United States Patent
Argiriadi et al.

(10) Patent No.: US 10,106,501 B2
(45) Date of Patent: Oct. 23, 2018

(54) NUCLEAR RECEPTOR MODULATORS

(71) Applicant: AbbVie Inc., North Chicago, IL (US)

(72) Inventors: Maria A. Argiriadi, Southborough, MA (US); Eric C. Breinlinger, Charlton, MA (US); Kevin P. Cusack, Holden, MA (US); Adrian D. Hobson, Shrewsbury, MA (US); Dominique Potin, Talant (FR); Martine Barth, Asniéres les Dijon (FR); Jerome Amaudrut, Dijon (FR); Olivia Poupardin, Varios es Chaignot (FR); Laurent Mounier, Marsannay le Bois (FR); Michael E. Kort, Lake Bluff, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/176,309

(22) Filed: Jun. 8, 2016

(65) Prior Publication Data

US 2016/0362370 A1  Dec. 15, 2016

Related U.S. Application Data

(60) Provisional application No. 62/343,905, filed on Jun. 1, 2016, provisional application No. 62/257,806, filed on Nov. 20, 2015.

(30) Foreign Application Priority Data

Jun. 9, 2015  (WO) ................. PCT/IB2015/001693

(51) Int. Cl.
| | | |
|---|---|---|
| C07D 209/08 | (2006.01) | |
| C07D 401/10 | (2006.01) | |
| C07D 403/10 | (2006.01) | |
| C07D 401/14 | (2006.01) | |
| C07D 405/12 | (2006.01) | |
| C07D 401/06 | (2006.01) | |
| C07D 491/107 | (2006.01) | |
| C07D 405/14 | (2006.01) | |
| C07D 235/06 | (2006.01) | |
| C07D 471/04 | (2006.01) | |
| C07D 487/04 | (2006.01) | |
| C07D 231/56 | (2006.01) | |
| C07D 235/16 | (2006.01) | |
| C07D 405/10 | (2006.01) | |
| C07D 491/10 | (2006.01) | |
| C07D 209/14 | (2006.01) | |
| C07D 209/18 | (2006.01) | |

(52) U.S. Cl.
CPC ......... *C07D 209/08* (2013.01); *C07D 209/14* (2013.01); *C07D 209/18* (2013.01); *C07D 231/56* (2013.01); *C07D 235/06* (2013.01); *C07D 235/16* (2013.01); *C07D 401/06* (2013.01); *C07D 401/10* (2013.01); *C07D 401/14* (2013.01); *C07D 403/10* (2013.01); *C07D 405/10* (2013.01); *C07D 405/12* (2013.01); *C07D 405/14* (2013.01); *C07D 471/04* (2013.01); *C07D 487/04* (2013.01); *C07D 491/10* (2013.01); *C07D 491/107* (2013.01)

(58) Field of Classification Search
CPC .................................................... C07D 209/08
See application file for complete search history.

(56) References Cited

U.S. PATENT DOCUMENTS

| | | |
|---|---|---|
| 5,290,798 A | 3/1994 | Gillard et al. |
| 5,468,898 A | 11/1995 | Huang et al. |
| 5,589,482 A | 12/1996 | Thompson |
| 5,962,695 A | 10/1999 | Nagahara et al. |
| 6,124,463 A | 9/2000 | Beck et al. |
| 7,157,487 B2 | 1/2007 | Nakayama et al. |
| 7,417,063 B2 | 8/2008 | Smallheer et al. |

(Continued)

FOREIGN PATENT DOCUMENTS

| | | |
|---|---|---|
| FR | 2890071 A1 | 3/2007 |
| JP | 3457694 B2 | 10/2003 |

(Continued)

OTHER PUBLICATIONS

Becker-Andre, Michael, et al., "Identification of Nuclear Receptor mRNAs by RT-PCR Amplification of Conserved Zinc-Finger Motif Sequences", Biochemical and Biophysical Research Communications, 194(3):1371-1379, Aug. 16, 1993.

(Continued)

*Primary Examiner* — Paul V Ward

(57) ABSTRACT

The invention provides compounds of Formula (I)

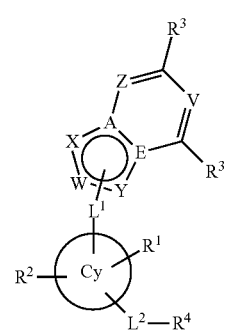

Formula (I)

pharmaceutically acceptable salts, thereof wherein the variable are defined herein. The compounds of the invention are useful for treating immunological conditions.

53 Claims, No Drawings

(56) References Cited

U.S. PATENT DOCUMENTS

| | | |
|---|---|---|
| 7,820,825 B2 | 10/2010 | Cole et al. |
| 9,095,583 B2 | 8/2015 | Karstens et al. |
| 9,603,838 B2 | 3/2017 | Karstens et al. |
| 2005/0043378 A1 | 2/2005 | Axe et al. |
| 2005/0043379 A1 | 2/2005 | Axe et al. |
| 2007/0219240 A1 | 9/2007 | Cole et al. |
| 2008/0153816 A1 | 6/2008 | Binet et al. |

FOREIGN PATENT DOCUMENTS

| | | | |
|---|---|---|---|
| WO | WO-2003/091211 A1 | 11/2003 | |
| WO | WO-2004/099192 A2 | 11/2004 | |
| WO | WO-2005/012297 A1 | 2/2005 | |
| WO | 2006050076 A1 | 5/2006 | |
| WO | 2007108936 A2 | 9/2007 | |
| WO | WO-2010/142801 A1 | 12/2010 | |
| WO | WO-2012/068589 A2 | 5/2012 | |
| WO | 2012/076672 A1 | 6/2012 | |
| WO | 2012/106995 A1 | 8/2012 | |
| WO | 2013015984 A1 | 1/2013 | |
| WO | 2014/026328 A1 | 2/2014 | |
| WO | WO-2014/179564 A1 | 11/2014 | |
| WO | 2015036411 A1 | 3/2015 | |
| WO | 2015/116904 A1 | 8/2015 | |
| WO | WO-2016/061160 A1 | 4/2016 | |

OTHER PUBLICATIONS

Chang Mi Ra, et al., "Pharmacologic Repression of Retinoic Acid Receptor-Related Orphan and Nuclear Receptor g Is Therapeutic in the Collagen-Induced Arthritis Experimental Model", Arthritis & Rheumatology, 66(3):579-588, Mar. 2014.

Codarri, Laura, et al., "RORgt drives production of the cytokine GM-CSF in helper T cells, whichis essnetion for the effector phase of autoimmune neuroinflammation", Nature Immunology, 12(6):560-568, Jun. 2011.

Dong, Zhaogang, et al., "Aberrant expression of circulating Th17, Th1 and Tc1 cells in patients with active and inactive ulcerative colitis", International Journal of Molecular Medicine, 31:989-997, 2013.

Eberl, Gérard, et al., "An essential function for the nuclear receptor RORgt in the generation of fetal lymphoid tissue inducer cells", Nature Immunology, 5(1):64-73, 2004.

Erbel, Christian, et al., "IL-17A Influences Essential Function of the Monocyte/Macrophage Lineage and is Involved in Advanced Murine and Human Atherosclerosis", J Immunol, 193:4344-4355, 2014.

Horai, Reiko, et al., "Cytokines in Autoimmune Uveitis", Journal of Interferon & Cytokine Research, 31(10):733-744, 2011.

International Search Report and Written Opinion for related PCT Application No. PCT/US2016/036283, dated Sep. 5, 2016.

Ivanov, Ivaylo I., et al., "The Orphan Nuclear Receptor RORgt Directs the Differentiation Program of Proinflammatory IL-17+ T Helper Cells", Cell, 126:1121-1133, Sep. 22, 2006.

Jellen, Anton M., "Retinoid-related orphan receptors (RORs): critical roles in development, immunity, circadian rythym, and cellular metabolism", NRS, 7:1-32, 2009.

Jin, Lihua, et al, "Structural Basis for Hydroxycholesterols as Natural Ligands of Orphan Nuclear Receptor RORg", Mol Endocrinol, 24(5)923-929, May 2010.

Kumawat, Ashok Kumar, et al., "Microscopic colitis patients demonstrate a mixed Th17/Tc17 and Th1/Tc1 mucosal cytokine profile", Molecular Immunology, 55:355-364, 2013.

Kurebayashi, Shogo, et al., "Retinoid-related orphan receptor g (RORg) is essential for lymphoid organogenesis and controls apoptosis during thymopoiesis", PNAS, 97(18):10132-10137.

Leonardi, Craig, et al., "Anti-Interleukin-17 Monoclonal Antibody Ixekizumab in Chronic Plaque Psoriasis", N Engl J Med 366(13):1190-1199, Mar. 29, 2012.

Leppkes, Maritz, et al., "RORg-Expressing Th17 Cells Induce Murine Chronic Intestinal Inflammation via Redundant Effects of IL-17A and IL-17F", Gastroenterology, 136(1):257-267, 2009.

Loubaki, Lionel, et al., "Co-Culture of Human Bronchial Fibroblasts and CD4+ T Cells Increases Th17 Cytokine Signature", Plos One, 8(12):1-12, Dec. 2013.

Ma, L., et al., "The Imbalance of Th17 cells and CD4+ CD25highFoxp3+ Treg cells in patients with atopic dermatitis", JEADV 28:1079-1086, 2014.

Martinez, Nicholas E., et al., "RORgt, but not T-bet, overexpression exacerbates an autoimmune model for multiple sclerosis", Journal of Neuroimmunology, 276:142-149, 2014.

Medvedev, Alexander, et al., "Cloning of a cDNA encoding the murine orphan receptor RZR/RORg and aharacterization of its response element", Gene, 181:199-206, 1996.

Meissburger, Bettina, et al., "Adipogenesis and insulin sensitivity in obesity are regulated by retinoid-related orphan receptor gamma", EMBO Mol Med, 3:637-651, 2011.

Dantelyushin, Stanislav, et al., "Rorgt+ innate lymphocytes and gd T cells initiate psoriasiform plaque formation in mice", The Journal of Clinical Investigation, 122(6):2252-2256, Jun. 2012.

Papp Kim A., et al., "Brodalumab, an Anti-Interleukin-17-Receptor Antibody for Psoriasis", N Engl J Med, 366 (13):1181-1189, Mar. 2012.

Park, Tae-Yoon, et al., "RORgt-specific transcriptional interactomic inhbition suppresses autoimmunity associated with TH17 cells", PNAS, 111(52):18673-18678, Dec. 30, 2014.

Peiser, Matthias, "Role of Th17 Cells in Skin Inflammation of Allergic Contact Dermatits", Clinical and Developmental Immunology, 2013(261037):1-10, 2013.

Purwar, Rahul, "Robust tumor immunity to melanoma mediated by interleukin-9-producing T cells", Nature Medicine, 18(8):1248-1254, Aug. 2012.

Raychaudhuri, Siba P., "Role of IL-17 in Psoriasis and Psoriatic Arthritis", Clinic Rev. Allerg Immunol, 44:183-193, 2013.

Solt, Laura A., et al., "Ligand regulation of retinoic acid receptor-related orphan receptors: implications for development of novel therapeutics", Current Opinion in Lipidology, 21:204-211, 2010.

Solt, Laura A., et al., "Action of RORs and their ligands in (patho)physiology", Trends in Endocrinology and Metabolism, 23(12):619-627, Dec. 2012.

Solt, Laura A., et al., "ROR inverse Agonist Suppresses Insulitis and Prevents Hyperglycemia in a Mouse Model of Type 1 Diabetes", Endocrinology 156(3):869-881, Mar. 2015.

Sun, Zuoming, et al., "Requirement for RORg in Thymocyte Survival and Lymphoid Organ Development", Science, 288(5475):2369-2373, Jun. 30, 2000.

Tilley, Stephen L., et al., "Retinoid-Related Orphan Receptor g Controls Immunoglobulin Production and Th1/Th2 Cytokine Balance in the Adaptive Immune Response to Allergen", J Immunol; 178:3208-3218, 2007.

Toussirot, Éric, "The IL23↑Th17 Pathway as a Therapeutic Target in Chronic Inflammatory Diseases", Inflammation & Allergy—Drug Targets, 11:159-168, 2012.

Troncone, Edoardo, et al., "Th17 Cytokines in Inflammatory Bowel Disease: Discerning the Good from the Bad", International Reviews of Immunology, 32:526-533, 2013.

Yang, Xuexian O., et al., "T Helper 17 Lineage Differentiation Is Programmed by Orphan Nuclear Receptors RORa and RORg", Immunity, 28:29-39, Jan. 2008.

Yoh, Keigyou, et al., "Overexpression of RORgt under control of the CD2 promoter induces polyclonal plasmacystosis and autoantibody production in transgenic mice", Eur. J. Immunol. 2012(42):1999-2009.

Yu, Yu, et al., "Prevention of GVHD while sparing GVL effect by targeting Th1 and Th17 transcription factor T-bet and RORgt in mice", Blood, 118(18):5011-5020, Nov. 3, 2011.

Bidad et al., "Effects of All-transretinoic Acid on Th17 and T Regulatory Cell Subsets in Patients with Ankylosing Spondylitis," The Journal of Rheumatology, 40(4): 476-483 (2013).

Bronner et al., "RORγAntagonists and Inverse Agonists: A Patent Review," Expert Opinion on Therapeutic Patents, 27(1): 101-112 (2017).

(56) References Cited

OTHER PUBLICATIONS

Fauber et al., "Reduction in Lipophilicity Improved the Solubility, Plasma-protein Binding, and Permeability of Tertiary Sulfonamide RORc Inverse Agonists," Bioorganic & Medicinal Chemistry Letters, 24: 3891-3897 (2014).

Gege et al., "Retinoid-related Orphan Receptor Gamma t (RORγt) Inhibitors from Vitae Pharmaceuticals (WO2015116904) and Structure Proposal for their Phase 1 Candidate VYP-43742," Expert Opinion on Therapeutic Patents, 26(6): 737-744 (2016).

Gege et al., "RORγt Inhibitors as Potential Back-Ups for the Phase II Candidate VYP-43742 from Vitae Pharmaceuticals: Patent Evaluation of WO2016061160 and US20160122345," Expert Opinion on Therapeutic Patents, 27(1): 1-8 (2017).

Wang et al., "Discovery of novel N-(5-(arylcarbonyl)thiazol-2-yl)amides and N-(5-(arylcarbonyl-thiophen-2-yl)amides as potent RORγt Inhibitors," Bioorganic & Medicinal Chemistry, 22: 692-702 (2014).

Fauber, et al, Modulators of the Nuclear Receptor Retinoic Acid Receptor-Related Orphan Receptor—(RORγ or RORc); Journal of Medicinal Chemistry, vol. 57, No. 14, pp. 5871-5892, Jul. 24, 2014.

International Preliminary Report on Patentability for International Application No. PCT/IB2015/001693 dated Dec. 12, 2017.

NUCLEAR RECEPTOR MODULATORS

REFERENCE TO RELATED APPLICATIONS

This application claims the benefit of the filing date, under 35 U.S.C. § 119(e), of U.S. Provisional Application No. 62/257,806, filed on Nov. 20, 2015; and U.S. Provisional Application No. 62/343,905, filed on Jun. 1, 2016. This application also claims foreign priority under 35 U.S.C. § 365(a), to International Application No. PCT/IB2015/001693, filed on Jun. 9, 2015. The entire contents of each of the aforementioned applications are incorporated herein by reference.

TECHNICAL FIELD

The present invention relates to novel compounds which modulate the activity of Rorc and the RORγt receptor, and their use as medicaments.

BACKGROUND OF THE INVENTION

The retinoic acid-related orphan receptor (ROR) isoforms RORα, RORβ, and RORγ are members of the steroid nuclear hormone receptor superfamily, and play prominent roles in a variety of biological processes including organ development, immunity, lipid homeostatsis and metabolism, and circadian rhythms (Jetten et al. *NURSA* 2009, 7, 1). The ROR family members are composed of both a ligand-binding domain (LBD) and a DNA-binding domain (DBD). Ligand binding causes a conformational change that modulates binding of co-regulatory proteins: agonists recruit co-activators; antagonists and inverse agonists disrupt the binding of co-activators or enhancing the binding of co-repressors thereby repressing the transcription of target genes (Fauber et al. *J. Med. Chem.* 2014, 57, 5871).

Retinoic acid-related orphan receptor γ thymus (RORγ, also referred to as RORc and NR1F3) is encoded by Rorc; human and mouse RORγ share high sequence homology, and nearly identical binding site homology (Jin, L. et al. *Mol. Endocrinol.* 2010, 24, 923). Mammalian RORγ exists in two distinct isoforms, RORγ and RORγt, which possess indentical LBDs and differ only in their N-terminal sequences (Medvedev et al. *Gene* 1996, 181, 199). Expression of the RORγt isoform is restricted to lymphoid organs including the thymus, whereas RORγ is more broadly expressed (liver, muscle, kidney), similar to RORαwhich is also found in brain and adipose tissue (Kurebayashi, S. et al. *Proc. Natl. Acad. Sci., U.S.A.* 2000, 97, 10132). RORβ is localized to the cerebral cortex (Hirose, T. et al. *Biochem. Biophys Res. Commun.* 1993, 194, 1371). RORγt is critical for the development of lymph nodes and Peyer's patches and for the normal differentiation of T helper-17 (Th17) cells, γδ T cells, and LTi cells (Sun et al. *Science* 2000, 288, 2369).

RORγt is an obligatory transcription factor that controls the differentiation of naive CD4+ T cells into Th17 lineage, and regulates transcription of the effector cytokine IL-17 in Th17 cells and cells of the innate immune response in both rodents and humans (Ivanov, I. et al. *Cell* 2006, 126, 1121). Pro-inflammatory cytokines including IL-17A, IL-17F, and IL-22 produced by Th17 cells and other RORγt+ lymphocytes activate and direct the immune response to extracellular pathogens (Ebert, G. et al. *Nat. Immunol.* 2004, 5, 64). Disruption of RORγ by genetic ablation of Rorc in mice attenuates disease severity in murine models of autoimmunity and inflammation including experimental autoimmune encephalomyelitis (EAE) induced by antigenic peptide, imiquimod-induced psoriasiform dermatitis, and allergic airway disease. Dysregulation of IL-17 transcription and secretion has been implicated multiple human autoimmune disorders including psoriasis, rheumatoid arthritis, inflammatory bowel disease (IBD), asthma, and multiple sclerosis (MS) (for example, see: Yang, X. et al. *Immunity* 2008, 28, 29; Pantelyushin, S. et al. *J. Clin. Invest.* 2012, 122, 2252; Leppkes, M. et al. *Gastroenterology* 2009, 136, 257; and Tilley, J. et al. *J. Immunol.* 2007, 178, 3208). The outcome of recent clinical trials with neutralizing antibodies to IL-17A and its receptor IL-17RA serve to highlight the role of this cytokine in psoriasis disease pathogenesis (Papp, K. et al. *New. Engl. J. Med.* 2012, 366, 1181; Leonardi, C. et al. *New. Engl. J. Med.* 2012, 366, 1190. The attenuation of IL-17 production from activated T cells and Th17, for example via inhibition or RORγt, may offer a similar therapeutic benefit.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In a first embodiment the invention provides a compound of Formula (I)

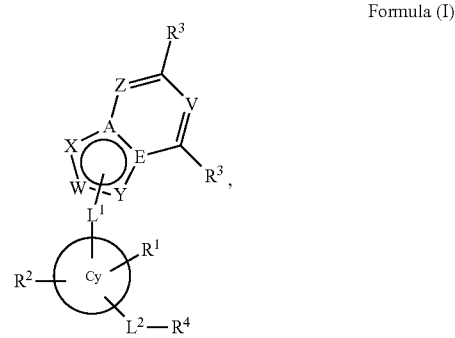

Formula (I)

a pharmaceutically acceptable salt, or a stereoisomer thereof, wherein
  W is C or $CR^a$, $L^1$ is connected to W or Y; and
    A and E are independently C or N provided both are not N;
    V is $CR^3$ or N;
    X is $CR^a$, $NR^a$, N, or O;
    Y is C, $CR^a$, $NR^a$, N, O or S;
    Z is $CR^3$ or N; or
  W is N or $NR^a$, $L^1$ is connected to W or Y; and
    A and E are independently C or N provided both are not N;
    V is $CR^3$ or N;
    X is $CR^a$, $NR^a$ or N;
    Y is C, $CR^a$ or N;
    Z is $CR^3$ or N; or
  Cy is a six-membered aromatic, heteroaromatic or partially saturated ring substituted with $R^1$ and $R^2$;
  $L^1$ is —$CH(R^b)$—, —$C(R^b)(R^d)$—, C(O) or —$N(R^c)$—;

L² is —C(O)—, —O—, —C(R^b)(R^d)—, —S—, —S(O)—, —S(O)₂—;

R¹ and R² are independently halo, —O—(C₁-C₃)alkyl, —O—(C₃-C₆)cycloalkyl, optionally substituted (C₃-C₆)cycloalkyl, or (C₁-C₃)alkyl;

each R³ is independently H, CF₃, CN, halo, —C(=O)(C₁-C₃)alkyl, —C(O)N(R^e)₂, —NR^eCOR^e, —OCHF₂, OCF₃, —O—(C₁-C₃)alkyl, —O—(C₃-C₆)cyclo alkyl, —S—(C₁-C₃)alkyl, optionally substituted (C₁-C₆)alkyl, optionally substituted (C₃-C₆)cycloalkyl, optionally substituted heteroaryl or optionally substituted heterocyclyl;

R⁴ is H, —OH, optionally substituted (C₁-C₆)alkyl, —NR⁵R⁶, optionally substituted (C₃-C₆)cycloalkyl or —(CH₂)ₘ-optionally substituted heterocyclyl;

wherein R⁵ is H or —(C₁-C₃)alkyl, and R⁶ is optionally substituted (C₁-C₄)alkyl, optionally substituted (C₃-C₆)cycloalkyl or —(CH₂)ₘ-optionally substituted heterocyclyl; or R⁵ and R⁶, together with the nitrogen atom to which they are attached, form an optionally substituted heterocyclyl;

each R^a is independently H, —C(O)CH₃, optionally substituted (C₁-C₆)alkyl, optionally substituted (C₃-C₆)cycloalkyl or S(O)₂-phenyl;

each R^b is independently H, F, OH, —O—(C₁-C₃)alkyl, or (C₁-C₃)alkyl; R^e is independently H or (C₁-C₃)alkyl;

each R^d is independently H, F, or (C₁-C₃)alkyl; or R^d and R^b form a (C₃—O₅) spirocycle;

R^e is independently H or (C₁-C₃)alkyl; and m is independently 0 or 1;

provided that not more than two of A, E, W, X and Y are N.

In a second embodiment the invention provides a compound according to the first embodiment, wherein Cy is

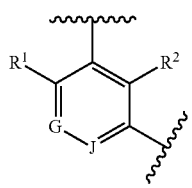

wherein G and J are independently CH or N.

In a third embodiment, the invention provides a compound according to any of the foregoing embodiments, wherein the compound is a compound of Formula (Ia)

Formula (Ia)

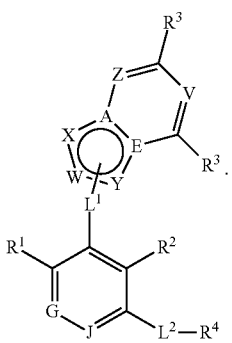

In a fourth embodiment, the invention provides a compound according to any of the foregoing embodiments, wherein L¹ is —CH₂—, —C(O)—, —C(H)(OH)—, —C(H)(OCH₃)—, or —C(H)(CH₃)—.

In a fifth embodiment, the invention provides a compound according to any of the foregoing embodiment, wherein L² is —C(O)—, —O— or —CH₂—.

In a sixth embodiment the invention provides a compound according to any of the foregoing embodiments, wherein R¹ and R² are independently halogen, —O—(C₁-C₃)alkyl, cyclopropyl, or (C₁-C₃)alkyl.

In a seventh embodiment, the invention provides a compound according to any of the foregoing embodiments, wherein R³ is independently H, —CF₃, —CN, halogen, —OCHF₂, —OCF₃, —C(O)N(R^e)₂, —NR^eCOR^e, —(C₁-C₃)alkyl, —O—(C₁-C₃)alkyl, —S—(C₁-C₃)alkyl, (C₃-C₆)cycloalkyl, or morpholinyl.

In an eighth embodiment, the invention provides a compound according to any of the foregoing embodiments, wherein R⁴ is H, OH, optionally substituted (C₁-C₆)alkyl, —CH₂-optionally substituted tetrahydro-2H-pyranyl, —N(CH₂CH₃)—CH₂CH₂OH, —NH—CH₂-optionally substituted tetrahydro-2H-pyranyl, —N(H)-optionally substituted (C₃-C₆)cycloalkyl, —NH-optionally substituted oxetanyl, —NH-optionally substituted tetrahydro-2H-pyranyl, optionally substituted (C₃-C₆)cycloalkyl, optionally substituted azabicyclo[2.2.1]heptanyl, optionally substituted azabicyclo[3.1.0]hexanyl, optionally substituted azaspiro[3.3]heptanyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted azepanyl, optionally substituted azetidinyl, optionally substituted 1,2-diazepanyl, optionally substituted 1,4-diazepanyl, optionally substituted morpholinyl, optionally substituted oxetanyl, optionally substituted piperazinyl, optionally substituted piperidinyl, optionally substituted pyrrolidinyl, or thiomorpholine 1,1-dioxide.

In a ninth embodiment, the invention provides a compound according any of the foregoing embodiments, wherein the (C₁-C₆)alkyl is optionally substituted with one or more halo, —CO₂H, or —CO₂(C₁-C₄)alkyl;

the —NH—CH₂-tetrahydro-2H-pyranyl is optionally substituted with one or two —OH or —O(C₁-C₄)alkyl;

the —N(H)—(C₃-C₆)cycloalkyl is optionally substituted with one or more F, —OH, —COOH, or —CO₂(C₁-C₄)alkyl;

the (C₃-C₆)cycloalkyl is optionally substituted with one or more F, —OH, —COOH, or —CO₂(C₁-C₄)alkyl;

the azabicyclo[2.2.1]heptanyl and the azabicyclo[3.1.0]hexanyl are each independently optionally substituted with —CO₂H or —CO₂(C₁-C₄)alkyl;

the azaspiro[3.3]heptanyl is optionally substituted with —CH₂CO₂H, —CH₂CO₂CH₃, —CO₂H, —CO₂CH₃;

the 2-oxa-6-azaspiro[3.3]heptanyl, the 2-oxa-7-azaspiro[3.5]nonanyl, the 2-oxa-8-azaspiro[4.5]decanyl are each independently optionally substituted with —CH₂CO₂H;

the azetidinyl is optionally substituted with one or two —CH₃, —OH, —OCH₃, —(C₁-C₄)alkylene-OH, —CH₂OCH₃, —(C₁-C₄)alkyleneO(C₁-C₄)alkyl, —CO₂(C₁-C₄)alkyl, —CO₂H, —(C₁-C₄)alkylene-CO₂H, —(C₁-C₄)alkylene-CO₂—(C₁-C₄)alkyl, —N(CH₃)₂, pyrrolidinyl;

the 1,2-diazepanyl or the 1,4-diazepanyl is optionally substituted with —(C₁-C₄)alkylene-OH;

the morpholinyl is optionally substituted with =O;

the piperazinyl, the piperidinyl and the pyrrolidinyl are each independently optionally substituted with one or more -halo, —CN, —($C_1$-$C_4$)alkyl, —$CH_2$-cyclopropyl, —($C_1$-$C_4$)alkylene-F, —$CF_3$, —$CH_2CF_3$, —COOH, —($C_1$-$C_4$)alkyleneCOOH, —CH(OH)$CO_2$H, —$COCH_3$, —$CO_2$($C_1$-$C_4$)alkyl, —CH(OH)$CO_2CH_3$, —($C_1$-$C_4$)alkylene-C(=O)O($C_1$-$C_4$)alkyl, —($C_1$-$C_4$)alkylene-OH, —O($C_1$-$C_4$)alkyl, —($C_1$-$C_4$)alkyleneO($C_1$-$C_4$)alkyl, —O($C_1$-$C_4$)alkyleneCO$_2$H, —O($C_1$-$C_4$)alkyleneC(=O)O($C_1$-$C_4$)alkyl, —$CONHCH_3$, —$SO_2$—($C_1$-$C_4$)alkyl, —$NH_2$, —NH($C_1$-$C_4$)alkyl, —N(($C_1$-$C_4$)alkyl)$_2$, cyclobutanecarboxylic acid, or oxetanyl.

In a tenth embodiment, the invention provides a compound according to any of the foregoing embodiments, wherein $R^1$ and $R^2$ are both halo or —$CH_3$.

In an eleventh embodiment, the invention provides a compound according to any of the foregoing embodiments, wherein W is C or CH, A is C and E is C.

In a twelfth embodiment, the invention provides a compound according to any of the foregoing embodiments, wherein $L^1$ is $CH_2$ or C(O) and $L^2$ is C(O).

In a thirteenth embodiment, the invention provides a compound according to any of the foregoing embodiments, wherein G is CH.

In a fourteenth embodiment, the invention provides a compound according to any of the foregoing embodiments, wherein J is CH.

In a fifteenth embodiment, the invention provides a compound according to any one of the first to fourteenth embodiments, wherein W is CH; X is $CR^a$, wherein $R^a$ is H or —$CH_3$; Y is N; A is C; E is C; V is $CR^3$, wherein $R^3$ is H; Z is N or $CR^3$, wherein $R^3$ is H, —$CH_3$, or —$CF_3$; $L^1$ is connected to Y; $L^1$ is —$CH_2$— or —C(O)—; $L^2$ is —C(O)—; $R^1$ is —Cl or —$CH_3$; $R^2$ is —Cl or —$CH_3$; each $R^3$ is independently H, —F, —Cl, —CN, —$CH_3$, —CH($CH_3$)$_2$, —$CF_3$, —$OCHF_2$, —$OCF_3$, —$SCH_3$, or cyclopropyl; and $R^4$ is optionally substituted 2-oxa-6-azaspiro[3.3]heptanyl, optionally substituted piperidinyl.

In a sixteenth embodiment, the invention provides a compound according to the fifteenth embodiment wherein the optionally substituted $R^4$ 2-oxa-6-azaspiro[3.3]heptanyl is optionally substituted by —$CH_2CO_2H$.

In a seventeenth embodiment, the invention provides a compound according to the fifteenth embodiment wherein the $R^4$ optionally substituted piperidinyl is optionally substituted by —$CH_3$, —COOH, —$CH_2CO_2H$, —$CH_2CH_2CO_2H$, —$CO_2CH_3$, —$CO_2CH_2CH_3$, or —OH.

In an eighteenth embodiment, the invention provides a compound according to any one of the first to fourteenth embodiments, wherein W is C; X is $NR^a$, wherein $R^a$ is —$CH_3$, —$CH_2CH_3$, —$CH_2CH(CH_3)_2$; Y is N; A is C; E is C; V is $CR^3$, wherein $R^3$ is H, Br, —CN, or —$CF_3$; Z is $CR^3$ or N, wherein $R^a$ is H or $CH_3$; $L^1$ is connected to W; $L^1$ is —$CH_2$— or —C(O)—; $L^2$ is —$CH_2$— or —C(O)—; $R^1$ is —Cl or —$CH_3$; $R^2$ is —Cl or —$CH_3$; each $R^3$ is independently —Br, —Cl, —CN, —$CH_3$, or —$CF_3$; and $R^4$ is —N($CH_2CH_3$)—$CH_2CH_2OH$, —NH-optionally substituted cyclohexyl, —NH-optionally substituted oxetanyl, optionally substituted azetidinyl, optionally substituted 1,4-diazepanyl, optionally substituted 3-azabicyclo[3.1.0]hexanyl, optionally substituted morpholinyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted piperazinyl, optionally substituted, or optionally substituted pyrrolidinyl.

In a nineteenth embodiment the invention provides a compound according to the eighteenth embodiment wherein t the $R^4$ optionally substituted the $R^4$ optionally substituted 1,4-diazepanyl is optionally substituted with —$CH_2CH_2OH$; the $R^4$ optionally substituted azetidinyl is optionally substituted with —OH, —$CH_2OH$, —$CH_2CH_2OH$, —$CH_2OCH_3$, —$CH_2CH_2OCH_3$, —N($CH_3$)$_2$, or pyrrolidinyl; the $R^4$ optionally substituted 1,4-diazepanyl is optionally substituted with —$CH_2CH_2OH$; the $R^4$ optionally substituted 3-azabicyclo[3.1.0]hexanyl is optionally substituted with —COOH or —$CO_2CH_3CH_3$, the $R^4$ optionally substituted morpholinyl is optionally substituted with =O; the $R^4$ optionally substituted piperazinyl is optionally substituted with —F, —$CH_3$, —CH($CH_3$)$_2$, —$CH_2CF_3$, —COOH, —$CH_2$-cyclopropyl, —$CH_2CH_2OH$, —$CH_2CH_2OCH_3$, —$CH_2CH(OH)CH_3$, —$CH_2CH(F)CH_3$, cyclobutanecarboxylic acid, or oxetanyl; the $R^4$ optionally substituted piperidinyl is optionally substituted with —$CH_3$, —$CH_2COOH$, —$CH_2OH$, —$CH_2CH_2OH$, —$CH_2CH_2OCH_3$, —C($CH_3$)$_2CH_2OH$, —C($CH_3$)$_2OH$, —C($CH_3$)$_2CH_2OH$, —CH(OH)$CH_3$, —$CH_2CH(OH)CH_3$, —$CH_2C(CH_3)_2OH$, —$CH_2OCH_3$, —COOH, —OH, —$OCH_3$, —N($CH_3$)$_2$, or oxetanyl; or the $R^4$ optionally substituted pyrrolidinyl is optionally substituted with —$CH_2CH_2OH$, —$CH_2OCH_3$, —$CONHCH_3$, —OH, or —$OCH_3$.

In a twentieth embodiment, the invention provides a compound according to any one of the first to fourteenth embodiments, wherein W is C; X is $NR^a$, wherein $R^a$ is H, —$CH_3$, —$CH_2CH_3$, —$COCH_3$, or —$CH_2CH(CH_3)_2$; Y is $CR^a$, wherein $R^a$ is H; Z is $CR^3$, wherein $R^3$ is H or —$CH_3$; A is C; E is C; V is $CR^3$, wherein $R^3$ is H, —CN, —$CH_3$, or —$CF_3$; $L^1$ is connected to W; $L^1$ is —$CH_2$—, —C(O)—, —CH(OH)—, or —CH($OCH_3$)—; $L^2$ is —O—, —$CH_2$—, or —C(O)—; $R^1$ is —Cl, —$CH_3$, or cyclopropyl; $R^2$ is —Cl or —$CH_3$; each $R^3$ is independently H, —F, —Br, —Cl, —CN, —$CH_3$, —$CF_3$, —$OCH_3$, —$OCHF_2$, —$OCF_3$, —$CONHCH_3$, —CON($CH_3$)$_2$, —$NHCOCH_3$, cyclopropyl, or morpholinyl; and $R^4$ is H, —OH, optionally substituted ($C_1$-$C_6$)alkyl (—$CO_2H$), —$CH_2$-optionally substituted tetrahydro-2H-pyranyl, —NH—$CH_2$-optionally substituted tetrahydro-2H-pyranyl, —NH-optionally substituted cyclohexyl (—OH, —COOH), —NH-optionally substituted oxetanyl, —NH-optionally substituted tetrahydro-2H-pyranyl, optionally substituted azabicyclo[2.2.1]heptanyl, optionally substituted 3-azabicyclo[3.1.0]hexanyl, optionally substituted azaspiro[3.3]heptanyl, optionally substituted azetidinyl, optionally substituted cyclobutyl, optionally substituted cyclohexyl, optionally substituted cyclopentyl, optionally substituted 1,4-diazepanyl, optionally substituted morpholinyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted piperazinyl, optionally substituted piperidinyl, or optionally substituted pyrrolidinyl.

In a twenty-first embodiment, the invention provides a compound according to the nineteenth embodiment wherein the $R^4$ optionally substituted ($C_1$-$C_6$)alkyl is optionally substituted by —$CO_2H$, the $R^4$ cyclohexyl of the —NH-optionally substituted cyclohexyl is optionally substituted by —OH or —COOH; optionally substituted azabicyclo[2.2.1]heptanyl (—$CO_2H$, —$CO_2Me$), the $R^4$ optionally substituted 3-azabicyclo[3.1.0]hexanyl is optionally substituted by —$CO_2H$ or —$CO_2CH_2CH_3$, the $R^4$ optionally substituted azaspiro[3.3]heptanyl is optionally substituted by —$CH_2CO_2H$, —$CH_2CO_2CH_3$, —$CO_2H$, or —$CO_2CH_3$; the $R^4$ optionally substituted azetidinyl is optionally substituted by —$CH_3$, —OH, —$OCH_3$, —$CO_2CH_3$, —$CO_2H$, —$CO_2CH_2CH_3$, —$CH_2CO_2H$, —$CH_2CO_2CH_2CH_3$, or pyrrolidinyl; the $R^4$ optionally substituted cyclobutyl is optionally substituted by —COOH or —CO$_2$(C$_1$-C$_4$)alkyl; the R$^4$ optionally substituted cyclohexyl is optionally substituted by —COOH or —CO$_2$(C$_1$-C$_4$)alkyl; the R$^4$ optionally substituted cyclopentyl is optionally substituted by —COOH or —CO$_2$(C$_1$-C$_4$)alkyl; the R$^4$ optionally substituted 1,4-diazepanyl is optionally substituted by —CH$_2$CH$_2$OH), the R$^4$ optionally substituted morpholinyl is optionally substituted by =O; optionally substituted 2-oxa-6-azaspiro[3.3]heptanyl, optionally substituted 2-oxa-7-azaspiro[3.5]nonanyl, the R$^4$ optionally substituted 2-oxa-8-azaspiro[4.5]decanyl, optionally substituted piperazinyl is optionally substituted by —CH$_3$, —CH(CH$_3$)$_2$, —CH$_2$CH$_2$OH, —CH$_2$CH(F)CH$_3$, —COCH$_3$, —CH$_2$CH$_2$OCH$_3$, —CH$_2$CO$_2$H, —CH(CH$_3$)CO$_2$H, —C(CH$_3$)$_2$CO$_2$H, —CH$_2$CO$_2$Me, —CH$_2$CO$_2$CH$_2$CH$_3$, oxetanyl, or cyclobutanecarboxylic acid; the R$^4$ optionally substituted piperidinyl is optionally substituted by —CH$_3$, —F, —CH$_2$OH, —CH$_2$CH$_2$OH, —CH$_2$CH$_2$OCH$_3$, —CH$_2$OCH$_3$, —C(CH$_3$)$_2$CH$_2$OH, —CH$_2$C(CH$_3$)$_2$OH, —CH$_2$CH(OH)CH$_3$, —CH(OH)CH$_3$, —C(OH)(CH$_3$)$_2$, —CO$_2$H, —CO$_2$Me, —CO$_2$CH$_2$CH$_3$, —CH$_2$CO$_2$H, —CH$_2$CH$_2$CO$_2$H, —CH(CH$_3$)CO$_2$H, —C(CH$_3$)$_2$CO$_2$H, —CH(OH)CO$_2$H, —CH(OH)CO$_2$CH$_3$, —CH(CH$_3$)CO$_2$CH$_2$CH$_3$, —CH$_2$CO$_2$CH$_3$, —CH$_2$CO$_2$CH$_2$CH$_3$, —N(CH$_3$)$_2$, —OH, —OCH$_3$, —OCH$_2$CO$_2$H, —OCH$_2$CO$_2$CH$_2$CH$_3$, —SO$_2$CH$_3$, or oxetanyl; or the R$^4$ optionally substituted pyrrolidinyl is optionally substituted by —OH, —CH$_2$OH, —CO$_2$H, —CO$_2$CH$_3$, —CH$_2$CO$_2$H, —CH$_2$CO$_2$CH$_3$, —CH$_2$OCH$_3$, —C(O)NHCH$_3$, or —N(CH$_3$)$_2$.

In a twenty-second embodiment, the invention provides a compound according to any one of the first to fourteenth embodiments, wherein W is C; X is CR$^a$, wherein R$^a$ is H; Y is NR$^a$, wherein R$^a$ is H or —CH$_3$; Z is N; A is C; E is C; V is CR$^3$, wherein R$^3$ is H or —CF$_3$; L$^1$ is connected to W; L$^1$ is —CH$_2$—, —C(O)—, or —CH(OH)—; L$^2$ is —C(O)—; R$^1$ is Cl; R$^2$ is Cl; each R$^3$ is independently H or —CF$_3$; and R$^4$ is optionally substituted morpholinyl.

In a twenty-third embodiment, the invention provides a compound according to any one of the first to fourteenth embodiments, wherein W is CH; X is N; Y is N; Z is CR$^3$; A is C; E is C; V is CR$^3$; and L$^1$ is connected to Y.

In a twenty-fourth embodiment, the invention provides a compound according to any one of the first to fourteenth embodiments, wherein W is C; X is NR$^a$, wherein R$^a$ is H or —CH$_3$; Y is CR$^a$, wherein R$^a$ is H; Z is N; A is C; E is C; V is CR$^3$, wherein R$^3$ is H; L$^1$ is connected to W; L$^1$ is —CH$_2$— or —C(O)—; L$^2$ is —C(O)—; R$^1$ is Cl; R$^2$ is Cl; each R$^3$ is independently H, —CH$_3$, or —CF$_3$; and R$^4$ is optionally substituted morpholinyl, optionally substituted piperazinyl, or optionally substituted piperidinyl.

In a twenty-fifth embodiment, the invention provides a compound according to the twenty-third embodiment, wherein the R4 optionally substituted piperazinyl is optionally substituted by —SO$_2$CH$_3$; the optionally substituted piperidinyl is optionally substituted by —CN, —CH$_3$, —OH, —COOH, —CH$_2$COOH, —CH$_2$CH$_2$OCH$_3$, or —SO$_2$CH$_3$.

In a twenty-sixth embodiment, the invention provides a compound according to any one of the first to fourteenth embodiments, wherein W is C; X is CR$^a$, wherein R$^a$ is H or —CH$_3$; Y is N; A is N; E is C; Z is N; V is CR$^3$, wherein R$^3$ is H or —CH$_3$; L$^1$ is connected to W; L$^1$ is —CH$_2$— or —C(O)—; L$^2$ is —C(O)—; R$^1$ is —Cl; R$^2$ is —Cl; each R$^3$ is independently H, —Cl, —CN, —CH$_3$, or —CF$_3$; and R$^4$ is optionally substituted, morpholinyl, optionally substituted piperazinyl (e.g., substituted with —CH$_3$, —SO$_2$CH$_3$, or oxetanyl), or optionally substituted piperidinyl (e.g., substituted with —CH$_2$COOH, oxetanyl).

In a twenty-seventh embodiment, the invention provides a compound according to any one of the first to fourteenth embodiments, wherein W is C; X is CR$^a$, wherein R$^a$ is H or —CH$_3$; Y is N; Z is CR$^3$, wherein R$^3$ is H; A is N; E is C; V is CR$^3$, wherein R$^3$ is H; L$^1$ is connected to W; L$^1$ is —CH$_2$—; L$^2$ is —C(O)—; R$^1$ is —Cl; R$^2$ is —Cl; each R$^3$ is independently H, —CN, —CH$_3$, or —CF$_3$; R$^4$ is optionally substituted morpholinyl, optionally substituted piperazinyl (e.g., substituted with oxetanyl), optionally substituted piperidinyl (e.g., substituted with —OH, —OCH$_3$, —CH$_2$OH, —CH$_2$CH$_2$OH, —CH$_2$CH$_2$OCH$_3$, —CH(OH)CH$_3$, —C(OH)(CH$_3$)$_2$, —CH$_2$CO$_2$H, —CH$_2$CO$_2$Me, —N(CH$_3$)$_2$, oxetanyl), or optionally substituted pyrrolidinyl (e.g., substituted with —OH).

In a twenty-eighth embodiment, the invention provides a compound according to any one of the first to fourteenth embodiments, wherein W is N; X is CR$^a$, wherein R$^a$ is H or —CH$_3$; Y is N; Z is CR$^3$, wherein R$^3$ is H; A is C; E is C; V is CR$^3$, wherein R$^3$ is H; L$^1$ is connected to W; L$^1$ is —CH$_2$— or —C(O)—; L$^2$ is —C(O)—; R$^1$ is —Cl; R$^2$ is —Cl; each R$^3$ is independently H, —CH$_3$, or —CF$_3$; and R$^4$ is optionally substituted morpholinyl or optionally substituted piperidinyl (e.g., substituted with —CH$_2$COOH).

In a twenty-ninth embodiment, the invention provides a compound according to any one of the first to fourteenth embodiments, wherein W is N; X is CR$^a$, wherein R$^a$ is H or —CH$_3$; Y is N; Z is CR$^3$, wherein R$^3$ is H; E is C; V is CR$^3$, wherein R$^3$ is H; L$^1$ is connected to Y; L$^1$ is —CH$_2$— or —C(O)—; L$^2$ is —C(O)—; R$^1$ is —Cl; R$^2$ is —Cl; each R$^3$ is independently H, —CH$_3$, or —CF$_3$; and R$^4$ is optionally substituted morpholinyl or optionally substituted piperidinyl (e.g., substituted with —CH$_2$COOH, oxetanyl).

In a thirtieth embodiment, the invention provides a compound according to any one of the first to fourteenth embodiments, wherein W is N; X is NR$^a$, wherein R$^a$ is H or —CH$_3$; Y is C; Z is CR$^3$, wherein R$^3$ is H; A is C; E is C; V is CR$^3$, wherein R$^3$ is H; L$^1$ is connected to Y; L$^1$ is —CH$_2$—; L$^2$ is —C(O)—; R$^1$ is —Cl; R$^2$ is —Cl; each R$^3$ is independently H, —CH$_3$, or —CF$_3$; and R$^4$ is optionally substituted piperidinyl (e.g., substituted with —CH$_2$COOH).

In a thirty-first embodiment, the invention provides a compound according to any one of the first to fourteenth embodiments, wherein W is C; X is NR$^a$, wherein R$^a$ is H or CH$_3$; Y is CR$^a$, wherein R$^a$ is H; Z is CR$^3$, wherein R$^3$ is H; A is C; E is C; V is N; L$^1$ is connected to W; L$^1$ is —CH$_2$—; L$^2$ is —C(O)—; R$^1$ is —Cl; R$^2$ is —Cl; each R$^3$ is independently H, —CN, —CF$_3$, or CH$_3$; and R$^4$ is optionally substituted morpholinyl or optionally substituted piperazinyl (e.g., substituted with oxetanyl).

In a thirty-second embodiment, the invention provides a compound according to any one of the first to fourteenth embodiments, wherein W is C; X is CR$^a$, wherein R$^a$ is H or CH$_3$; Y is N; Z is CR$^3$, wherein R$^3$ is H; A is C; E is C; V is N; L$^1$ is connected to Y; L$^1$ is —CH$_2$— or —C(O)—; L$^2$ is —C(O)—; R$^1$ is —Cl; R$^2$ is —Cl; each R$^3$ is independently H, —CF$_3$, or —CH$_3$; and R$^4$ is optionally substituted morpholinyl or optionally substituted piperidinyl (e.g., substituted with —CH$_2$COOH).

In a thirty-third embodiment, the invention provides a compound according to any one of the first to fourteenth embodiments, wherein W is CR$^a$, wherein R$^a$ is H; X is O or NR$^a$, wherein R$^a$ is H or CH$_3$; Y is C; Z is CR$^3$, wherein R$^3$ is H or —CF$_3$; A is C; E is C; V is CR$^3$, wherein R$^3$ is H; L$^1$ is connected to Y; L$^1$ is —CH$_2$—; L$^2$ is —C(O)—; R$^1$ is —Cl; R$^2$ is —Cl; each R$^3$ is independently H, —CH$_3$, —CF$_3$, or —OCF$_3$; and R$^4$ is optionally substituted piperidinyl (e.g., substituted with —CH$_3$, —COOH, —CH$_2$COOH, —CH$_2$CO$_2$CH$_3$, —CO$_2$CH$_2$CH$_3$).

In a thirty-fourth embodiment, the invention provides a compound according to any of the foregoing embodiments, wherein the compound is 1-(2,4-dichloro-3-((1,4-dimethyl-6-(trifluoromethyl)-1H-indol-2-yl)methyl)benzoyl)piperidine-4-carboxylic acid;

2-(2,6-dichloro-3-(morpholine-4-carbonyl)benzyl)-1,4-dimethyl-1H-pyrrolo[2,3-b]pyridine-6-carbonitrile;

2-(1-(2,4-dichloro-3-((3,7-dimethyl-5-(trifluoromethyl)-1H-indazol-1-yl)methyl)benzoyl)piperidin-4-yl)acetic acid;

(3R,4R)-1-(2,4-dichloro-3-((1,4-dimethyl-6-(trifluoromethyl)-1H-indol-2-yl)methyl)benzoyl)-3-methylpiperidine-4-carboxylic acid;

2-(1-(2,4-dichloro-3-((5-cyano-3,7-dimethyl-1H-indol-1-yl)methyl)benzoyl)piperidin-4-yl)acetic acid;

2-(1-(2,4-dichloro-3-(5-cyano-3,7-dimethyl-1H-indole-1-carbonyl)benzoyl)piperidin-4-yl)acetic acid;

2-(1-(2,4-dichloro-3-(3,7-dimethyl-5-(trifluoromethyl)-1H-indole-1-carbonyl)benzoyl)piperidin-4-yl)acetic acid;

2-(1-(2,4-dichloro-3-((1,4-dimethyl-6-(trifluoromethyl)-1H-indol-2-yl)methyl)benzoyl)piperidin-4-yl)propanoic acid;

2-(2,4-dichloro-3-((1,4-dimethyl-6-(trifluoromethyl)-1H-indol-2-yl)methyl)benzoyl)-2-azaspiro[3.3]heptane-6-carboxylic acid;

1-(2,4-dichloro-3-((1,4-dimethyl-6-(trifluoromethyl)-1H-indol-2-yl)methyl)benzoyl)piperidine-4-carboxylic acid;

3-(4-(2,4-dichloro-3-((1,4-dimethyl-6-(trifluoromethyl)-1H-indol-2-yl)methyl)benzoyl)piperazin-1-yl)cyclobutanecarboxylic acid;

2-((1-(2,4-dichloro-3-((1,4-dimethyl-6-(trifluoromethyl)-1H-indol-2-yl)methyl)benzoyl)piperidin-4-yl)oxy)acetic acid;

2-(4-(2,4-dichloro-3-((1,4-dimethyl-6-(trifluoromethyl)-1H-indol-2-yl)methyl)benzoyl)piperazin-1-yl)propanoic acid;

2-(4-(2,4-dichloro-3-((1,4-dimethyl-6-(trifluoromethyl)-1H-indol-2-yl)methyl)benzoyl)piperazin-1-yl)acetic acid;

(3S,4S)-1-(2,4-dichloro-3-((1,4-dimethyl-6-(trifluoromethyl)-1H-indol-2-yl)methyl)benzoyl)-3-methylpiperidine-4-carboxylic acid;

(3R,4R)-1-(2,4-dichloro-3-((1,4-dimethyl-6-(trifluoromethyl)-1H-indol-2-yl)methyl)benzoyl)-3-methylpiperidine-4-carboxylic acid;

2-(1-(2,4-dichloro-3-((1,4-dimethyl-6-(trifluoromethyl)-1H-benzo[d]imidazol-2-yl)methyl)benzoyl)piperidin-4-yl)acetic acid;

(2,4-dichloro-3-((1,4-dimethyl-6-(trifluoromethyl)-1H-pyrrolo[2,3-b]pyridin-2-yl)methyl)phenyl)(4-hydroxypiperidin-1-yl)methanone;

2-(2,6-dichloro-3-(4-(oxetan-3-yl)piperazine-1-carbonyl)benzoyl)-1,4-dimethyl-1H-indole-6-carbonitrile;

2-(1-(2,4-dichloro-3-((3,7-dimethyl-5-(trifluoromethyl)-1H-indol-1-yl)methyl)benzoyl)piperidin-4-yl)acetic acid;

2-(1-(2,4-dichloro-3-(3,7-dimethyl-5-(trifluoromethyl)-1H-indole-1-carbonyl)benzoyl)piperidin-4-yl)acetic acid;

2-(1-(2,4-dichloro-3-(1,4-dimethyl-6-(trifluoromethyl)-1H-indole-2-carbonyl)benzoyl)piperidin-4-yl)acetic acid;

2-(1-(2,4-dichloro-3-((3,7-dimethyl-5-(trifluoromethyl)-2H-indazol-2-yl)methyl)benzoyl)piperidin-4-yl)acetic acid;

2-(1-(2,4-dichloro-3-((1,4-dimethyl-6-(trifluoromethyl)-1H-indol-2-yl)methyl)benzoyl)piperidin-4-yl)propanoic acid;

2-(2-(2,4-dichloro-3-((1,4-dimethyl-6-(trifluoromethyl)-1H-indol-2-yl)methyl)benzoyl)-2-azaspiro[3.3]heptan-6-yl)acetic acid;

2-(1-(2,4-dichloro-3-((1,4-dimethyl-6-(trifluoromethoxy)-1H-indol-2-yl)methyl)benzoyl)piperidin-4-yl)acetic acid;

2-(1-(2,4-dichloro-3-((1,4-dimethyl-6-(trifluoromethyl)-1H-indol-2-yl)methyl)benzoyl)-3-methylpiperidin-4-yl)acetic acid;

2-(1-(2,4-dichloro-3-((7-methyl-5-(trifluoromethyl)-1H-indol-1-yl)methyl)benzoyl)piperidin-4-yl)acetic acid;

2-(1-(2,4-dichloro-3-((1,4-dimethyl-6-(trifluoromethyl)-1H-indol-2-yl)methyl)benzoyl)-3-methylpiperidin-4-yl)acetic acid;

(2,4-dichloro-3-((1,4-dimethyl-6-(trifluoromethyl)-1H-indol-2-yl)methyl)phenyl)(4-(oxetan-3-yl)piperazin-1-yl)methanone;

methyl 2-(1-(2,4-dichloro-3-((1,4-dimethyl-6-(trifluoromethyl)-1H-indol-2-yl)methyl)benzoyl)piperidin-4-yl)acetate;

(1R,5S)-ethyl 3-(2,4-dichloro-3-((1,4-dimethyl-6-(trifluoromethyl)-1H-indol-2-yl)methyl)benzoyl)-3-azabicyclo[3.1.0]hexane-6-carboxylate;

ethyl 2-(1-(2,4-dichloro-3-((1,4-dimethyl-6-(trifluoromethyl)-1H-indol-2-yl)methyl)benzoyl)azetidin-3-yl)acetate;

methyl 1-(2,4-dichloro-3-((1,4-dimethyl-6-(trifluoromethyl)-1H-indol-2-yl)methyl)benzoyl)-4-hydroxypiperidine-3-carboxylate;

methyl 1-(2,4-dichloro-3-((1,4-dimethyl-6-(trifluoromethyl)-1H-indol-2-yl)methyl)benzoyl)piperidine-3-carboxylate;

methyl 1-(2,4-dichloro-3-((1,4-dimethyl-6-(trifluoromethyl)-1H-indol-2-yl)methyl)benzoyl)-3-methoxyazetidine-3-carboxylate;

methyl 1-(2,4-dichloro-3-((1,4-dimethyl-6-(trifluoromethyl)-1H-indol-2-yl)methyl)benzoyl)-4-methylpiperidine-4-carboxylate;

ethyl 1-(2,4-dichloro-3-((1,4-dimethyl-6-(trifluoromethyl)-1H-indol-2-yl)methyl)benzoyl)-4-fluoropiperidine-4-carboxylate;

ethyl 2-(1-(2,4-dichloro-3-((1,4-dimethyl-6-(trifluoromethyl)-1H-indol-2-yl)methyl)benzoyl)piperidin-4-yl)propanoate;

methyl 2-(1-(2,4-dichloro-3-((1,4-dimethyl-6-(trifluoromethyl)-1H-indol-2-yl)methyl)benzoyl)-3-methylpiperidin-4-yl)acetate;

(2,4-dichloro-3-((1,4-dimethyl-6-(trifluoromethyl)-1H-indol-2-yl)methyl)phenyl)(4(methylsulfonyl)piperidin-1-yl)methanone;

1-(2,4-dichloro-3-((1,4-dimethyl-6-(trifluoromethyl)-1H-indol-2-yl)methyl)benzoyl)pyrrolidine-3-carboxylic acid;

1-(2,4-dichloro-3-((1,4-dimethyl-6-(trifluoromethyl)-1H-indol-2-yl)methyl)benzoyl)azetidine-3-carboxylic acid;

1-(2,4-dichloro-3-((1,4-dimethyl-6-(trifluoromethyl)-1H-indol-2-yl)methyl)benzoyl)-3-methylazetidine-3-carboxylic acid;

2-(1-(2,4-dichloro-3-((1,4-dimethyl-6-(trifluoromethyl)-1H-indol-2-yl)methyl)benzoyl)pyrrolidin-3-yl)acetic acid;

2-(1-(2,4-dichloro-3-((1,4-dimethyl-6-(trifluoromethyl)-1H-indol-2-yl)methyl)benzoyl)piperidin-4-yl)acetic acid;

(1R,5S)-3-(2,4-dichloro-3-((1,4-dimethyl-6-(trifluoromethyl)-1H-indol-2-yl)methyl)benzoyl)-3-azabicyclo[3.1.0]hexane-6-carboxylic acid;

2-(1-(2,4-dichloro-3-((1,4-dimethyl-6-(trifluoromethyl)-1H-indol-2-yl)methyl)benzoyl)azetidin-3-yl)acetic acid;

1-(2,4-dichloro-3-((1,4-dimethyl-6-(trifluoromethyl)-1H-indol-2-yl)methyl)benzoyl)-4-hydroxypiperidine-3-carboxylic acid;
1-(2,4-dichloro-3-((1,4-dimethyl-6-(trifluoromethyl)-1H-indol-2-yl)methyl)benzoyl)piperidine-3-carboxylic acid;
1-(2,4-dichloro-3-((1,4-dimethyl-6-(trifluoromethyl)-1H-indol-2-yl)methyl)benzoyl)-3-methoxyazetidine-3-carboxylic acid;
1-(2,4-dichloro-3-((1,4-dimethyl-6-(trifluoromethyl)-1H-indol-2-yl)methyl)benzoyl)-4-methylpiperidine-4-carboxylic acid;
1-(2,4-dichloro-3-((1,4-dimethyl-6-(trifluoromethyl)-1H-indol-2-yl)methyl)benzoyl)-4-fluoropiperidine-4-carboxylic acid;
(3S,4S)-1-(2,4-dichloro-3-((1,4-dimethyl-6-(trifluoromethyl)-1H-indol-2-yl)methyl)benzoyl)-4-(methoxymethyl)pyrrolidine-3-carboxylic acid;
(1R,4R)-2-(2,4-dichloro-3-((1,4-dimethyl-6-(trifluoromethyl)-1H-indol-2-yl)methyl)benzoyl)-2-azabicyclo[2.2.1]heptane-4-carboxylic acid;
2-(1-(4,6-dichloro-5-((1,4-dimethyl-6-(trifluoromethyl)-1H-indol-2-yl)methyl)nicotinoyl)piperidin-4-yl)acetic acid;
2-(1-(2,4-dichloro-3-((1,4-dimethyl-6-(trifluoromethyl)-1H-indol-2-yl)methyl)benzoyl)piperidin-4-yl)-2-methylpropanoic acid;
3-(1-(2,4-dichloro-3-((1,4-dimethyl-6-(trifluoromethyl)-1H-indol-2-yl)methyl)benzoyl)piperidin-4-yl)propanoic acid;
(1s,4s)-4-(2,4-dichloro-3-((1,4-dimethyl-6-(trifluoromethyl)-1H-indol-2-yl)methyl)benzamido)cyclohexanecarboxylic acid;
(2,4-dichloro-3-((4-methyl-6-(trifluoromethyl)-1H-indol-2-yl)methyl)phenyl)(morpholino)methanone;
(2,4-dichloro-3-((1,4-dimethyl-6-(trifluoromethyl)-1H-indol-2-yl)methyl)phenyl)(morpholino)methanone;
(2,4-dichloro-3-((1-ethyl-4-methyl-6-(trifluoromethyl)-1H-indol-2-yl)methyl)phenyl)(morpholino)methanone;
1-(2-(2,6-dichloro-3-(morpholine-4-carbonyl)benzyl)-4-methyl-6-(trifluoromethyl)-1H-indol-1-yl)ethanone;
(2,4-dichloro-3-((1-isobutyl-4-methyl-6-(trifluoromethyl)-1H-indol-2-yl)methyl)phenyl)(morpholino)methanone;
(2,4-dichloro-3-((1-methyl-6-(trifluoromethyl)-1H-indol-2-yl)methyl)phenyl)(morpholino)methanone;
2-(1-(2,4-dichloro-3-((1,4-dimethyl-6-(trifluoromethyl)-1H-indol-3-yl)methyl)benzoyl)piperidin-4-yl)acetic acid;
(1R,5S,6r)-3-(2,4-dichloro-3-((1,4-dimethyl-6-(trifluoromethyl)-1H-indol-3-yl)methyl)benzoyl)-3-azabicyclo[3.1.0]hexane-6-carboxylic acid;
(3S,4S)-1-(2,4-dichloro-3-((1,4-dimethyl-6-(trifluoromethyl)-1H-indol-3-yl)methyl)benzoyl)-3-methylpiperidine-4-carboxylic acid;
(3R,4R)-1-(2,4-dichloro-3-((1,4-dimethyl-6-(trifluoromethyl)-1H-indol-3-yl)methyl)benzoyl)-3-methylpiperidine-4-carboxylic acid;
(3-((1,4-dimethyl-6-(trifluoromethyl)-1H-indol-2-yl)methyl)-2,4-dimethylphenyl)(morpholino)methanone;
2,6-dimethyl-3-(morpholine-4-carbonyl)phenyl)(1,4-dimethyl-6-(trifluoromethyl)-1H-indol-2-yl)methanone;
(2,4-dichloro-3-((4-methyl-6-(trifluoromethyl)-1H-indol-2-yl)methyl)phenyl)(4-(dimethylamino)piperidin-1-yl)methanone;
(2,4-dichloro-3-((1,4-dimethyl-6-(trifluoromethyl)-1H-indol-2-yl)methyl)phenyl)(4-(dimethylamino)piperidin-1-yl)methanone;
(3-((1,4-dimethyl-6-(trifluoromethyl)-1H-indol-2-yl)(hydroxy)methyl)-2,4-dimethylphenyl)(morpholino)methanone;
(3-((1,4-dimethyl-6-(trifluoromethyl)-1H-indol-2-yl)(methoxy)methyl)-2,4-dimethylphenyl)(morpholino)methanone;
(2,4-dichloro-3-((1-methyl-6-(trifluoromethyl)-1H-indol-2-yl)methyl)phenyl)(4-hydroxypiperidin-1-yl)methanone;
(2,4-dichloro-3-((1-methyl-6-(trifluoromethyl)-1H-indol-2-yl)methyl)phenyl)(4-(dimethylamino)piperidin-1-yl)methanone;
(2,4-dichloro-3-((1-methyl-6-(trifluoromethyl)-1H-indol-2-yl)methyl)phenyl)(4-(hydroxymethyl)piperidin-1-yl)methanone;
1-(4-(2,4-dichloro-3-((1-methyl-6-(trifluoromethyl)-1H-indol-2-yl)methyl)benzoyl)piperazin-1-yl)ethanone;
(2,4-dichloro-3-((1-methyl-6-(trifluoromethyl)-1H-indol-2-yl)methyl)phenyl)(3-hydroxypiperidin-1-yl)methanone;
(2,4-dichloro-3-((1-methyl-6-(trifluoromethyl)-1H-indol-2-yl)methyl)phenyl)((3R,4R)-4-fluoro-3-hydroxypiperidin-1-yl)methanone;
1-(2,4-dichloro-3-((1-methyl-6-(trifluoromethyl)-1H-indol-2-yl)methyl)benzoyl)piperidine-4-carboxylic acid;
1-(2,4-dichloro-3-((1-methyl-6-(trifluoromethyl)-1H-indol-2-yl)methyl)benzoyl)-3-hydroxypiperidine-4-carboxylic acid;
3-(4-(2,4-dichloro-3-((1-methyl-6-(trifluoromethyl)-1H-indol-2-yl)methyl)benzoyl)piperazin-1-yl)cyclobutanecarboxylic acid;
(2,4-dichloro-3-((1-methyl-5-(trifluoromethyl)-1H-indol-2-yl)methyl)phenyl)(morpholino)methanone;
(2,4-dichloro-3-((1,4-dimethyl-6-(trifluoromethyl)indolin-2-yl)methyl)phenyl)(morpholino)methanone;
2-(1-(2,4-dichloro-3-((4-chloro-6-cyano-1-methyl-1H-indol-2-yl)methyl)benzoyl)piperidin-4-yl)acetic acid;
2-(4-(2,4-dichloro-3-((1,4-dimethyl-6-(trifluoromethyl)-1H-indol-2-yl)methyl)benzoyl)piperazin-1-yl)-2-methylpropanoic acid;
1-(2,4-dichloro-3-((1,5-dimethyl-6-(trifluoromethyl)-1H-indol-2-yl)methyl)benzoyl)piperidine-4-carboxylic acid;
2-(2,6-dichloro-3-methoxybenzyl)-1,4-dimethyl-6-(trifluoromethyl)-1H-indol;
2,4-dichloro-3-((1,4-dimethyl-6-(trifluoromethyl)-1H-indol-2-yl)methyl)phenol;
2-(2,4-dichloro-3-((1,4-dimethyl-6-(trifluoromethyl)-1H-indol-2-yl)methyl)phenoxy)acetic acid;
3-(2,4-dichloro-3-((1,4-dimethyl-6-(trifluoromethyl)-1H-indol-2-yl)methyl)phenoxy)propanoic acid;
2-((3,5-dichloro-2-methoxypyridin-4-yl)methyl)-1,4-dimethyl-6-(trifluoromethyl)-1H-indole;
2-(2,6-dichloro-3-(4-(oxetan-3-yl)piperazine-1-carbonyl)benzyl)-1,4-dimethyl-1H-indole-6-carbonitrile;
2-(2,6-dichloro-3-(4-(1-hydroxyethyl)piperidine-1-carbonyl)benzyl)-1,4-dimethyl-1H-indole-6-carbonitrile;
2-(2,6-dichloro-3-(4-(2-hydroxypropan-2-yl)piperidine-1-carbonyl)benzyl)-1,4-dimethyl-1H-indole-6-carbonitrile;
2-(2,6-dichloro-3-(4-methoxypiperidine-1-carbonyl)benzyl)-1,4-dimethyl-1H-indole-6-carbonitrile;
2-(2,6-dichloro-3-(4-hydroxypiperidine-1-carbonyl)benzyl)-1,4-dimethyl-1H-indole-6-carbonitrile;
2-(2,6-dichloro-3-(3-hydroxypiperidine-1-carbonyl)benzyl)-1,4-dimethyl-1H-indole-6-carbonitrile;
2-(2,6-dichloro-3-(4-(dimethylamino)piperidine-1-carbonyl)benzyl)-1,4-dimethyl-1H-indole-6-carbonitrile;
2-(2,6-dichloro-3-(4-(hydroxymethyl)piperidine-1-carbonyl)benzyl)-1,4-dimethyl-1H-indole-6-carbonitrile;

2-(2,6-dichloro-3-(4-(1-hydroxy-2-methylpropan-2-yl)piperidine-1-carbonyl)benzyl)-1,4-dimethyl-1H-indole-6-carbonitrile;
2-(2,6-dichloro-3-(4-methylpiperazine-1-carbonyl)benzyl)-1,4-dimethyl-1H-indole-6-carbonitrile;
2-(2,6-dichloro-3-(3,4-dimethylpiperazine-1-carbonyl)benzyl)-1,4-dimethyl-1H-indole-6-carbonitrile;
2-(2,6-dichloro-3-(4-isopropylpiperazine-1-carbonyl)benzyl)-1,4-dimethyl-1H-indole-6-carbonitrile;
2-(2,6-dichloro-3-(4-(2-hydroxyethyl)piperazine-1-carbonyl)benzyl)-1,4-dimethyl-1H-indole-6-carbonitrile;
2-(2,6-dichloro-3-(4-(2-hydroxyethyl)-1,4-diazepane-1-carbonyl)benzyl)-1,4-dimethyl-1H-indole-6-carbonitrile;
2-(2,6-dichloro-3-(3-(dimethylamino)pyrrolidine-1-carbonyl)benzyl)-1,4-dimethyl-1H-indole-6-carbonitrile;
2-(2,6-dichloro-3-(4-(2-methoxyethyl)piperazine-1-carbonyl)benzyl)-1,4-dimethyl-1H-indole-6-carbonitrile;
2-(2,6-dichloro-3-(3-(pyrrolidin-1-yl)azetidine-1-carbonyl)benzyl)-1,4-dimethyl-1H-indole-6-carbonitrile;
2-(2,6-dichloro-3-(4-(2-fluoropropyl)piperazine-1-carbonyl)benzyl)-1,4-dimethyl-1H-indole-6-carbonitrile;
2-(2,6-dichloro-3-(3-hydroxypyrrolidine-1-carbonyl)benzyl)-1,4-dimethyl-1H-indole-6-carbonitrile;
2-(2,6-dichloro-3-(3-(hydroxymethyl)pyrrolidine-1-carbonyl)benzyl)-1,4-dimethyl-1H-indole-6-carbonitrile;
2-(2,6-dichloro-3-(3-hydroxyazetidine-1-carbonyl)benzyl)-1,4-dimethyl-1H-indole-6-carbonitrile;
2-(2,6-dichloro-3-(3-methoxyazetidine-1-carbonyl)benzyl)-1,4-dimethyl-1H-indole-6-carbonitrile;
2,4-dichloro-3-((6-cyano-1,4-dimethyl-1H-indol-2-yl)methyl)-N-(4-hydroxycyclohexyl)benzamide;
2,4-dichloro-3-((6-cyano-1,4-dimethyl-1H-indol-2-yl)methyl)-N-(tetrahydro-2H-pyran-4-yl)benzamide;
2,4-dichloro-3-((6-cyano-1,4-dimethyl-1H-indol-2-yl)methyl)-N-(oxetan-3-yl)benzamide;
2-(2,6-dichloro-3-(2-oxa-7-azaspiro[3.5]nonane-7-carbonyl)benzyl)-1,4-dimethyl-1H-indole-6-carbonitrile;
2-(2,6-dichloro-3-(2-oxa-6-azaspiro[3.3]heptane-6-carbonyl)benzyl)-1,4-dimethyl-1H-indole-6-carbonitrile;
2-(2,6-dichloro-3-(4-(2-methoxyethyl)piperidine-1-carbonyl)benzyl)-1,4-dimethyl-1H-indole-6-carbonitrile;
2-(2,6-dichloro-3-(4-(oxetan-3-yl)piperidine-1-carbonyl)benzyl)-1,4-dimethyl-1H-indole-6-carbonitrile;
2-(2,6-dichloro-3-(4-(2-hydroxyethyl)piperidine-1-carbonyl)benzyl)-1,4-dimethyl-1H-indole-6-carbonitrile;
2-(2,6-dichloro-3-(4-(methoxymethyl)piperidine-1-carbonyl)benzyl)-1,4-dimethyl-1H-indole-6-carbonitrile;
2-(2,6-dichloro-3-(4-(2-hydroxy-2-methylpropyl)piperidine-1-carbonyl)benzyl)-1,4-dimethyl-1H-indole-6-carbonitrile;
(S)-1-(2,4-dichloro-3-((6-cyano-1,4-dimethyl-1H-indol-2-yl)methyl)benzoyl)-N-methylpyrrolidine-2-carboxamide;
methyl 1-(2,4-dichloro-3-((6-cyano-1,4-dimethyl-1H-indol-2-yl)methyl)benzoyl)-3-methylpiperidine-4-carboxylate;
methyl 1-(2,4-dichloro-3-((6-cyano-1,4-dimethyl-1H-indol-2-yl)methyl)benzoyl)piperidine-4-carboxylate;
2-(2,6-dichloro-3-(morpholine-4-carbonyl)benzyl)-1,4-dimethyl-1H-indole-6-carbonitrile;
2-(2,6-dichloro-3-(2-oxa-8-azaspiro[4.5]decane-8-carbonyl)benzyl)-1,4-dimethyl-1H-indole-6-carbonitrile;
2-(2,6-dichloro-3-(4-(2-hydroxypropyl)piperidine-1-carbonyl)benzyl)-1,4-dimethyl-1H-indole-6-carbonitrile;
methyl 2-(1-(2,4-dichloro-3-((6-cyano-1,4-dimethyl-1H-indol-2-yl)methyl)benzoyl)piperidin-4-yl)acetate;
(R)-2-(2,6-dichloro-3-(3-hydroxypyrrolidine-1-carbonyl)benzyl)-1,4-dimethyl-1H-indole-6-carbonitrile;
(S)-2-(2,6-dichloro-3-(3-hydroxypyrrolidine-1-carbonyl)benzyl)-1,4-dimethyl-1H-indole-6-carbonitrile;
2-(2,6-dichloro-3-(morpholine-4-carbonyl)benzyl)-1-methyl-1H-indo nitrile;
2-(2,6-dichloro-3-(morpholine-4-carbonyl)benzyl)-1-methyl-1H-indole-6-carbonitrile;
2-(2,6-dichloro-3-(morpholine-4-carbonyl)benzoyl)-1,4-dimethyl-1H-indole-6-carbonitrile;
2-(2,6-dimethyl-3-(morpholine-4-carbonyl)benzyl)-1,4-dimethyl-1H-indole-6-carbonitrile;
cis-4-(2,4-dichloro-3-((6-cyano-1,4-dimethyl-1H-indol-2-yl)methyl)phenoxy)cyclohexanecarboxylic acid;
trans-3-(2,4-dichloro-3-((6-cyano-1,4-dimethyl-1H-indol-2-yl)methyl)phenoxy)cyclopentanecarboxylic acid;
cis-3-(2,4-dichloro-3-((6-cyano-1,4-dimethyl-1H-indol-2-yl)methyl)phenoxy)cyclopentanecarboxylic acid;
trans-3-(2,4-dichloro-3-((6-cyano-1,4-dimethyl-1H-indol-2-yl)methyl)phenoxy)cyclobutanecarboxylic acid;
cis-3-(2,4-dichloro-3-((6-cyano-1,4-dimethyl-1H-indol-2-yl)methyl)phenoxy)cyclobutanecarboxylic acid;
trans-4-(2,4-dichloro-3-((1,4-dimethyl-6-(trifluoromethyl)-1H-indol-2-yl)methyl)phenoxy)cyclohexanecarboxylic acid;
cis-4-(2,4-dichloro-3-((1,4-dimethyl-6-(trifluoromethyl)-1H-indol-2-yl)methyl)phenoxy)cyclohexanecarboxylic acid;
trans-4-(2,4-dichloro-3-((1,4-dimethyl-6-(trifluoromethyl)-1H-indol-2-yl)methyl)phenoxy)cyclohexanecarboxylic acid;
cis-4-(2,4-dichloro-3-((1,4-dimethyl-6-(trifluoromethyl)-1H-indol-2-yl)methyl)phenoxy)cyclohexanecarboxylic acid;
trans-3-(2,4-dichloro-3-((1,4-dimethyl-6-(trifluoromethyl)-1H-indol-2-yl)methyl)phenoxy)cyclopentanecarboxylic acid;
cis-3-(2,4-dichloro-3-((1,4-dimethyl-6-(trifluoromethyl)-1H-indol-2-yl)methyl)phenoxy)cyclopentanecarboxylic acid;
2-((3,5-dichloro-2-((tetrahydro-2H-pyran-4-yl)methoxy)pyridin-4-yl)methyl)-1,4-dimethyl-6-(trifluoromethyl)-1H-indole;
2-((1-(2,4-dichloro-3-((6-cyano-1,4-dimethyl-1H-indol-2-yl)methyl)benzoyl)piperidin-4-yl)oxy)acetic acid;
1-(2,4-dichloro-3-((6-cyano-1,4-dimethyl-1H-indol-2-yl)methyl)benzoyl)-3-methylpiperidine-4-carboxylic acid;
1-(2,4-dichloro-3-((6-cyano-1,4-dimethyl-1H-indol-2-yl)methyl)benzoyl)piperidine-4-carboxylic acid;
2-(1-(2,4-dichloro-3-((6-cyano-1,4-dimethyl-1H-indol-2-yl)methyl)benzoyl)piperidin-4-yl)acetic acid;
2-(2,6-dichloro-3-(4-hydroxypiperidine-1-carbonyl)benzoyl)-1,4-dimethyl-1H-indole-6-carbonitrile;
2-(2,6-dichloro-3-(3-hydroxyazetidine-1-carbonyl)benzoyl)-1,4-dimethyl-1H-indole-6-carbonitrile;
2-(2,6-dichloro-3-(4-(1-hydroxy-2-methylpropan-2-yl)piperidine-1-carbonyl)benzoyl)-1,4-dimethyl-1H-indole-6-carbonitrile;
2-(2,6-dichloro-3-(4-(2-methoxyethyl)piperidine-1-carbonyl)benzoyl)-1,4-dimethyl-1H-indole-6-carbonitrile;
2-(2,6-dichloro-3-(4-(2-hydroxyethyl)piperidine-1-carbonyl)benzoyl)-1,4-dimethyl-1H-indole-6-carbonitrile;
methyl 2-(1-(2,4-dichloro-3-(6-cyano-1,4-dimethyl-1H-indole-2-carbonyl)benzoyl)piperidin-4-yl)acetate;
2-(1-(2,4-dichloro-3-(6-cyano-1,4-dimethyl-1H-indole-2-carbonyl)benzoyl)piperidin-4-yl)acetic acid;
(2,4-dichloro-3-(1,4-dimethyl-6-(trifluoromethyl)-1H-indole-2-carbonyl)phenyl)(morpholino)methanone;

(2,4-dichloro-3-(1,4-dimethyl-6-(trifluoromethyl)-1H-indole-2-carbonyl)phenyl)(4-(oxetan-3-yl)piperazin-1-yl)methanone;

methyl 2-(1-(2,4-dichloro-3-(1,4-dimethyl-6-(trifluoromethyl)-1H-indole-2-carbonyl)benzoyl)piperidin-4-yl)acetate;

ethyl 2-(4-(2,4-dichloro-3-(1,4-dimethyl-6-(trifluoromethyl)-1H-indole-2-carbonyl)benzoyl)piperazin-1-yl)acetate;

(1R,5S,6r)-ethyl 3-(2,4-dichloro-3-(1,4-dimethyl-6-(trifluoromethyl)-1H-indole-2-carbonyl)benzoyl)-3-azabicyclo[3.1.0]hexane-6-carboxylate;

(3S,4S)-methyl 1-(2,4-dichloro-3-(1,4-dimethyl-6-(trifluoromethyl)-1H-indole-2-carbonyl)benzoyl)-3-methylpiperidine-4-carboxylate;

(3S,4S)-methyl 1-(2,4-dichloro-3-(1,4-dimethyl-6-(trifluoromethyl)-1H-indole-2-carbonyl)benzoyl)-3-methylpiperidine-4-carboxylate;

(2,4-dichloro-3-(1,4-dimethyl-6-(trifluoromethyl)-1H-indole-2-carbonyl)phenyl)(4-(oxetan-3-yl)piperidin-1-yl)methanone;

(3S,4S)-ethyl 1-(2,4-dichloro-3-(1,4-dimethyl-6-(trifluoromethyl)-1H-indole-2-carbonyl)benzoyl)-3-methylpiperidine-4-carboxylate;

(3R,4R)-ethyl 1-(2,4-dichloro-3-(1,4-dimethyl-6-(trifluoromethyl)-1H-indole-2-carbonyl)benzoyl)-3-methylpiperidine-4-carboxylate;

2-(1-(2,4-dichloro-3-(1,4-dimethyl-6-(trifluoromethyl)-1H-indole-2-carbonyl)benzoyl)piperidin-4-yl)acetic acid;

2-(4-(2,4-dichloro-3-(1,4-dimethyl-6-(trifluoromethyl)-1H-indole-2-carbonyl)benzoyl)piperazin-1-yl)acetic acid;

(1R,5S,6r)-3-(2,4-dichloro-3-(1,4-dimethyl-6-(trifluoromethyl)-1H-indole-2-carbonyl)benzoyl)-3-azabicyclo[3.1.0]hexane-6-carboxylic acid;

(1R,5S,6r)-3-(2,4-dichloro-3-(1,4-dimethyl-6-(trifluoromethyl)-1H-indole-2-carbonyl)benzoyl)-3-azabicyclo[3.1.0]hexane-6-carboxylic acid;

(3S,4S)-1-(2,4-dichloro-3-(1,4-dimethyl-6-(trifluoromethyl)-1H-indole-2-carbonyl)benzoyl)-3-methylpiperidine-4-carboxylic acid;

(3R,4R)-1-(2,4-dichloro-3-(1,4-dimethyl-6-(trifluoromethyl)-1H-indole-2-carbonyl)benzoyl)-3-methylpiperidine-4-carboxylic acid;

(2,6-dichloro-3-(hydroxymethyl)phenyl)(1,4-dimethyl-6-(trifluoromethyl)-1H-indol-2-yl)methanone;

(2,4-dichloro-3-((7-methyl-5-(trifluoromethyl)-1H-indol-2-yl)methyl)phenyl)(morpholino)methanone;

(2,4-dichloro-3-((1,7-dimethyl-5-(trifluoromethyl)-1H-indol-2-yl)methyl)phenyl)(morpholino)methanone;

2-(2,6-dichloro-3-((3-oxomorpholino)methyl)benzyl)-1,4-dimethyl-1H-indole-6-carbonitrile;

2-(2,6-dichloro-3-((3-oxomorpholino)methyl)benzoyl)-1,4-dimethyl-1H-indole-6-carbonitrile;

ethyl 2-(4-(2,4-dichloro-3-((1,4-dimethyl-6-(trifluoromethyl)-1H-indol-2-yl)methyl)benzoyl)piperazin-1-yl)acetate;

(3-((6-bromo-1,4-dimethyl-1H-indol-2-yl)methyl)-2,4-dichlorophenyl)(morpholino)methanone;

(2,4-dichloro-3-((1,4-dimethyl-6-morpholino-1H-indol-2-yl)methyl)phenyl)(morpholino)methanone;

1-(2,4-dichloro-3-((1,4-dimethyl-6-(trifluoromethyl)-1H-indol-2-yl)methyl)benzoyl)-3,3-difluoropiperidine-4-carboxylic acid;

1-(2,4-dichloro-3-((1,4-dimethyl-6-(trifluoromethyl)-1H-indol-2-yl)methyl)benzoyl)-3-fluoropiperidine-4-carboxylic acid;

5-(((1,4-dimethyl-6-(trifluoromethyl)-1H-indol-2-yl)methyl)-4,6-dimethylpyridin-3-yl)(morpholino)methanone;

2-(1-(5-((1,4-dimethyl-6-(trifluoromethyl)-1H-indol-2-yl)methyl)-4,6-dimethylnicotinoyl)piperidin-4-yl)acetic acid;

2-[2,4-dimethyl-5-[4-(oxetan-3-yl)piperidine-1-carbonyl]pyridine-3-carbonyl]-1,4-dimethyl-indole-6-carbonitrile;

(3,5-dichloro-4-((1,4-dimethyl-6-(trifluoromethyl)-1H-indol-2-yl)methyl)pyridin-2-yl)(morpholino)methanone;

2-[[3,5-dichloro-2-(morpholine-4-carbonyl)-4-pyridyl]methyl]-1,4-dimethyl-indole-6-carbonitrile;

2-((3,5-dichloro-2-(4-(oxetan-3-yl)piperidine-1-carbonyl)pyridin-4-yl)methyl)-1,4-dimethyl-1H-indole-6-carbonitrile;

2-((3,5-dichloro-2-(4-hydroxypiperidine-1-carbonyl)pyridin-4-yl)methyl)-1,4-dimethyl-1H-indole-6-carbonitrile;

2-((3,5-dichloro-2-(3-hydroxyazetidine-1-carbonyl)pyridin-4-yl)methyl)-1,4-dimethyl-1H-indole-6-carbonitrile;

2-((3,5-dichloro-2-(4-(oxetan-3-yl)piperazine-1-carbonyl)pyridin-4-yl)methyl)-1,4-dimethyl-1H-indole-6-carbonitrile;

2-((3,5-dichloro-2-(3-hydroxypyrrolidine-1-carbonyl)pyridin-4-yl)methyl)-1,4-dimethyl-1H-indole-6-carbonitrile;

methyl 2-(1-(3,5-dichloro-4-((6-cyano-1,4-dimethyl-1H-indol-2-yl)methyl)picolinoyl)piperidin-4-yl)acetate;

2-[1-[3,5-dichloro-4-[(6-cyano-1,4-dimethyl-indol-2-yl)methyl]pyridine-2-carbonyl]-4-piperidyl]acetic acid;

(4,6-dichloro-5-((1,4-dimethyl-6-(trifluoromethyl)-1H-indol-2-yl)methyl)pyridin-3-yl)(morpholino)methanone;

methyl 2-(1-(4,6-dichloro-5-((1,4-dimethyl-6-(trifluoromethyl)-1H-indol-2-yl)methyl)nicotinoyl)piperidin-4-yl)acetate;

(4,6-dichloro-5-((1,4-dimethyl-6-(trifluoromethyl)-1H-indol-2-yl)methyl)pyridin-3-yl)(4-hydroxy-4-(2-hydroxyethyl)piperidin-1-yl)methanone;

3-(3,5-dichloro-4-((1,4-dimethyl-6-(trifluoromethyl)-1H-indol-2-yl)methyl)-2-oxopyridin-1(2H)-yl)propanoic acid;

(2,4-dichloro-3-((1,4-dimethyl-6-(trifluoromethyl)-1H-benzo[d]imidazol-2-yl)methyl)phenyl)(morpholino)methanone;

(S)-1-(2,4-dichloro-3-((1,4-dimethyl-6-(trifluoromethyl)-1H-benzo[d]imidazol-2-yl)methyl)benzoyl)-N-methylpyrrolidine-2-carboxamide;

(2,4-dichloro-3-((1,4-dimethyl-6-(trifluoromethyl)-1H-benzo[d]imidazol-2-yl)methyl)phenyl)(3-(2-hydroxyethyl)azetidin-1-yl)methanone;

A(2,4-dichloro-3-((1,4-dimethyl-6-(trifluoromethyl)-1H-benzo[d]imidazol-2-yl)methyl)phenyl)(3-hydroxyazetidin-1-yl)methanone;

(2,4-dichloro-3-((1,4-dimethyl-6-(trifluoromethyl)-1H-benzo[d]imidazol-2-yl)methyl)phenyl)(3-(2-hydroxyethyl)pyrrolidin-1-yl)methanone;

(2,4-dichloro-3-((1,4-dimethyl-6-(trifluoromethyl)-1H-benzo[d]imidazol-2-yl)methyl)phenyl)(3-(methoxymethyl)pyrrolidin-1-yl)methanone;

(2,4-dichloro-3-((1,4-dimethyl-6-(trifluoromethyl)-1H-benzo[d]imidazol-2-yl)methyl)phenyl)(3-methoxypyrrolidin-1-yl)methanone;

(2,4-dichloro-3-((1,4-dimethyl-6-(trifluoromethyl)-1H-benzo[d]imidazol-2-yl)methyl)phenyl)(3-hydroxypyrrolidin-1-yl)methanone;

(2,4-dichloro-3-((1,4-dimethyl-6-(trifluoromethyl)-1H-benzo[d]imidazol-2-yl)methyl)phenyl)(2-oxa-8-azaspiro[4.5]decan-8-yl)methanone;

(2,4-dichloro-3-((1,4-dimethyl-6-(trifluoromethyl)-1H-benzo[d]imidazol-2-yl)methyl)phenyl)(4-(2-hydroxypropan-2-yl)piperidin-1-yl)methanone;
(2,4-dichloro-3-((1,4-dimethyl-6-(trifluoromethyl)-1H-benzo[d]imidazol-2-yl)methyl)phenyl)(4-(1-hydroxy-2-methylpropan-2-yl)piperidin-1-yl)methanone;
(2,4-dichloro-3-((1,4-dimethyl-6-(trifluoromethyl)-1H-benzo[d]imidazol-2-yl)methyl)phenyl)(4-(hydroxymethyl)piperidin-1-yl)methanone;
(2,4-dichloro-3-((1,4-dimethyl-6-(trifluoromethyl)-1H-benzo[d]imidazol-2-yl)methyl)phenyl)(4-(1-hydroxyethyl)piperidin-1-yl)methanone;
(2,4-dichloro-3-((1,4-dimethyl-6-(trifluoromethyl)-1H-benzo[d]imidazol-2-yl)methyl)phenyl)(4-(methoxymethyl)piperidin-1-yl)methanone;
(2,4-dichloro-3-((1,4-dimethyl-6-(trifluoromethyl)-1H-benzo[d]imidazol-2-yl)methyl)phenyl)(4-(2-hydroxy-2-methylpropyl)piperidin-1-yl)methanone;
(2,4-dichloro-3-((1,4-dimethyl-6-(trifluoromethyl)-1H-benzo[d]imidazol-2-yl)methyl)phenyl)(4-methoxypiperidin-1-yl)methanone;
(2,4-dichloro-3-((1,4-dimethyl-6-(trifluoromethyl)-1H-benzo[d]imidazol-2-yl)methyl)phenyl)(4-(2-hydroxyethyl)piperidin-1-yl)methanone;
(2,4-dichloro-3-((1,4-dimethyl-6-(trifluoromethyl)-1H-benzo[d]imidazol-2-yl)methyl)phenyl)(4-(oxetan-3-yl)piperidin-1-yl)methanone;
(2,4-dichloro-3-((1,4-dimethyl-6-(trifluoromethyl)-1H-benzo[d]imidazol-2-yl)methyl)phenyl)(4-(2-methoxyethyl)piperidin-1-yl)methanone;
(2,4-dichloro-3-((1,4-dimethyl-6-(trifluoromethyl)-1H-benzo[d]imidazol-2-yl)methyl)phenyl)(4-(2-hydroxypropyl)piperidin-1-yl)methanone;
2,4-dichloro-3-((1,4-dimethyl-6-(trifluoromethyl)-1H-benzo[d]imidazol-2-yl)methyl)-N-(oxetan-3-yl)benzamide;
(2,4-dichloro-3-((1,4-dimethyl-6-(trifluoromethyl)-1H-benzo[d]imidazol-2-yl)methyl)phenyl)(3-(2-methoxyethyl)azetidin-1-yl)methanone;
2,4-dichloro-3-((1,4-dimethyl-6-(trifluoromethyl)-1H-benzo[d]imidazol-2-yl)methyl)-N-(4-methoxycyclohexyl)benzamide;
(2,4-dichloro-3-((1,4-dimethyl-6-(trifluoromethyl)-1H-benzo[d]imidazol-2-yl)methyl)phenyl)(3-(pyrrolidin-1-yl)azetidin-1-yl)methanone;
2,4-dichloro-3-((1,4-dimethyl-6-(trifluoromethyl)-1H-benzo[d]imidazol-2-yl)methyl)-N-(4-hydroxycyclohexyl)benzamide;
(2,4-dichloro-3-((1,4-dimethyl-6-(trifluoromethyl)-1H-benzo[d]imidazol-2-yl)methyl)phenyl)(2-oxa-7-azaspiro[3.5]nonan-7-yl)methanone;
2,4-dichloro-3-((1,4-dimethyl-6-(trifluoromethyl)-1H-benzo[d]imidazol-2-yl)methyl)-N-((tetrahydrofuran-2-yl)methyl)benzamide;
(2,4-dichloro-3-((1,4-dimethyl-6-(trifluoromethyl)-1H-benzo[d]imidazol-2-yl)methyl)phenyl)(3-(hydroxymethyl)azetidin-1-yl)methanone;
(2,4-dichloro-3-((1,4-dimethyl-6-(trifluoromethyl)-1H-benzo[d]imidazol-2-yl)methyl)phenyl)(2-oxa-6-azaspiro[3.3]heptan-6-yl)methanone;
(2,4-dichloro-3-((1,4-dimethyl-6-(trifluoromethyl)-1H-benzo[d]imidazol-2-yl)methyl)phenyl)(3-hydroxypiperidin-1-yl)methanone;
(2,4-dichloro-3-((1,4-dimethyl-6-(trifluoromethyl)-1H-benzo[d]imidazol-2-yl)methyl)phenyl)(4-(dimethylamino)piperidin-1-yl)methanone;
(2,4-dichloro-3-((1,4-dimethyl-6-(trifluoromethyl)-1H-benzo[d]imidazol-2-yl)methyl)phenyl)(3,4-dimethylpiperazin-1-yl)methanone;
(2,4-dichloro-3-((1,4-dimethyl-6-(trifluoromethyl)-1H-benzo[d]imidazol-2-yl)methyl)phenyl)(4-(2-hydroxyethyl)piperazin-1-yl)methanone;
(2,4-dichloro-3-((1,4-dimethyl-6-(trifluoromethyl)-1H-benzo[d]imidazol-2-yl)methyl)phenyl)(4-(2-hydroxypropyl)piperazin-1-yl)methanone;
(2,4-dichloro-3-((1,4-dimethyl-6-(trifluoromethyl)-1H-benzo[d]imidazol-2-yl)methyl)phenyl)(3-(dimethylamino)azetidin-1-yl)methanone;
(2,4-dichloro-3-((1,4-dimethyl-6-(trifluoromethyl)-1H-benzo[d]imidazol-2-yl)methyl)phenyl)(4-(2-methoxyethyl)piperazin-1-yl)methanone;
(2,4-dichloro-3-((1,4-dimethyl-6-(trifluoromethyl)-1H-benzo[d]imidazol-2-yl)methyl)phenyl)(4-(2-fluoropropyl)piperazin-1-yl)methanone;
(2,4-dichloro-3-((1,4-dimethyl-6-(trifluoromethyl)-1H-benzo[d]imidazol-2-yl)methyl)phenyl)(3-(methoxymethyl)azetidin-1-yl)methanone;
(2,4-dichloro-3-((1,4-dimethyl-6-(trifluoromethyl)-1H-benzo[d]imidazol-2-yl)methyl)phenyl)(4-(oxetan-3-yl)piperazin-1-yl)methanone;
(2,4-dichloro-3-((1,4-dimethyl-6-(trifluoromethyl)-1H-benzo[d]imidazol-2-yl)methyl)phenyl)(4-methylpiperazin-1-yl)methanone;
(2,4-dichloro-3-((1,4-dimethyl-6-(trifluoromethyl)-1H-benzo[d]imidazol-2-yl)methyl)phenyl)(4-isopropylpiperazin-1-yl)methanone;
(2,4-dichloro-3-((1,4-dimethyl-6-(trifluoromethyl)-1H-benzo[d]imidazol-2-yl)methyl)phenyl)(4-(2,2,2-trifluoroethyl)piperazin-1-yl)methanone;
(4-(cyclopropylmethyl)piperazin-1-yl)(2,4-dichloro-3-((1,4-dimethyl-6-(trifluoromethyl)-1H-benzo[d]imidazol-2-yl)methyl)phenyl)methanone;
(2,4-dichloro-3-((1,4-dimethyl-6-(trifluoromethyl)-1H-benzo[d]imidazol-2-yl)methyl)phenyl)(4-(2-hydroxyethyl)-1,4-diazepan-1-yl)methanone;
1-(2,4-dichloro-3-((1,4-dimethyl-6-(trifluoromethyl)-1H-benzo[d]imidazol-2-yl)methyl)benzoyl)-4-fluoropiperidine-4-carboxylic acid;
1-(2,4-dichloro-3-((1,4-dimethyl-6-(trifluoromethyl)-1H-benzo[d]imidazol-2-yl)methyl)benzoyl)piperidine-4-carboxylic acid;
(1R,5S,6r)-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylic acid;
1-[2,4-dichloro-3-[[1,4-dimethyl-6-(trifluoromethyl)benzimidazol-2-yl]methyl]benzoyl]-3-methyl-piperidine-4-carboxylic acid;
2-(2,6-dichloro-3-(4-(2-hydroxyethyl)piperidine-1-carbonyl)benzyl)-1,4-dimethyl-1H-benzo[d]imidazole-6-carbonitrile;
2-(2,6-dichloro-3-(morpholine-4-carbonyl)benzyl)-1,4-dimetethyl-1H-benzo[d]imidazole-6-carbonitrile;
2,4-dichloro-3-((6-cyano-1,4-dimethyl-1H-benzo[d]imidazol-2-yl)methyl)-N-((1s,4s)-4-hydroxycyclohexyl)benzamide;
2-(2,6-dichloro-3-(4-(2-methoxyethyl)piperidine-1-carbonyl)benzyl)-1,4-dimethyl-1H-benzo[d]imidazole-6-carbonitrile;
2-(2,6-dichloro-3-(4-(methoxymethyl)piperidine-1-carbonyl)benzyl)-1,4-dimethyl-1H-benzo[d]imidazole-6-carbonitrile;

2-(2,6-dichloro-3-(4-(hydroxymethyl)piperidine-1-carbonyl)benzyl)-1,4-dimethyl-1H-benzo[d]imidazole-6-carbonitrile;
2-(2,6-dichloro-3-(4-(1-hydroxy-2-methylpropan-2-yl)piperidine-1-carbonyl)benzyl)-1,4-dimethyl-1H-benzo[d]imidazole-6-carbonitrile;
2-(2,6-dichloro-3-(4-(2-hydroxypropan-2-yl)piperidine-1-carbonyl)benzyl)-1,4-dimethyl-1H-benzo[d]imidazole-6-carbonitrile;
2-(2,6-dichloro-3-(2-oxa-8-azaspiro[4.5]decane-8-carbonyl)benzyl)-1,4-dimethyl-1H-benzo[d]imidazole-6-carbonitrile;
2-(2,6-dichloro-3-(4-(2-hydroxyethyl)piperazine-1-carbonyl)benzyl)-1,4-dimethyl-1H-benzo[d]imidazole-6-carbonitrile;
2-(2,6-dichloro-3-(4-(2-fluoropropyl)piperazine-1-carbonyl)benzyl)-1,4-dimethyl-1H-benzo[d]imidazole-6-carbonitrile;
2-(2,6-dichloro-3-(4-(oxetan-3-yl)piperazine-1-carbonyl)benzyl)-1,4-dimethyl-1H-benzo[d]imidazole-6-carbonitrile;
2-(2,6-dichloro-3-(4-(oxetan-3-yl)piperidine-1-carbonyl)benzyl)-1,4-dimethyl-1H-benzo[d]imidazole-6-carbonitrile;
2-(2,6-dichloro-3-(4-methoxypiperidine-1-carbonyl)benzyl)-1,4-dimethyl-1H-benzo[d]imidazole-6-carbonitrile;
2-(2,6-dichloro-3-(4-(dimethylamino)piperidine-1-carbonyl)benzyl)-1,4-dimethyl-1H-benzo[d]imidazole-6-carbonitrile;
2-(2,6-dichloro-3-(4-(2-methoxyethyl)piperazine-1-carbonyl)benzyl)-1,4-dimethyl-1H-benzo[d]imidazole-6-carbonitrile;
2-(2,6-dichloro-3-(4-(2-hydroxy-2-methylpropyl)piperidine-1-carbonyl)benzyl)-1,4-dimethyl-1H-benzo[d]imidazole-6-carbonitrile;
2-(2,6-dichloro-3-(4-methylpiperazine-1-carbonyl)benzyl)-1,4-dimethyl-1H-benzo[d]imidazole-6-carbonitrile;
(2,4-dichloro-3-((1,4,6-trimethyl-1H-benzo[d]imidazol-2-yl)methyl)phenyl)(morpholino)methanone;
(2,4-dichloro-3-((1,7-dimethyl-5-(trifluoromethyl)-1H-benzo[d]imidazol-2-yl)methyl)phenyl)(morpholino)methanone;
(3-((6-bromo-1,4-dimethyl-1H-benzo[d]imidazol-2-yl)methyl)-2,4-dichlorophenyl)(morpholino)methanone;
(3-((6-bromo-1,4-dimethyl-1H-benzo[d]imidazol-2-yl)methyl)-2,4-dimethylphenyl)(morpholino)methanone;
2,4-dichloro-3-(1,4-dimethyl-6-(trifluoromethyl)-1H-benzo[d]imidazole-2-carbonyl)phenyl)(morpholino)methanone;
2-(2,6-dichloro-3-(morpholine-4-carbonyl)benzoyl)-1,4-dimethyl-1H-benzo[d]imidazole-6-carboxamide;
3-[4-[2,4-dichloro-3-[[1,4-dimethyl-6-(trifluoromethyl)benzimidazol-2-yl]methyl]benzoyl]piperazin-1-yl]cyclobutanecarboxylic acid;
2-[[2,6-dichloro-3-[[4-(2-methoxyethyl)-1-piperidyl]methyl]phenyl]methyl]-1,4-dimethyl-6-(trifluoromethyl)benzimidazole;
2-(2,6-dichloro-3-((4-(oxetan-3-yl)piperidin-1-yl)methyl)benzyl)-1,4-dimethyl-6-(trifluoromethyl)-1H-benzo[d]imidazole;
2-(2,6-dichloro-3-((4-methoxypiperidin-1-yl)methyl)benzyl)-1,4-dimethyl-6-(trifluoromethyl)-1H-benzo[d]imidazole;
2-(2,6-dichloro-3-((4-(methoxymethyl)piperidin-1-yl)methyl)benzyl)-1,4-dimethyl-6-(trifluoromethyl)-1H-benzo[d]imidazole;
1-(2,4-dichloro-3-((1,4-dimethyl-6-(trifluoromethyl)-1H-benzo[d]imidazol-2-yl)methyl)benzyl)piperidin-4-ol;
1-(2,4-dichloro-3-((1,4-dimethyl-6-(trifluoromethyl)-1H-benzo[d]imidazol-2-yl)methyl)benzyl)piperidin-3-ol;
2-(1-(2,4-dichloro-3-((1,4-dimethyl-6-(trifluoromethyl)-1H-benzo[d]imidazol-2-yl)methyl)benzyl)piperidin-4-yl)-2-methylpropan-1-ol;
2-(1-(2,4-dichloro-3-((1,4-dimethyl-6-(trifluoromethyl)-1H-benzo[d]imidazol-2-yl)methyl)benzyl)piperidin-4-yl)propan-2-ol;
8-(2,4-dichloro-3-((1,4-dimethyl-6-(trifluoromethyl)-1H-benzo[d]imidazol-2-yl)methyl)benzyl)-2-oxa-8-azaspiro[4.5]decane;
2-(2,6-dichloro-3-((4-(2-methoxyethyl)piperazin-1-yl)methyl)benzyl)-1,4-dimethyl-6-(trifluoromethyl)-1H-benzo[d]imidazole;
4-(2,4-dichloro-3-((1,4-dimethyl-6-(trifluoromethyl)-1H-benzo[d]imidazol-2-yl)methyl)benzyl)morpholine;
2-(1-(2,4-dichloro-3-((1,4-dimethyl-6-(trifluoromethyl)-1H-benzo[d]imidazol-2-yl)methyl)benzyl)piperidin-4-yl)ethanol;
1-(1-(2,4-dichloro-3-((1,4-dimethyl-6-(trifluoromethyl)-1H-benzo[d]imidazol-2-yl)methyl)benzyl)piperidin-4-yl)-2-methylpropan-2-ol;
1-(1-(2,4-dichloro-3-((1,4-dimethyl-6-(trifluoromethyl)-1H-benzo[d]imidazol-2-yl)methyl)benzyl)piperidin-4-yl)ethanol;
(1-(2,4-dichloro-3-((1,4-dimethyl-6-(trifluoromethyl)-1H-benzo[d]imidazol-2-yl)methyl)benzyl)piperidin-4-yl)methanol;
2-(2,6-dichloro-3-((4-(2,2,2-trifluoroethyl)piperazin-1-yl)methyl)benzyl)-1,4-dimethyl-6-(trifluoromethyl)-1H-benzo[d]imidazole;
1-(2,4-dichloro-3-((1,4-dimethyl-6-(trifluoromethyl)-1H-benzo[d]imidazol-2-yl)methyl)benzyl)-N,N-dimethylpiperidin-4-amine;
1-(2,4-dichloro-3-((1,4-dimethyl-6-(trifluoromethyl)-1H-benzo[d]imidazol-2-yl)methyl)benzyl)-3-methylpiperidin-3-ol;
2-((2,4-dichloro-3-((1,4-dimethyl-6-(trifluoromethyl)-1H-benzo[d]imidazol-2-yl)methyl)benzyl)(ethyl)amino)ethanol;
4-(2,4-dichloro-3-((1,4-dimethyl-6-(trifluoromethyl)-1H-benzo[d]imidazol-2-yl)methyl)benzyl)morpholin-3-one;
1-(2,4-dichloro-3-((1,4-dimethyl-5-(trifluoromethyl)-1H-benzo[d]imidazol-2-yl)methyl)benzoyl)piperidine-4-carboxylic acid;
2-(1-(2,4-dichloro-3-((1,4-dimethyl-5-(trifluoromethyl)-1H-benzo[d]imidazol-2-yl)methyl)benzoyl)piperidin-4-yl)acetic acid;
(2,4-dichloro-3-((1,4-dimethyl-5-(trifluoromethyl)-1H-benzo[d]imidazol-2-yl)methyl)phenyl)(morpholino)methanone;
(3-((5-bromo-1,4-dimethyl-1H-benzo[d]imidazol-2-yl)methyl)-2,4-dichlorophenyl)(morpholino)methanone;
2-(2,6-dichloro-3-(morpholine-4-carbonyl)benzyl)-1,4-dimethyl-1H-benzo[d]imidazole-5-carbonitrile;
2-(2,6-dichloro-3-(morpholine-4-carbonyl)benzyl)-1-methyl-H-benzo[d]imidazole-5-carbonitrile;
(3-((6-bromo-1-methyl-4-(trifluoromethyl)-1H-benzo[d]imidazol-2-yl)methyl)-2,4-dichlorophenyl)(morpholino)methanone;
2-(2,6-dichloro-3-(morpholine-4-carbonyl)benzyl)-1-methyl-4-(trifluoromethyl)-1H-benzo[d]imidazole-6-carbonitrile;
2-(2,6-dichloro-3-(morpholine-4-carbonyl)benzyl)-1-ethyl-4-methyl-1H-benzo[d]imidazole-6-carbonitrile;

2-(2,6-dichloro-3-(morpholine-4-carbonyl)benzyl)-1-isopropyl-4-methyl-1H-benzo[d]imidazole-6-carbonitrile;
2-(2,6-dichloro-3-(morpholine-4-carbonyl)benzyl)-3,7-dimethyl-3H-imidazo[4,5-b]pyridine-5-carbonitrile;
4-chloro-2-(2,6-dichloro-3-(morpholine-4-carbonyl)benzyl)-1-methyl-1H-indole-6-carbonitrile;
(2,4-dichloro-3-((1-methyl-1H-pyrrolo[2,3-b]pyridin-2-yl)methyl)phenyl)(morpholino)methanone;
2-(2,6-dichloro-3-(4-(oxetan-3-yl)piperidine-1-carbonyl)benzyl)-1,4-dimethyl-1H-pyrrolo[2,3-b]pyridine-6-carbonitrile;
(2,4-dichloro-3-((1,4-dimethyl-6-(trifluoromethyl)-1H-pyrrolo[2,3-b]pyridin-2-yl)methyl)phenyl)(morpholino)methanone;
(2,4-dichloro-3-((6-chloro-1,4-dimethyl-1H-pyrrolo[2,3-b]pyridin-2-yl)methyl)phenyl)(morpholino)methanone;
(2,4-dichloro-3-(hydroxy(1-methyl-5-(trifluoromethyl)-1H-pyrrolo[3,2-b]pyridin-2-yl)methyl)phenyl)(morpholino)methanone;
(2,4-dichloro-3-((1-methyl-6-(trifluoromethyl)-1H-pyrrolo[3,2-b]pyridin-2-yl)methyl)phenyl)(morpholino)methanone;
(2,4-dichloro-3-(1-methyl-6-(trifluoromethyl)-1H-pyrrolo[3,2-b]pyridine-2-carbonyl)phenyl)(morpholino)methanone;
(2,4-dichloro-3-((1-methyl-6-(trifluoromethyl)-1H-pyrrolo[3,2-c]pyridin-2-yl)methyl)phenyl)(morpholino)methanone;
(2,4-dichloro-3-((1,4-dimethyl-6-(trifluoromethyl)-1H-pyrrolo[3,2-c]pyridin-2-yl)methyl)phenyl)(morpholino)methanone;
2-(2,6-dichloro-3-(morpholine-4-carbonyl)benzyl)-1,4-dimethyl-1H-pyrrolo[3,2-c]pyridine-6-carbonitrile;
(2,4-dichloro-3-((3,8-dimethyl-6-(trifluoromethyl)imidazo[1,2-a]pyridin-2-yl)methyl)phenyl)(morpholino)methanone;
(2,4-dichloro-3-((3,8-dimethyl-6-(trifluoromethyl)imidazo[1,2-a]pyridin-2-yl)methyl)phenyl)(4-hydroxypiperidin-1-yl)methanone;
(2,4-dichloro-3-((3,8-dimethyl-6-(trifluoromethyl)imidazo[1,2-a]pyridin-2-yl)methyl)phenyl)(4-(2-hydroxyethyl)piperidin-1-yl)methanone;
(2,4-dichloro-3-((3,8-dimethyl-6-(trifluoromethyl)imidazo[1,2-a]pyridin-2-yl)methyl)phenyl)(4-(2-hydroxypropan-2-yl)piperidin-1-yl)methanone;
(2,4-dichloro-3-((3,8-dimethyl-6-(trifluoromethyl)imidazo[1,2-a]pyridin-2-yl)methyl)phenyl)(3-hydroxypyrrolidin-1-yl)methanone;
(2,4-dichloro-3-((3,8-dimethyl-6-(trifluoromethyl)imidazo[1,2-a]pyridin-2-yl)methyl)phenyl)(4-(dimethylamino)piperidin-1-yl)methanone;
(2,4-dichloro-3-((3,8-dimethyl-6-(trifluoromethyl)imidazo[1,2-a]pyridin-2-yl)methyl)phenyl)(4-methoxypiperidin-1-yl)methanone;
(2,4-dichloro-3-((3,8-dimethyl-6-(trifluoromethyl)imidazo[1,2-a]pyridin-2-yl)methyl)phenyl)(4-(2-methoxyethyl)piperidin-1-yl)methanone;
(2,4-dichloro-3-((3,8-dimethyl-6-(trifluoromethyl)imidazo[1,2-a]pyridin-2-yl)methyl)phenyl)(4-(oxetan-3-yl)piperidin-1-yl)methanone;
(2,4-dichloro-3-((3,8-dimethyl-6-(trifluoromethyl)imidazo[1,2-a]pyridin-2-yl)methyl)phenyl)(4-(oxetan-3-yl)piperazin-1-yl)methanone;
(2,4-dichloro-3-((3,8-dimethyl-6-(trifluoromethyl)imidazo[1,2-a]pyridin-2-yl)methyl)phenyl)(4-(hydroxymethyl)piperidin-1-yl)methanone;
(2,4-dichloro-3-((3,8-dimethyl-6-(trifluoromethyl)imidazo[1,2-a]pyridin-2-yl)methyl)phenyl)(4-(1-hydroxyethyl)piperidin-1-yl) methanone;
methyl 2-(1-(2,4-dichloro-3-((3,8-dimethyl-6-(trifluoromethyl)imidazo[1,2-a]pyridin-2-yl)methyl)benzoyl)piperidin-4-yl)acetate;
2-(1-(2,4-dichloro-3-((3,8-dimethyl-6-(trifluoromethyl)imidazo[1,2-a]pyridin-2-yl)methyl)benzoyl)piperidin-4-yl) acetic acid;
2-[[2,6-dichloro-3-[4-(2-hydroxyethyl)piperidine-1-carbonyl]phenyl]methyl]-3,8-dimethyl-imidazo[1,2-a]pyridine-6-carbonitrile;
2-(2,6-dichloro-3-(4-(hydroxymethyl)piperidine-1-carbonyl)benzyl)-3,8-dimethylimidazo[1,2-a]pyridine-6-carbonitrile;
2-(2,6-dichloro-3-(4-methoxypiperidine-1-carbonyl)benzyl)-3,8-dimethylimidazo[1,2-a]pyridine-6-carbonitrile;
2-(2,6-dichloro-3-(4-(2-hydroxypropan-2-yl)piperidine-1-carbonyl)benzyl)-3,8-dimethylimidazo[1,2-a]pyridine-6-carbonitrile;
2-(2,6-dichloro-3-(4-(1-hydroxyethyl)piperidine-1-carbonyl)benzyl)-3,8-dimethylimidazo[1,2-a]pyridine-6-carbonitrile;
2-(2,6-dichloro-3-(4-(oxetan-3-yl)piperidine-1-carbonyl)benzyl)-3,8-dimethylimidazo[1,2-a]pyridine-6-carbonitrile;
2-(2,6-dichloro-3-(4-(2-methoxyethyl)piperidine-1-carbonyl)benzyl)-3,8-dimethylimidazo[1,2-a]pyridine-6-carbonitrile;
(2,4-dichloro-3-((6-chloro-3,8-dimethylimidazo[1,2-b]pyridazin-2-yl)methyl)phenyl)(morpholino)methanone;
(2,4-dichloro-3-((6-chloro-3,7-dimethylimidazo[1,2-b]pyridazin-2-yl)methyl)phenyl)(morpholino)methanone;
(2,4-dichloro-3-((3,8-dimethyl-6-(trifluoromethyl)imidazo[1,2-b]pyridazin-2-yl)methyl)phenyl)(morpholino)methanone;
(2,4-dichloro-3-((3,8-dimethyl-6-(trifluoromethyl)imidazo[1,2-b]pyridazin-2-yl)methyl)phenyl)(4-(oxetan-3-yl)piperazin-1-yl)methanone;
(2,4-dichloro-3-((3,8-dimethyl-6-(trifluoromethyl)imidazo[1,2-b]pyridazin-2-yl)methyl)phenyl)(4-(oxetan-3-yl)piperidin-1-yl)methanone;
(R)-(2,4-dichloro-3-((3,8-dimethyl-6-(trifluoromethyl)imidazo[1,2-b]pyridazin-2-yl)methyl)phenyl)(3-methyl-4-(methylsulfonyl)piperazin-1-yl)methanone;
2-(1-(2,4-dichloro-3-(3,8-dimethyl-6-(trifluoromethyl)imidazo[1,2-b]pyridazine-2-carbonyl)benzoyl)piperidin-4-yl)acetic acid;
2-(2,6-dichloro-3-(morpholine-4-carbonyl)benzyl)-3,8-dimethylimidazo[1,2-b]pyridazine-6-carbonitrile;
2-(2,6-dichloro-3-(morpholine-4-carbonyl)benzyl)-3,7-dimethylimidazo[1,2-b]pyridazine-6-carbonitrile;
(2,4-dichloro-3-((3,7-dimethyl-5-(trifluoromethyl)-3H-imidazo[4,5-b]pyridin-2-yl)methyl)phenyl)(morpholino)methanone;
(2,4-dichloro-3-((3,7-dimethyl-5-(trifluoromethyl)-1H-indazol-1-yl)methyl)phenyl)(morpholino)methanone;
(2,4-dichloro-3-((3,7-dimethyl-5-(trifluoromethyl)-1H-indazol-1-yl)methyl)phenyl)(4-(oxetan-3-yl)piperidin-1-yl)methanone;
(2,4-dichloro-3-((3,7-dimethyl-5-(trifluoromethyl)-2H-indazol-2-yl)methyl)phenyl)(morpholino)methanone;
1-(2,4-dichloro-3-((3,7-dimethyl-5-(trifluoromethyl)-1H-indol-1-yl)methyl)benzoyl)piperidine-4-carboxylic acid;
(3S,4S)-ethyl 1-(2,4-dichloro-3-((3,7-dimethyl-5-(trifluoromethyl)-1H-indol-1-yl)methyl)benzoyl)-3-methylpiperidine-4-carboxylate;

(3R,4R)-ethyl 1-(2,4-dichloro-3-((3,7-dimethyl-5-(trifluoromethyl)-1H-indol-1-yl)methyl)benzoyl)-3-methylpiperidine-4-carboxylate;
(3S,4S)-1-(2,4-dichloro-3-((3,7-dimethyl-5-(trifluoromethyl)-1H-indol-1-yl)methyl)benzoyl)-3-methylpiperidine-4-carboxylic acid;
(3R,4R)-1-(2,4-dichloro-3-((3,7-dimethyl-5-(trifluoromethyl)-1H-indol-1-yl)methyl)benzoyl)-3-methylpiperidine-4-carboxylic acid;
methyl 1-(2,4-dichloro-3-(3,7-dimethyl-5-(trifluoromethyl)-1H-indole-1-carbonyl)benzoyl)piperidine-4-carboxylate;
(3S,4S)-ethyl 1-(2,4-dichloro-3-(3,7-dimethyl-5-(trifluoromethyl)-1H-indole-1-carbonyl)benzoyl)-3-methylpiperidine-4-carboxylate;
(3R,4R)-ethyl 1-(2,4-dichloro-3-(3,7-dimethyl-5-(trifluoromethyl)-1H-indole-1-carbonyl)benzoyl)-3-methylpiperidine-4-carboxylate;
1-(2,4-dichloro-3-(3,7-dimethyl-5-(trifluoromethyl)-1H-indole-1-carbonyl)benzoyl)piperidine-4-carboxylic acid;
(3S,4S)-1-(2,4-dichloro-3-(3,7-dimethyl-5-(trifluoromethyl)-1H-indole-1-carbonyl)benzoyl)-3-methylpiperidine-4-carboxylic acid;
(3R,4R)-1-(2,4-dichloro-3-(3,7-dimethyl-5-(trifluoromethyl)-1H-indole-1-carbonyl)benzoyl)-3-methylpiperidine-4-carboxylic acid;
1-(2,6-dichloro-3-(4-hydroxypiperidine-1-carbonyl)benzyl)-3,7-dimethyl-1H-indole-5-carbonitrile;
1-(2,6-dichloro-3-(4-hydroxypiperidine-1-carbonyl)benzyl)-3,7-dimethyl-1H-indole-5-carbonitrile;
(4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone;
(2,4-dichloro-3-((1,4-dimethyl-6-(trifluoromethoxy)-1H-indol-2-yl)methyl)phenyl)(morpholino)methanone;
(3S,4S)-1-(2,4-dichloro-3-((1,4-dimethyl-6-(trifluoromethoxy)-1H-indol-2-yl)methyl)benzoyl)-3-methylpiperidine-4-carboxylic acid;
(2,4-dichloro-3-((1,4-dimethyl-6-(trifluoromethoxy)-1H-indol-2-yl)methyl)phenyl)(morpholino)methanone;
(3S,4S)-1-(2,4-dichloro-3-((1,4-dimethyl-6-(trifluoromethoxy)-1H-indol-2-yl)methyl)benzoyl)-3-methylpiperidine-4-carboxylic acid;
(3R,4R)-1-(2,4-dichloro-3-((1,4-dimethyl-6-(trifluoromethoxy)-1H-indol-3-yl)methyl)benzoyl)-3-methylpiperidine-4-carboxylic acid;
(4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone;
1-[2,4-dichloro-3-[[1,4-dimethyl-6-(trifluoromethoxy)-1H-indol-3-yl]methyl]benzoyl]piperidine-4-carboxylic acid;
methyl 2-(1-(2,4-dichloro-3-((1,4-dimethyl-6-(trifluoromethoxy)-1H-indol-3-yl)methyl)benzoyl)piperidin-4-yl)acetate;
(3R,4R)-ethyl 1-(2,4-dichloro-3-((1,4-dimethyl-6-(trifluoromethoxy)-1H-indol-3-yl)methyl)benzoyl)-3-methylpiperidine-4-carboxylate;
2-(1-(2,4-dichloro-3-((1,4-dimethyl-6-(trifluoromethoxy)-1H-indol-3-yl)methyl)benzoyl)piperidin-4-yl)acetic acid;
(3R,4R)-1-(2,4-dichloro-3-((1,4-dimethyl-6-(trifluoromethoxy)-1H-indol-3-yl)methyl)benzoyl)-3-methylpiperidine-4-carboxylic acid;
2-[1-[4,6-dichloro-5-[[1,4-dimethyl-6-(trifluoromethyl)-1H-indol-3-yl]methyl]pyridine-3-carbonyl]-4-piperidyl]acetic acid;
2-[1-[3,5-dichloro-4-[[1,4-dimethyl-6-(trifluoromethyl)-1H-indol-3-yl]methyl]pyridine-2-carbonyl]-4-piperidyl]acetic acid;
2-[1-[3,5-dichloro-4-[[1,4-dimethyl-6-(trifluoromethoxy)-1H-indol-3-yl]methyl]pyridine-2-carbonyl]-4-piperidyl]acetic acid;
2-[1-[4,6-dichloro-5-[[1,4-dimethyl-6-(trifluoromethoxy)-H-indol-3-yl]methyl]pyridine-3-carbonyl]-4-piperidyl]acetic acid;
2-(1-(2,4-dichloro-3-((4-methyl-6-(trifluoromethyl)benzofuran-3-yl)methyl)benzoyl)piperidin-4-yl)acetic acid;
2-(1-(2,4-dichloro-3-(3,7-dimethyl-5-(trifluoromethyl)-1H-indazole-1-carbonyl)benzoyl)piperidin-4-yl)acetic acid;
2-(1-(2,4-dichloro-3-(3,7-dimethyl-5-(trifluoromethyl)-2H-indazole-2-carbonyl)benzoyl)piperidin-4-yl)acetic acid;
2-(1-(2,4-dichloro-3-((7-methyl-5-(trifluoromethyl)-1H-indazol-1-yl)methyl)benzoyl)piperidin-4-yl)acetic acid;
2-(1-(2,4-dichloro-3-((7-methyl-5-(trifluoromethyl)-2H-indazol-2-yl)methyl)benzoyl)piperidin-4-yl)acetic acid;
2-(1-(2,4-dichloro-3-((1,4-dimethyl-6-(trifluoromethyl)-1H-indazol-3-yl)methyl)benzoyl)piperidin-4-yl)acetic acid;
2-(1-(2,4-dichloro-3-((3-methyl-5-(trifluoromethyl)-1H-indazol-1-yl)methyl)benzoyl)piperidin-4-yl)acetic acid;
2-[1-[2,4-dichloro-3-[[3,7-dimethyl-5-(trifluoromethoxy)-1H-indol-1-yl]methyl]benzoyl]-4-piperidyl]acetic acid;
2-[1-[2,4-dichloro-3-[3,7-dimethyl-5-(trifluoromethoxy)indole-1-carbonyl]benzoyl]-4-piperidyl]acetic acid;
1-(2,4-dichloro-3-(3,7-dimethyl-5-(trifluoromethoxy)-1H-indole-1-carbonyl)benzoyl)piperidine-4-carboxylic acid;
2-(1-(2,4-dichloro-3-((5-(trifluoromethoxy)-1H-indol-1-yl)methyl)benzoyl)piperidin-4-yl)acetic acid;
2-(1-(2,4-dichloro-3-((7-methyl-5-(trifluoromethoxy)-1H-indol-1-yl)methyl)benzoyl)piperidin-4-yl)acetic acid;
2-(1-(2,4-dimethyl-3-((7-methyl-5-(trifluoromethoxy)-1H-indol-1-yl)methyl)benzoyl)piperidin-4-yl)acetic acid;
2-(1-(2,4-dichloro-3-(7-methyl-5-(trifluoromethoxy)-1H-indole-1-carbonyl)benzoyl)piperidin-4-yl)acetic acid;
2-(1-(2,4-dimethyl-3-((7-methyl-5-(trifluoromethoxy)-1H-indol-1-yl)methyl)benzoyl)piperidin-4-yl)acetic acid;
2-(1-(2,4-dichloro-3-(7-methyl-5-(trifluoromethoxy)-1H-indole-1-carbonyl)benzoyl)piperidin-4-yl)acetic acid;
2-(1-(2,4-dichloro-3-((5-(difluoromethoxy)-7-methyl-1H-indol-1-yl)methyl)benzoyl)piperidin-4-yl)acetic acid;
2-(1-(2,4-dichloro-3-((5-cyclopropyl-7-fluoro-1H-indol-1-yl)methyl)benzoyl)piperidin-4-yl)acetic acid;
2-(1-(2,4-dichloro-3-(5-cyclopropyl-7-fluoro-1H-indole-1-carbonyl)benzoyl)piperidin-4-yl)acetic acid;
2-(1-(2,4-dichloro-3-((7-fluoro-5-(trifluoromethyl)-1H-indol-1-yl)methyl)benzoyl)piperidin-4-yl)acetic acid;
2-(1-(4,6-dichloro-5-(3,7-dimethyl-5-(trifluoromethyl)-1H-indole-1-carbonyl)nicotinoyl)piperidin-4-yl)acetic acid;
2-(1-(4,6-dichloro-5-((3,7-dimethyl-5-(trifluoromethyl)-1H-indol-1-yl)methyl)nicotinoyl)piperidin-4-yl)acetic acid;
2-(1-(2,4-dichloro-3-(7-methyl-5-(trifluoromethyl)-1H-indole-1-carbonyl)benzoyl)piperidin-4-yl)acetic acid;
(2,4-dichloro-3-((3,7-dimethyl-5-(trifluoromethyl)-1H-pyrrolo[2,3-c]pyridin-1-yl)methyl)phenyl)(morpholino)methanone;
2-(1-(2,4-dichloro-3-((3,7-dimethyl-5-(trifluoromethyl)-1H-pyrrolo[2,3-c]pyridin-1-yl)methyl)benzoyl)piperidin-4-yl)acetic acid;
2-(1-(2,4-dichloro-3-(3,7-dimethyl-5-(trifluoromethyl)-1H-pyrrolo[2,3-c]pyridine-1-carbonyl)benzoyl)piperidin-4-yl)acetic acid;
2-(1-(2,4-dichloro-3-((3,7-dimethyl-5-(trifluoromethyl)-1H-pyrrolo[3,2-b]pyridin-1-yl)methyl)benzoyl)piperidin-4-yl)acetic acid;

2-(2,6-dichloro-3-(morpholine-4-carbonyl)benzyl)-1,4-dimethyl-1H-indole-5-carbonitrile;
2-(1-(2,4-dichloro-3-((5-cyano-1,4-dimethyl-1H-indol-2-yl)methyl)benzoyl)piperidin-4-yl)acetic acid;
(2,4-dichloro-3-((4,6-dichloro-1-methyl-1H-indol-2-yl)methyl)phenyl)(morpholino)methanone;
2-(1-(2,4-dichloro-3-((4,6-dichloro-1-methyl-1H-indol-2-yl)methyl)benzoyl)piperidin-4-yl)acetic acid;
2-((2,4-dichloro-5-(2-oxa-8-azaspiro[4.5]decane-8-carbonyl)pyridin-3-yl)methyl)-1,4-dimethyl-1H-indole-6-carbonitrile;
2-((2,4-dichloro-5-(4-(oxetan-3-yl)piperidine-1-carbonyl)pyridin-3-yl)methyl)-1,4-dimethyl-1H-indole-6-carbonitrile;
2-(1-(2,4-dichloro-3-((6-methoxy-1,4-dimethyl-1H-indol-2-yl)methyl)benzoyl)piperidin-4-yl)acetic acid;
2-(1-(2,4-dichloro-3-((4-fluoro-1-methyl-6-(trifluoromethyl)-1H-indol-2-yl)methyl)benzoyl)piperidin-4-yl)acetic acid;
2-(1-(2,4-dichloro-3-((6-(difluoromethoxy)-1,4-dimethyl-1H-indol-2-yl)methyl)benzoyl)piperidin-4-yl)acetic acid;
2-(1-(4,6-dichloro-5-(1,4-dimethyl-6-(trifluoromethyl)-1H-indole-2-carbonyl)nicotinoyl)piperidin-4-yl)acetic acid;
2-(1-(3,5-dichloro-4-((1,4-dimethyl-6-(trifluoromethyl)-1H-indol-2-yl)methyl)picolinoyl)piperidin-4-yl)acetic acid;
2-(1-(2,4-dichloro-3-((1-methyl-6-(trifluoromethoxy)-1H-indol-2-yl)methyl)benzoyl)piperidin-4-yl)acetic acid;
(2,4-dichloro-3-((1,4-dimethyl-6-(trifluoromethyl)-1H-pyrrolo[3,2-c]pyridin-2-yl)methyl)phenyl)(4-(oxetan-3-yl)piperazin-1-yl)methanone;
N-(2-(2,6-dichloro-3-(morpholine-4-carbonyl)benzyl)-1,4-dimethyl-1H-indol-6-yl)acetamide;
2-(1-(2-chloro-4-cyclopropyl-3-((1-methyl-6-(trifluoromethoxy)-1H-indol-2-yl)methyl)benzoyl)piperidin-4-yl)acetic acid;
2-(1-(2,4-dichloro-3-((6-cyclopropyl-4-fluoro-1-methyl-1H-indol-2-yl)methyl)benzoyl)piperidin-4-yl)acetic acid;
1-(2,4-dichloro-3-((6-cyclopropyl-4-fluoro-1-methyl-1H-indol-2-yl)methyl)benzoyl)piperidine-4-carboxylic acid;
2-[[2,6-dichloro-3-(morpholine-4-carbonyl)phenyl]methyl]-N,N,1,4-tetramethyl-indole-6-carboxamide;
2-[[2,6-dichloro-3-(morpholine-4-carbonyl)phenyl]methyl]-N,1,4-trimethyl-indole-6-carboxamide;
1-(2,4-dichloro-3-((1,4-dimethyl-6-(trifluoromethyl)-1H-indol-3-yl)methyl)benzoyl)piperidine-4-carboxylic acid;
2-(1-(3,5-dichloro-4-((3,7-dimethyl-5-(trifluoromethyl)-1H-indol-1-yl)methyl)picolinoyl)piperidin-4-yl)acetic acid;
1-(2,4-dichloro-3-((1,4-dimethyl-6-(trifluoromethyl)-1H-pyrrolo[2,3-b]pyridin-2-yl)methyl)benzoyl)piperidine-4-carboxylic acid;
(2,4-dichloro-3-((1,4-dimethyl-6-(trifluoromethyl)-1H-pyrrolo[2,3-b]pyridin-2-yl)methyl)phenyl)(4-(2-methoxyethyl)piperidin-1-yl)methanone;
2-(1-(2,4-dichloro-3-((1,4-dimethyl-6-(trifluoromethyl)-1H-pyrrolo[2,3-b]pyridin-2-yl)methyl)benzoyl)piperidin-4-yl)acetic acid;
ethyl 1-(2,4-dichloro-3-((1,4-dimethyl-6-(trifluoromethyl)-1H-pyrrolo[2,3-b]pyridin-2-yl)methyl)benzoyl)piperidine-4-carboxylate;
2-(1-(2,4-dichloro-3-(1,4-dimethyl-6-(trifluoromethyl)-1H-pyrrolo[2,3-b]pyridine-2-carbonyl)benzoyl)piperidin-4-yl)acetic acid;
1-(2,4-dichloro-3-(1,4-dimethyl-6-(trifluoromethyl)-1H-pyrrolo[2,3-b]pyridine-2-carbonyl)benzoyl)piperidine-4-carbonitrile;
(3R,4R)-1-(2,4-dichloro-3-(1,4-dimethyl-6-(trifluoromethyl)-1H-pyrrolo[2,3-b]pyridine-2-carbonyl)benzoyl)-3-methylpiperidine-4-carboxylic acid;
(2,4-dichloro-3-(1,4-dimethyl-6-(trifluoromethyl)-1H-pyrrolo[2,3-b]pyridine-2-carbonyl)phenyl)(4-(2-methoxyethyl)piperidin-1-yl)methanone;
(2,4-dichloro-3-(1,4-dimethyl-6-(trifluoromethyl)-1H-pyrrolo[2,3-b]pyridine-2-carbonyl)phenyl)(4-hydroxypiperidin-1-yl)methanone;
2-((3R,4S)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid;
(2,4-dichloro-3-(1,4-dimethyl-6-(trifluoromethyl)-1H-pyrrolo[2,3-b]pyridine-2-carbonyl)phenyl)(4-(methylsulfonyl)piperidin-1-yl)methanone;
2-((3S,4R)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetic acid;
(4,6-dichloro-5-((1,4-dimethyl-6-(trifluoromethyl)-1H-pyrrolo[2,3-b]pyridin-2-yl)methyl)pyridin-3-yl)(morpholino)methanone;
(4,6-dichloro-5-((1,4-dimethyl-6-(trifluoromethyl)-1H-pyrrolo[2,3-b]pyridin-2-yl)methyl)pyridin-3-yl)(4-(methylsulfonyl)piperidin-1-yl)methanone;
(3,5-dichloro-4-((1,4-dimethyl-6-(trifluoromethyl)-1H-pyrrolo[2,3-b]pyridin-2-yl)methyl)pyridin-2-yl)(morpholino)methanone;
2-(1-(2,4-dichloro-3-(1-methyl-6-(trifluoromethoxy)-1H-indole-2-carbonyl)benzoyl)piperidin-4-yl)acetic acid;
2-(1-(4,6-dichloro-5-((1-methyl-6-(trifluoromethoxy)-1H-indol-2-yl)methyl)nicotinoyl)piperidin-4-yl)acetic acid;
2-(1-(4,6-dichloro-5-((1-methyl-6-(trifluoromethoxy)-1H-indol-2-yl)methyl)nicotinoyl)piperidin-4-yl)acetic acid;
2-[1-[2,4-dichloro-3-[[1-methyl-7-(trifluoromethyl)-1H-indol-3-yl]methyl]benzoyl]-4-piperidyl]acetic acid;
2-[1-[4,6-dichloro-5-[(6-cyclopropyl-4-fluoro-1-methyl-1H-indol-2-yl)methyl]pyridine-3-carbonyl]-4-piperidyl]acetic acid;
2-(1-(2,4-dichloro-3-((4-(trifluoromethyl)-1H-indol-1-yl)methyl)benzoyl)piperidin-4-yl)acetic acid; or
2-[1-[2,4-dichloro-3-[[7-chloro-5-(trifluoromethyl)indol-1-yl]methyl]benzoyl]-4-piperidyl]acetic acid.

In a thirty-fifth embodiment, the invention provides a pharmaceutical composition comprising a compound according to any of the foregoing embodiments and one or more pharmaceutically acceptable excipients.

In a thirty-sixth embodiment, the invention provides a method of treating a disease comprising administering a therapeutically effective amount of a compound of any one of claims 1 to 29, wherein the disease is rheumatoid arthritis, juvenile rheumatoid arthritis, psoriasis, psoriatic arthritis, Crohn's disease, inflammatory bowel disease, ulcerative colitis, ankylosing spondylitis, reactive arthritis, arthritis associated with inflammatory bowel disease, undifferentiated spondyloarthritis, systemic lupus erythematosus, lupus nephritis, uveitis, atopic dermatitis, multiple sclerosis, axial spondyloarthritides or hidraenitis suppurativa.

In a thirty-seventh embodiment, the invention provides a kit comprising a packaged product comprising components with which to administer a compound of any one of the foregoing embodiments for treatment of an autoimmune disorder.

In a thirty-eighth embodiment, the invention provides the kit according to the thirty-seventh embodiment wherein the packaged product comprises a compound according to any of the foregoing embodiments and instructions for use.

DETAILED DESCRIPTION

The compounds of the present invention are useful to prevent, diagnose, and treat various medical disorders in humans or animals. The compounds of the present invention are used to inhibit or reduce one or more activities associated with RORγt receptors, relative to RORγt receptors in the absence of the same compounds. Thus, in one aspect of the invention, a method for treating a disease or disorder selected from an autoimmune disease or disorder, psoriasis, psoriatic arthritis, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. In certain embodiments, the autoimmune disease or disorder is selected from psoriasis, psoriatic arthritis, ankylosing spondylitis, rheumatoid arthritis, multiple sclerosis, inflammatory bowel disease, Crohn's disease, ulcerative colitis, uveitis, graft-versus-host disease, and lupus. In certain embodiments, the allergic disease or disorder is selected from atopic dermatitis, allergic rhinitis, asthma, or chronic obstructive pulmonary disease (COPD). In certain embodiments, the metabolic disease or disorder is selected from obesity, obesity-induced insulin resistance, atherosclerosis, and type II diabetes. In certain embodiments, the oncology disease or disorder is melanoma.

In one embodiment, the disease or disorder is psoriasis or psoriatic arthritis. See for example: Pantelyushin, S. et al. "RORγt+ innate lymphocytes and γδ T cells initiate psoriasiform plaque formation in mice" *J. Clin. Invest.* 2012, 122:2252; and Raychaudhuri, S. et al. "Role of IL-17 in psoriasis and psoriatic arthritis," *Clin. Rev. Allergy Immunol.* 2013, 44: 183.

In one embodiment, the disease or disorder is atopic dermatitis. See for example: Ma, L. et al. "The imbalance of Th17 cells and CD4+CD25highFoxp3+ Treg cells in patients with atopic dermatitis" *J. Eur. Acad. Dermatol. Venereol.* 2014, 28:1079; and Peiser, M. "Role of Th17 cells in skin inflammation of allergic contact dermatitis" *Clin. Dev. Immunol.* 2013, 261037.

In another embodiment, the disease or disorder is rheumatoid arthritis. See for example: Park, T.-Y. et al. "RORγt-specific transcriptional interactomic inhibition suppresses autoimmunity associated with TH17 cells" *Proc. Natl. Acad. Sci. USA* 2014, 111:18673; and Solt, L. et al. "Action of RORs and their ligands in (patho)\physiology" *Trends Endocrinol. Metab.* 2012, 23:619; and Chang, M. et al. "Pharmacologic repression of retinoic acid receptor-related orphan nuclear receptor γ is therapeutic in the collagen-induced arthritis experimental model" *Arthritis Rheumatol.*, 2014, 66:579.

In another embodiment, the disease or disorder is ankylosing spondylitis. See for example: Bidad, K. et al "Effect of all-transretinoic acid on Th17 and T regulatory cell subsets in patients with ankylosing spondylitis" *J. Rheumatol.* 2013, 40:476; and Toussirot, E. et al. "The IL-23/Th17 pathway as a therapeutic target in chronic inflammatory diseases," *Inflamm. Allergy Drug Targets* 2012, 1:159.

In another embodiment, the disease or disorder is multiple sclerosis. See for example: Martinez, N. et al. "RORγt, but not T-bet, overexpression exacerbates an autoimmune model for multiple sclerosis" *J. Neuroimmunol.* 2014, 276:(1/2) 142-149; and Codarri, L. et al., "RORγt drives production of the cytokine GM-CSF in helper T cells, which is essential for the effector phase of autoimmune neuroinflammation" *Nat. Immunol.* 2011, 12:560.

In another embodiment, the disease or disorder is inflammatory bowel disease. See for example: Troncone, E. et al. "Th17 cytokines in inflammatory bowel diseases: discerning the good from the bad" *Intl. Rev. Immunol.* 2013, 32:526; and Leppkes, M. et al. "RORgamma-expressing Th17 cells induce murine chronic intestinal inflammation via redundant effects of IL-17A and IL-17F" *Gastroenterology* 2009, 136: 257-267.

In another embodiment, the diseases or disorders are ulcerative colitis or Crohn's disease. See for example: Dong, Z. et al. "Aberrant expression of circulating Th17, Th1 and Tc1 cells in patients with active and inactive ulcerative colitis" *Intl. J. Mol. Med.* 2013, 31:989; and Kumawat, A. et al. "Microscopic colitis patients demonstrate a mixed Th17/Tc17 and Th1/Tc1 mucosal cytokine profile" *Mol Immunol.* 2013, 55:355.

In another embodiment, the disease or disorder is autoimmune uveitis. See for example: Horai, R. et al. "Cytokines in autoimmune uveitis" *J. Interferon Cytokine Res.* 2011, 31:733.

In another embodiment, the disease or disorder is lupus. See for example: Yoh, K. et al. "Overexpression of RORγt under control of the CD2 promoter induces polyclonal plasmacytosis and autoantibody production in transgenic mice" *Eur. J. Immunol.* 2012, 42:1999.

In another embodiment, the disease or disorder is graft-versus-host disease (GVHD). See for example: Yu, Y. et al. "Prevention of GVHD while sparing GVL effect by targeting Th1 and Th17 transcription factor T-bet and RORγt in mice" *Blood* 2011, 118:5011.

In another embodiment, the disease or disorder is atherosclerosis. See for example: Erbel, C. et al. "IL-17A influences essential functions of the monocyte/macrophage lineage and is involved in advanced murine and human atherosclerosis" *J. Immunol.* 2014, 193, 4344.

In another embodiment, the diseases or disorders are allergic rhinitis, asthma, or chronic obstructive pulmonary disease (COPD). See for example: Loubaki, L. et al. "Co-culture of human bronchial fibroblasts and CD4+ T cells increases Th17 cytokine signature" *PLoS One* 2013, 8:e81938/1; and Solt, L. et al. "Action of RORs and their ligands in (patho)\physiology" *Trends Endocrinol. Metab.* 2012, 23:619.

In another embodiment, the diseases or disorders are obesity, and/or insulin resistance, and/or type II diabetes. See for example: Solt, L. et al. "ROR inverse agonist suppresses insulitis and prevents hyperglycemia in a mouse model of type 1 diabetes" *Endocrinology* 2015, 156:869; and Meissburger, B. et al. "Adipogenesis and insulin sensitivity in obesity are regulated by retinoid-related orphan receptor gamma" *EMBO Mol. Med.* 2011, 3:637; and Solt, L. "Ligand regulation of retinoic acid receptor-related orphan receptors: implications for development of novel therapeutics" *Curr. Opin. Lipidology* 2010, 21:204.

In another embodiment, the disease or disorder is melanoma. See for example: Purwar, R. et al. "Robust tumor immunity to melanoma mediated by interleukin-9-producing T cells" *Nat. Med.* 2012, 18:1248.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. sIL-1RI, sIL-1RII, sIL-6R), antiinflammatory cytokines (e.g. IL-4, IL-10, IL-11, IL-13), celecoxib, folic acid, hydroxychloroquine sulfate, rofecoxib, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, tofacitinib, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, and cyclosporine.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as IL-1 (e.g. NIK, IKK, p38 or MAP kinase inhibitors); IL-1β converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. sIL-1RI, sIL-1RII, sIL-6R) and antiinflammatory cytokines (e.g. IL-4, IL-10, IL-11, IL-13). Preferred examples of therapeutic agents for Crohn's disease with which a compound of Formula (I) can be combined include PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/ trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, antibody or small molecule TNF inhibiotors, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, and prednisone Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, and alefacept Non-limiting examples of therapeutic agents for restenosis with which a compound of Formula (I) can be combined include the following: sirolimus, paclitaxel, everolimus, tacrolimus, ABT-578, and acetaminophen.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) (can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), and lymphostat-B (anti-BlyS antibody).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) (and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) (and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1$-$C_6$)alkanoyloxy)ethyl, 1-methyl-1-(($C_1$-$C_6$)alkanoyloxy)ethyl, ($C_1$-$C_{12}$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1$-$C_6)alkyl)_2$ or glycosyl (the radical resulting from detachment of the hydroxyl of the hemiacetal of a carbohydrate).

The term "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b;2'3'-d]pyridinyl, 6H-3-thia-2,5,6-triaza-as-indacenyl, 4,5-dihydro-1H-benzo[b]azepin-2(3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b]pyridine.

As used herein, "alkyl," "alkylene" or notations such as "($C_1$-$C_8$)" include straight chained or branched hydrocarbons which are completely saturated. Examples of alkyls are methyl, ethyl, propyl, isopropyl, butyl, pentyl, hexyl and isomers thereof. As used herein, "alkenyl," "alkenylene," "alkynylene" and "alkynyl" means $C_2$-$C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that is completely saturated. Examples of a cycloalkyl group are cyclopropyl, cyclobutyl, cyclopentyl, bicyclo[1.1.1]pentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of a cycloalkenyl group are cyclopentenyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, =O, =$CH_2$, —OH, —$CH_2$OH, —$CH_2NH_2$, ($C_1$-$C_4$)alkyl-OH, —$CH_2CH_2OCH_2CH_3$, —S—($C_1$-$C_8$)alkyl groups, —SH, —NH($C_1$-$C_8$)alkyl groups, —N(($C_1$-$C_8$)alkyl)$_2$ groups, —$NH_2$, —$C(O)NH_2$, —$CH_2NHC(O)(C_1$-$C_4)alkyl, —$CH_2NHC(O)CH_2Cl$, —$CH_2NHC(O)CH_2CN$, —$CH_2NHC(O)CH_2CH_2N(CH_3)_2$, —$CH_2NHC(O)C(=CH_2)CH_3$, —$CH_2NHC(O)(C_2$-$C_4)alkynyl, —$CH_2NHC(O)CH_2CH_2$-piperidinyl, —($C_1$-$C_4$)alkyl-morpholinyl, —$CH_2NHC(O)CH_2O$-phenyl wherein the phenyl is optionally substituted with halogen, ($C_1$-$C_4$)alkoxy, —C(O)($C_1$-$C_4$)alkyl, —C(O)($C_1$-$C_4$)alkoxy, —C(O)N(H)$_2$, —C(O)N(CH$_3$)$_2$, —C(O)($C_1$-$C_6$)heteroaryl, —N(CH$_3$)$_2$, —NHC(O)($C_1$-$C_4$)alkyl, —NHC(O)($C_2$-$C_4$)alkenyl, —NHC(O)CH$_2$CN, —S(O)$_2$($C_1$-$C_4$)alkyl, —S(O)$_2$($C_1$-$C_6$)hetero aryl, —S(O)$_2$($C_1$-$C_6$) ($C_1$-$C_6$)heterocyclyl, 4-methylpiperazinecarbonyl, —($C_1$-$C_4$)alkylC(O)NH$_2$, —C(O)NH($C_1$-$C_8$)alkyl groups, —C(O)N(($C_1$-$C_8$)alkyl)$_2$, —C(O)N(H)($C_3$-$C_8$)cycloalkyl groups, —C(O)($C_1$-$C_4$)alkoxy, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)NH$_2$, —NHC(O)NH($C_1$-$C_8$)alkyl groups, —N(($C_1$-$C_8$)alkyl)C(O)NH$_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —NHCH$_2$-heteroaryl, benzyl, —OCH$_2$-heteroaryl, —C(O)H, —C(O)($C_1$-$C_8$)alkyl groups, —CN, —NO$_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —OCF$_3$), —S(O)$_2$-halogenated ($C_1$-$C_8$)alkyl groups (for example but not limited to —S(O)$_2$CF$_3$), —S-halogenated ($C_1$-$C_8$)alkyl groups (for example but not limited to SCF$_3$), —($C_1$-$C_6$)heterocyclyl (for example but not limited to pyrrolidine, tetrahydrofuran, pyran or morpholine), —($C_1$-$C_6$) heteroaryl (for example but not limited to tetrazole, imidazole, furan, pyrazine or Pyrazole), -phenyl, optionally substituted benzyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$) alkyl groups, or —C(=N—O—($C_1$-$C_6$)alkyl)-($C_1$-$C_6$)alkyl groups.

The term "kit" as used herein refers to a packaged product comprising components with which to administer a compound of Formula (I) of the invention for treatment of an autoimmune disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering a compound of Formula (I).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5 W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples:

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in EtOH. The dry granulate can be blended with the magnesium stearate and the rest of the starch. The mixture is then compressed in a tabletting machine to give tablets each containing a unit dose or a part of a unit dose of active compound.

c) Enteric coated tablets

Tablets can be prepared by the method described in (b) above. The tablets can be enteric coated in a conventional manner using a solution of 20% cellulose acetate phthalate and 3% diethyl phthalate in EtOH:DCM (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically.

The present invention also comprises the use of a compound of Formula (I) as a medicament.

The present invention also provides a method of treating rheumatoid arthritis, juvenile rheumatoid arthritis, psoriasis, psoriatic arthritis, Crohn's disease, inflammatory bowel disease, ulcerative colitis, ankylosing spondylitis, reactive arthritis, arthritis associated with inflammatory bowel disease, undifferentiated spondyloarthritis, systemic lupus erythematosus, lupus nephritis, uveitis, atopic dermatitis, multiple sclerosis, axial spondyloarthritides or hidraenitis suppurativa and/or other disorders of the immune system which comprises the administration of a therapeutically effective amount of a compound of Formula (I) to a mammal, particularly a human being, in need thereof.

ABBREVIATIONS

| ACN | acetonitrile | g | gram |
|---|---|---|---|
| AcOH | Acetic acid | HATU | 1-[Bis(dimethylamino)methylene]-1H-1,2,3-triazolo[4,5-b]pyridinium 3-oxid hexafluorophosphate |
| aq | aqueous | L | liter |
| BOC$_2$O | di-tert-butyl dicarbonate | LDA | lithium diisopropylamide |
| BuLi | n-Butyl lithium | MeOH | methanol |
| concd | concentrated | MTBE | methyl tert-butyl ether |
| DCM | dichloromethane | NBS | N-bromo succinimide |
| DMAP | 4-dimethylaminopyridine | NH$_4$OAc | ammonium acetate |
| DME | dimethoxyethane | NMP | N-methyl-2-pyrrolidone |
| DMF | dimethylformamide | Pd(dppf)Cl$_2$ | [1,1'-bis(diphenylphosphino)-ferrocene]dichloropalladium(II) |
| DMSO | dimethylsulfoxide | rt | room temperature |
| Et$_2$O | diethyl ether | TBAF | tetrabutyl ammonium fluoride |
| EtOAc | ethyl acetate | TFA | trifluoroacetic acid |

-continued

| | | | |
|---|---|---|---|
| EtOH | EtOH | THF | tetrahydrofuran |
| eq | equivalents | TLC | thin layer chromatography |
| FCC | Flash column chromatography | T3P | 2,4,6-tripropyl-1,3,5,2,4,6-trioxatriphosphinane 2,4,6-trioxide |
| h | hour(s) | | |

General Synthetic Schemes

Compounds of the invention may be prepared using the synthetic transformations illustrated in Schemes I-XXIII. Starting materials are commercially available, may be prepared by the procedures described herein, by literature procedures, or by procedures that would be well known to one skilled in the art of organic chemistry.

Scheme I. General methods for preparing 2, 4-dichloro-3-((1-methyl-1H-indol-2-yl)methyl) benzamide compounds of the invention are illustrated in Scheme I, and further described in Example A, Al, L, M, V, AA, AC, AX:

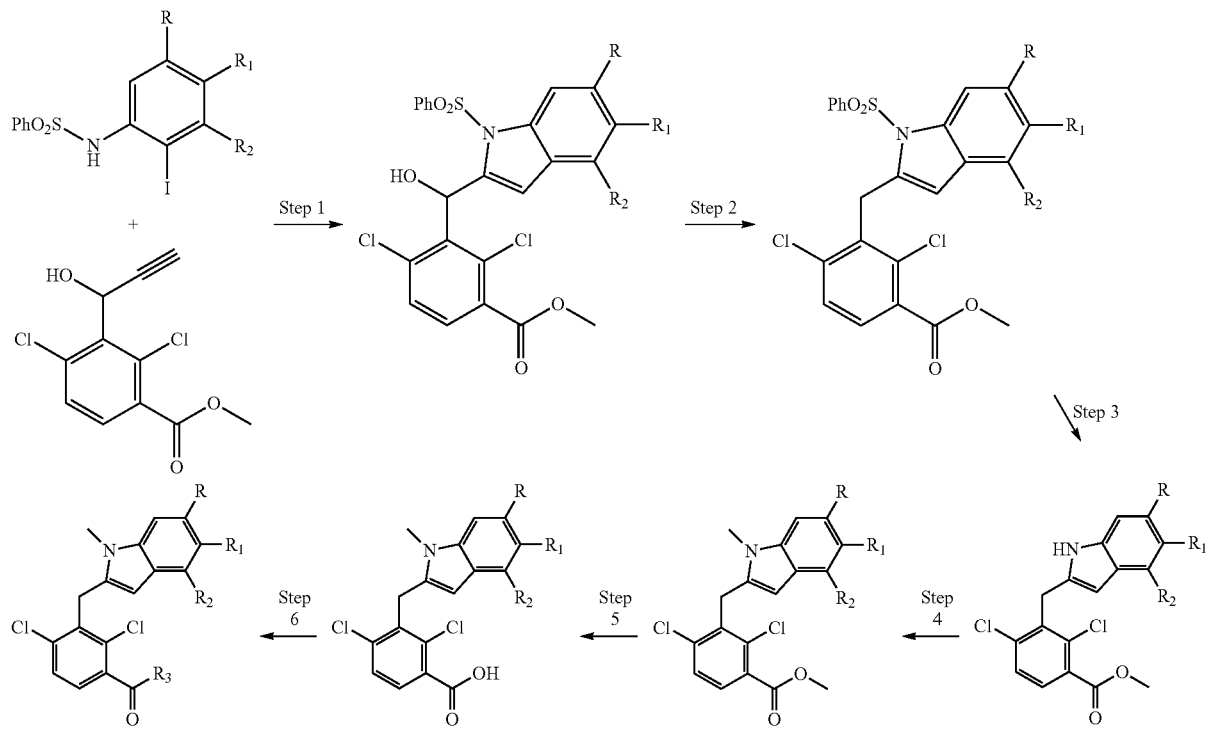

(R = Br, CN, CF$_3$, Me, H; R$_1$ = CN, CF$_3$, Me, H; R$_2$ = CN, CF$_3$, Me, H; R$_3$ = primary or secondary amine).

Scheme II. General methods for preparing (2,4-dichloro-3-((1-alkyl-1H-indol-2-yl)methyl)phenyl)(morpholino)methanone compounds of the invention are illustrated in Scheme II, and further described in Example C, D, E, P, AB, AE:

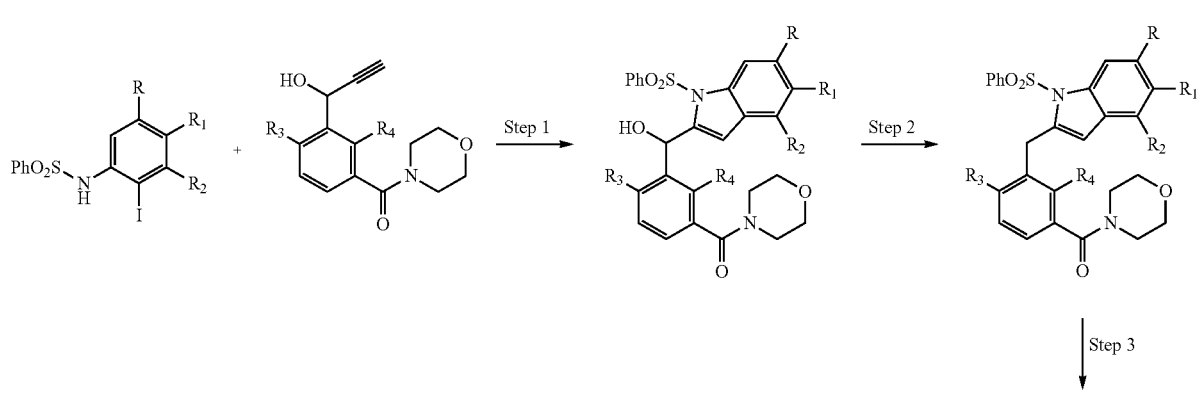

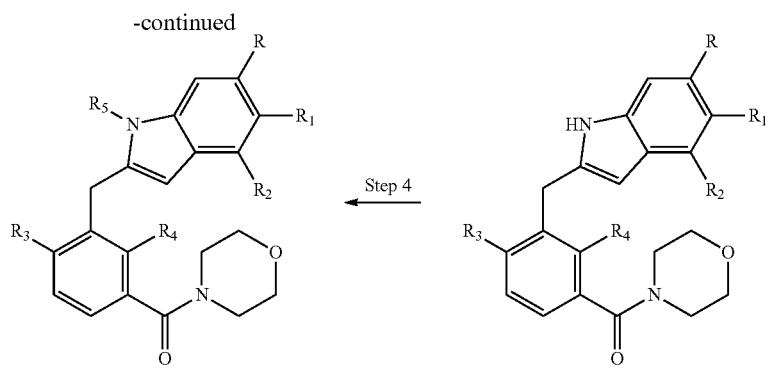
(R = CN, CF₃, Me, H; R₁ = CN, CF₃, Me, H; R₂ = CN, CF₃, Me, H; R₃ = Cl, Me, H; R₄ = Cl, Me, H: R₅ = H, alkyl or acyl substituent).
Scheme III. General methods for preparing 2-(1-(2, 4-dichloro-3-((1, 4-dimethyl-6-(trifluoromethyl)-1H-indol-3-yl)methyl)benzamide)) compounds of the invention are illustrated in Scheme III, and further described in Example F:
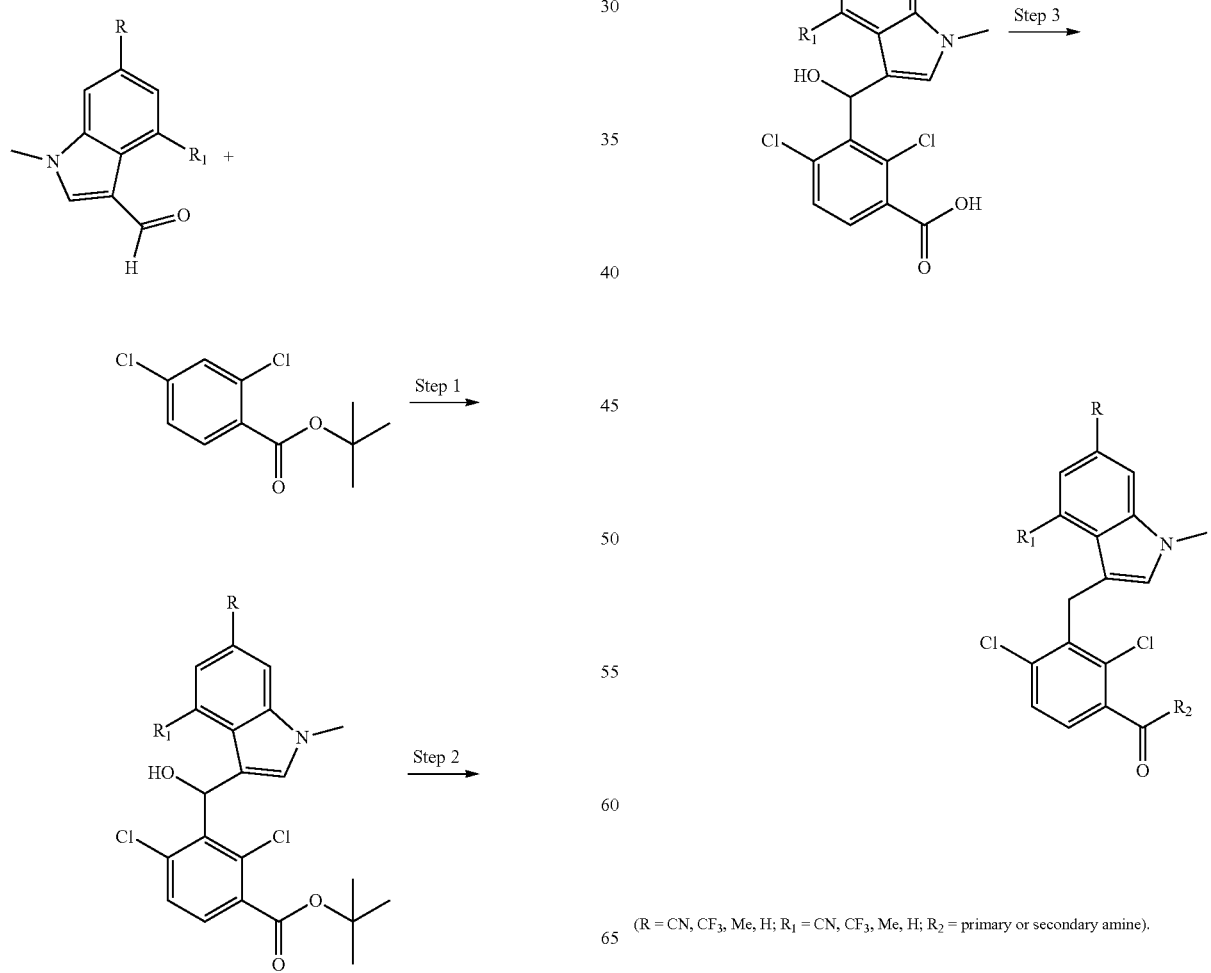
(R = CN, CF₃, Me, H; R₁ = CN, CF₃, Me, H; R₂ = primary or secondary amine).

Scheme IV. General methods for preparing 2-(2,6-dichloro-3-alkoxybenzyl)-1-methyl-1H-indole compounds of the invention are illustrated in Scheme IV, and are further described in Example W, X, Y, Z, AF, AG, AH, AI, AJ, AK, AL, BI:
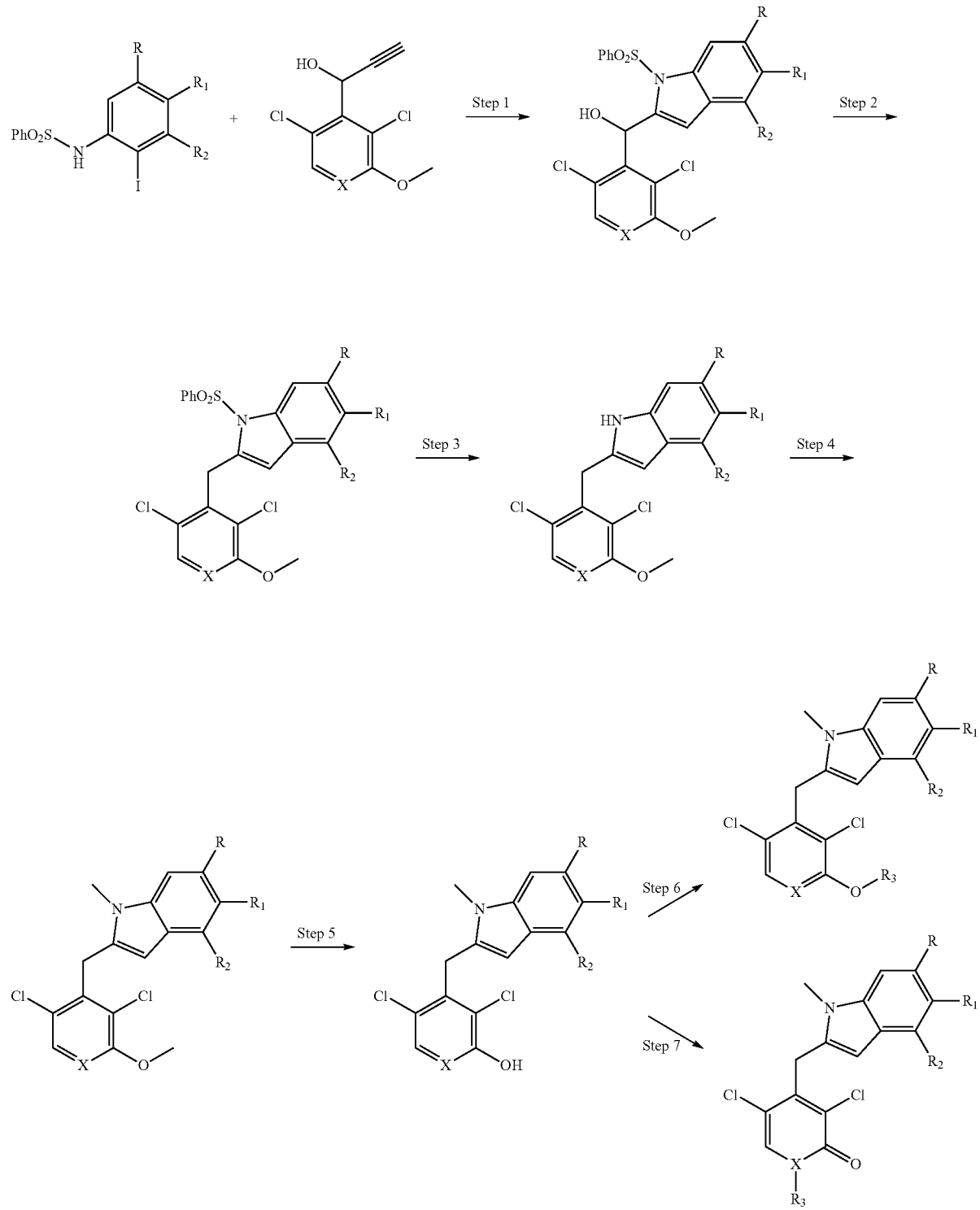
(R = CN, CF₃, Me, H; R₁ = CN, CF₃, Me, H; R₂ = CN, CF₃, Me, H; R₃ = H, alkyl, cycloalkyl, CH₂-heterocycle; X = C or N).

Scheme V. General methods for preparing 3,5-dichloro-4-((1-methyl-1H-indol-2-yl)methyl)benzamide compounds of the invention are illustrated in Scheme V, and are further described in Example R:

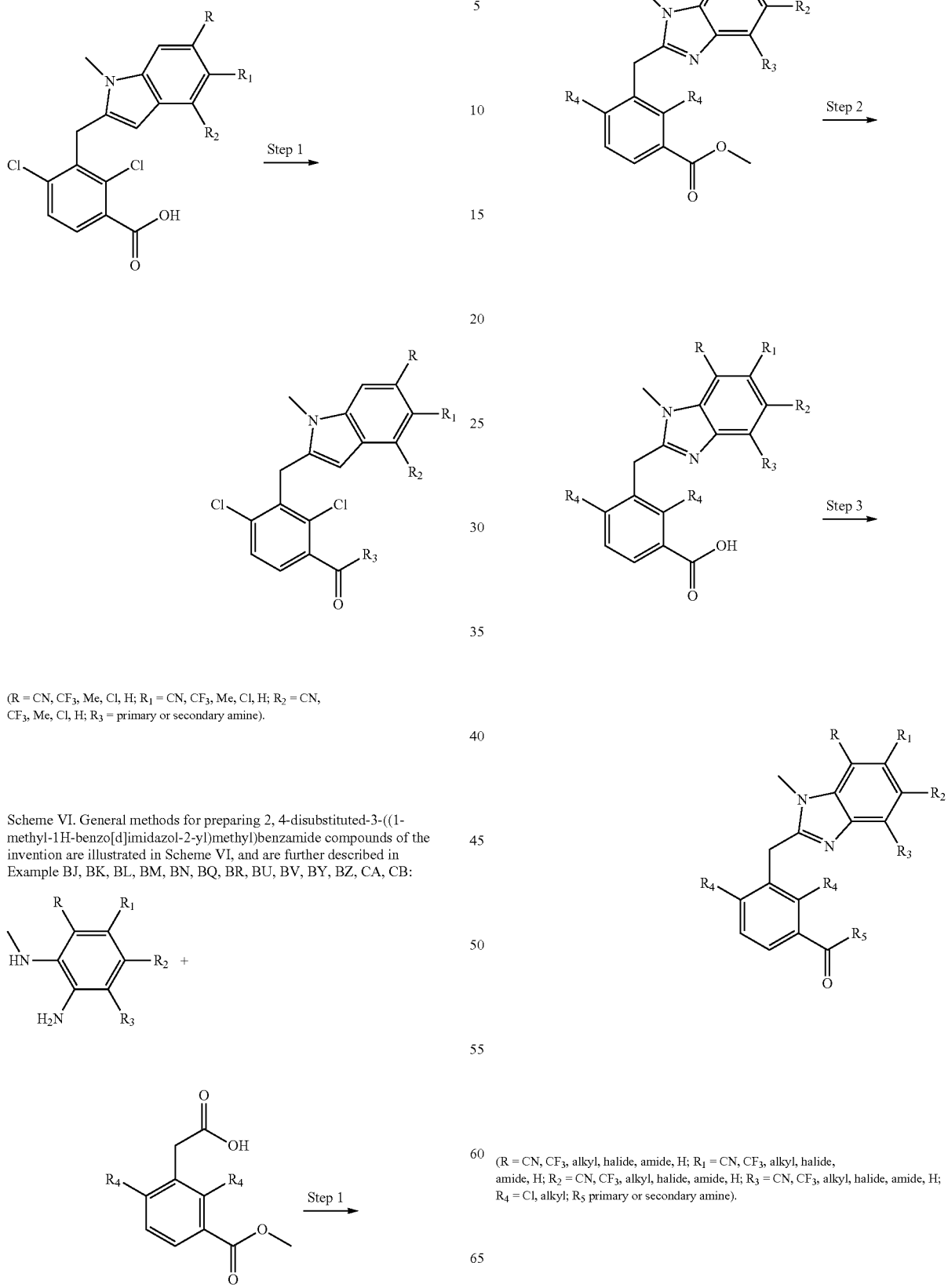

(R = CN, CF$_3$, Me, Cl, H; R$_1$ = CN, CF$_3$, Me, Cl, H; R$_2$ = CN, CF$_3$, Me, Cl, H; R$_3$ = primary or secondary amine).

Scheme VI. General methods for preparing 2,4-disubstituted-3-((1-methyl-1H-benzo[d]imidazol-2-yl)methyl)benzamide compounds of the invention are illustrated in Scheme VI, and are further described in Example BJ, BK, BL, BM, BN, BQ, BR, BU, BV, BY, BZ, CA, CB:

(R = CN, CF$_3$, alkyl, halide, amide, H; R$_1$ = CN, CF$_3$, alkyl, halide, amide, H; R$_2$ = CN, CF$_3$, alkyl, halide, amide, H; R$_3$ = CN, CF$_3$, alkyl, halide, amide, H; R$_4$ = Cl, alkyl; R$_5$ primary or secondary amine).

Scheme VII. General methods for preparing (2, 4-dichloro-3-((3-methyl-3H-imidazo[4, 5-b]pyridin-2-yl)methyl)phenyl)(morpholino)methanone compounds of the invention are illustrated in Scheme VII, and are further described in Example CI, DA:

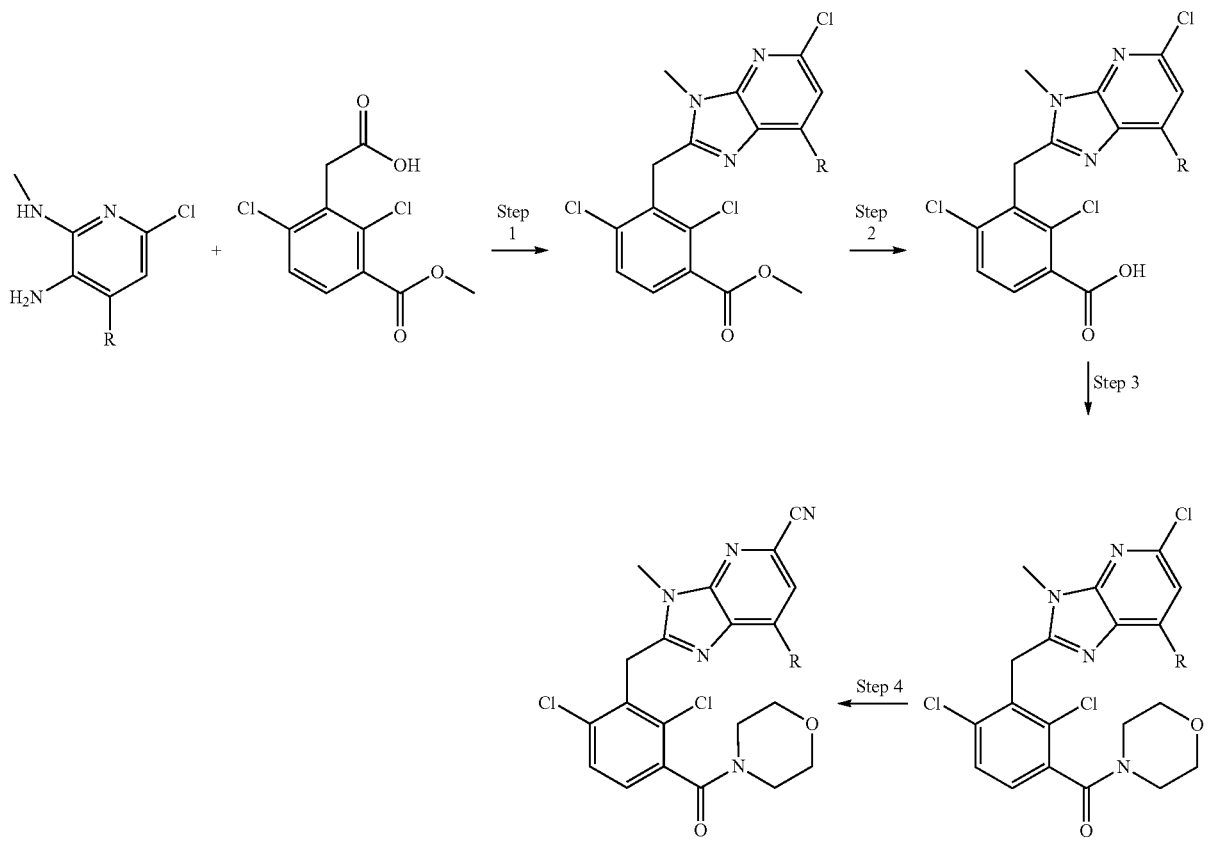

(R = CN, CF₃, alkyl, halide, amide, H).

Scheme VIII. General methods for preparing N-(3, 5-dichloro-4-((1-methyl-1H-benzo[d]imidazol-2-yl)methyl)phenyl)acetamide compounds of the invention are illustrated in Scheme VIII, and are further described in Example CJ:

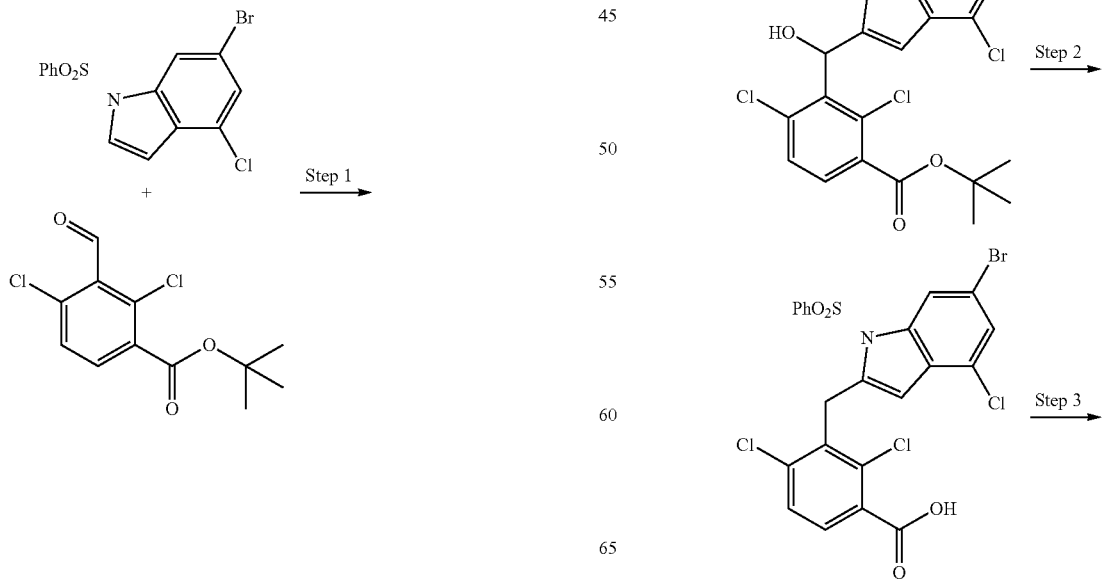

-continued

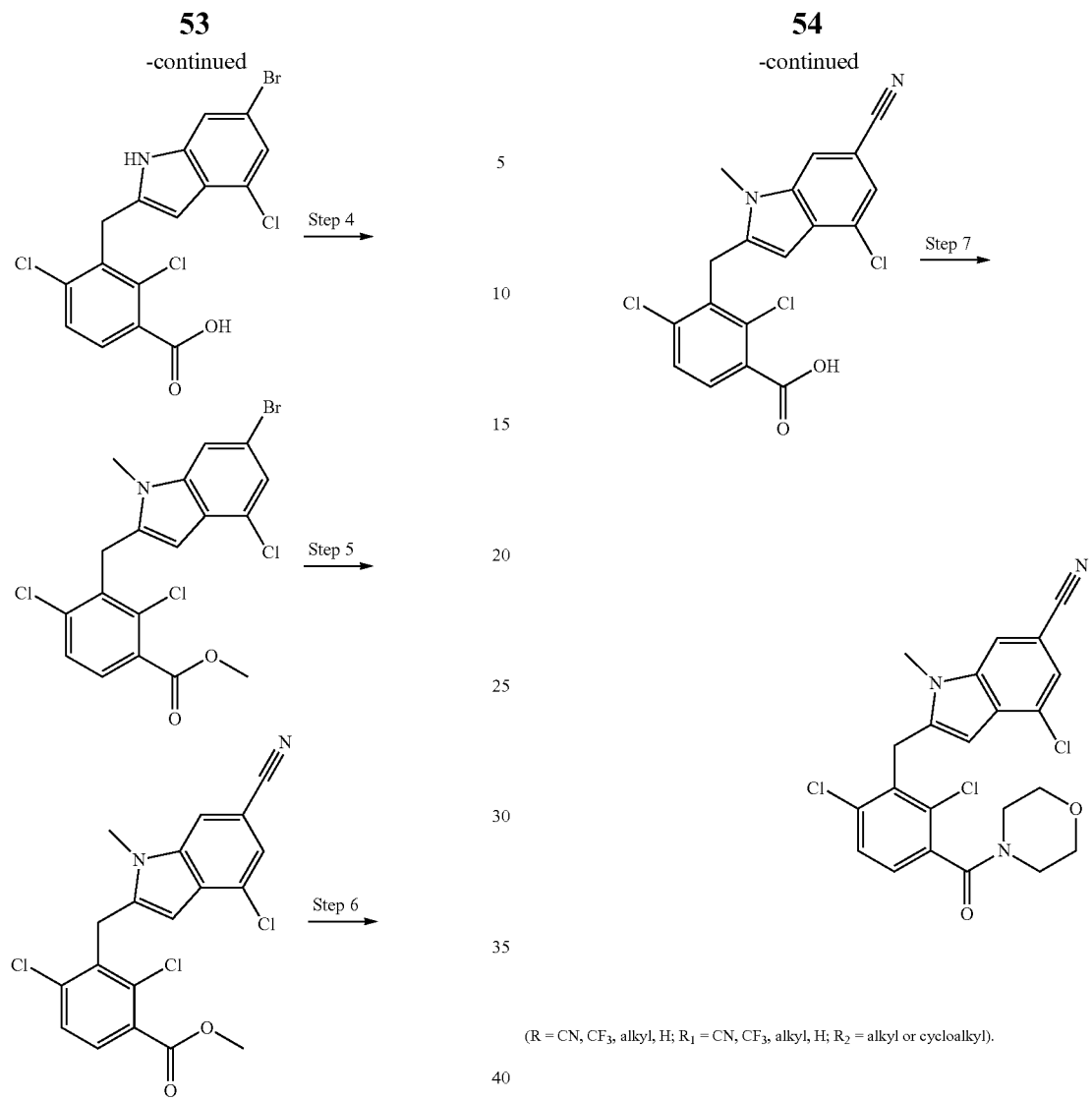
(R = CN, CF₃, alkyl, H; R₁ = CN, CF₃, alkyl, H; R₂ = alkyl or cycloalkyl).

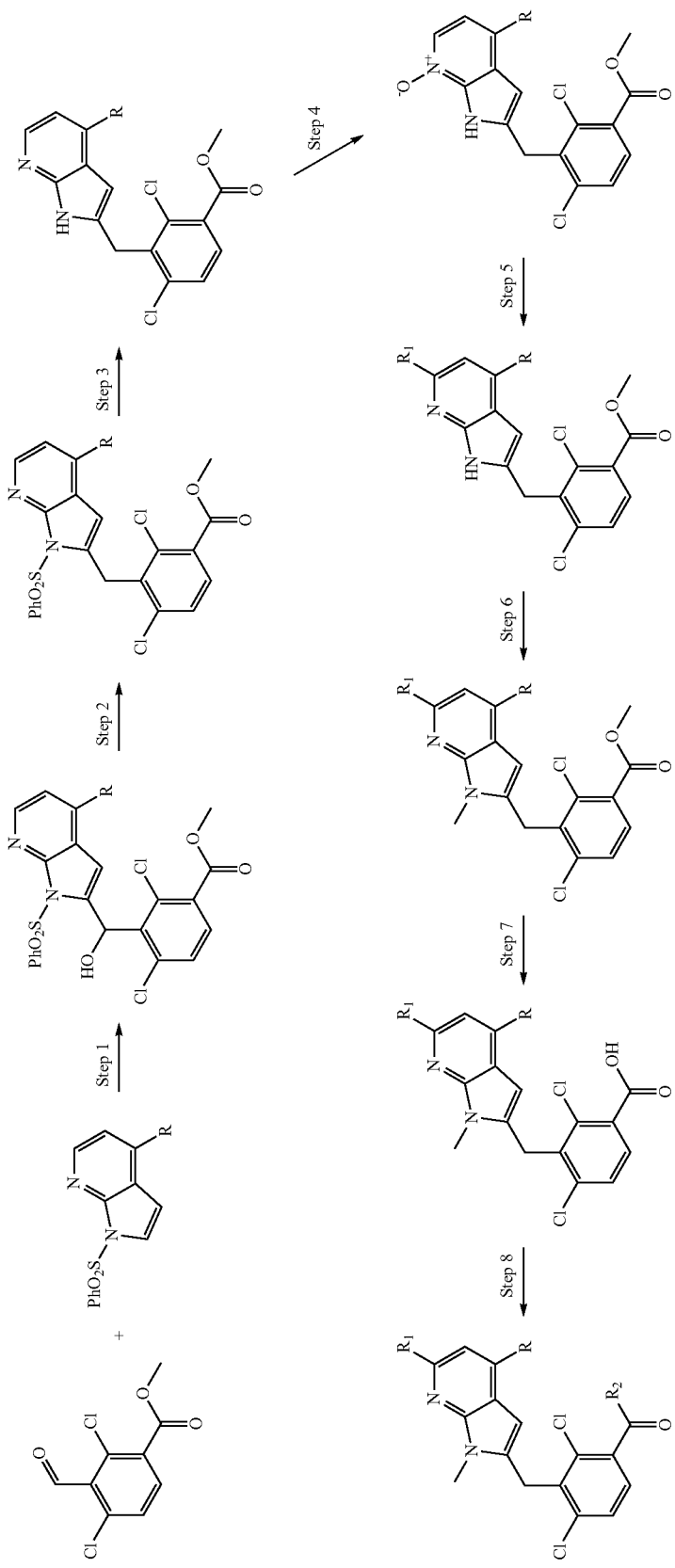

Scheme X. General methods for preparing (2, 4-dichloro-3-((1-methyl-1H-pyrrolo[3, 2-b]pyridin-2-yl)methyl)phenyl)(morpholino)methanone compounds of the invention are illustrated in Scheme X, and are further described in Example CO:

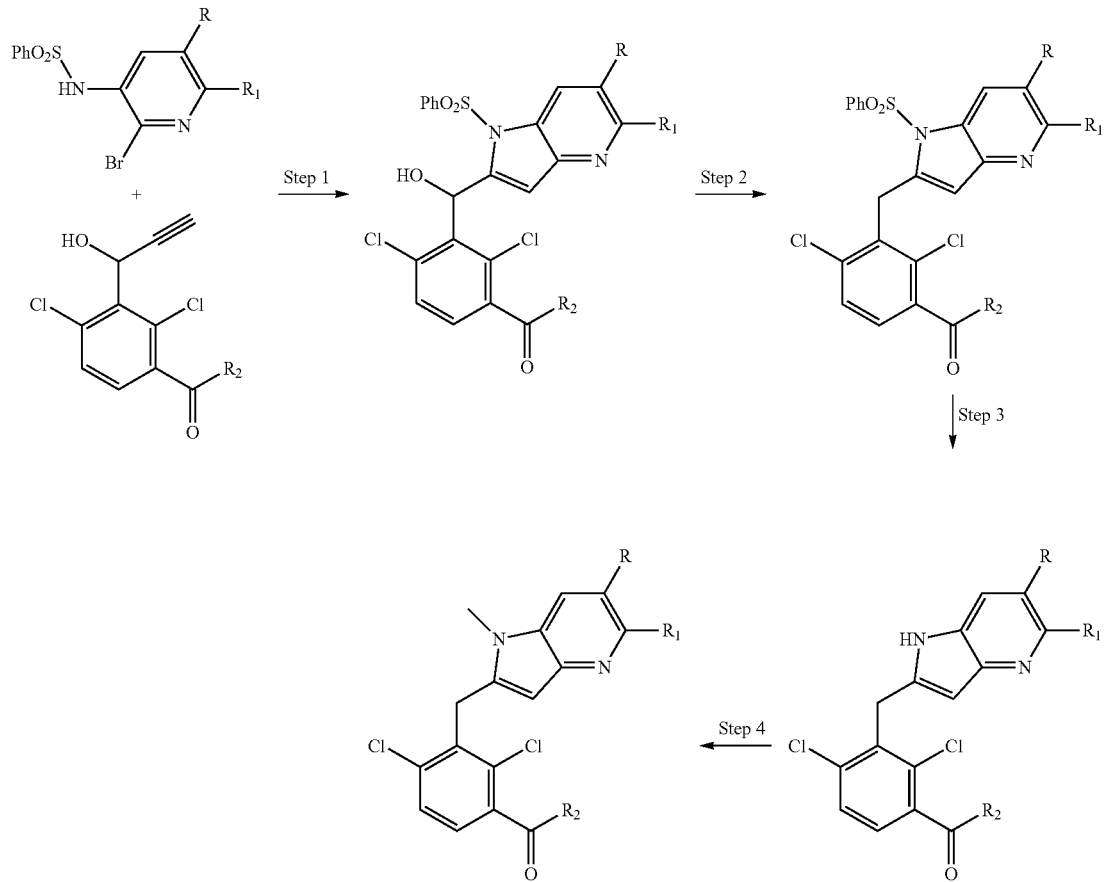

(R = CN, CF$_3$, alkyl, H; R$_1$ = CN, CF$_3$, alkyl, H; R$_2$ = primary or secondary amine).

Scheme XI. General methods for preparing 2,4-dichloro-3-((1-methyl-1H-pyrrolo[3,2-c]pyridin-2-yl)methyl)benzamide compounds of the invention are illustrated in Scheme XI, and are further described in Example CQ, CR and CS:

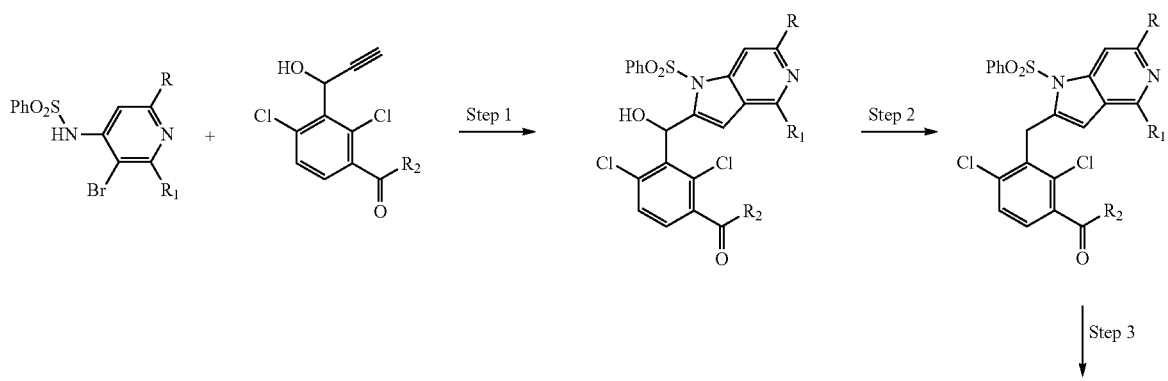

-continued

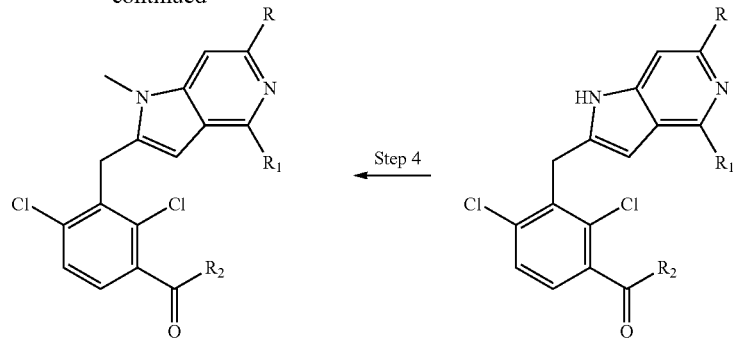

(R = CN, CF₃, alkyl, H; R₁ = CN, CF₃, alkyl, H; R₂ = primary or secondary amine).

Scheme XII. General methods for preparing 2, 4-dichloro-3-((3-methylimidazo[1, 2-a]pyridin-2-yl)methyl)benzamide compounds of the invention are illustrated in Scheme XII, and are further described in Example CT, CV, CW and CZ:

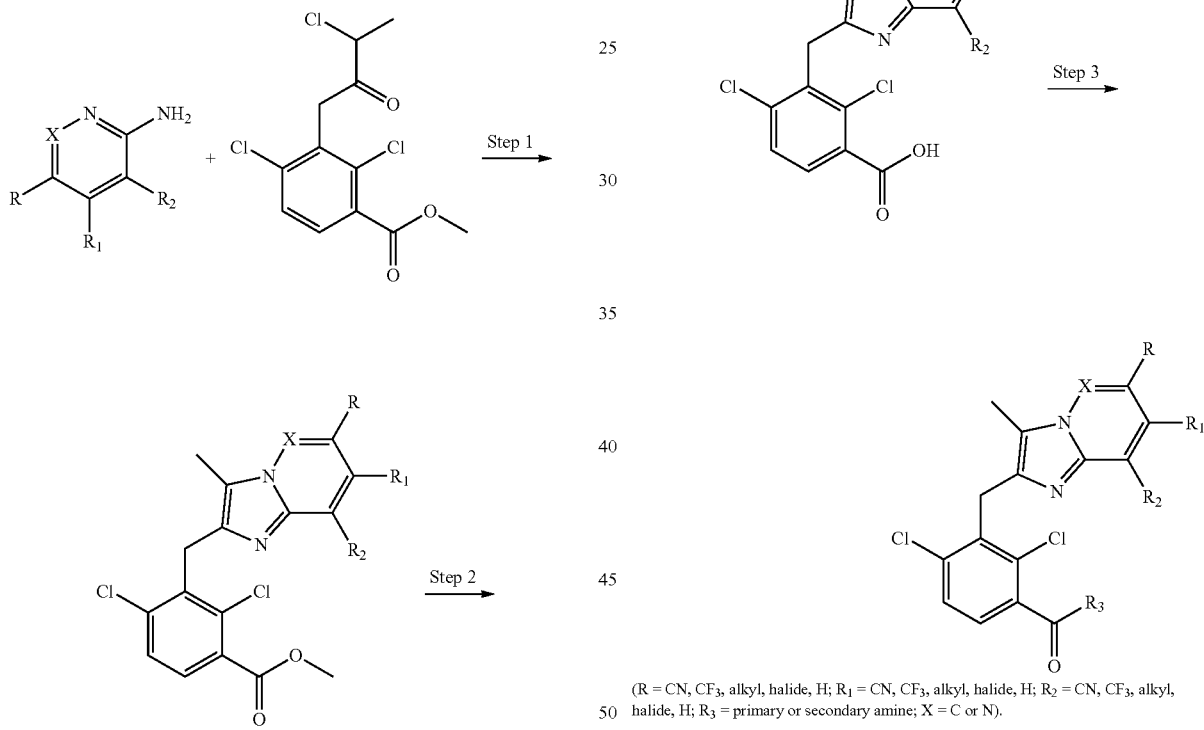

(R = CN, CF₃, alkyl, halide, H; R₁ = CN, CF₃, alkyl, halide, H; R₂ = CN, CF₃, alkyl, halide, H; R₃ = primary or secondary amine; X = C or N).

Scheme XIII. General methods for preparing 2, 4-dichloro-3-((1-methyl-3, 4-dihydroisoquinolin-2(1H)-yl)methyl)benzamide compounds of the invention are illustrated in Scheme XIII, and are further described in Example DO:

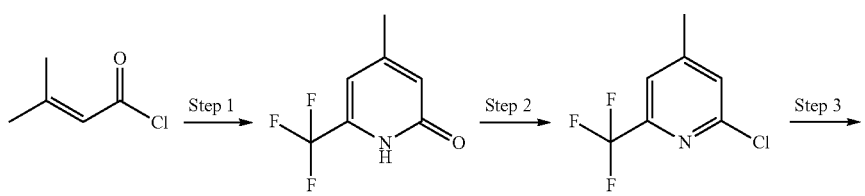

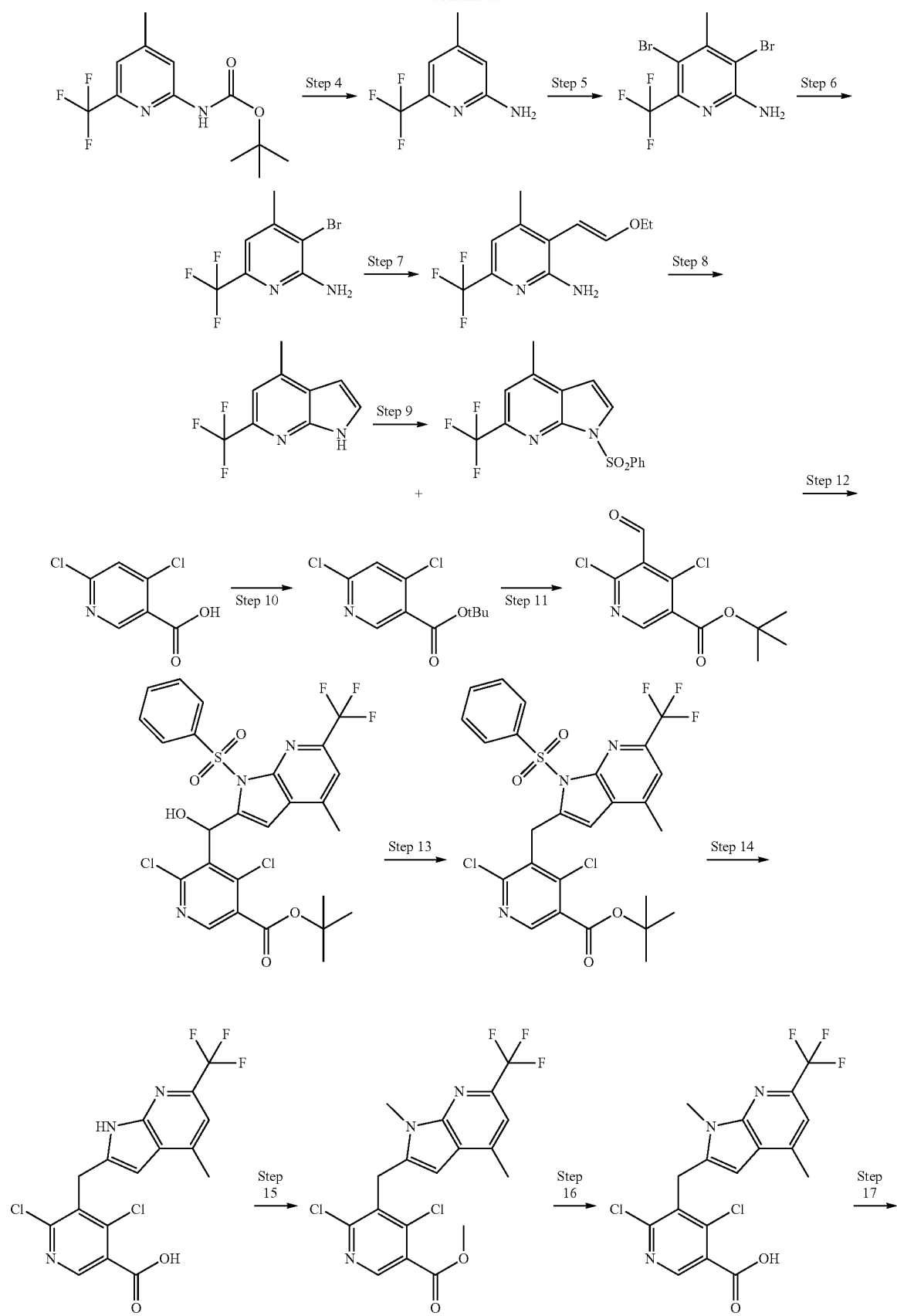

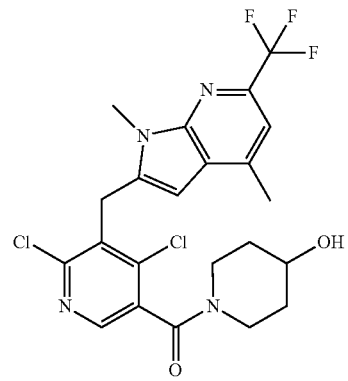

Scheme XIV. General methods for preparing 2, 4-disubstituted-3-((1-alkyl-1H-benzo[d]imidazol-2-yl)methyl)benzamide compounds of the invention are illustrated in Scheme XIV, and are further described in Examples CG and CH:

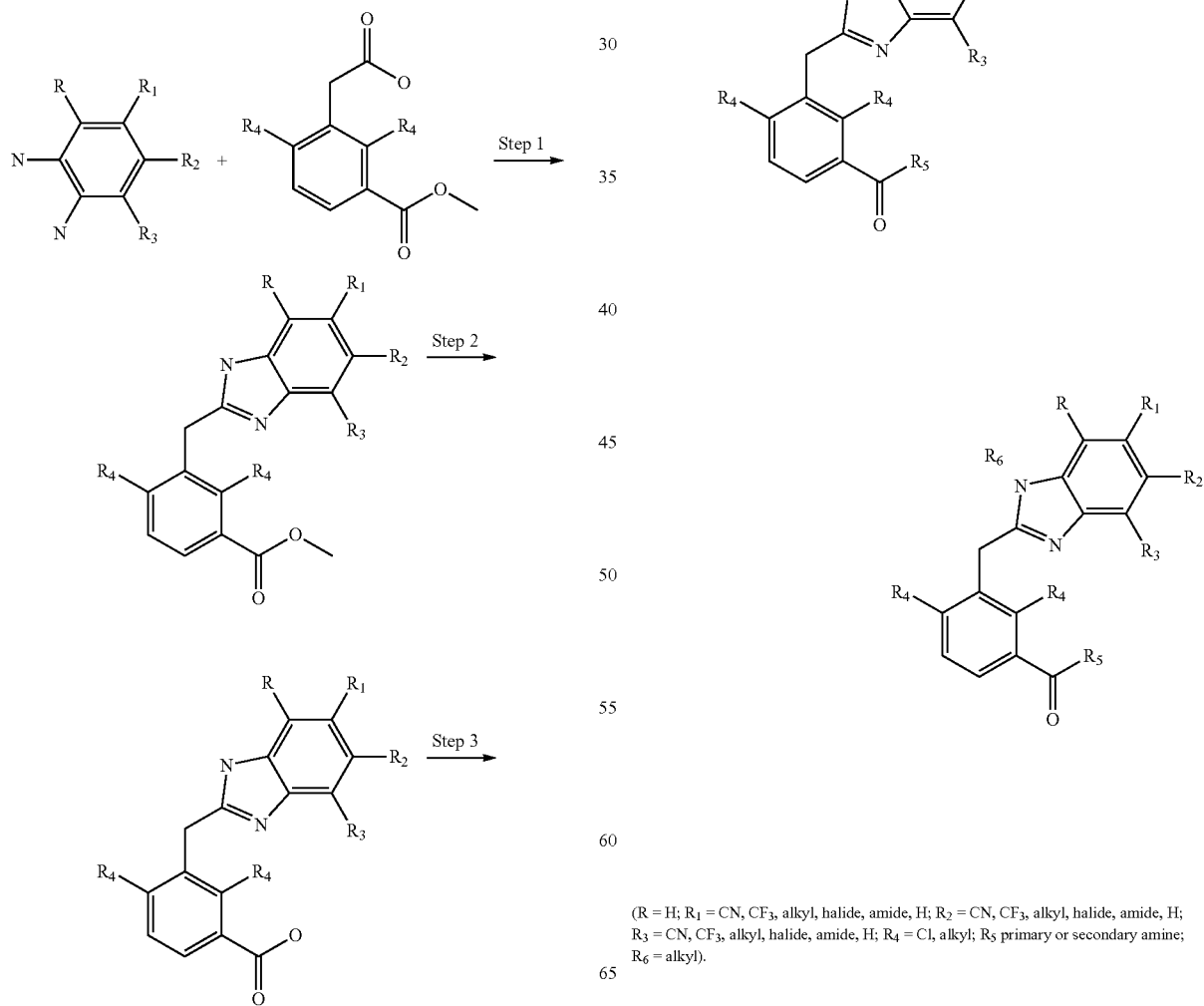

(R = H; $R_1$ = CN, $CF_3$, alkyl, halide, amide, H; $R_2$ = CN, $CF_3$, alkyl, halide, amide, H; $R_3$ = CN, $CF_3$, alkyl, halide, amide, H; $R_4$ = Cl, alkyl; $R_5$ primary or secondary amine; $R_6$ = alkyl).

Scheme XV. General methods for preparing 2,4-disubstituted-3-((1-methyl-1H-benzo[d]imidazol-2-yl)methyl)benzylamine compounds of the invention are illustrated in Scheme XV, and are further described in Examples BW and BX:

From Scheme XII

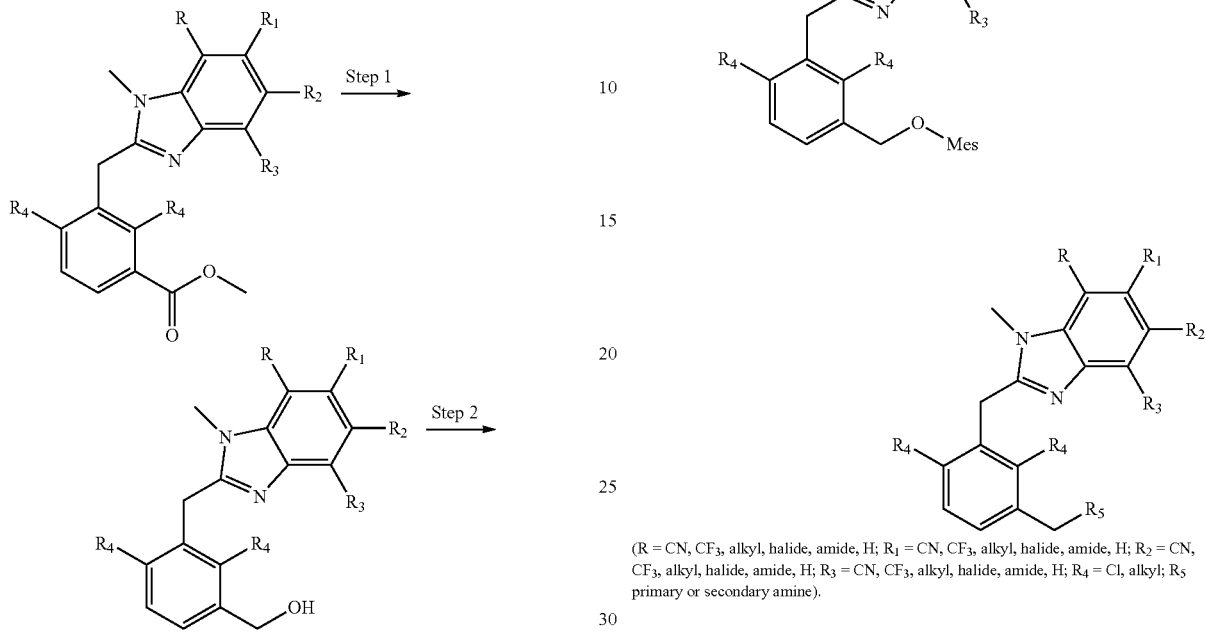

(R = CN, CF₃, alkyl, halide, amide, H; R₁ = CN, CF₃, alkyl, halide, amide, H; R₂ = CN, CF₃, alkyl, halide, amide, H; R₃ = CN, CF₃, alkyl, halide, amide, H; R₄ = Cl, alkyl; R₅ primary or secondary amine).

Scheme XVI. General methods for preparing (2,4-dichloro-3-((3-methyl-1H-indazol-1-yl)methyl)benzamide or (2,4-dichloro-3-((3-methyl-2H-indazol-2-yl)methyl)benzamide compounds of the invention are illustrated in Scheme XVI, and are further described in Examples DD, DD1, DE, DF and DG:

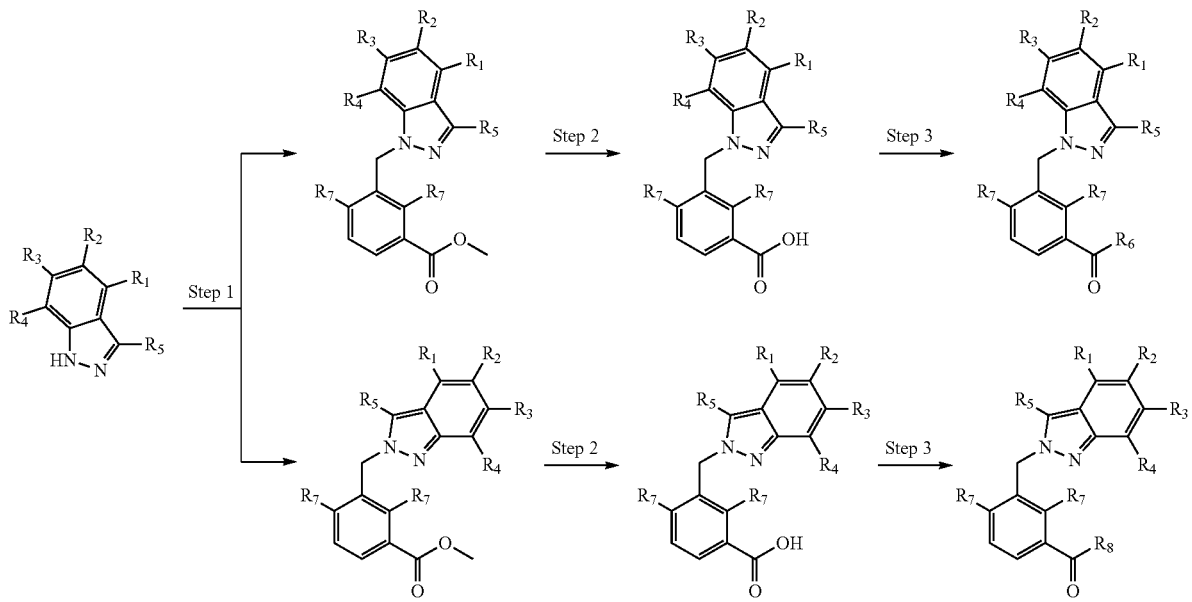

(R₁ = CN, CF₃, alkyl, halide, amide, H; R₂ = CN, CF₃, alkyl, halide, amide, H; R₃ = CN, CF₃, alkyl, halide, amide, H; R₄ = CN, CF₃, alkyl, halide, amide, H; R₅ = methyl; R₆ = primary or secondary amine; R₇ = chloro).

Scheme XVII. General methods for preparing (2, 4-dichloro-3-((3-methyl-3H-imidazo[4, 5-b]pyridin-2-yl)methyl)phenyl)(morpholino)methanone compounds of the invention are illustrated in Scheme XVII, and are further described in Example DC:

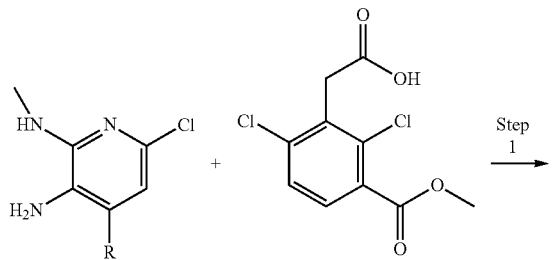

Step 1 →

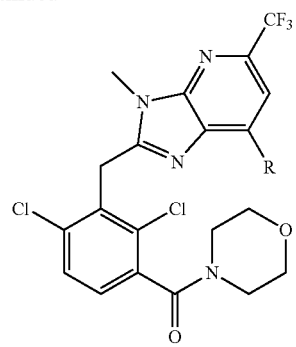

(R = CN, CF₃, alkyl, halide, amide, H).

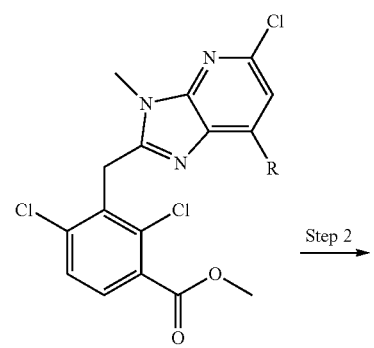

Step 2 →

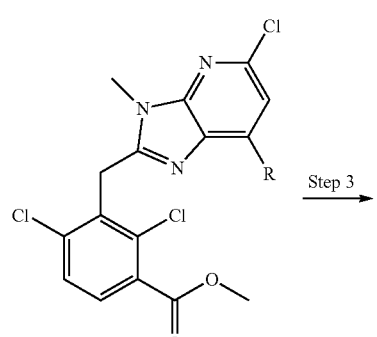

Step 3 →

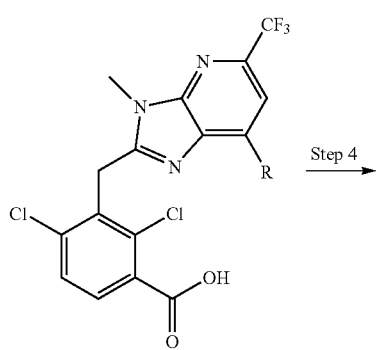

Step 4 →

Scheme XVIII. General methods for preparing 2, 4-dichloro-3-((1-methyl-1H-indol-2-yl)methyl)pyridylcarboxamide compounds of the invention are illustrated in Scheme XVIII, and further described in Examples BB, BC, BE, BF, BG and BH:

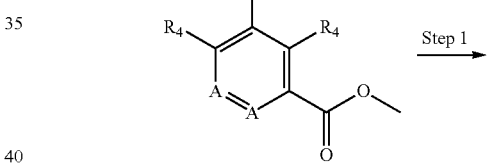

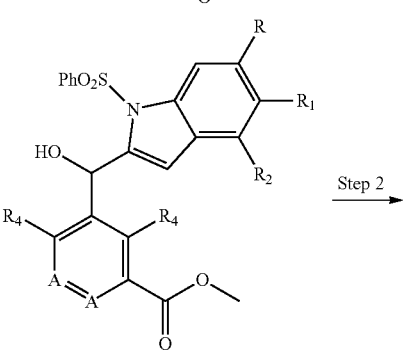

Step 2 →

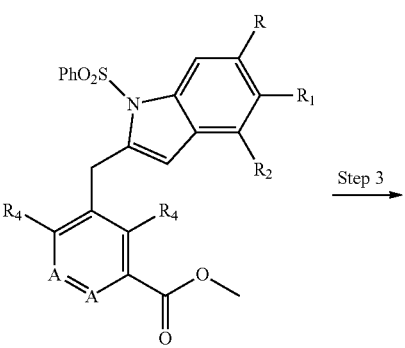

Step 3 →

-continued
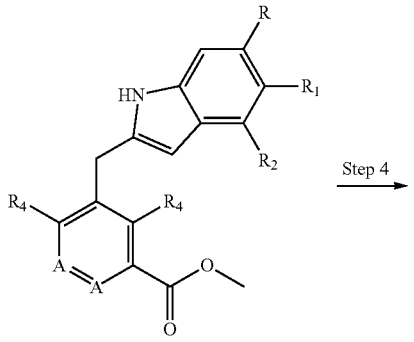
Step 4
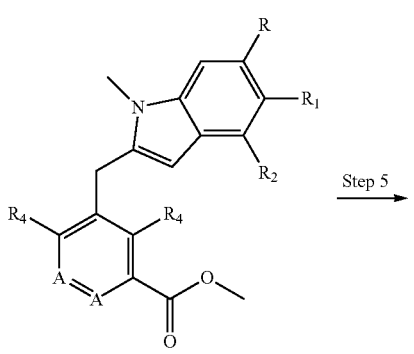
Step 5
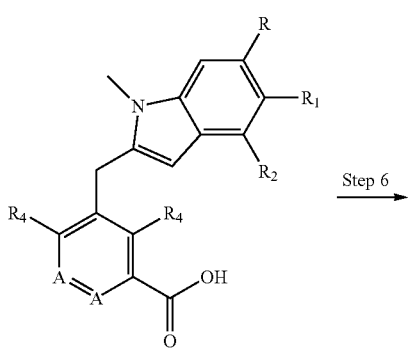
Step 6
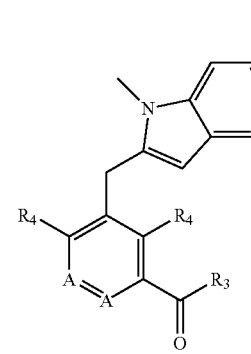
(A = A = C = N or N = C; R = CN, CF₃, Me, H; R₁ = CN, CF₃, Me, H; R₂ = CN, CF₃, Me, H; R₃ = primary or secondary amine, R₄ = Cl, Me, H).
Scheme XIX. General methods for preparing 2,4-disubstituted-3-((1H-indol-2-yl)methyl benzamide compounds of the invention are illustrated in Scheme XIX, and further described in Example AS:
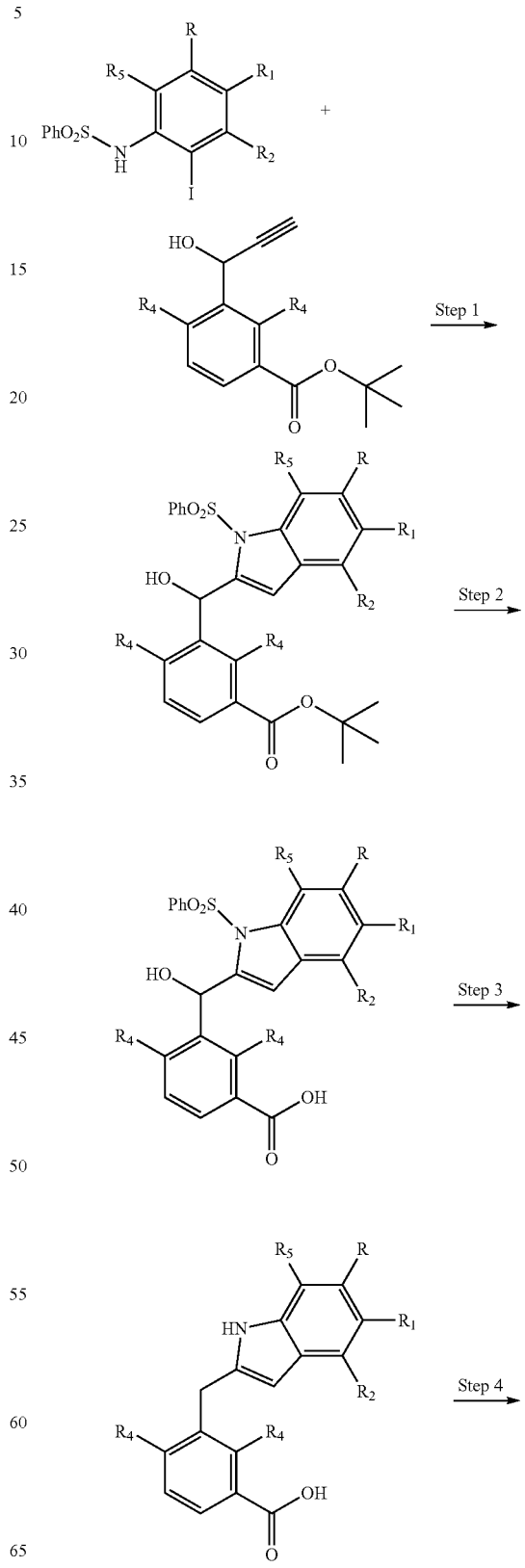

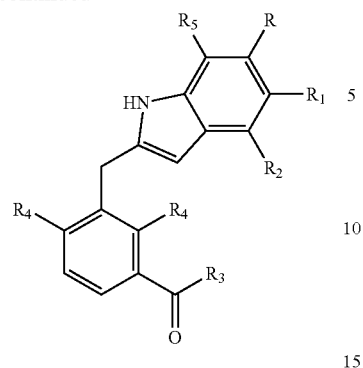
(R = CN, CF₃, Me, H; R₁ = CN, CF₃, Me, H; R₂ = CN, CF₃, Me, H; R₄ = Cl, Me; R₅ = CN, CF₃, Me, H; R₃ = primary or secondary amine).
Scheme XX. General methods for preparing 2,4-dichloro-3-(1-methyl-1H-indole-2-carbonyl)benzamide compounds of the invention are illustrated in Scheme XX, and further described in Examples AN, AO, AP and AQ:
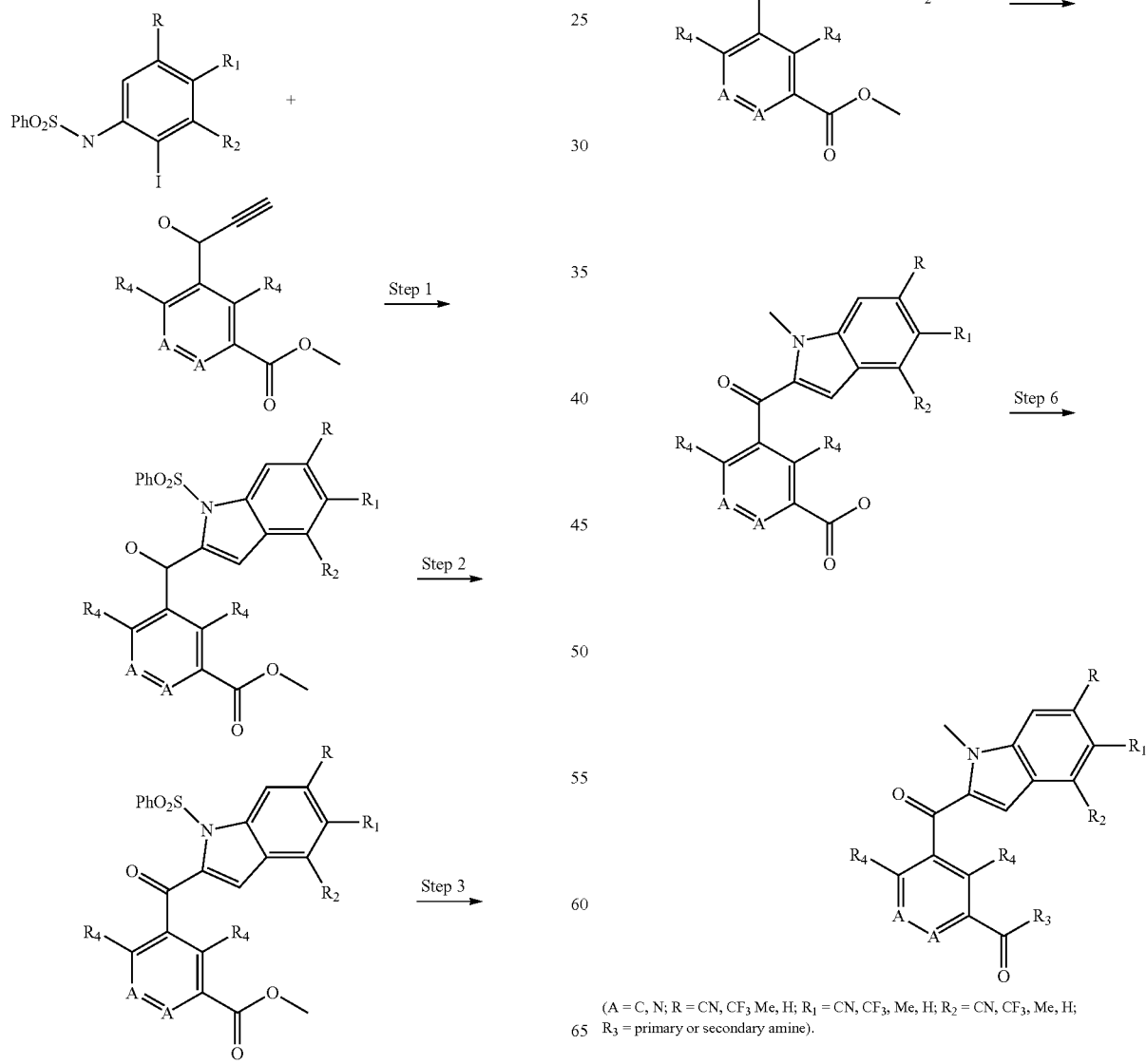
(A = C, N; R = CN, CF₃ Me, H; R₁ = CN, CF₃, Me, H; R₂ = CN, CF₃, Me, H; R₃ = primary or secondary amine).

Scheme XXI. General methods for preparing 2,4-disubstituted-3-((1-methyl-1H-indol-2-yl)methyl)benzylamine compounds of the invention are illustrated in Scheme XXI, and are further described in Example AU:

From scheme I

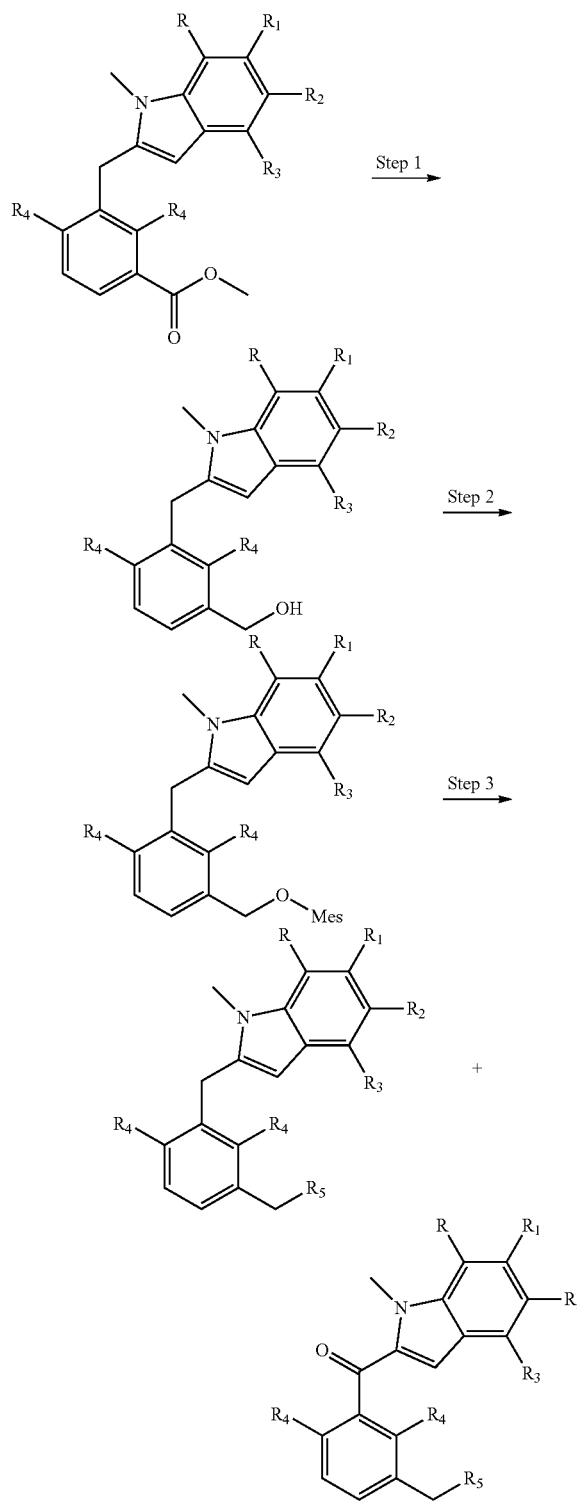

(R = CN, CF$_3$, alkyl, halide, amide, H; R$_1$ = CN, CF$_3$, alkyl, halide, amide, H; R$_2$ = CN, CF$_3$, alkyl, halide, amide, H; R$_3$ = CN, CF$_3$, alkyl, halide, amide, H; R$_4$ = Cl, alkyl; R$_5$ primary or secondary amine).

Scheme XXII. General methods for preparing 2,4-dichloro-3-((1-methyl-6-morpholino-1H-indol-2-yl)methyl)benzamide compounds of the invention are illustrated in Scheme XXII, and further described in Example AY:

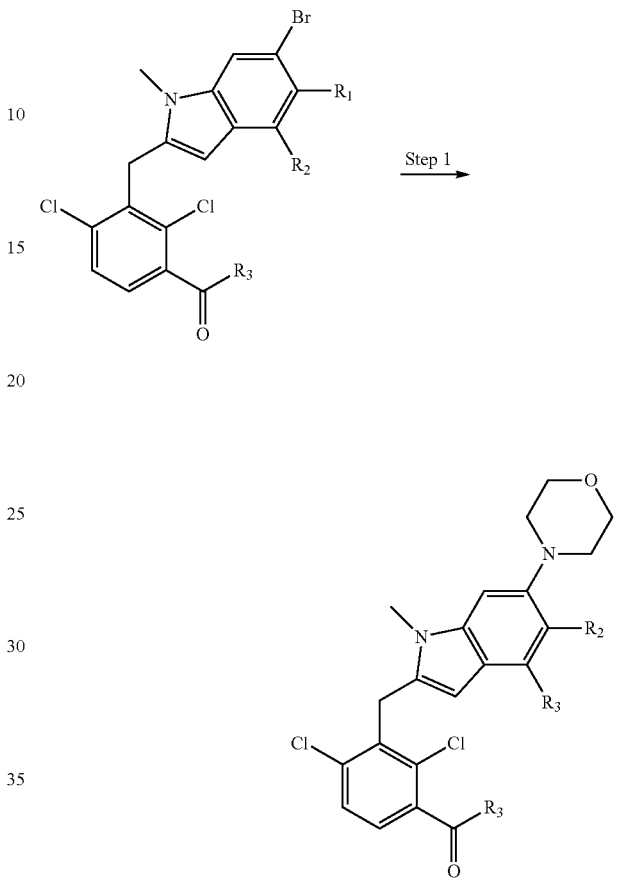

(R$_1$ = CN, CF$_3$, Me, H; R$_2$ = CN, CF$_3$, Me, H; R$_3$ = primary or secondary amine).

Scheme XXIII. General methods for preparing 2,4-dichloro-3-(1H-indol-1-yl)methyl benzamide compounds of the invention are illustrated in Scheme XXIII, and further described in Examples J, DH, DI, DJ, DK, DL, DM and DN:

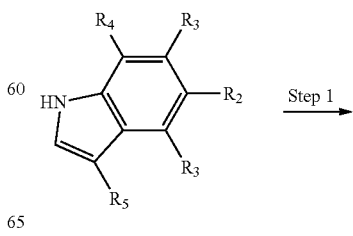

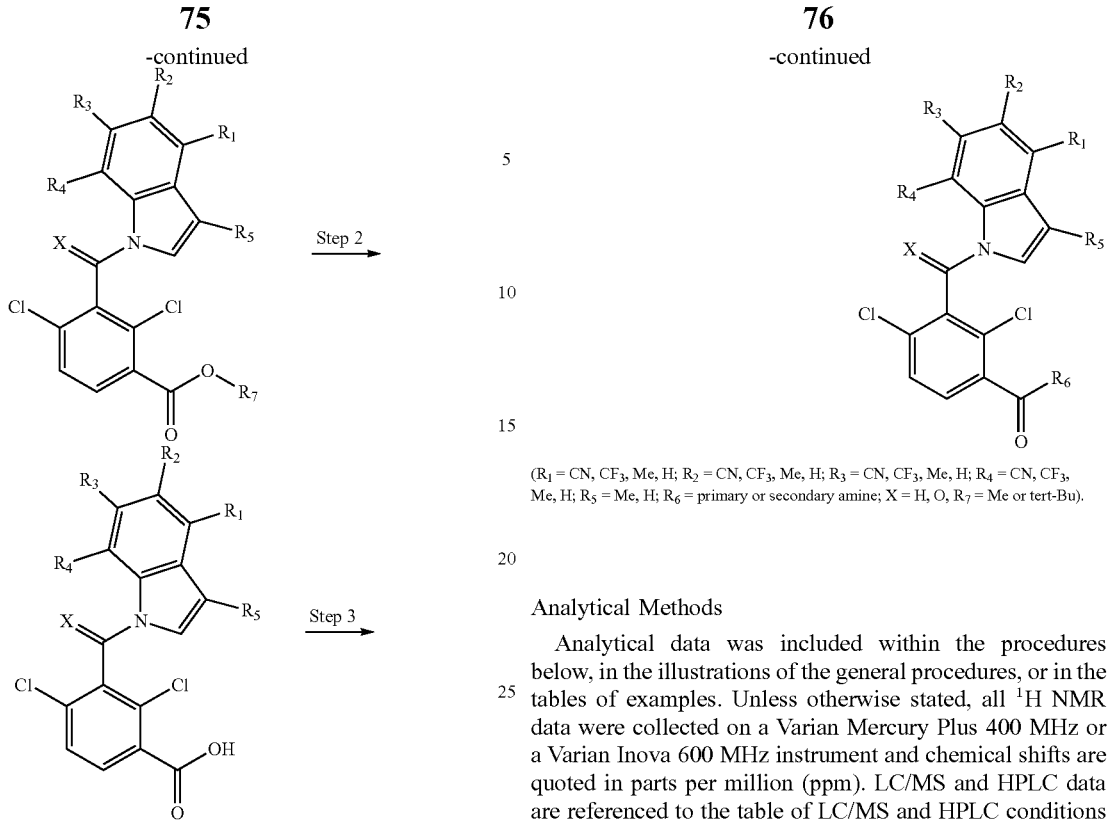

($R_1$ = CN, $CF_3$, Me, H; $R_2$ = CN, $CF_3$, Me, H; $R_3$ = CN, $CF_3$, Me, H; $R_4$ = CN, $CF_3$, Me, H; $R_5$ = Me, H; $R_6$ = primary or secondary amine; X = H, O, $R_7$ = Me or tert-Bu).

Analytical Methods

Analytical data was included within the procedures below, in the illustrations of the general procedures, or in the tables of examples. Unless otherwise stated, all $^1$H NMR data were collected on a Varian Mercury Plus 400 MHz or a Varian Inova 600 MHz instrument and chemical shifts are quoted in parts per million (ppm). LC/MS and HPLC data are referenced to the table of LC/MS and HPLC conditions using the lower case method letter provided in Table 1.

TABLE 1

LC/MS and HPLC methods.

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade ACN. The column used for the chromatography is a 4.6 × 50 mm MAC-MOD Halo C18 column (2.7 gm particles). Detection methods are diode array (DAD) and evaporative light scattering (ELSD) detection as well as positive/negative electrospray ionization. |
| b | CP Column: XBRIDGE C18 (4.6 × 50 mm, 3.5 μm) Mobile phase: $H_2O$ (10 mmol $NH_4HCO_3$) (A)/ACN(B) Elution program: Gradient from 10 to 95% of B in 1.5 min at 1.8 mL/min, Temperature: 45° C., Detection: UV (214, 4 nm) and MS (ESI, Pos mode, 70 to 900 amu) |
| c | LC/MS: The gradient was 10-95% B in 1.5 min (1.8 mL/min flow rate). Mobile phase A was 0.1% $NH_4HCO_3$ in water, mobile phase B was HPLC grade ACN. The column used for the chromatography was a 4.6 × 50 mm Xbridge C18 column (3.5 μm particles) at a temperature of 45° C. Detection methods are UV (214, 4 nm) and MS (ESI, Pos mode, 70 to 900 amu) |
| d | LC/MS: The gradient was 5-95% B in 1.4 min, then hold at 95% B for 1.4 min. then back to 5% B within 0.01 min. (1.8 mL/min flow rate). Mobile phase A was 0.1% $NH_4HCO_3$ in water, mobile phase B was HPLC grade ACN. The column used for the chromatography was a 4.6 × 50 mm Xbridge C18 column (3.5 μm particles) at a temperature of 50° C. Detection methods are UV (214, 4 nm) and MS (ESI, Pos mode, 70 to 900 amu). |
| e | LC/MS: The gradient was 5-100% B in 1.3 min. (2.0 mL/min flow rate). Mobile phase A was 0.05% TFA in water, mobile phase B was 0.05% TFA in HPLC grade ACN. The column used for the chromatography was a 4.6 × 50 mm SunFire C18 column (3.5 μm particles) at a temperature of 50° C. Detection methods are UV (214, 4 nm) and MS (ESI, Pos mode, 110 to 1000 amu) |
| f | LC/MS: The gradient was 5-95% B in 1.2 min. then 95% B for 1.3 min. back to 5% B for 0.01 min. (2.0 mL/min flow rate). Mobile phase A was 0.01% TFA in water, mobile phase B was 0.01% TFA in HPLC grade MeCN. The column used for the chromatography was a 4.6 × 50 mm SunFire C18 column (3.5 μm particles) at a temperature of 50° C. Detection methods are UV (214, 4 nm) and MS (ESI, Pos mode, 110 to 1000 amu) |
| g | LC/MS: The gradient was: 0-0.1 min: 5% B; 0.1-2.3 min: 5% B to 95% B; 2.3-2.5 min: 95% B; 2.51-3 min: 5% B (0.8 ml/min flow rate). Mobile Phase A: 0.1% $CH_3COOH$ in water. Mobile Phase B: 0.1% $CH_3COOH$ in ACN. Column: ACQUITY UPLC BEH C18 (Dimensions: 50 × 2.1 mm × 1.7 μm). Column temperature: 45° C. UV detection: DAD 210-260 nm. MS detection (ESI positive and negative). |
| h | LC/MS: The gradient was: 0-3.5 min: 10% B to 90% B; 3.5-4.2 min: 90% B; 4.21-5.2 min: 10% B (1.4 mL/min flow rate). Mobile Phase A: 0.1% $CH_3COOH$ in water. Mobile |

TABLE 1-continued

LC/MS and HPLC methods.

| Method | Conditions |
|---|---|
|  | Phase B: 0.1% CH3COOH in ACN. Column: Kinetex XB - C18 (Dimensions: 30 × 3.0 mm, 2.6 μm particles size). Column temperature: 45° C. UV detection: DAD 210-260 nm. MS detection (ESI positive and negative). |
| i | LC/MS: The gradient was: 0-2.8 min: 10% B to 100% B (1.4 mL/min flow rate); 2.8-2.9 min: 100% B (1.4 mL/min flow rate); 2.9.-3.5 min: 100% B (2.5 mL/min flow rate). Mobile Phase A: 0.1% $CH_3COOH$ in water. Mobile Phase B: 0.1% $CH_3COOH$ in ACN. Column: Kinetex XB - C18 (Dimensions: 30 × 3.0 mm, 2.6 μm particles size). Column temperature: 45° C. UV detection: DAD 210-260 nm. MS detection (ESI positive and negative). |
| j | LC/MS: The gradient was: 0-3.0 min: 40% B to 100% B (1.4 ml/min flow rate); 3.0.-3.1 min: 100% B (1.4 mL/min flow rate); 3.1.-3.4 min: 100% B (2.5 ml/min flow rate). Mobile Phase A: 0.1% $CH_3COOH$ in water. Mobile Phase B: 0.1% $CH_3COOH$ in ACN. Column: Kinetex XB - C18 (Dimensions: 30 × 3.0 mm, 2.6 μm particles size). Column temperature: 45° C. UV detection: DAD 210-260 nm. MS detection (ESI positive and negative). |
| k | LC/MS: The gradient was: 0-3.5 min: 10% B to 95% B; 3.5-4.0 min: 95% B; 4.1-5.2 min: 10% B (1.3 mL/min flow rate). Mobile Phase A: 0.1% HCOOH in water. Mobile Phase B: 0.1% HCOOH in ACN. Column: Kinetex XB - C18 (Dimensions: 30 × 3.0 mm, 2.6 μm particles size). Column temperature: room temperature. UV detection: DAD 210-260 nm. MS detection (ESI positive and negative). |
| l | The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| l-2 | The gradient was 30% B for 1 min, then to 85% B in 2 min, then hold at 85% B for 30 min, then to 50% B in one min, then hold at 50% B for 9 min, then to 90% B in 1 min, then hold at 90% for 2 min, then to 30% B in 1 min (15 ml/min flow rate). Mobile phase A was HPLC grade water, mobile phase B was HPLC grade MeOH. The column used for the chromatography is Discovery HS F5, 21.2 × 25 mm 5 μm (Supelco). |
| l-3 | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade ACN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization.)) |

TABLE 2

Chiral HPLC methods

| Method | Conditions |
|---|---|
| m | Isocratic 50% A for 25 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 gm particles). Detection methods were evaporative light scattering (ELSD) detection as well as optical rotation. |
| n | (preparative) 5-10% B in 1 min then 10-18% B in 62.5 min then step to 65% B for 5 min. Mobile phase B was an 80:20 mixture of HPLC grade isopropanol and HPLC grade ACN, mobile phase A was HPLC grade heptane with 0.1% formic acid added. The column used for the chromatography was a (R,R) Whelk-O 1 (Regis Technologies) 21 × 250 mm column (5 μm particles). |
| o | (analytical) 25% B co-solvent for 6 min (4 mL/min flow rate, 100 bar, 40° C.). Solvent A was SFC grade $CO_2$. Co-solvent B was an 80:20 mixture of HPLC grade isopropanol and HPLC grade ACN with 0.1% formic acid added. The column used for the chromatography was a (R,R) Whelk-O 1 (Regis Technologies) 4.6 × 100 mm column (3 μm particles). |
| p | (preparative) 5% B in 0.3 min, then 5-8% B in 0.3 min, then 8-11% B in 27.5 min then hold at 11% B for 5 min. Mobile phase A was heptane with 0.2% formic acid modifier, mobile phase B was (80:20 (1:1methanol:ethanol):methylene chloride). The column used for the chromatography was a Daicel IE column (20 × 250 mm). A second purification (preparative) was necessary for complete separation and used 8-12% B in 1 min, then 1-18% B in 24 min, then 18-20% B in 7 min then hold at 20% B for 1 min, then step to 50% B for 5 min. Mobile phase A was heptane with 0.2% formic acid modifier, mobile phase B was (80:20 isopropanol:methylene chloride). The column used for the chromatography was a Daicel IE column (20 × 250 mm). |

PREPARATIONS AND EXAMPLES

The general synthetic methods used in each preparation follow and include an illustration of a compound that was synthesized. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 9.0.7, CambridgeSoft® Chemistry E-Notebook 9.0.127, or AutoNom 2000. Compounds designated as salts (e.g. hydrochloride, acetate) may contain more than one molar equivalent of the salt. Compounds of the invention where the absolute stereochemistry has been determined by the use of a commercially available enantiomerically pure starting material or a stereochemically defined intermediate, or by X-ray diffraction are denoted by an asterisk after the example number.

Preparation #1. methyl 2,4-dichloro-3-(1-hydroxyprop-2-yn-1-yl)benzoate

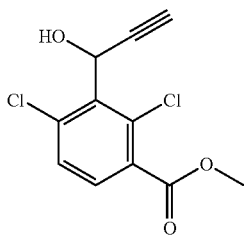 [SMILES: C#CC(O)c1c(Cl)ccc(C(=O)OC)c1Cl]

Step A: methyl 2,4-dichloro-3-methylbenzoate

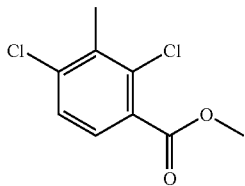

To a solution of 2,4-dichloro-3-methylbenzoic acid (250 g, 1219 mmol) in MeOH (1.5 L) was added sulfuric acid (78 mL, 1463 mmol) and the reaction was stirred under reflux for 20 hours. The reaction mixture was concentrated under vacuum. The crude product was dissolved in dichloromethane. The organic layer was washed with water, then with a $NaHCO_3$ saturated aqueous solution and brine, dried over magnesium sulfate and concentrated under vacuum to give methyl 2,4-dichloro-3-methylbenzoate (196 g, 73.4%) as a colorless oil that precipitates slowly. LC/MS (Method h) $R_t$=2.78 min.; MS m/z: 217 [M−H]$^-$. $^1$H NMR (DMSO-$d_6$, 300 MHz): δ 7.61 (d, J=8.4 Hz, 1H), 7.55 (d, J=8.4 Hz, 1H), 3.87 (s, 3H), 2.37 (s, 3H).

Step B: methyl 3-(bromomethyl)-2,4-dichlorobenzoate

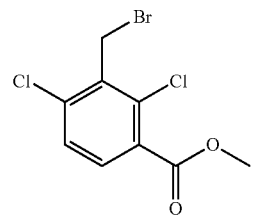

To a solution of methyl 2,4-dichloro-3-methylbenzoate (19.6 g, 89 mmol) in ACN (100 mL) was added N-bromosuccinimide (20.70 g, 116 mmol) and 2,2'-azobis(2-methylpropionitrile) (0.735 g, 4.47 mmol) by small fractions at room temperature. The reaction mixture was stirred under reflux 18 hours then concentrated under vacuum. The crude product was diluted with EtOAc and the solid was filtered off and washed with EtOAc. The organic layer was washed successively with a $NaHCO_3$ saturated aqueous solution, 10% $Na_2S_2O_3$ aqueous solution, dried over magnesium sulfate, filtered and evaporated to give methyl 3-(bromomethyl)-2,4-dichlorobenzoate (24.9 g, 93% yield) as a broken white solid. No LC/MS $^1$H NMR (DMSO-$d_6$, 300 MHz): δ 7.78 (d, J=9 Hz, 1H), 7.67 (d, J=9 Hz, 1H), 4.84 (s, 2H), 3.88 (s, 3H).

Step C: methyl 2,4-dichloro-3-formylbenzoate

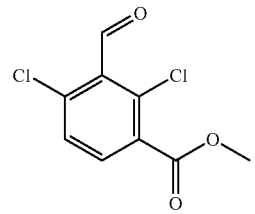

To a solution of methyl 3-(bromomethyl)-2,4-dichlorobenzoate (51.6 g, 173 mmol) in ACN (400 mL) was added 4-methylmorpholine N-oxide (81 g, 693 mmol) in solution in water (160 mL). The reaction mixture was stirred at reflux for 1.5 hours, cooled to room temperature and diluted with water until precipitation of the expected compound. The solid was filtered off, washed with water and dried under vacuum to give methyl 2,4-dichloro-3-formylbenzoate (25.48 g, 63.1%) as a white solid.

LC/MS (Method h) $R_t$=2.21 min.; no ionization $^1$H NMR (DMSO-$d_6$, 300 MHz): δ 10.33 (s, 1H), 7.95 (d, J=8.4 Hz, 1H), 7.72 (d, J=8.4 Hz, 1H), 3.89 (s, 3H).

Step D: methyl 2,4-dichloro-3-(1-hydroxyprop-2-yn-1-yl)benzoate

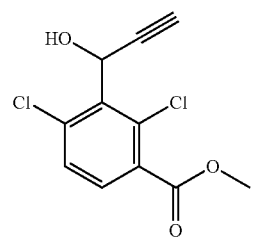 [SMILES: C#CC(O)c1c(Cl)ccc(C(=O)OC)c1Cl]

To a suspension of methyl 2,4-dichloro-3-formylbenzoate (19.36 g, 83 mmol) in THF (80 mL) was added dropwise ethynylmagnesium bromide (0.5M in THF, 199 mL, 100 mmol) and the reaction mixture was stirred at room temperature for 1 hour. It was then diluted with a 1N HCl solution and extracted EtOAc. The organic layer was dried over magnesium sulfate, filtered and concentrated under vacuum. The residue was purified by column chromatography on silica gel (eluting with 0-30% EtOAc in cyclohexane) to give methyl 2,4-dichloro-3-(1-hydroxyprop-2-yn-1-yl)benzoate (19.6 g, 91%) as a white solid. LC/MS (Method h) $R_f$=1.95 min.; MS m/z: 259 [M+H]$^+$. $^1$H NMR (DMSO-d$_6$, 300 MHz): δ 7.67 (d, J=9 Hz, 1H), 7.59 (d, J=9 Hz, 1H), 6.29 (s, 1H), 6.15 (d, J=2.48 Hz, 1H), 3.87 (s, 3H), 3.51 (d, J=2.48 Hz, 1H).

Preparation #2.
2-(2,6-dichloro-3-(methoxycarbonyl)phenyl)acetic acid

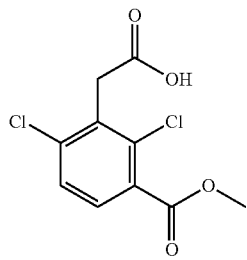 [SMILES: COC(=O)c1ccc(Cl)c(CC(=O)O)c1Cl]

Step A: methyl 2,4-dichloro-3-(cyanomethyl)benzoate

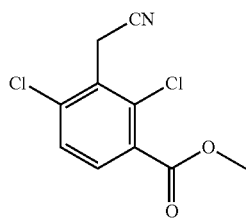

To a heated solution (40° C.) of KCN (8.52 g, 131 mmol) in DMSO (150 mL) was added dropwise a solution of methyl 3-(bromomethyl)-2,4-dichlorobenzoate (Preparation #1, Step B) (30 g, 101 mmol) in DMSO (90 mL). The reaction mixture was stirred at 40° C. for 2 h30. It was then cooled to room temperature and a NaHCO$_3$ saturated aqueous solution was added. The product was extracted with EtOAc. Organic layer was dried over magnesium sulfate, filtered and concentrated under vacuum. The residue was purified by column chromatography on silica gel (eluting with 5-50% EtOAc in cyclohexane) to give methyl 2,4-dichloro-3-(cyanomethyl)benzoate (19.1 g, 78%) as a white solid.

LC/MS (Method h) $R_f$=2.19 min.; MS m/z: 242 [M−H]$^-$. $^1$H NMR (DMSO-d$_6$, 300 MHz): δ 7.83 (d, J=9 Hz, 1H), 7.72 (d, J=9 Hz, 1H), 4.26 (s, 2H), 3.89 (s, 3H).

Step B: methyl 2,4-dichloro-3-(2-oxoethyl)benzoate

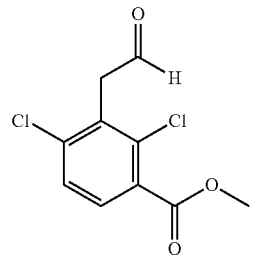

To a solution of methyl 2,4-dichloro-3-(cyanomethyl)benzoate (11 g, 45.1 mmol) in a mixture of pyridine (171 mL), acetic acid (85 mL) and water (85 mL), was added sodium hypophosphite (31.7 g, 361 mmol). The reaction mixture was stirred 15 min at room temperature. Activated Raney nickel (13.13 mL, 77 mmol) was added and the reaction mixture was stirred at 80° C. for 1.5 hours. The reaction mixture was filtered, washed with EtOAc and water. The layers were separated and the organic layer was washed with a 1M HCl solution, then dried over magnesium sulfate, filtered and concentrated under vacuum. The residue was purified by column chromatography on silica gel (eluting with 10-25% EtOAc in cyclohexane) to give methyl 2,4-dichloro-3-(2-oxoethyl)benzoate (10.24 g, 65.3% yield). LC/MS (Method h) $R_f$=2.19 min, 1.59 min (hydrate); MS m/z: 323 [M−H]$^-$+CH$_3$COOH $^1$H NMR (DMSO-d$_6$, 300 MHz): δ 9.76 (s, 1H), 7.72 (d, J=9 Hz, 1H), 7.64 (d, J=9 Hz, 1H), 4.27 (s, 2H), 3.87 (s, 3H).

Step C:
2-(2,6-dichloro-3-(methoxycarbonyl)phenyl)acetic acid

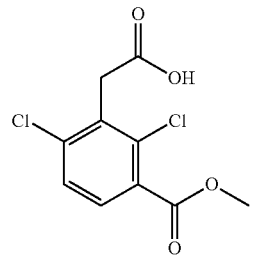 [SMILES: COC(=O)c1ccc(Cl)c(CC(=O)O)c1Cl]

To a solution of methyl 2,4-dichloro-3-(2-oxoethyl)benzoate (3 g, 12.14 mmol) in THF (50 mL) and water (50.0 mL) were added successively 2-methyl-2-butene (60.7 mL, 121 mmol), sodium chlorite (8.79 g, 97 mmol) and sodium phosphate, monobasic, monohydrate (15.08 g, 109 mmol). The mixture was stirred at room temperature for 1.5 hours then diluted with dichloromethane and a NaHCO3 saturated aqueous solution. The layers were separated and the aqueous layer was re-acidified by 1N HCl solution and extracted with dichloromethane. The organic layer was dried over magnesium sulfate and concentrated under reduced pressure. The residue was triturated in pentane to give 2-(2,6-dichloro-3-(methoxycarbonyl)phenyl)acetic acid (3 g, 94%). LC/MS (Method h) $R_f$=1.91 min.; MS m/z: 263 [M+H]$^+$ $^1$H NMR (DMSO-d$_6$, 300 MHz): δ 12.78 (broad, 1H), 7.70 (d, J=9 Hz, 1H), 7.62 (d, J=9 Hz, 1H), 3.97 (s, 2H), 3.87 (s, 3H).

Preparation #3. (2,4-dichloro-3-(1-hydroxyprop-2-yn-1-yl)phenyl)(morpholino)methanone

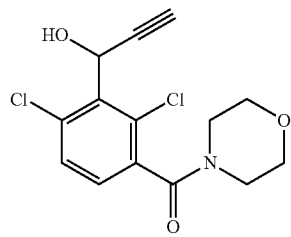 [SMILES: C#CC(O)c1c(Cl)ccc(C(=O)N2CCOCC2)c1Cl]

Step A: 2,4-dichloro-3-formylbenzoic acid

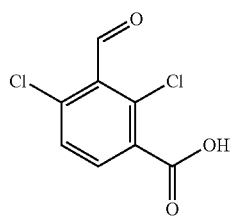 [SMILES: O=Cc1c(Cl)ccc(C(=O)O)c1Cl]

To a solution of methyl 2,4-dichloro-3-formylbenzoate (Preparation #1, Step C) (20 g, 86 mmol) in THF (240 mL) and water (120 mL) was added lithium hydroxide (3083 mg, 129 mmol) and the reaction mixture was stirred at room temperature overnight. The reaction mixture was partially evaporated. The resulting aqueous layer was washed with dichloromethane then acidified with a 1M HCl solution to (pH=2-3) and the compound was extracted successively with dichloromethane and EtOAc. The organic layers were dried over magnesium sulfate and concentrated under reduced pressure to give 2,4-dichloro-3-formylbenzoic acid (17.6 g, 94%). LC/MS (Method h) $R_t$=1.02 min.;

MS m/z: 217 [M−H]$^-$ $^1$H NMR (DMSO-d$_6$, 300 MHz): δ 13.88 (broad, 1H), 10.36 (s, 1H), 7.92 (d, J=9 Hz, 1H), 7.67 (d, J=9 Hz, 1H).

Step B: 2,6-dichloro-3-(morpholine-4-carbonyl)benzaldehyde

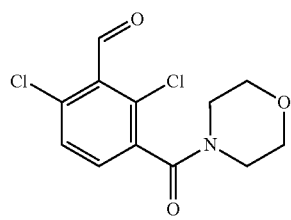 [SMILES: O=Cc1c(Cl)ccc(C(=O)N2CCOCC2)c1Cl]

To a suspension of 2,4-dichloro-3-formylbenzoic acid (17.2 g, 79 mmol) in dichloromethane (340 mL) was added HATU (32.8 g, 86 mmol) and 4-methylmorpholine (9.51 mL, 86 mmol) The reaction mixture was stirred at room temperature during 20 minutes, then morpholine (10.19 mL, 118 mmol) was added. The reaction mixture was stirred at room temperature during one night. The reaction mixture was diluted with dichloromethane and washed with a NaHCO$_3$ saturated aqueous solution. The obtained organic layer was dried over magnesium sulfate, filtered and concentrated under reduced pressure. The residue was purified by column chromatography on silica gel (eluting with 5-40% EtOAc in cyclohexane) to give 2,6-dichloro-3-(morpholine-4-carbonyl)benzaldehyde (23.8 g, 100%) as a white solid.

LC/MS (Method h) $R_t$=1.58 min.; MS m/z: 288 [M+H]$^+$ $^1$H NMR (DMSO-d$_6$, 300 MHz): δ 10.36 (s, 1H), 7.69 (d, J=9 Hz, 1H), 7.64 (d, J=9 Hz, 1H), 3.66 (m, 4H), 3.54 (m, 2H), 3.16 (m, 2H).

Step C: (2,4-dichloro-3-(1-hydroxyprop-2-yn-1-yl)phenyl)(morpholino)methanone

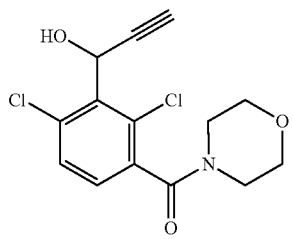

Using a procedure similar to Preparation #1, (2,4-dichloro-3-(1-hydroxyprop-2-yn-1-yl)phenyl)(morpholino)methanone (14.1 g, 99%) was prepared from 2,6-dichloro-3-(morpholine-4-carbonyl)benzaldehyde (13 g, 45.1 mmol). LC/MS (Method h) $R_t$=1.43 min.; MS m/z: 314 [M+H]$^+$.

$^1$H NMR (DMSO-d$_6$, 300 MHz): δ 7.55 (d, J=9 Hz, 1H), 7.38 (d, J=9 Hz, 1H), 6.26 (s, 1H), 6.09 (d d, J=3 Hz, 1H), 3.65 (m, 4H), 3.54 (m, 2H), 3.51 (d, J=3 Hz, 1H), 3.12 (m, 2H).

Preparation #4. (3-(1-hydroxyprop-2-yn-1-yl)-2,4-dimethylphenyl)(morpholino)methanone

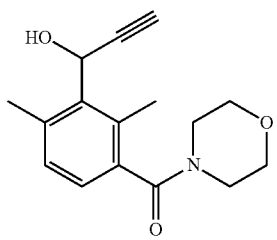 [SMILES: C#CC(O)c1c(C)ccc(C(=O)N2CCOCC2)c1C]

Step A: 3-bromo-2,6-dimethylbenzaldehyde

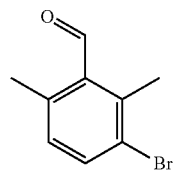

To a suspension of aluminum trichloride (14.91 g, 112 mmol) in dichloromethane (80 mL) were added dropwise at 0° C. 2,6-dimethylbenzaldehyde (10 g, 74.5 mmol) in solution in dichloromethane (80 mL) and dibromine (3.72 mL, 72.3 mmol) The mixture was stirred 4 hours at 0° C. The reaction mixture was poured onto ice and extracted twice with dichloromethane. The organic layers were washed with a 1N HCl solution, a NaHCO$_3$ saturated aqueous solution, dried over magnesium sulfate and concentrated under reduced pressure to give 3-bromo-2,6-dimethylbenzaldehyde (14.4 g, 91% yield) of as a yellow oil.

LC/MS (Method h) R$_t$=2.62 min.; no ionization. $^1$H NMR (DMSO-d$_6$, 300 MHz): δ 10.47 (s, 1H), 7.72 (d, J=9 Hz, 1H), 7.12 (d, J=9 Hz, 1H), 2.57 (s, 3H), 2.47 (s, 3H).

Step B: 3-formyl-2,4-dimethylbenzoic acid

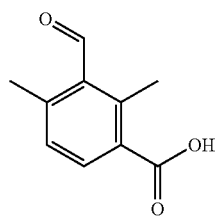

In a microwave reactor were added palladium(II) acetate (13.70 mg, 0.061 mmol), tri-tert-butylphosphonium tetrafluoroborate (17.70 mg, 0.061 mmol) and molybdenum hexacarbonyl (354 mg, 1.342 mmol), 3-bromo-2,6-dimethylbenzaldehyde (260 mg, 1.220 mmol) in solution in dimethoxyethane (2 mL) and sodium carbonate (194 mg, 1.830 mmol) in solution in water (0.5 mL). The reaction mixture was stirred one hour at 120° C. under microwave irradiation. Dimethoxyethane was evaporated and the residue was diluted with water and washed with EtOAc. The aqueous layer was acidified by 1N HCl solution (pH 1) and extracted with dichloromethane, dried over magnesium sulfate and concentrated under reduced pressure to give 3-formyl-2,4-dimethylbenzoic acid (150 mg, 69%) as a white powder. LC/MS (Method h) R$_t$=1.50 min.; MS m/z: 177 [M−H]$^−$. $^1$H NMR (DMSO-d$_6$, 300 MHz): δ 13.06 (broad, 1H), 10.56 (s, 1H), 7.78 (d, J=9 Hz, 1H), 7.24 (d, J=9 Hz, 1H), 2.65 (s, 3H), 2.52 (s, 3H).

Step C:
2,6-dimethyl-3-(morpholine-4-carbonyl)benzaldehyde

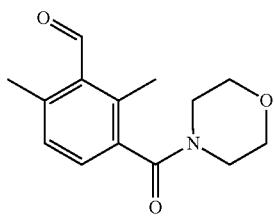 [SMILES: Cc1ccc(C(=O)N2CCOCC2)c(C)c1C=O]

To a solution of 3-formyl-2,4-dimethylbenzoic acid (1 g, 5.61 mmol) in DMF (5 mL) was added 1,1'-carbonyldiimidazole (1.183 g, 7.30 mmol) and the reaction mixture was stirred at room temperature for 4 hours. Morpholine (0.971 mL, 11.22 mmol) and triethylamine (1.564 mL, 11.22 mmol) were added and the reaction mixture was stirred at room temperature for one night. The reaction mixture was diluted with water and EtOAc. The layers were separated and the obtained aqueous layer was extracted with EtOAc. The obtained organic layer was dried over magnesium sulfate, filtered and concentrated under reduced pressure. The residue was purified by column chromatography on silica gel (eluting with 0.1-5% MeOH in dichloromethane) to give 2,6-dimethyl-3-(morpholine-4-carbonyl)benzaldehyde (780 mg, 56%).

LC/MS (Method h) R$_t$=1.46 min.; MS m/z: 248 [M+H]$^+$. $^1$H NMR (DMSO-d$_6$, 300 MHz): δ 10.53 (s, 1H), 7.32 (d, J=9 Hz, 1H), 7.24 (d, J=9 Hz, 1H), 3.65 (m, 4H), 3.48 (m, 2H), 3.11 (m, 2H), 2.54 (s, 3H), 2.42 (s, 3H).

Step D: (3-(1-hydroxyprop-2-yn-1-yl)-2,4-dimethylphenyl)(morpholino)methanone

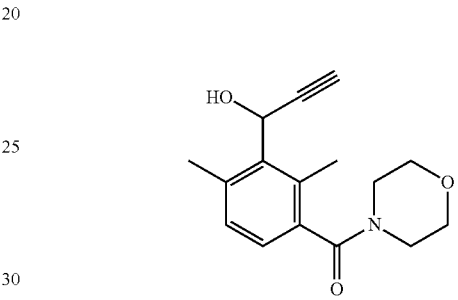

Using a procedure similar to Preparation #1, (3-(1-hydroxyprop-2-yn-1-yl)-2,4-dimethylphenyl)(morpholino)methanone (680 mg, 64%) was prepared from 2,6-dimethyl-3-(morpholine-4-carbonyl)benzaldehyde (953 mg, 3.85 mmol). LC/MS (Method h) R$_t$=1.39 min.; MS m/z: 274 [M+H]$^+$. $^1$H NMR (DMSO-d$_6$, 300 MHz): δ 7.06 (d, J=7.6 Hz, 1H), 6.98 (d, J=7.6 Hz, 1H), 5.83 (m, 1H), 5.76 (m, 1H), 3.64 (m, 4H), 3.47 (m, 2H), 3.41 (d, J=2.3 Hz, 1H), 3.10 (m, 2H), 2.44 (s, 3H), 2.34 (s, 3H).

Preparation #5. (3-(1-hydroxyprop-2-yn-1-yl)phenyl)(morpholino)methanone

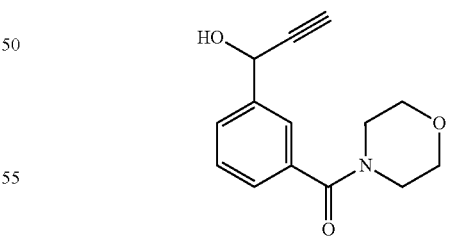

Using a procedure similar to Preparation #1, (3-(1-hydroxyprop-2-yn-1-yl)phenyl)(morpholino)methanone (2 g, 73%) was prepared from 3-(morpholine-4-carbonyl)benzaldehyde (described in WO2004/058762) (2.54 g, 11.59 mmol). LC/MS (Method h) R$_t$=1.09 min.; MS m/z: 246 [M+H]$^+$. $^1$H NMR (DMSO d-, 300 MHz): δ 7.62 (m, 2H), 7.47-7.34 (m, 2H), 5.47 (d, J=2 Hz, 1H), 3.90-3.30 (m broad, 9H), 2.67 (d, J=2 Hz, 1H).

Preparation #6: methyl 3,5-dichloro-4-(1-hydroxyprop-2-yn-1-yl)benzoate

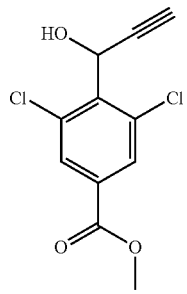 [SMILES: C#CC(O)c1c(Cl)cc(C(=O)OC)cc1Cl]

Using a procedure similar to Preparation #1, methyl 3,5-dichloro-4-(1-hydroxyprop-2-yn-1-yl)benzoate (1 g, 60%) was prepared from methyl 3,5-dichloro-4-formylbenzoate (described in WO2013/149997) (1.5 g, 6.44 mmol). LC/MS (Method h) $R_t$=2.14 min.; no ionization $^1$H NMR (DMSO-$d_6$, 300 MHz): δ 7.91 (s, 2H), 6.37 (s, 1H), 6.09 (d, J=2 Hz, 1H), 3.88 (s, 3H), 3.54 (d, J=2 Hz, 1H).

Preparation #7. 1-(2,6-dichloro-3-methoxyphenyl)prop-2-yn-1-ol

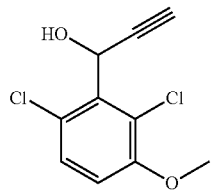

Using a procedure similar to Preparation #1, 1-(2,6-dichloro-3-methoxyphenyl)prop-2-yn-1-ol (1.68 g, 93%) was prepared from 2,6-dichloro-3-methoxybenzaldehyde (described in WO2006/049952) (1.6 g, 7.80 mmol). LC/MS (Method h) $R_t$=1.95 min.; no ionization $^1$H NMR (DMSO-$d_6$, 300 MHz): δ 7.42 (d, J=9 Hz, 1H), 7.14 (d, J=9 Hz, 1H), 6.12 (s, 1H), 6.05 (d, J=2.4 Hz, 1H), 3.86 (s, 3H), 3.41 (d, J=2.4 Hz, 1H).

Preparation #8. 2-(2,6-dichloro-3-(morpholine-4-carbonyl)phenyl)acetic acid

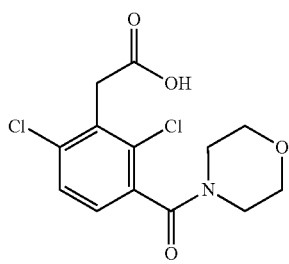 [SMILES: O=C(O)Cc1c(Cl)ccc(C(=O)N2CCOCC2)c1Cl]

Step A: methyl 2,4-dichloro-3-(2-hydroxyethyl)benzoate

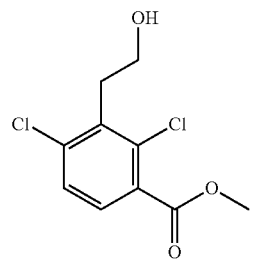

To a solution of methyl 2,4-dichloro-3-(2-oxoethyl)benzoate (Preparation #2, Step B) (1.88 g, 7.61 mmol) in MeOH (28 mL) and cooled to 0° C. was added sodium borohydride (0.288 g, 7.61 mmol) and reaction mixture was stirred at 0° C. for 30 minutes. Water was added and the MeOH was evaporated. The resulting aqueous layer was extracted with dichloromethane. The organic layer was dried over magnesium sulfate, filtered and concentrated under reduced pressure to give methyl 2,4-dichloro-3-(2-hydroxyethyl)benzoate (1.6 g, 84%). LC/MS (Method h) $R_t$=1.93 min.; MS m/z: 249 [M+H]$^+$. $^1$H NMR (DMSO-$d_6$, 300 MHz): δ 7.61 (d, J=8.4 Hz, 1H), 7.56 (d, J=8.4 Hz, 1H), 4.92 (broad, 1H), 3.85 (s, 3H), 3.56 (m, 2H), 3.13 (t, J=7.8 Hz, 2H)

Step B: 2,4-dichloro-3-(2-hydroxyethyl)benzoic acid

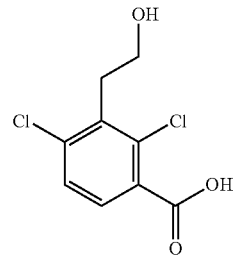 [SMILES: O=C(O)c1ccc(Cl)c(CCO)c1Cl]

Using a procedure similar to Preparation #3, Step A, 2,4-dichloro-3-(2-hydroxyethyl)benzoic acid (1.41 g, 93%) was prepared from methyl 2,4-dichloro-3-(2-hydroxyethyl)benzoate (1.60 g, 6.42 mmol). LC/MS (Method h) $R_t$=1.20 min.; MS m/z: 233 [M−H]$^−$. $^1$H NMR (DMSO-$d_6$, 300 MHz): δ 13.56 (broad, 1H), 7.56 (d, J=8.4 Hz, 1H), 7.51 (d, J=8.4 Hz, 1H), 4.92 (broad, 1H), 3.55 (t, J=2.7 Hz, 2H), 3.12 (t, J=7.8 Hz, 2H)

Step C: (2,4-dichloro-3-(2-hydroxyethyl)phenyl)(morpholino)methanone

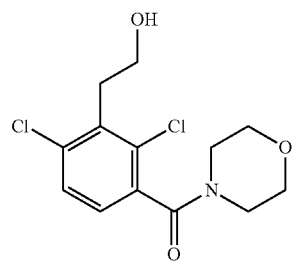 [SMILES: O=C(c1ccc(Cl)c(CCO)c1Cl)N1CCOCC1]

To a suspension of 2,4-dichloro-3-(2-hydroxyethyl)benzoic acid (1.4 g, 5.96 mmol) in dichloromethane (75 mL) was added 1-(3-dimethylaminopropyl)-3-ethylcarbodiimide hydrochloride (1.484 g, 7.74 mmol) and 1-hydroxybenzotriazole (1.046 g, 7.74 mmol) morpholine (1.031 mL, 11.91 mmol) and triethylamine (1.660 mL, 11.91 mmol) The reaction mixture was stirred at room temperature for one night. It was then diluted with dichloromethane. The layers were separated and the obtained organic layer was washed with water, dried over magnesium sulfate, filtered and concentrated under reduced pressure. The residue was purified by column chromatography on silica gel (eluting with 5-40% EtOAc in cyclohexane) to give (2,4-dichloro-3-(2-hydroxyethyl)phenyl)(morpholino)methanone (1.2 g, 66%) as a white solid.

LC/MS (Method h) $R_t$=1.41 min.; MS m/z: 304 [M+H]$^+$. $^1$H NMR (DMSO-d$_6$, 300 MHz): δ 7.53 (d, J=9 Hz, 1H), 7.27 (d, J=9 Hz, 1H), 4.91 (t, J=6 Hz, 1H), 3.65-3.50 (m, 8H), 3.10 (m, 4H).

Step D: 2-(2,6-dichloro-3-(morpholine-4-carbonyl)phenyl)acetic acid

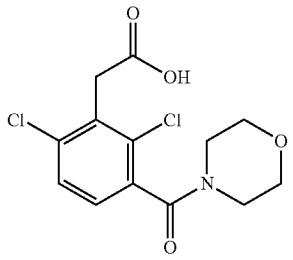 [SMILES: O=C(O)Cc1c(Cl)ccc(C(=O)N2CCOCC2)c1Cl]

To a solution of chromium(vi) oxide (182 mg, 1.816 mmol) in water (325 μl) and cooled at 0° C. was added sulfuric acid (162 μL, 3.05 mmol) and the reaction mixture was stirred at 0° C. for 10 min. This solution was added slowly to a solution of (2,4-dichloro-3-(2-hydroxyethyl)phenyl)(morpholino)methanone (325 mg, 1.068 mmol) in acetone (3898 μL) cooled to 0° C. The reaction mixture was stirred at 0° C. for 15 min, then at room temperature for 30 minutes. The reaction mixture was filtered and washed with acetone. The filtrate was concentrated. The residue was diluted in EtOAc and washed with a 1N HCl solution. The organic layer was dried over magnesium sulfate, filtered and concentrated to give 2-(2,6-dichloro-3-(morpholine-4-carbonyl)phenyl)acetic acid (283 mg, 83%). LC/MS (Method h) $R_t$=1.42 min.; MS m/z: 318 [M+H]$^+$. $^1$H NMR (DMSO-d$_6$, 300 MHz): δ 12.74 (broad, 1H), 7.59 (d, J=9 Hz, 1H), 7.36 (d, J=9 Hz, 1H), 3.93 (s, 2H), 3.66 (m, 4H), 3.52 (m, 2H), 3.11 (m, 2H).

Preparation #9.
2-(3-(methoxycarbonyl)-2,6-dimethylphenyl)acetic acid

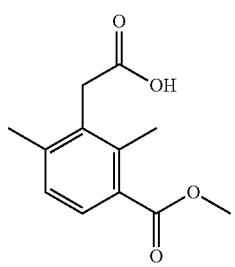

Step A: 2-(3-bromo-2,6-dimethylphenyl)acetic acid

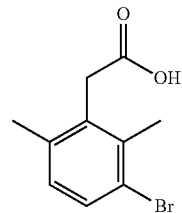

To a heated (40° C.) solution of 2-(2,6-dimethylphenyl)acetic acid (2 g, 12.18 mmol) in acetic acid (12 mL), was added dropwise over 1 hour a solution of dibromine (0.845 mL, 16.44 mmol) in acetic acid (5 mL). The reaction mixture was stirred at 45° C. for 18 hours then concentrated to dryness. The residue was triturated in cyclohexane and the solid was filtered and washed with cyclohexane to give 2-(3-bromo-2,6-dimethylphenyl)acetic acid (2.4 g, 71%) as a white solid. LC/MS (Method h) $R_t$=2.26 min.; MS m/z: 241 [M−H]$^−$. $^1$H NMR (DMSO-d$_6$, 300 MHz): δ 12.45 (broad, 1H), 7.38 (d, J=8.1 Hz, 1H), 6.97 (d, J=8.1 Hz, 1H), 3.69 (s, 2H), 2.33 (s, 3H), 2.24 (s, 3H)

Step B:
2-(3-(methoxycarbonyl)-2,6-dimethylphenyl)acetic acid

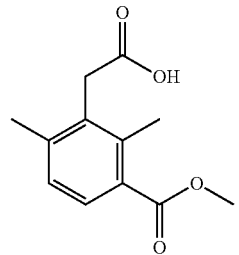

In a microwave vial was added 2-(3-bromo-2,6-dimethylphenyl)acetic acid (1.5 g, 6.17 mmol), trans-bis(acetato)bis[o-(di-o-tolylphosphino)benzyl]dipalladium(II) (0.289 g, 0.309 mmol), tri-tert-butylphosphonium tetrafluoroborate (0.358 g, 1.234 mmol) and molybdenum hexacarbonyl (1.629 g, 6.17 mmol) in MeOH (30 mL). 1,8-diazabicyclo[5.4.0]undec-7-ene (2.82 g, 18.51 mmol) was added dropwise and the mixture was stirred vigorously at room temperature for 5 minutes. Then the vial was heated under microwaves at 110° C. for 30 minutes and at 140° C. for 15 minutes. After being cooled to room temperature, the reaction mixture was filtered and the solvent was removed under reduced pressure. The residue was diluted with water and EtOAc. The phases were separated and the aqueous one was extracted with EtOAc. The organic layers were combined and discarded. The basic water layer was acidified to pH 2-3 with 1N HCl solution and thoroughly extracted with EtOAc. The organic phases were combined, washed with brine, dried over magnesium sulfate, filtered and concentrated under reduced pressure to give 2-(3-(methoxycarbonyl)-2,6-dimethylphenyl)acetic acid (1.17 g, 79%) as a green solid. LC/MS (Method h) $R_t$=1.86 min.; MS m/z: 223 [M+H]$^+$ $^1$H NMR (CDCl₃, 300 MHz): δ 7.66 (d, J=9 Hz, 1H), 7.11 (d, J=9 Hz, 1H), 3.89 (s, 3H), 3.81 (s, 2H), 2.54 (s, 3H), 2.39 (s, 3H).

Preparation #10.
2-(2,6-dichloro-4-nitrophenyl)acetic acid

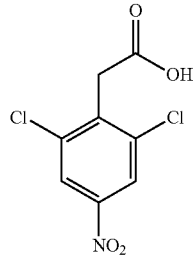 [SMILES: O=C(O)Cc1c(Cl)cc([N+](=O)[O-])cc1Cl]

To a suspension of diethyl malonate (1.006 mL, 6.62 mmol) and cesium carbonate (3.60 g, 11.04 mmol) in DMF (5 mL) heated at 70° C. was added 3,4,5-trichloronitrobenzene (1 g, 4.42 mmol) and the mixture was stirred at 70° C. for 3 hours. The mixture was cooled to room temperature. A 2M HCl solution was added and the reaction mixture was extracted with EtOAc. The combined organic layers were washed with brine, dried over magnesium sulfate and concentrated. The residue was suspended in hydrochloric acid (7.36 mL, 44.2 mmol) and stirred at 100° C. for 24 hours. The mixture was cooled to room temperature, pulled into cold water and the reaction mixture was extracted twice with EtOAc. The combined organic layers were washed with brine, dried over magnesium sulfate and concentrated. The residue was dissolved in dioxane (15 mL). Sodium hydroxide (11.99 mL, 11.99 mmol) was added and the mixture was stirred at room temperature for 48 hours. An excess of sodium hydroxide (11.99 mL, 11.99 mmol) was added and the stirring was continued for 24 hours. Another excess of sodium hydroxide (11.99 mL, 11.99 mmol) was added and the stirring was continued for 48 hours. The mixture was diluted with water and washed twice with EtOAc. The aqueous layers were acidified with 10M HCl solution (pH=2) and extracted with dichloromethane. The combined organic layers were washed with brine, dried over magnesium sulfate and concentrated to give 2-(2,6-dichloro-4-nitrophenyl)acetic acid (465 mg, 42%) as a white solid. LC/MS (Method h) $R_t$=1.98 min.; MS m/z: 497 [2M−H]⁻ ¹H NMR (DMSO-d₆, 300 MHz): δ 12.96 (broad, 1H), 8.32 (s, 2H), 4.03 (s, 2H)

Preparation #11. (2,4-dichloro-3-(chloromethyl)phenyl)(morpholino)methanone

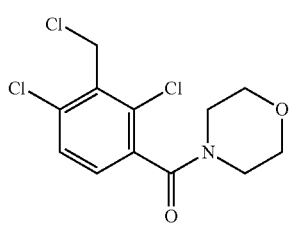 [SMILES: O=C(c1ccc(Cl)c(CCl)c1Cl)N1CCOCC1]

Step A: 2,4-dichloro-3-(hydroxymethyl)benzoic acid

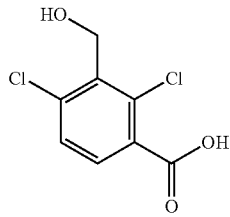 [SMILES: O=C(O)c1ccc(Cl)c(CO)c1Cl]

To a solution of methyl 3-(bromomethyl)-2,4-dichlorobenzoate (Preparation #1, Step B) (10 g, 33.6 mmol) in dioxane (100 mL) was added sodium hydroxide (84 mL, 84 mmol) and the reaction mixture was stirred under reflux for 5 hours The reaction mixture was concentrated to dryness. The residue was dissolved in water and acidified at pH1. The white solid was filtered, washed with water and dried under vacuum to give 2,4-dichloro-3-(hydroxymethyl)benzoic acid (5.9 g, 80%). LC/MS (Method h) $R_t$=0.70 min.; MS m/z: 219 [M−H]⁻ ¹H NMR (DMSO-d₆, 300 MHz): δ 13.58 (broad, 1H), 7.67 (d, J=9 Hz, 1H), 7.52 (d, J=9 Hz, 1H), 5.28 (m, 1H), 4.74 (s, 2H).

Step B: (2,4-dichloro-3-(hydroxymethyl)phenyl)(morpholino)methanone

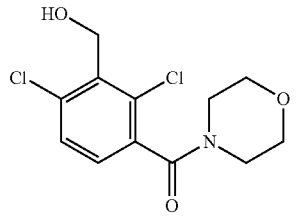 [SMILES: O=C(c1ccc(Cl)c(CO)c1Cl)N1CCOCC1]

Using a procedure similar to Preparation #8, (2,4-dichloro-3-(hydroxymethyl)phenyl)(morpholino)methanone (2.6 g, 41%) was prepared from 2,4-dichloro-3-(hydroxymethyl)benzoic acid (4.8 g, 21.72 mmol). LC/MS (Method h) $R_t$=1.19 min.; MS m/z: 290 [M+H]⁺. ¹H NMR (DMSO-d₆, 300 MHz): δ 7.53 (d, J=9 Hz, 1H), 7.34 (d, J=9 Hz, 1H), 5.28 (s, 1H), 4.70 (s, 2H), 3.64 (m, 4H), 3.52 (m, 2H), 3.12 (m, 2H).

Step C: (2,4-dichloro-3-(chloromethyl)phenyl)(morpholino)methanone

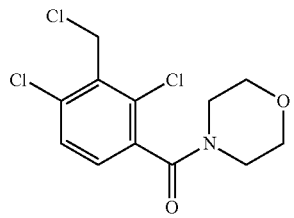 [SMILES: O=C(c1ccc(Cl)c(CCl)c1Cl)N1CCOCC1]

To a solution of (2,4-dichloro-3-(hydroxymethyl)phenyl)(morpholino)methanone (653 mg, 2.251 mmol) in DCM (18 mL) was added methanesulfonyl chloride (0.349 mL, 4.50 mmol) and triethylamine (0.627 mL, 4.50 mmol) and the reaction mixture was stirred at room temperature during 3 hours. The reaction mixture was diluted with DCM. The obtained organic layer was washed with water and brine. The obtained organic layer was dried over magnesium sulfate, filtered and concentrated under reduced pressure. The residue was purified by column chromatography on silica gel (eluting with 7-60% EtOAc in DCM) to give (2,4-dichloro-3-(chloromethyl)phenyl)(morpholino)methanone (548 mg, 79%). LC/MS (Method h) $R_t$=2.12 min.; MS m/z: 308 [M+H]$^+$. $^1$H NMR (DMSO-d$_6$, 300 MHz): δ 7.62 (d, J=9 Hz, 1H), 7.44 (d, J=9 Hz, 1H), 4.93 (s, 2H), 3.65 (m, 4H), 3.52 (m, 2H), 3.12 (m, 2H).

Preparation #12. ethyl 3-((methylsulfonyl)oxy)cyclopentanecarboxylate

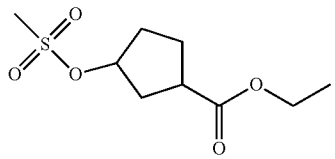

To a solution of ethyl 3-hydroxycyclopentanecarboxylate (0.8 g, 5.06 mmol) and triethylamine (1.762 mL, 12.64 mmol) in DCM (8 mL) and cooled at 0° C. was added a solution of methanesulfonyl chloride (0.588 mL, 7.59 mmol) in DCM (3 mL). The reaction was stirred at room temperature for 1 hour. Water was added, and the reaction mixture was extracted with DCM. The organic layer was washed with brine dried on MgSO$_4$, filtered and evaporated to give ethyl 3-((methylsulfonyl)oxy)cyclopentanecarboxylate (1.1 g, 92%) as a colorless liquid: No LC/MS. $^1$H NMR (DMSO-d$_6$, 300 MHz): δ 5.08 (m, 1H), 4.05 (m, 2H), 3.60 (m, 4H), 2.86 (m, 1H), 2.30 (m, 1H), 2.05 (m, 1H), 1.80 (m, 3H), 1.18 (m, 3H).

Preparation #13. methyl 2,4-dichloro-3-(3-chloro-2-oxobutyl)benzoate

A suspension of zinc (0.241 g, 3.69 mmol) in THF (1 mL) was heated to reflux and 1,2-dibromoethane (0.025 g, 0.134 mmol) and chlorotrimethylsilane (0.015 g, 0.134 mmol) were added. The reaction mixture was stirred 30 minutes. A solution of methyl 3-(bromomethyl)-2,4-dichlorobenzoate (1 g, 3.36 mmol) (Preparation #1, Step B) in THF (3 ml) was then added dropwise over 5 minutes and the mixture was stirred at reflux for 2 hours. This solution was added at room temperature to a mixture of copper(I) cyanide di(lithium chloride) complex (3.36 ml, 3.36 mmol) and N,N-dimethylformamide (246 mg, 3.36 mmol) and the solution was stirred 30 minutes at room temperature. Then, a solution of 2-chloropropionyl chloride (427 mg, 3.36 mmol) in toluene (4 mL) and tetrakis(triphenylphosphine)palladium(0) (116 mg, 0.101 mmol) were added. The reaction was stirred one hour at room temperature, diluted with 10 mL of hexane and 10 mL of EtOAc and solid silica gel was added. The mixture was stirred 5 minutes and the solid was filtered and washed with EtOAc. The organic layer was concentrated. The residue was purified by column chromatography on silica gel (eluting with 0-20% EtOAc in cyclohexane) to give methyl 2,4-dichloro-3-(3-chloro-2-oxobutyl)benzoate (560 mg, 54%) as a colorless oil. LC/MS (Method h) $R_t$=2.75 min.; MS m/z: 309 [M+H]$^+$. $^1$H NMR (DMSO-d$_6$, 300 MHz): δ 7.71 (d, J=9 Hz, 1H), 7.62 (d, J=9 Hz, 1H), 5.05 (q, J=7 Hz, 1H), 4.56 (d, J=15 Hz, 1H), 4.43 (d, J=15 Hz, 1H), 3.87 (s, 3H), 1.63 (d, J=7 Hz, 3H).

Preparation #14. methyl 3-(3-bromo-2-oxobutyl)-2,4-dichlorobenzoate

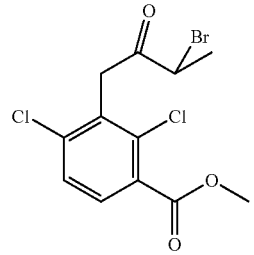 [SMILES: COC(=O)c1ccc(Cl)c(CC(=O)C(C)Br)c1Cl]

Step A: methyl 2,4-dichloro-3-(2-hydroxybutyl)benzoate

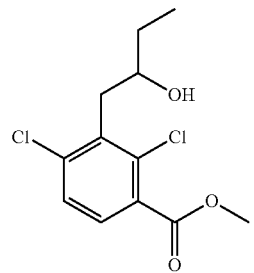 [SMILES: CCC(O)Cc1c(Cl)ccc(C(=O)OC)c1Cl]

To a solution of methyl 2,4-dichloro-3-(2-oxoethyl)benzoate (Preparation #2, Step B) (100 mg, 0.405 mmol) in THF (1 mL) was added ethylmagnesium bromide (1 M in THF, 0.486 mL, 0.486 mmol) and the reaction mixture was stirred at room temperature during 18 hours. The reaction mixture was diluted with a solution of 1N HCl aqueous solution and the obtained aqueous layer was extracted with EtOAc. The organic layer was dried over MgSO$_4$, filtered and concentrated under reduced pressure. The residue was purified by column chromatography on silica gel (eluting with 5-20% EtOAc in cyclohexane) to give methyl 2,4-dichloro-3-(2-hydroxybutyl)benzoate (100 mg, 89%) as a colorless oil. LC/MS (Method h) $R_t$=2.39 min.; MS m/z: 277 [M+H]$^+$. $^1$H NMR (DMSO-d$_6$, 300 MHz): δ 7.58 (m, 2H), 4.65 (d, J=6 Hz, 1H), 3.85 (s, 3H), 3.72 (m, 1H), 3.05 (m, 2H), 1.42 (m, 2H), 0.89 (t, J=6 Hz, 3H).

Step B: methyl 2,4-dichloro-3-(2-oxobutyl)benzoate

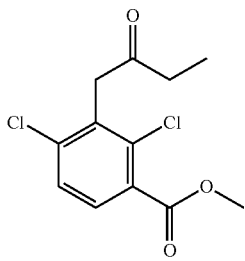 [SMILES: CCC(=O)Cc1c(Cl)ccc(C(=O)OC)c1Cl]

To a solution of methyl 2,4-dichloro-3-(2-hydroxybutyl)benzoate (100 mg, 0.361 mmol) in DCM (1.5 ml) was added Dess-Martin periodinane (0.750 ml, 0.361 mmol) The reaction mixture was stirred at room temperature for 18 hours. The reaction mixture was diluted with DCM. The organic layer was washed with a saturated Na$_2$S$_2$O$_3$ aqueous solution, then dried over MgSO$_4$, filtered and concentrated under reduced pressure. The residue was purified by column chromatography on silica gel (eluting with 5-20% EtOAc in cyclohexane) to give methyl 2,4-dichloro-3-(2-oxobutyl)benzoate (63 mg, 63%) as a colorless oil. LC/MS (Method h) R$_t$=2.53 min.; MS m/z: 275 [M+H]$^+$. $^1$H NMR (DMSO-d$_6$, 300 MHz): δ 7.69 (d, J=9 Hz, 1H), 7.60 (d, J=9 Hz, 1H), 4.21 (s, 2H), 3.86 (s, 3H), 2.64 (q, J=7.2 Hz, 2H), 0.99 (t, J=7.2, 3H).

Step C: methyl 3-(3-bromo-2-oxobutyl)-2,4-dichlorobenzoate

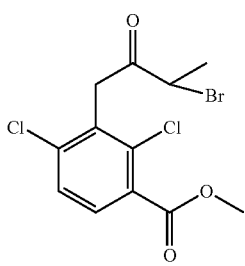 [SMILES: COC(=O)c1ccc(Cl)c(CC(=O)C(C)Br)c1Cl]

A suspension of cupric bromide (81 mg, 0.363 mmol) in chloroform (300 μL) and EtOAc (300 μL) was heated to reflux. Methyl 2,4-dichloro-3-(2-oxobutyl)benzoate (100 mg, 0.363 mmol) in solution in chloroform (80 μL) and EtOAc (80 μL) was added and the reaction mixture was stirred at reflux for 72 hours. The reaction mixture was concentrated under reduced pressure. The residue was purified by column chromatography on silica gel (eluting with 5-20% EtOAc in cyclohexane) to give methyl 3-(3-bromo-2-oxobutyl)-2,4-dichlorobenzoate (105 mg, 47%) as a colorless oil. LC/MS (Method h) R$_t$=2.82 min.; MS m/z: 353 [M+H]$^+$. $^1$H NMR (DMSO-d$_6$, 300 MHz): δ 7.70 (d, J=9 Hz, 1H), 7.63 (d, J=9 Hz, 1H), 5.10 (q, J=6.6 Hz, 1H), 4.63 (d, J=18 Hz, 1H), 4.46 (d, J=18 Hz, 1H), 3.86 (s, 3H), 1.72 (d, J=6.65 Hz, 3H).

Preparation #15. 1-(3,5-dichloro-2-methoxypyridin-4-yl)prop-2-yn-1-ol

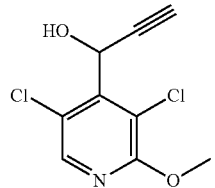

Step A: 3,5-dichloro-2-methoxyisonicotinaldehyde

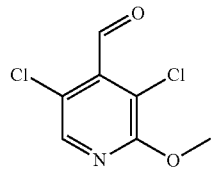

A solution of 3,5-dichloro-2-methoxypyridine (16 g, 90 mmol) in THF (100 mL) was slowly added to a solution of LDA (53.9 mL, 108 mmol) (2M in THF) at −78° C. DMF (14 mL, 180 mmol) was added to the reaction mixture and the resulting solution stirred at −78° C. for about 1 h. The reaction mixture was then poured into a NH$_4$Cl saturated aqueous solution. The aqueous layer was extracted with EtOAc (3×20 mL). The combined organic portion was dried over anhydrous Na$_2$SO$_4$, filtered, and concentrated under reduced pressure to give 3,5-dichloro-2-methoxyisonicotinaldehyde (17.54 g, 90%). LC/MS (Table 1, Method d) R$_t$=1.86 min.; MS m/z: 205, 207 [M+H]$^+$.

Step B: 1-(3,5-dichloro-2-methoxypyridin-4-yl)prop-2-yn-1-ol

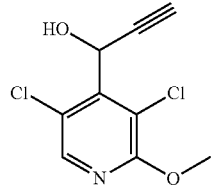

Using a procedure similar to Preparation #1, 1-(3,5-dichloro-2-methoxypyridin-4-yl)prop-2-yn-1-ol (8.74 g, 76%) was prepared from 3,5-dichloro-2-methoxyisonicotinaldehyde (10 g, 48.5 mmol).

LC/MS (Table 1, Method b) R$_t$=1.90 min.; MS(M+1)=231, 233

$^1$H NMR (DMSO-d$_6$, 400 MHz): δ 8.24 (s, 1H), 6.42 (s, 1H), 6.00 (s, 1H), 3.95 (s, 3H), 3.56 (s, 1H).

Preparation #16. N-(2-iodo-3-methyl-5-(trifluoromethyl)phenyl)benzenesulfonamide

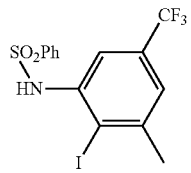

Step A: 2-iodo-3-methyl-5-(trifluoromethyl)aniline

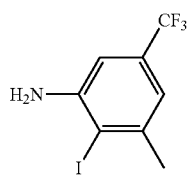

To a solution of 3-amino-5-methylbenzotrifluoride (10 g, 57.1 mmol) in DCM (200 mL) and MeOH (50 mL) was added benzyltrimethylammonium dichloroiodate (39.7 g, 114 mmol) and calcium carbonate (14.29 g, 143 mmol). The reaction mixture was stirred at room temperature overnight, filtered, and the solid was washed with DCM. The filtrate was washed with a saturated $Na_2S_2O_3$ aqueous solution, and the obtained organic layer was washed with water then dried over magnesium sulfate, filtered and concentrated under reduced pressure. The residue was purified by column chromatography on silica gel (eluting with 5-100% EtOAc in cyclohexane) to give 2-iodo-3-methyl-5-(trifluoromethyl) aniline (9.1 g, 53%) as an orange liquid. LC/MS (Method h) $R_t$=2.83 min.; MS m/z: 302 [M+H]$^+$. $^1$H NMR (DMSO-d$_6$, 300 MHz): δ 6.87 (d, J=1.8 Hz, 1H), 6.81 (d, J=1.8 Hz, 1H), 5.68 (s, 2H), 2.38 (s, 3H).

Step B: N-(2-iodo-3-methyl-5-(trifluoromethyl)phenyl)benzenesulfonamide

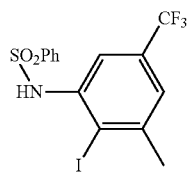

To a solution of 2-iodo-3-methyl-5-(trifluoromethyl)aniline (9.1 g, 30.2 mmol) in pyridine (50 mL) was added benzenesulfonyl chloride (7.75 mL, 60.5 mmol). The reaction was stirred at room temperature overnight, then partitioned between water and EtOAc. The organic layer was dried over magnesium sulfate, filtered and concentrated under reduced pressure. The residue was dissolved in 1,4-dioxane (66.7 mL) and 3N potassium hydroxide (40.3 mL, 121 mmol) was added to the reaction mixture. The reaction was refluxed for two hours, then diluted with water and acidified with concentrated HCl. The aqueous layer was extracted with DCM and the organic layer was dried over magnesium sulfate, filtered and concentrated under reduced pressure to give N-(2-iodo-3-methyl-5-(trifluoromethyl) phenyl)benzenesulfonamide (13.1 g, 98%) as a brown solid. LC/MS (Method h) $R_t$=2.96 min.; MS m/z: 440 [M−H]$^−$.
$^1$H NMR (DMSO-d$_6$, 300 MHz): δ 10.9 (s, 1H), 7.71 (m, 3H), 7.59 (m, 3H), 6.92 (s, 1H), 2.46 (s, 3H).

Preparation #17. N-(2-iodo-4-methyl-5-(trifluoromethyl)phenyl)benzenesulfonamide

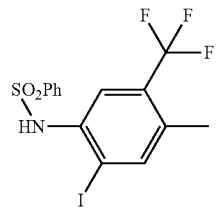

Using a procedure similar to Preparation #16 Step B, N-(2-iodo-4-methyl-5-(trifluoromethyl)phenyl)benzenesulfonamide (3 g, 100%) was prepared from 2-iodo-4-methyl-5-(trifluoromethyl)aniline (described in WO2006/002342) (2 g, 6.64 mmol). LC/MS (Method h) $R_t$=2.95 min.; MS m/z: 440 [M−H]$^−$ $^1$H NMR (DMSO-d$_6$, 300 MHz): δ 10.02 (s, 1H), 7.97 (s, 1H), 7.70 (m, 3H), 7.66 (m, 2H), 7.07 (s, 1H), 2.33 (s, 3H).

Preparation #18. N-(5-cyano-2-iodo-3-methylphenyl)benzenesulfonamide

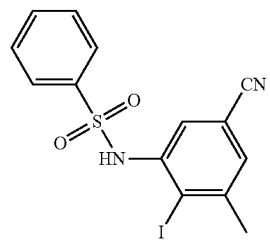 [SMILES: Cc1cc(C#N)cc(NS(=O)(=O)c2ccccc2)c1I]

Step A: 4-amino-3-methyl-5-nitrobenzonitrile

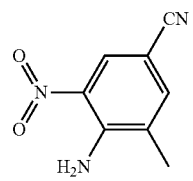

To a suspension of 4-bromo-2-methyl-6-nitroaniline (25 g, 108 mmol) in DMF (300 mL) was added copper(I) iodide (1.030 g, 5.41 mmol) and zinc cyanide (38.1 g, 325 mmol) The mixture was stirred at room temperature for 15 minutes, then palladium tetrakis (12.50 g, 10.82 mmol) was added and the mixture was stirred at 100° C. for 24 hours. More palladium tetrakis (12.50 g, 10.82 mmol) was added and the mixture was stirred at 130° C. for 6 hours. The reaction mixture was filtered and washed with EtOAc. The filtrate was washed successively with NaHCO₃ saturated aqueous solution and brine then dried over magnesium sulfate and concentrated under reduce pressure. The residue was recristallisated in 600 mL of EtOH and 4-amino-3-methyl-5-nitrobenzonitrile (12 g, 63%) was obtained as a yellow solid. LC/MS (Method h) R$_t$=1.77 min.; MS m/z: 176 [M−H]⁻. ¹H NMR (DMSO-d₆, 300 MHz): δ 8.35 (s, 1H), 7.65 (broad, 2H), 7.68 (s, 1H), 2.22 (s, 3H).

Step B: 4-iodo-3-methyl-5-nitrobenzonitrile

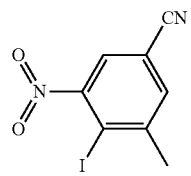

To a solution of 4-amino-3-methyl-5-nitrobenzonitrile (12 g, 67.7 mmol) in DMSO (176 mL) and cooled at 0° C. was added dropwise sulfuric acid (240 mL, 67.7 mmol). Temperature was maintained under 10° C. without freezing the DMSO. Then sodium nitrite (7.01 g, 102 mmol) in water (25 mL) was added drop by drop to the reaction mixture in order to keep the temperature at 0° C. and the reaction mixture was stirred for 1 hour between 0-5° C. A solution of potassium iodide (33.7 g, 203 mmol) and iodine (12.89 g, 50.8 mmol) in water (100 mL) was added dropwise keeping the temperature between 0-5° C. and the reaction mixture was stirred at 0° C. for 1 hour. A 20% Na₂S₂O₃ aqueous solution was added to the mixture and the solid was filtered and washed with water. The solid was recristallisated in pure EtOH (150 mL) and all the mother liquors were purified by column chromatography on silica gel (eluting with 5-100% EtOAc in cyclohexane). 4-iodo-3-methyl-5-nitrobenzonitrile (23.5 g, 70%) was obtained as a yellow solid.

LC/MS (Method h) R$_t$=1.77 min.; no ionization ¹H NMR (CDCl₃, 300 MHz): δ 7.69 (m, 2H), 2.64 (s, 3H).

Step C: 3-amino-4-iodo-5-methylbenzonitrile

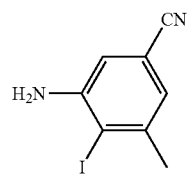

To a solution of 4-iodo-3-methyl-5-nitrobenzonitrile (3.11 g, 10.80 mmol) in EtOH (100 mL) was added iron (6.03 g, 108 mmol), ammonium chloride (1.733 g, 32.4 mmol) and water (30 mL). The reaction mixture was stirred at reflux for 1 hour. The reaction mixture was filtered through celite and washed with EtOH and EtOAc. The filtrate was concentrated, the residue was dissolved in EtOAc and washed successively with 2M NH₄Cl aqueous solution and brine, dried over magnesium sulfate and concentrated. The residue was purified by column chromatography on silica gel (eluting with 10% EtOAc in cyclohexane) to give 3-amino-4-iodo-5-methylbenzonitrile (2.55 g, 80%) as a brown solid.

LC/MS (Method h) R$_t$=2.29 min.; MS m/z: 259 [M+H]⁺. ¹H NMR (CDCl₃, 300 MHz): δ 6.87 (s, 1H), 6.77 (s, 1H), 4.41 (broad, 2H), 2.24 (s, 3H).

Step D: N-(5-cyano-2-iodo-3-methylphenyl)benzenesulfonamide

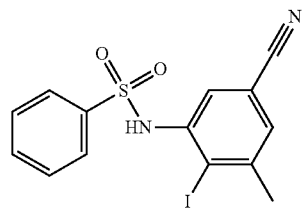 [SMILES: Cc1cc(C#N)cc(NS(=O)(=O)c2ccccc2)c1I]

Using a procedure similar to Preparation #16 Step B, N-(5-cyano-2-iodo-3-methylphenyl)benzenesulfonamide (9.43 g, 91%) was obtained as an orange solid from 3-amino-4-iodo-5-methylbenzonitrile (6.7 g, 26 mmol). LC/MS (Method k) R$_t$=2.68 min.; MS m/z: 397 [M−H]⁻.

¹H NMR (CDCl₃, 300 MHz): δ 7.72 (m, 2H), 7.64 (m, 1H), 7.50 (m, 1H), 7.41 (m, 2H), 7.16 (m, 1H), 7.09 (s, 1H), 2.34 (s, 3H).

Preparation #19.
N-(4-cyano-2-iodophenyl)benzenesulfonamide

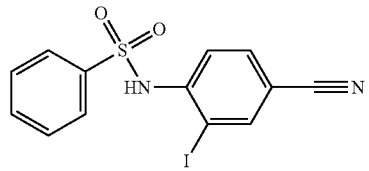 [SMILES: N#Cc1ccc(NS(=O)(=O)c2ccccc2)c(I)c1]

Using a procedure similar to Preparation #16 Step B, N-(4-cyano-2-iodophenyl)benzenesulfonamide (3.7 g, 100%) was obtained as an orange solid from 4-amino-3-iodobenzonitrile (2 g, 8.20 mmol).

LC/MS (Method h) R$_t$=2.41 min.; MS m/z: 383 [M−H]⁻
¹H NMR (CDCl₃, 300 MHz): δ 7.96 (m, 1H), 7.83 (m, 2H), 7.71 (m, 1H), 7.60 (m, 2H), 7.51 (m, 2H), 7.17 (m, 1H).

Preparation #20:
N-(5-cyano-2-iodophenyl)benzenesulfonamide

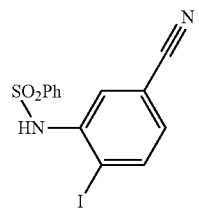

Using a procedure similar to Preparation #16 Step B, N-(5-cyano-2-iodophenyl)benzenesulfonamide (1.6 g, 51%) was obtained as an orange solid from 3-amino-4-iodobenzonitrile (2 g, 8.20 mmol).

LC/MS (Method h) R$_t$=2.38 min.; MS m/z: 383 [M−H]⁻

¹H NMR (DMSO-d₆, 300 MHz): δ 10.14 (broad, 1H), 8.05 (d, J=6 Hz, 1H), 7.70 (m, 3H), 7.61 (m, 2H), 7.42 (d, J=9 Hz, 1H), 7.36 (d, J=3 Hz, 1H).

Preparation #21: N-1,3-dimethyl-5-(trifluoromethyl)benzene-1,2-diamine

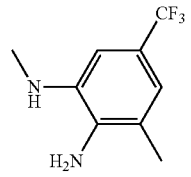

In a Parr reactor were introduced under nitrogen, 2-bromo-6-methyl-4-(trifluoromethyl)aniline (described in WO2009/009411) (14.5 g, 57.1 mmol) in THF (14.5 mL). Methylamine (40% in water) (72.5 mL, 2094 mmol) and copper(I) oxide (0.817 g, 5.71 mmol) were added. The reactor was closed under nitrogen and warmed at 110° C., during 16 hours. Water was added to the mixture and it was extracted with EtOAc. The organic layer was washed with water, dried over magnesium sulfate, filtered and evaporated. The residue was purified by column chromatography on silica gel (eluting with 5-40% EtOAc in cyclohexane) to give N-1,3-dimethyl-5-(trifluoromethyl)benzene-1,2-diamine (2.26 g, 19%). LC/MS (Method h) R$_f$=2.07 min.; MS m/z: 205 [M+H]⁺ ¹H NMR (DMSO-d₆, 300 MHz): δ 6.68 (s, 1H), 6.42 (s, 1H), 4.99 (d, J=5 Hz, 1H), 4.85 (s, 2H), 2.73 (d, J=5 Hz, 3H).

Preparation #22: 4-amino-3-methyl-5-(methylamino)benzonitrile

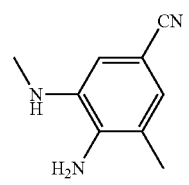

Step A: 5-bromo-N,3-dimethyl-2-nitroaniline

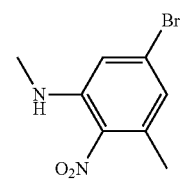

To a solution of 5-bromo-1-fluoro-3-methyl-2-nitrobenzene (5 g, 21.37 mmol) in EtOH, (50 mL) was added methylamine (2M in THF) (32.0 mL, 64.1 mmol) and the reaction mixture was stirred at 70° C. for 1.5 hours and overnight at room temperature. 0 (2M in THF) (32.0 mL, 64.1 mmol) was added and the reaction mixture was stirred at 70° C. for 1 hour. The reaction mixture was concentrated under reduced pressure. The residue was diluted with EtOAc and washed with brine, dried over magnesium sulfate, and evaporated to give 5-bromo-N,3-dimethyl-2-nitroaniline (5.13 g, 98%) as an orange solid.

LC/MS (Method h) R$_f$=2.77 min.; MS m/z: 245 [M+H]⁺. ¹H NMR (DMSO-d₆, 300 MHz): δ. 6.86 (s, 1H), 6.77 (s, 1H), 6.72 (m, 1H), 2.77 (d, J=3 Hz, 3H), 2.28 (s, 3H)

Step B: 3-methyl-5-(methylamino)-4-nitrobenzonitrile

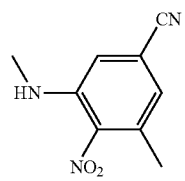

In a microwave reactor were added potassium ferrocyanide (3006 mg, 8.16 mmol), Pd(dppf)Cl₂ (179 mg, 0.245 mmol), sodium carbonate (865 mg, 8.16 mmol) and 5-bromo-N,3-dimethyl-2-nitroaniline (2000 mg, 8.16 mmol) in NMP (15 mL). The reaction mixture was stirred under microwave 2 hours at 130° C. The reaction mixture was filtered and washed with EtOAc. The filtrate was washed with water and brine. The organic layer was dried over magnesium sulfate, filtered and concentrated under vacuum. The residue was purified by column chromatography on silica gel (eluting with 5-25% EtOAc in cyclohexane) to give 3-methyl-5-(methylamino)-4-nitrobenzonitrile (1.21 g, 64%). LC/MS (Method h) R$_f$=2.28 min.; MS m/z: 192 [M+H]⁺. ¹H NMR (DMSO-d₆, 300 MHz): 6.7.13 (s, 1H), 7.01 (s, 1H), 6.60 (q, J=4.8 Hz, 1H), 2.76 (d, J=4.8 Hz, 3H), 2.25 (s, 3H)

Step C: 4-amino-3-methyl-5-(methylamino)benzonitrile

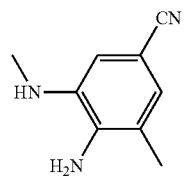

To a suspension of 3-methyl-5-(methylamino)-4-nitrobenzonitrile (1.795 g, 9.39 mmol) in EtOAc (84 mL) and MeOH (84 mL) was added Pd/C (0.400 g, 1.878 mmol) and the reaction mixture was stirred at room temperature under H₂ (1 bar) for 1 hour. The reaction mixture was filtered and washed with EtOAc. The filtrate was concentrated under reduced pressure to give 4-amino-3-methyl-5-(methylamino)benzonitrile (1.51 g, 100%) as a red solid. LC/MS (Method h) R$_f$=1.40 min.; MS m/z: 162 [M+H]⁺. ¹H NMR (DMSO-d₆, 300 MHz): 6.6.79 (s, 1H), 6.50 (s, 1H), 5.18 (s, 2H), 5.02 (m, 1H), 2.72 (d, J=5.1 Hz, 3H), 2.06 (s, 3H).

Preparation #23:
N-1,3,5-trimethylbenzene-1,2-diamine

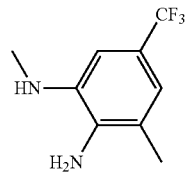

Step A:
N-(2-methyl-4-(trifluoromethyl)phenyl)acetamide

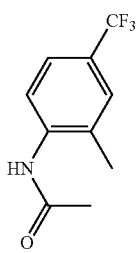

Acetic anhydride (8.08 mL, 86 mmol) was added to 2-methyl-4-(trifluoromethyl)aniline (5 g, 28.5 mmol) at 0° C., and the reaction mixture was stirred at 0° C. for 20 minutes. The solid formed was crushed with mortar, put in suspension in water and neutralized with ammonia. The precipitate was filtered and dry under vacuum to give N-(2-methyl-4-(trifluoromethyl)phenyl)acetamide (5.91 g, 95%) as a beige solid.

LC/MS (Method h) $R_t$=1.99 min.; MS m/z: 218 [M+H]$^+$.
$^1$H NMR (DMSO-d$_6$, 300 MHz): δ. 9.45 (s, 1H), 7.76 (d, J=8.4 Hz, 1H), 7.57 (s, 1H), 7.50 (d, J=8.4 Hz, 1H), 2.30 (s, 3H), 2.11 (s, 3H)

Step B: N-(2-methyl-6-nitro-4-(trifluoromethyl) phenyl)acetamide

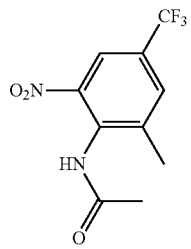 [SMILES: CC(=O)Nc1c(C)cc(C(F)(F)F)cc1[N+](=O)[O-]]

To a solution of N-(2-methyl-4-(trifluoromethyl)phenyl)acetamide (5.9 g, 27.2 mmol) in sulfuric acid (20 mL, 375 mmol) at 0° C. was added nitric acid dropwise (20 mL, 448 mmol) The reaction mixture was stirred at 0° C. for 2 hours and at room temperature overnight. The reaction mixture was diluted in water and extracted with EtOAc. The layers were separated and the organic layer was washed with NaHCO$_3$ saturated aqueous solution and brine. The organic layer was dried over magnesium sulfate, filtered and concentrated to give N-(2-methyl-6-nitro-4-(trifluoromethyl) phenyl)acetamide (6.6 g, 93%).

LC/MS (Method h) $R_t$=2.00 min.; MS m/z: 263 [M+H]$^+$.
$^1$H NMR (DMSO-d$_6$, 300 MHz): δ. 10.14 (broad, 1H), 8.08 (s, 1H), 8.04 (s, 1H), 2.39 (s, 3H), 2.07 (s, 3H).

Step C: 2-methyl-6-nitro-4-(trifluoromethyl)aniline

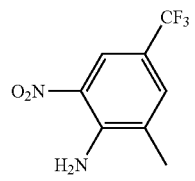

To a solution of N-(2-methyl-6-nitro-4-(trifluoromethyl) phenyl)acetamide (2.95 g, 11.25 mmol) in MeOH (2.5 mL) and water (1 mL) was added potassium hydroxide (0.189 g, 3.38 mmol) and the reaction mixture was stirred at 60° C. for 18 hours. Ice was poured into the reaction mixture and a precipitate was formed, filtered and washed with cold water. The solid was dried under vacuum to give 2-methyl-6-nitro-4-(trifluoromethyl)aniline (1.65 g, 67%). LC/MS (Method h) $R_t$=2.51 min.; MS m/z: 219 [M−H]$^−$.
$^1$H NMR (DMSO-d$_6$, 300 MHz): δ. 8.16 (s, 1H), 7.66 (s, 1H), 7.62 (s, 2H), 2.27 (s, 3H).

Step D:
3-methyl-5-(trifluoromethyl)benzene-1,2-diamine

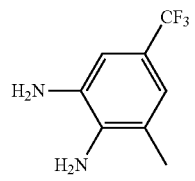

To a solution of 2-methyl-6-nitro-4-(trifluoromethyl)aniline (1.33 g, 6.04 mmol) in EtOH (22 mL) and water (11 mL) were added iron (1.687 g, 30.2 mmol) and calcium chloride (1.341 g, 12.08 mmol) and the reaction mixture was stirred at reflux for 5 hours. The reaction mixture was filtered and the filtrate was concentrated. The residue was purified by column chromatography on silica gel (eluting with 0-5% MeOH in DCM) to give 3-methyl-5-(trifluoromethyl)benzene-1,2-diamine (862 mg, 75%).

LC/MS (Method h) $R_t$=1.86 min.; MS m/z: 191 [M+H]$^+$.
$^1$H NMR (DMSO-d$_6$, 300 MHz): δ. 6.68 (s, 1H), 6.61 (s, 1H), 4.81 (m, 4H), 2.07 (s, 3H).

Step E: ethyl (2-amino-3-methyl-5-(trifluoromethyl) phenyl)carbamate

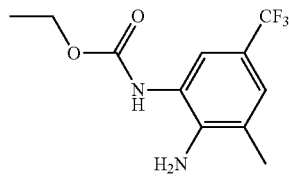 [SMILES: CCOC(=O)Nc1cc(C(F)(F)F)cc(C)c1N]

To a solution of 3-methyl-5-(trifluoromethyl)benzene-1,2-diamine (860 mg, 4.52 mmol) in DMF (9 mL) and cooled at 0° C. was added sodium hydride (109 mg, 4.52 mmol) and the reaction mixture was stirred at 0° C. for 1 hour. Ethyl chloroformate (0.432 mL, 4.52 mmol) was added and the reaction mixture was stirred at room temperature for 18 hours. The reaction mixture was hydrolysed with NH$_4$Cl saturated aqueous solution and extracted with EtOAc. The organic layer was dried over magnesium sulfate, filtered and concentrated. The residue was purified by column chromatography on silica gel (eluting with 0-40% EtOAc in DCM) to give ethyl (2-amino-3-methyl-5-(trifluoromethyl)phenyl)carbamate (512 mg, 43%) LC/MS (Method h) R$_t$=2.28 min.; MS m/z: 263 [M+H]$^+$. $^1$H NMR (DMSO-d$_6$, 300 MHz): δ. 8.69 (s, 1H), 7.44 (s, 1H), 7.10 (s, 1H), 5.30 (s, 2H), 4.11 (q, J=7.2 Hz, 2H), 2.13 (s, 3H), 1.24 (t, J=7.2 Hz, 3H).

Step F: N-1,3,5-trimethylbenzene-1,2-diamine

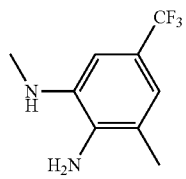

To a solution of ethyl (2-amino-3-methyl-5-(trifluoromethyl)phenyl)carbamate (510 mg, 1.945 mmol) in THF (12 mL) cooled at 0° C. was added a suspension of LiAlH$_4$ (9.72 mL, 9.72 mmol) in THF (5 mL) and the reaction mixture was refluxed for 18 hours. The reaction mixture was treated at room temperature with Glauber salts for 7 hours and filtered. The filtrate was concentrated. The residue was purified by column chromatography on silica gel (eluting with 0-40% EtOAc in DCM) to give N1,3,5-trimethylbenzene-1,2-diamine (197 mg, 67%). LC/MS (Method h) R$_t$=1.05 min.; MS m/z: 151 [M+H]$^+$. $^1$H NMR (DMSO-d$_6$, 300 MHz): δ. 6.16 (s, 1H), 6.10 (s, 1H), 4.53 (m, 1H), 3.95 (s, 2H), 2.67 (d, J=5.1 Hz, 3H), 2.10 (s, 3H), 2.00 (s, 3H).

Preparation #24:
5-bromo-N-1,3-dimethylbenzene-1,2-diamine

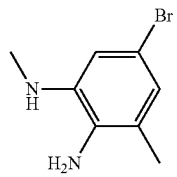

Using a procedure similar to Preparation #23, Step D, 5-bromo-N-1,3-dimethylbenzene-1,2-diamine (712 mg, 100%) was prepared from 5-bromo-N,3-dimethyl-2-nitroaniline (Preparation #22, Step A) (815 mg, 3.33 mmol). LC/MS (Method h) R$_t$=1.93 min.; MS m/z: 215 [M+H]$^+$. $^1$H NMR (DMSO-d$_6$, 300 MHz): δ. 6.49 (s, 1H), 6.32 (s, 1H), 4.91 (m, 1H), 4.34 (broad, 2H), 2.67 (d, J=4.8 Hz, 3H), 2.03 (s, 3H).

Preparation #25:
6-chloro-N-2,4-dimethylpyridine-2,3-diamine

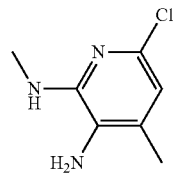

Step A:
6-chloro-N,4-dimethyl-3-nitropyridin-2-amine

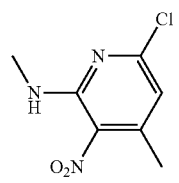

To a solution of 2,6-dichloro-4-methyl-3-nitropyridine (2.2 g, 10.63 mmol) in ACN (60 mL) were added triethylamine (4.44 mL, 31.9 mmol) and methylamine (2M in THF) (6.38 mL, 12.75 mmol) and the reaction mixture was stirred at room temperature for 4 hours. The reaction mixture was quenched with NaHCO$_3$ saturated aqueous solution and diluted with water and EtOAc. The layers were separated and the aqueous one was extracted with EtOAc. The organic layer was dried over magnesium sulfate, filtered and concentrated under reduced pressure. The residue was purified by column chromatography on silica gel (eluting with 0-30% EtOAc in cyclohexane) to give 6-chloro-N,4-dimethyl-3-nitropyridin-2-amine (2.05 g, 43%) as a yellow solid. LC/MS (Method h) R$_t$=2.45 min.; MS m/z: 202 [M+H]$^+$. $^1$H NMR (DMSO-d$_6$, 400 MHz): δ 7.93 (broad, 1H), 6.72 (s, 1H), 2.89 (s, 3H), 2.38 (s, 3H).

Step B:
6-chloro-N2,4-dimethylpyridine-2,3-diamine

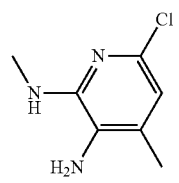

Using a procedure similar to example Preparation #23, Step D, 6-chloro-N2,4-dimethylpyridine-2,3-diamine (90 mg, 51%) was prepared from 6-chloro-N,4-dimethyl-3-nitropyridin-2-amine (200 mg, 0.992 mmol). LC/MS (Method h) R$_t$=1.40 min.; MS m/z: 172 [M+H]$^+$. $^1$H NMR (DMSO-d$_6$, 300 MHz): δ 6.30 (s, 1H), 5.93 (broad, 1H), 4.48 (broad, 2H), 2.78 (d, J=3 Hz, 3H), 2.00 (s, 3H).

Preparation #26: N-(2-bromo-5-(trifluoromethyl)pyridin-3-yl)benzenesulfonamide

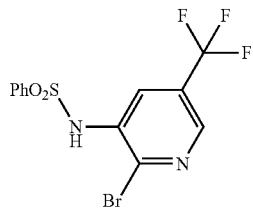

Step A: 2-bromo-5-(trifluoromethyl)pyridin-3-amine

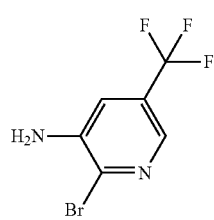 [SMILES: Nc1cc(C(F)(F)F)cnc1Br]

To a solution of 2-bromo-3-nitro-5-(trifluoromethyl)pyridine (described in WO2013/038381) (2.6 g, 9.59 mmol) is EtOH (40 mL) and water (16 mL) was added iron (4.02 g, 72.0 mmol) and acetic acid (3.7 mL). The reaction mixture was stirred at 110° C. for 3 hours, then it was filtered and the solvent was evaporated. The residue was diluted with EtOAc, and NaHCO$_3$ saturated aqueous solution, extracted, dried over magnesium sulfate, filtered and evaporated to give 2-bromo-5-(trifluoromethyl)pyridin-3-amine (2.35 g, 100%) as a white solid. LC/MS (Method h) R$_t$=1.91 min.; MS m/z: 241 [M+H]$^+$. $^1$H NMR (DMSO-d$_6$, 300 MHz): δ. 7.98 (s, 1H), 7.34 (s, 1H), 6.06 (s, 2H).

Step B: N-(2-bromo-5-(trifluoromethyl)pyridin-3-yl)benzenesulfonamide

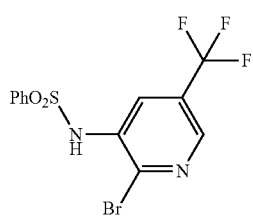

Using a procedure similar to Preparation #16 Step B, N-(2-bromo-5-(trifluoromethyl)pyridin-3-yl)benzenesulfonamide (954 m g, 50%) was prepared from 2-bromo-5-(trifluoromethyl)pyridin-3-amine (1.2 g, 4.98 mmol). LC/MS (Method h) R$_t$=2.52 min.; MS m/z: 381 [M+H]$^+$. $^1$H NMR (DMSO-d$_6$, 300 MHz,) δ 10.67 (broad, 1H), 8.66 (s, 1H), 7.85 (d, J=2.3 Hz, 1H), 7.73 (m, 3H), 7.59 (m, 2H).

Preparation #27: N-(5-iodo-2-(trifluoromethyl)pyridin-4-yl)benzenesulfonamide

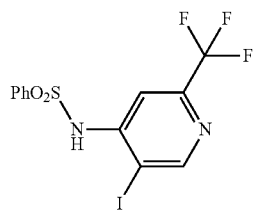

Using a procedure similar to Preparation #16 Step B, N-(5-iodo-2-(trifluoromethyl)pyridin-4-yl)benzenesulfonamide (13.32 g, 52%) was prepared from 5-iodo-2-(trifluoromethyl)pyridin-4-amine (described in WO2010/091310) (17.3 g, 60.1 mmol). LC/MS (Method h) R$_t$=2.57 min.; MS m/z: 429 [M+H]$^+$. $^1$H NMR (DMSO-d$_6$, 300 MHz,) δ 8.99 (s, 1H), 7.93 (m, 2H), 7.66 (m, 3H), 7.48 (s, 1H).

Preparation #28: 6-chloro-4-methylpyridazin-3-amine and 6-chloro-5-methylpyridazin-3-amine

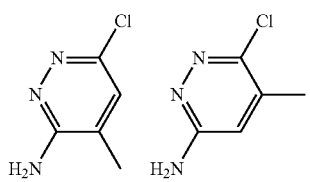

A suspension of 3,6-dichloro-4-methylpyridazine (3.38 g, 20.74 mmol) in ammonium hydroxide (55 mL, 1412 mmol) was heated in a reactor at 130° C. during for about 16 h. The reaction mixture was cooled to room temperature. A precipitate appeared which was filtered, washed with water and dried under vacuum to give an inseparable mixture of 6-chloro-4-methylpyridazin-3-amine and 6-chloro-5-methylpyridazin-3-amine (ratio 57/43) (2.25 g, 76%). $^1$H NMR (DMSO-d$_6$, 300 MHz,) δ 7.30 (s, 1H), 6.45 (broad, 2H), 2.08 (s, 3H) and 6.74 (s, 1H), 6.47 (broad, 2H), 2.19 (s, 3H).

Preparation #29: N-(2-iodo-5-(trifluoromethyl)phenyl)benzenesulfonamide

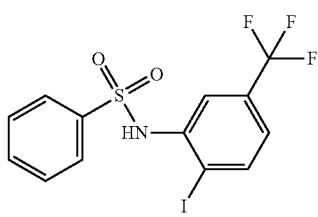 [SMILES: O=S(=O)(Nc1cc(C(F)(F)F)ccc1I)c1ccccc1]

Using a procedure similar to Preparation #16 Step B, N-[2-iodo-5-(trifluoromethyl)phenyl]benzenesulfonamide (136 g, 100%) was prepared from 2-iodo-5-(trifluoromethyl)aniline (85 g, 296 mmol) (described in US20070129334).

Preparation #30: N1,3-dimethyl-4-(trifluoromethyl)benzene-1,2-diamine

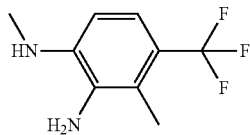

Step A: 1-fluoro-4-iodo-3-methyl-2-nitrobenzene

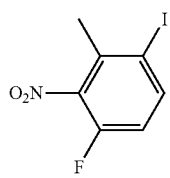

To a solution of 3-fluoro-2-nitrotoluene (1 g, 6.45 mmol) in trifluoromethanesulfonic acid (2.83 ml, 32.2 mmol) and cooled at 0° C. was added portionwise N-iodosuccinimide (1.740 g, 7.74 mmol) and the mixture was stirred at room temperature for 1 hour. The mixture was poured into water and extracted twice with diethylether. The organic layer was washed successively with a 10% $Na_2S_2O_3$ aqueous solution, then brine and concentrated to give 1-fluoro-4-iodo-3-methyl-2-nitrobenzene as a beige solid (1.86 g, 74%).

LC/MS (Method i) $R_t$=2.28 min.; no ionization $^1$H NMR (DMSO-$d_6$, 300 MHz): δ 8.16 (dd, J=6 Hz, 9 Hz, 1H), 7.31 (t, J=9 Hz, 1H), 2.39 ppm (s, 3H).

Step B: 1-fluoro-3-methyl-2-nitro-4-(trifluoromethyl)benzene

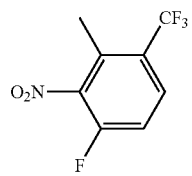

To a suspension of 1-fluoro-4-iodo-3-methyl-2-nitrobenzene (2.39 g, 8.50 mmol), copper(I) iodide (2.430 g, 12.76 mmol) and N,N-diisopropylethylamine (4.41 ml, 25.5 mmol) in DMF (8 ml) was added methyl 2,2-difluoro-2-(fluorosulfonyl)acetate (3.25 ml, 25.5 mmol) and the mixture was heated at 80° C. for 20 hours in a sealed tube. The reaction mixture was poured into water and extracted twice with EtOAc. The organic layer was washed successively with a 10% $NaHCO_3$ aqueous solution and brine, dried over magnesium sulfate and concentrated to give 1-fluoro-3-methyl-2-nitro-4-(trifluoromethyl)benzene (2.37 g, 62%). LC/MS (Method i) $R_t$=2.25 min.; no ionization $^1$H NMR (DMSO-$d_6$, 300 MHz): δ 8.09 (dd, J=6 Hz, 9 Hz, 1H), 7.71 (t, J=9 Hz, 1H), 2.43 (m, 1H).

Step C: N,3-dimethyl-2-nitro-4-(trifluoromethyl)aniline

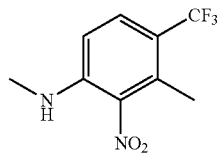 [SMILES: CNc1ccc(C(F)(F)F)c(C)c1[N+](=O)[O-]]

To a solution of 1-fluoro-3-methyl-2-nitro-4-(trifluoromethyl)benzene (2.3 g, 10.31 mmol) in MeOH (15 ml) was added methylamine (15.46 ml, 30.9 mmol) (2M in THF) and the reaction mixture was stirred at room temperature for 1 hour. The reaction mixture was concentrated under reduced pressure and the residue was diluted with EtOAc and washed with brine. The organic phase was dried over magnesium sulfate and evaporated. The residue was purified by column chromatography on silica gel (eluting with 5% EtOAc in cyclohexane) to give N,3-dimethyl-2-nitro-4-(trifluoromethyl)aniline (1 g, 43%) as a yellow solid. LC/MS (Method i) $R_t$=2.29 min.; MS m/z: 235 [M+H]$^+$.

$^1$H NMR (DMSO-$d_6$, 300 MHz): δ 7.63 (d, J=8.9 Hz, 1H), 6.77 (d, J=8.9 Hz, 1H), 6.59 (broad, 1H), 2.77 (d, J=4.5 Hz, 3H), 2.24 (m, 3H).

Step D: N1,3-dimethyl-4-(trifluoromethyl)benzene-1,2-diamine

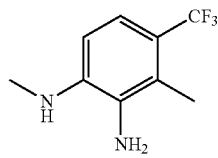

To a suspension of N,3-dimethyl-2-nitro-4-(trifluoromethyl)aniline (1 g, 4.27 mmol) in EtOH (48 ml) was added iron (2.385 g, 42.7 mmol), ammonium chloride (0.685 g, 12.81 mmol) and water (16 ml) and the reaction mixture was stirred at reflux for 1 hour. The reaction mixture was filtered through celite and the filtrate was concentrated. The residue was dissolved in DCM and washed successively with a 2M $NH_4Cl$ aqueous solution and brine; then the organic phase was dried over magnesium sulfate and concentrated to give N1,3-dimethyl-4-(trifluoromethyl)benzene-1,2-diamine as a yellow solid (884 mg, 77%). LC/MS (Method i) $R_t$=1.96 min.; MS m/z: 205 [M+H]$^+$.

$^1$H NMR (DMSO-$d_6$, 300 MHz): δ 6.87 (d, J=8.4 Hz, 1H), 6.33 (d, J=8.4 Hz, 1H), 5.28 (broad d, J=5.0 Hz, 1H), 4.57 (s, 2H), 2.75 (d, J=5.0 Hz, 3H), 2.12 ppm (m, 3H)

Preparation #31: 4-bromo-N1,3-dimethylbenzene-1,2-diamine

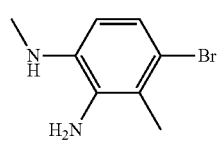

Step A: 4-bromo-N,3-dimethyl-2-nitroaniline

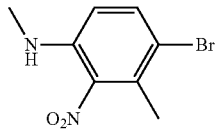

Using a procedure similar to Preparation #30 Step C, 4-bromo-N,3-dimethyl-2-nitroaniline (428 mg, 82%) was prepared from 1-bromo-4-fluoro-2-methyl-3-nitrobenzene (0.5 g, 2.14 mmol). LC/MS (Method h) $R_t$=2.73 min.; MS m/z: 245 [M+H]$^+$. $^1$H NMR (DMSO-d$_6$, 300 MHz): δ 7.55 (d, J=9.1 Hz, 1H), 6.65 (d, J=9.1 Hz, 1H), 6.23 (m, 1H), 2.71 (d, J=4.8 Hz, 3H), 2.24 (s, 3H).

Step B: 4-bromo-N1,3-dimethylbenzene-1,2-diamine

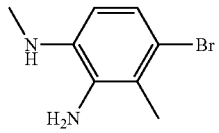

Using a procedure similar to Preparation #30 Step D, 4-bromo-N1,3-dimethylbenzene-1,2-diamine (360 mg, 82%) was prepared from 4-bromo-N,3-dimethyl-2-nitroaniline (425 mg, 1.73 mmol). LC/MS (Method h) $R_t$=1.73 min.; MS m/z: 215 [M+H]$^+$. $^1$H NMR (DMSO-d$_6$, 300 MHz): δ 6.73 (d, J=8.4 Hz, 1H), 6.21 (d, J=8.4 Hz, 1H), 4.60 (broad, 3H), 2.67 (s, 3H), 2.15 (s, 3H).

Preparation #32: 5-bromo-N1-methyl-3-(trifluoromethyl)benzene-1,2-diamine

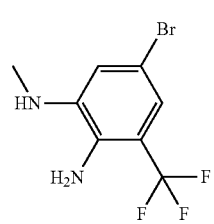

Step A: 5-bromo-1-chloro-2-nitroso-3-(trifluoromethyl)benzene

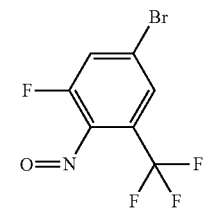 [SMILES: O=Nc1c(F)cc(Br)cc1C(F)(F)F]

To a solution of 4-bromo-2-chloro-6-(trifluoromethyl)aniline (1.396 ml, 9.00 mmol) in 1,2-dichloroethane (60 ml) was added 3-chloroperoxybenzoic acid (4.66 g, 27.0 mmol) and the reaction mixture was stirred at room temperature for 20 minutes and at 50° C. overnight. DCM was added and the organic layer was washed successively with a saturated aqueous solution of ammonium thiosulfate and a saturated solution of sodium bicarbonate, then the organic phase was dried over magnesium sulfate and concentrated. The residue was purified by column chromatography on silica gel (eluting with 5% to 20% EtOAc in cyclohexane) to give 5-bromo-1-chloro-2-nitroso-3-(trifluoromethyl)benzene as a beige solid (1.89 g, 69%). LC/MS (Method h) $R_t$=2.98 min.; no ionization $^1$H NMR (DMSO-d$_6$, 300 MHz): δ 8.48 (d, J=1.8 Hz, 1H), 8.33 (d, J=1.8 Hz, 1H).

Step B: 5-bromo-N-methyl-2-nitroso-3-(trifluoromethyl)aniline

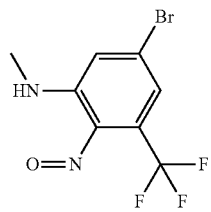

To a solution of 5-bromo-1-chloro-2-nitroso-3-(trifluoromethyl)benzene (2.7 g, 9.36 mmol) in THF (25 ml) was added methylamine (10.30 ml, 20.59 mmol) (2M in THF) and the reaction mixture was stirred at room temperature for 5 minutes. The reaction mixture was quenched with water and extracted with EtOAc. The organic layer was dried with magnesium sulfate, filtered and concentrated under reduced pressure to give 5-bromo-N-methyl-2-nitroso-3-(trifluoromethyl)aniline as a brown liquid (2.65 g, 89%).

LC/MS (Method h) $R_t$=2.60 min.; MS m/z: 283 [M+H]$^+$. $^1$H NMR (DMSO-d$_6$, 300 MHz): δ 11.56 (broad, 1H), 7.69 (d, J=1.8 Hz, 1H), 7.39 (d, J=1.8 Hz, 1H), 2.92 (d, J=5.3 Hz, 3H).

Step C: 5-bromo-N1-methyl-3-(trifluoromethyl)benzene-1,2-diamine

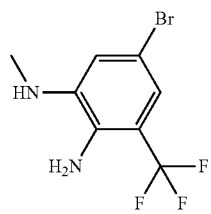

Using a procedure similar to Preparation #23 Step D, 5-bromo-N1-methyl-3-(trifluoromethyl)benzene-1,2-diamine (1.33 g, 51%) was prepared from 5-bromo-N-methyl-2-nitroso-3-(trifluoromethyl)aniline (2.65 g, 9.36 mmol). LC/MS (Method h) $R_t$=2.67 min.; MS m/z: 269 [M+H]$^+$.

$^1$H NMR (DMSO-d$_6$, 300 MHz): δ 6.77 (d, J=2.1 Hz, 1H), 6.60 (d, J=2.1 Hz, 1H), 5.48 (m, 1H), 5.10 (s, 2H), 2.73 (d, J=4.8 Hz, 3H).

Preparation #33: tert-butyl 2,4-dichloro-3-(1-hydroxyprop-2-yn-1-yl)benzoate

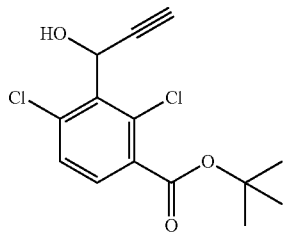 [SMILES: C#CC(O)c1c(Cl)ccc(C(=O)OC(C)(C)C)c1Cl]

Step A: tert-butyl 2,4-dichlorobenzoate

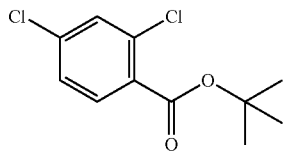

To a solution of 2,4-dichlorobenzoic acid (13.15 g, 68.8 mmol) in THF (68.5 ml) was added di-tert-butyl dicarbonate (15.98 ml, 68.8 mmol) and N,N-dimethylpyridin-4-amine (0.841 g, 6.88 mmol) and the reaction was stirred at 40° C. for 24 hours then evaporated to dryness. The residue was purified by column chromatography on silica gel (eluting with 5-10% EtOAc in cyclohexane) to give tert-butyl 2,4-dichlorobenzoate (13.1 g, 72%) as a colorless oil. LC/MS (Method i) $R_t$=2.60 min.; MS m/z: 247 [M+H]$^+$. $^1$H NMR (DMSO-d$_6$, 300 MHz): δ 7.75 (m, 2H), 7.53 (dd, J=8.3, 2.1 Hz, 1H), 1.55 ppm (s, 9H).

Step B: tert-butyl 2,4-dichloro-3-formylbenzoate

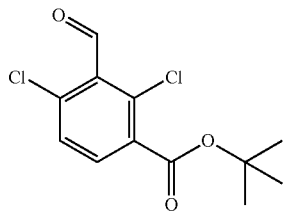 [SMILES: CC(C)(C)OC(=O)c1ccc(Cl)c(C=O)c1Cl]

To as solution of tert-butyl 2,4-dichlorobenzoate (13.1 g, 53.0 mmol) in THF (130 ml) and cooled to −78° C. was added dropwise over 10 minutes lithium diisopropylamide (31.8 ml, 63.6 mmol) diluted in THF (25 mL) and already cooled to 0° C. The reaction mixture was stirred for 90 minutes at −75° C. then DMF (12.31 ml, 159 mmol) was added and the reaction mixture was stirred for 10 minutes between −65° C. and −75° C. The reaction mixture was quenched with acetic acid (6 ml) and allowed to warm to room temperature. The reaction mixture was partitioned between diethyl ether and 1N HCl solution. The aqueous layer was extracted with diethyl ether, the organic layer was dried over magnesium sulfate, and concentrated. The residue was purified by column chromatography on silica gel (eluting with 5-10% EtOAc in cyclohexane) to give tert-butyl 2,4-dichloro-3-formylbenzoate (10.6 g, 71%) as a yellow oil.

LC/MS (Method h) $R_t$=2.88 min.; MS m/z: 275 [M+H]$^+$.
$^1$H NMR (DMSO-d$_6$, 300 MHz): δ 10.34 (s, 1H), 7.86 (d, J=8.4 Hz, 1H), 7.69 (d, J=8.4 Hz, 1H), 1.56 (s, 9H).

Step C: tert-butyl 2,4-dichloro-3-(1-hydroxyprop-2-yn-1-yl)benzoate

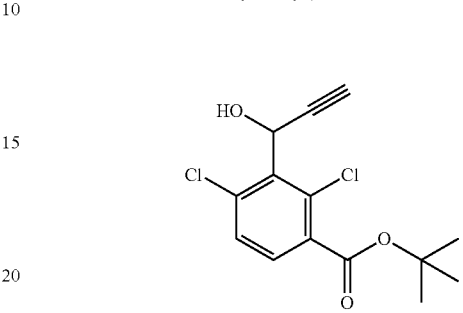

Using a procedure similar to Preparation #1 Step D, tert-butyl 2,4-dichloro-3-(1-hydroxyprop-2-yn-1-yl)benzoate (4 g, 100%) was prepared from tert-butyl 2,4-dichloro-3-formylbenzoate (3.39 g, 12.3 mmol). LC/MS (Method i) $R_t$=2.14 min.; MS m/z: 301 [M+H]$^+$.
$^1$H NMR (DMSO-d$_6$, 300 MHz): δ 7.56 (s, 2H), 6.26 (d, J=5.0 Hz, 1H), 6.10 (dd, d, J=5.0 Hz and 2.3 Hz, 1H), 3.51 (d, J=2.3 Hz, 1H), 1.55 (s, 9H).

Preparation #34: N-(2-iodo-6-methyl-4-(trifluoromethyl)phenyl)benzenesulfonamide

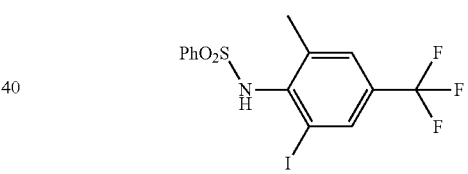

Step A: 2-iodo-6-methyl-4-(trifluoromethyl)aniline

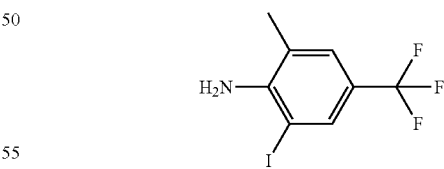

To a solution of 2-methyl-4-(trifluoromethyl)aniline (3.5 g, 19.98 mmol) in EtOH (80 ml) was added iodine (5.07 g, 19.98 mmol) and silver sulfate (6.23 g, 19.98 mmol), and the reaction mixture was stirred at room temperature for 2 hours. The reaction mixture was diluted with a 10% Na$_2$S$_2$O$_3$ aqueous solution. The obtained aqueous layer was extracted with EtOAc and the organic layer was dried over magnesium sulfate, filtered and concentrated under reduced pressure to give 2-iodo-6-methyl-4-(trifluoromethyl)aniline as an orange resin (6.3 g, 90%). LC/MS (Method i) $R_t$=2.32 min.;

MS m/z: 302 [M+H]$^+$. $^1$H NMR (DMSO-d$_6$, 300 MHz): δ 7.70 (s, 1H), 7.31 (s, 1H), 5.55 (s, 2H), 2.20 (s, 3H)

Step B: N-(2-iodo-6-methyl-4-(trifluoromethyl)phenyl)benzenesulfonamide

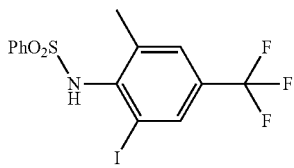

Using a procedure similar to Preparation #16 Step B, N-(2-iodo-6-methyl-4-(trifluoromethyl)phenyl)benzenesulfonamide (2.73 g, 32%) was prepared from 2-iodo-6-methyl-4-(trifluoromethyl)aniline (5.8 g, 19.3 mmol). LC/MS (Method i) R$_t$=2.35 min.; MS m/z: 442 [M+H]$^+$.

$^1$H NMR (DMSO-d$_6$, 300 MHz): δ 10.03 (s, 1H), 8.01 (d, J=2.1 Hz, 1H), 7.60 (m, 6H), 2.04 (s, 3H).

Preparation #35: N-(5-bromo-2-iodo-3-methylphenyl)benzenesulfonamide

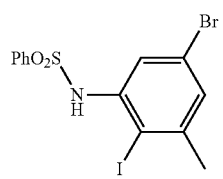

Step A: 5-bromo-2-iodo-1-methyl-3-nitrobenzene

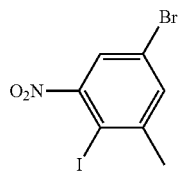

To a solution of 4-bromo-2-methyl-6-nitroaniline (250 mg, 1.082 mmol) in chloroform (1.6 ml) was added isoamyl nitrite (190 mg, 1.623 mmol) and iodine (549 mg, 2.164 mmol) and the reaction mixture was stirred at reflux for 3.5 hours. The reaction mixture was diluted with a 50% Na$_2$S$_2$O$_3$ aqueous solution. The obtained aqueous layer was extracted with EtOAc. The organic layer was dried over magnesium sulfate, filtered and concentrated under reduced pressure to give 5-bromo-2-iodo-1-methyl-3-nitrobenzene (350 mg, 30%) as a brown resin. It was used crude in the next step. LC/MS (Method h) R$_t$=2.90 min.; no ionization Step B: 5-bromo-2-iodo-3-methylaniline

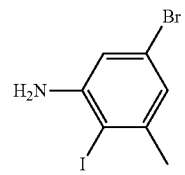

Using a procedure similar to Preparation #23 Step D, 5-bromo-2-iodo-3-methylaniline (1.6 g, 56%) was prepared from 5-bromo-2-iodo-1-methyl-3-nitrobenzene (7.25 g, 8.69 mmol). It was used crude in the next step. LC/MS (Method h) R$_t$=2.74 min.; MS m/z: 312 [M+H]$^+$. $^1$H NMR (DMSO-d$_6$, 300 MHz): δ 6.76 (d, J=2.5 Hz, 1H), 6.70 (m, 1H), 5.49 (s, 2H), 2.29 (s, 3H).

Step C: N-(5-bromo-2-iodo-3-methylphenyl)benzenesulfonamide

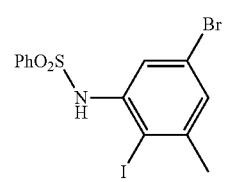

Using a procedure similar to Preparation #16 Step B, N-(5-bromo-2-iodo-3-methylphenyl)benzenesulfonamide (2.21 g, 95%) was prepared from 5-bromo-2-iodo-3-methylaniline (1.6 g, 5.13 mmol). LC/MS (Method h) R$_t$=2.94 min.; MS m/z: 450 [M−H]$^-$.

$^1$H NMR (DMSO-d$_6$, 300 MHz): δ 9.95 (s, 1H), 7.65 (m, 5H), 7.44 (d, J=2.1 Hz, 1H), 6.87 (d, J=2.1 Hz, 1H), 2.36 (s, 3H).

Preparation #36: Preparation of methyl 5-(1-hydroxyprop-2-yn-1-yl)-4,6-dimethylnicotinate

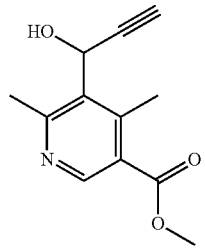

Step A: 5-bromo-4,6-dimethyl-2-oxo-1,2-dihydropyridine-3-carbonitrile

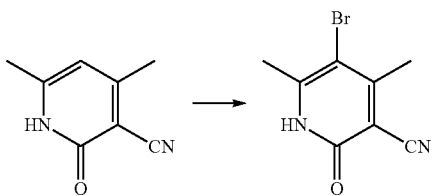

To a solution of 4,6-dimethyl-2-oxo-1,2-dihydropyridine-3-carbonitrile (35 g, 236 mmol) in Acetic Acid (200 ml) was added bromine (41.5 g, 260 mmol). The reaction mixture stirred for about 30 min at ambient temperature. The reaction mixture was then concentrated to dryness under reduced pressure. The resulting resin precipitated from aqueous EtOH to obtain 5-bromo-4,6-dimethyl-2-oxo-1,2-dihydropyridine-3-carbonitrile (70 g, 95%). LCMS (Table 1, Method c) RT=1.63 min.; MS m/z=226, 228 (M+H).

Step B:
5-bromo-2-chloro-4,6-dimethylnicotinonitrile

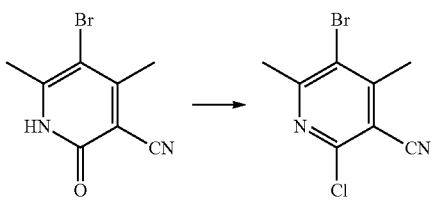

To a solution of 5-bromo-4,6-dimethyl-2-oxo-1,2-dihydropyridine-3-carbonitrile (14 g, 61.7 mmol) in $POCl_3$ (10 mL) was added pentachlorophosphorane (12.84 g, 61.7 mmol). The reaction was heated to reflux for about 8 h. The $POCl_3$ was concentrated under reduced pressure. The resulting residue was partitioned between DCM (100 mL) and 5% aqueous NaOH (100 mL). The combined organic extracts were dried over anhydrous $MgSO_4$, filtered, and concentrated in vacuo. The resulting residue was dissolved in $POCl_3$ (20 mL) and treated with pentachlorophosphorane (13 g, 62.4 mmol). The reaction was heated to reflux for about 12 h. The $POCl_3$ was concentrated under reduced pressure. The resulting residue was partitioned between DCM (100 mL) and 5% aqueous NaOH (100 mL). The combined organic extracts were dried over anhydrous $MgSO_4$, filtered, and concentrated in vacuo to provide 5-bromo-2-chloro-4,6-dimethylnicotinonitrile (12 g, 79%). LCMS (Table 1, Method d) RT=2.12 min.; MS m/z=246, 248 (M+H).

Step C: 5-bromo-4,6-dimethylnicotinonitrile

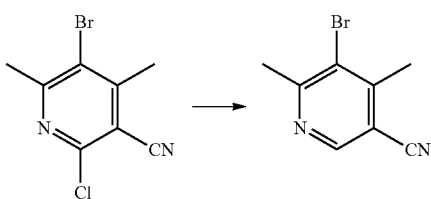

To a mixture of 5-bromo-2-chloro-4,6-dimethylnicotinonitrile (10 g, 40.7 mmol) and red phosphorus (12.62 g, 407 mmol) was added HI (44.7 mL, 489 mmol). The reaction was stirred at about 120° C. for about 4 h. The mixture was cooled to ambient temperature then poured into saturated aqueous $NaHCO_3$ (500 mL) and $Na_2SO_3$ (10 g). The solids were filtered off and the remaining filtrate was concentrated in vacuo. The resulting solid was extracted with MeOH, then concentrated under reduced pressure to provide 5-bromo-4,6-dimethylnicotinonitrile (7 g, 44.0%). LCMS (Table 1, Method f) RT=1.63 min.; MS m/z=211, 213 (M+H).

Step D: 5-bromo-4,6-dimethylnicotinic acid

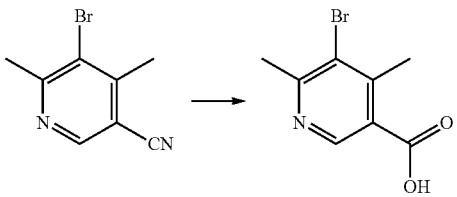

To a mixture of 5-bromo-4,6-dimethylnicotinonitrile (10 g, 47.4 mmol) in water (20 mL) was added KOH (26.6 g, 47.4 mmol). The reaction was stirred at about 110° C. for about 16 h. The reaction mixture was then cooled to ambient temperature and was neutralized by the addition of concentrated HCl. The resulting solid was filtered to provide 5-bromo-4,6-dimethylnicotinic acid (9 g, 79%).
LCMS (Table 1, Method e) RT=1.61 min.; MS m/z=232, 233 (M+H).

Step E: methyl 5-bromo-4,6-dimethylnicotinate

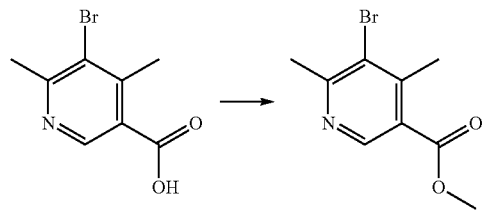

To a solution of 5-bromo-4,6-dimethylnicotinic acid (10 g, 43.5 mmol) in MeOH (10 ml) was added thionyl chloride (5.17 g, 43.5 mmol) at about 0° C. The reaction mixture was heated to about 80° C. After about 12 h, the reaction mixture was concentrated in vacuo. The resulting residue was diluted with DCM, dried over anhydrous $Na_2SO_4$, filtered, and concentrated under reduced pressure to provide methyl 5-bromo-4,6-dimethylnicotinate (9.6 g, 81%). LCMS (Table 1, Method e) RT=1.99 min.; MS m/z=245, 246 (M+H).

Step F: methyl 4,6-dimethyl-5-vinylnicotinate

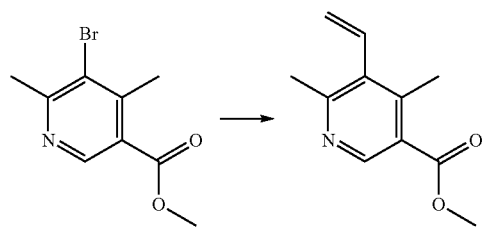

Methyl 5-bromo-4,6-dimethylnicotinate (15 g, 61.5 mmol), 4,4,5,5-tetramethyl-2-vinyl-1,3,2-dioxaborolane (14.2 g, 92 mmol), $Pd(PPh_3)_4$ (7.1 g, 6.1 mmol), and KF (5.4 g, 92 mmol) were combined in DMF (20 mL) The mixture was heated to about 100° C. for about 16 h. The mixture was cooled to rt and the solvent was concentrated in vacuo. The remaining residue was purified by silica gel chromatography (10:1 petroleum ether/EtOAc) to provide methyl 4,6-dimethyl-5-vinylnicotinate (9 g, 56%). LC/MS (Table 1, Method e) RT=1.23 min.; MS m/z=192 (M+H).

Step G: methyl 5-formyl-4,6-dimethylnicotinate

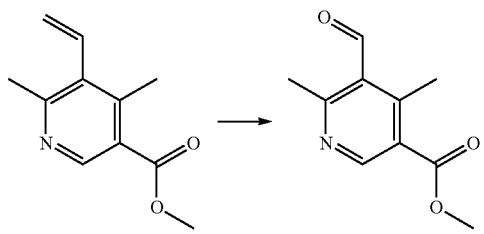

To a solution of methyl 4,6-dimethyl-5-vinylnicotinate (12 g, 62.8 mmol) and 2,6-dimethylpyridine (8 mL, 69 mmol) in a 3:1 mixture of 1,4-Dioxane:Water (50.0 ml) was added OsO$_4$ (12 mL, 0.94 mmol, 0.08 M in t-BuOH) and sodium periodate (40 g, 188 mmol). The mixture was stirred at rt for about 36 h. The reaction mixture was filtered, and the filtrate was washed with saturated aqueous Na$_2$S$_2$O$_3$. The mixture was extracted with EtOAc, dried over anhydrous Na$_2$SO$_4$, filtered, and concentrated in vacuo. The crude material was purified by silica gel chromatography (5:1 to 2:1 petroleum ether: EtOAc) to provide methyl 5-formyl-4,6-dimethylnicotinate (8 g, 59%). LCMS (Table 1, Method d) RT=1.55 min.; MS m/z=194 (M+H).

Step H: methyl 5-(1-hydroxyprop-2-yn-1-yl)-4,6-dimethylnicotinate

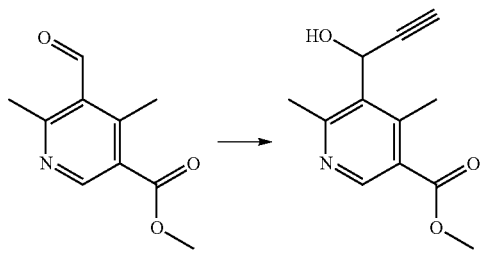

To a solution of methyl 5-formyl-4,6-dimethylnicotinate (8 g, 37.3 mmol) in anhydrous THF (100 ml) at about 0° C. was added ethynyl magnesium bromide (82 ml, 41 mmol) The resulting reaction was stirred at about 0° C. for about 1 h. The reaction was diluted with methylene chloride, washed with saturated aqueous NH$_4$Cl (3×100 mL). The organic layer was dried over anhydrous Na$_2$SO$_4$, filtered, and concentrated in vacuo. The crude material was purified by silica gel chromatography (2:1 hexanes:EtOAc) to provide methyl 5-(1-hydroxyprop-2-yn-1-yl)-4,6-dimethylnicotinate (6 g, 73%).

LCMS (Table 1, Method c) RT=1.73 min.; MS m/z=220 (M+H).

Preparation #37: ethyl 3,5-dichloro-4-(1-hydroxyprop-2-yn-1-yl)picolinate

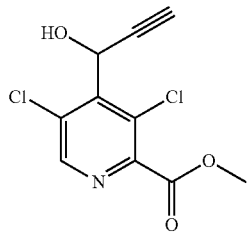 [SMILES: C#CC(O)c1c(Cl)cnc(C(=O)OC)c1Cl]

Step A: 2,3,5-trichloroisonicotinaldehyde

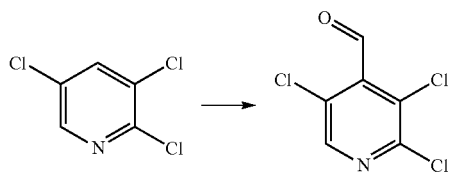 [SMILES: Clc1cnc(Cl)c(Cl)c1 ; O=Cc1c(Cl)cnc(Cl)c1Cl]

To a solution of LDA (99 mL, 197 mmol) in THF (100 mL), was added a solution of 2,3,5-trichloropyridine (30 g, 164 mmol) in THF (200 mL) at about −78° C. The resulting reaction was stirred at about −78° C. for about 1 h. Methyl formate (20 mL, 329 mmol) was added carefully to the reaction, then the mixture was stirred at about −78° C. for about 1 h, then warmed to rt and stirred for 16 h. The reaction was poured into saturated aqueous NH$_4$Cl. The aqueous layer was extracted with EtOAc (3×20 mL). The combined organic layers were dried over anhydrous Na$_2$SO$_4$, filtered through sintered glass funnel, and concentrated under reduced pressure to give 2,3,5-trichloroisonicotinaldehyde (26.2 g, 53%, 70% purity). LCMS (Table 1, Method c) RT=1.83 min.;
MS m/z=209, 211 (M+H).

Step B: 2,3,5-trichloro-4-(diethoxymethyl)pyridine

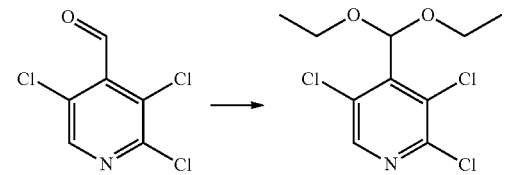 [SMILES: O=Cc1c(Cl)cnc(Cl)c1Cl ; CCOC(OCC)c1c(Cl)cnc(Cl)c1Cl]

A mixture of 2,3,5-trichloroisonicotinaldehyde (26.2 g, 87 mmol), p-toluenesulfonic acid monohydrate (18.23 g, 96 mmol), MgSO$_4$ (11.54 g, 96 mmol) and triethyl orthoformate (21.77 mL, 131 mmol) in DCE (300 mL) was heated to about 50° C. for about 5 h. The solution was diluted with water, extracted with DCM (3×50 mL). The combined organic layers were dried over anhydrous Na$_2$SO$_4$, filtered, and concentrated under reduced pressure to afford 2,3,5-trichloro-4-(diethoxymethyl)pyridine (20.67 g, 75%). LCMS (Table 1, Method d) RT=2.12 min.; MS m/z=284, 286 (M+H).

Step C: ethyl 3,5-dichloro-4-(diethoxymethyl)picolinate

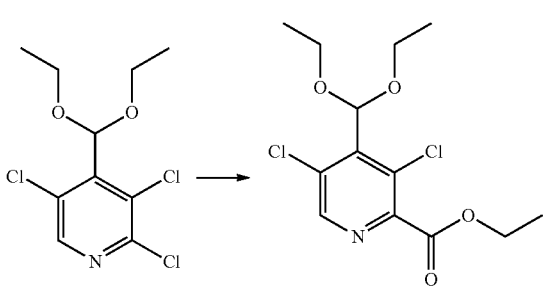 [SMILES: CCOC(OCC)c1c(Cl)cnc(Cl)c1Cl ; CCOC(=O)c1ncc(Cl)c(C(OCC)OCC)c1Cl]

A solution of 2,3,5-trichloro-4-(diethoxymethyl)pyridine (20 g, 70.3 mmol), PdCl$_2$(PPh$_3$)$_2$ (4.93 g, 7.03 mmol), and TEA (29 mL, 211 mmol) in EtOH (200 mL) was treated with CO at a pressure of 30 bar and was heated to about 100° C. in a sealed tube for about 24 h. The reaction was filtered through a pad of celite, and the filtrate was concentrated under reduced pressure. The crude material was purified via silicagel chromatography eluting with 5% EtOAc/Heptanes to give ethyl 3,5-dichloro-4-(diethoxymethyl)picolinate (14 g, 61.8%). LCMS (Table 1, Method d) RT=2.02 min.; MS m/z=322, 324 (M+H).

Step D: ethyl 3,5-dichloro-4-formylpicolinate

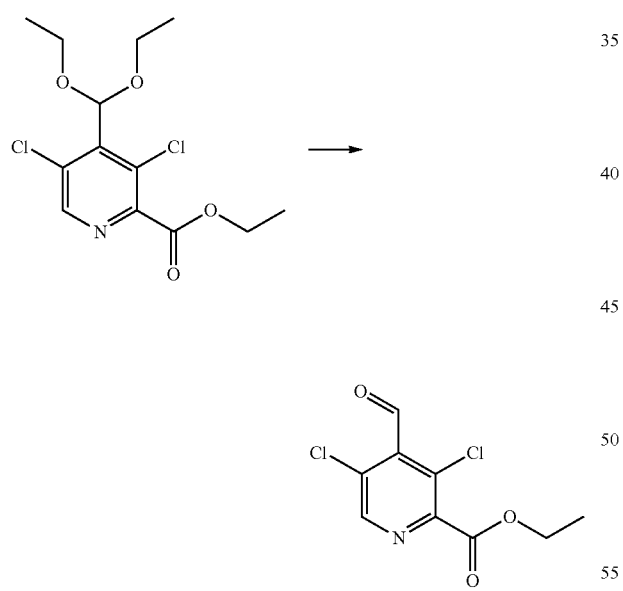

A round bottom flask was charged with a mixture of ethyl 3,5-dichloro-4-(diethoxymethyl)picolinate (14 g, 43.5 mmol) and HCl (100 mL, 3291 mmol). The reaction stirred for about 1 hour at rt. The reaction was diluted with EtOAc, washed with 1N aq. NaOH (3×50 mL). The organic portion was dried over anhydrous Na$_2$SO$_4$, filtered through sintered glass funnel, and concentrated under reduced pressure to give ethyl 3,5-dichloro-4-formylpicolinate (10 g, 93%). LCMS (Table 1, Method d) RT=1.92 min.; MS m/z=247, 249 (M+H).

Step E: ethyl 3,5-dichloro-4-(1-hydroxyprop-2-yn-1-yl)picolinate

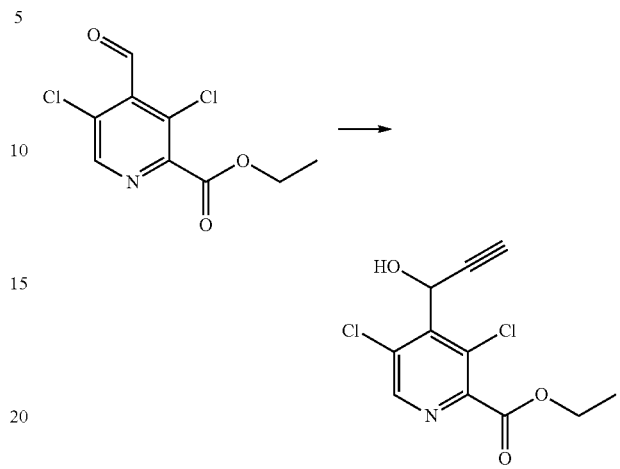

To a solution of ethyl 3,5-dichloro-4-formylpicolinate (9.6 g, 32.9 mmol) in anhydrous THF (100 ml) at about 0° C. was added ethynyl magnesium bromide (72 mL, 36.2 mmol) The resulting reaction was stirred at about 0° C. for about 1 h. The reaction was diluted with methylene chloride, washed with saturated aqueous NH$_4$Cl (3×100 mL). The organic layer was dried over anhydrous Na$_2$SO$_4$, filtered, and concentrated in vacuo. The crude material was purified by silica gel chromatography (10% EtOAc/Heptanes) to provide ethyl 3,5-dichloro-4-(1-hydroxyprop-2-yn-1-yl)picolinate (7.9 g, 88%).

LC/MS (Table 1, Method d) RT=1.65 min.; MS m/z=274, 276 (M+H).

Preparation #38: Preparation of ethyl 4,6-dichloro-5-(1-hydroxyprop-2-yn-1-yl)nicotinate

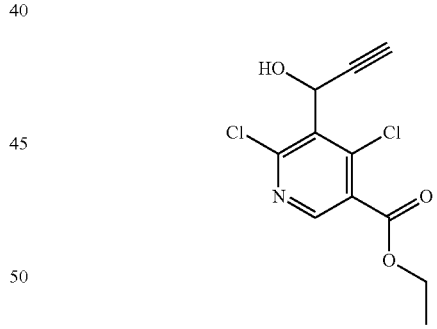

Step A: ethyl 4,6-dichloronicotinate

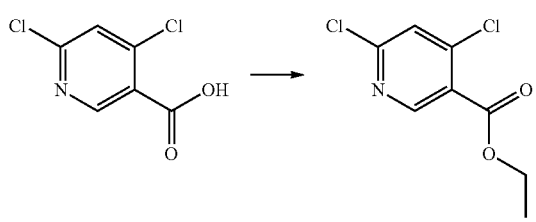

A mixture of 4,6-dichloronicotinic acid (20 g, 104 mmol) in DCM (200 mL) was cooled to 0° C. before the addition of DMF (0.807 ml, 10.42 mmol) and oxalyl chloride (10.94 ml, 125 mmol). The resulting reaction was stirred at about 0° C.-25° C. After about 2 h, EtOH (48.7 ml, 833 mmol) was slowly added and stirred at about 25° C. for 2 h. The reaction mixture was diluted with ether (50 mL) and the resulting solution was washed with saturated aqueous $NaHCO_3$ (3×50 mL). The extracts were combined and dried over anhydrous $Na_2SO_4$, filtered, and the solvent was removed in vacuo to provide ethyl 4,6-dichloronicotinate (18 g. 79%): LC/MS (Table 1, Method d) Rt=1.91 min.; MS m/z=220 (M+H).

Step B: ethyl 4,6-dichloro-5-formylnicotinate

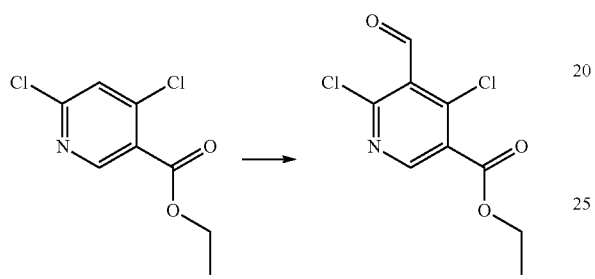

To a flask containing LDA (27.3 mL, 54.5 mmol) in THF (100 mL) was added a solution of ethyl 4,6-dichloronicotinate (10 g, 45.4 mmol) in THF (200 ml) such that the internal temperature was maintained at about −78° C. After about 30 min, methyl formate (5.57 ml, 91 mmol) was added dropwise to the reaction mixture and stirred at −78° C. for 1 h. The reaction mixture was then poured into saturated aqueous $Na_2SO_4$, filtered, and concentrated in vacuo. The residue was purified by silica gel chromatography (20:1 hexanes:EtOAc) to provide ethyl 4,6-dichloro-5-formylnicotinate (5.19 g, 46%). LCMS (Table 1, Method c) RT=1.95 min.; MS m/z=248 (M+H).

Step C: ethyl 4,6-dichloro-5-(1-hydroxyprop-2-yn-1-yl)nicotinate

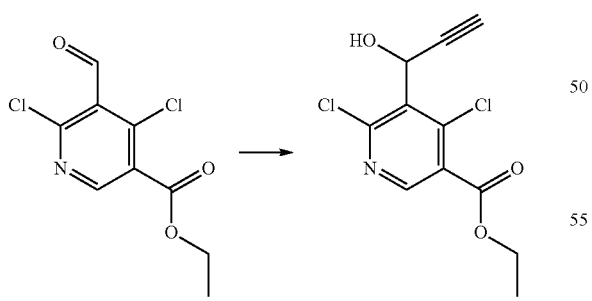

To a solution of ethyl 4,6-dichloro-5-formylnicotinate (12.9 g, 52.0 mmol) in anhydrous THF (120 mL) at about 0° C. was added ethynylmagnesium bromide (114 mL, 57.2 mmol). The resulting reaction was stirred at about 0° C. for about 1 h. The reaction was diluted with methylene chloride, washed with saturated aqueous $NH_4Cl$ (3×100 mL). The organic layer was dried over anhydrous $Na_2SO_4$, filtered, and concentrated in vacuo. The crude material was purified by silica gel chromatography (10:1 Hexanes/EtOAc) to provide ethyl 4,6-dichloro-5-(1-hydroxyprop-2-yn-1-yl) nicotinate (11.1 g, 78%). LCMS (Table 1, Method d) $R_t$=1.70 min.; MS m/z=274 (M+H).

Preparation #39: N-(3-iodo-2-methyl-6-(trifluoromethyl)pyridin-4-yl)benzenesulfonamide

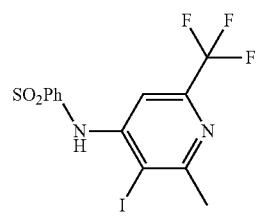

Step A: 2-methyl-4-nitro-6-(trifluoromethyl)pyridine

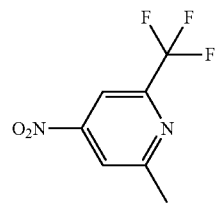

To a solution of 2-bromo-6-methyl-4-nitropyridine (WO2013/059587) (1.84 g, 8.48 mmol) and copper(I) iodide (1.938 g, 10.17 mmol) in NMP (15.73 ml) was added methyl 2,2-difluoro-2-(fluorosulfonyl)acetate (3.24 ml, 25.4 mmol) and the reaction was irradiated under microwave at 100° C. for 5 hours. The reaction mixture was washed with water and extracted with EtOAc. The organic layer was dried over magnesium sulfate, filtered and concentrated under reduced pressure to give 2-methyl-4-nitro-6-(trifluoromethyl)pyridine (1.48 g, 80%). LC/MS (Method h) $R_t$=2.16 min.; no ionization $^1$H NMR (DMSO-$d_6$, 300 MHz): δ 8.41 (d, J=1.8 Hz, 1H), 8.32 (d, J=1.8 Hz, 1H), 2.74 (s, 3H)

Step B: 2-methyl-6-(trifluoromethyl)pyridin-4-amine

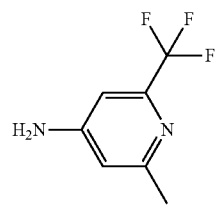

Using a procedure similar to described in Preparation #18 Step C, methyl-6-(trifluoromethyl)pyridin-4-amine (409 mg, 42%) was prepared from 2-methyl-4-nitro-6-(trifluoromethyl)pyridine (1.05 g, 5.09 mmol). LC/MS (Method k) $R_t$=2.15 min.; MS m/z: 177 [M+H]$^+$. $^1$H NMR (DMSO-$d_6$, 300 MHz): δ 6.73 (d, J=1.7 Hz, 1H), 6.49 (d, J=1.7 Hz, 1H), 6.42 (s, 2H), 2.29 (s, 3H).

Step C: 3-iodo-2-methyl-6-(trifluoromethyl)pyridin-4-amine

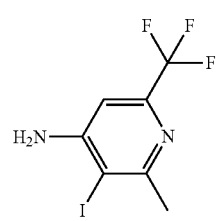

To a solution of 2-methyl-6-(trifluoromethyl)pyridin-4-amine (405 mg, 2.299 mmol) in EtOH (8 mL) was added silver sulfate (717 mg, 2.299 mmol) and iodine (584 mg, 2.299 mmol) and the reaction mixture was stirred at room temperature for 4 hours. The reaction mixture was quenched with a saturated $Na_2S_2O_3$ aqueous solution and extracted twice with EtOAc. The organic layer was dried over magnesium sulfate, filtered and concentrated under reduced pressure. The residue was purified by column chromatography on silica gel (eluting with 5-40% EtOAc in cyclohexane) to give 3-iodo-2-methyl-6-(trifluoromethyl)pyridin-4-amine (608 mg, 88%) as an amorphous solid. LC/MS (Method i) $R_t$=1.78 min.; MS m/z: 303 $[M+H]^+$. $^1H$ NMR (DMSO-$d_6$, 300 MHz): δ 6.86 (s, 1H), 6.63 (broad, 2H), 2.59 (s, 3H).

Step D: N-(3-iodo-2-methyl-6-(trifluoromethyl)pyridin-4-yl)benzenesulfonamide

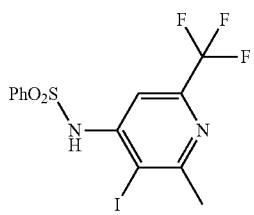

Using a procedure similar to Preparation #16 Step B, N-(3-iodo-2-methyl-6-(trifluoromethyl)pyridin-4-yl)benzenesulfonamide (414 mg, 33%) was prepared from 3-iodo-2-methyl-6-(trifluoromethyl)pyridin-4-amine (740 mg, 2.45 mmol). LC/MS (Method i) $R_t$=2.24 min.; MS m/z: 443 $[M+H]^+$. $^1H$ NMR (DMSO-$d_6$, 300 MHz): δ 7.90 (m, 2H), 7.64 (m, 3H), 7.22 (s, 1H), 2.70 (s, 3H).

Preparation #40: N-(6-cyano-3-iodo-2-methylpyridin-4-yl)benzenesulfonamide

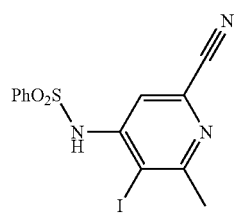

Step A: 4-amino-5-iodo-6-methylpicolinonitrile

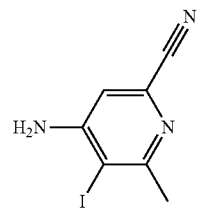

To a solution of 4-amino-6-methylpicolinonitrile (1.756 g, 13.19 mmol) (described in WO2005/030213) in ACN (44.0 ml) was added N-iodosuccinimide (3.26 g, 14.51 mmol) and the reaction mixture was stirred at reflux for 24 hours. The reaction mixture was hydrolyzed with a saturated $Na_2S_2O_3$ aqueous solution and extracted with EtOAc. The organic layer was dried over magnesium sulfate, filtered and concentrated under reduced pressure. The residue was purified by column chromatography on silica gel (eluting with 5-60% EtOAc in cyclohexane) to give 4-amino-5-iodo-6-methylpicolinonitrile (1.18 g, 34%) as a brown solid. LC/MS (Method h) $R_t$=1.55 min.; MS m/z: 260 $[M+H]^+$.

$^1H$ NMR (DMSO-$d_6$, 500 MHz): δ 6.88 (s, 1H), 6.66 (broad, 2H), 2.55 (s, 3H)

Step B: N-(6-cyano-3-iodo-2-methylpyridin-4-yl)benzenesulfonamide

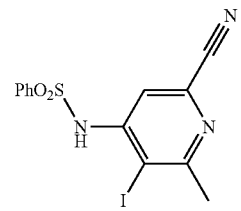

Using a procedure similar to Preparation #16 Step B, N-(6-cyano-3-iodo-2-methylpyridin-4-yl)benzenesulfonamide (400 mg, 23%) was prepared from 4-amino-5-iodo-6-methylpicolinonitrile (1.15 g, 4.44 mmol). The compound was used directly in the next step.

LC/MS (Method h) $R_t$=2.28 min.; MS m/z: 400 $[M+H]^+$.

Preparation #41: 4-methyl-6-(trifluoromethyl)pyridazin-3-amine

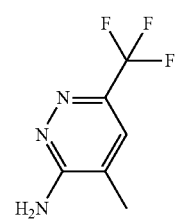

127

Step A:
4-bromo-6-(trifluoromethyl)pyridazin-3-amine

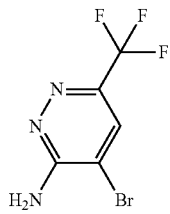 [SMILES: Nc1nnc(C(F)(F)F)cc1Br]

To a solution of 6-(trifluoromethyl)pyridazin-3-amine (730 mg, 4.48 mmol) and sodium bicarbonate (752 mg, 8.95 mmol) in MeOH (15 ml) was added bromine (0.231 ml, 4.48 mmol) dropwise. The reaction mixture was stirred at room temperature for one night, then hydrolyzed with a saturated $Na_2S_2O_3$ aqueous solution. The MeOH was evaporated and the resulting solution was diluted with EtOAc and the two phases were separated. The organic layer was washed with a saturated $Na_2S_2O_3$ aqueous solution, dried over magnesium sulfate, filtered and concentrated under reduced pressure. The residue was purified by column chromatography on silica gel (eluting with 7-60% EtOAc in cyclohexane) to give 4-bromo-6-(trifluoromethyl)pyridazin-3-amine (513 mg, 47%) as a beige solid.

LC/MS (Method i) $R_t$=1.33 min.; MS m/z: 242 [M+H]$^+$.
$^1$H NMR (DMSO-$d_6$, 300 MHz): δ 8.23 (s, 1H), 7.55 (broad, 2H).

Step B:
4-methyl-6-(trifluoromethyl)pyridazin-3-amine

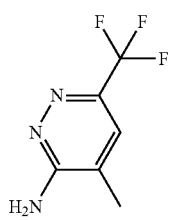

To a solution of 4-bromo-6-(trifluoromethyl)pyridazin-3-amine (460 mg, 1.901 mmol), tris(dibenzylideneacetone)dipalladium(0) (17.41 mg, 0.019 mmol), 2-(dicyclohexylphosphino)-2',4',6'-triisopropylbiphenyl (36.2 mg, 0.076 mmol) and potassium phosphate tribasic (807 mg, 3.80 mmol) in 1,4-dioxane (3.7 mL) was added trimethylboroxine (0.398 ml, 2.85 mmol). The reaction mixture was stirred at 100° C. for one night, then diluted with $H_2O$. The obtained aqueous layer was extracted with EtOAc and the obtained organic layer was dried over magnesium sulfate, filtered and concentrated under reduced pressure. The same procedure was done three times with the obtained residue to increase conversion. The residue was purified by column chromatography on silica gel (eluting with 7-60% EtOAc in cyclohexane) to give 4-methyl-6-(trifluoromethyl)pyridazin-3-amine (318 mg, 94%) as a beige solid. LC/MS (Method i) $R_t$=0.88 min.; MS m/z: 178 [M+H]$^+$.
$^1$H NMR (DMSO-$d_6$, 300 MHz): δ 7.54 (s, 1H), 6.94 (br. s., 2H), 2.09 (s, 3H)

128

Preparation #42:
3,7-dimethyl-5-(trifluoromethyl)-1H-indazole

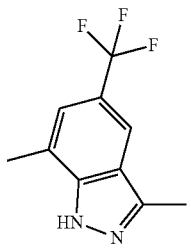

Step A:
2-fluoro-3-methyl-5-(trifluoromethyl)benzaldehyde

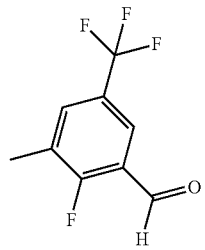

To a solution of 4-fluoro-3-methylbenzotrifluoride (1.5 g, 8.42 mmol) in THF (11 ml) and cooled at −78° C. was added butyllithium (5.42 ml, 8.67 mmol). The mixture was stirred for 30 minutes at −78° C., then a solution of DMF (0.724 ml, 9.35 mmol) in THF (3 ml) was added drop by drop. The reaction was stirred at −78° C. for 1 hour and then warmed to 0° C. A 10% solution of citric acid was added to the reaction mixture at 0° C. and the mixture was extracted with EtOAc. The organic layer was washed with brine and dried over magnesium sulfate, filtered and evaporated to give 2-fluoro-3-methyl-5-(trifluoromethyl)benzaldehyde (2 g, 100%) as a colorless liquid. LC/MS (Method h) $R_t$=2.52 min.; no ionization $^1$H NMR (DMSO-$d_6$, 300 MHz): δ 10.23 (s, 1H), 8.09 (m, 1H), 7.97 (m, 1H), 2.39 ppm (m, 3H)

Step B: 1-(2-fluoro-3-methyl-5-(trifluoromethyl)phenyl)ethanol

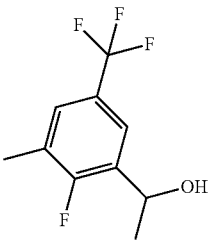

To a solution of 2-fluoro-3-methyl-5-(trifluoromethyl)benzaldehyde (2 g, 9.70 mmol) in THF (42 ml) and cooled at −50° C. was added methylmagnesium bromide (3.88 ml, 11.64 mmol) and the mixture was stirred at room temperature for 2 hours. The mixture was quenched with a NH₄Cl saturated aqueous solution and extracted with EtOAc. The organic layer was washed with brine dried over magnesium sulfate, filtered and evaporated to give 1-(2-fluoro-3-methyl-5-(trifluoromethyl)phenyl)ethanol (1.21 g, 41%) as a colorless liquid: LC/MS (Method h) $R_t$=2.42 min.; MS m/z: 281 [M−H]⁻+CH₃COOH ¹H NMR (DMSO-d₆, 300 MHz): δ 7.65 (m, 1H), 7.59 (m, 1H), 5.53 (d, J=4.6 Hz, 1H), 5.00 (m, 1H), 2.30 (d, J=2.3 Hz, 3H), 1.34 (d, J=6.6 Hz, 3H).

Step C: 1-(2-fluoro-3-methyl-5-(trifluoromethyl) phenyl)ethanone

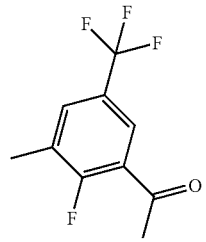

Using a procedure similar to Preparation #14 Step B, 1-(2-fluoro-3-methyl-5-(trifluoromethyl)phenyl)ethanone (854 mg, 75%) was prepared from 1-(2-fluoro-3-methyl-5-(trifluoromethyl)phenyl)ethanol (1.1 g, 4.95 mmol). LC/MS (Method h) $R_t$=2.63 min.; no ionization ¹H NMR (DMSO-d₆, 300 MHz): δ 7.99 (m, 1H), 7.91 (m, 1H), 2.63 (d, J=4.3 Hz, 3H), 2.37 (d, J=2.5 Hz, 3H).

Step D:
3,7-dimethyl-5-(trifluoromethyl)-1H-indazole

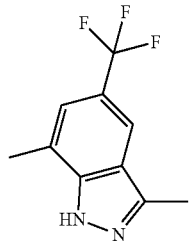

To a solution of 1-(2-fluoro-3-methyl-5-(trifluoromethyl) phenyl)ethanone (200 mg, 0.908 mmol) in ethane-1,2-diol (700 µl, 12.55 mmol) was added hydrazine hydrate (53.0 µL, 1.090 mmol) and the mixture was stirred at room temperature for 20 hours. More hydrazine hydrate (53.0 µL, 1.090 mmol) was added and the mixture was heated to 50° C. for 1 hour. The heated was increased to 170° C. and continued for 2 hours. The mixture was cooled to room temperature: the final indazole precipitated. It was diluted with water, filtrated; and rinsed with water and dried at 50° C. under vacuum to give 3,7-dimethyl-5-(trifluoromethyl)-1H-indazole (130 mg, 61%) as a white solid. LC/MS (Method i) $R_t$=1.99 min.; MS m/z: 215 [M+H]⁺ ¹H NMR (DMSO-d₆, 300 MHz): δ 13.14 (broad, 1H), 7.97 (s, 1H), 7.39 (s, 1H), 2.55 (s, 3H), 2.54 (s, 3H).

Preparation #43:
3,7-dimethyl-5-(trifluoromethyl)-1H-indole

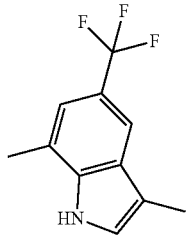

Step A:
N-allyl-2-iodo-6-methyl-4-(trifluoromethyl)aniline

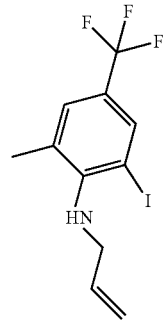 [SMILES: C=CCNc1c(C)cc(C(F)(F)F)cc1I]

To a solution of 2-iodo-6-methyl-4-(trifluoromethyl)aniline (Preparation #34, Step A) (11.1 g, 36.9 mmol) in toluene (56 ml) was added potassium carbonate (7.64 g, 55.3 mmol), tetrabutylammonium bromide (1.189 g, 3.69 mmol), potassium hydroxide (2.276 g, 40.6 mmol) and allyl bromide (5.80 g, 47.9 mmol) The reaction mixture was stirred at 65° C. for 18 hours. More potassium carbonate (0.8 eq), tetrabutylammonium bromide (0.05 eq), potassium hydroxide (0.5 eq) and allyl bromide (0.6 eq) were then added. The reaction mixture was stirred at 65° C. for 18 hours. More potassium carbonate (0.8 eq), tetrabutylammonium bromide (0.05 eq), potassium hydroxide (0.5 eq) and allyl bromide (0.6 eq) were then added. The reaction mixture was stirred at 65° C. for 18 hours. More potassium carbonate (0.8 eq), tetrabutylammonium bromide (0.05 eq), potassium hydroxide (0.5 eq) and allyl bromide (0.6 eq) were then added. The reaction mixture was stirred at 65° C. for 18 hours. The reaction mixture was cooled to 5° C. It was diluted with water and acidified with a 5N HCl solution until pH=3-4. The aqueous layer was extracted with EtOAc. The organic layer was washed with water, brine, dried over magnesium sulfate, filtered and concentrated under reduced pressure. The residue was purified twice by column chromatography on silica gel (eluting with 0-30% EtOAc in cyclohexane) then (eluting with 5-10% EtOAc in cyclohexane) to give N-allyl-2-iodo-6-methyl-4-(trifluoromethyl)aniline (7.25 g, 57%) as an orange oil. LC/MS (Method i) $R_t$=2.69 min.; MS m/z: 342 [M+H]⁺ ¹H NMR (CHLOROFORM-d, 300 MHz): δ 7.82 (s, 1H), 7.32 (s, 1H), 5.96 (dd, J=17.2, 10.2 Hz, 1H), 5.30 (dd, J=17.2, 1.4 Hz, 1.4H, 1H), 5.16 (dd, J=10.2, 1.4 Hz, 1H), 3.84 (broad, 1H), 3.73 (d, J=5.8 Hz, 2H), 2.38 (s, 3H), Step B: 3,7-dimethyl-5-(trifluoromethyl)-1H-indole

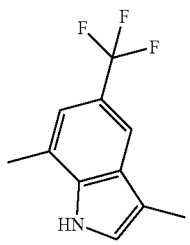

To a solution of N-allyl-2-iodo-6-methyl-4-(trifluoromethyl)aniline (1 g, 2.93 mmol) in ACN (5 ml) was added palladium(II) acetate (0.013 g, 0.059 mmol) and tri-o-tolylphosphine (0.036 g, 0.117 mmol) The reaction mixture was warmed-up to 45° C. and triethylamine (1.5 ml) was added. The reaction mixture was stirred at 75° C. for 15 hours. More palladium(II) acetate (0.05 eq) and tri-o-tolylphosphine (0.1 eq) were added and the stirring was continued for 2 hours. The reaction mixture was cooled to room temperature and the solvent was removed under reduced pressure. EtOAc was added to the residue and the obtained precipitate was filtered and washed with EtOAc. The filtrate was concentrated under reduce pressure. This residue was purified by column chromatography on silica gel (eluting with 0-15% EtOAc in cyclohexane) to give 3,7-dimethyl-5-(trifluoromethyl)-1H-indole (460 mg, 68%) as an orange oil. LC/MS (Method i) $R_t$=2.32 min.; MS m/z: 214 [M+H]$^+$
1H NMR (DMSO-d$_6$, 300 MHz): δ 11.18 (broad, 1H), 7.67 (s, 1H), 7.28 (s, 1H), 7.16 (s, 1H), 2.51 (s, 3H), 2.29 (s, 3H)

Preparation #44: tert-butyl 2,4-dichloro-3-(chlorocarbonyl)benzoate

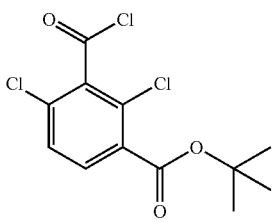 [SMILES: CC(C)(C)OC(=O)c1ccc(Cl)c(C(=O)Cl)c1Cl]

Step A: 3-(tert-butoxycarbonyl)-2,6-dichlorobenzoic acid

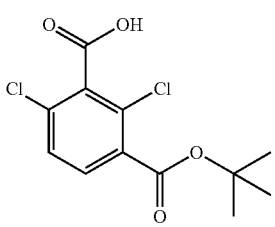 [SMILES: CC(C)(C)OC(=O)c1ccc(Cl)c(C(=O)O)c1Cl]

To a solution of tert-butyl 2,4-dichlorobenzoate (Preparation #33, Step A) (15 g, 60.7 mmol) in THF (100 ml). and cooled at −70° C. was added lithium diisopropylamide (36.4 mL, 72.8 mmol). The reaction mixture was stirred for 90 minutes at −70° C. then crushed carbon dioxide (30 g, 682 mmol) dried over magnesium sulfate was added. The reaction mixture was stirred for 15 minutes between −65° C. and −70° C. then warmed to room temperature. The reaction mixture was diluted with water and the THF was evaporated. The basic aqueous layer was washed with diethyl ether then acidified to pH=1 by addition of 1N HCl solution and extracted with EtOAc. The organic layer was washed with saturated NaCl solution, dried over magnesium sulfate, and concentrated to give 3-(tert-butoxycarbonyl)-2,6-dichlorobenzoic acid (13 g, 74%) a beige solid. LC/MS (Method i) $R_t$=1.53 min.; no ionization
$^1$H NMR (DMSO-d$_6$, 300 MHz): δ 7.76 (d, J=8.4 Hz, 1H), 7.65 (d, J=8.4 Hz, 1H), 1.55 (s, 9H).

Step B: tert-butyl 2,4-dichloro-3-(chlorocarbonyl)benzoate

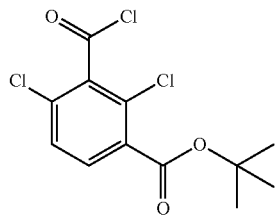 [SMILES: CC(C)(C)OC(=O)c1ccc(Cl)c(C(=O)Cl)c1Cl]

To a solution of 3-(tert-butoxycarbonyl)-2,6-dichlorobenzoic acid (455 mg, 1.563 mmol) in DCM (23 mL) and cooled at 0° C. was added oxalyl chloride (0.205 mL, 2.344 mmol) diluted in DCM (2 mL) with 2 drops of DMF. The reaction mixture was stirred for 45 minutes at 0° C. The reaction mixture was concentrated in vacuo to give tert-butyl 2,4-dichloro-3-(chlorocarbonyl)benzoate which was used directly crude in the next step.

Preparation #45: 3,7-dimethyl-1H-indole-5-carbonitrile

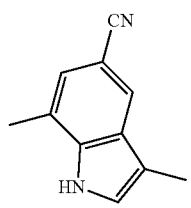

4-amino-3-chloro-5-methylbenzonitrile (250 mg, 1.501 mmol), potassium carbonate (622 mg, 4.50 mmol), 3-bromoprop-1-ene (0.130 mL, 1.501 mmol), dicyclohexyl(2',4',6'-triisopropyl-[1,1'-biphenyl]-2-yl)phosphine (71.5 mg, 0.150 mmol) were dissolved in DME (7.5 ml) and palladium (II) acetate (16.84 mg, 0.075 mmol) was added. The reaction mixture was stirred 95 minutes at 150° C. under microwave irradiation. The reaction mixture was concentrated to dryness and the residue was purified by column chromatography on silica gel (eluting with 15-20% EtOAc in cyclohexane) to give 3,7-dimethyl-1H-indole-5-carbonitrile (107 mg, 25%) as a pale yellow solid. LC/MS (Method i) $R_t$=1.91 min.; MS m/z: 171 [M+H]$^+$. $^1$H NMR (DMSO-d$_6$, 300

MHz): δ 11.34 (broad, 1H), 7.86 (s, 1H), 7.30 (s, 1H), 7.22 (s, 1H), 2.47 (s, 3H), 2.27 (s, 3H)

Preparation #46: N-(2-bromo-5-cyano-3-methylphenyl)benzenesulfonamide

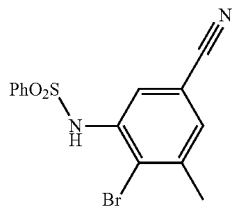

Using a procedure similar to Preparation #16 Step B, N-(2-bromo-5-cyano-3-methylphenyl)benzenesulfonamide (2.03 g, 67%) was obtained as an orange solid from 3-amino-4-bromo-5-methylbenzonitrile (described in Journal of Medicinal Chemistry, 2007, 50, 6519-6534) (1.5 g, 7.11 mmol). LC/MS (Method h) $R_t$=2.48 min.; MS m/z: 349 [M–H]⁻

¹H NMR (CDCl₃, 300 MHz): δ 7.81 (m, 3H), 7.59 (m, 1H), 7.49 (m, 2H), 7.24 (m, 2H), 2.36 (s, 3H).

Preparation #47: N-(2-iodo-3-methyl-5-(trifluoromethoxy)phenyl)benzenesulfonamide

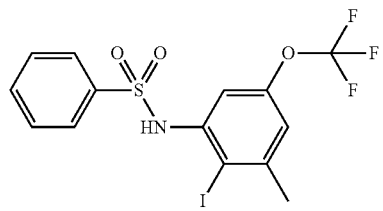 [SMILES: Cc1cc(OC(F)(F)F)cc(NS(=O)(=O)c2ccccc2)c1I]

Step A: 2,2,2-trifluoro-N-(2-methyl-6-nitro-4-(trifluoromethoxy)phenyl)acetamide

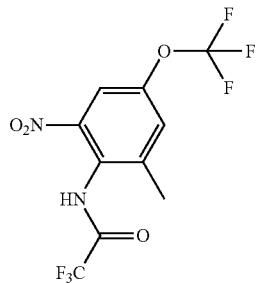 [SMILES: Cc1cc(OC(F)(F)F)cc([N+](=O)[O-])c1NC(=O)C(F)(F)F]

To a solution of 2-methyl-4-(trifluoromethoxy)aniline (1 g, 5.23 mmol) in DCM (4 ml) and cooled to 0° C. was added 2,2,2-trifluoroacetic anhydride (1.921 mL, 13.60 mmol) and the mixture was stirred for one hour at 0° C. Potassium nitrate (0.661 g, 6.54 mmol) was added slowly at 0° C. and the mixture was stirred at room temperature for 3 hours. The mixture was diluted with water and extracted three times with DCM. The organic phases were washed with a saturated NaCl solution, dried on magnesium sulfate, filtered and evaporated to give 2,2,2-trifluoro-N-(2-methyl-6-nitro-4-(trifluoromethoxy)phenyl)acetamide (1.7 g, 100%) as a yellow solid. LC/MS (Method i) $R_t$=2.17 min.; MS m/z: 331 [M–H]⁻ ¹H NMR (DMSO-d₆, 300 MHz): δ=11.59 (s, 1H), 8.05 (m, 1H), 7.88 (m, 1H), 2.35 (s, 3H).

Step B: 2-methyl-6-nitro-4-(trifluoromethoxy)aniline

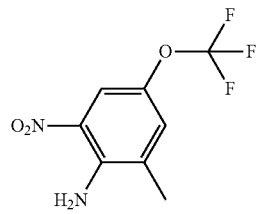 [SMILES: Cc1cc(OC(F)(F)F)cc([N+](=O)[O-])c1N]

To a solution of 2,2,2-trifluoro-N-(2-methyl-6-nitro-4-(trifluoromethoxy)phenyl)acetamide (4 g, 12.04 mmol) in MeOH (80 ml) was added potassium carbonate (6.66 g, 48.2 mmol) and the reaction mixture was stirred at 85° C. for 36 hours. The solvent was evaporated, the residue was diluted with ethylacetate and water and neutralised by addition of a 1N HCl solution. After two extraction with ethylacetate, the organic layers were washed with brine, dried on magnesium sulfate and evaporated to give 2-methyl-6-nitro-4-(trifluoromethoxy)aniline (3.24 g, 100%). LC/MS (Method i) $R_t$=2.16 min.; MS m/z: 235 [M–H]⁻

¹H NMR (DMSO-d₆, 300 MHz): d=7.83 (d, J=2.8 Hz, 1H), 7.47 (d, J=2.8 Hz, 1H), 7.33 (br, 2H), 2.25 (s, 3H)

Step C: 2-iodo-1-methyl-3-nitro-5-(trifluoromethoxy)benzene

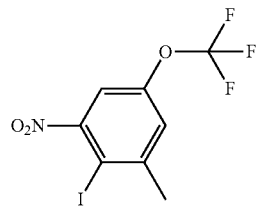 [SMILES: Cc1cc(OC(F)(F)F)cc([N+](=O)[O-])c1I]

To a solution of 2-methyl-6-nitro-4-(trifluoromethoxy)aniline (2.5 g, 10.59 mmol) in water (10.6 ml) was added drop by drop concentrated hydrochloric acid (10.61 ml, 349 mmol) The insoluble solution was cooled to 0° C., then a solution of sodium nitrite (1.169 g, 16.94 mmol) in water (15 ml) was added drop by drop in order to keep the temperature below 10° C. The reaction mixture was stirred 1 hour between 0° C. and 10° C. A solution of potassium iodide (5.27 g, 31.8 mmol) in water (15 ml) was added drop by drop in order to keep the temperature below 10° C. and the reaction mixture was stirred one hour at 5-10° C. A saturated sodium thiosulfate solution was added and the reaction was extracted three times with EtOAc. The organic layers were washed with a saturated NaCl solution, dried on magnesium sulfate, filtered and evaporated. The residue was purified by column chromatography on silica gel (eluting with 5-20% EtOAc in cyclohexane) to give 2-iodo-1-methyl-3-nitro-5-

(trifluoromethoxy)benzene (2.81 g, 76%) as a yellow oil. LC/MS (Method i) $R_t$=2.43 min.; no ionisation $^1$H NMR (DMSO-d$_6$, 300 MHz): d=7.89 (d, J=2.0 Hz, 1H), 7.72 (d, J=2.0 Hz, 1H), 2.55 (s, 3H).

Step D: 2-iodo-3-methyl-5-(trifluoromethoxy)aniline

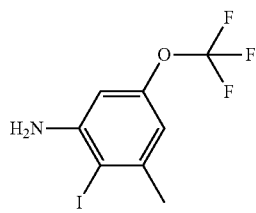

To a solution of 2-iodo-1-methyl-3-nitro-5-(trifluoromethoxy)benzene (2 g, 5.76 mmol) in EtOH (50 ml) was added iron (0.805 g, 14.41 mmol), water (10.42 ml) and hydrochloric acid (0.154 ml, 5.07 mmol) and the reaction mixture was stirred at 80° C. for one night. The reaction mixture was filtered and the solid was washed with EtOH. The filtrate was concentrated under reduced pressure and the residue was purified by column chromatography on silica gel (eluting with 5-20% EtOAc in cyclohexane) to give 2-iodo-3-methyl-5-(trifluoromethoxy)aniline (1.36 g, 75%) as a brown liquid.

LC/MS (Method i) $R_t$=2.38 min.; MS m/z: 318 [M+H]$^+$ $^1$H NMR (DMSO-d$_6$, 300 MHz): δ 6.56 (s, 1H), 6.52 (s, 1H), 5.62 (s, 2H), 2.33 (s, 3H)

Step E: N-(2-iodo-3-methyl-5-(trifluoromethoxy)phenyl)benzenesulfonamide

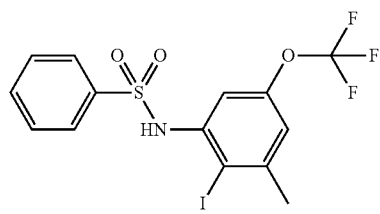 [SMILES: Cc1cc(OC(F)(F)F)cc(NS(=O)(=O)c2ccccc2)c1I]

Using a procedure similar to Preparation #16 Step B, N-(2-iodo-3-methyl-5-(trifluoromethoxy)phenyl)benzenesulfonamide (1.98 g, 100%) was prepared from 2-iodo-3-methyl-5-(trifluoromethoxy)aniline (1.36 g, 4.29 mmol). LC/MS (Method i) $R_t$=2.47 min.; MS m/z: 456 [M−H]$^-$ $^1$H NMR (DMSO-d$_6$, 300 MHz): δ 10.02 (s, 1H), 7.71 (m, 3H), 7.59 (m, 2H), 7.28 (m, 1H), 6.62-6.70 (m, 1H), 2.41 (s, 3H).

Preparation #48:
6-bromo-4-chloro-1-(phenylsulfonyl)-1H-indole

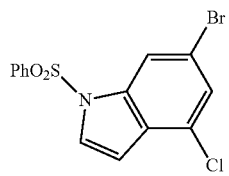

To a solution of 6-bromo-4-chloro-1H-indole (1 g, 4.34 mmol) in N,N-dimethylformamide (10 ml) and cooled to 0° C. was added sodium hydride (0.208 g, 5.21 mmol) and the reaction mixture was stirred at 0° C. during 1 hour. Benzenesulfonyl chloride (0.668 ml, 5.21 mmol) was added and the reaction mixture was stirred at room temperature for 2 hours. The reaction mixture was diluted with a saturated NH$_4$Cl solution and extracted with EtOAc. The organic layer was dried over magnesium sulfate, filtered and concentrated under reduced pressure. The residue was purified by column chromatography on silica gel (eluting with 5-40% EtOAc in cyclohexane) to give 6-bromo-4-chloro-1-(phenylsulfonyl)-1H-indole (1.57 g, 98%) as a beige solid. LC/MS (Method i) $R_t$=2.71 min.; no ionisation $^1$H NMR (DMSO-d$_6$, 300 MHz): δ 8.05 (m, 4H), 7.75 (m, 1H), 7.65 (m, 3H), 6.90 (dd, J=3.8, 0.8 Hz, 1H)

Preparation #49:
7-methyl-5-(trifluoromethyl)-1H-indole

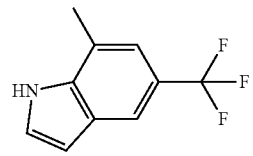

Step A: N-(2-methyl-4-(trifluoromethyl)-6-((trimethylsilyl)ethynyl)phenyl)benzenesulfonamide

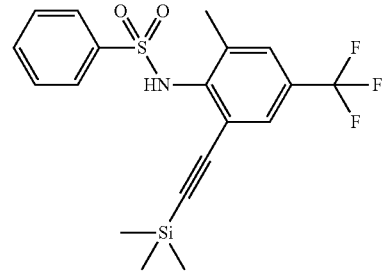 [SMILES: Cc1cc(C(F)(F)F)cc(C#C[Si](C)(C)C)c1NS(=O)(=O)c1ccccc1]

To a solution of N-(2-iodo-6-methyl-4-(trifluoromethyl)phenyl)benzenesulfonamide (Preparation #34) (400 mg, 0.907 mmol) in THF (4.5 mL) were added bis(triphenylphosphine)palladium dichloride (31.8 mg, 0.045 mmol), copper(I) iodide (17.27 mg, 0.091 mmol), trimethylsilylacetylene (351 μl, 2.54 mmol) and triethylamine (4.5 ml). The reaction mixture was stirred at 65° C. under microwaves for 1.5 hours. The reaction mixture was filtered, rinsed with EtOAc and the filtrate was evaporated to give N-(2-methyl-4-(trifluoromethyl)-6-((trimethylsilyl)ethynyl)phenyl)benzenesulfonamide (495 mg, 100%) as a brown solid. LC/MS (Method i) $R_t$=2.76 min.; MS m/z: 412 [M+H]$^+$ $^1$H NMR (DMSO-d$_6$, 300 MHz): δ 9.65 (br, 1H), 7.70 (m, 2H), 7.55 (m, 5H), 2.07 (s, 3H), 0.15 (m, 9H).

Step B: N-(2-ethynyl-6-methyl-4-(trifluoromethyl)phenyl)benzenesulfonamide

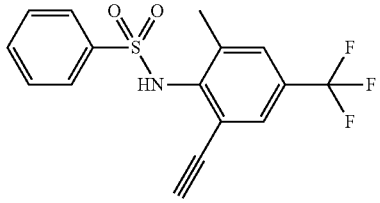 [SMILES: C#Cc1cc(C(F)(F)F)cc(C)c1NS(=O)(=O)c1ccccc1]

To a solution of N-(2-methyl-4-(trifluoromethyl)-6-((trimethylsilyl)ethynyl)phenyl)benzenesulfonamide (373 mg, 0.906 mmol) in THF (3.2 mL) and cooled 0° C. was added tetrabutylamonium fluoride (4.08 ml, 4.08 mmol) and the reaction mixture was stirred at 0° C. for 15 minutes. The reaction mixture was quenched with citric acid and diluted with water. It was then extracted with EtOAc. The organic layer was washed with brine, dried over magnesium sulfate, filtered and evaporated under reduced pressure to give N-(2-ethynyl-6-methyl-4-(trifluoromethyl)phenyl)benzenesulfonamide (413 mg, 100%). The compound was used crude in the next step. LC/MS (Method i) $R_t$=2.28 min.; MS m/z: 338 [M–H]$^-$

Step C: 7-methyl-1-(phenylsulfonyl)-5-(trifluoromethyl)-1H-indole

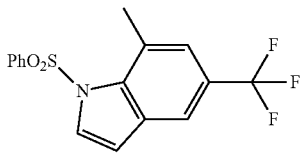

To a solution of N-(2-ethynyl-6-methyl-4-(trifluoromethyl)phenyl)benzenesulfonamide (308 mg, 0.908 mmol) in dichloroethane (4.5 ml) was added copper (II) acetate (165 mg, 0.908 mmol) and the reaction was heated at 150° C. under microwave The reaction mixture was filtered and the filtrate was concentrated under reduced pressure. The residue was purified by column chromatography on silica gel (eluting with 0-15% EtOAc in cyclohexane) to give 7-methyl-1-(phenylsulfonyl)-5-(trifluoromethyl)-1H-indole (231 mg, 75%) as a pink oil. LC/MS (Method i) $R_t$=2.59 min.; MS m/z: 340 [M+H]$^+$ $^1$H NMR (DMSO-d$_6$, 300 MHz): δ 8.06 (d, J=3.8 Hz, 1H), 7.93 (s, 1H), 7.76 (m, 3H), 7.64 (m, 2H), 7.41 (m, 1H), 7.05 (d, J=3.8 Hz, 1H), 2.53 (s, 3H).

Step D: 7-methyl-5-(trifluoromethyl)-1H-indole

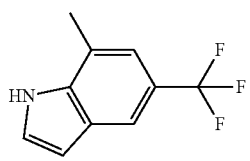

To a solution of 7-methyl-1-(phenylsulfonyl)-5-(trifluoromethyl)-1H-indole (230 mg, 0.68 mmol) in THF (8.4 mL) was added tetrabutylamonium fluoride (813 µL, 0.813 mmol) and the reaction mixture was stirred at 65 C for 2.5 hours. The reaction mixture was concentrated under reduced pressure. The residue was taken in DCM and washed with an saturated NaHCO$_3$ solution. The organic layer was then dried over magnesium sulfate, filtered and evaporated under reduced pressure. The residue was purified by column chromatography on silica gel (eluting with 0-20% EtOAc in cyclohexane) to give 7-methyl-5-(trifluoromethyl)-1H-indole (83 mg, 61%). LC/MS (Method i) $R_t$=2.20 min.; MS m/z: 198 [M–H]$^-$ $^1$H NMR (DMSO-d$_6$, 300 MHz): δ 11.52 (br, 1H), 7.77 (m, 1H), 7.50 (m, 1H), 7.17 (s, 1H), 6.60 (m, 1H), 2.54 (s, 3H).

Preparation #50: methyl 2-(3-methylpiperidin-4-yl)acetate hydrochloride

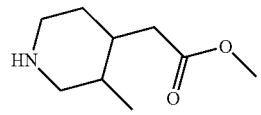

Step A: (E)-ethyl 4-(2-ethoxy-2-oxoethylidene)-3-methylpiperidine-1-carboxylate

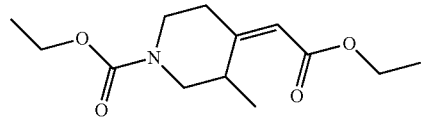 [SMILES: CCOC(=O)/C=C1/CCN(C(=O)OCC)CC1C]

To a suspension of sodium hydride (0.972 g, 24.30 mmol) in 1,2-dimethoxyethane (30 ml) and cooled to 0° C. was added triethyl phosphonoacetate (4.52 mL, 22.68 mmol) in solution in 1,2-dimethoxyethane (30.0 ml) and the reaction mixture was stirred at 0° C. during 30 minutes and 1 hour at room temperature. The reaction mixture was cooled to 10° C. and ethyl 3-methyl-4-oxopiperidine-1-carboxylate (3 g, 16.20 mmol) in 1,2-dimethoxyethane (30.0 mL) was added dropwise to the reaction mixture. The reaction mixture was stirred at room temperature during 3 hours. The reaction mixture was quenched with water and extracted with EtOAc. The obtained organic layer was dried over magnesium sulfate, filtered and concentrated under reduced pressure. The residue was purified by column chromatography on silica gel (eluting with 0-20% EtOAc in cyclohexane) to give (E)-ethyl 4-(2-ethoxy-2-oxoethylidene)-3-methylpiperidine-1-carboxylate (3.6 g, 87%) as a pale yellow liquid. LC/MS (Method i) $R_t$=2.05 min.; MS m/z: 256 [M+H]$^+$

Step B: ethyl 4-(2-ethoxy-2-oxoethyl)-3-methylpiperidine-1-carboxylate

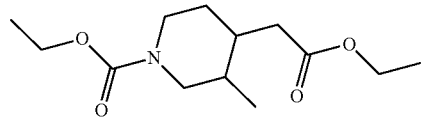 [SMILES: CCOC(=O)CC1CCN(C(=O)OCC)CC1C]

To a solution of (E)-ethyl 4-(2-ethoxy-2-oxoethylidene)-3-methylpiperidine-1-carboxylate (3.60 g, 14.10 mmol) in EtOH (100 mL) was added palladium on carbon (0.36 g, 3.38 mmol) and the reaction was stirred under hydrogen (1 atm) for 3 hours. The reaction mixture was filtered and the filtrate was concentrated under reduced pressure to give ethyl 4-(2-ethoxy-2-oxoethyl)-3-methylpiperidine-1-carboxylate (3.6 g, 100%).

Step C: 2-(3-methylpiperidin-4-yl)acetic acid hydrochloride

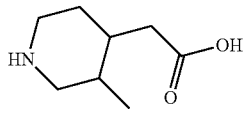

A solution of ethyl 4-(2-ethoxy-2-oxoethyl)-3-methylpiperidine-1-carboxylate (200 mg, 0.777 mmol) in hydrochloric acid (1 mL, 3.29 mmol) was stirred at reflux during one night. The reaction mixture was diluted with H2O and lyophilisated to give 2-(3-methylpiperidin-4-yl)acetic acid hydrochloride (151 mg, 100%).

Step D: methyl 2-(3-methylpiperidin-4-yl)acetate hydrochloride

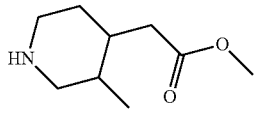

To a solution of 2-(3-methylpiperidin-4-yl)acetic acid hydrochloride (151 mg, 0.780 mmol in MeOH (2 ml) and cooled to 0° C. was added thionyl chloride (0.566 mL, 7.80 mmol) and d the reaction mixture was stirred at reflux during 4 hours. The reaction mixture was concentrated under vacuum to give methyl 2-(3-methylpiperidin-4-yl)acetate hydrochloride (151 mg, 93%) as a yellow oil. (70% of cis, 30% of trans).

Preparation #51: 1,4-dimethyl-6-(trifluoromethyl)-1H-indole-3-carbaldehyde

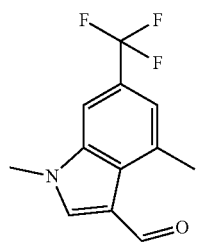

Step A: N-(3-methyl-5-(trifluoromethyl)-2-((trimethylsilyl)ethynyl)phenyl)benzenesulfonamide

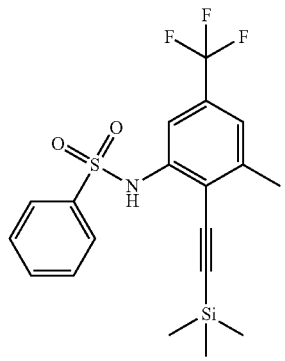 [SMILES: Cc1cc(C(F)(F)F)cc(NS(=O)(=O)c2ccccc2)c1C#C[Si](C)(C)C]

To a solution of N-(2-iodo-3-methyl-5-(trifluoromethyl)phenyl)benzenesulfonamide (5 g, 11.33 mmol) in THF (40 mL) was added bis(triphenylphosphine)palladium(II) dichloride (0.398 g, 0.567 mmol), cuprous iodide (0.216 g, 1.133 mmol), trimethylsilylacetylene (3.12 g, 31.7 mmol) and triethylamine (40.0 mL) and the reaction mixture was stirred at 65° C. under microwaves for 1.5 hours. The reaction mixture was filtered and concentrated under reduced pressure to give N-(3-methyl-5-(trifluoromethyl)-2-((trimethylsilyl)ethynyl)phenyl)benzenesulfonamide (4.5 g, 85%) as an orange resin. The product is used crude in the next step.

LC/MS (Method j) R$_t$=2.85 min.; MS m/z: 412 [M+H]$^+$

Step B: 4-methyl-1-(phenylsulfonyl)-6-(trifluoromethyl)-1H-indole

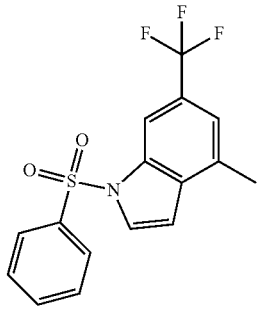 [SMILES: Cc1cc(C(F)(F)F)cc2c1ccn2S(=O)(=O)c1ccccc1]

To a solution of N-(3-methyl-5-(trifluoromethyl)-2-((trimethylsilyl)ethynyl)phenyl)benzenesulfonamide (4.5 g, 10.94 mmol) in THF (40 mL) and cooled to 0° C. was added tetrabutylammonium fluoride (12.87 g, 49.2 mmol) and the reaction mixture was stirred at 0° C. for 1 hour and at room temperature for 1 hour. The reaction mixture was quenched with citric acid and diluted with water. It was extracted with EtOAc. The organic layer was washed with brine, dried over magnesium sulfate, filtered and evaporated under reduced pressure to give 4-methyl-1-(phenylsulfonyl)-6-(trifluoromethyl)-1H-indole (3.5 g, 84%) as a brown solid. LC/MS (Method i) R$_t$=2.58 min.; MS m/z: 338 [M−H]$^-$ $^1$H NMR (CHLOROFORM-d, 300 MHz): δ 8.12 (s, 1H), 7.90 (m, 2H), 7.70 (d, J=3.3 Hz, 1H), 7.56 (m, 1H), 7.48 (m, 2H), 7.28 (m, 1H), 6.74 (d, J=3.3 Hz, 1H), 2.52 (s, 3H)

Step C: 4-methyl-6-(trifluoromethyl)-1H-indole

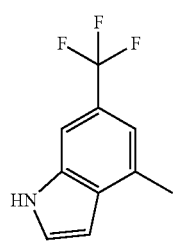

To a solution of 4-methyl-1-(phenylsulfonyl)-6-(trifluoromethyl)-1H-indole (3.1 g, 9.14 mmol) in THF (10 mL) was added tetrabutylammonium fluoride (10.96 mL, 10.96 mmol) and the reaction mixture was stirred at 60° C. for 1.5 hours. More tetrabutylammonium fluoride (0.6 eq) was added and the stirring was continued for 3 hours. More tetrabutylammonium fluoride (0.9 eq) was added and the stirring was continued for 18 hours. More tetrabutylammonium fluoride (0.9 eq) was added and the stirring was continued for 3 hours. The reaction mixture was concentrated under reduced pressure. The residue was taken in dichloromathane and washed with an saturated $NaHCO_3$ solution. The organic layer was then dried over magnesium sulfate, filtered and evaporated under reduced pressure. The residue was purified by column chromatography on silica gel (eluting with 0-20% EtOAc in cyclohexane) to give 4-methyl-6-(trifluoromethyl)-1H-indole (1.18 g, 62%) as a pale brown oil.

LC/MS (Method i) $R_t$=2.24 min.; MS m/z: 198 [M−H]$^−$ $^1$H NMR (CHLOROFORM-d, 300 MHz): δ 8.30 (br, 1H), 7.53 (s, 1H), 7.34 (t, J=2.9 Hz, 1H), 7.15 (s, 1H), 6.62 (td, J=2.9, 1.1 Hz, 1H), 2.60 (s, 3H)

Step D: 4-methyl-6-(trifluoromethyl)-1H-indole-3-carbaldehyde

To as solution of N,N-dimethylformamide (1.431 mL, 18.48 mmol) in DCM (15 ml) and cooled at 0° C. was added oxalyl chloride (1.617 mL, 18.48 mmol) diluted in DCM (15 mL) and the reaction mixture was stirred for 30 minutes. It was then added dropwise to a solution of 4-methyl-6-(trifluoromethyl)-1H-indole (920 mg, 4.62 mmol) in DCM (15 mL) and the reaction mixture was stirred at room temperature for 1 hour. A 5N NaOH solution was added until pH 10. The aqueous layer was extracted with DCM. The organic layer was dried over magnesium sulfate, filtered and concentrated under reduced pressure to give 4-methyl-6-(trifluoromethyl)-1H-indole-3-carbaldehyde (1 g, 78%) as a brown solid. The compound is used crude in the next step.

LC/MS (Method i) $R_t$=1.96 min.; MS m/z: 228 [M+H]$^+$

Step E: 1,4-dimethyl-6-(trifluoromethyl)-1H-indole-3-carbaldehyde

To a solution of 4-methyl-6-(trifluoromethyl)-1H-indole-3-carbaldehyde (1.09 g, 4.80 mmol) in DMF, (60 ml) was added sodium hydride (0.192 g, 4.80 mmol) and the reaction mixture was stirred at room temperature for 30 minutes. iodomethane (0.300 ml, 4.80 mmol) was added and the reaction mixture was stirred one hour at room temperature. The reaction mixture was diluted with water. The obtained precipitate was filtered, washed with water and concentrated to dryness to give 1,4-dimethyl-6-(trifluoromethyl)-1H-indole-3-carbaldehyde (815 mg, 70%) as a pink solid. LC/MS (Method i) $R_t$=2.09 min.; MS m/z: 242 [M+H]$^+$ $^1$H NMR (DMSO-$d_6$, 300 MHz): δ 9.98 (s, 1H), 8.46 (s, 1H), 7.83 (s, 1H), 7.35 (s, 1H), 3.96 (s, 3H), 2.84 (s, 3H)

Preparation #52: 1-methyl-6-(trifluoromethoxy)-1H-indole-2-carbaldehyde

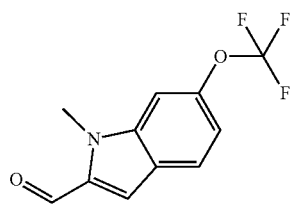 [SMILES: Cn1c(C=O)cc2ccc(OC(F)(F)F)cc21]

Step A: methyl (Z)-2-azido-3-(4-(trifluoromethoxy)phenyl)acrylate

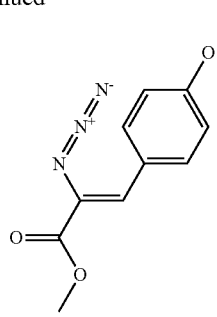

In a round-bottomed flask equipped with mechanical stirring, 25% sodium methoxide in MeOH (107 mL, 480 mmol) in was added to MeOH (MeOH) (80 mL) to give a colorless solution and it was cooled to approx. −20° C. A mixture of 4-(trifluoromethoxy)benzaldehyde (38.8 g, 204 mmol) and methyl-2-azidoacetate (55.22 g, 480 mmol) were added dropwise over 15 minutes, keeping the temperature at approx. −20° C. After the addition was complete the reaction became a thick yellow oil. Warmed to 0-5° C. After 1 h the mixture was poured into a 2 M aqueous HCl (400 mL)/MTBE (400 mL) mixture. Separated layers and extracted aqueous phase with MTBE (2×200 mL). Washed combined organics over brine, dried over sodium sulfate and removed solvent in vacuo. Gave 80.43 g of crude material as an orange oil. The crude material was chromatographed on the Intelliflash 280 system using a 330 g Silicycle SiliaSep Silica gel column using the following gradient: A: Heptane; B: 10% EtOAc in heptane; 0% B to 100% B over 30 min. The combined product fractions were concentrated in vacuo to give 37.85 g (65% yield) of methyl (Z)-2-azido-3-(4-(trifluoromethoxy)phenyl)acrylate. $^1$H NMR (400 MHz, DMSO-d6) δ8.00 (d, J=9.0 Hz, 1H), 7.40 (d, J=8.0 Hz, 1H), 6.97 (s, 1H), 3.87 (s, 3H).

Step B: methyl 6-(trifluoromethoxy)-1H-indole-2-carboxylate

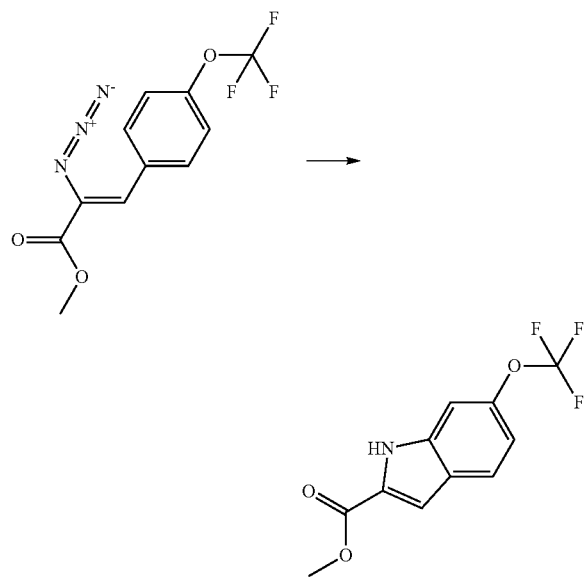

In a round-bottomed flask, Xylene (500 mL) which had been dried over the weekend over molecular sieves, and then purged with nitrogen for 1 hour was heated to 140° C. A solution of (Z)-methyl 2-azido-3-(4-(trifluoromethoxy)phenyl)acrylate (37.85 g, 132 mmol) in Xylene (75 mL) was added dropwise to the solution over 45 minutes. LC/MS of material after addition was complete shows complete consumption of starting material. Let cool to ambient temperature. Removed solvent in vacuo, triturated with heptanes (100 mL) over weekend. Filtered, washing with heptane. Dried in vacuo. Gave 25.08 g (73% yield) of methyl 6-(trifluoromethoxy)-1H-indole-2-carboxylate as a crystalline solid. $^1$H NMR (400 MHz, DMSO-d6) δ12.15 (s, 1H), 7.78 (d, J=8.8 Hz, 1H), 7.42-7.32 (m, 1H), 7.23 (dd, J=2.2, 0.9 Hz, 1H), 7.07 (ddt, J=8.7, 2.1, 1.0 Hz, 1H), 3.89 (s, 3H); LC/MS (Method i) $R_t$=1.59 min.; MS m/z: 258.17 (M−H)$^-$.

Step C: N-methoxy-N-methyl-6-(trifluoromethoxy)-1H-indole-2-carboxamide

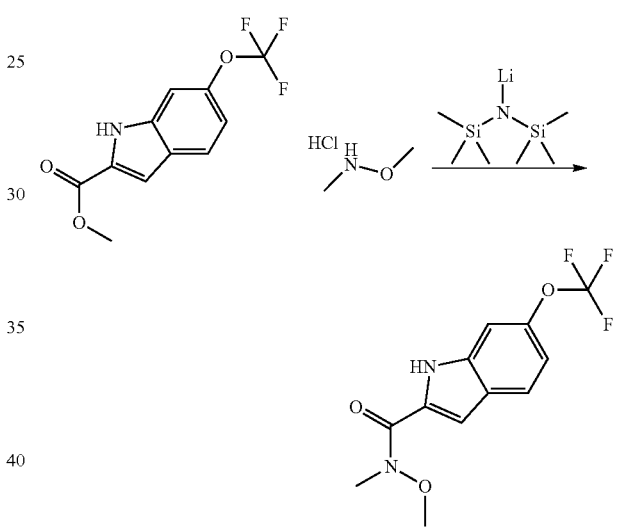

In a round-bottomed flask, methyl 6-(trifluoromethoxy)-1H-indole-2-carboxylate (25.08 g, 97 mmol) in THF (150 mL) was added to give a yellow solution. N,O-dimethylhydroxylamine hydrochloride (10.38 g, 106 mmol) was added and the mixture was cooled to 0° C. 1.0 M lithium bis(trimethylsilyl)amide in THF (300 mL, 300 mmol) was added dropwise, keeping the temperature <5° C. LC/MS 10 minutes after addition was complete indicated nearly complete. 2 N aqueous HCl (275 mL) was added, keeping the temperature <25° C. Extracted the aq layer with MTBE (275 mL) and washed organic with brine (75 mL). Dried over magnesium sulfate and removed solvent in vacuo. Slurried residue in heptane (100 mL) for 20 minutes, then filtered, washing with minimal heptane. The yellow solid was dried in vacuo to give 25.57 g (92% yield) of N-methoxy-N-methyl-6-(trifluoromethoxy)-1H-indole-2-carboxamide which was taken directly to the next step without further purification. $^1$H NMR (400 MHz, DMSO-d6) δ 11.77 (s, 1H), 7.78 (d, J=8.7 Hz, 1H), 7.42-7.38 (m, 1H), 7.22 (dd, J=2.2, 0.9 Hz, 1H), 7.03 (ddt, J=8.8, 2.1, 1.0 Hz, 1H), 3.81 (s, 3H), 3.34 (s, 3H);
LC/MS (Method i) $R_t$=1.48 min.; MS m/z: 289.26 (M+H)$^+$; MS m/z: 287.17 (M−H)$^-$.

145

Step D: N-methoxy-N,1-dimethyl-6-(trifluoromethoxy)-1H-indole-2-carboxamide

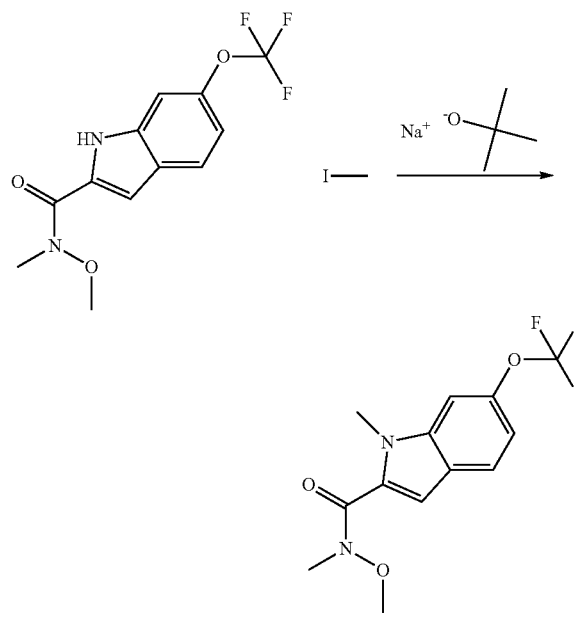

In a round-bottomed flask, N-methoxy-N-methyl-6-(trifluoromethoxy)-1H-indole-2-carboxamide (25.57 g, 89 mmol) in Dimethyl formamide (DMF) (250 mL) was added to give a yellow solution. Cooled to 0° C. and sodium tert-butoxide (8.95 g, 93 mmol) was added, keeping the temperature <5° C. The solution was stirred 30 minutes at 0° C., then a solution of 2.0 M iodomethane in MTBE (46.6 mL, 93 mmol) was added dropwise, keeping the temperature <5° C. Stirred at ~0° C. After 2 hours, nearly all starting material was consumed. MTBE (600 mL) and 2 N hydrochloric acid (250 mL) were added. The layers were separated and the aqueous layer was extracted with MTBE (200 mL) and then the combined organic layers were washed with brine (2×150 mL). The combined organic layers were dried over magnesium sulfate and removed solvent in vacuo. The crude material was chromatographed on the Intelliflash 280 system using a 220 g Silicycle SiliaSep Silica gel column using the following gradient: A: Heptane; B: EtOAc; 20% B to 100% B over 30 min to give 21.67 g (80% yield) of N-methoxy-N,1-dimethyl-6-(trifluoromethoxy)-1H-indole-2-carboxamide. $^1$H NMR (400 MHz, DMSO-d6) δ7.75 (dd, J=8.6, 0.5 Hz, 1H), 7.61 (tt, J=1.4, 0.8 Hz, 1H), 7.08 (ddq, J=8.6, 2.1, 1.0 Hz, 1H), 7.05 (d, J=0.9 Hz, 1H), 3.85 (s, 3H), 3.65 (s, 3H), 3.33 (s, 3H); LC/MS (Method i) $R_t$=1.57 min.; MS m/z: 303.14 (M+H)$^+$.

Step E: 1-methyl-6-(trifluoromethoxy)-1H-indole-2-carbaldehyde

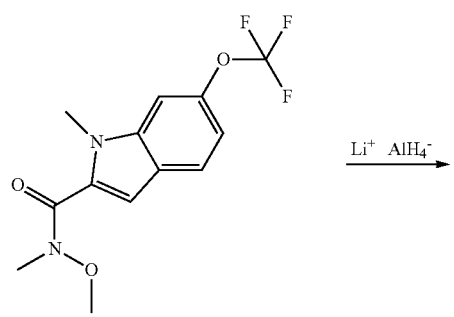

146

-continued

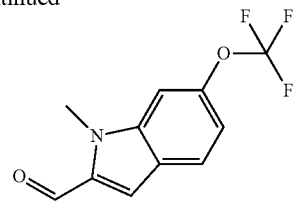

In a round-bottomed flask, N-methoxy-N,1-dimethyl-6-(trifluoromethoxy)-1H-indole-2-carboxamide (21.67 g, 71.7 mmol) in THF (200 mL) was added to give a yellow solution. The solution was cooled to −78° C., and 2.0 M lithium aluminum hydride in THF (50.2 mL, 100 mmol) was added dropwise, keeping the temperature <−65° C. After addition was complete, LC/MS indicated complete consumption of starting material. Sodium sulfate decahydrate (23.10 g, 71.7 mmol) was added portionwise, keeping the temperature <−60° C. followed by MTBE (300 mL). The solution was warmed to ambient temperature. At approximately −10° C. a precipitate formed. Additional MTBE was added until it freely stirred. Filtered through a pad of Celite® 545, washing with MTBE (2×120 mL). Solvent was removed in vacuo, chasing with heptane (2×120 mL), giving 14.29 g of a yellow oil mixture. The crude material was chromatographed on the Intelliflash 280 system using a 220 g Grace silica gel column using the following gradient: A: Heptane; B: EtOAc; 0% B to 60% B over 30 min, giving 11.21 g (64% yield) of 1-methyl-6-(trifluoromethoxy)-1H-indole-2-carbaldehyde. $^1$H NMR (400 MHz, DMSO-d6) δ9.93 (s, 1H), 7.89 (dd, J=8.7, 0.5 Hz, 1H), 7.68 (dp, J=2.5, 0.9 Hz, 1H), 7.51 (d, J=0.9 Hz, 1H), 7.14 (ddq, J=8.7, 2.1, 1.0 Hz, 1H), 4.04 (s, 3H). LC/MS (Method i) $R_t$=1.62 min.; MS m/z: 244.19 (M+H)$^+$.

Preparation #53: methyl 2-(1-(2,4-dichloro-3-(((methylsulfonyl)oxy)methyl)benzoyl)piperidin-4-yl)acetate

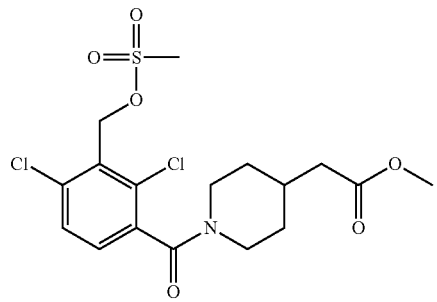 [SMILES: COC(=O)CC1CCN(C(=O)c2ccc(Cl)c(COS(C)(=O)=O)c2Cl)CC1]

Step A: tert-butyl 2,4-dichloro-3-(hydroxymethyl)benzoate

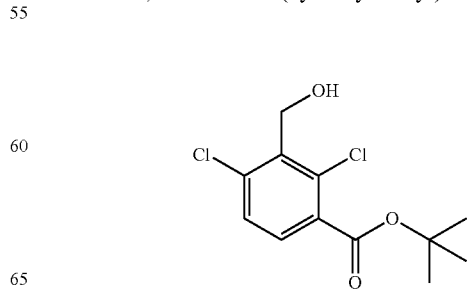

Using a procedure similar to Preparation #8, Step A, tert-butyl 2,4-dichloro-3-(hydroxymethyl)benzoate (11.8 g, 97%) was prepared from tert-butyl 2,4-dichloro-3-formylbenzoate (13.5 g, 44 mmol) (Preparation #33, Step B). LC/MS (Method i): Rt=2.02 min.; MS m/z: 277 [M+H]$^+$; $^1$H NMR (DMSO-d$_6$, 300 MHz): δ 7.55 (m, 2H), 5.28 (s, 1H), 4.72 (s, 2H), 1.54 (s, 9H).

Step B: tert-butyl 2,4-dichloro-3-(((methylsulfonyl)oxy)methyl)benzoate

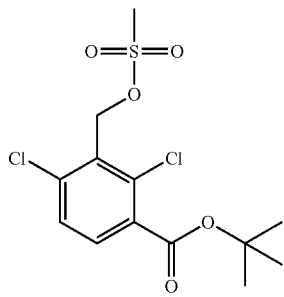 [SMILES: CC(C)(C)OC(=O)c1ccc(Cl)c(COS(C)(=O)=O)c1Cl]

To a solution of tert-butyl 2,4-dichloro-3-(hydroxymethyl)benzoate (11.9 g, 42.9 mmol) in DCM (472 ml) and cooled to −10° C. was added triethylamine (8.98 ml, 64.4 mmol) and methanesulfonyl chloride (5.33 ml, 68.7 mmol). The reaction mixture was stirred at −10° C. for 1 hour then diluted with DCM and washed with water. The organic layer was dried over magnesium sulfate, filtered, and concentrated under vacuum to give tert-butyl 2,4-dichloro-3-(((methylsulfonyl)oxy)methyl)benzoate (15.04 g, 99%) as a yellow oil. LC/MS (Method i): Rt=2.25 min.; MS m/z: 355 [M+H]$^+$; $^1$H NMR (DMSO-d$_6$, 300 MHz): δ 7.76 (d, J=8.9 Hz, 1H), 7.68 (d, J=8.9 Hz, 1H), 5.48 (s, 2H) 3.32 (s, 3H), 1.55 (s, 9H).

Step C: methyl 2-(1-(2,4-dichloro-3-(((methylsulfonyl)oxy)methyl)benzoyl)piperidin-4-yl)acetate

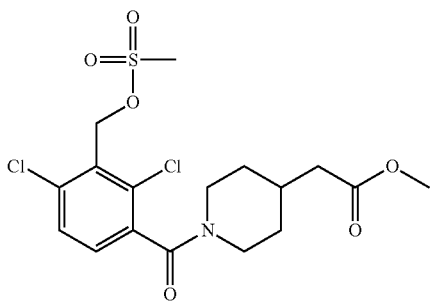 [SMILES: COC(=O)CC1CCN(C(=O)c2ccc(Cl)c(COS(C)(=O)=O)c2Cl)CC1]

To a solution of 2,4-dichloro-3-(((methylsulfonyl)oxy)methyl)benzoic acid (7.56 g, 25.3 mmol) in DCM (145 ml) and cooled to 0° C. were added 1-(3-dimethylaminopropyl)-3-ethylcarbodiimide hydrochloride (4.84 g, 25.3 mmol) and 1-hydroxybenzotriazole (3.42 g, 25.3 mmol). The reaction mixture was stirred for 10 minutes at 0° C. then methyl 2-(piperidin-4-yl)acetate hydrochloride (4.89 g, 25.3 mmol) and triethylamine (3.52 ml, 25.3 mmol) were added. The reaction mixture was stirred at 0° C. for 50 minutes and diluted with water and DCM. The layers were separated and the organic layer was dried over magnesium sulfate, filtered and concentrated under reduced pressure. The residue was purified by column chromatography on silica gel (eluting with 0-5% EtOAc in cyclohexane) to give methyl 2-(1-(2, 4-dichloro-3-(((methylsulfonyl)oxy)methyl)benzoyl)piperidin-4-yl)acetate (6.74 g, 61%). LC/MS (Method i): Rt=1.80 min.; MS m/z: 438 [M+H]$^+$; $^1$H NMR (DMSO-d$_6$, 300 MHz): δ 7.66 and 7.64 (d, J=8.3 Hz, 1H), 7.53 and 7.45 (m, 1H), 5.46 and 5.45 (s, 2H), 4.47 (m, 1H), 3.58 (s, 3H), 3.33 (broad, 3H), 3.20 (m, 1H), 3.03 (m, 1H), 2.81 (m, 1H), 2.27 (m, 2H), 1.96 (m, 1H), 1.75 (m, 1H), 1.58 (m, 1H), 1.16 (m, 2H).

Preparation #54: methyl 3-(chloromethyl)-2,4-dimethylbenzoate

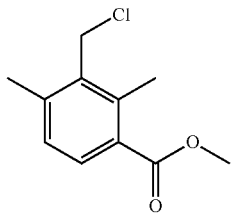

Step A: methyl 3-formyl-2,4-dimethylbenzoate

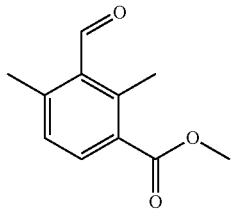

Using a procedure similar to Preparation #1, Step A, methyl 3-formyl-2,4-dimethylbenzoate (7 g, 93%) was prepared from 3-formyl-2,4-dimethylbenzoic acid (7 g, 39.3 mmol) (preparation #4, Step B). LC/MS (Method h): R$_t$=2.15 min.; $^1$H NMR (DMSO-d$_6$, 300 MHz): δ 10.55 (s, 1H), 7.78 (d, J=7.5 Hz, 1H), 7.27 (d, J=7.5 Hz, 1H), 3.83 (s, 3H), 2.51 (s, 3H), 2.46 (s, 3H).

Step B: methyl 3-(hydroxymethyl)-2,4-dimethylbenzoate

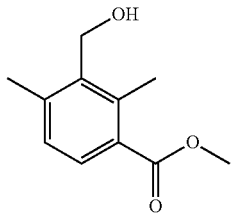

Using a procedure similar to Preparation #8, Step A, methyl 3-(hydroxymethyl)-2,4-dimethylbenzoate (6.08 g, 86%) was prepared from methyl 3-formyl-2,4-dimethylbenzoate (7 g, 36.4 mmol). LC/MS (Method h): R$_t$=1.65 min.; MS m/z: 195 [M+H]$^+$; $^1$H NMR (DMSO-d$_6$, 300 MHz): δ 7.52 (d, J=7.5 Hz, 1H), 7.09 (d, J=7.5 Hz, 1H), 4.83 (t, J=5.4 Hz, 1H), 4.53 (d, J=5.4 Hz, 2H), 3.80 (s, 3H), 2.49 (s, 3H), 2.39 (s, 3H).

Step C: methyl 3-(chloromethyl)-2,4-dimethylbenzoate

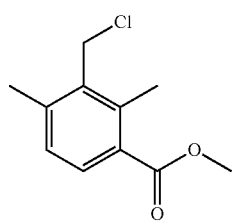

Using a procedure similar to Preparation #11, Step C, methyl 3-(chloromethyl)-2,4-dimethylbenzoate (2.6 g, 88%) was prepared from methyl 3-(hydroxymethyl)-2,4-dimethylbenzoate (2.5 g, 12.87 mmol).

LC/MS (Method h): R$_t$=2.66 min.; MS m/z: 213 [M+H]$^+$; $^1$H NMR (DMSO-d$_6$, 300 MHz): δ 7.60 (d, J=7.9 Hz, 1H), 7.19 (d, J=7.9 Hz, 1H), 4.84 (s, 2H), 3.82 (s, 3H), 2.52 (s, 3H), 2.43 (s, 3H).

Preparation #55: tert-butyl 2,4-dichloro-3-(fluorocarbonyl)benzoate

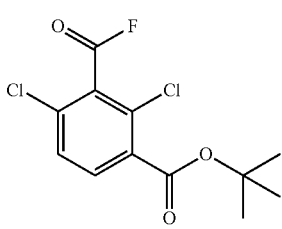

To a solution of 3-(tert-butoxycarbonyl)-2,6-dichlorobenzoic acid (0.95 g, 3.26 mmol) (Preparation #44, Step A) in DCM (32.6 ml) were added diisopropylethylamine (2.26 mL, 13.05 mmol) followed by bis(2-methoxyethyl)aminosulfur trifluoride (2.65 ml, 7.18 mmol) dropwise. The reaction is slightly exothermic was stirred at room temperature for 22 hours. The reaction mixture was washed with 10% aqueous citric acid, a saturated solution of NaHCO$_3$, and brine. The organic layer was dried over magnesium sulfate and concentrated under reduced pressure to give tert-butyl 2,4-dichloro-3-(fluorocarbonyl)benzoate (1 g, 100%) as an orange oil. LC/MS (Method j): R$_t$=1.98 min.; MS m/z: 291 [M−H]$^-$; H NMR (CDCl$_3$, 300 MHz): δ 7.83 (d, J=8.4 Hz, 1H), 7.44 (d, J=8.4 Hz, 1H), 1.60 (s, 9H).

Preparation #56: tert-butyl 4,6-dichloro-5-(chlorocarbonyl)nicotinate

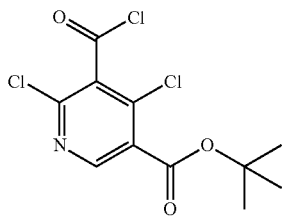 [SMILES: CC(C)(C)OC(=O)c1cnc(Cl)c(C(=O)Cl)c1Cl]

Step A: 5-(tert-butoxycarbonyl)-2,4-dichloronicotinic acid

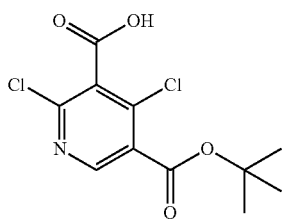 [SMILES: CC(C)(C)OC(=O)c1cnc(Cl)c(C(=O)Cl)c1Cl]

Using a procedure similar to Preparation #44, Step A, 5-(tert-butoxycarbonyl)-2,4-dichloronicotinic acid (1.96 g, 43%) was prepared from tert-butyl 4,6-dichloronicotinate (3.85 g, 15.5 mmol) ((Example DO, Step 11). LC/MS (Method i): Rt=1.31 min.; MS m/z: 292 [M+H]$^+$. $^1$H NMR (DMSO-d$_6$, 300 MHz): δ 8.78 (s, 1H), 1.56 (s, 9H).

Step 2: tert-butyl 4,6-dichloro-5-(chlorocarbonyl)nicotinate

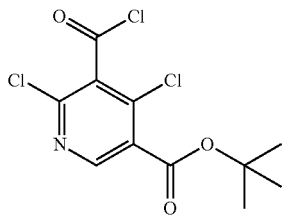

Using a procedure similar to Preparation #44, Step B, tert-butyl 4,6-dichloro-5-(chlorocarbonyl)nicotinate (2 g, 100%) was prepared from 5-(tert-butoxycarbonyl)-2,4-dichloronicotinic acid (1.96 g, 6.71 mmol) The residue was used in the next step without further purification.

Preparation #57: tert-butyl 4,6-dichloro-5-(((methylsulfonyl)oxy)methyl)nicotinate

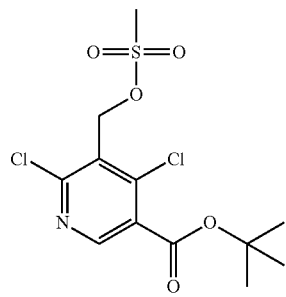 [SMILES: CC(C)(C)OC(=O)c1cnc(Cl)c(COS(C)(=O)=O)c1Cl]

Step A: tert-butyl 4,6-dichloro-5-(hydroxymethyl)nicotinate

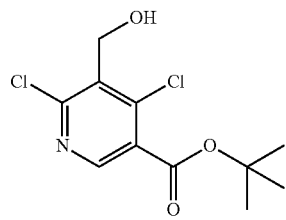 [SMILES: CC(C)(C)OC(=O)c1cnc(Cl)c(CO)c1Cl]

Using a procedure similar to Preparation #8, Step A, tert-butyl 4,6-dichloro-5-(hydroxymethyl)nicotinate (503 mg, 97%) were prepared from tert-butyl 4,6-dichloro-5-formylnicotinate (500 mg, 1.8 mmol) (Example DO, Step 12). LC/MS (Method i): $R_t$=1.83 min.; MS m/z: 278 [M+H]$^+$ $^1$H NMR (DMSO-d6, 300 MHz): δ 8.63 (s, 1H), 5.45 (t, J=5.4 Hz, 1H), 4.72 (d, J=5.4 Hz, 2H), 1.56 (s, 9H).

Step B: tert-butyl 4,6-dichloro-5-(((methylsulfonyl)oxy)methyl)nicotinate

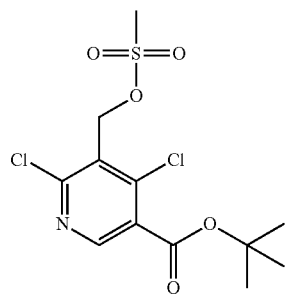 [SMILES: CC(C)(C)OC(=O)c1cnc(Cl)c(COS(C)(=O)=O)c1Cl]

Using a procedure similar to Preparation #11, Step C, tert-butyl 4,6-dichloro-5-(((methylsulfonyl)oxy)methyl) nicotinate and tert-butyl 4,6-dichloro-5-(chloromethyl)nicotinate (160 mg) were prepared from tert-butyl 4,6-dichloro-5-(hydroxymethyl)nicotinate (130 mg, 0.47 mmol). The residue was used crude in the next step. LC/MS (Method j): $R_t$=1.37 min.; MS m/z: 356 [M+H]$^+$;
$^1$H NMR (CDCl$_3$, 300 MHz): δ 8.73 (s, 1H), 5.55 (s, 2H), 3.67 (s, 3H), 161 (s, 9H).

Preparation #58: tert-butyl 2-chloro-4-cyclopropyl-3-(1-hydroxyprop-2-yn-1-yl)benzoate

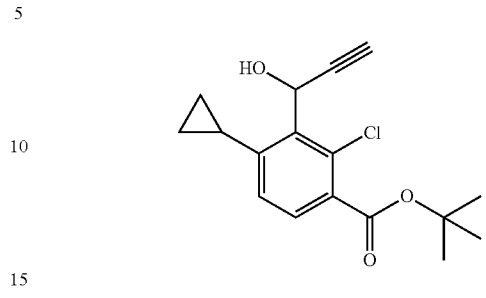

Step A: tert-butyl 4-bromo-2-chloro-3-formylbenzoate

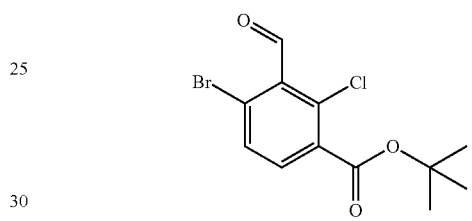

Using a procedure similar to Preparation #33, Step B, tert-butyl 4-bromo-2-chloro-3-formylbenzoate (2.66 g, 32%) was prepared from tert-butyl 4-bromo-2-chlorobenzoate (5 g, 17.15 mmol). LC/MS (Method i): $R_t$=2.38 min.; MS m/z: 319 [M+H]$^+$; $^1$H NMR (DMSO-d$_6$, 300 MHz): δ 10.23 (s, 1H), 7.85 (d, J=7.8 Hz, 1H), 7.75 (d, J=7.8 Hz, 1H), 1.55 (s, 9H).

Step B: tert-butyl 2-chloro-4-cyclopropyl-3-formylbenzoate

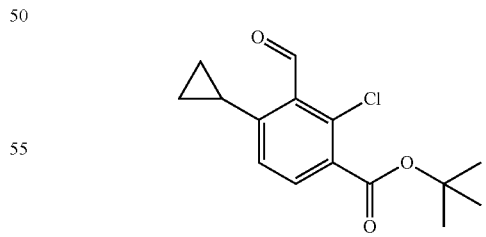

Using a procedure similar to Preparation #66, tert-butyl 2-chloro-4-cyclopropyl-3-formylbenzoate (1.18 g, 88%) was prepared from tert-butyl 4-cyclopropyl-2-chlorobenzoate (2 g, 4.17 mmol). LC/MS (Method i): Rt=2.49 min.; MS m/z: 281 [M+H]$^+$; $^1$H NMR (DMSO-d$_6$, 300 MHz): δ 10.56 (s, 1H), 7.71 (d, J=8.3 Hz, 1H), 7.12 (d, J=8.3 Hz, 1H), 2.45 (m, 1H), 1.53 (m, 9H), 1.03 (m, 2H), 0.77 (m, 2H).

Step C: tert-butyl 2-chloro-4-cyclopropyl-3-(1-hydroxyprop-2-yn-1-yl)benzoate

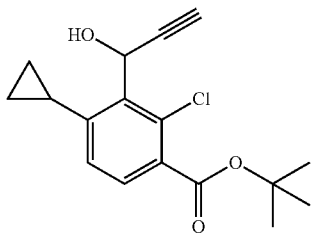 [SMILES: C#CC(O)c1c(C2CC2)ccc(C(=O)OC(C)(C)C)c1Cl]

Using a procedure similar to Preparation #1, Step D, tert-butyl 2-chloro-4-cyclopropyl-3-(1-hydroxyprop-2-yn-1-yl)benzoate (1.11 g, 86%) was prepared from tert-butyl 2-chloro-4-cyclopropyl-3-formylbenzoate (1.18 g, 4.2 mmol). LC/MS (Method j): $R_t$=1.28 min.; MS m/z: 365 [M−H]⁻+CH₃COOH; ¹H NMR (DMSO-d₆, 300 MHz): δ 7.41 (d, J=8.1 Hz, 1H), 6.91 (d, J=8.1 Hz, 1H), 6.26 (m, 1H), 6.19 (s, 1H), 3.49 (d, J=2.3 Hz, 1H), 2.73 (m, 1H), 1.53 (s, 9H), 1.03 (m, 2H), 0.83 (m, 1H), 0.70 (m, 1H).

Preparation #59: (E)-tert-butyl 2,4-dichloro-3-(3-((methylsulfonyl)oxy)prop-1-en-1-yl)benzoate

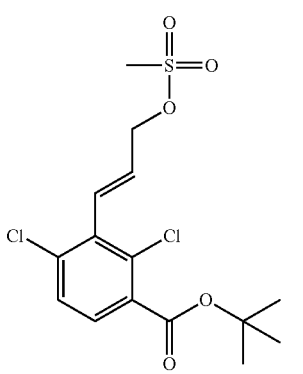 [SMILES: CC(C)(C)OC(=O)c1ccc(Cl)c(/C=C/COS(C)(=O)=O)c1Cl]

Step A: (E)-tert-butyl 2,4-dichloro-3-(3-ethoxy-3-oxoprop-1-en-1-yl)benzoate

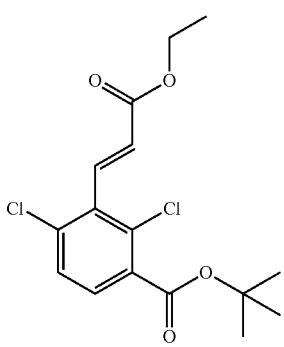 [SMILES: CCOC(=O)/C=C/c1c(Cl)ccc(C(=O)OC(C)(C)C)c1Cl]

To a suspension of sodium hydride (0.407 g, 10.18 mmol) in THF (6.2 mL) and cooled to 0° C. was added dropwise triethyl phosphonoacetate (2.03 mL, 10.18 mmol) and the reaction mixture was allowed to warm to room temperature and stirred until it was homogeneous. The reaction mixture was cooled to 0° C. and a solution of tert-butyl 2,4-dichloro-3-formylbenzoate (2.8 g, 10.18 mmol) (Preparation #33, Step B) in THF (16 mL) was added dropwise to the reaction mixture, a brown gum appeared and it was difficult to stir. The reaction mixture was allowed to warm to room temperature and the reaction mixture was quenched dropwise with a saturated solution of NaHCO₃. The obtained aqueous layer was extracted three times with EtOAc and the combined organic layers were dried over magnesium sulfate, filtered and concentrated under reduced pressure. The residue was purified by column chromatography on silica gel (eluting with 5-20% EtOAc in DCM) to give (E)-tert-butyl dichloro-3-(3-ethoxy-3-oxoprop-1-en-1-yl)benzoate (2.6 g, 77%) as a yellow oil. LC/MS (Method i): $R_t$=2.68 min.; MS m/z: 345 [M+H]⁺; ¹H NMR (DMSO-d₆, 300 MHz): δ 7.66 (s, 2H), 7.62 (d, J=16.3 Hz, 1H), 6.48 (d, J=16.3 Hz, 1H), 4.24 (q, J=7.1 Hz, 2H), 1.55 (s, 9H), 1.27 (t, J=7.1 Hz, 3H).

Step B: (E)-tert-butyl 2,4-dichloro-3-(3-hydroxyprop-1-en-1-yl)benzoate

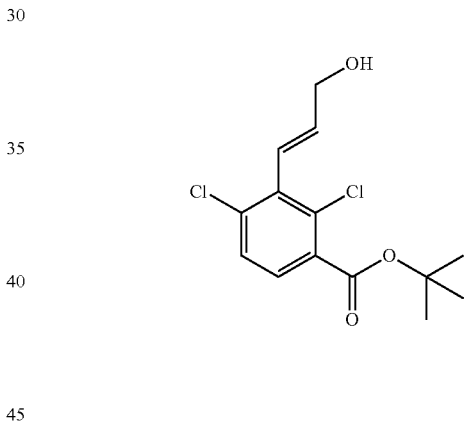

To a solution of (E)-tert-butyl 2,4-dichloro-3-(3-ethoxy-3-oxoprop-1-en-1-yl)benzoate (2.59 g, 7.50 mmol) in THF (68 mL) and cooled to −78° C. was added dropwise diisobutylaluminum hydride (24.38 mL, 29.3 mmol) and the reaction mixture was stirred during 30 minutes at −78° C. EtOAc was added slowly, followed by 68 mL of a 30% solution of potassium sodium tartrate. The mixture was stirred until there were two layers. The mixture was extracted twice with EtOAc and the obtained organic layer was dried over magnesium sulfate, filtered and concentrated under reduced pressure. The residue was purified by column chromatography on silica gel (eluting with 7-60% EtOAc in DCM) to give (E)-tert-butyl 2,4-dichloro-3-(3-hydroxyprop-1-en-1-yl)benzoate (2.19 g, 96%). LC/MS (Method i): Rt=2.19 min.; MS m/z: 303 [M+H]⁺; ¹H NMR (DMSO-d₆, 300 MHz): δ=7.56 (d, J=7.9 Hz, 1H), 7.51 (d, J=7.9 Hz, 1H), 6.53 (dd, J=15, 3.3 Hz, 1H), 6.26 (dd, J=15, 4.3 Hz, 1H), 5.08 (t, J=5.6 Hz, 1H), 4.19 (m, 2H), 1.54 (s, 9H).

155

Step C: (E)-tert-butyl 2,4-dichloro-3-(3-((methylsulfonyl)oxy)prop-1-en-1-yl)benzoate

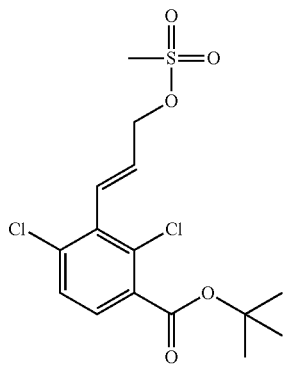 [SMILES: CC(C)(C)OC(=O)c1ccc(Cl)c(/C=C/COS(C)(=O)=O)c1Cl]

Using a procedure similar to Preparation 53, Step B, (E)-tert-butyl 2,4-dichloro-3-(3-((methylsulfonyl)oxy)prop-1-en-1-yl)benzoate (2.95 g, 86%) was prepared from (E)-tert-butyl 2,4-dichloro-3-(3-hydroxyprop-1-en-1-yl)benzoate (2.18 g, 7.19 mmol). LC/MS (Method i): $R_f$=2.39 min.; MS m/z: 381 [M+H]$^+$; $^1$H NMR (DMSO-d$_6$, 300 MHz): δ 7.60 (m, 2H), 6.77 (d, J=15 Hz, 1H), 6.26 (dt, J=15, 5.9 Hz, 1H), 4.98 (dd, J=5.9, 1.6 Hz, 2H), 3.26 (s, 3H), 1.54 (s, 9H).

Preparation #60: tert-butyl 4,6-dichloro-5-(1-hydroxyprop-2-yn-1-yl)nicotinate

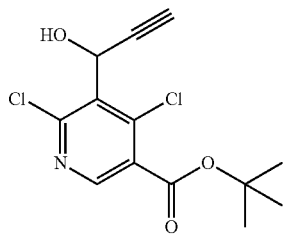 [SMILES: C#CC(O)c1c(Cl)ncc(C(=O)OC(C)(C)C)c1Cl]

Using a procedure similar to Preparation #1, Step D, tert-butyl 4,6-dichloro-5-(1-hydroxyprop-2-yn-1-yl)nicotinate (5.8 g, 79%) was prepared from tert-butyl 4,6-dichloro-5-formylnicotinate (6.75 g, 24.45 mmol) (Example DO, Step 12). LC/MS (Method i): $R_f$=2.00 min.; MS m/z: 302 [M+H]$^+$; $^1$H NMR (DMSO-d$_6$, 300 MHz): δ 8.65 (s, 1H), 6.43 (d, J=4.8 Hz, 1H), 6.10 (dd, J=4.8, 2.5 Hz, 1H), 3.60 (d, J=2.5 Hz, 1H), 1.56 (s, 9H).

Preparation #61:
3,7-dimethyl-5-(trifluoromethoxy)-1H-indole

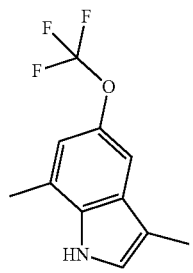

156

Step A: 2-iodo-6-methyl-4-(trifluoromethoxy)aniline

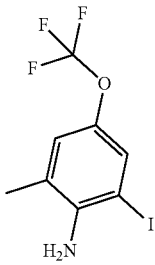

Using a procedure similar to Preparation #34, Step A, 2-iodo-6-methyl-4-(trifluoromethoxy)aniline (5.25 g, 79%) was prepared from 2-methyl-4-(trifluoromethoxy)aniline (4 g, 20.9 mmol). LC/MS (Method i): $R_f$=2.32 min.; MS m/z: 318 [M+H]$^+$; $^1$H NMR (DMSO-d$_6$, 300 MHz): δ 7.43 (s, 1H), 7.05 (s, 1H), 5.07 (s, 2H), 2.17 (s, 3H).

Step B:
3,7-dimethyl-5-(trifluoromethoxy)-1H-indole

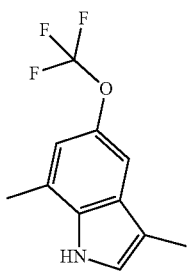

To a solution of 2-iodo-6-methyl-4-(trifluoromethoxy)aniline (500 mg, 1.57 mmol) in N,N-dimethylformamide (3 mL were added palladium(II) acetate (35.4 mg, 0.16 mmol), lithium chloride (66.9 mg, 1.58 mmol), triphenylphosphine (41.4 mg, 0.16 mmol), sodium acetate (259 mg, 3.15 mmol) and 1-(trimethylsilyl)-1-propyne (0.470 ml, 3.15 mmol) and the reaction mixture was heated at 140° C. for 1 hour under microwave irradiation. The reaction mixture was washed with water and extracted twice with EtOAc. The organic layer was washed successively with brine and water, dried over magnesium sulfate, filtered and concentrated under reduced pressure. The residue was dissolved in THF (8 mL) and tetrabutylammonium fluoride (0.718 mL, 2.481 mmol) was added. The reaction mixture was stirred at reflux for 4 hours then concentrated under reduced pressure. The residue was purified by column chromatography on silica gel (eluting with 5-60% EtOAc in cyclohexane) to give 3,7-dimethyl-5-(trifluoromethoxy)-1H-indole (285 mg, 79%) as a brown liquid. LC/MS (Method i): $R_f$=2.34 min.; MS m/z: 230 [M+H]$^+$; $^1$H NMR (DMSO-d$_6$, 300 MHz): δ 11.00 (s, 1H), 7.23 (s, 2H), 6.85 (s, 1H), 2.46 (s, 3H), 2.24 (s, 3H).

Preparation #62:
7-chloro-5-(trifluoromethyl)-1H-indole

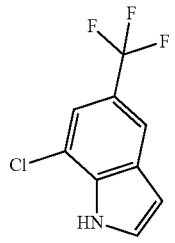 [SMILES: FC(F)(F)c1cc(Cl)c2[nH]ccc2c1]

To a solution of 2-chloro-6-iodo-4-(trifluoromethyl)aniline (3.2 g, 9.95 mmol) in DMF (64 mL) was added trimethylsilylacetylene (1.075 g, 10.95 mmol), palladium(II) acetate (0.335 g, 1.493 mmol) and sodium carbonate (3.17 g, 29.9 mmol) and the reaction mixture was stirred at 120° C. under microwaves for 20 minutes. The residue was suspended in brine and extracted twice with DMC. The organic layer was then dried over magnesium sulfate, filtered and concentrated under reduced pressure. The residue was purified by column chromatography on silica gel (eluting with 0-5% EtOAc in cyclohexane) to give 7-chloro-5-(trifluoromethyl)-2-(trimethylsilyl)-1H-indole (1 g, 20%). The residue was dissolved in THF (11 mL), tetrabutylammonium fluoride (3.65 ml, 3.65 mmol) was added and the reaction mixture was stirred at 50° C. for 30 minutes. The reaction mixture was concentrated under reduced pressure. The residue was taken in DCM and washed with an aqueous solution of NaHCO$_3$. The organic layer was then dried over magnesium sulfate, filtered and evaporated under reduced pressure. The residue was purified by column chromatography on silica gel (eluting with 0-10% EtOAc in cyclohexane) to give 7-chloro-5-(trifluoromethyl)-1H-indole (470 mg, 46%). LC/MS (Method i): R$_t$=2.23 min.; MS m/z: 218 [M−H]$^-$; $^1$H NMR (CDCl$_3$, 300 MHz): δ 8.54 (broad, 1H), 7.86 (s, 1H), 7.45 (m, 1H), 7.36 (m, 1H), 6.70 (m, 1H).

Preparation #63:
7-ethyl-5-(trifluoromethyl)-1H-indole

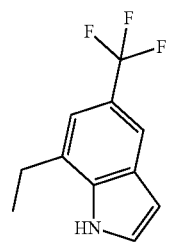

Step A: 5-(trifluoromethyl)-7-vinyl-1H-indole

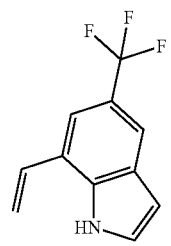

To a solution of 7-chloro-5-(trifluoromethyl)-1H-indole (115 mg, 0.52 mmol) (Preparation #62) in 1,4-dioxane (3.4 mL) were added cesium fluoride (159 mg, 1.05 mmol) and bis(tri-tert-butylphosphine)palladium(0) (53.5 mg, 0.10 mmol) and tributyl(vinyl)tin (830 mg, 2.62 mmol) and the reaction mixture was stirred at 120° C. for 45 minutes. The reaction mixture was allowed to cool to room temperature and the solvent was then removed under reduced pressure. The residue was purified by column chromatography on silica gel (eluting with 0-5% EtOAc in cyclohexane) to give 5-(trifluoromethyl)-7-vinyl-1H-indole (110 mg, 81%) as a brown oil. LC/MS (Method i): R$_t$=2.23 min.;

MS m/z: 212 [M+H]$^+$; $^1$H NMR (CDCl$_3$, 300 MHz): δ 8.56 (broad, 1H), 7.86 (s, 1H), 7.46 (s, 1H), 7.34 (s, 1H), 7.00 (dd, J=17.7, 11.2 Hz, 1H), 6.67 (m, 1H), 5.87 (d, J=17.7 Hz, 1H), 5.55 (d, J=11.2 Hz, 1H).

Step B: 7-ethyl-5-(trifluoromethyl)-1H-indole

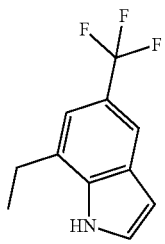

To as solution of 5-(trifluoromethyl)-7-vinyl-1H-indole (110 mg, 0.52 mmol) in EtOH (2 mL) under argon was added palladium on carbon (11.09 mg, 10.42 µmol). The reaction mixture was stirred at room temperature under atmospheric pressure of hydrogen for 5 hours. The reaction mixture was filtered and washed with EtOH. The solvent was removed under reduced pressure. The residue was purified by column chromatography on silica gel (eluting with 0-1% EtOAc in cyclohexane) to give 7-ethyl-5-(trifluoromethyl)-1H-indole (30 mg, 18%) as a beige resin. LC/MS (Method i): Rt=2.22 min.;

MS m/z: 214 [M+H]$^+$

Preparation #64:
7-methyl-5-(trifluoromethoxy)-1H-indole

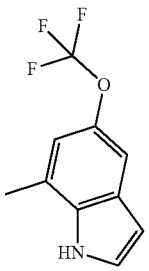

Step A: 2-iodo-6-methyl-4-(trifluoromethoxy)aniline

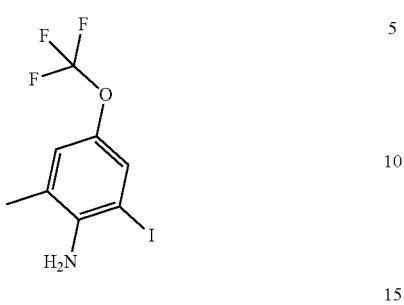

Using a procedure similar to Preparation #34, Step A, 2-iodo-6-methyl-4-(trifluoromethoxy)aniline (6.8 g, 82%) was prepared from 2-methyl-4-(trifluoromethoxy)aniline (5 g, 26.2 mmol). LC/MS (Method i): $R_t$=2.33 min.; MS m/z: 318 [M+H]$^+$; $^1$H NMR (DMSO-d$_6$, 300 MHz): δ 7.43 (s, 1H), 7.05 (s, 1H), 5.07 (s, 2H), 2.17 (s, 3H).

Step B: 7-methyl-5-(trifluoromethoxy)-1H-indole

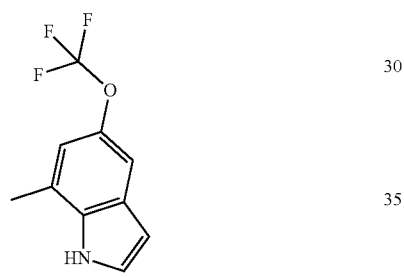

To a solution of 2-iodo-6-methyl-4-(trifluoromethoxy) aniline (3.3 g, 10.41 mmol) in N,N-dimethylformamide, (24 ml) were added Pd(PPh$_3$)$_2$Cl$_2$ (0.14 g, 0.21 mmol), copper(I) iodide (0.099 g, 0.520 mmol), ethynyltrimethylsilane (1.584 mL, 11.45 mmol) and diethylamine (2.392 mL, 22.90 mmol). The reaction mixture was stirred at 120° C. under microwaves irradiation for 40 minutes. The reaction mixture was filtered and washed with EtOAc. The mixture was diluted with water and extracted twice with EtOAc. The organic layer was washed with brine, dried on magnesium sulfate and concentrated. The residue was dissolved in DMF (30 mL) and calcium carbonate (1.045 g, 10.44 mmol) and copper(I) iodide (1.988 g, 10.44 mmol) were added, and the reaction mixture was stirred 20 minutes at 150° C. under microwave irradiation. The reaction mixture was diluted with water. The aqueous layer was extracted twice with EtOAc, and the combined organic layers were dried over magnesium sulfate, filtered and evaporated. The residue was purified by column chromatography on silica gel (eluting with 5-20% EtOAc in cyclohexane) to give 7-methyl-5-(trifluoromethoxy)-1H-indole (1 g, 49%) as a yellow solid. LC/MS (Method j): $R_t$=1.49 min.; MS m/z: 216 [M+H]$^+$; $^1$H NMR (DMSO-d$_6$, 300 MHz): δ 11.34 (s, 1H), 7.46 (t, J=2.9 Hz, 1H), 7.34 (s, 1H), 6.87 (m, 1H), 6.50 (m, 1H), 2.50 (s, 3H).

Preparation #65:
5-(difluoromethoxy)-7-methyl-1H-indole

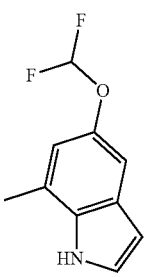

Step A:
5-bromo-7-methyl-1-(phenylsulfonyl)-1H-indole

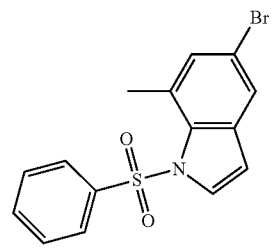 [SMILES: Cc1cc(Br)cc2ccn(S(=O)(=O)c3ccccc3)c12]

Using a procedure similar to Preparation #48, 5-bromo-7-methyl-1-(phenylsulfonyl)-1H-indole (1.6 g, 63%) was prepared from 5-bromo-7-methyl-1H-indole (1 g, 4.76 mmol). LC/MS (Method i): $R_t$=2.58 min.; MS m/z: 350 [M+H]$^+$; $^1$H NMR (CDCl$_3$, 300 MHz): δ=7.79 (d, J=3.8 Hz, 1H), 7.40-7.69 (m, 6H), 7.14 (m, 1H), 6.64 (d, J=3.8 Hz, 1H), 2.50 (s, 3H).

Step B: 7-methyl-1-(phenylsulfonyl)-5-(4,4,5,5-tetramethyl-1,3,2-dioxaborolan-2-yl)-1H-indole

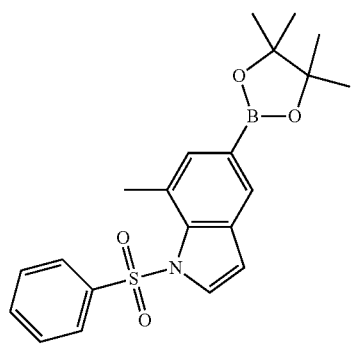 [SMILES: Cc1cc(B2OC(C)(C)C(C)(C)O2)cc2ccn(S(=O)(=O)c3ccccc3)c12]

To a solution of 5-bromo-7-methyl-1-(phenylsulfonyl)-1H-indole (1.6 g, 4.57 mmol) in THF (55 ml) were added bis(pinacolato)diboron (2.32 g, 9.14 mmol), [1,1'-bis(diphenylphosphino)ferrocene]dichloropalladium(II) (0.83 g, 1.14 mmol) and potassium acetate (1.12 g, 11.42 mmol) The tube was sealed and warmed at 80° C. for the night. The reaction mixture was allowed to cool-down to room temperature and it was quenched with water. The aqueous layer was extracted twice with DCM. The organic layer was washed with water and brine, dried over magnesium sulfate and concentrated to dryness. The residue was purified by column chromatography on silica gel (eluting with 0-10% EtOAc in cyclohexane) to give 7-methyl-1-(phenylsulfonyl)-5-(4,4,5,5-tetramethyl-1,3,2-dioxaborolan-2-yl)-1H-indole (1.45 g, 74%) as a yellow resin. LC/MS (Method i): $R_t$=2.73 min.; MS m/z: 398 [M+H]$^+$; $^1$H NMR (DMSO-d$_6$, 300 MHz): b=7.88 (d, J=3.8 Hz, 1H), 7.81 (s, 1H), 7.70 (m, 3H), 7.61 (m, 2H), 7.34 (s, 1H), 6.94 (d, J=3.8 Hz, 1H), 2.47 (s, 3H), 1.28 (s, 12H).

Step C: 7-methyl-1-(phenylsulfonyl)-1H-indol-5-ol

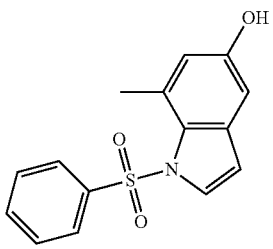 [SMILES: Cc1cc(O)cc2ccn(S(=O)(=O)c3ccccc3)c12]

To a solution of 7-methyl-1-(phenylsulfonyl)-5-(4,4,5,5-tetramethyl-1,3,2-dioxaborolan-2-yl)-1H-indole (1.6 g, 4.6 mmol) in THF (40 mL) and cooled-to 5° C. were added hydrogen peroxide (0.59 g, 8.68 mmol) and sodium hydroxide (0.27 g, 6.85 mmol) and the reaction mixture was stirred at 5° C. for 7 hours. The reaction mixture was quenched with water and extracted twice with DCM. The organic layer was washed with brine, dried over magnesium sulfate, filtered and concentrated to dryness to give 7-methyl-1-(phenylsulfonyl)-1H-indol-5-ol (1.1 g, 73%) as a brown resin. LC/MS (Method i): $R_t$=1.96 min.; MS m/z: 288 [M+H]$^+$; $^1$H NMR (DMSO-d$_6$, 300 MHz): b=9.27 (s, 1H), 7.68 (m, 4H), 7.57 (m, 2H), 6.72 (m, 2H), 6.52 (m, 1H), 2.42 (s, 3H).

Step D: 5-(difluoromethoxy)-7-methyl-1-(phenylsulfonyl)-1H-indole

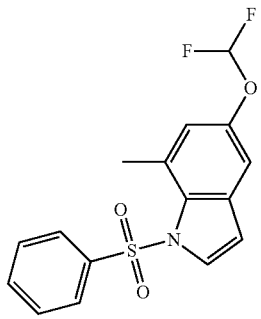 [SMILES: Cc1cc(OC(F)F)cc2ccn(S(=O)(=O)c3ccccc3)c12]

To a solution of 7-methyl-1-(phenylsulfonyl)-1H-indol-5-ol (1 g, 3.48 mmol) in ACN (11 mL and water (11 mL) and cooled to 0° C. was added potassium hydroxide (3.91 g, 69.6 mmol) and the reaction mixture was stirred at 0° C. for 15 minutes. Diethyl (bromodifluoromethyl)phosphonate (1.67 g, 6.26 mmol) was added and the reaction mixture was stirred at 0° C. for 5 minutes before being allowed to warm-to room temperature. The stirring was continued for 1.5 hours. The reaction mixture was quenched with water and acidified with (1N) HCl until pH=1. It was then extracted twice with DCM. The organic layer was washed with water and brine, dried over magnesium sulfate and concentrated under reduced pressure. The residue was purified by column chromatography on silica gel (eluting with 0-10% EtOAc in cyclohexane) to give 5-(difluoromethoxy)-7-methyl-1-(phenylsulfonyl)-1H-indole (550 mg, 43%) as a yellow resin. LC/MS (Method i): $R_t$=2.42 min.; MS m/z: 338 [M+H]$^+$; $^1$H NMR (DMSO-d$_6$, 300 MHz): δ 7.93 (d, J=3.8 Hz, 1H), 7.73 (m, 3H), 7.61 (m, 2H), 7.29 (d, J=2.3 Hz, 1H), 7.17 (t, J=74 Hz, 1H), 6.92 (d, J=2.3 Hz, 2H), 2.48 (s, 3H).

Step E: 5-(difluoromethoxy)-7-methyl-1H-indole

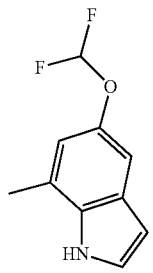

Using a procedure similar to Preparation #51, Step C, 5-(difluoromethoxy)-7-methyl-1H-indole (280 mg, 73%) was prepared from 5-(difluoromethoxy)-7-methyl-1-(phenylsulfonyl)-1H-indole (550 mg, 1.63 mmol). LC/MS (Method i): $R_t$=1.98 min.; MS m/z: 198 [M+H]$^+$; $^1$H NMR (DMSO-d$_6$, 300 MHz): δ 11.19 (s, 1H), 7.39 (m, 1H), 7.15 (s, 1H), 7.05 (t, J=74 Hz, 1H), 6.74 (s, 1H), 6.43 (m, 1H), 2.47 (s, 3H).

Preparation #66: 5-cyclopropyl-7-fluoro-1H-indole (10467249-0995

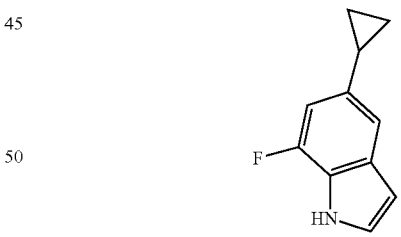

5-Bromo-7-fluoroindole (1 g, 4.67 mmol), cyclopropylboronic acid (0.602 g, 7.01 mmol), [1, F-bis(diphenylphosphino)ferrocene]dichloropalladium(II) (0.308 g, 0.420 mmol), and cesium carbonate (4.57 g, 14.02 mmol) were mixed and 1,4-dioxane (12.6 mL) and water (1.3 mL) were added. The reaction mixture was stirred at 110° C. under microwave irradiation for 30 minutes. Cyclopropylboronic acid (0.201 g, 2.336 mmol) and [1,1'-bis(diphenylphosphino)ferrocene]dichloropalladium(II) (0.154 g, 0.210 mmol) were added and the reaction mixture was stirred at 110° C. under microwave irradiation for 30 minutes. The reaction mixture was diluted with water. The aqueous layer was extracted with EtOAc. The obtained organic layer was dried over magnesium sulfate, filtered and concentrated under reduced pressure. The residue was purified by column chromatography on silica gel (eluting with 0-10% EtOAc in cyclohexane) to give 5-cyclopropyl-7-fluoro-1H-indole (1.19 g, 73%) as a yellow liquid. LC/MS (Method i): $R_t$=2.12 min.; MS m/z: 174 [M–H]$^-$; $^1$H NMR (DMSO-d$_6$, 300 MHz): δ 11.39 (broad, 1H), 7.33 (d, J=3.0 Hz, 1H), 7.10 (s, 1H), 6.63 (d, J=12.9, 1H), 6.39 (t, J=3.0 Hz, 1H), 1.97 (m, 1H), 0.89 (m, 2H), 0.63 (m, 2H).

Preparation #67:
7-fluoro-5-(trifluoromethyl)-1H-indole

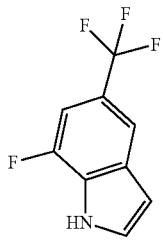 [SMILES: Fc1cc(C(F)(F)F)cc2cc[nH]c12]

Using a procedure similar to Preparation 64, Step B, 7-fluoro-5-(trifluoromethyl)-1H-indole (230 mg, 22%) was prepared from 2-fluoro-6-iodo-4-(trifluoromethyl)aniline (1 g, 3.61 mmol). LC/MS (Method i): $R_t$=2.12 min.; MS m/z: 202 [M–H]$^-$; $^1$H NMR (DMSO-d$_6$, 300 MHz): δ 12.10 (broad, 1H), 7.83 (s, 1H), 7.61 (d, J=3.1 Hz, 1H), 7.27 (d, J=11.5, 1H), 6.71 (t, J=3.1 Hz, 1H).

Preparation #68: 3,7-dimethyl-5-(trifluoromethyl)-1H-pyrrolo[2,3-c]pyridine

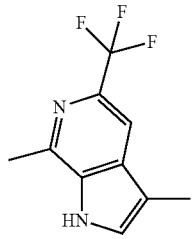

Step A:
4-iodo-2-methyl-6-(trifluoromethyl)pyridin-3-amine

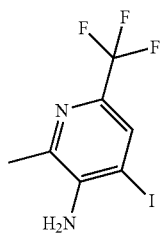

Using a procedure similar to Preparation #34, Step A, 4-iodo-2-methyl-6-(trifluoromethyl)pyridin-3-amine (3.4 g, 37%) was prepared from 2-methyl-6-(trifluoromethyl)pyridin-3-amine (4.9 g, 27.8 mmol). LC/MS (Method i): $R_t$=1.92 min.; MS m/z: 303 [M+H]$^+$; $^1$H NMR (CDCl$_3$, 300 MHz): δ 7.79 (s, 1H), 4.43 (broad, 2H), 2.53 (s, 3H).

Step B: N-allyl-4-iodo-2-methyl-6-(trifluoromethyl)pyridin-3-amine

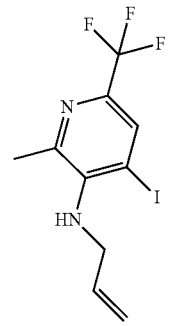 [SMILES: C=CCNc1c(I)cc(C(F)(F)F)nc1C]

Using a procedure similar to Preparation #43, Step A, N-allyl-4-iodo-2-methyl-6-(trifluoromethyl)pyridin-3-amine (3.7 g, 87%) was prepared from 4-iodo-2-methyl-6-(trifluoromethyl)pyridin-3-amine (3.4 g, 11.26 mmol). LC/MS (Method i): $R_t$=2.35 min.; MS m/z: 343 [M+H]$^+$; $^1$H NMR (CDCl$_3$, 300 MHz): δ 7.85 (s, 1H), 5.93 (m, 1H), 5.34 (d, J=17 Hz, 1H), 5.20 (d, J=9 Hz, 1H), 3.83 (broad, 3H), 2.62 (s, 3H).

Step C: 3,7-dimethyl-5-(trifluoromethyl)-1H-pyrrolo[2,3-c]pyridine

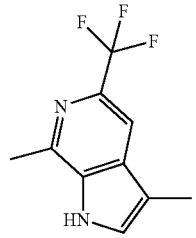

Using a procedure similar to Preparation #43, Step B, 3,7-dimethyl-5-(trifluoromethyl)-1H-pyrrolo[2,3-c]pyridine (2 g, 85%) was prepared from N-allyl-4-iodo-2-methyl-6-(trifluoromethyl)pyridin-3-amine (3.7 g, 10.82 mmol). LC/MS (Method i): $R_t$=1.81 min.; MS m/z: 215 [M+H]$^+$; $^1$H NMR (DMSO-d$_6$, 300 MHz): δ=11.78 (broad, 1H), 7.84 (s, 1H), 7.52 (s, 1H), 2.70 (s, 3H), 2.30 ppm (s, 3H)

Preparation #69: 3,7-dimethyl-5-(trifluoromethyl)-1H-pyrrolo[3,2-b]pyridine

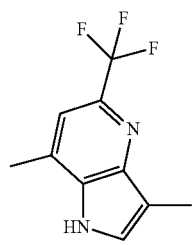

Step A: 2-bromo-4-methyl-6-(trifluoromethyl)pyridin-3-amine

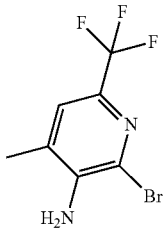

To a solution of 4-methyl-6-(trifluoromethyl)pyridin-3-amine (3.4 g, 19.30 mmol) in dimethyl sulfoxide (83 ml) and water (4.5 mL) was added 1-bromopyrrolidine-2,5-dione (8.59 g, 48.3 mmol) and the reaction mixture was stirred at room temperature for 24 hours. The reaction mixture was quenched with water, and the solid formed was filtrated. The filtrate was extracted twice with EtOAc. The organic layer was dried over magnesium sulfate, filtered and concentrated under reduced pressure. The two residues were purified by column chromatography on silica gel (eluting with 10-30% EtOAc in cyclohexane) to give 2-bromo-4-methyl-6-(trifluoromethyl)pyridin-3-amine (4.3 g, 85%). LC/MS (Method i): $R_t$=1.86 min.; MS m/z: 255 [M+H]$^+$; $^1$H NMR (DMSO-$d_6$, 300 MHz): δ 7.52 (s, 1H), 5.97 (s, 2H), 2.23 (s, 3H).

Step B: N-(2-bromo-4-methyl-6-(trifluoromethyl)pyridin-3-yl)-2,2,2-trifluoroacetamide

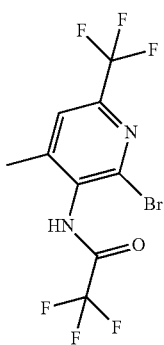 [SMILES: Cc1cc(C(F)(F)F)nc(Br)c1NC(=O)C(F)(F)F]

To a solution of 2-bromo-4-methyl-6-(trifluoromethyl)pyridin-3-amine (522 mg, 2.05 mmol in DCM (6 mL) was added pyridine (0.33 mL, 4.09 mmol) and trifluoroacetic anhydride (0.572 ml, 4.09 mmol) slowly. The reaction mixture was stirred at room temperature for 1 hour. The reaction mixture was washed with water and extracted twice with DCM. The organic layer was dried over magnesium sulfate, filtered and concentrated under reduced pressure to give N-(2-bromo-4-methyl-6-(trifluoromethyl)pyridin-3-yl)-2,2,2-trifluoroacetamide (764 mg, 100%) as a beige solid. LC/MS (Method i): $R_t$=2.01 min.; MS m/z: 351 [M+H]$^+$; $^1$H NMR (DMSO-$d_6$, 300 MHz): δ 11.80 (broad, 1H), 8.09 (s, 1H), 2.37 (s, 3H).

Step C: N-allyl-N-(2-bromo-4-methyl-6-(trifluoromethyl)pyridin-3-yl)-2,2,2-trifluoroacetamide

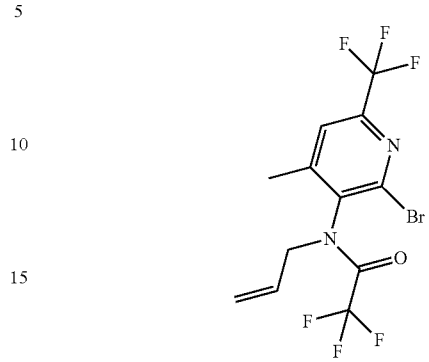

To a solution of N-(2-bromo-4-methyl-6-(trifluoromethyl)pyridin-3-yl)-2,2,2-trifluoroacetamide (719 mg, 2.048 mmol) in ACN (5 mL) was added sodium carbonate (651 mg, 6.14 mmol) and allyl bromide (0.71 mL, 8.19 mmol) and the reaction mixture was stirred at 70° C. for 2 hours. The reaction mixture was concentrated under reduced pressure, and the residue was diluted in EtOAc and washed with water. The organic layer was dried over magnesium sulfate, filtered and concentrated under reduced pressure to give N-allyl-N-(2-bromo-4-methyl-6-(trifluoromethyl)pyridin-3-yl)-2,2,2-trifluoroacetamide (795 mg, 99%). LC/MS (Method i): $R_t$=2.40 min.; MS m/z: 392 [M+H]$^+$; $^1$H NMR (DMSO-$d_6$, 300 MHz): δ 8.15 (s, 1H), 5.94 (m, 1H), 5.32 (dq, J=17, 1.5 Hz, 1H), 5.23 (m, 1H), 4.53 (dd, J=14.2, 6.3 Hz, 1H), 4.21 (dd, J=14.2, 7.6 Hz, 1H), 2.44 (s, 3H).

Step D: 3,7-dimethyl-5-(trifluoromethyl)-1H-pyrrolo[3,2-b]pyridine

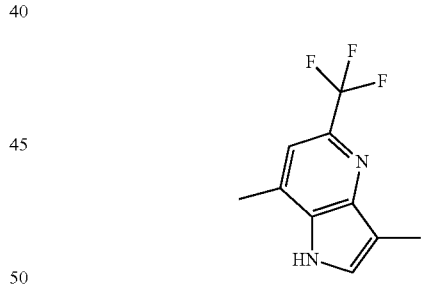

To a solution of N-allyl-N-(2-bromo-4-methyl-6-(trifluoromethyl)pyridin-3-yl)-2,2,2-trifluoroacetamide (200 mg, 0.256 mmol) in N,N-Dimethylformamide (1 ml) was added palladium(II) acetate (2.296 mg, 10.23 μmol), tetrabutylammonium chloride (78 mg, 0.281 mmol) and triethylamine (0.078 ml, 0.563 mmol) and the reaction mixture was stirred at 110° C. for 1.5 hour. The reaction mixture was washed with water and extracted with EtOAc. The organic layer was washed with water, then dried over magnesium sulfate, filtered and concentrated under reduced pressure. The residue was purified by column chromatography on silica gel (eluting with 10-60% EtOAc in cyclohexane) to give 3,7-dimethyl-5-(trifluoromethyl)-1H-pyrrolo[3,2-b]pyridine (29 mg, 53%). LC/MS (Method i): $R_t$=1.86 min.; MS m/z: 215 [M+H]$^+$; $^1$H NMR (DMSO-$d_6$, 300 MHz): δ 11.53 (broad, 1H), 7.61 (s, 1H), 7.39 (s, 1H), 2.57 (s, 3H), 2.30 (s, 3H).

Preparation #70: N-(4-cyano-2-iodo-3-methylphenyl)benzenesulfonamide

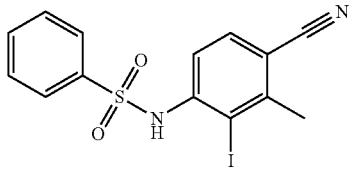 [SMILES: Cc1c(C#N)ccc(NS(=O)(=O)c2ccccc2)c1I]

Step A: 3-iodo-2-methyl-4-nitrobenzonitrile

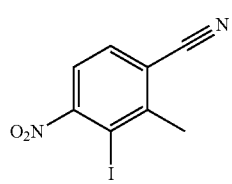

To a solution of 3-amino-2-methyl-4-nitrobenzonitrile (870 mg, 4.91 mmol) in THF (2.5 mL) and cooled to −10° C. was added drop by drop boron trifluoride diethyl etherate (1.079 mL, 8.59 mmol) and the reaction was stirred for 15 minutes at −10° C. Then isoamyl nitrite (0.986 mL, 7.37 mmol) was added dropwise and the reaction mixture was stirred for 2 hour to 0° C. Pentane (2 mL) was added to the reaction mixture and a beige precipitate was formed, filtrated and washed several time with diethylether. This residue was added to a mixture of iodine (935 mg, 3.68 mmol) and potassium iodide (1.6 g, 9.82 mmol) in acetone (6 mL) at 0° C. and the reaction mixture was stirred until the $N_2$ evolution ceased (15 minutes at 0° C. then 1 hour at room temperature. A 10% sodium thiosulfate aqueous solution was added to the reaction mixture and stirred for 15 minutes. Then it was extracted twice with DCM. The combined organic layers were washed with brine, and dried on magnesium sulfate and concentrated to give 3-iodo-2-methyl-4-nitrobenzonitrile (1.3 g, 88%) as a yellow solid. LC/MS (Method i): $R_t$=2.06 min.; MS m/z: 287 [M−H]−; 1H NMR (DMSO-$d_6$, 300 MHz): δ 8.08 (d, J=8.3 Hz, 1H), 7.84 (d, J=8.3 Hz, 1H), 2.73 (s, 3H).

Step B: 4-amino-3-iodo-2-methylbenzonitrile

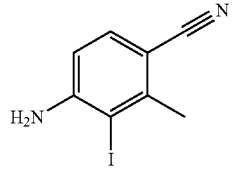

Using a procedure similar to Preparation #18, Step C, 4-amino-3-iodo-2-methylbenzonitrile (990 mg, 85%) were prepared from 3-iodo-2-methyl-4-nitrobenzonitrile (1.3 g, 4.51 mmol). LC/MS (Method i): $R_t$=1.84 min.; MS m/z: 259 [M+H]+; 1H NMR (DMSO-$d_6$, 300 MHz): δ 7.39 (d, J=8.4 Hz, 1H), 6.64 (d, J=8.4 Hz, 1H), 6.23 (s, 2H), 2.51 (s, 3H).

Step C: N-(4-cyano-2-iodo-3-methylphenyl)benzenesulfonamide

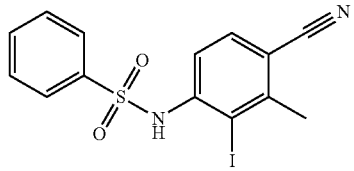 [SMILES: Cc1c(C#N)ccc(NS(=O)(=O)c2ccccc2)c1I]

Using a procedure similar to Preparation #16, Step B, N-(4-cyano-2-iodo-3-methylphenyl)benzenesulfonamide (1.8 g, 97%) were prepared from 4-amino-3-iodo-2-methylbenzonitrile (1.2 g, 4.65 mmol). LC/MS (Method i): $R_t$=2.15 min.; MS m/z: 397 [M−H]−; 1H NMR (DMSO-$d_6$, 300 MHz): δ 10.11 (m, 1H), 7.81 (m, 2H), 7.70 (m, 2H), 7.59 (m, 2H), 7.01 (d, J=8.4 Hz, 1H), 2.59 (s, 3H).

Preparation #71: 4,6-dichloro-1-(phenylsulfonyl)-1H-indole

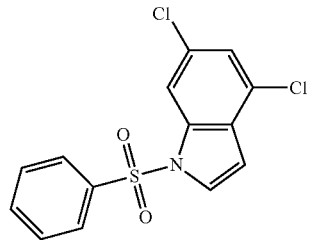 [SMILES: O=S(=O)(c1ccccc1)n1ccc2c(Cl)cc(Cl)cc21]

Using a procedure similar to Preparation #48, 4,6-dichloro-1-(phenylsulfonyl)-1H-indole (1.3 g, 74%) was prepared from 4,6-dichloro-1H-indole (1 g, 5.38 mmol). LC/MS (Method i): $R_t$=2.67 min.; MS m/z: 326 [M+H]+; 1H NMR (DMSO-$d_6$, 300 MHz): δ 8.10 (m, 1H), 8.06 (m, 1H), 8.03 (d, J=3.6 Hz, 1H), 7.94 (m, 1H), 7.75 (m, 1H), 7.65 (m, 2H), 7.54 (s, 1H), 6.90 (m, 1H).

Preparation #72: 6-methoxy-4-methyl-1-(phenylsulfonyl)-1H-indole

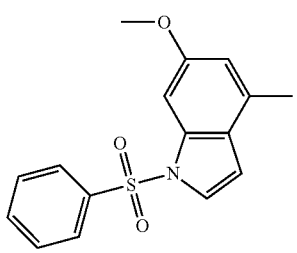 [SMILES: COc1cc(C)c2ccn(S(=O)(=O)c3ccccc3)c2c1]

Using a procedure similar to Preparation #48, 6-methoxy-4-methyl-1-(phenylsulfonyl)-1H-indole (1.3 g, 81%) was prepared from 6-methoxy-4-methyl-1H-indole (900 mg, 5.58 mmol). LC/MS (Method i): $R_t$=2.36 min.; MS m/z: 302 [M+H]+; 1H NMR (DMSO-$d_6$, 300 MHz): δ 7.96 (m, 2H), 7.63 (m, 4H), 7.25 (m, 1H), 6.80 (dd, J=3.6, 0.8 Hz, 1H), 6.72 (m, 1H), 3.80 (s, 3H), 2.37 (s, 3H).

Preparation #73: 4-fluoro-1-methyl-6-(trifluoromethyl)-1H-indole-2-carbaldehyde

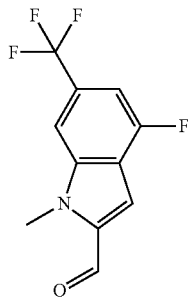 [SMILES: Cn1c(C=O)cc2c(F)cc(C(F)(F)F)cc21]

Step A: (Z)-ethyl 2-azido-3-(2-fluoro-4-(trifluoromethyl)phenyl)acrylate

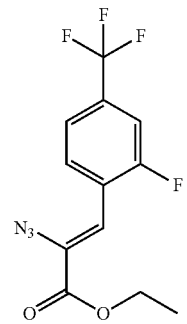 [SMILES: CCOC(=O)/C(=C/c1ccc(C(F)(F)F)cc1F)N=[N+]=[N-]]

To a solution of 2-fluoro-4-(trifluoromethyl)benzaldehyde (2.128 ml, 15.62 mmol) in EtOH (40 mL) the reaction mixture was cooled at −5° C. with a salt-ice bath fresh was added ethyl azidoacetate (7.14 mL, 62.5 mmol) and sodium ethanolate (5.31 g, 78 mmol). The reaction mixture was stirred at 0° C. for 1 hour and one night at room temperature. The reaction mixture was washed with water and extracted with EtOAc. The obtained organic layer was dried over magnesium sulfate, filtered and concentrated under reduced pressure. The residue was purified by column chromatography on silica gel (eluting with 5-20% EtOAc in cyclohexane) to give (Z)-ethyl 2-azido-3-(2-fluoro-4-(trifluoromethyl)phenyl)acrylate (1.75 g, 34%) as a yellow liquid. LC/MS (Method i): $R_t$=2.69 min.;

MS m/z: 276 [M-N2+H]$^+$; $^1$H NMR (DMSO-d$_6$, 300 MHz): δ 8.41 (dd, J=8.9, 7.8 Hz, 1H), 7.77 (dd, J=10.7, 1 Hz, 1H), 7.67 (dd, J=8.9, 1 Hz, 1H), 6.95 (s, 1H), 4.35 (q, J=7.1 Hz, 2H), 1.33 ppm (t, J=7.1 Hz, 3H)

Step B: ethyl 4-fluoro-6-(trifluoromethyl)-1H-indole-2-carboxylate

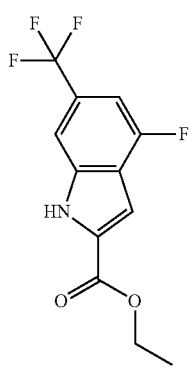 [SMILES: CCOC(=O)c1cc2c(F)cc(C(F)(F)F)cc2[nH]1]

A solution of (Z)-ethyl 2-azido-3-(2-fluoro-4-(trifluoromethyl)phenyl)acrylate (1.75 g, 5.77 mmol) in Xylene (5 mL) was stirred at 140° C. for 5 hours. The residue was directly purified by column chromatography on silica gel (eluting with 0-40% EtOAc in cyclohexane) to give ethyl 4-fluoro-6-(trifluoromethyl)-1H-indole-2-carboxylate (1.2 g, 64%) as a yellow solid. LC/MS (Method i): $R_t$=2.41 min.; MS m/z: 274 [M−H]$^−$; $^1$H NMR (DMSO-d$_6$, 300 MHz): δ 12.74 (broad, 1H), 7.64 (s, 1H), 7.29 (m, 2H), 4.39 (q, J=7.1 Hz, 2H), 1.36 ppm (t, J=7.1 Hz, 3H).

Step C: ethyl 4-fluoro-1-methyl-6-(trifluoromethyl)-1H-indole-2-carboxylate

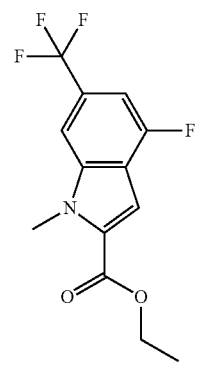

To a solution of ethyl 4-fluoro-6-(trifluoromethyl)-1H-indole-2-carboxylate (1 g, 3.63 mmol) in ACN (35 mL) was added dimethyl sulfate (1.7 mL, 18.17 mmol) and cesium carbonate (5.92 g, 18.17 mmol) and the reaction mixture was stirred at 50° C. overnight. The reaction mixture was diluted with H$_2$O and extracted with EtOAc. The organic layer was dried over magnesium sulfate, filtered and concentrated under reduced pressure. The residue was purified by column chromatography on silica gel (eluting with 5-20% EtOAc in cyclohexane) to give ethyl 4-fluoro-1-methyl-6-(trifluoromethyl)-1H-indole-2-carboxylate (240 mg, 23%). LC/MS (Method i): $R_t$=2.61 min.; MS m/z: 290 [M+H]$^+$; $^1$H NMR (DMSO-d$_6$, 300 MHz): δ 7.99 (s, 1H), 7.36 (s, 1H), 7.30 (d, J=10 Hz, 1H), 4.37 (q, J=7.1 Hz, 2H), 4.13 (s, 3H), 1.36 (t, J=7.1 Hz, 3H).

Step D: (4-fluoro-1-methyl-6-(trifluoromethyl)-1H-indol-2-yl)methanol

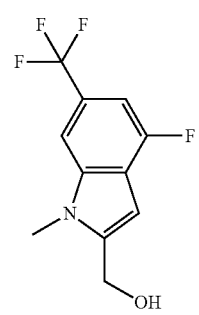 [SMILES: Cn1c(CO)cc2c(F)cc(C(F)(F)F)cc21]

To a solution of ethyl 4-fluoro-1-methyl-6-(trifluoromethyl)-1H-indole-2-carboxylate (232 mg, 0.802 mmol) in THF (5 mL) and cooled to 0° C. was added slowly lithium aluminum hydride (91 mg, 2.406 mmol) The reaction mixture was stirred at 0° C. during 30 minutes. Glauber's salt was added portionwise to the reaction mixture and stirred during one night. The salt was filtered and washed with DCM. The filtrate was concentrated under reduced pressure. The residue was purified by column chromatography on silica gel (eluting with 5-40% EtOAc in DCM) to give (4-fluoro-1-methyl-6-(trifluoromethyl)-1H-indol-2-yl)methanol (166 mg, 84%) as a white solid. LC/MS (Method i): $R_t$=2.02 min.; MS m/z: 248 [M+H]$^+$; $^1$H NMR (DMSO-$d_6$, 300 MHz): δ=7.78 (s, 1H), 7.13 (d, J=10.6 Hz, 1H), 6.56 (s, 1H), 5.43 (t, J=5.5 Hz, 1H), 4.69 (d, J=5.5 Hz, 2H), 3.84 (s, 3H).

Step E: 4-fluoro-1-methyl-6-(trifluoromethyl)-1H-indole-2-carbaldehyde

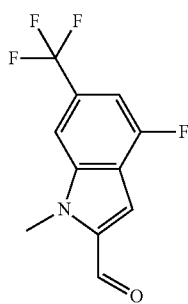 [SMILES: Cn1c(C=O)cc2c(F)cc(C(F)(F)F)cc21]

To a solution of (4-fluoro-1-methyl-6-(trifluoromethyl)-1H-indol-2-yl)methanol (162 mg, 0.65 mmol) in DCM (2 mL) was added manganese dioxide (342 mg, 3.93 mmol) and the reaction mixture was stirred at room temperature for 2 days. The reaction mixture was filtered and the solid was washed with DCM. The filtrate was concentrated under reduced pressure. The residue was purified by column chromatography on silica gel (eluting with 5-20% EtOAc in DCM) to give 4-fluoro-1-methyl-6-(trifluoromethyl)-1H-indole-2-carbaldehyde (117 mg, 73%) as a beige solid. LC/MS (Method i): $R_t$=2.28 min.; MS m/z: 246 [M+H]$^+$; $^1$H NMR (DMSO-$d_6$, 300 MHz): δ 10.02 (s, 1H), 8.01 (s, 1H), 7.63 (s, 1H), 7.32 (d, J=10.3 Hz, 1H), 4.14 (s, 3H).

Preparation #74: 6-(difluoromethoxy)-4-methyl-1-(phenylsulfonyl)-1H-indole

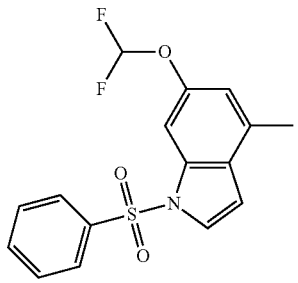 [SMILES: Cc1cc(OC(F)F)cc2c1ccn2S(=O)(=O)c1ccccc1]

Step A: 6-bromo-4-methyl-1-(phenylsulfonyl)-1H-indole

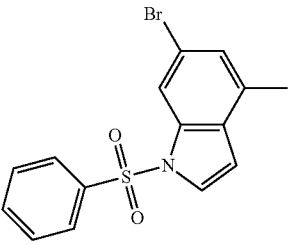

Using a procedure similar to described in Preparation #48, 6-bromo-4-methyl-1-(phenylsulfonyl)-1H-indole (3.49 g, 84%) was prepared from 6-bromo-4-methyl-1H-indole (2.5 g, 11.9 mmol). LC/MS (Method i): $R_t$=2.41 min.; MS m/z: 350 [M+H]$^+$; $^1$H NMR (DMSO-$d_6$, 300 MHz): δ 7.99 (m, 2H), 7.89 (m, 1H), 7.85 (d, J=3.8 Hz, 1H), 7.72 (m, 1H), 7.62 (m, 2H), 7.28 (m, 1H), 6.92 (d, J=3.6 Hz, 1H), 2.43 (s, 3H).

Step B: 4-methyl-1-(phenylsulfonyl)-1H-indol-6-ol

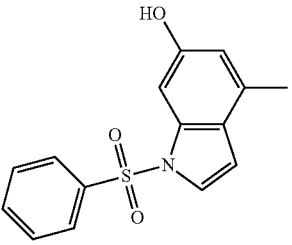 [SMILES: Cc1cc(O)cc2c1ccn2S(=O)(=O)c1ccccc1]

Using a procedure similar to described in Preparation #65, Step B and Step C, 4-methyl-1-(phenylsulfonyl)-1H-indol-6-ol (2.35 g, 82%) was prepared from 6-bromo-4-methyl-1-(phenylsulfonyl)-1H-indole (3.49 g, 9.96 mmol). LC/MS (Method i): $R_t$=2.03 min.; MS m/z: 288 [M+H]$^+$; $^1$H NMR (DMSO-$d_6$, 300 MHz): δ 9.48 (s, 1H), 7.87 (m, 2H), 7.69 (m, 1H), 7.61 (m, 2H), 7.54 (d, J=3.8 Hz, 1H), 7.14-7.19 (m, 1H), 6.74 (d, J=3.8 Hz, 1H), 6.55 (m, 1H), 2.32 (s, 3H).

Step C: 6-(difluoromethoxy)-4-methyl-1-(phenylsulfonyl)-1H-indole

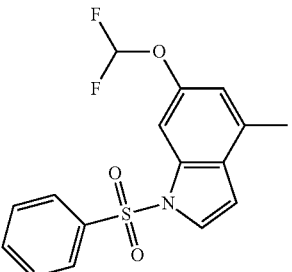

Using a procedure similar to Preparation 65, Step D, 6-(difluoromethoxy)-4-methyl-1-(phenylsulfonyl)-1H-indole (1.73 g, 63%) was prepared from 4-methyl-1-(phenylsulfonyl)-1H-indol-6-ol (2.35 g, 8.18 mmol). LC/MS (Method i): $R_t$=2.44 min.; MS m/z: 338 [M+H]$^+$; $^1$H NMR (DMSO-d$_6$, 300 MHz): δ=7.99 (m, 2H), 7.83 (d, J=3.6 Hz, 1H), 7.71 (m, 1H), 7.60 (m, 2H), 7.54 (m, 1H), 7.24 (t, J=74.0 Hz, 1H), 6.95 (m, 1H), 6.91 (d, J=3.8 Hz, 1H), 2.43 (s, 3H).

Preparation #75: N-(2-iodo-5-(trifluoromethoxy)phenyl)benzenesulfonamide

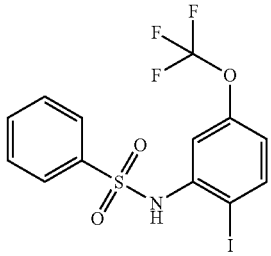 [SMILES: O=S(=O)(Nc1cc(OC(F)(F)F)ccc1I)c1ccccc1]

Using a procedure similar to described in Preparation #16, Step B, N-(2-iodo-5-(trifluoromethoxy)phenyl)benzenesulfonamide (4.28 g, 86%) was prepared from 2-iodo-5-(trifluoromethoxy)aniline (3.2 g, 10.56 mmol). LC/MS (Method i): $R_t$=2.28 min.; MS m/z: 444 [M+H]$^+$; $^1$H NMR (DMSO-d$_6$, 300 MHz): δ 10.06 (s, 1H), 7.95 (d, J=8.8 Hz, 1H), 7.70 (m, 3H), 759 (m, 2H), 7.04 (m, 1H), 6.88 (m, 1H).

Preparation #76: N-(2-bromo-3-methyl-5-nitrophenyl)benzenesulfonamide

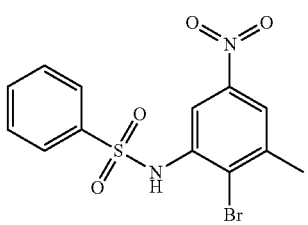 [SMILES: Cc1cc([N+](=O)[O-])cc(NS(=O)(=O)c2ccccc2)c1Br]

Using a procedure similar to described in Preparation #16, Step B, N-(2-bromo-3-methyl-5-nitrophenyl)benzenesulfonamide (3.24 g, 38%) was prepared from 2-bromo-3-methyl-5-nitroaniline (5.3 g, 22.94 mmol). LC/MS (Method i): $R_t$=2.16 min.; MS m/z: 369 [M–H]$^-$; $^1$H NMR (DMSO-d$_6$, 300 MHz): δ 10.42 (broad, 1H), 8.10 (d, J=2.5 Hz, 1H), 7.77 (m, 3H), 7.99 (m, 1H), 7.59 (m, 2H), 2.42 (s, 3H).

Preparation #77: 6-cyclopropyl-4-fluoro-1-(phenylsulfonyl)-1H-indole

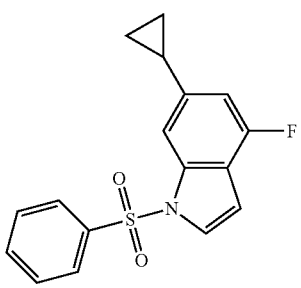 [SMILES: O=S(=O)(c1ccccc1)n1ccc2c(F)cc(C3CC3)cc21]

Step A: 6-bromo-4-fluoro-1-(phenylsulfonyl)-1H-indole

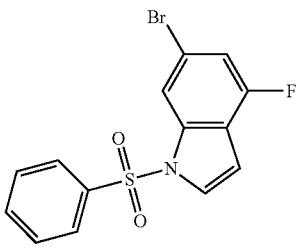 [SMILES: O=S(=O)(c1ccccc1)n1ccc2c(F)cc(Br)cc21]

Using a procedure similar to described in Preparation #48, 6-bromo-4-fluoro-1-(phenylsulfonyl)-1H-indole (251 mg, 76%) was prepared from 6-bromo-4-fluoro-1H-indole (200 mg, 0.93 mmol). LC/MS (Method j): $R_t$=1.93 min.; MS m/z: 354 [M+H]$^+$; $^1$H NMR (DMSO-d$_6$, 300 MHz): δ=8.06 (m, 2H), 7.95 (m, 2H), 7.76 (m, 1H), 7.65 (m, 2H), 7.44 (d, J=9.4 Hz, 1H), 6.96 ppm (d, J=3.8 Hz, 1H).

Step B: 6-cyclopropyl-4-fluoro-1-(phenylsulfonyl)-1H-indole

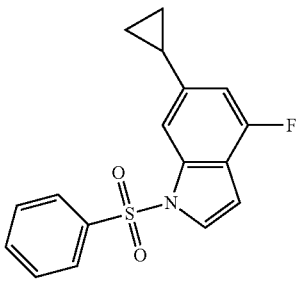 [SMILES: O=S(=O)(c1ccccc1)n1ccc2c(F)cc(C3CC3)cc21]

Using a procedure similar to described in Preparation #12, 6-cyclopropyl-4-fluoro-1-(phenylsulfonyl)-1H-indole (100 mg, 80%) was prepared from 6-bromo-4-fluoro-1H-indole (140 mg, 0.39 mmol). $^1$H NMR (DMSO-d$_6$, 300 MHz): δ 8.01 (m, 2H), 7.78 (d, J=3.8 Hz, 1H), 7.73 (m, 1H), 7.63 (m, 2H), 7.52 (s, 1H), 6.84 (dd, J=3.6, 0.7 Hz, 1H), 6.78 (dd, J=11.5, 1.2 Hz, 1H), 2.11 (m, 1H), 1.02 (m, 2H), 0.72 (m, 2H).

Preparation #78: 7-methyl-5-(trifluoromethyl)-1H-indazole

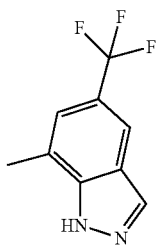

Using a procedure similar to described in Preparation #42, Step D, 7-methyl-5-(trifluoromethyl)-1H-indazole (550 mg, 46%) was prepared from 2-fluoro-3-methyl-5-(trifluoromethyl)benzaldehyde (1 g, 4.85 mmol) (Preparation #42, Step A). LC/MS (Method i): $R_t$=1.87 min.; MS m/z: 201 [M+H]$^+$; $^1$H NMR (DMSO-d$_6$, 300 MHz): δ=13.58 (m, 1H), 8.25 (s, 1H), 8.04 (s, 1H), 7.41 (s, 1H), 2.59 (s, 3H).

Preparation #79: 1,4-dimethyl-6-(trifluoromethyl)-1H-indazole-3-carbaldehyde

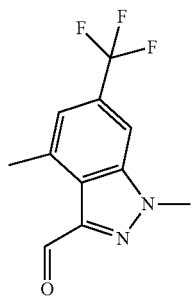

Step A: 4-methyl-6-(trifluoromethyl)-1H-indazole


Using a procedure similar to described in Preparation #41, Step B, 4-methyl-6-(trifluoromethyl)-1H-indazole (4.91 g, 72%) was prepared from 4-bromo-6-(trifluoromethyl)-1H-indazole (9 g, 34 mmol).

LC/MS (Method i): $R_t$=1.89 min.; MS m/z: 201 [M+H]$^+$; $^1$H NMR (DMSO-d$_6$, 300 MHz): δ 13.49 (broad, 1H), 8.30 (s, 1H), 7.73 (s, 1H), 7.18 (s, 1H), 2.64 (s, 3H).

Step B: 3-iodo-4-methyl-6-(trifluoromethyl)-1H-indazole

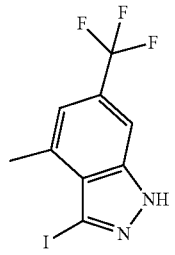

To a solution of 4-methyl-6-(trifluoromethyl)-1H-indazole (3 g, 14.99 mmol) in 1,4-dioxane (89.7 mL) was added 2N of sodium hydroxide solution (11.24 mL, 22.48 mmol) and the reaction mixture was stirred at room temperature 1 hour. Then diiodine (4.5 g, 17.99 mmol) was added and the reaction mixture was stirred at room temperature 20 hours. A 10% Na$_2$S$_2$O$_3$ solution was added, and the mixture was stirred 15 min at room temperature, then extracted with EtOAc. HCl 1M was added in the aqueous layer and it was extracted twice with EtOAc. The combined organic layers were dried over magnesium sulfate, filtered and concentrated under vacuum. The residue was purified by column chromatography on silica gel (eluting with 5-15% EtOAc in cyclohexane) to give 3-iodo-4-methyl-6-(trifluoromethyl)-1H-indazole (4.33 g, 89%) as a white powder. LC/MS (Method i): $R_t$=2.22 min.;

MS m/z: 327 [M+H]$^+$; $^1$H NMR (DMSO-d$_6$, 300 MHz): δ 13.89 (broad, 1H), 7.80 (s, 1H), 7.20 (s, 1H), 2.85 (s, 3H).

Step C: 3-iodo-1,4-dimethyl-6-(trifluoromethyl)-1H-indazole

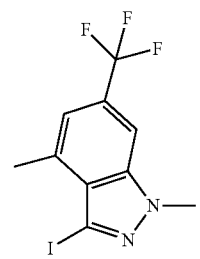

Using a procedure similar to described in Preparation #51, Step E, 3-iodo-1,4-dimethyl-6-(trifluoromethyl)-1H-indazole (3.5 g, 67%) was prepared from 3-iodo-4-methyl-6-(trifluoromethyl)-1H-indazole (4.3 g, 13.3 mmol). LC/MS (Method i): $R_t$=2.44 min.; MS m/z: 341 [M+H]$^+$; $^1$H NMR (DMSO-d$_6$, 300 MHz): δ 8.06 (s, 1H), 7.22 (s, 1H), 4.12 (s, 3H), 2.83 (s, 3H).

Step D: 1,4-dimethyl-6-(trifluoromethyl)-3-vinyl-1H-indazole

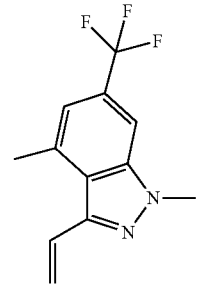

To a solution of 3-iodo-1,4-dimethyl-6-(trifluoromethyl)-1H-indazole (3.3 g, 9.70 mmol) in toluene (105 mL) was added bis(triphenylphosphine)palladium(II) chloride (681 mg, 0.970 mmol) and tributyl(vinyl)tin (3.97 mL, 13.58 mmol), and the reaction mixture was stirred 2 hours at 90° C. SiO$_2$ was added, and the reaction mixture was evaporated to dryness and purified by column chromatography on silica gel (eluting with 0-20% EtOAc in cyclohexane) to give 1,4-dimethyl-6-(trifluoromethyl)-3-vinyl-1H-indazole (2.33 g, 90%) as a white powder. LC/MS (Method i): $R_t$=2.33 min.; MS m/z: 241 [M+H]$^+$; $^1$H NMR (DMSO-d$_6$, 300

MHz): δ 7.95 (s, 1H), 7.19 (s, 1H), 7.22 (dd, J=17.3, 11.1 Hz, 1H), 6.02 (dd, J=17.3, 2.1 Hz, 1H), 5.40 (dd, J=11.1, 2.1 Hz, 1H), 4.12 (s, 3H), 2.71 (s, 3H).

Step E: 1,4-dimethyl-6-(trifluoromethyl)-1H-indazole-3-carbaldehyde

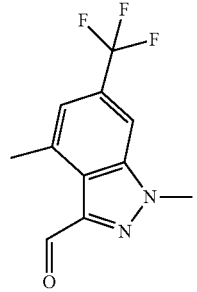

To a solution of 1,4-dimethyl-6-(trifluoromethyl)-3-vinyl-1H-indazole (2.3 g, 9.70 mmol) in ACN (66 mL) and water (14.51 mL) was added a solution of ruthenium(III) chloride hydrate (9.70 mL, 0.388 mmol) in water (9.70 mL), followed by sodium periodate (4.1 g, 19.40 mmol). The reaction mixture was stirred overnight at room temperature. A saturated solution of sodium thiosulfate was added, and the mixture was extracted twice with EtOAc. The organic layer was dried over magnesium sulfate, filtered and concentrated under vacuum. The residue was purified by column chromatography on silica gel (eluting with 0-20% EtOAc in cyclohexane) to give 1,4-dimethyl-6-(trifluoromethyl)-1H-indazole-3-carbaldehyde (1.1 g, 47%) as a white powder. LC/MS (Method i): $R_t$=2.15 min.; MS m/z: 243 [M+H]$^+$; $^1$H NMR (DMSO-d$_6$, 300 MHz): δ 10.14 (s, 1H), 8.15 (s, 1H), 7.45 (s, 1H), 4.29 (s, 3H), 2.87 (s, 3H).

Preparation #80: 4-methyl-6-(trifluoromethoxy)-1H-indole

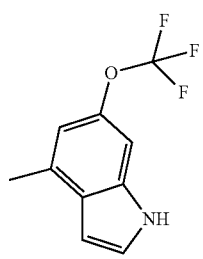

Using a procedure similar to described in Preparation 64, Step B, 4-methyl-6-(trifluoromethoxy)-1H-indole (373 mg, 57%) was prepared from 2-iodo-3-methyl-5-(trifluoromethoxy)aniline (1.1 g, 3.47 mmol) (Preparation #47, Step D). LC/MS (Method i): $R_t$=2.24 min.; MS m/z: 214 [M–H]$^-$; $^1$H NMR (DMSO-d$_6$, 300 MHz): δ=11.27 (broad, 1H), 7.42 (m, 1H), 7.17 (m, 1H), 6.79 (m, 1H), 6.50 (m, 1H), 2.49 (s, 3H).

Preparation #81: methyl 2-azaspiro[3.3]heptane-6-carboxylate 2,2,2-trifluoroacetate

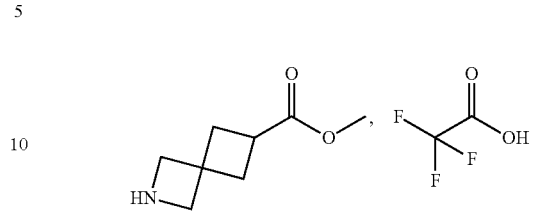

To a solution of methyl 2-boc-2-aza-spiro[3.3]heptane-6-carboxylate (400 mg, 1.57 mmol) in DCM (6 mL) was added TFA (3.02 mL, 39.2 mmol) and the reaction mixture was stirred at room temperature for 18 hours. The reaction mixture was concentrated under reduced pressure to give methyl 2-azaspiro[3.3]heptane-6-carboxylate 2,2,2-trifluoroacetate (422 mg, 100%). $^1$H NMR (DMSO-d$_6$, 300 MHz): δ 3.98 (t, J=6.2 Hz, 2H), 3.90 (t, J=6.2 Hz, 2H), 3.59 (s, 3H), 3.01 (m, 1H), 2.50 (m, 4H).

Preparation #82: methyl 2-(2-azaspiro[3.3]heptan-6-yl)acetate hydrochloride

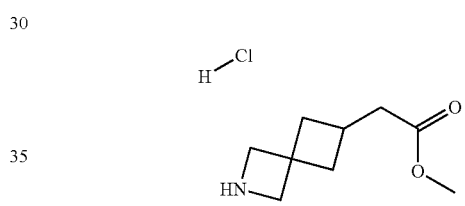

To a solution of 2-(2-(tert-butoxycarbonyl)-2-azaspiro [3.3]heptan-6-yl)acetic acid (309 mg, 1.21 mmol) in EtOHMeOH (2.3 mL) was added dropwise oxalyl chloride (0.21 mL, 2.42 mmol) and the reaction mixture was stirred at room temperature for 20 hours, then concentrated under reduced pressure to give methyl 2-(2-azaspiro[3.3]heptan-6-yl)acetate hydrochloride (249 mg, 100%) as a white solid. $^1$H NMR (DMSO-d$_6$, 300 MHz): δ 3.94 (m, 2H), 3.81 (m, 2H), 3.76 (s, 1H), 3.56 (s, 3H), 2.38 (m, 4H), 1.88 (m, 2H).

Preparation #83: (3S,4S)-ethyl 3-methylpiperidine-4-carboxylate, Hydrochloric Acid

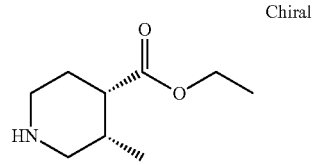

Step 1: (cis)-ethyl 3-methylpiperidine-4-carboxylate

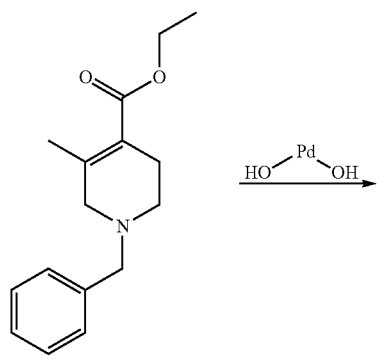

A flask was charged with Pd(OH)$_2$ (2.71 g, 3.86 mmol) and dissolved in EtOH (100 mL) under a blanket of nitrogen. A solution of ethyl 1-benzyl-5-methyl-1,2,3,6-tetrahydropyridine-4-carboxylate (10 g, 38.6 mmol) (*Journal of Med Chem*, 2010, vol. 53, #21 p. 7682-7698) in EtOH (50 mL) was added and the reaction was purged with hydrogen balloon and stirred at room temperature. The catalyst was filtered off and the solvent was concentrated under reduced pressure to afford an oil (cis)-ethyl 3-methylpiperidine-4-carboxylate (29 g, 169 mmol, 97% yield). LC/MS (Method i) R$_t$=0.1 min.; MS m/z: 130 (M+H)$^+$.

Step 2: (3R,4R)-ethyl 3-methylpiperidine-4-carboxylate, Hydrochloric Acid and (3S,4S)-ethyl 3-methylpiperidine-4-carboxylate, hydrochloric acid

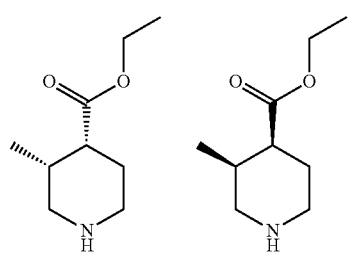

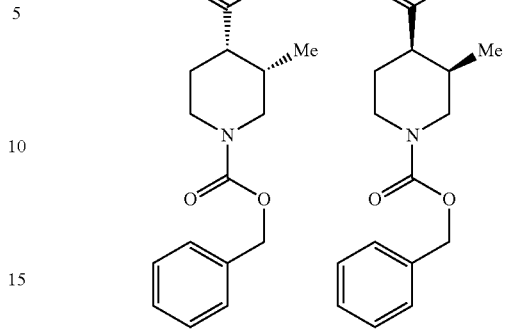

N-ethyl-N-isopropylpropan-2-amine (5.35 ml, 30.7 mmol) was added to a solution of rac-(3R,4R)-ethyl 3-methylpiperidine-4-carboxylate (5.00 g, 29.2 mmol) (10:1 mixture of cis/trans isomers) dissolved in DCM (97 mL) at room temperature in a 250 mL flask. benzyl 2,5-dioxopyrrolidine-1-carboxylate (6.81 g, 28.6 mmol) was added batchwise at room temperature. After 3 hours the reaction was concentrated to dryness then redissolved in ether. The solution was washed with water, 10% HCl solution (2×20 mL), followed by a brine solution (20 mL), and then dried over magnesium sulfate. The cis-isomers were separated by prep SFC: 10% isopropanol in CO$_2$ (60 mL/min, 140 bar, 40° C.). Cycle time was 4.40 min, with single run time of 22 min HPLC grade isopropanol was used with SFC grade CO$_2$. The chromatography used a YMC-SC, 30×150 mm column (5 μm particles).

LC/MS (Method i) Rt=1.60 min.; MS m/z: 306 (M+H)+.

Step 3: (3S,4S)-ethyl 3-methylpiperidine-4-carboxylate, hydrochloric acid

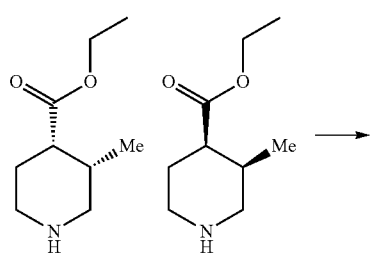

Palladium on carbon (4.18 g, 3.93 mmol) was added to a 50 mL round bottom flask under a blank of nitrogen. (3S,4S)-1-benzyl 4-ethyl 3-methylpiperidine-1,4-dicarboxylate (12 g, 39.3 mmol) was dissolved in EtOH (7 mL) and added to the reaction flask. The flask was purged with an atmosphere of hydrogen and then stirred for about 18 hr. Upon completion, the hydrogen was removed and the mixture was filtered through a pad of Celite®. The solution was concentrated to dryness. Ether (10 mL) was added followed by HCl in ether (58.9 mL, 58.9 mmol), which precipitated out a white solid. the solid was filtered under a stream of nitrogen and then dried in a vacuum oven for about two hours. The material was collected as a pure white solid (3S,4S)-ethyl 3-methylpiperidine-4-carboxylate, hydrochloric acid (5.3 g, 25.5 mmol, 64.9% yield). LC/MS (Method i) $R_t$=0.1 min.; MS m/z: 130 (M+H)+.

Preparation #84: (3R,4R)-ethyl 3-methylpiperidine-4-carboxylate, hydrochloric acid

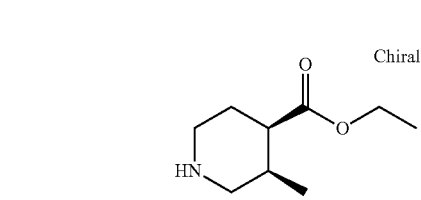

Step 1: (cis)-ethyl 3-methylpiperidine-4-carboxylate

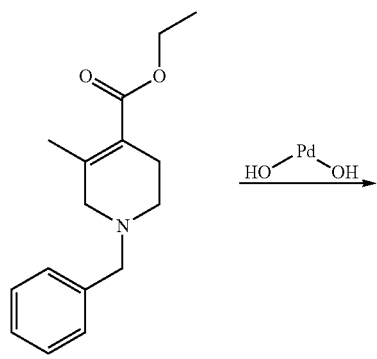

A flask was charged with Pd(OH)$_2$ (2.71 g, 3.86 mmol) and dissolved in EtOH (100 mL) under a blanket of nitrogen. A solution of ethyl 1-benzyl-5-methyl-1,2,3,6-tetrahydropyridine-4-carboxylate (10 g, 38.6 mmol) (*Journal of Med Chem*, 2010, vol. 53, #21 p. 7682-7698) in EtOH (50 mL) was added and the reaction was purged with hydrogen balloon and stirred at room temperature for about 18 hours. The catalyst was filtered off and the solvent was concentrated under reduced pressure to afford (cis)-ethyl 3-methylpiperidine-4-carboxylate (29 g, 169 mmol, 97%) as an oil. LC/MS (Method i) $R_t$=0.1 min.; MS m/z: 130 (M+H)+.

Step 2: (3R,4R)-ethyl 3-methylpiperidine-4-carboxylate, hydrochloric acid

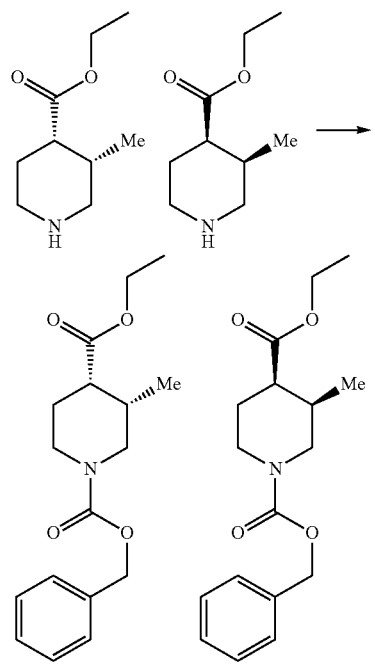

N-ethyl-N-isopropylpropan-2-amine (5.35 mL, 30.7 mmol) was added to a solution of rac-(3R,4R)-ethyl 3-methylpiperidine-4-carboxylate (5.00 g, 29.2 mmol) (10:1 mixture of cis/trans isomers) dissolved in DCM (97 mL) at room temperature in a 250 mL flask. Benzyl 2,5-dioxopyrrolidine-1-carboxylate (6.81 g, 28.6 mmol) was added batchwise at room temperature. After 3 hours the reaction was concentrated to dryness then redissolved in ether. The solution was washed with water, 10% HCl solution (2×20 mL), followed by a brine solution (20 mL), and then dried over magnesium sulfate. The cis-isomers were separated by prep SFC: 10% isopropanol in CO$_2$ (60 mL/min, 140 bar, 40° C.). Cycle time was 4.40 min, with single run time of 22 min HPLC grade isopropanol was used with SFC grade CO$_2$. The chromatography used a YMC-SC, 30×150 mm column (5 μm particles).

LC/MS (Method i) $R_t$=1.60 min.; MS m/z: 306 (M+H)+.

Step 3: (3R,4R)-ethyl 3-methylpiperidine-4-carboxylate, hydrochloric acid

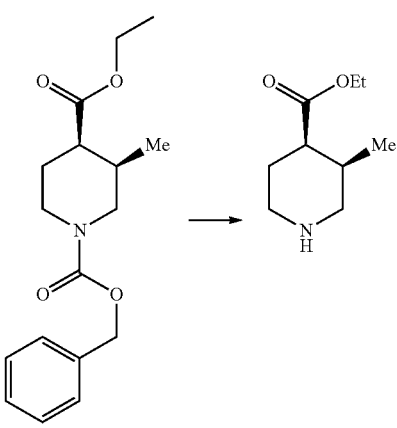 [SMILES: CCOC(=O)[C@@H]1CCN(C(=O)OCc2ccccc2)C[C@@H]1C ; CCOC(=O)[C@@H]1CCNC[C@@H]1C]

Palladium on carbon (2.67 g, 2.505 mmol) was added to a dry nitrogen flushed 2-neck 500 mL flask. A minimal amount of EtOAc was added to wet the catalyst, and then EtOH (200 mL) was carefully added to the flask while stirring. (3R,4R)-1-benzyl 4-ethyl 3-methylpiperidine-1,4-dicarboxylate (15.3 g, 50.1 mmol) was added in 50 mL of EtOH and then the flask was flushed three times with an atmosphere of hydrogen. The reaction was allowed to stir overnight. The mixture was then evacuated with nitrogen and then filtered through a pad of Celite® and the filtrate was concentrated to a crude oil. The oil was dissolved in ether (50 mL) and then 4M HCl in ether was added. The solution was filtered into a fitted funnel under a stream a nitrogen and then dried in a vacuum oven for couple of hours to provide (3R,4R)-ethyl 3-methylpiperidine-4-carboxylate, hydrochloric acid (6.88 g, 66%). LC/MS (Method i) Rt=0.1 min.; MS m/z: 130 (M+H)+.

Preparation #85:
2-iodo-3-methyl-5-(trifluoromethyl)phenol

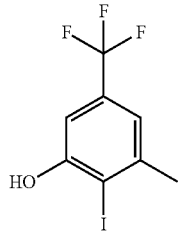

To a solution of 2-iodo-3-methyl-5-(trifluoromethyl)aniline (3 g, 9.97 mmol) (Preparation #16, Step A) in acetic acid (30 mL, 9.97 mmol) and cooled to 10° C. was added drop by drop sodium nitrite (1.031 g, 14.95 mmol) in solution in sulfuric acid (18 mL, 9.97 mmol). The reaction mixture was stirred 30 minutes between 10 and 15° C. This solution was added drop by drop to a refluxed solution of water (54 mL) and the reaction mixture was stirred 30 minutes at reflux. The reaction was cooled to room temperature and the mixture was extracted twice with EtOAc. The organic layer was dried over magnesium sulfate, filtered and concentrated under reduced pressure to give 2-iodo-3-methyl-5-(trifluoromethyl)phenol (3 g, 100%) as an orange oil. LC/MS (Method i): R$_f$=2.19 min.; MS m/z: 301 [M−H]⁻; ¹H NMR (DMSO-d$_6$, 300 MHz): δ 10.96 (s, 1H), 7.13 (s, 1H), 6.93 (s, 1H), 2.44 (s, 3H).

Example A: (2,4-dichloro-3-((1,4-dimethyl-6-(trifluoromethyl)-1H-indol-2-yl)methyl)phenyl)(4-(2-methoxyethyl)piperazin-1-yl)methanone

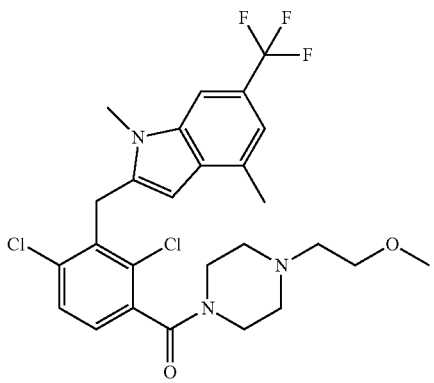

Step 1: methyl 2,4-dichloro-3-(hydroxy(4-methyl-1-(phenylsulfonyl)-6-(trifluoromethyl)-1H-indol-2-yl)methyl)benzoate

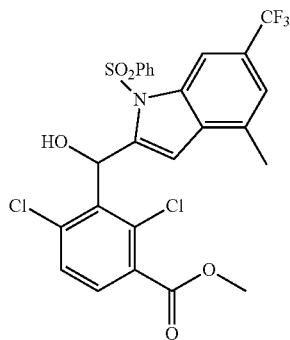

To a solution of N-(2-iodo-3-methyl-5-(trifluoromethyl)phenyl)benzenesulfonamide (Preparation #16) (300 mg, 0.680 mmol) in DMF (2 mL) was added Pd(PPh$_3$)$_2$Cl$_2$ (23.86 mg, 0.034 mmol), copper(I) iodide (6.47 mg, 0.034 mmol), triethylamine (2 mL) and methyl 2,4-dichloro-3-(1-hydroxyprop-2-yn-1-yl)benzoate (229 mg, 0.884 mmol) (Preparation #1). The reaction mixture was heated at about 110° C. under microwave for 20 minutes, and then diluted with water. The aqueous layer was extracted with EtOAc, dried over magnesium sulfate, filtered and concentrated under reduced pressure. The residue was purified by column chromatography on silica gel (eluting with 0-60% EtOAc in cyclohexane) to give methyl 2,4-dichloro-3-(hydroxy(4-methyl-1-(phenylsulfonyl)-6-(trifluoromethyl)-1H-indol-2-yl)methyl)benzoate (400 mg, 99%) as a brown oil. LC/MS (Method h) R$_f$=3.33 min.; MS m/z: 630 [M−H]⁻+ CH$_3$COOH. ¹H NMR (DMSO-d$_6$, 300 MHz): δ 8.08 (s, 1H) 7.80 (m, 1H), 7.78 (m, 1H), 7.68 (m, 2H), 5.56 (m, 3H), 7.43 (s, 1H), 7.02 (d, 1H), 6.88 (s, 1H), 6.75 (d, 1H), 3.86 (s, 3H), 2.47 (s, 3H).

Step 2: methyl 2,4-dichloro-3-((4-methyl-1-(phenylsulfonyl)-6-(trifluoromethyl)-1H-indol-2-yl)methyl)benzoate

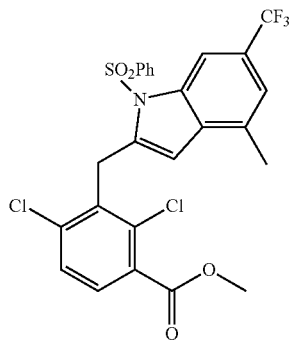

To a solution of methyl 2,4-dichloro-3-(hydroxy(4-methyl-1-(phenylsulfonyl)-6-(trifluoromethyl)-1H-indol-2-yl)methyl)benzoate (440 mg, 0.769 mmol) in DCM (4.6 mL) cooled at 0° C. was added triethylsilane (0.613 mL, 3.84 mmol), boron trifluoride diethyl etherate (0.483 mL, 3.84 mmol) and TFA (0.046 mL). The reaction mixture was stirred at room temperature for one hour, then diluted with water. The obtained aqueous layer was extracted with DCM and the organic layer was washed with NaHCO₃ saturated aqueous solution, dried over magnesium sulfate, filtered and concentrated under reduced pressure to give methyl 2,4-dichloro-3-((4-methyl-1-(phenylsulfonyl)-6-(trifluoromethyl)-1H-indol-2-yl)methyl)benzoate (413 mg, 94%) as a black solid. LC/MS (Method h) R$_f$=3.79 min.; MS m/z: 556 [M+H]⁺. ¹H NMR (DMSO-d₆, 300 MHz): δ 8.24 (s, 1H), 7.92 (m, 2H), 7.81 (m, 2H), 7.70 (m, 3H), 7.42 (s, 1H), 5.98 (s, 1H), 4.61 (s, 2H), 3.86 (s, 3H), 2.35 (s, 3H)

Step 3: methyl 2,4-dichloro-3-((4-methyl-6-(trifluoromethyl)-1H-indol-2-yl)methyl)benzoate

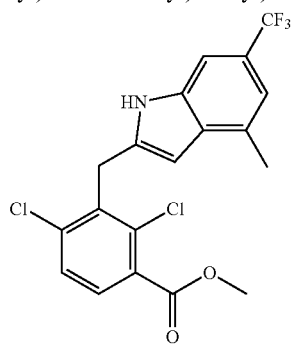

To a solution of methyl 2,4-dichloro-3-((4-methyl-1-(phenylsulfonyl)-6-(trifluoromethyl)-1H-indol-2-yl)methyl)benzoate (6.16 g, 11.07 mmol) in THF (200 mL) was added dropwise tetrabutylammonium fluoride (13.29 mL, 13.29 mmol). The reaction mixture was stirred at reflux for one hour and tetrabutylammonium fluoride (3.3 mL, 3.3 mmol) was added and refluxed for one more hour. The reaction mixture was concentrated under reduced pressure and the residue was taken in EtOAc and washed with NaHCO₃ saturated aqueous solution. The organic layer was then dried over magnesium sulfate, filtered and evaporated under reduced. The residue was purified by column chromatography on silica gel (eluting with 0-20% EtOAc in cyclohexane) to give methyl 2,4-dichloro-3-((4-methyl-6-(trifluoromethyl)-1H-indol-2-yl)methyl)benzoate (3.8 g, 66%) as a yellow solid. LC/MS (Method h) R$_f$=3.39 min.; MS m/z: 416 [M+H]⁺. ¹H NMR (CDCl₃, 300 MHz): δ 8.36 (s, 1H), 7.64 (d, J=9.0 Hz, 1H), 7.43 (m, 2H), 7.09 (s, 1H), 6.39 (s, 1H), 4.56 (s, 2H), 3.94 (s, 3H), 2.52 (s, 3H)

Step 4: methyl 2,4-dichloro-3-((1,4-dimethyl-6-(trifluoromethyl)-1H-indol-2-yl)methyl)benzoate

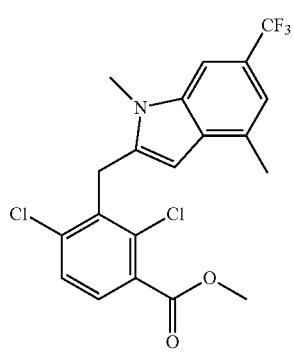 [SMILES: COC(=O)c1ccc(Cl)c(Cc2cc3c(C)cc(C(F)(F)F)cc3n2C)c1Cl]

To a solution of methyl 2,4-dichloro-3-((4-methyl-6-(trifluoromethyl)-1H-indol-2-yl)methyl)benzoate (3.80 g, 9.13 mmol) in DMF (100 mL) was added portionwise sodium hydride (0.402 g, 10.04 mmol). The reaction mixture was stirred at room temperature for 10 minutes then iodomethane (0.628 mL, 10.04 mmol) was added and the reaction mixture was stirred for one hour. The reaction mixture was diluted with water. The resulting precipitate was filtered, washed with water and dried to obtain methyl 2,4-dichloro-3-((1,4-dimethyl-6-(trifluoromethyl)-1H-indol-2-yl)methyl)benzoate (3.7 g, 94%) as beige solid.

LC/MS (Method h) R$_f$=3.51 min.; MS m/z: 430 [M+H]⁺. ¹H NMR (DMSO-d₆, 300 MHz): δ 7.80 (d, J=9.0 Hz, 1H), 7.70 (m, 2H), 7.06 (s, 1H), 5.67 (s, 1H), 4.50 (s, 2H), 3.92 (s, 3H), 3.88 (s, 3H), 2.36 (s, 3H)

Step 5: 2,4-dichloro-3-((1,4-dimethyl-6-(trifluoromethyl)-1H-indol-2-yl)methyl)benzoic acid

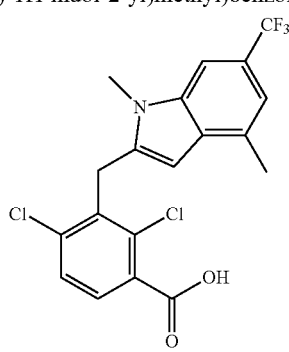

To a solution of methyl 2,4-dichloro-3-((1,4-dimethyl-6-(trifluoromethyl)-1H-indol-2-yl)methyl)benzoate (3.7 g, 8.60 mmol) in THF (100 mL) was added lithium hydroxide (0.722 g, 17.20 mmol) in water (50 mL). The reaction mixture was stirred at room temperature for the night then concentrated under reduced pressure. The residue was taken in water and acidified to pH=3-4 by addition of 1N HCl solution. The obtained precipitate was filtered, washed with water and dried to give 2,4-dichloro-3-((1,4-dimethyl-6-(trifluoromethyl)-1H-indol-2-yl)methyl)benzoic acid (3.5 g, 95% yield) as a white powder.

LC/MS (Method h) R$_f$=3.08 min.; MS m/z: 416 [M+H]⁺. ¹H NMR (DMSO-d₆, 300 MHz): δ 13.55 (broad, 1H), 7.76 (d, J=9.0 Hz, 1H), 7.68 (m, 2H), 7.06 (s, 1H), 5.67 (s, 1H), 4.84 (s, 2H), 3.92 (s, 3H), 2.49 (s, 3H)

Step 6: (2,4-dichloro-3-((1,4-dimethyl-6-(trifluoromethyl)-1H-indol-2-yl)methyl)phenyl)(4-(2-methoxyethyl)piperazin-1-yl)methanone

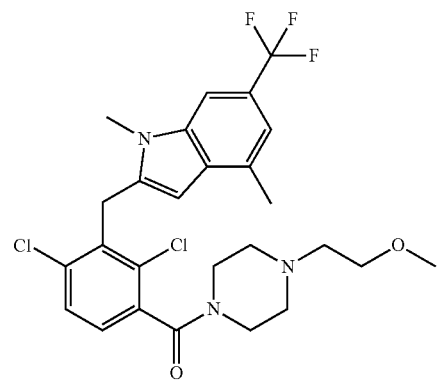 [SMILES: COCCN1CCN(C(=O)c2ccc(Cl)c(Cc3cc4c(C)cc(C(F)(F)F)cc4n3C)c2Cl)CC1]

To a solution of 2,4-dichloro-3-((1,4-dimethyl-6-(trifluoromethyl)-1H-indol-2-yl)methyl)benzoic acid (102 mg, 0.245 mmol) in DCM (2 ml) was added triethylamine (0.044 ml, 0.319 mmol), 1-(3-dimethylaminopropyl)-3-ethylcarbodiimide (49.5 mg, 0.319 mmol) and 1-hydroxybenzotriazole (43.0 mg, 0.319 mmol). The reaction mixture was stirred at room temperature for 30 minutes. 1-(2-methoxyethyl)piperazine (0.044 ml, 0.294 mmol) was added and the reaction mixture was stirred at room temperature overnight, then diluted with water and extracted with DCM. The organic layer was dried over magnesium sulfate, filtered and concentrated under reduced pressure. The residue was purified by column chromatography on silica gel (eluting with 0-5% MeOH in DCM) to give (2,4-dichloro-3-((1,4-dimethyl-6-(trifluoromethyl)-1H-indol-2-yl)methyl)phenyl)(4-(2-methoxyethyl)piperazin-1-yl)methanone (59 mg, 43.6%) as a white solid. LC/MS (Method g) R$_t$=1.34 min.; MS m/z: 542 [M+H]$^+$.

$^1$H NMR (DMSO-d$_6$, 400 MHz): δ 7.70 (s, 1H), 7.67 (d, J=8.1 Hz, 1H), 7.41 (d, J=8.1 Hz, 1H), 7.07 (s, 1H), 5.67 (s, 1H), 4.49 (d, J=16.7 Hz, 1H), 4.43 (d, J=16.7 Hz, 1H), 3.92 (s, 3H), 3.68-3.56 (m, 2H), 3.42 (t, J=5.7 Hz, 2H), 3.21 (s, 3H), 3.16 (m, 2H), 2.50-2.34 (m, 6H), 2.36 (s, 3H).

TABLE A

The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.

| Example # | Product | Amine | R$_t$ min | m/z ESI+ (M + H)$^+$ |
|---|---|---|---|---|
| A-1 | 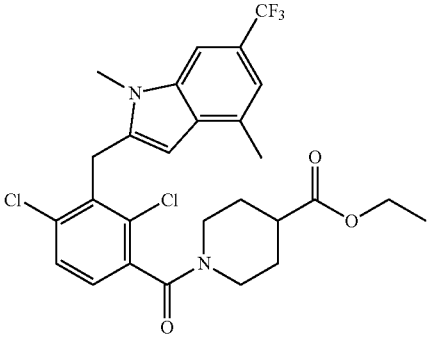 [SMILES: CCOC(=O)C1CCN(C(=O)c2ccc(Cl)c(Cc3cc4c(C)cc(C(F)(F)F)cc4n3C)c2Cl)CC1] | 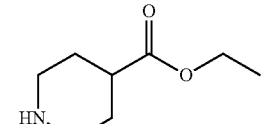 | 3.38 (Method h) | 555 |
| A-2 | 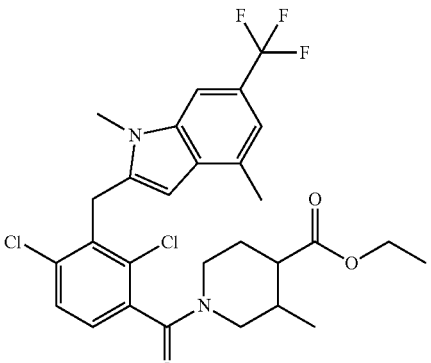 | 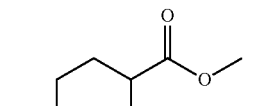 | 3.35 (Method h) | 555 |
| A-3 | 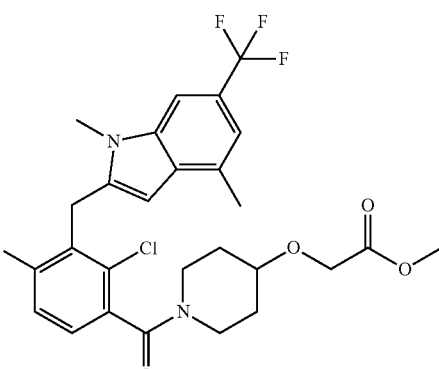 | 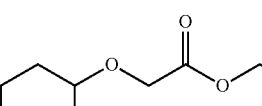 | 3.28 (Method h) | 585 |

TABLE A-continued

*The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.*

| Example # | Product | Amine | $R_t$ min | m/z ESI+ $(M + H)^+$ |
|---|---|---|---|---|
| A-4 | | | 3.15 (Method h) | 527 |
| A-5 | | | 3.10 (Method h) | 513 |
| A-6 | | | 3.35 (Method h) | 541 |

TABLE A-continued
*The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.*
| Example # | Product | Amine | R$_t$ min | m/z ESI+ (M + H)+ |
|---|---|---|---|---|
| A-7 | 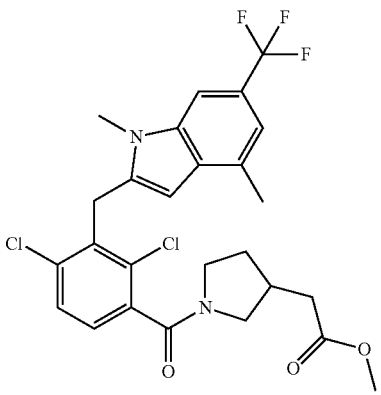 [SMILES: COC(=O)CC1CCN(C(=O)c2ccc(Cl)c(Cc3cc4c(C)cc(C(F)(F)F)cc4n3C)c2Cl)C1] | 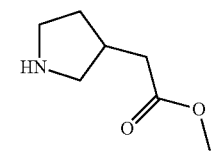 | 3.19 (Method h) | 541 |
| A-8 | 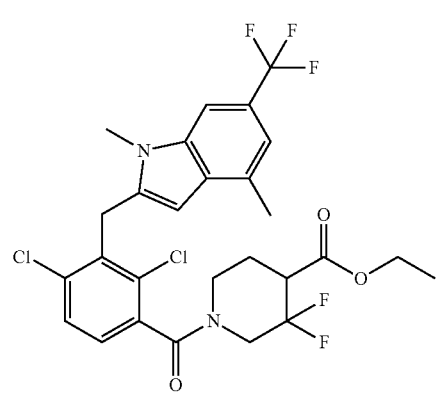 [SMILES: CCOC(=O)C1CCN(C(=O)c2ccc(Cl)c(Cc3cc4c(C)cc(C(F)(F)F)cc4n3C)c2Cl)CC1(F)F] | 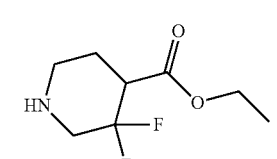 | 3.43 min (Method h) | 591 |
| A-9 | 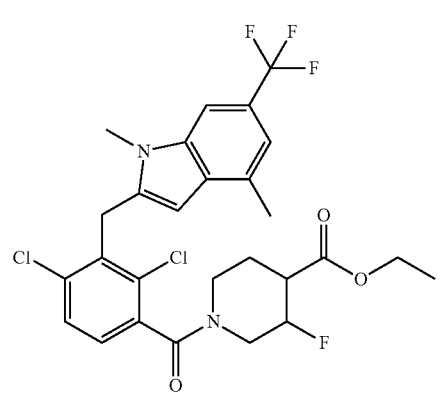 | 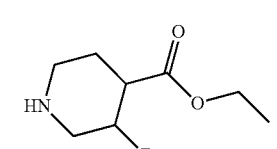 | 2.72 min (Method i) | 573 |

TABLE A-continued
The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.
| Example # | Product | Amine | R, min | m/z ESI+ (M + H)+ |
|---|---|---|---|---|
| A-10 | Chiral 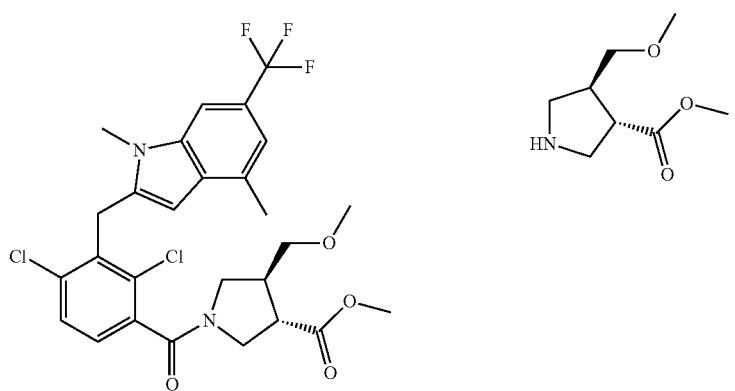 | Chiral 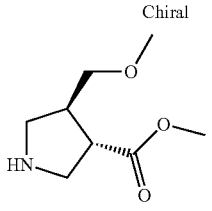 | 2.59 min (Method i) | 571 |
| A-11 | Chiral 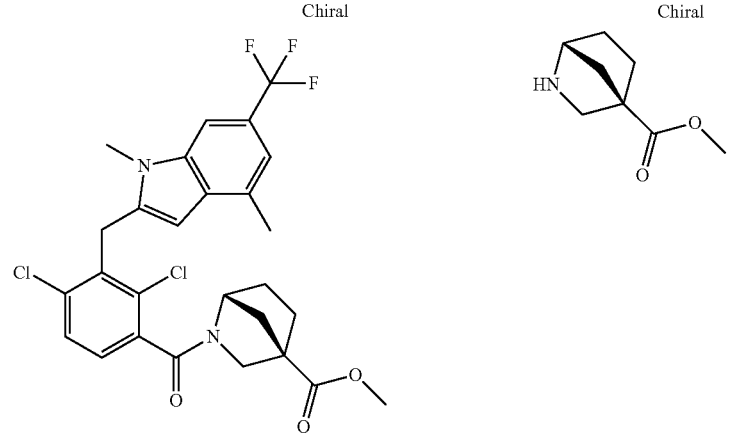 | Chiral 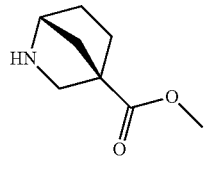 | 2.63 (Method i) | 553 |
| A-12 | 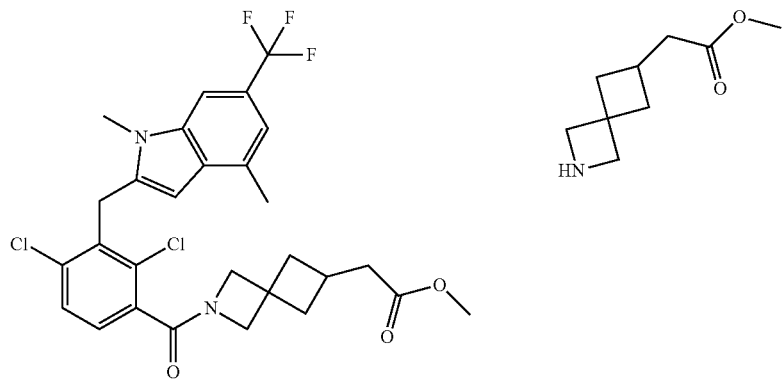 | 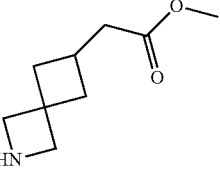 | 2.66 (Method i) | 567 |

TABLE A-continued
*The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.*
| Example # | Product | Amine | R, min | m/z ESI+ (M + H)+ |
|---|---|---|---|---|
| A-13 | 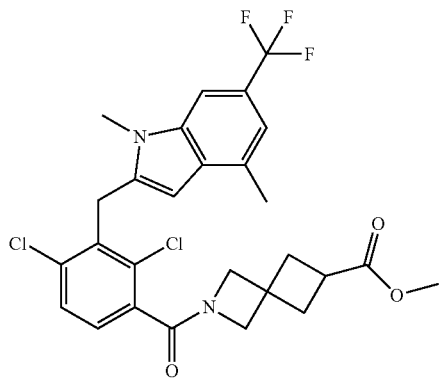 [SMILES: COC(=O)C1CC2(C1)CN(C(=O)c1ccc(Cl)c(Cc3cc4c(C)cc(C(F)(F)F)cc4n3C)c1Cl)C2] | 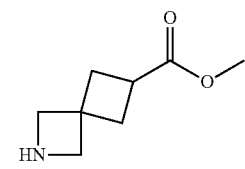 | 2.60 (Method i) | 553 |
| A-14 | 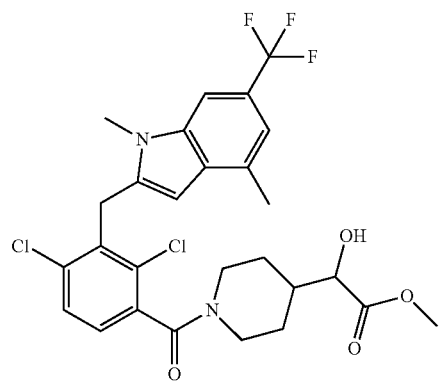 [SMILES: COC(=O)C(O)C1CCN(C(=O)c2ccc(Cl)c(Cc3cc4c(C)cc(C(F)(F)F)cc4n3C)c2Cl)CC1] | 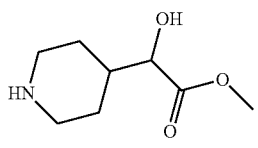 | 2.42 (Method i) | 571 |
| A-15 | 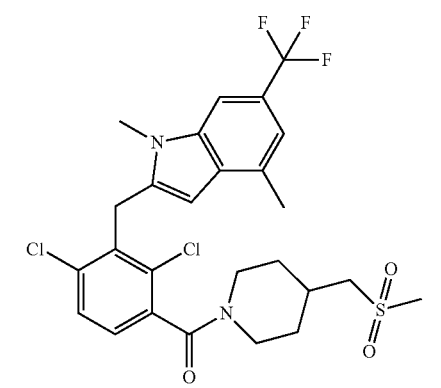 [SMILES: Cc1cc(C(F)(F)F)cc2c1cc(Cc1c(Cl)ccc(C(=O)N3CCC(CS(C)(=O)=O)CC3)c1Cl)n2C] | 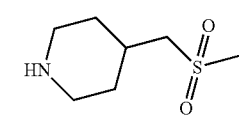 | 1.84 (Method g) | 575 |

TABLE A-continued
The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.
| Example # | Product | Amine | R, min | m/z ESI+ (M + H)+ |
|---|---|---|---|---|
| A-16 | 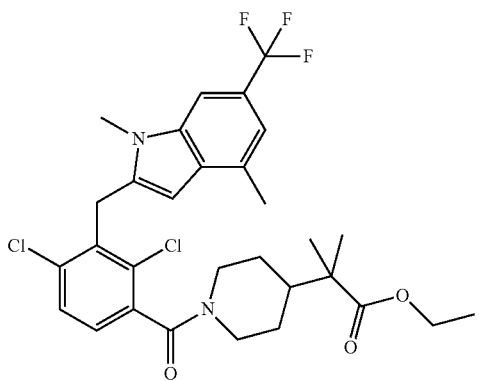 [SMILES: CCOC(=O)C(C)(C)C1CCN(C(=O)c2ccc(Cl)c(Cc3cc4c(C)cc(C(F)(F)F)cc4n3C)c2Cl)CC1] | 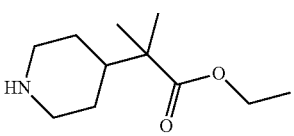 | 2.84 (Method i) | 597 |
| A-17 | 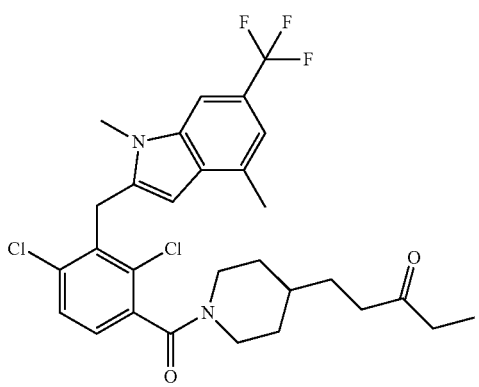 [SMILES: CCC(=O)CCC1CCN(C(=O)c2ccc(Cl)c(Cc3cc4c(C)cc(C(F)(F)F)cc4n3C)c2Cl)CC1] | 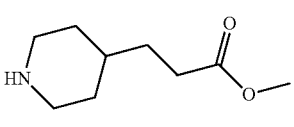 | 2.62 (Method i) | 569 |
| A-18 | 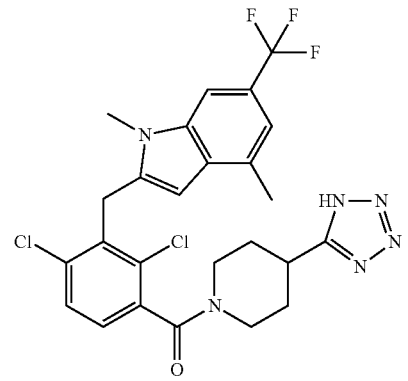 [SMILES: Cc1cc(C(F)(F)F)cc2c1cc(Cc1c(Cl)ccc(C(=O)N3CCC(c4nnn[nH]4)CC3)c1Cl)n2C] | 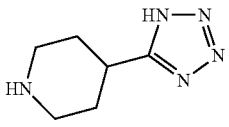 | 1.79 (Method g) | 551 |

TABLE A-continued
The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.
| Example # | Product | Amine | R, min | m/z ESI+ (M + H)+ |
|---|---|---|---|---|
| A-19 | 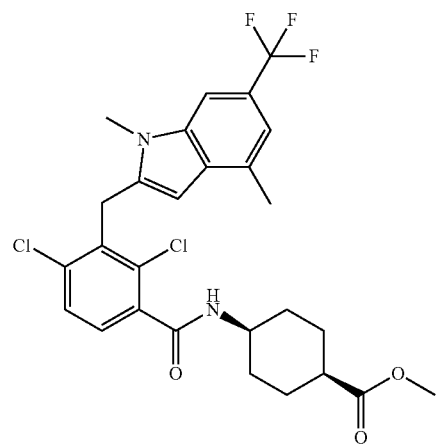<br>And enantiomer | 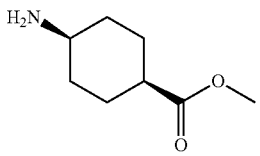<br>And enantiomer | 2.63 (Method i) | 555 |
| A-20 | 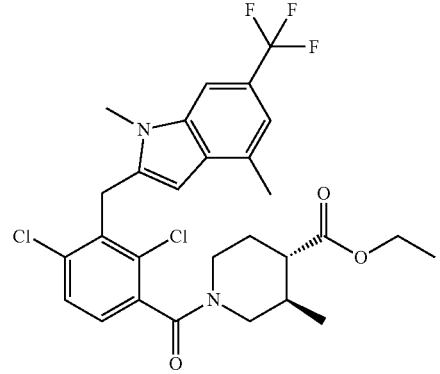 [SMILES: CCOC(=O)[C@H]1CCN(C(=O)c2ccc(Cl)c(Cc3cc4c(C)cc(C(F)(F)F)cc4n3C)c2Cl)C[C@@H]1C] | 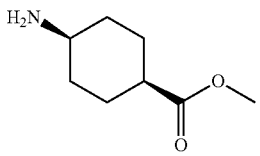 | 3.05 (Method i) | 569 |
| A-21 | 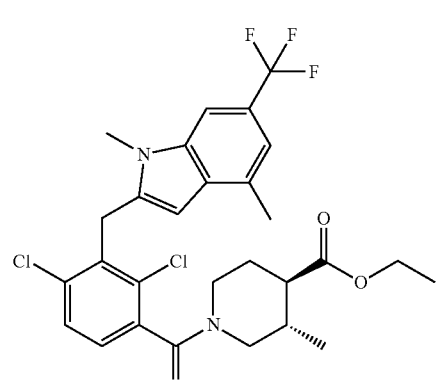 | 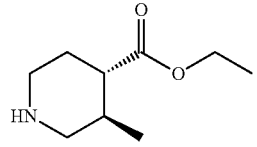 | 3.05 (Method i) | 569 |

TABLE A-continued

The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.

| Example # | Product | Amine | R$_t$ min | m/z ESI+ (M + H)$^+$ |
|---|---|---|---|---|
| A-22 | 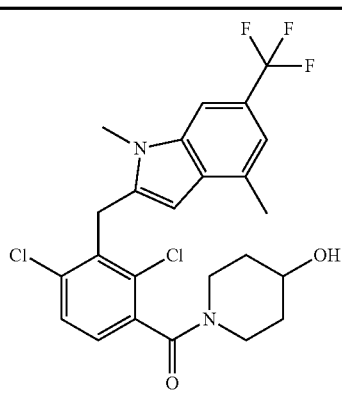 | 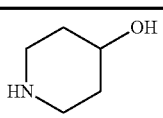 | 2.90 (Method g) | 501 |

Example A1: (2,4-dichloro-3-((1,4-dimethyl-6-(trifluoromethyl)-1H-indol-2-yl)methyl)phenyl)(4-(oxetan-3-yl)piperazin-1-yl)methanone

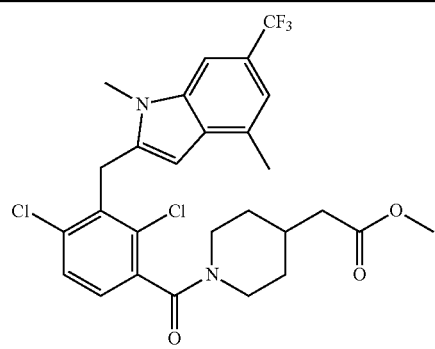

To a solution of 2,4-dichloro-3-((1,4-dimethyl-6-(trifluoromethyl)-1H-indol-2-yl)methyl)benzoic acid (Example A, Step 5) (100 mg, 0.240 mmol) in DMF (519 μL) was added HATU (110 mg, 0.288 mmol) and 4-methylmorpholine (106 μL, 0.961 mmol). The reaction mixture was stirred at room temperature for 15 minutes then 1-(oxetan-3-yl)piperazine (41.0 mg, 0.288 mmol) was added. The reaction mixture was stirred at room temperature overnight. Water was added and the formed precipitate was filtered and washed with water and triturated in diethylether to give (2,4-dichloro-3-((1,4-dimethyl-6-(trifluoromethyl)-1H-indol-2-yl)methyl)phenyl)(4-(oxetan-3-yl)piperazin-1-yl)methanone (81 mg, 62%) as a white solid. LC/MS (Method g) R$_t$=1.73 min.; MS m/z: 540 [M+H]$^+$. $^1$H NMR (DMSO-d$_6$, 400 MHz): δ 7.70 (s, 1H), 7.68 (d, J=8.1 Hz, 1H), 7.43 (d, J=8.1 Hz, 1H), 7.06 (s, 1H), 5.68 (s, 1H), 4.52 (m, 2H), 4.43 (m, 4H), 3.92 (s, 3H), 3.67 (m; 2H), 3.43 (m, 1H), 3.20 (m, 2H), 2.36 (s, 3H), 2.38-2.18 (m, 4H).

TABLE A1

The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.

| Example # | Product | Amine | R$_t$ min | m/z ESI+ (M + H)$^+$ |
|---|---|---|---|---|
| A1-1 | 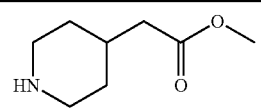 | 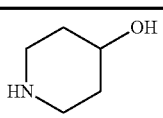 | 3.30 (Method h) | 555 |

TABLE A1-continued
The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.
| Example # | Product | | Amine | | $R_t$ min | m/z ESI+ (M + H)+ |
|---|---|---|---|---|---|---|
| A1-2 | 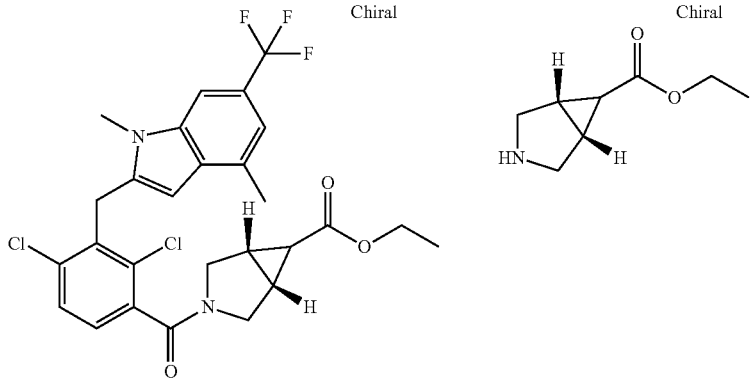 | Chiral | 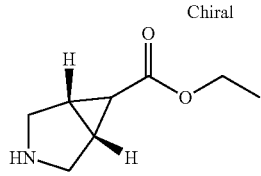 | Chiral | 3.32 (Method h) | 553 |
| A1-3 | 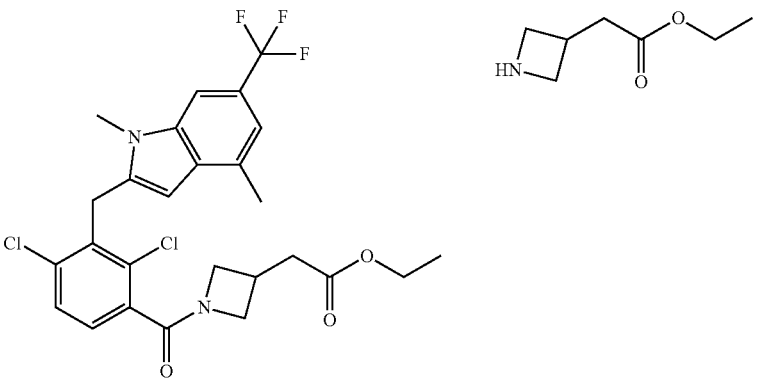 | | 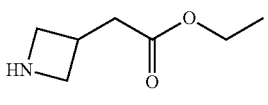 | | 3.24 (Method h) | 541 |
| A1-4 | 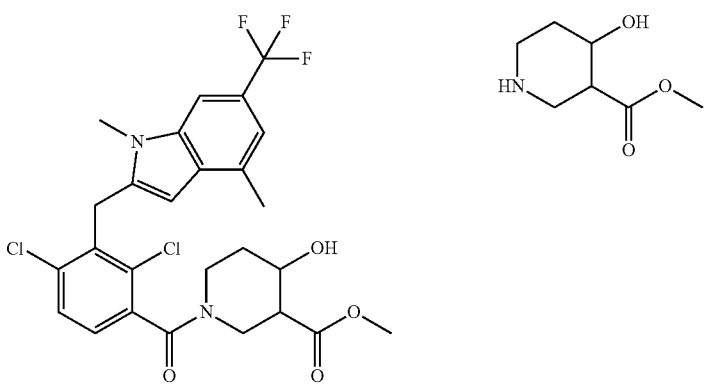 | | 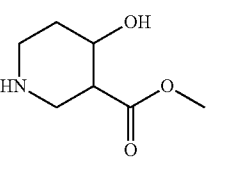 | | 2.95 (Method h) | 557 |

TABLE A1-continued

The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.

| Example # | Product | Amine | $R_t$ min | m/z ESI+ (M + H)+ |
|---|---|---|---|---|
| A1-5 | | | 3.30 (Method h) | 541 |
| A1-6 | | | 3.16 (Method h) | 543 |
| A1-7 | | | 3.41 (Method h) | 555 |
| A1-8 | | | 3.38 (Method h) | 573 |

TABLE A1-continued
The following intermediates were prepared from 2,4-dichloro-3-((1,4-dimethyl-6-(trifluoromethyl)-1H-indol-2-yl)methyl)benzoic acid (Example A, Step 5) using the same procedure with the appropriate amine.
| Example # | Product | Amine | $R_t$ min | m/z ESI+ (M + H)+ |
|---|---|---|---|---|
| A1-9 | 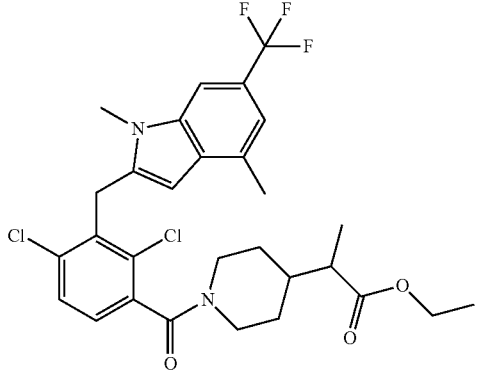 [SMILES: CCOC(=O)C(C)C1CCN(C(=O)c2ccc(Cl)c(Cc3cc4c(C)cc(C(F)(F)F)cc4n3C)c2Cl)CC1] | 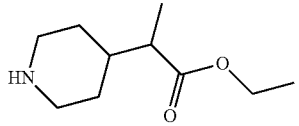 | 2.80 (Method i) | 583 |
| A1-10 | 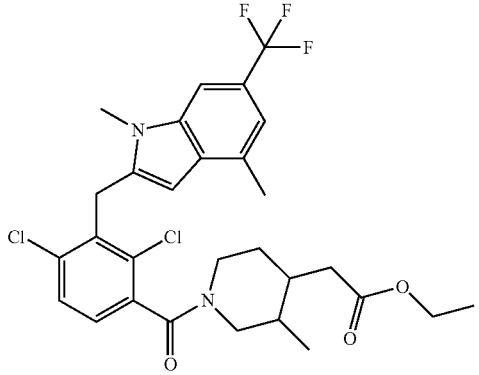 [SMILES: CCOC(=O)CC1CCN(C(=O)c2ccc(Cl)c(Cc3cc4c(C)cc(C(F)(F)F)cc4n3C)c2Cl)CC1C] | 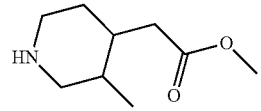 (Preparation #50) | 2.71 (Method i) | 569 |
| A1-11 | 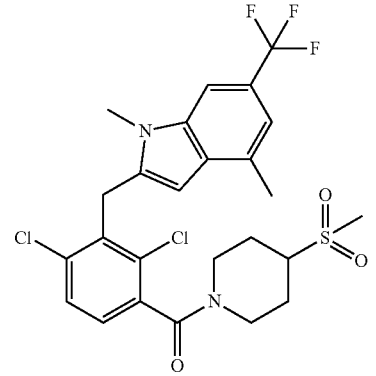 [SMILES: Cc1cc(C(F)(F)F)cc2c1cc(Cc1c(Cl)ccc(C(=O)N3CCC(S(C)(=O)=O)CC3)c1Cl)n2C] | 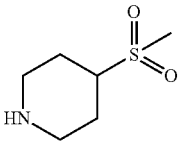 | 1.78 (Method g) | 561 |

Example B: 1-(2,4-dichloro-3-((1,4-dimethyl-6-(trifluoromethyl)-1H-indol-2-yl)methyl)benzoyl)piperidine-4-carboxylic acid

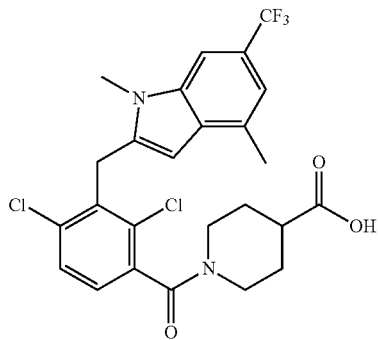 [SMILES: Cc1cc(C(F)(F)F)cc2c1cc(Cc1c(Cl)ccc(C(=O)N3CCC(C(=O)O)CC3)c1Cl)n2C]

Using a procedure similar to Example A, Step 5, 1-(2,4-dichloro-3-((1,4-dimethyl-6-(trifluoromethyl)-1H-indol-2-yl)methyl)benzoyl)piperidine-4-carboxylic acid (1.465 g, 95% yield) was prepared from ethyl 1-(2,4-dichloro-3-((1,4-dimethyl-6-(trifluoromethyl)-1H-indol-2-yl)methyl)benzoyl)piperidine-4-carboxylate (Table A. A-1) (1.6 g, 2.88 mmol). LC/MS (Method g) $R_t$=1.79 min.; MS m/z: 527 [M+H]$^+$. $^1$H NMR (DMSO-d$_6$, 500 MHz): δ 13.36 (broad, 1H), 7.87 (s, 1H), 7.67 (m, 1H), 7.42 (m, 1H), 6.87 (s, 1H), 5.67 (m, 1H), 4.48 (m, 2H), 4.35 (m, 1H), 3.92 (s, 3H), 3.31 (m, 1H), 3.08 (m, 1H), 2.97 (m, 1H), 2.58 (m, 1H), 2.35 (s, 3H), 1.93 (m, 1H), 1.75 (m, 1H), 1.50 (m, 2H)

TABLE B

The following Examples were prepared using the same peocedure starting from the appropriate esters (as described in Tables A and A1, BH).

| Example | Product | Ester | $R_t$ min (Method g) | m/z ESI+ (M + H)$^+$ |
|---|---|---|---|---|
| B-1 | | A-2 | 1.82 | 541 |
| B-2 | | A-3 | 1.79 | 557 |

TABLE B-continued

The following Examples were prepared using the same peocedure starting from the appropriate esters (as described in Tables A and A1, BH).

| Example | Product | Ester | R$_t$ min (Method g) | m/z ESI+ (M + H)$^+$ |
|---|---|---|---|---|
| B-3 | (structure) | A-4 | 1.76 | 513 |
| B-4 | (structure) | A-5 | 1.74 | 499 |
| B-5 | (structure) | A-6 | 1.80 | 513 |

TABLE B-continued
The following Examples were prepared using the same peocedure starting from the appropriate esters (as described in Tables A and A1, BH).
| Example | Product | Ester | R$_t$ min (Method g) | m/z ESI+ (M + H)+ |
|---|---|---|---|---|
| B-6 | 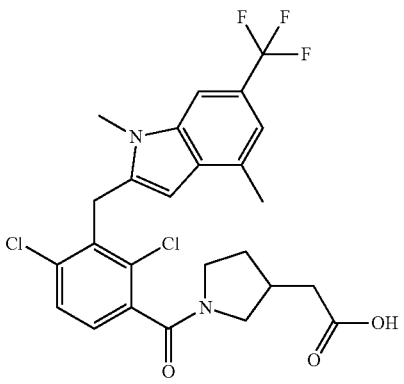 [SMILES: Cc1cc(C(F)(F)F)cc2c1cc(Cc1c(Cl)ccc(C(=O)N3CCC(CC(=O)O)C3)c1Cl)n2C] | A-7 | 1.80 | 527 |
| B-7 | 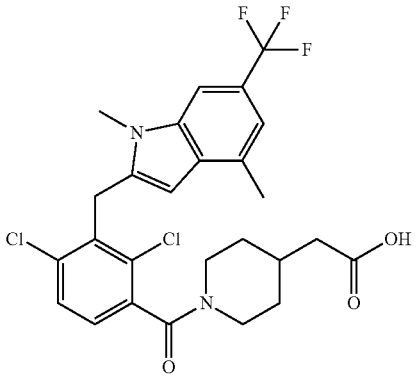 [SMILES: Cc1cc(C(F)(F)F)cc2c1cc(Cc1c(Cl)ccc(C(=O)N3CCC(CC(=O)O)CC3)c1Cl)n2C] | A1-1 | 1.82 | 541 |
| B-8 | Chiral 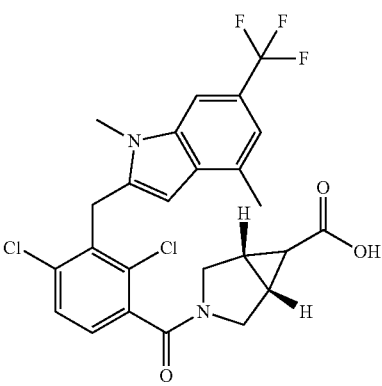 | A1-2 | 1.76 | 525 |

TABLE B-continued

The following Examples were prepared using the same peocedure starting from the appropriate esters (as described in Tables A and A1, BH).

| Example | Product | Ester | R$_t$ min (Method g) | m/z ESI+ (M + H)+ |
|---|---|---|---|---|
| B-9 | | A1-3 | 1.74 | 513 |
| B-10 | | A1-4 | 1.70 | 543 |
| B-11 | | A1-5 | 2.92 | 527 |

TABLE B-continued
The following Examples were prepared using the same peocedure starting from the appropriate esters (as described in Tables A and A1, BH).
| Example | Product | Ester | R$_t$ min (Method g) | m/z ESI+ (M + H)+ |
|---|---|---|---|---|
| B-12 | 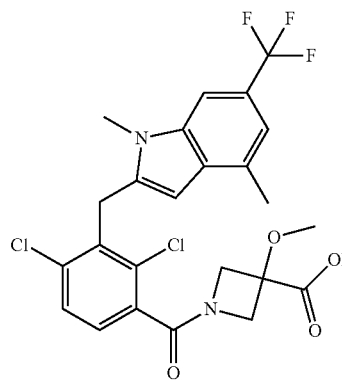 | A1-6 | 2.76 | 529 |
| B-13 | 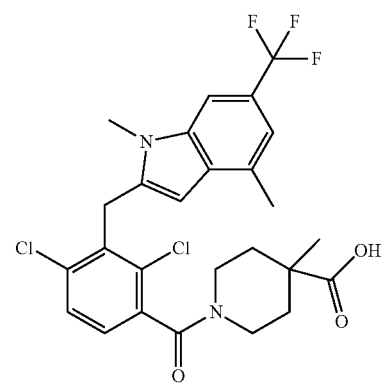 [SMILES: Cc1cc(C(F)(F)F)cc2c1cc(Cc1c(Cl)ccc(C(=O)N3CCC(C)(C(=O)O)CC3)c1Cl)n2C] | A1-7 | 1.86 | 541 |
| B-14 | 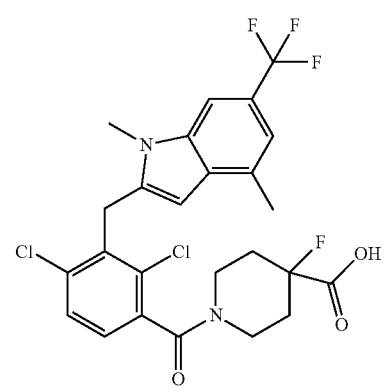 [SMILES: Cc1cc(C(F)(F)F)cc2c1cc(Cc1c(Cl)ccc(C(=O)N3CCC(F)(C(=O)O)CC3)c1Cl)n2C] | A1-8 | 1.92 | 545 |

TABLE B-continued

The following Examples were prepared using the same peocedure starting from the appropriate esters (as described in Tables A and A1, BH).

| Example | Product | Ester | R$_t$ min (Method g) | m/z ESI+ (M + H)+ |
|---|---|---|---|---|
| B-15 | Chiral | A-10 | 1.82 | 557 |
| B-16 | Chiral | A-11 | 1.85 | 539 |
| B-17 | | A-12 | 1.86 | 553 |

TABLE B-continued

The following Examples were prepared using the same peocedure starting from the appropriate esters (as described in Tables A and A1, BH).

| Example | Product | Ester | R$_t$ min (Method g) | m/z ESI+ (M + H)+ |
|---|---|---|---|---|
| B-18 | | A-13 | 1.82 | 539 |
| B-19 | | A1-9 | 1.87 | 555 |
| B-20 | | A-14 | 1.79 | 557 |

TABLE B-continued

The following Examples were prepared using the same peocedure starting from the appropriate esters (as described in Tables A and A1, BH).

| Example | Product | Ester | R$_t$ min (Method g) | m/z ESI+ (M + H)+ |
|---|---|---|---|---|
| B-21 | | A1-10 | 1.88 | 555 |
| B-22 | | BH-1 | 1.74 | 542 |
| B-23 | | A-16 | 2.51 (Method i) | 569 |

TABLE B-continued
The following Examples were prepared using the same peocedure starting from the appropriate esters (as described in Tables A and A1, BH).
| Example | Product | Ester | R, min (Method g) | m/z ESI+ (M + H)+ |
|---|---|---|---|---|
| B-24 | 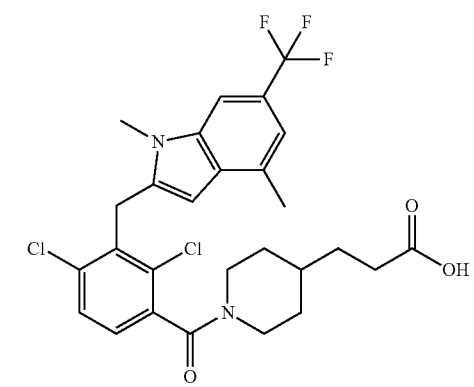 [SMILES: Cc1cc(C(F)(F)F)cc2c1cc(Cc1c(Cl)ccc(C(=O)N3CCC(CCC(=O)O)CC3)c1Cl)n2C] | A-17 | 1.89 (method g) | 555 |
| B-25 | AND Enantion 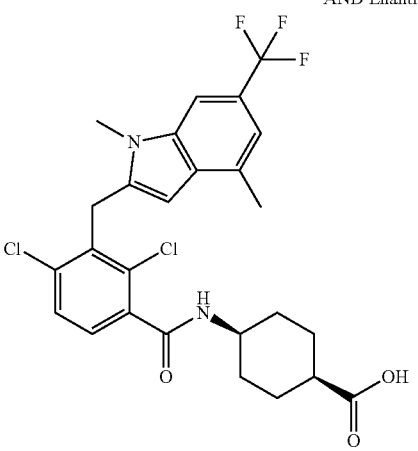 | A-19 | 1.84 (method g) | 541 |
| B-26 | 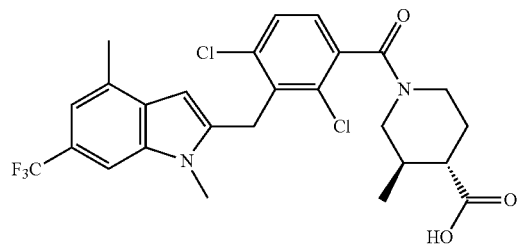 [SMILES: Cc1cc(C(F)(F)F)cc2c1cc(Cc1c(Cl)ccc(C(=O)N3CC[C@H](C(=O)O)[C@@H](C)C3)c1Cl)n2C] | A-20 | 2.32 (method i) | 541 |
| B-27 | 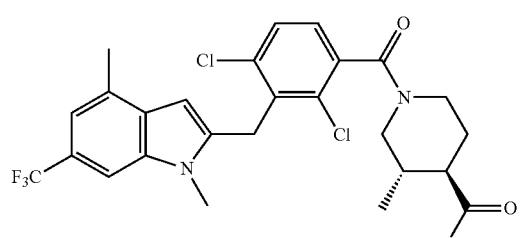 | A-21 | 2.32 (method i) | 541 |

Example B.2: (3S,4S)-1-(2,4-dichloro-3-((1,4-dimethyl-6-(trifluoromethyl)-1H-indol-2-yl)methyl)benzoyl)-3-methylpiperidine-4-carboxylic acid and (3R,4R)-1-(2,4-dichloro-3-((1,4-dimethyl-6-(trifluoromethyl)-1H-indol-2-yl)methyl)benzoyl)-3-methylpiperidine-4-carboxylic acid

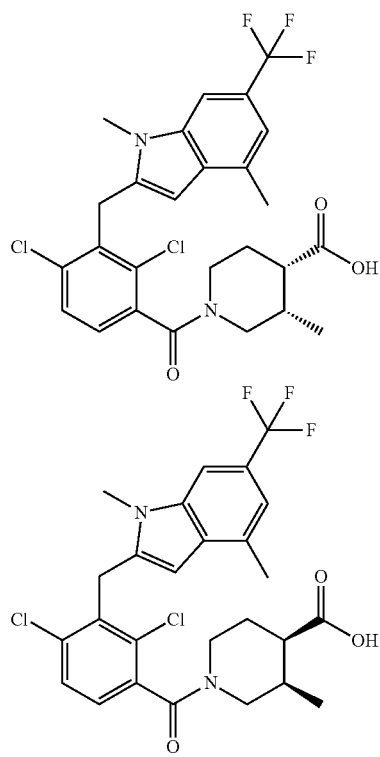

1-(2,4-dichloro-3-((1,4-dimethyl-6-(trifluoromethyl)-1H-indol-2-yl)methyl)benzoyl)-3-methylpiperidine-4-carboxylic acid (Example B1, Table B, 400 mg) was dissolved in methylene chloride and purified using Method o of the chiral purification methods (Table 2). Fractions of the first eluting isomer were pooled and analyzed.

(3S,4S)-1-(2,4-dichloro-3-((1,4-dimethyl-6-(trifluoromethyl)-1H-indol-2-yl)methyl)benzoyl)-3-methylpiperidine-4-carboxylic acid (0.123 g, 0.227 mmol, 28.7% yield) LC/MS (Method l) $R_f$=2.5 min.; MS m/z: 539 [M−H]⁻, 541 [M+H]⁺. ¹H NMR (CDCl₃, 400 MHz): δ 12.33 (bs, 1H), 7.73-7.64 (m, 2H), 7.47-7.37 (m, 1H), 7.07 (s, 1H), 4.15-4.55 (m, 3H), 3.91-3.94 (m, 3H), 3.28-3.22 (m, 1H), 3.18-2.92 (m, 2H), 2.72-2.63 (m, 1H), 2.38-2.34 (m, 3H), 2.34-2.06 (m, 1H), 1.74-1.50 (m, 2H), 0.95-0.70 (m, 4H)

Chiral HPLC 2.9 min (Method n, >99% ee).

Fractions of the second eluting peak were pooled and analyzed.

(3R,4R)-1-(2,4-dichloro-3-((1,4-dimethyl-6-(trifluoromethyl)-1H-indol-2-yl)methyl)benzoyl)-3-methylpiperidine-4-carboxylic acid (0.138 g, 0.255 mmol, 32.2% yield) LC/MS (Method l) $R_f$=2.5 min.; MS m/z: 539 [M−H]⁻, 541 [M+H]⁺. ¹H NMR (CDCl₃, 400 MHz): δ 12.33 (bs, 1H), 7.73-7.64 (m, 2H), 7.47-7.37 (m, 1H), 7.07 (s, 1H), 4.15-4.55 (m, 3H), 3.91-3.94 (m, 3H), 3.28-3.22 (m, 1H), 3.18-2.92 (m, 2H), 2.72-2.63 (m, 1H), 2.38-2.34 (m, 3H), 2.34-2.06 (m, 1H), 1.74-1.50 (m, 2H), 0.95-0.70 (m, 4H).

Chiral HPLC 3.7 min (Method n, >99% ee).

Example C: (2,4-dichloro-3-((4-methyl-6-(trifluoromethyl)-1H-indol-2-yl)methyl)phenyl)(morpholino)methanone

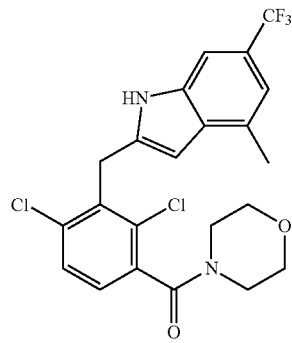 [SMILES: Cc1cc(C(F)(F)F)cc2[nH]c(Cc3c(Cl)ccc(C(=O)N4CCOCC4)c3Cl)cc12]

Step 1: (2,4-dichloro-3-(hydroxy(4-methyl-1-(phenylsulfonyl)-6-(trifluoromethyl)-1H-indol-2-yl)methyl)phenyl)(morpholino)methanone

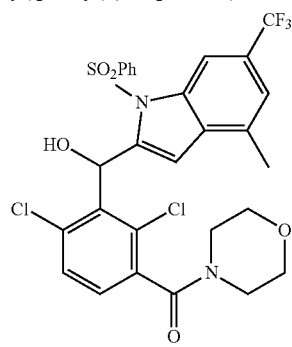

Using a procedure similar to Example A, Step 1, (2,4-dichloro-3-(hydroxy(4-methyl-1-(phenylsulfonyl)-6-(trifluoromethyl)-1H-indol-2-yl)methyl)phenyl)(morpholino)methanone (3.7 g, 87%) was prepared from N-(2-iodo-3-methyl-5-(trifluoromethyl)phenyl)benzenesulfonamide (Preparation #16) (3 g, 6.80 mmol) and (2,4-dichloro-3-(1-hydroxyprop-2-yn-1-yl)phenyl)(morpholino)methanone (2.78 g, 8.84 mmol) (Preparation #3). LC/MS (Method k) $R_f$=3.10 min.; MS m/z: 627[M+H]⁺.

¹H NMR (CDCl₃, 300 MHz): δ 8.25 (s, 1H), 7.90 (m, 2H), 7.52 (m, 1H), 7.45 (m, 3H), 7.30 (m, 2H), 7.12 (m, 1H), 6.35 (m, 1H), 4.02 (m, 1H), 3.82 (m, 4H), 3.79 (m, 2H), 3.30 (m, 2H), 2.41 (s, 3H).

Step 2: (2,4-dichloro-3-((4-methyl-1-(phenylsulfonyl)-6-(trifluoromethyl)-1H-indol-2-yl)methyl)phenyl)(morpholino)methanone

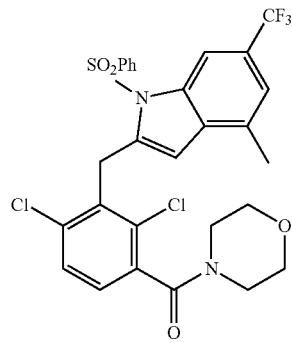

Using a procedure similar to Example A, Step 2, (2,4-dichloro-3-((4-methyl-1-(phenylsulfonyl)-6-(trifluoromethyl)-1H-indol-2-yl)methyl)phenyl)(morpholino)methanone (3 g, 86%) was prepared from (2,4-dichloro-3-(hydroxy(4-methyl-1-(phenylsulfonyl)-6-(trifluoromethyl)-1H-indol-2-yl)methyl)phenyl)(morpholino)methanone (3.67 g, 5.85 mmol). LC/MS (Method k) $R_t$=3.56 min.;

MS m/z: 611[M+H]$^+$. $^1$H NMR (DMSO-d$_6$, 300 MHz): δ 8.24 (s, 1H), 7.92 (m, 2H), 7.68 (m, 1H), 7.65 (m, 3H), 7.46 (m, 1H), 7.42 (s, 1H), 6.00 (s, 1H), 4.57 (m, 2H), 3.62 (m, 4H), 3.47 (m, 2H), 3.18 (m, 2H), 2.35 (s, 3H).

Step 3: (2,4-dichloro-3-((4-methyl-6-(trifluoromethyl)-1H-indol-2-yl)methyl)phenyl)(morpholino)methanone

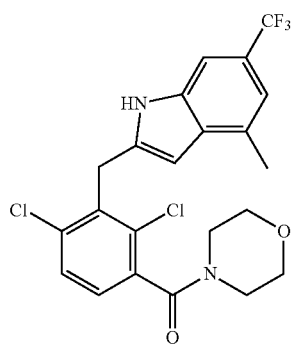 [SMILES: Cc1cc(C(F)(F)F)cc2[nH]c(Cc3c(Cl)ccc(C(=O)N4CCOCC4)c3Cl)cc12]

Using a procedure similar to Example A, Step 3, (2,4-dichloro-3-((4-methyl-6-(trifluoromethyl)-1H-indol-2-yl)methyl)phenyl)(morpholino)methanone (130 mg, 59%) was prepared from (2,4-dichloro-3-((4-methyl-1-(phenylsulfonyl)-6-(trifluoromethyl)-1H-indol-2-yl)methyl)phenyl)(morpholino)methanone (286 mg, 0.468 mmol). LC/MS (Method g) $R_t$=1.36 min.;

MS m/z: 471 [M+H]$^+$ $^1$H NMR (DMSO-d$_6$, 400 MHz): δ 11.55 (s, 1H), 7.66 (m, 1H), 7.48 (m, 1H), 7.42 (m, 1H), 7.02 (s, 1H), 5.97 (s, 1H), 4.48 (m, 2H), 3.65 (m, 4H), 3.52 (m, 2H), 3.18 (m, 2H), 2.40 (s, 3H).

Example D: (2,4-dichloro-3-((1,4-dimethyl-6-(trifluoromethyl)-1H-indol-2-yl)methyl)phenyl)(morpholino)methanone Using a procedure similar to Example A, Step 4, (2,4-dichloro-3-((1,4-dimethyl-6-(trifluoromethyl)-1H-indol-2-yl)methyl)phenyl)(morpholino)methanone (26 mg, 50%) was prepared from (2,4-dichloro-3-((4-methyl-6-(trifluoromethyl)-1H-indol-2-yl)methyl)phenyl)(morpholino)methanone (Example C) (50 mg, 0.106 mmol). LC/MS (Method g) $R_t$=1.91 min.; MS m/z: 485[M+H]$^+$.

$^1$H NMR (DMSO-d$_6$, 400 MHz): δ 7.75 (s, 1H), 7.70 (d, J=9.0 Hz, 1H), 7.49 (d, J=9.0 Hz, 1H), 7.06 (s, 1H), 5.67 (s, 1H), 4.48 (m, 2H), 3.92 (s, 3H), 3.62 (m, 4H), 3.51 (m, 2H), 3.20 (m, 2H), 2.36 (s, 3H).

TABLE D

The following analogs were prepared from (2,4-dichloro-3-((4-methyl-6-(trifluoromethyl)-1H-indol-2-yl)methyl)phenyl)(morpholino)methanone (Example C) using the same procedure and using the appropriate electrophile.

| Example | Product | Electrophile | $R_t$ min (Method g) | m/z ESI+ (M + H)$^+$ |
|---|---|---|---|---|
| D-1 | | EtI | 1.96 | 499 |

TABLE D-continued

The following analogs were prepared from (2,4-dichloro-3-((4-methyl-6-(trifluoromethyl)-1H-indol-2-yl)methyl)phenyl)(morpholino)methanone (Example C) using the same procedure and using the appropriate electrophile.

| Example | Product | Electrophile | R$_t$ min (Method g) | m/z ESI+ (M + H)+ |
|---|---|---|---|---|
| D-2 | | | 1.86 | 513 |
| D-3 | | | 2.11 | 527 |

Example E: (2,4-dichloro-3-((1-methyl-6-(trifluoromethyl)-1H-indol-2-yl)methyl)phenyl)(morpholino)methanone

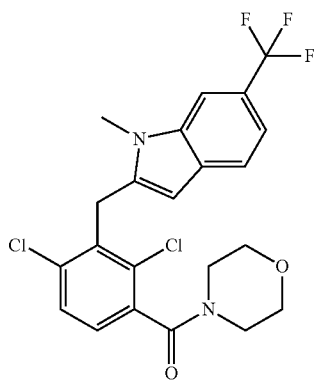 [SMILES: Cn1c(Cc2c(Cl)ccc(C(=O)N3CCOCC3)c2Cl)cc2ccc(C(F)(F)F)cc21]

Step 1: (2,4-dichloro-3-(hydroxy(1-(phenylsulfonyl)-6-(trifluoromethyl)-1H-indol-2-yl)methyl)phenyl)(morpholino)methanone

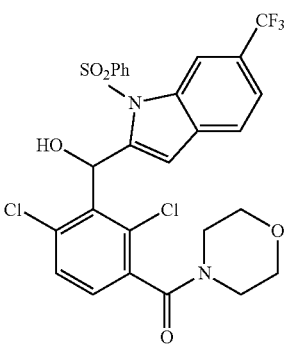

Using a procedure similar to Example A, Step 1, (2,4-dichloro-3-(hydroxy(1-(phenylsulfonyl)-6-(trifluoromethyl)-1H-indol-2-yl)methyl)phenyl)(morpholino)methanone (491 mg, 81%) was prepared from N-(2-iodo-5-(trifluoromethyl)phenyl)benzenesulfonamide (420 mg, 0.983 mmol) (Preparation #29) and (2,4-dichloro-3-(1-hydroxyprop-2-yn-1-yl)phenyl)(morpholino)methanone (402 mg, 1.28 mmol) (Preparation #3). LC/MS (Method g) R$_t$=1.77 min.; MS m/z: 612[M+H]$^+$. $^1$H NMR (DMSO-d$_6$, 400 MHz): δ 8.21 (s, 1H), 7.91 (m, 1H), 7.85 (m, 2H), 7.72 (m, 1H), 7.61 (m, 3H), 7.53 (m, 1H), 7.38 (m, 1H), 6.98 (m, 1H), 6.82 (m, 1H), 6.65 (m, 1H), 3.68 (m, 4H), 3.57 (m, 2H), 3.15 (m, 2H).

Step 2: (2,4-dichloro-3-((1-(phenylsulfonyl)-6-(trifluoromethyl)-1H-indol-2-yl)methyl)phenyl)(morpholino)methanone

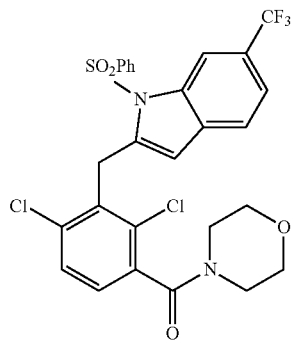

Using a procedure similar to Example A, Step 2, (2,4-dichloro-3-((1-(phenylsulfonyl)-6-(trifluoromethyl)-1H-indol-2-yl)methyl)phenyl)(morpholino)methanone (196 mg, 47%) was prepared from (2,4-dichloro-3-(hydroxy(1-(phenylsulfonyl)-6-(trifluoromethyl)-1H-indol-2-yl)methyl)phenyl)(morpholino)methanone (430 mg, 0.701 mmol). LC/MS (Method g) R$_t$=2.00 min.;
MS m/z: 597 [M+H]$^+$ $^1$H NMR (DMSO-d$_6$, 400 MHz): δ 8.41 (s, 1H), 7.94 (m, 2H), 7.80 (m, 1H), 7.68 (m, 4H), 7.60 (m, 1H), 6.48 (m, 1H), 6.06 (s, 1H), 4.55 (m, 2H), 3.65 (m, 4H), 3.51 (m, 2H), 3.21 (m, 2H).

Step 3: (2,4-dichloro-3-((6-(trifluoromethyl)-1H-indol-2-yl)methyl)phenyl)(morpholino)methanone

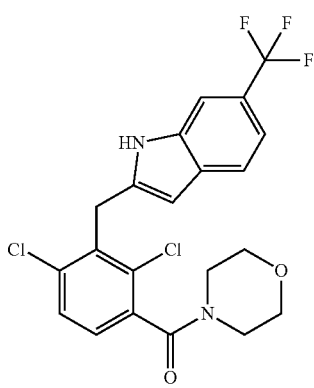 [SMILES: O=C(c1ccc(Cl)c(Cc2cc3ccc(C(F)(F)F)cc3[nH]2)c1Cl)N1CCOCC1]

Using a procedure similar to Example A, Step 3, (2,4-dichloro-3-((6-(trifluoromethyl)-1H-indol-2-yl)methyl)phenyl)(morpholino)methanone (103 mg, 69%) was prepared from (2,4-dichloro-3-((1-(phenylsulfonyl)-6-(trifluoromethyl)-1H-indol-2-yl)methyl)phenyl)(morpholino)methanone (182 mg, 0.305 mmol). LC/MS (Method g) R$_t$=1.76 min.; MS m/z: 457 [M+H]$^+$. $^1$H NMR (DMSO-d$_6$, 400 MHz): δ 11.53 (s, 1H), 7.65 (m, 2H), 7.57 (d, J=8.0 Hz, 1H), 7.41 (d, J=8.0 Hz, 1H), 7.21 (dd, J=8.0 Hz, J=4.0 Hz, 1H), 5.97 (s, 1H), 4.46 (s, 2H), 3.64 (m, 4H), 3.53 (m, 2H), 3.18 (m, 2H).

Step 4: (2,4-dichloro-3-((1-methyl-6-(trifluoromethyl)-1H-indol-2-yl)methyl)phenyl)(morpholino)methanone

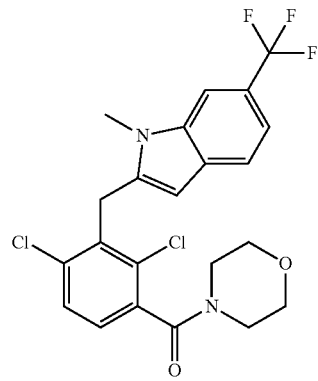 [SMILES: Cn1c(Cc2c(Cl)ccc(C(=O)N3CCOCC3)c2Cl)cc2ccc(C(F)(F)F)cc21]

Using a procedure similar to Example A, Step 4, (2,4-dichloro-3-((1-methyl-6-(trifluoromethyl)-1H-indol-2-yl)methyl)phenyl)(morpholino)methanone (68 mg, 77%) was prepared from (2,4-dichloro-3-((6-(trifluoromethyl)-1H-indol-2-yl)methyl)phenyl)(morpholino)methanone (86 mg, 0.188 mmol).

LC/MS (Method g) R$_t$=1.83 min.; MS m/z: 471 [M+H]$^+$. $^1$H NMR (DMSO-d$_6$, 400 MHz): δ 7.87 (s, 1H), 7.67 (d, J=8.0 Hz, 1H), 7.56 (d, J=8.0 Hz, 1H), 7.45 (d, J=8.0 Hz, 1H), 7.25 (d, J=8.0 Hz, 1H), 5.72 (s, 1H), 4.45 (s, 2H), 3.93 (s, 3H), 4.65 (m, 4H), 3.52 (m, 2H), 3.18 (m, 2H).

Example F: 2-(1-(2,4-dichloro-3-((1,4-dimethyl-6-(trifluoromethyl)-1H-indol-3-yl)methyl)benzoyl)piperidin-4-yl)acetic acid

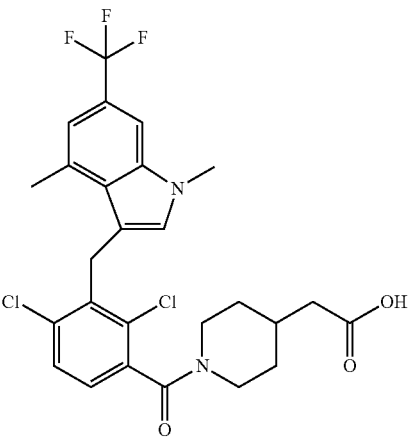 [SMILES: Cc1cc(C(F)(F)F)cc2c1c(Cc1c(Cl)ccc(C(=O)N3CCC(CC(=O)O)CC3)c1Cl)cn2C]

Step 1: tert-butyl 2,4-dichloro-3-((1,4-dimethyl-6-(trifluoromethyl)-1H-indol-3-yl)(hydroxy)methyl)benzoate

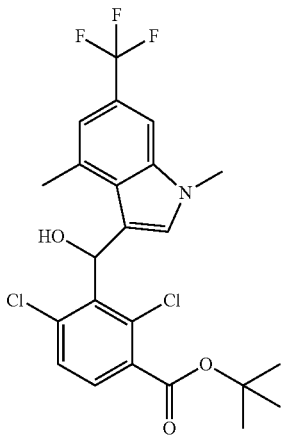 [SMILES: Cc1cc(C(F)(F)F)cc2c1c(C(O)c1c(Cl)ccc(C(=O)OC(C)(C)C)c1Cl)cn2C]

To a solution of tert-butyl 2,4-dichlorobenzoate (Preparation #33, Step A) (748 mg, 3.03 mmol) in THF (20 mL) and cooled to −78° C. was added lithium diisopropylamide (1.816 ml, 3.63 mmol) diluted in THF (10 mL) and already cooled to 0° C. The reaction mixture was stirred at −78° C. for 1 hour. At −78° C., 1,4-dimethyl-6-(trifluoromethyl)-1H-indole-3-carbaldehyde (Preparation #51) (730 mg, 3.03 mmol) was added and the reaction mixture was stirred for 15 minutes. It was then allowed to warm-up to room temperature and the stirring was continued for 30 minutes. The reaction mixture was quenched with a saturated NH$_4$Cl solution. The aqueous layer was extracted with EtOAc. The organic layer was dried over magnesium sulfate, filtered and concentrated to dryness under reduced pressure. The residue was purified by column chromatography on silica gel (eluting with 0-50% EtOAc in cyclohexane) to give tert-butyl 2,4-dichloro-3-((1,4-dimethyl-6-(trifluoromethyl)-1H-indol-3-yl)(hydroxy)methyl)benzoate (355 mg, 23%) as an orange solid. LC/MS (Method i) R$_f$=2.79 min.;

MS m/z: 546 [M−H]$^-$+CH$_3$COOH $^1$H NMR (DMSO-d$_6$, 300 MHz): δ 7.64 (s, 1H), 7.58 (s, 2H), 7.13 (s, 1H), 6.98 (s, 1H), 6.87 (d, J=5.6 Hz, 1H), 5.93 (d, J=5.6 Hz, 1H), 3.75 (s, 3H), 2.85 (s, 3H), 1.54 (s, 9H)

Step 2: 2,4-dichloro-3-((1,4-dimethyl-6-(trifluoromethyl)-1H-indol-3-yl)methyl)benzoic acid

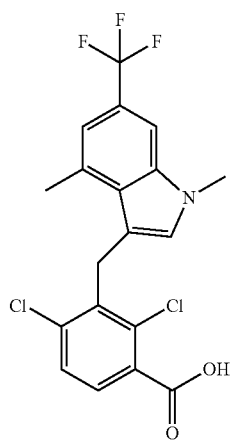 [SMILES: Cc1cc(C(F)(F)F)cc2c1c(Cc1c(Cl)ccc(C(=O)O)c1Cl)cn2C]

Using a procedure similar to Example A, Step 2, 2,4-dichloro-3-((1,4-dimethyl-6-(trifluoromethyl)-1H-indol-3-yl)methyl)benzoic acid (20 mg, 31%) was prepared from tert-butyl 2,4-dichloro-3-((1,4-dimethyl-6-(trifluoromethyl)-1H-indol-3-yl)(hydroxy)methyl)benzoate (50 mg, 0.10 mmol). Mixture with the corresponding indoline (30%) LC/MS (Method i) R$_f$=2.56 min.; MS m/z: 416 [M+H]$^+$

Step 3: methyl 2-(1-(2,4-dichloro-3-((1,4-dimethyl-6-(trifluoromethyl)-1H-indol-3-yl)methyl)benzoyl)piperidin-4-yl)acetate

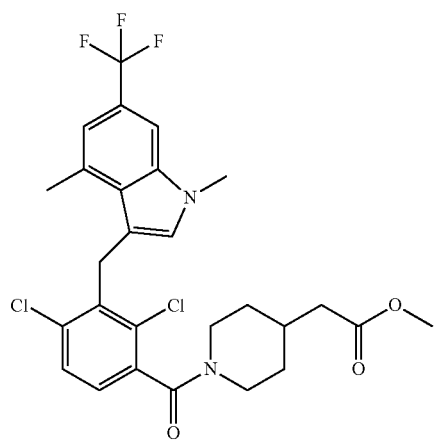 [SMILES: COC(=O)CC1CCN(C(=O)c2ccc(Cl)c(Cc3cn(C)c4cc(C(F)(F)F)cc(C)c34)c2Cl)CC1]

Using a procedure similar to Example A, Step 6, methyl 2-(1-(2,4-dichloro-3-((1,4-dimethyl-6-(trifluoromethyl)-1H-indol-3-yl)methyl)benzoyl)piperidin-4-yl)acetate (65 mg, 77%) was prepared from 2,4-dichloro-3-((1,4-dimethyl-6-(trifluoromethyl)-1H-indol-3-yl)methyl)benzoic acid (50 mg, 0.12 mmol) and methyl (4-piperidyl)acetate hydrochloride (26 mg, 0.13 mmol). Mixture with the corresponding indoline (22%). LC/MS (Method i) R$_f$=2.72 min.; MS m/z: 555 [M+H]$^+$

Step 4: 2-(1-(2,4-dichloro-3-((1,4-dimethyl-6-(trifluoromethyl)-1H-indol-3-yl)methyl)benzoyl)piperidin-4-yl)acetic acid

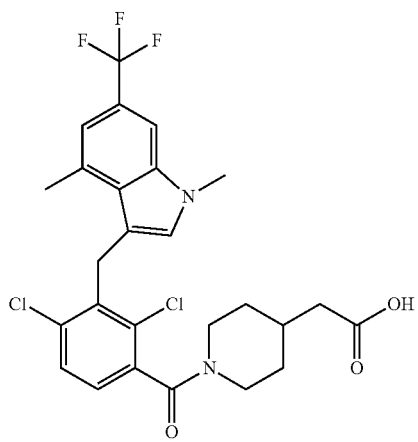 [SMILES: Cc1cc(C(F)(F)F)cc2c1c(Cc1c(Cl)ccc(C(=O)N3CCC(CC(=O)O)CC3)c1Cl)cn2C]

To a solution of methyl 2-(1-(2,4-dichloro-3-((1,4-dimethyl-6-(trifluoromethyl)-1H-indol-3-yl)methyl)benzoyl)piperidin-4-yl)acetate (65 mg, 0.117 mmol) in dioxane, (1.25 ml) and water (0.5 ml) was added sodium hydroxide (11.70 mg, 0.293 mmol) and the reaction mixture was stirred at 45° C. for 1 hour. The reaction mixture was concentrated under reduced pressure. The residue was taken in water and acidified until pH=3-4 by addition of a 1N HCl solution. The obtained precipitate was washed with water and dried under reduced pressure. The residue was purified by preparative LC/MS (method 12) to give 2-(1-(2,4-dichloro-3-((1,4-dimethyl-6-(trifluoromethyl)-1H-indol-3-yl)methyl)benzoyl)piperidin-4-yl)acetic acid (18 mg, 28%) as a white solid. LC/MS (Method g) $R_t$=1.92 min.; MS m/z: 541 [M+H]$^+$. $^1$H NMR (DMSO-d$_6$, 400 MHz): δ 12.12 (br, 1H), 7.63 (m, 2H), 7.39 and 7.32 (d, J=8.1 Hz, 1H), 7.09 (s, 1H), 6.53 (m, 1H), 4.60 (m, 2H), 4.47 (m, 1H), 3.70 (m, 3H), 3.30 (m, 1H), 3.03 (m, 1H), 2.78 (m, 4H), 2.17 (m, 2H), 1.91 (m, 1H), 1.77 (m, 1H), 1.62 (m, 1H), 1.16 (m, 2H).

TABLE F

The following examples were prepared from 2,4-dichloro-3-((1,4-dimethyl-6-(trifluoromethyl)-1H-indol-3-yl)methyl)benzoic acid (Example F, Step 2) using the same procedure with the appropriate amine.

| | Structure | Starting amine | $R_t$ min (method) | m/z ESI+ (M + H)$^+$ |
|---|---|---|---|---|
| F1-1 | 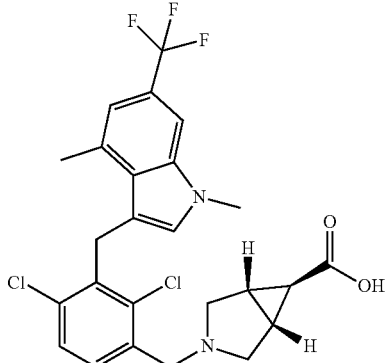 | 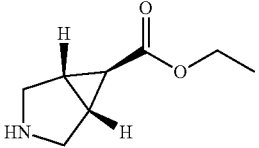 | 1.87 (method g) | 525 |
| F1-2 | 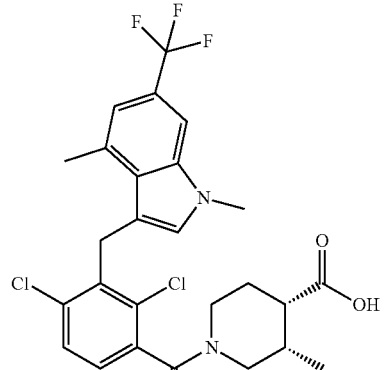 | 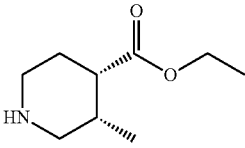 | 1.95 (method g) | 541 |
| F1-3 | 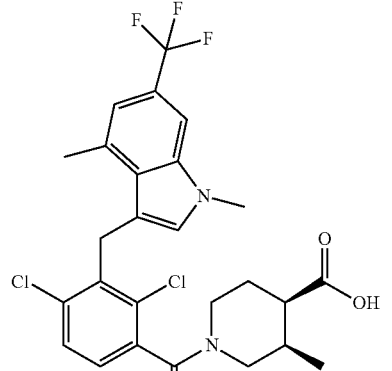 | 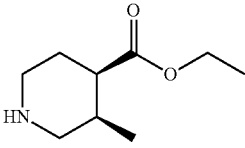 | 1.90 (method g) | 541 |

Example G: (3-((1,4-dimethyl-6-(trifluoromethyl)-1H-indol-2-yl)methyl)-2,4-dimethylphenyl)(morpholino)methanone

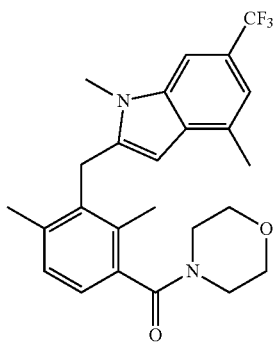 [SMILES: Cc1ccc(C(=O)N2CCOCC2)c(C)c1Cc1cc2c(C)cc(C(F)(F)F)cc2n1C]

Example G1: (2,6-dimethyl-3-(morpholine-4-carbonyl)phenyl)(1,4-dimethyl-6-(trifluoromethyl)-1H-indol-2-yl)methanone

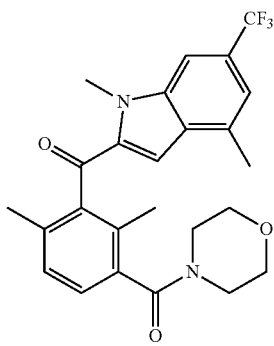 [SMILES: Cc1ccc(C(=O)N2CCOCC2)c(C)c1C(=O)c1cc2c(C)cc(C(F)(F)F)cc2n1C]

Step 1: (3-(hydroxy(4-methyl-1-(phenylsulfonyl)-6-(trifluoromethyl)-1H-indol-2-yl)methyl)-2,4-dimethylphenyl)(morpholino)methanone

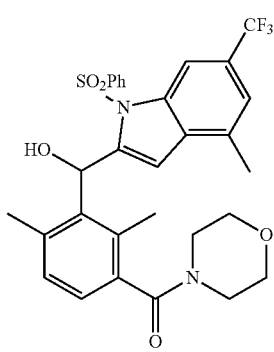

Using a procedure similar to Example A, Step 1, (3-(hydroxy(4-methyl-1-(phenylsulfonyl)-6-(trifluoromethyl)-1H-indol-2-yl)methyl)-2,4-dimethylphenyl)(morpholino)methanone (374 mg, 94%) was prepared from N-(2-iodo-3-methyl-5-(trifluoromethyl)phenyl)benzenesulfonamide (Preparation #16) (300 mg, 0.680 mmol) and (3-(1-hydroxy-prop-2-yn-1-yl)-2,4-dimethylphenyl)(morpholino)methanone (223 mg, 0.816 mmol) (Preparation #4). LC/MS (Method h) $R_t$=3.05 min.; MS m/z: 587 [M+H]$^+$. $^1$H NMR (DMSO-d$_6$, 300 MHz): δ 8.08 (m, 1H), 7.98 (m, 2H), 7.85 (m, 1H), 7.68 (m, 1H), 7.60 (m, 2H), 7.48 (s, 1H), 7.06 (m, 2H), 6.75 (m, 1H), 6.25 (m, 1H), 3.63 (m, 4H), 3.46 (m, 2H), 3.12 (m, 2H), 2.89 (s, 3H), 2.73 (s, 3H), 2.45 (m, 3H).

Step 2: (2,4-dimethyl-3-((4-methyl-1-(phenylsulfonyl)-6-(trifluoromethyl)-1H-indol-2-yl)methyl)phenyl)(morpholino)methanone

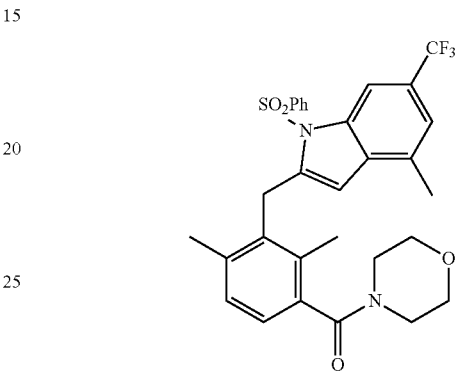

Using a procedure similar to Example A, Step 2, (2,4-dimethyl-3-((4-methyl-1-(phenylsulfonyl)-6-(trifluoromethyl)-1H-indol-2-yl)methyl)phenyl)(morpholino)methanone (346 mg, 95%) was prepared from (3-(hydroxy(4-methyl-1-(phenylsulfonyl)-6-(trifluoromethyl)-1H-indol-2-yl)methyl)-2,4-dimethylphenyl)(morpholino)methanone (374 mg, 0.638 mmol). LC/MS (Method h) $R_t$=3.30 min.; MS m/z: 571 [M+H]$^+$ $^1$H NMR (DMSO-d$_6$, 300 MHz): δ 8.29 (s, 1H), 7.96 (m, 2H), 7.76 (m, 1H), 7.68 (m, 2H), 7.41 (s, 1H), 7.17 (m, 1H), 7.08 (m, 1H), 5.73 (s, 1H), 4.25 (m, 2H), 3.62 (m, 4H), 3.44 (m, 2H), 3.10 (m, 2H), 2.30 (s, 3H), 2.05 (s, 3H), 1.90 (s, 3H).

Step 3: (2,4-dimethyl-3-((4-methyl-6-(trifluoromethyl)-1H-indol-2-yl)methyl)phenyl)(morpholino)methanone

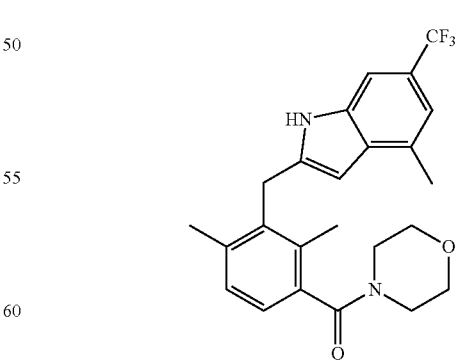

Using a procedure similar to Example A, Step 3, (2,4-dimethyl-3-((4-methyl-6-(trifluoromethyl)-1H-indol-2-yl)methyl)phenyl)(morpholino)methanone (198 mg, 76%) was prepared from (2,4-dimethyl-3-((4-methyl-1-(phenylsulfonyl)-6-(trifluoromethyl)-1H-indol-2-yl)methyl)phenyl)(morpholino)methanone (346 mg, 0.606 mmol). LC/MS (Method g) $R_t$=1.80 min.;

MS m/z: 431 [M+H]$^+$ $^1$H NMR (DMSO-d$_6$, 400 MHz): δ 11.39 (s, 1H), 7.46 (s, 1H), 7.17 (d, J=8.0 Hz, 1H), 7.02 (m, 2H), 5.81 (s, 1H), 4.19 (s, 2H), 3.64 (m, 4H), 3.48 (m, 2H), 3.13 (m, 2H), 2.38 (s, 3H), 2.30 (s, 3H), 2.15 (s, 3H).

Step 4: (3-((1,4-dimethyl-6-(trifluoromethyl)-1H-indol-2-yl)methyl)-2,4-dimethylphenyl)(morpholino)(methanone and (2,6-dimethyl-3-(morpholine-4-carbonyl)phenyl)(1,4-dimethyl-6-(trifluoromethyl)-1H-indol-2-yl)methanone

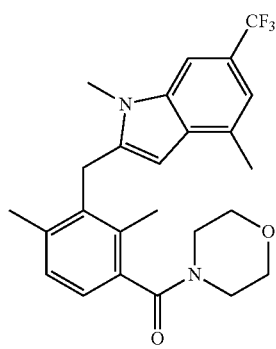

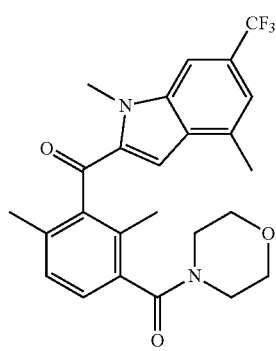

Using a procedure similar to Example A, Step 4, (3-((1,4-dimethyl-6-(trifluoromethyl)-1H-indol-2-yl)methyl)-2,4-dimethylphenyl)(morpholino)methanone (30 mg, 19%) was prepared from (2,4-dimethyl-3-((4-methyl-6-(trifluoromethyl)-1H-indol-2-yl)methyl)phenyl)(morpholino)methanone (154 mg, 0.358 mmol). LC/MS (Method g) $R_t$=1.87 min.; MS m/z: 445[M+H]$^+$. $^1$H NMR (DMSO-d$_6$, 400 MHz): δ 7.69 (s, 1H), 7.19 (d, J=8 Hz, 1H), 7.06 (m, 2H), 5.51 (s, 1H), 4.17 (m, 2H), 3.91 (s, 3H), 3.65 (m, 4H), 3.48 (m, 2H), 3.13 (m, 2H), 2.33 (s, 3H), 2.25 (s, 3H), 2.11 (s, 3H).

This reaction also afforded an oxidation product which was isolated and characterized: (2,6-dimethyl-3-(morpholine-4-carbonyl)phenyl)(1,4-dimethyl-6-(trifluoromethyl)-1H-indol-2-yl)methanone (32 mg, 19%). LC/MS (Method g) $R_t$=1.84 min.; MS m/z: 459[M+H]$^+$.

$^1$H NMR (DMSO-d$_6$, 400 MHz): δ 7.95 (s, 1H), 7.26 (s, 2H), 7.22 (s, 1H), 6.82 (s, 1H), 4.24 (s, 3H), 3.62 (m, 4H), 3.48 (m, 2H), 3.16 (m, 2H), 2.44 (s, 3H), 2.17 (s, 3H), 2.00 (s, 3H).

Example H: (2,4-dichloro-3-((4-methyl-6-(trifluoromethyl)-1H-indol-2-yl)methyl)phenyl)(4-(dimethylamino)piperidin-1-yl)methanone

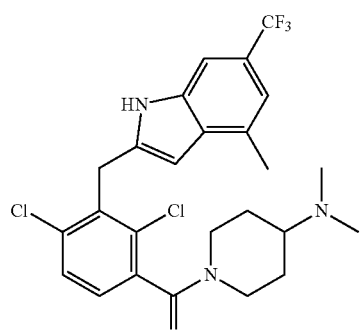

Step 1: 2,4-dichloro-3-((4-methyl-1-(phenylsulfonyl)-6-(trifluoromethyl)-1H-indol-2-yl)methyl)benzoic acid

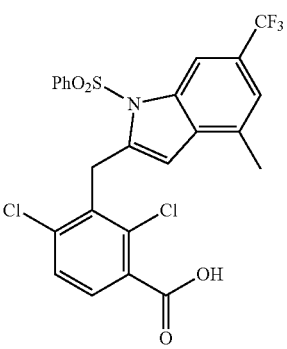

Using a procedure similar to Example A, Step 5, 2,4-dichloro-3-((4-methyl-1-(phenylsulfonyl)-6-(trifluoromethyl)-1H-indol-2-yl)methyl)benzoic acid (280 mg, 82%) was prepared from methyl 2,4-dichloro-3-((4-methyl-1-(phenylsulfonyl)-6-(trifluoromethyl)-1H-indol-2-yl)methyl)benzoate (Example A, Step 2,) (350 mg, 0.629 mmol). LC/MS (Method h) $R_t$=3.33 min.; MS m/z: 542 [M+H]$^+$. $^1$H NMR (DMSO-d$_6$, 300 MHz): δ 8.25 (s, 1H), 7.92 (m, 2H), 7.75 (m, 1H), 7.67 (m, 3H), 7.58 (m, 1H), 7.41 (s, 1H), 5.93 (s, 1H), 4.58 (s, 2H), 2.35 (s, 3H).

Step 2: (2,4-dichloro-3-((4-methyl-1-(phenylsulfonyl)-6-(trifluoromethyl)-1H-indol-2-yl)methyl)phenyl)(4-(dimethylamino)piperidin-1-yl)methanone

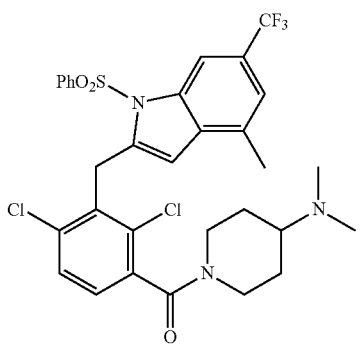

Using a procedure similar to Example A, Step 6, (2,4-dichloro-3-((4-methyl-1-(phenylsulfonyl)-6-(trifluoromethyl)-1H-indol-2-yl)methyl)phenyl)(4-(dimethylamino)piperidin-1-yl)methanone (305 mg, 72%) was prepared from 2,4-dichloro-3-((4-methyl-1-(phenylsulfonyl)-6-(trifluoromethyl)-1H-indol-2-yl)methyl)benzoic acid (350 mg, 0.645 mmol) and N,N-dimethylpiperidin-4-amine (165 mg, 1.29 mmol). LC/MS (Method h) $R_t$=3.34 min.; MS m/z: 652 [M+H]$^+$.

$^1$H NMR (DMSO-d$_6$, 300 MHz): δ 8.25 (s, 1H), 7.92 (m, 2H), 7.75 (m, 1H), 7.66 (m, 3H), 7.48 (m, 2H), 5.98 (m, 1H), 4.50 (m, 2H), 4.41 (m, 1H), 2.98 (m, 1H), 2.80 (m, 1H), 2.36 (s, 3H), 2.30 (m, 2H), 2.20 (s, 3H), 2.09 (s, 3H), 1.82 (m, 1H), 1.64 (m, 1H), 1.27 (m, 2H).

Step 3: (2,4-dichloro-3-((4-methyl-6-(trifluoromethyl)-1H-indol-2-yl)methyl)phenyl)(4-(dimethylamino)piperidin-1-yl)methanone

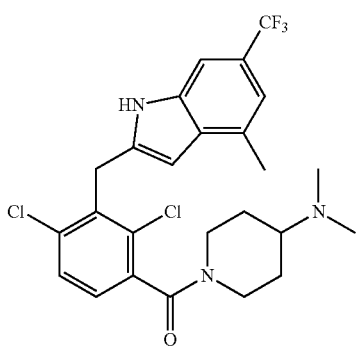 [SMILES: Cc1cc(C(F)(F)F)cc2[nH]c(Cc3c(Cl)ccc(C(=O)N4CCC(N(C)C)CC4)c3Cl)cc12]

Using a procedure similar to Example A, Step 3, (2,4-dichloro-3-((4-methyl-6-(trifluoromethyl)-1H-indol-2-yl)methyl)phenyl)(4-(dimethylamino)piperidin-1-yl)methanone (190 mg, 86%) was prepared from (2,4-dichloro-3-((4-methyl-1-(phenylsulfonyl)-6-(trifluoromethyl)-1H-indol-2-yl)methyl)phenyl)(4-(dimethylamino)piperidin-1-yl)methanone (280 mg, 0.429 mmol).

LC/MS (Method g) $R_t$=1.22 min.; MS m/z: 512 [M+H]$^+$.
$^1$H NMR (DMSO-d$_6$, 400 MHz): δ 11.40 (s, 1H), 7.64 (m, 1H), 7.48 (s, 1H), 7.38 (m, 1H), 7.03 (s, 1H), 5.95 (s, 1H), 4.46 (m, 3H), 3.30 (m, 1H), 3.00 (m, 1H), 2.85 (m, 1H), 2.41 (s, 3H), 2.32 (m, 1H), 2.16 (s, 3H), 2.12 (s, 3H), 1.82 (m, 1H), 1.65 (m, 1H), 1.32 (m, 2H).

Example I: (2,4-dichloro-3-((1,4-dimethyl-6-(trifluoromethyl)-1H-indol-2-yl)methyl)phenyl)(4-(dimethylamino)piperidin-1-yl)methanone

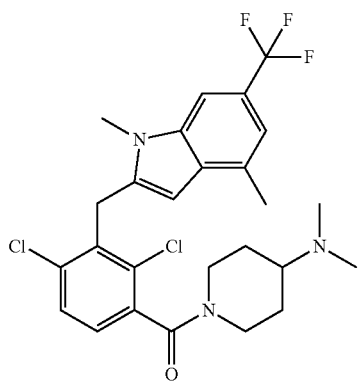 [SMILES: Cc1cc(C(F)(F)F)cc2c1cc(Cc1c(Cl)ccc(C(=O)N3CCC(N(C)C)CC3)c1Cl)n2C]

Using a procedure similar to Example A, Step 4, (2,4-dichloro-3-((1,4-dimethyl-6-(trifluoromethyl)-1H-indol-2-yl)methyl)phenyl)(4-(dimethylamino)piperidin-1-yl)methanone (10 mg, 13%) was prepared from (2,4-dichloro-3-((4-methyl-6-(trifluoromethyl)-1H-indol-2-yl)methyl)phenyl)(4-(dimethylamino)piperidin-1-yl)methanone (Example H, Step 3) (75 mg, 0.146 mmol). LC/MS (Method g) $R_t$=1.29 min.; MS m/z: 526 [M+H]$^+$. $^1$H NMR (DMSO-d$_6$, 300 MHz): δ 7.70 (m, 1H), 7.65 (m, 1H), 7.43 (m, 1H), 7.07 (s, 1H), 5.68 (m, 1H), 4.46 (m, 3H), 3.92 (m, 3H), 2.99 (m, 1H), 2.85 (m, 1H), 2.36 (s, 3H), 2.32 (m, 1H), 2.17 (s, 3H), 2.11 (s, 3H), 1.83 (m, 1H), 1.68 (m, 1H), 1.32 (m, 2H).

Example J: 2-(1-(2,4-dichloro-3-((7-methyl-5-(trifluoromethyl)-1H-indol-1-yl)methyl)benzoyl)piperidin-4-yl)acetic acid

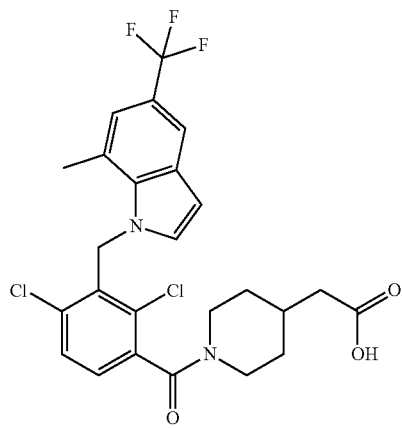 [SMILES: Cc1cc(C(F)(F)F)cc2ccn(Cc3c(Cl)ccc(C(=O)N4CCC(CC(=O)O)CC4)c3Cl)c12]

Step 1: methyl 2,4-dichloro-3-((7-methyl-5-(trifluoromethyl)-1H-indol-1-yl)methyl)benzoate

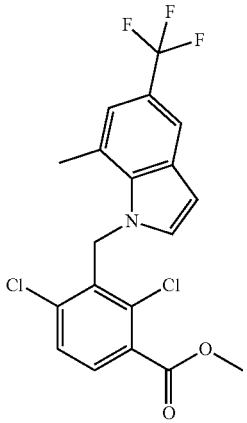 [SMILES: COC(=O)c1ccc(Cl)c(Cn2ccc3cc(C(F)(F)F)cc(C)c32)c1Cl]

To a solution of 7-methyl-5-(trifluoromethyl)-1H-indole (Preparation #49) (0.850 g, 4.27 mmol) in N,N-dimethylformamide (10.67 ml) and cooled to 0° C. was added sodium hydride (0.188 g, 4.69 mmol) and the reaction was stirred 30 minutes. Methyl 3-(bromomethyl)-2,4-dichlorobenzoate (Preparation #1, Step B) (1.272 g, 4.27 mmol) was added and the reaction mixture was stirred 1 hour at 0° C. The reaction mixture was diluted with water and EtOAc. The layers were separated and the aqueous one was extracted with EtOAc. The combined organic layers were washed with water then a saturated NaCl solution, dried over magnesium sulfate, filtered and concentrated under reduced pressure. The residue was purified by column chromatography on silica gel (eluting with 0-10% EtOAc in cyclohexane) to give methyl 2,4-dichloro-3-((7-methyl-5-(trifluoromethyl)-1H-indol-1-yl)methyl)benzoate (1.55 g, 80%). LC/MS (Method j) $R_t$=2.32 min.; MS m/z: 416 [M+H]$^+$ $^1$H NMR (DMSO-d$_6$, 300 MHz): δ 7.89 (d, J=8.4 Hz, 1H), 7.79 (m, 1H), 7.76 (d, J=8.4 Hz, 1H), 7.23 (m, 1H), 6.74 (d, J=3.3 Hz, 1H), 6.56 (d, J=3.3 Hz, 1H), 5.98 (s, 2H), 3.88 (s, 3H), 2.94 (s, 3H).

Step 2: 2,4-dichloro-3-((7-methyl-5-(trifluoromethyl)-1H-indol-1-yl)methyl)benzoic acid

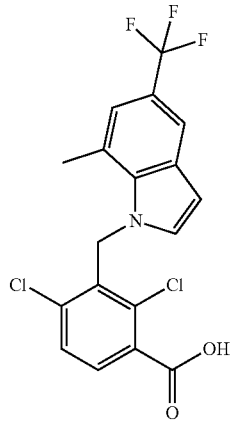 [SMILES: Cc1cc(C(F)(F)F)cc2ccn(Cc3c(Cl)ccc(C(=O)O)c3Cl)c12]

Using a procedure similar to Example F, Step 4, 2,4-dichloro-3-((7-methyl-5-(trifluoromethyl)-1H-indol-1-yl)methyl)benzoic acid (1.44 g, 96%) was prepared from methyl 2,4-dichloro-3-((7-methyl-5-(trifluoromethyl)-1H-indol-1-yl)methyl)benzoate (1.55 g, 3.72 mmol). LC/MS (Method j) $R_t$=1.86 min.; MS m/z: 402 [M+H]$^+$ $^1$H NMR (DMSO-d$_6$, 300 MHz): δ 13.8 (br, 1H), 7.82 (d, J=8.3 Hz, 1H), 7.79 (s, 1H), 7.69 (d, J=8.3 Hz, 1H), 7.23 (s, 1H), 6.73 (d, J=3.3 Hz, 1H), 6.56 (d, J=3.3 Hz, 1H), 5.97 (s, 2H), 2.95 (s, 3H).

Step 3: methyl 2-(1-(2,4-dichloro-3-((7-methyl-5-(trifluoromethyl)-1H-indol-1-yl)methyl)benzoyl)piperidin-4-yl)acetate

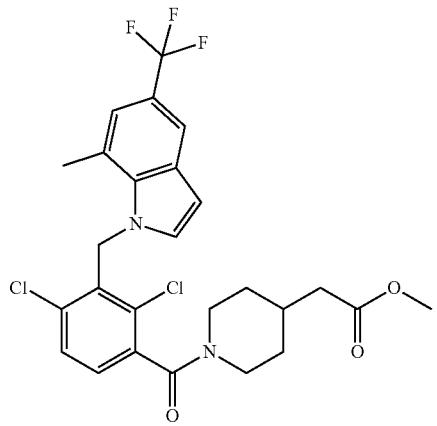 [SMILES: COC(=O)CC1CCN(C(=O)c2ccc(Cl)c(Cn3ccc4cc(C(F)(F)F)cc(C)c43)c2Cl)CC1]

Using a procedure similar to Example A, Step 6, methyl 2-(1-(2,4-dichloro-3-((7-methyl-5-(trifluoromethyl)-1H-indol-1-yl)methyl)benzoyl)piperidin-4-yl)acetate (118 mg, 88%) was prepared from 2,4-dichloro-3-((7-methyl-5-(trifluoromethyl)-1H-indol-1-yl)methyl)benzoic acid (100 mg, 0.25 mmol) and methyl 2-(piperidin-4-yl)acetate hydrochloride (62.6, 0.32 mmol).

LC/MS (Method j) $R_t$=2.10 min.; MS m/z: 541 [M+H]$^+$ $^1$H NMR (DMSO-d$_6$, 300 MHz): δ 7.79 (s, 1H), 7.70 and 7.69 (d, J=8.3 Hz, 1H), 7.53 and 7.46 (d, J=8.3 Hz, 1H), 7.23 (s, 1H), 6.76 (m, 1H), 6.57 (m, 1H), 5.94 (m, 2H), 4.46 (m, 1H), 3.59 and 3.57 (s, 3H), 3.21 (m, 1H), 3.03 (m, 1H), 2.94 (s, 3H), 2.80 (m, 1H), 2.28 (m, 2H), 1.96 (m, 1H), 1.75 (m, 1H), 1.59 (m, 1H), 1.17 (m, 2H)

Step 4: 2-(1-(2,4-dichloro-3-((7-methyl-5-(trifluoromethyl)-1H-indol-1-yl)methyl)benzoyl)piperidin-4-yl)acetic acid

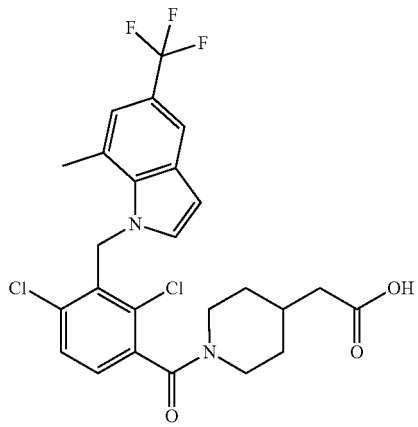 [SMILES: Cc1cc(C(F)(F)F)cc2ccn(Cc3c(Cl)ccc(C(=O)N4CCC(CC(=O)O)CC4)c3Cl)c12]

247

Using a procedure similar to Example A, Step 5, 2-(1-(2,4-dichloro-3-((7-methyl-5-(trifluoromethyl)-1H-indol-1-yl)methyl)benzoyl)piperidin-4-yl)acetic acid (99 mg, 89%) was prepared from methyl 2-(1-(2,4-dichloro-3-((7-methyl-5-(trifluoromethyl)-1H-indol-1-yl)methyl)benzoyl)piperidin-4-yl)acetate (114 mg, 0.21 mmol). LC/MS (Method g) $R_t$=1.85 min.; MS m/z: 527 [M+H]$^+$ $^1$H NMR (DMSO-d$_6$, 400 MHz): δ 12.10 (br, 1H), 7.79 (s, 1H), 7.70 and 7.69 (d, J=8.3 Hz, 1H), 7.53 and 7.46 (d, J=8.3 Hz, 1H), 7.23 (s, 1H), 6.76 (m, 1H), 6.58 (m, 1H), 5.94 (m, 2H), 4.46 (m, 1H), 3.27 (m, 1H), 3.03 (m, 1H), 2.94 (s, 3H), 2.80 (m, 1H), 2.17 (m, 2H), 1.93 (m, 1H), 1.77 (m, 1H), 1.61 (m, 1H), 1.14 (m, 2H).

Example K: (3-((1,4-dimethyl-6-(trifluoromethyl)-1H-indol-2-yl)(hydroxy)methyl)-2,4-dimethylphenyl)(morpholino)methanone

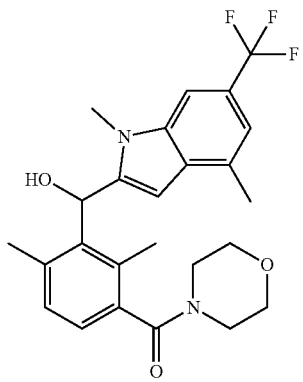 [SMILES: Cc1ccc(C(=O)N2CCOCC2)c(C)c1C(O)c1cc2c(C)cc(C(F)(F)F)cc2n1C]

Example K1: (3-((1,4-dimethyl-6-(trifluoromethyl)-1H-indol-2-yl)(methoxy)methyl)-2,4-dimethylphenyl)(morpholino)methanone

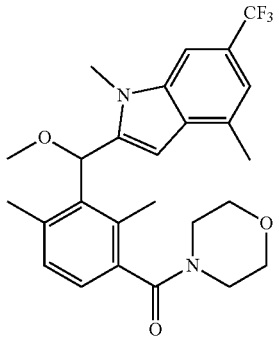 [SMILES: COC(c1c(C)ccc(C(=O)N2CCOCC2)c1C)c1cc2c(C)cc(C(F)(F)F)cc2n1C]

Step 1: (3-(hydroxy(4-methyl-6-(trifluoromethyl)-1H-indol-2-yl)methyl)-2,4-dimethylphenyl)(morpholino)methanone

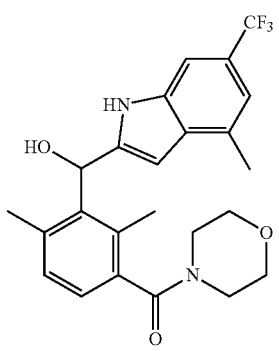 [SMILES: Cc1ccc(C(=O)N2CCOCC2)c(C)c1C(O)c1cc2c(C)cc(C(F)(F)F)cc2[nH]1]

Using a procedure similar to Example A, Step 3, (3-(hydroxy(4-methyl-6-(trifluoromethyl)-1H-indol-2-yl)methyl)-2,4-dimethylphenyl)(morpholino)methanone (189 mg, 39%) was prepared from (3-(hydroxy(4-methyl-1-(phenylsulfonyl)-6-(trifluoromethyl)-1H-indol-2-yl)methyl)-2,4-dimethylphenyl)(morpholino)methanone (Example G, Step 1) (629 mg, 1.072 mmol). LC/MS (Method h) $R_t$=2.66 min.; MS m/z: 447 [M+H]$^+$. $^1$H NMR (DMSO-d$_6$, 300 MHz): δ 11.32 (s, 1H), 7.52 (d, J=4.8 Hz, 1H), 7.12 (m, 1H), 7.03 (m, 2H) 6.38 (s, 1H), 6.24 (d, J=4 Hz, 1H), 5.94 (s, 1H), 3.62 (m, 4H), 3.49 (m, 2H), 3.136 (m, 2H), 2.41 (s, 3H), 2.40 (s, 3H), 2.12 (s, 3H).

Step 2: (3-((1,4-dimethyl-6-(trifluoromethyl)-1H-indol-2-yl)(hydroxy)methyl)-2,4-dimethylphenyl)(morpholino)methanone and (3-((1,4-dimethyl-6-(trifluoromethyl)-1H-indol-2-yl)(methoxy)methyl)-2,4-dimethylphenyl)(morpholino)methanone

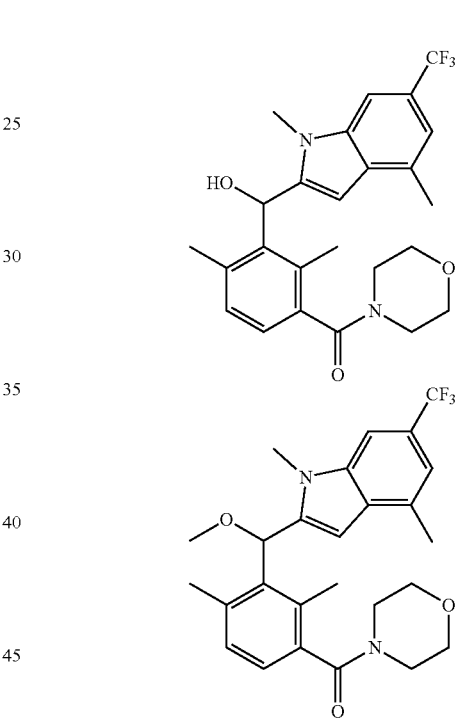

Using a procedure similar to Example A, Step 4, (3-((1,4-dimethyl-6-(trifluoromethyl)-1H-indol-2-yl)(hydroxy)methyl)-2,4-dimethylphenyl)(morpholino)methanone (14 mg, 7%) was prepared from (3-(hydroxy(4-methyl-6-(trifluoromethyl)-1H-indol-2-yl)methyl)-2,4-dimethylphenyl)(morpholino)methanone (189 mg, 0.423 mmol). LC/MS (Method g) $R_t$=1.70 min.;

MS m/z: 461 [M+H]$^+$ $^1$H NMR (DMSO-d$_6$, 500 MHz): δ 7.68 (s, 1H), 7.14 (m, 1H), 7.07 (m, 2H), 6.39 (s, 1H), 6.10 (s, 1H), 5.96 and 5.92 (s, 1H), 3.86 and 3.82 (s, 3H), 3.63 (m, 4H), 3.48 (m, 2H), 3.16 (m, 2H), 2.39 and 2.38 (s, 3H), 2.34 and 2.31 (s, 3H), 2.21 and 2.19 (s, 3H).

During this reaction a double methylation product was also isolated and characterized as (3-((1,4-dimethyl-6-(trifluoromethyl)-1H-indol-2-yl)(methoxy)methyl)-2,4-dimethylphenyl)(morpholino)methanone (0.5 mg, 0.2%). LC/MS (Method g) $R_t$=1.85 min.; MS m/z: 475 [M+H]$^+$ $^1$H NMR (DMSO-d$_6$, 500 MHz): δ 7.72 (s, 1H), 7.20 (m, 1H), 7.14

(m, 1H), 7.08 (s, 1H), 6.05 (s, 1H), 5.80 (s, 1H), 3.91 (s, 3H), 3.65-3.48 (m, 6H), 3.33 (s, 3H), 3.12 (m, 2H), 2.36 (s, 3H), 2.32 (s, 3H), 2.19 (s, 3H).

Example L: (2,4-dichloro-3-((1-methyl-6-(trifluoromethyl)-1H-indol-2-yl)methyl)phenyl)(4-hydroxypiperidin-1-yl)methanone

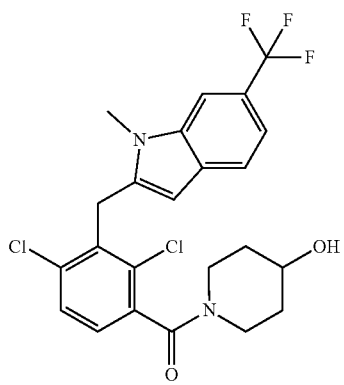 [SMILES: Cn1c(Cc2c(Cl)ccc(C(=O)N3CCC(O)CC3)c2Cl)cc2ccc(C(F)(F)F)cc21]

Step 1: methyl 2,4-dichloro-3-(hydroxy(1-(phenylsulfonyl)-6-(trifluoromethyl)-1H-indol-2-yl)methyl)benzoate

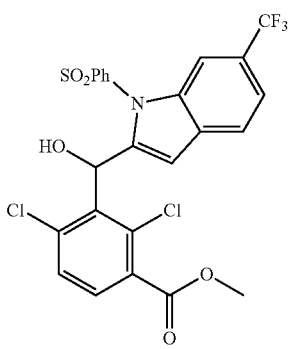

Using a procedure similar to Example A, Step 1, methyl 2,4-dichloro-3-(hydroxy(1-(phenylsulfonyl)-6-(trifluoromethyl)-1H-indol-2-yl)methyl)benzoate (7.8 g, 78%) was prepared from N-(2-iodo-5-(trifluoromethyl)phenyl)benzenesulfonamide (Preparation #29) (7.00 g, 16.4 mmol) and methyl 2,4-dichloro-3-(1-hydroxyprop-2-yn-1-yl)benzoate (Preparation #1) (4.7 g, 18.1 mmol).

LC/MS (Method h) $R_t$=3.27 min.; MS m/z: 540 [M−H]⁻+CH₃COOH ¹H NMR (DMSO-d₆, 300 MHz): δ 8.24 (s, 1H), 7.85 (m, 3H), 7.69 (m, 2H), 7.58 (m, 4H), 7.03 (m, 1H), 6.84 (s, 1H), 6.73 (m, 1H), 3.87 (s, 3H).

Step 2: methyl 2,4-dichloro-3-((1-(phenylsulfonyl)-6-(trifluoromethyl)-1H-indol-2-yl)methyl)benzoate

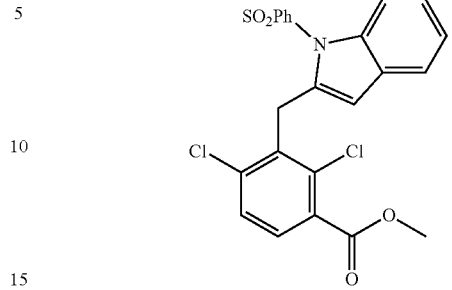

Using a procedure similar to Example A, Step 2, methyl 2,4-dichloro-3-((1-(phenylsulfonyl)-6-(trifluoromethyl)-1H-indol-2-yl)methyl)benzoate (6.3 g, 90%) was prepared from methyl 2,4-dichloro-3-(hydroxy(1-(phenylsulfonyl)-6-(trifluoromethyl)-1H-indol-2-yl)methyl)benzoate (7.15 g, 12.8 mmol). LC/MS (Method h) $R_t$=3.73 min.; MS m/z: 540 [M−H]⁻.

¹H NMR (CDCl₃, 300 MHz): δ 8.45 (s, 1H), 7.80 (m, 2H), 7.63 (d, J=9 Hz, 1H), 7.51 (m, 1H), 7.38 (m, 5H), 5.68 (s, 1H), 4.63 (m, 2H), 3.86 (s, 3H).

Step 3: methyl 2,4-dichloro-3-((6-(trifluoromethyl)-1H-indol-2-yl)methyl)benzoate

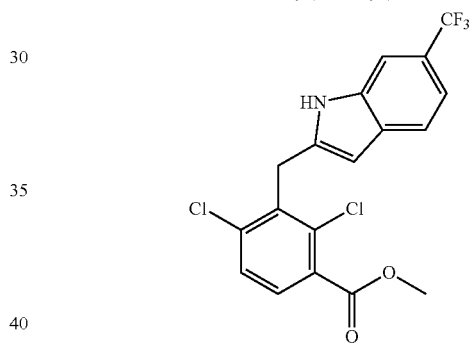

Using a procedure similar to Example A, Step 3, methyl 2,4-dichloro-3-((6-(trifluoromethyl)-1H-indol-2-yl)methyl)benzoate (4.3 g, 93%) was prepared from methyl 2,4-dichloro-3-((1-(phenylsulfonyl)-6-(trifluoromethyl)-1H-indol-2-yl)methyl)benzoate (6.2 g, 11.4 mmol).

LC/MS (Method h) $R_t$=3.23 min.; MS m/z: 402 [M+H]⁺.
¹H NMR (DMSO-d₆, 300 MHz): δ 11.5 (broad, 1H), 7.75 (d, J=9 Hz, 1H), 7.69 (d, J=9 Hz, 1H), 7.65 (s, 1H), 7.57 (d, J=6 Hz, 1H), 7.23 (dd, J=6 Hz, J=1.5 Hz, 1H), 5.96 (s, 1H), 4.50 (s, 2H), 2.87 (s, 3H).

Step 4: methyl 2,4-dichloro-3-((1-methyl-6-(trifluoromethyl)-1H-indol-2-yl)methyl)benzoate

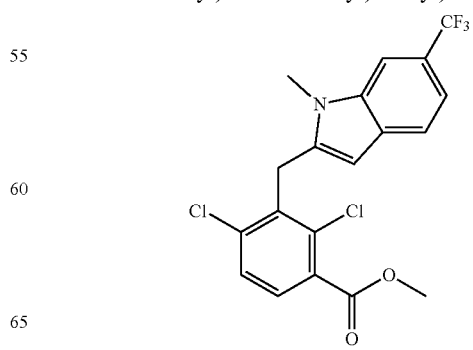

Using a procedure similar to Example A, Step 4, methyl 2,4-dichloro-3-((1-methyl-6-(trifluoromethyl)-1H-indol-2-yl)methyl)benzoate (3.86 g, 89%) was prepared from methyl 2,4-dichloro-3-((6-(trifluoromethyl)-1H-indol-2-yl)methyl)benzoate (4.17 g, 10.37 mmol). LC/MS (Method g) R$_t$=2.06 min.; MS m/z: 416 [M+H]$^+$. $^1$H NMR (DMSO-d$_6$, 300 MHz): δ 7.87 (s, 1H), 7.79 (d, J=9 Hz, 1H), 7.71 (d, J=9 Hz, 1H), 7.55 (d, J=9 Hz, 1H), 7.24 (d, J=9 Hz, 1H), 5.68 (s, 1H), 4.50 (s, 2H), 3.94 (s, 3H), 3.88 (s, 3H).

Step 5: 2,4-dichloro-3-((1-methyl-6-(trifluoromethyl)-1H-indol-2-yl)methyl)benzoic acid

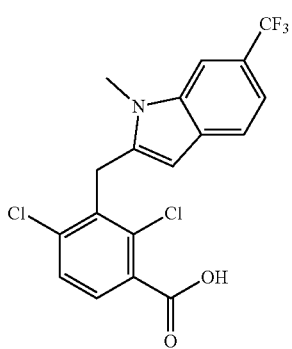 [SMILES: Cn1c(Cc2c(Cl)ccc(C(=O)O)c2Cl)cc2ccc(C(F)(F)F)cc21]

Using a procedure similar to Example A, Step 5, 2,4-dichloro-3-((1-methyl-6-(trifluoromethyl)-1H-indol-2-yl)methyl)benzoic acid (1.53 g, 87%) was prepared from methyl 2,4-dichloro-3-((1-methyl-6-(trifluoromethyl)-1H-indol-2-yl)methyl)benzoate (1.81 g, 4.35 mmol).

LC/MS (Method h) R$_t$=3.08 min.; MS m/z: 402 [M+H]$^+$.

$^1$H NMR (DMSO-d$_6$, 300 MHz): δ 7.87 (s, 1H), 7.74 (d, J=9 Hz, 1H), 7.67 (d, J=9 Hz, 1H), 7.56 (d, J=9 Hz, 1H), 7.24 (dd, J=9 Hz, J=1.5 Hz, 1H), 5.68 (s, 1H), 4.49 (s, 2H), 3.94 (s, 3H).

Step 6: (2,4-dichloro-3-((1-methyl-6-(trifluoromethyl)-1H-indol-2-yl)methyl)phenyl)(4-hydroxypiperidin-1-yl)methanone

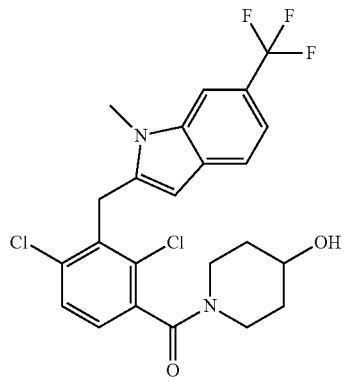 [SMILES: Cn1c(Cc2c(Cl)ccc(C(=O)N3CCC(O)CC3)c2Cl)cc2ccc(C(F)(F)F)cc21]

Using a procedure similar to Example A, Step 6, (2,4-dichloro-3-((1-methyl-6-(trifluoromethyl)-1H-indol-2-yl)methyl)phenyl)(4-hydroxypiperidin-1-yl)methanone (65 mg, 53%) was prepared from 2,4-dichloro-3-((1-methyl-6-(trifluoromethyl)-1H-indol-2-yl)methyl)benzoic acid (100 mg, 0.249 mmol) and piperidin-4-ol (37.7 mg, 0.37 mmol). LC/MS (Method g) R$_t$=1.70 min.; MS m/z: 485 [M+H]$^+$.

$^1$H NMR (DMSO-d$_6$, 400 MHz): δ 7.87 (s, 1H), 7.65 (dd, J=6.3 Hz, J=1.8 Hz, 1H), 7.56 (d, J=6.3 Hz, 1H), 7.41 (m, 1H), 7.25 (d, J=6 Hz, 1H), 5.70 (m, 1H), 4.80 (m, 1H), 4.38 (m, 2H), 4.05 (m, 1H), 3.96 (s, 3H), 3.73 (m, 1H), 3.20 (m, 2H), 3.07 (m, 1H), 1.81 (m, 1H), 1.75 (m, 1H), 1.39 (m, 2H).

TABLE L

The following analogs were prepared from 2,4-dichloro-3-((1-methyl-6-(trifluoromethyl)-1H-indol-2-yl)methyl)benzoic acid (Example L, Step 5) using the same procedure with the appropriate amine.

| Example # | Product | amine | R$_t$ min (Method g) | m/z ESI+ (M + H)$^+$ |
|---|---|---|---|---|
| L-1 | (structure) | (structure) | 1.21 | 512 |

TABLE L-continued
The following analogs were prepared from 2,4-dichloro-3-((1-methyl-6-(trifluoromethyl)-1H-indol-2-yl)methyl)benzoic acid (Example L, Step 5) using the same procedure with the appropriate amine.
| Example # | Product | amine | R$_t$ min (Method g) | m/z ESI+ (M + H)+ |
|---|---|---|---|---|
| L-2 | 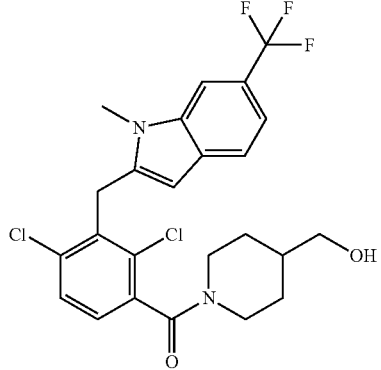 [SMILES: Cn1c(Cc2c(Cl)ccc(C(=O)N3CCC(CO)CC3)c2Cl)cc2ccc(C(F)(F)F)cc21] | 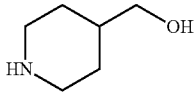 | 1.74 | 499 |
| L-3 | 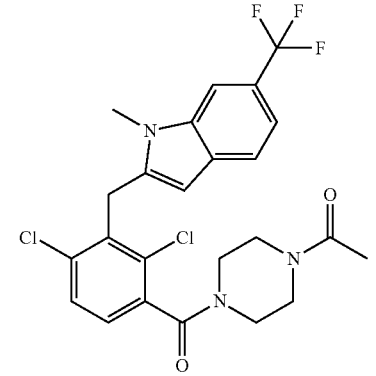 [SMILES: CC(=O)N1CCN(C(=O)c2ccc(Cl)c(Cc3cc4ccc(C(F)(F)F)cc4n3C)c2Cl)CC1] | 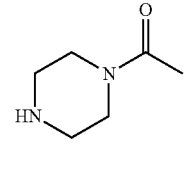 | 1.69 | 510 ( |
| L-4 | 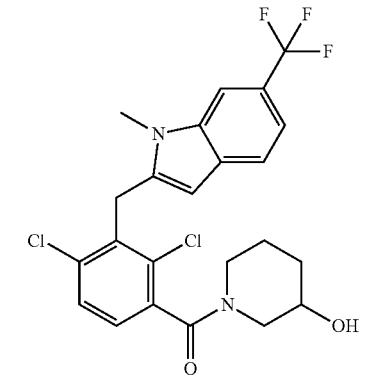 [SMILES: Cn1c(Cc2c(Cl)ccc(C(=O)N3CCCC(O)C3)c2Cl)cc2ccc(C(F)(F)F)cc21] | 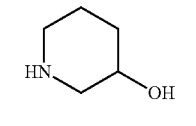 | 1.75 | 485 |

TABLE L-continued

The following analogs were prepared from 2,4-dichloro-3-((1-methyl-6-(trifluoromethyl)-1H-indol-2-yl)methyl)benzoic acid (Example L, Step 5) using the same procedure with the appropriate amine.

| Example # | Product | amine | R$_t$ min (Method g) | m/z ESI+ (M + H)+ |
|---|---|---|---|---|
| L-5 | (structure) | (structure) | 1.76 | 503 |

Example M: 1-(2,4-dichloro-3-((1-methyl-6-(trifluoromethyl)-1H-indol-2-yl)methyl)benzoyl)piperidine-4-carboxylic acid

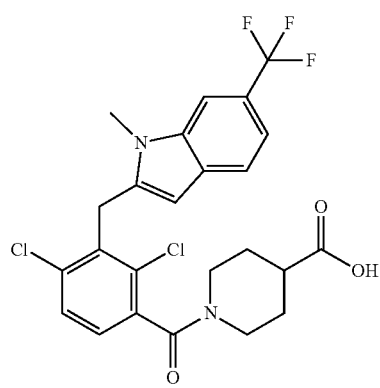 [SMILES: Cn1c(Cc2c(Cl)ccc(C(=O)N3CCC(C(=O)O)CC3)c2Cl)cc2ccc(C(F)(F)F)cc21]

Step 1: methyl 1-(2,4-dichloro-3-((1-methyl-6-(trifluoromethyl)-1H-indol-2-yl)methyl)benzoyl)piperidine-4-carboxylate

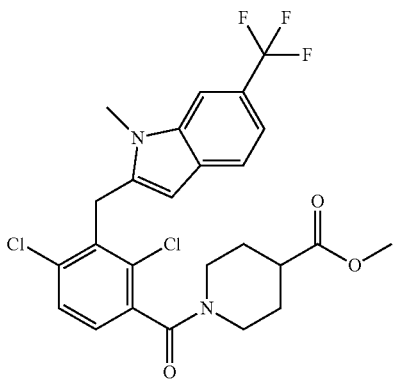 [SMILES: COC(=O)C1CCN(C(=O)c2ccc(Cl)c(Cc3cc4ccc(C(F)(F)F)cc4n3C)c2Cl)CC1]

Using a procedure similar to Example A, Step 6, methyl 1-(2,4-dichloro-3-((1-methyl-6-(trifluoromethyl)-1H-indol-2-yl)methyl)benzoyl)piperidine-4-carboxylate (172 mg, 73%) was prepared from 2,4-dichloro-3-((1-methyl-6-(trifluoromethyl)-1H-indol-2-yl)methyl)benzoic acid (Example L, Step 5) (180 mg, 0.448 mmol) and methyl 4-piperidinecarboxylate (96 mg, 0.67 mmol).

LC/MS (Method h) R$_t$=3.17 min.; MS m/z: 527 [M+H]+.
$^1$H NMR (DMSO-d$_6$, 300 MHz): δ 7.81 (s, 1H), 7.65 (d, J=8.4 Hz, 1H), 7.56 (d, J=7.8 Hz, 1H), 7.46 (d, J=8.4 Hz, 0.5H), 7.39 (d, J=8.4 Hz, 0.5H), 7.26 (d, J=7.8 Hz, 1H), 5.72 and 5.69 (s, 1H), 4.46 (m, 2H), 4.38 (m, 1H), 3.93 (s, 3H), 3.62 and 3.58 (s, 3H), 3.27 (m, 1H), 3.13-2.94 (m, 2H), 2.67 (m, 1H), 1.82 (m, 2H), 1.52 (m, 2H).

Step 2: 1-(2,4-dichloro-3-((1-methyl-6-(trifluoromethyl)-1H-indol-2-yl)methyl)benzoyl)piperidine-4-carboxylic acid Using a procedure similar to Example A, Step 5, 1-(2,4-dichloro-3-((1-methyl-6-(trifluoromethyl)-1H-indol-2-yl)methyl)benzoyl)piperidine-4-carboxylic acid (154 mg, 93%) was prepared from methyl 1-(2,4-dichloro-3-((1-methyl-6-(trifluoromethyl)-1H-indol-2-yl)methyl)benzoyl)piperidine-4-carboxylate (170 mg, 0.32 mmol). LC/MS (Method g) $R_t$=1.73 min.; MS m/z: 513 [M+H]$^+$. $^1$H NMR (DMSO-d$_6$, 400 MHz): δ 12.32 (broad, 1H), 7.87 (s, 1H), 7.65 (d, J=8.4 Hz, 1H), 7.56 (d, J=8.4 Hz, 1H), 7.46 (d, J=8.4 Hz, 0.5H), 7.39 (d, J=8.4 Hz, 0.5H), 7.24 (d, J=8.4 Hz, 1H), 5.71 (m, 1H), 4.51 (m, 2H), 4.45 (m, 1H), 3.93 (s, 3H), 3.29 (m, 1H), 3.12 (m, 1H), 2.95 (m, 1H), 2.54 (m, 1H), 1.95 (m, 1H), 1.76 (m, 1H), 1.50 (m, 2H).

Example N: 1-(2,4-dichloro-3-((1-methyl-6-(trifluoromethyl)-1H-indol-2-yl)methyl)benzoyl)-3-hydroxypiperidine-4-carboxylic acid

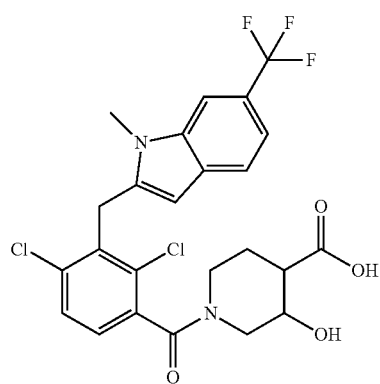 [SMILES: Cn1c(Cc2c(Cl)ccc(C(=O)N3CCC(C(=O)O)C(O)C3)c2Cl)cc2ccc(C(F)(F)F)cc21]

Step 1: ethyl 1-(2,4-dichloro-3-((1-methyl-6-(trifluoromethyl)-1H-indol-2-yl)methyl)benzoyl)-3-oxopiperidine-4-carboxylate

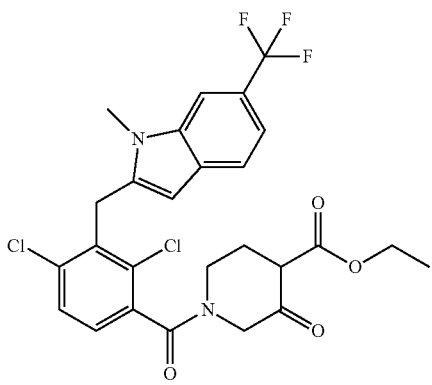 [SMILES: CCOC(=O)C1CCN(C(=O)c2ccc(Cl)c(Cc3cc4ccc(C(F)(F)F)cc4n3C)c2Cl)CC1=O]

Using a procedure similar to Example A, Step 6, ethyl 1-(2,4-dichloro-3-((1-methyl-6-(trifluoromethyl)-1H-indol-2-yl)methyl)benzoyl)-3-oxopiperidine-4-carboxylate (221 mg, 59%) was prepared from 2,4-dichloro-3-((1-methyl-6-(trifluoromethyl)-1H-indol-2-yl)methyl)benzoic acid (Example L, Step 5) (250 mg, 0.62 mmol) and ethyl 3-oxopiperidine-4-carboxylate hydrochloride (194 mg, 0.93 mmol). LC/MS (Method h) $R_t$=3.52 min.; MS m/z: 555 [M+H]$^+$. $^1$H NMR (DMSO-d$_6$, 300 MHz): 7.87 (s, 1H), 7.69 (m, 1H), 7.65 (m, 1H), 7.46 (m, 1H), 7.26 (m, 1H), 5.74 (s, 1H), 5.73 and 5.69 (s, 1H), 4.48 (s, 2H), 4.30 (m, 1H), 4.17 (m, 2H), 3.92 (m, 3H), 3.51 (m, 2H), 3.32 (m, 1H), 3.30 (m, 2H), 1.20 (m, 3H).

Step 2: ethyl 1-(2,4-dichloro-3-((1-methyl-6-(trifluoromethyl)-1H-indol-2-yl)methyl)benzoyl)-3-hydroxypiperidine-4-carboxylate

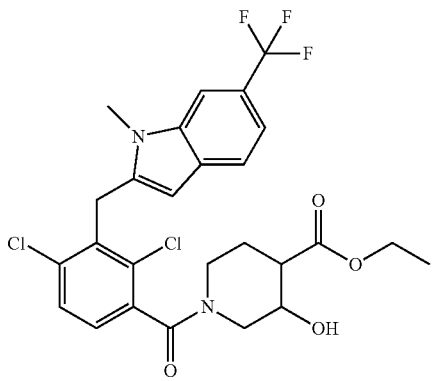 [SMILES: CCOC(=O)C1CCN(C(=O)c2ccc(Cl)c(Cc3cc4ccc(C(F)(F)F)cc4n3C)c2Cl)CC1O]

To a suspension of ethyl 1-(2,4-dichloro-3-((1-methyl-6-(trifluoromethyl)-1H-indol-2-yl)methyl)benzoyl)-3-oxopiperidine-4-carboxylate (218 mg, 0.393 mmol) in EtOHMeOH (4 mL) cooled at 0° C. was added NaBH$_4$ (7.43 mg, 0.196 mmol) and the mixture was stirred at 5° C. for 4 hours. NaBH$_4$ (7.43 mg, 0.196 mmol) was added again and the reaction was stirred for 5 hours at 5° C.

The reaction was hydrolyzed with NH$_4$Cl saturated aqueous solution and extracted with DCM. The organic layer was washed with brine, dried over magnesium sulfate, filtered and concentrated under reduced pressure. The residue was purified by column chromatography on silica gel (eluting with 0-70% EtOAc in cyclohexane) to give ethyl 1-(2,4-dichloro-3-((1-methyl-6-(trifluoromethyl)-1H-indol-2-yl)methyl)benzoyl)-3-hydroxypiperidine-4-carboxylate (150 mg, 69%). LC/MS (Method g) $R_t$=1.85 min.; MS m/z: 557 [M+H]$^+$. $^1$H NMR (DMSO-d$_6$, 400 MHz): δ 7.87 (s, 1H), 7.69 (m, 1H), 7.51 (m, 1H), 7.38 (m, 1H), 7.25 (m, 1H), 5.72 (m, 1H), 5.40 and 5.22 and 5.13 and 5.00 and 4.82 (m, 1H), 4.52-4.25 (m, 3H), 4.22-4.00 (m, 3H), 3.94 (s, 3H), 3.60 (m, 0.5H), 3.38-3.18 (m, 0.5H), 3.10-2.55 (m, 2.5H), 2.45 (m, 0.5H), 2.00-1.40 (m, 2H), 1.18 (m, 3H).

Step 3: 1-(2,4-dichloro-3-((1-methyl-6-(trifluoromethyl)-1H-indol-2-yl)methyl)benzoyl)-3-hydroxypiperidine-4-carboxylic acid

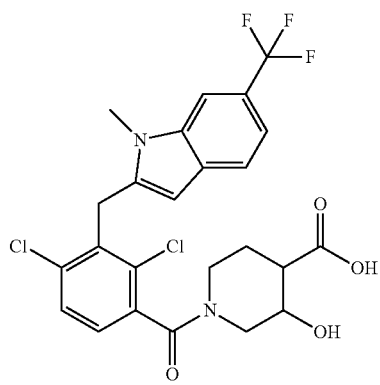 [SMILES: Cn1c(Cc2c(Cl)ccc(C(=O)N3CCC(C(=O)O)C(O)C3)c2Cl)cc2ccc(C(F)(F)F)cc21]

Using a procedure similar to Example A, Step 5, 1-(2,4-dichloro-3-((1-methyl-6-(trifluoromethyl)-1H-indol-2-yl)methyl)benzoyl)-3-hydroxypiperidine-4-carboxylic acid (73 mg, 66%) was prepared from ethyl 1-(2,4-dichloro-3-((1-methyl-6-(trifluoromethyl)-1H-indol-2-yl)methyl)benzoyl)-3-hydroxypiperidine-4-carboxylate (Example M, Step 2) (116 mg, 0.208 mmol). LC/MS (Method g) R$_t$=2.60 min.; MS m/z: 527 [M−H]⁻. ¹H NMR (DMSO-d$_6$, 400 MHz): δ 7.87 (s, 1H), 7.68 (m, 1H), 7.58 (m, 1H), 7.38 (m, 1H), 7.23 (m, 1H), 5.70 (m, 1H), 4.47 (m, 3H), 4.19 and 4.02 (m, 1H), 3.93 (s, 3H), 3.20 (m, 1H), 3.09 (m, 1H), 2.70 (m, 2H), 1.85 (m, 1H), 1.63 and 1.50 (m, 1H).

Example O: 3-(4-(2,4-dichloro-3-((1-methyl-6-(trifluoromethyl)-1H-indol-2-yl)methyl)benzoyl)piperazin-1-yl)cyclobutanecarboxylic acid

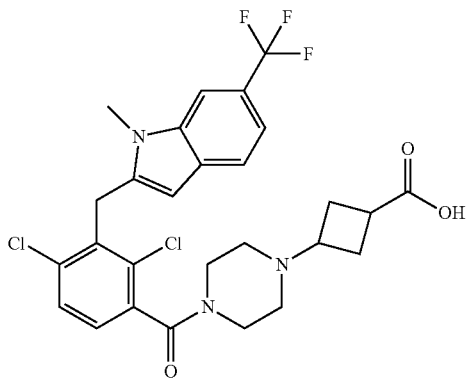 [SMILES: Cn1c(Cc2c(Cl)ccc(C(=O)N3CCN(C4CC(C(=O)O)C4)CC3)c2Cl)cc2ccc(C(F)(F)F)cc21]

Step 1: tert-butyl 4-(2,4-dichloro-3-((1-methyl-6-(trifluoromethyl)-1H-indol-2-yl)methyl)benzoyl)piperazine-1-carboxylate

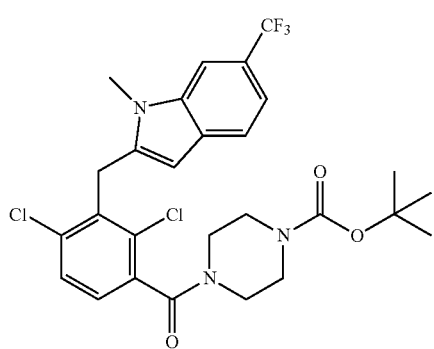 [SMILES: Cn1c(Cc2c(Cl)ccc(C(=O)N3CCN(C(=O)OC(C)(C)C)CC3)c2Cl)cc2ccc(C(F)(F)F)cc21]

Using a procedure similar to Example A, Step 6, tert-butyl 4-(2,4-dichloro-3-((1-methyl-6-(trifluoromethyl)-1H-indol-2-yl)methyl)benzoyl)piperazine-1-carboxylate (840 mg, 100%) was prepared from 2,4-dichloro-3-((1-methyl-6-(trifluoromethyl)-1H-indol-2-yl)methyl)benzoic acid (Example L, Step 5) (500 mg, 1.243 mmol) and 1-boc-piperazine (347 mg, 1.86 mmol). LC/MS (Method h) R$_t$=3.42 min.; MS m/z: 570 [M+H]⁺. ¹H NMR (DMSO-d$_6$, 300 MHz): δ 7.88 (s, 1H), 7.68 (d, J=9 Hz, 1H), 7.56 (d, J=9 Hz, 1H), 7.46 (d, J=9 Hz, 1H), 7.26 (J=9 Hz, 1H), 5.74 (s, 1H), 4.46 (s, 2H), 3.94 (s, 3H), 3.60 (m, 2H), 3.42 (m, 2H), 3.20 (m, 4H), 1.40 (s, 9H).

Step 2: (2,4-dichloro-3-((1-methyl-6-(trifluoromethyl)-1H-indol-2-yl)methyl)phenyl)(piperazin-1-yl)methanone

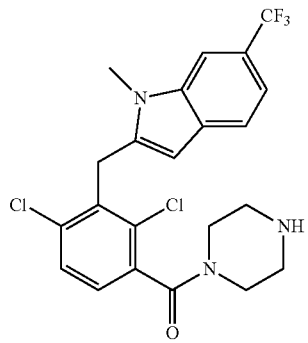 [SMILES: Cn1c(Cc2c(Cl)ccc(C(=O)N3CCNCC3)c2Cl)cc2ccc(C(F)(F)F)cc21]

To a solution of tert-butyl 4-(2,4-dichloro-3-((1-methyl-6-(trifluoromethyl)-1H-indol-2-yl)methyl)benzoyl)piperazine-1-carboxylate (840 mg, 1.473 mmol) in DCM (32 mL) and cooled at 0° C. was added TFA (8 mL, 104 mmol). The ice bath was removed and the reaction mixture was stirred at room temperature for 1.5 hours. The reaction mixture was concentrated under reduced pressure. The crude was diluted with DCM and it was washed with NaHCO$_3$ saturated aqueous solution. The organic layer was washed with water, dried over magnesium sulfate, filtered and concentrated under reduced pressure to give (2,4-dichloro-3-((1-methyl-6-(trifluoromethyl)-1H-indol-2-yl)methyl)phenyl)(piperazin-1-yl)methanone (850 mg, 100%) as an orange powder. LC/MS (Method h) R$_t$=2.07 min.; MS m/z: 470 [M+H]⁺. ¹H NMR (CDCl$_3$, 300 MHz): δ 7.51 (s, 1H), 7.40 (m, 2H), 7.19 (m, 2H), 5.73 (s, 1H), 4.36 (s, 2H), 3.81 (s, 3H), 3.72 (m, 2H), 3.16 (m, 2H), 2.89 (m, 2H), 2.73 (m, 2H).

Step 3: methyl 3-(4-(2,4-dichloro-3-((1-methyl-6-(trifluoromethyl)-1H-indol-2-yl)methyl)benzoyl)piperazin-1-yl)cyclobutanecarboxylate

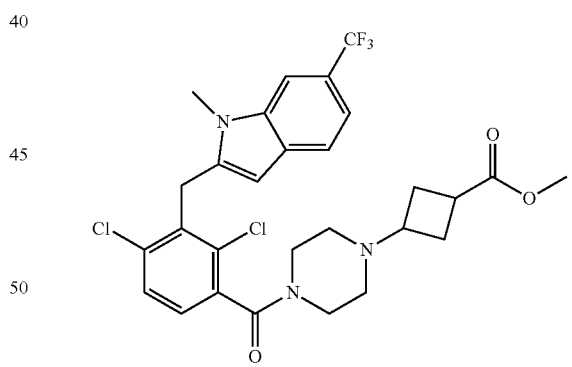

To a solution of (2,4-dichloro-3-((1-methyl-6-(trifluoromethyl)-1H-indol-2-yl)methyl)phenyl)(piperazin-1-yl)methanone (50 mg, 0.106 mmol) and methyl 3-oxocyclobutanecarboxylate (31.8 mg, 0.149 mmol) in 1,2-dichloroethane (1.4 mL) was added acetic acid (50 μl, 0.873 mmol) and the reaction mixture was stirred at room temperature for 45 minutes. Sodium triacetoxyborohydride (33.8 mg, 0.159 mmol) was then added and the stirring was continued for 2.5 hours. The reaction mixture was concentrated under reduced pressure to give methyl 3-(4-(2,4-dichloro-3-((1-methyl-6-(trifluoromethyl)-1H-indol-2-yl)methyl)benzoyl)piperazin-1-yl)cyclobutanecarboxylate (80 mg, 100%). LC/MS (Method h) R$_t$=2.46 min.; MS m/z: 582 [M+H]⁺.

¹H NMR (CDCl₃, 300 MHz): δ 7.51 (s, 1H), 7.41 (m, 2H), 7.18 (m, 2H), 5.72 (s, 1H), 4.36 (s, 2H), 3.81 (s, 3H), 3.75 (m, 2H), 3.60 (s, 3H), 3.20 (m, 2H), 2.68 (m, 2H), 2.36-2.05 (m, 8H).

Step 4: 3-(4-(2,4-dichloro-3-((1-methyl-6-(trifluoromethyl)-1H-indol-2-yl)methyl)benzoyl)piperazin-1-yl)cyclobutanecarboxylic acid

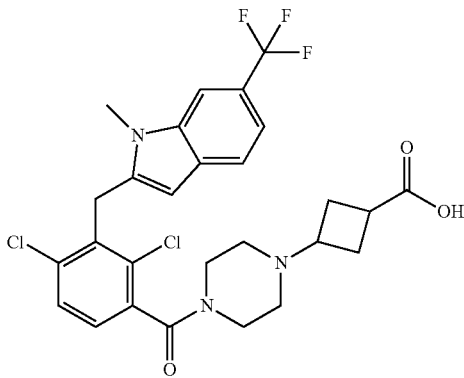 [SMILES: Cn1c(Cc2c(Cl)ccc(C(=O)N3CCN(C4CC(C(=O)O)C4)CC3)c2Cl)cc2ccc(C(F)(F)F)cc21]

To a solution of methyl 3-(4-(2,4-dichloro-3-((1-methyl-6-(trifluoromethyl)-1H-indol-2-yl)methyl)benzoyl)piperazin-1-yl)cyclobutanecarboxylate (200 mg, 0.343 mmol) in dioxane (3.75 mL) and water (1.5 mL) was added sodium hydroxide (54.9 mg, 1.374 mmol) The reaction mixture was stirred at room temperature for 1 hour and concentrated under reduced pressure. The residue was taken in water and acidified until pH=3-4 by addition of 1N HCl solution. After extraction with EtOAc, the organic layer was dried over magnesium sulfate, filtered and concentrated under reduced pressure. The residue was purified by column chromatography on silica gel (eluting with 0-10% MeOH in DCM) to give 3-(4-(2,4-dichloro-3-((1-methyl-6-(trifluoromethyl)-1H-indol-2-yl)methyl)benzoyl)piperazin-1-yl)cyclobutanecarboxylic acid (115 mg, 57%). LC/MS (Method g) R$_t$=1.30 min, 1.33 min.; MS m/z: 568 [M+H]⁺. ¹H NMR (DMSO-d₆, 400 MHz): δ 7.87 (s, 1H), 7.65 (d, J=8 Hz, 1H), 7.56 (d, J=8.4 Hz, 1H), 7.41 (d, J=8 Hz, 1H), 7.25 (d, J=8.4 Hz, 1H), 5.71 (s, 1H), 4.49 (s, 2H), 3.93 (s, 3H), 3.62 (m, 2H), 3.17 (m, 2H), 2.69 (m, 2H), 2.31 (m, 2H), 2.21 (m, 4H), 1.90 (m, 2H).

Example P: (2,4-dichloro-3-((1-methyl-5-(trifluoromethyl)-1H-indol-2-yl)methyl)phenyl)(morpholino)methanone

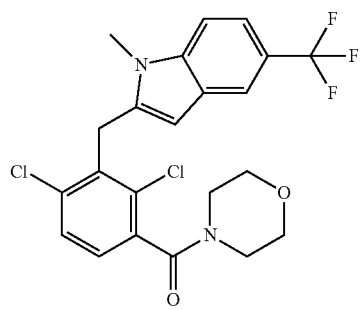 [SMILES: Cn1c(Cc2c(Cl)ccc(C(=O)N3CCOCC3)c2Cl)cc2cc(C(F)(F)F)ccc21]

Step 1: (2,4-dichloro-3-(hydroxy(1-(phenylsulfonyl)-5-(trifluoromethyl)-1H-indol-2-yl)methyl)phenyl)(morpholino)methanone

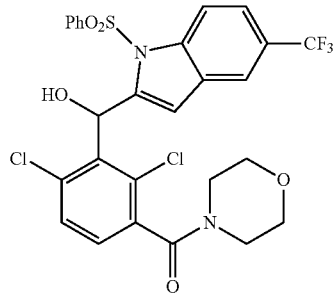

Using a procedure similar to Example A, Step 1, (2,4-dichloro-3-(hydroxy(1-(phenylsulfonyl)-5-(trifluoromethyl)-1H-indol-2-yl)methyl)phenyl)(morpholino)methanone (850 mg, 74%) was prepared from N-(2-iodo-4-(trifluoromethyl)phenyl)benzenesulfonamide (described in patent FR2890071) (800 mg, 1.873 mmol), and (2,4-dichloro-3-(1-hydroxyprop-2-yn-1-yl)phenyl)(morpholino)methanone (647 mg, 2.060 mmol) (Preparation #3). LC/MS (Method h) R$_t$=2.92 min.; MS m/z: 613 [M+H]⁺. ¹H NMR (DMSO-d₆, 300 MHz): δ 8.01 (m, 1H), 7.95 (m, 2H), 7.91 (m, 1H), 7.65 (m, 4H), 7.53 (m, 1H), 7.40 (m, 1H), 6.95 (m, 1H), 6.77 and 6.71 (s, 1H), 6.69 (m, 1H), 3.64 (m, 4H), 3.52 (m, 2H), 3.16 (m, 2H).

Step 2: (2,4-dichloro-3-((1-(phenylsulfonyl)-5-(trifluoromethyl)-1H-indol-2-yl)methyl)phenyl)(morpholino)methanone

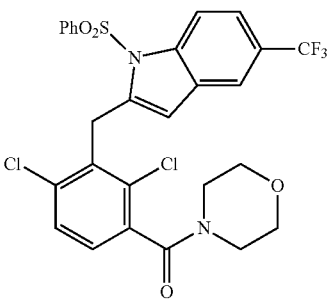

Using a procedure similar to Example A, Step 2, (2,4-dichloro-3-((1-(phenylsulfonyl)-5-(trifluoromethyl)-1H-indol-2-yl)methyl)phenyl)(morpholino)methanone (540 mg, 58%) was prepared from (2,4-dichloro-3-(hydroxy(1-(phenylsulfonyl)-5-(trifluoromethyl)-1H-indol-2-yl)methyl)phenyl)(morpholino)methanone (840 mg, 1.369 mmol). LC/MS (Method h) R$_t$=3.33 min.;

MS m/z: 597 [M+H]⁺. ¹H NMR (DMSO-d₆, 300 MHz): δ 8.33 (d, J=8.4 Hz, 1H), 7.98 (m, 2H), 7.90 (s, 1H), 7.77 (m, 1H), 7.67 (m, 4H), 7.49 (d, J=8.1 Hz, 1H), 6.03 (s, 1H), 4.59 (m, 2H), 3.63 (m, 4H), 3.51 (m, 2H), 3.17 (m, 2H).

Step 3: (2,4-dichloro-3-((5-(trifluoromethyl)-1H-indol-2-yl)methyl)phenyl)(morpholino)methanone

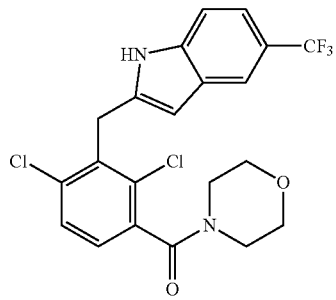 [SMILES: O=C(c1ccc(Cl)c(Cc2cc3cc(C(F)(F)F)ccc3[nH]2)c1Cl)N1CCOCC1]

Using a procedure similar to Example A, Step 3 (2,4-dichloro-3-((5-(trifluoromethyl)-1H-indol-2-yl)methyl)phenyl)(morpholino)methanone (230 mg, 69%) was prepared from (2,4-dichloro-3-((1-(phenylsulfonyl)-5-(trifluoromethyl)-1H-indol-2-yl)methyl)phenyl)(morpholino)methanone (500 mg, 0.837 mmol). LC/MS (Method h) $R_t$=2.86 min.; MS m/z: 457 [M+H]$^+$. $^1$H NMR (DMSO-d$_6$, 300 MHz): δ 11.55 (broad, 1H), 7.78 (s, 1H), 7.65 (d, J=8.1 Hz, 1H), 7.50 (d, J=8.7 Hz, 1H), 7.41 (d, J=8.7 Hz, 1H), 7.30 (d, J=8.1 Hz, 1H), 5.97 (s, 1H), 4.44 (s, 2H), 3.65 (m, 4H), 3.52 (m, 2H), 3.17 (m, 2H).

Step 4: (2,4-dichloro-3-((1-methyl-5-(trifluoromethyl)-1H-indol-2-yl)methyl)phenyl)(morpholino)methanone

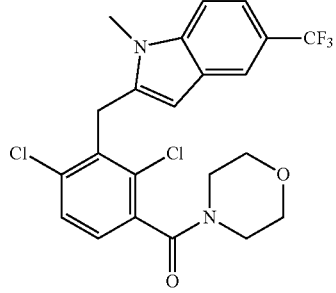 [SMILES: Cn1c(Cc2c(Cl)ccc(C(=O)N3CCOCC3)c2Cl)cc2cc(C(F)(F)F)ccc21]

To a solution of (2,4-dichloro-3-((5-(trifluoromethyl)-1H-indol-2-yl)methyl)phenyl)(morpholino)methanone (100 mg, 0.219 mmol) in ACNACN (2 mL) was added dimethyl sulfate (0.031 mL, 0.328 mmol) and cesium carbonate (143 mg, 0.437 mmol). The mixture was stirred at room temperature for 24 hours then diluted with water and extracted with DCM. The organic layer was washed with brine and dried over magnesium sulfate. The residue was purified by preparative LC/MS to give (2,4-dichloro-3-((1-methyl-5-(trifluoromethyl)-1H-indol-2-yl)methyl)phenyl)(morpholino)methanone (50 mg, 45%). LC/MS (Method g) $R_t$=1.78 min.; MS m/z: 471 [M+H]$^+$. $^1$H NMR (DMSO-d$_6$, 400 MHz): δ 7.78 (s, 1H), 7.66 (m, 2H), 7.45 (d, J=8.4 Hz, 1H), 7.38 (d, J=8.8 Hz, 1H), 5.75 (s, 1H), 4.44 (s, 2H), 3.91 (s, 3H), 3.66 (m, 4H), 3.55 (m, 2H), 3.17 (m, 2H).

Example Q: (2,4-dichloro-3-((1,4-dimethyl-6-(trifluoromethyl)indolin-2-yl)methyl)phenyl)(morpholino)methanone

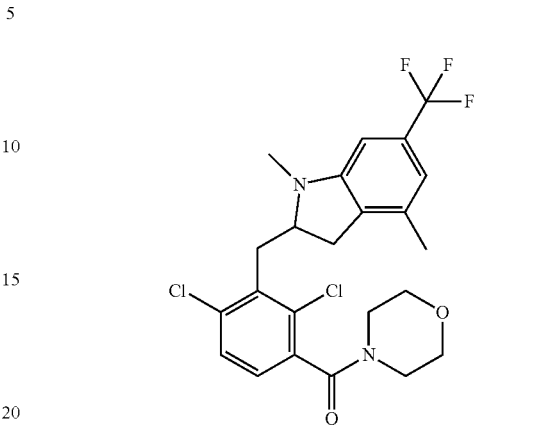

Step 1: (2,4-dichloro-3-((4-methyl-6-(trifluoromethyl)indolin-2-yl)methyl)phenyl)(morpholino)methanone

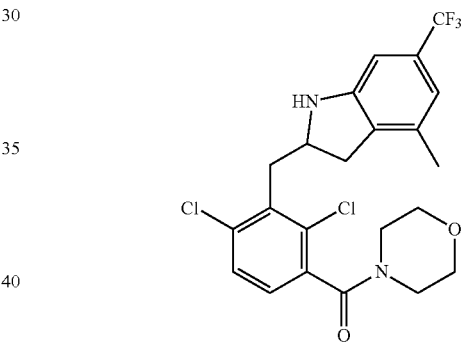

To a solution of (2,4-dichloro-3-((4-methyl-6-(trifluoromethyl)-1H-indol-2-yl)methyl)phenyl)(morpholino)methanone (Example C) (256 mg, 0.543 mmol) in TFA (4 mL) was added sodium cyanoborohydride (170 mg, 2.71 mmol) per fraction. The reaction mixture was stirred at room temperature during 2 hours and a 1N NaOH aqueous solution was added (pH 7). The aqueous layer was extracted with DCM. The organic layer was dried over magnesium sulfate, filtered and concentrated under reduced pressure. The residue was purified by preparative LC/MS to give (2,4-dichloro-3-((4-methyl-6-(trifluoromethyl)indolin-2-yl)methyl)phenyl)(morpholino)methanone (82 mg, 43%) as a yellow solid. LC/MS (Method h) $R_t$=3.08 min.; MS m/z: 473 [M+H]$^+$. $^1$H NMR (DMSO-d$_6$, 300 MHz): δ 7.58 (d, J=9 Hz, 1H), 7.32 (J=9 Hz, 1H), 6.67 (s, 1H), 6.49 (dm, 1H), 6.14 (m, 1H), 4.22 (m, 1H), 3.65 (m, 4H), 3.54 (m, 2H), 3.16 (m, 4H), 2.90 (m, 1H), 2.72 (m, 1H), 2.17 (s, 3H).

Step 2: (2,4-dichloro-3-((1,4-dimethyl-6-(trifluoromethyl)indolin-2-yl)methyl)phenyl)(morpholino)methanone

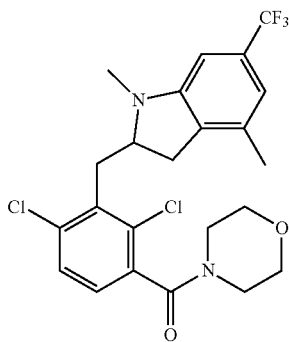 [SMILES: Cc1cc(C(F)(F)F)cc2c1CC(Cc1c(Cl)ccc(C(=O)N3CCOCC3)c1Cl)N2C]

Using a procedure similar to Example A, Step 4, (2,4-dichloro-3-((1,4-dimethyl-6-(trifluoromethyl)indolin-2-yl)methyl)phenyl)(morpholino)methanone (5 mg, 20%) was prepared from (2,4-dichloro-3-((4-methyl-6-(trifluoromethyl)indolin-2-yl)methyl)phenyl)(morpholino)methanone (24 mg, 0.051 mmol). LC/MS (Method g) $R_f$=1.97 min.; MS m/z: 487 [M+H]$^+$. $^1$H NMR (DMSO-d$_6$, 400 MHz): δ 7.61 (d, J=8.4 Hz, 1H), 7.35 (d, J=8.4 Hz, 1H), 6.76 (s, 1H), 6.57 (s, 1H), 3.90 (m, 1H), 3.69 (m, 4H), 3.54 (m, 2H), 3.40 (m, 1H), 3.13 (m, 3H), 2.93 (m, 1H), 2.82 (m, 3H), 2.72 (m, 1H), 2.14 (s, 3H).

Example R: 2-(1-(2,4-dichloro-3-((4-chloro-6-cyano-1-methyl-1H-indol-2-yl)methyl)benzoyl)piperidin-4-yl)acetic acid

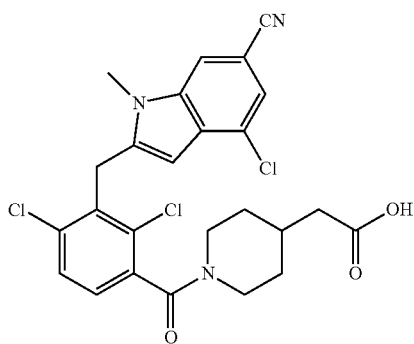

Step 1: methyl 2-(1-(2,4-dichloro-3-((4-chloro-6-cyano-1-methyl-1H-indol-2-yl)methyl)benzoyl)piperidin-4-yl)acetate

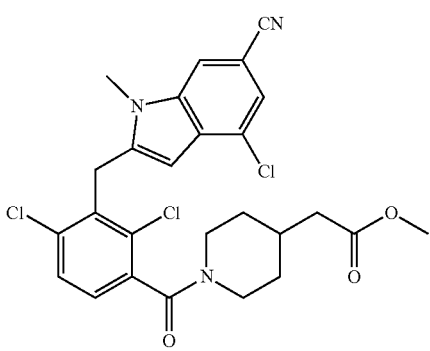 [SMILES: COC(=O)CC1CCN(C(=O)c2ccc(Cl)c(Cc3cc4c(Cl)cc(C#N)cc4n3C)c2Cl)CC1]

Using a procedure similar to Example A1, methyl 2-(1-(2,4-dichloro-3-((4-chloro-6-cyano-1-methyl-1H-indol-2-yl)methyl)benzoyl)piperidin-4-yl)acetate (101 mg, 83%) was prepared from 2,4-dichloro-3-((4-chloro-6-cyano-1-methyl-1H-indol-2-yl)methyl)benzoic acid (Example DQ, Step 6) (90 mg, 0.23 mmol) and methyl (4-piperidyl)acetate hydrochloride (66.4 mg, 0.34 mmol).

LC/MS (Method i) $R_f$=2.43 min.; MS m/z: 532 [M+H]$^+$
$^1$H NMR (DMSO-d$_6$, 300 MHz): δ 8.17 (m, 1H), 7.68 and 7.67 (d, J=8.4 Hz, 1H), 7.51 and 7.50 (s, 1H), 7.47 and 7.40 (d, J=8.4 Hz, 1H), 5.68 and 5.65 (m, 1H), 4.47 (m, 3H), 3.96 and 3.95 (s, 3H), 3.59 and 3.56 (s, 3H), 3.25 (m, 1H), 3.05 (m, 1H), 2.80 (m, 1H), 2.25 (m, 2H), 1.95 (m, 1H), 1.75 (m, 1H), 1.59 (m, 1H), 1.17 (m, 2H).

Step 2: 2-(1-(2,4-dichloro-3-((4-chloro-6-cyano-1-methyl-1H-indol-2-yl)methyl)benzoyl)piperidin-4-yl)acetic acid

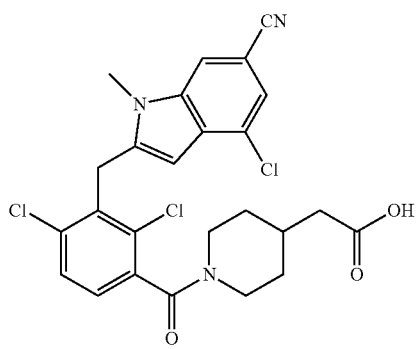

Using a procedure similar to Example A, Step 5, 2-(1-(2,4-dichloro-3-((4-chloro-6-cyano-1-methyl-1H-indol-2-yl)methyl)benzoyl)piperidin-4-yl)acetic acid (93 mg, 95%) was prepared from methyl 2-(1-(2,4-dichloro-3-((4-chloro-6-cyano-1-methyl-1H-indol-2-yl)methyl)benzoyl)piperidin-4-yl)acetate (101 mg, 0.19 mmol). LC/MS (Method g) $R_f$=1.63 min.; MS m/z: 518 [M+H]$^+$
$^1$H NMR (DMSO-d$_6$, 400 MHz): δ 12.09 (m, 1H), 8.17 (s, 1H), 7.68 and 7.67 (d, J=8.4 Hz, 1H), 7.50 (m, 1H), 7.46 and 7.39 (d, J=8.4 Hz, 1H), 5.68 and 5.66 (m, 1H), 4.49 (m, 3H), 3.96 and 3.95 (s, 3H), 3.27 (m, 1H), 3.05 (m, 1H), 2.80 (m, 1H), 2.15 (m, 2H), 193 (m, 1H), 1.77 (m, 1H), 1.61 (m, 1H), 1.15 (m, 2H).

Example S: 3-(4-(2,4-dichloro-3-((1,4-dimethyl-6-(trifluoromethyl)-1H-indol-2-yl)methyl)benzoyl)piperazin-1-yl)cyclobutanecarboxylic acid

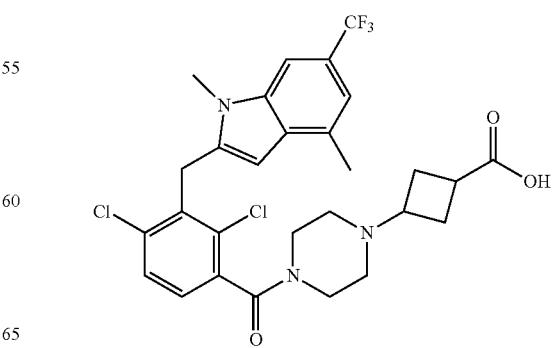

Step 1: tert-butyl 4-(2,4-dichloro-3-((1,4-dimethyl-6-(trifluoromethyl)-1H-indol-2-yl)methyl)benzoyl)piperazine-1-carboxylate

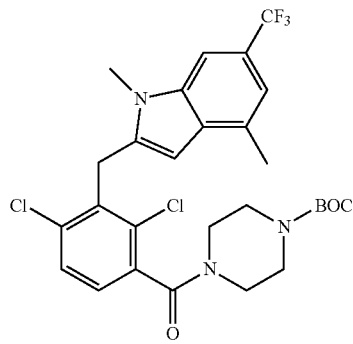 [SMILES: Cc1cc(C(F)(F)F)cc2c1cc(Cc1c(Cl)ccc(C(=O)N3CCN(C(=O)OC(C)(C)C)CC3)c1Cl)n2C]

Using a procedure similar to Example A, Step 6, tert-butyl 4-(2,4-dichloro-3-((1,4-dimethyl-6-(trifluoromethyl)-1H-indol-2-yl)methyl)benzoyl)piperazine-1-carboxylate (700 mg, 100%) was prepared from 2,4-dichloro-3-((1,4-dimethyl-6-(trifluoromethyl)-1H-indol-2-yl)methyl)benzoic acid (Example A, Step 5) (500 mg, 1.201 mmol) and 1-boc-piperazine (336 mg, 1.8 mmol). LC/MS (Method h) $R_t$=3.49 min.; MS m/z: 584 [M+H]$^+$ $^1$H NMR (CDCl$_3$, 300 MHz): δ 7.49 (d, J=9 Hz, 1H), 7.43 (s, 1H), 7.26 (d, J=9 Hz, 1H), 7.09 (s, 1H), 5.76 (s, 1H), 4.44 (m, 2H), 3.87 (s, 3H), 3.75 (m, 2H), 3.53 (m, 2H), 3.39 (m, 2H), 3.22 (m, 2H), 2.43 (s, 3H), 1.46 (m, 9H).

Step 2: (2,4-dichloro-3-((1,4-dimethyl-6-(trifluoromethyl)-1H-indol-2-yl)methyl)phenyl)(piperazin-1-yl)methanone

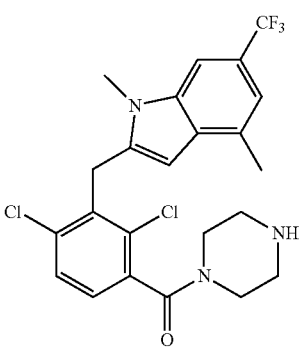 [SMILES: Cc1cc(C(F)(F)F)cc2c1cc(Cc1c(Cl)ccc(C(=O)N3CCNCC3)c1Cl)n2C]

Using a procedure similar to Example O, Step 2, (2,4-dichloro-3-((1,4-dimethyl-6-(trifluoromethyl)-1H-indol-2-yl)methyl)phenyl)(piperazin-1-yl)methanone (535 mg, 92%) was prepared from tert-butyl 4-(2,4-dichloro-3-((1,4-dimethyl-6-(trifluoromethyl)-1H-indol-2-yl)methyl)benzoyl)piperazine-1-carboxylate (700 mg, 1.198 mmol). LC/MS (Method h) $R_t$=2.73 min.; MS m/z: 483 [M+H]$^+$ $^1$H NMR (CDCl$_3$, 300 MHz): δ 7.49 (d, J=9 Hz, 1H), 7.43 (s, 1H), 7.26 (d, J=9 Hz, 1H), 7.08 (s, 1H), 5.78 (s, 1H), 4.43 (m, 2H), 3.87 (s, 3H), 3.80 (m, 2H), 3.23 (m, 2H), 2.95 (m, 2H), 2.88 (m, 1H), 2.80 (m, 1H), 2.42 (s, 3H).

Step 3: tert-butyl 3-(4-(2,4-dichloro-3-((1,4-dimethyl-6-(trifluoromethyl)-1H-indol-2-yl)methyl)benzoyl)piperazin-1-yl)cyclobutanecarboxylate

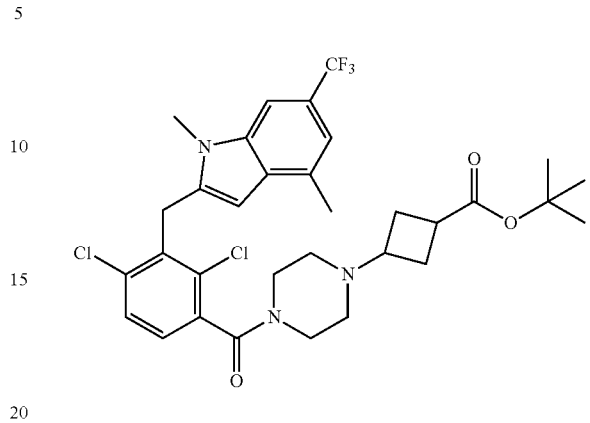

Using a procedure similar to Example O, Step 3, tert-butyl 3-(4-(2,4-dichloro-3-((1,4-dimethyl-6-(trifluoromethyl)-1H-indol-2-yl)methyl)benzoyl)piperazin-1-yl)cyclobutanecarboxylate (105 mg, 80%) was prepared from (2,4-dichloro-3-((1,4-dimethyl-6-(trifluoromethyl)-1H-indol-2-yl)methyl)phenyl)(piperazin-1-yl)methanone (100 mg, 0.206 mmol) and tert-butyl 3-oxocyclobutanecarboxylate (52.7 mg, 0.310 mmol). LC/MS (Method h) $R_t$=3.39 min.; MS m/z: 638 [M+H]$^+$ $^1$H NMR (DMSO-d$_6$, 300 MHz): δ 7.70 (s, 1H), 7.67 (d, J=9 Hz, 1H), 7.42 (d, J=9 Hz, 1H), 7.06 (s, 1H), 5.67 (s, 1H), 4.46 (m, 2H), 3.92 (s, 3H), 3.60 (m, 2H), 3.15 (m, 2H), 2.70 (m, 2H), 2.28 (s, 3H), 2.20 (m, 6H), 2.17 (m, 2H), 1.39 (s, 9H).

Step 4: 3-(4-(2,4-dichloro-3-((1,4-dimethyl-6-(trifluoromethyl)-1H-indol-2-yl)methyl)benzoyl)piperazin-1-yl)cyclobutanecarboxylic acid

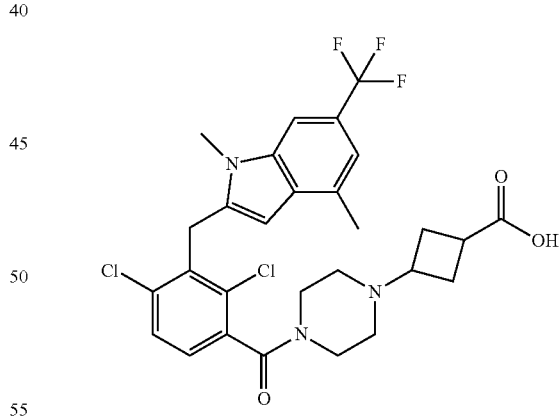

To a solution of tert-butyl 3-(4-(2,4-dichloro-3-((1,4-dimethyl-6-(trifluoromethyl)-1H-indol-2-yl)methyl)benzoyl)piperazin-1-yl)cyclobutanecarboxylate (105 mg, 0.164 mmol) in DCM (3.5 mL) and cooled to 0° C. was added TFA (0.8 mL, 10.38 mmol). The ice bath was removed and the reaction mixture was stirred at room temperature for 3 hours. The reaction mixture was concentrated under reduced pressure. The crude was diluted with DCM and was washed with NaHCO$_3$ saturated aqueous solution. The organic layer was washed with water, dried over magnesium sulfate, filtered and concentrated under reduced pressure. The crude was taken in water and the pH was adjusted to 7. The aqueous layer was extracted with DCM. The organic layer was dried over magnesium sulfate, filtered and concentrated under reduced pressure to give 3-(4-(2,4-dichloro-3-((1,4-dimethyl-6-(trifluoromethyl)-1H-indol-2-yl)methyl)benzoyl)piperazin-1-yl)cyclobutanecarboxylic acid (45 mg, 45.8%). LC/MS (Method g) R$_t$=1.38 min.; MS m/z: 582 [M+H]$^+$ $^1$H NMR (Pyridine-d$_5$, 500 MHz): δ 7.66 (s, 1H), 7.53 (d, J=8 Hz, 1H), 7.44 (d, J=8 Hz, 1H), 7.18 (s, 1H), 6.10 (s, 1H), 4.48 (m, 2H), 3.90 (m, 2H), 3.76 (s, 3H), 3.32 (m, 2H), 2.98 (m, 1H), 2.56 (m, 1H), 2.32 (m, 8H), 2.26 (s, 3H).

Example T: 2-(4-(2,4-dichloro-3-((1,4-dimethyl-6-(trifluoromethyl)-1H-indol-2-yl)methyl)benzoyl)piperazin-1-yl)-2-methylpropanoic acid

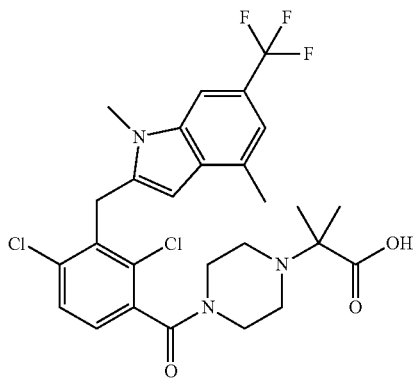 [SMILES: Cc1cc(C(F)(F)F)cc2c1cc(Cc1c(Cl)ccc(C(=O)N3CCN(C(C)(C)C(=O)O)CC3)c1Cl)n2C]

Step 1: ethyl 2-(4-(2,4-dichloro-3-((1,4-dimethyl-6-(trifluoromethyl)-1H-indol-2-yl)methyl)benzoyl)piperazin-1-yl)-2-methylpropanoate

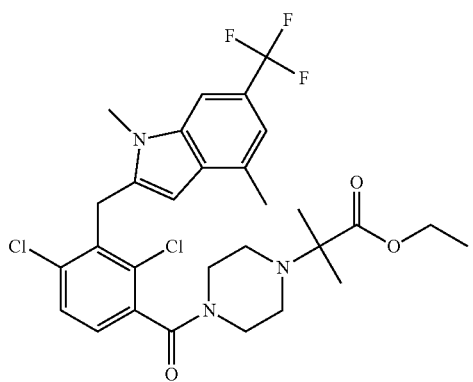 [SMILES: CCOC(=O)C(C)(C)N1CCN(C(=O)c2ccc(Cl)c(Cc3cc4c(C)cc(C(F)(F)F)cc4n3C)c2Cl)CC1]

To a solution of (2,4-dichloro-3-((1,4-dimethyl-6-(trifluoromethyl)-1H-indol-2-yl)methyl)phenyl)(piperazin-1-yl)methanone (Example S, Step 2) (50 mg, 0.103 mmol) and ethyl 2-bromoisobutyrate (60.4 mg, 0.310 mmol) in DMF (0.3 mL) was added potassium carbonate (42.8 mg, 0.310 mmol) and the reaction mixture was stirred at 60° C. for the night. Potassium carbonate (3 eq) and ethyl 2-bromoisobutyrate (3 eq) were added and the stirring was continued for 24 hours. The reaction mixture was diluted with water and EtOAc. The aqueous layer was extracted with EtOAc. The organic layers were combined, dried over magnesium sulfate, filtered and concentrated under reduced pressure. The residue was purified by column chromatography on silica gel (eluting with 20-80% EtOAc in cyclohexane) to give ethyl 2-(4-(2,4-dichloro-3-((1,4-dimethyl-6-(trifluoromethyl)-1H-indol-2-yl)methyl)benzoyl)piperazin-1-yl)-2-methylpropanoate (30 mg, 49%).

LC/MS (Method h) R$_t$=3.35 min.; MS m/z: 598 [M+H]$^+$

Step 2: 2-(4-(2,4-dichloro-3-((1,4-dimethyl-6-(trifluoromethyl)-1H-indol-2-yl)methyl)benzoyl)piperazin-1-yl)-2-methylpropanoic acid

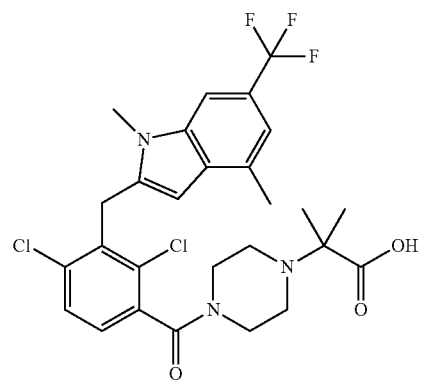 [SMILES: Cc1cc(C(F)(F)F)cc2c1cc(Cc1c(Cl)ccc(C(=O)N3CCN(C(C)(C)C(=O)O)CC3)c1Cl)n2C]

Using a procedure similar to Example O, Step 4, 2-(4-(2,4-dichloro-3-((1,4-dimethyl-6-(trifluoromethyl)-1H-indol-2-yl)methyl)benzoyl)piperazin-1-yl)-2-methylpropanoic acid (60 mg, 96%) was prepared from ethyl 2-(4-(2,4-dichloro-3-((1,4-dimethyl-6-(trifluoromethyl)-1H-indol-2-yl)methyl)benzoyl)piperazin-1-yl)-2-methylpropanoate (60 mg, 0.100 mmol). LC/MS (Method g) R$_t$=1.59 min.; MS m/z: 570 [M+H]$^+$ $^1$H NMR (DMSO-d$_6$, 400 MHz): δ 7.70 (s, 1H), 7.66 (d, J=8 Hz, 1H), 7.47 (d, J=8 Hz, 1H), 7.06 (s, 1H), 5.68 (s, 1H), 4.49 (m, 2H), 3.90 (s, 3H), 3.65 (m, 2H), 3.18 (m, 2H), 2.62 (m, 2H), 2.58 (m, 2H), 2.36 (s, 3H), 1.19 (s, 6H).

Example U: 2-(4-(2,4-dichloro-3-((1,4-dimethyl-6-(trifluoromethyl)-1H-indol-2-yl)methyl)benzoyl)piperazin-1-yl)propanoic acid

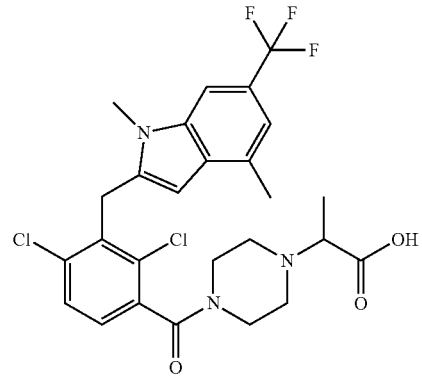 [SMILES: Cc1cc(C(F)(F)F)cc2c1cc(Cc1c(Cl)ccc(C(=O)N3CCN(C(C)C(=O)O)CC3)c1Cl)n2C]

Step 1: ethyl 2-(4-(2,4-dichloro-3-((1,4-dimethyl-6-(trifluoromethyl)-1H-indol-2-yl)methyl)benzoyl)piperazin-1-yl)propanoate

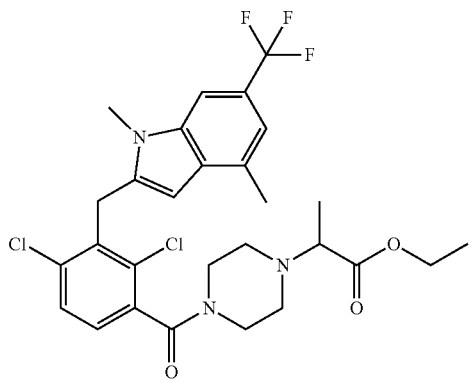 [SMILES: CCOC(=O)C(C)N1CCN(C(=O)c2ccc(Cl)c(Cc3cc4c(C)cc(C(F)(F)F)cc4n3C)c2Cl)CC1]

Using a procedure similar to Example T, Step 1, ethyl 2-(4-(2,4-dichloro-3-((1,4-dimethyl-6-(trifluoromethyl)-1H-indol-2-yl)methyl)benzoyl)piperazin-1-yl)propanoate (43 mg, 66%) was prepared from (2,4-dichloro-3-((1,4-dimethyl-6-(trifluoromethyl)-1H-indol-2-yl)methyl)phenyl)(piperazin-1-yl)methanone (Example S, Step 2) (50 mg, 0.103 mmol) and ethyl 2-bromopropionate (28 mg, 0.155 mmol). LC/MS (Method k) $R_t$=3.05 min.; MS m/z: 584 [M+H]$^+$ $^1$H NMR (CDCl$_3$, 300 MHz): δ 7.48 (d, J=9 Hz, 1H), 7.43 (s, 1H), 7.25 (d, J=9 Hz, 1H), 7.08 (s, 1H), 5.78 (s, 1H), 4.42 (m, 2H), 4.14 (m, 2H), 3.86 (s, 3H), 3.84 (m, 2H), 3.28 (m, 3H), 2.71 (m, 4H), 2.43 (s, 3H), 1.28 (m, 6H).

Step 2: 2-(4-(2,4-dichloro-3-((1,4-dimethyl-6-(trifluoromethyl)-1H-indol-2-yl)methyl)benzoyl)piperazin-1-yl)propanoic acid

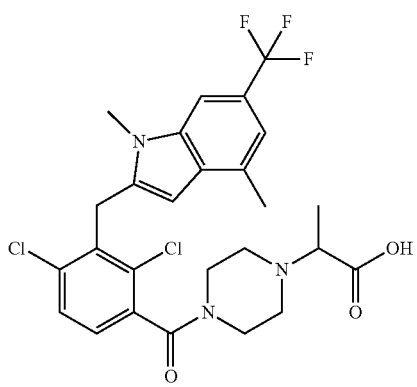

Using a procedure similar to Example O, Step 4, 2-(4-(2,4-dichloro-3-((1,4-dimethyl-6-(trifluoromethyl)-1H-indol-2-yl)methyl)benzoyl)piperazin-1-yl)propanoic acid (45 mg, 53%) was prepared from ethyl 2-(4-(2,4-dichloro-3-((1,4-dimethyl-6-(trifluoromethyl)-1H-indol-2-yl)methyl)benzoyl)piperazin-1-yl)propanoe (85 mg, 0.145 mmol). LC/MS (Method g) $R_t$=1.52 min.;

MS m/z: 556 [M+H]$^+$ $^1$H NMR (DMSO-d$_6$, 300 MHz): δ 7.70 (s, 1H), 7.66 (d, J=8 Hz, 1H), 7.40 (d, J=8 Hz, 1H), 7.06 (s, 1H), 5.67 (s, 1H), 4.46 (m, 2H), 3.92 (s, 3H), 3.63 (m, 3H), 3.16 (m, 4H), 2.57 (m, 2H), 2.36 (s, 3H), 1.73 (m, 3H).

Example V: 1-(2,4-dichloro-3-((1,5-dimethyl-6-(trifluoromethyl)-1H-indol-2-yl)methyl)benzoyl)piperidine-4-carboxylic acid

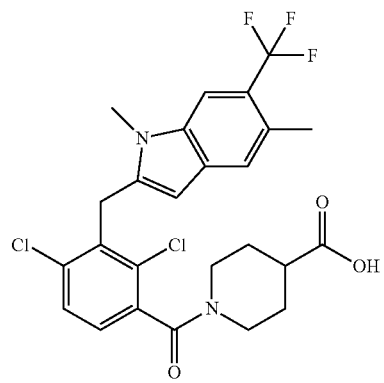 [SMILES: Cc1cc2cc(Cc3c(Cl)ccc(C(=O)N4CCC(C(=O)O)CC4)c3Cl)n(C)c2cc1C(F)(F)F]

Step 1: methyl 2,4-dichloro-3-(hydroxy(5-methyl-1-(phenylsulfonyl)-6-(trifluoromethyl)-1H-indol-2-yl)methyl)benzoate

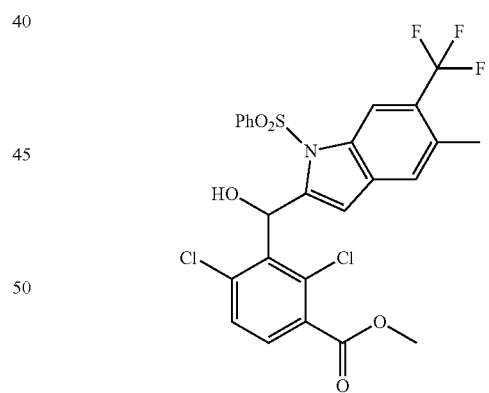

Using a procedure similar to Example A, Step 1, methyl 2,4-dichloro-3-(hydroxy(5-methyl-1-(phenylsulfonyl)-6-(trifluoromethyl)-1H-indol-2-yl)methyl)benzoate (1 g, 96%) was prepared from N-(2-iodo-4-methyl-5-(trifluoromethyl)phenyl)benzenesulfonamide (Preparation #17) (800 mg, 1.813 mmol) and methyl 2,4-dichloro-3-(1-hydroxyprop-2-yn-1-yl)benzoate (Preparation #1) (564 mg, 2.176 mmol). LC/MS (Method h) $R_t$=3.36 min.; MS m/z: 630 [M−H]$^-$+ CH$_3$COOH $^1$H NMR (DMSO-d$_6$, 300 MHz): δ 8.29 (s, 1H), 7.79 (m, 2H), 7.68-7.53 (m, 6H), 6.97 (d, J=3 Hz, 1H), 6.77 (s, 1H), 6.72 (d, J=8 Hz, 1H), 3.86 (s, 3H), 2.46 (s, 3H).

Step 2: methyl 2,4-dichloro-3-((5-methyl-1-(phenyl-sulfonyl)-6-(trifluoromethyl)-1H-indol-2-yl)methyl)benzoate

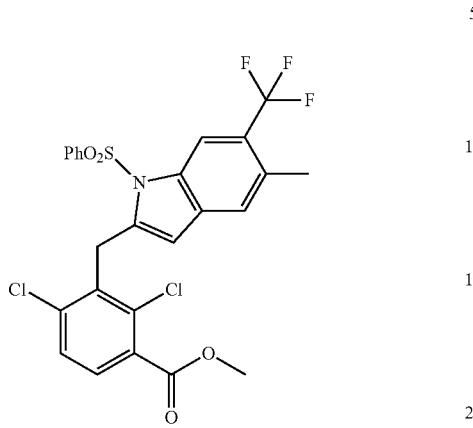

Using a procedure similar to Example A, Step 2, methyl 2,4-dichloro-3-((5-methyl-1-(phenylsulfonyl)-6-(trifluoromethyl)-1H-indol-2-yl)methyl)benzoate (841 mg, 87%) was prepared from methyl 2,4-dichloro-3-(hydroxy(5-methyl-1-(phenylsulfonyl)-6-(trifluoromethyl)-1H-indol-2-yl)methyl) (1 g, 1.747 mmol). LC/MS (Method h) $R_f$=3.80 min.; MS m/z: 556 [M+H]$^+$ $^1$H NMR (DMSO-d$_6$, 300 MHz): δ 8.38 (s, 1H), 7.90 (d, J=8 Hz, 1H), 7.79 (m, 3H), 7.69 (m, 3H), 7.50 (s, 1H), 5.88 (s, 1H), 4.58 (s, 2H), 3.87 (s, 3H), 2.44 (s, 3H).

Step 3: methyl 2,4-dichloro-3-((5-methyl-6-(trifluoromethyl)-1H-indol-2-yl)methyl)benzoate

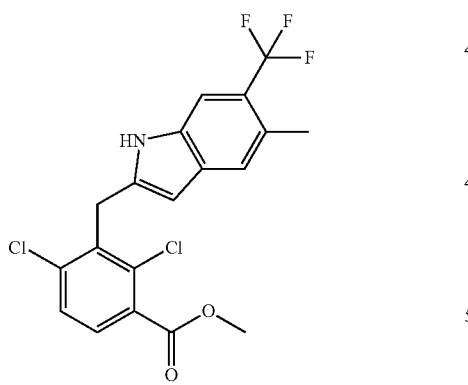

Using a procedure similar to Example A, Step 3, methyl 2,4-dichloro-3-((5-methyl-6-(trifluoromethyl)-1H-indol-2-yl)methyl)benzoate (420 mg, 67%) was prepared from methyl 2,4-dichloro-3-((5-methyl-1-(phenylsulfonyl)-6-(trifluoromethyl)-1H-indol-2-yl)methyl)benzoate (841 mg, 1.512 mmol). LC/MS (Method h) $R_f$=3.43 min.; MS m/z: 416 [M+H]$^+$ $^1$H NMR (DMSO-d$_6$, 300 MHz): δ 11.35 (s, 1H), 7.75 (d, J=9 Hz, 1H), 7.68 (d, J=9 Hz, 1H), 7.62 (s, 1H), 7.37 (s, 1H), 5.87 (s, 1H), 4.47 (s, 2H), 3.87 (s, 3H), 2.42 (s, 3H).

Step 4: methyl 2,4-dichloro-3-((1,5-dimethyl-6-(trifluoromethyl)-1H-indol-2-yl)methyl)benzoate

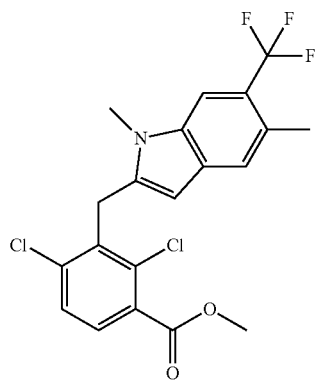 [SMILES: COC(=O)c1ccc(Cl)c(Cc2cc3cc(C)c(C(F)(F)F)cc3n2C)c1Cl]

Using a procedure similar to Example P, Step 4, methyl 2,4-dichloro-3-((1,5-dimethyl-6-(trifluoromethyl)-1H-indol-2-yl)methyl)benzoate (530 mg, 84%) was prepared from methyl 2,4-dichloro-3-((5-methyl-6-(trifluoromethyl)-1H-indol-2-yl)methyl)benzoate (592 mg, 1.422 mmol).

LC/MS (Method h) $R_f$=3.57 min.; MS m/z: 430 [M+H]$^+$ $^1$H NMR (DMSO-d$_6$, 300 MHz): δ 7.79 (s, 1H), 7.78 (d, J=8 Hz, 1H), 7.71 (d, J=8 Hz, 1H), 7.36 (s, 1H), 5.56 (s, 1H), 4.47 (s, 2H), 3.90 (s, 3H), 3.86 (s, 3H), 2.42 (s, 3H).

Step 5: 2,4-dichloro-3-((1,5-dimethyl-6-(trifluoromethyl)-1H-indol-2-yl)methyl)benzoic acid

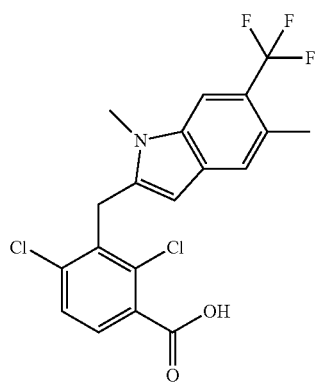 [SMILES: Cc1cc2cc(Cc3c(Cl)ccc(C(=O)O)c3Cl)n(C)c2cc1C(F)(F)F]

Using a procedure similar to Example A, Step 5, 2,4-dichloro-3-((1,5-dimethyl-6-(trifluoromethyl)-1H-indol-2-yl)methyl)benzoic acid (424 mg, 100%) was prepared from methyl 2,4-dichloro-3-((1,5-dimethyl-6-(trifluoromethyl)-1H-indol-2-yl)methyl)benzoate (438 mg, 1.018 mmol). LC/MS (Method h) $R_f$=3.13 min.; MS m/z: 416 [M+H]$^+$ $^1$H NMR (DMSO-d$_6$, 300 MHz): δ 13.67 (broad, 1H), 7.79 (s, 1H), 7.75 (d, J=9 Hz, 1H), 7.67 (d, J=9 Hz, 1H), 7.36 (s, 1H), 5.57 (s, 1H), 4.47 (d, 2H), 3.90 (s, 3H), 2.43 (s, 3H).

Step 6: ethyl 1-(2,4-dichloro-3-((1,5-dimethyl-6-(trifluoromethyl)-1H-indol-2-yl)methyl)benzoyl)piperidine-4-carboxylate

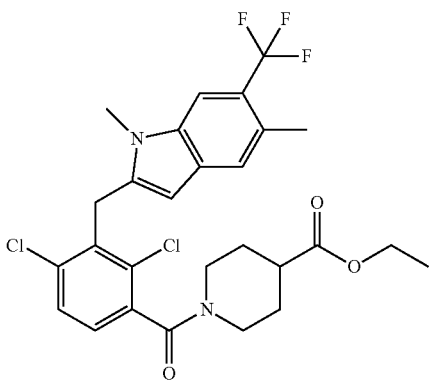 [SMILES: CCOC(=O)C1CCN(C(=O)c2ccc(Cl)c(Cc3cc4cc(C)c(C(F)(F)F)cc4n3C)c2Cl)CC1]

Using a procedure similar to Example A1, ethyl 1-(2,4-dichloro-3-((1,5-dimethyl-6-(trifluoromethyl)-1H-indol-2-yl)methyl)benzoyl)piperidine-4-carboxylate (133 mg, 100%) was prepared from 2,4-dichloro-3-((1,5-dimethyl-6-(trifluoromethyl)-1H-indol-2-yl)methyl)benzoic acid (100 mg, 0.240 mmol) and ethyl piperidine-4-carboxylate (37.8 mg, 0.24 mmol). LC/MS (Method h) $R_t$=3.43 min.;

MS m/z: 555 [M+H]$^+$. $^1$H NMR (DMSO-d$_6$, 300 MHz): δ 7.79 (s, 1H), 7.65 (d, J=6 Hz, 1H), 7.46 (d, J=6 Hz, 0.5H), 7.38 (m, 1.5H), 5.60 and 5.58 (s, 1H), 4.43 (m, 2H), 4.37 (m, 1H), 4.07 (m, 2H), 3.89 (s, 3H), 3.27 (m, 1H), 3.13 (m, 2H), 2.65 (m, 1H), 2.43 (s, 3H), 1.93 (m, 1H), 1.81 (m, 1H), 1.51 (m, 2H), 1.18 (m, 3H).

Step 7: 1-(2,4-dichloro-3-((1,5-dimethyl-6-(trifluoromethyl)-1H-indol-2-yl)methyl)benzoyl)piperidine-4-carboxylic acid

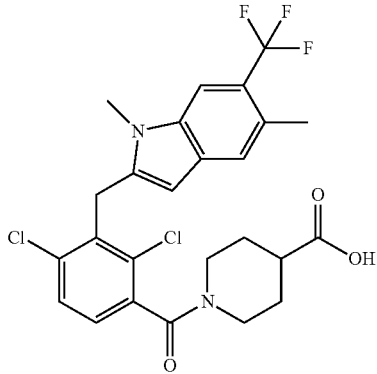 [SMILES: Cc1cc2cc(Cc3c(Cl)ccc(C(=O)N4CCC(C(=O)O)CC4)c3Cl)n(C)c2cc1C(F)(F)F]

Using a procedure similar to Example A, Step 5, 1-(2,4-dichloro-3-((1,5-dimethyl-6-(trifluoromethyl)-1H-indol-2-yl)methyl)benzoyl)piperidine-4-carboxylic acid (102 mg, 77%) was prepared from ethyl 1-(2,4-dichloro-3-((1,5-dimethyl-6-(trifluoromethyl)-1H-indol-2-yl)methyl)benzoyl)piperidine-4-carboxylate (133 mg, 0.239 mmol). LC/MS (Method g) $R_t$=1.82 min.; MS m/z: 527 [M+H]$^+$ $^1$H NMR (DMSO-d$_6$, 400 MHz): δ 12.40 (broad, 1H), 7.79 (s, 1H), 7.67 (d, J=10 Hz, 1H), 7.45 (d, J=10 Hz, 0.5H), 7.37 (m, 1.5H), 5.60 and 5.58 (s, 1H), 4.46 (s, 2H), 4.36 (m, 1H), 3.96 (s, 3H), 3.29 (m, 1H), 3.12 (m, 1H), 3.01 (m, 1H), 2.56 (m, 1H), 2.49 (s, 3H), 1.92 (m, 1H), 1.78 (m, 1H), 1.53 (m, 2H).

Example W: 2-(2,6-dichloro-3-methoxybenzyl)-1,4-dimethyl-6-(trifluoromethyl)-1H-indole

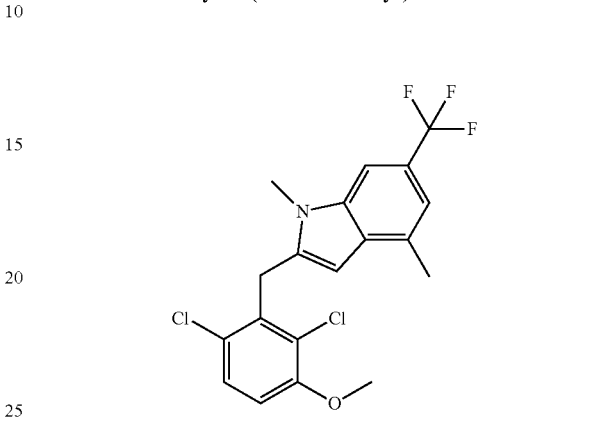

Step 1: (2,6-dichloro-3-methoxyphenyl)(4-methyl-1-(phenylsulfonyl)-6-(trifluoromethyl)-1H-indol-2-yl)methanol

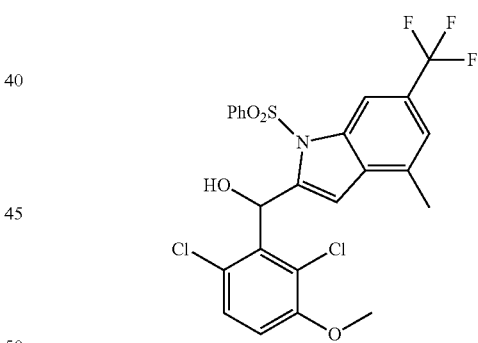

Using a procedure similar to Example A, Step 1, (2,6-dichloro-3-methoxyphenyl)(4-methyl-1-(phenylsulfonyl)-6-(trifluoromethyl)-1H-indol-2-yl)methanol (2.51 g, 90%) was prepared from N-(2-iodo-3-methyl-5-(trifluoromethyl)phenyl)benzenesulfonamide (Preparation #16) (2.262 g, 5.13 mmol) and 1-(2,6-dichloro-3-methoxyphenyl)prop-2-yn-1-ol (Preparation #7 (1.54 g, 6.66 mmol). LC/MS (Method h) $R_t$=3.39 min.; MS m/z: 602 [M–H]$^-$+ CH$_3$COOH $^1$H NMR (DMSO-d$_6$, 300 MHz): δ 8.08 (m, 1H), 7.82 (m, 2H), 7.67 (m, 1H), 7.56 (m, 2H), 7.40 (m, 2H), 7.14 (d, J=9 Hz, 1H), 6.98 (d, 6 Hz, 1H), 6.79 (s, 1H), 6.57 (d, J=6 Hz, 1H), 3.87 (s, 3H), 2.45 (s, 3H).

Step 2: 2-(2,6-dichloro-3-methoxybenzyl)-4-methyl-1-(phenylsulfonyl)-6-(trifluoromethyl)-1H-indole

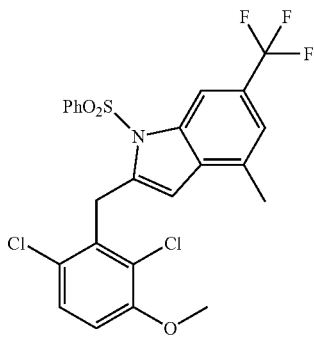

Using a procedure similar to Example A, Step 2, 2-(2,6-dichloro-3-methoxybenzyl)-4-methyl-1-(phenylsulfonyl)-6-(trifluoromethyl)-1H-indole (2.12 g, 87%) was prepared from (2,6-dichloro-3-methoxyphenyl)(4-methyl-1-(phenylsulfonyl)-6-(trifluoromethyl)-1H-indol-2-yl)methanol (2.5 g, 4.59 mmol). LC/MS (Method h) $R_t$=3.85 min.; MS m/z: 528 [M+H]$^+$ $^1$H NMR (DMSO-d$_6$, 300 MHz): δ 8.24 (s, 1H), 7.93 (m, 2H), 7.76 (m, 1H), 7.68 (m, 2H), 7.53 (d, J=9 Hz, 1H), 7.41 (s, 1H), 7.23 (d, J=9 Hz, 1H), 5.90 (s, 1H), 4.54 (s, 2H), 3.90 (s, 3H), 2.34 (s, 3H).

Step 3: 2-(2,6-dichloro-3-methoxybenzyl)-4-methyl-6-(trifluoromethyl)-1H-indole

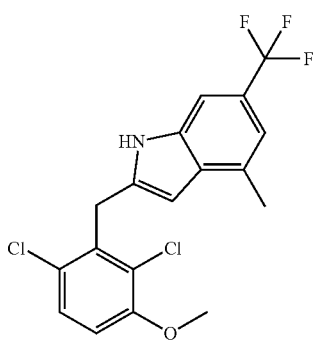 [SMILES: COc1ccc(Cl)c(Cc2cc3c(C)cc(C(F)(F)F)cc3[nH]2)c1Cl]

Using a procedure similar to Example A, Step 3, 2-(2,6-dichloro-3-methoxybenzyl)-4-methyl-6-(trifluoromethyl)-1H-indole (1.52 g, 98%) was prepared from 2-(2,6-dichloro-3-methoxybenzyl)-4-methyl-1-(phenylsulfonyl)-6-(trifluoromethyl)-1H-indole (2.12 g, 4.01 mmol). LC/MS (Method h) $R_t$=3.47 min.; MS m/z: 388 [M+H]$^+$ $^1$H NMR (DMSO-d$_6$, 300 MHz): δ 11.50 (broad, 1H), 7.52 (d, J=9 Hz, 1H), 7.48 (s, 1H), 7.17 (d, J=9 Hz, 1H), 7.02 (s, 1H), 5.95 (s, 1H), 4.42 (s, 2H), 3.89 (s, 3H), 2.40 (s, 3H).

Step 4: 2-(2,6-dichloro-3-methoxybenzyl)-1,4-dimethyl-6-(trifluoromethyl)-1H-indole

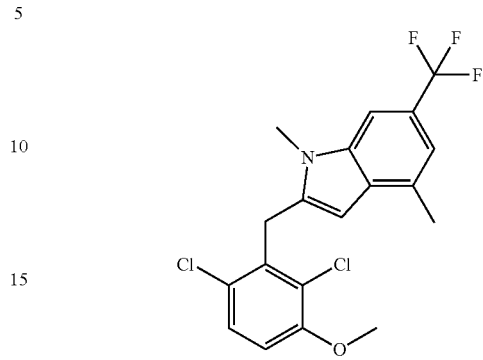

Using a procedure similar to Example P, Step 4, 2-(2,6-dichloro-3-methoxybenzyl)-1,4-dimethyl-6-(trifluoromethyl)-1H-indole (517 mg, 93%) was prepared from 2-(2,6-dichloro-3-methoxybenzyl)-4-methyl-6-(trifluoromethyl)-1H-indole (1.36 g, 3.50 mmol). LC/MS (Method g) k 2.17 min.; MS m/z: 402 [M+H]$^+$ $^1$H NMR (DMSO-d$_6$, 300 MHz): δ 7.69 (s, 1H), 7.54 (d, J=9 Hz, 1H), 7.22 (d, J=9 Hz, 1H), 7.05 (s, 1H), 5.65 (s, 1H), 4.41 (s, 2H), 3.91 (s, 6H), 2.35 (s, 3H).

Example X: 2,4-dichloro-3-((1,4-dimethyl-6-(trifluoromethyl)-1H-indol-2-yl)methyl)phenol

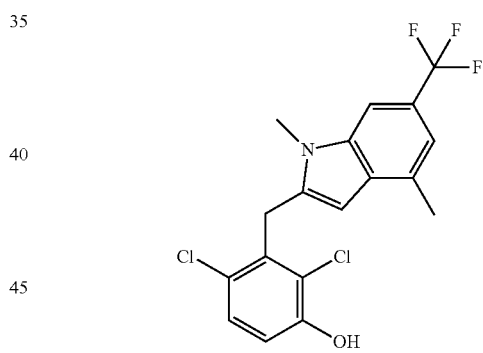

To a solution of 2-(2,6-dichloro-3-methoxybenzyl)-1,4-dimethyl-6-(trifluoromethyl)-1H-indole (Example W) (0.517 g, 1.285 mmol) in DCM (51.4 mL) and cooled at −10° C. was added BBr$_3$ (3.86 mL, 3.86 mmol). The reaction was stirred at −10° C. for 1 hour and warmed at room temperature for 1.5 hours. The reaction was hydrolysed by addition of saturated NaHCO$_3$ aqueous solution, and the basic mixture was extracted with DCM. The organic layer was washed successively with water and saturated NaCl solution, dried over magnesium sulfate, filtered and evaporated. The residue was purified by column chromatography on silica gel (eluting with 0-30% EtOAc in cyclohexane) to give 2,4-dichloro-3-((1,4-dimethyl-6-(trifluoromethyl)-1H-indol-2-yl)methyl)phenol (389 mg, 78%). LC/MS (Method g) $R_t$ 1.97 min.; MS m/z: 388 [M+H]$^+$ $^1$H NMR (DMSO-d$_6$, 400 MHz): δ 10.58 (broad, 1H), 7.68 (s, 1H), 7.35 (d, J=8.8 Hz, 1H), 7.05 (s, 1H), 7.01 (d, J=8.8 Hz, 1H), 5.66 (s, 1H), 4.37 (s, 2H), 3.90 (s, 3H), 2.36 (s, 3H).

Example Y: 2-(2,4-dichloro-3-((1,4-dimethyl-6-(trifluoromethyl)-1H-indol-2-yl)methyl)phenoxy)acetic acid

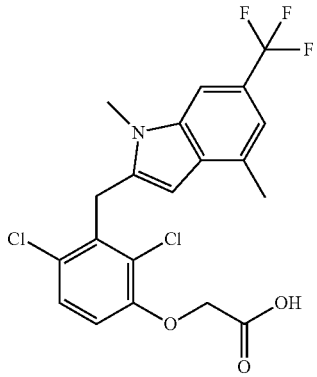 [SMILES: Cc1cc(C(F)(F)F)cc2c1cc(Cc1c(Cl)ccc(OCC(=O)O)c1Cl)n2C]

Step 1: methyl 2-(2,4-dichloro-3-((1,4-dimethyl-6-(trifluoromethyl)-1H-indol-2-yl)methyl)phenoxy)acetate

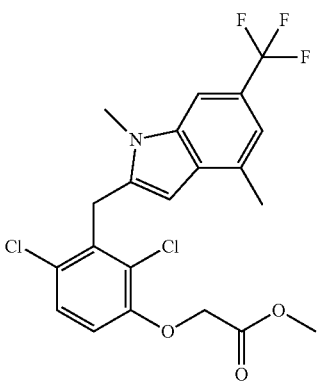 [SMILES: COC(=O)COc1ccc(Cl)c(Cc2cc3c(C)cc(C(F)(F)F)cc3n2C)c1Cl]

To a solution of 2,4-dichloro-3-((1,4-dimethyl-6-(trifluoromethyl)-1H-indol-2-yl)methyl)phenol (Example X) (100 mg, 0.258 mmol) in ACN (1 mL) was added $Cs_2CO_3$ (92 mg, 0.283 mmol) and the mixture was stirred at room temperature for 10 minutes. methyl bromoacetate (0.036 mL, 0.386 mmol) was added and the mixture was stirred at room temperature for 7 hours. The reaction mixture was diluted with water and extracted with DCM. The organic layer was washed with brine, dried over magnesium sulfate, filtered and concentrated under reduced pressure. The residue was purified by column chromatography on silica gel (eluting with 0-30% EtOAc in cyclohexane) to give methyl 2-(2,4-dichloro-3-((1,4-dimethyl-6-(trifluoromethyl)-1H-indol-2-yl)methyl)phenoxy)acetate (98 mg, 83%). LC/MS (Method h) k 3.46 min.; MS m/z: 460 [M+H]$^+$ $^1$H NMR (DMSO-d$_6$, 300 MHz): δ 7.70 (s, 1H), 7.52 (d, J=9 Hz, 1H), 7.16 (d, J=9 Hz, 1H), 7.06 (s, 1H), 5.65 (s, 1H), 5.00 (s, 2H), 4.43 (s, 2H), 3.92 (s, 3H), 3.72 (s, 3H), 2.36 (s, 3H).

Step 2: 2-(2,4-dichloro-3-((1,4-dimethyl-6-(trifluoromethyl)-1H-indol-2-yl)methyl)phenoxy)acetic acid

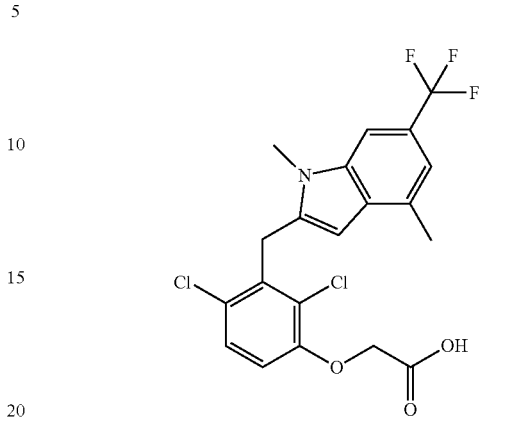

Using a procedure similar to Example A, Step 5, 2-(2,4-dichloro-3-((1,4-dimethyl-6-(trifluoromethyl)-1H-indol-2-yl)methyl)phenoxy)acetic acid (88 mg, 93%) was prepared from methyl 2-(2,4-dichloro-3-((1,4-dimethyl-6-(trifluoromethyl)-1H-indol-2-yl)methyl)phenoxy)acetate (98 mg, 0.213 mmol)

LC/MS (Method g) k 1.98 min.; MS m/z: 446 [M+H]$^+$ $^1$H NMR (DMSO-d$_6$, 400 MHz): δ 13.30 (broad, 1H), 7.70 (s, 1H), 7.50 (d, J=8.8 Hz, 1H), 7.09 (d, J=8.8 Hz, 1H), 7.06 (s, 1H), 5.66 (s, 1H), 4.83 (s, 2H), 4.42 (s, 2H), 3.91 (s, 3H), 2.34 (s, 3H).

Example Y1: 3-(2,4-dichloro-3-((1,4-dimethyl-6-(trifluoromethyl)-1H-indol-2-yl)methyl)phenoxy)propanoic acid

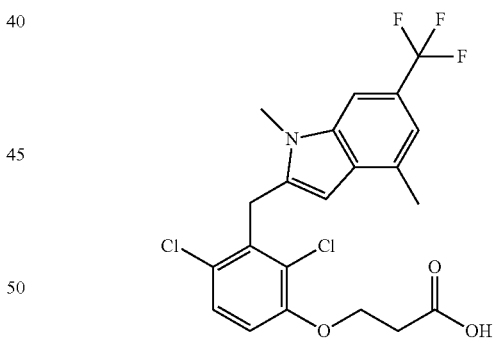

To a solution of 2,4-dichloro-3-((1,4-dimethyl-6-(trifluoromethyl)-1H-indol-2-yl)methyl)phenol (Example X) (150 mg, 0.386 mmol) in DMF (2 mL) was added NaH (23.18 mg, 0.580 mmol) and the mixture was stirred at room temperature for 10 minutes. Beta-propiolactone (0.036 mL, 0.580 mmol) was added and the mixture was stirred at room temperature overnight. Water was added to the mixture, and the mixture was acidified to pH=3-4 with 1N HCl solution. The solid was filtered, washed with water and diethyl ether and dried under vacuum. The residue was purified by column chromatography on silica gel (eluting with 0-20% MeOH in DCM) to give 3-(2,4-dichloro-3-((1,4-dimethyl-6-(trifluoromethyl)-1H-indol-2-yl)methyl)phenoxy)propanoic acid (101 mg, 37%) as a white solid.

LC/MS (Method g) k 1.97 min.; MS m/z: 460 [M+H]+ 1H NMR (DMSO-d6, 400 MHz): δ 12.56 (broad, 1H), 7.67 (s, 1H), 7.52 (d, J=9.2 Hz, 1H), 7.24 (d, J=9.2 Hz, 1H), 7.05 (s, 1H), 5.65 (s, 1H), 4.40 (s, 2H), 4.30 (t, J=6 Hz, 2H), 3.90 (s, 3H), 2.74 (t, J=6 Hz, 2H), 2.36 (s, 3H).

Example Z: 2-((3,5-dichloro-2-methoxypyridin-4-yl)methyl)-1,4-dimethyl-6-(trifluoromethyl)-1H-indole

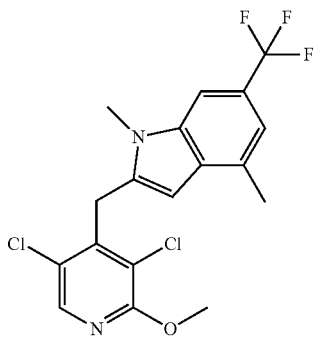 [SMILES: COc1ncc(Cl)c(Cc2cc3c(C)cc(C(F)(F)F)cc3n2C)c1Cl]

Step 1: (3,5-dichloro-2-methoxypyridin-4-yl)(4-methyl-1-(phenylsulfonyl)-6-(trifluoromethyl)-1H-indol-2-yl)methanol

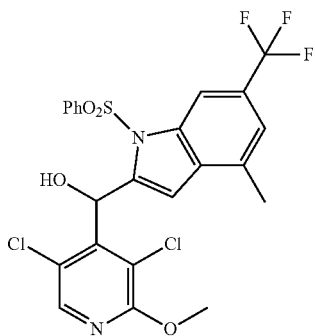

Using a procedure similar to Example A, Step 1, (3,5-dichloro-2-methoxypyridin-4-yl)(4-methyl-1-(phenylsulfonyl)-6-(trifluoromethyl)-1H-indol-2-yl)methanol (3.47 g, 94%) was prepared from N-(2-iodo-3-methyl-5-(trifluoromethyl)phenyl)benzenesulfonamide (Preparation #16) (3 g, 6.80 mmol) and 1-(3,5-dichloro-2-methoxypyridin-4-yl)prop-2-yn-1-ol (Preparation #15) (1.894 g, 8.16 mmol).

LC/MS (Method k) k 3.59 min.; MS m/z: 545 [M+H]+ 1H NMR (DMSO-d6, 300 MHz): δ 8.21 (s, 1H), 8.09 (s, 1H), 7.82 (m, 2H), 7.71 (m, 1H), 7.58 (m, 1H), 7.44 (s, 1H), 6.94 (s, 1H), 6.87 (m, 2H), 3.95 (s, 3H), 2.48 (s, 3H).

Step 2: 2-((3,5-dichloro-2-methoxypyridin-4-yl)methyl)-4-methyl-1-(phenylsulfonyl)-6-(trifluoromethyl)-1H-indole

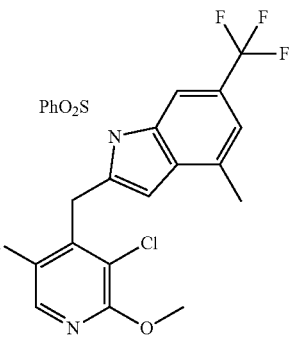

To a solution of (3,5-dichloro-2-methoxypyridin-4-yl)(4-methyl-1-(phenylsulfonyl)-6-(trifluoromethyl)-1H-indol-2-yl)methanol (50 mg, 0.092 mmol) in chloroform (420 μL) was added thionyl chloride (19.95 μL, 0.275 mmol) and the reaction mixture was stirred at room temperature during one night. The reaction mixture was basified (pH 8) with NaHCO3 saturated aqueous solution. The obtained aqueous layer was extracted with EtOAc. The obtained organic layer was dried over magnesium sulfate, filtered and concentrated under reduced pressure. The residue was dissolved in acetic acid (420 μL) and zinc (30.0 mg, 0.458 mmol) was added. The reaction mixture was stirred at room temperature during 2 hours, then filtered, washed with DCM and the filtrate was concentrated under reduced pressure. The residue was diluted with EtOAc and washed with water. The obtained organic layer was dried over magnesium sulfate, filtered and concentrated under reduced pressure to give 2-((3,5-dichloro-2-methoxypyridin-4-yl)methyl)-4-methyl-1-(phenylsulfonyl)-6-(trifluoromethyl)-1H-indole (50 mg, 94%) as a beige solid. LC/MS (Method k) R$_t$ 4.19 min.; MS m/z: 529 [M+H]+ 1H NMR (DMSO-d6, 300 MHz): δ 8.32 (s, 1H), 8.22 (s, 1H), 7.92 (m, 2H), 7.77 (m, 1H), 7.67 (m, 2H), 7.41 (s, 1H), 6.21 (s, 1H), 4.54 (s, 2H), 3.39 (s, 3H), 2.37 (s, 3H).

Step 3: 2-((3,5-dichloro-2-methoxypyridin-4-yl)methyl)-4-methyl-6-(trifluoromethyl)-1H-indole

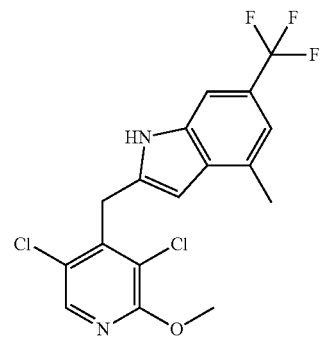 [SMILES: COc1ncc(Cl)c(Cc2cc3c(C)cc(C(F)(F)F)cc3[nH]2)c1Cl]

Using a procedure similar to Example A, Step 3, 2-((3,5-dichloro-2-methoxypyridin-4-yl)methyl)-4-methyl-6-(trifluoromethyl)-1H-indole (1.2 g, 86%) was prepared from 2-((3,5-dichloro-2-methoxypyridin-4-yl)methyl)-4-methyl- 1-(phenylsulfonyl)-6-(trifluoromethyl)-1H-indole (1.9 g, 3.59 mmol). LC/MS (Method h) $R_t$ 3.45 min.; MS m/z: 389 [M+H]$^+$ $^1$H NMR (DMSO-d$_6$, 300 MHz): δ 11.49 (s, 1H), 8.31 (s, 1H), 7.48 (s, 1H), 7.03 (s, 1H), 6.06 (s, 1H), 4.42 (s, 2H), 3.98 (s, 3H), 2.42 (s, 3H).

Step 4: 2-((3,5-dichloro-2-methoxypyridin-4-yl)methyl)-1,4-dimethyl-6-(trifluoromethyl)-1H-indole

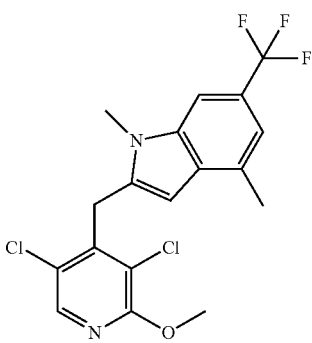 [SMILES: COc1ncc(Cl)c(Cc2cc3c(C)cc(C(F)(F)F)cc3n2C)c1Cl]

Using a procedure similar to Example A, Step 4, 2-((3,5-dichloro-2-methoxypyridin-4-yl)methyl)-1,4-dimethyl-6-(trifluoromethyl)-1H-indole (963 mg, 77%) was prepared from 2-((3,5-dichloro-2-methoxypyridin-4-yl)methyl)-4-methyl-6-(trifluoromethyl)-1H-indole (1.2 g, 3.08 mmol). LC/MS (Method h) $R_t$ 3.60 min.; MS m/z: 403 [M+H]$^+$ $^1$H NMR (DMSO-d$_6$, 300 MHz): δ 8.35 (s, 1H), 7.70 (s, 1H), 7.07 (s, 1H), 5.80 (s, 1H), 4.43 (s, 2H), 4.00 (s, 3H), 3.92 (s, 3H), 2.38 (s, 3H).

Example AA: 2-(2,6-dichloro-3-(4-(oxetan-3-yl)piperazine-1-carbonyl)benzyl)-1,4-dimethyl-1H-indole-6-carbonitrile

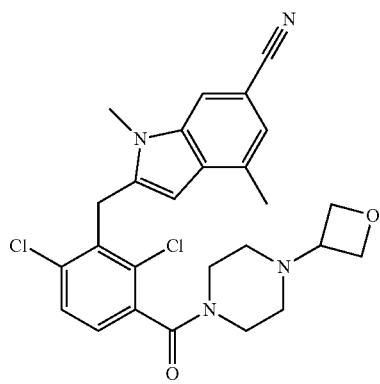 [SMILES: Cc1cc(C#N)cc2c1cc(Cc1c(Cl)ccc(C(=O)N3CCN(C4COC4)CC3)c1Cl)n2C]

Step 1: methyl 2,4-dichloro-3-((6-cyano-4-methyl-1-(phenylsulfonyl)-1H-indol-2-yl)(hydroxy)methyl)benzoate

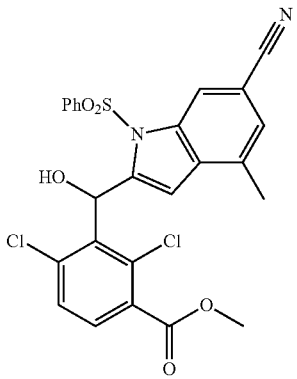

Using a procedure similar to Example A, Step 1, methyl 2,4-dichloro-3-((6-cyano-4-methyl-1-(phenylsulfonyl)-1H-indol-2-yl)(hydroxy)methyl)benzoate (1.32 g, 71%) was obtained as a brown solid from N-(5-cyano-2-iodo-3-methylphenyl)benzenesulfonamide (Preparation #18) (1.4 g, 3.52 mmol) and methyl 2,4-dichloro-3-(1-hydroxyprop-2-yn-1-yl)benzoate (Preparation #1) (1.093 g, 4.22 mmol). LC/MS (Method h) $R_t$=2.97 min.; MS m/z: 587[M−H]$^-$+ CH$_3$COOH.

$^1$H NMR (DMSO-d$_6$, 300 MHz): δ 8.24 (s, 1H), 7.90 (m, 2H), 7.67 (m, 2H), 7.53 (m, 4H), 7.02 (m, 1H), 6.89 (s, 1H), 6.77 (d, J=6 Hz, 1H), 3.87 (s, 3H), 2.43 (s, 3H).

Step 2: methyl 2,4-dichloro-3-((6-cyano-4-methyl-1-(phenylsulfonyl)-1H-indol-2-yl)methyl)benzoate

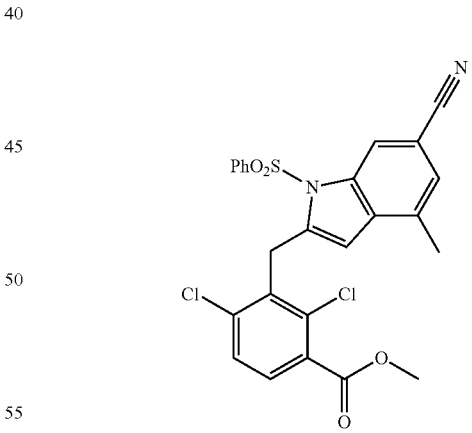

Using a procedure similar to Example A, Step 2, methyl 2,4-dichloro-3-((6-cyano-4-methyl-1-(phenylsulfonyl)-1H-indol-2-yl)methyl)benzoate (1.6 g, 100%) was obtained as a yellow solid from methyl 2,4-dichloro-3-((6-cyano-4-methyl-1-(phenylsulfonyl)-1H-indol-2-yl)(hydroxy)methyl)benzoate (1.52 g, 2.87 mmol). LC/MS (Method h) $R_t$=3.45 min.; MS m/z: 513 [M+H]$^+$. $^1$H NMR (DMSO-d$_6$, 300 MHz): δ 8.36 (s, 1H), 8.07 (d, J=9 Hz, 2H), 7.81 (m, 2H), 7.69 (m, 3H), 7.48 (s, 1H), 5.98 (s, 1H), 4.63 (s, 2H), 3.86 (s, 3H), 2.31 (s, 3H).

Step 3: methyl 2,4-dichloro-3-((6-cyano-4-methyl-1H-indol-2-yl)methyl)benzoate

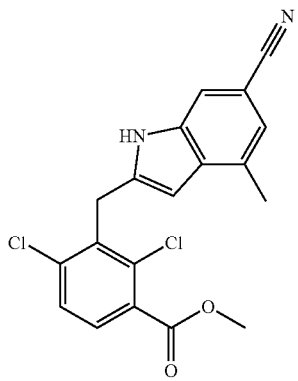 [SMILES: COC(=O)c1ccc(Cl)c(Cc2cc3c(C)cc(C#N)cc3[nH]2)c1Cl]

Using a procedure similar to Example A, Step 3, methyl 2,4-dichloro-3-((6-cyano-4-methyl-1H-indol-2-yl)methyl)benzoate (850 mg, 67%) was obtained as a brown solid from methyl 2,4-dichloro-3-((6-cyano-4-methyl-1-(phenylsulfonyl)-1H-indol-2-yl)methyl)benzoate (1.6 g, 3.12 mmol).

LC/MS (Method h) $R_t$=3.03 min.; MS m/z: 373 [M+H]$^+$. $^1$H NMR (DMSO-d$_6$, 300 MHz): δ 11.66 (broad, 1H), 7.76 (d, J=6 Hz, 1H), 7.68 (d, J=6 Hz, 1H), 7.64 (s, 1H), 7.08 (s, 1H), 5.99 (s, 1H), 4.50 (s, 2H), 3.87 (s, 3H), 2.37 (s, 3H).

Step 4: methyl 2,4-dichloro-3-((6-cyano-1,4-dimethyl-1H-indol-2-yl)methyl)benzoate

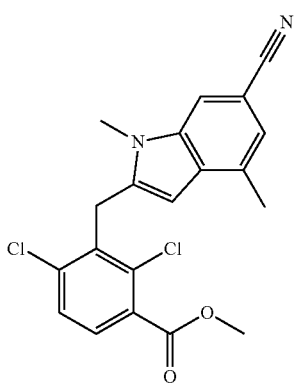 [SMILES: COC(=O)c1ccc(Cl)c(Cc2cc3c(C)cc(C#N)cc3n2C)c1Cl]

Using a procedure similar to Example A, Step 4, methyl 2,4-dichloro-3-((6-cyano-1,4-dimethyl-1H-indol-2-yl)methyl)benzoate (660 mg, 75%) was obtained as a beige solid from methyl 2,4-dichloro-3-((6-cyano-4-methyl-1H-indol-2-yl)methyl)benzoate (847 mg, 2.27 mmol).

LC/MS (Method k) $R_t$=3.29 min.; MS m/z: 387 [M+H]$^+$. $^1$H NMR (DMSO-d$_6$, 300 MHz): δ 7.92 (s, 1H), 7.80 (d, J=9 Hz, 1H), 7.72 (d, J=9 Hz, 1H), 7.11 (s, 1H), 5.70 (s, 1H), 4.50 (s, 2H), 3.91 (s, 3H), 3.88 (s, 3H), 2.33 (s, 3H).

Step 5: 2,4-dichloro-3-((6-cyano-1,4-dimethyl-1H-indol-2-yl)methyl)benzoic acid

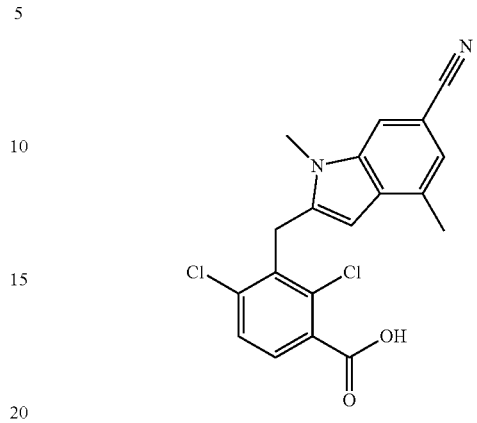

Using a procedure similar to Example A, Step 5, 2,4-dichloro-3-((6-cyano-1,4-dimethyl-1H-indol-2-yl)methyl)benzoic acid (660 mg, 100%) was obtained as a white solid from methyl 2,4-dichloro-3-((6-cyano-1,4-dimethyl-1H-indol-2-yl)methyl)benzoate (655 mg, 1.69 mmol). LC/MS (Method k) $R_t$=2.82 min.; MS m/z: 373 [M+H]$^+$. $^1$H NMR (DMSO-d$_6$, 300 MHz): δ 7.92 (s, 1H), 7.77 (d, J=9 Hz, 1H), 7.68 (d, J=9 Hz, 1H), 7.11 (s, 1H), 5.70 (s, 1H), 4.49 (s, 2H), 3.91 (s, 3H), 2.33 (s, 3H).

Step 6: 2-(2,6-dichloro-3-(4-(oxetan-3-yl)piperazine-1-carbonyl)benzyl)-1,4-dimethyl-1H-indole-6-carbonitrile

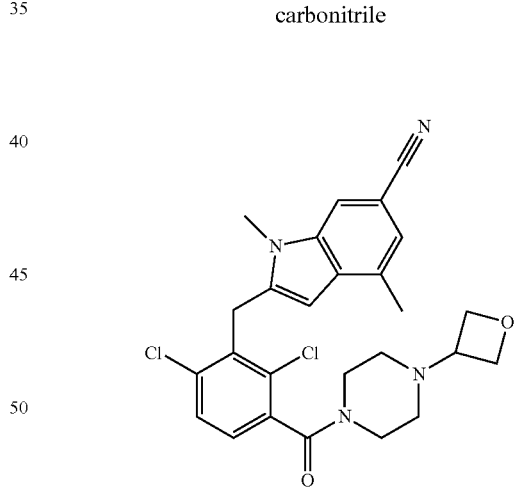

Using a procedure similar to Example A.1, 2-(2,6-dichloro-3-(4-(oxetan-3-yl)piperazine-1-carbonyl)benzyl)-1,4-dimethyl-1H-indole-6-carbonitrile (700 mg, 88%) was obtained as a white solid from 2,4-dichloro-3-((6-cyano-1,4-dimethyl-1H-indol-2-yl)methyl)benzoic acid (600 mg, 1.608 mmol) and 1-(oxetan-3-yl)piperazine (260 mg, 1.83 mmol). LC/MS (Method g) $R_t$=1.47 min.; MS m/z: 497 [M+H]$^+$ $^1$H NMR (DMSO-d$_6$, 400 MHz): δ 7.92 (s, 1H), 7.67 (d, J=8 Hz, 1H), 7.43 (d, J=8 Hz, 1H), 7.11 (s, 1H), 5.71 (s, 1H), 4.53 (m, 2H), 4.47 (m, 4H), 3.90 (s, 3H), 3.69 (m, 2H), 3.48 (m, 1H), 3.20 (m, 2H), 2.38 (m, 2H), 2.23 (s, 3H), 2.18 (m, 2H).

TABLE AA
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)+ |
|---|---|---|---|---|
| AA-1 | 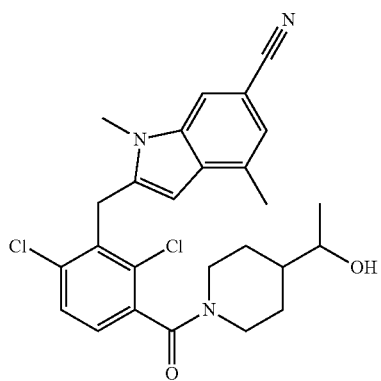 [SMILES: Cc1cc(C#N)cc2c1cc(Cc1c(Cl)ccc(C(=O)N3CCC(C(C)O)CC3)c1Cl)n2C] | 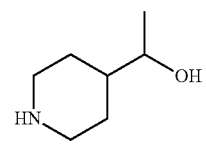 | 1.62 (Method g) | 484 |
| AA-2 | 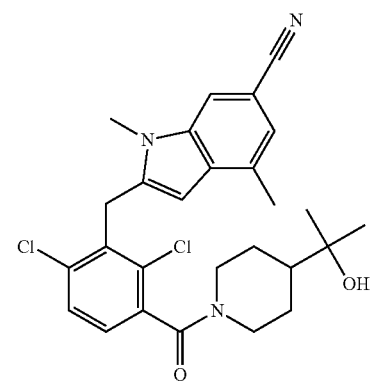 [SMILES: Cc1cc(C#N)cc2c1cc(Cc1c(Cl)ccc(C(=O)N3CCC(C(C)(C)O)CC3)c1Cl)n2C] | 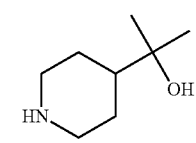 | 1.67 (Method g) | 498 |
| AA-3 | 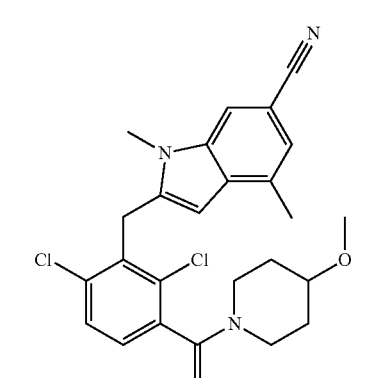 | 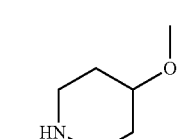 | 1.73 (Method g) | 470 |

TABLE AA-continued
*The following examples were prepared from 2,4-dichloro-3-((6-cyano-1,4-dimethyl-1H-indol-2-yl)methyl)benzoic acid (Example AA, Step 5) using the same procedure with the appropriate amine.*
| Example | Product | amine | $R_t$ min (method) | m/z ESI+ (M + H)+ |
|---|---|---|---|---|
| AA-4 | 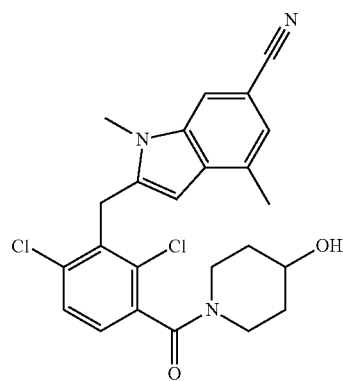 | 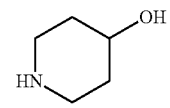 | 1.51 (Method g) | 456 |
| AA-5 | 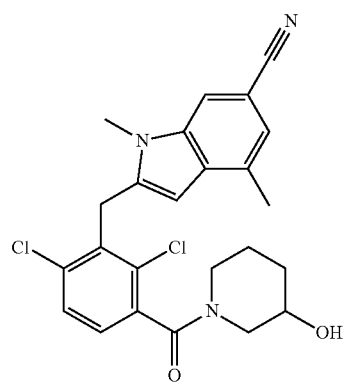 [SMILES: Cc1cc(C#N)cc2c1cc(Cc1c(Cl)ccc(C(=O)N3CCCC(O)C3)c1Cl)n2C] | 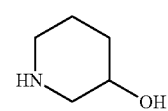 | 1.56 (Method g) | 456 |
| AA-6 | 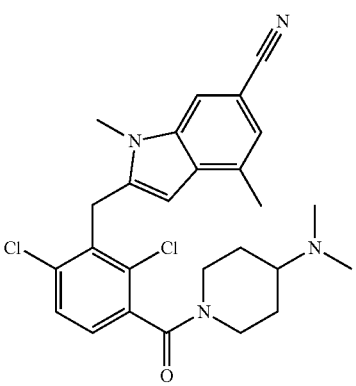 [SMILES: Cc1cc(C#N)cc2c1cc(Cc1c(Cl)ccc(C(=O)N3CCC(N(C)C)CC3)c1Cl)n2C] | 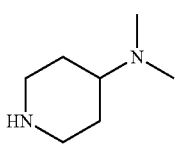 | 1.09 (Method g) | 483 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)+ |
|---------|---------|-------|--------------------|-----|
| AA-7 | 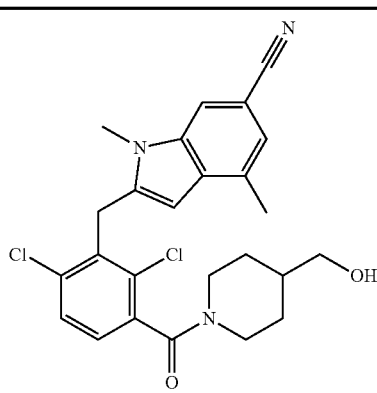 | 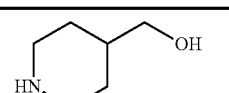 | 1.55 (Method g) | 470 |
| AA-8 | 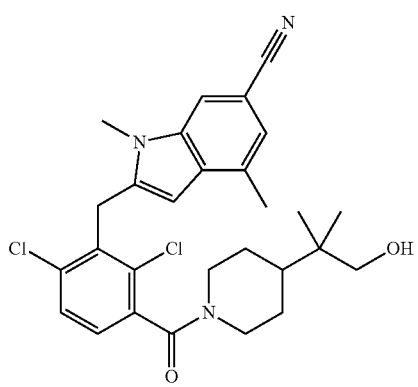 [SMILES: Cc1cc(C#N)cc2c1cc(Cc1c(Cl)ccc(C(=O)N3CCC(C(C)(C)CO)CC3)c1Cl)n2C] | 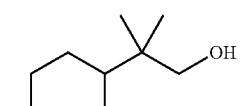 | 1.75 (Method g) | 512 |
| AA-9 | 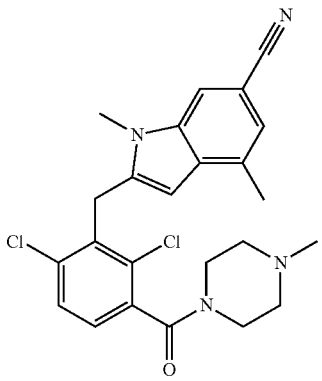 [SMILES: Cc1cc(C#N)cc2c1cc(Cc1c(Cl)ccc(C(=O)N3CCN(C)CC3)c1Cl)n2C] | 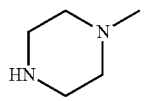 | 1.08 (Method g) | 455 |
| AA-10 | 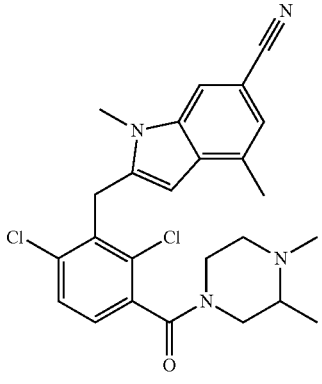 [SMILES: Cc1cc(C#N)cc2c1cc(Cc1c(Cl)ccc(C(=O)N3CCN(C)C(C)C3)c1Cl)n2C] | 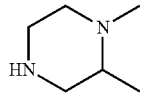 | 1.10 (Method g) | 469 |

TABLE AA-continued

The following examples were prepared from 2,4-dichloro-3-((6-cyano-1,4-dimethyl-1H-indol-2-yl)methyl)benzoic acid (Example AA, Step 5) using the same procedure with the appropriate amine.

| Example | Product | amine | R$_t$ min (method) | m/z ESI+ (M + H)+ |
|---|---|---|---|---|
| AA-11 | | | 1.12 (Method g) | 483 |
| AA-12 | | | 1.07 (Method g) | 485 |
| AA-13 | | | 1.08 (Method g) | 499 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)$^+$ |
|---|---|---|---|---|
| AA-14 | 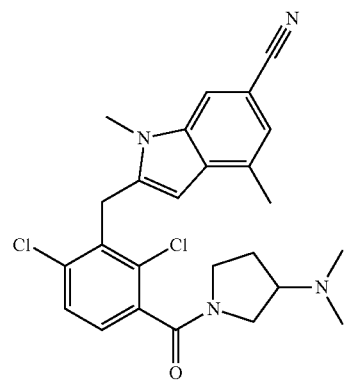 [SMILES: Cc1cc(C#N)cc2c1cc(Cc1c(Cl)ccc(C(=O)N3CCC(N(C)C)C3)c1Cl)n2C] | 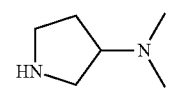 | 1.08 (Method g) | 469 |
| AA-15 | 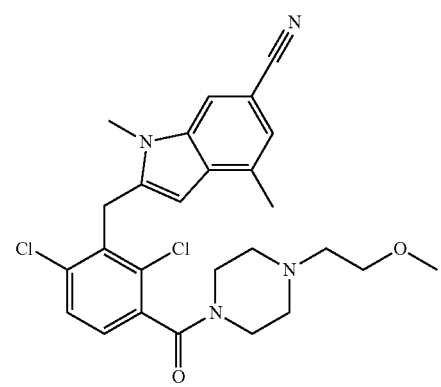 [SMILES: COCCN1CCN(C(=O)c2ccc(Cl)c(Cc3cc4c(C)cc(C#N)cc4n3C)c2Cl)CC1] | 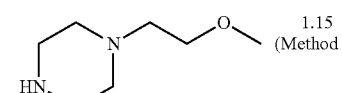 | 1.15 (Method g) | 499 |
| AA-16 | 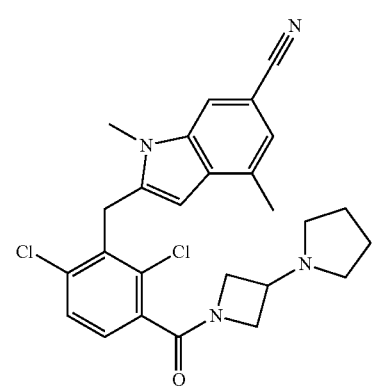 [SMILES: Cc1cc(C#N)cc2c1cc(Cc1c(Cl)ccc(C(=O)N3CC(N4CCCC4)C3)c1Cl)n2C] | 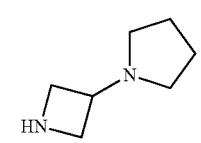 | 1.10 (Method g) | 481 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)+ |
|---------|---------|-------|--------------------|--------------------|
| AA-17 | 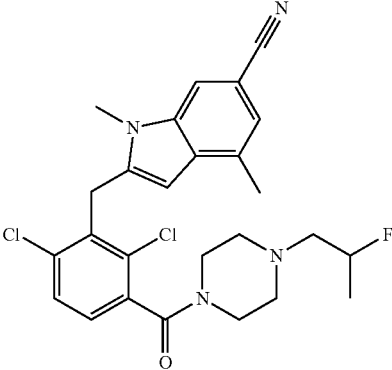 [SMILES: Cc1cc(C#N)cc2c1cc(Cc1c(Cl)ccc(C(=O)N3CCN(CC(C)F)CC3)c1Cl)n2C] | 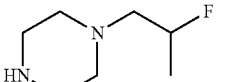 | 1.38 (Method g) | 501 |
| AA-18 | 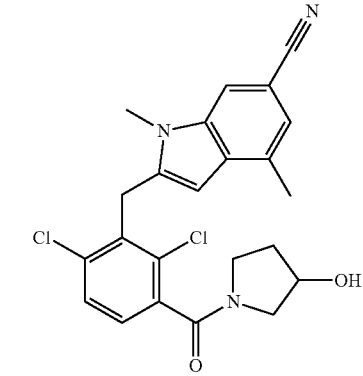 [SMILES: Cc1cc(C#N)cc2c1cc(Cc1c(Cl)ccc(C(=O)N3CCC(O)C3)c1Cl)n2C] | 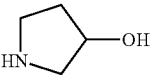 | 1.49 (Method g) | 442 |
| AA-19 | 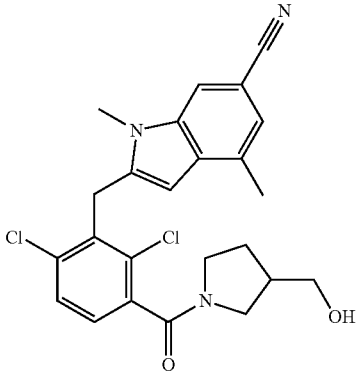 [SMILES: Cc1cc(C#N)cc2c1cc(Cc1c(Cl)ccc(C(=O)N3CCC(CO)C3)c1Cl)n2C] | 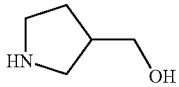 | 1.52 (Method g) | 456 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)+ |
|---|---|---|---|---|
| AA-20 | 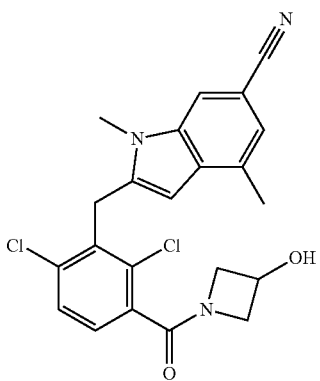 [SMILES: Cc1cc(C#N)cc2c1cc(Cc1c(Cl)ccc(C(=O)N3CC(O)C3)c1Cl)n2C] | 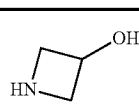 | 1.47 (Method g) | 428 |
| AA-21 | 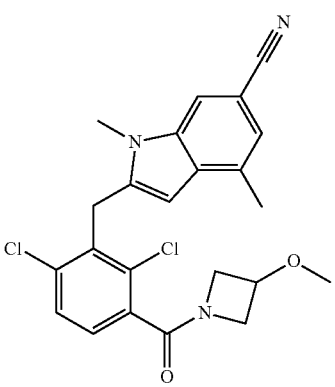 [SMILES: COC1CN(C(=O)c2ccc(Cl)c(Cc3cc4c(C)cc(C#N)cc4n3C)c2Cl)C1] | 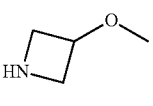 | 1.65 (Method g) | 442 |
| AA-22 | 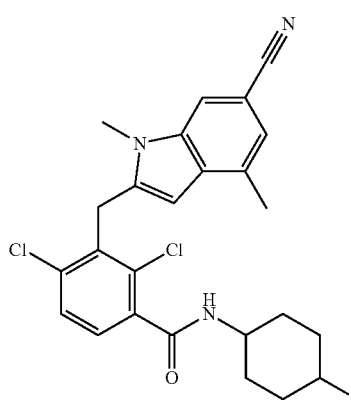 | 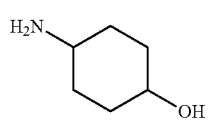 | 1.52 (Method g) | 470 |

TABLE AA-continued

The following examples were prepared from 2,4-dichloro-3-((6-cyano-1,4-dimethyl-1H-indol-2-yl)methyl)benzoic acid (Example AA, Step 5) using the same procedure with the appropriate amine.

| Example | Product | amine | $R_t$ min (method) | m/z ESI+ (M + H)+ |
|---|---|---|---|---|
| AA-23 | | | 1.60 (Method g) | 456 |
| AA-24 | | | 1.52 (Method g) | 428 |
| AA-25 | | | 1.63 (Method g) | 482 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)$^+$ |
|---|---|---|---|---|
| AA-26 | 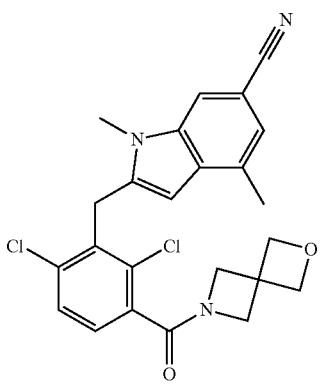 [SMILES: Cc1cc(C#N)cc2c1cc(Cc1c(Cl)ccc(C(=O)N3CC4(COC4)C3)c1Cl)n2C] |  | 1.55 (Method g) | 454 |
| AA-27 | 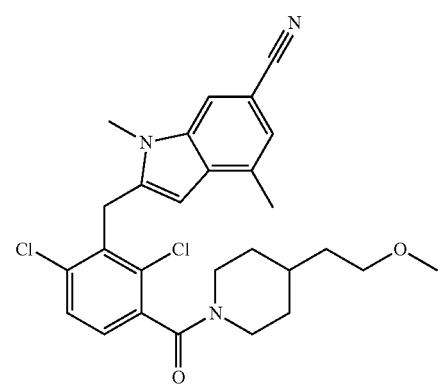 | 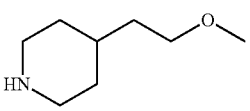 | 1.85 (Method g) | 498 |
| AA-28 | 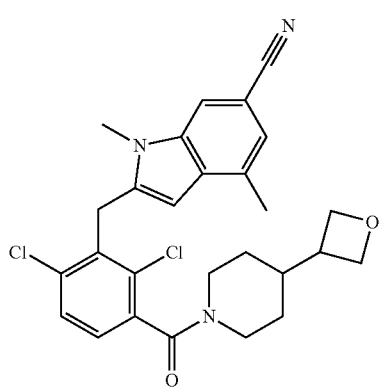 | 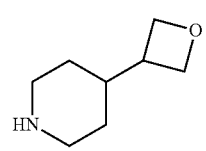 | 1.68 (Method g) | 496 |

TABLE AA-continued
The following examples were prepared from 2,4-dichloro-3-((6-cyano-1,4-dimethyl-1H-indol-2-yl)methyl)benzoic acid (Example AA, Step 5) using the same procedure with the appropriate amine.
| Example | Product | amine | R$_t$ min (method) | m/z ESI+ (M + H)⁺ |
|---|---|---|---|---|
| AA-29 | 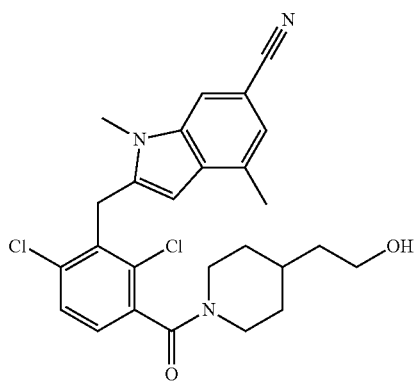 | 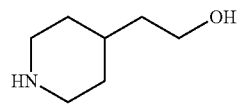 | 1.60 (Method g) | 484 |
| AA-30 | 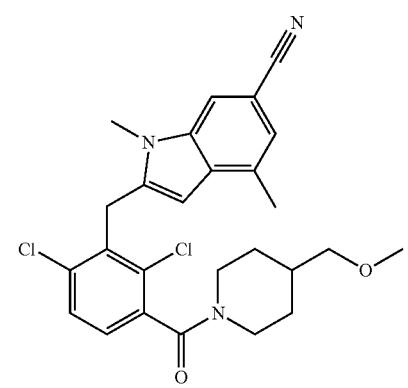 [SMILES: COCC1CCN(C(=O)c2ccc(Cl)c(Cc3cc4c(C)cc(C#N)cc4n3C)c2Cl)CC1] | 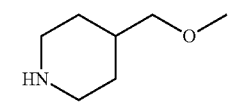 | 1.80 (Method g) | 484 |
| AA-31 | 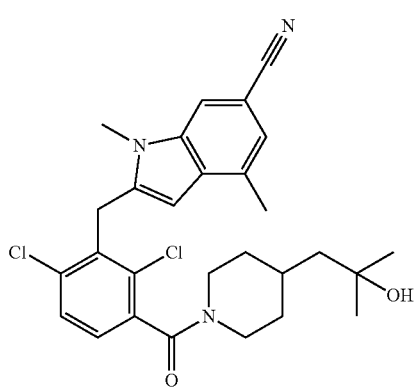 [SMILES: Cc1cc(C#N)cc2c1cc(Cc1c(Cl)ccc(C(=O)N3CCC(CC(C)(C)O)CC3)c1Cl)n2C] | 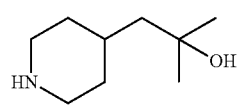 | 1.74 (Method g) | 512 |

TABLE AA-continued

The following examples were prepared from 2,4-dichloro-3-((6-cyano-1,4-dimethyl-1H-indol-2-yl)methyl)benzoic acid (Example AA, Step 5) using the same procedure with the appropriate amine.

| Example | Product | amine | R$_t$ min (method) | m/z ESI+ (M + H)+ |
|---|---|---|---|---|
| AA-32 | Chiral | Chiral | 1.49 (Method g) | 483 |
| AA-33 | | | 1.80 (Method g) | 512 |
| AA-34 | | | 2.85 (Method h) | 498 |

TABLE AA-continued

The following examples were prepared from 2,4-dichloro-3-((6-cyano-1,4-dimethyl-1H-indol-2-yl)methyl)benzoic acid (Example AA, Step 5) using the same procedure with the appropriate amine.

| Example | Product | amine | R$_t$ min (method) | m/z ESI+ (M + H)+ |
|---------|---------|-------|--------------------|-------------------|
| AA-35 | | | 1.61 (Method g) | 442 |
| AA-36 | | | 1.68 (Method g) | 496 |
| AA-37 | | | 1.63 (Method g) | 498 |
| AA-38 | | | 2.89 (Method h) | 512 |

TABLE AA-continued

The following examples were prepared from 2,4-dichloro-3-((6-cyano-1,4-dimethyl-1H-indol-2-yl)methyl)benzoic acid (Example AA, Step 5) using the same procedure with the appropriate amine.

| Example | Product | amine | R$_t$ min (method) | m/z ESI+ (M + H)+ |
|---|---|---|---|---|
| AA-39 | Chiral | Chiral | 1.46 min (Method g) | 442 |
| AA-40 | Chiral | Chiral | 1.46 min (Method g) | 442 |

Example AB: 2-(2,6-dichloro-3-(morpholine-4-carbonyl)benzyl)-1-methyl-1H-indole-5-carbonitrile

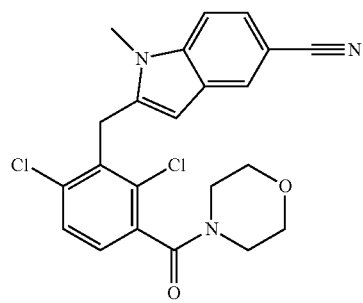 [SMILES: Cn1c(Cc2c(Cl)ccc(C(=O)N3CCOCC3)c2Cl)cc2cc(C#N)ccc21]

Step 1: 2-((2,6-dichloro-3-(morpholine-4-carbonyl)phenyl)(hydroxy)methyl)-1-(phenylsulfonyl)-1H-indole-5-carbonitrile

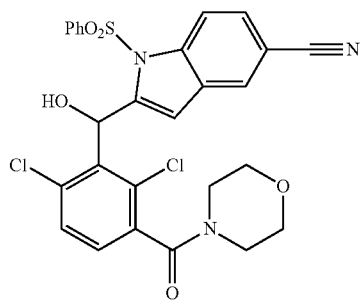

Using a procedure similar to using a procedure similar to Example A, Step 1, 2-((2,6-dichloro-3-(morpholine-4-carbonyl)phenyl)(hydroxy)methyl)-1-(phenylsulfonyl)-1H-indole-5-carbonitrile (500 mg, 100%) was obtained as a brown solid from (2,4-dichloro-3-(1-hydroxyprop-2-yn-1-yl)phenyl)(morpholino)methanone (Preparation #3) (319 mg, 1.015 mmol) and N-(4-cyano-2-iodophenyl)benzenesulfonamide (Preparation #19) (300 mg, 0.781 mmol). LC/MS (Method h) $R_t$=2.52 min.; MS m/z: 570 [M+H]$^+$ $^1$H NMR (DMSO-d$_6$, 300 MHz): δ 8.14 (m, 2H), 7.94 (m, 2H), 7.70 (m, 1H), 7.55 (m, 4H), 7.52 (m, 2H), 7.01 (m, 1H), 6.71 (m, 1H), 3.65 (m, 4H), 3.53 (m, 2H), 3.17 (m, 2H).

Step 2: 2-(2,6-dichloro-3-(morpholine-4-carbonyl)benzyl)-1-(phenylsulfonyl)-1H-indole-5-carbonitrile

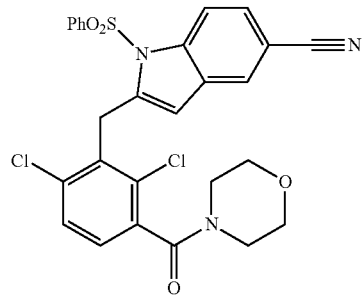

Using a procedure similar to Example A, Step 2, 2-(2,6-dichloro-3-(morpholine-4-carbonyl)benzyl)-1-(phenylsulfonyl)-1H-indole-5-carbonitrile (20 mg, 29%) was obtained as a white solid from 2-((2,6-dichloro-3-(morpholine-4-carbonyl)phenyl)(hydroxy)methyl)-1-(phenylsulfonyl)-1H-indole-5-carbonitrile (70 mg, 0.123 mmol). LC/MS (Method g) $R_t$=1.78 min.; MS m/z: 554 [M+H]$^+$ $^1$H NMR (DMSO-d$_6$, 300 MHz): δ 8.30 (d, J=9 Hz, 1H), 7.98 (m, 3H), 7.77 (m, 2H), 7.68 (m, 3H), 7.48 (d, J=9 Hz, 1H), 5.99 (s, 1H), 4.58 (m, 2H), 3.65 (m, 4H), 3.53 (m, 2H), 3.17 (m, 2H).

Step 3: 2-(2,6-dichloro-3-(morpholine-4-carbonyl)benzyl)-1H-indole-5-carbonitrile

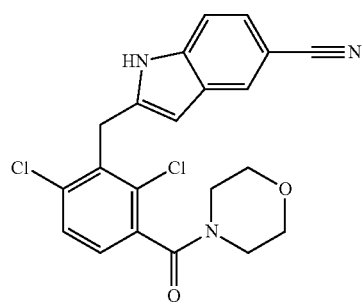 [SMILES: N#Cc1ccc2[nH]c(Cc3c(Cl)ccc(C(=O)N4CCOCC4)c3Cl)cc2c1]

Using a procedure similar to Example A, Step 3, 2-(2,6-dichloro-3-(morpholine-4-carbonyl)benzyl)-1H-indole-5-carbonitrile (465 mg, 85%) was obtained as a yellow solid from 2-(2,6-dichloro-3-(morpholine-4-carbonyl)benzyl)-1-(phenylsulfonyl)-1H-indole-5-carbonitrile (670 mg, 1.208 mmol).

LC/MS (Method h) $R_t$=2.40 min.; MS m/z: 414 [M+H]$^+$ $^1$H NMR (DMSO-d$_6$, 300 MHz): δ 11.70 (s, 1H), 7.90 (s, 1H), 7.64 (d, J=9 Hz, 1H), 7.47 (m, 1H), 7.39 (m, 2H), 5.96 (s, 1H), 4.44 (s, 2H), 3.65 (m, 4H), 3.52 (m, 2H), 3.17 (m, 2H).

Step 4: 2-(2,6-dichloro-3-(morpholine-4-carbonyl)benzyl)-1-methyl-1H-indole-5-carbonitrile

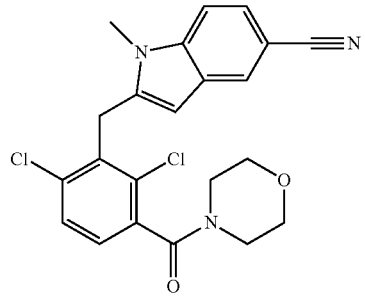 [SMILES: Cn1c(Cc2c(Cl)ccc(C(=O)N3CCOCC3)c2Cl)cc2cc(C#N)ccc21]

Using a procedure similar to Example P, Step 4, 2-(2,6-dichloro-3-(morpholine-4-carbonyl)benzyl)-1-methyl-1H-indole-5-carbonitrile (115 mg, 56%) was obtained as a white solid from 2-(2,6-dichloro-3-(morpholine-4-carbonyl)benzyl)-1H-indole-5-carbonitrile (200 mg, 0.483 mmol).

LC/MS (Method g) $R_t$=1.49 min.; MS m/z: 428 [M+H]$^+$ $^1$H NMR (DMSO-d$_6$, 400 MHz): δ 7.90 (m, 1H), 7.68 (d, J=8 Hz, 1H), 7.65 (d, J=8 Hz, 1H), 7.46 (m, 2H), 5.73 (s, 1H), 4.44 (s, 2H), 3.90 (s, 3H), 3.65 (m, 4H), 3.55 (m, 2H), 3.19 (m, 2H).

Example AC: 2-(2,6-dichloro-3-(morpholine-4-carbonyl)benzyl)-1-methyl-1H-indole-6-carbonitrile

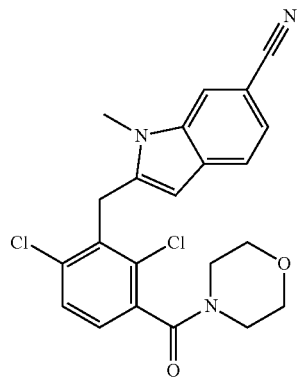 [SMILES: Cn1c(Cc2c(Cl)ccc(C(=O)N3CCOCC3)c2Cl)cc2ccc(C#N)cc21]

315

Step 1: methyl 2,4-dichloro-3-((6-cyano-1-(phenyl-sulfonyl)-1H-indol-2-yl)(hydroxy)methyl)benzoate

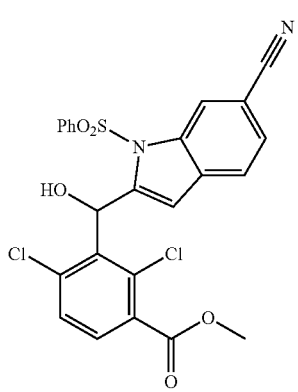

Using a procedure similar to Example A, Step 1, methyl 2,4-dichloro-3-((6-cyano-1-(phenylsulfonyl)-1H-indol-2-yl)(hydroxy)methyl)benzoate (715 mg, 89%) was obtained as a white solid from N-(5-cyano-2-iodophenyl)benzenesulfonamide (Preparation #20) (600 mg, 1.562 mmol) and methyl 2,4-dichloro-3-(1-hydroxyprop-2-yn-1-yl)benzoate (Preparation #1) (445 mg, 1.718 mmol). LC/MS (Method h) $R_t$=2.87 min.; MS m/z: 573 [M–H]⁻+CH₃COOH ¹H NMR (DMSO-d₆, 300 MHz): δ 8.40 (s, 1H), 7.98 (dd, J=3 Hz, 9 Hz, 2H), 7.79 (d, J=6 Hz, 1H), 7.68 (m, 3H), 7.58 (m, 3H), 7.03 (dd, J=3 Hz, 6 Hz, 1H), 6.82 (s, 1H), 6.76 (d, J=6 Hz, 1H), 3.86 (s, 3H).

Step 2: methyl 2,4-dichloro-3-((6-cyano-1-(phenyl-sulfonyl)-1H-indol-2-yl)methyl)benzoate

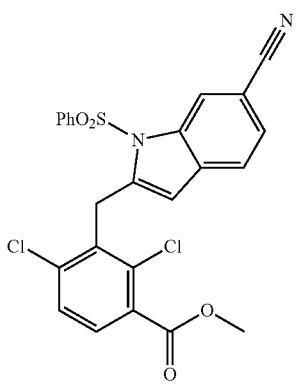

Using a procedure similar to Example A, Step 2, methyl 2,4-dichloro-3-((6-cyano-1-(phenylsulfonyl)-1H-indol-2-yl)methyl)benzoate (400 mg, 100%) was obtained as a yellow solid from methyl 2,4-dichloro-3-((6-cyano-1-(phenylsulfonyl)-1H-indol-2-yl)(hydroxy)methyl)benzoate (400 mg, 0.776 mmol). LC/MS (Method h) $R_t$=3.39 min.; MS m/z: 497 [M–H]⁻ ¹H NMR (DMSO-d₆, 300 MHz): δ 8.51 (s, 1H), 8.07 (d, J=9 Hz, 2H), 7.80 (m, 2H), 7.68 (m, 5H), 6.00 (s, 1H), 4.62 (s, 2H), 3.86 (s, 3H).

316

Step 3: methyl 2,4-dichloro-3-((6-cyano-1H-indol-2-yl)methyl)benzoate

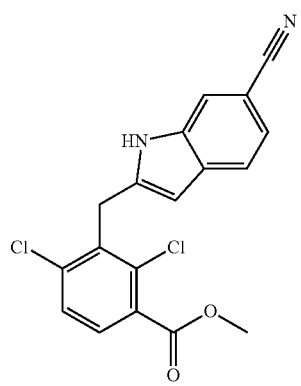 [SMILES: COC(=O)c1ccc(Cl)c(Cc2cc3ccc(C#N)cc3[nH]2)c1Cl]

Using a procedure similar to Example A, Step 3, methyl 2,4-dichloro-3-((6-cyano-1H-indol-2-yl)methyl)benzoate (213 mg, 74%) was obtained as a yellow solid from methyl 2,4-dichloro-3-((6-cyano-1-(phenylsulfonyl)-1H-indol-2-yl)methyl)benzoate (400 mg, 0.801 mmol). LC/MS (Method h) $R_t$=2.93 min.; MS m/z: 359 [M+H]⁺ ¹H NMR (DMSO-d₆, 300 MHz): δ 11.65 (broad, 1H), 7.79 (d, J=9 Hz, 1H), 7.74 (s, 1H), 7.68 (d, J=9 Hz, 1H), 7.54 (d, J=9 Hz, 1H), 7.27 (dd, J=3 Hz, 9 Hz, 1H), 7.98 (s, 1H), 4.50 (s, 2H), 3.87 (s, 3H).

Step 4: methyl 2,4-dichloro-3-((6-cyano-1-methyl-1H-indol-2-yl)methyl)benzoate

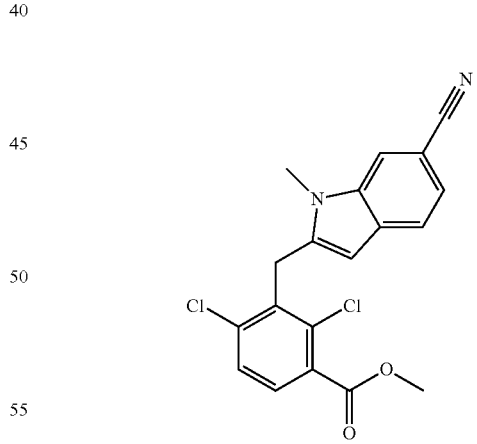

Using a procedure similar to Example P, Step 4, methyl 2,4-dichloro-3-((6-cyano-1-methyl-1H-indol-2-yl)methyl)benzoate (210 mg, 93%) was obtained as a white solid from methyl 2,4-dichloro-3-((6-cyano-1H-indol-2-yl)methyl)benzoate (210 mg, 0.585 mmol). LC/MS (Method h) $R_t$=3.04 min.; MS m/z: 373 [M+H]⁺ ¹H NMR (DMSO-d₆, 300 MHz): δ 8.08 (s, 1H), 7.80 (d, J=9 Hz, 1H), 7.72 (d, J=9 Hz, 1H), 7.53 (d, J=9 Hz, 1H), 7.30 (dd, J=3 Hz, 9 Hz, 1H), 5.71 (s, 1H), 4.50 (s, 2H), 3.92 (s, 3H), 3.88 (s, 3H).

Step 5: 2,4-dichloro-3-((6-cyano-1-methyl-1H-indol-2-yl)methyl)benzoic acid

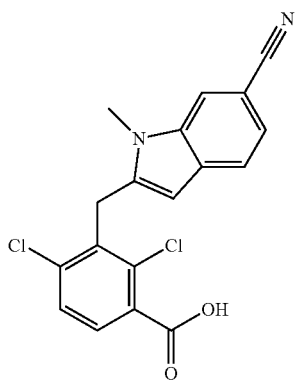 [SMILES: Cn1c(Cc2c(Cl)ccc(C(=O)O)c2Cl)cc2ccc(C#N)cc21]

Using a procedure similar to Example A, Step 5, 2,4-dichloro-3-((6-cyano-1-methyl-1H-indol-2-yl)methyl)benzoic acid (170 mg, 88%) was obtained as a white solid from methyl 2,4-dichloro-3-((6-cyano-1-methyl-1H-indol-2-yl)methyl)benzoate (200 mg, 0.536 mmol). LC/MS (Method h) R$_t$=2.61 min.; MS m/z: 359 [M+H]$^+$ $^1$H NMR (DMSO-d$_6$, 300 MHz): δ 8.08 (d, J=3 Hz, 1H), 7.75 (d, J=9 Hz, 1H), 7.66 (d, J=9 Hz, 1H), 7.54 (d, J=9 Hz, 1H), 7.30 (dd, J=3 Hz, 9 Hz, 1H), 5.71 (s, 1H), 4.50 (s, 2H), 3.92 (s, 3H).

Step 6: 2-(2,6-dichloro-3-(morpholine-4-carbonyl)benzyl)-1-methyl-1H-indole-6-carbonitrile

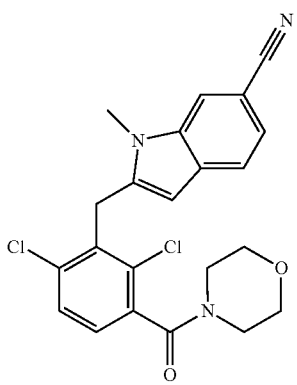 [SMILES: Cn1c(Cc2c(Cl)ccc(C(=O)N3CCOCC3)c2Cl)cc2ccc(C#N)cc21]

Using a procedure similar to Example A, Step 6, 2-(2,6-dichloro-3-(morpholine-4-carbonyl)benzyl)-1-methyl-1H-indole-6-carbonitrile (100 mg, 50%) was obtained as a white solid from 2,4-dichloro-3-((6-cyano-1-methyl-1H-indol-2-yl)methyl)benzoic acid (165 mg, 0.459 mmol) and morpholine (80 mg, 0.92 mmol). LC/MS (Method g) R$_t$=1.53 min.; MS m/z: 428 [M+H]$^+$ $^1$H NMR (DMSO-d$_6$, 400 MHz): δ 8.08 (s, 1H), 7.67 (d, J=8 Hz, 1H), 7.54 (d, J=8 Hz, 1H), 7.45 (d, J=8 Hz, 1H), 7.30 (dd, J=3 Hz, 8 Hz, 1H), 5.75 (s, 1H), 4.46 (s, 2H), 3.92 (s, 3H), 3.65 (m, 4H), 3.54 (m, 2H), 3.18 (m, 2H).

Example AD: 2-(2,6-dichloro-3-(morpholine-4-carbonyl)benzoyl)-1,4-dimethyl-1H-indole-6-carbonitrile

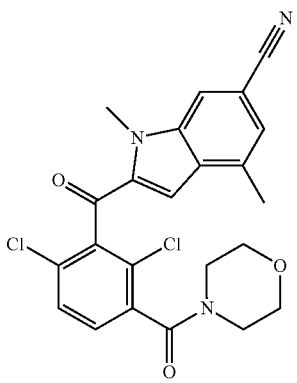 [SMILES: Cc1cc(C#N)cc2c1cc(C(=O)c1c(Cl)ccc(C(=O)N3CCOCC3)c1Cl)n2C]

Step 1: 2-((2,6-dichloro-3-(morpholine-4-carbonyl)phenyl)(hydroxyl)methyl)-4-methyl-1-(phenylsulfonyl)-1H-indole-6-carbonitrile

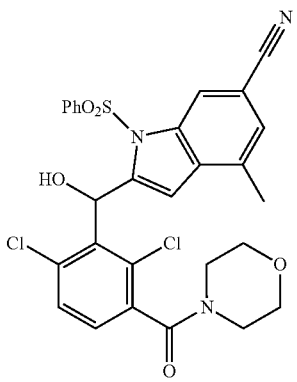

Using a procedure similar to example A, Step 1, 2-((2,6-dichloro-3-(morpholine-4-carbonyl)phenyl)(hydroxy)methyl)-4-methyl-1-(phenylsulfonyl)-1H-indole-6-carbonitrile (3 g, 41%) was obtained as an orange solid from N-(2-bromo-5-cyano-3-methylphenyl)benzenesulfonamide (Preparation #46) (3.6 g, 10.25 mmol) and (2,4-dichloro-3-(1-hydroxyprop-2-yn-1-yl)phenyl)(morpholino)methanone (Preparation #3) (4.83 g, 15.38 mmol). LC/MS (Method h) R$_t$=2.60 min.; MS m/z: 584 [M+H]$^+$ $^1$H NMR (CDCl$_3$, 300 MHz): δ 8.30 (s, 1H), 7.92 (m, 2H), 7.54 (m, 2H), 7.47 (m, 3H), 7.28 (m, 3H), 6.43 and 6.31 (s, 1H), 3.81 (m, 4H), 3.67 (m, 2H), 3.29 (m, 2H), 2.40 (s, 3H).

Step 2: 2-(2,6-dichloro-3-(morpholine-4-carbonyl)benzoyl)-4-methyl-1-(phenylsulfonyl)-1H-indole-6-carbonitrile

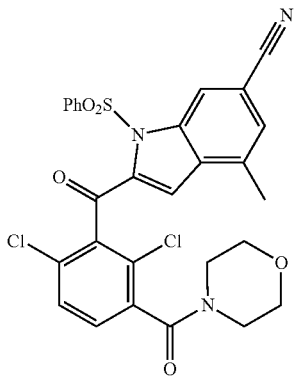

To a solution of 2-((2,6-dichloro-3-(morpholine-4-carbonyl)phenyl)(hydroxy)methyl)-4-methyl-1-(phenylsulfonyl)-1H-indole-6-carbonitrile (321 mg, 0.549 mmol) in DCM (5 mL) was added Dess-Martin periodinane (2.284 mL, 1.098 mmol). The reaction was stirred at room temperature for 2 hours then filtered and washed with ACN. The filtrate was washed with NaHCO₃ saturated aqueous solution, brine and dried over magnesium sulfate; then concentrated to give 2-(2,6-dichloro-3-(morpholine-4-carbonyl)benzoyl)-4-methyl-1-(phenylsulfonyl)-1H-indole-6-carbonitrile as a yellow solid (252 mg, 72%). LC/MS (Method h) $R_t$=2.79 min.; MS m/z: 582 [M+H]⁺

¹H NMR (DMSO-d₆, 300 MHz): δ 8.53 (s, 1H), 8.28 (m, 2H), 7.80 (m, 1H), 7.73 (m, 4H), 7.65 (m, 2H), 3.63 (m, 4H), 3.52 (m, 2H), 3.23 (m, 2H), 2.48 (s, 3H).

Step 3: 2-(2,6-dichloro-3-(morpholine-4-carbonyl)benzoyl)-4-methyl-1H-indole-6-carbonitrile

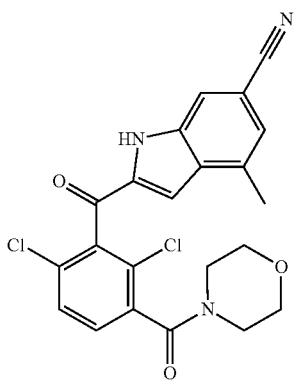 [SMILES: Cc1cc(C#N)cc2[nH]c(C(=O)c3c(Cl)ccc(C(=O)N4CCOCC4)c3Cl)cc12]

Using a procedure similar to Example A, Step 3, 2-(2,6-dichloro-3-(morpholine-4-carbonyl)benzoyl)-4-methyl-1H-indole-6-carbonitrile (165 mg, 73%) was obtained as a yellow solid from 2-(2,6-dichloro-3-(morpholine-4-carbonyl)benzoyl)-4-methyl-1-(phenylsulfonyl)-1H-indole-6-carbonitrile (250 mg, 0.429 mmol). LC/MS (Method h) $R_t$=2.34 min.; MS m/z: 442 [M+H]⁺

¹H NMR (DMSO-d₆, 300 MHz): δ 12.72 (broad, 1H), 7.79 (m, 2H), 7.66 (d, J=6 Hz, 1H), 7.33 and 7.12 (s, 1H), 7.24 (s, 1H), 3.66 (m, 4H), 3.56 (m, 2H), 3.18 (m, 2H), 2.48 (s, 3H).

Step 4: 2-(2,6-dichloro-3-(morpholine-4-carbonyl)benzoyl)-1,4-dimethyl-1H-indole-6-carbonitrile

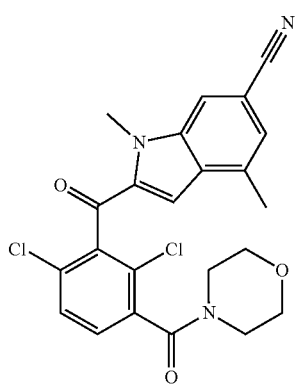 [SMILES: Cc1cc(C#N)cc2c1cc(C(=O)c1c(Cl)ccc(C(=O)N3CCOCC3)c1Cl)n2C]

Using a procedure similar to Example A, Step 4, 2-(2,6-dichloro-3-(morpholine-4-carbonyl)benzoyl)-1,4-dimethyl-1H-indole-6-carbonitrile (49 mg, 29%) was obtained as a yellow solid from 2-(2,6-dichloro-3-(morpholine-4-carbonyl)benzoyl)-4-methyl-1H-indole-6-carbonitrile (160 mg, 0.362 mmol). LC/MS (Method g) $R_t$=1.58 min.; MS m/z: 456 [M+H]⁺

¹H NMR (DMSO-d₆, 400 MHz): δ 8.21 (s, 1H), 7.75 (d, J=8 Hz, 1H), 7.65 (d, J=8 Hz, 1H), 7.30 and 7.10 (broad, 1H), 7.29 (s, 1H), 4.20 (s, 3H), 3.65 (m, 4H), 3.54 (m, 2H), 3.19 (m, 2H), 2.48 (s, 3H).

Example AE: 2-(2,6-dimethyl-3-(morpholine-4-carbonyl)benzyl)-1,4-dimethyl-1H-indole-6-carbonitrile

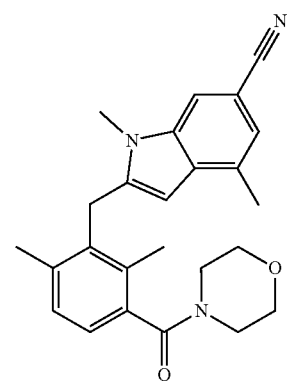 [SMILES: Cc1ccc(C(=O)N2CCOCC2)c(C)c1Cc1cc2c(C)cc(C#N)cc2n1C]

Step 1: 2-((2,6-dimethyl-3-(morpholine-4-carbonyl)phenyl)(hydroxy)methyl)-4-methyl-1-(phenylsulfonyl)-1H-indole-6-carbonitrile

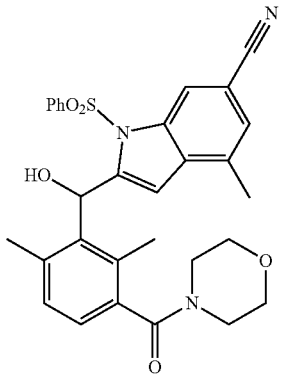

Using a procedure similar to Example A, Step 1, 2-((2,6-dimethyl-3-(morpholine-4-carbonyl)phenyl)(hydroxy)methyl)-4-methyl-1-(phenylsulfonyl)-1H-indole-6-carbonitrile (730 mg, 71%) was obtained as a yellow oil from N-(5-cyano-2-iodo-3-methylphenyl)benzenesulfonamide (Preparation #18) (730 mg, 1.833 mmol) and (3-(1-hydroxyprop-2-yn-1-yl)-2,4-dimethylphenyl)(morpholino)methanone (Preparation #4) (601 mg, 2.2 mmol).

LC/MS (Method h) $R_t$=2.66 min.; MS m/z: 544 [M+H]$^+$ $^1$H NMR (DMSO-d$_6$, 300 MHz): δ 8.24 (d, J=9 Hz, 1H), 8.08 (d, J=9 Hz, 1H), 7.97 (d, J=9 Hz, 1H), 7.95 (s, 1H), 7.71 (t, J=9 Hz, 1H), 7.59 (t, J=9 Hz, 2H), 7.48 (s, 1H), 7.06 (m, 1H), 6.78 and 6.72 (s, 1H), 6.80 and 6.42 (s, 1H), 6.30 (broad, 1H), 3.64 (m, 4H), 3.47 (m, 2H), 3.12 (m, 2H), 2.89 (s, 3H), 2.73 (s, 3H), 2.36 and 2.39 (s, 3H).

Step 2: 2-(2,6-dimethyl-3-(morpholine-4-carbonyl)benzyl)-4-methyl-1-(phenylsulfonyl)-1H-indole-6-carbonitrile

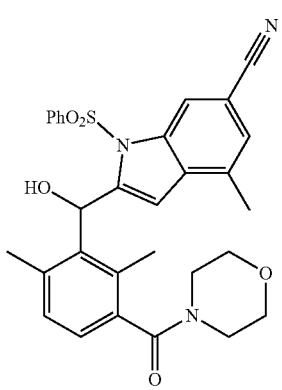

Using a procedure similar to Example A, Step 2, 2-(2,6-dimethyl-3-(morpholine-4-carbonyl)benzyl)-4-methyl-1-(phenylsulfonyl)-1H-indole-6-carbonitrile (700 mg, 100%) was obtained as a yellow solid from 2-((2,6-dimethyl-3-(morpholine-4-carbonyl)phenyl)(hydroxy)methyl)-4-methyl-1-(phenylsulfonyl)indoline-6-carbonitrile (725 mg, 1.329 mmol). LC/MS (Method h) $R_t$=2.94 min.; MS m/z: 528 [M+H]$^+$. $^1$H NMR (DMSO-d$_6$, 300 MHz): δ 8.39 (s, 1H), 8.08 (m, 2H), 7.81 (m, 1H), 7.67 (m, 2H), 7.47 (s, 1H), 7.18 (d, J=9 Hz, 1H), 7.07 (d, J=9 Hz, 1H), 5.73 (s, 1H), 4.28 (m, 2H), 3.62 (m, 4H), 3.44 (m, 2H), 3.09 (m, 2H), 2.26 (s, 3H), 2.06 (s, 3H), 1.89 (s, 3H).

Step 3: 2-(2,6-dimethyl-3-(morpholine-4-carbonyl)benzyl)-4-methyl-1H-indole-6-carbonitrile

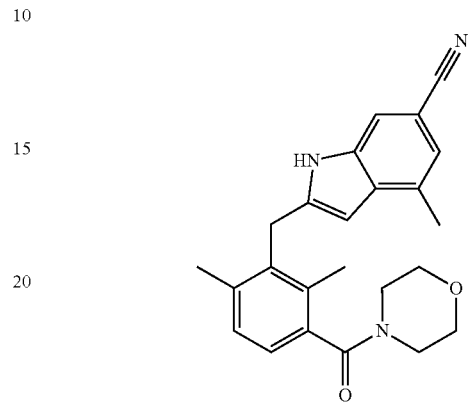

Using a procedure similar to Example A, Step 3, 2-(2,6-dimethyl-3-(morpholine-4-carbonyl)benzyl)-4-methyl-1H-indole-6-carbonitrile (380 mg, 64%) was obtained as a yellow solid from 2-(2,6-dimethyl-3-(morpholine-4-carbonyl)benzyl)-4-methyl-1-(phenylsulfonyl)-1H-indole-6-carbonitrile (700 mg, 1.327 mmol). LC/MS (Method h) $R_t$=2.52 min.; MS m/z: 388 [M+H]$^+$ $^1$H NMR (DMSO-d$_6$, 300 MHz): δ 11.56 (broad, 1H), 7.61 (s, 1H), 7.17 (d, J=6 Hz, 1H), 7.06 (m, 1H), 7.03 (d, J=6 Hz, 1H), 5.83 (s, 1H), 4.18 (s, 2H), 3.64 (m, 4H), 3.47 (m, 2H), 3.12 (m, 2H), 2.35 (s, 3H), 2.30 (s, 3H), 2.13 (s, 3H).

Step 4: 2-(2,6-dimethyl-3-(morpholine-4-carbonyl)benzyl)-1,4-dimethyl-1H-indole-6-carbonitrile

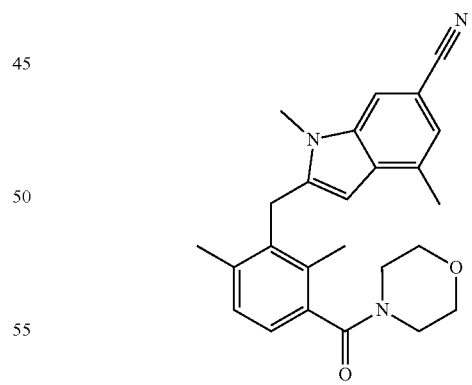

Using a procedure similar to Example P, Step 4, 2-(2,6-dimethyl-3-(morpholine-4-carbonyl)benzyl)-1,4-dimethyl-1H-indole-6-carbonitrile (70 mg, 33%) was obtained as a pink solid from 2-(2,6-dimethyl-3-(morpholine-4-carbonyl)benzyl)-4-methyl-1H-indole-6-carbonitrile (200 mg, 0.516 mmol).

LC/MS (Method g) $R_t$=1.56 min.; MS m/z: 402 [M+H]$^+$. $^1$H NMR (DMSO-d$_6$, 400 MHz): δ 7.90 (s, 1H), 7.19 (d, J=8 Hz, 1H), 7.09 (m, 1H), 7.07 (d, J=8 Hz, 1H), 5.53 (s, 1H), 4.18 (m, 2H), 3.90 (s, 3H), 3.65 (m, 4H), 3.50 (m, 2H), 3.13 (m, 2H), 2.29 (s, 3H), 2.25 (s, 3H), 2.10 (s, 3H).

Example AF: trans-4-(2,4-dichloro-3-((6-cyano-1,4-dimethyl-1H-indol-2-yl)methyl)phenoxy)cyclohexanecarboxylic acid Example AF1: cis-4-(2,4-dichloro-3-((6-cyano-1,4-dimethyl-1H-indol-2-yl)methyl)phenoxy)cyclohexanecarboxylic acid

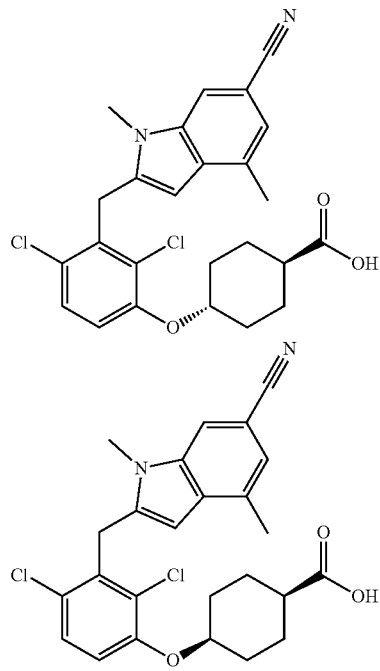

Step 1: 2-((2,6-dichloro-3-methoxyphenyl)(hydroxy)methyl)-4-methyl-1-(phenylsulfonyl)-1H-indole-6-carbonitrile

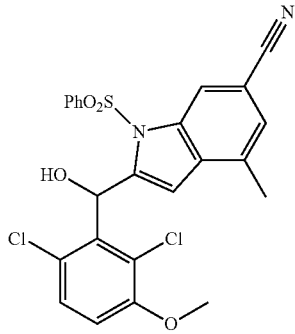

Using a procedure similar to Example A, Step 1, 2-((2,6-dichloro-3-methoxyphenyl)(hydroxy)methyl)-4-methyl-1-(phenylsulfonyl)-1H-indole-6-carbonitrile (2.25 g, 67%) was obtained as a beige solid from 1-(2,6-dichloro-3-methoxyphenyl)prop-2-yn-1-ol (Preparation #7) (1.810 g, 7.83 mmol) and N-(5-cyano-2-iodo-3-methylphenyl)benzenesulfonamide (Preparation #18) (2.4 g, 6.03 mmol). LC/MS (Method h) $R_t$=2.99 min.; MS m/z: 559 [M−H]⁻+ CH₃COOH.
$^1$H NMR (DMSO-d$_6$, 300 MHz): δ 8.24 (s, 1H), 7.90 (m, 2H), 7.68 (m, 1H), 7.57 (m, 2H), 7.49 (s, 1H), 7.40 (d, J=9 Hz, 1H), 7.14 (d, J=9 Hz, 1H), 6.98 (dd, J=3 Hz, 6 Hz, 1H), 6.79 (s, 1H), 6.62 (d, J=6 Hz, 1H), 3.86 (s, 3H), 2.41 (s, 3H).

Step 2: 2-(2,6-dichloro-3-methoxybenzyl)-4-methyl-1-(phenylsulfonyl)-1H-indole-6-carbonitrile

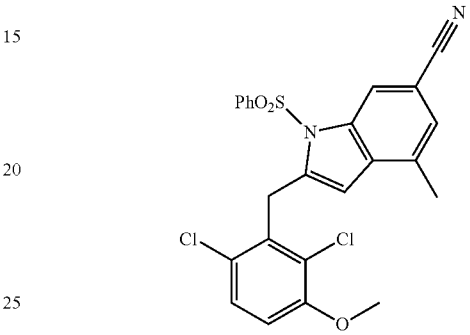

Using a procedure similar to Example A, Step 2, 2-(2,6-dichloro-3-methoxybenzyl)-4-methyl-1-(phenylsulfonyl)-1H-indole-6-carbonitrile (1.99 g, 84%) was obtained as a yellow solid from 2-((2,6-dichloro-3-methoxyphenyl)(hydroxy)methyl)-4-methyl-1-(phenylsulfonyl)-1H-indole-6-carbonitrile (2.2 g, 4.39 mmol). LC/MS (Method h) $R_t$=3.50 min.; MS m/z: 485 [M+H]⁺ $^1$H NMR (DMSO-d$_6$, 300 MHz): δ 8.36 (s, 1H), 8.06 (m, 2H), 7.79 (t, J=9 Hz, 1H), 7.67 (t, J=9 Hz, 2H), 7.52 (d, J=9 Hz, 1H), 7.48 (s, 1H), 7.28 (d, J=9H, 1H), 7.89 (s, 1H), 4.56 (s, 2H), 3.89 (s, 3H), 2.30 (s, 3H).

Step 3: 2-(2,6-dichloro-3-methoxybenzyl)-4-methyl-1H-indole-6-carbonitrile

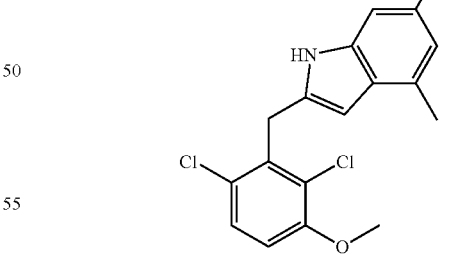

Using a procedure similar to Example A, Step 3, 2-(2,6-dichloro-3-methoxybenzyl)-4-methyl-1H-indole-6-carbonitrile (1.22 g, 78%) was obtained as a beige solid from 2-(2,6-dichloro-3-methoxybenzyl)-4-methyl-1-(phenylsulfonyl)-1H-indole-6-carbonitrile (1.99 g, 4.10 mmol).
LC/MS (Method h) $R_t$=3.10 min.; MS m/z: 345 [M+H]⁺.
$^1$H NMR (DMSO-d$_6$, 300 MHz): δ 11.61 (broad, 1H), 7.63 (s, 1H), 7.52 (d, J=9 Hz, 1H), 7.18 (d, J=9 Hz, 1H), 7.07 (s, 1H), 5.96 (s, 1H), 4.42 (s, 2H), 3.89 (s, 3H), 2.36 (s, 3H).

Step 4: 2-(2,6-dichloro-3-methoxybenzyl)-1,4-dimethyl-1H-indole-6-carbonitrile

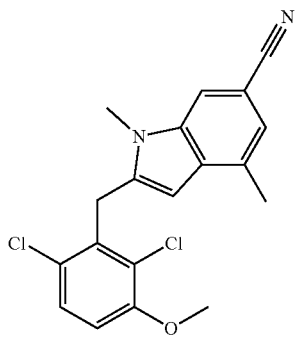 [SMILES: COc1ccc(Cl)c(Cc2cc3c(C)cc(C#N)cc3n2C)c1Cl]

Using a procedure similar to Example P, Step 4, 2-(2,6-dichloro-3-methoxybenzyl)-1,4-dimethyl-1H-indole-6-carbonitrile (1.20 g, 80%) was obtained as a pink solid from 2-(2,6-dichloro-3-methoxybenzyl)-4-methyl-1H-indole-6-carbonitrile (1.2 g, 3.48 mmol). LC/MS (Method g) $R_t$=1.96 min.; MS m/z: 359 [M+H]$^+$ $^1$H NMR (DMSO-d$_6$, 300 MHz): δ 7.91 (s, 1H), 7.55 (d, J=9 Hz, 1H), 7.21 (d, J=9 Hz, 1H), 7.10 (s, 1H), 5.68 (s, 1H), 4.41 (s, 2H), 3.91 (s, 3H), 3.90 (s, 3H), 2.32 (s, 3H).

Step 5: 2-(2,6-dichloro-3-hydroxybenzyl)-1,4-dimethyl-1H-indole-6-carbonitrile

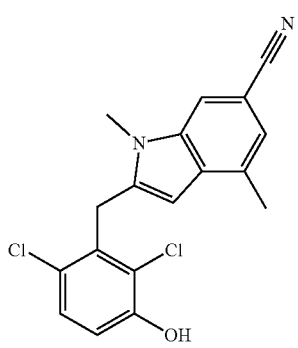 [SMILES: Cc1cc(C#N)cc2c1cc(Cc1c(Cl)ccc(O)c1Cl)n2C]

Using a procedure similar to Example X, 2-(2,6-dichloro-3-hydroxybenzyl)-1,4-dimethyl-1H-indole-6-carbonitrile (63 mg, 67%) was obtained as a white solid from 2-(2,6-dichloro-3-methoxybenzyl)-1,4-dimethyl-1H-indole-6-carbonitrile (200 mg, 0.557 mmol). LC/MS (Method g) $R_t$=1.71 min.; MS m/z: 345 [M+H]$^+$ $^1$H NMR (DMSO-d$_6$, 400 MHz): δ 10.58 (broad, 1H), 7.90 (s, 1H), 7.36 (d, J=8 Hz, 1H), 7.10 (s, 1H), 7.02 (d, J=8 Hz, 1H), 5.69 (s, 1H), 4.38 (s, 2H), 3.89 (s, 3H), 2.33 (s, 3H).

Step 6: ethyl trans-4-(2,4-dichloro-3-((6-cyano-1,4-dimethyl-1H-indol-2-yl)methyl)phenoxy)cyclohexanecarboxylate and ethyl cis-4-(2,4-dichloro-3-((6-cyano-1,4-dimethyl-1H-indol-2-yl)methyl)phenoxy)cyclohexanecarboxylate

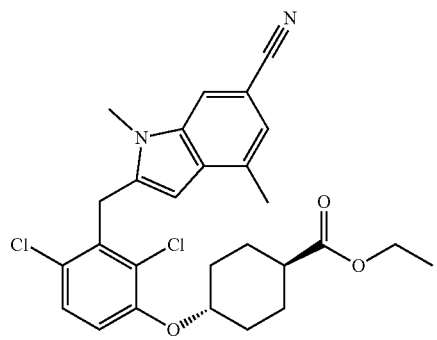

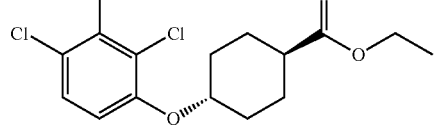

To a solution of ethyl 4-((methylsulfonyl)oxy)cyclohexanecarboxylate (described in WO2011/035159) (75 mg, 0.300 mmol) in DMSO (0.5 mL) was added 2-(2,6-dichloro-3-hydroxybenzyl)-1,4-dimethyl-1H-indole-6-carbonitrile (100 mg, 0.290 mmol) and cesium carbonate (123 mg, 0.377 mmol) in DMSO (0.5 mL). The reaction was stirred at 90° C. for 26 hours. The mixture was diluted with water and extracted with EtOAc. The organic layer was washed with brine and concentrated. The residue was purified by column chromatography on silica gel (eluting with 10% EtOAc in cyclohexane) to give ethyl trans-4-(2,4-dichloro-3-((6-cyano-1,4-dimethyl-1H-indol-2-yl)methyl)phenoxy)cyclohexanecarboxylate (15 mg, 10%) LC/MS (Method k) $R_t$=4.04 min.; MS m/z: 499 [M+H]$^+$ $^1$H NMR (DMSO-d$_6$, 300 MHz): δ 7.91 (s, 1H), 7.48 (d, J=9 Hz, 1H), 7.31 (d, J=9 Hz, 1H), 7.11 (s, 1H), 5.68 (s, 1H), 4.47 (m, 1H), 4.40 (s, 2H), 4.08 (m, 2H), 3.89 (s, 3H), 2.37 (m, 1H), 2.32 (s, 3H), 2.06 (m, 2H), 1.94 (m, 2H), 1.51 (m, 4H), 1.16 (m, 3H) and ethyl cis-4-(2,4-dichloro-3-((6-cyano-1,4-dimethyl-1H-indol-2-yl)methyl)phenoxy)cyclohexanecarboxylate (26 mg, 18%) as white solids. LC/MS (Method k) $R_t$=4.04 min.; MS m/z: 499 [M+H]$^+$. $^1$H NMR (DMSO-d$_6$, 300 MHz): δ 7.91 (s, 1H), 7.48 (d, J=9 Hz, 1H), 7.31 (d, J=9 Hz, 1H), 7.11 (s, 1H), 5.68 (s, 1H), 4.47 (m, 1H), 4.40 (s, 2H), 4.08 (m, 2H), 3.89 (s, 3H), 2.37 (m, 1H), 2.32 (s, 3H), 2.06 (m, 2H), 1.94 (m, 2H), 1.51 (m, 4H), 1.16 (m, 3H).

Step 7: trans-4-(2,4-dichloro-3-((6-cyano-1,4-dimethyl-1H-indol-2-yl)methyl)phenoxy)cyclohexanecarboxylic acid

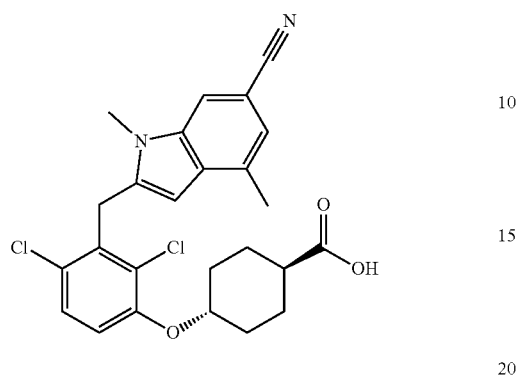

Using a procedure similar to Example A, Step 5, trans-4-(2,4-dichloro-3-((6-cyano-1,4-dimethyl-1H-indol-2-yl)methyl)phenoxy)cyclohexanecarboxylic acid (16.5 mg, 45%) was obtained as a white solid from ethyl trans-4-(2,4-dichloro-3-((6-cyano-1,4-dimethyl-1H-indol-2-yl)methyl)phenoxy)cyclohexanecarboxylate (37 mg, 0.074 mmol). LC/MS (Method g) $R_t$=1.87 min.;

MS m/z: 471 [M+H]$^+$ $^1$H NMR (DMSO-d$_6$, 500 MHz): δ 12.12 (broad, 1H), 7.90 (s, 1H), 7.48 (d, J=9 Hz, 1H), 7.30 (d, J=9 Hz, 1H), 7.10 (s, 1H), 5.69 (s, 1H), 4.45 (m, 1H), 4.40 (s, 2H), 3.89 (s, 3H), 2.32 (s, 3H), 2.28 (m, 1H), 2.08 (m, 2H), 1.95 (m, 2H), 1.49 (m, 4H).

Step 7a: cis-4-(2,4-dichloro-3-((6-cyano-1,4-dimethyl-1H-indol-2-yl)methyl)phenoxy)cyclohexanecarboxylic acid

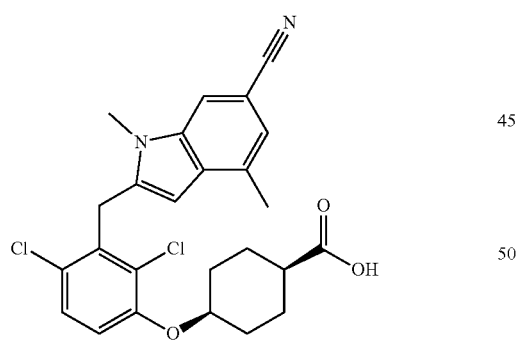

Using a procedure similar to Example A, Step 5, cis-4-(2,4-dichloro-3-((6-cyano-1,4-dimethyl-1H-indol-2-yl)methyl)phenoxy)cyclohexanecarboxylic acid (14.5 mg, 54%) was obtained as a white solid from ethyl cis-4-(2,4-dichloro-3-((6-cyano-1,4-dimethyl-1H-indol-2-yl)methyl)phenoxy)cyclohexanecarboxylate (26 mg, 0.052 mmol). LC/MS (Method g) $R_t$=1.89 min.;

MS m/z: 471 [M+H]$^+$ $^1$H NMR (DMSO-d$_6$, 500 MHz): δ 12.10 (broad, 1H), 7.91 (s, 1H), 7.49 (d, J=9 Hz, 1H), 7.26 (d, J=9 Hz, 1H), 7.11 (s, 1H), 5.69 (s, 1H), 4.72 (m, 1H), 4.41 (s, 2H), 3.90 (s, 3H), 2.39 (m, 1H), 2.32 (s, 3H), 1.87 (m, 2H), 1.77 (m, 2H), 1.69 (m, 4H).

Example AG: trans-3-(2,4-dichloro-3-((6-cyano-1,4-dimethyl-1H-indol-2-yl)methyl)phenoxy)cyclopentanecarboxylic acid Example AG1: cis-3-(2,4-dichloro-3-((6-cyano-1,4-dimethyl-1H-indol-2-yl)methyl)phenoxy)cyclopentanecarboxylic acid

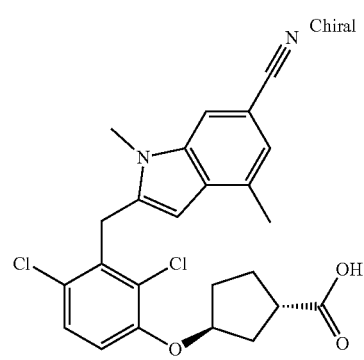

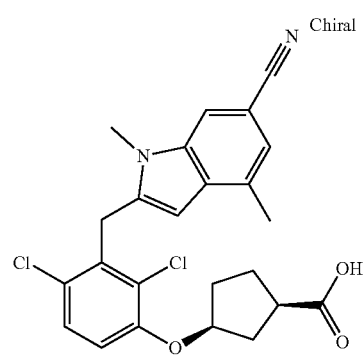

Step 1: ethyl trans-3-(2,4-dichloro-3-((6-cyano-1,4-dimethyl-1H-indol-2-yl)methyl)phenoxy)cyclopentanecarboxylate and ethyl cis-3-(2,4-dichloro-3-((6-cyano-1,4-dimethyl-1H-indol-2-yl)methyl)phenoxy)cyclopentanecarboxylate

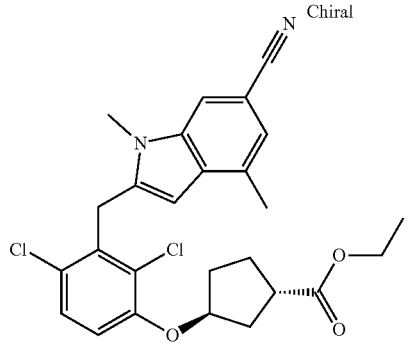

-continued

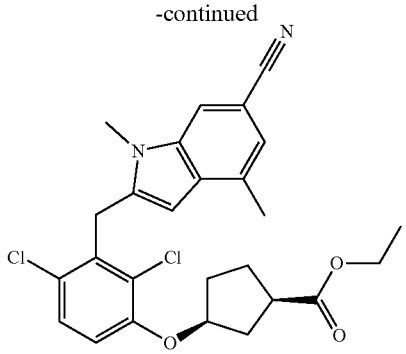

Using a procedure similar to Example AF, Step 6, ethyl trans-3-(2,4-dichloro-3-((6-cyano-1,4-dimethyl-1H-indol-2-yl)methyl)phenoxy)cyclopentanecarboxylate (52 mg, 32%) LC/MS (Method h) $R_t$=3.62 min.; MS m/z: 485 [M+H]$^+$ $^1$H NMR (DMSO-d$_6$, 300 MHz): δ 7.90 (s, 1H), 7.51 (d, J=9 Hz, 1H), 7.21 (d, J=9 Hz, 1H), 7.11 (s, 1H), 5.68 (s, 1H), 5.05 (m, 1H), 4.40 (s, 2H), 4.07 (q, J=6 Hz, 2H), 3.89 (s, 3H), 3.01 (m, 1H), 2.32 (s, 3H), 2.09 (m, 4H), 1.81 (m, 2H), 1.18 (t, J=6 Hz, 3H); and ethyl cis-3-(2,4-dichloro-3-((6-cyano-1,4-dimethyl-1H-indol-2-yl)methyl)phenoxy)cyclopentanecarboxylate (15 mg, 9%) were obtained from 2-(2,6-dichloro-3-hydroxybenzyl)-1,4-dimethyl-1H-indole-6-carbonitrile (Example AF, Step 5) (100 mg, 0.290 mmol) and ethyl 3-((methylsulfonyl)oxy)cyclopentanecarboxylate (Preparation #12) (90 mg, 0.381 mmol)

LC/MS (Method h) $R_t$=3.54 min.; MS m/z: 485 [M+H]$^+$ $^1$H NMR (DMSO-d$_6$, 300 MHz): δ 7.90 (s, 1H), 7.50 (d, J=9 Hz, 1H), 7.20 (d, J=9 Hz, 1H), 7.11 (s, 1H), 5.70 (s, 1H), 4.97 (m, 1H), 4.40 (s, 2H), 4.01 (q, J=6 Hz, 2H), 3.89 (s, 3H), 2.92 (m, 1H), 2.32 (s, 3H), 2.28 (m, 1H), 2.09 (m, 2H), 1.94 (m, 3H), 1.10 (t, J=6 Hz, 3H).

Step 2: trans-3-(2,4-dichloro-3-((6-cyano-1,4-dimethyl-1H-indol-2-yl)methyl)phenoxy)cyclopentanecarboxylic acid

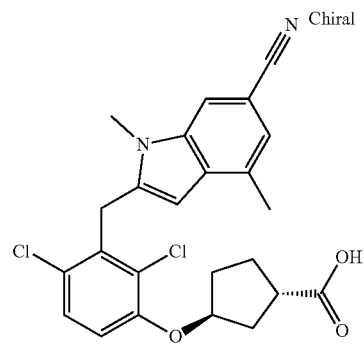 [SMILES: Cc1cc(C#N)cc2c1cc(Cc1c(Cl)ccc(O[C@H]3CC[C@H](C(=O)O)C3)c1Cl)n2C]

Using a procedure similar to Example A, Step 5, trans-3-(2,4-dichloro-3-((6-cyano-1,4-dimethyl-1H-indol-2-yl)methyl)phenoxy)cyclopentanecarboxylic acid (35 mg, 48%) was obtained from ethyl trans-3-(2,4-dichloro-3-((6-cyano-1,4-dimethyl-1H-indol-2-yl)methyl)phenoxy)cyclopentanecarboxylate (73 mg, 0.150 mmol). LC/MS (Method g) $R_t$=1.85 min.; MS m/z: 457 [M+H]$^+$ $^1$H NMR (DMSO-d$_6$, 500 MHz): δ 12.21 (broad, 1H), 7.90 (s, 1H), 7.50 (d, J=9 Hz, 1H), 7.22 (d, J=9 Hz, 1H), 7.10 (s, 1H), 5.69 (s, 1H), 5.04 (m, 1H), 4.40 (s, 2H), 3.89 (s, 3H), 2.94 (m, 1H), 2.32 (s, 3H), 2.11 (m, 2H), 2.05 (m, 2H), 1.80 (m, 2H).

Step 2a: cis-3-(2,4-dichloro-3-((6-cyano-1,4-dimethyl-1H-indol-2-yl)methyl)phenoxy)cyclopentanecarboxylic acid

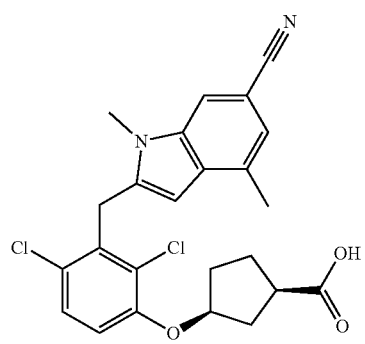 [SMILES: Cc1cc(C#N)cc2c1cc(Cc1c(Cl)ccc(O[C@H]3CC[C@@H](C(=O)O)C3)c1Cl)n2C]

Using a procedure similar to Example A, Step 5, cis-3-(2,4-dichloro-3-((6-cyano-1,4-dimethyl-1H-indol-2-yl)methyl)phenoxy)cyclopentanecarboxylic acid (5 mg, 21%) was obtained from ethyl cis-3-(2,4-dichloro-3-((6-cyano-1,4-dimethyl-1H-indol-2-yl)methyl)phenoxy)cyclopentanecarboxylate (24 mg, 0.049 mmol). LC/MS (Method g) $R_t$=1.83 min.; MS m/z: 457 [M+H]$^+$ $^1$H NMR (DMSO-d$_6$, 500 MHz): δ 12.15 (broad, 1H), 7.90 (s, 1H), 7.50 (d, J=9 Hz, 1H), 7.19 (d, J=9 Hz, 1H), 7.10 (s, 1H), 5.69 (s, 1H), 4.94 (m, 1H), 4.40 (s, 2H), 3.89 (s, 3H), 2.81 (s, 1H), 2.36 (m, 1H), 2.32 (s, 3H), 1.94 (m, 5H).

Example AH: trans-3-(2,4-dichloro-3-((6-cyano-1,4-dimethyl-1H-indol-2-yl)methyl)phenoxy)cyclobutanecarboxylic acid Example AH1: cis-3-(2,4-dichloro-3-((6-cyano-1,4-dimethyl-1H-indol-2-yl)methyl)phenoxy)cyclobutanecarboxylic acid

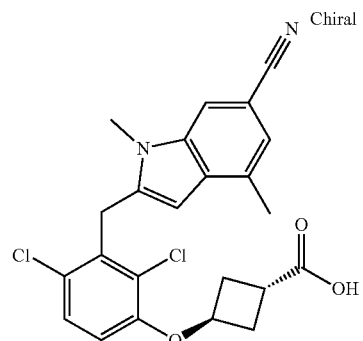

-continued

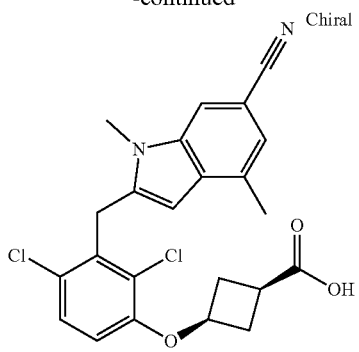

Step 1: ethyl trans-3-(2,4-dichloro-3-((6-cyano-1,4-dimethyl-1H-indol-2-yl)methyl)phenoxy)cyclobutanecarboxylate and ethyl cis-3-(2,4-dichloro-3-((6-cyano-1,4-dimethyl-1H-indol-2-yl)methyl)phenoxy)cyclobutanecarboxylate

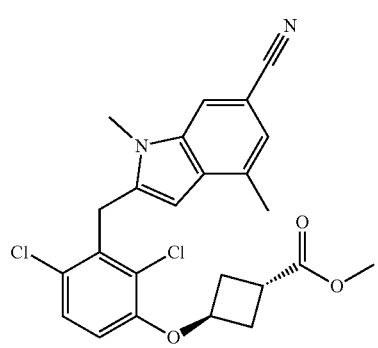

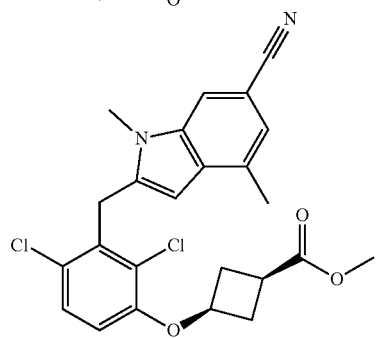

Using a procedure similar to Example AF, Step 6, methyl trans-3-(2,4-dichloro-3-((6-cyano-1,4-dimethyl-1H-indol-2-yl)methyl)phenoxy)cyclobutanecarboxylate (200 mg, 29%) LC/MS (Method h) $R_t$=3.37 min.; MS m/z: 457 [M+H]⁺ ¹H NMR (DMSO-d₆, 300 MHz): δ 7.91 (s, 1H), 7.49 (d, J=8.9 Hz, 1H), 7.11 (s, 1H), 6.99 (d, J=8.9 Hz, 1H), 5.68 (s, 1H), 4.96 (m, 1H), 4.41 (s, 2H), 3.90 (s, 3H), 3.67 (s, 3H), 3.23 (m, 1H), 2.73 (m, 2H), 2.43 (m, 2H), 2.32 (s, 3H) and methyl cis-3-(2,4-dichloro-3-((6-cyano-1,4-dimethyl-1H-indol-2-yl)methyl)phenoxy)cyclobutanecarboxylate (75 mg, 11%) LC/MS (Method h) $R_t$=3.30 min.; MS m/z: 457 [M+H]⁺ ¹H NMR (DMSO-d₆, 300 MHz): δ 7.91 (s, 1H), 7.50 (d, J=8.9 Hz, 1H), 7.11 (s, 1H), 7.05 (d, J=9.1 Hz, 1H), 5.68 (m, 1H), 4.79 (m, 1H), 4.41 (s, 2H), 3.90 (s, 3H), 3.63 (s, 3H), 2.80 (m, 3H), 2.32 (s, 3H), 2.25 (m, 2H) were obtained from 2-(2,6-dichloro-3-hydroxybenzyl)-1,4-dimethyl-1H-indole-6-carbonitrile (Example AF, Step 5) (400 mg, 1.16 mmol) and methyl 3-((methylsulfonyl)oxy)cyclobutanecarboxylate (described in WO2011/035159) (314 mg, 1.50 mmol).

Step 2: trans-3-(2,4-dichloro-3-((6-cyano-1,4-dimethyl-1H-indol-2-yl)methyl)phenoxy)cyclobutanecarboxylic acid

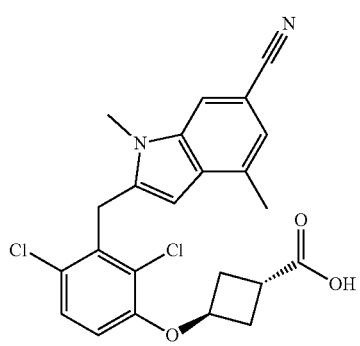 [SMILES: Cc1cc(C#N)cc2c1cc(Cc1c(Cl)ccc(O[C@H]3C[C@H](C(=O)O)C3)c1Cl)n2C]

Using a procedure similar to Example A, Step 5 trans-3-(2,4-dichloro-3-((6-cyano-1,4-dimethyl-1H-indol-2-yl)methyl)phenoxy)cyclobutanecarboxylic acid (130 mg, 71%) was prepared from methyl trans-3-(2,4-dichloro-3-((6-cyano-1,4-dimethyl-1H-indol-2-yl)methyl)phenoxy)cyclobutanecarboxylate (180 mg, 0.38 mmol). LC/MS (Method g) $R_t$=1.79 min.;
MS m/z: 443 [M+H]⁺ ¹H NMR (DMSO-d₆, 500 MHz): δ 12.40 (broad, 1H), 7.91 (s, 1H), 7.49 (d, J=8.9 Hz, 1H), 7.11 (s, 1H), 7.00 (d, J=9.1 Hz, 1H), 5.70 (s, 1H), 4.96 (m, 1H), 4.42 (s, 2H), 3.91 (s, 3H), 3.11 (m, 1H), 2.72 (m, 2H), 2.41 (m, 2H), 2.33 (s, 3H).

Step 2a: cis-3-(2,4-dichloro-3-((6-cyano-1,4-dimethyl-1H-indol-2-yl)methyl)phenoxy)cyclobutanecarboxylic acid

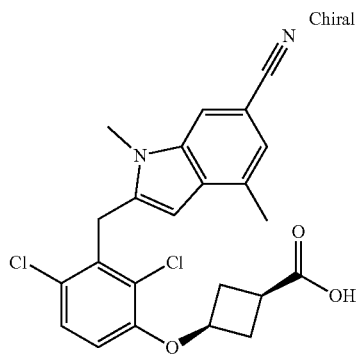 [SMILES: Cc1cc(C#N)cc2c1cc(Cc1c(Cl)ccc(O[C@H]3C[C@@H](C(=O)O)C3)c1Cl)n2C]

Using a procedure similar to Example A, Step 5, cis-3-(2,4-dichloro-3-((6-cyano-1,4-dimethyl-1H-indol-2-yl)methyl)phenoxy)cyclobutanecarboxylic acid (35 mg, 44%) was prepared from methyl cis-3-(2,4-dichloro-3-((6-cyano-1,4-dimethyl-1H-indol-2-yl)methyl)phenoxy)cyclobutanecarboxylate (70 mg, 0.15 mmol). LC/MS (Method g) $R_t$=1.76 min.; MS m/z: 443 [M+H]⁺ ¹H NMR (DMSO-d₆, 500 MHz): δ 12.34 (broad, 1H), 7.91 (s, 1H), 7.50 (d, J=8.9

Hz, 1H), 7.10-7.15 (m, 1H), 7.06 (d, J=8.9 Hz, 1H), 5.69 (s, 1H), 4.78 (m, 1H), 4.42 (s, 2H), 3.91 (s, 3H), 2.77 (m, 3H), 2.33 (s, 3H), 2.24 (m, 2H).

Example AI: trans-4-(2,4-dichloro-3-((1,4-dimethyl-6-(trifluoromethyl)-1H-indol-2-yl)methyl)phenoxy)cyclohexanecarboxylic acid Example AII: cis-4-(2,4-dichloro-3-((1,4-dimethyl-6-(trifluoromethyl)-1H-indol-2-yl)methyl)phenoxy)cyclohexanecarboxylic acid

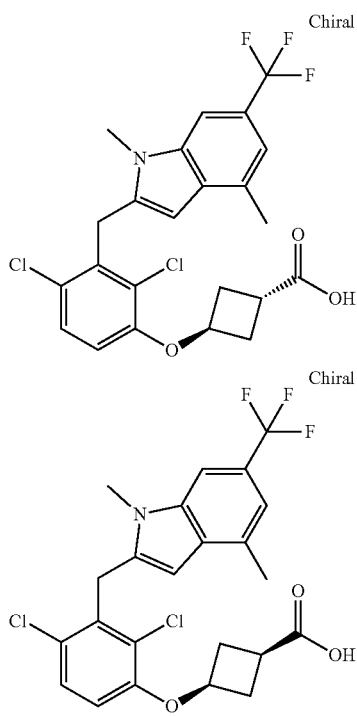

Step 1: ethyl trans-4-(2,4-dichloro-3-((1,4-dimethyl-6-(trifluoromethyl)-1H-indol-2-yl)methyl)phenoxy)cyclohexanecarboxylate and ethyl cis-4-(2,4-dichloro-3-((1,4-dimethyl-6-(trifluoromethyl)-1H-indol-2-yl)methyl)phenoxy)cyclohexanecarboxylate

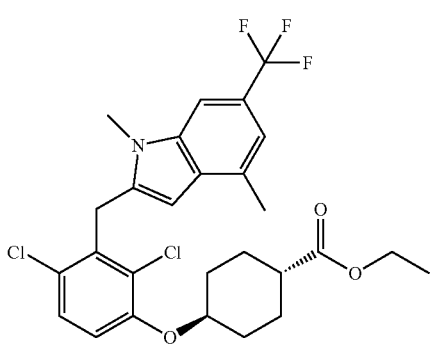

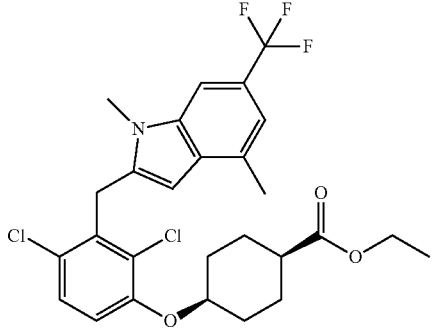

Using a procedure similar to Example AF, Step 6 ethyl trans-4-(2,4-dichloro-3-((1,4-dimethyl-6-(trifluoromethyl)-1H-indol-2-yl)methyl)phenoxy)cyclohexanecarboxylate (48 mg, 14%)

LC/MS (Method h) $R_t$=3.99 min.; MS m/z: 542 [M+H]$^+$ 1H NMR (DMSO-d$_6$, 300 MHz): δ 7.69 (s, 1H), 7.49 (d, J=9.1 Hz, 1H), 7.30 (d, J=9.1 Hz, 1H), 7.05 (s, 1H), 5.66 (s, 1H), 4.47 (m, 2H), 4.40 (q, J=7.1 Hz, 2H), 4.07 (m, 2H), 3.91 (s, 3H), 3.30 (s, 1H), 2.32 (m, 4H), 2.08 (m, 1H), 1.95 (m, 1H), 1.52 (m, 4H), 1.19 (t, J=7.1 Hz, 3H) and ethyl cis-4-(2,4-dichloro-3-((1,4-dimethyl-6-(trifluoromethyl)-1H-indol-2-yl)methyl)phenoxy)cyclohexanecarboxylate (70 mg, 25%) LC/MS (Method h) $R_t$=3.96 min.; MS m/z: 542 [M+H]$^+$ $^1$H NMR (DMSO-d$_6$, 300 MHz): δ 7.69 (s, 1H), 7.49 (d, J=9.1 Hz, 1H), 7.26 (d, J=9.1 Hz, 1H), 7.06 (s, 1H), 5.66 (s, 1H), 4.74 (m, 1H), 4.41 (m, 2H), 4.05 (q, J=7.0 Hz, 2H), 3.91 (m, 4H), 3.30 (s, 1H), 2.36 (m, 4H), 1.87 (m, 2H), 1.65 (m, 4H), 1.16 (t, J=7.1 Hz, 3H) was prepared from 2,4-dichloro-3-((1,4-dimethyl-6-(trifluoromethyl)-1H-indol-2-yl)methyl)phenol (200 mg, 0.51 mmol) (Example X) and ethyl 4-((methylsulfonyl)oxy)cyclohexanecarboxylate (193 mg, 0.77 mmol).

Step 7: trans-4-(2,4-dichloro-3-((1,4-dimethyl-6-(trifluoromethyl)-1H-indol-2-yl)methyl)phenoxy)cyclohexanecarboxylic acid

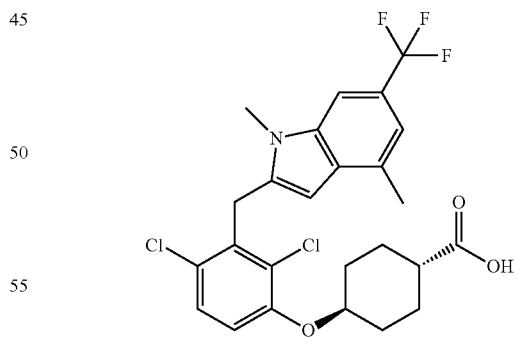

Using a procedure similar to Example A, Step 5, trans-4-(2,4-dichloro-3-((1,4-dimethyl-6-(trifluoromethyl)-1H-indol-2-yl)methyl)phenoxy)cyclohexanecarboxylic acid (13 mg, 28%) was prepared from ethyl trans-4-(2,4-dichloro-3-((1,4-dimethyl-6-(trifluoromethyl)-1H-indol-2-yl)methyl)phenoxy)cyclohexanecarboxylate (48 mg, 0.088 mmol).
LC/MS (Method g) $R_t$=2.12 min.;
MS m/z: 514 [M+H]$^+$ $^1$H NMR (DMSO-d$_6$, 400 MHz): δ 12.15 (broad 1H), 7.69 (s, 1H), 7.49 (d, J=9.0 Hz, 1H), 7.30

(d, J=9.0 Hz, 1H), 7.05 (s, 1H), 5.66 (s, 1H), 4.46 (m, 1H), 4.40 (s, 2H), 3.91 (s, 3H), 2.32 (s, 3H), 2.30 (m, 1H), 2.08 (m, 2H), 1.97 (m, 2H), 149 (m, 4H).

Step 7a: cis-4-(2,4-dichloro-3-((1,4-dimethyl-6-(trifluoromethyl)-1H-indol-2-yl)methyl)phenoxy)cyclohexanecarboxylic acid

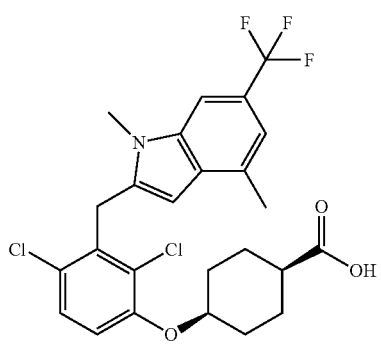 [SMILES: Cc1cc(C(F)(F)F)cc2c1cc(Cc1c(Cl)ccc(O[C@H]3CC[C@@H](C(=O)O)CC3)c1Cl)n2C]

Using a procedure similar to Example A, Step 5, cis-4-(2,4-dichloro-3-((1,4-dimethyl-6-(trifluoromethyl)-1H-indol-2-yl)methyl)phenoxy)cyclohexanecarboxylic acid (23 mg, 46%) was prepared from ethyl cis-4-(2,4-dichloro-3-((1,4-dimethyl-6-(trifluoromethyl)-1H-indol-2-yl)methyl)phenoxy)cyclohexanecarboxylate (52 mg, 0.096 mmol). LC/MS (Method g) $R_t$=2.11 min.;

MS m/z: 514 [M+H]$^+$ $^1$H NMR (DMSO-d$_6$, 400 MHz): δ 12.08 (broad, 1H), 7.69 (s, 1H), 7.49 (d, J=9.0 Hz, 1H), 7.26 (d, J=9.0 Hz, 1H), 7.05 (s, 1H), 5.66 (s, 1H), 4.72 (m, 1H), 4.41 (s, 2H), 3.91 (s, 3H), 2.36 (s, 4H), 1.87 (broad, 2H), 1.78 (t, J=10.2 Hz, 2H), 1.61-1.74 (m, 4H).

Example AJ: trans-4-(2,4-dichloro-3-((1,4-dimethyl-6-(trifluoromethyl)-1H-indol-2-yl)methyl)phenoxy)cyclohexanecarboxylic acid Example AJ1: cis-4-(2,4-dichloro-3-((1,4-dimethyl-6-(trifluoromethyl)-1H-indol-2-yl)methyl)phenoxy)cyclohexanecarboxylic acid

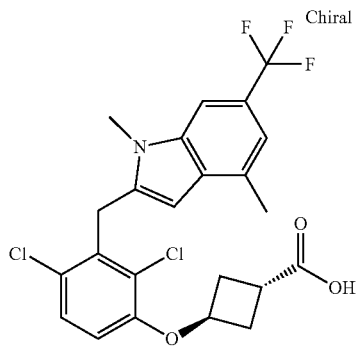

-continued

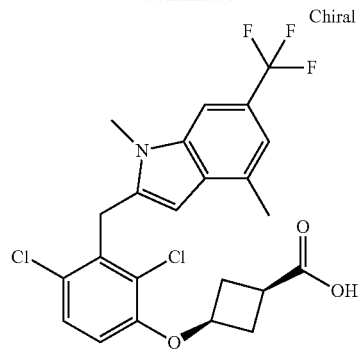

Step 1: methyl trans-3-(2,4-dichloro-3-((1,4-dimethyl-6-(trifluoromethyl)-1H-indol-2-yl)methyl)phenoxy)cyclobutanecarboxylate and methyl cis-3-(2,4-dichloro-3-((1,4-dimethyl-6-(trifluoromethyl)-1H-indol-2-yl)methyl)phenoxy)cyclobutanecarboxylate

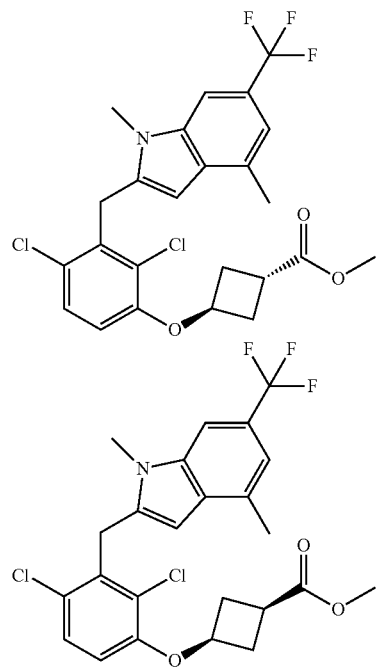

Using a procedure similar to Example AF, Step 6, methyl trans-3-(2,4-dichloro-3-((1,4-dimethyl-6-(trifluoromethyl)-1H-indol-2-yl)methyl)phenoxy)cyclobutanecarboxylate (200 mg, 63%)

LC/MS (Method h) $R_t$=3.72 min.; MS m/z: 500 [M+H]$^+$ $^1$H NMR (DMSO-d$_6$, 300 MHz): δ 7.69 (s, 1H), 7.49 (d, J=8.9 Hz, 1H), 7.06 (s, 1H), 6.99 (d, J=8.9 Hz, 1H), 5.66 (s, 1H), 4.97 (m, 1H), 4.41 (s, 2H), 3.91 (s, 3H), 3.67 (s, 3H), 3.23 (m, 1H), 2.72 (m, 2H), 2.44 (m, 2H), 2.36 (s, 3H) and methyl cis-3-(2,4-dichloro-3-((1,4-dimethyl-6-(trifluoromethyl)-1H-indol-2-yl)methyl)phenoxy)cyclobutanecarboxylate LC/MS (Method h) $R_t$=3.65 min.; MS m/z: 500 [M+H]$^+$ $^1$H NMR (DMSO-d$_6$, 300 MHz): δ 7.69 (s, 1H), 7.50 (d, J=8.9 Hz, 1H), 7.02-7.09 (m, 2H), 5.65 (s, 1H), 4.80 (m, 1H), 4.40 (s, 2H), 3.91 (s, 3H), 3.63 (s, 3H), 2.86 (m, 3H), 2.36 (s, 3H), 2.26 (m, 2H) were prepared from 2,4-dichloro-3-((1,4-dimethyl-6-(trifluoromethyl)-1H-indol-2-yl)methyl)phenol (Example AI, Step 5) (200 mg, 0.51 mmol) and methyl 3-((methylsulfonyl)oxy)cyclobutanecarboxylate (161 mg, 0.77 mmol).

Step 2: trans-4-(2,4-dichloro-3-((1,4-dimethyl-6-(trifluoromethyl)-1H-indol-2-yl)methyl)phenoxy)cyclohexanecarboxylic acid

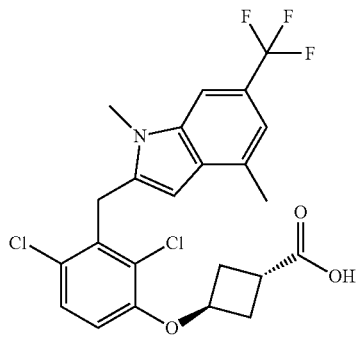 [SMILES: Cc1cc(C(F)(F)F)cc2c1cc(Cc1c(Cl)ccc(O[C@H]3C[C@H](C(=O)O)C3)c1Cl)n2C]

Using a procedure similar to Example A, Step 5, trans-4-(2,4-dichloro-3-((1,4-dimethyl-6-(trifluoromethyl)-1H-indol-2-yl)methyl)phenoxy)cyclohexanecarboxylic acid (125 mg, 98%) was prepared from methyl trans-3-(2,4-dichloro-3-((1,4-dimethyl-6-(trifluoromethyl)-1H-indol-2-yl)methyl)phenoxy)cyclobutanecarboxylate (130 mg, 0.26 mmol). LC/MS (Method g) $R_t$=2.05 min.;

MS m/z: 486 [M+H]$^+$ $^1$H NMR (DMSO-d$_6$, 400 MHz): δ 12.36 (broad, 1H), 7.69 (s, 1H), 7.48 (d, J=9.0 Hz, 1H), 7.05 (s, 1H), 6.99 (d, J=9.0 Hz, 1H), 5.66 (s, 1H), 4.95 (m, 1H), 4.41 (s, 2H), 3.91 (s, 3H), 3.12 (m, 1H), 2.70 (m, 2H), 2.41 (m, 2H), 2.36 (s, 3H).

Step 2a: cis-4-(2,4-dichloro-3-((1,4-dimethyl-6-(trifluoromethyl)-1H-indol-2-yl)methyl)phenoxy)cyclohexanecarboxylic acid

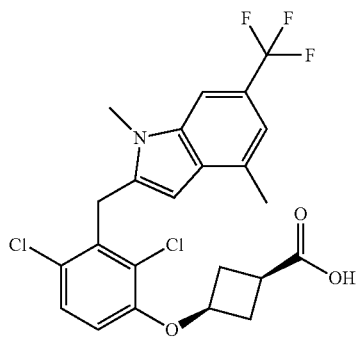 [SMILES: Cc1cc(C(F)(F)F)cc2c1cc(Cc1c(Cl)ccc(O[C@H]3C[C@@H](C(=O)O)C3)c1Cl)n2C]

Using a procedure similar to Example A, Step 5, cis-4-(2,4-dichloro-3-((1,4-dimethyl-6-(trifluoromethyl)-1H-indol-2-yl)methyl)phenoxy)cyclohexanecarboxylic acid (25 mg, 70%) was prepared from methyl cis-3-(2,4-dichloro-3-((1,4-dimethyl-6-(trifluoromethyl)-1H-indol-2-yl)methyl)phenoxy)cyclobutanecarboxylate (33 mg, 0.066 mmol). LC/MS (Method g) $R_t$=2.02 min.;

MS m/z: 486 [M+H]$^+$ $^1$H NMR (DMSO-d$_6$, 400 MHz): δ 12.35 (broad, 1H), 7.69 (s, 1H), 7.49 (d, J=8.8 Hz, 1H), 7.03-7.08 (m, 2H), 5.66 (s, 1H), 4.78 (m, 1H), 4.40 (s, 2H), 3.91 (s, 3H), 2.76 (m, 3H), 2.36 (s, 3H), 2.22 (m, 2H).

Example AK: trans-3-(2,4-dichloro-3-((1,4-dimethyl-6-(trifluoromethyl)-1H-indol-2-yl)methyl)phenoxy)cyclopentanecarboxylic acid Example AK1: cis-3-(2,4-dichloro-3-((1,4-dimethyl-6-(trifluoromethyl)-1H-indol-2-yl)methyl)phenoxy)cyclopentanecarboxylic acid

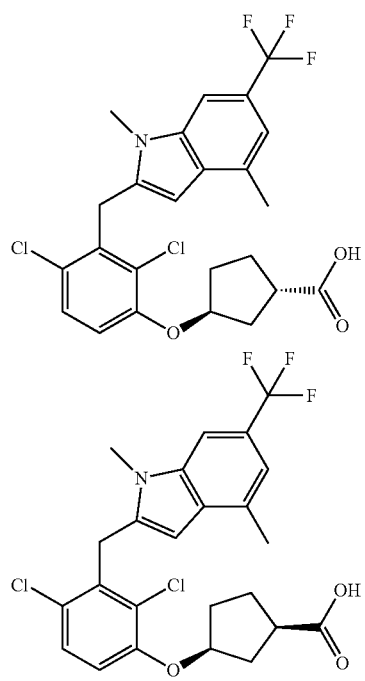

Step 1: ethyl trans-3-(2,4-dichloro-3-((1,4-dimethyl-6-(trifluoromethyl)-1H-indol-2-yl)methyl)phenoxy)cyclopentanecarboxylate and ethyl cis-3-(2,4-dichloro-3-((1,4-dimethyl-6-(trifluoromethyl)-1H-indol-2-yl)methyl)phenoxy)cyclopentanecarboxylate

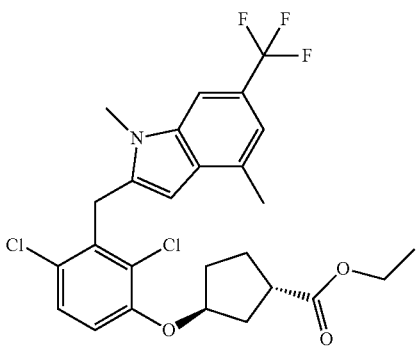

-continued

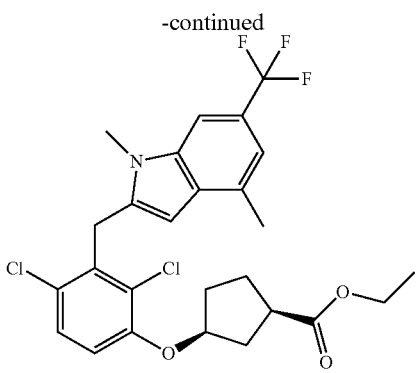

Using a procedure similar to Example AF, Step 6, ethyl trans-3-(2,4-dichloro-3-((1,4-dimethyl-6-(trifluoromethyl)-1H-indol-2-yl)methyl)phenoxy)cyclopentanecarboxylate (125 mg, 46%)

LC/MS (Method h) $R_t$=3.94 min.; MS m/z: 528 [M+H]+ 1H NMR (DMSO-d6, 300 MHz): δ 7.69 (s, 1H), 7.51 (d, J=9.1 Hz, 1H), 7.22 (d, J=9.1 Hz, 1H), 7.06 (s, 1H), 5.66 (s, 1H), 5.06 (m, 1H), 4.40 (s, 2H), 4.03 (q, J=7.1 Hz, 2H), 3.91 (s, 3H), 3.02 (m, 1H), 2.36 (s, 3H), 2.10 (m, 4H), 1.80 (m, 2H), 1.20 (t, J=7.1 Hz, 3H) and ethyl cis-3-(2,4-dichloro-3-((1,4-dimethyl-6-(trifluoromethyl)-1H-indol-2-yl)methyl)phenoxy)cyclopentanecarboxylate (55 mg, 20%) (containing 20% of isomer trans)

LC/MS (Method h) $R_t$=3.86 min.; MS m/z: 528 [M+H]+ 1H NMR (DMSO-d6, 300 MHz): δ 7.69 (s, 1H), 7.50 (d, J=9.1 Hz, 1H), 7.19 (d, J=9.1 Hz, 1H), 7.05 (s, 1H), 5.67 (s, 1H), 4.97 (m, 1H), 4.39 (s, 3H), 3.02 (q, J=7.1 Hz, 2H), 3.91 (s, 3H), 2.92 (m, 1H), 2.32 (m, 4H), 1.95 (m, 4H), 1.11 (t, J=7.1 Hz, 3H)

were prepared from 2,4-dichloro-3-((1,4-dimethyl-6-(trifluoromethyl)-1H-indol-2-yl)methyl)phenol (Example AI, Step 5) (200 mg, 0.51 mmol) and ethyl 3-((methylsulfonyl)oxy)cyclopentanecarboxylate (Preparation #12) (183 mg, 0.77 mmol).

Step 2: trans-3-(2,4-dichloro-3-((1,4-dimethyl-6-(trifluoromethyl)-1H-indol-2-yl)methyl)phenoxy)cyclopentanecarboxylic acid

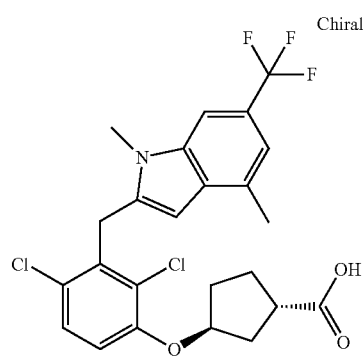 [SMILES: Cc1cc(C(F)(F)F)cc2c1cc(Cc1c(Cl)ccc(O[C@H]3CC[C@H](C(=O)O)C3)c1Cl)n2C]

Using a procedure similar to Example A, Step 5, trans-3-(2,4-dichloro-3-((1,4-dimethyl-6-(trifluoromethyl)-1H-indol-2-yl)methyl)phenoxy)cyclopentanecarboxylic acid (80 mg, 68%) was prepared from ethyl trans-3-(2,4-dichloro-3-((1,4-dimethyl-6-(trifluoromethyl)-1H-indol-2-yl)methyl) phenoxy)cyclopentanecarboxylate (122 mg, 0.23 mmol). LC/MS (Method g) $R_t$=2.09 min.;

MS m/z: 500 [M+H]+ 1H NMR (DMSO-d6, 400 MHz): δ 12.21 (broad, 1H), 7.69 (s, 1H), 7.51 (d, J=9.0 Hz, 1H), 7.22 (d, J=9.0 Hz, 1H), 7.05 (s, 1H), 5.66 (s, 1H), 5.04 (m, 1H), 4.40 (s, 2H), 3.91 (s, 3H), 2.95 (m, 1H), 2.36 (s, 3H), 2.08 (m, 4H), 1.81 (m, 2H).

Step 2a: cis-3-(2,4-dichloro-3-((1,4-dimethyl-6-(trifluoromethyl)-1H-indol-2-yl)methyl)phenoxy)cyclopentanecarboxylic acid

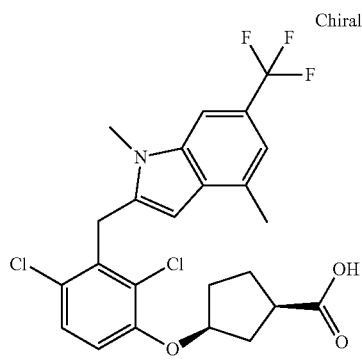 [SMILES: Cc1cc(C(F)(F)F)cc2c1cc(Cc1c(Cl)ccc(O[C@H]3CC[C@@H](C(=O)O)C3)c1Cl)n2C]

Using a procedure similar to Example A, Step 5, cis-3-(2,4-dichloro-3-((1,4-dimethyl-6-(trifluoromethyl)-1H-indol-2-yl)methyl)phenoxy)cyclopentanecarboxylic acid (18 mg, 34%) (containing 20% of trans isomer) was prepared from ethyl cis-3-(2,4-dichloro-3-((1,4-dimethyl-6-(trifluoromethyl)-1H-indol-2-yl)methyl)phenoxy)cyclopentanecarboxylate (52 mg, 0.098 mmol).

LC/MS (Method g) $R_t$=2.07 min.; MS m/z: 500 [M+H]+ 1H NMR (DMSO-d6, 400 MHz): δ 12.14 (broad, 1H), 7.69 (s, 1H), 7.50 (d, J=9.2 Hz, 1H), 7.19 (d, J=9.2 Hz, 1H), 7.05 (s, 1H), 5.66 (s, 1H), 4.95 (m, 1H), 4.39 (s, 2H), 3.91 (s, 3H), 2.80 (m, 1H), 2.36 (m, 4H), 1.92 (m, 5H).

Example AL: 2-((3,5-dichloro-2-((tetrahydro-2H-pyran-4-yl)methoxy)pyridin-4-yl)methyl)-1,4-dimethyl-6-(trifluoromethyl)-1H-indole

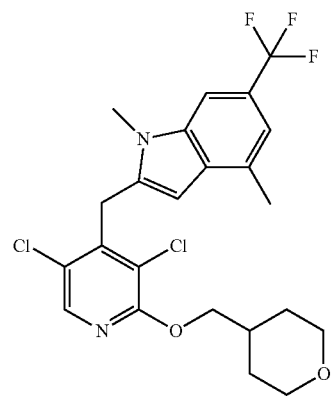 [SMILES: Cc1cc(C(F)(F)F)cc2c1cc(Cc1c(Cl)cnc(OCC3CCOCC3)c1Cl)n2C]

Step 1: 3,5-dichloro-4-((1,4-dimethyl-6-(trifluoromethyl)-1H-indol-2-yl)methyl)pyridin-2-ol

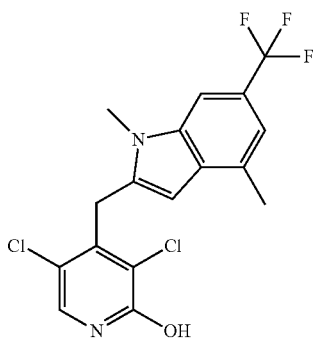 [SMILES: Cc1cc(C(F)(F)F)cc2c1cc(Cc1c(Cl)cnc(O)c1Cl)n2C]

Using a procedure similar to Example X, 3,5-dichloro-4-((1,4-dimethyl-6-(trifluoromethyl)-1H-indol-2-yl)methyl)pyridin-2-ol (716 mg, 100%) was prepared from 2-((3,5-dichloro-2-methoxypyridin-4-yl)methyl)-1,4-dimethyl-6-(trifluoromethyl)-1H-indole (example Z, step 4) (647 mg, 1.6 mmol). LC/MS (Method h) $R_t$=2.68 min.; MS m/z: 389 [M+H]$^+$ $^1$H NMR (DMSO-d$_6$, 300 MHz): δ 12.60 (broad, 1H), 7.81 (s, 1H), 7.70 (s, 1H), 7.07 (s, 1H), 5.97 (s, 1H), 4.31 (s, 2H), 3.89 (s, 3H), 2.41 (s, 3H).

Step 2: 2-((3,5-dichloro-2-((tetrahydro-2H-pyran-4-yl)methoxy)pyridin-4-yl)methyl)-1,4-dimethyl-6-(trifluoromethyl)-1H-indole and 3,5-dichloro-4-((1,4-dimethyl-6-(trifluoromethyl)-1H-indol-2-yl)methyl)-1-((tetrahydro-2H-pyran-4-yl)methyl)pyridin-2(1H)-one

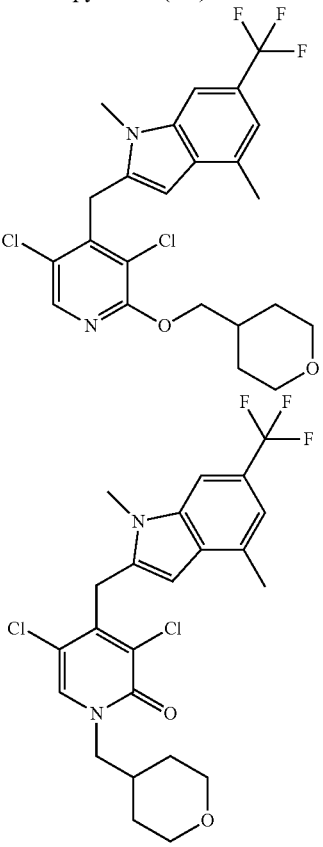

To a solution of 3,5-dichloro-4-((1,4-dimethyl-6-(trifluoromethyl)-1H-indol-2-yl)methyl)pyridin-2-ol (200 mg, 0.514 mmol) in DMF (2.6 ml) was added potassium carbonate (284 mg, 2.056 mmol) and 4-(bromomethyl)tetrahydropyran (0.135 ml, 1.028 mmol) and reaction mixture was stirred at 100° C. for 2 hours. The reaction mixture was diluted with water and the obtained aqueous layer was extracted with EtOAc. The obtained organic layer was dried over magnesium sulfate, filtered and concentrated under reduced pressure. The residue was purified by column chromatography on silica gel (eluting with 5-100% EtOAc in DCM) then by preparative LCMS to give 2-((3,5-dichloro-2-((tetrahydro-2H-pyran-4-yl)methoxy)pyridin-4-yl)methyl)-1,4-dimethyl-6-(trifluoromethyl)-1H-indole (108 mg, 40%) as a white solid LC/MS (Method g) $R_t$=2.26 min.; MS m/z: 487 [M+H]$^+$ $^1$H NMR (DMSO-d$_6$, 400 MHz): δ 8.32 (m, 1H), 7.70 (s, 1H), 7.07 (s, 1H), 5.80 (s, 1H), 4.42 (s, 2H), 4.24 (d, J=6.3 Hz, 2H), 3.91 (s, 3H), 3.88 (m, 2H), 3.34 (m, 2H), 2.38 (s, 3H), 2.07 (m, 1H), 1.68 (m, 2H), 1.39 (m, 2H) and 3,5-dichloro-4-((1,4-dimethyl-6-(trifluoromethyl)-1H-indol-2-yl)methyl)-1-((tetrahydro-2H-pyran-4-yl)methyl)pyridin-2(1H)-one (46 mg, 18%) as a white solid. LC/MS (Method g) $R_t$=1.84 min.; MS m/z: 487 [M+H]$^+$ $^1$H NMR (DMSO-d$_6$, 400 MHz): δ 8.14 (s, 1H), 7.69 (s, 1H), 7.07 (s, 1H), 6.00 (s, 1H), 4.30 (s, 2H), 3.82-3.95 (m, 7H), 3.20-3.30 (m, 2H), 2.41 (s, 3H), 2.09 (m, 1H), 1.48 (m, 2H), 1.30 (m, 2H).

Example AM: 2-((1-(2,4-dichloro-3-((6-cyano-1,4-dimethyl-1H-indol-2-yl)methyl)benzoyl)piperidin-4-yl)oxy)acetic acid

Step 1: ethyl 2-((1-(2,4-dichloro-3-((6-cyano-1,4-dimethyl-1H-indol-2-yl)methyl)benzoyl)piperidin-4-yl)oxy)acetate


Using a procedure similar to Example A, Step 6, ethyl 2-((1-(2,4-dichloro-3-((6-cyano-1,4-dimethyl-1H-indol-2-yl)methyl)benzoyl)piperidin-4-yl)oxy)acetate (337 mg, 88%) was obtained as an orange oil from 2,4-dichloro-3-((6-cyano-1,4-dimethyl-1H-indol-2-yl)methyl)benzoic acid (Example AA, Step 5) (150 mg, 0.402 mmol) and N-1-((ethylimino)methylene)-N3,N3-dimethylpropane-1,3-diamine hydrochloride (100 mg, 0.52 mmol) and used crude in the next step.

LC/MS (Method h) $R_t$=2.90 min.; MS m/z: 542 [M+H]$^+$

Step 2: 2-((1-(2,4-dichloro-3-((6-cyano-1,4-dimethyl-1H-indol-2-yl)methyl)benzoyl)piperidin-4-yl)oxy)acetic acid

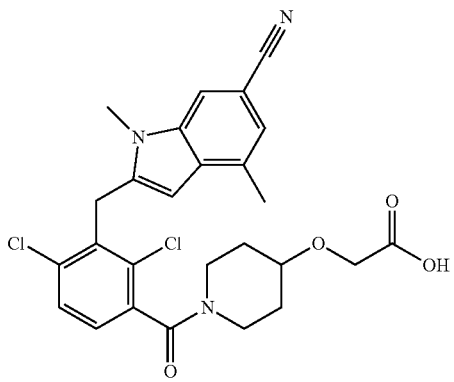 [SMILES: Cc1cc(C#N)cc2c1cc(Cc1c(Cl)ccc(C(=O)N3CCC(OCC(=O)O)CC3)c1Cl)n2C]

Using a procedure similar to Example A, Step 5, 2-((1-(2,4-dichloro-3-((6-cyano-1,4-dimethyl-1H-indol-2-yl)methyl)benzoyl)piperidin-4-yl)oxy)acetic acid (33 mg, 18%) was obtained as a white solid from ethyl 2-((1-(2,4-dichloro-3-((6-cyano-1,4-dimethyl-1H-indol-2-yl)methyl)benzoyl)piperidin-4-yl)oxy)acetate (336 mg, 0.353 mmol). LC/MS (Method g) $R_t$=1.52 min.; MS m/z: 514 [M+H]$^+$ $^1$H NMR (DMSO-d$_6$, 400 MHz): δ 12.57 (broad, 1H), 7.92 (s, 1H), 7.66 (d, J=9 Hz, 1H), 7.46 and 7.42 (d, J=9 Hz, 1H), 7.12 (s, 1H), 5.70 (m, 1H), 4.47 (m, 2H), 4.05 and 4.03 (s, 2H), 3.96 (m, 1H), 3.90 (s, 3H), 3.63 (m, 1H), 3.37 (m, 2H), 3.05 (m, 1H), 2.33 (s, 3H), 1.91 (m, 1H), 1.78 (m, 1H), 1.60-1.40 (m, 2H).

TABLE AM

The following Examples were prepared using the same procedure starting from the appropriate esters from Table AA.

| Example | Structure | Starting ester | $R_t$ min (Method g) | m/z ESI+ (M + H)$^+$ |
|---------|-----------|----------------|----------------------|----------------------|
| AM-1 | 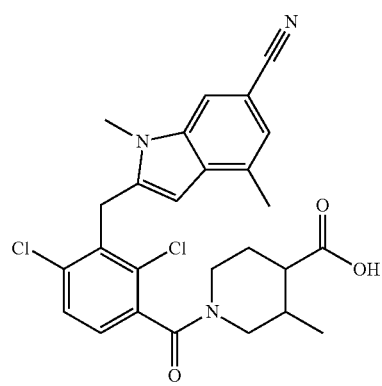 [SMILES: Cc1cc(C#N)cc2c1cc(Cc1c(Cl)ccc(C(=O)N3CCC(C(=O)O)C(C)C3)c1Cl)n2C] | AA-33 | 1.60 | 498 |
| AM-2 | 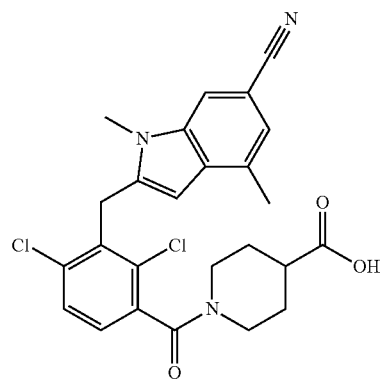 [SMILES: Cc1cc(C#N)cc2c1cc(Cc1c(Cl)ccc(C(=O)N3CCC(C(=O)O)CC3)c1Cl)n2C] | AA-34 | 1.56 | 484 |

TABLE AM-continued

The following Examples were prepared using the same procedure starting from the appropriate esters from Table AA.

| Example | Structure | Starting ester | R$_t$ min (Method g) | m/z ESI+ (M + H)+ |
|---|---|---|---|---|
| AM-3 | (structure shown) | AA-38 | 1.55 | 498 |

Example AN: 2-(2,6-dichloro-3-(4-hydroxypiperidine-1-carbonyl)benzoyl)-1,4-dimethyl-1H-indole-6-carbonitrile

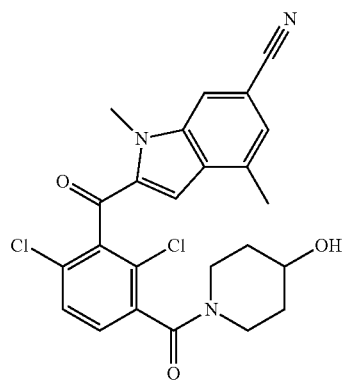 [SMILES: Cc1cc(C#N)cc2c1cc(C(=O)c1c(Cl)ccc(C(=O)N3CCC(O)CC3)c1Cl)n2C]

Step 1: methyl 2,4-dichloro-3-(6-cyano-4-methyl-1-(phenylsulfonyl)-1H-indole-2-carbonyl)benzoate

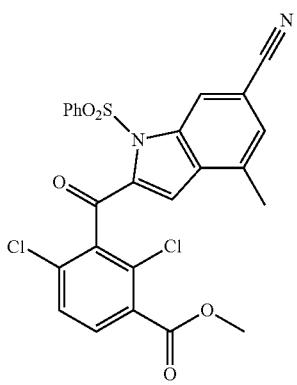

Using a procedure similar to Example AD, Step 2, methyl 2,4-dichloro-3-(6-cyano-4-methyl-1-(phenylsulfonyl)-1H-indole-2-carbonyl)benzoate (5.98 g, 100%) was obtained as a beige foam from methyl 2,4-dichloro-3-((6-cyano-4-methyl-1-(phenylsulfonyl)-1H-indol-2-yl)(hydroxy)methyl)benzoate (Example AA, Step 1) (6 g, 11.33 mmol). LC/MS (Method i) R$_t$=2.57 min.; MS m/z: 527 [M+H]+ $^1$H NMR (DMSO-d$_6$, 300 MHz): δ 8.54 (s, 1H), 8.29 (m, 2H), 8.05 (m, 2H), 7.68-7.91 (m, 4H), 7.63 (m, 1H), 3.88 (s, 3H), 2.26 (s, 3H)

Step 2: methyl 2,4-dichloro-3-(6-cyano-4-methyl-1-(phenylsulfonyl)-1H-indole-2-carbonyl)benzoate

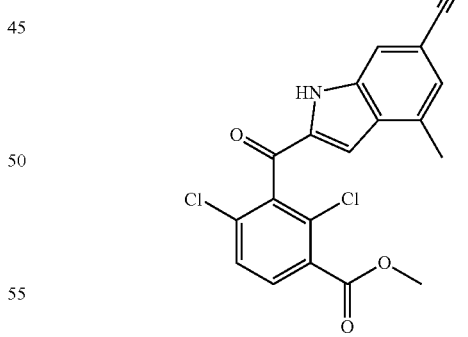

Using a procedure similar to Example A, Step 3, methyl 2,4-dichloro-3-(6-cyano-4-methyl-1-(phenylsulfonyl)-1H-indole-2-carbonyl)benzoate (3.32 g, 76%) was obtained as a beige foam from methyl 2,4-dichloro-3-(6-cyano-4-methyl-1-(phenylsulfonyl)-1H-indole-2-carbonyl)benzoate (5.98 g, 11.34 mmol). LC/MS (Method i) R$_t$=2.33 min.; MS m/z: 387 [M+H]+ $^1$H NMR (DMSO-d$_6$, 300 MHz): δ 12.72 (s, 1H), 8.03 (d, J=8.4 Hz, 1H), 7.80 (m, 2H), 7.15 (m, 2H), 3.90 (s, 3H), 2.50 (s, 3H).

Step 3: methyl 2,4-dichloro-3-(6-cyano-1,4-dimethyl-1H-indole-2-carbonyl)benzoate

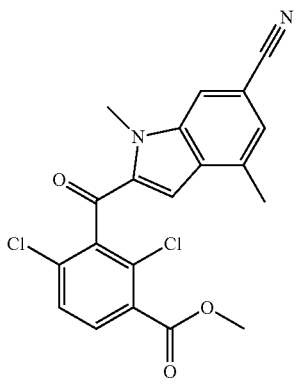 [SMILES: COC(=O)c1ccc(Cl)c(C(=O)c2cc3c(C)cc(C#N)cc3n2C)c1Cl]

Using a procedure similar to Example A, Step 4, methyl 2,4-dichloro-3-(6-cyano-1,4-dimethyl-1H-indole-2-carbonyl)benzoate (3.34 g, 97%) was obtained as a white solid from methyl 2,4-dichloro-3-(6-cyano-4-methyl-1-(phenylsulfonyl)-1H-indole-2-carbonyl)benzoate (3.32 g, 8.57 mmol).

LC/MS (Method i) $R_t$=2.49 min.; MS m/z: 401 [M+H]$^+$ $^1$H NMR (DMSO-d$_6$, 300 MHz): δ 8.20 (s, 1H), 8.03 (d, J=8.1 Hz, 1H), 7.79 (d, J=8.1 Hz, 1H), 7.26-7.34 (m, 1H), 7.20 (s, 1H), 4.20 (s, 3H), 3.90 (s, 3H), 2.47 (s, 3H)

Step 4: 2,4-dichloro-3-(6-cyano-1,4-dimethyl-1H-indole-2-carbonyl)benzoic acid

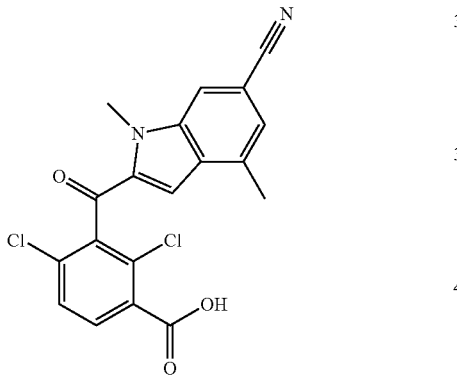

Using a procedure similar to Example A, Step 5, 2,4-dichloro-3-(6-cyano-1,4-dimethyl-1H-indole-2-carbonyl)benzoic acid (3.22 g, 100%) was obtained as a white solid from methyl 2,4-dichloro-3-(6-cyano-1,4-dimethyl-1H-indole-2-carbonyl)benzoate (3.34 g, 8.32 mmol).

LC/MS (Method i) $R_t$=2.12 min.; MS m/z: 387 [M+H]$^+$ $^1$H NMR (DMSO-d$_6$, 300 MHz): δ 8.20 (s, 1H), 8.00 (d, J=8.6 Hz, 1H), 7.75 (d, J=8.6 Hz, 1H), 7.29 (m, 1H), 7.17 (m, 1H), 4.20 (s, 3H), 2.47 (s, 3H).

Step 5: 2-(2,6-dichloro-3-(4-hydroxypiperidine-1-carbonyl)benzoyl)-1,4-dimethyl-1H-indole-6-carbonitrile

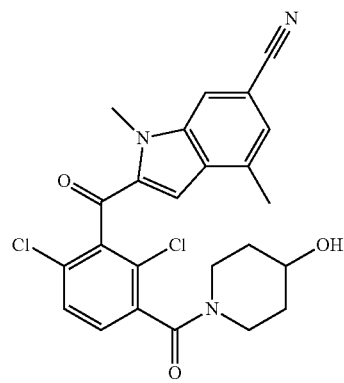 [SMILES: Cc1cc(C#N)cc2c1cc(C(=O)c1c(Cl)ccc(C(=O)N3CCC(O)CC3)c1Cl)n2C]

Using a procedure similar to Example A, Step 6, 2-(2,6-dichloro-3-(4-hydroxypiperidine-1-carbonyl)benzoyl)-1,4-dimethyl-1H-indole-6-carbonitrile (101 mg, 83%) was obtained as a yellow solid from 2,4-dichloro-3-(6-cyano-1,4-dimethyl-1H-indole-2-carbonyl)benzoic acid (100 mg, 0.26 mmol) and piperidin-4-ol (39 mg, 0.38 mmol). LC/MS (Method g) $R_t$=1.47 min.; MS m/z: 470 [M+H]$^+$ $^1$H NMR (DMSO-d$_6$, 400 MHz): δ 8.20 (s, 1H), 7.74 (d, J=8.4 Hz, 1H), 7.61 (m, 1H), 7.29 (s, 1H), 7.20 and 7.07 (m, 1H), 4.81 and 4.76 (m, 1H), 4.20 and 4.19 (s, 3H), 4.02 (m, 1H), 3.75 (m, 1H), 3.25 (m, 1H), 3.08 (m, 1H), 2.48 (s, 3H), 1.70 (m, 2H), 1.35 (m, 2H).

TABLE AN

The following intermediates were prepared from 2,4-dichloro-3-(6-cyano-1,4-dimethyl-1H-indole-2-carbonyl)benzoic acid (Example AN, Step 4) using the same procedure with the appropriate amine.

| Example # | Product | Amine | $R_t$ min | m/z ESI+ (M + H)$^+$ |
|---|---|---|---|---|
| AN-1 | (structure) | (structure) | 1.43 (Method g) | 442 |

TABLE AN-continued

The following intermediates were prepared from 2,4-dichloro-3-(6-cyano-1,4-dimethyl-1H-indole-2-carbonyl)benzoic acid (Example AN, Step 4) using the same procedure with the appropriate amine.

| Example # | Product | Amine | R$_t$ min | m/z ESI+ (M + H)$^+$ |
|---|---|---|---|---|
| AN-2 | | | 1.42 (Method g) | 511 |
| AN-3 | | | 1.70 (Method g) | 526 |
| AN-4 | | | 1.80 (Method g) | 512 |

TABLE AN-continued

The following intermediates were prepared from 2,4-dichloro-3-(6-cyano-1,4-dimethyl-1H-indole-2-carbonyl)benzoic acid (Example AN, Step 4) using the same procedure with the appropriate amine.

| Example # | Product | Amine | R$_t$, min | m/z ESI+ (M + H)+ |
|---|---|---|---|---|
| AN-5 | 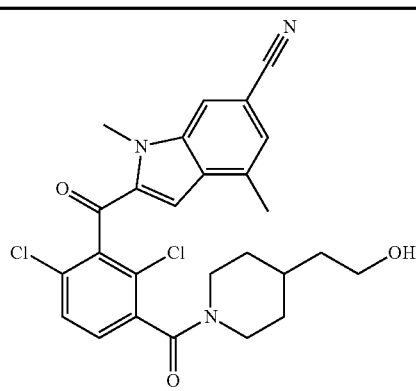 | 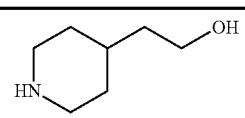 | 1.56 (Method g) | 498 |
| AN-6 | 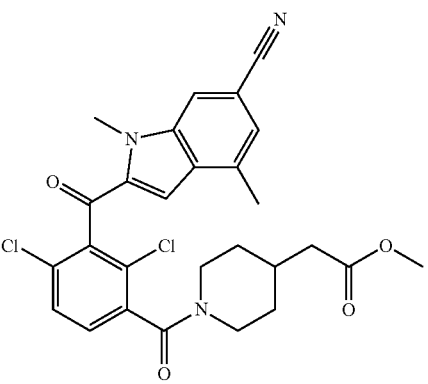 [SMILES: COC(=O)CC1CCN(C(=O)c2ccc(Cl)c(C(=O)c3cc4c(C)cc(C#N)cc4n3C)c2Cl)CC1] | 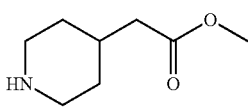 | 2.36 (Method i) | 526 |

Example AO: 2-(1-(2,4-dichloro-3-(6-cyano-1,4-dimethyl-1H-indole-2-carbonyl)benzoyl)piperidin-4-yl)acetic acid

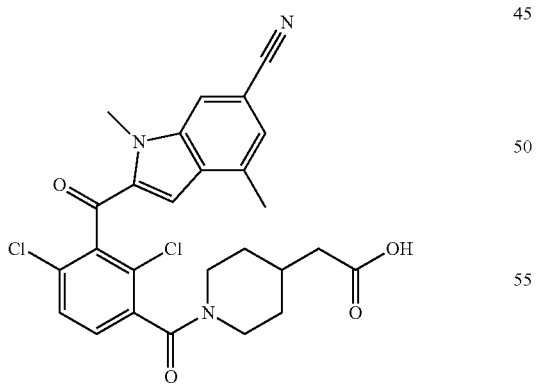

Using a procedure similar to Example A, Step 5, 2-(1-(2,4-dichloro-3-(6-cyano-1,4-dimethyl-1H-indole-2-carbonyl)benzoyl)piperidin-4-yl)acetic acid (107 mg, 94%) was obtained as a white solid from methyl 2-(1-(2,4-dichloro-3-(6-cyano-1,4-dimethyl-1H-indole-2-carbonyl)benzoyl)piperidin-4-yl)acetate (Table AN, Example AN-6) (116 mg, 0.22 mmol). LC/MS (Method g) R$_t$=1.54 min.; MS m/z: 512 [M+H]+ $^1$H NMR (DMSO-d$_6$, 400 MHz): δ 12.12 (broad., 1H), 8.20 (s, 1H), 7.75 (m, 1H), 7.63 and 7.57 (d, J=8.4 Hz, 1H), 7.29 (s, 1H), 7.01-7.26 (m, 1H), 4.47 (m, 1H), 4.20 and 4.19 (s, 3H), 3.55 (m, 1H), 3.06 (m, 1H), 2.81 (m, 1H), 2.48 (m, 3H), 2.19 (m, 1H), 2.13 (m, 1H), 1.95 (m, 1H), 1.77 (m, 1H), 1.64 (m, 1H), 1.14 (m, 2H).

Example AP: (2,4-dichloro-3-(1,4-dimethyl-6-(trifluoromethyl)-1H-indole-2-carbonyl)phenyl)(morpholino)methanone

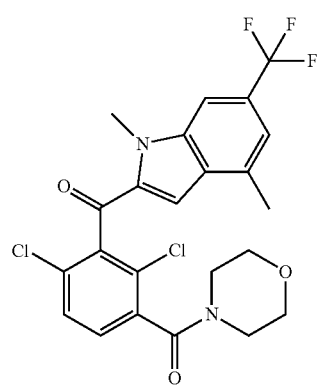 [SMILES: Cc1cc(C(F)(F)F)cc2c1cc(C(=O)c1c(Cl)ccc(C(=O)N3CCOCC3)c1Cl)n2C]

Step 1: methyl 2,4-dichloro-3-(4-methyl-1-(phenylsulfonyl)-6-(trifluoromethyl)-1H-indole-2-carbonyl)benzoate

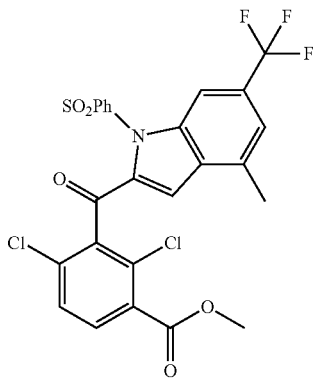

Using a procedure similar to Example AD, Step 2, methyl 2,4-dichloro-3-(4-methyl-1-(phenylsulfonyl)-6-(trifluoromethyl)-1H-indole-2-carbonyl)benzoate (5.88 g, 100%) was obtained as a beige foam from methyl 2,4-dichloro-3-(hydroxy(4-methyl-1-(phenylsulfonyl)-6-(trifluoromethyl)-1H-indol-2-yl)methyl)benzoate (example A, step 1) (5.9 g, 10.3 mmol). LC/MS (Method i) $R_t$=2.80 min.;

MS m/z: 570 [M+H]$^+$ $^1$H NMR (DMSO-d$_6$, 300 MHz): δ 8.37 (s, 1H), 8.12 (m, 2H), 8.01 (d, J=8.4 Hz, 1H), 7.70 (m, 5H), 7.58 (s, 1H), 3.88 (s, 3H), 2.56 (s, 3H).

Step 2: methyl 2,4-dichloro-3-(4-methyl-1-(phenylsulfonyl)-6-(trifluoromethyl)-1H-indole-2-carbonyl)benzoate

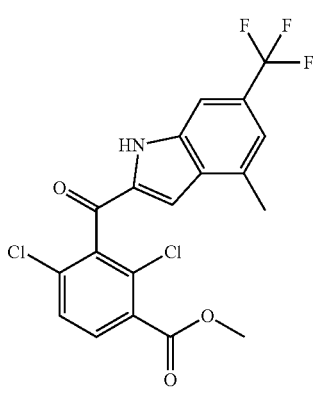 [SMILES: COC(=O)c1ccc(Cl)c(C(=O)c2cc3c(C)cc(C(F)(F)F)cc3[nH]2)c1Cl]

Using a procedure similar to Example A, Step 3, methyl 2,4-dichloro-3-(4-methyl-1-(phenylsulfonyl)-6-(trifluoromethyl)-1H-indole-2-carbonyl)benzoate (4 g, 79%) was obtained as a colorless foam from methyl 2,4-dichloro-3-(4-methyl-1-(phenylsulfonyl)-6-(trifluoromethyl)-1H-indole-2-carbonyl)benzoate (5.88 g, 10.3 mmol). LC/MS (Method i) $R_t$=2.59 min.; MS m/z: 430 [M+H]$^+$ $^1$H NMR (DMSO-d$_6$, 300 MHz): δ 12.64 (s, 1H), 8.03 (d, J=8.4 Hz, 1H), 7.80 (d, J=8.4 Hz, 1H), 7.62 (s, 1H), 7.18 (s, 2H), 3.90 (s, 3H), 2.56 (s, 3H).

Step 3: methyl 2,4-dichloro-3-(1,4-dimethyl-6-(trifluoromethyl)-1H-indole-2-carbonyl)benzoate

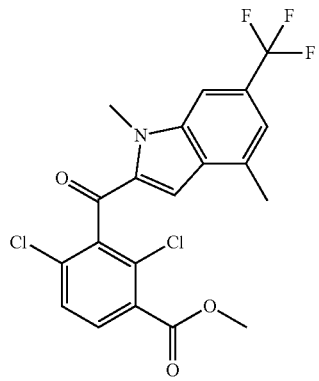 [SMILES: COC(=O)c1ccc(Cl)c(C(=O)c2cc3c(C)cc(C(F)(F)F)cc3n2C)c1Cl]

Using a procedure similar to Example A, Step 4, methyl 2,4-dichloro-3-(1,4-dimethyl-6-(trifluoromethyl)-1H-indole-2-carbonyl)benzoate (2.45 g, 92%) was obtained as a white solid from methyl 2,4-dichloro-3-(4-methyl-6-(trifluoromethyl)-1H-indole-2-carbonyl)benzoate (2.58 g, 6 mmol).

LC/MS (Method i) $R_t$=2.75 min.; MS m/z: 444 [M+H]$^+$ $^1$H NMR (DMSO-d$_6$, 300 MHz): δ 8.02 (d, J=8.5 Hz, 1H), 7.96 (s, 1H), 7.79 (d, J=8.5 Hz, 1H), 7.24 (s, 1H), 7.18 (s, 1H), 4.24 (s, 3H), 3.32 (s, 3H), 2.50 (s, 3H).

Step 4: 2,4-dichloro-3-(1,4-dimethyl-6-(trifluoromethyl)-1H-indole-2-carbonyl)benzoic acid

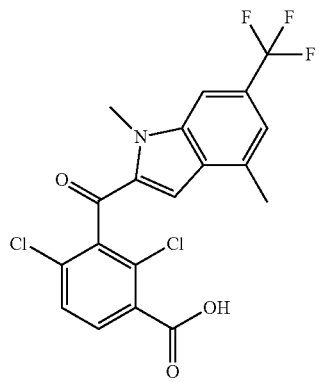 [SMILES: Cc1cc(C(F)(F)F)cc2c1cc(C(=O)c1c(Cl)ccc(C(=O)O)c1Cl)n2C]

Using a procedure similar to Example A, Step 5, 2,4-dichloro-3-(1,4-dimethyl-6-(trifluoromethyl)-1H-indole-2-carbonyl)benzoic acid (2.37 g, 100%) was obtained as a white solid from methyl 2,4-dichloro-3-(1,4-dimethyl-6-(trifluoromethyl)-1H-indole-2-carbonyl)benzoate (2.45 g, 5.52 mmol).

LC/MS (Method i) $R_t$=2.42 min.; MS m/z: 430 [M+H]$^+$ $^1$H NMR (DMSO-d$_6$, 300 MHz): δ 13.84 (broad, 1H), 7.99 (d, J=8.4 Hz, 1H), 7.96 (s, 1H), 7.75 (d, J=8.4 Hz, 1H), 7.24 (s, 1H), 7.15 (s, 1H), 4.24 (s, 3H), 2.50 (s, 3H).

Step 5: (2,4-dichloro-3-(1,4-dimethyl-6-(trifluoromethyl)-1H-indole-2-carbonyl)phenyl)(morpholino)methanone

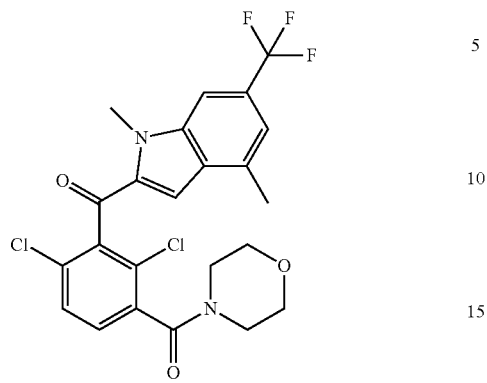

Using a procedure similar to Example A1, (2,4-dichloro-3-(1,4-dimethyl-6-(trifluoromethyl)-1H-indole-2-carbonyl)phenyl)(morpholino)methanone (101 mg, 87%) was obtained as a white solid from 2,4-dichloro-3-(1,4-dimethyl-6-(trifluoromethyl)-1H-indole-2-carbonyl)benzoic acid (100 mg, 0.23 mmol) and morpholine (26.3 mg, 0.30 mmol).

LC/MS (Method g) $R_t$=1.87 min.; MS m/z: 499 [M+H]$^+$ $^1$H NMR (DMSO-d$_6$, 400 MHz): δ 7.96 (s, 1H), 7.76 (d, J=8.1 Hz, 1H), 7.65 (d, J=8.1 Hz, 1H), 7.30 and 7.09 (m, 1H), 7.24 (s, 1H), 4.23 (s, 3H), 3.65 (m, 4H), 3.55 (m, 2H), 3.36 (m, 1H), 3.15 (m, 1H), 2.50 (s, 3H).

TABLE AP

The following intermediates were prepared from 2,4-dichloro-3-(1,4-dimethyl-6-(trifluoromethyl)-1H-indole-2-carbonyl)benzoic acid (Example AP, Step 4) using the same procedure with the appropriate amine.

| Example # | Product | Amine | $R_t$ min | m/z ESI+ (M + H)$^+$ |
|---|---|---|---|---|
| AP-1 | (structure) | (structure) | 1.72 (Method g) | 554 |
| AP-2 | (structure) | (structure) | 2.63 (Method i) | 569 |

TABLE AP-continued
The following intermediates were prepared from 2,4-dichloro-3-(1,4-dimethyl-6-(trifluoromethyl)-1H-indole-2-carbonyl)benzoic acid (Example AP, Step 4) using the same procedure with the appropriate amine.
| Example # | Product | Amine | R, min | m/z ESI+ (M + H)+ |
|---|---|---|---|---|
| AP-3 | 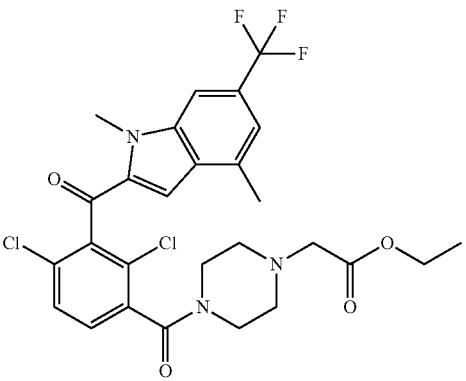 [SMILES: CCOC(=O)CN1CCN(C(=O)c2ccc(Cl)c(C(=O)c3cc4c(C)cc(C(F)(F)F)cc4n3C)c2Cl)CC1] | 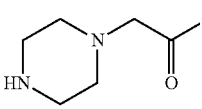 | 2.66 (Method i) | 584 |
| AP-4 | Chiral 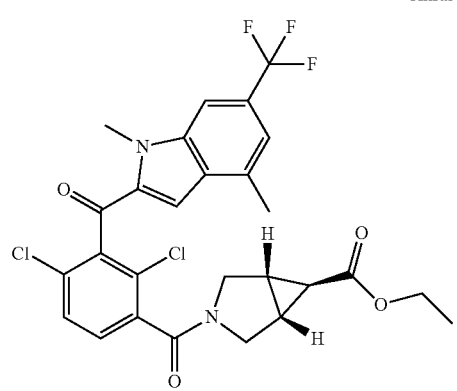 | Chiral 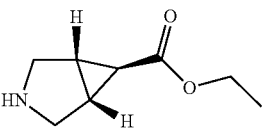 | 2.65 (Method i) | 567 |
| AP-5 | AND Enantiomer 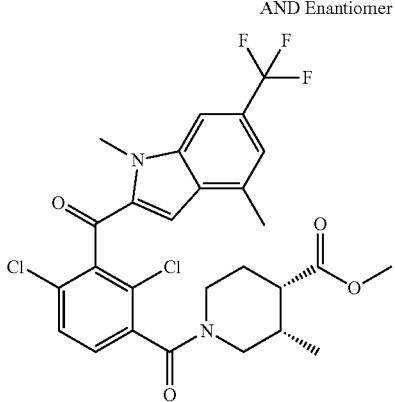 [SMILES: COC(=O)[C@H]1CCN(C(=O)c2ccc(Cl)c(C(=O)c3cc4c(C)cc(C(F)(F)F)cc4n3C)c2Cl)C[C@H]1C] | AND Enantiomer 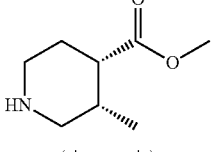 (cis racemic) | 2.66 (Method i) | 569 |

TABLE AP-continued
The following intermediates were prepared from 2,4-dichloro-3-(1,4-dimethyl-6-(trifluoromethyl)-1H-indole-2-carbonyl)benzoic acid (Example AP, Step 4) using the same procedure with the appropriate amine.
| Example # | Product | Amine | R$_t$ min | m/z ESI+ (M + H)+ |
|---|---|---|---|---|
| AP-6 | 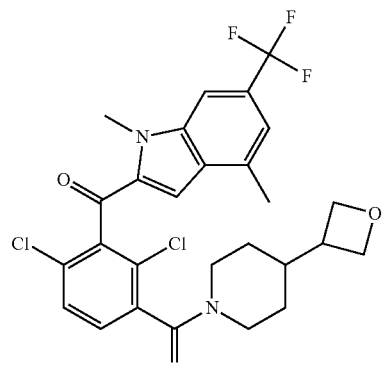 | 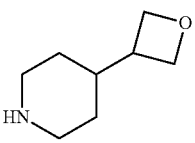 | 1.93 (Method g) | 553 |
| AP-7 | 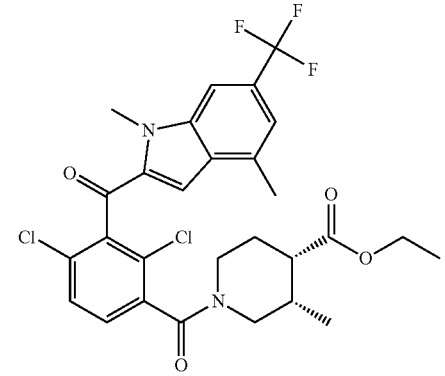 [SMILES: CCOC(=O)[C@H]1CCN(C(=O)c2ccc(Cl)c(C(=O)c3cc4c(C)cc(C(F)(F)F)cc4n3C)c2Cl)C[C@H]1C] | 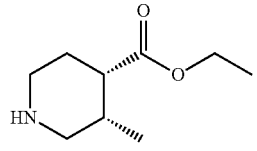 Preparation #83 | 2.73 (Method i) | 583 |
| AP-8 | 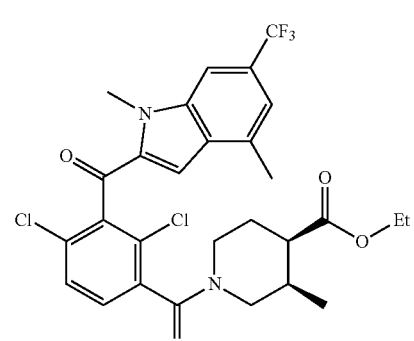 | 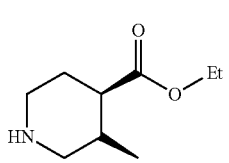 Preparation 84 | 2.73 (Method i) | 583 |

Example AQ: 2-(1-(2,4-dichloro-3-(1,4-dimethyl-6-(trifluoromethyl)-1H-indole-2-carbonyl)benzoyl)piperidin-4-yl)acetic acid

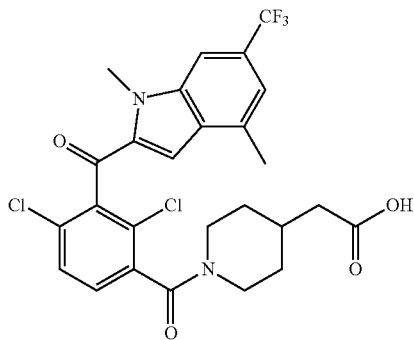 [SMILES: Cc1cc(C(F)(F)F)cc2c1cc(C(=O)c1c(Cl)ccc(C(=O)N3CCC(CC(=O)O)CC3)c1Cl)n2C]

Using a procedure similar to Example A, Step 5, 2-(1-(2,4-dichloro-3-(1,4-dimethyl-6-(trifluoromethyl)-1H-indole-2-carbonyl)benzoyl)piperidin-4-yl)acetic acid (108 mg, 82%) was obtained as a white solid from 2,4-dichloro-3-(1,4-dimethyl-6-(trifluoromethyl)-1H-indole-2-carbonyl)benzoic acid (Example AP, Step 4) (100 mg, 0.23 mmol). LC/MS (Method g) $R_t$=1.80 min.;

MS m/z: 555 $[M+H]^+$ $^1$H NMR (DMSO-$d_6$, 400 MHz): δ 12.10 (broad, 1H), 7.96 (s, 1H), 7.74 (m, 1H), 7.63 and 7.57 (d, J=8 Hz, 1H), 7.24-7.00 (m, 2H), 4.47 (m, 1H), 4.23 and 4.22 (s, 3H), 3.20 (m, 1H), 3.06 (m, 1H), 2.81 (m, 1H), 2.50 (s, 3H), 2.20 (m, 2H), 1.94 (m, 1H), 1.78 (m, 1H), 1.65 (m, 1H), 1.15 (m, 2H).

TABLE AQ

The following Examples were prepared using the same procedure starting from the appropriate esters (as described in Table AP).

| Example # | Product | Ester | $R_t$ min (Method g) | m/z ESI+ $(M + H)^+$ |
|---|---|---|---|---|
| AQ-1 | | AP-3 | 1.50 | 556 |
| AQ-2 | Chiral | AP-4 | 1.76 | 539 |

TABLE AQ-continued
The following Examples were prepared using the same procedure starting from the appropriate esters (as described in Table AP).
| Example # | Product | Ester | R$_t$ min (Method g) | m/z ESI+ (M + H)+ |
|---|---|---|---|---|
| AQ-3 (racemic) | AND Enantiomer 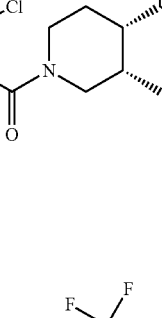 | AP-5 | 1.82 (method g) | 555 |
| AQ-4 | 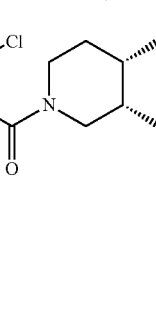 | AP-7 | 1.85 (method g) | 555 |
| AQ-5 | 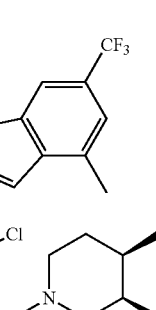 | AP-8 | 1.74 (method i) | 555 |

Example AR: (2,6-dichloro-3-(hydroxymethyl)phenyl)(1,4-dimethyl-6-(trifluoromethyl)-1H-indol-2-yl)methanone

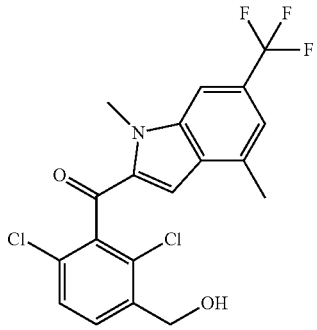 [SMILES: Cc1cc(C(F)(F)F)cc2c1cc(C(=O)c1c(Cl)ccc(CO)c1Cl)n2C]

To a solution of methyl 2,4-dichloro-3-(1,4-dimethyl-6-(trifluoromethyl)-1H-indole-2-carbonyl)benzoate (Example AP, Step 3) (250 mg, 0.563 mmol) in EtOHMeOH (10 ml) was added at room temperature sodium tetrahydroborate (63.9 mg, 1.688 mmol) and the reaction mixture was stirred at room temperature for 1 hour. More sodium tetrahydroborate (63.9 mg, 1.688 mmol) was added and the reaction mixture was stirred at room temperature for 24 hours. The reaction was quenched with NH$_4$Cl saturated aqueous solution. The reaction mixture was extracted with EtOAc and the organic layer was dried over magnesium sulfate and concentrated to dryness. The crude product was purified by preparative LCMS to give (2,6-dichloro-3-(hydroxymethyl)phenyl)(1,4-dimethyl-6-(trifluoromethyl)-1H-indol-2-yl)methanone (71 mg, 29%). LC/MS (Method g) R$_t$=1.92 min.; MS m/z: 416 [M+H]$^+$ $^1$H NMR (DMSO-d$_6$, 400 MHz): δ 7.95 (s, 1H), 7.73 (d, J=8 Hz, 1H), 7.66 (d, J=8 Hz, 1H), 7.23 (s, 1H), 7.02 (s, 1H), 5.62 (t, J=5.4 Hz, 1H), 4.61 (d, J=5.4 Hz, 2H), 4.23 (s, 3H), 2.50 (s, 3H).

Example AS: (2,4-dichloro-3-((7-methyl-5-(trifluoromethyl)-1H-indol-2-yl)methyl)phenyl)(morpholino)methanone

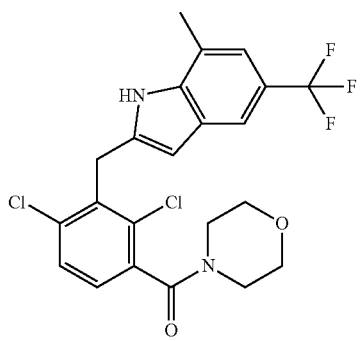 [SMILES: Cc1cc(C(F)(F)F)cc2cc(Cc3c(Cl)ccc(C(=O)N4CCOCC4)c3Cl)[nH]c12]

Step 1: tert-butyl 2,4-dichloro-3-(hydroxy(7-methyl-1-(phenylsulfonyl)-5-(trifluoromethyl)-1H-indol-2-yl)methyl)benzoate

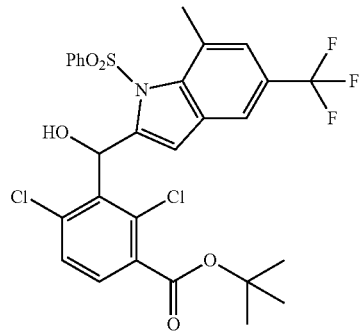

Using a procedure similar to Example A, Step 1, tert-butyl 2,4-dichloro-3-(hydroxy(7-methyl-1-(phenylsulfonyl)-5-(trifluoromethyl)-1H-indol-2-yl)methyl)benzoate (1.75 g, 49%) was obtained as an orange resin from N-(2-iodo-6-methyl-4-(trifluoromethyl)phenyl)benzenesulfonamide (Preparation #34) (2 g, 4.53 mmol) and tert-butyl 2,4-dichloro-3-(1-hydroxyprop-2-yn-1-yl)benzoate (Preparation #33) (1.23 g, 4.08 mmol). LC/MS (Method i) R$_t$=2.84 min.; MS m/z: 672 [M−H]$^-$+CH$_3$COOH $^1$H NMR (DMSO-d$_6$, 300 MHz): δ 7.60 (m, 8H), 7.44 (s, 1H), 6.97 (dd, J=5.9 and 1.5 Hz, 1H), 6.74 (d, J=1.5 Hz, 1H), 6.66 (d, J=5.9 Hz, 1H), 2.45 (s, 3H), 1.49 (s, 9H).

Step 2: 2,4-dichloro-3-((7-methyl-1-(phenylsulfonyl)-5-(trifluoromethyl)-1H-indol-2-yl)methyl)benzoic acid

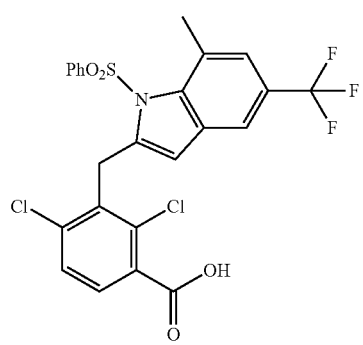

Using a procedure similar to Example A, Step 2, 2,4-dichloro-3-((7-methyl-1-(phenylsulfonyl)-5-(trifluoromethyl)-1H-indol-2-yl)methyl)benzoic acid (800 mg, 52%) was obtained as a yellow powder from tert-butyl 2,4-dichloro-3-(hydroxy(7-methyl-1-(phenylsulfonyl)-5-(trifluoromethyl)-1H-indol-2-yl)methyl)benzoate (1.7 g, 2.77 mmol). LC/MS (Method i) R$_t$=2.67 min.; MS m/z: 542 [M+H]$^+$ $^1$H NMR (DMSO-d$_6$, 300 MHz): δ 7.51-7.80 (m, 6H), 7.40 (m, 3H), 5.98 (s, 1H), 4.49 (s, 2H), 2.66 (s, 3H).

367

Step 3: 2,4-dichloro-3-((7-methyl-5-(trifluoromethyl)-1H-indol-2-yl)methyl)benzoic acid

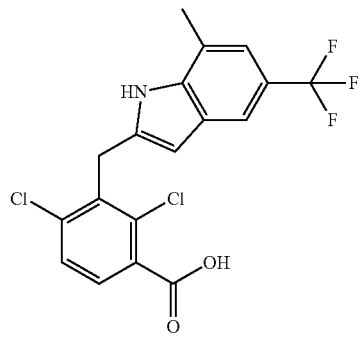 [SMILES: Cc1cc(C(F)(F)F)cc2cc(Cc3c(Cl)ccc(C(=O)O)c3Cl)[nH]c12]

Using a procedure similar to Example A, Step 3, 2,4-dichloro-3-((7-methyl-5-(trifluoromethyl)-1H-indol-2-yl)methyl)benzoic acid (620 mg, 99%) was obtained as an orange powder from 2,4-dichloro-3-((7-methyl-1-(phenylsulfonyl)-5-(trifluoromethyl)-1H-indol-2-yl)methyl)benzoic acid (800 mg, 1.47 mmol). LC/MS (Method i) $R_t$=2.37 min.; MS m/z: 402 [M+H]$^+$ $^1$H NMR (DMSO-d$_6$, 300 MHz): δ 11.57 (s, 1H), 7.55 (s, 1H), 7.41 (m, 1H), 7.29 (m, 2H), 7.10 (s, 1H), 5.77 (s, 1H), 4.40 (s, 2H), 2.54 (s, 3H).

Step 4: (2,4-dichloro-3-((7-methyl-5-(trifluoromethyl)-1H-indol-2-yl)methyl)phenyl)(morpholino)methanone

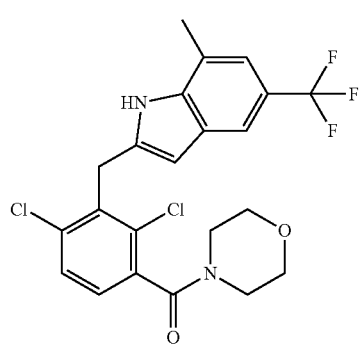 [SMILES: Cc1cc(C(F)(F)F)cc2cc(Cc3c(Cl)ccc(C(=O)N4CCOCC4)c3Cl)[nH]c12]

Using a procedure similar to Example A, Step 6, (2,4-dichloro-3-((7-methyl-5-(trifluoromethyl)-1H-indol-2-yl)methyl)phenyl)(morpholino)methanone (95 mg, 20%) was obtained as an orange powder from 2,4-dichloro-3-((7-methyl-5-(trifluoromethyl)-1H-indol-2-yl)methyl)benzoic acid (400 mg, 0.99 mmol). LC/MS (Method g) $R_t$=1.79 min.; MS m/z: 471 [M+H]$^+$ $^1$H NMR (DMSO-d$_6$, 500 MHz): δ 11.56 (s, 1H), 7.65 (d, J=8.4 Hz, 1H), 7.58 (s, 1H), 7.42 (d, J=8.4 Hz, 1H), 7.12 (s, 1H), 5.80 (m, 1H), 4.45 (s, 2H), 3.65 (m, 4H), 3.55 (m, 2H), 3.17 (m, 2H), 2.54 (s, 3H).

368

Example AT: (2,4-dichloro-3-((1,7-dimethyl-5-(trifluoromethyl)-1H-indol-2-yl)methyl)phenyl)(morpholino)methanone

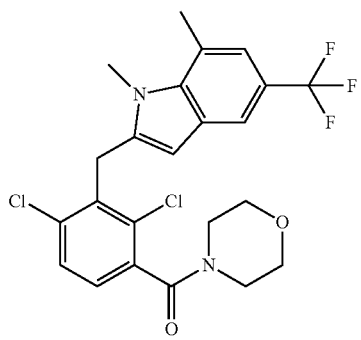 [SMILES: Cc1cc(C(F)(F)F)cc2cc(Cc3c(Cl)ccc(C(=O)N4CCOCC4)c3Cl)n(C)c12]

Using a procedure similar to Example A, Step 4, (2,4-dichloro-3-((1,7-dimethyl-5-(trifluoromethyl)-1H-indol-2-yl)methyl)phenyl)(morpholino)methanone (48 mg, 63%) was obtained as a beige powder from (2,4-dichloro-3-((7-methyl-5-(trifluoromethyl)-1H-indol-2-yl)methyl)phenyl)(morpholino)methanone (example AS, step 4) (70 mg, 0.149 mmol).

LC/MS (Method g) $R_t$=1.88 min.; MS m/z: 485 [M+H]$^+$ $^1$H NMR (DMSO-d$_6$, 400 MHz): δ 7.67 (d, J=8.1 Hz, 1H), 7.59 (s, 1H), 7.45 (d, J=8.1 Hz, 1H), 7.09 (s, 1H), 5.67 (s, 1H), 4.39 (m, 2H), 4.12 (s, 3H), 3.65 (m, 4H), 3.55 (m, 2H), 3.20 (m, 2H), 2.83 (s, 3H).

Example AU: 2-(2,6-dichloro-3-((3-oxomorpholino)methyl)benzyl)-1,4-dimethyl-1H-indole-6-carbonitrile Example AU1: 2-(2,6-dichloro-3-((3-oxomorpholino)methyl)benzoyl)-1,4-dimethyl-1H-indole-6-carbonitrile

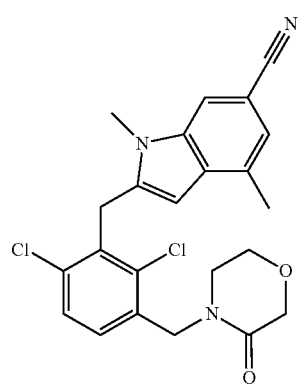

-continued

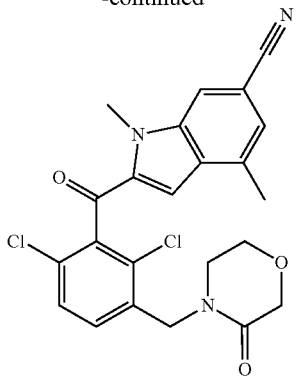

Step 1: 2-(2,6-dichloro-3-(hydroxymethyl)benzyl)-1,4-dimethyl-1H-indole-6-carbonitrile

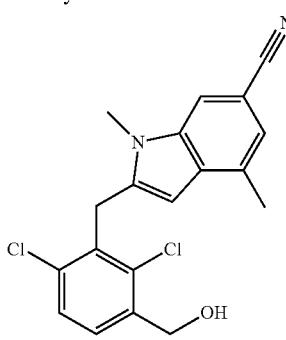

To a solution of methyl 2,4-dichloro-3-((6-cyano-1,4-dimethyl-1H-indol-2-yl)methyl)benzoate (Example AA, Step 4) (300 mg, 0.775 mmol) in THF (10 mL) was added lithium borohydride (1.162 mL, 2.32 mmol) (2M in THF) and the mixture was stirred at room temperature overnight. More lithium borohydride (0.5 ml, 1.17 mmol) (2M in THF) was added and the mixture was stirred at 50° C. for one hour, then cooled to 0° C. and quenched slowly by addition of 1M HCl aqueous solution. THF was concentrated, the precipitate was filtered, washed with water and dried under vacuum. The residue was dissolved in DCM, dried with magnesium sulfate and concentrated to give 2-(2,6-dichloro-3-(hydroxymethyl)benzyl)-1,4-dimethyl-1H-indole-6-carbonitrile (290 mg, 89%) as a white solid.

LC/MS (Method h) $R_t$=2.77 min.; MS m/z: 359 [M+H]$^+$ $^1$H NMR (DMSO-d$_6$, 300 MHz): δ 7.91 (s, 1H), 7.60 (m, 2H), 7.11 (s, 1H), 5.67 (s, 1H), 5.55 (t, J=5.5 Hz, 1H), 4.59 (d, J=5.5 Hz, 2H), 4.44 (s, 2H), 3.91 (s, 3H), 2.31 (s, 3H).

Step 2: 2,4-dichloro-3-((6-cyano-1,4-dimethyl-1H-indol-2-yl)methyl)benzyl methanesulfonate

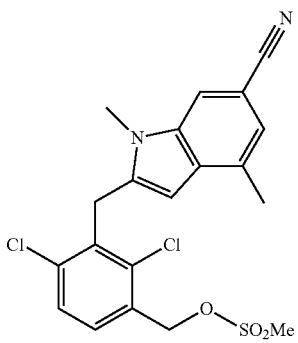 [SMILES: Cc1cc(C#N)cc2c1cc(Cc1c(Cl)ccc(COS(C)(=O)=O)c1Cl)n2C]

Using a procedure similar to Preparation #12, 2,4-dichloro-3-((6-cyano-1,4-dimethyl-1H-indol-2-yl)methyl)benzyl methanesulfonate (327 mg, 54%) was obtained as a yellow solid from 2-(2,6-dichloro-3-(hydroxymethyl)benzyl)-1,4-dimethyl-1H-indole-6-carbonitrile (290 mg, 0.80 mmol).

LC/MS (Method h) $R_t$=2.95 min.; MS m/z: 437 [M+H]$^+$ $^1$H NMR (DMSO-d$_6$, 300 MHz): δ 7.92 (s, 1H), 7.67 (m, 2H), 7.10 (m, 1H), 5.70 (m, 1H), 5.39 (s, 2H), 4.48 (s, 2H), 3.92 (s, 3H), 3.30 (s, 3H), 2.32 (m, 3H).

Step 3: 2-(2,6-dichloro-3-((3-oxomorpholino)methyl)benzyl)-1,4-dimethyl-1H-indole-6-carbonitrile

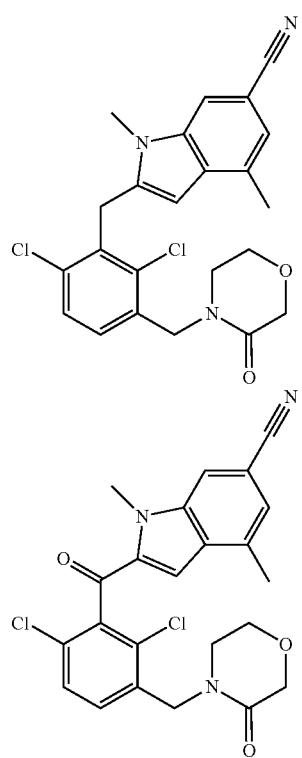

To a solution of morpholin-3-one (139 mg, 1.372 mmol) in DMF (9 ml) was added sodium hydride (63.1 mg, 1.578 mmol) and the reaction mixture was stirred at room temperature for 15 minutes. 2,4-dichloro-3-((6-cyano-1,4-dimethyl-1H-indol-2-yl)methyl)benzyl methanesulfonate (300 mg, 0.686 mmol) was added to the reaction mixture and it was stirred at room temperature for 20 hours. The reaction mixture was poured in a solution of water and EtOAc; the organic layer was extracted, washed with brine; dried over magnesium sulfate and concentrated. The residue was purified by column chromatography on silica gel (eluting with 30-70% EtOAc in cyclohexane) then purified by preparative LCMS to give 2-(2,6-dichloro-3-((3-oxomorpholino)methyl)benzyl)-1,4-dimethyl-1H-indole-6-carbonitrile (35 mg, 11%) as a yellow solid. LC/MS (Method g) $R_t$=1.65 min.; MS m/z: 443 [M+H]$^+$ $^1$H NMR (DMSO-d6, 400 MHz): δ 7.91 (s, 1H), 7.60 (d, J=8.4 Hz, 1H), 7.30 (d, J=8.4 Hz, 1H), 7.04-7.14 (m, 1H), 5.70 (s, 1H), 4.66 (s, 2H), 4.46 (s, 2H), 4.16 (s, 2H), 3.91 (s, 3H), 3.89 (m, 2H), 3.35 (m, 2H), 2.32 (s, 3H).

During this reaction, an oxidation side product was isolated and characterized as 2-(2,6-dichloro-3-((3-oxomorpholino)methyl)benzoyl)-1,4-dimethyl-1H-indole-6-carbonitrile (30 mg, 9%) as a white solid.

LC/MS (Method g) $R_t$=1.62 min.; MS m/z: 456 [M+H]+ 1H NMR (DMSO-d6, 400 MHz): δ 8.20 (s, 1H), 7.66 (d, J=8.4 Hz, 1H), 7.46 (d, J=8.4 Hz, 1H), 7.29 (m, 1H), 7.09 (s, 1H), 4.67 (m, 2H), 4.20 (s, 3H), 4.17 (s, 2H), 3.91 (m, 2H), 3.40 (m, 2H), 2.47 (s, 3H).

Example AV: ethyl 2-(4-(2,4-dichloro-3-((1,4-dimethyl-6-(trifluoromethyl)-1H-indol-2-yl)methyl)benzoyl)piperazin-1-yl)acetate

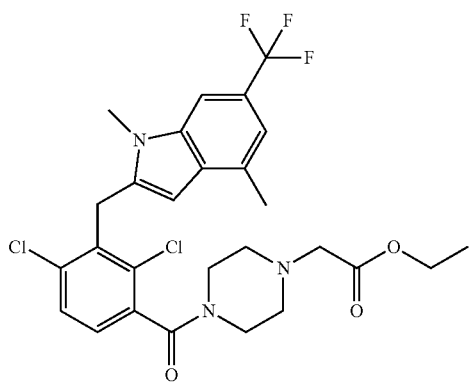 [SMILES: CCOC(=O)CN1CCN(C(=O)c2ccc(Cl)c(Cc3cc4c(C)cc(C(F)(F)F)cc4n3C)c2Cl)CC1]

Using a procedure similar to Example T, Step 1, ethyl 2-(4-(2,4-dichloro-3-((1,4-dimethyl-6-(trifluoromethyl)-1H-indol-2-yl)methyl)benzoyl)piperazin-1-yl)acetate (51 mg, 49%) was prepared from (2,4-dichloro-3-((1,4-dimethyl-6-(trifluoromethyl)-1H-indol-2-yl)methyl)phenyl)(piperazin-1-yl)methanone (Example S, Step 2) (85 mg, 0.17 mmol) and ethyl bromoacetate (30 mg, 0.18 mmol).

LC/MS (Method g) $R_t$=1.90 min.; MS m/z: 570 [M+H]+ 1H NMR (DMSO-d6, 400 MHz): δ 7.70 (s, 1H), 7.67 (d, J=8.1 Hz, 1H), 7.41 (d, J=8.1 Hz, 1H), 7.06 (s, 1H), 5.68 (s, 1H), 4.48 (d, J=16 Hz, 1H), 4.43 (d, J=16 Hz, 1H), 4.06 (q, J=7.2 Hz, 2H), 3.92 (s, 3H), 3.68 (m, 1H), 3.61 (m, 1H), 3.27 (s, 2H), 3.16 (m, 2H), 2.60 (m, 2H), 2.50 (m, 2H), 2.36 (s, 3H), 1.16 (t, J=7.2 Hz, 3H).

Example AW: 2-(4-(2,4-dichloro-3-((1,4-dimethyl-6-(trifluoromethyl)-1H-indol-2-yl)methyl)benzoyl)piperazin-1-yl)acetic acid

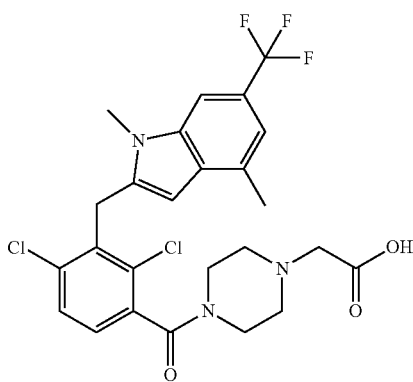 [SMILES: Cc1cc(C(F)(F)F)cc2c1cc(Cc1c(Cl)ccc(C(=O)N3CCN(CC(=O)O)CC3)c1Cl)n2C]

Step 1: methyl 2-(4-(2,4-dichloro-3-((1,4-dimethyl-6-(trifluoromethyl)-1H-indol-2-yl)methyl)benzoyl)piperazin-1-yl)acetate

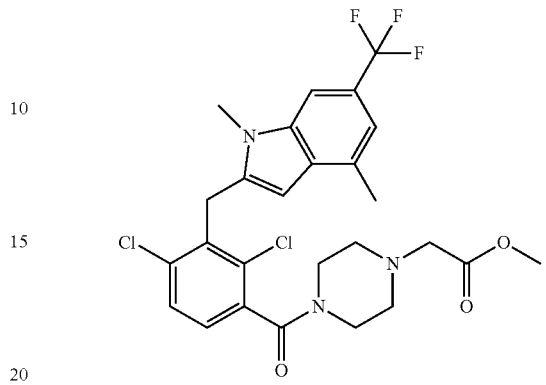

Using a procedure similar to Example T, Step 1, methyl 2-(4-(2,4-dichloro-3-((1,4-dimethyl-6-(trifluoromethyl)-1H-indol-2-yl)methyl)benzoyl)piperazin-1-yl)acetate (115 mg, 100%) was prepared from (2,4-dichloro-3-((1,4-dimethyl-6-(trifluoromethyl)-1H-indol-2-yl)methyl)phenyl)(piperazin-1-yl)methanone (Example S, Step 2) (100 mg, 0.206 mmol) and methyl bromoacetate (42.8 mg, 0.31 mmol). LC/MS (Method h) $R_t$=3.11 min.; MS m/z: 556 [M+H]+ 1H NMR (CHLOROFORM-d, 300 MHz): δ 7.41 (d, J=8.1 Hz, 1H), 7.36 (s, 1H), 7.19 (d, J=8.1 Hz, 1H), 7.01 (s, 1H), 5.70 (s, 1H), 4.36 (m, 2H), 3.80 (m, 5H), 3.65 (s, 3H), 3.25 (m, 2H), 3.20 (s, 2H), 2.62 (m, 2H), 2.50 (m, 2H), 2.35 (s, 3H).

Step 2: 2-(4-(2,4-dichloro-3-((1,4-dimethyl-6-(trifluoromethyl)-1H-indol-2-yl)methyl)benzoyl)piperazin-1-yl)acetic acid

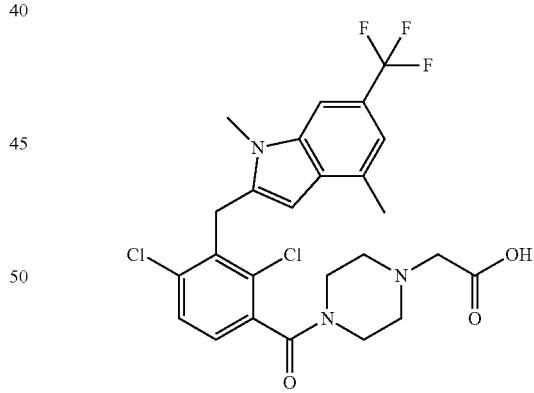

Using a procedure similar to Example O, Step 4, 2-(4-(2,4-dichloro-3-((1,4-dimethyl-6-(trifluoromethyl)-1H-indol-2-yl)methyl)benzoyl)piperazin-1-yl)acetic acid (25 mg, 15%) was prepared from methyl 2-(4-(2,4-dichloro-3-((1,4-dimethyl-6-(trifluoromethyl)-1H-indol-2-yl)methyl)benzoyl)piperazin-1-yl)acetate (170 mg, 0.30 mmol). LC/MS (Method g) $R_t$=1.50 min.;

MS m/z: 542 [M+H]+ 1H NMR (DMSO-d6, 500 MHz): δ 7.70 (s, 1H), 7.66 (d, J=8.4 Hz, 1H), 7.41 (d, J=8.4 Hz, 1H), 7.06 (s, 1H), 5.68 (s, 1H), 4.46 (m, 2H), 3.91 (s, 3H), 3.65 (m, 2H), 3.19 (m, 4H), 3.06 (m, 2H), 2.58 (m, 1H), 2.48 (m, 1H), 2.36 (s, 3H).

Example AX: (3-((6-bromo-1,4-dimethyl-1H-indol-2-yl)methyl)-2,4-dichlorophenyl)(morpholino)methanone

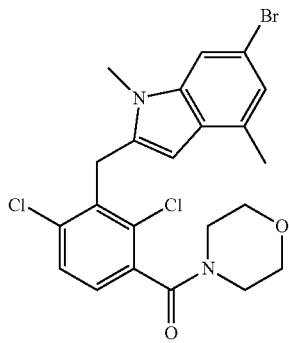 [SMILES: Cc1cc(Br)cc2c1cc(Cc1c(Cl)ccc(C(=O)N3CCOCC3)c1Cl)n2C]

Step 1: methyl 3-((6-bromo-4-methyl-1-(phenylsulfonyl)-1H-indol-2-yl)(hydroxy)methyl)-2,4-dichlorobenzoate

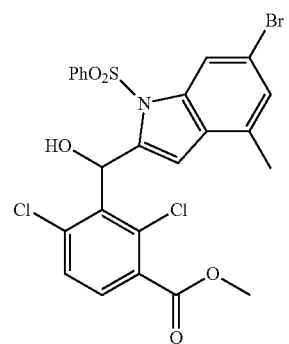

Using a procedure similar to Example A, Step 1, methyl 3-((6-bromo-4-methyl-1-(phenylsulfonyl)-1H-indol-2-yl)(hydroxy)methyl)-2,4-dichlorobenzoate (1.9 g, 66%) was prepared from N-(5-bromo-2-iodo-3-methylphenyl)benzenesulfonamide (Preparation #35) (2.21 g, 4.89 mmol) and methyl 2,4-dichloro-3-(1-hydroxyprop-2-yn-1-yl)benzoate (Preparation #1) (1.39 g, 5.38 mmol). LC/MS (Method h) $R_t$=3.33 min.; MS m/z: 640 [M−H]−+CH$_3$COOH $^1$H NMR (DMSO-d$_6$, 300 MHz): δ 7.94 (s, 1H), 7.85 (m, 2H), 7.60 (m, 5H), 7.28 (s, 1H), 6.98 (dd, J=5.8, 1.2 Hz, 1H), 6.71 (s, 1H), 6.64 (d, J=5.8 Hz, 1H, 3.86 (s, 3H), 2.37 (s, 3H).

Step 2: methyl 3-((6-bromo-4-methyl-1-(phenylsulfonyl)-1H-indol-2-yl)methyl)-2,4-dichlorobenzoate

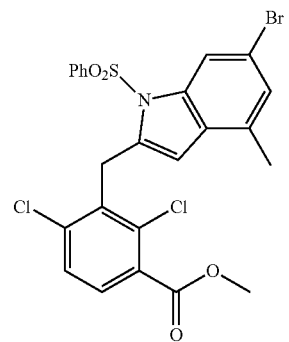

Using a procedure similar to Example A, Step 2, methyl 3-((6-bromo-4-methyl-1-(phenylsulfonyl)-1H-indol-2-yl)methyl)-2,4-dichlorobenzoate (1.73 g, 94%) was prepared from methyl 3-((6-bromo-4-methyl-1-(phenylsulfonyl)-1H-indol-2-yl)(hydroxy)methyl)-2,4-dichlorobenzoate (1.9 g, 3.26 mmol).

LC/MS (Method h) $R_t$=3.77 min.; MS m/z: 566 [M+H]$^+$ $^1$H NMR (DMSO-d$_6$, 300 MHz): δ 8.10 (s, 1H), 7.93 (m, 2H), 7.79 (m, 2H), 7.69 (m, 3H), 7.27 (s, 1H), 5.84 (s, 1H), 4.55 (s, 2H), 3.86 (s, 3H), 2.26 (s, 3H).

Step 3: methyl 3-((6-bromo-4-methyl-1H-indol-2-yl)methyl)-2,4-dichlorobenzoate

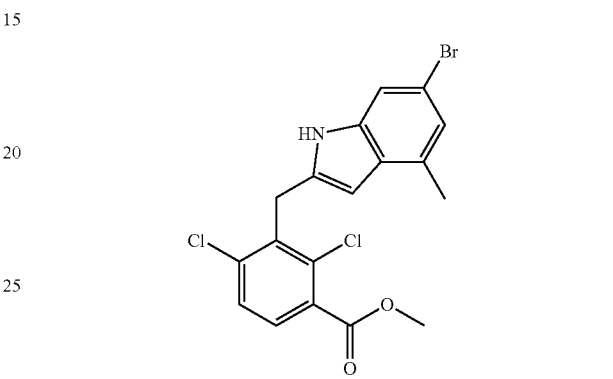

Using a procedure similar to Example A, Step 3 methyl 3-((6-bromo-4-methyl-1H-indol-2-yl)methyl)-2,4-dichlorobenzoate (1.05 g, 81%) was prepared from methyl 3-((6-bromo-4-methyl-1-(phenylsulfonyl)-1H-indol-2-yl)methyl)-2,4-dichlorobenzoate (1.73 g, 3.05 mmol). LC/MS (Method h) $R_t$=3.36 min.; MS m/z: 426 [M+H]$^+$ $^1$H NMR (DMSO-d$_6$, 300 MHz): δ 11.19 (s, 1H), 7.75 (m, 1H), 7.65 (m, 1H), 7.32 (s, 1H), 6.88 (s, 1H), 5.84 (s, 1H), 4.43 (s, 2H), 3.87 (s, 3H), 2.32 (s, 3H).

Step 4: methyl 3-((6-bromo-1,4-dimethyl-1H-indol-2-yl)methyl)-2,4-dichlorobenzoate

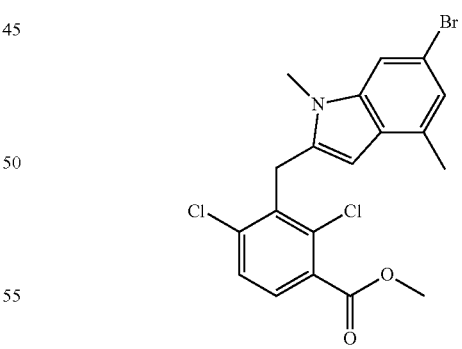

Using a procedure similar to Example P, Step 4, methyl 3-((6-bromo-1,4-dimethyl-1H-indol-2-yl)methyl)-2,4-dichlorobenzoate (916 mg, 89%) was prepared from methyl 3-((6-bromo-4-methyl-1H-indol-2-yl)methyl)-2,4-dichlorobenzoate (1 g, 2.34 mmol). LC/MS (Method h) $R_t$=3.52 min.; MS m/z: 440 [M+H]$^+$ $^1$H NMR (DMSO-d$_6$, 300 MHz): δ 7.80 (m, 1H), 7.70 (m, 1H), 7.54 (s, 1H), 6.91 (s, 1H), 5.54 (m, 1H), 4.43 (s, 2H), 3.88 (s, 3H), 3.82 (s, 3H), 2.27 (s, 3H).

Step 5: 3-((6-bromo-1,4-dimethyl-1H-indol-2-yl)methyl)-2,4-dichlorobenzoic acid

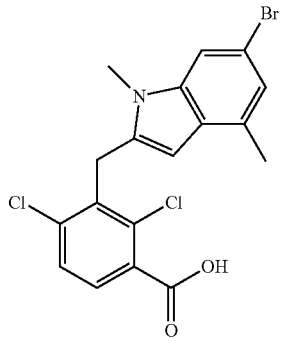

Using a procedure similar to Example A, Step 5, 3-((6-bromo-1,4-dimethyl-1H-indol-2-yl)methyl)-2,4-dichlorobenzoic acid (850 mg, 96%) was prepared from methyl 3-((6-bromo-1,4-dimethyl-1H-indol-2-yl)methyl)-2,4-dichlorobenzoate (916 mg, 2.07 mmol). The compound was used directly in the next step. LC/MS (Method h) $R_t$=3.06 min.; MS m/z: 426 [M+H]$^+$

Step 6: (3-((6-bromo-1,4-dimethyl-1H-indol-2-yl)methyl)-2,4-dichlorophenyl)(morpholino)methanone

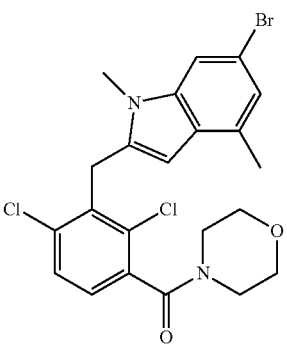

Using a procedure similar to Example A1, (3-((6-bromo-1,4-dimethyl-1H-indol-2-yl)methyl)-2,4-dichlorophenyl)(morpholino)methanone (970 mg, 97%) was prepared from 3-((6-bromo-1,4-dimethyl-1H-indol-2-yl)methyl)-2,4-dichlorobenzoic acid (850 mg, 1.99 mmol) and morpholine (260 mg, 2.99 mmol). LC/MS (Method g) $R_t$=1.90 min.; MS m/z: 495 [M+H]$^+$ $^1$H NMR (DMSO-d$_6$, 400 MHz): δ 7.67 (d, J=8.4 Hz, 1H), 7.53 (m, 1H), 7.44 (d, J=8.4 Hz, 1H), 6.92 (s, 1H), 5.57 (s, 1H), 4.39 (m, 2H), 3.81 (s, 3H), 3.65 (m, 4H), 3.53 (m, 2H), 3.17 (m, 2H), 2.28 (s, 3H).

Example AY: (2,4-dichloro-3-((1,4-dimethyl-6-morpholino-1H-indol-2-yl)methyl)phenyl)(morpholino)methanone

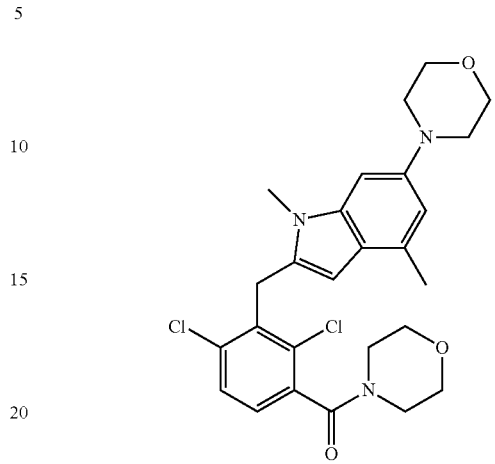

To a suspension of (3-((6-bromo-1,4-dimethyl-1H-indol-2-yl)methyl)-2,4-dichlorophenyl)(morpholino)methanone (Example AW, Step 6), (200 mg, 0.403 mmol) and potassium phosphate tribasic (171 mg, 0.806 mmol) in dioxane (2.5 mL) was added 2-dicyclohexylphosphino-2',6'-di-isopropoxy-1,1'-biphenyl (11.28 mg, 0.024 mmol), chloro(2-dicyclohexylphosphino-2',6'-di-isopropoxy-1,1'-biphenyl)[2-(2-aminoethylphenyl)]palladium(II), methyl-t-butylether adduct (9.88 mg, 0.012 mmol) and morpholine (38.6 mg, 0.443 mmol). The mixture was stirred at reflux for 8 hours. More potassium phosphate tribasic (171 mg, 0.806 mmol), 2-dicyclohexylphosphino-2',6'-di-isopropoxy-1,1'-biphenyl (11.28 mg, 0.024 mmol), chloro(2-dicyclohexylphosphino-2',6'-di-isopropoxy-1,1'-biphenyl)[2-(2-aminoethylphenyl)]palladium(II), methyl-tert-butylether adduct (9.88 mg, 0.012 mmol) and morpholine (38.6 mg, 0.443 mmol) were added and the mixture was stirred at reflux overnight. The mixture was diluted with EtOAc and the organic phase was washed successively with water and a saturated NaCl aqueous solution, dried over magnesium sulfate and concentrated.

The residue was purified by preparative LCMS to give (2,4-dichloro-3-((1,4-dimethyl-6-morpholino-1H-indol-2-yl)methyl)phenyl)(morpholino)methanone (25 mg, 12%) as a beige solid. LC/MS (Method g) $R_t$=1.38 min.; MS m/z: 502 [M+H]$^+$ $^1$H NMR (DMSO-d$_6$, 400 MHz): δ 7.65 (d, J=8.1 Hz, 1H), 7.42 (d, J=8.1 Hz, 1H), 6.73 (s, 1H), 6.55 s, 1H), 5.40 (s, 1H), 4.36 (m, 2H), 3.76 (m, 7H), 3.65 (m, 4H), 3.54 (m, 2H), 3.17 (m, 2H), 3.07 (m, 4H), 2.23 (s, 3H).

Example AZ: 1-(2,4-dichloro-3-((1,4-dimethyl-6-(trifluoromethyl)-1H-indol-2-yl)methyl)benzoyl)-3,3-difluoropiperidine-4-carboxylic acid

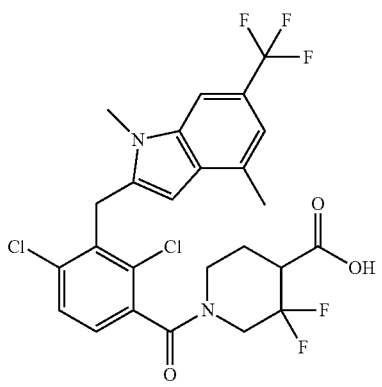 [SMILES: Cc1cc(C(F)(F)F)cc2c1cc(Cc1c(Cl)ccc(C(=O)N3CCC(C(=O)O)C(F)(F)C3)c1Cl)n2C]

To a solution of ethyl 1-(2,4-dichloro-3-((1,4-dimethyl-6-(trifluoromethyl)-1H-indol-2-yl)methyl)benzoyl)-3,3-difluoropiperidine-4-carboxylate (Table A, Example A-8) (100 mg, 0.169 mmol) in acetic acid (6.5 mL) was added at room temperature hydrochloric acid (323 µl, 3.34 mmol) and the reaction mixture was stirred at reflux for 18 hours. More hydrogen chloride (140 µl, 1.449 mmol) was added at room temperature and the reaction mixture was stirred at reflux for 24 hours. The reaction mixture was concentrated to dryness and the residue was purified by column chromatography on silica gel (eluting with 7-10% MeOH in DCM) to give 1-(2,4-dichloro-3-((1,4-dimethyl-6-(trifluoromethyl)-1H-indol-2-yl)methyl)benzoyl)-3,3-difluoropiperidine-4-carboxylic acid (16 mg, 16%) as a white solid. LC/MS (Method g) $R_t$=1.86 min.; MS m/z: 563 [M+H]$^+$ $^1$H NMR (DMSO-d$_6$, 500 MHz): δ 7.70 (m, 2H), 7.38 (m, 1H), 7.06 (s, 1H), 5.67 (m, 1H), 4.47 (m, 2H), 4.28 (m, 1H), 4.10 (m, 1H), 3.92 (s, 3H), 3.39 (m, 1H), 3.17 (m, 1H), 2.82 (m, 1H), 2.36 and 2.34 (s, 3H), 1.90 (m, 2H).

Example BA: 1-(2,4-dichloro-3-((1,4-dimethyl-6-(trifluoromethyl)-1H-indol-2-yl)methyl)benzoyl)-3-fluoropiperidine-4-carboxylic acid

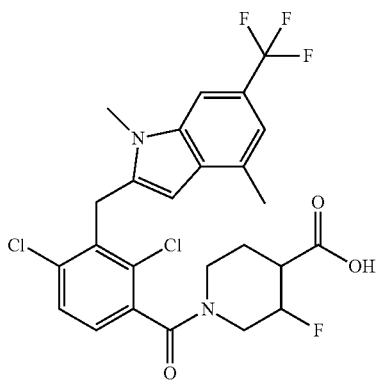 [SMILES: Cc1cc(C(F)(F)F)cc2c1cc(Cc1c(Cl)ccc(C(=O)N3CCC(C(=O)O)C(F)C3)c1Cl)n2C]

Using a procedure similar to Example AZ, 1-(2,4-dichloro-3-((1,4-dimethyl-6-(trifluoromethyl)-1H-indol-2-yl)methyl)benzoyl)-3-fluoropiperidine-4-carboxylic acid (11 mg, 13%) was prepared from ethyl 1-(2,4-dichloro-3-((1,4-dimethyl-6-(trifluoromethyl)-1H-indol-2-yl)methyl)benzoyl)-3-fluoropiperidine-4-carboxylate (Table A, Example A-9) (80 mg, 0.14 mmol). LC/MS (Method i) $R_t$=2.42 min.; MS m/z: 545 [M+H]$^+$ $^1$H NMR (DMSO-d$_6$, 500 MHz): δ 12.81 (broad, 1H), 7.70 (m, 2H), 7.50 and 7.40 (m, 1H), 7.06 (s, 1H), 5.68 (m, 1H), 4.89-4.70 (m, 1H), 4.39-4.58 (m, 2H), 4.31-3.90 (m, 4H), 3.40-3.58 (m, 2H), 3.10-3.26 (m, 2H), 2.38 (m, 3H), 1.85-2.08 (m, 1H), 1.56-1.76 (m, 1H)

Example BB: (5-((1,4-dimethyl-6-(trifluoromethyl)-1H-indol-2-yl)methyl)-4,6-dimethylpyridin-3-yl)(morpholino)methanone

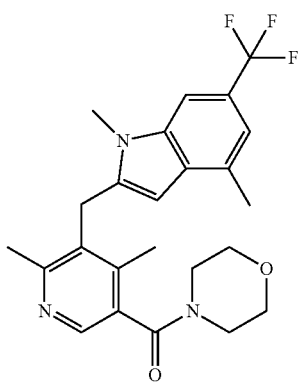 [SMILES: Cc1ncc(C(=O)N2CCOCC2)c(C)c1Cc1cc2c(C)cc(C(F)(F)F)cc2n1C]

Step 1: methyl 5-(hydroxy(4-methyl-1-(phenylsulfonyl)-6-(trifluoromethyl)-1H-indol-2-yl)methyl)-4,6-dimethylnicotinate

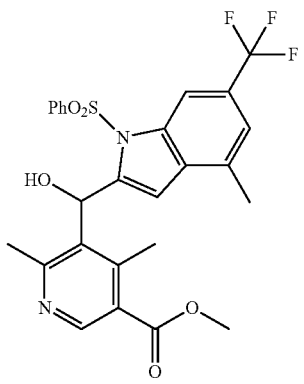

Using a procedure similar to Example A, Step 1, methyl 5-(hydroxy(4-methyl-1-(phenylsulfonyl)-6-(trifluoromethyl)-1H-indol-2-yl)methyl)-4,6-dimethylnicotinate (1.4 g, 69%) was prepared from N-(2-iodo-3-methyl-5-(trifluoromethyl)phenyl)benzenesulfonamide (Preparation #16) (1.8 g, 4.16 mmol) and methyl 5-(1-hydroxyprop-2-yn-1-yl)-4,6-dimethylnicotinate (Preparation #36) (830 mg, 3.79 mmol) the compound was used directly in the next step. LC/MS (Method i) $R_t$=2.51 min.; MS m/z: 533 [M+H]$^+$

Step 2: methyl 4,6-dimethyl-5-((4-methyl-1-(phenylsulfonyl)-6-(trifluoromethyl)-1H-indol-2-yl)methyl)nicotinate

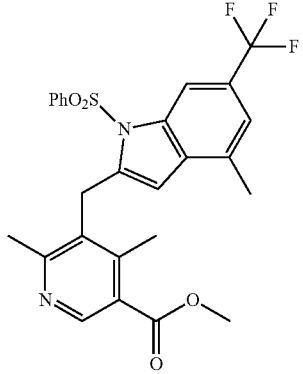

Using a procedure similar to Example Z, Step 2, methyl 4,6-dimethyl-5-((4-methyl-1-(phenylsulfonyl)-6-(trifluoromethyl)-1H-indol-2-yl)methyl)nicotinate (1.28 g, 94%) was prepared from methyl 5-(hydroxy(4-methyl-1-(phenylsulfonyl)-6-(trifluoromethyl)-1H-indol-2-yl)methyl)-4,6-dimethylnicotinate (1.4 g, 2.63 mmol). The crude product was used directly in the next step. LC/MS (Method i) $R_t$=2.74 min.; MS m/z: 517 $[M+H]^+$

Step 3: methyl 4,6-dimethyl-5-((4-methyl-6-(trifluoromethyl)-1H-indol-2-yl)methyl)nicotinate

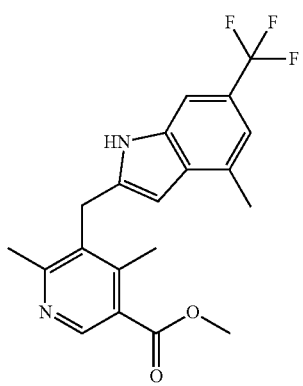 [SMILES: COC(=O)c1cnc(C)c(Cc2cc3c(C)cc(C(F)(F)F)cc3[nH]2)c1C]

Using a procedure similar to Example A, Step 3, methyl 4,6-dimethyl-5-((4-methyl-6-(trifluoromethyl)-1H-indol-2-yl)methyl)nicotinate (700 mg, 75%) was prepared from methyl 4,6-dimethyl-5-((4-methyl-1-(phenylsulfonyl)-6-(trifluoromethyl)-1H-indol-2-yl)methyl)nicotinate (1.28 g, 2.48 mmol). LC/MS (Method i) $R_t$=2.45 min.; MS m/z: 377 $[M+H]^+$ $^1$H NMR (DMSO-d$_6$, 300 MHz): δ 11.42 (s, 1H), 8.72 (s, 1H), 7.46 (s, 1H), 7.02 (s, 1H), 5.91 (s, 1H), 4.26 (s, 2H), 3.32 (s, 3H), 2.54 (s, 3H), 2.47 (s, 3H), 2.40 (s, 3H).

Step 4: methyl 5-((1,4-dimethyl-6-(trifluoromethyl)-1H-indol-2-yl)methyl)-4,6-dimethylnicotinate

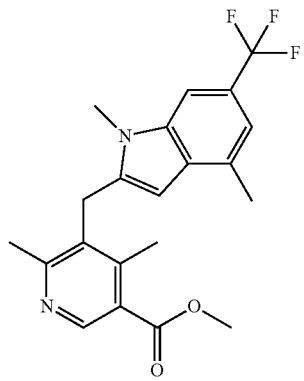 [SMILES: COC(=O)c1cnc(C)c(Cc2cc3c(C)cc(C(F)(F)F)cc3n2C)c1C]

Using a procedure similar to Example A, Step 4, methyl 5-((1,4-dimethyl-6-(trifluoromethyl)-1H-indol-2-yl)methyl)-4,6-dimethylnicotinate (540 mg, 75%) was prepared from methyl 4,6-dimethyl-5-((4-methyl-6-(trifluoromethyl)-1H-indol-2-yl)methyl)nicotinate (700 mg, 1.86 mmol). LC/MS (Method i) $R_t$=2.53 min.; MS m/z: 391 $[M+H]^+$ $^1$H NMR (DMSO-d$_6$, 300 MHz): δ 8.76 (s, 1H), 7.70 (s, 1H), 7.05 (s, 1H), 5.57 (s, 1H), 4.27 (s, 2H), 3.93 (s, 3H), 3.32 (s, 3H), 2.50 (s, 3H), 2.43 (s, 3H), 2.34 (s, 3H)

Step 5: 5-((1,4-dimethyl-6-(trifluoromethyl)-1H-indol-2-yl)methyl)-4,6-dimethylnicotinic acid

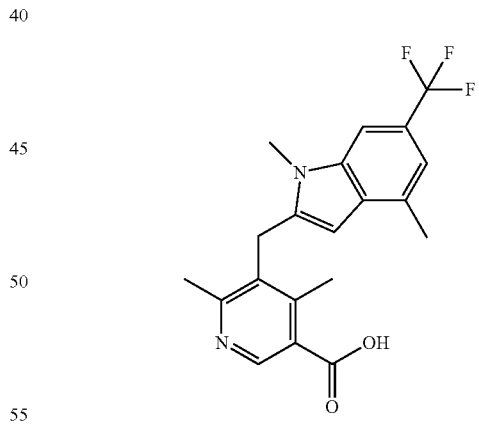

Using a procedure similar to Example A, Step 5, 5-((1,4-dimethyl-6-(trifluoromethyl)-1H-indol-2-yl)methyl)-4,6-dimethylnicotinic acid (420 mg, 81%) was prepared from methyl 5-((1,4-dimethyl-6-(trifluoromethyl)-1H-indol-2-yl)methyl)-4,6-dimethylnicotinate (540 mg, 1.38 mmol). LC/MS (Method i) $R_t$=1.89 min.; MS m/z: 377 $[M+H]^+$ $^1$H NMR (DMSO-d$_6$, 300 MHz): δ 13.21 (broad, 1H), 8.76 (s, 1H), 7.70 (s, 1H), 7.05 (s, 1H), 5.57 (s, 1H), 4.25 (s, 2H), 3.92 (s, 3H), 2.48 (s, 3H), 2.45 (s, 3H), 2.34 (s, 3H).

Step 6: (5-((1,4-dimethyl-6-(trifluoromethyl)-1H-indol-2-yl)methyl)-4,6-dimethylpyridin-3-yl)(morpholino)methanone

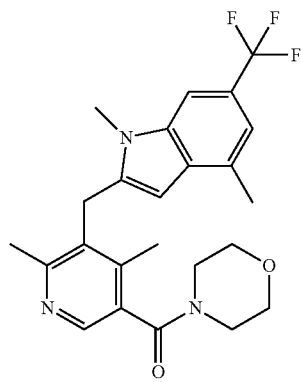 [SMILES: Cc1ncc(C(=O)N2CCOCC2)c(C)c1Cc1cc2c(C)cc(C(F)(F)F)cc2n1C]

Using a procedure similar to Example A1, (5-((1,4-dimethyl-6-(trifluoromethyl)-1H-indol-2-yl)methyl)-4,6-dimethylpyridin-3-yl)(morpholino)methanone (19 mg, 26%) was prepared from 5-((1,4-dimethyl-6-(trifluoromethyl)-1H-indol-2-yl)methyl)-4,6-dimethylnicotinic acid (59 mg, 0.16 mmol) and morpholine (25 mg, 0.29 mmol). LC/MS (Method g) $R_t$=1.50 min.; MS m/z: 446 [M+H]$^+$ $^1$H NMR (DMSO-d$_6$, 400 MHz): δ 8.26 (s, 1H), 7.70 (s, 1H), 7.05 (s, 1H), 5.58 (s, 1H), 4.23 (s, 2H), 3.92 (s, 3H), 3.67 (m, 4H), 3.51 (m, 2H), 3.18 (m, 2H), 2.46 (s, 3H), 2.35 (s, 3H), 2.14 (s, 3H).

Example BC: 2-(1-(5-((1,4-dimethyl-6-(trifluoromethyl)-1H-indol-2-yl)methyl)-4,6-dimethylnicotinoyl)piperidin-4-yl)acetic acid

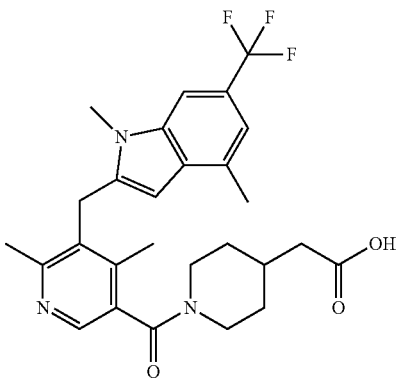 [SMILES: Cc1ncc(C(=O)N2CCC(CC(=O)O)CC2)c(C)c1Cc1cc2c(C)cc(C(F)(F)F)cc2n1C]

Step 1: methyl 2-(1-(5-((1,4-dimethyl-6-(trifluoromethyl)-1H-indol-2-yl)methyl)-4,6-dimethylnicotinoyl)piperidin-4-yl)acetate

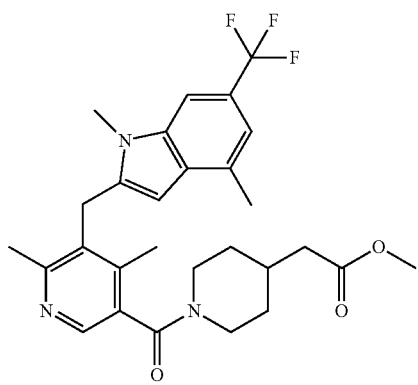

Using a procedure similar to Example A1, methyl 2-(1-(5-((1,4-dimethyl-6-(trifluoromethyl)-1H-indol-2-yl)methyl)-4,6-dimethylnicotinoyl)piperidin-4-yl)acetate (137 mg, 100%) was prepared from 5-((1,4-dimethyl-6-(trifluoromethyl)-1H-indol-2-yl)methyl)-4,6-dimethylnicotinic acid (Example BB, Step 5) (100 mg, 0.26 mmol) and methyl (4-piperidyl)acetate hydrochloride (66.9 mg, 0.34 mmol). the compound was used crude in the next step. LC/MS (Method i) $R_t$=2.41 min.; MS m/z: 516 [M+1-1]$^+$ Step 2: 2-(1-(5-((1,4-dimethyl-6-(trifluoromethyl)-1H-indol-2-yl)methyl)-4,6-dimethylnicotinoyl)piperidin-4-yl)acetic acid

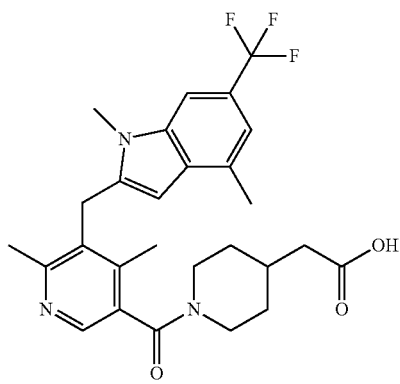 [SMILES: Cc1ncc(C(=O)N2CCC(CC(=O)O)CC2)c(C)c1Cc1cc2c(C)cc(C(F)(F)F)cc2n1C]

Using a procedure similar to Example A, Step 5, 2-(1-(5-((1,4-dimethyl-6-(trifluoromethyl)-1H-indol-2-yl)methyl)-4,6-dimethylnicotinoyl)piperidin-4-yl)acetic acid (116 mg, 87%) was prepared from methyl 2-(1-(5-((1,4-dimethyl-6-(trifluoromethyl)-1H-indol-2-yl)methyl)-4,6-dimethylnicotinoyl)piperidin-4-yl)acetate (137 mg, 0.26 mmol).

LC/MS (Method g) $R_t$=1.43 min.; MS m/z: 502 [M+H]$^+$ $^1$H NMR (DMSO-d$_6$, 400 MHz): δ 12.09 (broad, 1H), 8.30 and 8.24 (s, 1H), 7.70 (s, 1H), 7.05 (s, 1H), 5.57 (m, 1H), 4.52 (m, 1H), 4.25 (m, 2H), 3.92 (s, 3H), 3.34 (m, 1H), 3.05 (m, 1H), 2.81 (m, 1H), 2.48 (s, 3H), 2.35 and 2.34 (s, 3H), 2.06-2.25 (m, 5H), 1.92 (m, 1H), 1.78 (m, 1H), 1.63 (m, 1H), 1.17 (m, 2H).

Example BD: 2-[2,4-dimethyl-5-[4-(oxetan-3-yl)piperidine-1-carbonyl]pyridine-3-carbonyl]-1,4-dimethyl-indole-6-carbonitrile

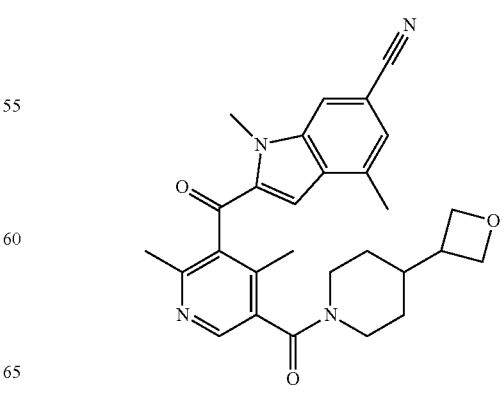

Step 1: methyl 5-((6-cyano-4-methyl-1-(phenylsulfonyl)-1H-indol-2-yl)(hydroxy)methyl)-4,6-dimethylnicotinate

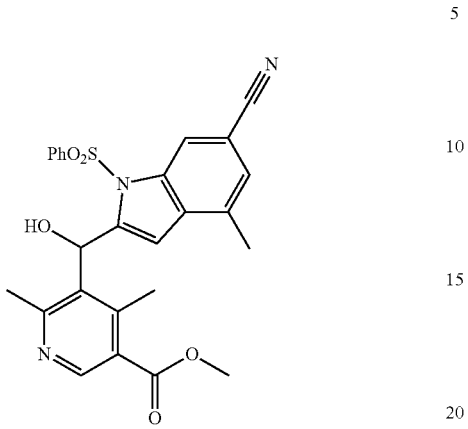

Using a procedure similar to Example A, Step 1, methyl 5-((6-cyano-4-methyl-1-(phenylsulfonyl)-1H-indol-2-yl)(hydroxy)methyl)-4,6-dimethylnicotinate (14 g, 81%) was prepared from N-(5-cyano-2-iodo-3-methylphenyl)benzenesulfonamide (Preparation #18) (14 g, 35.2 mmol) and methyl 5-(1-hydroxyprop-2-yn-1-yl)-4,6-dimethylnicotinate (Preparation #36) (8.86 g, 40.4 mmol). LC/MS (Method i) $R_t$=2.22 min.; MS m/z: 490 [M+H]$^+$ $^1$H NMR (DMSO-$d_6$, 300 MHz): δ 8.65 (s, 1H), 8.25 (s, 1H), 7.93 (m, 2H), 7.69 (m, 1H), 7.52-7.64 (m, 2H), 7.50 (s, 1H), 6.75 (s, 2H), 6.54 (s, 1H), 3.85 (s, 3H), 2.46 (s, 3H), 2.42 (s, 3H), 2.41 (s, 3H).

Step 2: methyl 5-(6-cyano-4-methyl-1-(phenylsulfonyl)-1H-indole-2-carbonyl)-4,6-dimethylnicotinate

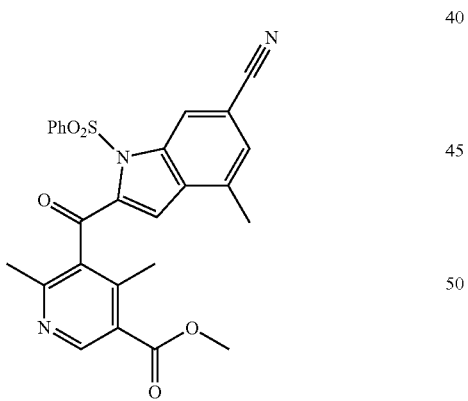

Using a procedure similar to Example AD, Step 2, methyl 5-(6-cyano-4-methyl-1-(phenylsulfonyl)-1H-indole-2-carbonyl)-4,6-dimethylnicotinate (7.5 g, 100%) was prepared from methyl 5-((6-cyano-4-methyl-1-(phenylsulfonyl)-1H-indol-2-yl)(hydroxy)methyl)-4,6-dimethylnicotinate (6.9 g, 14 mmol).

LC/MS (Method i) $R_t$=2.40 min.; MS m/z: 488 [M+H]$^+$ $^1$H NMR (DMSO-$d_6$, 300 MHz): δ 8.96 (s, 1H), 8.51 (s, 1H), 8.37 (m, 2H), 7.88 (m, 1H), 7.75 (m, 2H), 7.62 (m, 1H), 7.55 (s, 1H), 3.88 (s, 3H), 2.50 (s, 3H), 2.37 (s, 3H), 2.36 (s, 3H).

Step 3: methyl 5-(6-cyano-4-methyl-1H-indole-2-carbonyl)-4,6-dimethylnicotinate

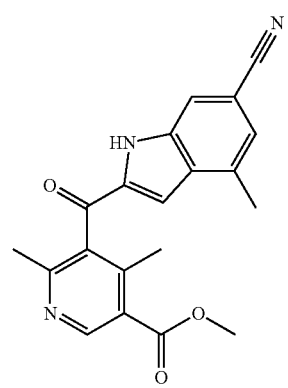 [SMILES: COC(=O)c1cnc(C)c(C(=O)c2cc3c(C)cc(C#N)cc3[nH]2)c1C]

Using a procedure similar to Example A, Step 3, methyl 5-(6-cyano-4-methyl-1H-indole-2-carbonyl)-4,6-dimethylnicotinate (5 g, 100%) was prepared from methyl 5-(6-cyano-4-methyl-1-(phenylsulfonyl)-1H-indole-2-carbonyl)-4,6-dimethylnicotinate (6.87 g, 14 mmol). LC/MS (Method i) $R_t$=2.05 min.; MS m/z: 348 [M+H]$^+$ $^1$H NMR (DMSO-$d_6$, 300 MHz): δ 12.64 (broad, 1H), 8.97 (s, 1H), 7.78 (s, 1H), 7.23 (s, 1H), 7.09 (s, 1H), 3.89 (s, 3H), 2.47 (s, 3H), 2.36 (s, 6H).

Step 4: methyl 5-(6-cyano-1,4-dimethyl-1H-indole-2-carbonyl)-4,6-dimethylnicotinate

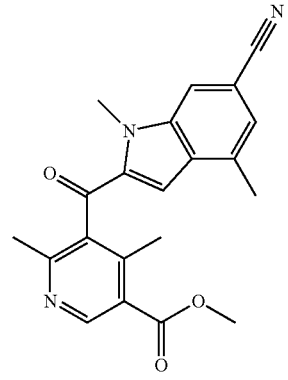 [SMILES: COC(=O)c1cnc(C)c(C(=O)c2cc3c(C)cc(C#N)cc3n2C)c1C]

Using a procedure similar to Example A, Step 4, methyl 5-(6-cyano-1,4-dimethyl-1H-indole-2-carbonyl)-4,6-dimethylnicotinate (2.6 g, 51%) was prepared from methyl 5-(6-cyano-4-methyl-1H-indole-2-carbonyl)-4,6-dimethylnicotinate (4.89 g, 14 mmol). LC/MS (Method i) $R_t$=2.20 min.; MS m/z: 362 [M+H]$^+$ $^1$H NMR (DMSO-$d_6$, 300 MHz): δ 8.96 (s, 1H), 8.21 (s, 1H), 7.27 (s, 1H), 7.06 (s, 1H), 4.23 (s, 3H), 3.32 (s, 3H), 2.45 (s, 3H), 2.38 (s, 3H), 2.37 (s, 3H).

Step 5: 5-(6-cyano-1,4-dimethyl-1H-indole-2-carbonyl)-4,6-dimethylnicotinic acid

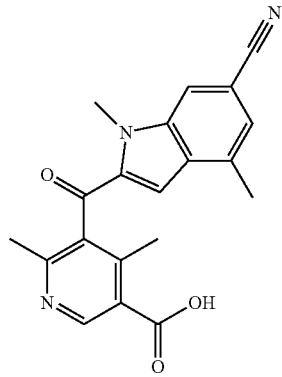 [SMILES: Cc1ncc(C(=O)O)c(C)c1C(=O)c1cc2c(C)cc(C#N)cc2n1C]

Using a procedure similar to Example A, Step 5, 5-(6-cyano-1,4-dimethyl-1H-indole-2-carbonyl)-4,6-dimethylnicotinic acid (2 g, 95%) was prepared from methyl 5-(6-cyano-1,4-dimethyl-1H-indole-2-carbonyl)-4,6-dimethylnicotinate (2.19 g, 6.06 mmol). LC/MS (Method i) $R_t$=1.80 min.; MS m/z: 348 [M+H]$^+$ $^1$H NMR (DMSO-d$_6$, 300 MHz): δ 13.42 (broad, 1H), 8.96 (s, 1H), 8.21 (s, 1H), 7.27 (s, 1H), 7.05 (s, 1H), 4.23 (s, 3H), 2.45 (s, 3H), 2.39 (s, 3H), 2.36 (s, 3H).

Step 6: 2-[2,4-dimethyl-5-[4-(oxetan-3-yl)piperidine-1-carbonyl]pyridine-3-carbonyl]-1,4-dimethyl-indole-6-carbonitrile

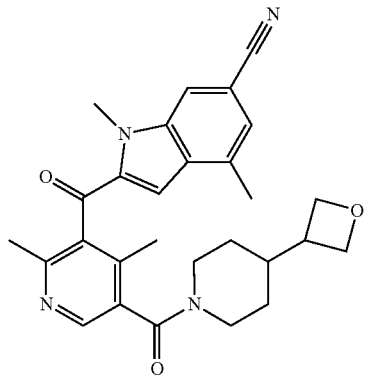 [SMILES: Cc1ncc(C(=O)N2CCC(C3COC3)CC2)c(C)c1C(=O)c1cc2c(C)cc(C#N)cc2n1C]

Using a procedure similar to Example A1, 2-[2,4-dimethyl-5-[4-(oxetan-3-yl)piperidine-1-carbonyl]pyridine-3-carbonyl]-1,4-dimethyl-indole-6-carbonitrile (73 mg, 54%) was prepared from 5-(6-cyano-1,4-dimethyl-1H-indole-2-carbonyl)-4,6-dimethylnicotinic acid (100 mg, 0.28 mmol) and 4-(oxetan-3-yl)piperidine (53 mg, 0.374 mmol). LC/MS (Method g) $R_t$=1.42 min.; MS m/z: 471 [M+H]$^+$ $^1$H NMR (DMSO-d$_6$, 400 MHz): δ 8.44 (broad, 1H), 8.20 (s, 1H), 7.27 (s, 1H), 7.02 (broad, 1H), 4.58 (m, 3H), 4.34 (m, 2H), 4.21 (s, 3H), 3.44 (m, 1H), 3.08 (m, 1H), 2.78 (m, 2H), 2.46 (m, 3H), 2.35 (s, 3H), 2.04 (m, 3H), 1.90 (m, 1H), 1.69 (m, 1H), 1.56 (m, 1H), 1.06 (m, 2H).

Example BE: (3,5-dichloro-4-((1,4-dimethyl-6-(trifluoromethyl)-1H-indol-2-yl)methyl)pyridin-2-yl)(morpholino)methanone

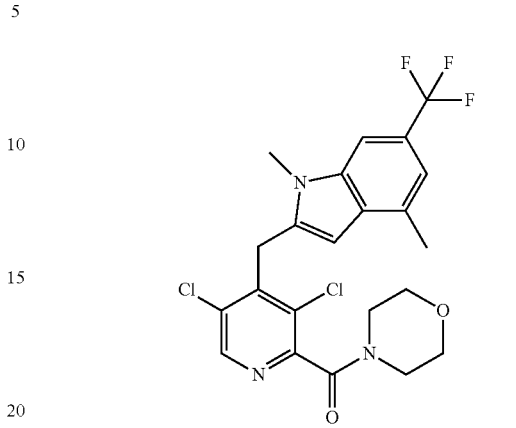

Step 1: ethyl 3,5-dichloro-4-(hydroxy(4-methyl-1-(phenylsulfonyl)-6-(trifluoromethyl)-1H-indol-2-yl)methyl)picolinate

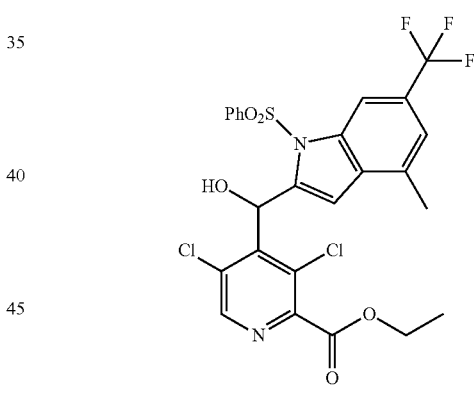

Using a procedure similar to Example A, Step 1, ethyl 3,5-dichloro-4-(hydroxy(4-methyl-1-(phenylsulfonyl)-6-(trifluoromethyl)-1H-indol-2-yl)methyl)picolinate (702 mg, 53%) was prepared from N-(2-iodo-3-methyl-5-(trifluoromethyl)phenyl)benzenesulfonamide (Preparation #16) (1 g, 0.267 mmol) and ethyl 3,5-dichloro-4-(1-hydroxyprop-2-yn-1-yl)picolinate (Preparation #37)(0.87 mg, 3.17 mmol). LC/MS (Method h) $R_t$=3.30 min.; MS m/z: 587 [M+H]$^+$ $^1$H NMR (DMSO-d$_6$, 300 MHz): δ 8.65 (s, 1H), 8.08 (s, 1H), 7.84 (m, 2H), 7.70 (m, 1H), 7.61 (m, 2H), 7.45 (s, 1H), 7.03 (m, 2H), 6.94 (s, 1H), 4.40 (q, J=7.1 Hz, 2H), 2.50 (s, 3H), 1.33 (t, J=7.1 Hz, 3H).

Step 2: ethyl 3,5-dichloro-4-((4-methyl-1-(phenyl-sulfonyl)-6-(trifluoromethyl)-1H-indol-2-yl)methyl)picolinate

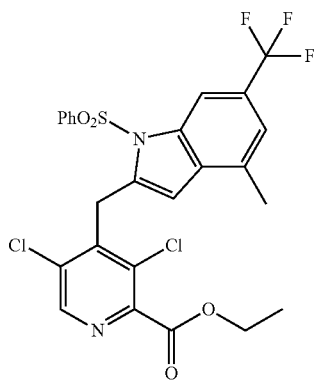

Using a procedure similar to Example Z, Step 2, ethyl 3,5-dichloro-4-((4-methyl-1-(phenylsulfonyl)-6-(trifluoromethyl)-1H-indol-2-yl)methyl)picolinate (474 mg, 69%) was prepared from ethyl 3,5-dichloro-4-(hydroxy(4-methyl-1-(phenylsulfonyl)-6-(trifluoromethyl)-1H-indol-2-yl)methyl)picolinate (702 mg, 1.19 mmol). LC/MS (Method h) $R_t$=3.65 min.; MS m/z: 571 [M+H]+ 1H NMR (DMSO-d$_6$, 300 MHz): δ 8.77 (s, 1H), 8.23 (s, 1H), 7.91 (m, 2H), 7.77 (m, 1H), 7.69 (m, 2H), 7.42 (s, 1H), 6.31 (s, 1H), 4.61 (s, 2H), 4.39 (q, J=7.1 Hz, 2H), 2.38 (s, 3H), 1.32 (t, J=7.1 Hz, 3H).

Step 3: ethyl 3,5-dichloro-4-((4-methyl-6-(trifluoromethyl)-1H-indol-2-yl)methyl)picolinate

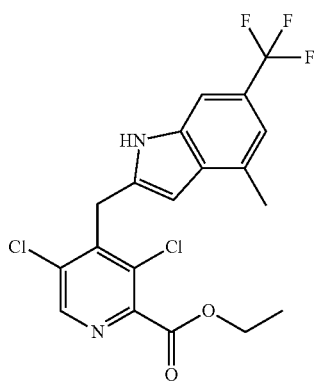 [SMILES: CCOC(=O)c1ncc(Cl)c(Cc2cc3c(C)cc(C(F)(F)F)cc3[nH]2)c1Cl]

Using a procedure similar to Example A, Step 3, ethyl 3,5-dichloro-4-((4-methyl-6-(trifluoromethyl)-1H-indol-2-yl)methyl)picolinate (221 mg, 51%) was prepared from ethyl 3,5-dichloro-4-((4-methyl-1-(phenylsulfonyl)-6-(trifluoromethyl)-1H-indol-2-yl)methyl)picolinate (427 mg, 0.82 mmol). LC/MS (Method h) $R_t$=3.27 min.; MS m/z: 431 [M+H]+ 1H NMR (DMSO-d$_6$, 300 MHz): δ 11.53 (s, 1H), 8.77 (s, 1H), 7.48 (s, 1H), 7.04 (s, 1H), 6.10 (m, 1H), 4.50 (s, 2H), 4.40 (q, J=7.1 Hz, 2H), 2.43 (s, 3H), 1.32 (t, J=7.1 Hz, 3H).

Step 4: ethyl 3,5-dichloro-4-((1,4-dimethyl-6-(trifluoromethyl)-1H-indol-2-yl)methyl)picolinate

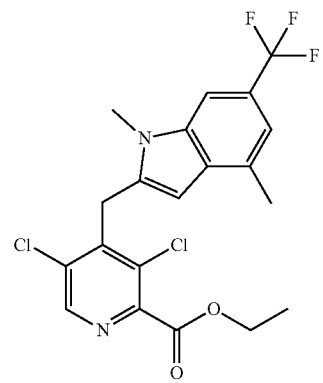 [SMILES: CCOC(=O)c1ncc(Cl)c(Cc2cc3c(C)cc(C(F)(F)F)cc3n2C)c1Cl]

Using a procedure similar to Example P, Step 4, ethyl 3,5-dichloro-4-((1,4-dimethyl-6-(trifluoromethyl)-1H-indol-2-yl)methyl)picolinate (191 mg, 69%) was prepared from ethyl 3,5-dichloro-4-((4-methyl-6-(trifluoromethyl)-1H-indol-2-yl)methyl)picolinate (220 mg, 0.51 mmol).

LC/MS (Method h) $R_t$=3.37 min.; MS m/z: 445 [M+H]+ 1H NMR (DMSO-d$_6$, 300 MHz): δ 8.80 (s, 1H), 7.72 (s, 1H), 7.07 (s, 1H), 5.83 (s, 1H), 4.51 (s, 2H), 4.41 (d, J=7.1 Hz, 2H), 3.92 (s, 3H), 2.38 (s, 3H), 1.33 (t, J=7.1 Hz, 3H).

Step 5: 3,5-dichloro-4-((1,4-dimethyl-6-(trifluoromethyl)-1H-indol-2-yl)methyl)picolinic acid

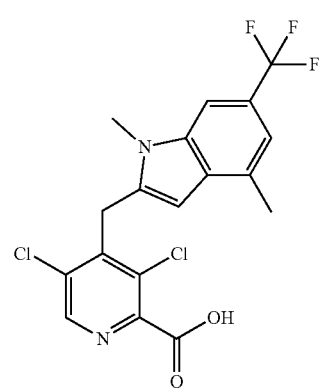 [SMILES: Cc1cc(C(F)(F)F)cc2c1cc(Cc1c(Cl)cnc(C(=O)O)c1Cl)n2C]

Using a procedure similar to Example A, Step 5, 3,5-dichloro-4-((1,4-dimethyl-6-(trifluoromethyl)-1H-indol-2-yl)methyl)picolinic acid (154 mg, 97%) was prepared from ethyl 3,5-dichloro-4-((1,4-dimethyl-6-(trifluoromethyl)-1H-indol-2-yl)methyl)picolinate (170 mg, 0.38 mmol). LC/MS (Method h) $R_t$=2.61 min.; MS m/z: 417 [M+H]+ 1H NMR (DMSO-d$_6$, 300 MHz): δ 8.74 (s, 1H), 7.72 (s, 1H), 7.07 (s, 1H), 5.79 (s, 1H), 4.50 (s, 2H), 3.93 (s, 3H), 2.38 (s, 3H).

Step 6: (3,5-dichloro-4-((1,4-dimethyl-6-(trifluoromethyl)-1H-indol-2-yl)methyl)pyridin-2-yl)(morpholino)methanone

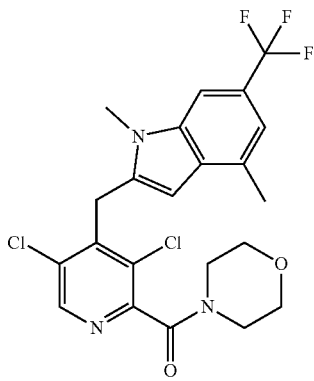

Using a procedure similar to Example A, Step 6, (3,5-dichloro-4-((1,4-dimethyl-6-(trifluoromethyl)-1H-indol-2-yl)methyl)pyridin-2-yl)(morpholino)methanone (108 mg, 72%) was prepared from 3,5-dichloro-4-((1,4-dimethyl-6-(trifluoromethyl)-1H-indol-2-yl)methyl)picolinic acid (129 mg, 0.30 mmol). LC/MS (Method g) $R_t$=1.79 min.; MS m/z: 486 [M+H]$^+$ $^1$H NMR (DMSO-d$_6$, 300 MHz): δ 8.78 (s, 1H), 7.72 (s, 1H), 7.07 (s, 1H), 5.83 (s, 1H), 4.48 (s, 2H), 3.92 (s, 3H), 3.54 (s, 2H), 3.31 (m, 4H), 3.21 (m, 2H), 2.38 (s, 3H).

Example BF: 2-[[3,5-dichloro-2-(morpholine-4-carbonyl)-4-pyridyl]methyl]-1,4-dimethyl-indole-6-carbonitrile

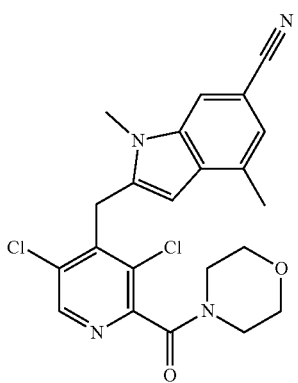 [SMILES: Cc1cc(C#N)cc2c1cc(Cc1c(Cl)cnc(C(=O)N3CCOCC3)c1Cl)n2C]

Step 1: ethyl 3,5-dichloro-4-((6-cyano-4-methyl-1-(phenylsulfonyl)-1H-indol-2-yl)(hydroxy)methyl)picolinate

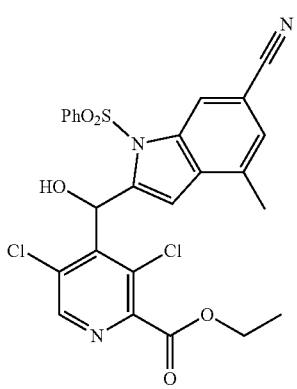

Using a procedure similar to Example A, Step 1, ethyl 3,5-dichloro-4-((6-cyano-4-methyl-1-(phenylsulfonyl)-1H-indol-2-yl)(hydroxy)methyl)picolinate (7.6 mg, 39%) was prepared from N-(5-cyano-2-iodo-3-methylphenyl)benzenesulfonamide (Preparation #18) (12 g, 30 mmol) and ethyl 3,5-dichloro-4-(1-hydroxyprop-2-yn-1-yl)picolinate (Preparation #37) (9.42 g, 34.4 mmol). LC/MS (Method i) $R_t$=2.39 min.; MS m/z: 544 [M+H]$^+$ $^1$H NMR (DMSO-d$_6$, 300 MHz): δ 8.64 (s, 1H), 8.25 (s, 1H), 7.95 (m, 2H), 7.71 (m, 1H), 7.60 (m, 2H), 7.52 (m, 1H), 7.06 (s, 1H), 7.02 (m, 1H), 6.92 (m, 1H), 4.40 (q, J=7.1 Hz, 2H), 2.44 (s, 3H), 1.32 (t, J=7.1 Hz, 3H).

Step 2: ethyl 3,5-dichloro-4-((6-cyano-4-methyl-1-(phenylsulfonyl)-1H-indol-2-yl)methyl)picolinate

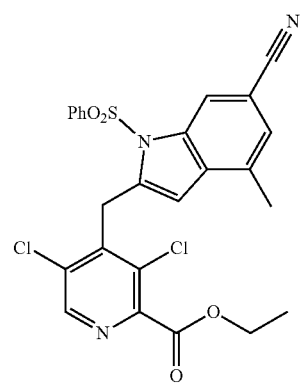

Using a procedure similar to Example Z, Step 2, ethyl 3,5-dichloro-4-((6-cyano-4-methyl-1-(phenylsulfonyl)-1H-indol-2-yl)methyl)picolinate (5.3 g, 56%) was prepared from ethyl 3,5-dichloro-4-((6-cyano-4-methyl-1-(phenylsulfonyl)-1H-indol-2-yl)(hydroxy)methyl)picolinate (7.3 g, 13.4 mmol). LC/MS (Method i) $R_t$=2.67 min.; MS m/z: 528 [M+H]$^+$ $^1$H NMR (DMSO-d$_6$, 300 MHz): δ 8.77 (s, 1H), 8.35 (s, 1H), 8.05 (m, 2H), 7.78 (m, 1H), 7.65 (m, 2H), 7.48 (s, 1H), 6.32 (s, 1H), 4.63 (s, 2H), 4.39 (q, J=7.1 Hz, 2H), 2.33 (s, 3H), 1.32 (t, J=7.1 Hz, 3H).

Step 3: ethyl 3,5-dichloro-4-((6-cyano-4-methyl-1H-indol-2-yl)methyl)picolinate

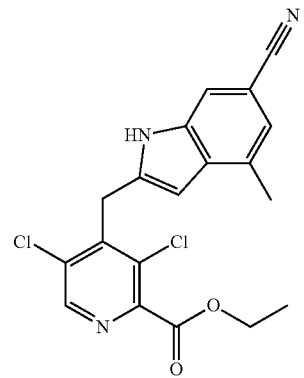 [SMILES: CCOC(=O)c1ncc(Cl)c(Cc2cc3c(C)cc(C#N)cc3[nH]2)c1Cl]

Using a procedure similar to Example A, Step 3, ethyl 3,5-dichloro-4-((6-cyano-4-methyl-1H-indol-2-yl)methyl)picolinate (4.9 g, 100%) was prepared from ethyl 3,5-dichloro-4-((6-cyano-4-methyl-1-(phenylsulfonyl)-1H-indol-2-yl)methyl)picolinate (5.3 g, 10 mmol). The product is used crude in the next step. LC/MS (Method i) $R_t$=2.36 min.; MS m/z: 388 [M+H]$^+$ Step 4: ethyl 3,5-dichloro-4-((6-cyano-1,4-dimethyl-1H-indol-2-yl)methyl)picolinate

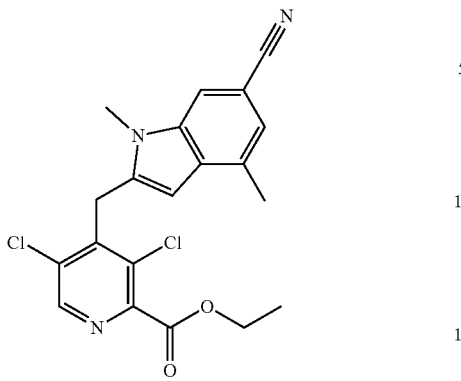

Using a procedure similar to Example P, Step 4, ethyl 3,5-dichloro-4-((6-cyano-1,4-dimethyl-1H-indol-2-yl) methyl)picolinate (1.25 g, 31%) was prepared from ethyl 3,5-dichloro-4-((6-cyano-4-methyl-1H-indol-2-yl)methyl) picolinate (3.89 g, 10.02 mmol). The product was used directly in the next step. LC/MS (Method i) $R_t$=2.41 min.; MS m/z: 402 [M+H]$^+$ Step 5: 3,5-dichloro-4-((6-cyano-1,4-dimethyl-1H-indol-2-yl)methyl)picolinic acid

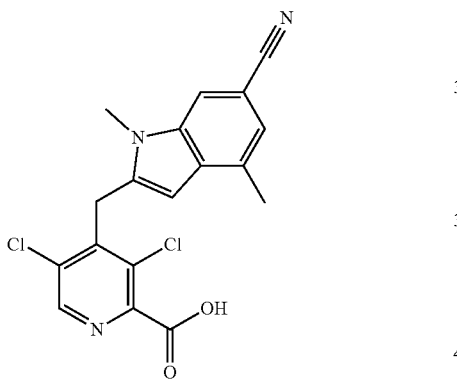

Using a procedure similar to Example A, Step 5, 3,5-dichloro-4-((6-cyano-1,4-dimethyl-1H-indol-2-yl)methyl) picolinic acid (1.06 g, 88%) was prepared from ethyl 3,5-dichloro-4-((6-cyano-1,4-dimethyl-1H-indol-2-yl)methyl) picolinate (1.25 g, 3.11 mmol). LC/MS (Method i) $R_t$=1.80 min.;

MS m/z: 374 [M+H]$^+$ $^1$H NMR (DMSO-d$_6$, 300 MHz): δ 14.15 (broad., 1H), 8.76 (s, 1H), 7.93 (s, 1H), 7.13 (s, 1H), 5.83 (s, 1H), 4.51 (s, 2H), 3.91 (s, 3H), 2.35 (s, 3H).

Step 6: 2-[[3,5-dichloro-2-(morpholine-4-carbonyl)-4-pyridyl]methyl]-1,4-dimethyl-indole-6-carbonitrile

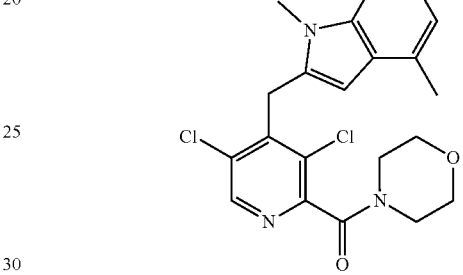

Using a procedure similar to Example A1, 2-[[3,5-dichloro-2-(morpholine-4-carbonyl)-4-pyridyl]methyl]-1,4-dimethyl-indole-6-carbonitrile (49 mg, 41%) was prepared from 3,5-dichloro-4-((6-cyano-1,4-dimethyl-1H-indol-2-yl) methyl)picolinic acid (100 mg, 0.26 mmol) and morpholine (30 mg, 0.347 mmol). LC/MS (Method g) $R_t$=1.53 min.; MS m/z: 443 [M+H]$^+$. $^1$H NMR (DMSO-d$_6$, 400 MHz): δ 8.78 (s, 1H), 7.93 (s, 1H), 7.12 (m, 1H), 5.87 (s, 1H), 4.49 (s, 2H), 3.91 (s, 3H), 3.67 (s, 4H), 3.53 (m, 2H), 3.22 (m, 2H), 2.35 (s, 3H).

TABLE BF

The following examples were prepared from 3,5-dichloro-4-((6-cyano-1,4-dimethyl-1H-indol-2-yl)methyl)picolinic acid (Example BA, Step 5) using the same procedure with the appropriate amine.

| Example | Product | Amine | $R_t$ min (Method g) | m/z ESI+ (M + H)$^+$ |
|---|---|---|---|---|
| BF-1 | 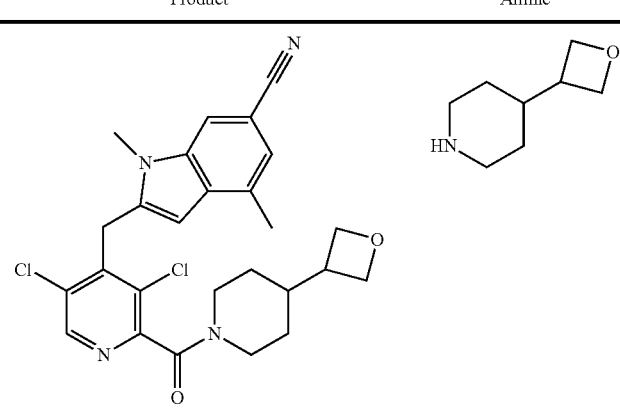 | 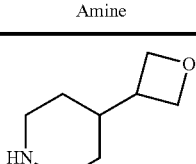 | 1.57 | 497 |

TABLE BF-continued
The following examples were prepared from 3,5-dichloro-4-((6-cyano-1,4-dimethyl-1H-indol-2-yl)methyl)picolinic acid (Example BA, Step 5) using the same procedure with the appropriate amine.
| Example | Product | Amine | $R_t$ min (Method g) | m/z ESI+ $(M + H)^+$ |
|---|---|---|---|---|
| BF-2 | 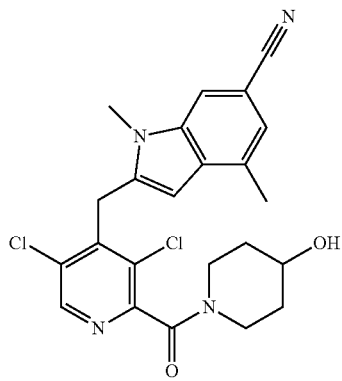 [SMILES: Cc1cc(C#N)cc2c1cc(Cc1c(Cl)cnc(C(=O)N3CCC(O)CC3)c1Cl)n2C] | 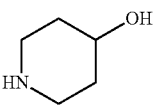 | 1.41 | 457 |
| BF-3 | 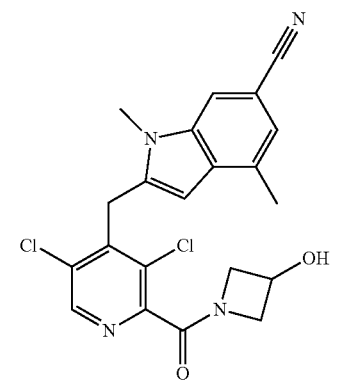 [SMILES: Cc1cc(C#N)cc2c1cc(Cc1c(Cl)cnc(C(=O)N3CC(O)C3)c1Cl)n2C] | 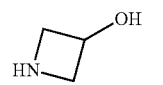 | 1.38 | 429 |
| BF-4 | 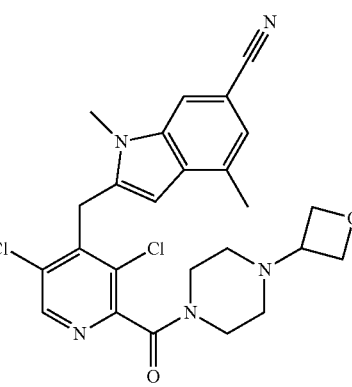 | 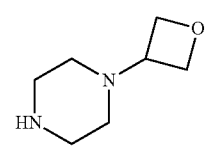 | 1.36 | 498 |

TABLE BF-continued

The following examples were prepared from 3,5-dichloro-4-((6-cyano-1,4-dimethyl-1H-indol-2-yl)methyl)picolinic acid (Example BA, Step 5) using the same procedure with the appropriate amine.

| Example | Product | Amine | $R_t$ min (Method g) | m/z ESI+ $(M + H)^+$ |
|---|---|---|---|---|
| BF-5 | 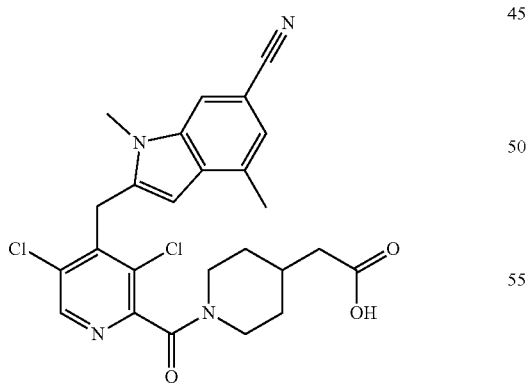 | | 1.40 | 443 |
| BF-6 | | | 1.69 | 513 |

Example BG: 2-[1-[3,5-dichloro-4-[(6-cyano-1,4-dimethyl-indol-2-yl)methyl]pyridine-2-carbonyl]-4-piperidyl]acetic acid Using a procedure similar to Example A, Step 5, 2-[1-[3,5-dichloro-4-[(6-cyano-1,4-dimethyl-indol-2-yl)methyl]pyridine-2-carbonyl]-4-piperidyl]acetic acid (49 mg, 37%) was prepared from methyl 2-[1-[3,5-dichloro-4-[(6-cyano-1,4-dimethyl-indol-2-yl)methyl]pyridine-2-carbonyl]-4-piperidyl]acetate (Table BF, Example BF-6) (0.27 mmol). LC/MS (Method g) $R_t$=1.48 min.; MS m/z: 499 [M+H]+ $^1$H NMR (DMSO-$d_6$, 400 MHz): δ 12.11 (broad, 1H), 8.76 (s, 1H), 7.93 (s, 1H), 7.10 (m, 1H), 5.83 (s, 1H), 4.49 (m, 2H), 4.44 (m, 1H), 3.91 (s, 3H), 3.25 (m, 1H), 3.07 (m, 1H), 2.85 (m, 1H), 2.34 (s, 3H), 2.17 (m, 2H), 1.96 (m, 1H), 1.79 (m, 1H), 1.63 (m, 1H), 1.14 (m, 2H).

Example BH: (4,6-dichloro-5-((1,4-dimethyl-6-(trifluoromethyl)-1H-indol-2-yl)methyl)pyridin-3-yl)(morpholino)methanone

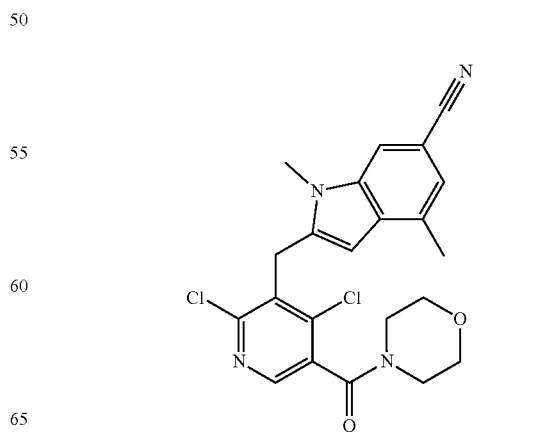

Step 1: (4,6-dichloro-5-((1,4-dimethyl-6-(trifluoromethyl)-1H-indol-2-yl)methyl)pyridin-3-yl)(morpholino)methanone

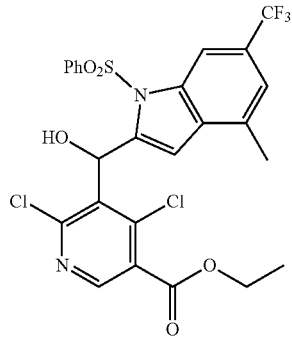

Using a procedure similar to Example A, Step 1, (4,6-dichloro-5-((1,4-dimethyl-6-(trifluoromethyl)-1H-indol-2-yl)methyl)pyridin-3-yl)(morpholino)methanone (4.3 mg, 32%) was prepared from N-(2-iodo-3-methyl-5-(trifluoromethyl)phenyl)benzenesulfonamide (Preparation #16) (8.72 g, 19.7 mmol) and ethyl 4,6-dichloro-5-(1-hydroxyprop-2-yn-1-yl)nicotinate (Preparation #38) (6.5 g, 23.7 mmol).

LC/MS (Method h) $R_t$=2.65 min.; MS m/z: 587 [M+H]$^+$ $^1$H NMR (DMSO-d$_6$, 300 MHz): δ 8.69 (s, 1H), 8.08 (s, 1H), 7.80 (m, 2H), 7.69 (m, 1H), 7.60 (m, 2H), 7.45 (s, 1H), 7.07 (s, 1H), 6.91 (m, 2H), 4.37 (q, J=7.1 Hz, 2H), 2.50 (s, 3H), 1.33 (t, J=7.1 Hz, 3H).

Step 2: ethyl 4,6-dichloro-5-((4-methyl-1-(phenylsulfonyl)-6-(trifluoromethyl)-1H-indol-2-yl)methyl)nicotinate

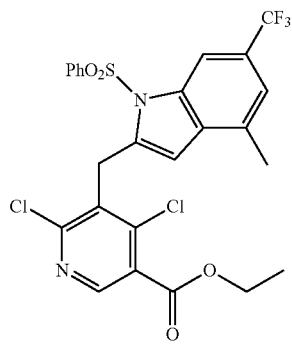

Using a procedure similar to Example Z, Step 2, ethyl 4,6-dichloro-5-((4-methyl-1-(phenylsulfonyl)-6-(trifluoromethyl)-1H-indol-2-yl)methyl)nicotinate (3.35 g, 80%) was prepared from (4,6-dichloro-5-((1,4-dimethyl-6-(trifluoromethyl)-1H-indol-2-yl)methyl)pyridin-3-yl)(morpholino)methanone (4.3 g, 7.32 mmol). LC/MS (Method h) $R_t$=2.57 min.; MS m/z: 571 [M+H]$^+$ $^1$H NMR (DMSO-d$_6$, 300 MHz): δ 8.84 (s, 1H), 8.23 (s, 1H), 7.93 (m, 2H), 7.77 (m, 1H), 7.69 (m, 2H), 7.42 (s, 1H), 6.33 (s, 1H), 4.60 (s, 2H), 4.38 (q, J=7.1 Hz, 2H), 2.38 (s, 3H), 1.34 (t, J=7.1 Hz, 3H).

Step 3: 4,6-dichloro-5-((4-methyl-6-(trifluoromethyl)-1H-indol-2-yl)methyl)nicotinic acid

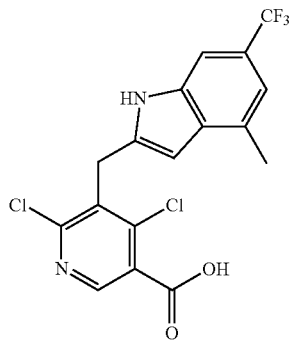 [SMILES: Cc1cc(C(F)(F)F)cc2[nH]c(Cc3c(Cl)ncc(C(=O)O)c3Cl)cc12]

To a solution of ethyl 4,6-dichloro-5-((4-methyl-1-(phenylsulfonyl)-6-(trifluoromethyl)-1H-indol-2-yl)methyl)nicotinate (3.29 g, 5.76 mmol) in THF (30 mL) and MeOH (30 mL) was added sodium hydroxide (28 mL) and the mixture was stirred at room temperature overnight. Solvents were concentrated under vacuum and the residue was diluted with water. pH was adjusted to 5 with addition of 1N HCl aqueous solution, and the obtained precipitate was filtered, washed by water and dried to give 4,6-dichloro-5-((4-methyl-6-(trifluoromethyl)-1H-indol-2-yl)methyl)nicotinic acid (2.27 g, 98%) as a beige powder. The product was used directly in the next step. LC/MS (Method h) $R_t$=1.46 min.; MS m/z: 403 [M+H]$^+$

Step 4: methyl 4,6-dichloro-5-((1,4-dimethyl-6-(trifluoromethyl)-1H-indol-2-yl)methyl)nicotinate

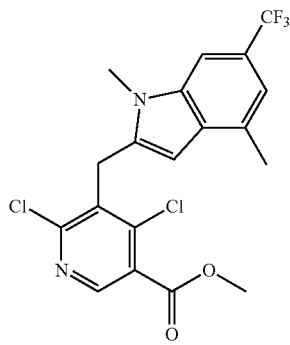 [SMILES: COC(=O)c1cnc(Cl)c(Cc2cc3c(C)cc(C(F)(F)F)cc3n2C)c1Cl]

To a solution of 4,6-dichloro-5-((4-methyl-6-(trifluoromethyl)-1H-indol-2-yl)methyl)nicotinic acid (2 g, 4.96 mmol) in ACN (50 mL) was added cesium carbonate (4.85 g, 14.88 mmol) and dimethyl sulfate (1.176 mL, 12.40 mmol) and the mixture was stirred overnight at 45° C. More dimethyl sulfate (624 mg, 4.9 mmol) was added and the mixture was stirred for 6 hours. Water was added to the mixture and the aqueous layer was extracted with EtOAc. The organic phase was washed by a saturated NaCl aqueous solution, dried over magnesium sulfate and concentrated. The residue was purified by column chromatography on silica gel (eluting with 0-80% EtOAc in cyclohexane) to give methyl 4,6-dichloro-5-((1,4-dimethyl-6-(trifluoromethyl)-1H-indol-2-yl)methyl)nicotinate (1 g, 47%) as a pink powder. LC/MS (Method h) $R_t$=2.13 min.; MS m/z: 431 [M+H]$^+$ $^1$H NMR (DMSO-d$_6$, 300 MHz): δ 8.84 (s, 1H), 7.71 (s, 1H), 7.07 (s, 1H), 5.82 (s, 1H), 4.50 (s, 2H), 3.92 (s, 6H), 2.38 (s, 3H).

Step 5: 4,6-dichloro-5-((1,4-dimethyl-6-(trifluoromethyl)-1H-indol-2-yl)methyl)nicotinic acid

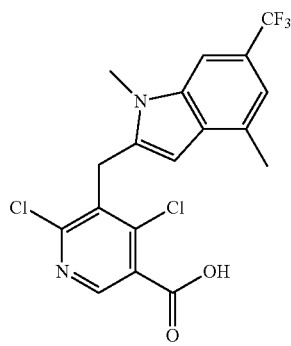 [SMILES: Cc1cc(C(F)(F)F)cc2c1cc(Cc1c(Cl)ncc(C(=O)O)c1Cl)n2C]

Using a procedure similar to Example A, Step 5, 4,6-dichloro-5-((1,4-dimethyl-6-(trifluoromethyl)-1H-indol-2-yl)methyl)nicotinic acid (88 mg, 100%) was prepared from methyl 4,6-dichloro-5-((1,4-dimethyl-6-(trifluoromethyl)-1H-indol-2-yl)methyl)nicotinate (92 mg, 0.21 mmol). LC/MS (Method h) $R_t$=2.70 min.; MS m/z: 417 [M+H]$^+$ $^1$H NMR (DMSO-d$_6$, 300 MHz): δ 8.79 (s, 1H), 7.71 (s, 1H), 7.07 (s, 1H), 5.81 (s, 1H), 4.49 (s, 2H), 3.92 (s, 3H), 2.38 (s, 3H).

Step 6: (4,6-dichloro-5-((1,4-dimethyl-6-(trifluoromethyl)-1H-indol-2-yl)methyl)pyridin-3-yl)(morpholino)methanone

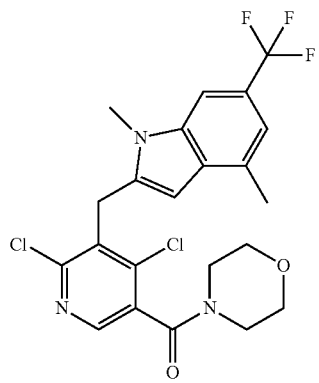 [SMILES: Cc1cc(C(F)(F)F)cc2c1cc(Cc1c(Cl)ncc(C(=O)N3CCOCC3)c1Cl)n2C]

Using a procedure similar to Example A, Step 6, (4,6-dichloro-5-((1,4-dimethyl-6-(trifluoromethyl)-1H-indol-2-yl)methyl)pyridin-3-yl)(morpholino)methanone (81 mg, 78%) was prepared from 4,6-dichloro-5-((1,4-dimethyl-6-(trifluoromethyl)-1H-indol-2-yl)methyl)nicotinic acid (85 mg, 0.20 mmol). LC/MS (Method g) $R_t$=1.78 min.; MS m/z: 486 [M+H]$^+$ $^1$H NMR (DMSO-d$_6$, 400 MHz): δ 8.51 (s, 1H), 7.71 (s, 1H), 7.07 (s, 1H), 5.85 (s, 1H), 4.46 (m, 2H), 3.92 (s, 3H), 3.70 (m, 4H), 3.55 (m, 2H), 3.25 (m, 2H), 2.39 (s, 3H).

TABLE BH

The following examples were prepared from 4,6-dichloro-5-((1,4-dimethyl-6-(trifluoromethyl)-1H-indol-2-yl)methyl)nicotinic acid (Example BH, Step 5) using the same procedure with the appropriate amine.

| Example | Product | Amine | $R_t$ min (Method j) | m/z ESI+ (M + H)$^+$ |
|---|---|---|---|---|
| BH-1 | (structure) | (structure) | 1.92 | 556 |
| BH-2 | (structure) | (structure) | 1.60 (method i) | 544 |

401

Example BI: 3-(3,5-dichloro-4-((1,4-dimethyl-6-(trifluoromethyl)-1H-indol-2-yl)methyl)-2-oxopyridin-1(2H)-yl)propanoic acid

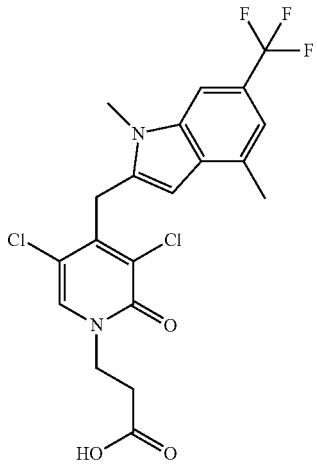 [SMILES: Cc1cc(C(F)(F)F)cc2c1cc(Cc1c(Cl)cn(CCC(=O)O)c(=O)c1Cl)n2C]

To a suspension of 3,5-dichloro-4-((1,4-dimethyl-6-(trifluoromethyl)-1H-indol-2-yl)methyl)pyridin-2-ol (example AL, step 1) (50 mg, 0.128 mmol) in DMF (700 µL) was added sodium hydride (4.62 mg, 0.193 mmol) and the reaction mixture was stirred at room temperature for 15 minutes. Beta-propiolactone (12.12 µL, 0.193 mmol) was added to the reaction mixture and the reaction mixture was stirred at 50° C. for 24 hours. The reaction mixture was diluted with water. The obtained aqueous layer was extracted with EtOAc. The obtained organic layer was dried over magnesium sulfate, filtered and concentrated under reduced pressure. The residue was purified by preparative LCMS to give 3-(3,5-dichloro-4-((1,4-dimethyl-6-(trifluoromethyl)-1H-indol-2-yl)methyl)-2-oxopyridin-1 (2H)-yl) propanoic acid (7 mg, 12%) as a white solid. LC/MS (Method g) $R_t$=1.68 min.; MS m/z: 461 [M+H]$^+$ $^1$H NMR (DMSO-$d_6$, 500 MHz): δ 8.15 (s, 1H), 7.69 (s, 1H), 7.07 (s, 1H), 5.98 (s, 1H), 4.30 (s, 2H), 4.17 (t, J=6.9 Hz, 2H), 3.89 (s, 3H), 2.66 (m, 2H), 2.41 ppm (s, 3H)

Example BJ: (2,4-dichloro-3-((1,4-dimethyl-6-(trifluoromethyl)-1H-benzo[d]imidazol-2-yl)methyl)phenyl)(morpholino)methanone

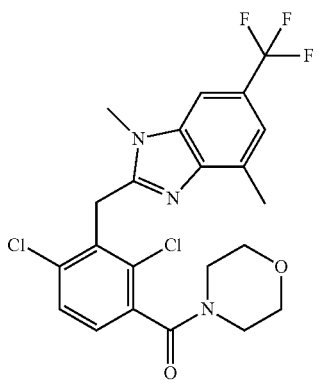 [SMILES: Cc1cc(C(F)(F)F)cc2c1nc(Cc1c(Cl)ccc(C(=O)N3CCOCC3)c1Cl)n2C]

402

Step 1: methyl 2,4-dichloro-3-((1,4-dimethyl-6-(trifluoromethyl)-1H-benzo[d]imidazol-2-yl)methyl)benzoate

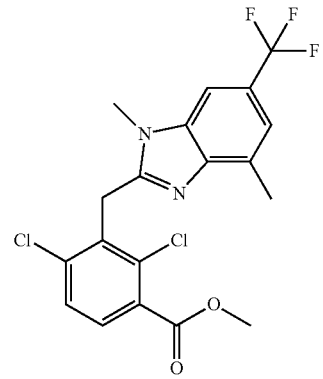 [SMILES: COC(=O)c1ccc(Cl)c(Cc2nc3c(C)cc(C(F)(F)F)cc3n2C)c1Cl]

A mixture of N-1,3-dimethyl-5-(trifluoromethyl)benzene-1,2-diamine (Preparation #21) (100 mg, 0.490 mmol), 2-(2,6-dichloro-3-(methoxycarbonyl)phenyl)acetic acid (Preparation #2) (129 mg, 0.490 mmol), HATU (186 mg, 0.490 mmol) and 4-methylmorpholine (216 µL, 1.959 mmol) was warmed at 100° C. under fast agitation for 18 hours. Acetic acid (245 µl) was added and the mixture was stirred at 100° C. for 1 additional hour. The reaction mixture was diluted with water, extracted with EtOAc. The organic layer was washed with NaHCO$_3$ saturated aqueous solution, water and brine, dried over magnesium sulfate, filtered and concentrated to give methyl 2,4-dichloro-3-((1,4-dimethyl-6-(trifluoromethyl)-1H-benzo[d]imidazol-2-yl)methyl)benzoate (199 mg, 94%) as a beige solid. LC/MS (Method k) $R_t$=2.98 min.; MS m/z: 431 [M+H]$^+$ $^1$H NMR (DMSO-$d_6$, 300 MHz): δ 7.83 (s, 1H), 7.76 (d, J=9 Hz, 1H), 7.67 (d, J=9 Hz, 1H), 7.27 (s, 1H), 4.63 (s, 2H), 3.98 (s, 3H), 3.87 (s, 3H), 2.41 (s, 3H).

Step 2: 2,4-dichloro-3-((1,4-dimethyl-6-(trifluoromethyl)-1H-benzo[d]imidazol-2-yl)methyl)benzoic acid

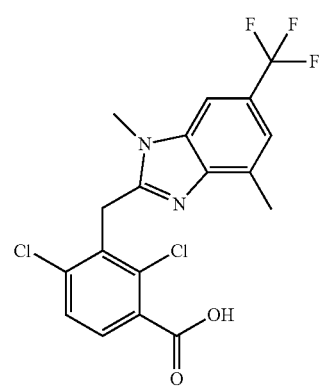 [SMILES: Cc1cc(C(F)(F)F)cc2c1nc(Cc1c(Cl)ccc(C(=O)O)c1Cl)n2C]

Using a procedure similar to Example A, Step 5, 2,4-dichloro-3-((1,4-dimethyl-6-(trifluoromethyl)-1H-benzo[d]imidazol-2-yl)methyl)benzoic acid (7.4 g, 98%) was prepared from methyl 2,4-dichloro-3-((1,4-dimethyl-6-(trifluoromethyl)-1H-benzo[d]imidazol-2-yl)methyl)benzoate (7.81 g, 18.16 mmol). LC/MS (Method h) $R_t$=2.41 min.; MS m/z: 417 [M+H]$^+$.

$^1$H NMR (DMSO-$d_6$, 300 MHz): δ 13.67 (broad, 1H), 7.82 (s, 1H), 7.73 (d, J=9 Hz, 1H), 7.62 (d, J=9 Hz, 1H), 7.27 (s, 1H), 4.63 (s, 2H), 3.97 (s, 3H), 2.41 (s, 3H).

Step 3: (2,4-dichloro-3-((1,4-dimethyl-6-(trifluoromethyl)-1H-benzo[d]imidazol-2-yl)methyl)phenyl)(morpholino)methanone

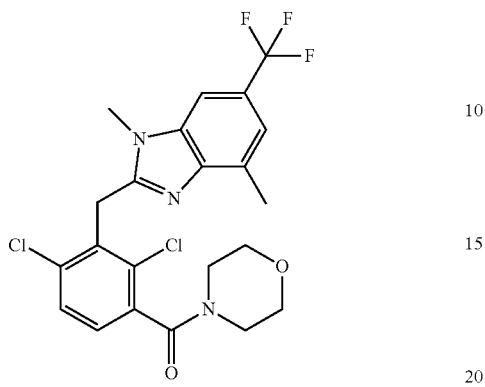

Using a procedure similar to Example A1, (2,4-dichloro-3-((1,4-dimethyl-6-(trifluoromethyl)-1H-benzo[d]imidazol-2-yl)methyl)phenyl)(morpholino)methanone (191 mg, 56%) was prepared from 2,4-dichloro-3-((1,4-dimethyl-6-(trifluoromethyl)-1H-benzo[d]imidazol-2-yl)methyl)benzoic acid (290 mg, 0.695 mmol) and morpholine (79 mg, 0.90 mmol).

LC/MS (Method h) $R_t$=2.59 min.; MS m/z: 486 [M+H]$^+$. $^1$H NMR (DMSO-d$_6$, 400 MHz): δ 7.82 (s, 1H), 7.65 (d, J=8 Hz, 1H), 7.41 (d, J=8 Hz, 1H), 7.26 (s, 1H), 4.63 (d, J=16 Hz, 1H), 4.56 (d, J=16 Hz, 1H), 3.97 (s, 3H), 3.63 (m, 4H), 3.52 (m, 2H), 3.17 (m, 2H), 2.39 (s, 3H).

TABLE BJ

The following examples were prepared from 2,4-dichloro-3-((1,4-dimethyl-6-(trifluoromethyl)-1H-benzo[d]imidazol-2-yl)methyl)benzoic acid using the same procedure with the appropriate amine

| Example | Structure | Starting amine | $R_t$ min (Method g) | m/z ESI+ (M + H)$^+$ |
|---------|-----------|----------------|----------------------|----------------------|
| BJ-1 | Chiral | Chiral | 1.64 | 527 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | R<sub>t</sub> min (Method g) | m/z ESI+ (M + H)+ |
|---|---|---|---|---|
| BJ-2 | 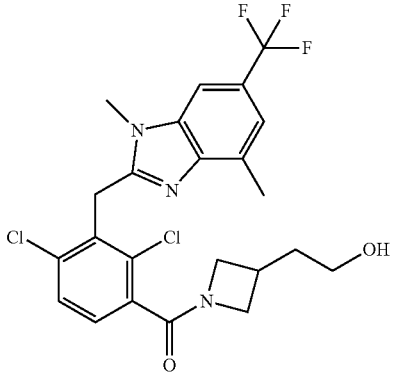 [SMILES: Cc1cc(C(F)(F)F)cc2c1nc(Cc1c(Cl)ccc(C(=O)N3CC(CCO)C3)c1Cl)n2C] | 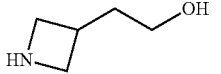 | 1.51 | 500 |
| BJ-3 | 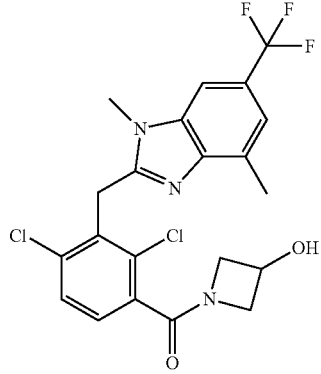 [SMILES: Cc1cc(C(F)(F)F)cc2c1nc(Cc1c(Cl)ccc(C(=O)N3CC(O)C3)c1Cl)n2C] | 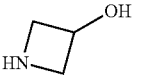 | 1.48 | 472 |
| BJ-4 | 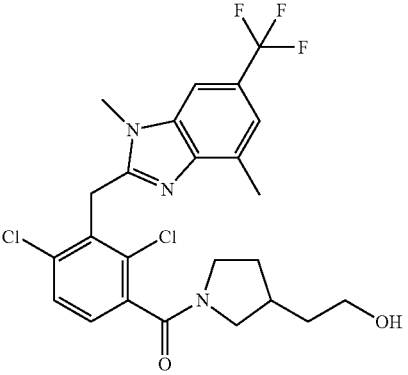 [SMILES: Cc1cc(C(F)(F)F)cc2c1nc(Cc1c(Cl)ccc(C(=O)N3CCC(CCO)C3)c1Cl)n2C] | 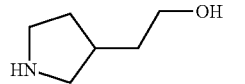 | 1.58 | 514 |

TABLE BJ-continued

The following examples were prepared from 2,4-dichloro-3-((1,4-dimethyl-6-(trifluoromethyl)-1H-benzo[d]imidazol-2-yl)methyl)benzoic acid using the same procedure with the appropriate amine

| Example | Structure | Starting amine | $R_t$ min (Method g) | m/z ESI+ (M + H)+ |
|---|---|---|---|---|
| BJ-5 | 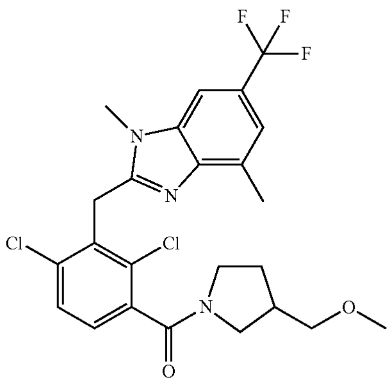 [SMILES: COCC1CCN(C(=O)c2ccc(Cl)c(Cc3nc4c(C)cc(C(F)(F)F)cc4n3C)c2Cl)C1] | | 1.74 | 514 |
| BJ-6 | 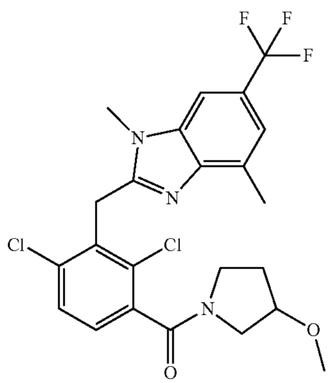 [SMILES: COC1CCN(C(=O)c2ccc(Cl)c(Cc3nc4c(C)cc(C(F)(F)F)cc4n3C)c2Cl)C1] | | 1.68 | 500 |
| BJ-7 | 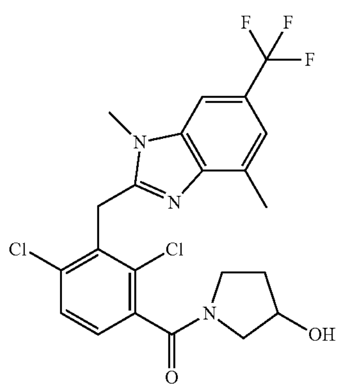 [SMILES: Cc1cc(C(F)(F)F)cc2c1nc(Cc1c(Cl)ccc(C(=O)N3CCC(O)C3)c1Cl)n2C] | | 1.48 | 486 |
| BJ-8 | 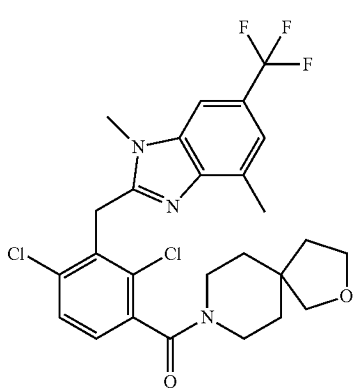 [SMILES: Cc1cc(C(F)(F)F)cc2c1nc(Cc1c(Cl)ccc(C(=O)N3CCC4(CCOC4)CC3)c1Cl)n2C] | | 1.73 | 540 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ $(M + H)^+$ |
|---|---|---|---|---|
| BJ-9 | 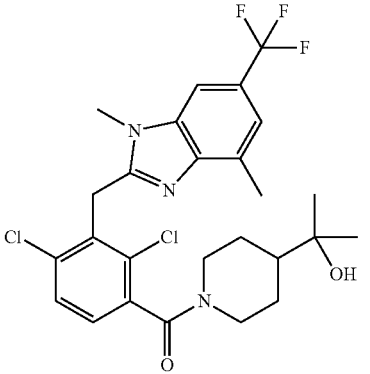 [SMILES: Cc1cc(C(F)(F)F)cc2c1nc(Cc1c(Cl)ccc(C(=O)N3CCC(C(C)(C)O)CC3)c1Cl)n2C] | 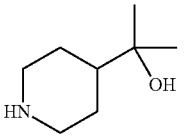 | 1.68 | 542 |
| BJ-10 | 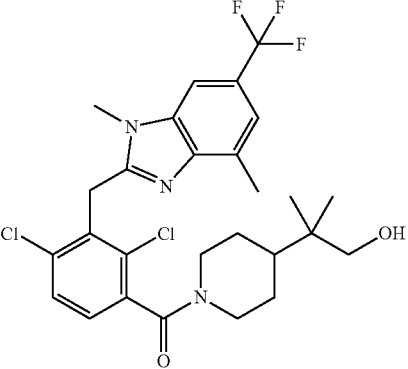 [SMILES: Cc1cc(C(F)(F)F)cc2c1nc(Cc1c(Cl)ccc(C(=O)N3CCC(C(C)(C)CO)CC3)c1Cl)n2C] | 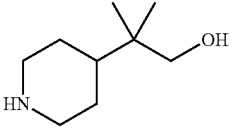 | 1.75 | 556 |
| BJ-11 | 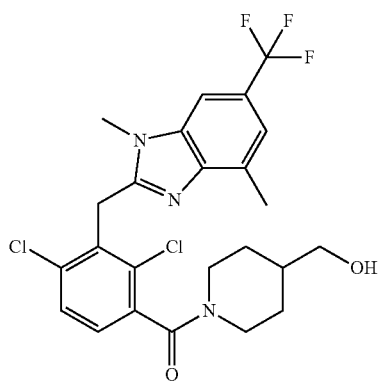 [SMILES: Cc1cc(C(F)(F)F)cc2c1nc(Cc1c(Cl)ccc(C(=O)N3CCC(CO)CC3)c1Cl)n2C] | 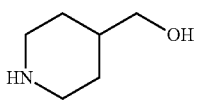 | 1.57 | 514 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ (M + H)+ |
|---|---|---|---|---|
| BJ-12 | 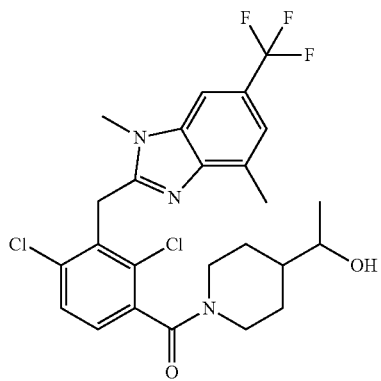 [SMILES: Cc1cc(C(F)(F)F)cc2c1nc(Cc1c(Cl)ccc(C(=O)N3CCC(C(C)O)CC3)c1Cl)n2C] | 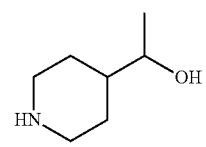 | 1.63 | 528 |
| BJ-13 | 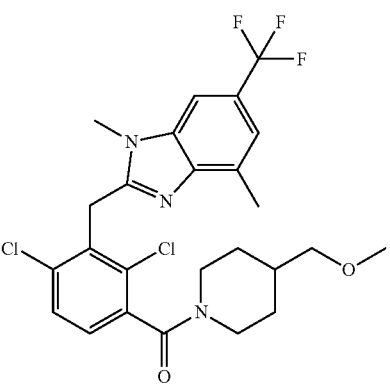 [SMILES: COCC1CCN(C(=O)c2ccc(Cl)c(Cc3nc4c(C)cc(C(F)(F)F)cc4n3C)c2Cl)CC1] | 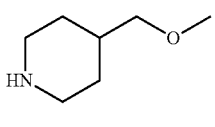 | 1.81 | 528 |
| BJ-14 | 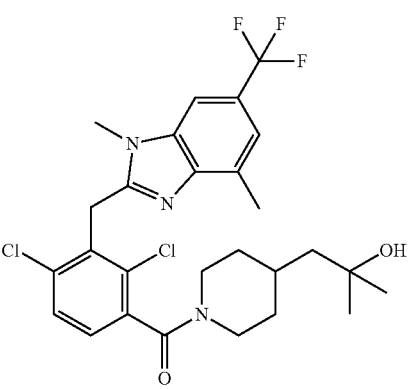 [SMILES: Cc1cc(C(F)(F)F)cc2c1nc(Cc1c(Cl)ccc(C(=O)N3CCC(CC(C)(C)O)CC3)c1Cl)n2C] | 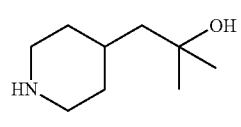 | 1.75 | 556 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ (M + H)+ |
|---|---|---|---|---|
| BJ-15 | 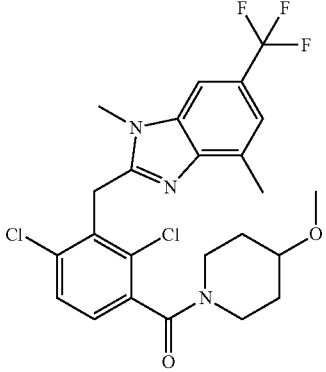 [SMILES: COC1CCN(C(=O)c2ccc(Cl)c(Cc3nc4c(C)cc(C(F)(F)F)cc4n3C)c2Cl)CC1] | 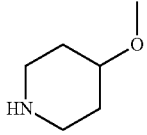 | 1.74 | 514 |
| BJ-16 | 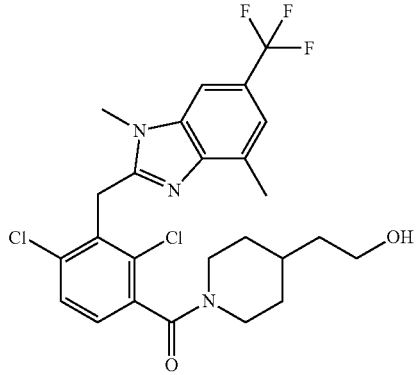 [SMILES: Cc1cc(C(F)(F)F)cc2c1nc(Cc1c(Cl)ccc(C(=O)N3CCC(CCO)CC3)c1Cl)n2C] | 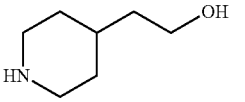 | 1.61 | 528 |
| BJ-17 | 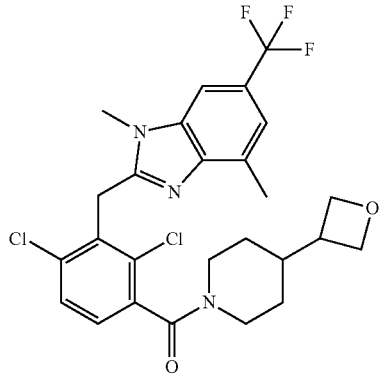 [SMILES: Cc1cc(C(F)(F)F)cc2c1nc(Cc1c(Cl)ccc(C(=O)N3CCC(C4COC4)CC3)c1Cl)n2C] | 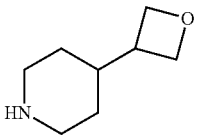 | 1.69 | 540 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | R$_t$ min (Method g) | m/z ESI+ (M + H)+ |
|---|---|---|---|---|
| BJ-18 | 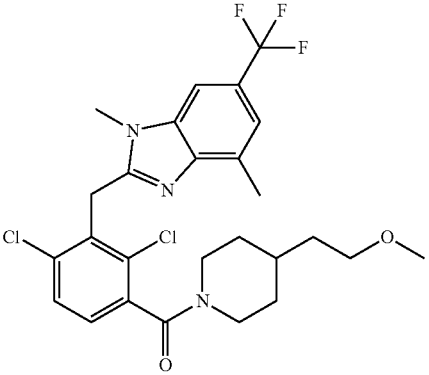 [SMILES: COCCC1CCN(C(=O)c2ccc(Cl)c(Cc3nc4c(C)cc(C(F)(F)F)cc4n3C)c2Cl)CC1] | 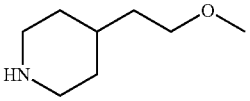 | 1.86 | 542 |
| BJ-19 | 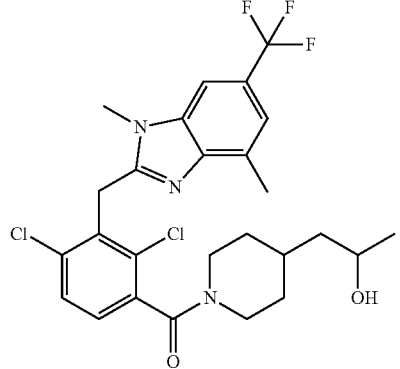 [SMILES: Cc1cc(C(F)(F)F)cc2c1nc(Cc1c(Cl)ccc(C(=O)N3CCC(CC(C)O)CC3)c1Cl)n2C] | 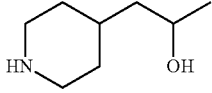 | 1.68 | 542 |
| BJ-20 | 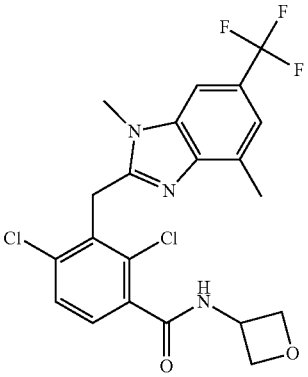 [SMILES: Cc1cc(C(F)(F)F)cc2c1nc(Cc1c(Cl)ccc(C(=O)NC3COC3)c1Cl)n2C] | 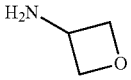 | 1.55 | 472 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ $(M + H)^+$ |
|---|---|---|---|---|
| BJ-21 | 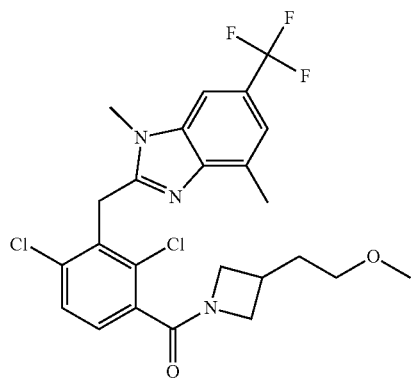 [SMILES: COCCC1CN(C(=O)c2ccc(Cl)c(Cc3nc4c(C)cc(C(F)(F)F)cc4n3C)c2Cl)C1] | 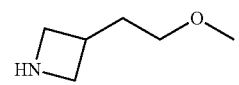 | 1.73 | 514 |
| BJ-22 | 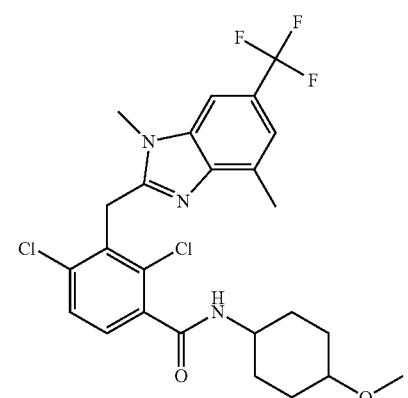 | 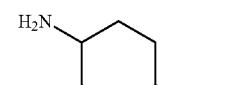 | 1.74 | 528 |
| BJ-23 | 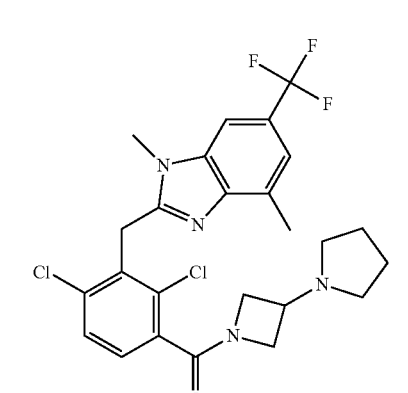 | 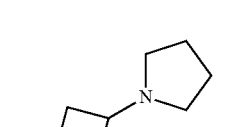 | 1.13 | 525 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ $(M + H)^+$ |
|---|---|---|---|---|
| BJ-24 | 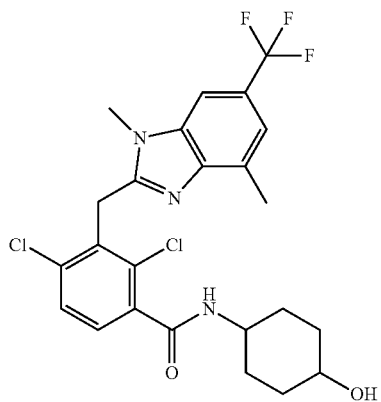 [SMILES: Cc1cc(C(F)(F)F)cc2c1nc(Cc1c(Cl)ccc(C(=O)NC3CCC(O)CC3)c1Cl)n2C] | 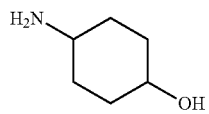 | 1.55 | 514 |
| BJ-25 | 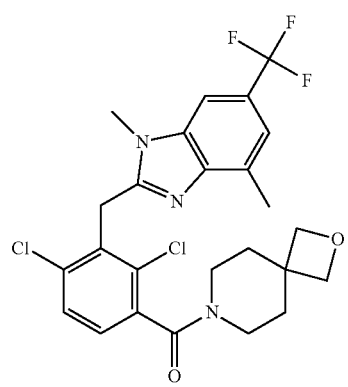 [SMILES: Cc1cc(C(F)(F)F)cc2c1nc(Cc1c(Cl)ccc(C(=O)N3CCC4(CC3)COC4)c1Cl)n2C] | 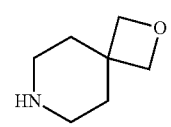 | 1.65 | 526 |
| BJ-26 | 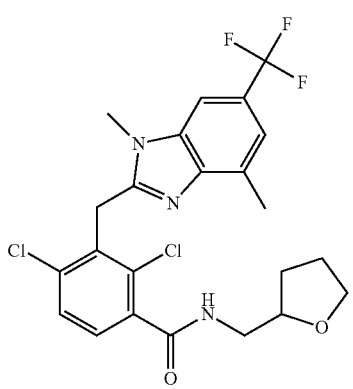 [SMILES: Cc1cc(C(F)(F)F)cc2c1nc(Cc1c(Cl)ccc(C(=O)NCC3CCCO3)c1Cl)n2C] | 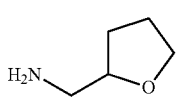 | 1.67 | 500 |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ (M + H)+ |
|---|---|---|---|---|
| BJ-27 | 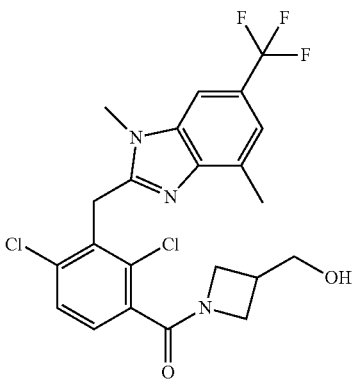 [SMILES: Cc1cc(C(F)(F)F)cc2c1nc(Cc1c(Cl)ccc(C(=O)N3CC(CO)C3)c1Cl)n2C] | 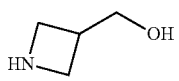 | 1.48 | 486 |
| BJ-28 | 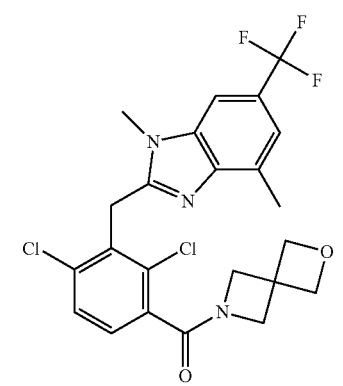 [SMILES: Cc1cc(C(F)(F)F)cc2c1nc(Cc1c(Cl)ccc(C(=O)N3CC4(COC4)C3)c1Cl)n2C] | 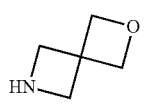 | 1.56 | 498 |
| BJ-29 | 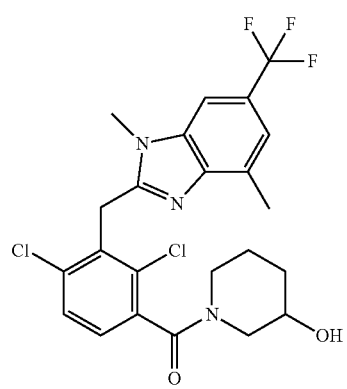 [SMILES: Cc1cc(C(F)(F)F)cc2c1nc(Cc1c(Cl)ccc(C(=O)N3CCCC(O)C3)c1Cl)n2C] | 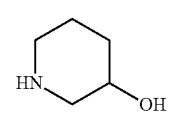 | 1.58 | 500 |

TABLE BJ-continued

The following examples were prepared from 2,4-dichloro-3-((1,4-dimethyl-6-(trifluoromethyl)-1H-benzo[d]imidazol-2-yl)methyl)benzoic acid using the same procedure with the appropriate amine

| Example | Structure | Starting amine | R$_t$ min (Method g) | m/z ESI+ (M + H)+ |
|---------|-----------|----------------|----------------------|-------------------|
| BJ-30 | 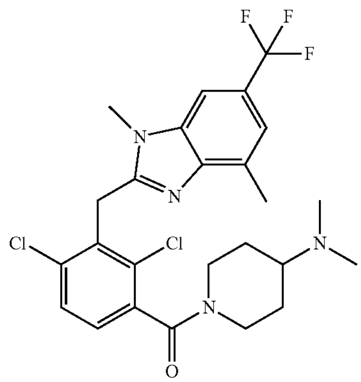 [SMILES: Cc1cc(C(F)(F)F)cc2c1nc(Cc1c(Cl)ccc(C(=O)N3CCC(N(C)C)CC3)c1Cl)n2C] | | 1.12 | 527 |
| BJ-31 | 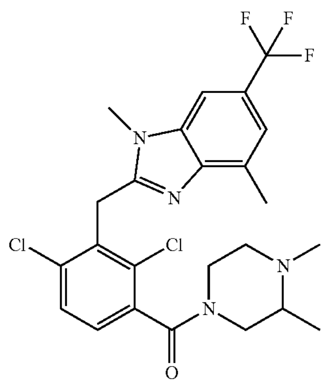 [SMILES: Cc1cc(C(F)(F)F)cc2c1nc(Cc1c(Cl)ccc(C(=O)N3CCN(C)C(C)C3)c1Cl)n2C] | | 1.13 | 513 |
| BJ-32 | 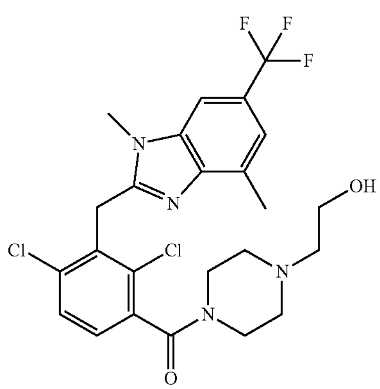 [SMILES: Cc1cc(C(F)(F)F)cc2c1nc(Cc1c(Cl)ccc(C(=O)N3CCN(CCO)CC3)c1Cl)n2C] | | 1.11 | 529 |
| BJ-33 | 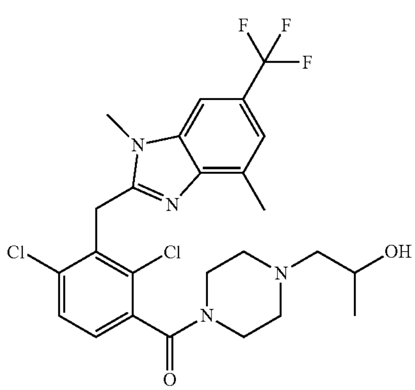 [SMILES: Cc1cc(C(F)(F)F)cc2c1nc(Cc1c(Cl)ccc(C(=O)N3CCN(CC(C)O)CC3)c1Cl)n2C] | | 1.13 | 543 |

TABLE BJ-continued

The following examples were prepared from 2,4-dichloro-3-((1,4-dimethyl-6-(trifluoromethyl)-1H-benzo[d]imidazol-2-yl)methyl)benzoic acid using the same procedure with the appropriate amine

| Example | Structure | Starting amine | $R_t$ min (Method g) | m/z ESI+ $(M + H)^+$ |
|---------|-----------|----------------|----------------------|----------------------|
| BJ-34   | 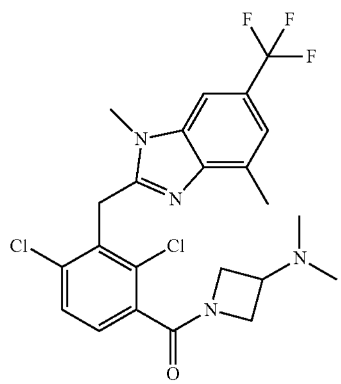 [SMILES: Cc1cc(C(F)(F)F)cc2c1nc(Cc1c(Cl)ccc(C(=O)N3CC(N(C)C)C3)c1Cl)n2C]          |                | 1.11                 | 499                  |
| BJ-35   | 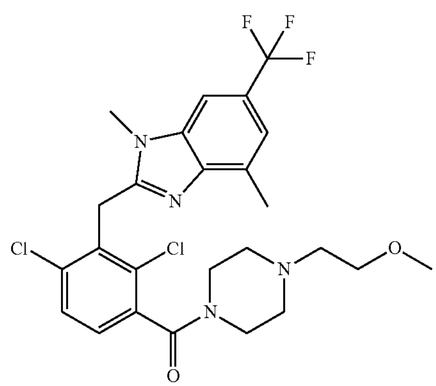 [SMILES: COCCN1CCN(C(=O)c2ccc(Cl)c(Cc3nc4c(C)cc(C(F)(F)F)cc4n3C)c2Cl)CC1]          |                | 1.17                 | 543                  |
| BJ-36   | 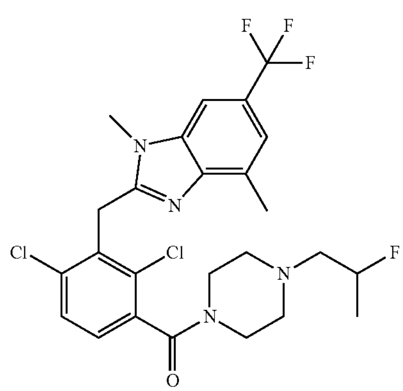 [SMILES: Cc1cc(C(F)(F)F)cc2c1nc(Cc1c(Cl)ccc(C(=O)N3CCN(CC(C)F)CC3)c1Cl)n2C]          |                | 1.36                 | 545                  |

TABLE BJ-continued
The following examples were prepared from 2,4-dichloro-3-((1,4-dimethyl-6-(trifluoromethyl)-1H-benzo[d]imidazol-2-yl)methyl)benzoic acid using the same procedure with the appropriate amine
| Example | Structure | Starting amine | $R_t$ min (Method g) | m/z ESI+ (M + H)+ |
|---|---|---|---|---|
| BJ-37 | 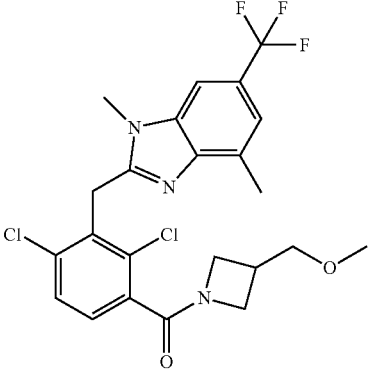 [SMILES: COCC1CN(C(=O)c2ccc(Cl)c(Cc3nc4c(C)cc(C(F)(F)F)cc4n3C)c2Cl)C1] | 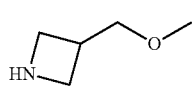 | 1.68 | 500 |
| BJ-38 | 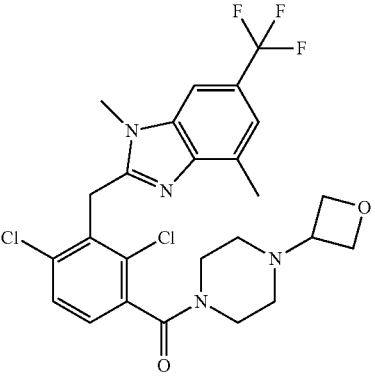 [SMILES: Cc1cc(C(F)(F)F)cc2c1nc(Cc1c(Cl)ccc(C(=O)N3CCN(C4COC4)CC3)c1Cl)n2C] | 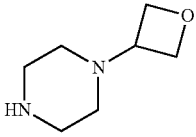 | 1.46 | 541 |
| BJ-39 | 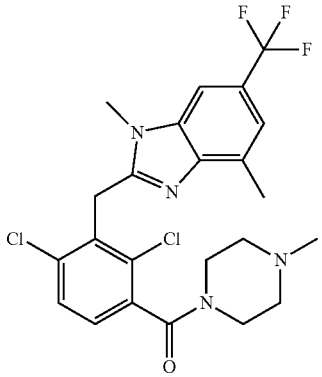 | 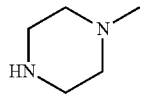 | 1.11 | 499 |

TABLE BJ-continued

The following examples were prepared from 2,4-dichloro-3-((1,4-dimethyl-6-(trifluoromethyl)-1H-benzo[d]imidazol-2-yl)methyl)benzoic acid using the same procedure with the appropriate amine

| Example | Structure | Starting amine | R$_t$ min (Method g) | m/z ESI+ (M + H)+ |
|---|---|---|---|---|
| BJ-40 | 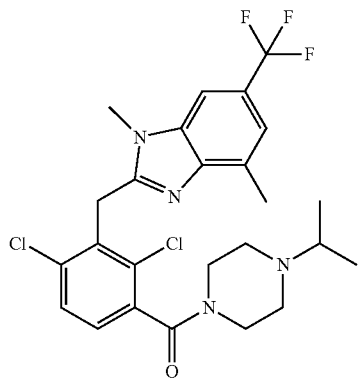 | | 1.15 | 527 |
| BJ-41 | 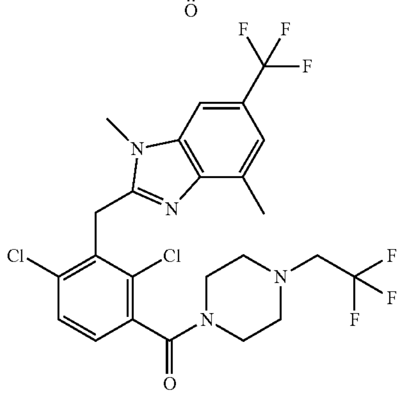 | | 1.88 | 567 |
| BJ-42 | 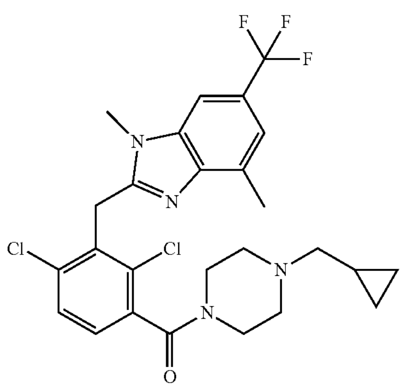 [SMILES: Cc1cc(C(F)(F)F)cc2c1nc(Cc1c(Cl)ccc(C(=O)N3CCN(CC4CC4)CC3)c1Cl)n2C] | | 1.18 | 539 |
| BJ-43 | 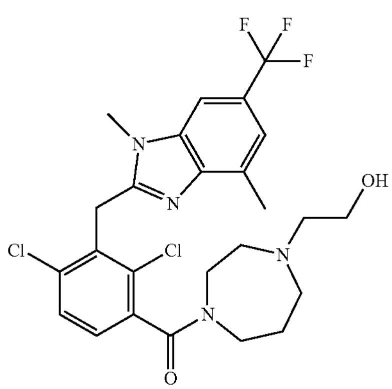 [SMILES: Cc1cc(C(F)(F)F)cc2c1nc(Cc1c(Cl)ccc(C(=O)N3CCCN(CCO)CC3)c1Cl)n2C] | | 1.11 | 543 |

Example BK: 1-(2,4-dichloro-3-((1,4-dimethyl-6-(trifluoromethyl)-1H-benzo[d]imidazol-2-yl)methyl)benzoyl)piperidine-4-carboxylic acid

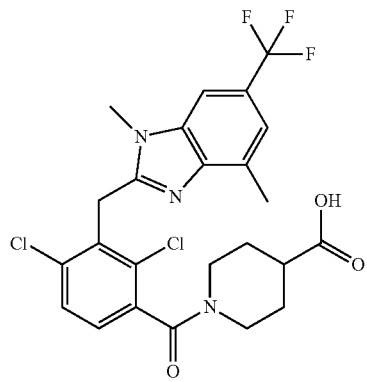 [SMILES: Cc1cc(C(F)(F)F)cc2c1nc(Cc1c(Cl)ccc(C(=O)N3CCC(C(=O)O)CC3)c1Cl)n2C]

Step 1: ethyl 1-(2,4-dichloro-3-((1,4-dimethyl-6-(trifluoromethyl)-1H-benzo[d]imidazol-2-yl)methyl)benzoyl)piperidine-4-carboxylate

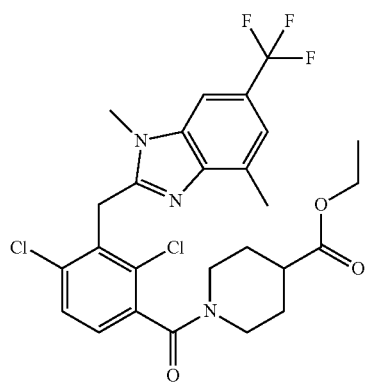 [SMILES: CCOC(=O)C1CCN(C(=O)c2ccc(Cl)c(Cc3nc4c(C)cc(C(F)(F)F)cc4n3C)c2Cl)CC1]

Using a procedure similar to Example A, Step 6, ethyl 1-(2,4-dichloro-3-((1,4-dimethyl-6-(trifluoromethyl)-1H-benzo[d]imidazol-2-yl)methyl)benzoyl)piperidine-4-carboxylate (110 mg, 63%) was prepared from 2,4-dichloro-3-((1,4-dimethyl-6-(trifluoromethyl)-1H-benzo[d]imidazol-2-yl)methyl)benzoic acid (Example BJ, Step 2) (130 mg, 0.312 mmol) and ethyl piperidine-4-carboxylate (73.5 mg, 0.467 mmol). LC/MS (Method h) $R_t$=2.97 min.; MS m/z: 556 [M+H]$^+$. $^1$H NMR (DMSO-d$_6$, 300 MHz): δ 7.82 (s, 1H), 7.62 (d, J=9 Hz, 1H), 7.42 and 7.35 (d, J=9 Hz, 1H), 7.26 (s, 1H), 4.65 (m, 1H), 4.56 (d, J=16 Hz, 1H), 4.38 and 4.34 (m, 1H), 4.04 (m, 2H), 3.97 (s, 3H), 3.27 (m, 1H), 3.09 (m, 1H), 2.97 (m, 1H), 2.64 (m, 1H), 2.40 (s, 3H), 1.93 (m, 1H), 1.76 (m, 1H), 1.50 (m, 2H), 1.16 (m, 3H).

Step 2: 1-(2,4-dichloro-3-((1,4-dimethyl-6-(trifluoromethyl)-1H-benzo[d]imidazol-2-yl)methyl)benzoyl)piperidine-4-carboxylic acid

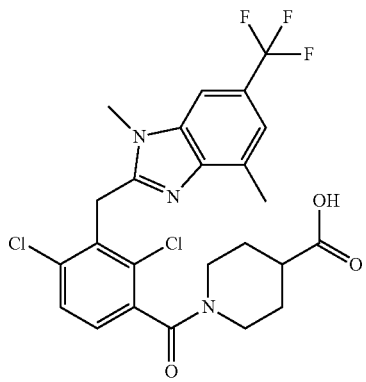 [SMILES: Cc1cc(C(F)(F)F)cc2c1nc(Cc1c(Cl)ccc(C(=O)N3CCC(C(=O)O)CC3)c1Cl)n2C]

Using a procedure similar to Example A, Step 5, 1-(2,4-dichloro-3-((1,4-dimethyl-6-(trifluoromethyl)-1H-benzo[d]imidazol-2-yl)methyl)benzoyl)piperidine-4-carboxylic acid (88 mg, 83%) was prepared from ethyl 1-(2,4-dichloro-3-((1,4-dimethyl-6-(trifluoromethyl)-1H-benzo[c]imidazol-2-yl)methyl)benzoyl)piperidine-4-carboxylate (110 mg, 0.198 mmol). LC/MS (Method g) $R_t$=1.53 min.; MS m/z: 528 [M+H]$^+$. $^1$H NMR (DMSO-d$_6$, 400 MHz): δ 7.83 (s, 1H), 7.62 (d, J=8 Hz, 1H), 7.42 and 7.35 (d, J=8 Hz, 1H), 7.27 (s, 1H), 4.65 (dd, J=6 Hz, 12 Hz, 1H), 4.56 (d, J=12 Hz, 1H), 4.36 and 4.33 (m, 1H), 3.97 (s, 3H), 3.28 (m, 1H), 3.07 (m, 1H), 2.96 (m, 1H), 2.54 (m, 1H), 2.40 (s, 3H), 1.92 (m, 1H), 1.76 (m, 1H), 1.60-1.40 (m, 2H).

Example BL: (1R,5S,6r)-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylic acid

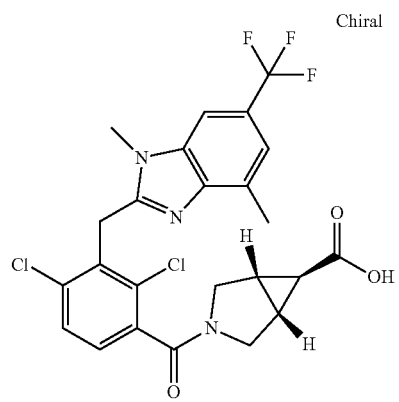 [SMILES: Cc1cc(C(F)(F)F)cc2c1nc(Cc1c(Cl)ccc(C(=O)N3C[C@@H]4[C@H](C3)[C@H]4C(=O)O)c1Cl)n2C]

Step 1: (1R,5S)-ethyl-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylate

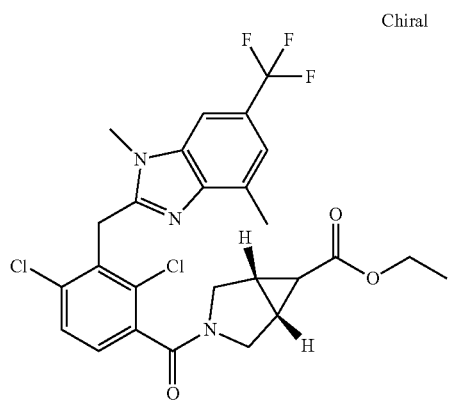 [SMILES: CCOC(=O)C1[C@H]2CN(C(=O)c3ccc(Cl)c(Cc4nc5c(C)cc(C(F)(F)F)cc5n4C)c3Cl)C[C@@H]12]

Using a procedure similar to Example A, Step 6, (1R,5S)-ethyl-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylate (110 mg, 52%) was prepared from 2,4-dichloro-3-((1,4-dimethyl-6-(trifluoromethyl)-1H-benzo[c]imidazol-2-yl)methyl)benzoic acid (Example BJ, Step 2) (160 mg, 0.384 mmol) and (1R,5S)-ethyl 3-azabicyclo[3.1.0]hexane-6-carboxylate hydrochloride (89 mg, 0.464 mmol).

LC/MS (Method g) $R_t$=1.77 min.; MS m/z: 554 [M+H]$^+$. $^1$H NMR (DMSO-d$_6$, 300 MHz): δ 7.82 (s, 1H), 7.63 (d, J=9 Hz, 1H), 7.42 (d, J=9 Hz, 1H), 7.26 (s, 1H), 4.60 (m, 2H), 4.05 (m, 2H), 3.97 (s, 3H), 3.91 (m, 1H), 3.50 (m, 2H), 3.29 (m, 1H), 3.20 (m, 1H), 2.40 (s, 3H), 2.13 (m, 1H), 2.05 (m, 1H), 1.15 (m, 3H).

Step 2: (1R,5S,6r)-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylic acid

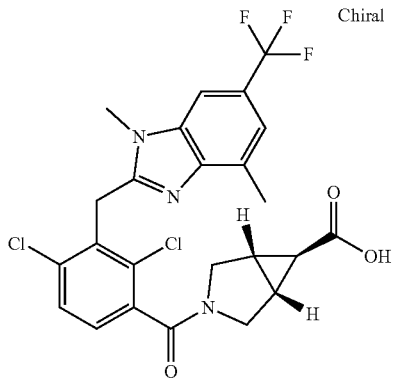 [SMILES: Cc1cc(C(F)(F)F)cc2c1nc(Cc1c(Cl)ccc(C(=O)N3C[C@@H]4[C@H](C3)[C@H]4C(=O)O)c1Cl)n2C]

Using a procedure similar to Example A, Step 5 (1R,5S,6r)-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylic acid (74 mg, 62%) was prepared from ethyl (1R,5S,6r)-3-(2,4-dichloro-3-((1,4-dimethyl-6-(trifluoromethyl)-1H-benzo[d]imidazol-2-yl)methyl)benzoyl)-3-azabicyclo[3.1.0]hexane-6-carboxylate (122 mg, 0.220 mmol). LC/MS (Method g) $R_t$=1.50 min.; MS m/z: 526 [M+H]$^+$. $^1$H NMR (DMSO-d$_6$, 400 MHz): δ 7.82 (s, 1H), 7.62 (d, J=9 Hz, 1H), 7.41 (d, J=9 Hz, 1H), 7.26 (s, 1H), 4.60 (m, 2H), 3.97 (s, 3H), 3.88 (m, 1H), 3.48 (m, 2H), 3.20 (m, 1H), 2.40 (s, 3H), 2.07 (m, 1H), 1.99 (m, 1H), 1.33 (m, 1H).

Example BM: 1-[2,4-dichloro-3-[[1,4-dimethyl-6-(trifluoromethyl)benzimidazol-2-yl]methyl]benzoyl]-3-methyl-piperidine-4-carboxylic acid

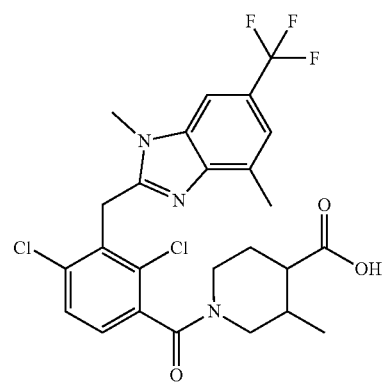 [SMILES: Cc1cc(C(F)(F)F)cc2c1nc(Cc1c(Cl)ccc(C(=O)N3CCC(C(=O)O)C(C)C3)c1Cl)n2C]

Using a procedure similar to Example A, Step 6 and 5, 1-[2,4-dichloro-3-[[1,4-dimethyl-6-(trifluoromethyl)benzimidazol-2-yl]methyl]benzoyl]-3-methyl-piperidine-4-carboxylic acid was prepared from 2,4-dichloro-3-((1,4-dimethyl-6-(trifluoromethyl)-1H-benzo[c]imidazol-2-yl)methyl)benzoic acid (Example BJ, Step 2) (60 mg, 0.144 mmol) and methyl 3-methylpiperidine-4-carboxylate hydrochloride (0.216 mmol). LC/MS (Method g) $R_t$=1.61 min.; MS m/z: 542 [M+H]$^+$.
$^1$H NMR (DMSO-d$_6$, 400 MHz): δ 12.26 (broad, 1H), 7.83 (s, 1H), 7.61 (m, 1H), 7.37 (m, 1H), 7.27 (s, 1H), 4.62 (m, 2H), 4.38 and 4.23 (m, 1H), 3.97 (m, 3H), 3.28-2.95 (m, 3H), 2.69 (m, 1H), 2.40 (m, 3H), 2.29 and 2.10 (m, 1H), 1.75-1.48 (m, 2H), 0.89 and 0.74 (m, 3H).

Example BM-1

1-(2,4-dichloro-3-((1,4-dimethyl-6-(trifluoromethyl)-1H-indol-2-yl)methyl)benzoyl)-4-fluoropiperidine-4-carboxylic acid

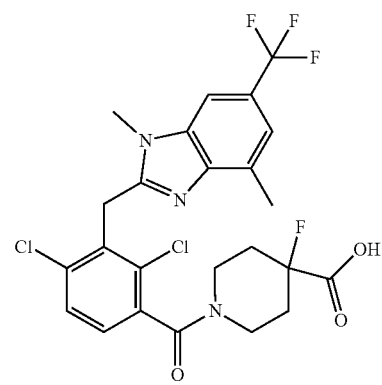 [SMILES: Cc1cc(C(F)(F)F)cc2c1nc(Cc1c(Cl)ccc(C(=O)N3CCC(F)(C(=O)O)CC3)c1Cl)n2C]

Using a procedure similar to Example A, Step 6 and 5, 1-(2,4-dichloro-3-((1,4-dimethyl-6-(trifluoromethyl)-1H-indol-2-yl)methyl)benzoyl)-4-fluoropiperidine-4-carboxylic acid (91 mg, 99%) was prepared from 2,4-dichloro-3-((1,4-dimethyl-6-(trifluoromethyl)-1H-benzo[d]imidazol-2-yl)methyl)benzoic acid (Example BJ, Step 2) (95 mg, 0.166 mmol) and ethyl 4-fluoropiperidine-4-carboxylate hydrochloride (76 mg, 0.36 mmol). LC/MS (Method g) R$_t$=1.92 min.; MS m/z: 545 [M+H]$^+$.

$^1$H NMR (DMSO-d$_6$, 400 MHz): δ 7.69 (m, 2H), 7.54 and 7.44 (d, J=, 8 Hz 1H), 7.06 (s, 1H), 5.69 (m, 1H), 4.48 (m, 3H), 3.92 (s, 3H), 3.26 (m, 1H), 3.08 (m, 1H), 2.37 and 2.36 (s, 3H), 2.00 (m, 2H), 1.88 (m, 2H)

Example BN: 2-(2,6-dichloro-3-(4-(2-hydroxyethyl)piperidine-1-carbonyl)benzyl)-1,4-dimethyl-1H-benzo[d]imidazole-6-carbonitrile

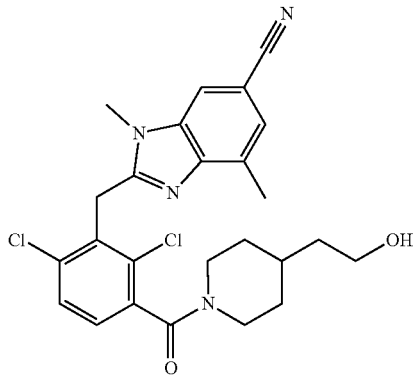 [SMILES: Cc1cc(C#N)cc2c1nc(Cc1c(Cl)ccc(C(=O)N3CCC(CCO)CC3)c1Cl)n2C]

Step 1: methyl 2,4-dichloro-3-((6-cyano-1,4-dimethyl-1H-benzo[d]imidazol-2-yl)methyl)benzoate

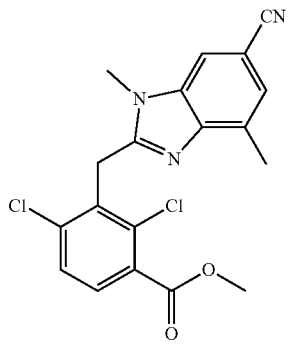 [SMILES: COC(=O)c1ccc(Cl)c(Cc2nc3c(C)cc(C#N)cc3n2C)c1Cl]

Using a procedure similar to Example BJ, Step 1, methyl 2,4-dichloro-3-((6-cyano-1,4-dimethyl-1H-benzo[d]imidazol-2-yl)methyl)benzoate (1.65 g, 44%) was prepared from 4-amino-3-methyl-5-(methylamino)benzonitrile (Preparation #22) (1.55 g, 9.62 mmol) and 2-(2,6-dichloro-3-(methoxycarbonyl)phenyl)acetic acid (Preparation #2) (2.53 g, 9.62 mmol). LC/MS (Method k) 2.69 min.; MS m/z: 388 [M+H]$^+$. $^1$H NMR (DMSO-d$_6$, 300 MHz): δ. 8.02 (s, 1H), 7.76 (d, J=9 Hz, 1H), 7.68 (d, J=9 Hz, 1H), 7.34 (s, 1H), 4.64 (s, 2H), 3.95 (s, 3H), 3.87 (s, 3H), 2.37 (s, 3H).

Step 2: 2,4-dichloro-3-((6-cyano-1,4-dimethyl-1H-benzo[d]imidazol-2-yl)methyl)benzoic acid

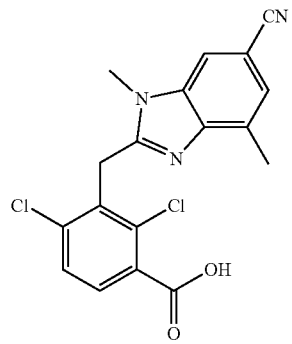 [SMILES: Cc1cc(C#N)cc2c1nc(Cc1c(Cl)ccc(C(=O)O)c1Cl)n2C]

Using a procedure similar to Example A, Step 5, 2,4-dichloro-3-((6-cyano-1,4-dimethyl-1H-benzo[d]imidazol-2-yl)methyl)benzoic acid (1.7 g, 87%) was prepared from methyl 2,4-dichloro-3-((6-cyano-1,4-dimethyl-1H-benzo[c]imidazol-2-yl)methyl)benzoate (2.028 g, 5.22 mmol).

LC/MS (Method h) R$_t$=2.04 min.; MS m/z: 374 [M+H]$^+$.
$^1$H NMR (DMSO-d$_6$, 300 MHz): δ. 13.63 (broad, 1H), 8.02 (s, 1H), 7.73 (d, J=9 Hz, 1H), 7.63 (d, J=9 Hz, 1H), 7.34 (s, 1H), 4.63 (s, 2H), 3.95 (s, 3H), 2.37 (s, 3H).

Step 3: 2-(2,6-dichloro-3-(4-(2-hydroxyethyl)piperidine-1-carbonyl)benzyl)-1,4-dimethyl-1H-benzo[d]imidazole-6-carbonitrile

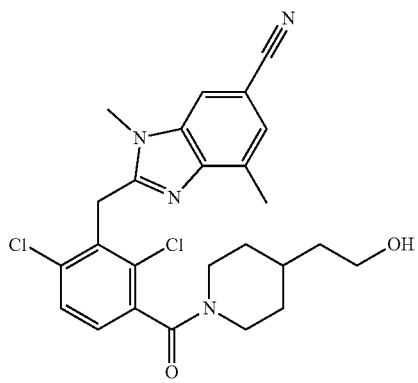 [SMILES: Cc1cc(C#N)cc2c1nc(Cc1c(Cl)ccc(C(=O)N3CCC(CCO)CC3)c1Cl)n2C]

Using a procedure similar to Example A1, 2-(2,6-dichloro-3-(4-(2-hydroxyethyl)piperidine-1-carbonyl)benzyl)-1,4-dimethyl-1H-benzo[d]imidazole-6-carbonitrile (55 mg, 65%) was prepared from 2,4-dichloro-3-((6-cyano-1,4-dimethyl-1H-benzo[d]imidazol-2-yl)methyl)benzoic acid (65 mg, 0.174 mmol) and 4-piperidineethanol (0.26 mmol). LC/MS (Method h) R$_t$=2.04 min.; MS m/z: 485 [M+H]$^+$.

$^1$H NMR (DMSO-d$_6$, 300 MHz): δ. 8.02 (s, 1H), 7.61 and 7.60 (d, J=8.1 Hz, 1H), 7.40 and 7.32 (d, J=8.1 Hz, 1H), 7.34 (s, 1H), 4.66 and 6.64 (d, J=17.1, 1H), 4.56 (d, J=17.1, 1H), 4.46 (m, 1H), 3.95 (s, 3H), 3.42 (m, 3H), 3.27 (m, 1H), 2.99 (m, 1H), 2.75 (m, 1H), 2.36 (m, 3H), 1.75 (m, 1H), 1.86 (m, 1H), 1.57 (m, 1H), 1.35 (m, 2H), 1.06 (m, 2H)

TABLE BN

The following examples were prepared from 2,4-dichloro-3-((6-cyano-1,4-dimethyl-1H-benzo[d]imidazol-2-yl)methyl)benzoic acid (Example BN, Step 2) using the same procedure with the appropriate amine.

| Example | Structure | Starting amine | R$_t$ min (Method g) | m/z ESI+ (M + H)+ |
|---|---|---|---|---|
| BN-1 | 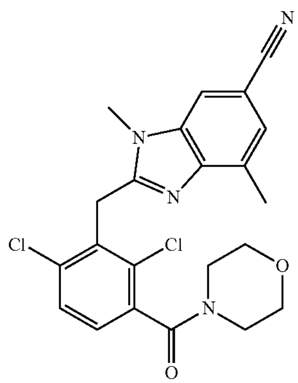 [SMILES: Cc1cc(C#N)cc2c1nc(Cc1c(Cl)ccc(C(=O)N3CCOCC3)c1Cl)n2C] | | 1.33 | 443 |
| BN-2 | Chiral | Chiral | 1.18 | 471 |
| BN-3 | 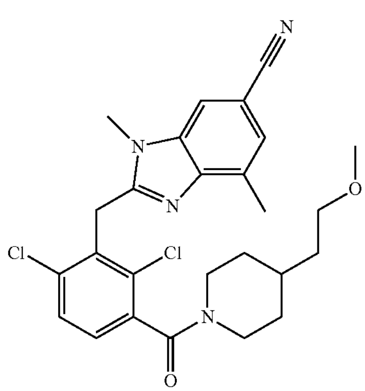 [SMILES: COCCC1CCN(C(=O)c2ccc(Cl)c(Cc3nc4c(C)cc(C#N)cc4n3C)c2Cl)CC1] | | 1.61 | 499 |

TABLE BN-continued

The following examples were prepared from 2,4-dichloro-3-(((6-cyano-1,4-dimethyl-1H-benzo[d]imidazol-2-yl)methyl)benzoic acid (Example BN, Step 2) using the same procedure with the appropriate amine.

| Example | Structure | Starting amine | $R_t$ min (Method g) | m/z ESI+ $(M + H)^+$ |
|---|---|---|---|---|
| BN-4 | 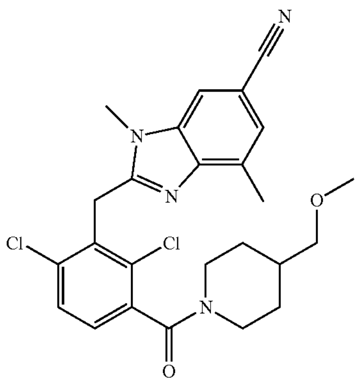 [SMILES: COCC1CCN(C(=O)c2ccc(Cl)c(Cc3nc4c(C)cc(C#N)cc4n3C)c2Cl)CC1] | | 1.55 | 485 |
| BN-5 | 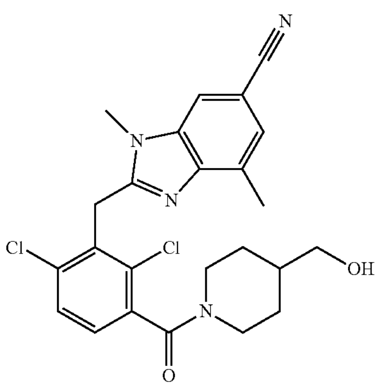 [SMILES: Cc1cc(C#N)cc2c1nc(Cc1c(Cl)ccc(C(=O)N3CCC(CO)CC3)c1Cl)n2C] | | 1.30 | 471 |
| BN-6 | 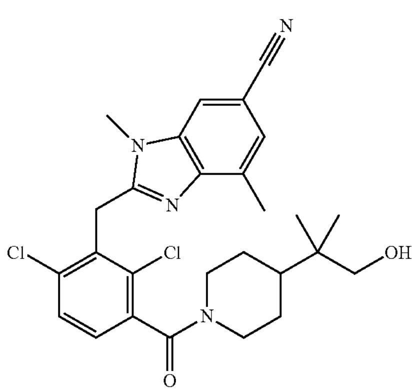 [SMILES: Cc1cc(C#N)cc2c1nc(Cc1c(Cl)ccc(C(=O)N3CCC(C(C)(C)CO)CC3)c1Cl)n2C] | | 1.51 | 513 |

TABLE BN-continued

The following examples were prepared from 2,4-dichloro-3-((6-cyano-1,4-dimethyl-1H-benzo[d]imidazol-2-yl)methyl)benzoic acid (Example BN, Step 2) using the same procedure with the appropriate amine.

| Example | Structure | Starting amine | R$_t$ min (Method g) | m/z ESI+ (M + H)+ |
|---|---|---|---|---|
| BN-7 | 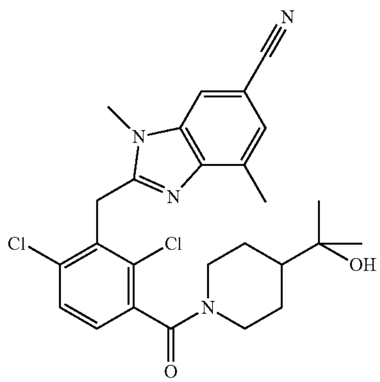 [SMILES: Cc1cc(C#N)cc2c1nc(Cc1c(Cl)ccc(C(=O)N3CCC(C(C)(C)O)CC3)c1Cl)n2C] | | 1.42 | 499 |
| BN-8 | 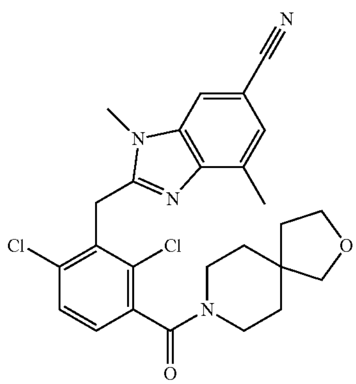 [SMILES: Cc1cc(C#N)cc2c1nc(Cc1c(Cl)ccc(C(=O)N3CCC4(CCOC4)CC3)c1Cl)n2C] | | 1.47 | 497 |
| BN-9 | 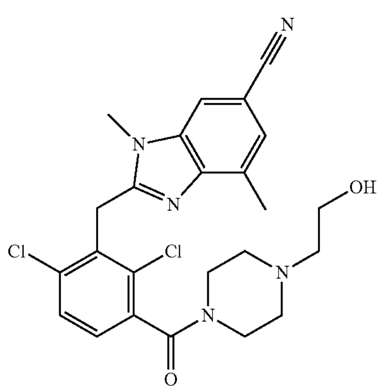 [SMILES: Cc1cc(C#N)cc2c1nc(Cc1c(Cl)ccc(C(=O)N3CCN(CCO)CC3)c1Cl)n2C] | | 0.90 | 486 |

TABLE BN-continued
The following examples were prepared from 2,4-dichloro-3-((6-cyano-1,4-dimethyl-1H-benzo[d]imidazol-2-yl)methyl)benzoic acid (Example BN, Step 2) using the same procedure with the appropriate amine.
| Example | Structure | Starting amine | R$_t$ min (Method g) | m/z ESI+ (M + H)$^+$ |
|---|---|---|---|---|
| BN-10 | 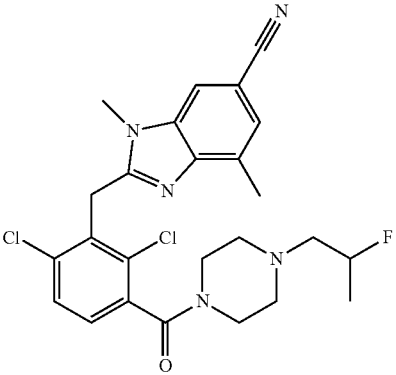 [SMILES: Cc1cc(C#N)cc2c1nc(Cc1c(Cl)ccc(C(=O)N3CCN(CC(C)F)CC3)c1Cl)n2C] | 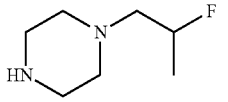 | 1.09 | 502 |
| BN-11 | 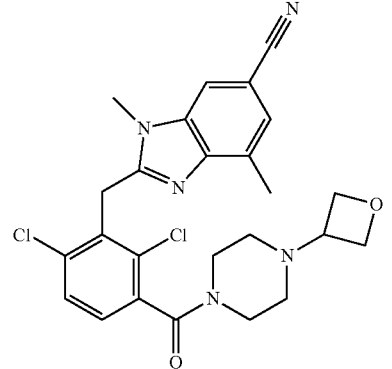 [SMILES: Cc1cc(C#N)cc2c1nc(Cc1c(Cl)ccc(C(=O)N3CCN(C4COC4)CC3)c1Cl)n2C] | 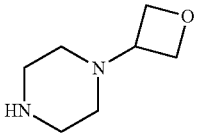 | 1.18 | 498 |
| BN-12 | 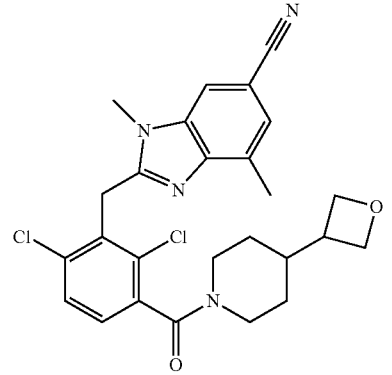 [SMILES: Cc1cc(C#N)cc2c1nc(Cc1c(Cl)ccc(C(=O)N3CCC(C4COC4)CC3)c1Cl)n2C] | 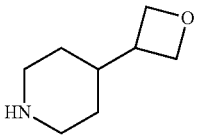 | 1.43 | 497 |

TABLE BN-continued

The following examples were prepared from 2,4-dichloro-3-((6-cyano-1,4-dimethyl-1H-benzo[d]imidazol-2-yl)methyl)benzoic acid (Example BN, Step 2) using the same procedure with the appropriate amine.

| Example | Structure | Starting amine | R$_t$ min (Method g) | m/z ESI+ (M + H)+ |
|---|---|---|---|---|
| BN-13 | 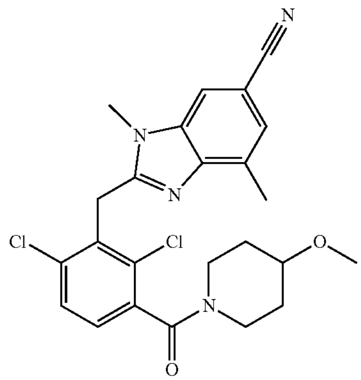 [SMILES: COC1CCN(C(=O)c2ccc(Cl)c(Cc3nc4c(C)cc(C#N)cc4n3C)c2Cl)CC1] | | 1.47 | 471 |
| BN-14 | 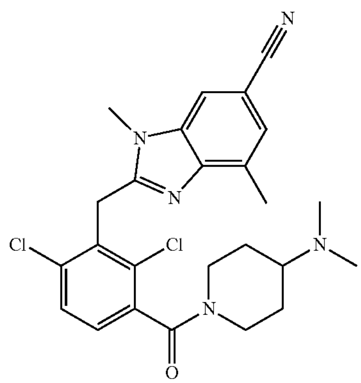 [SMILES: Cc1cc(C#N)cc2c1nc(Cc1c(Cl)ccc(C(=O)N3CCC(N(C)C)CC3)c1Cl)n2C] | | 0.92 | 484 |
| BN-15 | 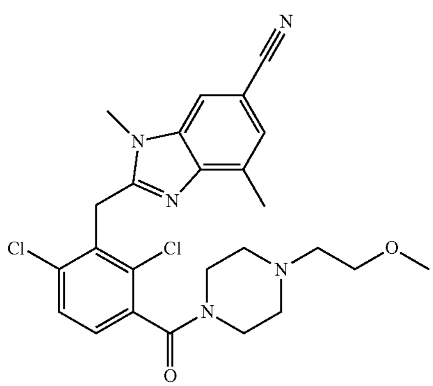 [SMILES: COCCN1CCN(C(=O)c2ccc(Cl)c(Cc3nc4c(C)cc(C#N)cc4n3C)c2Cl)CC1] | | 0.95 | 500 |
| BN-16 | 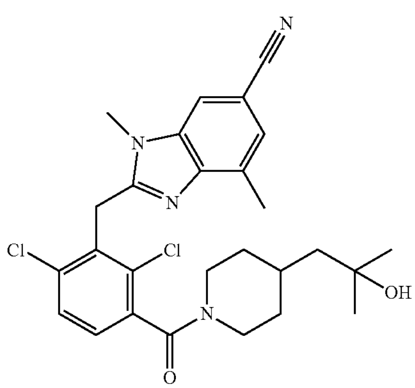 [SMILES: Cc1cc(C#N)cc2c1nc(Cc1c(Cl)ccc(C(=O)N3CCC(CC(C)(C)O)CC3)c1Cl)n2C] | | 1.51 | 513 |

TABLE BN-continued

The following examples were prepared from 2,4-dichloro-3-((6-cyano-1,4-dimethyl-1H-benzo[d]imidazol-2-yl)methyl)benzoic acid (Example BN, Step 2) using the same procedure with the appropriate amine.

| Example | Structure | Starting amine | R$_t$ min (Method g) | m/z ESI+ (M + H)+ |
|---|---|---|---|---|
| BN-17 | 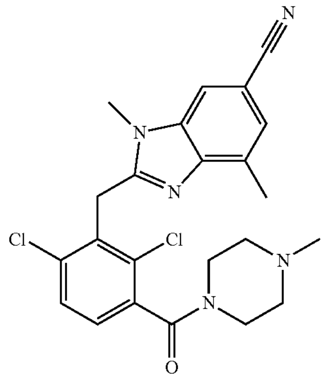 [SMILES: Cc1cc(C#N)cc2c1nc(Cc1c(Cl)ccc(C(=O)N3CCN(C)CC3)c1Cl)n2C] | | 0.90 | 456 |

Example BO: (2,4-dichloro-3-((1,4,6-trimethyl-1H-benzo[d]imidazol-2-yl)methyl)phenyl)(morpholino)methanone

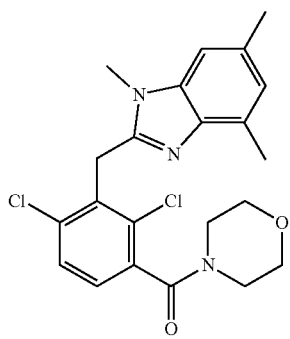 [SMILES: Cc1cc(C)c2nc(Cc3c(Cl)ccc(C(=O)N4CCOCC4)c3Cl)n(C)c2c1]

Step 1: (2,4-dichloro-3-((1,4,6-trimethyl-1H-benzo[d]imidazol-2-yl)methyl)phenyl)(morpholino)methanone

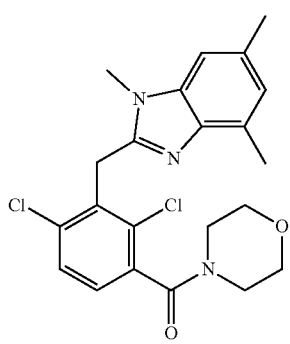 [SMILES: Cc1cc(C)c2nc(Cc3c(Cl)ccc(C(=O)N4CCOCC4)c3Cl)n(C)c2c1]

Using a procedure similar to Example BJ, Step 1, (2,4-dichloro-3-((1,4,6-trimethyl-1H-benzo[d]imidazol-2-yl)methyl)phenyl)(morpholino)methanone (17 mg, 12%) was prepared from N1,3,5-trimethylbenzene-1,2-diamine (Preparation #23) (50 mg, 0.333 mmol) and 2-(2,6-dichloro-3-(morpholine-4-carbonyl)phenyl)acetic acid (Preparation #8) (100 mg, 0.314 mmol).

LC/MS (Method g) R$_t$=1.05 min.; MS m/z: 432 [M+H]$^+$. $^1$H NMR (DMSO-d$_6$, 300 MHz): δ. 7.62 (d, J=9 Hz, 1H), 7.38 (d, J=9 Hz, 1H), 7.11 (s, 1H), 6.75 (s, 1H), 4.55 (d, J=15 Hz, 1H), 4.46 (d, J=15 Hz, 1H), 3.82 (s, 3H), 3.64 (m, 4H), 3.53 (m, 2H), 3.17 (m, 2H), 2.38 (s, 3H), 2.27 (s, 3H).

Example BP: (2,4-dichloro-3-((1,7-dimethyl-5-(trifluoromethyl)-1H-benzo[d]imidazol-2-yl)methyl)phenyl)(morpholino)methanone

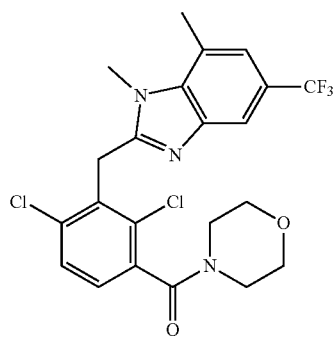 [SMILES: Cc1cc(C(F)(F)F)cc2nc(Cc3c(Cl)ccc(C(=O)N4CCOCC4)c3Cl)n(C)c12]

449

Step 1: (2,4-dichloro-3-((4-methyl-6-(trifluoromethyl)-1H-benzo[d]imidazol-2-yl)methyl)phenyl)(morpholino)methanone

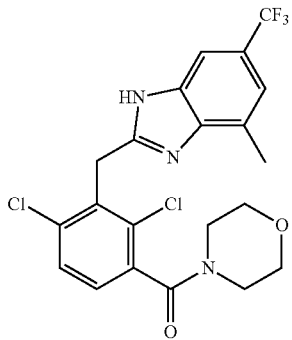

Using a procedure similar to Example BJ, Step 1, (2,4-dichloro-3-((4-methyl-6-(trifluoromethyl)-1H-benzo[d]imidazol-2-yl)methyl)phenyl)(morpholino)methanone (70 mg, 11%) was prepared from 3-methyl-5-(trifluoromethyl)benzene-1,2-diamine (Preparation #23, Step 4) (251 mg, 1.320 mmol) and 2-(2,6-dichloro-3-(morpholine-4-carbonyl)phenyl)acetic acid (Preparation #8) (420 mg, 1.320 mmol).

LC/MS (Method h) $R_t$=2.32 min.; MS m/z: 472 [M+H]$^+$.

$^1$H NMR (DMSO-d$_6$, 300 MHz): δ. 12.92 and 12.62 (broad, 1H), 7.63 (m, 2H), 7.41 (m, 1H), 7.24 and 7.16 (m, 1H), 4.56 (m, 2H), 3.64 (m, 4H), 3.53 (m, 2H), 3.17 (m, 2H), 2.56 and 2.50 (s, 3H).

Step 2: (2,4-dichloro-3-((1,7-dimethyl-5-(trifluoromethyl)-1H-benzo[d]imidazol-2-yl)methyl)phenyl)(morpholino)methanone

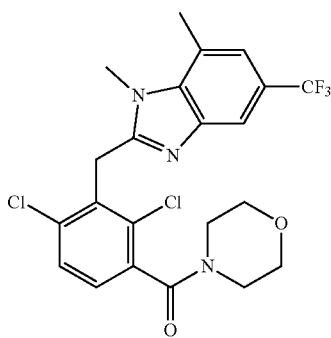 [SMILES: Cc1cc(C(F)(F)F)cc2nc(Cc3c(Cl)ccc(C(=O)N4CCOCC4)c3Cl)n(C)c12]

Using a procedure similar to Example A, Step 4, (2,4-dichloro-3-((1,7-dimethyl-5-(trifluoromethyl)-1H-benzo[d]imidazol-2-yl)methyl)phenyl)(morpholino)methanone (8 mg, 11%) was prepared from (2,4-dichloro-3-((4-methyl-6-(trifluoromethyl)-1H-benzo[c]imidazol-2-yl)methyl)phenyl)(morpholino)methanone (70 mg, 0.148 mmol). LC/MS (Method g) $R_t$=1.54 min.;

MS m/z: 486 [M+H]$^+$. $^1$H NMR (DMSO-d$_6$, 400 MHz): δ. 7.69 (s, 1H), 7.62 (d, J=9 Hz, 1H), 7.41 (d, J=9 Hz, 1H), 7.25 (s, 1H), 4.56 (m, 2H), 4.15 (s, 3H), 3.65 (m, 4H), 3.53 (m, 2H), 3.16 (m, 2H), 2.81 (s, 3H).

450

Example BQ: (3-((6-bromo-1,4-dimethyl-1H-benzo[d]imidazol-2-yl)methyl)-2,4-dichlorophenyl)(morpholino)methanone

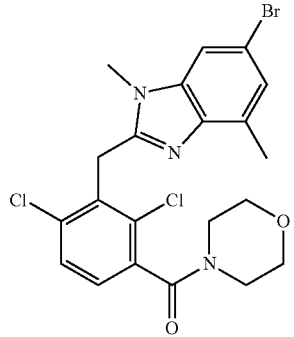

Step 1: methyl 3-((6-bromo-1,4-dimethyl-1H-benzo[d]imidazol-2-yl)methyl)-2,4-dichlorobenzoate

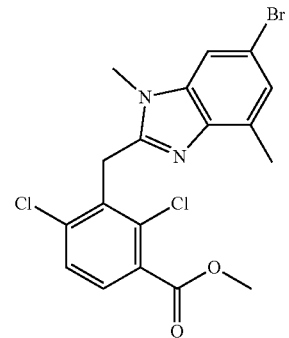 [SMILES: COC(=O)c1ccc(Cl)c(Cc2nc3c(C)cc(Br)cc3n2C)c1Cl]

Using a procedure similar to Example BJ, Step 1, methyl 3-((6-bromo-1,4-dimethyl-1H-benzo[d]imidazol-2-yl)methyl)-2,4-dichlorobenzoate (451 mg, 42%) was prepared from 5-bromo-N-1,3-dimethylbenzene-1,2-diamine (Preparation #24) (440 mg, 2.046 mmol) and 2-(2,6-dichloro-3-(methoxycarbonyl)phenyl)acetic acid (Preparation #2) (538 mg, 2.046 mmol). LC/MS (Method h) $R_t$=2.89 min.; MS m/z: 441 [M+H]$^+$. $^1$H NMR (DMSO-d$_6$, 300 MHz): δ. 7.75 (d, J=9 Hz, 1H), 7.67 (d, J=9 Hz, 1H), 7.63 (m, 1H), 7.10 (m, 1H), 4.57 (s, 2H), 3.88 (s, 3H), 3.87 (s, 3H), 2.32 (s, 3H).

Step 2: 3-((6-bromo-1,4-dimethyl-1H-benzo[d]imidazol-2-yl)methyl)-2,4-dichlorobenzoic acid

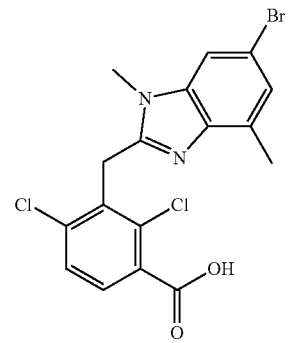 [SMILES: Cc1cc(Br)cc2c1nc(Cc1c(Cl)ccc(C(=O)O)c1Cl)n2C]

Using a procedure similar to Example A, Step 5, 3-((6-bromo-1,4-dimethyl-1H-benzo[d]imidazol-2-yl)methyl)-2,4-dichlorobenzoic acid (248 mg, 57%) was prepared from methyl 3-((6-bromo-1,4-dimethyl-1H-benzo[d]imidazol-2-yl)methyl)-2,4-dichlorobenzoate (445 mg, 1.006 mmol).

LC/MS (Method h) $R_t$=2.16 min.; MS m/z: 427 [M+H]$^+$. $^1$H NMR (DMSO-d$_6$, 300 MHz): δ. 7.72 (d, J=9 Hz, 1H), 7.65 (s, 1H), 7.62 (d, J=9 Hz, 1H), 7.11 (s, 1H), 4.57 (s, 2H), 3.88 (s, 3H), 2.33 (s, 3H).

Step 3: (3-((6-bromo-1,4-dimethyl-1H-benzo[d]imidazol-2-yl)methyl)-2,4-dichlorophenyl)(morpholino)methanone

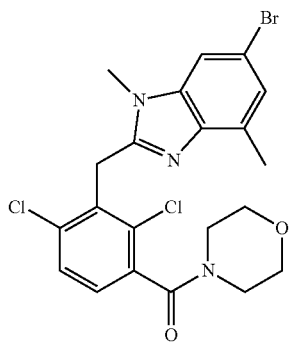

Using a procedure similar to Example A1, (3-((6-bromo-1,4-dimethyl-1H-benzo[d]imidazol-2-yl)methyl)-2,4-dichlorophenyl)(morpholino)methanone (223 mg, 78%) was prepared from 3-((6-bromo-1,4-dimethyl-1H-benzo[d]imidazol-2-yl)methyl)-2,4-dichlorobenzoic acid (245 mg, 0.572 mmol) and morpholine (64.8 mg, 0.744 mmol). LC/MS (Method g) $R_t$=1.53 min.; MS m/z: 496 [M+H]$^+$. $^1$H NMR (DMSO-d$_6$, 300 MHz): δ. 7.63 (s, 1H), 7.62 (d, J=9 Hz, 1H), 7.40 (d, J=9 Hz, 1H), 7.10 (s, 1H), 4.56 (d, J=15 Hz, 1H), 4.48 (d, J=15 Hz, 1H), 3.87 (s, 3H), 3.64 (m, 4H), 3.52 (m, 2H), 3.17 (m, 2H), 2.31 (s, 3H).

Example BR: (3-((6-bromo-1,4-dimethyl-1H-benzo[d]imidazol-2-yl)methyl)-2,4-dimethylphenyl)(morpholino)methanone

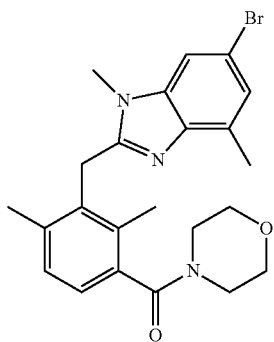 [SMILES: Cc1ccc(C(=O)N2CCOCC2)c(C)c1Cc1nc2c(C)cc(Br)cc2n1C]

Step 1: methyl 3-((6-bromo-1,4-dimethyl-1H-benzo[d]imidazol-2-yl)methyl)-2,4-dimethylbenzoate

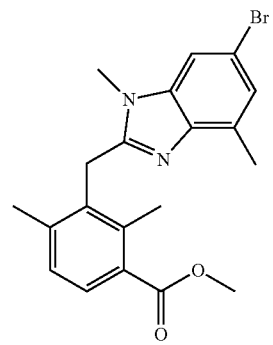 [SMILES: COC(=O)c1ccc(C)c(Cc2nc3c(C)cc(Br)cc3n2C)c1C]

Using a procedure similar to Example BJ, Step 1, methyl 3-((6-bromo-1,4-dimethyl-1H-benzo[d]imidazol-2-yl)methyl)-2,4-dimethylbenzoate (620 mg, 70%) was prepared from 2-(3-(methoxycarbonyl)-2,6-dimethylphenyl)acetic acid (Preparation #9) (500 mg, 2.250 mmol) and 5-bromo-N1,3-dimethylbenzene-1,2-diamine (Preparation #24) (484 mg, 2.250 mmol). LC/MS (Method h) $R_t$=2.62 min.; MS m/z: 401 [M+H]$^+$. $^1$H NMR (DMSO-d$_6$, 300 MHz): δ 7.61 (m, 1H), 7.55 (d, J=9 Hz, 1H), 7.18 (d, J=9 Hz, 1H), 7.08 (m, 1H), 4.28 (s, 2H), 3.85 (s, 3H), 3.81 (s, 3H), 2.36 (s, 3H), 2.33 (s, 3H), 2.28 (s, 3H).

Step 2: 3-((6-bromo-1,4-dimethyl-1H-benzo[d]imidazol-2-yl)methyl)-2,4-dimethylbenzoic acid

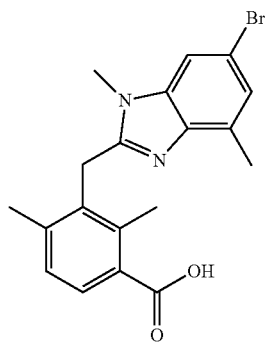 [SMILES: Cc1ccc(C(=O)O)c(C)c1Cc1nc2c(C)cc(Br)cc2n1C]

Using a procedure similar to Example E, Step 1, 3-((6-bromo-1,4-dimethyl-1H-benzo[d]imidazol-2-yl)methyl)-2,4-dimethylbenzoic acid (580 mg, 94%) was prepared from methyl 3-((6-bromo-1,4-dimethyl-1H-benzo[d]imidazol-2-yl)methyl)-2,4-dimethylbenzoate 620 mg, 1.545 mmol). LC/MS (Method h) $R_t$=2.09 min.; MS m/z: 387 [M+H]$^+$. $^1$H NMR (DMSO-d$_6$, 400 MHz): δ 12.72 (broad, 1H), 7.63 (s, 1H), 7.57 (d, J=9 Hz, 1H), 7.14 (d, J=9 Hz, 1H), 7.09 (s, 1H), 4.27 (s, 2H), 3.33 (s, 3H), 2.38 (s, 3H), 2.33 (s, 3H), 2.28 (s, 3H).

Step 3: (3-((6-bromo-1,4-dimethyl-1H-benzo[d]imidazol-2-yl)methyl)-2,4-dimethylphenyl)(morpholino)methanone

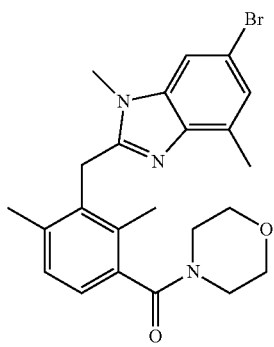 [SMILES: Cc1ccc(C(=O)N2CCOCC2)c(C)c1Cc1nc2c(C)cc(Br)cc2n1C]

Using a procedure similar to Example A, Step 6, (3-((6-bromo-1,4-dimethyl-1H-benzo[d]imidazol-2-yl)methyl)-2,4-dimethylphenyl)(morpholino)methanone (580 mg, 97%) was prepared from 3-((6-bromo-1,4-dimethyl-1H-benzo[d]imidazol-2-yl)methyl)-2,4-dimethylbenzoic acid (465 mg, 1.201 mmol) and morpholine (157 mg, 1.80 mmol). LC/MS (Method g) $R_t$=1.99 min.; MS m/z: 456 [M+H]$^+$. $^1$H NMR (DMSO-d$_6$, 300 MHz): δ 7.61 (m, 1H), 7.12 (d, J=9 Hz, 1H), 7.08 (m, 1H), 7.01 (d, J=9 Hz, 1H), 4.26 (m, 2H), 3.83 (s, 3H), 3.64 (m, 4H), 3.48 (m, 2H), 3.14 (m, 2H), 2.32 (s, 3H), 2.25 (s, 3H), 2.12 (s, 3H).

Example BS: (2,4-dichloro-3-(1,4-dimethyl-6-(trifluoromethyl)-1H-benzo[d]imidazole-2-carbonyl)phenyl)(morpholino)methanone

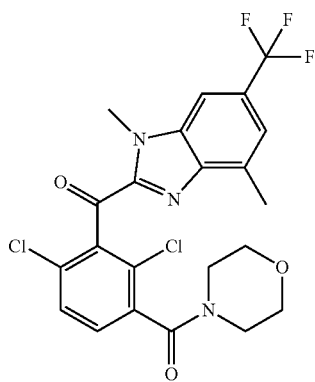 [SMILES: Cc1cc(C(F)(F)F)cc2c1nc(C(=O)c1c(Cl)ccc(C(=O)N3CCOCC3)c1Cl)n2C]

To a solution of (2,4-dichloro-3-((1,4-dimethyl-6-(trifluoromethyl)-1H-benzo[c]imidazol-2-yl)methyl)phenyl)(morpholino)methanone (Example BJ, Step 3) (35 mg, 0.072 mmol) in dioxane (500 μL) was added manganese dioxide (67 mg, 0.771 mmol). The reaction mixture was stirred at 65° C. for 24 hours. Manganese dioxide (55 mg, 0.633 mmol) was added and the reaction mixture was stirred at 65° C. for 24 hours. Manganese dioxide (55 mg, 0.633 mmol) was added and the reaction mixture was stirred at 80° C. for 24 hours. Manganese dioxide (55 mg, 0.633 mmol) was added and the reaction mixture was stirred at 80° C. for 36 hours. The reaction mixture was filtered and washed with EtOAc. The filtrate was concentrated under reduced pressure. The residue was purified by preparative LCMS to give (2,4-dichloro-3-(1,4-dimethyl-6-(trifluoromethyl)-1H-benzo[c]imidazole-2-carbonyl)phenyl)(morpholino)methanone (20 mg, 55%). LC/MS (Method g) $R_t$=1.77 min.; MS m/z: 500 [M+H]$^+$. $^1$H NMR (DMSO-d$_6$, 400 MHz): δ 8.16 (s, 1H), 7.76 (d, J=9 Hz, 1H), 7.66 (d, J=9 Hz, 1H), 7.51 (s, 1H), 4.31 (s, 3H), 3.65 (m, 4H), 3.56 (m, 2H), 3.20 (m, 2H), 2.51 (s, 3H).

Example BT: 2-(2,6-dichloro-3-(morpholine-4-carbonyl)benzoyl)-1,4-dimethyl-1H-benzo[d]imidazole-6-carboxamide

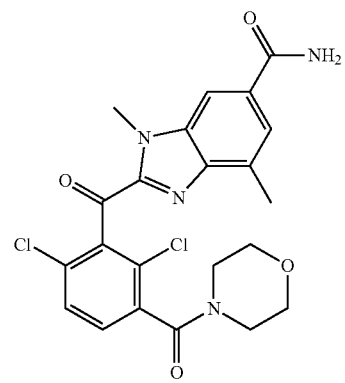 [SMILES: Cc1cc(C(N)=O)cc2c1nc(C(=O)c1c(Cl)ccc(C(=O)N3CCOCC3)c1Cl)n2C]

Using a procedure similar to Example BS, 2-(2,6-dichloro-3-(morpholine-4-carbonyl)benzoyl)-1,4-dimethyl-1H-benzo[d]imidazole-6-carboxamide (15 mg, 18%) was prepared from 2-(2,6-dichloro-3-(morpholine-4-carbonyl)benzyl)-1,4-dimethyl-1H-benzo[d]imidazole-6-carbonitrile (Table BN, Example BN-1) (180 mg, 0.406 mmol). LC/MS (Method g) $R_t$=1.12 min.; MS m/z: 475 [M+H]$^+$. $^1$H NMR (DMSO-d$_6$, 300 MHz): δ 8.18 (s, 1H), 8.06 (broad, 1H), 7.75 (d, J=9 Hz, 1H), 7.71 (m, 1H), 7.64 (d, J=9 Hz, 1H), 7.46 (broad, 1H), 4.27 (s, 3H), 3.65 (m, 4H), 3.55 (m, 2H), 3.20 (m, 2H), 2.46 (s, 3H).

Example BU: 2-(1-(2,4-dichloro-3-((1,4-dimethyl-6-(trifluoromethyl)-1H-benzo[d]imidazol-2-yl)methyl)benzoyl)piperidin-4-yl)acetic acid

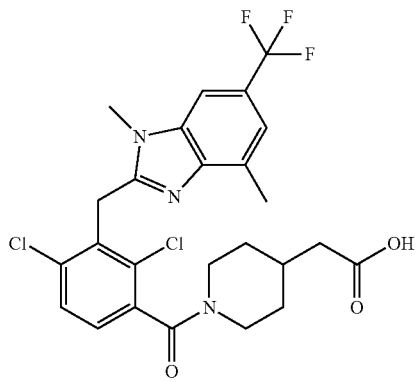 [SMILES: Cc1cc(C(F)(F)F)cc2c1nc(Cc1c(Cl)ccc(C(=O)N3CCC(CC(=O)O)CC3)c1Cl)n2C]

Step 1: methyl 2-(1-(2,4-dichloro-3-((1,4-dimethyl-6-(trifluoromethyl)-1H-benzo[d]imidazol-2-yl)methyl)benzoyl)piperidin-4-yl)acetate

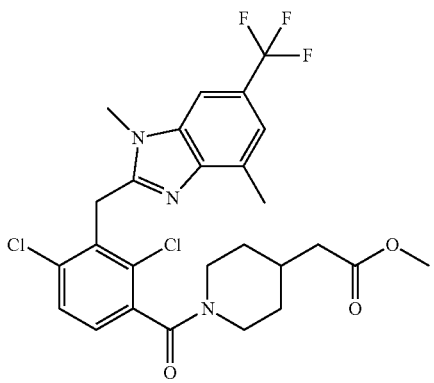

Using a procedure similar to Example A1, methyl 2-(1-(2,4-dichloro-3-((1,4-dimethyl-6-(trifluoromethyl)-1H-benzo[c]imidazol-2-yl)methyl)benzoyl)piperidin-4-yl)acetate (163 mg, 100%) was prepared from 2,4-dichloro-3-((1,4-dimethyl-6-(trifluoromethyl)-1H-benzo[d]imidazol-2-yl)methyl)benzoic acid (Example BJ, Step 2) (120 mg, 0.288 mmol) and methyl (4-piperidyl)acetate hydrochloride (67 mg, 0.345 mmol). LC/MS (Method i) $R_t$=2.37 min.; MS m/z: 556 [M+H]$^+$.

$^1$H NMR (DMSO-d$_6$, 300 MHz): δ 7.85 (s, 1H), 7.62 (m, 1H), 7.40 and 7.33 (d, J=8.3 Hz, 1H), 7.29 (s, 1H), 4.64 (m, 2H), 4.47 (m, 1H), 3.98 and 3.97 (s, 3H), 3.59 and 3.56 (s, 3H), 3.28 (m, 1H), 3.04 (m, 1H), 2.80 (m, 1H), 2.40 (s, 3H), 2.26 (m, 2H), 1.95 (m, 1H), 1.74 (m, 1H), 1.56 (m, 1H), 1.13 (m, 2H).

Step 2: 2-(1-(2,4-dichloro-3-((1,4-dimethyl-6-(trifluoromethyl)-1H-benzo[d]imidazol-2-yl)methyl)benzoyl)piperidin-4-yl)acetic acid

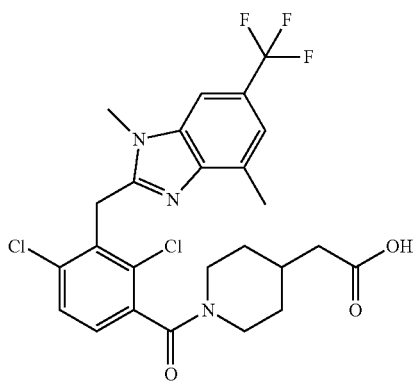

Using a procedure similar to Example A, Step 5, 2-(1-(2,4-dichloro-3-((1,4-dimethyl-6-(trifluoromethyl)-1H-benzo[c]imidazol-2-yl)methyl)benzoyl)piperidin-4-yl)acetic acid (130 mg, 81%) was prepared from methyl 2-(1-(2,4-dichloro-3-((1,4-dimethyl-6-(trifluoromethyl)-1H-benzo[d]imidazol-2-yl)methyl)benzoyl)piperidin-4-yl)acetate (163 mg, 0.0.293 mmol). LC/MS (Method g) $R_t$=1.56 min.; MS m/z: 542 [M+H]$^+$. $^1$H NMR (DMSO-d$_6$, 400 MHz): δ 12.01 (s, 1H), 7.85 (s, 1H), 7.61 (m, 1H), 7.40 and 7.33 (d, J=8.4 Hz, 1H), 7.29 (s, 1H), 4.65 (m, 2H), 4.47 (m, 1H), 3.98 and 3.97 (s, 3H), 3.29 (m, 1H), 3.04 (m, 1H), 2.79 (m, 1H), 2.40 (s, 3H), 2.18 (m, 1H), 2.13 (m, 1H), 1.91 (m, 1H), 1.62 (m, 1H), 1.59 (m, 1H), 1.17 (m, 2H).

Example BV: 3-[4-[2,4-dichloro-3-[[1,4-dimethyl-6-(trifluoromethyl)benzimidazol-2-yl]methyl]benzoyl]piperazin-1-yl]cyclobutanecarboxylic acid

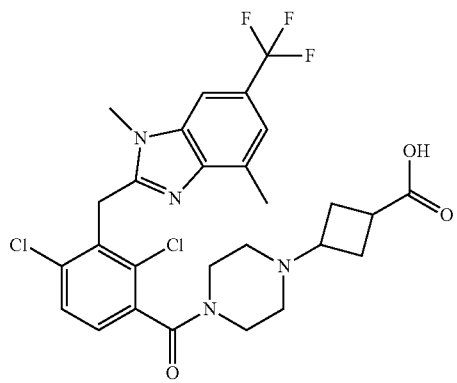 [SMILES: Cc1cc(C(F)(F)F)cc2c1nc(Cc1c(Cl)ccc(C(=O)N3CCN(C4CC(C(=O)O)C4)CC3)c1Cl)n2C]

Step 1: tert-butyl 4-(2,4-dichloro-3-((1,4-dimethyl-6-(trifluoromethyl)-1H-benzo[d]imidazol-2-yl)methyl)benzoyl)piperazine-1-carboxylate

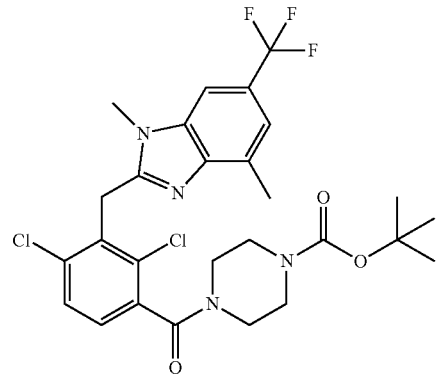 [SMILES: Cc1cc(C(F)(F)F)cc2c1nc(Cc1c(Cl)ccc(C(=O)N3CCN(C(=O)OC(C)(C)C)CC3)c1Cl)n2C]

Using a procedure similar to Example A, Step 6, tert-butyl 4-(2,4-dichloro-3-((1,4-dimethyl-6-(trifluoromethyl)-1H-benzo[c]imidazol-2-yl)methyl)benzoyl)piperazine-1-carboxylate (480 mg, 100%) was prepared from 2,4-dichloro-3-((1,4-dimethyl-6-(trifluoromethyl)-1H-benzo[c]imidazol-2-yl)methyl)benzoic acid (Example BJ, Step 2) (300 mg, 0.719 mmol) and tert-butyl piperazine-1-carboxylate (201 mg, 1.079 mmol). LC/MS (Method h) $R_t$=3.11 min.; MS m/z: 585 [M+H]$^+$.

$^1$H NMR (DMSO-d$_6$, 300 MHz): δ 7.83 (s, 1H), 7.64 (d, J=8.3 Hz, 1H), 7.41 (d, J=8.3 Hz, 1H), 7.27 (s, 1H), 4.65 (d, J=16 Hz, 1H), 4.53 (d, J=16 Hz, 1H), 3.97 (s, 3H), 3.61 (m, 2H), 3.21 (m, 2H), 3.15 (m, 2H), 2.58 (m, 2H), 2.41 (s, 3H), 1.30 (s, 9H).

Step 2: (2,4-dichloro-3-((1,4-dimethyl-6-(trifluoromethyl)-1H-benzo[d]imidazol-2-yl)methyl)phenyl)(piperazin-1-yl)methanone

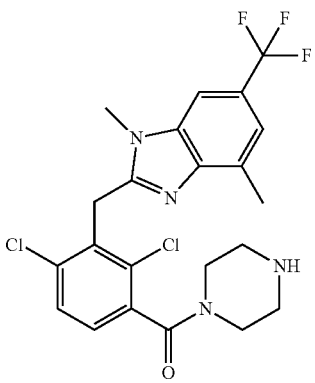 [SMILES: Cc1cc(C(F)(F)F)cc2c1nc(Cc1c(Cl)ccc(C(=O)N3CCNCC3)c1Cl)n2C]

Using a procedure similar to Example O, Step 2, (2,4-dichloro-3-((1,4-dimethyl-6-(trifluoromethyl)-1H-benzo[d]imidazol-2-yl)methyl)phenyl)(piperazin-1-yl)methanone (340 mg, 98%) was prepared from tert-butyl 4-(2,4-dichloro-3-((1,4-dimethyl-6-(trifluoromethyl)-1H-benzo[c]imidazol-2-yl)methyl)benzoyl)piperazine-1-carboxylate (420 mg, 0.717 mmol). LC/MS (Method h) $R_t$=2.46 min.; MS m/z: 485 [M+H]$^+$. $^1$H NMR (DMSO-d$_6$, 300 MHz): δ 7.82 (s, 1H), 7.61 (d, J=8.3 Hz, 1H), 7.37 (d, J=8.3 Hz, 1H), 7.26 (s, 1H), 4.66 (d, J=16 Hz, 1H), 4.53 (d, J=16 Hz, 1H), 3.97 (s, 3H), 3.53 (m, 2H), 3.07 (m, 2H), 2.6770 (m, 2H), 2.60 (m, 2H), 2.39 (s, 3H).

Step 3: methyl 3-(4-(2,4-dichloro-3-((1,4-dimethyl-6-(trifluoromethyl)-1H-benzo[d]imidazol-2-yl)methyl)benzoyl)piperazin-1-yl)cyclobutanecarboxylate

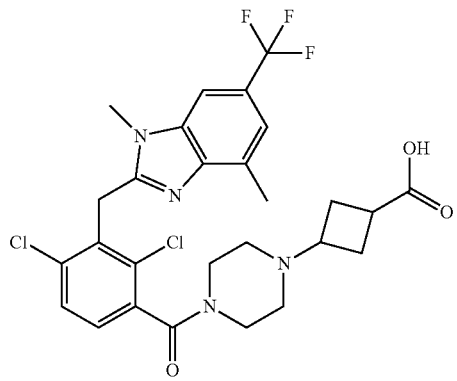 [SMILES: Cc1cc(C(F)(F)F)cc2c1nc(Cc1c(Cl)ccc(C(=O)N3CCN(C4CC(C(=O)O)C4)CC3)c1Cl)n2C]

Using a procedure similar to Example O, Step 3, methyl 3-(4-(2,4-dichloro-3-((1,4-dimethyl-6-(trifluoromethyl)-1H-benzo[c]imidazol-2-yl)methyl)benzoyl)piperazin-1-yl)cyclobutanecarboxylate (105 mg, 65%) was prepared from (2,4-dichloro-3-((1,4-dimethyl-6-(trifluoromethyl)-1H-benzo[d]imidazol-2-yl)methyl)phenyl)(piperazin-1-yl)methanone (130 mg, 0.268 mmol) and methyl 3-oxocyclobutanecarboxylate (85.8 mg, 0.67 mmol). LC/MS (Method h) $R_t$=2.89 min.; MS m/z: 597 [M+H]$^+$. $^1$H NMR (DMSO-d$_6$, 300 MHz): δ 7.82 (s, 1H), 7.62 (d, J=8.1 Hz, 1H), 7.37 (d, J=8.1 Hz, 1H), 7.27 (s, 1H), 4.65 (d, J=16 Hz, 1H), 4.53 (d, J=16 Hz, 1H), 3.97 (s, 3H), 3.65 (m, 1H), 3.58 (s, 3H), 3.14 (m, 2H), 2.82 (m, 1H), 2.65 (m, 1H), 2.39 (s, 3H), 2.32 (m, 1H), 2.20 (m, 6H), 1.93 (m, 2H).

Step 4: 3-[4-[2,4-dichloro-3-[[1,4-dimethyl-6-(trifluoromethyl)benzimidazol-2-yl]methyl]benzoyl]piperazin-1-yl]cyclobutanecarboxylic acid

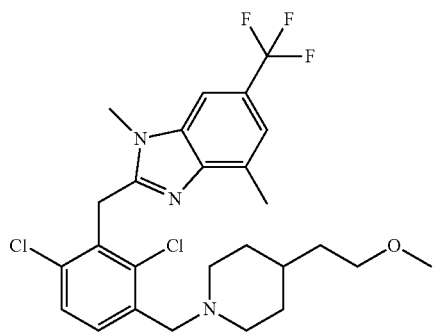 [SMILES: COCCC1CCN(Cc2ccc(Cl)c(Cc3nc4c(C)cc(C(F)(F)F)cc4n3C)c2Cl)CC1]

Using a procedure similar to Example A, Step 5, 3-[4-[2,4-dichloro-3-[[1,4-dimethyl-6-(trifluoromethyl)benzimidazol-2-yl]methyl]benzoyl]piperazin-1-yl]cyclobutanecarboxylic acid (65 mg, 63%) was prepared from methyl 3-(4-(2,4-dichloro-3-((1,4-dimethyl-6-(trifluoromethyl)-1H-benzo[c]imidazol-2-yl)methyl)benzoyl)piperazin-1-yl)cyclobutanecarboxylate (105 mg, 0.176 mmol).

LC/MS (Method g) $R_t$=1.16 min.; MS m/z: 583 [M+H]$^+$. $^1$H NMR (DMSO-d$_6$, 300 MHz,): δ 7.82 (s, 1H), 7.61 (d, J=8.3 Hz, 1H), 7.37 (d, J=8.3 Hz, 1H), 7.27 (s, 1H), 4.65 (d, J=16 Hz, 1H), 4.53 (d, J=16 Hz, 1H), 3.96 (s, 3H), 3.61 (m, 2H), 3.13 (m, 2H), 2.40 (s, 3H), 2.18 (m, 6H), 1.97 (m, 2H), 1.81 (m, 2H)

Example BW: 2-[[2,6-dichloro-3-[[4-(2-methoxyethyl)-1-piperidyl]methyl]phenyl]methyl]-1,4-dimethyl-6-(trifluoromethyl)benzimidazole Step 1: (2,4-dichloro-3-((1,4-dimethyl-6-(trifluoromethyl)-1H-benzo[d]imidazol-2-yl)methyl)phenyl)methanol

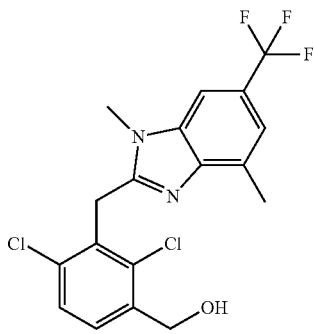 [SMILES: Cc1cc(C(F)(F)F)cc2c1nc(Cc1c(Cl)ccc(CO)c1Cl)n2C]

To a solution of methyl 2,4-dichloro-3-((1,4-dimethyl-6-(trifluoromethyl)-1H-benzo[c]imidazol-2-yl)methyl)benzoate (Example BJ, Step 1) (2.45 g, 5.68 mmol) in THF (100 mL) was added by portion lithium borohydride (0.371 g, 17.04 mmol) and the mixture was stirred at room temperature overnight. More lithium borohydride (0.185 g, 8.5 mmol) was added and the reaction was stirred at 50° C. for 3 hours. The mixture was cooled to 0° C. and quenched slowly by addition of a 1N HCl aqueous solution. A white precipitate was obtained. The THF was concentrated and the precipitate was filtered, washed with water and dried under vacuum to give (2,4-dichloro-3-((1,4-dimethyl-6-(trifluoromethyl)-1H-benzo[d]imidazol-2-yl)methyl)phenyl)methanol (1.83 g, 80%) as a white powder.

LC/MS (Method h) $R_t$=2.66 min.; MS m/z: 403 [M+H]$^+$.
$^1$H NMR (DMSO-d$_6$, 300 MHz): δ 7.82 (s, 1H), 7.55 (s, 2H), 7.26 (s, 1H), 5.54 (t, J=5.6 Hz, 1H), 4.53-4.60 (m, 4H), 3.97 (s, 3H), 2.41 (s, 3H).

Step 2: 2,4-dichloro-3-((1,4-dimethyl-6-(trifluoromethyl)-1H-benzo[d]imidazol-2-yl)methyl)benzyl methanesulfonate

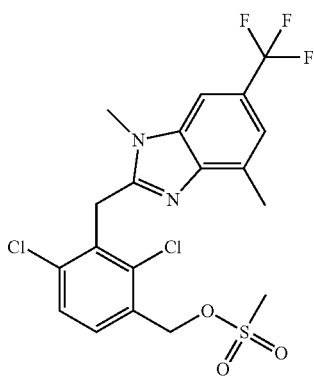 [SMILES: Cc1cc(C(F)(F)F)cc2c1nc(Cc1c(Cl)ccc(COS(C)(=O)=O)c1Cl)n2C]

To a suspension of (2,4-dichloro-3-((1,4-dimethyl-6-(trifluoromethyl)-1H-benzo[d]imidazol-2-yl)methyl)phenyl)methanol (1.820 g, 4.51 mmol) in DCM (150 mL) was added triethylamine (0.913 g, 9.03 mmol) and methanesulfonyl chloride (0.776 g, 6.77 mmol) and the mixture was stirred at room temperature for 2 hours. The reaction mixture was diluted with DCM. The obtained organic layer was washed successively with water and a 1N HCl aqueous solution. The obtained organic layer was dried over magnesium sulfate, filtered and concentrated under reduced pressure to give 2,4-dichloro-3-((1,4-dimethyl-6-(trifluoromethyl)-1H-benzo[d]imidazol-2-yl)methyl)benzyl methanesulfonate (2.1 g, 97%) as a white powder. LC/MS (Method h) $R_t$=2.92 min.; MS m/z: 481 [M+H]$^+$. $^1$H NMR (DMSO-d$_6$, 300 MHz): δ 7.83 (s, 1H), 7.64 (m, 2H), 7.26 (s, 1H), 5.37 (s, 2H), 4.62 (s, 2H), 3.98 (s, 3H), 3.28 (s, 3H), 2.40 ppm (s, 3H).

Step 3: 2-[[2,6-dichloro-3-[[4-(2-methoxyethyl)-1-piperidyl]methyl]phenyl]methyl]-1,4-dimethyl-6-(trifluoromethyl)benzimidazole To a solution of 4-(2-methoxyethyl)piperidine hydrochloride (52 mg, 0.29 mmol) in DMF (0.5 mL) was added potassium carbonate (40 mg, 0.29 mmol) and 2,4-dichloro-3-((1,4-dimethyl-6-(trifluoromethyl)-1H-benzo[c]imidazol-2-yl)methyl)benzyl methanesulfonate (70 mg, 0.145 mmol) in solution in DMF (1.5 mL). The mixture was stirred at 60° C. for 18 hours. Water was added and the mixture was extracted with DCM. The organic phase was dried by filtration through a hydrophobic membrane and concentrated. The residue was purified by preparative LCMS to give 2-[[2,6-dichloro-3-[[4-(2-methoxyethyl)-1-piperidyl]methyl]phenyl]methyl]-1,4-dimethyl-6-(trifluoromethyl)benzimidazole (52 mg, 68%). LC/MS (HPLC) $R_t$=1.24 min.; MS m/z: 528 [M+H]$^+$.

$^1$H NMR (DMSO-d$_6$, 400 MHz): δ 7.79 (s, 1H), 7.50 (d, J=8 Hz, 1H), 7.45 (d, J=8 Hz, 1H), 7.23 (s, 1H), 4.58 (s, 2H), 3.96 (s, 3H), 3.54 (s, 2H), 3.32 (t, J=6 Hz, 2H), 3.21 (s, 3H), 2.80 (m, 2H), 2.40 (s, 3H), 2.00 (m, 2H), 1.60 (m, 2H), 1.42 (m, 2H), 1.32 (m, 1H), 1.10 (m, 2H)

TABLE BW

The following examples were prepared from 2,4-dichloro-3-((1,4-dimethyl-6-(trifluoromethyl)-1H-benzo[d]imidazol-2-yl)methyl)benzyl methanesulfonate using the same procedure with the appropriate amine.

| Example | Structure | Starting amine | $R_t$ min (Method g) | m/z ESI+ (M + H)+ |
|---|---|---|---|---|
| BW-1 | 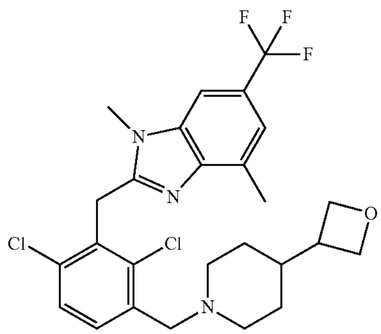 [SMILES: Cc1cc(C(F)(F)F)cc2c1nc(Cc1c(Cl)ccc(CN3CCC(C4COC4)CC3)c1Cl)n2C] | | 1.18 | 526 |
| BW-2 | 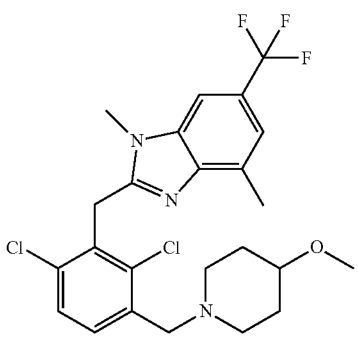 [SMILES: COC1CCN(Cc2ccc(Cl)c(Cc3nc4c(C)cc(C(F)(F)F)cc4n3C)c2Cl)CC1] | | 1.20 | 500 |
| BW-3 | 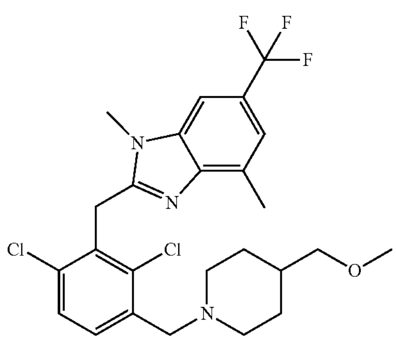 [SMILES: COCC1CCN(Cc2ccc(Cl)c(Cc3nc4c(C)cc(C(F)(F)F)cc4n3C)c2Cl)CC1] | | 1.22 | 514 |
| BW-4 | 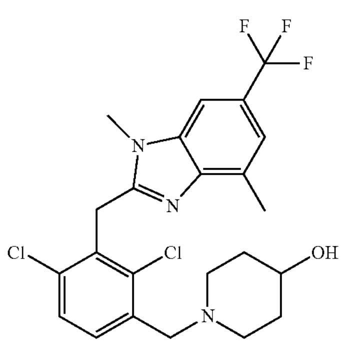 [SMILES: Cc1cc(C(F)(F)F)cc2c1nc(Cc1c(Cl)ccc(CN3CCC(O)CC3)c1Cl)n2C] | | 1.12 | 486 |

TABLE BW-continued
The following examples were prepared from 2,4-dichloro-3-((1,4-dimethyl-6-(trifluoromethyl)-1H-benzo[d]imidazol-2-yl)methyl)benzyl methanesulfonate using the same procedure with the appropriate amine.
| Example | Structure | Starting amine | R$_t$ min (Method g) | m/z ESI+ (M + H)+ |
|---|---|---|---|---|
| BW-5 | 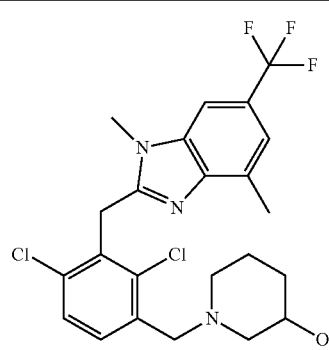 | 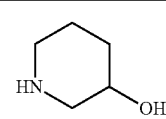 | 1.14 | 486 |
| BW-6 | 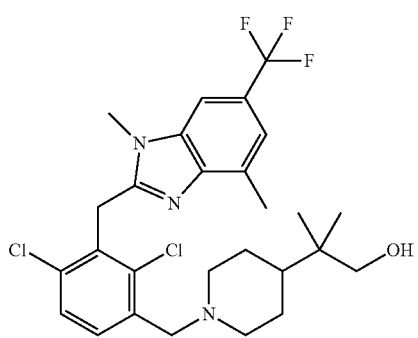 [SMILES: Cc1cc(C(F)(F)F)cc2c1nc(Cc1c(Cl)ccc(CN3CCC(C(C)(C)CO)CC3)c1Cl)n2C] | 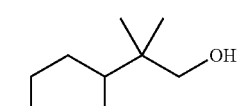 | 1.23 | 542 |
| BW-7 | 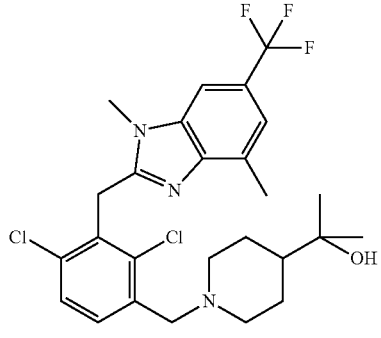 [SMILES: Cc1cc(C(F)(F)F)cc2c1nc(Cc1c(Cl)ccc(CN3CCC(C(C)(C)O)CC3)c1Cl)n2C] | 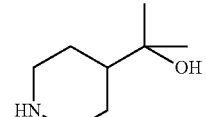 | 1.19 | 528 |
| BW-8 | 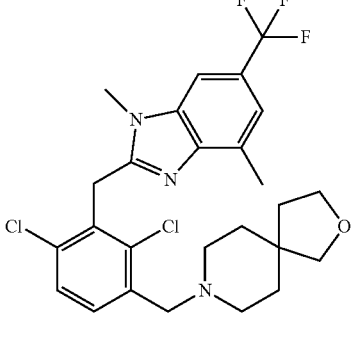 | 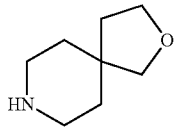 | 1.19 | 526 |

TABLE BW-continued

The following examples were prepared from 2,4-dichloro-3-((1,4-dimethyl-6-(trifluoromethyl)-1H-benzo[d]imidazol-2-yl)methyl)benzyl methanesulfonate using the same procedure with the appropriate amine.

| Example | Structure | Starting amine | $R_t$ min (Method g) | m/z ESI+ (M + H)+ |
|---|---|---|---|---|
| BW-9 | 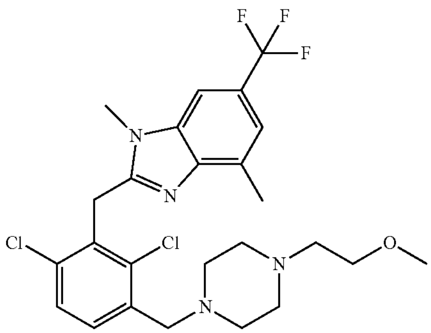 [SMILES: COCCN1CCN(Cc2ccc(Cl)c(Cc3nc4c(C)cc(C(F)(F)F)cc4n3C)c2Cl)CC1] | | 1.23 | 529 |
| BW-10 | 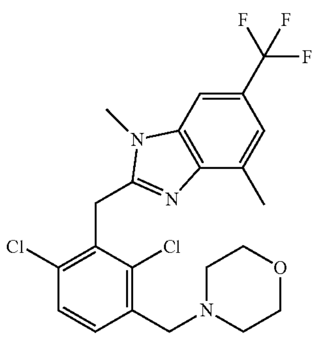 [SMILES: Cc1cc(C(F)(F)F)cc2c1nc(Cc1c(Cl)ccc(CN3CCOCC3)c1Cl)n2C] | | 1.28 | 472 |
| BW-11 | 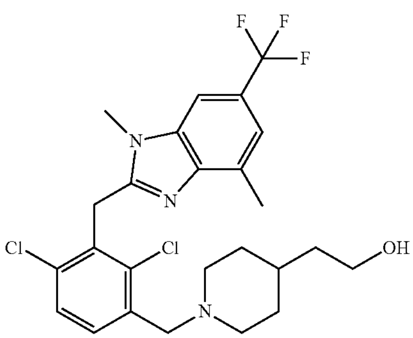 [SMILES: Cc1cc(C(F)(F)F)cc2c1nc(Cc1c(Cl)ccc(CN3CCC(CCO)CC3)c1Cl)n2C] | | 1.15 | 514 |
| BW-12 | 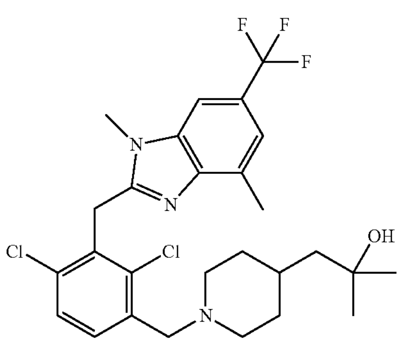 [SMILES: Cc1cc(C(F)(F)F)cc2c1nc(Cc1c(Cl)ccc(CN3CCC(CC(C)(C)O)CC3)c1Cl)n2C] | | 1.22 | 542 |

TABLE BW-continued

*The following examples were prepared from 2,4-dichloro-3-((1,4-dimethyl-6-(trifluoromethyl)-1H-benzo[d]imidazol-2-yl)methyl)benzyl methanesulfonate using the same procedure with the appropriate amine.*

| Example | Structure | Starting amine | $R_t$ min (Method g) | m/z ESI+ (M + H)+ |
|---------|-----------|----------------|----------------------|-------------------|
| BW-13 | 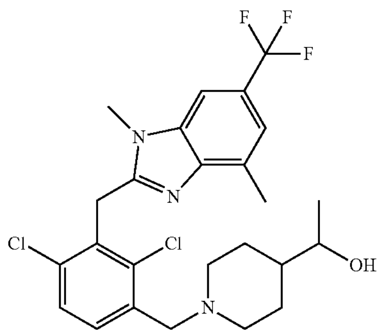 [SMILES: Cc1cc(C(F)(F)F)cc2c1nc(Cc1c(Cl)ccc(CN3CCC(C(C)O)CC3)c1Cl)n2C] | | 1.16 | 514 |
| BW-14 | 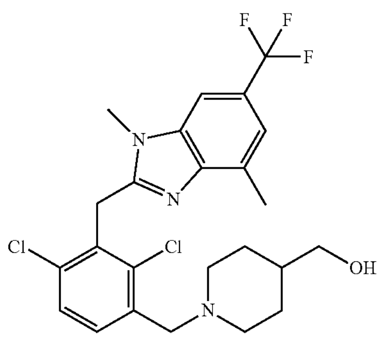 [SMILES: Cc1cc(C(F)(F)F)cc2c1nc(Cc1c(Cl)ccc(CN3CCC(CO)CC3)c1Cl)n2C] | | 1.14 | 500 |
| BW-15 | 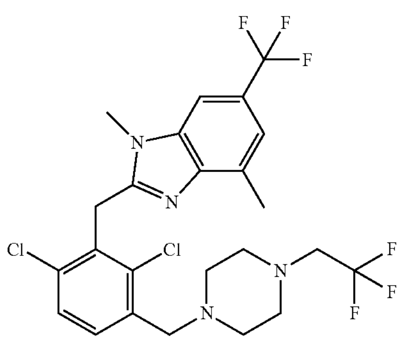 [SMILES: Cc1cc(C(F)(F)F)cc2c1nc(Cc1c(Cl)ccc(CN3CCN(CC(F)(F)F)CC3)c1Cl)n2C] | | 1.45 | 553 |
| BW-16 | 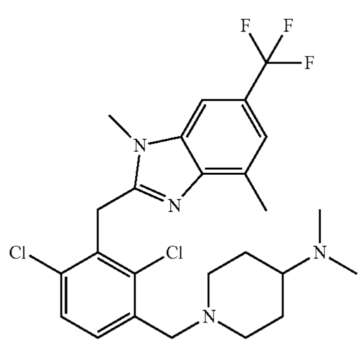 [SMILES: Cc1cc(C(F)(F)F)cc2c1nc(Cc1c(Cl)ccc(CN3CCC(N(C)C)CC3)c1Cl)n2C] | | 0.97 | 513 |

TABLE BW-continued

The following examples were prepared from 2,4-dichloro-3-((1,4-dimethyl-6-(trifluoromethyl)-1H-benzo[d]imidazol-2-yl)methyl)benzyl methanesulfonate using the same procedure with the appropriate amine.

| Example | Structure | Starting amine | $R_t$ min (Method g) | m/z ESI+ (M + H)+ |
|---|---|---|---|---|
| BW-17 | 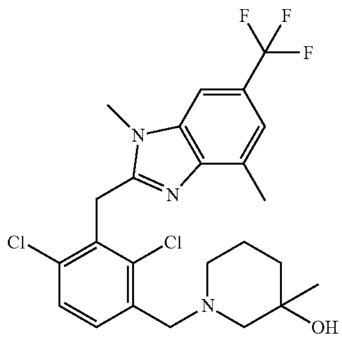 [SMILES: Cc1cc(C(F)(F)F)cc2c1nc(Cc1c(Cl)ccc(CN3CCCC(C)(O)C3)c1Cl)n2C] | | 1.18 | 500 |
| BW-18 | 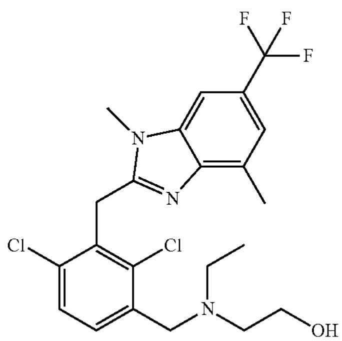 [SMILES: CCN(CCO)Cc1ccc(Cl)c(Cc2nc3c(C)cc(C(F)(F)F)cc3n2C)c1Cl] | | 1.14 | 474 |

Example BX: 4-(2,4-dichloro-3-((1,4-dimethyl-6-(trifluoromethyl)-1H-benzo[d]imidazol-2-yl)methyl)benzyl)morpholin-3-one

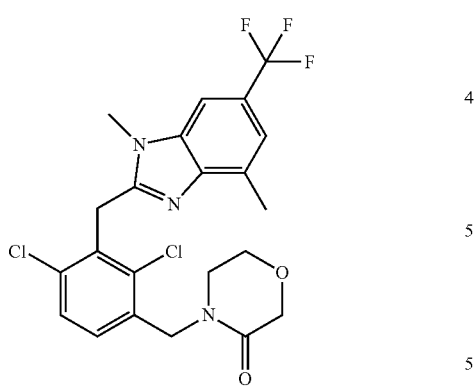

To a solution of morpholin-3-one (42.0 mg, 0.416 mmol) in DMF (3 mL) was added sodium hydride (19.11 mg, 0.478 mmol) and the reaction was stirred at room temperature during 15 minutes. 2,4-dichloro-3-((1,4-dimethyl-6-(trifluoromethyl)-1H-benzo[d]imidazol-2-yl)methyl)benzyl methanesulfonate (Example BW, Step 2) (100 mg, 0.208 mmol) was added and the reaction mixture was stirred at room temperature for 1 hour then water and EtOAc was added. The organic layer was decanted, washed with brine; dried over magnesium sulfate and concentrated. The residue was purified by column chromatography on silica gel (eluting with 40-70% EtOAc in cyclohexane) to give 4-(2,4-dichloro-3-((1,4-dimethyl-6-(trifluoromethyl)-1H-benzo[d]imidazol-2-yl)methyl)benzyl)morpholin-3-one (20 mg, 19%) as a white solid. LC/MS (HPLC) $R_t$=1.62 min.; MS m/z: 486 [M+H]+.

$^1$H NMR (DMSO-$d_6$, 400 MHz): δ 7.82 (s, 1H), 7.55 (d, J=8.4 Hz, 1H), 7.26 (m, 2H), 4.64 (s, 2H), 4.60 (s, 2H), 4.16 (s, 2H), 3.97 (s, 3H), 3.89 (m, 2H), 3.34 (m, 2H), 2.41 (s, 3H).

Example BY: 1-(2,4-dichloro-3-((1,4-dimethyl-5-(trifluoromethyl)-1H-benzo[d]imidazol-2-yl)methyl)benzoyl)piperidine-4-carboxylic acid

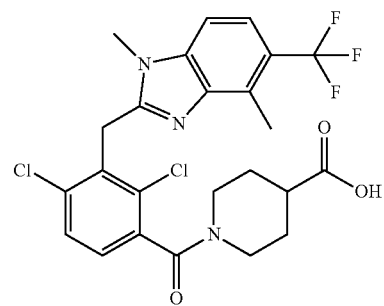 [SMILES: Cc1c(C(F)(F)F)ccc2c1nc(Cc1c(Cl)ccc(C(=O)N3CCC(C(=O)O)CC3)c1Cl)n2C]

Step 1: methyl 2,4-dichloro-3-((1,4-dimethyl-5-(trifluoromethyl)-1H-benzo[d]imidazol-2-yl)methyl)benzoate

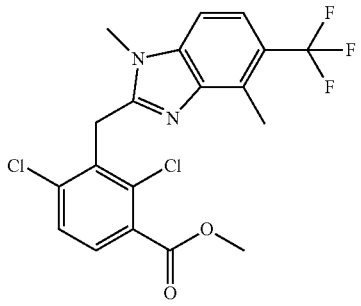 [SMILES: COC(=O)c1ccc(Cl)c(Cc2nc3c(C)c(C(F)(F)F)ccc3n2C)c1Cl]

Using a procedure similar to Example BJ, Step 1, methyl 2,4-dichloro-3-((1,4-dimethyl-5-(trifluoromethyl)-1H-benzo[c]imidazol-2-yl)methyl)benzoate (1.2 g, 61%) was prepared from N1,3-dimethyl-4-(trifluoromethyl)benzene-1,2-diamine (Preparation #30) (880 mg, 4.31 mmol) and 2-(2,6-dichloro-3-(methoxycarbonyl)phenyl)acetic acid (Preparation #2) (1.13 g, 4.31 mmol). LC/MS (Method i) $R_t$=2.50 min.; MS m/z: 431 [M+H]$^+$.

$^1$H NMR (DMSO-d$_6$, 300 MHz): δ 7.6 (d, J=9 Hz, 1H), 7.68 (d, J=9 Hz, 1H), 7.54 (d, J=9 Hz, 1H), 7.50 (d, J=9 Hz, 1H), 4.63 (s, 2H), 3.95 (s, 3H), 3.87 (s, 3H), 2.49 (s, 3H).

Step 2: 2,4-dichloro-3-((1,4-dimethyl-5-(trifluoromethyl)-1H-benzo[d]imidazol-2-yl)methyl)benzoic acid

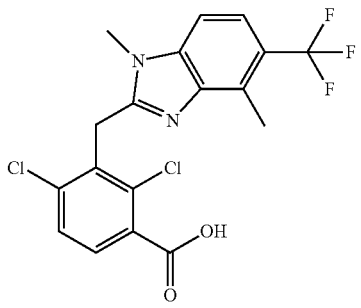

Using a procedure similar to Example A, Step 5, 2,4-dichloro-3-((1,4-dimethyl-5-(trifluoromethyl)-1H-benzo[d]imidazol-2-yl)methyl)benzoic acid (1.09 g, 98%) was prepared from methyl 2,4-dichloro-3-((1,4-dimethyl-5-(trifluoromethyl)-1H-benzo[d]imidazol-2-yl)methyl)benzoate (1.1 g, 2.55 mmol).

LC/MS (Method i) $R_t$=2.08 min.; MS m/z: 417 [M+H]$^+$.

$^1$H NMR (DMSO-d$_6$, 300 MHz): δ 13.63 (broad, 1H), 7.73 (d, J=9 Hz, 1H), 7.63 (d, J=9 Hz, 1H), 7.54 (d, J=9 Hz, 1H), 7.50 (d, J=9 Hz, 1H), 4.62 (s, 2H), 3.95 (s, 3H), 2.50 (s, 3H).

Step 3: methyl 1-(2,4-dichloro-3-((1,4-dimethyl-5-(trifluoromethyl)-1H-benzo[d]imidazol-2-yl)methyl)benzoyl)piperidine-4-carboxylate

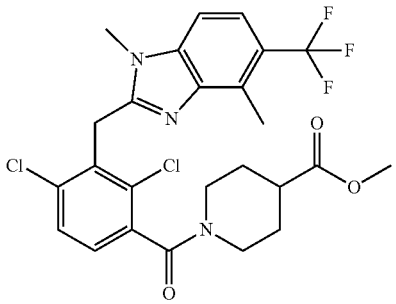 [SMILES: COC(=O)C1CCN(C(=O)c2ccc(Cl)c(Cc3nc4c(C)c(C(F)(F)F)ccc4n3C)c2Cl)CC1]

Using a procedure similar to Example A1, methyl 1-(2,4-dichloro-3-((1,4-dimethyl-5-(trifluoromethyl)-1H-benzo[d]imidazol-2-yl)methyl)benzoyl)piperidine-4-carboxylate (255 mg, 70%) was prepared from 2,4-dichloro-3-((1,4-dimethyl-5-(trifluoromethyl)-1H-benzo[d]imidazol-2-yl)methyl)benzoic acid (200 mg, 0.479 mmol) and methyl piperidine-4-carboxylate hydrochloride (103 mg, 0.575 mmol). LC/MS (Method i) $R_t$=2.34 min.; MS m/z: 542 [M+H]$^+$. $^1$H NMR (DMSO-d$_6$, 300 MHz): δ 7.62 (d, J=8.3 Hz, 1H), 7.56 (d, J=9 Hz, 1H), 7.50 (d, J=9 Hz, 1H), 7.43 and 7.35 (d, J=8.3 Hz, 1H), 4.60 (m, 2H), 4.36 (m, 1H), 3.94 (m, 3H), 3.62 and 3.57 (s, 3H), 3.30 (m., 1H), 3.10 (m, 1H), 2.94 (m, 1H), 2.69 (m, 1H), 2.50 (m, 3H), 1.93 (m, 1H), 1.77 (m, 1H), 1.38-1.66 (m, 2H)

Step 4: 1-(2,4-dichloro-3-((1,4-dimethyl-5-(trifluoromethyl)-1H-benzo[d]imidazol-2-yl)methyl)benzoyl)piperidine-4-carboxylic acid

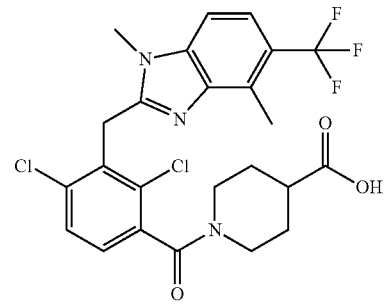 [SMILES: Cc1c(C(F)(F)F)ccc2c1nc(Cc1c(Cl)ccc(C(=O)N3CCC(C(=O)O)CC3)c1Cl)n2C]

Using a procedure similar to Example A, Step 5, 1-(2,4-dichloro-3-((1,4-dimethyl-5-(trifluoromethyl)-1H-benzo[d]imidazol-2-yl)methyl)benzoyl)piperidine-4-carboxylic acid (80 mg, 32%) was prepared from methyl 1-(2,4-dichloro-3-((1,4-dimethyl-5-(trifluoromethyl)-1H-benzo[c]imidazol-2-yl)methyl)benzoyl)piperidine-4-carboxylate (254 mg, 0.468 mmol). LC/MS (Method g) $R_t$=1.55 min.; MS m/z: 528 [M+H]$^+$. $^1$H NMR (DMSO-d$_6$, 400 MHz): δ 12.31 (broad, 1H), 7.61 (m, 1H), 7.52 (d, J=9 Hz, 1H), 7.50 (d, J=9 Hz, 1H), 7.42 and 7.35 (d, J=8 Hz, 1H), 4.59 (m, 2H), 4.35 (m, 1H), 3.94 (m, 3H), 3.21 (m, 1H), 3.09 (m, 1H), 2.96 (m, 1H), 2.54 (m, 1H), 2.50 (m, 3H), 1.91 (m, 1H), 1.74 (m, 1H), 1.50 (m, 2H).

Example BZ: 2-(1-(2,4-dichloro-3-((1,4-dimethyl-5-(trifluoromethyl)-1H-benzo[d]imidazol-2-yl)methyl)benzoyl)piperidin-4-yl)acetic acid

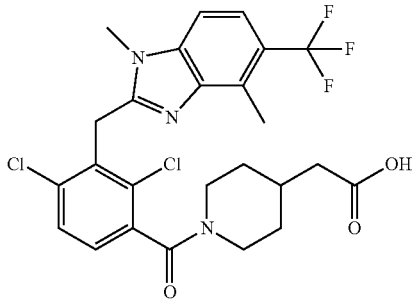 [SMILES: Cc1c(C(F)(F)F)ccc2c1nc(Cc1c(Cl)ccc(C(=O)N3CCC(CC(=O)O)CC3)c1Cl)n2C]

Step 1: methyl 2-(1-(2,4-dichloro-3-((1,4-dimethyl-5-(trifluoromethyl)-1H-benzo[d]imidazol-2-yl)methyl)benzoyl)piperidin-4-yl)acetate

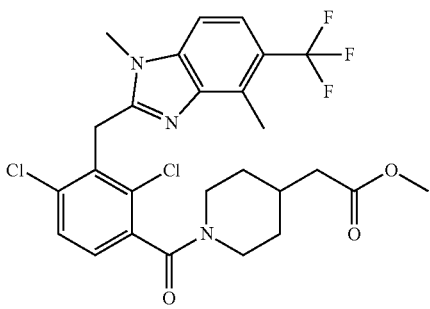 [SMILES: COC(=O)CC1CCN(C(=O)c2ccc(Cl)c(Cc3nc4c(C)c(C(F)(F)F)ccc4n3C)c2Cl)CC1]

Using a procedure similar to Example A1, methyl 2-(1-(2,4-dichloro-3-((1,4-dimethyl-5-(trifluoromethyl)-1H-benzo[d]imidazol-2-yl)methyl)benzoyl)piperidin-4-yl)acetate (275 mg, 100%) was prepared from 2,4-dichloro-3-((1,4-dimethyl-5-(trifluoromethyl)-1H-benzo[c]imidazol-2-yl)methyl)benzoic acid (Example BY, Step 2) (200 mg, 0.479 mmol) and methyl (4-piperidyl)acetate hydrochloride (111 mg, 0.57 mmol). LC/MS (Method i) R$_t$=2.39 min.; MS m/z: 556 [M+H]$^+$. $^1$H NMR (DMSO-d$_6$, 300 MHz): δ 7.61 (m, 1H), 7.55 (d, J=9 Hz, 1H), 7.51 (d, J=9 Hz, 1H), 7.40 and 7.33 (d, J=8.3 Hz, 1H), 4.62 (m, 2H), 4.46 (m, 1H), 3.94 (m, 3H), 3.59 and 3.55 (s, 3H), 3.28 (m, 1H), 3.06 (m, 1H), 2.78 (m, 1H), 2.47 (m, 3H), 2.25 (m, 2H), 1.94 (m, 1H), 1.75 (m, 1H), 1.57 (m, 1H), 1.14 (m, 2H).

Step 2: 2-(1-(2,4-dichloro-3-((1,4-dimethyl-5-(trifluoromethyl)-1H-benzo[d]imidazol-2-yl)methyl)benzoyl)piperidin-4-yl)acetic acid

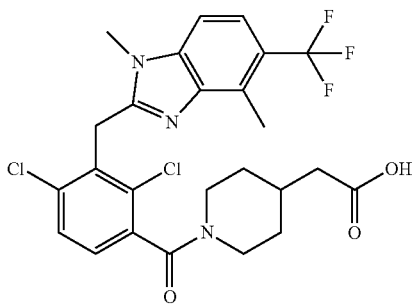 [SMILES: Cc1c(C(F)(F)F)ccc2c1nc(Cc1c(Cl)ccc(C(=O)N3CCC(CC(=O)O)CC3)c1Cl)n2C]

Using a procedure similar to Example A, Step 5, 2-(1-(2,4-dichloro-3-((1,4-dimethyl-5-(trifluoromethyl)-1H-benzo[c]imidazol-2-yl)methyl)benzoyl)piperidin-4-yl)acetic acid (210 mg, 76%) was prepared from methyl 2-(1-(2,4-dichloro-3-((1,4-dimethyl-5-(trifluoromethyl)-1H-benzo[d]imidazol-2-yl)methyl)benzoyl)piperidin-4-yl)acetate (272 mg, 0.46 mmol). LC/MS (Method g) R$_t$=1.57 min.; MS m/z: 542 [M+H]$^+$. $^1$H NMR (DMSO-d$_6$, 400 MHz): δ 12.07 (broad, 1H), 7.61 (m, 1H), 7.54 (d, J=9 Hz, 1H), 7.50 (d, J=9 Hz, 1H), 7.40 and 7.32 (d, J=8.1 Hz, 1H), 4.4.62 (m, 2H), 4.47 (m, 1H), 3.94 (m, 3H), 3.30 (m, 1H), 3.04 (m, 1H), 2.79 (m, 1H), 2.48, 2.47 (s, 3H), 2.10 (m, 2H), 1.93 (m, 1H), 1.77 (m, 1H), 1.57 (m, 1H), 1.10 (m, 2H).

Example CA: (2,4-dichloro-3-((1,4-dimethyl-5-(trifluoromethyl)-1H-benzo[d]imidazol-2-yl)methyl)phenyl)(morpholino)methanone

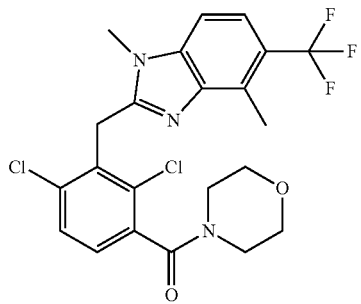 [SMILES: Cc1c(C(F)(F)F)ccc2c1nc(Cc1c(Cl)ccc(C(=O)N3CCOCC3)c1Cl)n2C]

Using a procedure similar to Example A1, (2,4-dichloro-3-((1,4-dimethyl-5-(trifluoromethyl)-1H-benzo[d]imidazol-2-yl)methyl)phenyl)(morpholino)methanone (90 mg, 76%) was prepared from 2,4-dichloro-3-((1,4-dimethyl-5-(trifluoromethyl)-1H-benzo[d]imidazol-2-yl)methyl)benzoic acid (Example BY, Step 2) (200 mg, 0.479 mmol) and morpholine (31 mg, 0.360 mmol). LC/MS (Method g) R$_t$=1.63 min.; MS m/z: 486 [M+H]$^+$. $^1$H NMR (DMSO-d$_6$, 400 MHz): δ=7.63 (d, J=8.1 Hz, 1H), 7.55 (d, J=8 Hz, 1H), 7.50 (d, J=8 Hz, 1H), 7.41 (d, J=8.1 Hz, 1H), 4.64 (d, J=16 Hz, 1H), 4.56 (d, J=16 Hz, 1H), 3.94 (s, 3H), 3.64 (m, 4H), 3.53 (m, 2H), 3.17 (m, 2H), 2.48 (s, 3H).

Example CB: (3-((5-bromo-1,4-dimethyl-1H-benzo[d]imidazol-2-yl)methyl)-2,4-dichlorophenyl)(morpholino)methanone

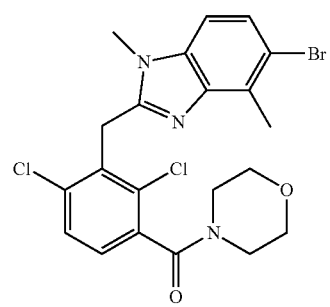 [SMILES: Cc1c(Br)ccc2c1nc(Cc1c(Cl)ccc(C(=O)N3CCOCC3)c1Cl)n2C]

Step 1: methyl 3-((5-bromo-1,4-dimethyl-1H-benzo[d]imidazol-2-yl)methyl)-2,4-dichlorobenzoate

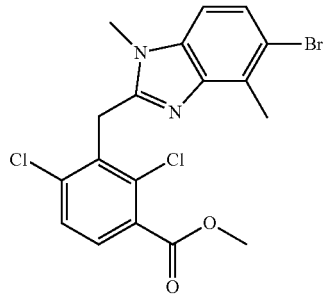 [SMILES: COC(=O)c1ccc(Cl)c(Cc2nc3c(C)c(Br)ccc3n2C)c1Cl]

Using a procedure similar to Example BJ, Step 1, methyl 3-((5-bromo-1,4-dimethyl-1H-benzo[d]imidazol-2-yl)methyl)-2,4-dichlorobenzoate (508 mg, 67%) was prepared from 4-bromo-N1,3-dimethylbenzene-1,2-diamine (Preparation #31) (350 mg, 1.63 mmol) and 2-(2,6-dichloro-3-(methoxycarbonyl)phenyl)acetic acid (Preparation #2) (428 mg, 1.63 mmol). LC/MS (Method h) $R_t$=2.98 min.; MS m/z: 441 [M+H]$^+$. $^1$H NMR (DMSO-d$_6$, 300 MHz): δ 7.75 (d, J=9 Hz, 1H), 7.66 (d, J=9 Hz, 1H), 7.38 (d, J=9 Hz, 1H), 7.34 (d, J=9 Hz, 1H), 4.58 (s, 2H), 3.88 (s, 3H), 3.86 (s, 3H), 2.37 (s, 3H).

Step 2: 3-((5-bromo-1,4-dimethyl-1H-benzo[d]imidazol-2-yl)methyl)-2,4-dichlorobenzoic acid

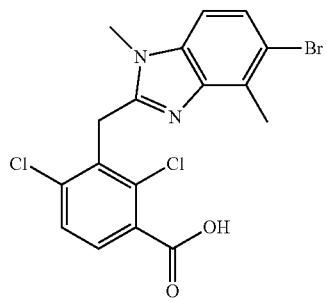 [SMILES: Cc1c(Br)ccc2c1nc(Cc1c(Cl)ccc(C(=O)O)c1Cl)n2C]

Using a procedure similar to Example A, Step 5, 3-((5-bromo-1,4-dimethyl-1H-benzo[d]imidazol-2-yl)methyl)-2,4-dichlorobenzoic acid (450 mg, 93%) was prepared from methyl 3-((5-bromo-1,4-dimethyl-1H-benzo[d]imidazol-2-yl)methyl)-2,4-dichlorobenzoate (500 mg, 1.13 mmol).

LC/MS (Method h) $R_t$=2.14 min.; MS m/z: 427 [M+H]$^+$. $^1$H NMR (DMSO-d$_6$, 300 MHz): δ 7.71 (d, J=9 Hz, 1H), 7.63 (d, J=9 Hz, 1H), 7.37 (d, J=9 Hz, 1H), 7.34 (d, J=9 Hz, 1H), 4.57 (s, 2H), 3.88 (s, 3H), 2.37 (s, 3H).

Step 3: (3-((5-bromo-1,4-dimethyl-1H-benzo[d]imidazol-2-yl)methyl)-2,4-dichlorophenyl)(morpholino)methanone

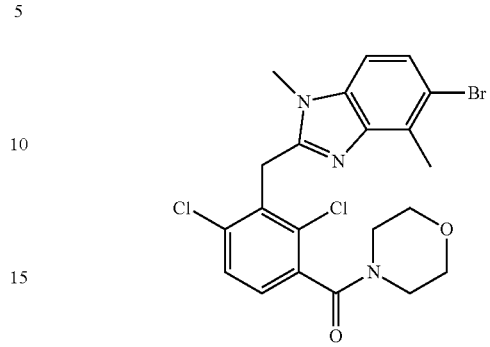

Using a procedure similar to Example A1, (3-((5-bromo-1,4-dimethyl-1H-benzo[d]imidazol-2-yl)methyl)-2,4-dichlorophenyl)(morpholino)methanone (465 mg, 84%) was prepared from 3-((5-bromo-1,4-dimethyl-1H-benzo[d]imidazol-2-yl)methyl)-2,4-dichlorobenzoic acid (436 mg, 4.02 mmol) and morpholine (133 mg, 1.53 mmol). LC/MS (Method g) $R_t$=1.53 min.; MS m/z: 496 [M+H]$^+$. $^1$H NMR (DMSO-d$_6$, 400 MHz): δ 7.63 (d, J=8.1 Hz, 1H), 7.40 (m, 3H), 4.63 (d, J=16 Hz, 1H), 4.55 (d, J=16 Hz, 1H), 3.89 (s, 3H), 3.65 (m, 4H), 3.52 (m, 2H), 3.17 (m, 2H), 2.38 (s, 3H).

Example CC: 2-(2,6-dichloro-3-(morpholine-4-carbonyl)benzyl)-1,4-dimethyl-1H-benzo[d]imidazole-5-carbonitrile

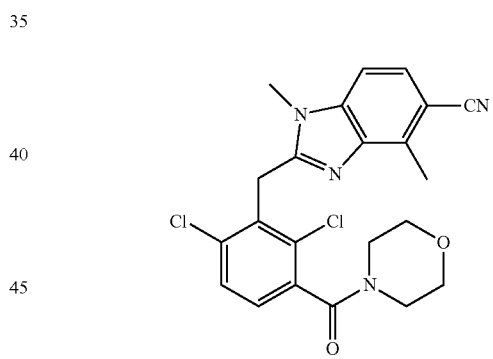

In a microwave vial were put (3-((5-bromo-1,4-dimethyl-1H-benzo[d]imidazol-2-yl)methyl)-2,4-dichlorophenyl)(morpholino)methanone (Example CB, Step 3) (140 mg, 0.28 mmol), zinc cyanide (24.8 mg, 0.211 mmol) and Pd(Ph$_3$P)$_4$ (32.5 mg, 0.028 mmol) in DMF (800 μL) and the reaction mixture was stirred at 120° C. for 60 minutes under microwave irradiation. The reaction mixture was diluted with EtOAc and filtered. Water was added on the filtrate. The layers were separated and the aqueous one was washed with EtOAc. The organic layers was dried over magnesium sulfate, filtered and concentrated under reduced pressure. The residue was purified by column chromatography on silica gel (eluting with 50-60% EtOAc in cyclohexane) to give 2-(2,6-dichloro-3-(morpholine-4-carbonyl)benzyl)-1,4-dimethyl-1H-benzo[c]imidazole-5-carbonitrile (30 mg, 23%). LC/MS (Method g) $R_t$=1.32 min.; MS m/z: 443 [M+H]$^+$. $^1$H NMR (DMSO-d$_6$, 400 MHz): δ 7.63 (d, J=8.1 Hz, 1H), 7.56 (m, 2H), 7.41 (d, J=8.1 Hz, 1H), 4.64 (d, J=16

Hz, 1H), 4.56 (d, J=16 Hz, 1H), 3.94 (s, 3H), 3.60 (m, 4H), 3.53 (m, 2H), 3.17 (m, 2H), 2.50 (s, 3H).

Example CD: 2-(2,6-dichloro-3-(morpholine-4-carbonyl)benzyl)-1-methyl-1H-benzo[d]imidazole-5-carbonitrile

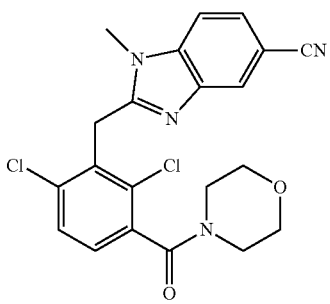 [SMILES: Cn1c(Cc2c(Cl)ccc(C(=O)N3CCOCC3)c2Cl)nc2cc(C#N)ccc21]

Step 1: methyl 2,4-dichloro-3-((5-cyano-1-methyl-1H-benzo[d]imidazol-2-yl)methyl)benzoate

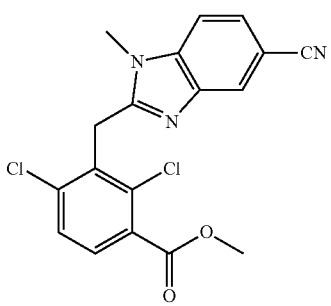 [SMILES: COC(=O)c1ccc(Cl)c(Cc2nc3cc(C#N)ccc3n2C)c1Cl]

Using a procedure similar to Example BJ, Step 1, methyl 2,4-dichloro-3-((5-cyano-1-methyl-1H-benzo[d]imidazol-2-yl)methyl)benzoate (460 mg, 82%) was prepared from 3-amino-4-(methylamino)benzonitrile (WO 2003060078) (220 mg, 1.49 mmol) and 2-(2,6-dichloro-3-(methoxycarbonyl)phenyl)acetic acid (Preparation #2) (393 mg, 1.49 mmol). LC/MS (Method h) $R_t$=2.39 min.; MS m/z: 374 [M+H]$^+$. $^1$H NMR (DMSO-d$_6$, 300 MHz): δ 8.04 (d, J=1.5 Hz, 1H), 7.76 (m, 2H), 7.66 (d, J=9 Hz, 1H), 7.62 (dd, J=9, 1.5 Hz, 1H), 4.64 (s, 2H), 3.97 (s, 3H), 3.87 (s, 3H).

Step 2: 2,4-dichloro-3-((5-cyano-1-methyl-1H-benzo[d]imidazol-2-yl)methyl)benzoic acid

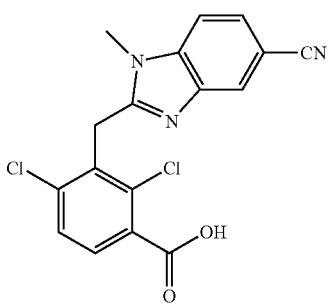 [SMILES: Cn1c(Cc2c(Cl)ccc(C(=O)O)c2Cl)nc2cc(C#N)ccc21]

Using a procedure similar to Example A, Step 5, 2,4-dichloro-3-((5-cyano-1-methyl-1H-benzo[d]imidazol-2-yl)methyl)benzoic acid (400 mg, 92%) was prepared from methyl 2,4-dichloro-3-((5-cyano-1-methyl-1H-benzo[c]imidazol-2-yl)methyl)benzoate (450 mg, 1.20 mmol).

LC/MS (Method h) $R_t$=1.80 min.; MS m/z: 360 [M+H]$^+$. $^1$H NMR (DMSO-d$_6$, 300 MHz): δ 8.04 (d, J=1.3 Hz, 1H), 7.77 (d, J=8.4 Hz, 1H), 7.72 (d, J=9 Hz, 1H), 7.62 (m, 2H), 4.63 (s, 2H), 3.97 (s, 3H).

Step 3: 2-(2,6-dichloro-3-(morpholine-4-carbonyl)benzyl)-1-methyl-1H-benzo[d]imidazole-5-carbonitrile

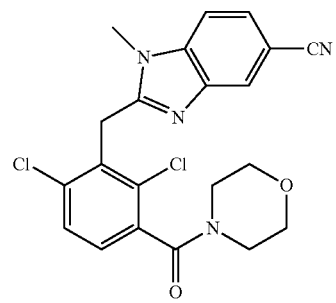 [SMILES: Cn1c(Cc2c(Cl)ccc(C(=O)N3CCOCC3)c2Cl)nc2cc(C#N)ccc21]

Using a procedure similar to Example A1, 2-(2,6-dichloro-3-(morpholine-4-carbonyl)benzyl)-1-methyl-1H-benzo[c]imidazole-5-carbonitrile (178 mg, 38%) was prepared from 2,4-dichloro-3-((5-cyano-1-methyl-1H-benzo[d]imidazol-2-yl)methyl)benzoic acid (387 mg, 1.07 mmol) and morpholine (140 mg, 1.61 mmol). LC/MS (HPLC) $R_t$=1.19 min.; MS m/z: 429 [M+H]$^+$.

$^1$H NMR (DMSO-d$_6$, 400 MHz): δ 8.05 (s, 1H), 7.77 (d, J=8.4 Hz, 1H), 7.62 (m, 2H), 7.41 (d, J=8.4 Hz, 1H), 4.61 (m, 2H), 3.97 (s, 3H), 3.64 (m, 4H), 3.54 (m, 2H), 3.16 (m, 2H).

Example CE: (3-((6-bromo-1-methyl-4-(trifluoromethyl)-1H-benzo[d]imidazol-2-yl)methyl)-2,4-dichlorophenyl)(morpholino)methanone

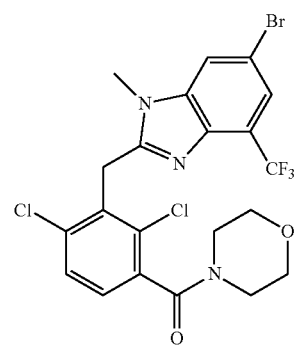 [SMILES: Cn1c(Cc2c(Cl)ccc(C(=O)N3CCOCC3)c2Cl)nc2c(C(F)(F)F)cc(Br)cc21]

Step 1: methyl 3-((6-bromo-1-methyl-4-(trifluoromethyl)-1H-benzo[d]imidazol-2-yl)methyl)-2,4-dichlorobenzoate Step 3: (3-((6-bromo-1-methyl-4-(trifluoromethyl)-1H-benzo[d]imidazol-2-yl)methyl)-2,4-dichlorophenyl)(morpholino)methanone

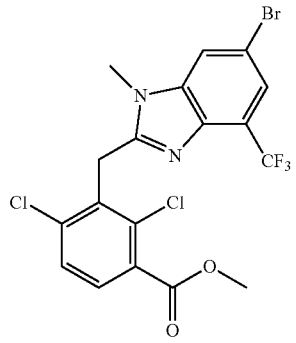 [SMILES: COC(=O)c1ccc(Cl)c(Cc2nc3c(C(F)(F)F)cc(Br)cc3n2C)c1Cl]

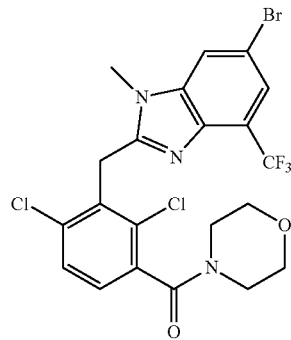

Using a procedure similar to Example BJ, Step 1, methyl 3-((6-bromo-1-methyl-4-(trifluoromethyl)-1H-benzo[d]imidazol-2-yl)methyl)-2,4-dichlorobenzoate (827 mg) was prepared from 5-bromo-N1-methyl-3-(trifluoromethyl)benzene-1,2-diamine (Preparation #32) (450 mg, 1.67 mmol) and 2-(2,6-dichloro-3-(methoxycarbonyl)phenyl)acetic acid (Preparation #2) (440 mg, 1.67 mmol). It was used crude in the next step. LC/MS (Method h) $R_t$=3.19 min.; MS m/z: 494 [M+H]$^+$.

Step 2: 3-((6-bromo-1-methyl-4-(trifluoromethyl)-1H-benzo[d]imidazol-2-yl)methyl)-2,4-dichlorobenzoic acid

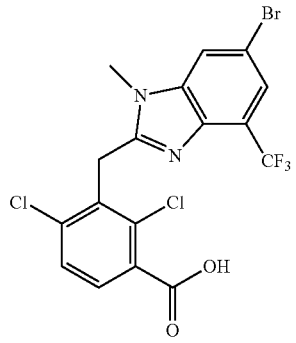 [SMILES: Cn1c(Cc2c(Cl)ccc(C(=O)O)c2Cl)nc2c(C(F)(F)F)cc(Br)cc21]

Using a procedure similar to Example A, Step 5, 3-((6-bromo-1-methyl-4-(trifluoromethyl)-1H-benzo[d]imidazol-2-yl)methyl)-2,4-dichlorobenzoic acid (487 mg, 88%) was prepared from methyl 3-((6-bromo-1-methyl-4-(trifluoromethyl)-1H-benzo[d]imidazol-2-yl)methyl)-2,4-dichlorobenzoate (830 mg, 1.67 mmol). LC/MS (Method h) $R_t$=2.77 min.; MS m/z: 481 [M+H]$^+$.

$^1$H NMR (DMSO-d$_6$, 300 MHz): δ 8.24 (d, J=1.0 Hz, 1H), 7.74 (d, J=9 Hz, 1H), 7.63 (d, J=9 Hz, 1H), 7.59 (d, J=1.0 Hz, 1H), 4.64 (s, 2H), 3.97 (s, 3H).

Using a procedure similar to Example A1, (3-((6-bromo-1-methyl-4-(trifluoromethyl)-1H-benzo[c]imidazol-2-yl)methyl)-2,4-dichlorophenyl)(morpholino)methanone (442 mg, 79%) was prepared from 3-((6-bromo-1-methyl-4-(trifluoromethyl)-1H-benzo[d]imidazol-2-yl)methyl)-2,4-dichlorobenzoic acid (478 mg, 0.99 mmol) and morpholine (86 mg, 0.99 mmol). LC/MS (Method g) $R_t$=1.76 min.; MS m/z: 550 [M+H]$^+$. $^1$H NMR (DMSO-d$_6$, 400 MHz): δ 8.23 (s, 1H), 7.63 (d, J=8.4 Hz, 1H), 7.58 (s, 1H), 7.40 (d, J=8.4 Hz, 1H), 4.66 (d, J=16 Hz, 1H), 4.56 (d, J=16 Hz, 1H), 3.96 (s, 3H), 3.63 (m, 4H), 3.40-3.54 (m, 2H), 3.12 (m, 2H).

Example CF: 2-(2,6-dichloro-3-(morpholine-4-carbonyl)benzyl)-1-methyl-4-(trifluoromethyl)-1H-benzo[d]imidazole-6-carbonitrile

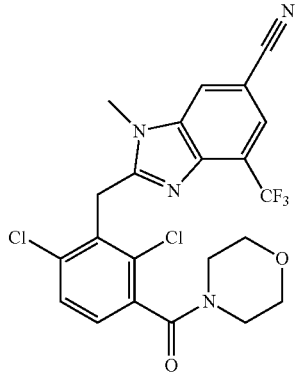 [SMILES: Cn1c(Cc2c(Cl)ccc(C(=O)N3CCOCC3)c2Cl)nc2c(C(F)(F)F)cc(C#N)cc21]

Using a procedure similar to Example CC, 2-(2,6-dichloro-3-(morpholine-4-carbonyl)benzyl)-1-methyl-4-(trifluoromethyl)-1H-benzo[d]imidazole-6-carbonitrile (57 mg, 42%) was prepared from (3-((6-bromo-1-methyl-4-(trifluoromethyl)-1H-benzo[c]imidazol-2-yl)methyl)-2,4-dichlorophenyl)(morpholino)methanone (Example CE, Step 3) (151 mg, 0.0.27 mmol). LC/MS (Method g) $R_t$=1.50 min.; MS m/z: 497 [M+H]$^+$. $^1$H NMR (DMSO-d$_6$, 400 MHz): δ 8.58 (s, 1H), 7.94 (m, 1H), 7.64 (d, J=8.4 Hz, 1H), 7.41 (d, J=8.4 Hz, 1H), 4.74 (d, J=16 Hz, 1H), 4.64 (d, J=16 Hz, 1H), 4.03 (s, 3H), 3.63 (m, 4H), 3.48 (m, 2H), 3.12 (m, 2H).

Example CG: 2-(2,6-dichloro-3-(morpholine-4-carbonyl)benzyl)-1-ethyl-4-methyl-1H-benzo[d]imidazole-6-carbonitrile

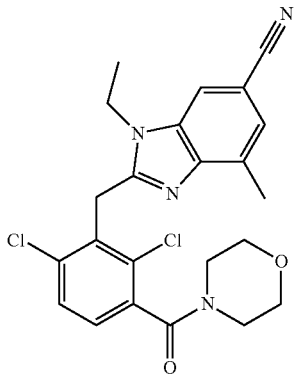 [SMILES: CCn1c(Cc2c(Cl)ccc(C(=O)N3CCOCC3)c2Cl)nc2c(C)cc(C#N)cc21]

Step 1: methyl 2,4-dichloro-3-((6-cyano-4-methyl-1H-benzo[d]imidazol-2-yl)methyl)benzoate

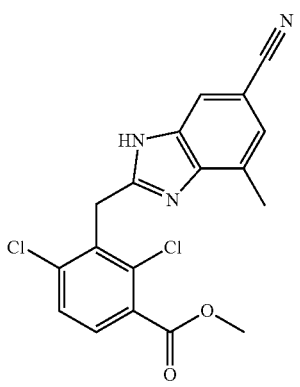 [SMILES: COC(=O)c1ccc(Cl)c(Cc2nc3c(C)cc(C#N)cc3[nH]2)c1Cl]

Using a procedure similar to Example BJ, Step 1, methyl 2,4-dichloro-3-((6-cyano-4-methyl-1H-benzo[d]imidazol-2-yl)methyl)benzoate (1.16 g, 76%) was prepared from 3,4-diamino-5-methylbenzonitrile (WO2005021510) (600 mg, 4.08 mmol) and 2-(2,6-dichloro-3-(methoxycarbonyl)phenyl)acetic acid (Preparation #2) (440 mg, 1.67 mmol). LC/MS (Method h) $R_t$=2.35 min.; MS m/z: 374 [M+H]$^+$. $^1$H NMR (DMSO-d$_6$, 300 MHz): δ 13.07 and 12.78 (broad, 1H), 7.77 (m, 2H), 7.66 (d, J=9 Hz, 1H), 7.36 (s, 1H), 4.61 (s, 2H), 3.87 (s, 3H), 2.48 (s, 3H).

Step 2: 2,4-dichloro-3-((6-cyano-4-methyl-1H-benzo[d]imidazol-2-yl)methyl)benzoic acid

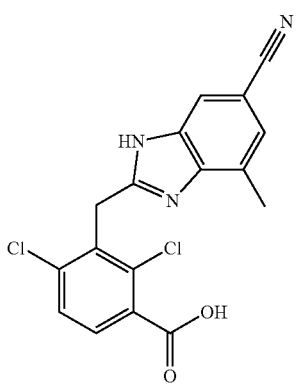 [SMILES: Cc1cc(C#N)cc2[nH]c(Cc3c(Cl)ccc(C(=O)O)c3Cl)nc12]

Using a procedure similar to Example A, Step 5, 2,4-dichloro-3-((6-cyano-4-methyl-1H-benzo[d]imidazol-2-yl)methyl)benzoic acid (462 mg, 76%) was prepared from methyl 2,4-dichloro-3-((6-cyano-4-methyl-1H-benzo[d]imidazol-2-yl)methyl)benzoate (600 mg, 1.60 mmol).

LC/MS (Method h) $R_t$=1.72 min.; MS m/z: 360 [M+H]$^+$. $^1$H NMR (DMSO-d$_6$, 300 MHz): δ 7.85 (d, J=8.4 Hz, 1H), 7.78 (s, 1H), 7.52 (d, J=8.4 Hz, 1H), 7.47 (s, 1H), 5.03 (s, 2H), 2.74 (s, 3H).

Step 3: 2-(2,6-dichloro-3-(morpholine-4-carbonyl)benzyl)-4-methyl-1H-benzo[d]imidazole-6-carbonitrile

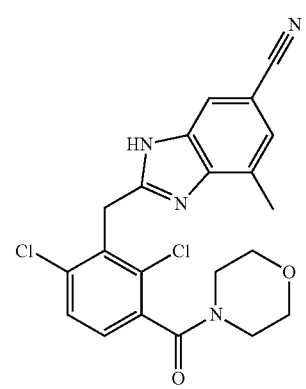 [SMILES: Cc1cc(C#N)cc2[nH]c(Cc3c(Cl)ccc(C(=O)N4CCOCC4)c3Cl)nc12]

Using a procedure similar to Example A1, 2-(2,6-dichloro-3-(morpholine-4-carbonyl)benzyl)-4-methyl-1H-benzo[d]imidazole-6-carbonitrile (129 mg, 71%) was prepared from 2,4-dichloro-3-((6-cyano-4-methyl-1H-benzo[d]imidazol-2-yl)methyl)benzoic acid (150 mg, 0.416 mmol) and morpholine (43.5 mg, 0.5 mmol). LC/MS (Method h) $R_t$=1.97 min.; MS m/z: 429 [M+H]$^+$.

$^1$H NMR (DMSO-d$_6$, 300 MHz): δ 13.04 and 12.76 (s, 1H), 7.85 and 7.76 (s, 1H), 7.63 (m, 1H), 7.39 (m, 2H), 4.57 (m, 2H), 3.65 (m, 4H), 3.53 (m, 2H), 3.16 (m, 2H), 2.50 and 2.45 (s, 3H).

Step 4: 2-(2,6-dichloro-3-(morpholine-4-carbonyl)benzyl)-1-ethyl-4-methyl-W-benzo[d]imidazole-6-carbonitrile

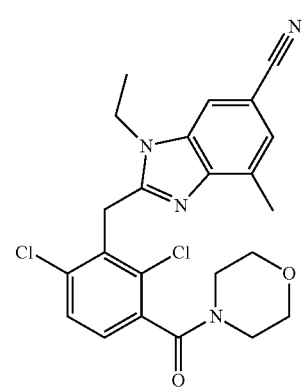 [SMILES: CCn1c(Cc2c(Cl)ccc(C(=O)N3CCOCC3)c2Cl)nc2c(C)cc(C#N)cc21]

Using a procedure similar to Example A Step 4, 2-(2,6-dichloro-3-(morpholine-4-carbonyl)benzyl)-1-ethyl-4- methyl-1H-benzo[d]imidazole-6-carbonitrile (63 mg, 47%) was prepared from 2-(2,6-dichloro-3-(morpholine-4-carbonyl)benzyl)-4-methyl-1H-benzo[d]imidazole-6-carbonitrile (125 mg, 0.29 mmol) and bromoethane (56 mg, 0.52 mmol). LC/MS (Method g) $R_t$=1.43 min.; MS m/z: 457 [M+H]$^+$. $^1$H NMR (DMSO-d$_6$, 500 MHz): δ 8.05 (s, 1H), 7.64 (d, J=8.2 Hz, 1H), 7.42 (d, J=8.4 Hz, 1H), 7.34 (s, 1H), 4.65 (d, J=16 Hz, 1H), 4.57 (d, J=8.2 Hz, 1H), 4.45 (q, J=7.1 Hz, 2H), 3.65 (m, 4H), 3.53 (m, 2H), 3.16 (m, 2H), 2.34 (s, 3H), 1.39 (t, J=7.1 Hz, 3H).

Example CH: 2-(2,6-dichloro-3-(morpholine-4-carbonyl)benzyl)-1-isopropyl-4-methyl-W-benzo[d]imidazole-6-carbonitrile

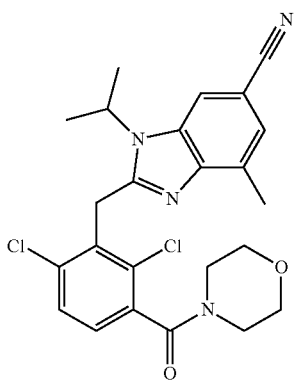 [SMILES: Cc1cc(C#N)cc2c1nc(Cc1c(Cl)ccc(C(=O)N3CCOCC3)c1Cl)n2C(C)C]

Using a procedure similar to Example A1 Step 4, 2-(2,6-dichloro-3-(morpholine-4-carbonyl)benzyl)-1-isopropyl-4-methyl-1H-benzo[d]imidazole-6-carbonitrile (20 mg, 14%) was prepared from 2-(2,6-dichloro-3-(morpholine-4-carbonyl)benzyl)-4-methyl-1H-benzo[c]imidazole-6-carbonitrile (Example CG, Step 3) (130 mg, 0.30 mmol) and 2-iodopropane (61 mg, 0.36 mmol). LC/MS (Method g) $R_t$=1.52 min.; MS m/z: 471 [M+H]$^+$. $^1$H NMR (DMSO-d$_6$, 500 MHz): δ 8.15 (s, 1H), 7.63 (d, J=8.2 Hz, 1H), 7.41 (d, J=8.2 Hz, 1H), 7.33 (s, 1H), 5.05 (sept, J=6.9 Hz, 1H), 4.66 (d, J=16 Hz, 1H), 4.58 (d, J=16 Hz, 1H), 3.65 (m, 4H), 3.52 (m, 2H), 3.16 (m, 2H), 2.31 (s, 3H), 1.64 (d, J=6.9 Hz, 6H).

Example CI: 2-(2,6-dichloro-3-(morpholine-4-carbonyl)benzyl)-3,7-dimethyl-3H-imidazo[4,5-b]pyridine-5-carbonitrile

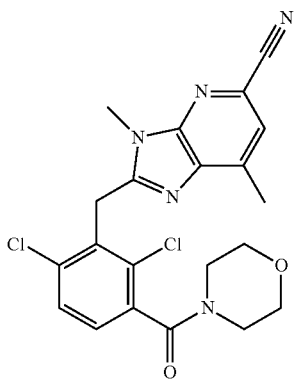 [SMILES: Cc1cc(C#N)nc2c1nc(Cc1c(Cl)ccc(C(=O)N3CCOCC3)c1Cl)n2C]

Step 1: methyl 2,4-dichloro-3-((5-chloro-3,7-dimethyl-3H-imidazo[4,5-b]pyridin-2-yl)methyl)benzoate

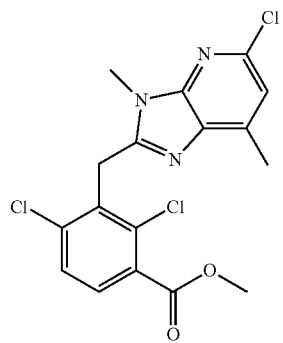 [SMILES: COC(=O)c1ccc(Cl)c(Cc2nc3c(C)cc(Cl)nc3n2C)c1Cl]

Using a procedure similar to Example BJ, Step 1, methyl 2,4-dichloro-3-((5-chloro-3,7-dimethyl-3H-imidazo[4,5-b]pyridin-2-yl)methyl)benzoate (350 mg, 50%) was prepared from 6-chloro-N2,4-dimethylpyridine-2,3-diamine (Preparation #25) (150 mg, 0.874 mmol) and 2-(2,6-dichloro-3-(methoxycarbonyl)phenyl)acetic acid (Preparation #2) (230 mg, 0.874 mmol) and was used crude in the next step. LC/MS (Method h) $R_t$=2.78 min.; MS m/z: 398 [M+H]$^+$.

Step 2: 2,4-dichloro-3-((5-chloro-3,7-dimethyl-3H-imidazo[4,5-b]pyridin-2-yl)methyl)benzoic acid

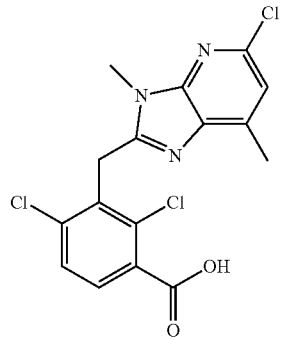 [SMILES: Cc1cc(Cl)nc2c1nc(Cc1c(Cl)ccc(C(=O)O)c1Cl)n2C]

Using a procedure similar to Example F, Step 4, 2,4-dichloro-3-((5-chloro-3,7-dimethyl-3H-imidazo[4,5-b]pyridin-2-yl)methyl)benzoic acid (250 mg, 86%) was prepared from methyl 2,4-dichloro-3-((5-chloro-3,7-dimethyl-3H-imidazo[4,5-b]pyridin-2-yl)methyl)benzoate (300 mg, 0.753 mmol). LC/MS (Method h) $R_t$=2.21 min.; MS m/z: 384 [M+H]$^+$. $^1$H NMR (DMSO-d$_6$, 300 MHz): δ 13.64 (broad, 1H), 7.72 (d, J=9 Hz, 1H), 7.62 (d, J=9 Hz, 1H), 7.14 (s, 1H), 4.62 (s, 2H), 3.88 (s, 3H), 2.39 (s, 3H).

Step 3: (2,4-dichloro-3-((5-chloro-3,7-dimethyl-3H-imidazo[4,5-b]pyridin-2-yl)methyl)phenyl)(morpholino)methanone

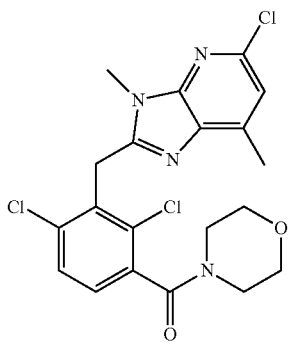 [SMILES: Cc1cc(Cl)nc2c1nc(Cc1c(Cl)ccc(C(=O)N3CCOCC3)c1Cl)n2C]

Using a procedure similar to Example A, Step 6, (2,4-dichloro-3-((5-chloro-3,7-dimethyl-3H-imidazo[4,5-b]pyridin-2-yl)methyl)phenyl)(morpholino)methanone (160 mg, 87%) was prepared from 2,4-dichloro-3-((5-chloro-3,7-dimethyl-3H-imidazo[4,5-b]pyridin-2-yl)methyl)benzoic acid (150 mg, 0.390 mmol) and morpholine (51 mg, 0.585 mmol). LC/MS (Method g) $R_t$=1.43 min.; MS m/z: 453 [M+H]$^+$. $^1$H NMR (DMSO-d$_6$, 400 MHz): δ 7.63 (d, J=9 Hz, 1H), 7.41 (d, J=9 Hz, 1H), 7.13 (s, 1H), 4.63 (d, J=12 Hz, 1H), 4.56 (d, J=12 Hz, 1H), 3.87 (s, 3H), 3.64 (m, 4H), 3.52 (m, 2H), 3.15 (m, 2H), 2.38 (s, 3H).

Step 4: 2-(2,6-dichloro-3-(morpholine-4-carbonyl)benzyl)-3,7-dimethyl-3H-imidazo[4,5-b]pyridine-5-carbonitrile

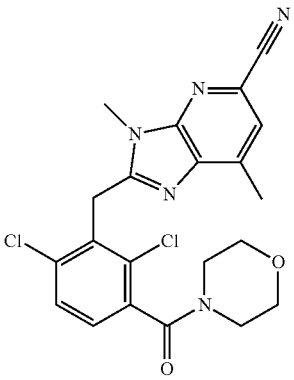

In a microwave vial were put (2,4-dichloro-3-((5-chloro-3,7-dimethyl-3H-imidazo[4,5-b]pyridin-2-yl)methyl)phenyl)(morpholino)methanone (70 mg, 0.154 mmol), zinc cyanide (15.40 mg, 0.131 mmol) and Pd(Ph$_3$P)$_4$ (17.83 mg, 0.015 mmol) in DMF (250 μL) and the reaction mixture was stirred at 110° C. for 30 minutes under microwave irradiation. The reaction mixture was diluted with EtOAc and filtered. The filtrate was then washed with water. The layers were separated and the aqueous one was washed with EtOAc. The organic layers were combined, dried over magnesium sulfate, filtered and concentrated under reduced pressure. The residue was purified by column chromatography on silica gel (eluting with 0-100% EtOAc in cyclohexane) to give 2-(2,6-dichloro-3-(morpholine-4-carbonyl)benzyl)-3,7-dimethyl-3H-imidazo[4,5-b]pyridine-5-carbonitrile (18 mg, 26%). LC/MS (Method g) $R_t$=1.32 min.; MS m/z: 444 [M+H]$^+$. $^1$H NMR (DMSO-d$_6$, 400 MHz): δ 7.70 (s, 1H), 7.64 (d, J=9 Hz, 1H), 7.43 (d, J=9 Hz, 1H), 4.72 (d, J=16 Hz, 1H), 4.64 (d, J=16 Hz, 1H), 3.94 (s, 3H), 3.65 (m, 4H), 3.53 (m, 2H), 3.15 (m, 2H), 2.43 (s, 3H).

Example CJ: 4-chloro-2-(2,6-dichloro-3-(morpholine-4-carbonyl)benzyl)-1-methyl-1H-indole-6-carbonitrile

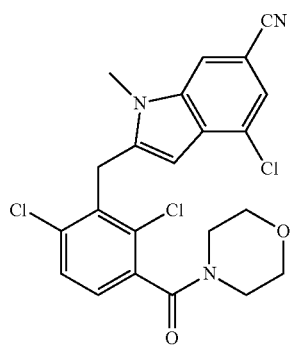

Step 1: tert-butyl 3-((6-bromo-4-chloro-1-(phenylsulfonyl)-1H-indol-2-yl)(hydroxy)methyl)-2,4-dichlorobenzoate

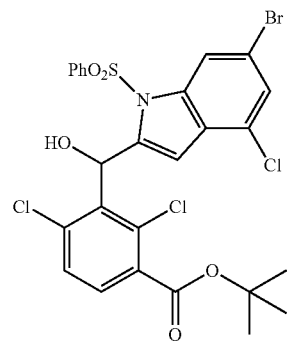

To a solution of 6-bromo-4-chloro-1-(phenylsulfonyl)-1H-indole (Preparation #48) (200 mg, 0.54 mmol) in THF (1.5 mL) and cooled to −78° C. was added lithium diisopropylamide (0.30 mL, 0.59 mmol) and the reaction mixture was stirred for 1 hour at −78° C. Tert-butyl 2,4-dichloro-3-formylbenzoate (Preparation #33, Step B) (178 mg, 0.65 mmol) in solution in THF (1.5 mL) was added to the reaction mixture and the reaction mixture was stirred for 2 hours at −78° C. The reaction mixture was quenched with a saturated NH$_4$Cl solution and extracted with EtOAc. The organic layer was dried over magnesium sulfate, filtered and concentrated under reduced pressure. The residue was purified by column chromatography on silica gel (eluting with 0-10% EtOAc in cyclohexane) to give tert-butyl 3-((6-bromo-4-chloro-1-(phenylsulfonyl)-1H-indol-2-yl)(hydroxy)methyl)-2,4-dichlorobenzoate (262 mg, 75%). LC/MS (Method j) $R_t$=2.75 min.; MS m/z: 702 [M−H]$^-$+ CH$_3$COOH ¹H NMR (DMSO-d₆, 300 MHz): δ 8.11 (m, 1H), 7.85 (m, 2H), 7.72 (m, 1H), 7.66 (d, J=6 Hz, 1H), 7.55 (m, 4H), 6.95 (m, 1H), 6.75 (m, 1H), 6.66 (m, 1H), 1.54 ppm (s, 9H)

Step 2: 3-((6-bromo-4-chloro-1-(phenylsulfonyl)-1H-indol-2-yl)methyl)-2,4-dichlorobenzoic acid

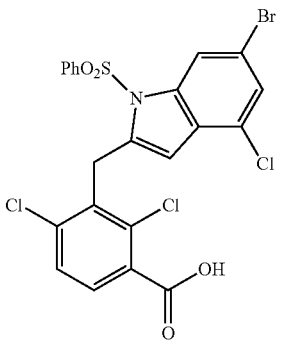

Using a procedure similar to Example A, Step 2, 3-((6-bromo-4-chloro-1-(phenylsulfonyl)-1H-indol-2-yl)methyl)-2,4-dichlorobenzoic acid (1.17 g, 93%) was prepared from tert-butyl 3-((6-bromo-4-chloro-1-(phenylsulfonyl)-1H-indol-2-yl)(hydroxy)methyl)-2,4-dichlorobenzoate (1.42 g, 2.2 mmol).

LC/MS (Method i) $R_t$=2.81 min.; MS m/z: 570 [M−H]⁻
¹H NMR (DMSO-d₆, 300 MHz): δ 8.27 (m, 1H), 8.00 (m, 2H), 7.80 (m, 2H), 7.69 (m, 4H), 5.70 (m, 1H), 4.55 (s, 2H).

Step 3: 3-((6-bromo-4-chloro-1H-indol-2-yl)methyl)-2,4-dichlorobenzoic acid

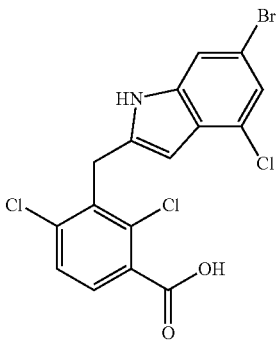 [SMILES: O=C(O)c1ccc(Cl)c(Cc2cc3c(Cl)cc(Br)cc3[nH]2)c1Cl]

Using a procedure similar to Example A, Step 3, 3-((6-bromo-4-chloro-1H-indol-2-yl)methyl)-2,4-dichlorobenzoic acid (657 mg, 100%) was prepared from 3-((6-bromo-4-chloro-1-(phenylsulfonyl)-1H-indol-2-yl)methyl)-2,4-dichlorobenzoic acid (870 mg, 1.52 mmol). The compound was used directly in the next step. LC/MS (Method i) $R_t$=2.48 min.; MS m/z: 432 [M+H]⁺

Step 4: methyl 3-((6-bromo-4-chloro-1-methyl-1H-indol-2-yl)methyl)-2,4-dichlorobenzoate

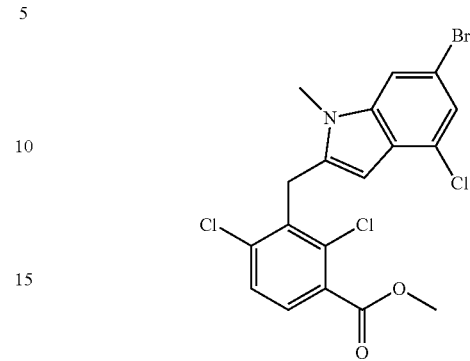

Using a procedure similar to Example P, Step 4, methyl 3-((6-bromo-4-chloro-1-methyl-1H-indol-2-yl)methyl)-2,4-dichlorobenzoate (568 mg, 81%) was prepared from 3-((6-bromo-4-chloro-1H-indol-2-yl)methyl)-2,4-dichlorobenzoic acid (657 mg, 1.52 mmol). LC/MS (Method j) $R_t$=2.46 min.; MS m/z: 460 [M+H]⁺ ¹H NMR (DMSO-d₆, 300 MHz): δ 7.80 (m, 2H), 7.72 (m, 1H), 7.23 (d, J=1.5 Hz, 1H), 5.52 (m, 1H), 4.46 (s, 2H), 3.89 (s, 3H), 3.88 (s, 3H).

Step 5: methyl 2,4-dichloro-3-((4-chloro-6-cyano-1-methyl-1H-indol-2-yl)methyl)benzoate

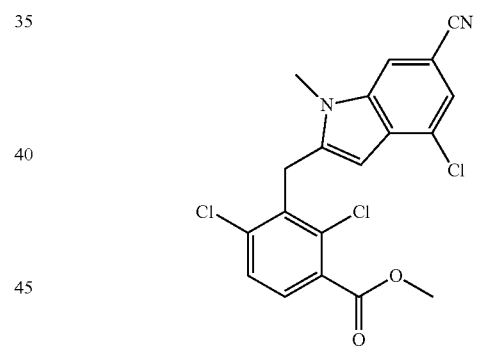

To a solution of methyl 3-((6-bromo-4-chloro-1-methyl-1H-indol-2-yl)methyl)-2,4-dichlorobenzoate (559 mg, 1.211 mmol) in N,N-dimethylformamide (4.3 mL) was added zinc cyanide (107 mg, 0.908 mmol) and tetrakis(triphenylphosphine)palladium (140 mg, 0.121 mmol) and the reaction mixture was heated at 120° C. under microwave during 1 hour. The reaction mixture was diluted with water and extracted with EtOAc. The obtained organic layer was dried over magnesium sulfate, filtered and concentrated under reduced pressure. The residue was purified by column chromatography on silica gel (eluting with 0-40% EtOAc in cyclohexane) to give methyl 2,4-dichloro-3-((4-chloro-6-cyano-1-methyl-1H-indol-2-yl)methyl)benzoate (200 mg, 40%). LC/MS (Method i) $R_t$=2.59 min.; MS m/z: 405 [M−H]⁻

¹H NMR (DMSO-d₆, 300 MHz): δ=8.18 (m, 1H), 7.83 (d, J=8.4 Hz, 1H), 7.73 (d, J=8.4 Hz, 1H), 7.50 (d, J=1.2 Hz, 1H), 5.67 (m, 1H), 4.54 (s, 2H), 3.96 (s, 3H), 3.88 (s, 3H).

Step 6: 2,4-dichloro-3-((4-chloro-6-cyano-1-methyl-1H-indol-2-yl)methyl)benzoic acid

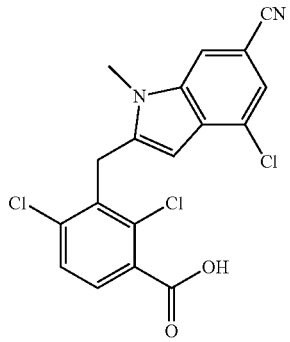 [SMILES: Cn1c(Cc2c(Cl)ccc(C(=O)O)c2Cl)cc2c(Cl)cc(C#N)cc21]

Using a procedure similar to Example A, Step 5, 2,4-dichloro-3-((4-chloro-6-cyano-1-methyl-1H-indol-2-yl)methyl)benzoic acid (180 mg, 94%) was prepared from methyl 2,4-dichloro-3-((4-chloro-6-cyano-1-methyl-1H-indol-2-yl)methyl)benzoate (198 mg, 0.48 mmol). LC/MS (Method i) $R_t$=2.25 min.; MS m/z: 393 [M+H]$^+$ $^1$H NMR (DMSO-$d_6$, 300 MHz): δ 13.60 (br, 1H), 8.18 (m, 1H), 7.79 (d, J=8.4 Hz 1H), 7.69 (d, J=8.4 Hz 1H), 7.50 (d, J=1.2 Hz, 1H), 5.67 (m, 1H), 4.53 (s, 2H), 3.96 (s, 3H).

Step 7: 4-chloro-2-(2,6-dichloro-3-(morpholine-4-carbonyl)benzyl)-1-methyl-1H-indole-6-carbonitrile

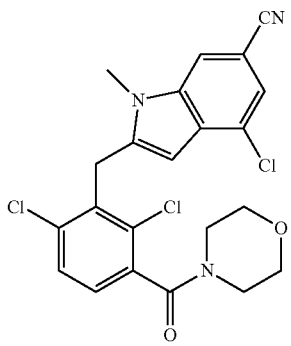 [SMILES: Cn1c(Cc2c(Cl)ccc(C(=O)N3CCOCC3)c2Cl)cc2c(Cl)cc(C#N)cc21]

Using a procedure similar to Example A1, 4-chloro-2-(2,6-dichloro-3-(morpholine-4-carbonyl)benzyl)-1-methyl-1H-indole-6-carbonitrile (89 mg, 82%) was prepared from 2,4-dichloro-3-((4-chloro-6-cyano-1-methyl-1H-indol-2-yl)methyl)benzoic acid (90 mg, 0.23 mmol) and morpholine (23.9 mg, 0.27 mmol). LC/MS (Method g) $R_t$=1.69 min.; MS m/z: 462 [M+H]$^+$ $^1$H NMR (DMSO-$d_6$, 400 MHz): δ 8.17 (s, 1H), 7.69 (d, J=8.1 Hz, 1H), 7.50 (d, J=1.3 Hz, 1H), 7.47 (d, J=8.1 Hz, 1H), 5.70 (m, 1H), 4.50 (m, 2H), 3.96 (s, 3H), 3.65 (m, 4H), 3.55 (m, 2H), 3.15 (m, 2H).

Example CK: (2,4-dichloro-3-((1-methyl-1H-pyrrolo[2,3-b]pyridin-2-yl)methyl)phenyl)(morpholino)methanone

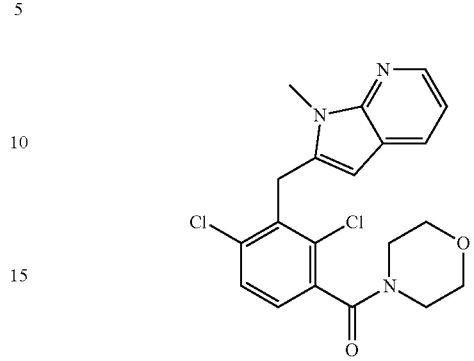

Step 1: methyl 2,4-dichloro-3-((1-(phenylsulfonyl)-1H-pyrrolo[2,3-b]pyridin-2-yl)methyl)benzoate To a solution of 1-(phenylsulfonyl)-1H-pyrrolo[2,3-b]pyridine (described in WO2006/050076) 1.5 g, 5.81 mmol) in THF (45 mL) and cooled at −78° C. was added dropwise butyl lithium (2.439 mL, 6.10 mmol) and the reaction mixture was stirred for 45 minutes at −78° C. The reaction mixture was warmed to −20° C. and stirred 5 minutes at this temperature. At −78° C., methyl 3-(bromomethyl)-2,4-dichlorobenzoate (Preparation #1, Step B) (2.249 g, 7.55 mmol) previously dissolved in THF, (20 mL) was added dropwise and the reaction mixture was stirred for 10 minutes at −78° C. and for 18 hours at room temperature. The reaction mixture was quenched with NH$_4$Cl saturated aqueous solution and extracted with EtOAc. The organic layer was washed with brine, dried over magnesium sulfate, filtered and concentrated to dryness under vacuum. The residue was purified by column chromatography on silica gel (eluting with 10-20% EtOAc in cyclohexane) to give methyl 2,4-dichloro-3-((1-(phenylsulfonyl)-1H-pyrrolo[2,3-b]pyridin-2-yl)methyl)benzoate (1 g, 22%). LC/MS (Method h) $R_t$=3.09 min.; MS m/z: 475 [M+H]$^+$. $^1$H NMR (DMSO-$d_6$, 300 MHz): δ 8.32 (dd, J=4.8 Hz, 1.6 Hz, 1H), 8.15 (m, 2H), 7.87-7.62 (m, 6H), 7.23 (dd, J=4.8 Hz, 7.7 Hz, 1H), 5.81 (m, 1H), 4.79 (s, 2H), 3.88 (s, 3H).

Step 2: methyl 3-0H-pyrrolo[2,3-b]pyridin-2-yl)
methyl)-2,4-dichlorobenzoate

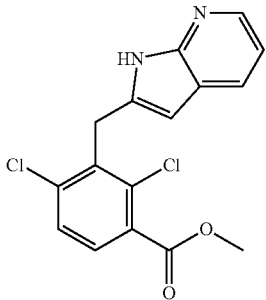 [SMILES: COC(=O)c1ccc(Cl)c(Cc2cc3cccnc3[nH]2)c1Cl]

Using a procedure similar to Example A, Step 3, methyl 34(1H-pyrrolo[2,3-b]pyridin-2-yl)methyl)-2,4-dichlorobenzoate (125 mg, 71%) was obtained as a white solid from methyl 2,4-dichloro-3-((1-(phenylsulfonyl)-1H-pyrrolo[2,3-b]pyridin-2-yl)methyl)benzoate (250 mg, 0.526 mmol). LC/MS (Method h) $R_t$=2.34 min.; MS m/z: 335 [M+H]$^+$ $^1$H NMR (DMSO-d$_6$, 300 MHz): δ 11.71 (broad, 1H), 8.12 (dd, J=5 Hz, 1.6 Hz, 1H), 7.75 (d, J=8.4 Hz, 1H), 7.74 (dd, J=7.7 Hz, 1.6 Hz, 1H), 7.68 (d, J=8.4 Hz, 1H), 6.97 (dd, J=7.7 Hz, 5 Hz, 1H), 5.68 (m, 1H), 4.46 (s, 2H), 3.87 (s, 3H).

Step 3: methyl 2,4-dichloro-3-((1-methyl-1H-pyrrolo[2,3-b]pyridin-2-yl)methyl)benzoate

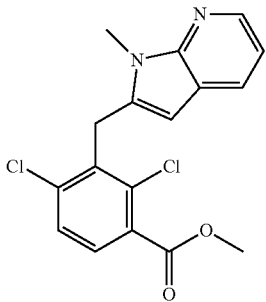 [SMILES: COC(=O)c1ccc(Cl)c(Cc2cc3cccnc3n2C)c1Cl]

Using a procedure similar to Example A, Step 4, methyl 2,4-dichloro-3-((1-methyl-1H-pyrrolo[2,3-b]pyridin-2-yl)methyl)benzoate (97 mg, 76%) was obtained as a yellow solid from methyl 34(1H-pyrrolo[2,3-b]pyridin-2-yl)methyl)-2,4-dichlorobenzoate (123 mg, 0.367 mmol). LC/MS (Method h) $R_t$=2.70 min.; MS m/z: 349 [M+H]$^+$. $^1$H NMR (DMSO-d$_6$, 300 MHz): δ 8.19 (dd, J=4.6 Hz and 1.5 Hz, 1H), 7.80 (d, J=8.4 Hz, 1H), 7.76 (dd, J=7.1 Hz and 1.5 Hz, 1H), 7.71 (d, J=8.4 Hz, 1H), 7.01 (dd, J=4.6 Hz and 7.1 Hz, 1H), 5.56 (m, 1H), 4.50 (s, 2H), 3.90 (s, 3H), 3.88 (s, 3H).

Step 4: 2,4-dichloro-3-((1-methyl-1H-pyrrolo[2,3-b]pyridin-2-yl)methyl)benzoic acid

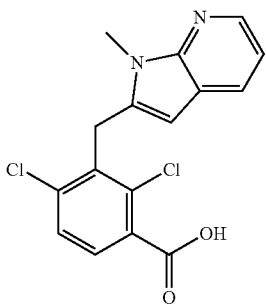 [SMILES: Cn1c(Cc2c(Cl)ccc(C(=O)O)c2Cl)cc2cccnc21]

Using a procedure similar to Example A, Step 5, 2,4-dichloro-3-((1-methyl-1H-pyrrolo[2,3-b]pyridin-2-yl)methyl)benzoic acid (87 mg, 96%) was obtained from methyl 2,4-dichloro-3-((1-methyl-1H-pyrrolo[2,3-b]pyridin-2-yl)methyl)benzoate (94 mg, 0.269 mmol).

LC/MS (Method h) $R_t$=2.44 min.; MS m/z: 335 [M+H]$^+$

Step 5: (2,4-dichloro-3-((1-methyl-1H-pyrrolo[2,3-b]pyridin-2-yl)methyl)phenyl)(morpholino)methanone

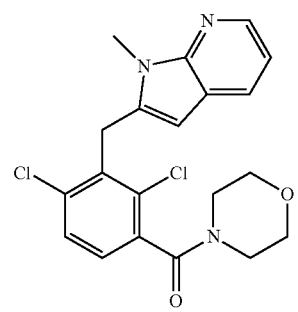 [SMILES: Cn1c(Cc2c(Cl)ccc(C(=O)N3CCOCC3)c2Cl)cc2cccnc21]

Using a procedure similar to Example A, Step 6, (2,4-dichloro-3-((1-methyl-1H-pyrrolo[2,3-b]pyridin-2-yl)methyl)phenyl)(morpholino)methanone (82 mg, 79%) was obtained as a yellow solid from 2,4-dichloro-3-((1-methyl-1H-pyrrolo[2,3-b]pyridin-2-yl)methyl)benzoic acid (86 mg, 0.257 mmol) and morpholine (33.5 mg, 0.385 mmol). LC/MS (Method g) $R_t$=1.34 min.; MS m/z: 404 [M+H]$^+$ $^1$H NMR (DMSO-d$_6$, 400 MHz): δ 8.19 (dd, J=4.6 Hz, and 1.5 Hz, 1H), 7.77 (dd, J=7.9 Hz, and 1.5 Hz, 1H), 7.67 (d, J=8.4 Hz, 1H), 7.45 (d, J=8.4 Hz, 1H), 7.02 (dd, J=4.6 Hz, and 7.9 Hz, 1H), 5.60 (m, 1H), 4.46 (s, 2H), 3.90 (s, 3H), 3.65 (m, 4H), 3.55 (m, 2H), 3.18 (m, 2H).

Example CL: 2-(2,6-dichloro-3-(morpholine-4-carbonyl)benzyl)-1,4-dimethyl-1H-pyrrolo[2,3-b]pyridine-6-carbonitrile

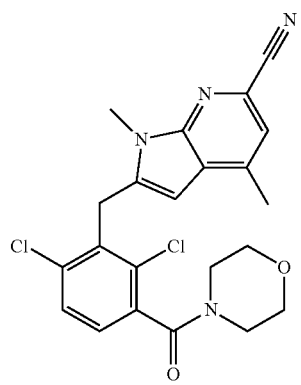 [SMILES: Cc1cc(C#N)nc2c1cc(Cc1c(Cl)ccc(C(=O)N3CCOCC3)c1Cl)n2C]

Step 1: methyl 2,4-dichloro-3-(hydroxy(4-methyl-1-(phenylsulfonyl)-1H-pyrrolo[2,3-b]pyridin-2-yl)methyl)benzoate

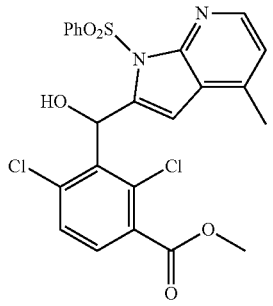

To a solution of lithium diisopropylamide (8.81 mL, 17.63 mmol) in THF (27 mL) cooled at −25° C. was added dropwise over 10 minutes 4-methyl-1-(phenylsulfonyl)-1H-pyrrolo[2,3-b]pyridine (described in WO2013/015984) (2.40 g, 8.81 mmol) in solution in THF (44 mL) and the reaction mixture was stirred for 20-25 minutes at −25° C. Methyl 2,4-dichloro-3-formylbenzoate (Preparation #1, Step C) (2.157 g, 9.25 mmol) previously dissolved in THF (22 mL) was added dropwise over 15 minutes at −25° C. The reaction mixture was stirred for 1.5 hour at −25° C. The reaction mixture was quenched with NH$_4$Cl saturated aqueous solution, and extracted with EtOAc. The organic layer was washed with brine, dried over magnesium sulfate, and concentrated to dryness. The residue was purified by column chromatography on silica gel (eluting with 10-20% EtOAc in cyclohexane) to give methyl 2,4-dichloro-3-(hydroxy(4-methyl-1-(phenylsulfonyl)-1H-pyrrolo[2,3-b]pyridin-2-yl)methyl)benzoate (1.32 g, 27%) as an orange foam. LC/MS (Method h) R$_f$=2.69 min.; MS m/z: 505 [M+H]$^+$ $^1$H NMR (DMSO-d$_6$, 300 MHz): δ 8.20 (d, J=4.9 Hz, 1H), 8.00 (m, 2H), 7.68 (m, 2H), 7.56 (m, 3H), 7.13 (dd, J=1.1 Hz, 6.1 Hz, 1H), 7.10 (d, J=4.9 Hz, 1H), 6.70 (d, J=1.1 Hz, 1H), 6.68 (d, J=6.1 Hz, 1H), 3.86 (s, 3H), 2.42 (s, 3H).

Step 2: methyl 2,4-dichloro-3-((4-methyl-1-(phenylsulfonyl)-1H-pyrrolo[2,3-b]pyridin-2-yl)methyl)benzoate

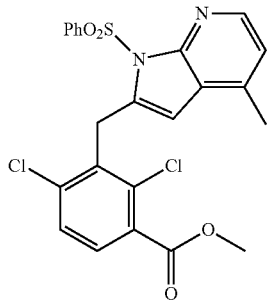

Using a procedure similar to Example Z, Step 2, methyl 2,4-dichloro-3-((4-methyl-1-(phenylsulfonyl)-1H-pyrrolo[2,3-b]pyridin-2-yl)methyl)benzoate (1.85 g, 70%) (mixture with exocyclic double bond) was obtained from methyl 2,4-dichloro-3-(hydroxy(4-methyl-1-(phenylsulfonyl)-1H-pyrrolo[2,3-b]pyridin-2-yl)methyl)benzoate (2.12 g, 4.19 mmol). LC/MS (Method h) R$_f$=3.00 min And 3.11 min.; MS m/z: 489 [M+H]$^+$ $^1$H NMR (DMSO-d$_6$, 300 MHz): δ 8.15 (m, 3H), 7.85 (d, J=8.4 Hz, 1H), 7.76-7.60 (m, 4H), 7.06 (d, J=5.2 Hz, 1H), 5.85 (m, 1H), 4.79 (s, 2H), 3.88 (s, 3H), 2.29 (s, 3H).

Step 3: methyl 2,4-dichloro-3-((4-methyl-1H-pyrrolo[2,3-b]pyridin-2-yl)methyl)benzoate

Using a procedure similar to Example A, Step 3, methyl 2,4-dichloro-3-((4-methyl-1H-pyrrolo[2,3-b]pyridin-2-yl)methyl)benzoate (86 mg, 93%) was obtained as a yellow solid from methyl 2,4-dichloro-3-((4-methyl-1-(phenylsulfonyl)-1H-pyrrolo[2,3-b]pyridin-2-yl)methyl)benzoate (130 mg, 0.266 mmol). LC/MS (Method h) R$_f$=2.27 min.; MS m/z: 349 [M+H]$^+$ $^1$H NMR (DMSO-d$_6$, 300 MHz): δ 11.55 (broad, 1H), 8.00 (d, J=4.9 Hz, 1H), 7.75 (d, J=8.4 Hz, 1H), 7.68 (d, J=8.4 Hz, 1H), 6.80 (d, J=4.9 Hz, 1H), 5.72 (m, 1H), 4.45 (s, 2H), 3.87 (s, 3H), 2.34 (s, 3H).

Step 4: 2-(2,6-dichloro-3-(methoxycarbonyl)benzyl)-4-methyl-W-pyrrolo[2,3-b]pyridine 7-oxide

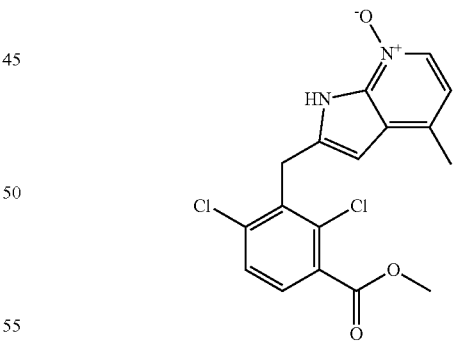

To a solution of methyl 2,4-dichloro-3-((4-methyl-1H-pyrrolo[2,3-b]pyridin-2-yl)methyl)benzoate (160 mg, 0.458 mmol) in DME (6 mL) and cooled at 0° C. was added 3-chlorobenzoperoxoic acid (138 mg, 0.802 mmol) and the reaction was stirred at room temperature for 1 hour. The reaction mixture was concentrated to dryness, the residue was solubilized in EtOAc and washed with NaHCO$_3$ saturated aqueous solution and brine. The organic layer was dried over magnesium sulfate, filtered and concentrated to dryness to give 2-(2,6-dichloro-3-(methoxycarbonyl)benzyl)-4-methyl-1H-pyrrolo[2,3-b]pyridine 7-oxide (140 mg, 84%). LC/MS (Method h) R$_t$=2.14 min.; MS m/z: 365 [M+H]$^+$ $^1$H NMR (DMSO-d$_6$, 300 MHz): δ 12.60 (broad, 1H), 7.95 (d, J=6.2 Hz, 1H), 7.77 (d, J=8.4 Hz, 1H), 7.69 (d, J=8.4 Hz, 1H), 6.82 (d, J=6.4 Hz, 1H), 5.78 (s, 1H), 4.46 (s, 2H), 3.87 (s, 3H), 2.33 (s, 3H).

Step 5: methyl 2,4-dichloro-3-((6-cyano-4-methyl-1H-pyrrolo[2,3-b]pyridin-2-yl)methyl)benzoate

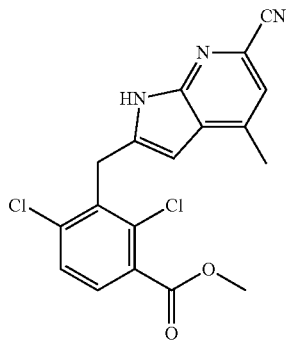 [SMILES: COC(=O)c1ccc(Cl)c(Cc2cc3c(C)cc(C#N)nc3[nH]2)c1Cl]

To a solution of 2-(2,6-dichloro-3-(methoxycarbonyl)benzyl)-4-methyl-1H-pyrrolo[2,3-b]pyridine 7-oxide (70 mg, 0.192 mmol) in ACN (4 mL) was added triethylamine (0.067 mL, 0.479 mmol) then trimethylsilyl cyanide (0.154 mL, 1.150 mmol). The reaction mixture was stirred at reflux overnight. More triethylamine (0.067 mL, 0.479 mmol) and trimethylsilyl cyanide (0.154 mL, 1.150 mmol) were added. The reaction mixture was stirred at reflux during 24 hours. The reaction mixture was quenched with NaHCO$_3$ saturated aqueous solution and extracted with DCM. The organic layer was dried over magnesium sulfate, filtered and concentrated to dryness. The residue was purified by column chromatography on silica gel (eluting with 5-20% EtOAc in cyclohexane) to give methyl 2,4-dichloro-3-((6-cyano-4-methyl-1H-pyrrolo[2,3-b]pyridin-2-yl)methyl)benzoate (22 mg, 30%).

LC/MS (Method k) R$_t$=2.93 min.; MS m/z: 374 [M+H]$^+$ $^1$H NMR (DMSO-d$_6$, 300 MHz): δ 12.29 (broad, 1H), 7.78 (d, J=8.4 Hz, 1H), 7.69 (d, J=8.4 Hz, 1H), 7.41 (s, 1H), 5.95 (s, 1H), 4.51 (s, 2H), 3.87 (s, 3H), 2.43 (s, 3H).

Step 6: methyl 2,4-dichloro-3-((6-cyano-1,4-dimethyl-1H-pyrrolo[2,3-b]pyridin-2-yl)methyl)benzoate

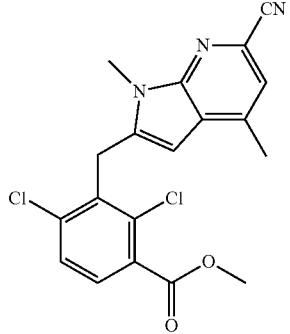 [SMILES: COC(=O)c1ccc(Cl)c(Cc2cc3c(C)cc(C#N)nc3n2C)c1Cl]

Using a procedure similar to Example P, Step 4, methyl 2,4-dichloro-3-((6-cyano-1,4-dimethyl-1H-pyrrolo[2,3-b]pyridin-2-yl)methyl)benzoate (63 mg, 95%) was obtained from methyl 2,4-dichloro-3-((6-cyano-4-methyl-1H-pyrrolo[2,3-b]pyridin-2-yl)methyl)benzoate (64 mg, 0.171 mmol).

LC/MS (Method h) R$_t$=3.06 min.; MS m/z: 388 [M+H]$^+$ $^1$H NMR (DMSO-d$_6$, 300 MHz): δ 7.83 (d, J=8.4 Hz, 1H), 7.73 (d, J=8.4 Hz, 1H), 7.45 (s, 1H), 5.82 (s, 1H), 4.56 (s, 2H), 3.93 (s, 3H), 3.88 (s, 3H), 2.41 (s, 3H).

Step 7: 2,4-dichloro-3-((6-cyano-1,4-dimethyl-1H-pyrrolo[2,3-b]pyridin-2-yl)methyl)benzoic acid

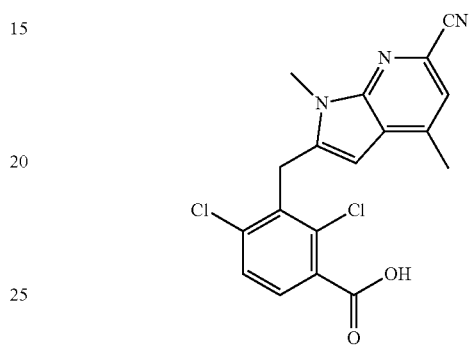

Using a procedure similar to Example A, Step 5, 2,4-dichloro-3-((6-cyano-1,4-dimethyl-1H-pyrrolo[2,3-b]pyridin-2-yl)methyl)benzoic acid (59 mg, 99%) was obtained from methyl 2,4-dichloro-3-((6-cyano-1,4-dimethyl-1H-pyrrolo[2,3-b]pyridin-2-yl)methyl)benzoate (62 mg, 0.160 mmol).

LC/MS (Method h) R$_t$=2.56 min.; MS m/z: 374 [M+H]$^+$
$^1$H NMR (DMSO-d$_6$, 300 MHz): δ 13.66 (broad, 1H), 7.76 (d, J=8.4 Hz, 1H), 7.67 (d, J=8.4 Hz, 1H), 7.45 (s, 1H), 5.81 (s, 1H), 4.55 (s, 2H), 3.93 (s, 3H), 2.42 (s, 3H).

Step 8: 2-(2,6-dichloro-3-(morpholine-4-carbonyl)benzyl)-1,4-dimethyl-W-pyrrolo[2,3-b]pyridine-6-carbonitrile

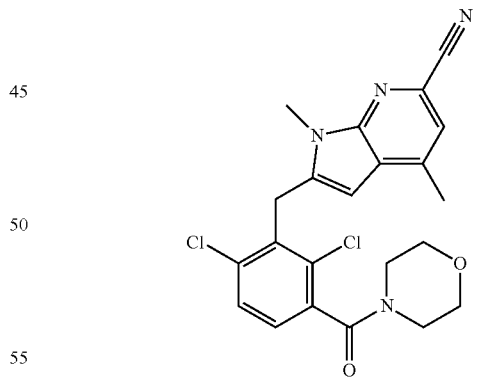

Using a procedure similar to Example A, Step 6, 2-(2,6-dichloro-3-(morpholine-4-carbonyl)benzyl)-1,4-dimethyl-1H-pyrrolo[2,3-b]pyridine-6-carbonitrile (55 mg, 79%) was obtained from 2,4-dichloro-3-((6-cyano-1,4-dimethyl-1H-pyrrolo[2,3-b]pyridin-2-yl)methyl)benzoic acid (58 mg, 0.155 mmol) and morpholine (23.5 mg, 0.23 mmol). LC/MS (Method g) R$_t$=1.57 min.; MS m/z: 443 [M+H]$^+$ $^1$H NMR (DMSO-d$_6$, 400 MHz): δ 7.69 (d, J=8.4 Hz, 1H), 7.47 (d, J=8.4 Hz, 1H), 7.46 (m, 1H), 5.76 (s, 1H), 4.53 (m, 2H), 3.92 (s, 3H), 3.65 (m, 4H), 3.53 (m, 2H), 3.18 (m, 2H), 2.42 (s, 3H).

TABLE CL

The following intermediates were prepared from 2,4-dichloro-3-((6-cyano-1,4-dimethyl-1H-pyrrolo[2,3-b]pyridin-2-yl)methyl)benzoic acid (Example CL, Step 7) using the same procedure with the appropriate amine.

| Example # | Product | Amine | R$_t$ min (Method g) | m/z ESI+ (M + H)$^+$ |
|---|---|---|---|---|
| CL-1 | 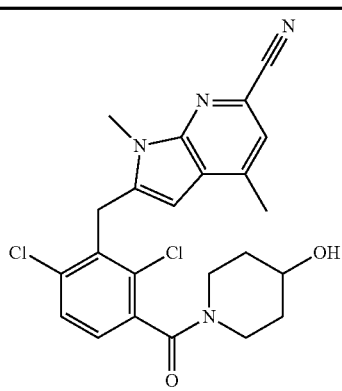 | 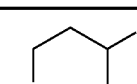 | 1.44 | 457 |
| CL-2 | 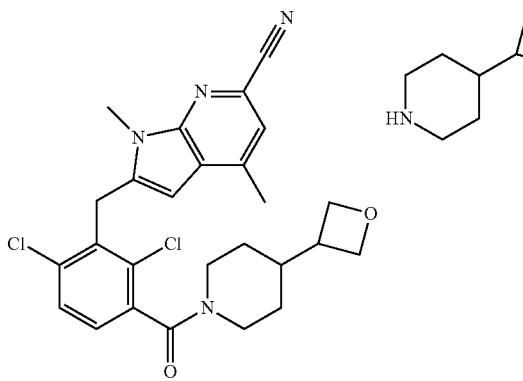 | 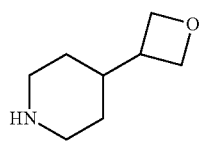 | 1.61 | 497 |

Example CM: (2,4-dichloro-3-((1,4-dimethyl-6-(trifluoromethyl)-1H-pyrrolo[2,3-b]pyridin-2-yl)methyl)phenyl)(morpholino)methanone

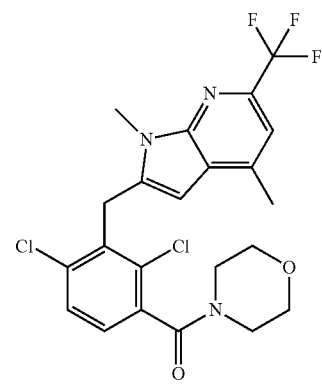

Example CM1: (2,4-dichloro-3-((6-chloro-1,4-dimethyl-1H-pyrrolo[2,3-b]pyridin-2-yl)methyl)phenyl)(morpholino)methanone

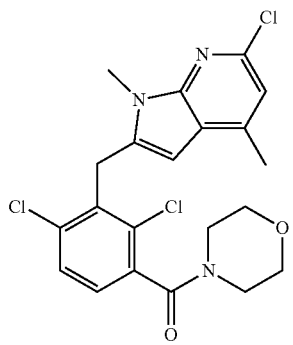

Step 1: methyl 2-(2,6-dichloro-3-(methoxycarbonyl)benzyl)-6-iodo-4-methyl-1H-pyrrolo[2,3-b]pyridine-1-carboxylate

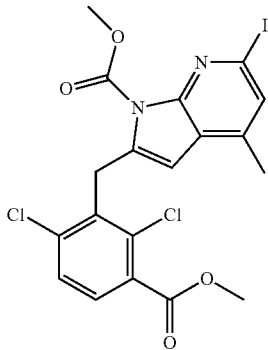 [SMILES: COC(=O)c1ccc(Cl)c(Cc2cc3c(C)cc(I)nc3n2C(=O)OC)c1Cl]

To a solution of 2-(2,6-dichloro-3-(methoxycarbonyl)benzyl)-4-methyl-1H-pyrrolo[2,3-b]pyridine 7-oxide (prepared similar to Example CL, Step 4) (60 mg, 0.164 mmol) in THF (3 mL) was added bis(trimethylsilyl)amine (0.034 mL, 0.164 mmol), iodotrimethylsilane (0.067 mL, 0.493 mmol) then methyl chloroformate (0.025 mL, 0.33 mmol) dropwise. The reaction was stirred 20 hours at room temperature. The reaction mixture was concentrated under reduced pressure ant the residue was dissolved in EtOAc. The organic layer was washed successively with saturated NaHCO₃ aqueous solution, brine and dried over magnesium sulfate, filtered then concentrated. The residue was purified by column chromatography on silica gel (eluting with 0-5% EtOAc in cyclohexane) to give methyl 2-(2,6-dichloro-3-(methoxycarbonyl)benzyl)-6-iodo-4-methyl-1H-pyrrolo[2,3-b]pyridine-1-carboxylate (33 mg, 14%) as a pale yellow solid. The compound was used directly in the next step. LC/MS (Method h) $R_t$=3.30 min.; MS m/z: 533 [M+H]⁺

Step 2: methyl 2-(2,6-dichloro-3-(methoxycarbonyl)benzyl)-4-methyl-6-(trifluoromethyl)-1H-pyrrolo[2,3-b]pyridine-1-carboxylate and methyl 6-chloro-2-(2,6-dichloro-3-(methoxycarbonyl)benzyl)-4-methyl-W-pyrrolo[2,3-b]pyridine-1-carboxylate

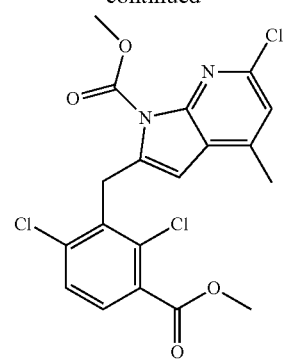

To a solution of methyl 2-(2,6-dichloro-3-(methoxycarbonyl)benzyl)-6-iodo-4-methyl-1H-pyrrolo[2,3-b]pyridine-1-carboxylate (134 mg, 0.251 mmol) in DMF (3 mL) were added at room temperature methyl 2,2-difluoro-2-(fluorosulfonyl)acetate (0.127 mL, 1.005 mmol) and copper(I) iodide (47.9 mg, 0.251 mmol), and the reaction mixture was stirred at 115° C. for 24 hours in a sealed tube. The residue was diluted in EtOAc. The organic layer was washed successively with water, with 10% LiCl aqueous solution and brine and dried over magnesium sulfate, filtered then concentrated. The residue was purified by column chromatography on silica gel (eluting with 10-20% EtOAc in cyclohexane) to give a mixture of methyl 2-(2,6-dichloro-3-(methoxycarbonyl)benzyl)-4-methyl-6-(trifluoromethyl)-1H-pyrrolo[2,3-b]pyridine-1-carboxylate LC/MS (Method h) $R_t$=3.30 min.; MS m/z: 475 [M+H]⁺ and methyl 6-chloro-2-(2,6-dichloro-3-(methoxycarbonyl)benzyl)-4-methyl-1H-pyrrolo[2,3-b]pyridine-1-carboxylate (120 mg) with a 43/57 ratio. LC/MS (Method h) $R_t$=3.12 min.; MS m/z: 441 [M+H]⁺

Step 3: 2,4-dichloro-3-((4-methyl-6-(trifluoromethyl)-1H-pyrrolo[2,3-b]pyridin-2-yl)methyl)benzoic acid and 2,4-dichloro-3-((6-chloro-4-methyl-1H-pyrrolo[2,3-b]pyridin-2-yl)methyl)benzoic acid

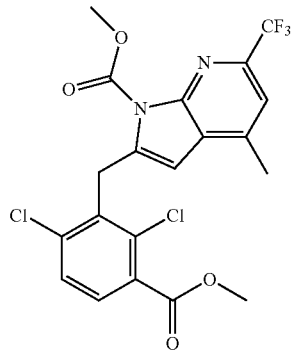


-continued

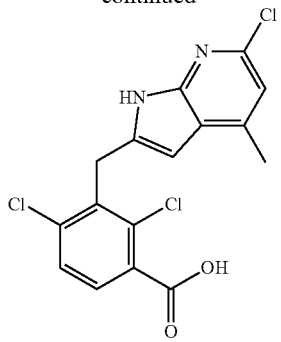

Using a procedure similar to Example F, Step 4, 2,4-dichloro-3-((4-methyl-6-(trifluoromethyl)-1H-pyrrolo[2,3-b]pyridin-2-yl)methyl)benzoic acid LC/MS (Method h) $R_t$=2.65 min.; MS m/z: 403 [M+H]$^+$ and 2,4-dichloro-3-((6-chloro-4-methyl-1H-pyrrolo[2,3-b]pyridin-2-yl)methyl)benzoic acid (85 mg) LC/MS (Method h) $R_t$=2.48 min.; MS m/z: 369 [M+H]$^+$ were obtained with a 35/65 ratio from a mixture of methyl 2-(2,6-dichloro-3-(methoxycarbonyl)benzyl)-4-methyl-6-(trifluoromethyl)-1H-pyrrolo[2,3-b]pyridine-1-carboxylate and methyl 6-chloro-2-(2,6-dichloro-3-(methoxycarbonyl)benzyl)-4-methyl-1H-pyrrolo[2,3-b]pyridine-1-carboxylate (120 mg) with a 43/57 ratio.

Step 4: (2,4-dichloro-3-((4-methyl-6-(trifluoromethyl)-1H-pyrrolo[2,3-b]pyridin-2-yl)methyl)phenyl)(morpholino)methanone and (2,4-dichloro-3-((6-chloro-4-methyl-1H-pyrrolo[2,3-b]pyridin-2-yl)methyl)phenyl)(morpholino)methanone

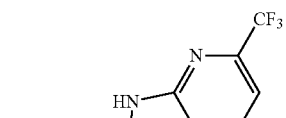

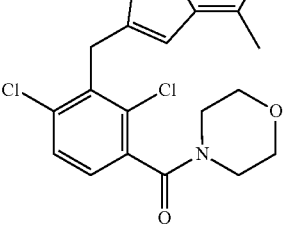

Using a procedure similar to Example A, Step 6, (2,4-dichloro-3-((4-methyl-6-(trifluoromethyl)-1H-pyrrolo[2,3-b]pyridin-2-yl)methyl)phenyl)(morpholino)methanone LC/MS (Method h) $R_t$=2.68 min.;

MS m/z: 472 [M+H]$^+$ and (2,4-dichloro-3-((6-chloro-4-methyl-1H-pyrrolo[2,3-b]pyridin-2-yl)methyl)phenyl)(morpholino)methanone (102 mg) LC/MS (Method h) $R_t$=2.51 min.; MS m/z: 438 [M+H]$^+$ were obtained with a 39/61 ratio from a mixture of 2,4-dichloro-3-((4-methyl-6-(trifluoromethyl)-1H-pyrrolo[2,3-b]pyridin-2-yl)methyl)benzoic acid and 2,4-dichloro-3-((6-chloro-4-methyl-1H-pyrrolo[2,3-b]pyridin-2-yl)methyl)benzoic acid (102 mg) with a 35/65 ratio.

Step 5: (2,4-dichloro-3-((1,4-dimethyl-6-(trifluoromethyl)-1H-pyrrolo[2,3-b]pyridin-2-yl)methyl)phenyl)(morpholino)methanone and (2,4-dichloro-3-((6-chloro-1,4-dimethyl-1H-pyrrolo[2,3-b]pyridin-2-yl)methyl)phenyl)(morpholino)methanone

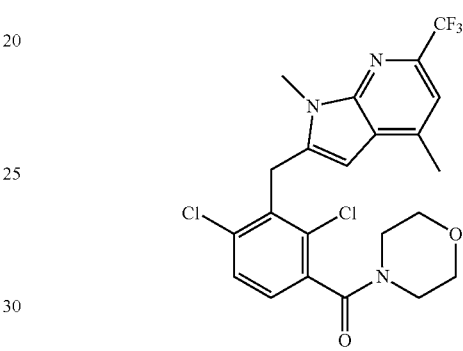

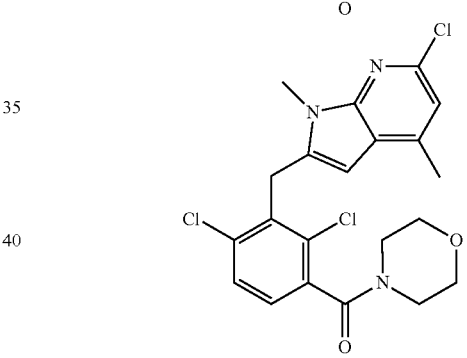

Using a procedure similar to Example P, Step 4, (2,4-dichloro-3-((1,4-dimethyl-6-(trifluoromethyl)-1H-pyrrolo[2,3-b]pyridin-2-yl)methyl)phenyl)(morpholino)methanone (24 mg, 23%)

LC/MS (Method g) $R_t$=1.83 min.; MS m/z: 486 [M+H]$^+$. $^1$H NMR (DMSO-d$_6$, 400 MHz): δ 7.69 (d, J=8.4 Hz, 1H), 7.47 (d, J=8.4 Hz, 1H), 7.34 (d, J=0.9 Hz, 1H), 5.81 (m, 1H), 4.51 (m, 2H), 3.93 (s, 3H), 3.65 (m, 4H), 3.54 (m, 2H), 3.20 (m, 2H), 2.46 (s, 3H) and (2,4-dichloro-3-((6-chloro-1,4-dimethyl-1H-pyrrolo[2,3-b]pyridin-2-yl)methyl)phenyl)(morpholino)methanone (30 mg, 31%)

LC/MS (Method g) $R_t$=1.72 min.; MS m/z: 452 [M+H]$^+$ $^1$H NMR (DMSO-d$_6$, 400 MHz): δ 7.67 (d, J=8.4 Hz, 1H), 7.45 (d, J=8.4 Hz, 1H), 6.94 (d, J=0.9 Hz, 1H), 5.68 (m, 1H), 4.44 (m, 2H), 3.84 (s, 3H), 3.65 (m, 4H), 3.52 (m, 2H), 3.19 (m, 2H), 2.35 (s, 3H) were obtained from a mixture of (2,4-dichloro-3-((4-methyl-6-(trifluoromethyl)-1H-pyrrolo[2,3-b]pyridin-2-yl)methyl)phenyl)(morpholino)methanone and (2,4-dichloro-3-((6-chloro-4-methyl-1H-pyrrolo[2,3-b]pyridin-2-yl)methyl)phenyl)(morpholino)methanone (100 mg) with a 39/61 ratio.

Example CN: (2,4-dichloro-3-(hydroxy(1-methyl-5-(trifluoromethyl)-1H-pyrrolo[3,2-b]pyridin-2-yl)methyl)phenyl)(morpholino)methanone

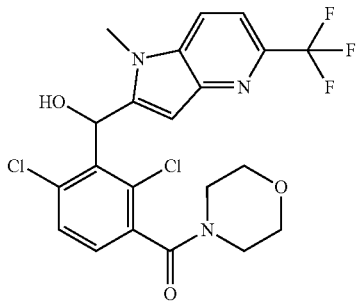 [SMILES: Cn1c(C(O)c2c(Cl)ccc(C(=O)N3CCOCC3)c2Cl)cc2nc(C(F)(F)F)ccc21]

Step 1: methyl 3-((1-((3-(tert-butyl)phenyl)sulfonyl)-5-(trifluoromethyl)-1H-pyrrolo[3,2-b]pyridin-2-yl)(hydroxy)methyl)-2,4-dichlorobenzoate

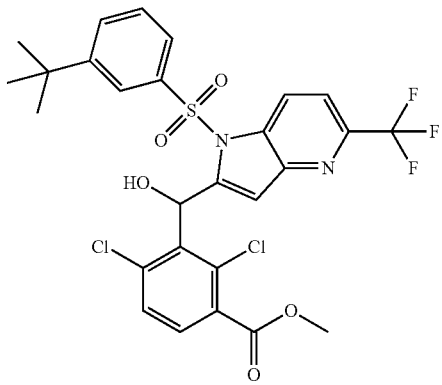 [SMILES: COC(=O)c1ccc(Cl)c(C(O)c2cc3nc(C(F)(F)F)ccc3n2S(=O)(=O)c2cccc(C(C)(C)C)c2)c1Cl]

Using a procedure similar to Example A, Step 1, methyl 3-((1-((3-(tert-butyl)phenyl)sulfonyl)-5-(trifluoromethyl)-1H-pyrrolo[3,2-b]pyridin-2-yl)(hydroxy)methyl)-2,4-dichlorobenzoate (540 mg, 76%) was prepared from 3-(tert-butyl)-N-(2-iodo-6-(trifluoromethyl)pyridin-3-yl)benzenesulfonamide (described in WO2007/026104) (500 mg, 1.032 mmol) and methyl 2,4-dichloro-3-(1-hydroxyprop-2-yn-1-yl)benzoate (Preparation #1) (348 mg, 1.342 mmol). LC/MS (Method h) $R_t$=3.43 min.; MS m/z: 615 [M+H]$^+$. $^1$H NMR (DMSO-d$_6$, 300 MHz,) δ 8.70 (d, J=8.7 Hz, 1H), 7.94 (m, 1H), 7.87 (d, J=8.7 Hz, 1H), 7.76 (d, J=7.9 Hz, 1H), 7.70 (d, J=7.9 Hz, 1H), 7.68 (d, J=8.7 Hz, 1H), 7.53 (m, 2H), 7.02 (broad, 1H), 6.95 (broad, 1H), 6.92 (s, 1H), 3.86 (s, 3H), 1.21 (s, 9H).

Step 2: 2,4-dichloro-3-(hydroxy(5-(trifluoromethyl)-1H-pyrrolo[3,2-b]pyridin-2-yl)methyl)benzoic acid

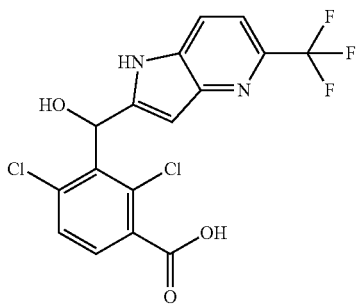 [SMILES: O=C(O)c1ccc(Cl)c(C(O)c2cc3nc(C(F)(F)F)ccc3[nH]2)c1Cl]

To a solution of methyl 3-((1-((3-(tert-butyl)phenyl)sulfonyl)-5-(trifluoromethyl)-1H-pyrrolo[3,2-b]pyridin-2-yl)(hydroxy)methyl)-2,4-dichlorobenzoate (500 mg, 0.812 mmol) in THF (5 mL) and water (2 mL) was added lithium hydroxide (97 mg, 4.06 mmol) The reaction mixture was stirred at room temperature overnight. Lithium hydroxide (97 mg, 4.06 mmol) (10 mg, 1 eq) was added and the reaction was refluxed for 5 hours and stirred overnight at room temperature. The reaction mixture was diluted with water and acidified with 1M HCl aqueous solution. The obtained aqueous layer was extracted with DCM and the obtained organic layer was washed with brine, dried over magnesium sulfate, filtered and concentrated under reduced pressure to give 2,4-dichloro-3-(hydroxy(5-(trifluoromethyl)-1H-pyrrolo[3,2-b]pyridin-2-yl)methyl)benzoic acid (374 mg, 45%) as a brown solid.

LC/MS (Method h) $R_t$=1.85 min.; MS m/z: 405 [M+H]$^+$. $^1$H NMR (DMSO-d$_6$, 300 MHz,) δ 11.76 (s, 1H), 7.90 (d, J=9 Hz, 1H), 7.68 (d, J=9 Hz, 1H), 7.56 (d, J=9 Hz, 1H), 7.50 (d, J=9 Hz, 1H), 6.82 (broad, 1H), 6.20 (s, 1H).

Step 3: (2,4-dichloro-3-(hydroxy(5-(trifluoromethyl)-1H-pyrrolo[3,2-b]pyridin-2-yl)methyl)phenyl)(morpholino)methanone

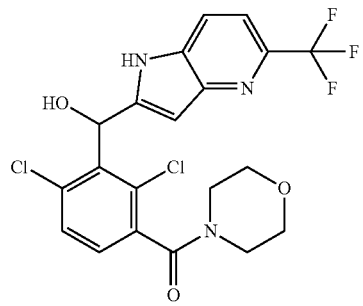 [SMILES: O=C(c1ccc(Cl)c(C(O)c2cc3nc(C(F)(F)F)ccc3[nH]2)c1Cl)N1CCOCC1]

Using a procedure similar to Example A, Step 6, (2,4-dichloro-3-(hydroxy(5-(trifluoromethyl)-1H-pyrrolo[3,2-b]pyridin-2-yl)methyl)phenyl)(morpholino)methanone (87 mg, 15%) was prepared from 2,4-dichloro-3-(hydroxy(5-(trifluoromethyl)-1H-pyrrolo[3,2-b]pyridin-2-yl)methyl)benzoic acid (370 mg, 0.913 mmol) and used crude in the next step and morpholine (239 mg, 2.74 mmol). LC/MS (Method h) $R_t$=2.07 min.; MS m/z: 474 [M+H]$^+$.

Step 4: (2,4-dichloro-3-(hydroxy(1-methyl-5-(trifluoromethyl)-1H-pyrrolo[3,2-b]pyridin-2-yl)methyl)phenyl)(morpholino)methanone

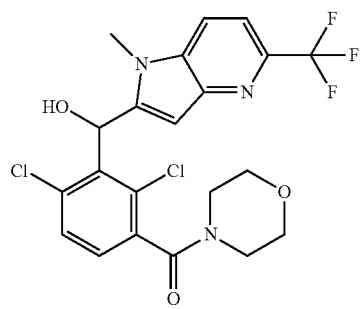 [SMILES: Cn1c(C(O)c2c(Cl)ccc(C(=O)N3CCOCC3)c2Cl)cc2nc(C(F)(F)F)ccc21]

Using a procedure similar to Example P, Step 4 (2,4-dichloro-3-(hydroxy(1-methyl-5-(trifluoromethyl)-1H-pyrrolo[3,2-b]pyridin-2-yl)methyl)phenyl)(morpholino)methanone (28 mg, 34%) was prepared from (2,4-dichloro-3-(hydroxy(5-(trifluoromethyl)-1H-pyrrolo[3,2-b]pyridin-2-yl)methyl)phenyl)(morpholino)methanone (80 mg, 0.169 mmol). LC/MS (Method g) R$_t$=1.36 min.;

MS m/z: 488 [M+H]$^+$. $^1$H NMR (DMSO-d$_6$, 400 MHz,) δ 8.13 (m, 1H), 7.62 (m, 2H), 7.46 (d, J=8 Hz, 1H), 6.73 (m, 1H), 6.65 (m, 1H), 6.32 and 6.29 (s, 1H), 3.88 and 3.86 (s, 3H), 3.66 (m, 3H), 3.55 (m, 3H), 3.21 (m, 2H).

Example CO: (2,4-dichloro-3-((1-methyl-6-(trifluoromethyl)-1H-pyrrolo[3,2-b]pyridin-2-yl)methyl)phenyl)(morpholino)methanone

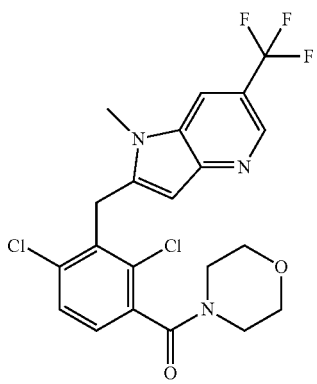 [SMILES: Cn1c(Cc2c(Cl)ccc(C(=O)N3CCOCC3)c2Cl)cc2ncc(C(F)(F)F)cc21]

Step 1: (2,4-dichloro-3-(hydroxy(1-(phenylsulfonyl)-6-(trifluoromethyl)-1H-pyrrolo[3,2-b]pyridin-2-yl)methyl)phenyl)(morpholino)methanone

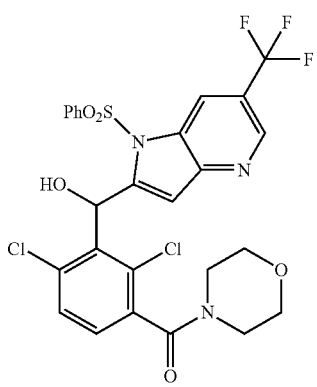

Using a procedure similar to Example A, Step 1, (2,4-dichloro-3-(hydroxy(1-(phenylsulfonyl)-6-(trifluoromethyl)-1H-pyrrolo[3,2-b]pyridin-2-yl)methyl)phenyl)(morpholino)methanone (520 mg, 87%) was prepared from N-(2-bromo-5-(trifluoromethyl)pyridin-3-yl)benzenesulfonamide (Preparation #26) (370 mg, 0.971 mmol) and (2,4-dichloro-3-(1-hydroxyprop-2-yn-1-yl)phenyl)(morpholino)methanone (Preparation #3) (396 mg, 1.262 mmol). LC/MS (Method g) R$_t$=1.62 min.; MS m/z: 614 [M+H]$^+$. $^1$H NMR (DMSO-d$_6$, 400 MHz,) δ 8.92 (s, 1H), 8.56 (m, 1H), 7.89 (m, 2H), 7.74 (m, 1H), 7.60 (m, 2H), 7.52 and 7.45 (d, J=8 Hz, 1H), 7.39 (m, 1H), 7.03 and 6.92 (s, 1H), 6.98 and 6.88 (m, 1H), 6.87 and 6.83 (d, J=8 Hz, 1H), 3.64 (m, 4H), 3.54 (m, 2H), 3.17 (m, 2H).

Step 2: (2,4-dichloro-3-((1-(phenylsulfonyl)-6-(trifluoromethyl)-1H-pyrrolo[3,2-b]pyridin-2-yl)methyl)phenyl)(morpholino)methanone

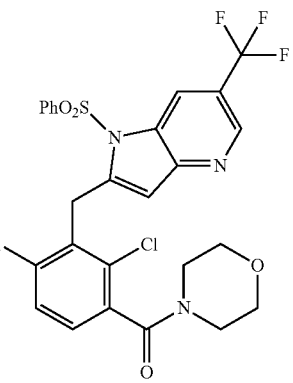

Using a procedure similar to Example Z, Step 2, (2,4-dichloro-3-((1-(phenylsulfonyl)-6-(trifluoromethyl)-1H-pyrrolo[3,2-b]pyridin-2-yl)methyl)phenyl)(morpholino)methanone (314 mg, 96%) was prepared from (2,4-dichloro-3-(hydroxy(1-(phenylsulfonyl)-6-(trifluoromethyl)-1H-pyrrolo[3,2-b]pyridin-2-yl)methyl)phenyl)(morpholino)methanone (336 mg, 0.547 mmol).

LC/MS (Method h) R$_t$=3.05 min.; MS m/z: 598 [M+H]$^+$.
$^1$H NMR (DMSO-d$_6$, 300 MHz,) δ 8.89 (m, 1H), 8.70 (m, 1H), 8.05 (m, 2H), 7.83 (m, 1H), 7.67 (m, 3H), 7.46 (d, J=9 Hz, 1H), 6.18 (s, 1H), 4.58 (m, 2H), 3.64 (m, 4H), 3.49 (m, 2H), 3.21 (m, 2H).

Step 3: (2,4-dichloro-3-((6-(trifluoromethyl)-1H-pyrrolo[3,2-b]pyridin-2-yl)methyl)phenyl)(morpholino)methanone

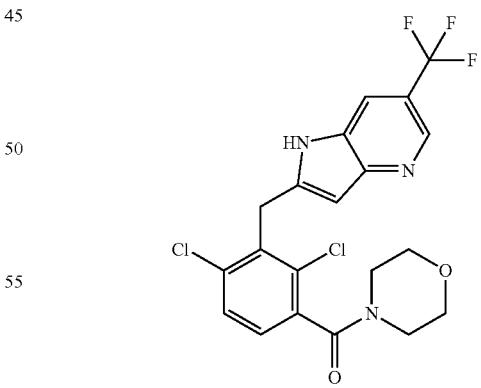

Using a procedure similar to Example A, Step 3, (2,4-dichloro-3-((6-(trifluoromethyl)-1H-pyrrolo[3,2-b]pyridin-2-yl)methyl)phenyl)(morpholino)methanone (237 mg, 100%) was prepared from (2,4-dichloro-3-((1-(phenylsulfonyl)-6-(trifluoromethyl)-1H-pyrrolo[3,2-b]pyridin-2-yl)methyl)phenyl)(morpholino)methanone (310 mg, 0.518 mmol). LC/MS (Method h) R$_t$=2.10 min.;

MS m/z: 456 [M−H]⁻. ¹H NMR (DMSO-d₆, 300 MHz,) δ 11.83 (broad, 1H), 8.56 (m, 1H), 8.02 (m, 1H), 7.66 (d, J=9 Hz, 1H), 7.46 (d, J=9 Hz, 1H), 6.13 (s, 1H), 4.53 (s, 2H), 3.65 (m, 4H), 3.54 (m, 2H), 3.19 (m, 2H).

Step 4: (2,4-dichloro-3-((1-methyl-6-(trifluoromethyl)-1H-pyrrolo[3,2-b]pyridin-2-yl)methyl)phenyl)(morpholino)methanone

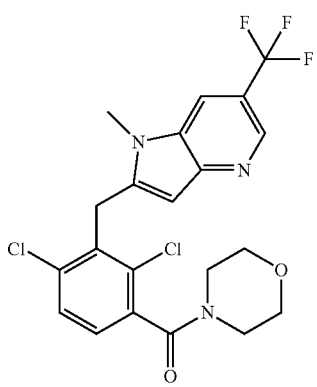 [SMILES: Cn1c(Cc2c(Cl)ccc(C(=O)N3CCOCC3)c2Cl)cc2ncc(C(F)(F)F)cc21]

Using a procedure similar to Example A, Step 4, (2,4-dichloro-3-((1-methyl-6-(trifluoromethyl)-1H-pyrrolo[3,2-b]pyridin-2-yl)methyl)phenyl)(morpholino)methanone (16 mg, 31%) was prepared from (2,4-dichloro-3-((6-(trifluoromethyl)-1H-pyrrolo[3,2-b]pyridin-2-yl)methyl)phenyl)(morpholino)methanone (50 mg, 0.109 mmol). LC/MS (Method g) R$_t$=1.46 min.;

MS m/z: 472 [M+H]⁺. ¹H NMR (DMSO-d₆, 400 MHz,) δ 8.57 (m, 1H), 8.37 (m, 1H), 7.69 (d, J=8 Hz, 1H), 7.47 (d, J=8 Hz, 1H), 5.85 (s, 1H), 4.52 (s, 2H), 3.98 (s, 3H), 3.56 (m, 4H), 3.55 (m, 2H), 3.21 (m, 2H).

Example CP: (2,4-dichloro-3-(1-methyl-6-(trifluoromethyl)-1H-pyrrolo[3,2-b]pyridine-2-carbonyl)phenyl)(morpholino)methanone

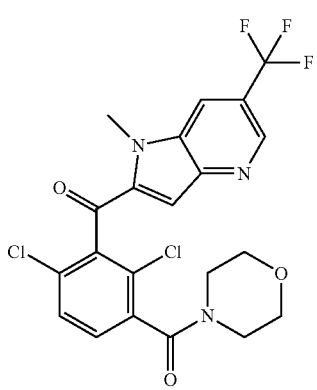 [SMILES: Cn1c(C(=O)c2c(Cl)ccc(C(=O)N3CCOCC3)c2Cl)cc2ncc(C(F)(F)F)cc21]

Step 1: (2,4-dichloro-3-(1-(phenylsulfonyl)-6-(trifluoromethyl)-1H-pyrrolo[3,2-b]pyridine-2-carbonyl)phenyl)(morpholino)methanone

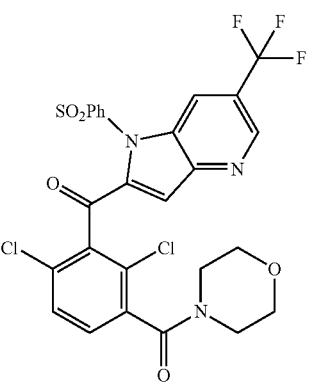

To a solution of (2,4-dichloro-3-(hydroxy(1-(phenylsulfonyl)-6-(trifluoromethyl)-1H-pyrrolo[3,2-b]pyridin-2-yl)methyl)phenyl)(morpholino)methanone (Example CO, Step 1) (580 mg, 0.944 mmol) in dichloroethane (10 mL) was added manganese dioxide (821 mg, 9.44 mmol). and the mixture was stirred at 85° C. for 24 hours. The mixture was filtered and washed with DCM, and ACN. The filtrate was concentrated to give (2,4-dichloro-3-(1-(phenylsulfonyl)-6-(trifluoromethyl)-1H-pyrrolo[3,2-b]pyridine-2-carbonyl)phenyl)(morpholino)methanone (540 mg, 80%) as a beige powder.

LC/MS (Method h) R$_t$=2.92 min.; MS m/z: 612 [M+H]⁺.

¹H NMR (DMSO-d₆, 300 MHz,) δ 9.13 (s, 1H), 8.93 (s, 1H), 8.26 (d, J=9 Hz, 2H), 7.85 (broad, 1H), 7.84 (m, 1H), 7.71 (m, 3H), 7.64 (d, J=9 Hz, 1H), 3.66 (m, 4H), 3.53 (m, 2H), 3.25 (m, 2H).

Step 2: (2,4-dichloro-3-(6-(trifluoromethyl)-1H-pyrrolo[3,2-b]pyridine-2-carbonyl)phenyl)(morpholino)methanone

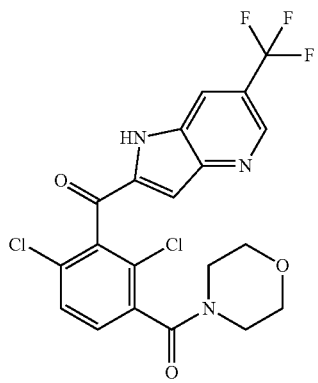 [SMILES: O=C(c1cc2ncc(C(F)(F)F)cc2[nH]1)c1c(Cl)ccc(C(=O)N2CCOCC2)c1Cl]

Using a procedure similar to Example A, Step 3, (2,4-dichloro-3-(6-(trifluoromethyl)-1H-pyrrolo[3,2-b]pyridine-2-carbonyl)phenyl)(morpholino)methanone (363 mg, 86%) was prepared from (2,4-dichloro-3-(1-(phenylsulfonyl)-6-(trifluoromethyl)-1H-pyrrolo[3,2-b]pyridine-2-carbonyl)phenyl)(morpholino)methanone (530 mg, 0.865 mmol). LC/MS (Method h) R$_t$=2.31 min.;

MS m/z: 472 [M+H]⁺. ¹H NMR (DMSO-$d_6$, 300 MHz,) δ 13.00 (broad, 1H), 8.84 (m, 1H), 8.20 (m, 1H), 7.77 (d, J=9 Hz, 1H), 7.68 (d, J=9 Hz, 1H), 7.50 and 7.20 (broad, 1H), 3.66 (m, 4H), 3.57 (m, 2H), 3.40 (m, 1H), 3.19 (m, 1H).

Step 3: (2,4-dichloro-3-(1-methyl-6-(trifluoromethyl)-1H-pyrrolo[3,2-b]pyridine-2-carbonyl)phenyl)(morpholino)methanone

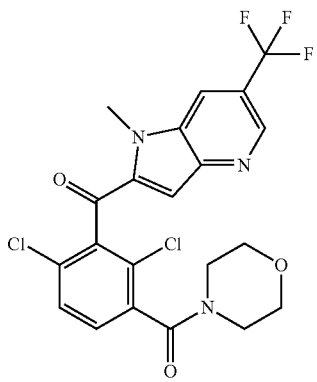 [SMILES: Cn1c(C(=O)c2c(Cl)ccc(C(=O)N3CCOCC3)c2Cl)cc2ncc(C(F)(F)F)cc21]

Using a procedure similar to Example A, Step 4, (2,4-dichloro-3-(1-methyl-6-(trifluoromethyl)-1H-pyrrolo[3,2-b]pyridine-2-carbonyl)phenyl)(morpholino)methanone (28 mg, 27%) was prepared from (2,4-dichloro-3-(6-(trifluoromethyl)-1H-pyrrolo[3,2-b]pyridine-2-carbonyl)phenyl)(morpholino)methanone (100 mg, 0.212 mmol). LC/MS (Method g) $R_t$=1.56 min.;

MS m/z: 486 [M+H]⁺. ¹H NMR (DMSO-$d_6$, 400 MHz,) δ 8.87 (m, 1H), 8.75 (m, 1H), 7.77 (d, J=8 Hz, 1H), 7.66 (d, J=8 Hz, 1H), 7.45 (broad, 1H), 4.27 (s, 3H), 3.66 (m, 4H), 3.55 (m, 2H), 3.26 (m, 2H).

Example CQ: (2,4-dichloro-3-((1-methyl-6-(trifluoromethyl)-1H-pyrrolo[3,2-c]pyridin-2-yl)methyl)phenyl)(morpholino)methanone

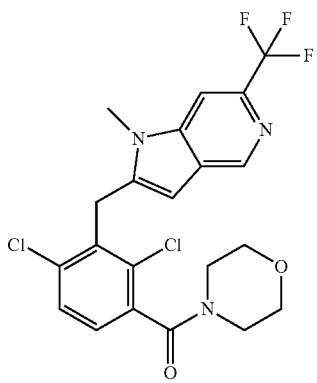 [SMILES: Cn1c(Cc2c(Cl)ccc(C(=O)N3CCOCC3)c2Cl)cc2cnc(C(F)(F)F)cc21]

Step 1: (2,4-dichloro-3-(hydroxy(1-(phenylsulfonyl)-6-(trifluoromethyl)-1H-pyrrolo[3,2-c]pyridin-2-yl)methyl)phenyl)(morpholino)methanone

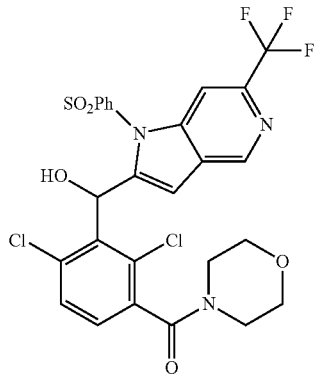

Using a procedure similar to Example A, Step 1, (2,4-dichloro-3-(hydroxy(1-(phenylsulfonyl)-6-(trifluoromethyl)-1H-pyrrolo[3,2-c]pyridin-2-yl)methyl)phenyl)(morpholino)methanone (1.94 g, 68%) was prepared from N-(5-iodo-2-(trifluoromethyl)pyridin-4-yl)benzenesulfonamide (Preparation #27) (2 g, 4.67 mmol) and (2,4-dichloro-3-(1-hydroxyprop-2-yn-1-yl)phenyl)(tetrahydro-2H-pyran-4-yl)methanone (Preparation #3) (1.902 g, 6.07 mmol). LC/MS (Method h) $R_t$=2.63 min.; MS m/z: 614 [M+H]⁺. ¹H NMR (DMSO-$d_6$, 300 MHz) δ 9.07 and 9.05 (s, 1H), 8.32 and 8.29 (s, 1H), 7.95 (m, 2H), 7.75 (m, 1H), 7.63 (m, 2H), 7.51 (m, 1H), 7.40 (m, 1H), 6.97 (m, 2H), 6.79 and 6.74 (d, J=8 Hz, 1H), 3.65 (m, 4H), 3.54 (m, 2H), 3.16 (m, 2H).

Step 2: (2,4-dichloro-3-((1-(phenylsulfonyl)-6-(trifluoromethyl)-1H-pyrrolo[3,2-c]pyridin-2-yl)methyl)phenyl)(morpholino)methanone

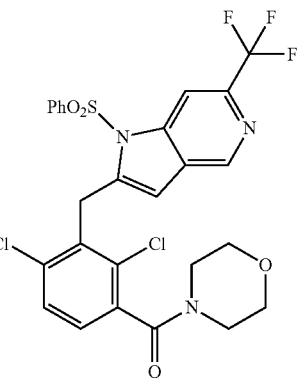

Using a procedure similar to Example Z, Step 2, (2,4-dichloro-3-((1-(phenylsulfonyl)-6-(trifluoromethyl)-1H-pyrrolo[3,2-c]pyridin-2-yl)methyl)phenyl)(morpholino)methanone (2.1 g, 100%) was prepared from (2,4-dichloro-3-(hydroxy(1-(phenylsulfonyl)-6-(trifluoromethyl)-1H-pyrrolo[3,2-c]pyridin-2-yl)methyl)phenyl)(morpholino)methanone (1.93 g, 3.14 mmol). LC/MS (Method k) $R_t$=3.14 min.; MS m/z: 598 [M+H]⁺. ¹H NMR (DMSO-$d_6$, 300 MHz,) δ 8.94 (s, 1H), 8.48 (s, 1H), 8.05 (m, 1H), 7.96 (m, 1H), 7.81 (m, 1H), 7.66 (m, 2H), 7.47 (m, 1H), 7.41 (m, 1H), 6.21 (s, 1H), 4.52 (m, 2H), 3.64 (m, 4H), 3.49 (m, 2H), 3.16 (m, 2H).

Step 3: (2,4-dichloro-3-((6-(trifluoromethyl)-1H-pyrrolo[3,2-c]pyridin-2-yl)methyl)phenyl)(morpholino)methanone

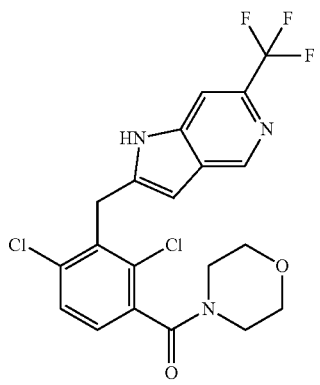 [SMILES: O=C(c1ccc(Cl)c(Cc2cc3cnc(C(F)(F)F)cc3[nH]2)c1Cl)N1CCOCC1]

Using a procedure similar to Example A, Step 3, (2,4-dichloro-3-((6-(trifluoromethyl)-1H-pyrrolo[3,2-c]pyridin-2-yl)methyl)phenyl)(morpholino)methanone (1.05 g, 65%) was prepared from (2,4-dichloro-3-((1-(phenylsulfonyl)-6-(trifluoromethyl)-1H-pyrrolo[3,2-c]pyridin-2-yl)methyl)phenyl)(morpholino)methanone (2.1 g, 3.51 mmol). LC/MS (Method k) $R_t$=2.35 min.; MS m/z: 458 [M+H]$^+$. $^1$H NMR (DMSO-d$_6$, 300 MHz,) δ 12.05 (broad, 1H), 8.80 (s, 1H), 7.78 (s, 1H), 7.66 (d, J=9 Hz, 1H), 7.43 (d, J=9 Hz, 1H), 6.14 (s, 1H), 4.49 (s, 2H), 3.66 (m, 4H), 3.54 (m, 2H), 3.18 (m, 2H).

Step 4: (2,4-dichloro-3-((1-methyl-6-(trifluoromethyl)-1H-pyrrolo[3,2-c]pyridin-2-yl)methyl)phenyl)(morpholino)methanone

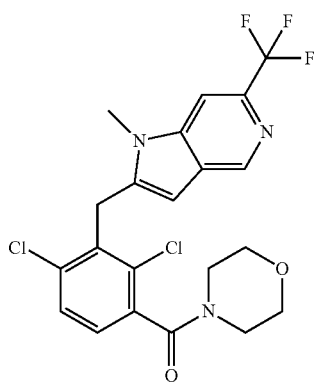 [SMILES: Cn1c(Cc2c(Cl)ccc(C(=O)N3CCOCC3)c2Cl)cc2cnc(C(F)(F)F)cc21]

Using a procedure similar to Example A, Step 4 (2,4-dichloro-3-((1-methyl-6-(trifluoromethyl)-1H-pyrrolo[3,2-c]pyridin-2-yl)methyl)phenyl)(morpholino)methanone (78 mg, 50%) was prepared from (2,4-dichloro-3-((6-(trifluoromethyl)-1H-pyrrolo[3,2-c]pyridin-2-yl)methyl)phenyl)(morpholino)methanone (150 mg, 0.327 mmol). LC/MS (Method g) $R_t$=2.36 min.;

MS m/z: 472 [M+H]$^+$. $^1$H NMR (DMSO-d$_6$, 400 MHz,) δ 8.76 (s, 1H), 8.09 (s, 1H), 7.69 (d, J=8 Hz, 1H), 7.47 (d, J=8 Hz, 1H), 5.91 (s, 1H), 4.49 (s, 2H), 3.98 (s, 3H), 3.65 (m, 4H), 3.55 (m, 2H), 3.19 (m, 2H).

Example CR: (2,4-dichloro-3-((1,4-dimethyl-6-(trifluoromethyl)-1H-pyrrolo[3,2-c]pyridin-2-yl)methyl)phenyl)(morpholino)methanone

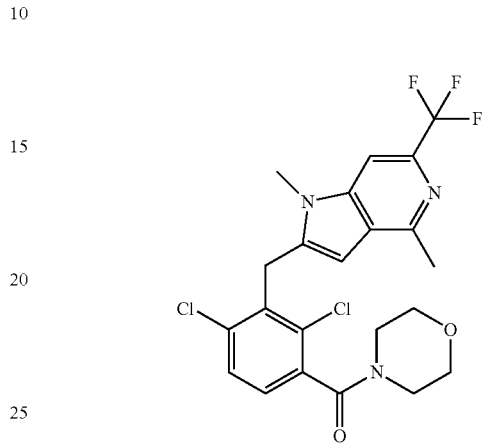

Step 1: (2,4-dichloro-3-(hydroxy(4-methyl-1-(phenylsulfonyl)-6-(trifluoromethyl)-1H-pyrrolo[3,2-c]pyridin-2-yl)methyl)phenyl)(morpholino)methanone

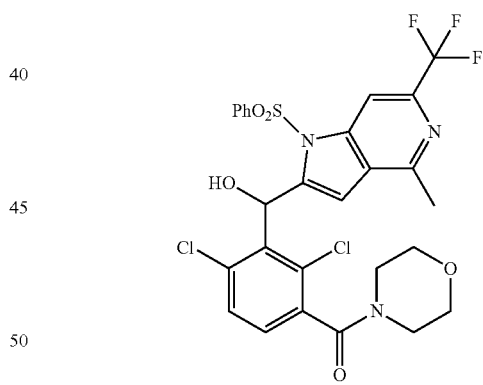

Using a procedure similar to Example A, Step 1, (2,4-dichloro-3-((1,4-dimethyl-6-(trifluoromethyl)-1H-pyrrolo[3,2-c]pyridin-2-yl)methyl)phenyl)(morpholino)methanone (180 mg, 50%) was prepared from N-(3-iodo-2-methyl-6-(trifluoromethyl)pyridin-4-yl)benzenesulfonamide (Preparation #39) (233 mg, 0.53 mmol), and (2,4-dichloro-3-(1-hydroxyprop-2-yn-1-yl)phenyl)(morpholino)methanone (199 mg, 0.63 mmol) (Preparation #3). LC/MS (Method i) $R_t$=2.21 min.; MS m/z: 628 [M+H]$^+$ $^1$H NMR (DMSO-d$_6$, 300 MHz): δ 8.14 (m, 1H), 7.94 (d, J=7.8 Hz, 1H), 7.86 (d, J=7.8 Hz, 1H), 7.75 (m, 1H), 7.62 (m, 2H), 7.50 (m, 1H), 7.40 (m, 1H), 7.00 (m, 1H), 6.91 (m, 1H), 6.74 and 6.81 (d, J=6 Hz, 1H), 3.65 (m, 4H), 3.55 (m, 2H), 3.18 (m, 2H), 2.68 and 2.69 (s, 3H).

Step 2: (2,4-dichloro-3-((4-methyl-1-(phenylsulfonyl)-6-(trifluoromethyl)-1H-pyrrolo[3,2-c]pyridin-2-yl)methyl)phenyl)(morpholino)methanone

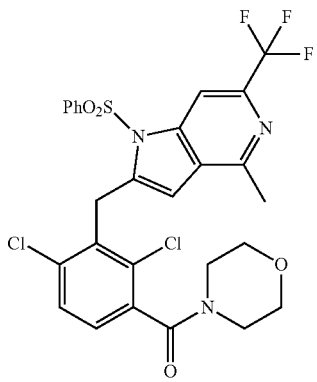

Using a procedure similar to Example Z, Step 2, (2,4-dichloro-3-((4-methyl-1-(phenylsulfonyl)-6-(trifluoromethyl)-1H-pyrrolo[3,2-c]pyridin-2-yl)methyl)phenyl)(morpholino)methanone (202 mg, 100%) was prepared from (2,4-dichloro-3-(hydroxy(4-methyl-1-(phenylsulfonyl)-6-(trifluoromethyl)-1H-pyrrolo[3,2-c]pyridin-2-yl)methyl)phenyl)(morpholino)methanone (175 mg, 0.28 mmol) as a yellow resin. The compound is used directly in the next step. LC/MS (Method i) $R_t$=2.48 min.; MS m/z: 612 [M+H]$^+$

Step 3: (2,4-dichloro-3-((4-methyl-6-(trifluoromethyl)-1H-pyrrolo[3,2-c]pyridin-2-yl)methyl)phenyl)(morpholino)methanone

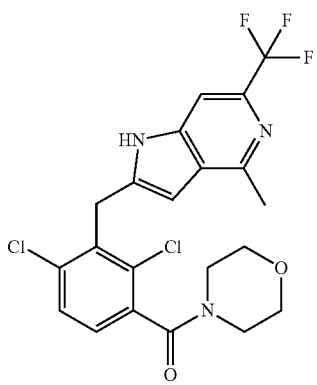 [SMILES: Cc1nc(C(F)(F)F)cc2[nH]c(Cc3c(Cl)ccc(C(=O)N4CCOCC4)c3Cl)cc12]

Using a procedure similar to Example A, Step 3, (2,4-dichloro-3-((4-methyl-6-(trifluoromethyl)-1H-pyrrolo[3,2-c]pyridin-2-yl)methyl)phenyl)(morpholino)methanone (115 mg, 87%) was prepared from (2,4-dichloro-3-((4-methyl-1-(phenylsulfonyl)-6-(trifluoromethyl)-1H-pyrrolo[3,2-c]pyridin-2-yl)methyl)phenyl)(morpholino)methanone (171 mg, 0.28 mmol). LC/MS (Method i) $R_t$=1.98 min.;

MS m/z: 472 [M+H]$^+$ $^1$H NMR (DMSO-d$_6$, 300 MHz): δ 11.96 (s, 1H), 7.65 (m, 2H), 7.43 (d, J=8.3 Hz, 1H), 6.13 (s, 1H), 4.48 (s, 2H), 3.65 (dm, 4H), 3.53 (m, 2H), 3.17 (m, 2H), 2.58 (s, 3H).

Step 4: (2,4-dichloro-3-((1,4-dimethyl-6-(trifluoromethyl)-1H-pyrrolo[3,2-c]pyridin-2-yl)methyl)phenyl)(morpholino)methanone

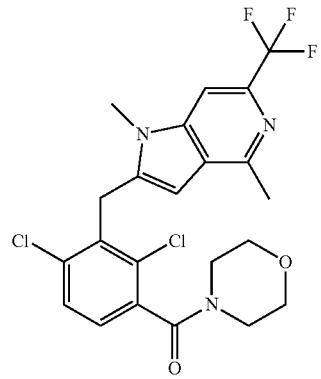 [SMILES: Cc1nc(C(F)(F)F)cc2c1cc(Cc1c(Cl)ccc(C(=O)N3CCOCC3)c1Cl)n2C]

Using a procedure similar to Example A, Step 4, (2,4-dichloro-3-((1,4-dimethyl-6-(trifluoromethyl)-1H-pyrrolo[3,2-c]pyridin-2-yl)methyl)phenyl)(morpholino)methanone (25 mg, 21%) was prepared from (2,4-dichloro-3-((4-methyl-6-(trifluoromethyl)-1H-pyrrolo[3,2-c]pyridin-2-yl)methyl)phenyl)(morpholino)methanone (112 mg, 0.24 mmol). LC/MS (Method g) $R_t$=1.53 min.;

MS m/z: 486 [M+H]$^+$ $^1$H NMR (DMSO-d$_6$, 400 MHz): δ 7.92 (s, 1H), 7.69 (d, J=8.4 Hz, 1H), 7.47 (d, J=8.4 Hz, 1H), 5.88 (s, 1H), 4.48 (m, 2H), 3.96 (s, 3H), 3.65 (m, 4H), 3.55 (m, 2H), 3.21 (m, 2H), 2.54 (s, 3H).

Example CS: 2-(2,6-dichloro-3-(morpholine-4-carbonyl)benzyl)-1,4-dimethyl-1H-pyrrolo[3,2-c]pyridine-6-carbonitrile

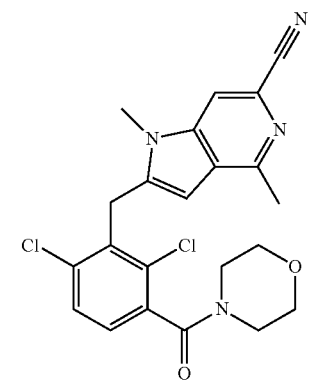 [SMILES: Cc1nc(C#N)cc2c1cc(Cc1c(Cl)ccc(C(=O)N3CCOCC3)c1Cl)n2C]

Step 1: 2-((2,6-dichloro-3-(morpholine-4-carbonyl)phenyl)(hydroxy)methyl)-4-methyl-1-(phenylsulfonyl)-1H-pyrrolo[3,2-c]pyridine-6-carbonitrile

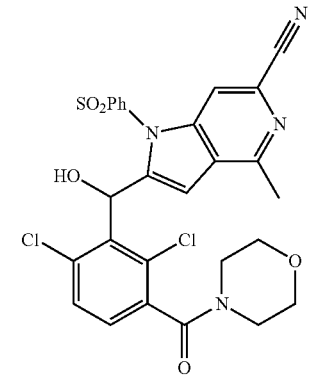

Using a procedure similar to Example A, Step 1, 2-((2,6-dichloro-3-(morpholine-4-carbonyl)phenyl)(hydroxy)methyl)-4-methyl-1-(phenylsulfonyl)-1H-pyrrolo[3,2-c]pyridine-6-carbonitrile (204 mg, 42%) was prepared from N-(6-cyano-3-iodo-2-methylpyridin-4-yl)benzenesulfonamide (Preparation #40) (300 mg, 0.75 mmol), and (2,4-dichloro-3-(1-hydroxyprop-2-yn-1-yl)phenyl)(morpholino)methanone (283 mg, 0.90 mmol) (Preparation #3). LC/MS (Method h) R$_t$=2.37 min.; MS m/z: 585 [M+H]$^+$ $^1$H NMR (DMSO-d$_6$, 300 MHz): δ 8.44 and 8.42 (s, 1H), 8.07 (m, 1H), 7.99 (m, 1H), 7.75 (m, 1H), 7.63 (m, 2H), 7.52 and 7.49 (d, J=8.1 Hz, 1H), 7.40 and 7.39 (d, J=8.1 Hz, 1H), 7.06 and 6.89 (d, J=5.5 Hz, 1H), 7.03 and 6.93 (d, J=5.5 Hz, 1H), 6.83 and 6.77 (d, J=5.5 Hz, 1H), 3.64 (m, 4H), 3.55 (m, 2H), 3.16 (m, 2H), 2.65 and 2.63 (s, 3H).

Step 2: 2-(2,6-dichloro-3-(morpholine-4-carbonyl)benzyl)-4-methyl-1-(phenylsulfonyl)-1H-pyrrolo[3,2-c]pyridine-6-carbonitrile

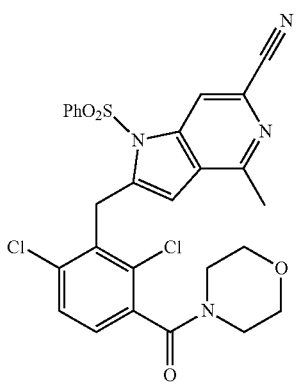

Using a procedure similar to Example Z, Step 2, 2-(2,6-dichloro-3-(morpholine-4-carbonyl)benzyl)-4-methyl-1-(phenylsulfonyl)-1H-pyrrolo[3,2-c]pyridine-6-carbonitrile (248 mg, 100%) was prepared from 2-((2,6-dichloro-3-(morpholine-4-carbonyl)phenyl)(hydroxy)methyl)-4-methyl-1-(phenylsulfonyl)-1H-pyrrolo[3,2-c]pyridine-6-carbonitrile (200 mg, 0.34 mmol) as a yellow resin. The compound is used directly in the next step. LC/MS (Method h) R$_t$=2.77 min.; MS m/z: 569 [M+H]$^+$ Step 3: 2-(2,6-dichloro-3-(morpholine-4-carbonyl)benzyl)-4-methyl-1H-pyrrolo[3,2-c]pyridine-6-carbonitrile

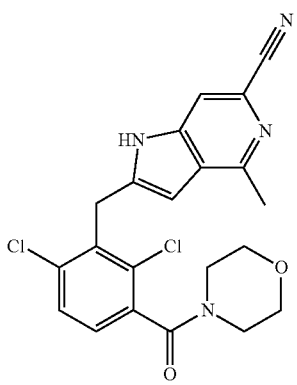 [SMILES: Cc1nc(C#N)cc2[nH]c(Cc3c(Cl)ccc(C(=O)N4CCOCC4)c3Cl)cc12]

Using a procedure similar to Example A, Step 3, 2-(2,6-dichloro-3-(morpholine-4-carbonyl)benzyl)-4-methyl-1H-pyrrolo[3,2-c]pyridine-6-carbonitrile (100 mg, 47%) was prepared from 2-(2,6-dichloro-3-(morpholine-4-carbonyl)benzyl)-4-methyl-1-(phenylsulfonyl)-1H-pyrrolo[3,2-c]pyridine-6-carbonitrile (248 mg, 0.43 mmol). LC/MS (Method h) R$_t$=2.07 min.; MS m/z: 429 [M+H]$^+$ $^1$H NMR (DMSO-d$_6$, 300 MHz): δ 12.14 (broad, 1H), 7.85 (s, 1H), 7.66 (d, J=8.3 Hz, 1H), 7.43 (d, J=8.3 Hz, 1H), 6.15 (s, 1H), 4.48 (s, 2H), 3.65 (m, 4H), 3.53 (m, 2H), 3.17 (m, 2H), 2.56 (s, 3H).

Step 4: 2-(2,6-dichloro-3-(morpholine-4-carbonyl)benzyl)-1,4-dimethyl-1H-pyrrolo[3,2-c]pyridine-6-carbonitrile

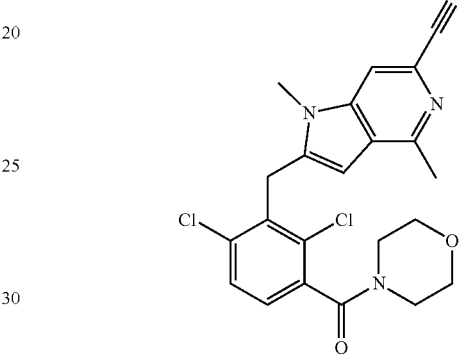

Using a procedure similar to Example A, Step 4, 2-(2,6-dichloro-3-(morpholine-4-carbonyl)benzyl)-1,4-dimethyl-1H-pyrrolo[3,2-c]pyridine-6-carbonitrile (18 mg, 16%) was prepared from 2-(2,6-dichloro-3-(morpholine-4-carbonyl)benzyl)-4-methyl-1H-pyrrolo[3,2-c]pyridine-6-carbonitrile (100 mg, 0.23 mmol). LC/MS (Method g) R$_t$=1.31 min.; MS m/z: 443 [M+H]$^+$ $^1$H NMR (DMSO-d$_6$, 400 MHz): δ 8.17 (s, 1H), 7.69 (d, J=8.1 Hz, 1H), 7.47 (d, J=8.1 Hz, 1H), 5.92 (s, 1H), 4.48 (m, 2H), 3.94 (s, 3H), 3.64 (m, 4H), 3.54 (m, 2H), 3.20 (m, 2H), 2.52 (s, 3H).

Example CT: (2,4-dichloro-3-((3,8-dimethyl-6-(trifluoromethyl)imidazo[1,2-a]pyridin-2-yl)methyl)phenyl)(morpholino)methanone

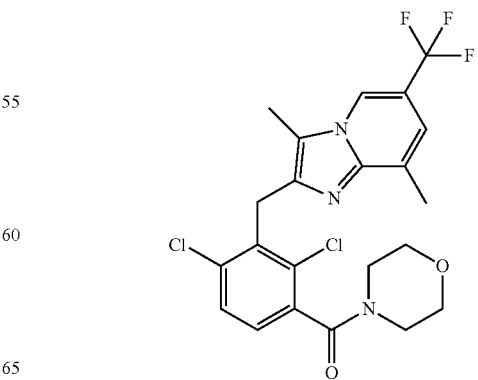

Step 1: methyl 2,4-dichloro-3-((3,8-dimethyl-6-(trifluoromethyl)imidazo[1,2-a]pyridin-2-yl)methyl)benzoate

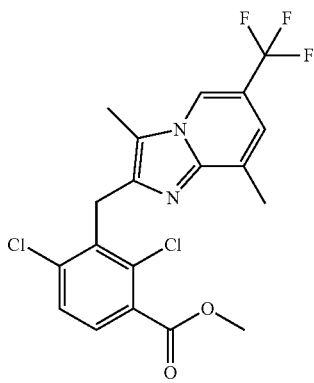 [SMILES: COC(=O)c1ccc(Cl)c(Cc2nc3c(C)cc(C(F)(F)F)cn3c2C)c1Cl]

To a solution of methyl 2,4-dichloro-3-(3-chloro-2-oxobutyl)benzoate (Preparation #13) (176 mg, 0.568 mmol) in N-methyl-2-pyrrolidinone (300 μL) was added 3-methyl-5-(trifluoromethyl)pyridin-2-amine (described in WO2007/089034) (100 mg, 0.568 mmol) The reaction mixture was stirred at 120° C. for 48 hours and concentrated under reduced pressure. The residue was purified by column chromatography on silica gel (eluting with 5-20% EtOAc in cyclohexane) to give methyl 2,4-dichloro-3-((3,8-dimethyl-6-(trifluoromethyl)imidazo[1,2-a]pyridin-2-yl)methyl)benzoate (55 mg, 22%)

LC/MS (Method h) $R_t$=2.96 min.; MS m/z: 431 [M+H]$^+$. $^1$H NMR (DMSO-d$_6$, 300 MHz) δ 8.59 (s, 1H), 7.67 (d, J=8 Hz, 1H), 7.62 (d, J=8 Hz, 1H), 7.22 (s, 1H), 4.43 (s, 2H), 3.85 (s, 3H), 2.48 (s, 3H), 2.42 (s, 3H).

Step 2: 2,4-dichloro-3-((3,8-dimethyl-6-(trifluoromethyl)imidazo[1,2-a]pyridin-2-yl)methyl)benzoic acid

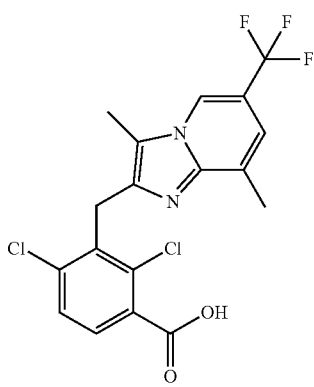 [SMILES: Cc1cc(C(F)(F)F)cn2c(C)c(Cc3c(Cl)ccc(C(=O)O)c3Cl)nc12]

Using a procedure similar to Example A, Step 5, 2,4-dichloro-3-((3,8-dimethyl-6-(trifluoromethyl)imidazo[1,2-a]pyridin-2-yl)methyl)benzoic acid (18 mg, 35%) was prepared from methyl 2,4-dichloro-3-((3,8-dimethyl-6-(trifluoromethyl)imidazo[1,2-a]pyridin-2-yl)methyl)benzoate (53 mg, 0.123 mmol). LC/MS (Method h) $R_t$=2.03 min.; MS m/z: 417 [M+H]$^+$. $^1$H NMR (DMSO-d$_6$, 300 MHz,) δ 13.57 (broad, 1H), 8.59 (s, 1H), 7.61 (d, J=9 Hz, 1H), 7.55 (d, J=9 Hz, 1H), 7.22 (s, 1H), 4.42 (s, 2H), 2.47 (s, 3H), 2.43 (s, 3H).

Step 3: (2,4-dichloro-3-((3,8-dimethyl-6-(trifluoromethyl)imidazo[1,2-a]pyridin-2-yl)methyl)phenyl)(morpholino)methanone

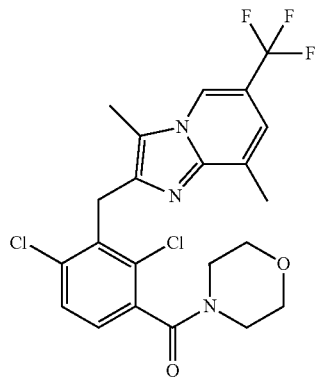 [SMILES: Cc1cc(C(F)(F)F)cn2c(C)c(Cc3c(Cl)ccc(C(=O)N4CCOCC4)c3Cl)nc12]

Using a procedure similar to Example A1, (2,4-dichloro-3-((3,8-dimethyl-6-(trifluoromethyl)imidazo[1,2-a]pyridin-2-yl)methyl)phenyl)(morpholino)methanone (14 mg, 19%) was prepared from 2,4-dichloro-3-((3,8-dimethyl-6-(trifluoromethyl)imidazo[1,2-a]pyridin-2-yl)methyl)benzoic acid (62 mg, 0.149 mmol) and morpholine (19.4 mg, 0.22 mmol). LC/MS (Method g) $R_t$=1.47 min.; MS m/z: 486 [M+H]$^+$. $^1$H NMR (DMSO-d$_6$, 400 MHz,) δ 8.59 (s, 1H), 7.56 (d, J=8 Hz, 1H), 7.32 (d, J=8 Hz, 1H), 7.22 (s, 1H), 4.40 (m, 2H), 3.66 (m, 4H), 3.55 (m, 2H), 3.14 (m, 2H), 2.48 (s, 3H), 2.41 (s, 3H).

TABLE CT
The following intermediates were prepared from 2,4-dichloro-3-((3,8-dimethyl-6-(trifluoromethyl)imidazo[1,2-a]pyridin-2-yl)methyl)benzoic acid (Example CT, Step 2) using the same procedure with the appropriate amine.
| Example # | Product | Amine | R$_t$ min | m/z ESI+ (M + H)$^+$ |
|---|---|---|---|---|
| CT-1 | 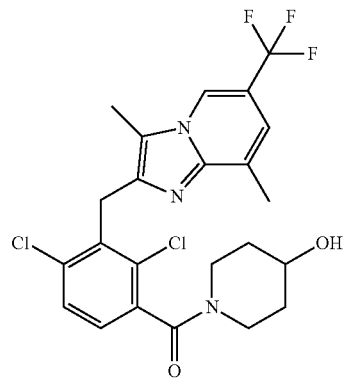 [SMILES: Cc1cc(C(F)(F)F)cn2c(C)c(Cc3c(Cl)ccc(C(=O)N4CCC(O)CC4)c3Cl)nc12] | 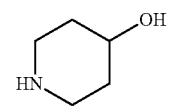 | 1.36 (Method g) | 500 |
| CT-2 | 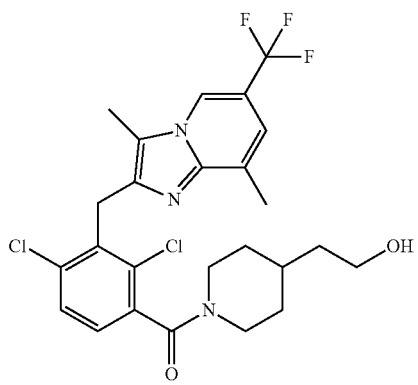 [SMILES: Cc1cc(C(F)(F)F)cn2c(C)c(Cc3c(Cl)ccc(C(=O)N4CCC(CCO)CC4)c3Cl)nc12] | 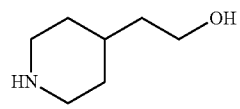 | 1.48 (Method g) | 528 |
| CT-3 | 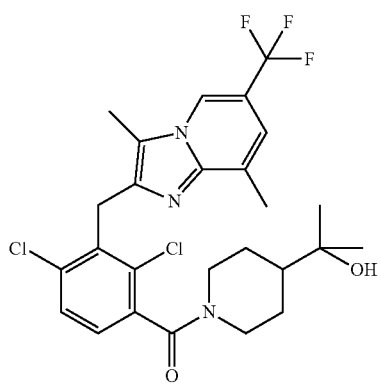 [SMILES: Cc1cc(C(F)(F)F)cn2c(C)c(Cc3c(Cl)ccc(C(=O)N4CCC(C(C)(C)O)CC4)c3Cl)nc12] | 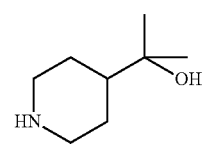 | 1.56 (Method g) | 542 |

TABLE CT-continued
*The following intermediates were prepared from 2,4-dichloro-3-((3,8-dimethyl-6-(trifluoromethyl)imidazo[1,2-a]pyridin-2-yl)methyl)benzoic acid (Example CT, Step 2) using the same procedure with the appropriate amine.*
| Example # | Product | Amine | R$_t$ min | m/z ESI+ (M + H)+ |
|---|---|---|---|---|
| CT-4 | 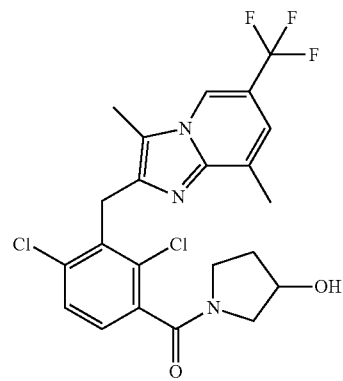 [SMILES: Cc1cc(C(F)(F)F)cn2c(C)c(Cc3c(Cl)ccc(C(=O)N4CCC(O)C4)c3Cl)nc12] | 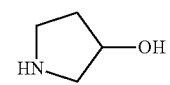 | 1.34 (Method g) | 486 |
| CT-5 | 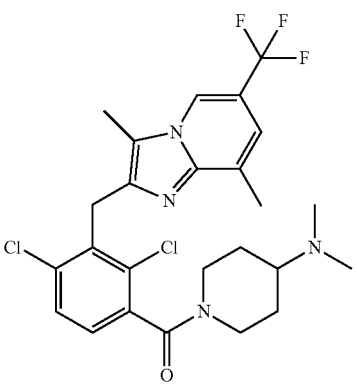 [SMILES: Cc1cc(C(F)(F)F)cn2c(C)c(Cc3c(Cl)ccc(C(=O)N4CCC(N(C)C)CC4)c3Cl)nc12] | 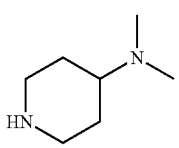 | 1.02 (Method g) | 527 |
| CT-6 | 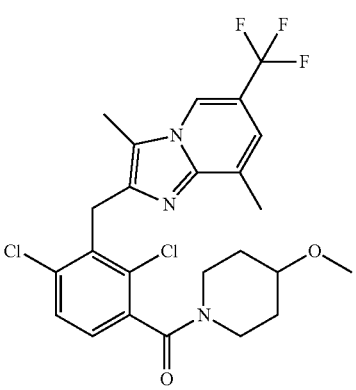 [SMILES: COC1CCN(C(=O)c2ccc(Cl)c(Cc3nc4c(C)cc(C(F)(F)F)cn4c3C)c2Cl)CC1] | 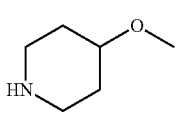 | 1.64 (Method g) | 514 |

TABLE CT-continued
The following intermediates were prepared from 2,4-dichloro-3-((3,8-dimethyl-6-(trifluoromethyl)imidazo[1,2-a]pyridin-2-yl)methyl)benzoic acid (Example CT, Step 2) using the same procedure with the appropriate amine.
| Example # | Product | Amine | $R_t$, min | m/z ESI+ $(M + H)^+$ |
|---|---|---|---|---|
| CT-7 | 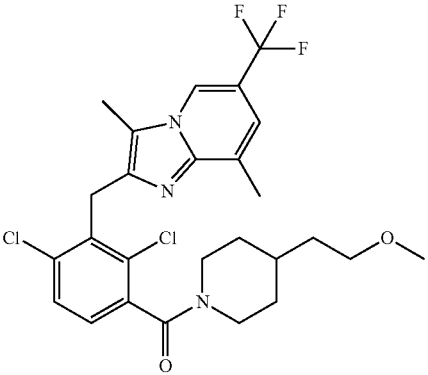 [SMILES: COCCC1CCN(C(=O)c2ccc(Cl)c(Cc3nc4c(C)cc(C(F)(F)F)cn4c3C)c2Cl)CC1] | 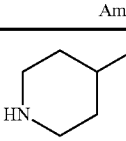 | 1.79 (Method g) | 542 |
| CT-8 | 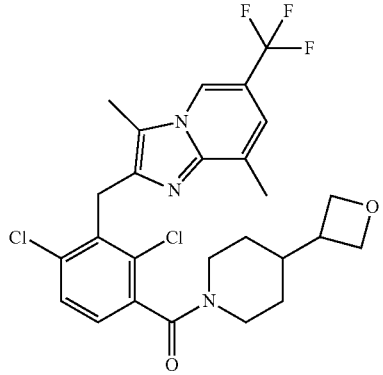 [SMILES: Cc1cc(C(F)(F)F)cn2c(C)c(Cc3c(Cl)ccc(C(=O)N4CCC(C5COC5)CC4)c3Cl)nc12] | 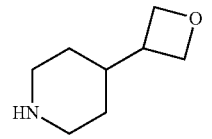 | 1.59 (Method g) | 540 |
| CT-9 | 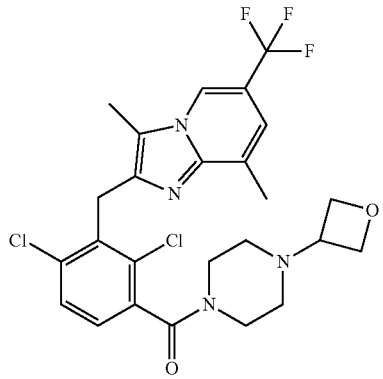 [SMILES: Cc1cc(C(F)(F)F)cn2c(C)c(Cc3c(Cl)ccc(C(=O)N4CCN(C5COC5)CC4)c3Cl)nc12] | 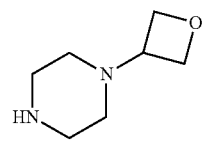 | 1.35 (Method g) | 541 |
| CT-10 | 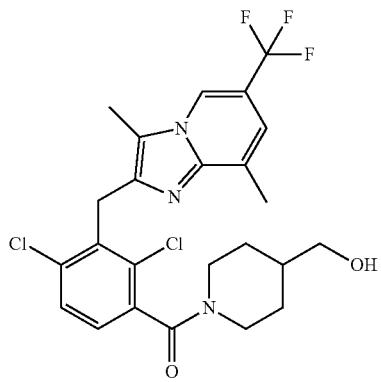 [SMILES: Cc1cc(C(F)(F)F)cn2c(C)c(Cc3c(Cl)ccc(C(=O)N4CCC(CO)CC4)c3Cl)nc12] | 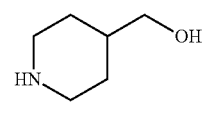 | 1.42 (Method g) | 514 |

TABLE CT-continued

The following intermediates were prepared from 2,4-dichloro-3-((3,8-dimethyl-6-(trifluoromethyl)imidazo[1,2-a]pyridin-2-yl)methyl)benzoic acid (Example CT, Step 2) using the same procedure with the appropriate amine.

| Example # | Product | Amine | R, min | m/z ESI+ (M + H)+ |
|---|---|---|---|---|
| CT-11 | | | 1.50 (Method g) | 528 |
| CT-12 | | | 2.40 (Method i) | 556 |

Example CU: 2-(1-(2,4-dichloro-3-((3,8-dimethyl-6-(trifluoromethyl)imidazo[1,2-a]pyridin-2-yl)methyl)benzoyl)piperidin-4-yl)acetic acid

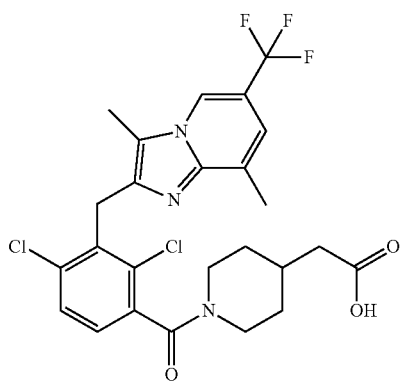 [SMILES: COC(=O)CC1CCN(C(=O)c2ccc(Cl)c(Cc3nc4c(C)cc(C(F)(F)F)cn4c3C)c2Cl)CC1]

Using a procedure similar to Example A, Step 5, 2-(1-(2,4-dichloro-3-((3,8-dimethyl-6-(trifluoromethyl)imidazo[1,2-a]pyridin-2-yl)methyl)benzoyl)piperidin-4-yl)acetic acid (73 mg, 48%) was prepared from methyl 2-(1-(2,4-dichloro-3-((3,8-dimethyl-6-(trifluoromethyl)imidazo[1,2-a]pyridin-2-yl)methyl)benzoyl)piperidin-4-yl)acetate (table CT, CT-12) (155 mg, 0.28 mmol). LC/MS (Method g) $R_t$=1.43 min.; MS m/z: 542 [M+H]+ $^1$H NMR (DMSO-$d_6$, 400 MHz): δ 12.08 (broad, 1H), 8.60 (s, 1H), 7.54 (m, 1H), 7.32 and 7.24 (d, J=8.1 Hz, 1H), 7.22 (s, 1H), 4.43 (m, 3H), 3.23 (m, 1H), 3.02 (m, 1H), 2.79 (m, 1H), 2.47 (s, 3H), 2.41 (s, 3H), 2.15 (m, 2H), 1.96 (m, 1H), 1.75 (m, 1H), 1.61 (m, 1H), 1.15 (m, 2H).

Example CV: 2-[[2,6-dichloro-3-[4-(2-hydroxyethyl)piperidine-1-carbonyl]phenyl]methyl]-3,8-dimethyl-imidazo[1,2-a]pyridine-6-carbonitrile

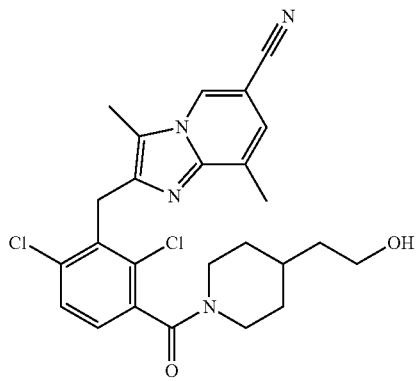 [SMILES: Cc1cc(C#N)cn2c(C)c(Cc3c(Cl)ccc(C(=O)N4CCC(CCO)CC4)c3Cl)nc12]

527

Step 1: 2,4-dichloro-3-((6-cyano-3,8-dimethylimidazo[1,2-a]pyridin-2-yl)methyl)benzoic acid

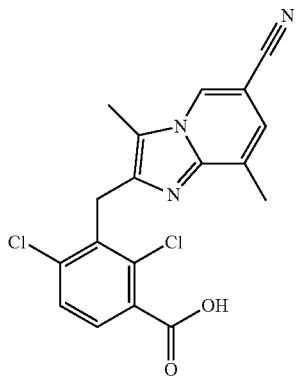 [SMILES: Cc1cc(C#N)cn2c(C)c(Cc3c(Cl)ccc(C(=O)O)c3Cl)nc12]

Using a procedure similar to Example CT, Step 1, followed by Example A, Step 5, 2,4-dichloro-3-((6-cyano-3,8-dimethylimidazo[1,2-a]pyridin-2-yl)methyl)benzoic acid (1.17 g, 34%) was prepared from methyl 2,4-dichloro-3-(3-chloro-2-oxobutyl)benzoate (Preparation #13) (2.67 g, 8.64 mmol) and 6-amino-5-methylnicotinonitrile (1.15 g, 8.64 mmol). LC/MS (Method g) $R_t$=1.74 min.; MS m/z: 374 [M+H]$^+$ $^1$H NMR (DMSO-d$_6$, 300 MHz): δ 13.55 (broad, 1H), 8.95 (s, 1H), 7.63 (d, J=9 Hz, 1H), 7.57 (d, J=9 Hz, 1H), 7.24 (s, 1H), 4.42 (s, 2H), 2.44 (s, 3H), 2.38 (s, 3H).

528

Step 2: 2-[[2,6-dichloro-3-[4-(2-hydroxyethyl)piperidine-1-carbonyl]phenyl]methyl]-3,8-dimethyl-imidazo[1,2-a]pyridine-6-carbonitrile

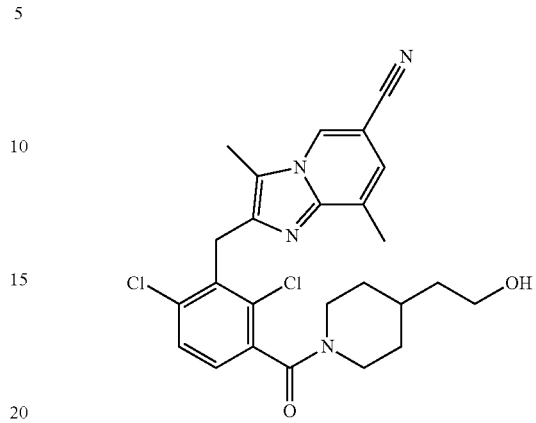

Using a procedure similar to Example A1, 2-[[2,6-dichloro-3-[4-(2-hydroxyethyl)piperidine-1-carbonyl]phenyl]methyl]-3,8-dimethyl-imidazo[1,2-a]pyridine-6-carbonitrile (40 mg, 52%) was prepared from 2,4-dichloro-3-((6-cyano-3,8-dimethylimidazo[1,2-a]pyridin-2-yl)methyl)benzoic acid (60 mg, 0.16 mmol). LC/MS (Method g) $R_t$=1.33 min.; MS m/z: 485 [M+H]$^+$ $^1$H NMR (DMSO-d$_6$, 400 MHz): δ 8.94 (s, 1H), 7.54 and 7.53 (d, J=8.1, 1H), 7.31 and 7.24 (d, J=8.4 Hz, 1H), 7.22 (m, 1H), 4.45 (m, 1H), 4.38 (m, 3H), 3.42 (m, 2H), 3.24 (m, 1H), 2.98 (m, 1H), 2.75 (m, 1H), 2.44 (s, 3H), 2.35 (m, 3H), 1.75 (m, 1H), 1.66 (m, 1H), 1.57 (m, 1H), 1.36 (m, 2H), 0.94-1.20 (m, 2H).

TABLE CV

The following intermediates were prepared from 2,4-dichloro-3-((6-cyano-3,8-dimethylimidazo[1,2-a]pyridin-2-yl)methyl)benzoic acid (Example CV, Step 1) using the same procedure with the appropriate amine.

| Example # | Product | Amine | $R_t$, min | m/z ESI+ (M + H)$^+$ |
|---|---|---|---|---|
| CV-1 | ![structure] | ![amine] | 1.27 (Method g) | 471 |

TABLE CV-continued
The following intermediates were prepared from 2,4-dichloro-3-((6-cyano-3,8-dimethylimidazo[1,2-a]pyridin-2-yl)methyl)benzoic acid (Example CV, Step 1) using the same procedure with the appropriate amine.
| Example # | Product | Amine | R$_t$, min | m/z ESI+ (M + H)+ |
|---|---|---|---|---|
| CV-2 | 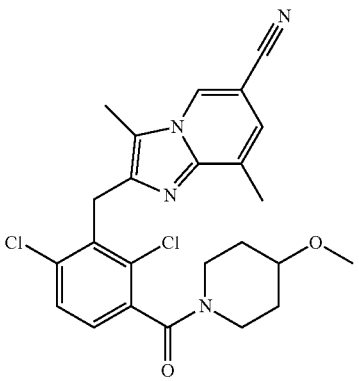 [SMILES: COC1CCN(C(=O)c2ccc(Cl)c(Cc3nc4c(C)cc(C#N)cn4c3C)c2Cl)CC1] | 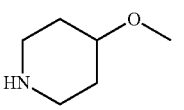 | 1.46 (Method g) | 471 |
| CV-3 | 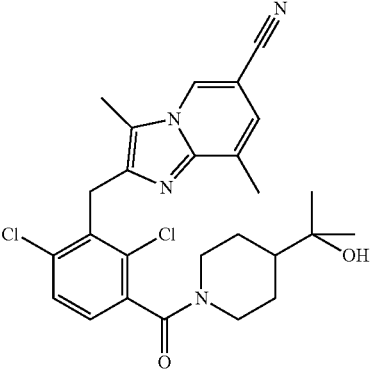 [SMILES: Cc1cc(C#N)cn2c(C)c(Cc3c(Cl)ccc(C(=O)N4CCC(C(C)(C)O)CC4)c3Cl)nc12] | 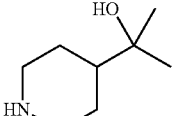 | 1.41 (Method g) | 499 |
| CV-4 | 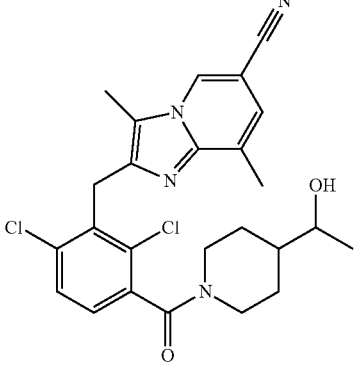 | 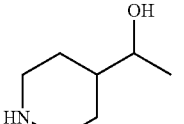 | 1.35 (Method g) | 485 |
| CV-5 | 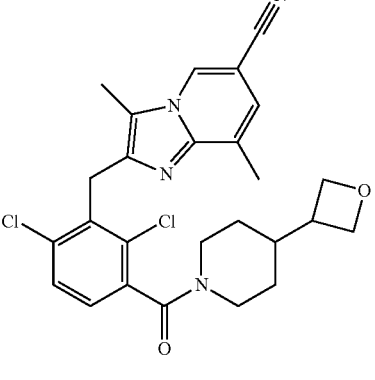 | 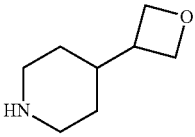 | 1.43 (Method g) | 497 |

TABLE CV-continued

The following intermediates were prepared from 2,4-dichloro-3-((6-cyano-3,8-dimethylimidazo[1,2-a]pyridin-2-yl)methyl)benzoic acid (Example CV, Step 1) using the same procedure with the appropriate amine.

| Example # | Product | Amine | R, min | m/z ESI+ (M + H)+ |
|---|---|---|---|---|
| CV-6 | (structure) | (structure) | 1.62 (Method g) | 499 |

Example CW: (2,4-dichloro-3-((6-chloro-3,8-dimethylimidazo[1,2-b]pyridazin-2-yl)methyl)phenyl)(morpholino)methanone

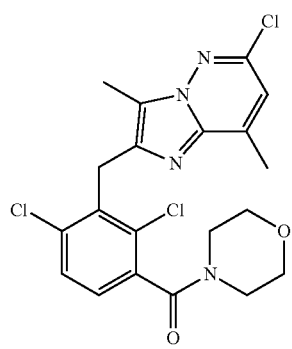 [SMILES: Cc1cc(Cl)nn2c(C)c(Cc3c(Cl)ccc(C(=O)N4CCOCC4)c3Cl)nc12]

Step 1: methyl 2,4-dichloro-3-((6-chloro-3,8-dimethylimidazo[1,2-b]pyridazin-2-yl)methyl)benzoate and methyl 2,4-dichloro-3-((6-chloro-3,7-dimethylimidazo[1,2-b]pyridazin-2-yl)methyl)benzoate

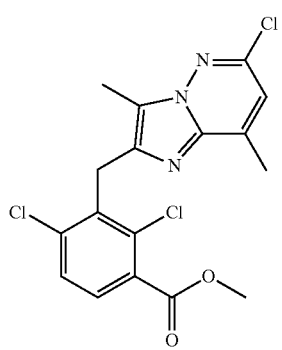

-continued

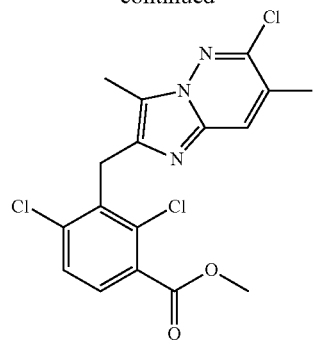

Using a procedure similar to Example CT, Step 1, methyl 2,4-dichloro-3-((6-chloro-3,8-dimethylimidazo[1,2-b]pyridazin-2-yl)methyl)benzoate (47 mg, 34%)

LC/MS (Method h) $R_t$=3.10 min.; MS m/z: 398 [M+H]+. $^1$H NMR (DMSO-$d_6$, 400 MHz) δ 7.68 (d, J=8 Hz, 1H), 7.63 (d, J=8 Hz, 1H), 7.15 (s, 1H), 4.45 (s, 2H), 3.87 (s, 3H), 2.44 (s, 6H); and methyl 2,4-dichloro-3-((6-chloro-3,7-dimethylimidazo[1,2-b]pyridazin-2-yl)methyl)benzoate (38 mg, 28%) were prepared from a mixture of 6-chloro-5-methylpyridazin-3-amine and 6-chloro-4-methylpyridazin-3-amine (Preparation #28) (23.12 mg, 0.161 mmol) and methyl 3-(3-bromo-2-oxobutyl)-2,4-dichlorobenzoate (Preparation #14) (57 mg, 0.161 mmol). LC/MS (Method h) $R_t$=2.98 min.; MS m/z: 398 [M+H]+. $^1$H NMR (DMSO-$d_6$, 400 MHz,) δ 7.98 (s, 1H), 7.66 (d, J=8 Hz, 1H), 7.60 (d, J=8 Hz, 1H), 4.43 (s, 2H), 3.85 (s, 3H), 2.49 (s, 3H), 2.33 (s, 3H).

Step 2: 2,4-dichloro-3-((6-chloro-3,8-dimethylimidazo[1,2-b]pyridazin-2-yl)methyl)benzoic acid

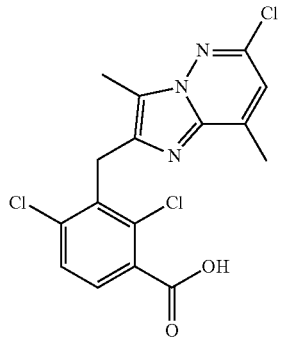 [SMILES: Cc1cc(Cl)nn2c(C)c(Cc3c(Cl)ccc(C(=O)O)c3Cl)nc12]

Using a procedure similar to Example A, Step 5, 2,4-dichloro-3-((6-chloro-3,8-dimethylimidazo[1,2-b]pyridazin-2-yl)methyl)benzoic acid (330 mg, 93%) was prepared from methyl 2,4-dichloro-3-((6-chloro-3,8-dimethylimidazo[1,2-b]pyridazin-2-yl)methyl)benzoate (366 mg, 0.918 mmol). LC/MS (Method h) $R_t$=2.47 min.; MS m/z: 384 [M+H]$^+$. $^1$H NMR (DMSO-d$_6$, 300 MHz,) δ 13.57 (broad, 1H), 7.65 (d, J=9 Hz, 1H), 7.57 (d, J=9 Hz, 1H), 7.15 (s, 1H), 4.45 (s, 2H), 2.45 (s, 3H), 2.43 (s, 3H).

Step 3: (2,4-dichloro-3-((6-chloro-3,8-dimethylimidazo[1,2-b]pyridazin-2-yl)methyl)phenyl)(morpholino)methanone

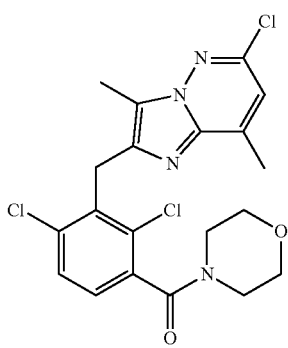 [SMILES: Cc1cc(Cl)nn2c(C)c(Cc3c(Cl)ccc(C(=O)N4CCOCC4)c3Cl)nc12]

Using a procedure similar to Example A1, (2,4-dichloro-3-((6-chloro-3,8-dimethylimidazo[1,2-b]pyridazin-2-yl)methyl)phenyl)(morpholino)methanone (356 mg, 92%) was prepared from 2,4-dichloro-3-((6-chloro-3,8-dimethylimidazo[1,2-b]pyridazin-2-yl)methyl)benzoic acid (327 mg, 0.850 mmol) and morpholine (89 mg, 1.02 mmol). LC/MS (Method g) $R_t$=1.62 min.; MS m/z: 453 [M+H]$^+$.

$^1$H NMR (DMSO-d$_6$, 300 MHz,) δ 7.57 (d, J=8 Hz, 1H), 7.33 (d, J=8 Hz, 1H), 7.15 (m, 1H), 4.42 (m, 2H), 3.65 (m, 4H), 3.54 (m, 2H), 3.14 (m, 2H), 2.44 (s, 6H).

Example CY: (2,4-dichloro-3-((6-chloro-3,7-dimethylimidazo[1,2-b]pyridazin-2-yl)methyl)phenyl)(morpholino)methanone

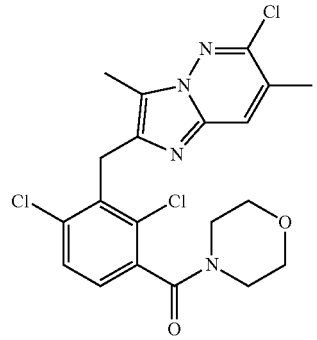 [SMILES: Cc1cc2nc(Cc3c(Cl)ccc(C(=O)N4CCOCC4)c3Cl)c(C)n2nc1Cl]

Step 1: 2,4-dichloro-3-((6-chloro-3,7-dimethylimidazo[1,2-b]pyridazin-2-yl)methyl)benzoic acid Using a procedure similar to Example A, Step 5, 2,4-dichloro-3-((6-chloro-3,7-dimethylimidazo[1,2-b]pyridazin-2-yl)methyl)benzoic acid (21 mg, 66%) was prepared from methyl 2,4-dichloro-3-((6-chloro-3,7-dimethylimidazo[1,2-b]pyridazin-2-yl)methyl)benzoate (Example CW, Step 1) (33 mg, 0.083 mmol). LC/MS (Method h) $R_t$=2.30 min.; MS m/z: 384 [M+H]$^+$. $^1$H NMR (DMSO-d$_6$, 300 MHz,) δ 13.55 (broad, 1H), 8.01 (s, 1H), 7.64 (d, J=9 Hz, 1H), 7.56 (d, J=9 Hz, 1H), 4.45 (s, 2H), 2.48 (s, 3H), 2.36 (s, 3H).

Step 2: (2,4-dichloro-3-((6-chloro-3,7-dimethylimidazo[1,2-b]pyridazin-2-yl)methyl)phenyl)(morpholino)methanone

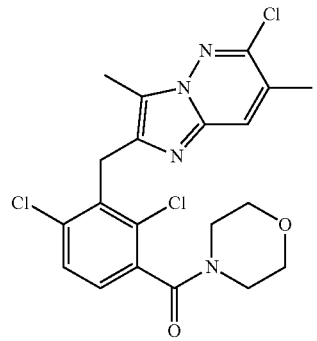 [SMILES: Cc1cc2nc(Cc3c(Cl)ccc(C(=O)N4CCOCC4)c3Cl)c(C)n2nc1Cl]

Using a procedure similar to Example A1, (2,4-dichloro-3-((6-chloro-3,7-dimethylimidazo[1,2-b]pyridazin-2-yl)methyl)phenyl)(morpholino)methanone (15 mg, 70%) was prepared from 2,4-dichloro-3-((6-chloro-3,7-dimethylimidazo[1,2-b]pyridazin-2-yl)methyl)benzoic acid (18 mg, 0.047 mmol) and morpholine (6.12 mg, 0.07 mmol). LC/MS (Method g) $R_t$=1.56 min.; MS m/z: 453 [M+H]$^+$. $^1$H NMR (DMSO-$d_6$, 400 MHz,) δ 7.99 (s, 1H), 7.55 (d, J=8 Hz, 1H), 7.33 (d, J=8 Hz, 1H), 4.40 (m, 2H), 3.63 (m, 4H), 3.52 (m, 2H), 3.12 (m, 2H), 2.48 (s, 3H), 2.34 (s, 3H).

Example CZ: (2,4-dichloro-3-((3,8-dimethyl-6-(trifluoromethyl)imidazo[1,2-b]pyridazin-2-yl)methyl)phenyl)(morpholino)methanone

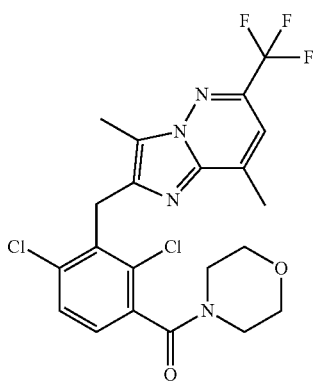 [SMILES: Cc1cc(C(F)(F)F)nn2c(C)c(Cc3c(Cl)ccc(C(=O)N4CCOCC4)c3Cl)nc12]

Step 1: methyl 2,4-dichloro-3-((3,8-dimethyl-6-(trifluoromethyl)imidazo[1,2-b]pyridazin-2-yl)methyl)benzoate

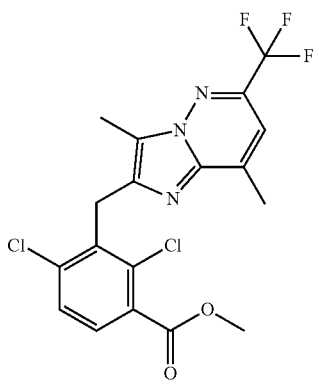 [SMILES: COC(=O)c1ccc(Cl)c(Cc2nc3c(C)cc(C(F)(F)F)nn3c2C)c1Cl]

Using a procedure similar to Example CT, Step 1, methyl 2,4-dichloro-3-((3,8-dimethyl-6-(trifluoromethyl)imidazo[1,2-b]pyridazin-2-yl)methyl)benzoate (135 mg, 37%) was prepared from methyl 2,4-dichloro-3-(3-chloro-2-oxobutyl)benzoate (Preparation #13) (262 mg, 0.847 mmol) and 4-methyl-6-(trifluoromethyl)pyridazin-3-amine (Preparation #41) (150 mg, 0.847 mmol). LC/MS (Method i) $R_t$=2.65 min.; MS m/z: 432 [M+H]$^+$ $^1$H NMR (DMSO-$d_6$, 300 MHz): δ 7.69 (d, J=9 Hz, 1H), 7.64 (J=9 Hz, 1H), 7.47 (d, J=1.0 Hz, 1H), 4.52 (s, 2H), 3.86 (s, 3H), 2.55 (d, J=1 Hz, 3H), 2.51 (s, 3H).

Step 2: 2,4-dichloro-3-((3,8-dimethyl-6-(trifluoromethyl)imidazo[1,2-b]pyridazin-2-yl)methyl)benzoic acid

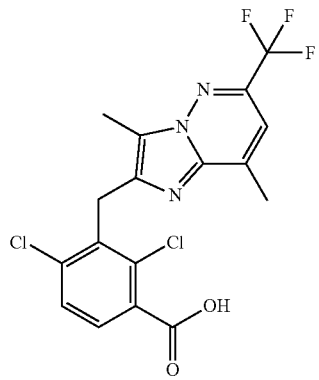 [SMILES: Cc1cc(C(F)(F)F)nn2c(C)c(Cc3c(Cl)ccc(C(=O)O)c3Cl)nc12]

Using a procedure similar to Example A, Step 5, 2,4-dichloro-3-((3,8-dimethyl-6-(trifluoromethyl)imidazo[1,2-b]pyridazin-2-yl)methyl)benzoic acid (100 mg, 80%) was prepared from methyl 2,4-dichloro-3-((3,8-dimethyl-6-(trifluoromethyl)imidazo[1,2-b]pyridazin-2-yl)methyl)benzoate (129 mg, 0.29 mmol). LC/MS (Method i) $R_t$=2.27 min.; MS m/z: 418 [M+H]$^+$ $^1$H NMR (DMSO-$d_6$, 300 MHz): δ 13.61 (broad, 1H), 7.65 (d, J=9 Hz, 1H), 7.61 (d, J=9 Hz, 1H), 7.47 (d, J=1.0 Hz, 1H), 4.52 (s, 2H), 2.55 (d, J=0.8 Hz, 3H), 2.50 (s, 3H).

Step 3: (2,4-dichloro-3-((3,8-dimethyl-6-(trifluoromethyl)imidazo[1,2-b]pyridazin-2-yl)methyl)phenyl)(morpholino)methanone

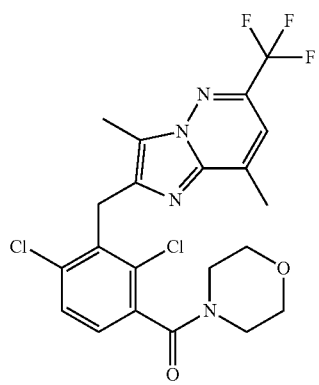 [SMILES: Cc1cc(C(F)(F)F)nn2c(C)c(Cc3c(Cl)ccc(C(=O)N4CCOCC4)c3Cl)nc12]

Using a procedure similar to Example A1, (2,4-dichloro-3-((3,8-dimethyl-6-(trifluoromethyl)imidazo[1,2-b]pyridazin-2-yl)methyl)phenyl)(morpholino)methanone (22 mg, 38%) was prepared from methyl 2,4-dichloro-3-((3,8-dimethyl-6-(trifluoromethyl)imidazo[1,2-b]pyridazin-2-yl)methyl)benzoate (48 mg, 0.11 mmol). LC/MS (Method g) $R_t$=1.75 min.; MS m/z: 487 [M+H]$^+$ $^1$H NMR (DMSO-$d_6$, 400 MHz): δ 7.58 (d, J=8.4 Hz, 1H), 7.46 (d, J=1.1 Hz, 1H), 7.35 (d, J=8.4 Hz, 1H), 4.49 (m, 2H), 3.64 (m, 4H), 3.54 (m, 2H), 3.15 (m, 2H), 2.54 (d, J=0.9 Hz, 3H) 2.50 (s, 3H).

TABLE CZ
The following examples were prepared using the same procedure as example CZ, step 3 with the appropriate amines.
| Example # | Product | Amine | R$_t$ min | m/z ESI+ (M + H)$^+$ |
|---|---|---|---|---|
| CZ-1 | 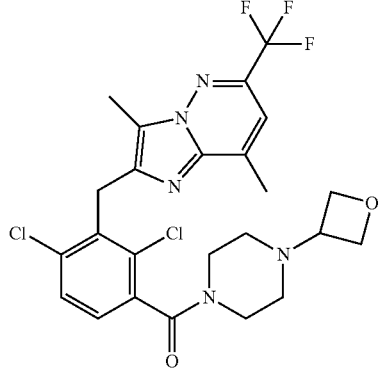 | 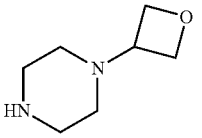 | 1.58 (method g) | 542 |
| CZ-2 | 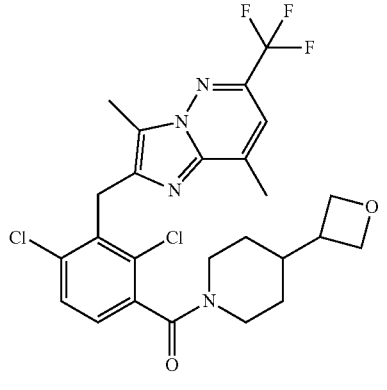 [SMILES: Cc1cc(C(F)(F)F)nn2c(C)c(Cc3c(Cl)ccc(C(=O)N4CCC(C5COC5)CC4)c3Cl)nc12] | 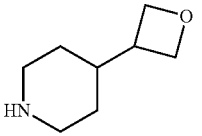 | 1.83 (method g) | 541 |
| CZ-3 | 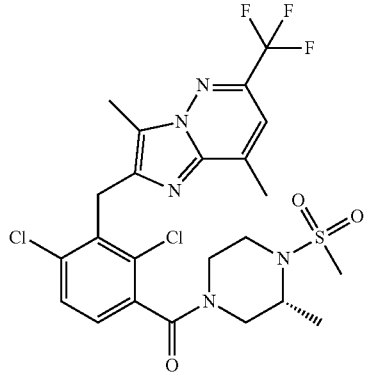 [SMILES: Cc1cc(C(F)(F)F)nn2c(C)c(Cc3c(Cl)ccc(C(=O)N4CCN(S(C)(=O)=O)[C@H](C)C4)c3Cl)nc12] | 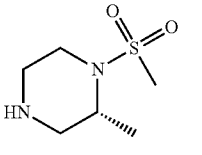 | 1.78 (method g) | 578 |

Example CZ-1A: 2-(1-(2,4-dichloro-3-(3,8-dimethyl-6-(trifluoromethyl)imidazo[1,2-b]pyridazine-2-carbonyl)benzoyl)piperidin-4-yl)acetic acid

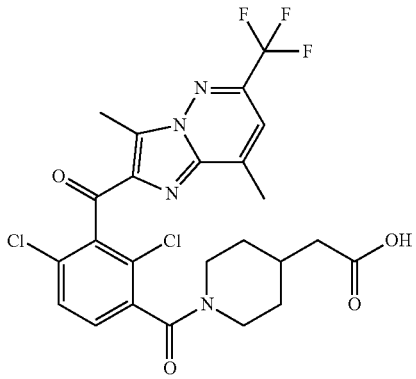 [SMILES: Cc1cc(C(F)(F)F)nn2c(C)c(C(=O)c3c(Cl)ccc(C(=O)N4CCC(CC(=O)O)CC4)c3Cl)nc12]

Step 1: 2,4-dichloro-3-(3,8-dimethyl-6-(trifluoromethyl)imidazo[1,2-b]pyridazine-2-carbonyl)benzoic acid

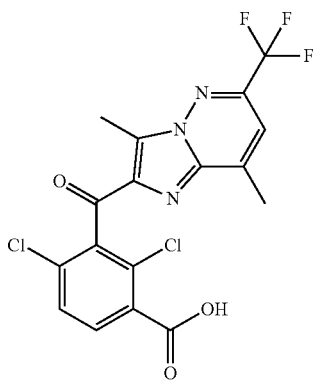 [SMILES: Cc1cc(C(F)(F)F)nn2c(C)c(C(=O)c3c(Cl)ccc(C(=O)O)c3Cl)nc12]

Using a procedure similar to Example AD, Step 2, 2,4-dichloro-3-(3,8-dimethyl-6-(trifluoromethyl)imidazo[1,2-b]pyridazine-2-carbonyl)benzoic acid (347 mg, 43%) was prepared from 2,4-dichloro-3-((3,8-dimethyl-6-(trifluoromethyl)imidazo[1,2-b]pyridazin-2-yl)methyl)benzoic acid (420 mg, 1 mmol) (example CZ, Step 2). LC/MS (Method g): Rt=1.78 min.; MS m/z: 432 [M+H]+;

$^1$H NMR (DMSO-d$_6$, 500 MHz): δ 13.67 (broad, 1H), 7.92 (d, J=8.5 Hz, 1H), 7.70 (d, J=8.5 Hz, 1H), 7.68 (s, 1H), 2.87 (s, 3H), 2.56 (s, 3H)

Step 2: methyl 2-(1-(2,4-dichloro-3-(3,8-dimethyl-6-(trifluoromethyl)imidazo[1,2-b]pyridazine-2-carbonyl)benzoyl)piperidin-4-yl)acetate

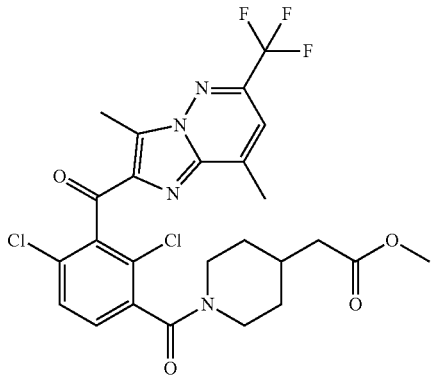 [SMILES: COC(=O)CC1CCN(C(=O)c2ccc(Cl)c(C(=O)c3nc4c(C)cc(C(F)(F)F)nn4c3C)c2Cl)CC1]

Using a procedure similar to Example A, Step 6, methyl 2-(1-(2,4-dichloro-3-(3,8-dimethyl-6-(trifluoromethyl)imidazo[1,2-b]pyridazine-2-carbonyl)benzoyl)piperidin-4-yl)acetate (45 mg, 57%) was prepared from 2,4-dichloro-3-(3,8-dimethyl-6-(trifluoromethyl)imidazo[1,2-b]pyridazine-2-carbonyl)benzoic acid (60 mg, 0.14 mmol) and methyl (4-piperidyl)acetate hydrochloride (40 mg, 0.21 mmol). LC/MS (Method i): Rt=2.33 min.; MS m/z: 571 [M+H]+; $^1$H NMR (DMSO-d$_6$, 300 MHz): δ 7.95 (s, 1H), 7.60 (m, 2H), 4.47 (m, 1H), 3.60 (m, 3H), 3.27 (m, 1H), 3.09 (m, 1H), 2.87 (s, 3H), 2.80 (m, 1H), 2.55 (m, 3H), 2.27 (m, 2H), 1.97 (m, 1H), 1.75 (m, 1H), 1.62 (m, 1H), 1.15 (m, 2H).

Step 3: 2-(1-(2,4-dichloro-3-(3,8-dimethyl-6-(trifluoromethyl)imidazo[1,2-b]pyridazine-2-carbonyl)benzoyl)piperidin-4-yl)acetic acid

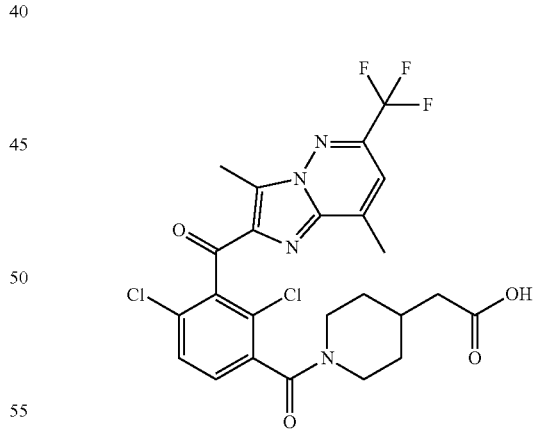

Using a procedure similar to Example A, Step 5, 2-(1-(2,4-dichloro-3-(3,8-dimethyl-6-(trifluoromethyl)imidazo[1,2-b]pyridazine-2-carbonyl)benzoyl)piperidin-4-yl)acetic acid (31 mg, 70%) was prepared from methyl 2-(1-(2,4-dichloro-3-(3,8-dimethyl-6-(trifluoromethyl)imidazo[1,2-b]pyridazine-2-carbonyl)benzoyl)piperidin-4-yl)acetate (45 mg, 0.08 mmol). LC/MS (Method g): Rt=1.66 min.; MS m/z: 557 [M+H]+; $^1$H NMR (DMSO-d$_6$, 400 MHz): δ=12.11 (broad, 1H), 7.69 (m, 2H), 7.59 and 7.52 (d, J=8.6 Hz, 1H), 4.46 (m, 1H), 3.24 (m, 1H), 3.10 (m, 1H), 2.87 (s, 3H), 2.81

(m, 1H), 2.57 (m, 3H), 2.16 (m, 2H), 1.95 (m, 1H), 1.77 (m, 1H), 1.64 (m, 1H), 1.18 (m, 2H).

Example DA: 2-(2,6-dichloro-3-(morpholine-4-carbonyl)benzyl)-3,8-dimethylimidazo[1,2-b]pyridazine-6-carbonitrile

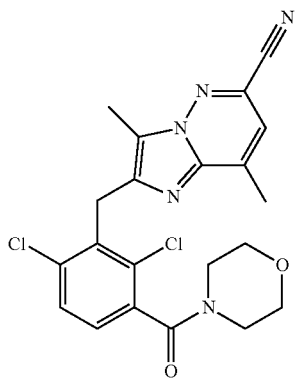 [SMILES: Cc1cc(C#N)nn2c(C)c(Cc3c(Cl)ccc(C(=O)N4CCOCC4)c3Cl)nc12]

Using a procedure similar to Example CI, Step 4, 2-(2,6-dichloro-3-(morpholine-4-carbonyl)benzyl)-3,8-dimethylimidazo[1,2-b]pyridazine-6-carbonitrile (41 mg, 79%) was prepared from (2,4-dichloro-3-((6-chloro-3,8-dimethylimidazo[1,2-b]pyridazin-2-yl)methyl)phenyl)(morpholino)methanone (Example CW, Step 3) (50 mg, 0.11 mmol). LC/MS (Method g) $R_t$=1.52 min.; MS m/z: 444 [M+H]$^+$ $^1$H NMR (DMSO-d$_6$, 400 MHz): δ 7.58 (d, J=8.4 Hz, 1H), 7.53 (d, J=1.1 Hz, 1H), 7.35 (d, J=8.4 Hz, 1H), 4.49 (m, 2H), 3.64 (m, 4H), 3.54 (m, 2H), 3.14 (m, 2H), 2.54 m (s, 3H), 2.50 (s, 3H).

Example DB: 2-(2,6-dichloro-3-(morpholine-4-carbonyl)benzyl)-3,7-dimethylimidazo[1,2-b]pyridazine-6-carbonitrile

Using a procedure similar to Example CI, Step 4, 2-(2,6-dichloro-3-(morpholine-4-carbonyl)benzyl)-3,7-dimethylimidazo[1,2-b]pyridazine-6-carbonitrile (30 mg, 13%) was prepared from (2,4-dichloro-3-((6-chloro-3,7-dimethylimidazo[1,2-b]pyridazin-2-yl)methyl)phenyl)(morpholino)methanone (Example CY, Step 2) (100 mg, 0.22 mmol). LC/MS (Method g) $R_t$=1.48 min.; MS m/z: 444 [M+H]$^+$ $^1$H NMR (DMSO-d$_6$, 400 MHz): δ 8.10 (d, J=1.1 Hz, 1H), 7.56 (d, J=8.4 Hz, 1H), 7.34 (d, J=8.4 Hz, 1H), 4.47 (m, 2H), 3.65 (m, 4H), 3.53 (m, 2H), 3.13 (m, 2H), 2.53 (s, 3H), 2.47 (m, 3H).

Example DC: (2,4-dichloro-3-((3,7-dimethyl-5-(trifluoromethyl)-3H-imidazo[4,5-b]pyridin-2-yl)methyl)phenyl)(morpholino)methanone

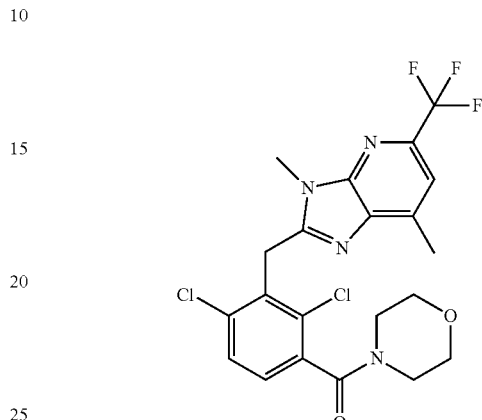

Step 1: methyl 2,4-dichloro-3-((3,7-dimethyl-5-(trifluoromethyl)-3H-imidazo[4,5-b]pyridin-2-yl)methyl)benzoate

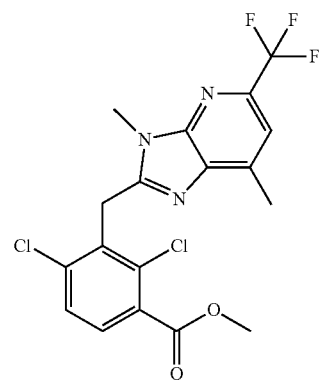 [SMILES: COC(=O)c1ccc(Cl)c(Cc2nc3c(C)cc(C(F)(F)F)nc3n2C)c1Cl]

To a solution of methyl 2,4-dichloro-3-((5-chloro-3,7-dimethyl-3H-imidazo[4,5-b]pyridin-2-yl)methyl)benzoate (Example CI, Step 1) (350 mg, 0.878 mmol) in DMF (2.5 mL) were added methyl 2,2-difluoro-2-(fluorosulfonyl)acetate (0.333 mL, 2.63 mmol) and copper(I) iodide (167 mg, 0.878 mmol) and the reaction mixture was stirred at 115° C. for 24 hours. The reaction mixture was diluted with EtOAc. The organic layer was washed with water, with 10% LiCl aqueous solution, with brine and it was dried over magnesium sulfate, filtered concentrated under reduced pressure. The residue was purified by column chromatography on silica gel (eluting with 0-5% EtOAc in cyclohexane) to give methyl 2,4-dichloro-3-((3,7-dimethyl-5-(trifluoromethyl)-3H-imidazo[4,5-b]pyridin-2-yl)methyl)benzoate (165 mg, 17%) as a pale yellow powder. The product was used directly in the next step.

LC/MS (Method h) $R_t$=2.86 min.; MS m/z: 432 [M+H]$^+$

543

Step 2: 2,4-dichloro-3-((3,7-dimethyl-5-(trifluoromethyl)-3H-imidazo[4,5-b]pyridin-2-yl)methyl)benzoic acid

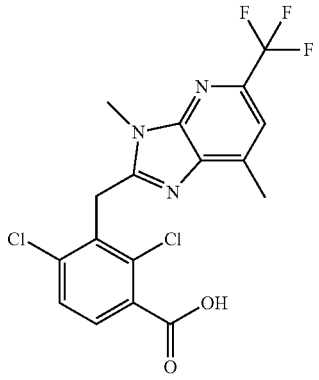 [SMILES: Cc1cc(C(F)(F)F)nc2c1nc(Cc1c(Cl)ccc(C(=O)O)c1Cl)n2C]

Using a procedure similar to Example F, Step 4, 2,4-dichloro-3-((3,7-dimethyl-5-(trifluoromethyl)-3H-imidazo[4,5-b]pyridin-2-yl)methyl)benzoic acid (210 mg, 94%) was prepared from methyl 2,4-dichloro-3-((3,7-dimethyl-5-(trifluoromethyl)-3H-imidazo[4,5-b]pyridin-2-yl)methyl)benzoate (230 mg, 0.53 mmol). LC/MS (Method h) $R_t$=2.15 min.; MS m/z: 418 [M+H]$^+$ $^1$H NMR (DMSO-d$_6$, 300 MHz): δ 7.84 and 7.66 (d, J=8.4 Hz, 1H), 7.50 (m, 1H), 7.13 (m, 1H), 4.61 (s, 1H), 4.53 (s, 1H), 3.87 (m, 3H), 2.39 and 2.37 (s, 3H).

Step 3: (2,4-dichloro-3-((3,7-dimethyl-5-(trifluoromethyl)-3H-imidazo[4,5-b]pyridin-2-yl)methyl)phenyl)(morpholino)methanone

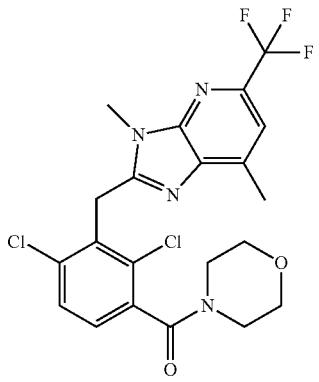 [SMILES: Cc1cc(C(F)(F)F)nc2c1nc(Cc1c(Cl)ccc(C(=O)N3CCOCC3)c1Cl)n2C]

Using a procedure similar to Example A, Step 6, (2,4-dichloro-3-((3,7-dimethyl-5-(trifluoromethyl)-3H-imidazo[4,5-b]pyridin-2-yl)methyl)phenyl)(morpholino)methanone (33 mg, 13%) was prepared from 2,4-dichloro-3-((3,7-dimethyl-5-(trifluoromethyl)-3H-imidazo[4,5-b]pyridin-2-yl)methyl)benzoic acid (210 mg, 0.50 mmol) and morpholine (125 mg, 0.65 mmol).

LC/MS (Method g) $R_t$=1.49 min.; MS m/z: 487 [M+H]$^+$
$^1$H NMR (DMSO-d$_6$, 500 MHz): δ 7.93 (d, J=8.4 Hz, 1H), 7.49 (d, J=8.4 Hz, 1H), 7.13 (d, J=0.7 Hz, 1H), 4.55 (s, 2H), 3.86 (m, 3H), 3.53-3.73 (m, 5H), 3.47 (m, 1H), 3.20 (m, 1H), 3.10 (m, 1H), 2.37 (s, 3H).

544

Example DD: (2,4-dichloro-3-((3,7-dimethyl-5-(trifluoromethyl)-1H-indazol-1-yl)methyl)phenyl)(morpholino)methanone

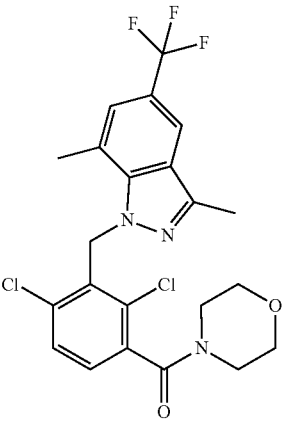

Step 1: methyl 2,4-dichloro-3-((3,7-dimethyl-5-(trifluoromethyl)-1H-indazol-1-yl)methyl)benzoate and methyl 2,4-dichloro-3-((3,7-dimethyl-5-(trifluoromethyl)-2H-indazol-2-yl)methyl)benzoate

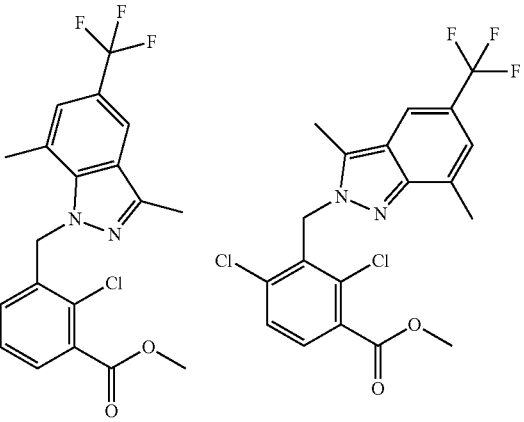

To a solution of 3,7-dimethyl-5-(trifluoromethyl)-1H-indazole (Preparation #42) (140 mg, 0.654 mmol) in DMF (5 mL) was added potassium carbonate (117 mg, 0.850 mmol) and the reaction mixture was stirred 30 minutes at room temperature. Methyl 3-(bromomethyl)-2,4-dichlorobenzoate (Preparation #1, Step B) (214 mg, 0.719 mmol) was added and the reaction was heated at 50° C. for 2 hours. The reaction mixture was poured into water (100 mL), and extracted with EtOAc. The combined organic layer was washed with brine and concentrated. The residue was purified by column chromatography on silica gel (eluting with 10-20% EtOAc in cyclohexane) to give methyl 2,4-dichloro-3-((3,7-dimethyl-5-(trifluoromethyl)-1H-indazol-1-yl)methyl)benzoate (82 mg, 17%) LC/MS (Method h) $R_t$=3.39 min.; MS m/z: 431 [M+H]$^+$ $^1$H NMR (DMSO-d$_6$, 500 MHz): δ 7.98 (s, 1H), 7.78 (d, J=8.5 Hz, 1H), 7.67 (d, J=8.5 Hz, 1H), 7.47 (s, 1H), 6.02 (s, 2H), 3.86 (s, 3H), 2.94 (s, 3H), 2.39 (s, 3H) and methyl 2,4-dichloro-3-((3,7-dimethyl-5-

(trifluoromethyl)-2H-indazol-2-yl)methyl)benzoate (215 mg, 49%). LC/MS (Method h) R$_t$=3.28 min.; MS m/z: 431 [M+H]$^+$. $^1$H NMR (DMSO-d$_6$, 300 MHz): δ 8.05 (s, 1H), 7.82 (d, J=8.5 Hz, 1H), 7.70 (d, J=8.5 Hz, 1H), 7.15 (s, 1H), 5.85 (s, 2H), 3.86 (s, 3H), 2.83 (s, 3H), 2.36 (s, 3H).

Step 2: 2,4-dichloro-3-((3,7-dimethyl-5-(trifluoromethyl)-1H-indazol-1-yl)methyl)benzoic acid

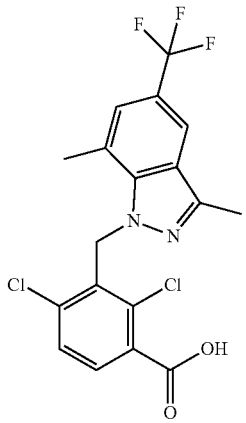 [SMILES: Cc1nn(Cc2c(Cl)ccc(C(=O)O)c2Cl)c2c(C)cc(C(F)(F)F)cc12]

Using a procedure similar to Example A, Step 5, 2,4-dichloro-3-((3,7-dimethyl-5-(trifluoromethyl)-1H-indazol-1-yl)methyl)benzoic acid (75 mg, 90%) was prepared from methyl 2,4-dichloro-3-((3,7-dimethyl-5-(trifluoromethyl)-1H-indazol-1-yl)methyl)benzoate (80 mg, 0.18 mmol).

LC/MS (Method h) R$_t$=2.93 min.; MS m/z: 417 [M+H]$^+$ $^1$H NMR (DMSO-d$_6$, 300 MHz): δ 7.98 (s, 1H), 7.74 (d, J=8.5 Hz, 1H), 7.62 (d, J=8.5 Hz, 1H), 7.48 (s, 1H), 6.01 (s, 2H), 2.94 (s, 3H), 2.39 (s, 3H).

Step 3: (2,4-dichloro-3-((3,7-dimethyl-5-(trifluoromethyl)-1H-indazol-1-yl)methyl)phenyl)(morpholino)methanone

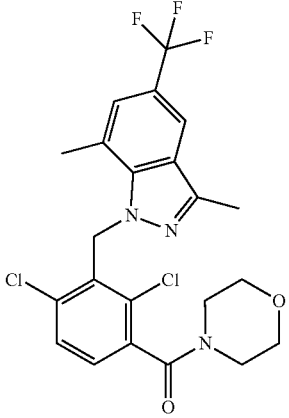 [SMILES: Cc1nn(Cc2c(Cl)ccc(C(=O)N3CCOCC3)c2Cl)c2c(C)cc(C(F)(F)F)cc12]

Using a procedure similar to Example A1, (2,4-dichloro-3-((3,7-dimethyl-5-(trifluoromethyl)-1H-indazol-1-yl)methyl)phenyl)(morpholino)methanone (25 mg, 30%) was prepared from 2,4-dichloro-3-((3,7-dimethyl-5-(trifluoromethyl)-1H-indazol-1-yl)methyl)benzoic acid (70 mg, 0.17 mmol) and morpholine (29 mg, 0.33 mmol). LC/MS (Method g) R$_t$=1.83 min.; MS m/z: 486 [M+H]$^+$ $^1$H NMR (DMSO-d$_6$, 400 MHz): δ 7.98 (s, 1H), 7.62 (d, J=8.4 Hz, 1H), 7.47 (s, 1H), 7.44 (d, J=8.4 Hz, 1H), 6.00 (d, J=12 Hz, 1H), 5.97 (d, J=12 Hz, 1H), 3.60 (m, 4H), 3.52 (m, 2H), 3.13 (m, 2H), 2.93 (s, 3H), 2.39 (s, 3H)

Example DD-1

(2,4-dichloro-3-((3,7-dimethyl-5-(trifluoromethyl)-1H-indazol-1-yl)methyl)phenyl)(4-(oxetan-3-yl)piperidin-1-yl)methanone

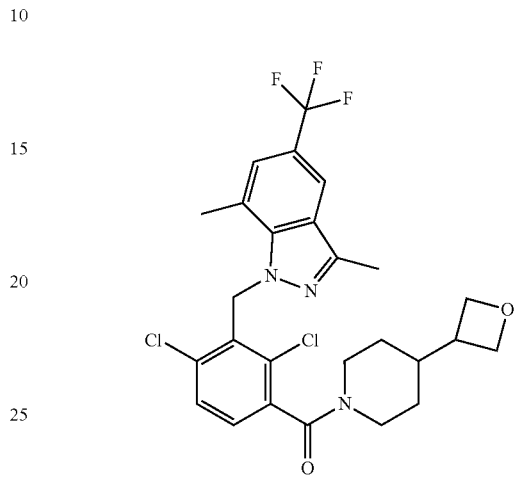

Using a procedure similar to Example A1, (2,4-dichloro-3-((3,7-dimethyl-5-(trifluoromethyl)-1H-indazol-1-yl)methyl)phenyl)(4-(oxetan-3-yl)piperidin-1-yl)methanone (128 mg, 72%) was prepared from 2,4-dichloro-3-((3,7-dimethyl-5-(trifluoromethyl)-1H-indazol-1-yl)methyl)benzoic acid (133 mg, 0.32 mmol) (Example DD, Step 1) and 4-(oxetan-3-yl)piperidine (58 mg, 0.41 mmol). LC/MS (Method g): Rt=1.91 min.; MS m/z: 540 [M+H]$^+$ $^1$H NMR (DMSO-d$_6$, 400 MHz): δ 7.98 (s, 1H), 7.61 and 7.60 (d, J=8.3 Hz, 1H), 7.47 (s, 1H), 7.44 and 7.37 (d, J=8.3 Hz, 1H), 5.99 (m, 2H), 4.58 (m, 2H), 4.49 (m, 1H), 4.33 (m, 2H), 3.25 (m, 1H), 3.02 (m, 1H), 2.93 (s, 3H), 2.76 (m, 2H), 2.39 and 2.38 (s, 3H), 1.89 (m, 1H), 1.67 (m, 1H), 1.51 (m, 1H), 0.96 (m, 2H).

Example DE: 2-(1-(2,4-dichloro-3-((3,7-dimethyl-5-(trifluoromethyl)-1H-indazol-1-yl)methyl)benzoyl)piperidin-4-yl)acetic acid

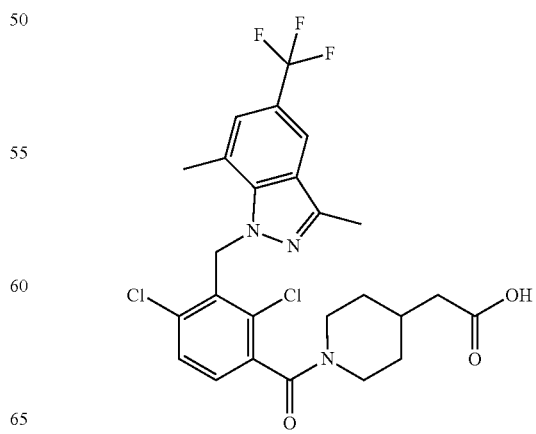

Step 1: methyl 2-(1-(2,4-dichloro-3-((3,7-dimethyl-5-(trifluoromethyl)-1H-indazol-1-yl)methyl)benzoyl)piperidin-4-yl)acetate

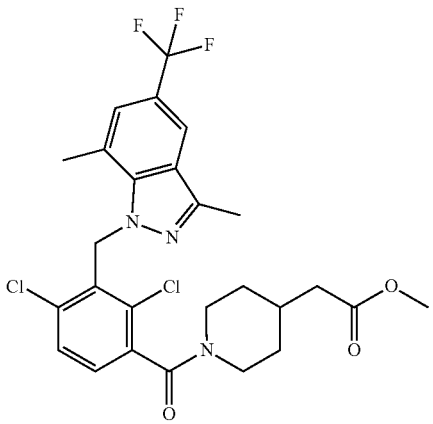 [SMILES: COC(=O)CC1CCN(C(=O)c2ccc(Cl)c(Cn3nc(C)c4cc(C(F)(F)F)cc(C)c43)c2Cl)CC1]

Using a procedure similar to Example A1, methyl 2-(1-(2,4-dichloro-3-((3,7-dimethyl-5-(trifluoromethyl)-1H-indazol-1-yl)methyl)benzoyl)piperidin-4-yl)acetate (90 mg, 73%) was prepared from 2,4-dichloro-3-((3,7-dimethyl-5-(trifluoromethyl)-1H-indazol-1-yl)methyl)benzoic acid (Example DD, Step 2) (92 mg, 0.22 mmol) and methyl (4-piperidyl)acetate hydrochloride (51 mg, 0.26 mmol). LC/MS (Method i) $R_t$=2.59 min.; MS m/z: 556 [M+H]$^+$ $^1$H NMR (DMSO-d$_6$, 300 MHz): δ 7.98 (s, 1H), 7.60 and 7.59 (d, J=8.3 Hz, 1H), 7.47 (s, 1H), 7.43 and 7.36 (d, J=8.3 Hz, 1H), 5.90 (m, 2H), 4.46 (m, 1H), 3.59 and 3.57 (s, 3H), 3.22 (m, 1H), 3.02 (m, 1H), 2.93 (s, 3H), 2.79 (m, 1H), 2.39 (m, 3H), 2.27 (m, 2H), 1.97 (m, 1H), 1.74 (m, 1H), 1.57 (m, 1H), 1.15 (m, 2H).

Step 2: 2-(1-(2,4-dichloro-3-((3,7-dimethyl-5-(trifluoromethyl)-1H-indazol-1-yl)methyl)benzoyl)piperidin-4-yl)acetic acid

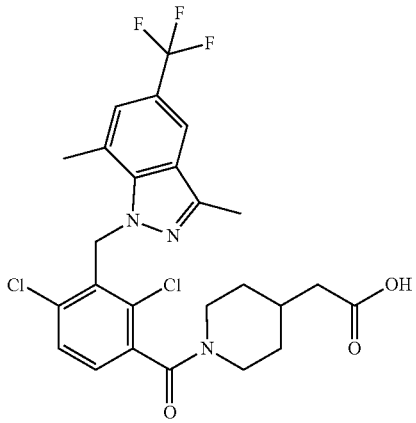 [SMILES: Cc1nn(Cc2c(Cl)ccc(C(=O)N3CCC(CC(=O)O)CC3)c2Cl)c2c(C)cc(C(F)(F)F)cc12]

Using a procedure similar to Example A, Step 5, 2-(1-(2,4-dichloro-3-((3,7-dimethyl-5-(trifluoromethyl)-1H-indazol-1-yl)methyl)benzoyl)piperidin-4-yl)acetic acid (64 mg, 71%) was prepared from methyl 2-(1-(2,4-dichloro-3-((3,7-dimethyl-5-(trifluoromethyl)-1H-indazol-1-yl)methyl)benzoyl)piperidin-4-yl)acetate (90 mg, 0.16 mmol). LC/MS (Method g) $R_t$=1.77 min.; MS m/z: 542 [M+H]$^+$ $^1$H NMR (DMSO-d$_6$, 500 MHz): δ 12.09 (broad, 1H), 7.98 (s, 1H), 7.60 (m, 1H), 7.47 (s, 1H), 7.43 and 7.36 (d, J=8.3 Hz, 1H), 5.96 (m, 2H), 4.46 (m, 1H), 3.23 (m, 1H), 2.02 (m, 1H), 2.93 (s, 3H), 2.79 (m, 1H), 2.39 (m, 3H), 2.15 (m, 2H), 1.92 (m, 1H), 1.76 (m, 1H), 1.60 (m, 1H), 1.10 (m, 2H).

Example DF: (2,4-dichloro-3-((3,7-dimethyl-5-(trifluoromethyl)-2H-indazol-2-yl)methyl)phenyl)(morpholino)methanone

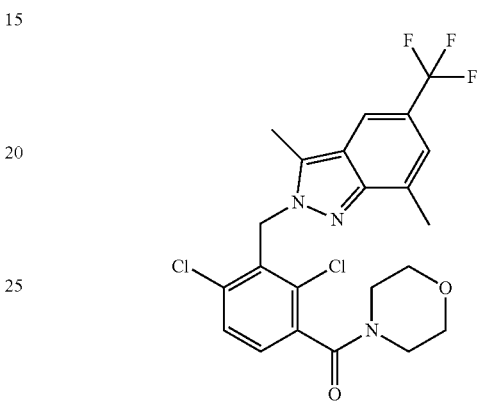

Step 1: 2,4-dichloro-3-((3,7-dimethyl-5-(trifluoromethyl)-2H-indazol-2-yl)methyl)benzoic acid

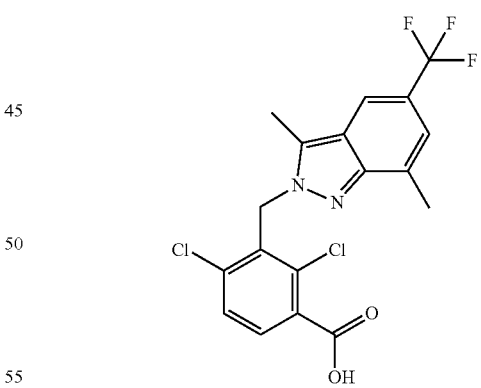

Using a procedure similar to Example A, Step 5, 2,4-dichloro-3-((3,7-dimethyl-5-(trifluoromethyl)-2H-indazol-2-yl)methyl)benzoic acid (160 mg, 76%) was prepared from methyl 2,4-dichloro-3-((3,7-dimethyl-5-(trifluoromethyl)-2H-indazol-2-yl)methyl)benzoate (Example DD, Step 1) (200 mg, 0.46 mmol). LC/MS (Method h) $R_t$=2.81 min.; MS m/z: 417 [M+H]$^+$ $^1$H NMR (DMSO-d$_6$, 300 MHz): δ 13.68 (s, 1H), 8.05 (s, 1H), 7.78 (d, J=9 Hz, 1H), 7.65 (d, J=9 Hz, 1H), 7.15 (s, 1H), 5.84 (s, 2H), 2.83 (s, 3H), 2.36 (s, 3H).

Step 2: (2,4-dichloro-3-((3,7-dimethyl-5-(trifluoromethyl)-2H-indazol-2-yl)methyl)phenyl)(morpholino)methanone

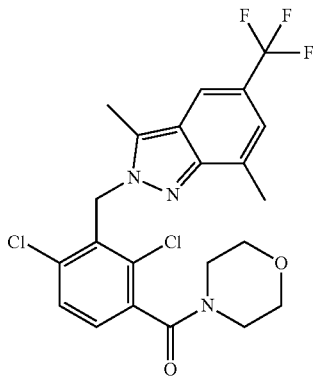 [SMILES: Cc1cc(C(F)(F)F)cc2c(C)n(Cc3c(Cl)ccc(C(=O)N4CCOCC4)c3Cl)nc12]

Using a procedure similar to Example A1, (2,4-dichloro-3-((3,7-dimethyl-5-(trifluoromethyl)-2H-indazol-2-yl)methyl)phenyl)(morpholino)methanone (153 mg, 82%) was prepared from 2,4-dichloro-3-((3,7-dimethyl-5-(trifluoromethyl)-2H-indazol-2-yl)methyl)benzoic acid (156 mg, 0.37 mmol) and morpholine (65 mg, 0.75 mmol). LC/MS (Method g) $R_f$=1.78 min.; MS m/z: 486 [M+H]$^+$ $^1$H NMR (DMSO-$d_6$, 400 MHz): δ 8.05 (s, 1H), 7.64 (d, J=8.4 Hz, 1H), 7.47 (d, J=8.4 Hz, 1H), 7.15 (s, 1H), 5.81 (m, 2H), 3.60 (m, 4H), 3.53 (m, 2H), 3.14 (m, 2H), 2.83 (s, 3H), 2.34 (s, 3H).

Example DG: 2-(1-(2,4-dichloro-3-((3,7-dimethyl-5-(trifluoromethyl)-2H-indazol-2-yl)methyl)benzoyl)piperidin-4-yl)acetic acid

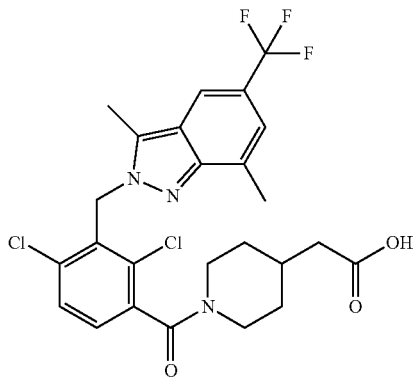 [SMILES: Cc1cc(C(F)(F)F)cc2c(C)n(Cc3c(Cl)ccc(C(=O)N4CCC(CC(=O)O)CC4)c3Cl)nc12]

Step 1: methyl 2-(1-(2,4-dichloro-3-((3,7-dimethyl-5-(trifluoromethyl)-2H-indazol-2-yl)methyl)benzoyl)piperidin-4-yl)acetate

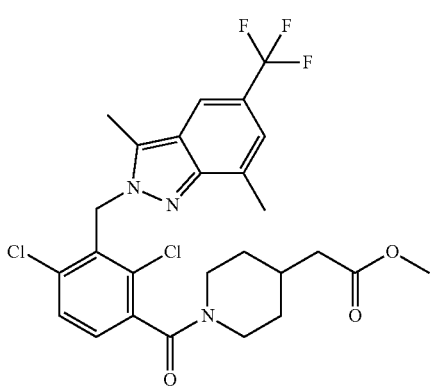 [SMILES: COC(=O)CC1CCN(C(=O)c2ccc(Cl)c(Cn3nc4c(C)cc(C(F)(F)F)cc4c3C)c2Cl)CC1]

Using a procedure similar to Example A1, methyl 2-(1-(2,4-dichloro-3-((3,7-dimethyl-5-(trifluoromethyl)-2H-indazol-2-yl)methyl)benzoyl)piperidin-4-yl)acetate (192 mg, 56%) was prepared from 2,4-dichloro-3-((3,7-dimethyl-5-(trifluoromethyl)-2H-indazol-2-yl)methyl)benzoic acid (Example DF, Step 1) (237 mg, 0.56 mmol) and methyl (4-piperidyl)acetate hydrochloride (132 mg, 0.68 mmol). LC/MS (Method i): $R_f$=2.52 min.; MS m/z: 556 [M+H]$^+$ $^1$H NMR (DMSO-$d_6$, 300 MHz): δ 8.05 (s, 1H), 7.63 and 7.60 (d, J=8.3 Hz, 1H), 7.46 and 7.38 (d, J=8.3 Hz, 1H), 7.15 (s, 1H), 5.82 (m, 2H), 4.46 (m, 1H), 3.59 and 3.57 (s, 3H), 3.22 (m, 1H), 3.03 (m, 1H), 2.83 (m, 3H), 2.79 (m, 1H), 2.34 (s, 3H), 2.20 (m, 2H), 1.99 (m, 1H), 1.75 (m, 1H), 1.56 (m, 1H), 1.15 (m, 2H).

Step 2: 2-(1-(2,4-dichloro-3-((3,7-dimethyl-5-(trifluoromethyl)-2H-indazol-2-yl)methyl)benzoyl)piperidin-4-yl)acetic acid

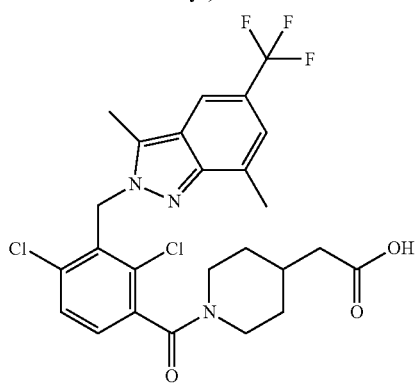

Using a procedure similar to Example A, Step 5, 2-(1-(2,4-dichloro-3-((3,7-dimethyl-5-(trifluoromethyl)-2H-indazol-2-yl)methyl)benzoyl)piperidin-4-yl)acetic acid (170 mg, 89%) was prepared from methyl 2-(1-(2,4-dichloro-3-((3,7-dimethyl-5-(trifluoromethyl)-2H-indazol-2-yl)methyl)benzoyl)piperidin-4-yl)acetate (190 mg, 0.34 mmol). LC/MS (Method g): $R_f$=1.71 min.;

MS m/z: 542 [M+H]$^+$ $^1$H NMR (DMSO-$d_6$, 400 MHz): δ 12.15 (s, 1H), 8.04 (s, 1H), 7.61 (m, 1H), 7.46 and 7.38 (d, J=8.3 Hz, 1H), 7.14 (s, 1H), 5.73-5.91 (m, 2H), 4.47 (m, 1H), 3.21 (m, 1H), 3.03 (m, 1H), 2.83 (s, 3H), 2.78 (m, 1H), 2.34 (s, 3H), 2.10 (m, 2H), 1.93 (m, 1H), 1.77 (m, 1H), 1.58 (m, 1H), 1.10 (m, 2H).

Example DH: 1-(2,4-dichloro-3-((3,7-dimethyl-5-(trifluoromethyl)-1H-indol-1-yl)methyl)benzoyl)piperidine-4-carboxylic acid

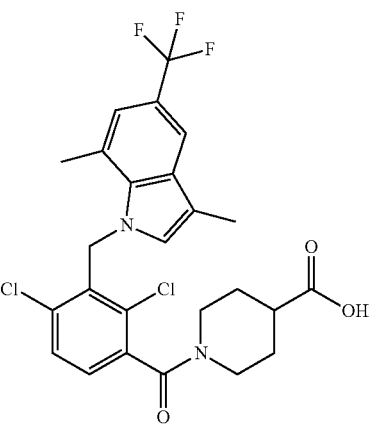 [SMILES: Cc1cn(Cc2c(Cl)ccc(C(=O)N3CCC(C(=O)O)CC3)c2Cl)c2c(C)cc(C(F)(F)F)cc12]

Step 1: methyl 2,4-dichloro-3-((3,7-dimethyl-5-(trifluoromethyl)-1H-indol-1-yl)methyl)benzoate

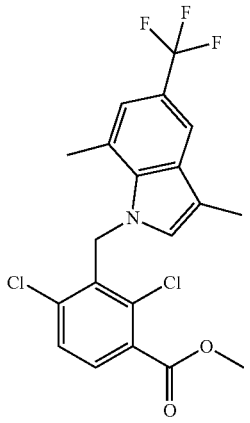 [SMILES: COC(=O)c1ccc(Cl)c(Cn2cc(C)c3cc(C(F)(F)F)cc(C)c32)c1Cl]

To a solution of 3,7-dimethyl-5-(trifluoromethyl)-1H-indole (Preparation #43) (90 mg, 0.422 mmol) in DMF (1.1 mL) and cooled to 0° C. was added sodium hydride (18.57 mg, 0.464 mmol). After 30 minutes of stirring, methyl 3-(bromomethyl)-2,4-dichlorobenzoate (Preparation #1, Step B) (126 mg, 0.422 mmol) was added and the stirring was continued for 1 hour at 0° C. The reaction mixture was diluted with water and EtOAc. The layers were separated and the aqueous one was extracted with EtOAc. The organic layers were combined, dried over magnesium sulfate, filtered and concentrated under reduced pressure. The residue was purified by column chromatography on silica gel (eluting with 0-5% EtOAc in cyclohexane) to give methyl 2,4-dichloro-3-((3,7-dimethyl-5-(trifluoromethyl)-1H-indol-1-yl)methyl)benzoate (100 mg, 53%) as a white powder. LC/MS (Method i): $R_t$=2.86 min.;
MS m/z: 430 [M+H]$^+$ $^1$H NMR (DMSO-d$_6$, 300 MHz): δ 7.88 (d, J=8.4 Hz, 1H), 7.75 (d, J=8.4 Hz, 1H), 7.68 (s, 1H), 7.23 (s, 1H), 6.55 (d, J=1.2 Hz, 1H), 5.92 (s, 2H), 3.88 (s, 3H), 2.93 (s, 3H), 2.17 (s, 3H).

Step 2: 2,4-dichloro-3-((3,7-dimethyl-5-(trifluoromethyl)-1H-indol-1-yl)methyl)benzoic acid

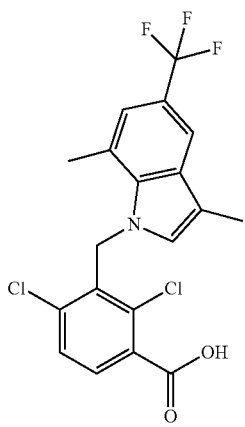 [SMILES: Cc1cn(Cc2c(Cl)ccc(C(=O)O)c2Cl)c2c(C)cc(C(F)(F)F)cc12]

Using a procedure similar to Example F, Step 4, 2,4-dichloro-3-((3,7-dimethyl-5-(trifluoromethyl)-1H-indol-1-yl)methyl)benzoic acid (90 mg, 93%) was prepared from methyl 2,4-dichloro-3-((3,7-dimethyl-5-(trifluoromethyl)-1H-indol-1-yl)methyl)benzoate (100 mg, 0.23 mmol).
LC/MS (Method i): $R_t$=2.57 min.; MS m/z: 416 [M+H]$^+$ $^1$H NMR (DMSO-d$_6$, 300 MHz): δ 7.67 (s, 1H), 7.55 (s, 2H), 7.22 (s, 1H), 6.52 (s, 1H), 5.87 (s, 2H), 2.93 (s, 3H), 2.16 (s, 3H).

Step 3: methyl 1-(2,4-dichloro-3-((3,7-dimethyl-5-(trifluoromethyl)-1H-indol-1-yl)methyl)benzoyl)piperidine-4-carboxylate

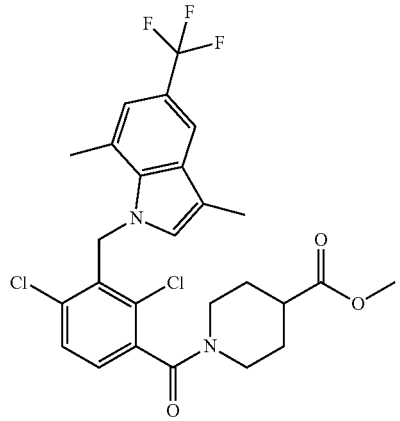 [SMILES: COC(=O)C1CCN(C(=O)c2ccc(Cl)c(Cn3cc(C)c4cc(C(F)(F)F)cc(C)c43)c2Cl)CC1]

Using a procedure similar to Example A, Step 6, methyl 1-(2,4-dichloro-3-((3,7-dimethyl-5-(trifluoromethyl)-1H-indol-1-yl)methyl)benzoyl)piperidine-4-carboxylate (84 mg, 72%) was prepared from 2,4-dichloro-3-((3,7-dimethyl-5-(trifluoromethyl)-1H-indol-1-yl)methyl)benzoic acid (90 mg, 0.12 mmol) and methyl piperidine-4-carboxylate hydrochloride (43 mg, 0.24 mmol). LC/MS (Method i): $R_t$=2.69 min.; MS m/z: 541 [M+H]$^+$ $^1$H NMR (DMSO-d$_6$, 300 MHz): δ 7.69 (m, 2H), 7.55 and 7.48 (d, J=8.3 Hz, 1H), 7.23 (s, 1H), 6.56 (m, 1H), 5.90 (m, 2H), 4.35 (m, 1H), 3.62 and 3.60 (s, 3H), 3.31 (m, 1H), 2.94-3.15 (m, 2H), 2.92 (s, 3H), 2.67 (m, 1H), 2.18 (m, 3H), 1.90 (m, 1H), 1.77 (m, 1H), 1.50 (m, 2H)

Step 4: 1-(2,4-dichloro-3-((3,7-dimethyl-5-(trifluoromethyl)-1H-indol-1-yl)methyl)benzoyl)piperidine-4-carboxylic acid

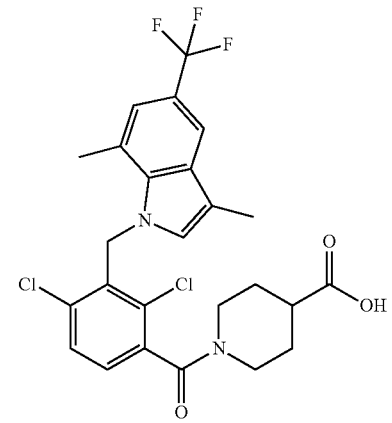 [SMILES: Cc1cn(Cc2c(Cl)ccc(C(=O)N3CCC(C(=O)O)CC3)c2Cl)c2c(C)cc(C(F)(F)F)cc12]

Using a procedure similar to Example F, Step 4, 1-(2,4-dichloro-3-((3,7-dimethyl-5-(trifluoromethyl)-1H-indol-1-yl)methyl)benzoyl)piperidine-4-carboxylic acid (67 mg, 82%) was prepared from methyl 1-(2,4-dichloro-3-((3,7-dimethyl-5-(trifluoromethyl)-1H-indol-1-yl)methyl)benzoyl)piperidine-4-carboxylate (84 mg, 0.15 mmol). LC/MS (Method g): $R_t$=1.87 min.; MS m/z: 527 [M+H]$^+$ $^1$H NMR (DMSO-d$_6$, 400 MHz): δ 12.30 (broad, 1H), 7.70 (m, 2H), 7.55 and 7.48 (d, J=8.1 Hz, 1H), 7.22 (s, 1H), 6.57 and 6.55 (d, 1H), 5.90 (m, 2H), 4.34 (m, 1H), 3.29 (m, 1H), 3.00 (m, 2H), 2.92 (s, 3H), 2.54 (m, 1H), 2.18 (s, 3H), 1.92 (m, 1H), 1.76 (m, 1H), 1.49 (m, 2H).

TABLE DH

The following intermediates were prepared from 2,4-dichloro-3-((3,7-dimethyl-5-(trifluoromethyl)-1H-indol-1-yl)methyl)benzoic acid (Example DH, Step 2) using the same procedure as in example DH, step 3, with the appropriate amine.

| Example # | Product | Amine | $R_t$ min | m/z ESI+ (M + H)$^+$ |
|---|---|---|---|---|
| DH-1 | 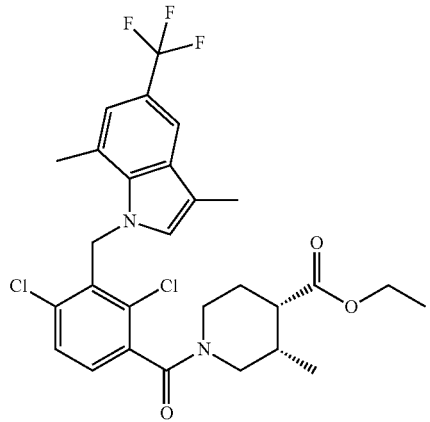 [SMILES: CCOC(=O)[C@H]1CCN(C(=O)c2ccc(Cl)c(Cn3cc(C)c4cc(C(F)(F)F)cc(C)c43)c2Cl)C[C@H]1C] | 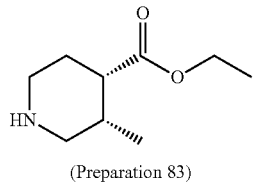 (Preparation 83) | 2.41 (Method j) | 569 |
| DH-2 | 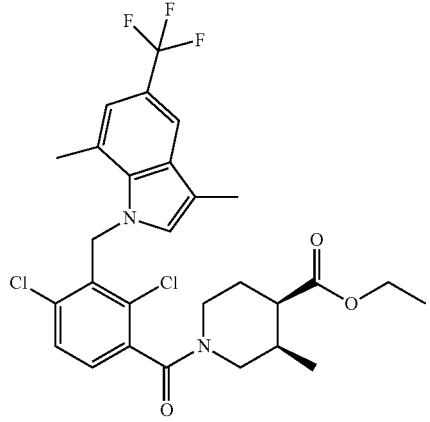 [SMILES: CCOC(=O)[C@@H]1CCN(C(=O)c2ccc(Cl)c(Cn3cc(C)c4cc(C(F)(F)F)cc(C)c43)c2Cl)C[C@@H]1C] | 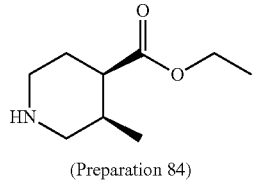 (Preparation 84) | 2.86 (Method i) | 569 |

TABLE DH1

The following examples were prepared using the same procedure as example DH, step 4 with the appropriate esters described in Table DH.

| Example # | Product | Ester | R, min | m/z ESI+ (M + H)+ |
|---|---|---|---|---|
| DH1-1 | (structure) | DH-1 | 1.95 (Method g) | 541 |
| DH1-2 | (structure) | DH-2 | 1.94 (Method g) | 541 |

Example DI: 2-(1-(2,4-dichloro-3-((3,7-dimethyl-5-(trifluoromethyl)-1H-indol-1-yl)methyl)benzoyl)piperidin-4-yl)acetic acid Step 1: methyl 2-(1-(2,4-dichloro-3-((3,7-dimethyl-5-(trifluoromethyl)-1H-indol-1-yl)methyl)benzoyl)piperidin-4-yl)acetate

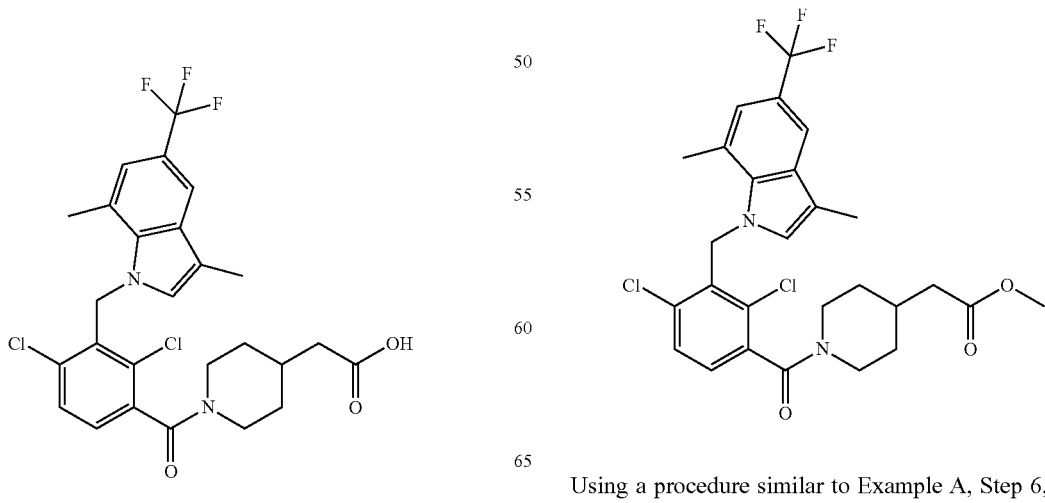

Using a procedure similar to Example A, Step 6, methyl 2-(1-(2,4-dichloro-3-((3,7-dimethyl-5-(trifluoromethyl)-

1H-indol-1-yl)methyl)benzoyl)piperidin-4-yl)acetate (120 mg, 84%) was prepared from 2,4-dichloro-3-((3,7-dimethyl-5-(trifluoromethyl)-1H-indol-1-yl)methyl)benzoic acid (Example DH, Step 2) (105 mg, 0.25 mmol) and methyl (4-piperidyl)acetate hydrochloride (54 mg, 0.27 mmol).

LC/MS (Method i): $R_t$=2.73 min.; MS m/z: 555 [M+H]$^+$ $^1$H NMR (DMSO-d$_6$, 300 MHz): δ 7.69 (m, 2H), 7.52 and 7.45 (d, J=8.3 Hz, 1H), 7.23 (s, 1H), 6.55 (m, 1H), 5.88 (m, 2H), 4.46 (m, 1H), 3.59 and 3.57 (s, 3H), 3.25 (m, 1H), 3.04 (m, 1H), 2.92 (s, 3H), 2.80 (m, 1H), 2.27 (m, 2H), 2.17 (s, 3H), 1.95 (m, 1H), 1.75 (m, 1H), 1.58 (m, 1H), 1.10 (m, 2H).

Step 2: 2-(1-(2,4-dichloro-3-((3,7-dimethyl-5-(trifluoromethyl)-1H-indol-1-yl)methyl)benzoyl)piperidin-4-yl)acetic acid

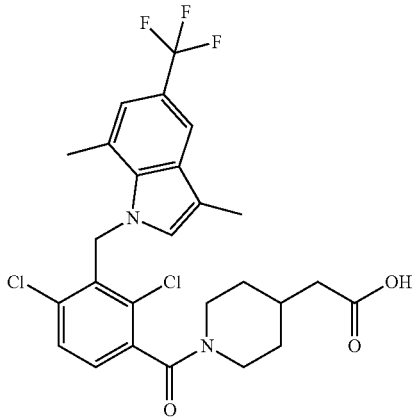 [SMILES: Cc1cn(Cc2c(Cl)ccc(C(=O)N3CCC(CC(=O)O)CC3)c2Cl)c2c(C)cc(C(F)(F)F)cc12]

Using a procedure similar to Example F, Step 4, 2-(1-(2,4-dichloro-3-((3,7-dimethyl-5-(trifluoromethyl)-1H-indol-1-yl)methyl)benzoyl)piperidin-4-yl)acetic acid (70 mg, 58%) was prepared from methyl 2-(1-(2,4-dichloro-3-((3,7-dimethyl-5-(trifluoromethyl)-1H-indol-1-yl)methyl)benzoyl)piperidin-4-yl)acetate (120 mg, 0.21 mmol). LC/MS (Method g): $R_t$=1.89 min.;

MS m/z: 541 [M+H]$^+$ $^1$H NMR (DMSO-d$_6$, 400 MHz): δ 12.10 (broad, 1H), 7.71 (m, 2H), 7.52 and 7.45 (d, J=8.4 Hz, 1H), 7.22 (s, 1H), 6.55 and 6.53 (s, 1H), 5.85 (m, 2H), 4.46 (m, 1H), 3.26 (m, 1H), 3.03 (m, 1H), 2.92 (s, 3H), 2.80 (m, 1H), 2.19 (m, 5H), 1.90 (m, 1H), 1.77 (m, 1H), 1.60 (m, 1H), 1.10 (m, 2H).

Example DJ: 2-(1-(2,4-dichloro-3-(3,7-dimethyl-5-(trifluoromethyl)-1H-indole-1-carbonyl)benzoyl)piperidin-4-yl)acetic acid

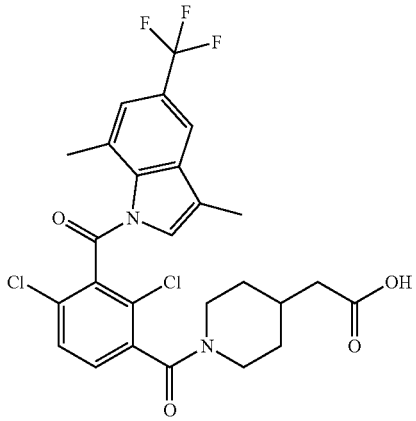 [SMILES: Cc1cn(C(=O)c2c(Cl)ccc(C(=O)N3CCC(CC(=O)O)CC3)c2Cl)c2c(C)cc(C(F)(F)F)cc12]

Step 1: tert-butyl 2,4-dichloro-3-(3,7-dimethyl-5-(trifluoromethyl)-1H-indole-1-carbonyl)benzoate

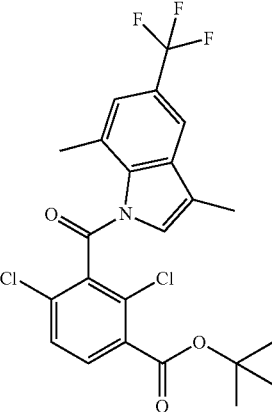 [SMILES: Cc1cn(C(=O)c2c(Cl)ccc(C(=O)OC(C)(C)C)c2Cl)c2c(C)cc(C(F)(F)F)cc12]

To a solution of 3,7-dimethyl-5-(trifluoromethyl)-1H-indole (Preparation #43) (170 mg, 0.797 mmol) in DMF (5 mL) and cooled at 0° C. was added sodium hydride (57.4 mg, 1.435 mmol) and the reaction mixture was stirred at 0° C. for 20 minutes. Tert-butyl 2,4-dichloro-3-(chlorocarbonyl)benzoate (Preparation #44) (443 mg, 1.435 mmol) diluted in DMF (4 mL) was then added and the reaction mixture was stirred at room temperature for 3 hours. The reaction mixture was quenched with a NH$_4$Cl saturated aqueous solution and extracted with EtOAc. The organic layer was washed with water and brine, dried over magnesium sulfate, filtered and concentrated to dryness. The residue was purified by column chromatography on silica gel (eluting with 0-10% EtOAc in cyclohexane) to give tert-butyl 2,4-dichloro-3-(3,7-dimethyl-5-(trifluoromethyl)-1H-indole-1-carbonyl)benzoate (300 mg, 76%) as a yellow resin. LC/MS (Method j): $R_t$=2.87 min.; MS m/z: 486 [M+H]$^+$. $^1$H NMR (DMSO-d$_6$, 300 MHz): δ 7.99 (d, J=8.4 Hz, 1H), 7.82 (m, 2H), 7.61 (s, 1H), 7.27 (s, 1H), 2.73 (s, 3H), 2.21 (s, 3H), 1.57 (s, 9H)

Step 2: 2,4-dichloro-3-(3,7-dimethyl-5-(trifluoromethyl)-1H-indole-1-carbonyl)benzoic acid

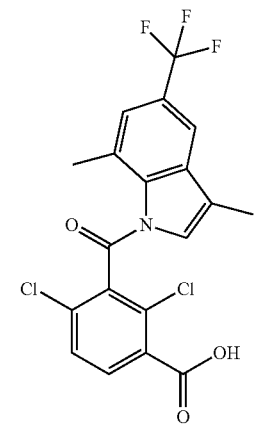 [SMILES: Cc1cn(C(=O)c2c(Cl)ccc(C(=O)O)c2Cl)c2c(C)cc(C(F)(F)F)cc12]

To a solution of tert-butyl 2,4-dichloro-3-(3,7-dimethyl-5-(trifluoromethyl)-1H-indole-1-carbonyl)benzoate (300 mg, 0.617 mmol) in DCM (5 mL) was added TFA (2.5 mL, 32.4 mmol) and the reaction mixture was stirred at room temperature for 1 hour. The reaction mixture was concentrated with toluene under reduced pressure to give 2,4-dichloro-3-(3,7-dimethyl-5-(trifluoromethyl)-1H-indole-1-carbonyl)benzoic acid (260 mg, 96%) as a beige solid.

LC/MS (Method i): $R_t$=2.50 min.; MS m/z: 430 [M+H]$^+$ $^1$H NMR (DMSO-d$_6$, 300 MHz): δ 13.87 (broad, 1H), 8.05 (d, J=8.4 Hz, 1H), 7.81 (m, 2H), 7.61 (s, 1H), 7.25 (s, 1H), 2.74 (s, 3H), 2.21 (s, 3H).

Step 3: methyl 2-(1-(2,4-dichloro-3-(3,7-dimethyl-5-(trifluoromethyl)-1H-indole-1-carbonyl)benzoyl)piperidin-4-yl)acetate

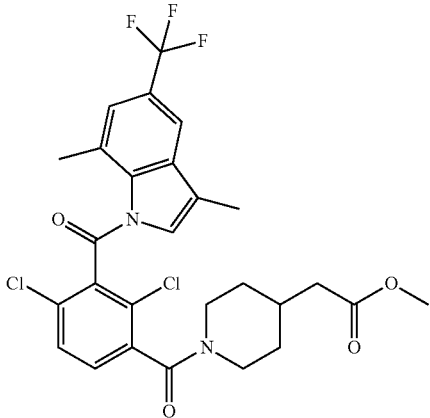 [SMILES: COC(=O)CC1CCN(C(=O)c2ccc(Cl)c(C(=O)n3cc(C)c4cc(C(F)(F)F)cc(C)c43)c2Cl)CC1]

Using a procedure similar to Example A, Step 6, methyl 2-(1-(2,4-dichloro-3-(3,7-dimethyl-5-(trifluoromethyl)-1H-indole-1-carbonyl)benzoyl)piperidin-4-yl)acetate (150 mg, 81%) was prepared from 2,4-dichloro-3-(3,7-dimethyl-5-(trifluoromethyl)-1H-indole-1-carbonyl)benzoic acid (105 mg, 0.25 mmol) and methyl (4-piperidyl)acetate hydrochloride (64 mg, 0.33 mmol). LC/MS (Method i): $R_t$=2.71 min.; MS m/z: 569 [M+H]$^+$ $^1$H NMR (DMSO-d$_6$, 300 MHz): δ 7.76-81 (m, 2H), 7.65 (m, 2H), 7.43, 7.37 and 7.17 (m, 1H), 4.47 (m, 1H), 3.60 (m, 3H), 3.23 (m, 1H), 3.07 (m, 1H), 2.85 (m, 1H), 2.72 (s, 3H), 2.30 (m, 2H), 2.23 (m, 3H), 1.92 (m, 1H), 1.77 (m, 1H), 1.62 (m, 1H), 1.06-1.27 (m, 2H).

Step 4: 2-(1-(2,4-dichloro-3-(3,7-dimethyl-5-(trifluoromethyl)-1H-indole-1-carbonyl)benzoyl)piperidin-4-yl)acetic acid

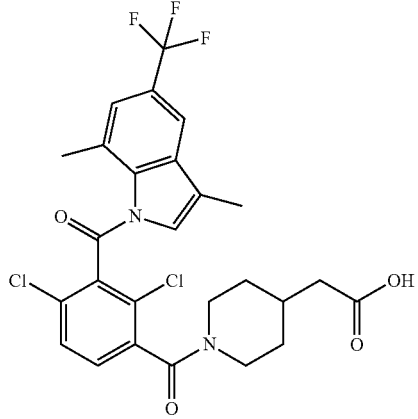 [SMILES: Cc1cn(C(=O)c2c(Cl)ccc(C(=O)N3CCC(CC(=O)O)CC3)c2Cl)c2c(C)cc(C(F)(F)F)cc12]

Using a procedure similar to Example F, Step 4, 2-(1-(2,4-dichloro-3-(3,7-dimethyl-5-(trifluoromethyl)-1H-indole-1-carbonyl)benzoyl)piperidin-4-yl)acetic acid (96 mg, 65%) was prepared from methyl 2-(1-(2,4-dichloro-3-(3,7-dimethyl-5-(trifluoromethyl)-1H-indole-1-carbonyl)benzoyl)piperidin-4-yl)acetate (150 mg, 0.26 mmol). LC/MS (Method g): $R_t$=1.89 min.; MS m/z: 555 [M+H]$^+$ $^1$H NMR (DMSO-d$_6$, 400 MHz): δ 12.10 (s, 1H), 7.82 (m, 2H), 7.57-7.72 (m, 2H), 7.42, 7.37 and 7.16 (m, 1H), 4.48 (m, 1H), 3.57 and 3.26 (m, 1H), 3.08 (m, 1H), 2.82 (m, 1H), 2.72 (s, 3H), 2.23 (m, 3H), 2.19 (m, 2H), 1.95 (m, 1H), 1.77 (m, 1H), 1.63 (m, 1H), 1.16 (m, 2H).

TABLE DJ

The following intermediates were prepared from (Example DJ, Step 2) using the same procedure as in example DJ, step 3, with the appropriate amine.

| Example # | Product | Amine | $R_t$ min | m/z ESI+ (M + H)$^+$ |
|---|---|---|---|---|
| DJ-1 | | | 2.67 (Method i) | 555 |

TABLE DJ-continued

The following intermediates were prepared from (Example DJ, Step 2) using the same procedure as in example DJ, step 3, with the appropriate amine.

| Example # | Product | Amine | R, min | m/z ESI+ (M + H)+ |
|---|---|---|---|---|
| DJ-2 | 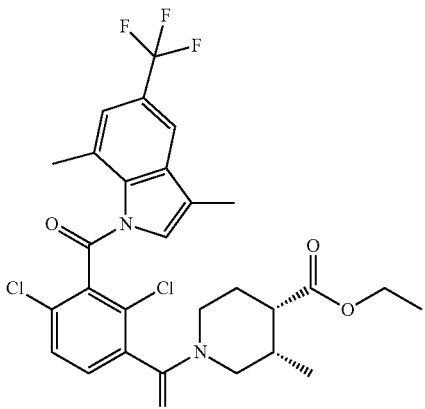 | 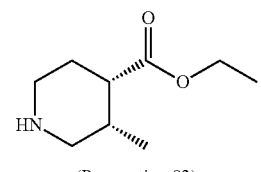 (Preparation 83) | 2.84 (Method i) | 583 |
| DJ-3 | 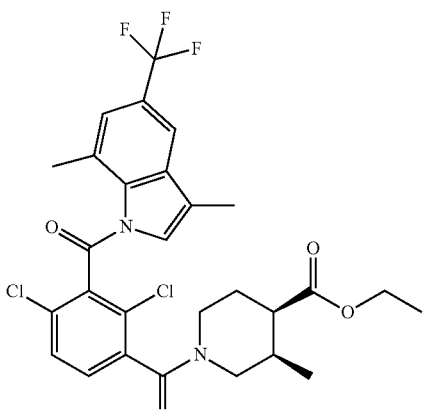 | 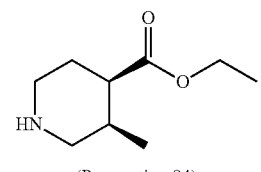 (Preparation 84) | 2.84 (Method i) | 583 |

TABLE DJ1

The following examples were prepared using the same procedure as example DJ, step 4, with the appropriate esters described in Table DJ.

| Example # | Product | Ester | R, min | m/z ESI+ (M + H)+ |
|---|---|---|---|---|
| DJ1-1 | 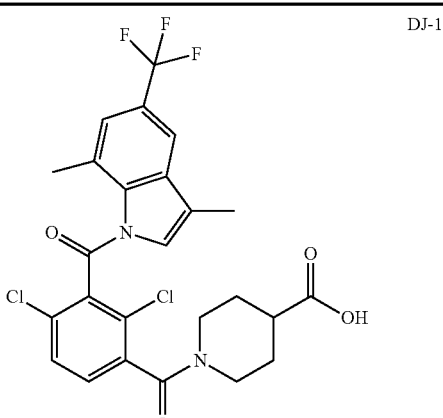 | DJ-1 | 1.87 (Method g) | 541 |

TABLE DJ1-continued

The following examples were prepared using the same procedure as example DJ, step 4, with the appropriate esters described in Table DJ.

| Example # | Product | Ester | R$_t$ min | m/z ESI+ (M + H)+ |
|---|---|---|---|---|
| DJ1-2 | *(structure)* | DJ-2 | 1.94 (Method g) | 555 |
| DJ1-3 | *(structure)* | DJ-3 | 1.94 (Method g) | 555 |

Example DK: 1-(2,6-dichloro-3-(4-hydroxypiperidine-1-carbonyl)benzyl)-3,7-dimethyl-1H-indole-5-carbonitrile

Step 1: methyl 2,4-dichloro-3-((5-cyano-3,7-dimethyl-1H-indol-1-yl)methyl)benzoate

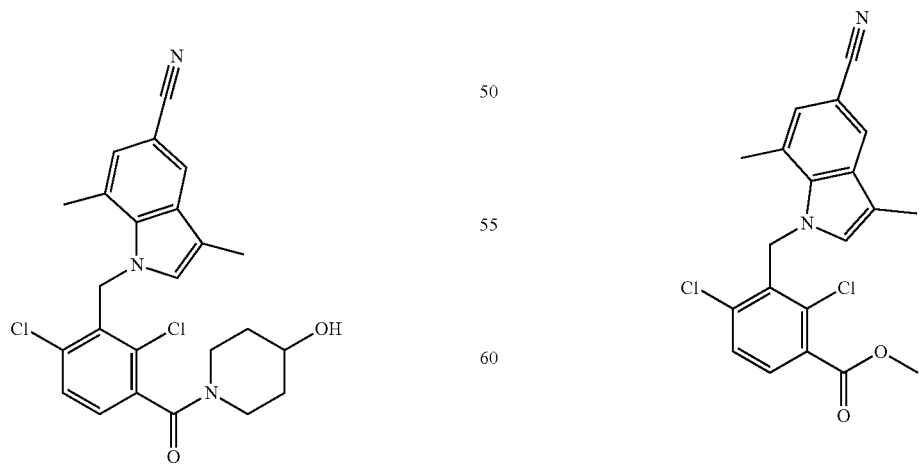

Using a procedure similar to Example DH, Step 1, methyl 2,4-dichloro-3-((5-cyano-3,7-dimethyl-1H-indol-1-yl)methyl)benzoate (262 mg, 56%) was prepared from 3,7- dimethyl-1H-indole-5-carbonitrile (Preparation #45) (242 mg, 0.87 mmol) and methyl 3-(bromomethyl)-2,4-dichlorobenzoate (Preparation #1, Step B) (466 mg, 1.56 mmol). The compound is used directly in the next step
LC/MS (Method i): $R_t$=2.58 min.; MS m/z: 387 [M+H]$^+$ Step 2: 2,4-dichloro-3-((5-cyano-3,7-dimethyl-1H-indol-1-yl)methyl)benzoic acid

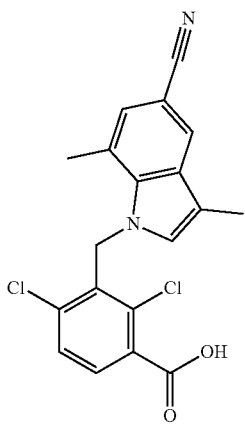 [SMILES: Cc1cn(Cc2c(Cl)ccc(C(=O)O)c2Cl)c2c(C)cc(C#N)cc12]

Using a procedure similar to Example A, Step 5, 2,4-dichloro-3-((5-cyano-3,7-dimethyl-1H-indol-1-yl)methyl) benzoic acid (100 mg, 90%) was prepared from methyl 2,4-dichloro-3-((5-cyano-3,7-dimethyl-1H-indol-1-yl) methyl)benzoate (113 mg, 0.29 mmol). LC/MS (Method i): $R_t$=2.22 min.; MS m/z: 373 [M+H]$^+$ $^1$H NMR (DMSO-d$_6$, 400 MHz): δ 7.88 (s, 1H), 7.82 (d, J=8.4 Hz, 1H), 7.69 (d, J=8.4 Hz, 1H), 7.29 (s, 1H), 6.56 (d, J=1 Hz, 1H), 5.90 (s, 2H), 2.89 (s, 3H), 2.15 (d, J=1 Hz, 3H).

Step 3: 1-(2,6-dichloro-3-(4-hydroxypiperidine-1-carbonyl)benzyl)-3,7-dimethyl-1H-indole-5-carbonitrile

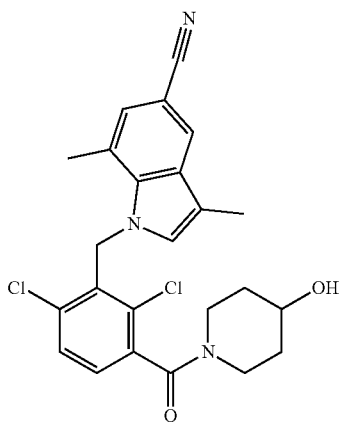 [SMILES: Cc1cn(Cc2c(Cl)ccc(C(=O)N3CCC(O)CC3)c2Cl)c2c(C)cc(C#N)cc12]

Using a procedure similar to Example A, Step 6, 1-(2,6-dichloro-3-(4-hydroxypiperidine-1-carbonyl)benzyl)-3,7-dimethyl-1H-indole-5-carbonitrile (48 mg, 65%) was prepared from 2,4-dichloro-3-((5-cyano-3,7-dimethyl-1H-indol-1-yl)methyl)benzoic acid (60 mg, 0.16 mmol) and 4-hydroxypiperidine (19.5 mg, 0.19 mmol). LC/MS (Method g): $R_t$=1.54 min.; MS m/z: 456 [M+H]$^+$ $^1$H NMR (DMSO-d$_6$, 400 MHz): δ 7.89 (s, 1H), 7.69 and 7.68 (d, J=8.4 Hz, 1H), 7.49 and 7.48 (d, 8.4 Hz, 1H), 7.29 (d, J=1 Hz, 1H), 6.57 and 7.56 (d, J=1 Hz, 1H), 5.88 (m, 2H), 4.79 (m, 1H), 4.01 (m, 1H), 3.73 (m, 1H), 3.26 (m, 2H), 3.01 (m, 1H), 2.88 (m, 3H), 2.16 (s, 3H), 1.78 (m, 1H), 1.66 (m, 1H), 137 (m, 2H).

Example DL: 2-(1-(2,4-dichloro-3-((5-cyano-3,7-dimethyl-1H-indol-1-yl)methyl)benzoyl)piperidin-4-yl)acetic acid

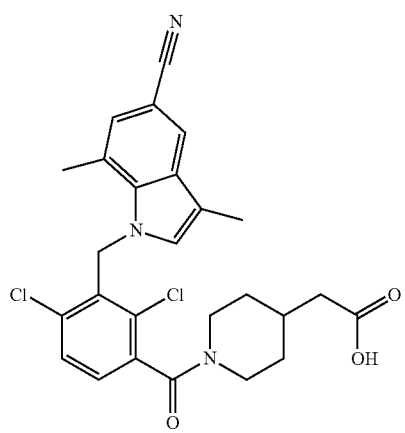 [SMILES: Cc1cn(Cc2c(Cl)ccc(C(=O)N3CCC(CC(=O)O)CC3)c2Cl)c2c(C)cc(C#N)cc12]

Step 1: methyl 2-(1-(2,4-dichloro-3-((5-cyano-3,7-dimethyl-1H-indol-1-yl)methyl)benzoyl)piperidin-4-yl)acetate

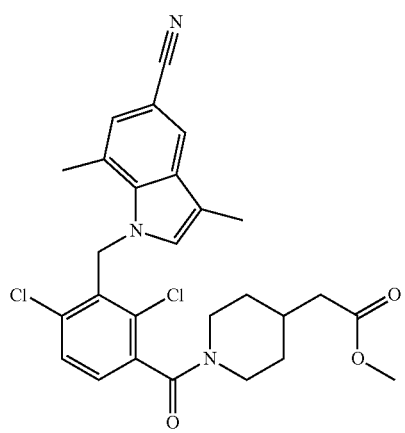 [SMILES: COC(=O)CC1CCN(C(=O)c2ccc(Cl)c(Cn3cc(C)c4cc(C#N)cc(C)c43)c2Cl)CC1]

Using a procedure similar to Example A, Step 6, methyl 2-(1-(2,4-dichloro-3-((5-cyano-3,7-dimethyl-1H-indol-1-yl) methyl)benzoyl)piperidin-4-yl)acetate (111 mg, 99%) was prepared from 2,4-dichloro-3-((5-cyano-3,7-dimethyl-1H-indol-1-yl)methyl)benzoic acid (Example DK, Step 2) (80 mg, 0.21 mmol) and methyl (4-piperidyl)acetate hydrochloride (49.8 mg, 0.27 mmol) The compound is used directly in the next step. LC/MS (Method i): $R_t$=2.43 min.; MS m/z: 512 [M+H]+

Step 2: 2-(1-(2,4-dichloro-3-((5-cyano-3,7-dimethyl-1H-indol-1-yl)methyl)benzoyl)piperidin-4-yl)acetic acid

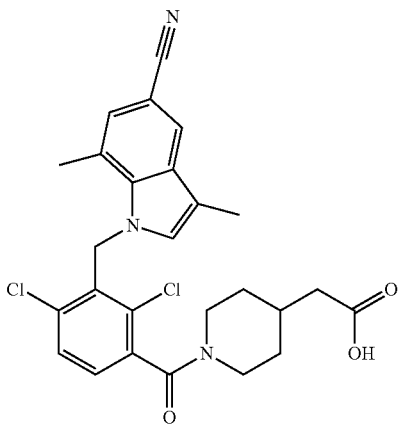 [SMILES: Cc1cn(Cc2c(Cl)ccc(C(=O)N3CCC(CC(=O)O)CC3)c2Cl)c2c(C)cc(C#N)cc12]

Using a procedure similar to Example A, Step 5, 2-(1-(2,4-dichloro-3-((5-cyano-3,7-dimethyl-1H-indol-1-yl)methyl)benzoyl)piperidin-4-yl)acetic acid (51 mg, 45%) was prepared from methyl 2-(1-(2,4-dichloro-3-((5-cyano-3,7-dimethyl-1H-indol-1-yl)methyl)benzoyl)piperidin-4-yl)acetate (110 mg, 0.21 mmol). LC/MS (Method g): $R_t$=1.62 min.; MS m/z: 498 [M+H]$^+$ $^1$H NMR (DMSO-d$_6$, 400 MHz): δ 12.09 (broad, 1H), 7.88 (m, 1H), 7.69 and 7.68 (d, J=8.4 Hz, 1H), 7.52 and 7.46 (d, J=8.4 Hz, 1H), 7.29 (s, 1H), 6.58 and 6.55 (s, 1H), 5.87 (m, 2H), 4.46 (m, 1H), 3.27 (m, 1H), 3.03 (m, 1H), 2.88 (s, 3H), 2.80 (m, 1H), 2.16 (m, 5H), 1.93 (m, 1H), 1.77 (m, 1H), 1.60 (m, 1H), 1.15 (m, 2H).

Example DM: 1-(2,6-dichloro-3-(4-hydroxypiperidine-1-carbonyl)benzoyl)-3,7-dimethyl-1H-indole-5-carbonitrile

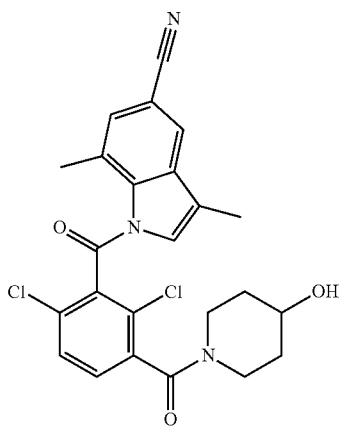 [SMILES: Cc1cn(C(=O)c2c(Cl)ccc(C(=O)N3CCC(O)CC3)c2Cl)c2c(C)cc(C#N)cc12]

Step 1: tert-butyl 2,4-dichloro-3-(5-cyano-3,7-dimethyl-1H-indole-1-carbonyl)benzoate

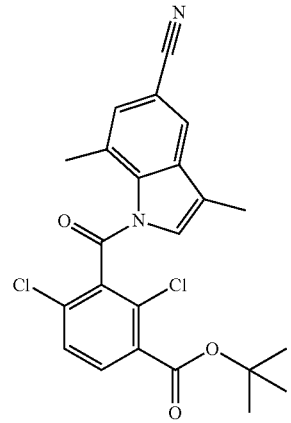 [SMILES: Cc1cn(C(=O)c2c(Cl)ccc(C(=O)OC(C)(C)C)c2Cl)c2c(C)cc(C#N)cc12]

Using a procedure similar to Example DJ, Step 1, tert-butyl 2,4-dichloro-3-(5-cyano-3,7-dimethyl-1H-indole-1-carbonyl)benzoate (290 mg, 75%) was prepared from 3,7-dimethyl-1H-indole-5-carbonitrile (Preparation #45) (242 mg, 0.87 mmol) and tert-butyl 2,4-dichloro-3-(chlorocarbonyl)benzoate (Preparation #44) (483 mg, 1.56 mmol). The product is used directly in the next step. LC/MS (Method i): $R_t$=2.87 min.; MS m/z: 443 [M+H]$^+$

Step 2: 2,4-dichloro-3-(5-cyano-3,7-dimethyl-1H-indole-1-carbonyl)benzoic acid

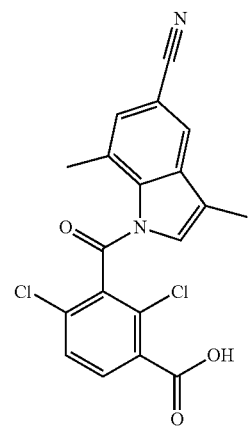 [SMILES: Cc1cn(C(=O)c2c(Cl)ccc(C(=O)O)c2Cl)c2c(C)cc(C#N)cc12]

Using a procedure similar to Example DJ, Step 2, 2,4-dichloro-3-(5-cyano-3,7-dimethyl-1H-indole-1-carbonyl)benzoic acid (232 mg, 82%) was prepared from tert-butyl 2,4-dichloro-3-(5-cyano-3,7-dimethyl-1H-indole-1-carbonyl)benzoate (290 mg, 0.65 mmol). LC/MS (Method i): $R_t$=2.17 min.; MS m/z: 387 [M+H]$^+$ $^1$H NMR (DMSO-d$_6$, 300 MHz): δ 13.91 (broad, 1H), 8.05 (d, J=8.6 Hz, 1H), 8.02 (m, 1H), 7.81 (d, J=8.6 Hz, 1H), 7.71 (s, 1H), 7.27 (d, J=1.3 Hz, 1H), 2.69 (s, 3H), 2.19 (d, J=1.3 Hz, 3H).

569

Step 3: 1-(2,6-dichloro-3-(4-hydroxypiperidine-1-carbonyl)benzoyl)-3,7-dimethyl-1H-indole-5-carbonitrile

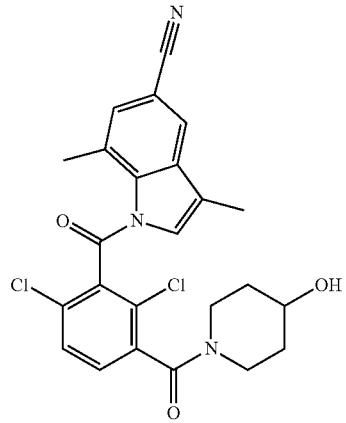 [SMILES: Cc1cn(C(=O)c2c(Cl)ccc(C(=O)N3CCC(O)CC3)c2Cl)c2c(C)cc(C#N)cc12]

Using a procedure similar to Example A, Step 6, 1-(2,6-dichloro-3-(4-hydroxypiperidine-1-carbonyl)benzoyl)-3,7-dimethyl-1H-indole-5-carbonitrile (65 mg, 45%) was prepared from 2,4-dichloro-3-(5-cyano-3,7-dimethyl-1H-indole-1-carbonyl)benzoic acid (113 mg, 0.3 mmol) and 4-hydroxypiperidine (36.4 mg, 0.36 mmol). LC/MS (Method g): $R_t$=1.54 min.; MS m/z: 470 [M+H]$^+$ $^1$H NMR (DMSO-d$_6$, 400 MHz): δ 8.03 (s, 1H), 7.80 (m, 1H), 7.70 (m, 1H), 7.67 (m, 1H), 7.45, 7.41 and 7.19 (m, 1H), 4.80 (m, 1H), 4.02 (m, 1H), 3.75 (m, 1H), 3.50 (m, 1H), 3.27 (m, 1H), 3.12 (m, 1H), 2.67 (s, 3H), 2.20 (s, 3H), 1.80 (m, 1H), 1.70 (m, 1H), 1.35 (m, 2H).

Example DN: 2-(1-(2,4-dichloro-3-(5-cyano-3,7-dimethyl-1H-indole-1-carbonyl)benzoyl)piperidin-4-yl)acetic acid

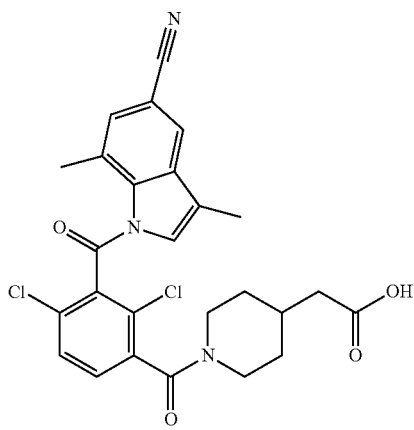 [SMILES: Cc1cn(C(=O)c2c(Cl)ccc(C(=O)N3CCC(CC(=O)O)CC3)c2Cl)c2c(C)cc(C#N)cc12]

570

Step 1: methyl 2-(1-(2,4-dichloro-3-(5-cyano-3,7-dimethyl-1H-indole-1-carbonyl)benzoyl)piperidin-4-yl)acetate

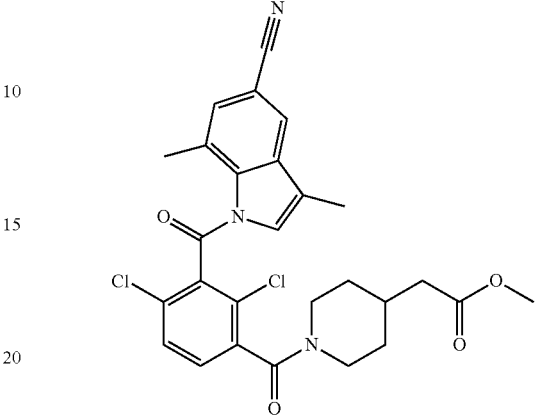

Using a procedure similar to Example A, Step 6, methyl 2-(1-(2,4-dichloro-3-(5-cyano-3,7-dimethyl-1H-indole-1-carbonyl)benzoyl)piperidin-4-yl)acetate (140 mg, 72%) was prepared from 2,4-dichloro-3-(5-cyano-3,7-dimethyl-1H-indole-1-carbonyl)benzoic acid (Example DM, Step 2) (115 mg, 0.29 mmol) and methyl (4-piperidyl)acetate hydrochloride (69 mg, 0.35 mmol). The product is used directly in the next step. LC/MS (Method i): $R_t$=2.42 min.; MS m/z: 526 [M+H]$^+$ Step 2: 2-(1-(2,4-dichloro-3-(5-cyano-3,7-dimethyl-1H-indole-1-carbonyl)benzoyl)piperidin-4-yl)acetic acid

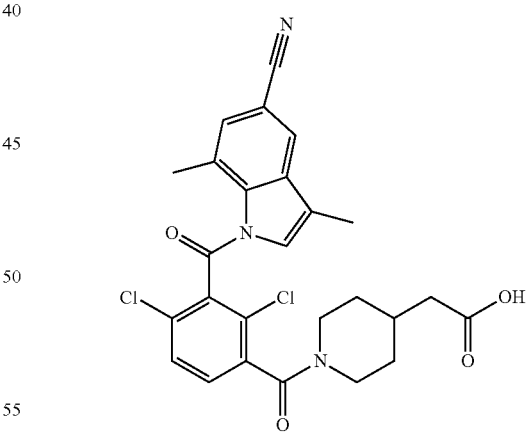

Using a procedure similar to Example A, Step 5, 2-(1-(2,4-dichloro-3-(5-cyano-3,7-dimethyl-1H-indole-1-carbonyl)benzoyl)piperidin-4-yl)acetic acid (123 mg, 85%) was prepared from methyl 2-(1-(2,4-dichloro-3-(5-cyano-3,7-dimethyl-1H-indole-1-carbonyl)benzoyl)piperidin-4-yl)acetate (138 mg, 0.26 mmol). LC/MS (Method i): $R_t$=2.18 min.; MS m/z: 512 [M+H]$^+$ $^1$H NMR (DMSO-d$_6$, 400 MHz): δ 12.10 (broad, 1H), 8.02 (s, 1H), 7.80 (m, 1H), 7.65 (m, 2H), 7.45 and 7.39 and 7.19 (m, 1H), 4.48 (m, 1H), 3.57 (m, 1H), 3.24 (m, 1H), 3.07

(m, 1H), 2.82 (m, 1H), 2.67 (s, 3H), 2.18 (m, 4H), 1.95 (m, 1H), 1.78 (m, 1H), 1.63 (m, 1H), 1.17 (m, 2H).

Example DO: (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone

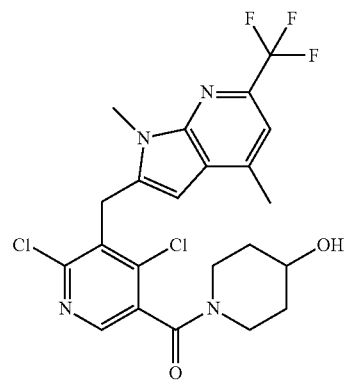 [SMILES: Cc1cc(C(F)(F)F)nc2c1cc(Cc1c(Cl)ncc(C(=O)N3CCC(O)CC3)c1Cl)n2C]

Step 1:
4-methyl-6-(trifluoromethyl)pyridin-2(1H)-one

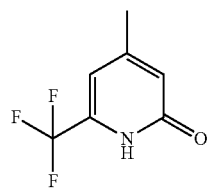

A solution of CHCl3 (1.25 L) was cooled down to about 0° C. and 2,2,2-trifluoroacetic anhydride (0.141 L, 1012 mmol) was added followed by the addition of 3-methylbut-2-enoyl chloride (0.094 L, 843 mmol). Triethylamine (0.259 L, 1856 mmol) was added dropwise such that the internal temperature was maintained below about 10° C. (exothermic). After addition, the mixture was stirred at about 0° C. for about 1 h and then warmed up to rt slowly and stirred overnight. The reaction mixture was washed with water (1 L), sat NaHCO3 (1 L), water/brine (1:1, 500 mL), dried over MgSO4, filtered and concentrated in vacuo. The residue was dissolved in acetic acid (1.250 L) and acetic acid/ammonia salt (130 g, 1687 mmol) was added. The reaction flask was capped with a balloon and the mixture was heated at about 115° C. overnight. After about 20 h the reaction mixture was cooled to about 40° C. and concentrated in vacuo. The syrup was poured onto water (~2 L) with stirring. After about 1 h the solids were collected by filtration to provide 4-methyl-6-(trifluoromethyl)pyridin-2(1H)-one (101 g, 68%) as a tan solid. LC/MS (Method a) $R_t$=1.59 min.; MS m/z: 178 [M+H]$^+$. $^1$H NMR (CDCl$_3$, 400 MHz): δ 6.79 (s, 1H), 6.70 (s, 1H), 2.34 (s, 3H).

Step 2:
2-chloro-4-methyl-6-(trifluoromethyl)pyridine

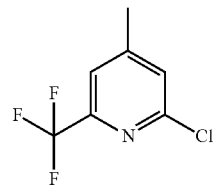

A 50 mL pear-shaped flask fitted with a short path distillation head was charged with 4-methyl-6-(trifluoromethyl)pyridin-2(1H)-one (20 g, 113 mmol). To the flask was added phenylphosphonic dichloride (19.2 mL, 135 mmol). The reaction mixture was heated to about 160° C. After about 3 h the pressure on the reaction mixture was slowly reduced to 100 mBar and distillation starts with a head temp about 120-130° C. Periodically when distillation had significantly slowed the pressure over the reaction mixture was reduced to 80 mBar and the bath temp was raised to about 170° C. After about 3 h the distillation had ceased providing 2-chloro-4-methyl-6-(trifluoromethyl)pyridine (12 g, 54%).

LC/MS (Method a) $R_t$=2.4 min.; MS m/z: 196 [M+H]$^+$. $^1$H NMR (DMSO-d6, 400 MHz): 7.79 (s, 1H), 7.71 (s, 1H), 2.43 (s, 3H).

Step 3: tert-butyl (4-methyl-6-(trifluoromethyl)pyridin-2-yl)carbamate

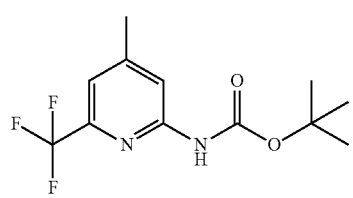 [SMILES: Cc1cc(NC(=O)OC(C)(C)C)nc(C(F)(F)F)c1]

A flask charged with 2-chloro-4-methyl-6-(trifluoromethyl)pyridine (35.1 g, 180 mmol), tert-butyl carbamate (42.1 g, 359 mmol), Pd$_2$(dba)$_3$ (4.11 g, 4.49 mmol), dicyclohexyl(2',4',6'-triisopropyl-[1,1'-biphenyl]-2-yl)phosphine (X-Phos) (4.28 g, 8.98 mmol) and cesium carbonate (205 g, 629 mmol) was evacuated and filled with N$_2$ (repeated 3 times) before addition of degassed 1,4-dioxane (350 mL). The mixture was then heated at about 80° C. for about 2 h. The reaction mixture was cooled to rt and the reaction mixture was partitioned between water and EtOAc. The aqueous layer was further extracted with EtOAc (2×100 mL). Organic layer was dried over Na$_2$SO$_4$, filtered and concentrated to dryness to give a dark red oil. The material was used without additional purification, assuming a 100% yield.

LC/MS (Method a) $R_t$=2.71 min.; MS m/z: 275 [M+H]$^+$. $^1$H NMR (400 MHz, DMSO-d6) δ 10.13 (s, 1H), 7.90 (dt, J=1.3, 0.7 Hz, 1H), 7.34 (dd, J=1.3, 0.7 Hz, 1H), 2.38 (t, J=0.6 Hz, 3H), 1.45 (s, 9H).

Step 4: 4-methyl-6-(trifluoromethyl)pyridin-2-amine

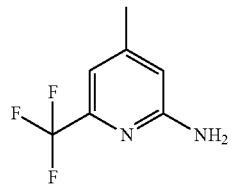

A mixture of tert-butyl (4-methyl-6-(trifluoromethyl)pyridin-2-yl)carbamate (49.6 g, 180 mmol) and hydrogen chloride (4M in dioxane) (597 mL, 2388 mmol) was stirred at rt for about 2 h. The solvent was removed under reduced pressure and the residue was filtered. The insoluble was washed with EtOAc and the filtrate was diluted with EtOAc and extracted with 6 N HCl (3×). The aqueous layer was washed with DCM (4×100 mL) and then adjusted to pH 8 with addition of Na$_2$CO$_3$ slowly. The bright yellow solid was collected by filtration and washed with water. The solid was then dissolved in DCM, washed with brine, dried over Na$_2$SO$_4$, filtered and concentrated to almost dryness. The solid was triturated with petroleum ether and collected by filtration, washed with petroleum ether and air dried to give 4-methyl-6-(trifluoromethyl)pyridin-2-amine (27.7 g, 88%) as a pale yellow solid.

LC/MS (Method a) R$_t$=1.92 min.; MS m/z: 177 [M+H]$^+$. $^1$H NMR (400 MHz, DMSO-d6) δ 6.72 (s, 1H), 6.45 (s, 1H), 6.35 (s, 2H), 2.20 (s, 3H).

Step 5: 3,5-dibromo-4-methyl-6-(trifluoromethyl)pyridin-2-amine

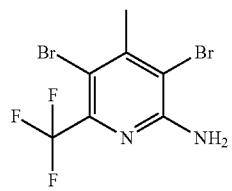

A mixture of 4-methyl-6-(trifluoromethyl)pyridin-2-amine (31.4 g, 179 mmol) and NBS (66.7 g, 375 mmol) in ACN (250 mL) was heated at about 70° C. for about 2 h. To the reaction flask was added water (~500 mL). The resulting solid was collected by filtration, washed with water and air dried for about 5 minutes. The solid was solubilized in DCM, washed with water, dried over Na$_2$SO$_4$, filtered and concentrated to almost dryness. The solid was triturated with heptane and collected by filtration, washed with heptane and dried to give 3,5-dibromo-4-methyl-6-(trifluoromethyl)pyridin-2-amine (56.9 g, 96%) as light yellow solid. LC/MS (Method a) R$_t$=2.55 min.; MS m/z: 333 [M+H]$^+$. $^1$H NMR (400 MHz, DMSO-d6) δ 6.90 (s, 2H), 2.53 (s, 3H).

Step 6: 3-bromo-4-methyl-6-(trifluoromethyl)pyridin-2-amine

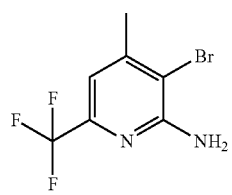

To a light orange solution of 3,5-dibromo-4-methyl-6-(trifluoromethyl)pyridin-2-amine (56.98 g, 171 mmol) in THF (570 mL) at about −78° C. was added n-butyllithium (2.5 M in hexane) (68.3 mL, 171 mmol) dropwise (turned into a brown solution). The mixture was stirred at about −78° C. for about 45 minutes. LCMS indicated only partial conversion and a second portion of BuLi (2.5 M in hexane) (20.48 mL, 51.2 mmol) was added dropwise. A third portion of butyllithium (2.5 M in hexane) (13.65 mL, 34.1 mmol) was added dropwise to complete conversion to product. The reaction flask was transferred to an ice-water bath and 20 mL water was added quickly. The reaction mixture was then warmed to room temperature. The reaction mixture was partitioned between saturated NH$_4$Cl and EtOAc. The organic layer was washed with NaHCO$_3$, dried over Na$_2$SO$_4$, filtered and concentrated to almost dryness. The solid was triturated with heptane and collected by filtration, washed with hepane to give the first crop of product as a off-white solid (38.9 g, 85%). The filtrate was concentrated to dryness and heptane was added. The solid was collected by vacuum filtration and washed with heptane and dried to give the second crop of product as a pale yellow solid (1.9 g, 3%). LC/MS (Method a) R$_t$=2.29 min.; MS m/z: 255 [M+H]$^+$. $^1$H NMR (400 MHz, DMSO-d6) δ 6.96 (s, 1H), 6.74 (s, 1H), 2.32 (s, 3H).

Step 7: (E)-2-(2-Ethoxyvinyl)-4,4,5,5-tetramethyl-1,3,2-dioxaborolane

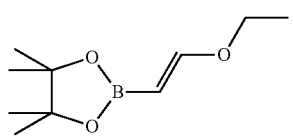

Under an atmosphere of nitrogen in a round bottom flask ethoxyethyne, 50% solution in hexanes (100 g, 710 mmol) and DCM (996 mL) was stirred at about 0-5° C. To the stirred solution was added 4,4,5,5-tetramethyl-1,3,2-dioxaborolane (113 mL, 781 mmol) in one portion followed by the addition of bis(cyclopentadienyl)zirconium hydridochloride (9.16 g, 35.5 mmol) at about 0-5° C. The suspension (orange) was allowed to gradually warm to room temperature over about 30 min Dissolution occurred within about 10 min. The reaction mixture was stirred at RT overnight (very dark red). To the reaction solution was added ether (2 L) and the solution was washed with saturated aqueous NH$_4$Cl. The solvents were removed under reduced pressure, minimal DCM (100 mL) was added and the solution was filtered through a pad of alumina, topped with Celite. The alumina was washed with DCM and the filtrate solvent was removed in vacuo to yield (E)-2-(2-ethoxyvinyl)-4,4,5,5-tetramethyl-1,3,2-dioxaborolane (114.9 g, 82%) as a very dark red oil. $^1$H NMR (400 MHz, DMSO-d6) δ 7.05 (d, 1H), 4.45 (d, 1H), 3.83 (q, 2H), 1.30 (t, 3H), 1.28 (s, 12H).

Step 8: (E)-3-(2-ethoxyvinyl)-4-methyl-6-(trifluoromethyl)pyridin-2-amine

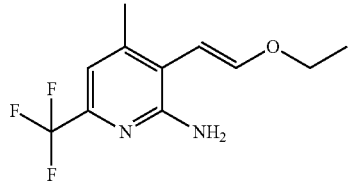 [SMILES: CCO/C=C/c1c(C)cc(C(F)(F)F)nc1N]

A flask charged with 3-bromo-4-methyl-6-(trifluoromethyl)pyridin-2-amine (38.3 g, 143 mmol), (E)-2-(2-ethoxyvinyl)-4,4,5,5-tetramethyl-1,3,2-dioxaborolane (56.5 g, 285 mmol), diacetoxypalladium (0.960 g, 4.28 mmol), dicyclohexyl(2',4',6'-triisopropyl-[1,1'-biphenyl]-2-yl)phosphine (XPhos) (4.28 g, 8.98 mmol) and cesium carbonate (116 g, 356 mmol) was degassed with $N_2$ for 15 min before addition of 320 mL degassed 1,4-dioxane/$H_2O$ (4:1). The mixture was heated at about 80° C. for about 2 h. The mixture was cooled down to room temperature. The reaction mixture was partitioned between EtOAc and water and the aqueous layer was further extracted with EtOAc (2×50 mL). The organic layer was dried over $Na_2SO_4$, filtered and concentrated to dryness. To the residue was added heptane and the resulting solid was collected by filtration and washed with heptane to give an off-white solid (1.45 g). The filtrate was concentrated to dryness again to give a thick black oil that was left at rt overnight. Significant solid formation was noticed and the solid was diluted with heptane, sonicated and filtered, washed with heptane to give a light brown solid (15.2 g, 42%). The filtrate was concentrated to dryness to give a black oil that was purified by flash chromatography (0-25% EtOAc/heptane over 30 min) The product containing fractions was concentrated to almost dryness. The solid was collected by filtration, washed with a small amount of heptane and dried to give the second crop of product as a light yellow solid (12.7 g, 35%). LC/MS (Method 1) $R_t$=1.48 min.; MS m/z: 247 [M+H]$^+$. $^1$H NMR (400 MHz, DMSO-d6) δ 6.82 (s, 1H), 6.73 (d, J=13.1 Hz, 1H), 6.12 (s, 2H), 5.45 (d, J=13.1 Hz, 1H), 3.93 (q, J=7.0 Hz, 2H), 2.23 (s, 3H), 1.25 (t, J=7.0 Hz, 3H).

Step 9: 4-methyl-6-(trifluoromethyl)-1H-pyrrolo[2,3-b]pyridine

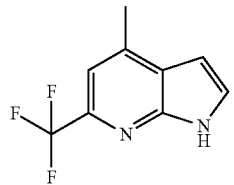

A mixture of (E)-3-(2-ethoxyvinyl)-4-methyl-6-(trifluoromethyl)pyridin-2-amine (27.9 g, 113 mmol) and acetic acid (130 mL) was heated at about 100° C. overnight. The mixture was cooled to rt and the precipitate was collected by filtration, washed with ACN and dried to give the first crop of product.

The filtrate was concentrated to approximately 50 mL. and the solid was collected by filtration, washed with ACN and dried to give the second crop of product. Both looked similar purity and therefore combined. Filtrate still had some product in it and was set aside. The solid was suspended in approximately 250 mL EtOAc and heated to reflux to dissolve. Most of the solvent was removed under reduced pressure and heptane was added. The solid was collected by vacuum filtration, dried to give the product as an off-white solid (19.8 g, 87%). LC/MS (Method 1-3) $R_t$=1.30 min.; MS m/z: 201 [M+H]$^+$. $^1$H NMR (400 MHz, DMSO-d6) δ 12.13-11.98 (br, 1H), 7.67 (t, J=3.1 Hz, 1H), 7.34 (d, J=1.0 Hz, 1H), 6.63 (dd, J=3.5, 1.9 Hz, 1H), 2.59 (s, 3H).

Step 10: 4-methyl-1-(phenylsulfonyl)-6-(trifluoromethyl)-1H-pyrrolo[2,3-b]pyridine

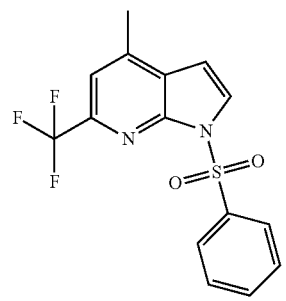 [SMILES: Cc1cc(C(F)(F)F)nc2c1ccn2S(=O)(=O)c1ccccc1]

To a suspension of sodium hydride (60% in mineral oil) (4.35 g, 109 mmol) in DMF (40 mL) at about 0° C. was added a solution of 4-methyl-6-(trifluoromethyl)-1H-pyrrolo[2,3-b]pyridine (19.8 g, 99 mmol) under $N_2$. After addition, the ice-water bath was removed and the mixture was stirred at room temperature for about 30 min. It was cooled down to about 0° C. again, benzenesulfonyl chloride (13.27 mL, 104 mmol) was added dropwise. After addition, the reaction was allowed to warm up to rt and stirred at room temperature for about 1 hour.

The reaction was quenched with the addition of 100 mL saturated $NH_4Cl$ solution followed by the addition of 350 mL water. The solid was collected by filtration, washed with water and dried in a vacuum oven at about 70° C. for about 2 days to give an off-white solid. The solid was dissolved in EtOAc, filtered through 70 g silica gel and the pad was washed with EtOAc. The filtrate was dried over $Na_2SO_4$, filtered and concentrated to dryness. The solid was triturated with EtOAc/heptane to give the first crop of 4-methyl-1-(phenylsulfonyl)-6-(trifluoromethyl)-1H-pyrrolo[2,3-b]pyridine (28.5 g, 85%) as white solid.

The filtrate was concentrated to dryness and the solid was triturated with ether/hepatane. The resulting solid was collected by filtration, washed with heptane and dried to give the second crop of 4-methyl-1-(phenylsulfonyl)-6-(trifluoromethyl)-1H-pyrrolo[2,3-b]pyridine (3.65 g, 11%) as an off-white solid.

LC/MS (Method 1-3) $R_t$=1.84 min.; MS m/z: 341 [M+H]$^+$. $^1$H NMR (400 MHz, DMSO-d6) δ 8.15-8.07 (m, 3H), 7.75-7.67 (m, 1H), 7.64-7.56 (m, 3H), 7.03 (d, J=4.1 Hz, 1H), 2.57 (s, 3H).

Step 11: tert-butyl 4,6-dichloronicotinate

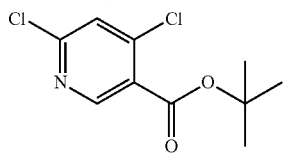

A mixture of 4,6-dichloronicotinic acid (8.2 g, 42.7 mmol) and BOC₂O (19.83 mL, 85 mmol) in THF (100 mL) was stirred at room temperature, then DMAP (1.044 g, 8.54 mmol) was added to the solution. The resulting mixture was stirred at about 70° C. for about 1 h. The sample was deposited onto silica gel and loaded onto a silica gel column and eluted with 5% EtOAc/heptane. The following fractions were collected to give the tert-butyl 4,6-dichloronicotinate (10 g, 94%) as a colorless oil. $^1$H NMR (400 MHz, CDCl₃) δ 8.76 (s, 1H), 7.43 (s, 1H), 1.61 (s, 9H).

Step 12: tert-butyl 4,6-dichloro-5-formylnicotinate

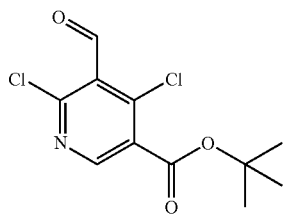 [SMILES: CC(C)(C)OC(=O)c1cnc(Cl)c(C=O)c1Cl]

The tert-butyl 4,6-dichloronicotinate (10 g, 40.3 mmol) was dissolved in THF (100 mL), stirred and cooled to about −78° C. To the solution was added LDA (22.2 mL, 44.3 mmol) at a rate to maintain the temperature below about −70° C. The resulting solution was stirred at about −78° C. for about 10 min. Then methyl formate (4.94 mL, 81 mmol) was added to the solution and the mixture was stirred at about −78° C. for about 30 min. The mixture was poured into saturated NH₄Cl, extracted with EtOAc (3×) and the combined organic layers were dried with Na₂SO₄, filtered and concentrated to afford a brown oil. The sample was deposited onto silica gel and purified by silica gel chromatography eluting with 2% EtOAc/heptane. The following fractions were collected to give tert-butyl 4,6-dichloro-5-formylnicotinate (5.0 g, 45% yield) as a yellow solid. $^1$H NMR (400 MHz, CDCl₃) δ 10.47 (s, 1H), 8.7 (s, 1H), 1.65 (s, 9H).

Step 13: tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate

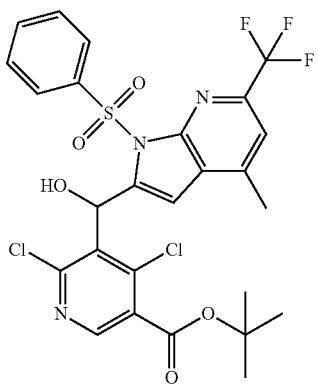 [SMILES: Cc1cc(C(F)(F)F)nc2c1cc(C(O)c1c(Cl)ncc(C(=O)OC(C)(C)C)c1Cl)n2S(=O)(=O)c1ccccc1]

Using a procedure similar to described in Example CL, Step 1, tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate was prepared from 4-methyl-1-(phenylsulfonyl)-6-(trifluoromethyl)-1H-pyrrolo[2,3-b]pyridine (6.0 g, 17.6 mmol) and tert-butyl 4,6-dichloro-5-formylnicotinate (5.35 g, 19.4 mmol). LC/MS (Method 1-3) R$_t$=2.15 min.; MS m/z: 616 [M+H]⁺. $^1$H NMR (400 MHz, DMSO-d6) δ 8.67 (s, 1H), 7.95 (d, 2H), 7.69 (m, 1H), 7.61 (s, 1H), 7.55 (m, 2H), 7.05 (s, 1H), 7.04 (d, 1H), 6.92 (d, 1H), 2.54 (s, 3H), 1.54 (s, 9H).

Step 14: tert-butyl 4,6-dichloro-5-((4-methyl-1-(phenylsulfonyl)-6-(trifluoromethyl)-1H-pyrrolo[2,3-b]pyridin-2-yl)methyl)nicotinate

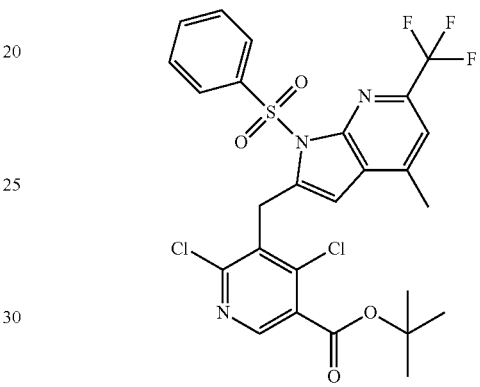

Using a procedure similar to Example Z, Step 2, tert-butyl 4,6-dichloro-5-((4-methyl-1-(phenylsulfonyl)-6-(trifluoromethyl)-1H-pyrrolo[2,3-b]pyridin-2-yl)methyl)nicotinate was prepared from tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate (1.51 g, 2.44 mmol). LC/MS (Method 1-3) R$_t$=2.33 min.; MS m/z: 600 [M+H]⁺.

Step 15: 4,6-dichloro-5-((4-methyl-6-(trifluoromethyl)-1H-pyrrolo[2,3-b]pyridin-2-yl)methyl)nicotinic acid

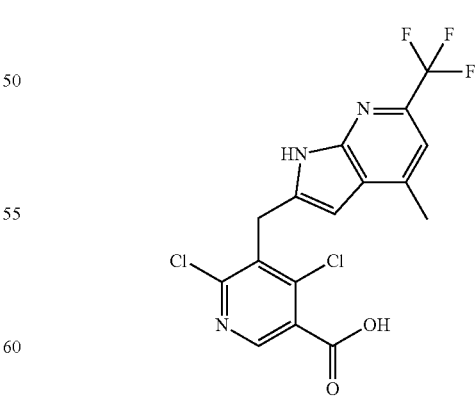

To a solution of tert-butyl 4,6-dichloro-5-((4-methyl-1-(phenylsulfonyl)-6-(trifluoromethyl)-1H-pyrrolo[2,3-b]pyridin-2-yl)methyl)nicotinate (334.9 mg, 0.558 mmol) in 1,4-dioxane (7339 μL) was added sodium hydroxide (2M)

(1394 µL, 2.79 mmol) The mixture was heated at about 50° C. overnight. The reaction mixture was cooled to room temperature, diluted with water and acidified with HCl (1M). The mixture was extracted twice with EtOAc and the combined organic extracts were dried over Na₂SO₄, filtered and evaporated to give 4,6-dichloro-5-((4-methyl-6-(trifluoromethyl)-1H-pyrrolo[2,3-b]pyridin-2-yl)methyl)nicotinic acid (0.23 g, 100%) as a pale brown solid. LC/MS (Method 1-3) $R_f$=1.02 min.; MS m/z: 404 [M+H]⁺. ¹H NMR (400 MHz, DMSO-d6) δ 12.16 (s, 1H), 8.75 (s, 1H), 7.29 (d, J=0.8 Hz, 1H), 6.09 (dd, J=2.1, 1.0 Hz, 1H), 4.48 (s, 3H).

Step 16: methyl 4,6-dichloro-5-((1,4-dimethyl-6-(trifluoromethyl)-1H-pyrrolo[2,3-b]pyridin-2-yl)methyl)nicotinate

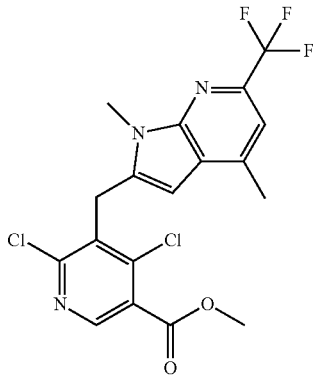 [SMILES: COC(=O)c1cnc(Cl)c(Cc2cc3c(C)cc(C(F)(F)F)nc3n2C)c1Cl]

Using a procedure similar to Example P, Step 4, methyl 4,6-dichloro-5-((1,4-dimethyl-6-(trifluoromethyl)-1H-pyrrolo[2,3-b]pyridin-2-yl)methyl)nicotinate was prepared from 4,6-dichloro-5-((4-methyl-6-(trifluoromethyl)-1H-pyrrolo[2,3-b]pyridin-2-yl)methyl)nicotinic acid (0.23 g, 0.567 mmol). LC/MS (Method 1-3) $R_f$=2.01 min.; MS m/z: 432 [M+H]⁺.

Step 17: 4,6-dichloro-5-((1,4-dimethyl-6-(trifluoromethyl)-1H-pyrrolo[2,3-b]pyridin-2-yl)methyl)nicotinic acid

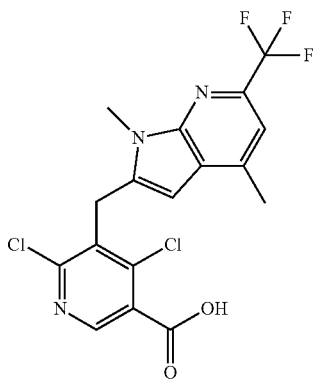 [SMILES: Cc1cc(C(F)(F)F)nc2c1cc(Cc1c(Cl)ncc(C(=O)O)c1Cl)n2C]

Using a procedure similar to Example A, Step 5, 4,6-dichloro-5-((1,4-dimethyl-6-(trifluoromethyl)-1H-pyrrolo[2,3-b]pyridin-2-yl)methyl)nicotinic acid was prepared from methyl 4,6-dichloro-5-((1,4-dimethyl-6-(trifluoromethyl)-1H-pyrrolo[2,3-b]pyridin-2-yl)methyl)nicotinate (0.25 g, 0.578 mmol). LC/MS (Method 1-3) $R_f$=1.14 min.; MS m/z: 418 [M+H]⁺.

Step 18: (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone

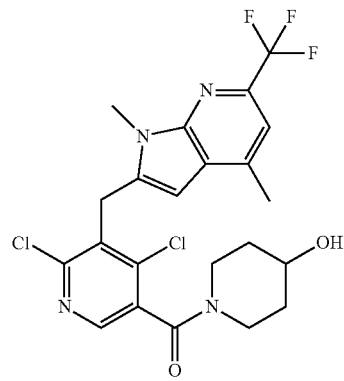 [SMILES: Cc1cc(C(F)(F)F)nc2c1cc(Cc1c(Cl)ncc(C(=O)N3CCC(O)CC3)c1Cl)n2C]

Using a procedure similar to Example A, Step 6, (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone was prepared from 4,6-dichloro-5-((1,4-dimethyl-6-(trifluoromethyl)-1H-pyrrolo[2,3-b]pyridin-2-yl)methyl)nicotinic acid (0.116 g, 0.278 mmol) and piperidin-4-ol (0.042 g, 0.42 mmol). LC/MS (Method a) $R_f$=2.28 min.; MS m/z: 501 [M+H]⁺. ¹H NMR (400 MHz, DMSO-d6) δ 8.31 (s, 1H), 7.26 (s, 1H), 7.22 (s, 1H), 5.81 (s, 1H), 4.46 (m, 2H), 4.15 (m, 1H), 4.04 (m, 1H), 3.98 (s, 3H), 3.65-3.45 (m, 3H), 3.13 (m, 2H), 2.00 (m, 1H), 1.87 (m, 2H), 1.70 (m, 2H).

Example DP: 2-(1-(2,4-dichloro-3-((1,4-dimethyl-6-(trifluoromethoxy)-1H-indol-2-yl)methyl)benzoyl)piperidin-4-yl)acetic acid

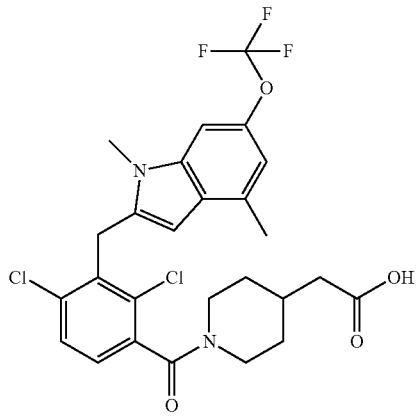 [SMILES: Cc1cc(OC(F)(F)F)cc2c1cc(Cc1c(Cl)ccc(C(=O)N3CCC(CC(=O)O)CC3)c1Cl)n2C]

Step 1: methyl 2,4-dichloro-3-(hydroxy(4-methyl-1-(phenylsulfonyl)-6-(trifluoromethoxy)-1H-indol-2-yl)methyl)benzoate

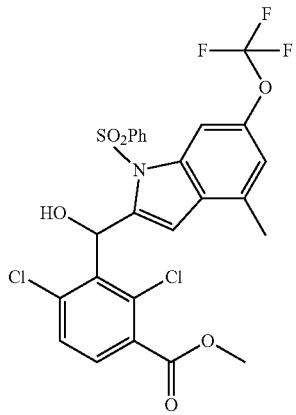

Using a procedure similar to Example A, Step 1, methyl 2,4-dichloro-3-(hydroxy(4-methyl-1-(phenylsulfonyl)-6-(trifluoromethoxy)-1H-indol-2-yl)methyl)benzoate (814 mg, 79%) was prepared from N-(2-iodo-3-methyl-5-(trifluoromethoxy)phenyl)benzenesulfonamide (Preparation #47) (800 mg, 1.75 mmol) and methyl 2,4-dichloro-3-(1-hydroxyprop-2-yn-1-yl)benzoate (Preparation #1) (544 mg, 2.1 mmol). LC/MS (Method i) $R_t$=2.69 min.; MS m/z: 646 [M−H]⁻+CH₃COOH ¹H NMR (DMSO-d₆, 300 MHz): δ 7.89 (m, 2H), 7.74 (s, 1H), 7.69 (m, 2H), 7.58 (m, 3H), 7.12 (m, 1H), 7.03 (dd, J=5.9, 1.2 Hz, 1H), 6.74 (m, 1H), 6.67 (d, J=5.9 Hz, 1H), 3.87 (s, 3H), 2.40 (s, 3H).

Step 2: methyl 2,4-dichloro-3-((4-methyl-1-(phenylsulfonyl)-6-(trifluoromethoxy)-1H-indol-2-yl)methyl)benzoate

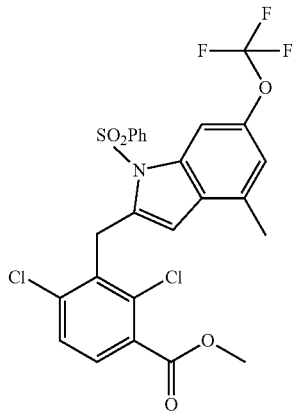

Using a procedure similar to Example A, Step 2, methyl 2,4-dichloro-3-((4-methyl-1-(phenylsulfonyl)-6-(trifluoromethoxy)-1H-indol-2-yl)methyl)benzoate (540 mg, 68%) was prepared from methyl 2,4-dichloro-3-(hydroxy(4-methyl-1-(phenylsulfonyl)-6-(trifluoromethoxy)-1H-indol-2-yl)methyl)benzoate (811 mg, 1.38 mmol). LC/MS (Method j) $R_t$=2.65 min.; MS m/z: 572 [M+H]⁺

¹H NMR (DMSO-d₆, 300 MHz): δ 7.96 (m, 2H), 7.88 (s, 1H), 7.83 (m, 1H), 7.76 (d, J=7.6 Hz, 1H), 7.68 (m, 3H), 7.12 (m, 1H), 5.89 (m, 1H), 4.61 (m, 2H), 3.87 (s, 3H), 2.29 (s, 3H).

Step 3: methyl 2,4-dichloro-3-((4-methyl-6-(trifluoromethoxy)-1H-indol-2-yl)methyl)benzoate

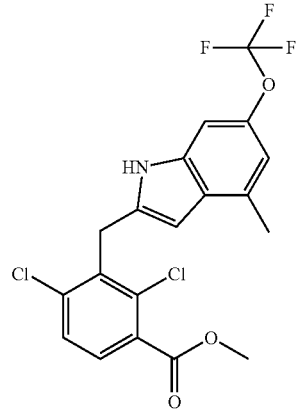 [SMILES: COC(=O)c1ccc(Cl)c(Cc2cc3c(C)cc(OC(F)(F)F)cc3[nH]2)c1Cl]

Using a procedure similar to Example A, Step 3, methyl 2,4-dichloro-3-((4-methyl-6-(trifluoromethoxy)-1H-indol-2-yl)methyl)benzoate (408 mg, 100%) was prepared from methyl 2,4-dichloro-3-((4-methyl-1-(phenylsulfonyl)-6-(trifluoromethoxy)-1H-indol-2-yl)methyl)benzoate (540 mg, 0.94 mmol). LC/MS (Method j) $R_t$=2.25 min.; MS m/z: 432 [M+H]⁺

¹H NMR (DMSO-d₆, 300 MHz): δ 11.26 (s, 1H), 7.74 (d, J=8.4 Hz, 1H), 7.68 (d, J=8.4 Hz, 1H), 7.11 (s, 1H), 6.73 (s, 1H), 5.90 (s, 1H), 4.45 (s, 2H), 3.87 (s, 3H), 2.36 (s, 3H)

Step 4: methyl 2,4-dichloro-3-((1,4-dimethyl-6-(trifluoromethoxy)-1H-indol-2-yl)methyl)benzoate

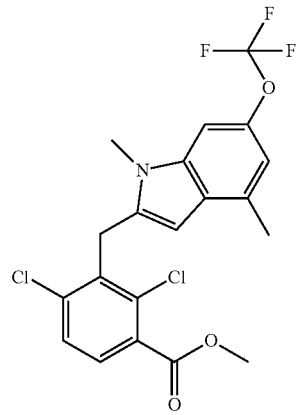 [SMILES: COC(=O)c1ccc(Cl)c(Cc2cc3c(C)cc(OC(F)(F)F)cc3n2C)c1Cl]

Using a procedure similar to Example P, Step 4, methyl 2,4-dichloro-3-((1,4-dimethyl-6-(trifluoromethoxy)-1H-indol-2-yl)methyl)benzoate (178 mg, 42%) was obtained from methyl 2,4-dichloro-3-((4-methyl-6-(trifluoromethoxy)-1H-indol-2-yl)methyl)benzoate (408 mg, 0.944 mmol).

LC/MS (Method j) $R_t$=2.42 min.; MS m/z: 446 [M+H]⁺ ¹H NMR (DMSO-d₆, 300 MHz): δ 7.80 (d, J=8.4 Hz, 1H), 7.71 (d, J=8.4 Hz, 1H), 7.34 (s, 1H), 6.77 (s, 1H), 5.59 (s, 1H), 4.46 (s, 2H), 3.88 (s, 3H), 3.85 (s, 3H), 2.31 (s, 3H).

Step 5: 2,4-dichloro-3-((1,4-dimethyl-6-(trifluoromethoxy)-1H-indol-2-yl)methyl)benzoic acid

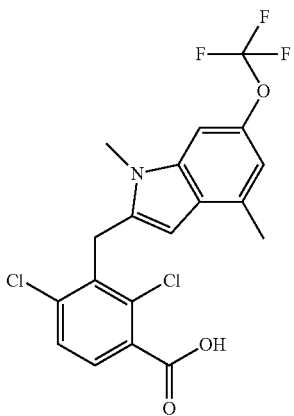 [SMILES: Cc1cc(OC(F)(F)F)cc2c1cc(Cc1c(Cl)ccc(C(=O)O)c1Cl)n2C]

Using a procedure similar to Example A, Step 5, 2,4-dichloro-3-((1,4-dimethyl-6-(trifluoromethoxy)-1H-indol-2-yl)methyl)benzoic acid (170 mg, 97%) was prepared from methyl 2,4-dichloro-3-((1,4-dimethyl-6-(trifluoromethoxy)-1H-indol-2-yl)methyl)benzoate (178 mg, 0.4 mmol).

LC/MS (Method i) $R_t$=2.53 min.; MS m/z: 432 [M+H]$^+$ $^1$H NMR (DMSO-d$_6$, 300 MHz): δ 13.60 (br, 1H), 7.75 (d, J=8.4 Hz, 1H), 7.66 (d, J=8.4 Hz, 1H), 7.34 (s, 1H), 6.77 (s, 1H), 5.59 (s, 1H), 4.45 (s, 2H), 3.85 (s, 3H), 2.32 (s, 3H)

Step 6: methyl 2-(1-(2,4-dichloro-3-((1,4-dimethyl-6-(trifluoromethoxy)-1H-indol-2-yl)methyl)benzoyl)piperidin-4-yl)acetate

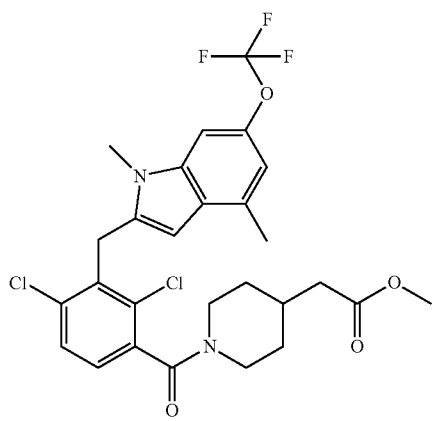 [SMILES: COC(=O)CC1CCN(C(=O)c2ccc(Cl)c(Cc3cc4c(C)cc(OC(F)(F)F)cc4n3C)c2Cl)CC1]

Using a procedure similar to Example A1, methyl 2-(1-(2,4-dichloro-3-((1,4-dimethyl-6-(trifluoromethoxy)-1H-indol-2-yl)methyl)benzoyl)piperidin-4-yl)acetate (102 mg, 96%) was prepared from 2,4-dichloro-3-((1,4-dimethyl-6-(trifluoromethoxy)-1H-indol-2-yl)methyl)benzoic acid (80 mg, 0.18 mmol) and methyl (4-piperidyl)acetate hydrochloride (54 mg, 0.28 mmol).

LC/MS (Method i) $R_t$=2.68 min.; MS m/z: 571 [M+H]$^+$ $^1$H NMR (DMSO-d$_6$, 300 MHz): δ 7.66 and 7.65 (d, J=8.4 Hz, 1H), 7.42 and 7.37 (d, J=8.4 Hz, 1H), 7.34 (m, 1H), 6.77 (m, 1H), 5.59 and 5.56 (m, 1H), 4.44 (m, 3H), 3.85 and 3.84 (s, 3H), 3.59 and 3.55 (s, 3H), 3.25 (m, 1H), 3.05 (m, 1H), 2.80 (m, 1H), 2.31 and 2.30 (s, 3H), 2.24 (m, 2H), 1.95 (m, 1H), 1.74 (m, 1H), 1.58 (m, 1H), 1.17 (m, 2H).

Step 7: 2-(1-(2,4-dichloro-3-((1,4-dimethyl-6-(trifluoromethoxy)-1H-indol-2-yl)methyl)benzoyl)piperidin-4-yl)acetic acid

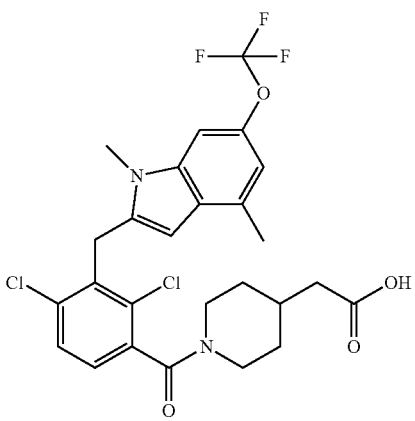 [SMILES: Cc1cc(OC(F)(F)F)cc2c1cc(Cc1c(Cl)ccc(C(=O)N3CCC(CC(=O)O)CC3)c1Cl)n2C]

Using a procedure similar to Example A, Step 5, 2-(1-(2,4-dichloro-3-((1,4-dimethyl-6-(trifluoromethoxy)-1H-indol-2-yl)methyl)benzoyl)piperidin-4-yl)acetic acid (90 mg, 89%) was prepared from methyl 2-(1-(2,4-dichloro-3-((1,4-dimethyl-6-(trifluoromethoxy)-1H-indol-2-yl)methyl)benzoyl)piperidin-4-yl)acetate (102 mg, 0.18 mmol).

LC/MS (Method g) $R_t$=1.88 min.; MS m/z: 557 [M+H]$^+$ $^1$H NMR (DMSO-d$_6$, 400 MHz): δ 12.10 (m, 1H), 7.66 and 7.65 (d, J=8.3 Hz, 1H), 7.43 and 7.36 (d, J=8.3 Hz, 1H), 7.34 (s, 1H), 6.77 (m, 1H), 5.59 and 5.56 (s, 1H), 4.42 (m, 3H), 3.84 (m, 3H), 3.26 (m, 1H), 3.05 (m, 1H), 2.80 (m, 1H), 2.31 and 2.30 (s, 3H), 2.15 (m, 2H), 1.95 (m, 1H), 1.77 (m, 1H), 1.62 (m, 1H), 1.15 (m, 2H).

Example DP-1: (2,4-dichloro-3-((1,4-dimethyl-6-(trifluoromethoxy)-1H-indol-2-yl)methyl)phenyl)(morpholino)methanone

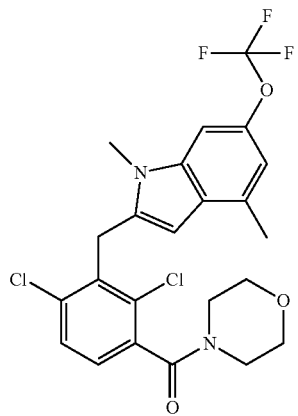 [SMILES: Cc1cc(OC(F)(F)F)cc2c1cc(Cc1c(Cl)ccc(C(=O)N3CCOCC3)c1Cl)n2C]

Using a procedure similar to Example A1, (2,4-dichloro-3-((1,4-dimethyl-6-(trifluoromethoxy)-1H-indol-2-yl)methyl)phenyl)(morpholino)methanone (79 mg, 83%) was prepared from 2,4-dichloro-3-((1,4-dimethyl-6-(trifluoromethoxy)-1H-indol-2-yl)methyl)benzoic acid (80 mg, 0.18 mmol) (example DP, step 5) and morpholine (19 mg, 0.22 mmol). LC/MS (Method g): $R_t$=1.96 min.; MS m/z: 501 [M+H]$^+$; $^1$H NMR (DMSO-d$_6$, 400 MHz): δ 7.67 (d, J=8.4 Hz, 1H), 7.44 (d, J=8.4 Hz, 1H), 7.34 (s, 1H), 6.77 (s, 1H), 5.61 (s, 1H), 4.42 (m, 2H), 3.84 (s, 3H), 3.65 (m, 4H), 3.54 (m, 2H), 3.17 (m, 2H), 2.32 (s, 3H).

Example DP-2: (3S,4S)-1-(2,4-dichloro-3-((1,4-dimethyl-6-(trifluoromethoxy)-1H-indol-2-yl)methyl)benzoyl)-3-methylpiperidine-4-carboxylic acid

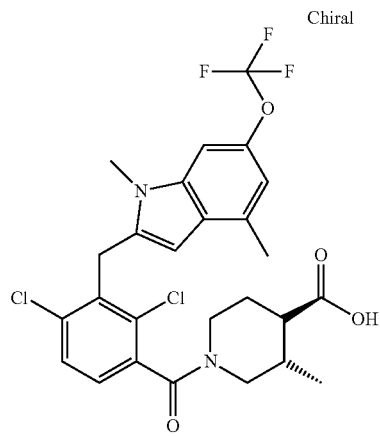

Step 1: (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate

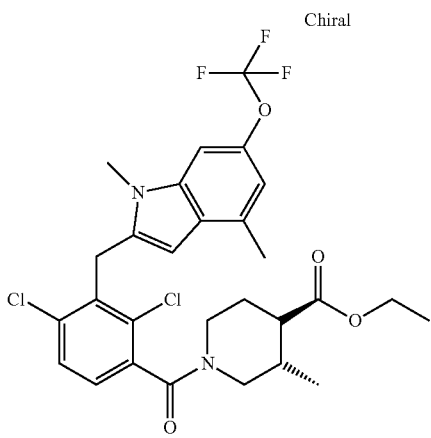

Using a procedure similar to Example A, Step 6, (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate (166 mg, 82%) was prepared from 2,4-dichloro-3-((1,4-dimethyl-6-(trifluoromethoxy)-1H-indol-2-yl)methyl)benzoic acid (80 mg, 0.18 mmol) (example DP, step 5) and (3S,4S)-ethyl 3-methylpiperidine-4-carboxylate hydrochloride (108 mg, 0.52 mmol) (Preparation 83). LC/MS (Method i): Rt=2.80 min.; MS m/z: 585 [M+H]$^+$ $^1$H NMR (DMSO-d$_6$, 300 MHz): δ 7.66 (d, J=8.3 Hz, 1H), 7.42 (m, 1H), 7.34 (s, 1H), 6.77 (s, 1H), 5.59 (m, 1H), 4.41 (m, 2H), 4.08 (m, 2H), 3.85 and 3.84 (s, 3H), 3.16 (m, 3H), 2.79 (m, 1H), 2.32 (m, 3H), 2.27 (m, 1H), 2.12 (m, 1H), 1.72 (m, 2H), 1.16 (m, 3H), 0.82 (m, 3H).

Step 2: (3S,4S)-1-(2,4-dichloro-3-((1,4-dimethyl-6-(trifluoromethoxy)-1H-indol-2-yl)methyl)benzoyl)-3-methylpiperidine-4-carboxylic acid

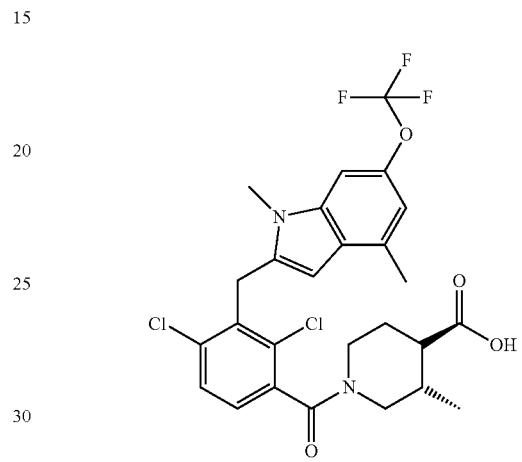

Using a procedure similar to Example A, Step 5, (3S,4S)-1-(2,4-dichloro-3-((1,4-dimethyl-6-(trifluoromethoxy)-1H-indol-2-yl)methyl)benzoyl)-3-methylpiperidine-4-carboxylic acid (72 mg, 46%) was prepared from (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate (160 mg, 0.27 mmol). LC/MS (Method g): Rt=1.90 min.; MS m/z: 557 [M+H]$^+$; $^1$H NMR (DMSO-d$_6$, 400 MHz): δ 12.25 (broad, 1H), 7.65 (m, 1H), 7.41 (m, 1H), 7.34 (s, 1H), 6.77 (m, 1H), 5.58 (m, 1H), 4.30 (m, 3H), 3.85 and 3.84 (s, 3H), 3.08 (m, 3H), 2.67 (m, 1H), 2.32 (m, 3H), 2.28 and 2.11 (m, 1H), 1.65 (m, 2H), 0.84 (m, 3H).

Example DQ: 4-chloro-2-(2,6-dichloro-3-(morpholine-4-carbonyl)benzyl)-1-methyl-1H-indole-6-carbonitrile

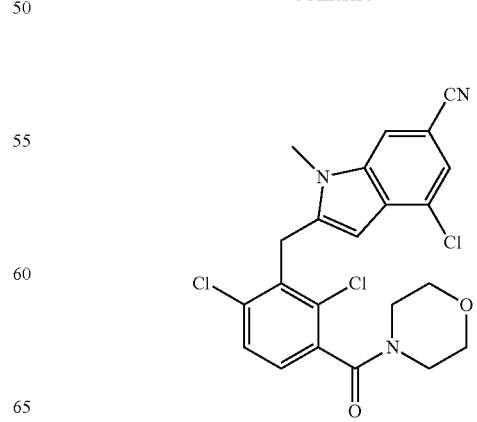

Step 1: tert-butyl 3-((6-bromo-4-chloro-1-(phenylsulfonyl)-1H-indol-2-yl)(hydroxyl)methyl)-2,4-dichlorobenzoate

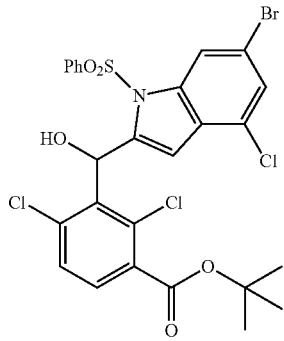

To a solution of 6-bromo-4-chloro-1-(phenylsulfonyl)-1H-indole (Preparation #48) (200 mg, 0.54 mmol) in THF (1.5 mL) and cooled to −78° C. was added lithium diisopropylamide (0.30 mL, 0.59 mmol) and the reaction mixture was stirred for 1 hour at −78° C. tert-butyl 2,4-dichloro-3-formylbenzoate (Preparation #33, Step B) (178 mg, 0.65 mmol) in solution in THF (1.5 mL) was added to the reaction mixture and the reaction mixture was stirred for 2 hours at −78° C. The reaction mixture was quenched with a saturated NH$_4$Cl solution and extracted with EtOAc. The organic layer was dried over magnesium sulfate, filtered and concentrated under reduced pressure. The residue was purified by column chromatography on silica gel (eluting with 0-10% EtOAc in cyclohexane) to give tert-butyl 3-((6-bromo-4-chloro-1-(phenylsulfonyl)-1H-indol-2-yl)(hydroxy)methyl)-2,4-dichlorobenzoate (262 mg, 75%). LC/MS (Method j) R$_t$=2.75 min.; MS m/z: 702 [M−H]$^-$+CH$_3$COOH $^1$H NMR (DMSO-d$_6$, 300 MHz): δ 8.11 (m, 1H), 7.85 (m, 2H), 7.72 (m, 1H), 7.66 (d, J=6 Hz, 1H), 7.55 (m, 4H), 6.95 (m, 1H), 6.75 (m, 1H), 6.66 (m, 1H), 1.54 ppm (s, 9H)

Step 2: 3-((6-bromo-4-chloro-1-(phenylsulfonyl)-1H-indol-2-yl)methyl)-2,4-dichlorobenzoic acid

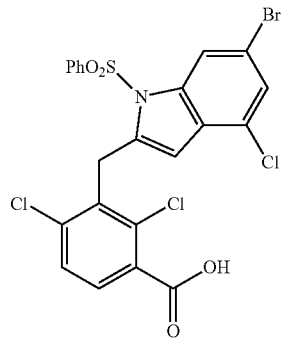

Using a procedure similar to Example A, Step 2, 3-((6-bromo-4-chloro-1-(phenylsulfonyl)-1H-indol-2-yl)methyl)-2,4-dichlorobenzoic acid (1.17 g, 93%) was prepared from tert-butyl 3-((6-bromo-4-chloro-1-(phenylsulfonyl)-1H-indol-2-yl)(hydroxy)methyl)-2,4-dichlorobenzoate (1.42 g, 2.2 mmol).

LC/MS (Method i) R$_t$=2.81 min.; MS m/z: 570 [M−H]$^-$ $^1$H NMR (DMSO-d$_6$, 300 MHz): δ 8.27 (m, 1H), 8.00 (m, 2H), 7.80 (m, 2H), 7.69 (m, 4H), 5.70 (m, 1H), 4.55 (s, 2H).

Step 3: 3-((6-bromo-4-chloro-1H-indol-2-yl)methyl)-2,4-dichlorobenzoic acid

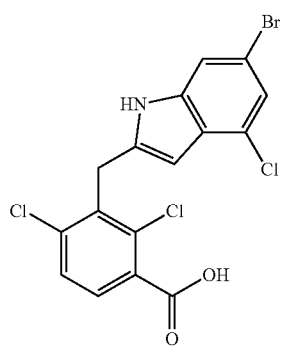 [SMILES: O=C(O)c1ccc(Cl)c(Cc2cc3c(Cl)cc(Br)cc3[nH]2)c1Cl]

Using a procedure similar to Example A, Step 3, 3-((6-bromo-4-chloro-1H-indol-2-yl)methyl)-2,4-dichlorobenzoic acid (657 mg, 100%) was prepared from 3-((6-bromo-4-chloro-1-(phenylsulfonyl)-1H-indol-2-yl)methyl)-2,4-dichlorobenzoic acid (870 mg, 1.52 mmol). The compound was used directly in the next step. LC/MS (Method i) R$_t$=2.48 min.; MS m/z: 432 [M+H]$^+$

Step 4: methyl 3-((6-bromo-4-chloro-1-methyl-1H-indol-2-yl)methyl)-2,4-dichlorobenzoate

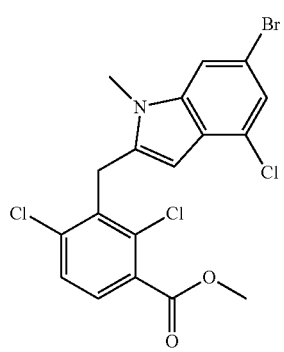 [SMILES: COC(=O)c1ccc(Cl)c(Cc2cc3c(Cl)cc(Br)cc3n2C)c1Cl]

Using a procedure similar to Example P, Step 4, methyl 3-((6-bromo-4-chloro-1-methyl-1H-indol-2-yl)methyl)-2,4-dichlorobenzoate (568 mg, 81%) was prepared from 3-((6-bromo-4-chloro-1H-indol-2-yl)methyl)-2,4-dichlorobenzoic acid (657 mg, 1.52 mmol).

LC/MS (Method j) R$_t$=2.46 min.; MS m/z: 460 [M+H]$^+$ $^1$H NMR (DMSO-d$_6$, 300 MHz): δ 7.80 (m, 2H), 7.72 (m, 1H), 7.23 (d, J=1.5 Hz, 1H), 5.52 (m, 1H), 4.46 (s, 2H), 3.89 (s, 3H), 3.88 (s, 3H).

Step 5: methyl 2,4-dichloro-3-((4-chloro-6-cyano-1-methyl-1H-indol-2-yl)methyl)benzoate

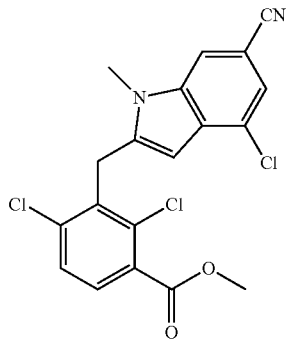 [SMILES: COC(=O)c1ccc(Cl)c(Cc2cc3c(Cl)cc(C#N)cc3n2C)c1Cl]

To a solution of methyl 3-((6-bromo-4-chloro-1-methyl-1H-indol-2-yl)methyl)-2,4-dichlorobenzoate (559 mg, 1.211 mmol) in N,N-dimethylformamide (4.3 mL) was added zinc cyanide (107 mg, 0.908 mmol) and tetrakis(triphenylphosphine)palladium (140 mg, 0.121 mmol) and the reaction mixture was heated at 120° C. under microwave during 1 hour. The reaction mixture was diluted with water and extracted with EtOAc. The obtained organic layer was dried over magnesium sulfate, filtered and concentrated under reduced pressure. The residue was purified by column chromatography on silica gel (eluting with 0-40% EtOAc in cyclohexane) to give methyl 2,4-dichloro-3-((4-chloro-6-cyano-1-methyl-1H-indol-2-yl)methyl)benzoate (200 mg, 40%). LC/MS (Method i) $R_f$=2.59 min.; MS m/z: 405 [M−H]⁻

¹H NMR (DMSO-d₆, 300 MHz): δ=8.18 (m, 1H), 7.83 (d, J=8.4 Hz, 1H), 7.73 (d, J=8.4 Hz, 1H), 7.50 (d, J=1.2 Hz, 1H), 5.67 (m, 1H), 4.54 (s, 2H), 3.96 (s, 3H), 3.88 (s, 3H).

Step 6: 2,4-dichloro-3-((4-chloro-6-cyano-1-methyl-1H-indol-2-yl)methyl)benzoic acid

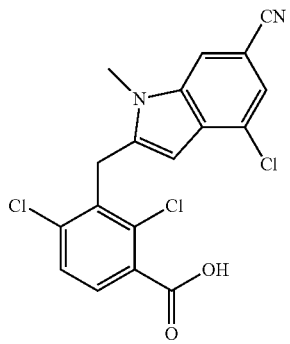 [SMILES: Cn1c(Cc2c(Cl)ccc(C(=O)O)c2Cl)cc2c(Cl)cc(C#N)cc21]

Using a procedure similar to Example A, Step 5, 2,4-dichloro-3-((4-chloro-6-cyano-1-methyl-1H-indol-2-yl)methyl)benzoic acid (180 mg, 94%) was prepared from methyl 2,4-dichloro-3-((4-chloro-6-cyano-1-methyl-1H-indol-2-yl)methyl)benzoate (198 mg, 0.48 mmol). LC/MS (Method i) $R_f$=2.25 min.; MS m/z: 393 [M+H]⁺

¹H NMR (DMSO-d₆, 300 MHz): δ 13.60 (br, 1H), 8.18 (m, 1H), 7.79 (d, J=8.4 Hz 1H), 7.69 (d, J=8.4 Hz 1H), 7.50 (d, J=1.2 Hz, 1H), 5.67 (m, 1H), 4.53 (s, 2H), 3.96 (s, 3H).

Step 7: 4-chloro-2-(2,6-dichloro-3-(morpholine-4-carbonyl)benzyl)-1-methyl-1H-indole-6-carbonitrile

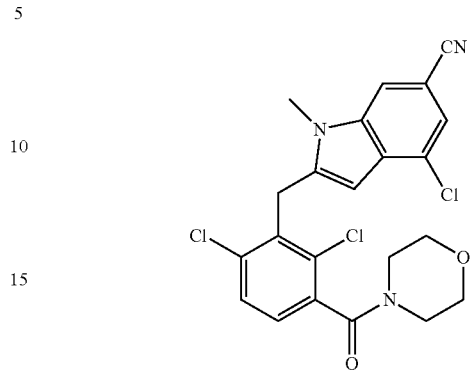

Using a procedure similar to Example A1, 4-chloro-2-(2,6-dichloro-3-(morpholine-4-carbonyl)benzyl)-1-methyl-1H-indole-6-carbonitrile (89 mg, 82%) was prepared from 2,4-dichloro-3-((4-chloro-6-cyano-1-methyl-1H-indol-2-yl)methyl)benzoic acid (90 mg, 0.23 mmol) and morpholine (23.9 mg, 0.27 mmol). LC/MS (Method g) $R_f$=1.69 min.; MS m/z: 462 [M+H]⁺ ¹H NMR (DMSO-d₆, 400 MHz): δ 8.17 (s, 1H), 7.69 (d, J=8.1 Hz, 1H), 7.50 (d, J=1.3 Hz, 1H), 7.47 (d, J=8.1 Hz, 1H), 5.70 (m, 1H), 4.50 (m, 2H), 3.96 (s, 3H), 3.65 (m, 4H), 3.55 (m, 2H), 3.15 (m, 2H).

Example DP-1: (2,4-dichloro-3-((1,4-dimethyl-6-(trifluoromethoxy)-1H-indol-2-yl)methyl)phenyl)(morpholino)methanone

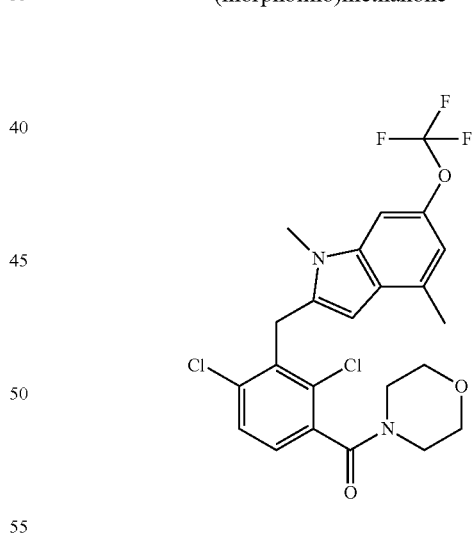

Using a procedure similar to Example A1, (2,4-dichloro-3-((1,4-dimethyl-6-(trifluoromethoxy)-1H-indol-2-yl)methyl)phenyl)(morpholino)methanone (79 mg, 83%) was prepared from 2,4-dichloro-3-((1,4-dimethyl-6-(trifluoromethoxy)-1H-indol-2-yl)methyl)benzoic acid (80 mg, 0.18 mmol) (example DP, step 5) and morpholine (19 mg, 0.22 mmol). LC/MS (Method g): Rt=1.96 min.; MS m/z: 501 [M+H]⁺; ¹H NMR (DMSO-d₆, 400 MHz): δ 7.67 (d, J=8.4 Hz, 1H), 7.44 (d, J=8.4 Hz, 1H), 7.34 (s, 1H), 6.77 (s, 1H), 5.61 (s, 1H), 4.42 (m, 2H), 3.84 (s, 3H), 3.65 (m, 4H), 3.54 (m, 2H), 3.17 (m, 2H), 2.32 (s, 3H).

Example DP-2: (3S,4S)-1-(2,4-dichloro-3-((1,4-dimethyl-6-(trifluoromethoxy)-1H-indol-2-yl)methyl)benzoyl)-3-methylpiperidine-4-carboxylic acid

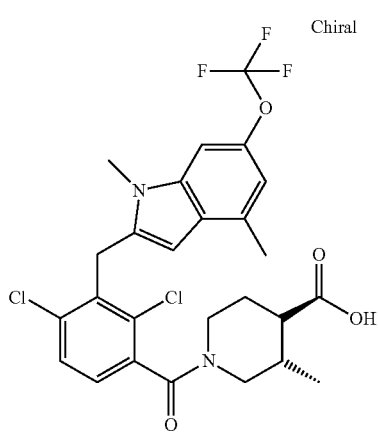

Step 1: (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate

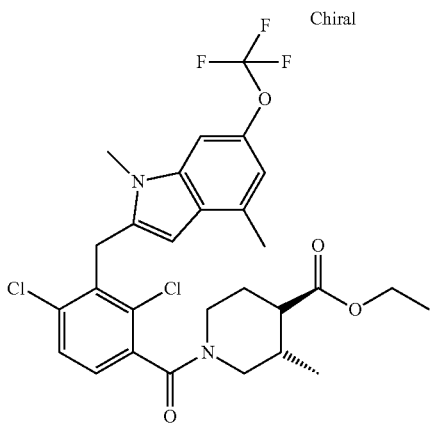

Using a procedure similar to Example A, Step 6, (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate (166 mg, 82%) was prepared from 2,4-dichloro-3-((1,4-dimethyl-6-(trifluoromethoxy)-1H-indol-2-yl)methyl)benzoic acid (80 mg, 0.18 mmol) (example DP, step 5) and (3S,4S)-ethyl 3-methylpiperidine-4-carboxylate hydrochloride (108 mg, 0.52 mmol) (Preparation 83). LC/MS (Method i): Rt=2.80 min.; MS m/z: 585 [M+H]+ ¹H NMR (DMSO-d₆, 300 MHz): δ 7.66 (d, J=8.3 Hz, 1H), 7.42 (m, 1H), 7.34 (s, 1H), 6.77 (s, 1H), 5.59 (m, 1H), 4.41 (m, 2H), 4.08 (m, 2H), 3.85 and 3.84 (s, 3H), 3.16 (m, 3H), 2.79 (m, 1H), 2.32 (m, 3H), 2.27 (m, 1H), 2.12 (m, 1H), 1.72 (m, 2H), 1.16 (m, 3H), 0.82 (m, 3H).

Step 2: (3S,4S)-1-(2,4-dichloro-3-((1,4-dimethyl-6-(trifluoromethoxy)-1H-indol-2-yl)methyl)benzoyl)-3-methylpiperidine-4-carboxylic acid

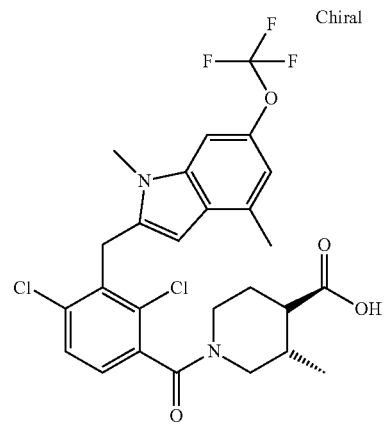

Using a procedure similar to Example A, Step 5, (3S,4S)-1-(2,4-dichloro-3-((1,4-dimethyl-6-(trifluoromethoxy)-1H-indol-2-yl)methyl)benzoyl)-3-methylpiperidine-4-carboxylic acid (72 mg, 46%) was prepared from (3S,4S)-ethyl 1-(2,4-dichloro-3-((1,4-dimethyl-6-(trifluoromethoxy)-1H-indol-2-yl)methyl)benzoyl)-3-methylpiperidine-4-carboxylate (160 mg, 0.27 mmol). LC/MS (Method g): R$_t$=1.90 min.; MS m/z: 557 [M+H]+; ¹H NMR (DMSO-d₆, 400 MHz): δ 12.25 (broad, 1H), 7.65 (m, 1H), 7.41 (m, 1H), 7.34 (s, 1H), 6.77 (m, 1H), 5.58 (m, 1H), 4.30 (m, 3H), 3.85 and 3.84 (s, 3H), 3.08 (m, 3H), 2.67 (m, 1H), 2.32 (m, 3H), 2.28 and 2.11 (m, 1H), 1.65 (m, 2H), 0.84 (m, 3H).

Example DP-3: (3R,4R)-1-(2,4-dichloro-3-((1,4-dimethyl-6-(trifluoromethoxy)-1H-indol-2-yl)methyl)benzoyl)-3-methylpiperidine-4-carboxylic acid

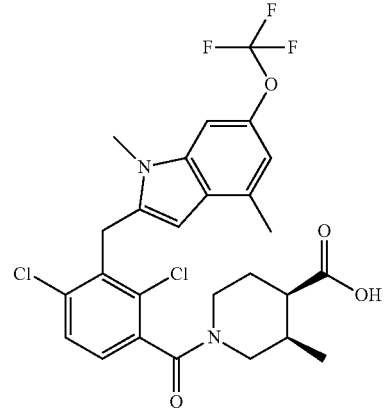 [SMILES: Cc1cc(OC(F)(F)F)cc2c1cc(Cc1c(Cl)ccc(C(=O)N3CC[C@@H](C(=O)O)[C@@H](C)C3)c1Cl)n2C]

(3R,4R)-1-(2,4-dichloro-3-((1,4-dimethyl-6-(trifluoromethoxy)-1H-indol-2-yl)methyl)benzoyl)-3-methylpiperidine-4-carboxylic acid was prepared in a similar way as example DP-2 using (3R,4R)-ethyl 3-methylpiperidine-4-carboxylate hydrochloride (Preparation 84) in step 1. LC/MS (Method g): Rt=1.90 min.; MS m/z: 557 [M+H]+

593

Example DQ: 4-chloro-2-(2,6-dichloro-3-(morpholine-4-carbonyl)benzyl)-1-methyl-1H-indole-6-carbonitrile

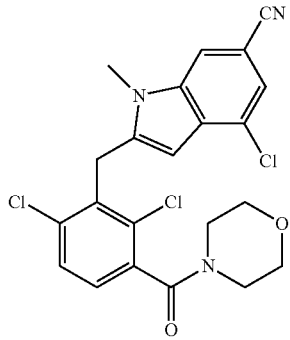

Step 1: tert-butyl 3-((6-bromo-4-chloro-1-(phenylsulfonyl)-1H-indol-2-yl)(hydroxyl)methyl)-2,4-dichlorobenzoate

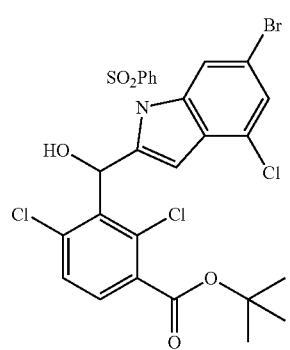 [SMILES: CC(C)(C)OC(=O)c1ccc(Cl)c(C(O)c2cc3c(Cl)cc(Br)cc3[nH]2)c1Cl ; "SO2Ph"]

To a solution of 6-bromo-4-chloro-1-(phenylsulfonyl)-1H-indole (Preparation #48) (200 mg, 0.54 mmol) in THF (1.5 mL) and cooled to −78° C. was added lithium diisopropylamide (0.30 mL, 0.59 mmol) and the reaction mixture was stirred for 1 hour at −78° C. tert-Butyl 2,4-dichloro-3-formylbenzoate (Preparation #33, Step B) (178 mg, 0.65 mmol) in solution in THF (1.5 mL) was added to the reaction mixture and the reaction mixture was stirred for 2 hours at −78° C. The reaction mixture was quenched with a saturated NH$_4$Cl solution and extracted with EtOAc. The organic layer was dried over magnesium sulfate, filtered and concentrated under reduced pressure. The residue was purified by column chromatography on silica gel (eluting with 0-10% EtOAc in cyclohexane) to give tert-butyl 3-((6-bromo-4-chloro-1-(phenylsulfonyl)-1H-indol-2-yl)(hydroxy)methyl)-2,4-dichlorobenzoate (262 mg, 75%). LC/MS (Method j) R$_t$=2.75 min.; MS m/z: 702 [M−H]$^-$+CH$_3$COOH; $^1$H NMR (DMSO-d$_6$, 300 MHz): δ 8.11 (m, 1H), 7.85 (m, 2H), 7.72 (m, 1H), 7.66 (d, J=6 Hz, 1H), 7.55 (m, 4H), 6.95 (m, 1H), 6.75 (m, 1H), 6.66 (m, 1H), 1.54 ppm (s, 9H)

594

Step 2: 3-((6-bromo-4-chloro-1-(phenylsulfonyl)-1H-indol-2-yl)methyl)-2,4-dichlorobenzoic acid

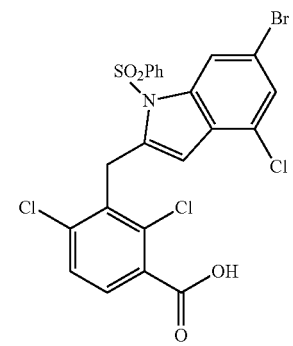

Using a procedure similar to Example A, Step 2, 3-((6-bromo-4-chloro-1-(phenylsulfonyl)-1H-indol-2-yl)methyl)-2,4-dichlorobenzoic acid (1.17 g, 93%) was prepared from tert-butyl 3-((6-bromo-4-chloro-1-(phenylsulfonyl)-1H-indol-2-yl) (hydroxy)methyl)-2,4-dichlorobenzoate (1.42 g, 2.2 mmol).

LC/MS (Method i) R$_t$=2.81 min.; MS m/z: 570 [M−H]$^-$; $^1$H NMR (DMSO-d$_6$, 300 MHz): δ 8.27 (m, 1H), 8.00 (m, 2H), 7.80 (m, 2H), 7.69 (m, 4H), 5.70 (m, 1H), 4.55 (s, 2H).

Step 3: 3-((6-bromo-4-chloro-1H-indol-2-yl)methyl)-2,4-dichlorobenzoic acid

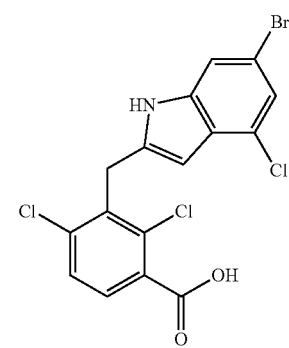 [SMILES: O=C(O)c1ccc(Cl)c(Cc2cc3c(Cl)cc(Br)cc3[nH]2)c1Cl]

Using a procedure similar to Example A, Step 3, 3-((6-bromo-4-chloro-1H-indol-2-yl)methyl)-2,4-dichlorobenzoic acid (657 mg, 100%) was prepared from 3-((6-bromo-4-chloro-1-(phenylsulfonyl)-1H-indol-2-yl)methyl)-2,4-dichlorobenzoic acid (870 mg, 1.52 mmol). The compound was used directly in the next step. LC/MS (Method i) R$_t$=2.48 min.; MS m/z: 432 [M+H]$^+$ Step 4: methyl 3-((6-bromo-4-chloro-1-methyl-1H-indol-2-yl)methyl)-2,4-dichlorobenzoate

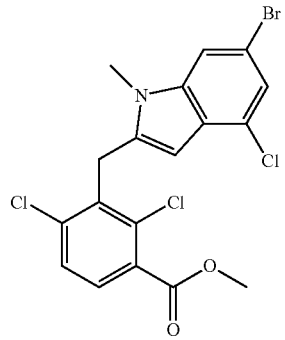 [SMILES: COC(=O)c1ccc(Cl)c(Cc2cc3c(Cl)cc(Br)cc3n2C)c1Cl]

Using a procedure similar to Example P, Step 4, methyl 3-((6-bromo-4-chloro-1-methyl-1H-indol-2-yl)methyl)-2,4-dichlorobenzoate (568 mg, 81%) was prepared from 3-((6-bromo-4-chloro-1H-indol-2-yl)methyl)-2,4-dichlorobenzoic acid (657 mg, 1.52 mmol). LC/MS (Method j) $R_t$=2.46 min.; MS m/z: 460 [M+H]$^+$; $^1$H NMR (DMSO-d$_6$, 300 MHz): δ 7.80 (m, 2H), 7.72 (m, 1H), 7.23 (d, J=1.5 Hz, 1H), 5.52 (m, 1H), 4.46 (s, 2H), 3.89 (s, 3H), 3.88 (s, 3H).

Step 5: methyl 2,4-dichloro-3-((4-chloro-6-cyano-1-methyl-1H-indol-2-yl)methyl)benzoate

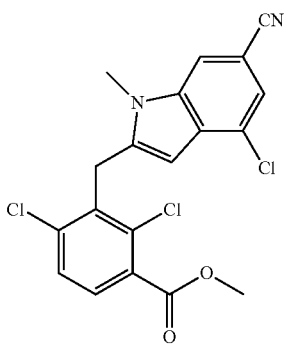 [SMILES: COC(=O)c1ccc(Cl)c(Cc2cc3c(Cl)cc(C#N)cc3n2C)c1Cl]

To a solution of methyl 3-((6-bromo-4-chloro-1-methyl-1H-indol-2-yl)methyl)-2,4-dichlorobenzoate (559 mg, 1.211 mmol) in N,N-dimethylformamide (4.3 mL) was added zinc cyanide (107 mg, 0.908 mmol) and tetrakis(triphenylphosphine)palladium (140 mg, 0.121 mmol) and the reaction mixture was heated at 120° C. under microwave during 1 hour. The reaction mixture was diluted with water and extracted with EtOAc. The obtained organic layer was dried over magnesium sulfate, filtered and concentrated under reduced pressure. The residue was purified by column chromatography on silica gel (eluting with 0-40% EtOAc in cyclohexane) to give methyl 2,4-dichloro-3-((4-chloro-6-cyano-1-methyl-1H-indol-2-yl)methyl)benzoate (200 mg, 40%). LC/MS (Method i) $R_t$=2.59 min.; MS m/z: 405 [M–H]$^-$; $^1$H NMR (DMSO-d$_6$, 300 MHz): δ=8.18 (m, 1H), 7.83 (d, J=8.4 Hz, 1H), 7.73 (d, J=8.4 Hz, 1H), 7.50 (d, J=1.2 Hz, 1H), 5.67 (m, 1H), 4.54 (s, 2H), 3.96 (s, 3H), 3.88 (s, 3H).

Step 6: 2,4-dichloro-3-((4-chloro-6-cyano-1-methyl-1H-indol-2-yl)methyl)benzoic acid

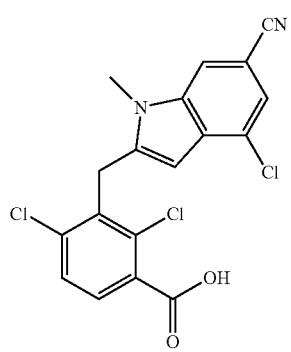

Using a procedure similar to Example A, Step 5, 2,4-dichloro-3-((4-chloro-6-cyano-1-methyl-1H-indol-2-yl)methyl)benzoic acid (180 mg, 94%) was prepared from methyl 2,4-dichloro-3-((4-chloro-6-cyano-1-methyl-1H-indol-2-yl)methyl)benzoate (198 mg, 0.48 mmol). LC/MS (Method i) $R_t$=2.25 min.; MS m/z: 393 [M+H]$^+$; $^1$H NMR (DMSO-d$_6$, 300 MHz): δ 13.60 (br, 1H), 8.18 (m, 1H), 7.79 (d, J=8.4 Hz 1H), 7.69 (d, J=8.4 Hz 1H), 7.50 (d, J=1.2 Hz, 1H), 5.67 (m, 1H), 4.53 (s, 2H), 3.96 (s, 3H).

Step 7: 4-chloro-2-(2,6-dichloro-3-(morpholine-4-carbonyl)benzyl)-1-methyl-1H-indole-6-carbonitrile

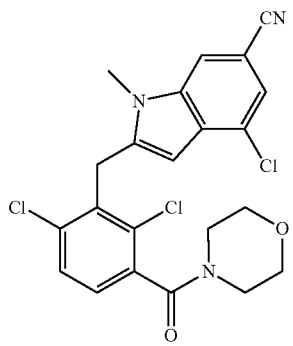 [SMILES: Cn1c(Cc2c(Cl)ccc(C(=O)N3CCOCC3)c2Cl)cc2c(Cl)cc(C#N)cc21]

Using a procedure similar to Example A1, 4-chloro-2-(2,6-dichloro-3-(morpholine-4-carbonyl)benzyl)-1-methyl-1H-indole-6-carbonitrile (89 mg, 82%) was prepared from 2,4-dichloro-3-((4-chloro-6-cyano-1-methyl-1H-indol-2-yl)methyl)benzoic acid (90 mg, 0.23 mmol) and morpholine (23.9 mg, 0.27 mmol). LC/MS (Method g) $R_t$=1.69 min.; MS m/z: 462 [M+H]$^+$; $^1$H NMR (DMSO-d$_6$, 400 MHz): δ 8.17 (s, 1H), 7.69 (d, J=8.1 Hz, 1H), 7.50 (d, J=1.3 Hz, 1H), 7.47 (d, J=8.1 Hz, 1H), 5.70 (m, 1H), 4.50 (m, 2H), 3.96 (s, 3H), 3.65 (m, 4H), 3.55 (m, 2H), 3.15 (m, 2H).

Example DR: 2-(1-(2,4-dichloro-3-((4-chloro-6-cyano-1-methyl-1H-indol-2-yl)methyl)benzoyl)piperidin-4-yl)acetic acid

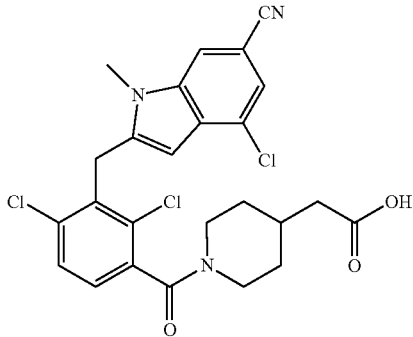

Step 1: methyl 2-(1-(2,4-dichloro-3-((4-chloro-6-cyano-1-methyl-1H-indol-2-yl)methyl)benzoyl)piperidin-4-yl)acetate

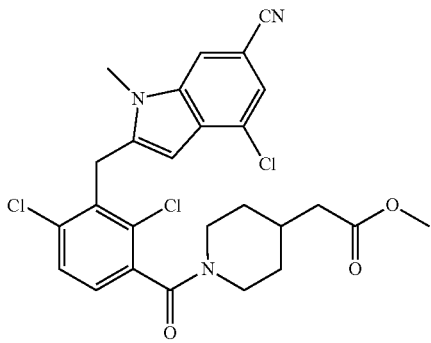

Using a procedure similar to Example A1, methyl 2-(1-(2,4-dichloro-3-((4-chloro-6-cyano-1-methyl-1H-indol-2-yl)methyl)benzoyl)piperidin-4-yl)acetate (101 mg, 83%) was prepared from 2,4-dichloro-3-((4-chloro-6-cyano-1-methyl-1H-indol-2-yl)methyl)benzoic acid (Example DQ, Step 6) (90 mg, 0.23 mmol) and methyl (4-piperidyl)acetate hydrochloride (66.4 mg, 0.34 mmol).

LC/MS (Method i) $R_f$=2.43 min.; MS m/z: 532 [M+H]$^+$ 1H NMR (DMSO-d$_6$, 300 MHz): δ 8.17 (m, 1H), 7.68 and 7.67 (d, J=8.4 Hz, 1H), 7.51 and 7.50 (s, 1H), 7.47 and 7.40 (d, J=8.4 Hz, 1H), 5.68 and 5.65 (m, 1H), 4.47 (m, 3H), 3.96 and 3.95 (s, 3H), 3.59 and 3.56 (s, 3H), 3.25 (m, 1H), 3.05 (m, 1H), 2.80 (m, 1H), 2.25 (m, 2H), 1.95 (m, 1H), 1.75 (m, 1H), 1.59 (m, 1H), 1.17 (m, 2H).

Step 2: 2-(1-(2,4-dichloro-3-((4-chloro-6-cyano-1-methyl-1H-indol-2-yl)methyl)benzoyl)piperidin-4-yl)acetic acid

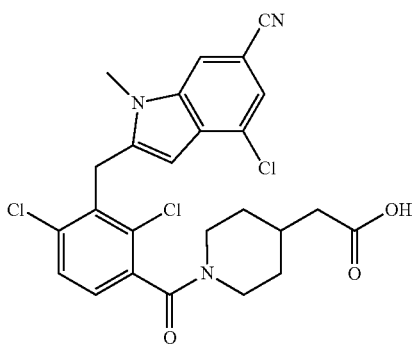

Using a procedure similar to Example A, Step 5, 2-(1-(2,4-dichloro-3-((4-chloro-6-cyano-1-methyl-1H-indol-2-yl)methyl)benzoyl)piperidin-4-yl)acetic acid (93 mg, 95%) was prepared from methyl 2-(1-(2,4-dichloro-3-((4-chloro-6-cyano-1-methyl-1H-indol-2-yl)methyl)benzoyl)piperidin-4-yl)acetate (101 mg, 0.19 mmol). LC/MS (Method g) $R_f$=1.63 min.; MS m/z: 518 [M+H]$^+$ 1H NMR (DMSO-d$_6$, 400 MHz): δ 12.09 (m, 1H), 8.17 (s, 1H), 7.68 and 7.67 (d, J=8.4 Hz, 1H), 7.50 (m, 1H), 7.46 and 7.39 (d, J=8.4 Hz, 1H), 5.68 and 5.66 (m, 1H), 4.49 (m, 3H), 3.96 and 3.95 (s, 3H), 3.27 (m, 1H), 3.05 (m, 1H), 2.80 (m, 1H), 2.15 (m, 2H), 193 (m, 1H), 1.77 (m, 1H), 1.61 (m, 1H), 1.15 (m, 2H).

Example DS: 2-(1-(2,4-dichloro-3-((7-methyl-5-(trifluoromethyl)-1H-indol-1-yl)methyl)benzoyl)piperidin-4-yl)acetic acid

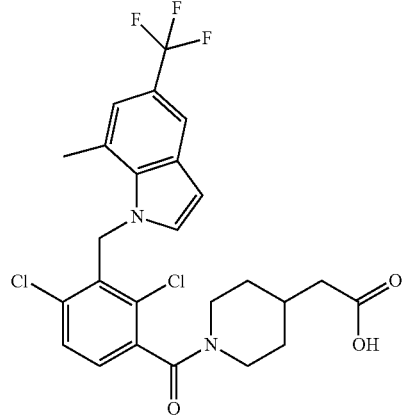 [SMILES: Cc1cc(C(F)(F)F)cc2ccn(Cc3c(Cl)ccc(C(=O)N4CCC(CC(=O)O)CC4)c3Cl)c12]

Step 1: methyl 2,4-dichloro-3-((7-methyl-5-(trifluoromethyl)-1H-indol-1-yl)methyl)benzoate

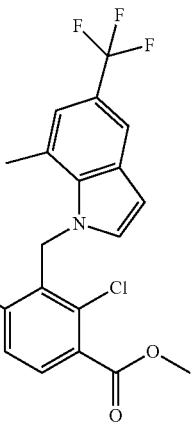

Using a procedure similar to Example DH, Step 1, methyl 2,4-dichloro-3-((7-methyl-5-(trifluoromethyl)-1H-indol-1-yl)methyl)benzoate (1.55 g, 80%) was prepared from 7-methyl-5-(trifluoromethyl)-1H-indole (Preparation #49) (0.85 mg, 4.27 mmol) and methyl 3-(bromomethyl)-2,4-dichlorobenzoate (Preparation #1, Step B) (1.27 g, 0.27 mmol).

LC/MS (Method j) $R_t$=2.32 min.; MS m/z: 416 [M+H]+ 1H NMR (DMSO-$d_6$, 300 MHz): δ 7.89 (d, J=8.4 Hz, 1H), 7.79 (m, 1H), 7.76 (d, J=8.4 Hz, 1H), 7.23 (m, 1H), 6.74 (d, J=3.3 Hz, 1H), 6.56 (d, J=3.3 Hz, 1H), 5.98 (s, 2H), 3.88 (s, 3H), 2.94 (s, 3H).

Step 2: 2,4-dichloro-3-((7-methyl-5-(trifluoromethyl)-1H-indol-1-yl)methyl)benzoic acid

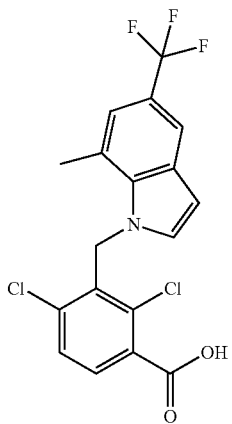 [SMILES: Cc1cc(C(F)(F)F)cc2ccn(Cc3c(Cl)ccc(C(=O)O)c3Cl)c12]

Using a procedure similar to Example F, Step 3, 2,4-dichloro-3-((7-methyl-5-(trifluoromethyl)-1H-indol-1-yl)methyl)benzoic acid (1.44 g, 96%) was prepared from methyl 2,4-dichloro-3-((7-methyl-5-(trifluoromethyl)-1H-indol-1-yl)methyl)benzoate (1.55 g, 3.72 mmol). LC/MS (Method j) $R_t$=1.86 min.; MS m/z: 402 [M+H]+ 1H NMR (DMSO-$d_6$, 300 MHz): δ 13.8 (br, 1H), 7.82 (d, J=8.3 Hz, 1H), 7.79 (s, 1H), 7.69 (d, J=8.3 Hz, 1H), 7.23 (s, 1H), 6.73 (d, J=3.3 Hz, 1H), 6.56 (d, J=3.3 Hz, 1H), 5.97 (s, 2H), 2.95 (s, 3H).

Step 3: methyl 2-(1-(2,4-dichloro-3-((7-methyl-5-(trifluoromethyl)-1H-indol-1-yl)methyl)benzoyl)piperidin-4-yl)acetate

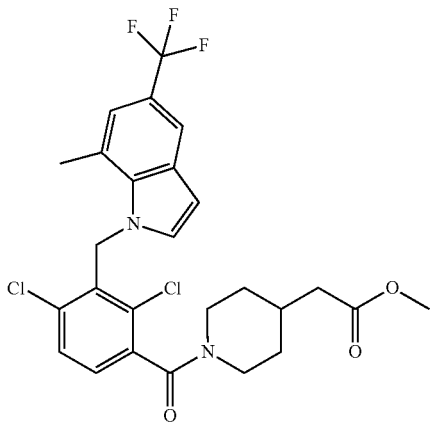

Using a procedure similar to Example A, Step 6, methyl 2-(1-(2,4-dichloro-3-((7-methyl-5-(trifluoromethyl)-1H-indol-1-yl)methyl)benzoyl)piperidin-4-yl)acetate (118 mg, 88%) was prepared from 2,4-dichloro-3-((7-methyl-5-(trifluoromethyl)-1H-indol-1-yl)methyl)benzoic acid (100 mg, 0.25 mmol) and methyl 2-(piperidin-4-yl)acetate hydrochloride (62.6, 0.32 mmol). LC/MS (Method j) $R_t$=2.10 min.; MS m/z: 541 [M+H]+

1H NMR (DMSO-$d_6$, 300 MHz): δ 7.79 (s, 1H), 7.70 and 7.69 (d, J=8.3 Hz, 1H), 7.53 and 7.46 (d, J=8.3 Hz, 1H), 7.23 (s, 1H), 6.76 (m, 1H), 6.57 (m, 1H), 5.94 (m, 2H), 4.46 (m, 1H), 3.59 and 3.57 (s, 3H), 3.21 (m, 1H), 3.03 (m, 1H), 2.94 (s, 3H), 2.80 (m, 1H), 2.28 (m, 2H), 1.96 (m, 1H), 1.75 (m, 1H), 1.59 (m, 1H), 1.17 (m, 2H)

Step 4: 2-(1-(2,4-dichloro-3-((7-methyl-5-(trifluoromethyl)-1H-indol-1-yl)methyl)benzoyl)piperidin-4-yl)acetic acid

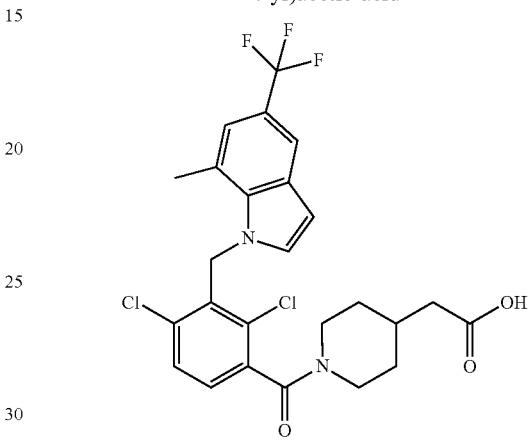

Using a procedure similar to Example A, Step 5, 2-(1-(2,4-dichloro-3-((7-methyl-5-(trifluoromethyl)-1H-indol-1-yl)methyl)benzoyl)piperidin-4-yl)acetic acid (99 mg, 89%) was prepared from methyl 2-(1-(2,4-dichloro-3-((7-methyl-5-(trifluoromethyl)-1H-indol-1-yl)methyl)benzoyl)piperidin-4-yl)acetate (114 mg, 0.21 mmol).

LC/MS (Method g) $R_t$=1.85 min.; MS m/z: 527 [M+H]+ 1H NMR (DMSO-$d_6$, 400 MHz): δ 12.10 (br, 1H), 7.79 (s, 1H), 7.70 and 7.69 (d, J=8.3 Hz, 1H), 7.53 and 7.46 (d, J=8.3 Hz, 1H), 7.23 (s, 1H), 6.76 (m, 1H), 6.58 (m, 1H), 5.94 (m, 2H), 4.46 (m, 1H), 3.27 (m, 1H), 3.03 (m, 1H), 2.94 (s, 3H), 2.80 (m, 1H), 2.17 (m, 2H), 1.93 (m, 1H), 1.77 (m, 1H), 1.61 (m, 1H), 1.14 (m, 2H).

Example DT: (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone

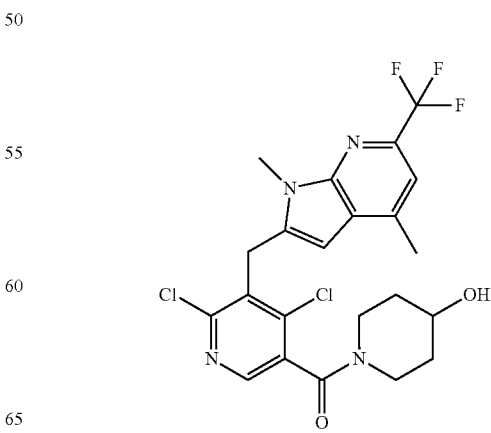

Step 1: 4-methyl-6-(trifluoromethyl)pyridin-2(1H)-one

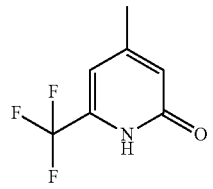

A solution of CHCl₃ (1.25 L) was cooled down to about 0° C. and 2,2,2-trifluoroacetic anhydride (0.141 L, 1012 mmol) was added followed by the addition of 3-methylbut-2-enoyl chloride (0.094 L, 843 mmol). Triethylamine (0.259 L, 1856 mmol) was added dropwise such that the internal temperature was maintained below about 10° C. (exothermic). After addition, the mixture was stirred at about 0° C. for about 1 h and then warmed up to room temperature slowly and stirred overnight. The reaction mixture was washed with water (1 L), saturated NaHCO₃ (1 L), water/brine (1:1, 500 mL), dried over MgSO₄, filtered and concentrated in vacuo. The residue was dissolved in acetic acid (1.250 L) and acetic acid/ammonia salt (130 g, 1687 mmol) was added. The reaction flask was capped with a balloon and the mixture was heated at about 115° C. overnight. After about 20 h the reaction mixture was cooled to about 40° C. and concentrated in vacuo. The syrup was poured onto water (~2 L) with stirring. After about 1 h the solids were collected by filtration to provide 4-methyl-6-(trifluoromethyl)pyridin-2(1H)-one (101 g, 68%) as a tan solid. LC/MS (Method a) $R_t$=1.59 min.; MS m/z: 178 [M+H]⁺. ¹H NMR (CDCl₃, 400 MHz): δ 6.79 (s, 1H), 6.70 (s, 1H), 2.34 (s, 3H).

Step 2: 2-chloro-4-methyl-6-(trifluoromethyl)pyridine

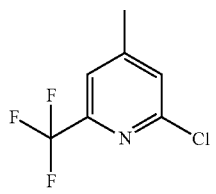

A 50 mL pear-shaped flask fitted with a short path distillation head was charged with 4-methyl-6-(trifluoromethyl)pyridin-2(1H)-one (20 g, 113 mmol). To the flask was added phenylphosphonic dichloride (19.2 mL, 135 mmol). The reaction mixture was heated to about 160° C. After about 3 hours the pressure on the reaction mixture was slowly reduced to 100 mBar and distillation starts with a head temp about 120-130° C. Periodically when distillation had significantly slowed the pressure over the reaction mixture was reduced to 80 mBar and the bath temperature was raised to about 170° C. After about 3 hours the distillation had ceased, providing 2-chloro-4-methyl-6-(trifluoromethyl)pyridine (12 g, 54%). LC/MS (Method a) $R_t$=2.4 min.; MS m/z: 196 [M+H]⁺. ¹H NMR (DMSO-d6, 400 MHz): 7.79 (s, 1H), 7.71 (s, 1H), 2.43 (s, 3H).

Step 3: tert-butyl (4-methyl-6-(trifluoromethyl)pyridin-2-yl)carbamate

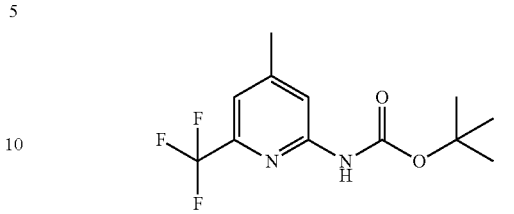

A flask charged with 2-chloro-4-methyl-6-(trifluoromethyl)pyridine (35.1 g, 180 mmol), tert-butyl carbamate (42.1 g, 359 mmol), Pd₂(dba)₃ (4.11 g, 4.49 mmol), dicyclohexyl(2',4',6'-triisopropyl-[1,1'-biphenyl]-2-yl)phosphine (X-Phos) (4.28 g, 8.98 mmol) and cesium carbonate (205 g, 629 mmol) was evacuated and filled with N₂ (repeated 3 times) before addition of degassed 1,4-dioxane (350 mL). The mixture was then heated at about 80° C. for about 2 h. The reaction mixture was cooled to room temperature and the reaction mixture was partitioned between water and EtOAc. The aqueous layer was further extracted with EtOAc (2×100 mL). The organic layer was dried over Na₂SO₄, filtered and concentrated to dryness to give a dark red oil. The material was used without additional purification, 100% yield. LC/MS (Method a) $R_t$=2.71 min.; MS m/z: 275 [M+H]⁺. ¹H NMR (400 MHz, DMSO-d6) δ 10.13 (s, 1H), 7.90 (dt, J=1.3, 0.7 Hz, 1H), 7.34 (dd, J=1.3, 0.7 Hz, 1H), 2.38 (t, J=0.6 Hz, 3H), 1.45 (s, 9H).

Step 4: 4-methyl-6-(trifluoromethyl)pyridin-2-amine

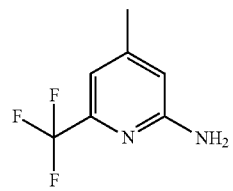

A mixture of tert-butyl (4-methyl-6-(trifluoromethyl)pyridin-2-yl)carbamate (49.6 g, 180 mmol) and hydrogen chloride (4M in 1,4-dioxane) (597 mL, 2388 mmol) was stirred at room temperature for about 2 h. The solvent was removed under reduced pressure and the residue was filtered. The insoluble material was washed with EtOAc and the filtrate was diluted with EtOAc and extracted with 6 N HCl (3×). The aqueous layer was washed with DCM (4×100 mL) and then adjusted to pH 8 with addition of Na₂CO₃ slowly. The bright yellow solid was collected by filtration and washed with water. The solid was then dissolved in DCM, washed with brine, dried over Na₂SO₄, filtered and concentrated to almost dryness. The solid was triturated with petroleum ether and collected by filtration, washed with petroleum ether and air dried to give 4-methyl-6-(trifluoromethyl)pyridin-2-amine (27.7 g, 88%) as a pale yellow solid. LC/MS (Method a) $R_t$=1.92 min.; MS m/z: 177 [M+H]⁺. ¹H NMR (400 MHz, DMSO-d6) δ 6.72 (s, 1H), 6.45 (s, 1H), 6.35 (s, 2H), 2.20 (s, 3H).

Step 5: 3,5-dibromo-4-methyl-6-(trifluoromethyl)pyridin-2-amine

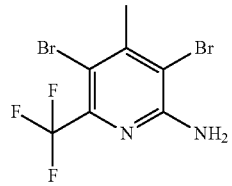

A mixture of 4-methyl-6-(trifluoromethyl)pyridin-2-amine (31.4 g, 179 mmol) and N-bromosuccinimide (66.7 g, 375 mmol) in ACN (250 mL) was heated at about 70° C. for about 2 h. To the reaction flask was added water (~500 mL). The resulting solid was collected by filtration, washed with water and air dried for about 5 minutes. The solid was solubilized in DCM, washed with water, dried over Na$_2$SO$_4$, filtered and concentrated to almost dryness. The solid was triturated with heptane and collected by filtration, washed with heptane and dried to give 3,5-dibromo-4-methyl-6-(trifluoromethyl)pyridin-2-amine (56.9 g, 96%) as light yellow solid. LC/MS (Method a) R$_f$=2.55 min.; MS m/z: 333 [M+H]$^+$. $^1$H NMR (400 MHz, DMSO-d6) δ 6.90 (s, 2H), 2.53 (s, 3H).

Step 6: 3-bromo-4-methyl-6-(trifluoromethyl)pyridin-2-amine

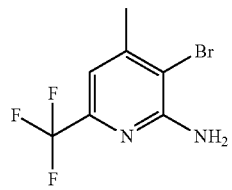

To a light orange solution of 3,5-dibromo-4-methyl-6-(trifluoromethyl)pyridin-2-amine (56.98 g, 171 mmol) in THF (570 mL) at about −78° C. was added n-butyllithium (2.5 M in hexane) (68.3 mL, 171 mmol) dropwise (turned into a brown solution). The mixture was stirred at about −78° C. for about 45 minutes. LC/MS indicated only partial conversion and a second portion of BuLi (2.5 M in hexane) (20.48 mL, 51.2 mmol) was added dropwise. A third portion of BuLi (2.5 M in hexane) (13.65 mL, 34.1 mmol) was added dropwise to complete conversion to product. The reaction flask was transferred to an ice-water bath and 20 mL water was added quickly. The reaction mixture was then warmed to room temperature. The reaction mixture was partitioned between saturated NH$_4$Cl and EtOAc. The organic layer was washed with NaHCO$_3$, dried over Na$_2$SO$_4$, filtered and concentrated to almost dryness. The solid was triturated with heptane and collected by filtration, washed with hepane to give the first crop of product as a off-white solid (38.9 g, 85%). The filtrate was concentrated to dryness and heptane was added. The solid was collected by vacuum filtration and washed with heptane and dried to give the second crop of product as a pale yellow solid (1.9 g, 3%). LC/MS (Method a) R$_f$=2.29 min.; MS m/z: 255 [M+H]$^+$. $^1$H NMR (400 MHz, DMSO-d6) δ 6.96 (s, 1H), 6.74 (s, 1H), 2.32 (s, 3H).

Step 7: (E)-2-(2-Ethoxyvinyl)-4,4,5,5-tetramethyl-1,3,2-dioxaborolane

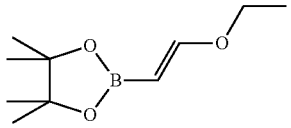

Under an atmosphere of nitrogen in a round bottom flask ethoxyethyne, 50% solution in hexanes (100 g, 710 mmol) and DCM (996 mL) were stirred at about 0-5° C. To the stirred solution was added 4,4,5,5-tetramethyl-1,3,2-dioxaborolane (113 mL, 781 mmol) in one portion followed by the addition of bis(cyclopentadienyl)zirconium hydridochloride (9.16 g, 35.5 mmol) at about 0-5° C. The suspension (orange) was allowed to gradually warm to room temperature over about 30 min Dissolution occurred within about 10 min. The reaction mixture was stirred at room temperature overnight (very dark red). To the reaction solution was added ether (2 L) and the solution was washed with saturated aqueous NH$_4$Cl. The solvents were removed under reduced pressure, DCM (100 mL) was added and the solution was filtered through a pad of alumina, topped with Celite®. The alumina was washed with dichlormethane and the filtrate solvent was removed in vacuo to yield (E)-2-(2-ethoxyvinyl)-4,4,5,5-tetramethyl-1,3,2-dioxaborolane (114.9 g, 82%) as a very dark red oil. $^1$H NMR (400 MHz, DMSO-d6) δ 7.05 (d, 1H), 4.45 (d, 1H), 3.83 (q, 2H), 1.30 (t, 3H), 1.28 (s, 12H).

Step 8: (E)-3-(2-ethoxyvinyl)-4-methyl-6-(trifluoromethyl)pyridin-2-amine

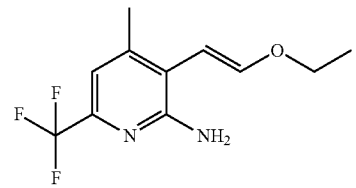 [SMILES: CCO/C=C/c1c(C)cc(C(F)(F)F)nc1N]

A flask charged with 3-bromo-4-methyl-6-(trifluoromethyl)pyridin-2-amine (38.3 g, 143 mmol), (E)-2-(2-ethoxyvinyl)-4,4,5,5-tetramethyl-1,3,2-dioxaborolane (56.5 g, 285 mmol), diacetoxypalladium (0.960 g, 4.28 mmol), dicyclohexyl(2',4',6'-triisopropyl-[1,1'-biphenyl]-2-yl)phosphine (XPhos) (4.28 g, 8.98 mmol) and cesium carbonate (116 g, 356 mmol) was degassed with N$_2$ for 15 min before addition of 320 mL degassed 1,4-dioxane/H$_2$O (4:1). The mixture was heated at about 80° C. for about 2 hours. The mixture was cooled to room temperature. The reaction mixture was partitioned between EtOAc and water and the aqueous layer was further extracted with EtOAc (2×50 mL). The organic layer was dried over Na$_2$SO$_4$, filtered and concentrated to dryness. To the residue was added heptane and the resulting solid was collected by filtration and washed with heptane to give an off-white solid (1.45 g). The filtrate was concentrated to dryness again to give a thick black oil that was left at room temperature overnight. Significant solid formation was noticed and the solid was diluted with heptane, sonicated and filtered, washed with heptane to give a light brown solid (15.2 g, 42%). The filtrate was concentrated to dryness to give a black oil that was purified by flash chromatography (0-25% EtOAc/heptane over 30 min) The product containing fractions was concentrated to almost dryness. The solid was collected by filtration, washed with a small amount of heptane and dried to give the second crop of product as a light yellow solid (12.7 g, 35%). LC/MS (Method 1) $R_t$=1.48 min.; MS m/z: 247 [M+H]$^+$. $^1$H NMR (400 MHz, DMSO-d6) δ 6.82 (s, 1H), 6.73 (d, J=13.1 Hz, 1H), 6.12 (s, 2H), 5.45 (d, J=13.1 Hz, 1H), 3.93 (q, J=7.0 Hz, 2H), 2.23 (s, 3H), 1.25 (t, J=7.0 Hz, 3H).

Step 9: 4-methyl-6-(trifluoromethyl)-1H-pyrrolo[2,3-b]pyridine

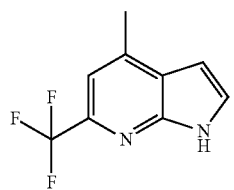

A mixture of (E)-3-(2-ethoxyvinyl)-4-methyl-6-(trifluoromethyl)pyridin-2-amine (27.9 g, 113 mmol) and acetic acid (130 mL) was heated at about 100° C. overnight. The mixture was cooled to room temperature and the precipitate was collected by filtration, washed with ACN and dried to give the first crop of product. The filtrate was concentrated to ~50 mL. and the solid was collected by filtration, washed with ACN and dried to give the second crop of product. Both crops were combined. The filtrate still had some product in it and was set aside. The solid was suspended in ~250 mL EtOAc and heated to reflux to dissolve. Most of the solvent was removed under reduced pressure and heptane was added. The solid was collected by vacuum filtration, dried to give the product as an off-white solid (19.8 g, 87%). LC/MS (Method 1) $R_t$=1.30 min.; MS m/z: 201 [M+H]$^+$. $^1$H NMR (400 MHz, DMSO-d6) δ 12.13-11.98 (br, 1H), 7.67 (t, J=3.1 Hz, 1H), 7.34 (d, J=1.0 Hz, 1H), 6.63 (dd, J=3.5, 1.9 Hz, 1H), 2.59 (s, 3H).

Step 10: 4-methyl-1-(phenylsulfonyl)-6-(trifluoromethyl)-1H-pyrrolo[2,3-b]pyridine

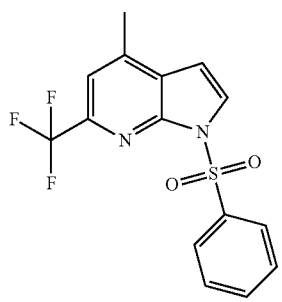 [SMILES: Cc1cc(C(F)(F)F)nc2c1ccn2S(=O)(=O)c1ccccc1]

To a suspension of sodium hydride (60% in mineral oil) (4.35 g, 109 mmol) in N,N-dimethylformamide (40 mL) at about 0° C. was added a solution of 4-methyl-6-(trifluoromethyl)-1H-pyrrolo[2,3-b]pyridine (19.8 g, 99 mmol) under N$_2$. After addition, the ice-water bath was removed and the mixture was stirred at room temperature for about 30 minutes. It was cooled down to about 0° C. again, benzenesulfonyl chloride (13.27 mL, 104 mmol) was added dropwise. After addition, the reaction was allowed to warm to room temperature and stirred for about 1 h. The reaction was quenched with the addition of 100 mL saturated NH$_4$Cl solution followed by the addition of 350 mL water. The solid was collected by filtration, washed with water and dried in a vacuum oven at about 70° C. for about 2 days to give an off-white solid. The solid was dissolved in EtOAc, filtered through 70 g silica gel and the pad was washed with EtOAc. The filtrate was dried over Na$_2$SO$_4$, filtered and concentrated to dryness. The solid was triturated with EtOAc/heptane to give the first crop of 4-methyl-1-(phenylsulfonyl)-6-(trifluoromethyl)-1H-pyrrolo[2,3-b]pyridine (28.5 g, 85%) as white solid. The filtrate was concentrated to dryness and the solid was triturated with ether/heptane. The resulting solid was collected by filtration, washed with heptane and dried to give the second crop of 4-methyl-1-(phenylsulfonyl)-6-(trifluoromethyl)-1H-pyrrolo[2,3-b]pyridine (3.65 g, 11%) as an off-white solid. LC/MS (Method 1) $R_t$=1.84 min.; MS m/z: 341 [M+H]$^+$. $^1$H NMR (400 MHz, DMSO-d6) δ 8.15-8.07 (m, 3H), 7.75-7.67 (m, 1H), 7.64-7.56 (m, 3H), 7.03 (d, J=4.1 Hz, 1H), 2.57 (s, 3H).

Step 11: tert-butyl 4,6-dichloronicotinate

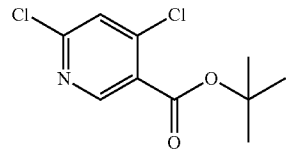

A mixture of 4,6-dichloronicotinic acid (8.2 g, 42.7 mmol) and di-tert-butyl dicarbonate (19.83 mL, 85 mmol) in THF (100 mL) was stirred at room temperature, then 4-(N,N-dimethylamino)pyridine (1.044 g, 8.54 mmol) was added to the solution. The resulting mixture was stirred at about 70° C. for about 1 h. The sample was deposited onto silica gel and loaded onto a silica gel column and eluted with 5% EtOAc/heptane. The following fractions were collected to give the tert-butyl 4,6-dichloronicotinate (10 g, 94%) as a colorless oil. $^1$H NMR (400 MHz, CDCl$_3$) δ 8.76 (s, 1H), 7.43 (s, 1H), 1.61 (s, 9H).

Step 12: tert-butyl 4,6-dichloro-5-formylnicotinate

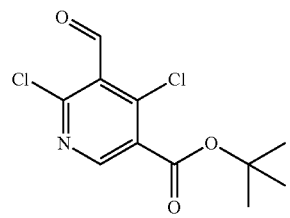 [SMILES: CC(C)(C)OC(=O)c1cnc(Cl)c(C=O)c1Cl]

The tert-butyl 4,6-dichloronicotinate (10 g, 40.3 mmol) was dissolved in THF (100 mL), stirred and cooled to about −78° C. To the solution was added lithium diisopropylamide (22.2 mL, 44.3 mmol) at a rate to maintain the temperature below about −70° C. The resulting solution was stirred at about −78° C. for about 10 minutes. Then methyl formate (4.94 mL, 81 mmol) was added to the solution and the mixture was stirred at about −78° C. for about 30 minutes. The mixture was poured into saturated NH₄Cl, extracted with EtOAc (3×) and the combined organic layers were dried with Na₂SO₄, filtered and concentrated to afford a brown oil. The sample was deposited onto silica gel and purified by silica gel chromatography eluting with 2% EtOAc/heptane. The following fractions were collected to give tert-butyl 4,6-dichloro-5-formylnicotinate (5.0 g, 45% yield) as a yellow solid. ¹H NMR (400 MHz, CDCl₃) δ 10.47 (s, 1H), 8.7 (s, 1H), 1.65 (s, 9H).

Step 13: tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate

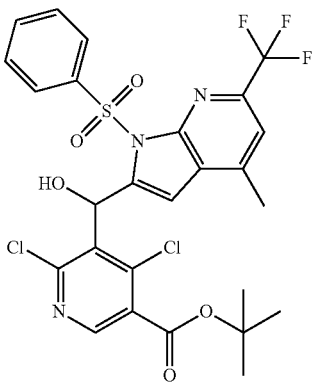 [SMILES: Cc1cc(C(F)(F)F)nc2c1cc(C(O)c1c(Cl)ncc(C(=O)OC(C)(C)C)c1Cl)n2S(=O)(=O)c1ccccc1]

Using a procedure similar to Example CL, Step 1, tert-butyl 4,6-dichloro-5-(hydroxy(4-methyl-1-(phenylsulfonyl)-6-(trifluoromethyl)-1H-pyrrolo[2,3-b]pyridin-2-yl) methyl)nicotinate was prepared from 4-methyl-1-(phenylsulfonyl)-6-(trifluoromethyl)-1H-pyrrolo[2,3-b] pyridine (6.0 g, 17.6 mmol) and tert-butyl 4,6-dichloro-5-formylnicotinate (5.35 g, 19.4 mmol). LC/MS (Method 1) R$_f$=2.15 min.; MS m/z: 616 [M+H]⁺. ¹H NMR (400 MHz, DMSO-d6) δ 8.67 (s, 1H), 7.95 (d, 2H), 7.69 (m, 1H), 7.61 (s, 1H), 7.55 (m, 2H), 7.05 (s, 1H), 7.04 (d, 1H), 6.92 (d, 1H), 2.54 (s, 3H), 1.54 (s, 9H).

Step 14: tert-butyl 4,6-dichloro-5-((4-methyl-1-(phenylsulfonyl)-6-(trifluoromethyl)-1H-pyrrolo[2,3-b]pyridin-2-yl)methyl)nicotinate

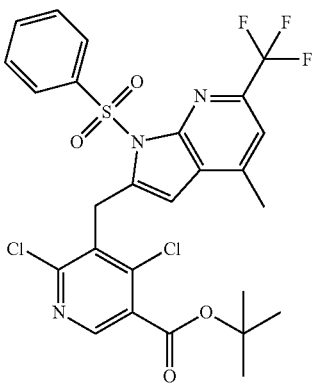 [SMILES: Cc1cc(C(F)(F)F)nc2c1cc(Cc1c(Cl)ncc(C(=O)OC(C)(C)C)c1Cl)n2S(=O)(=O)c1ccccc1]

Using a procedure similar to Example Z, Step 2, tert-butyl 4,6-dichloro-5-((4-methyl-1-(phenylsulfonyl)-6-(trifluoromethyl)-1H-pyrrolo[2,3-b]pyridin-2-yl)methyl)nicotinate was prepared from tert-butyl 4,6-dichloro-5-(hydroxy(4-methyl-1-(phenylsulfonyl)-6-(trifluoromethyl)-1H-pyrrolo [2,3-b]pyridin-2-yl)methyl)nicotinate (1.51 g, 2.44 mmol). LC/MS (Method 1) R$_f$=2.33 min.; MS m/z: 600 [M+H]⁺.

Step 15: 4,6-dichloro-5-((4-methyl-6-(trifluoromethyl)-1H-pyrrolo[2,3-b]pyridin-2-yl)methyl)nicotinic acid

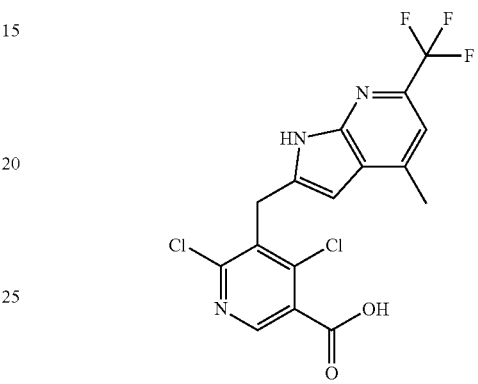

To a solution of tert-butyl 4,6-dichloro-5-((4-methyl-1-(phenylsulfonyl)-6-(trifluoromethyl)-1H-pyrrolo[2,3-b] pyridin-2-yl)methyl)nicotinate (334.9 mg, 0.558 mmol) in 1,4-dioxane (7339 μL) was added sodium hydroxide (2M) (1394 μL, 2.79 mmol) The mixture was heated at about 50° C. overnight. The reaction mixture was cooled to room temperature, diluted with water and acidified with HCl (1M). The mixture was extracted twice with EtOAc and the combined organic extracts were dried over Na₂SO₄, filtered and evaporated to give 4,6-dichloro-5-((4-methyl-6-(trifluoromethyl)-1H-pyrrolo[2,3-b]pyridin-2-yl)methyl)nicotinic acid (0.23 g, 100%) as a pale brown solid. LC/MS (Method 1) R$_f$=1.02 min.; MS m/z: 404 [M+H]⁺. ¹H NMR (400 MHz, DMSO-d6) δ 12.16 (s, 1H), 8.75 (s, 1H), 7.29 (d, J=0.8 Hz, 1H), 6.09 (dd, J=2.1, 1.0 Hz, 1H), 4.48 (s, 3H).

Step 16: methyl 4,6-dichloro-5-((1,4-dimethyl-6-(trifluoromethyl)-1H-pyrrolo[2,3-b]pyridin-2-yl)methyl)nicotinate

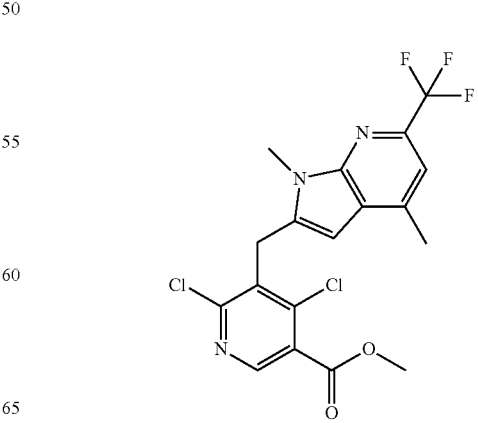

609

Using a procedure similar to Example P, Step 4, methyl 4,6-dichloro-5-((1,4-dimethyl-6-(trifluoromethyl)-1H-pyrrolo[2,3-b]pyridin-2-yl)methyl)nicotinate was prepared from 4,6-dichloro-5-((4-methyl-6-(trifluoromethyl)-1H-pyrrolo[2,3-b]pyridin-2-yl)methyl)nicotinic acid (0.23 g, 0.567 mmol). LC/MS (Method 1) $R_t$=2.01 min.; MS m/z: 432 [M+H]$^+$.

Step 17: 4,6-dichloro-5-((1,4-dimethyl-6-(trifluoromethyl)-1H-pyrrolo[2,3-b]pyridin-2-yl)methyl)nicotinic acid

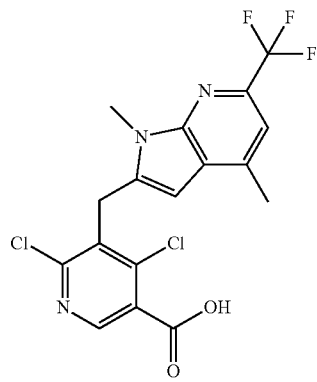 [SMILES: Cc1cc(C(F)(F)F)nc2c1cc(Cc1c(Cl)ncc(C(=O)O)c1Cl)n2C]

Using a procedure similar to Example A, Step 5, 4,6-dichloro-5-((1,4-dimethyl-6-(trifluoromethyl)-1H-pyrrolo[2,3-b]pyridin-2-yl)methyl)nicotinic acid was prepared from methyl 4,6-dichloro-5-((1,4-dimethyl-6-(trifluoromethyl)-1H-pyrrolo[2,3-b]pyridin-2-yl)methyl)nicotinate (0.25 g, 0.578 mmol). LC/MS (Method 1) $R_t$=1.14 min.; MS m/z: 418 [M+H]$^+$.

Step 18: (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone

Using a procedure similar to Example A, Step 6, (4,6-dichloro-5-((1,4-dimethyl-6-(trifluoromethyl)-1H-pyrrolo[2,3-b]pyridin-2-yl)methyl)pyridin-3-yl)(4-hydroxypiperidin-1-yl)methanone was prepared from 4,6-dichloro-5-((1,4-dimethyl-6-(trifluoromethyl)-1H-pyrrolo[2,3-b]pyridin-2-yl)methyl)nicotinic acid (0.116 g, 0.278 mmol) and piperidin-4-ol (0.042 g, 0.42 mmol). LC/MS (Method a) $R_t$=2.28 min.; MS m/z: 501 [M+H]$^+$. $^1$H NMR (400 MHz, DMSO-d6) δ 8.31 (s, 1H), 7.26 (s, 1H), 7.22 (s, 1H), 5.81 (s, 1H), 4.46 (m, 2H), 4.15 (m, 1H), 4.04 (m, 1H), 3.98 (s, 3H), 3.65-3.45 (m, 3H), 3.13 (m, 2H), 2.00 (m, 1H), 1.87 (m, 2H), 1.70 (m, 2H).

Example DU: 1-[2,4-dichloro-3-[[1,4-dimethyl-6-(trifluoromethoxy)-1H-indol-3-yl]methyl]benzoyl]piperidine-4-carboxylic acid

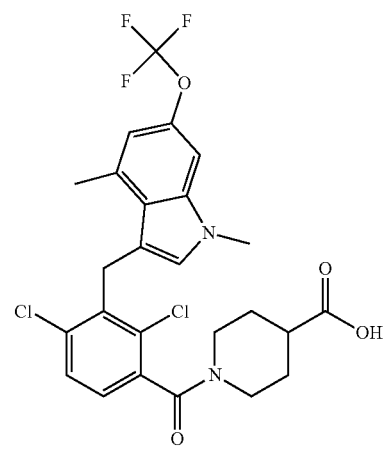 [SMILES: Cc1cc(OC(F)(F)F)cc2c1c(Cc1c(Cl)ccc(C(=O)N3CCC(C(=O)O)CC3)c1Cl)cn2C]

Step 1: tert-butyl 2,4-dichloro-3-[[4-methyl-6-(trifluoromethoxy)-1H-indol-3-yl]methyl]benzoate

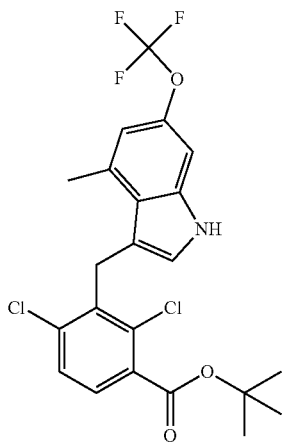 [SMILES: Cc1cc(OC(F)(F)F)cc2[nH]cc(Cc3c(Cl)ccc(C(=O)OC(C)(C)C)c3Cl)c12]

A solution of 4-methyl-6-(trifluoromethoxy)-1H-indole (200 mg, 0.93 mmol) (Preparation 80) and tert-butyl 2,4-dichloro-3-formylbenzoate (281 mg, 1.02 mmol) (Preparation #33, Step B) in DCM (3 mL) was added dropwise, to a cold (ice bath) DCM (1.25 mL) solution of 2,2,2-TFA (0.11 mL, 1.39 mmol) and triethylsilane (0.44 mL, 2.79 mmol) in a 5 mL round-bottom flask under nitrogen, keeping the temperature below 5° C. (yellow then brown coloration). After 20 minutes at 0° C., the reaction mixture was stirred 2 hours at room temperature. The reaction mixture was diluted with DCM, washed with water, then with a saturated NaHCO3 aqueous solution and finally with brine. The organic layer was dried over magnesium sulfate, filtered and concentrated under vacuum. The obtained brown resin was chromatographed over silica gel (15 g column, eluent Cyclohexane/EtOAc 95:5 to 80/20) to give tert-butyl 2,4-dichloro sodium hydride (42.1 mg, 1.054 mmol) was added portionwise -6-(trifluoromethoxy)-1H-indol-3-yl)methyl)benzoate (266 mg, 56%) as a colourless resin. LC/MS (Method j): Rt=2.69 min.; MS m/z: 474 [M+H]+; 1H NMR (DMSO-d6, 300 MHz): δ 10.96 (m, 1H), 7.63 (s, 2H), 7.13 (s, 1H), 6.77 (s, 1H), 6.32 (m, 1H), 4.59 (s, 2H), 2.77 (s, 3H), 1.55 (s, 9H).

Step 2: tert-butyl 2,4-dichloro-3-[[1,4-dimethyl-6-(trifluoromethoxy)-1H-indol-3-yl]methyl]benzoate

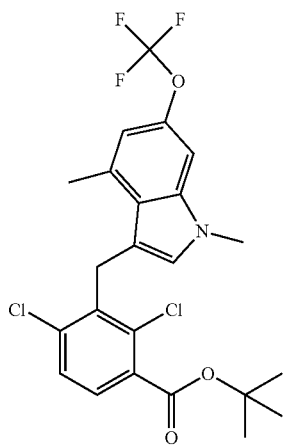 [SMILES: Cc1cc(OC(F)(F)F)cc2c1c(Cc1c(Cl)ccc(C(=O)OC(C)(C)C)c1Cl)cn2C]

Using a procedure similar to Example A, Step 4, tert-butyl 2,4-dichloro-3-[[1,4-dimethyl-6-(trifluoromethoxy)-1H-indol-3-yl]methyl]benzoate (383 mg, 74%) was prepared from tert-butyl dichloro-3-((4-methyl-6-(trifluoromethoxy)-1H-indol-3-yl)methyl)benzoate (476 mg, 1.0 mmol).

LC/MS (Method j): Rt=2.90 min.; MS m/z: 488 [M+H]+; 1H NMR (DMSO-d6, 300 MHz): δ 7.64 (s, 2H), 7.23 (s, 1H), 6.81 (s, 1H), 6.39 (s, 1H), 4.59 (s, 2H), 3.62 (s, 3H), 2.78 (s, 3H), 1.55 (s, 9H).

Step 3: 2,4-dichloro-3-[[1,4-dimethyl-6-(trifluoromethoxy)-1H-indol-3-yl]methyl]benzoic acid

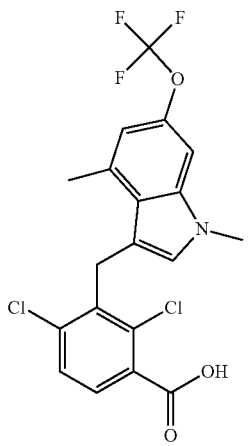 [SMILES: Cc1cc(OC(F)(F)F)cc2c1c(Cc1c(Cl)ccc(C(=O)O)c1Cl)cn2C]

Using a procedure similar to Example DJ, Step 2, 2,4-dichloro-3-((1,4-dimethyl-6-(trifluoromethoxy)-1H-indol-3-yl)methyl)benzoic acid as a brown solid (335 mg, 99%) was prepared from tert-butyl 2,4-dichloro-3-((1,4-dimethyl-6-(trifluoromethoxy)-1H-indol-3-yl)methyl)benzoate (381 mg, 0.78 mmol).

LC/MS (Method j): Rt=2.01 min.; MS m/z: 432 [M+H]+; 1H NMR ((DMSO-d6, 300 MHz): δ 13.58 (broad, 1H), 7.71 (d, J=8.4 Hz, 1H), 7.64 (d, J=8.4 Hz, 1H), 7.23 (s, 1H), 6.81 (s, 1H), 6.37 (s, 1H), 4.60 (s, 2H), 3.61 (s, 3H), 2.78 (s, 3H).

Step 4: methyl 1-[2,4-dichloro-3-[[1,4-dimethyl-6-(trifluoromethoxy)-1H-indol-3-yl]methyl]benzoyl]piperidine-4-carboxylate

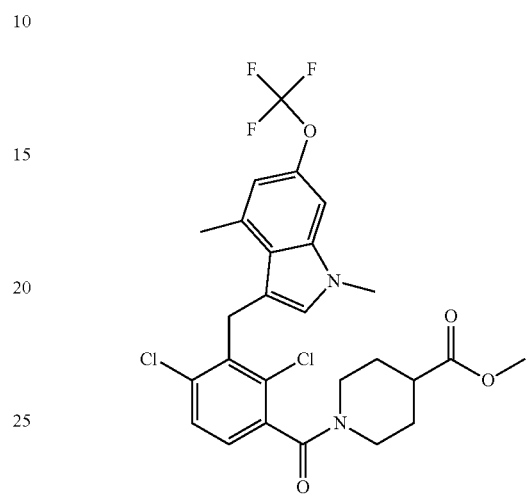

Using a procedure similar to Example A, Step 6, methyl 1-[2,4-dichloro-3-[[1,4-dimethyl-6-(trifluoromethoxy)-1H-indol-3-yl]methyl]benzoyl]piperidine-4-carboxylate (104 mg, 63%) was prepared from 2,4-dichloro-3-[[1,4-dimethyl-6-(trifluoromethoxy)-1H-indol-3-yl]methyl]benzoic acid (125 mg) and methyl piperidine-4-carboxylate hydrochloride (67 mg, 0.38 mmol). LC/MS (Method i): Rt=2.74 min.; MS m/z: 557 [M+H]+; 1H NMR ((DMSO-d6, 300 MHz): δ 7.62 (d, J=8.3 Hz, 1H), 7.41 and 7.34 (d, J=8.3 Hz, 1H), 7.23 (s, 1H), 6.80 (s, 1H), 6.40 and 6.38 (s, 1H), 4.57 (m, 2H), 4.35 (m, 1H), 3.60 (m, 6H), 3.33 (m, 1H), 3.03 (m, 2H), 2.77 (s, 3H), 2.68 (m, 1H), 1.99 (m, 1H), 1.78 (m, 1H), 1.53 (m, 2H).

Step 5: 1-[2,4-dichloro-3-[[1,4-dimethyl-6-(trifluoromethoxy)-1H-indol-3-yl]methyl]benzoyl]piperidine-4-carboxylic acid

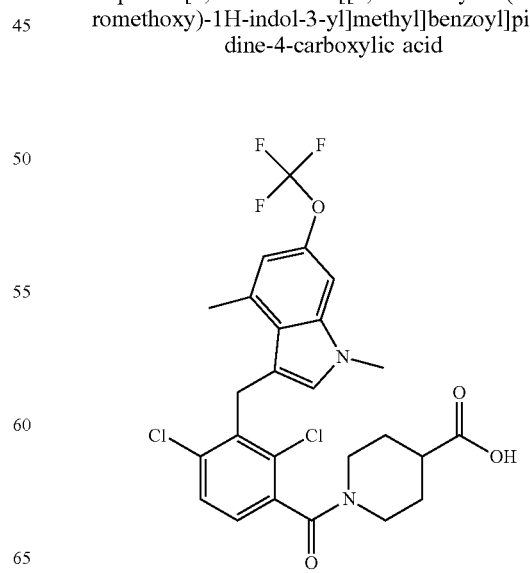

Using a procedure similar to Example A, Step 5, 1-[2,4-dichloro-3-[[1,4-dimethyl-6-(trifluoromethoxy)-1H-indol-3-yl]methyl]benzoyl]piperidine-4-carboxylic acid (85 mg, 83%) was prepared from methyl 1-[2,4-dichloro-3-[[1,4-dimethyl-6-(trifluoromethoxy)-1H-indol-3-yl]methyl]benzoyl]piperidine-4-carboxylate (103 mg, 0.18 mmol). LC/MS (Method g): Rt=1.93 min.;

MS m/z: 543 [M+H]$^+$; $^1$H NMR ((DMSO-d$_6$, 400 MHz): b=7.63 (d, J=8.4 Hz, 1H), 7.40 and 7.34 (d, J=8.4 Hz, 1H), 7.23 (s, 1H), 6.81 (s, 1H), 6.39 and 6.36 (s, 1H), 4.57 (m, 2H), 4.35 (m, 1H), 3.62 and 3.61 (s, 3H), 3.32 (m, 1H), 3.08 (m, 1H), 2.95 (m, 1H), 2.77 (s, 3H), 2.55 (m, 1H), 1.94 (m, 1H), 1.79 (m, 1H), 1.50 (m, 2H).

TABLE DU

The following intermediates were prepared from 2,4-dichloro-3-[[1,4-dimethyl-6-(trifluoromethoxy)-1H-indol-3-yl]methyl]benzoic acid (Example DU, Step 5) using the same procedure with the appropriate amine.

| Example # | Structure | ANumber | Starting amine | R$_t$ min (method) | m/z ESI+ (M + H)$^+$ |
|---|---|---|---|---|---|
| DU-1 | 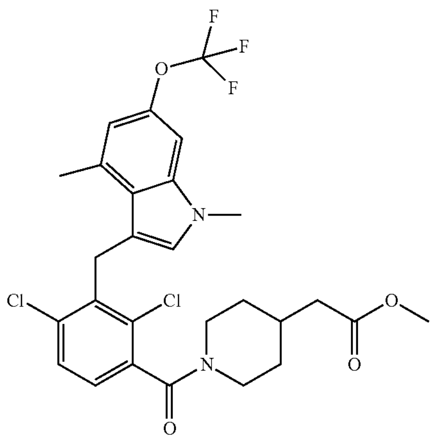 [SMILES: COC(=O)CC1CCN(C(=O)c2ccc(Cl)c(Cc3cn(C)c4cc(OC(F)(F)F)cc(C)c34)c2Cl)CC1] | | | 2.78 (method i) | 571 |
| DU-2 | 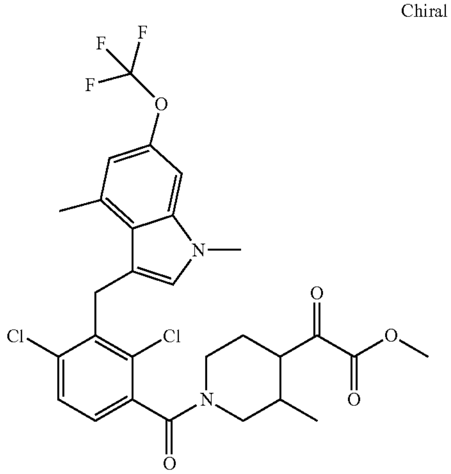 [SMILES: COC(=O)C(=O)C1CCN(C(=O)c2ccc(Cl)c(Cc3cn(C)c4cc(OC(F)(F)F)cc(C)c34)c2Cl)CC1C] | Chiral | Chiral | 2.89 (method i) | 585 |

TABLE DU1

The following Examples were prepared using the same procedure as in Example A Step 5 starting from the appropriate esters (from Table DU).

| Example # | Structure | Ester | R$_t$ min (method) | m/z ESI+ (M + H)+ |
|---|---|---|---|---|
| DU1-1 | 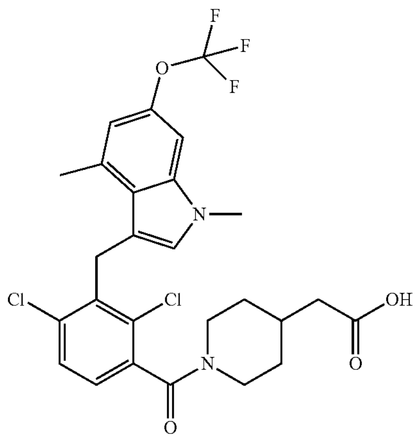 [SMILES: Cc1cc(OC(F)(F)F)cc2c1c(Cc1c(Cl)ccc(C(=O)N3CCC(CC(=O)O)CC3)c1Cl)cn2C] | DU-1 | 1.96 (method g) | 557 |
| DU1-2 | Chiral | DU-2 | 1.93 (method g) | 557 |

Example DV: 2-[1-[4,6-dichloro-5-[[1,4-dimethyl-6-(trifluoromethyl)-1H-indol-3-yl]methyl]pyridine-3-carbonyl]-4-piperidyl]acetic acid Step 1: tert-butyl 4,6-dichloro-5-[[4-methyl-6-(trifluoromethyl)-1H-indol-3-yl]methyl]pyridine-3-carboxylate

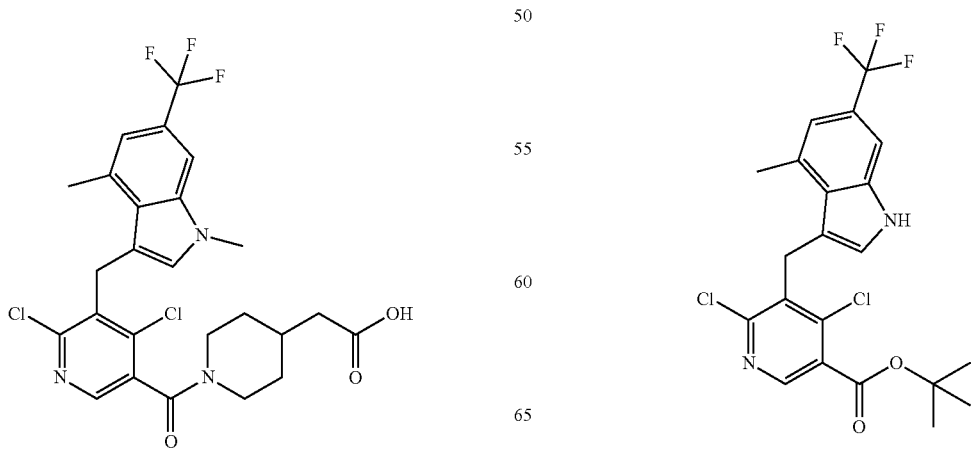

Using a procedure similar to Example DU Step 1, tert-butyl 4,6-dichloro-5-[[4-methyl-6-(trifluoromethyl)-1H-indol-3-yl]methyl]pyridine-3-carboxylate (544 mg, 79%) was obtained from 4-methyl-6-(trifluoromethyl)-1H-indole (250 mg, 1.255 mmol) (Preparation #51, Step C) and tert-butyl 4,6-dichloro-5-formyl-pyridine-3-carboxylate (381 mg, 1.38 mmol) (example DO, Step 12). LC/MS (Method i): $R_t$=2.89 min.; MS m/z: 459 [M+H]$^+$; $^1$H NMR ((DMSO-d$_6$, 300 MHz): δ=11.26 (s, 1H), 8.71 (s, 1H), 7.51 (s, 1H), 7.05 (s, 1H), 6.68 (m, 1H), 4.62 (s, 2H), 2.82 (s, 3H), 1.57 (s, 9H).

Step 2: tert-butyl 4,6-dichloro-5-[[1,4-dimethyl-6-(trifluoromethyl)-1H-indol-3-yl]methyl]pyridine-3-carboxylate

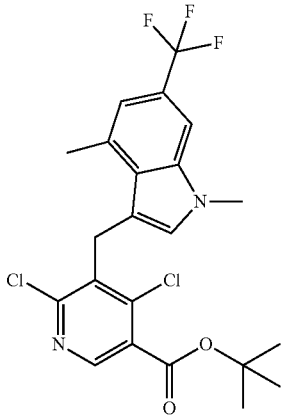 [SMILES: Cc1cc(C(F)(F)F)cc2c1c(Cc1c(Cl)ncc(C(=O)OC(C)(C)C)c1Cl)cn2C]

Using a procedure similar to Example A, Step 4 tert-butyl 4,6-dichloro-5-[[1,4-dimethyl-6-(trifluoromethyl)-1H-indol-3-yl]methyl]pyridine-3-carboxylate (353 mg, 70%) was obtained from tert-butyl 4,6-dichloro-5-[[4-methyl-6-(trifluoromethyl)-1H-indol-3-yl]methyl]pyridine-3-carboxylate (490 mg, 1.07 mmol) and methyl iodide (80 µl, 1.28 mmol). LC/MS (Method j): Rt=2.67 min.; MS m/z: 473 [M+H]$^+$; $^1$H NMR ((DMSO-d$_6$, 300 MHz): δ 8.73 (s, 1H), 7.62 (s, 1H), 7.10 (s, 1H), 6.74 (s, 1H), 4.61 (s, 2H), 3.70 (s, 3H), 2.82 (s, 3H), 1.57 (s, 9H).

Step 3: 4,6-dichloro-5-[[1,4-dimethyl-6-(trifluoromethyl)-1H-indol-3-yl]methyl]pyridine-3-carboxylic acid

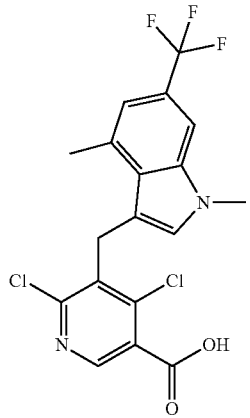 [SMILES: Cc1cc(C(F)(F)F)cc2c1c(Cc1c(Cl)ncc(C(=O)O)c1Cl)cn2C]

Using a procedure similar to Example DJ, Step 2, 4,6-dichloro-5-[[1,4-dimethyl-6-(trifluoromethyl)-1H-indol-3-yl]methyl]pyridine-3-carboxylic acid was obtained (281 mg, 91%) from tert-butyl 4,6-dichloro-5-[[1,4-dimethyl-6-(trifluoromethyl)-1H-indol-3-yl]methyl]pyridine-3-carboxylate (350 mg, 0.739 mmol). LC/MS (Method j): Rt=1.63 min.; MS m/z: 417 [M+H]$^+$; $^1$H NMR ((DMSO-d$_6$, 300 MHz): δ 13.99 (broad, 1H), 8.76 (s, 1H), 7.62 (s, 1H), 7.10 (s, 1H), 6.71 (s, 1H), 4.62 (s, 2H), 3.70 (s, 3H), 2.83 (s, 3H).

Step 4: methyl 2-[1-[4,6-dichloro-5-[[1,4-dimethyl-6-(trifluoromethyl)-1H-indol-3-yl]methyl]pyridine-3-carbonyl]-4-piperidyl]acetate

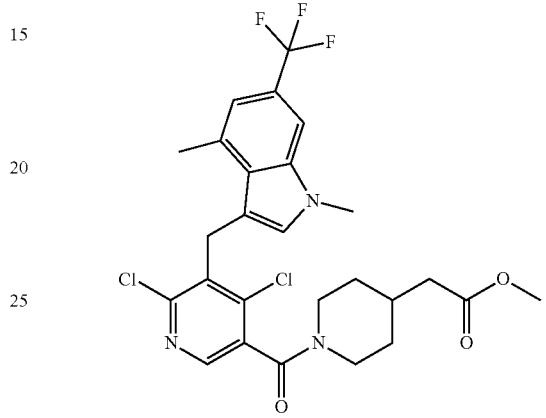

Using a procedure similar to Example A, Step 6, methyl 2-[1-[4,6-dichloro-5-[[1,4-dimethyl-6-(trifluoromethyl)-1H-indol-3-yl]methyl]pyridine-3-carbonyl]-4-piperidyl]acetate (87 mg, 73%) was obtained from 4,6-dichloro-5-[[1,4-dimethyl-6-(trifluoromethyl)-1H-indol-3-yl]methyl]pyridine-3-carboxylic acid (90 mg, 0.216 mmol) and methyl 2-(4-piperidyl)acetate hydrochloride (46 mg, 0.237 mmol). LC/MS (Method j): $R_t$=2.01 min.; MS m/z: 556 [M+H]$^+$; $^1$H NMR ((DMSO-d$_6$, 300 MHz): δ 8.46 and 8.39 (s, 1H), 7.62 (s, 1H), 7.10 (s, 1H), 6.76 and 6.71 (s, 1H), 4.50 (m, 3H), 3.71 (s, 3H), 3.60 and 3.57 (s, 3H), 3.44 (m, 1H), 3.07 (m, 1H), 2.82 (m, 4H), 2.29 (m, 2H), 1.98 (m, 1H), 1.77 (m, 1H), 1.62 (br s, 1H), 1.17 (m, 2H).

Step 5: 2-[1-[4,6-dichloro-5-[[1,4-dimethyl-6-(trifluoromethyl)-1H-indol-3-yl]methyl]pyridine-3-carbonyl]-4-piperidyl]acetic acid

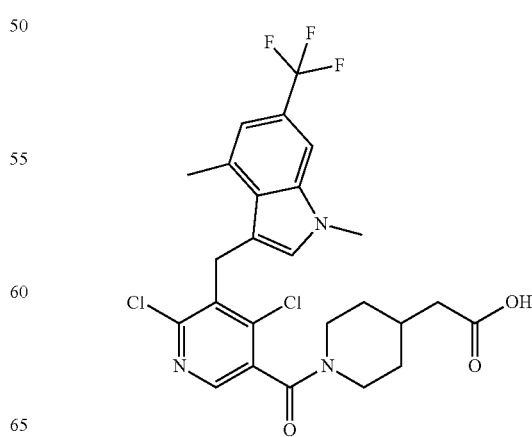

Using a procedure similar to Example A, Step 5, 2-[1-[4,6-dichloro-5-[[1,4-dimethyl-6-(trifluoromethyl)-1H-indol-3-yl]methyl]pyridine-3-carbonyl]-4-piperidyl]acetic acid (71 mg, 83%) was obtained from methyl 2-[1-[4,6-dichloro-5-[[1,4-dimethyl-6-(trifluoromethyl)-1H-indol-3-yl]methyl]pyridine-3-carbonyl]-4-piperidyl]acetate (85 mg, 0.15 mmol). LC/MS (Method g): $R_t$=1.82 min.; MS m/z: 542 [M+H]$^+$ $^1$H NMR ((DMSO-d$_6$, 400 MHz): δ 8.45 and 8.39 (s, 1H), 7.61 (s, 1H), 7.09 (s, 1H), 6.75 and 7.71 (s, 1H), 4.54 (m, 3H), 3.71 (s, 3H), 3.40 (m, 1H), 3.06 (m, 1H), 2.82 (s, 4H), 2.15 (m, 2H), 1.93 (m, 1H), 1.79 (m, 1H), 1.64 (m, 1H), 1.14 (m, 2H).

Example DW: 2-[1-[3,5-dichloro-4-[[1,4-dimethyl-6-(trifluoromethyl)-1H-indol-3-yl]methyl]pyridine-2-carbonyl]-4-piperidyl]acetic acid

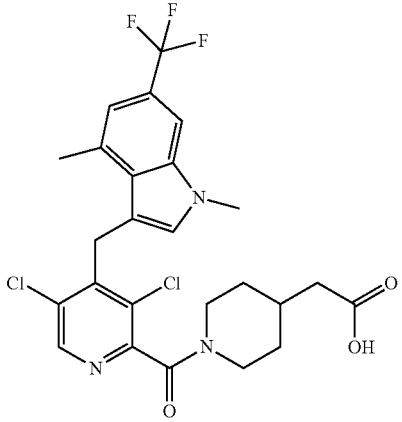 [SMILES: Cc1cc(C(F)(F)F)cc2c1c(Cc1c(Cl)cnc(C(=O)N3CCC(CC(=O)O)CC3)c1Cl)cn2C]

Step 1: ethyl 3,5-dichloro-4-[[4-methyl-6-(trifluoromethyl)-1H-indol-3-yl]methyl]pyridine-2-carboxylate

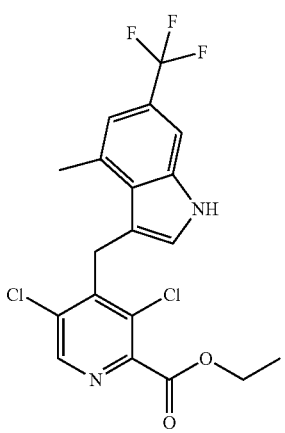 [SMILES: CCOC(=O)c1ncc(Cl)c(Cc2c[nH]c3cc(C(F)(F)F)cc(C)c23)c1Cl]

Using a procedure similar to Example DU Step 1, ethyl 3,5-dichloro-4-[[4-methyl-6-(trifluoromethyl)-1H-indol-3-yl]methyl]pyridine-2-carboxylate (444 mg, 68%) was obtained from 4-methyl-6-(trifluoromethyl)-1H-indole (250 mg, 1.255 mmol) (Preparation #51, Step C) and ethyl 3,5-dichloro-4-formyl-pyridine-2-carboxylate (343 mg, 1.381 mmol) (Preparation #37, Step D). LC/MS (Method i): $R_t$=2.67 min.; MS m/z: 431 [M+H]$^+$; $^1$H NMR ((DMSO-d$_6$, 300 MHz): δ 11.28 (s, 1H), 8.75 (s, 1H), 7.52 (s, 1H), 7.06 (s, 1H), 6.66 (m, 1H), 4.64 (s, 2H), 4.40 (q, J=7.1 Hz, 2H), 2.82 (s, 3H), 1.33 (t, J=7.1 Hz, 3H).

Step 2: ethyl 3,5-dichloro-4-[[1,4-dimethyl-6-(trifluoromethyl)-1H-indol-3-yl]methyl]pyridine-2-carboxylate

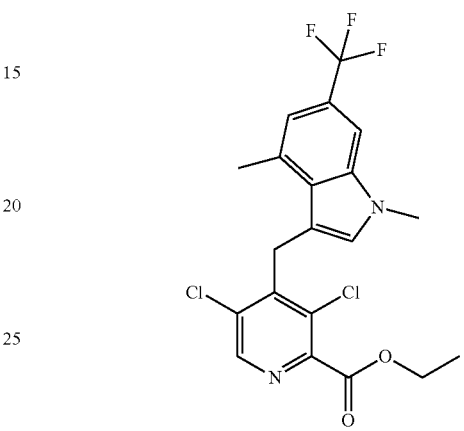

Using a procedure similar to Example A, Step 4, ethyl 3,5-dichloro-4-[[1,4-dimethyl-6-(trifluoromethyl)-1H-indol-3-yl]methyl]pyridine-2-carboxylate (190 mg, 47%) was obtained from ethyl 3,5-dichloro-4-[[4-methyl-6-(trifluoromethyl)-1H-indol-3-yl]methyl]pyridine-2-carboxylate (390 mg, 0.90 mmol) and methyl iodide (79 μL, 1.27 mmol). LC/MS (Method j): $R_t$=2.32 min.; MS m/z: 445 [M+H]$^+$; $^1$H NMR ((DMSO-d$_6$, 300 MHz): δ 8.76 (s, 1H), 7.62 (s, 1H), 7.10 (s, 1H), 6.72 (s, 1H), 4.63 (s, 2H), 4.40 (q, J=7.1 Hz, 2H), 3.70 (s, 3H), 2.82 (s, 3H), 1.33 (t, J=7.1 Hz, 3H).

Step 3: 3,5-dichloro-4-[[1,4-dimethyl-6-(trifluoromethyl)-1H-indol-3-yl]methyl]pyridine-2-carboxylic acid

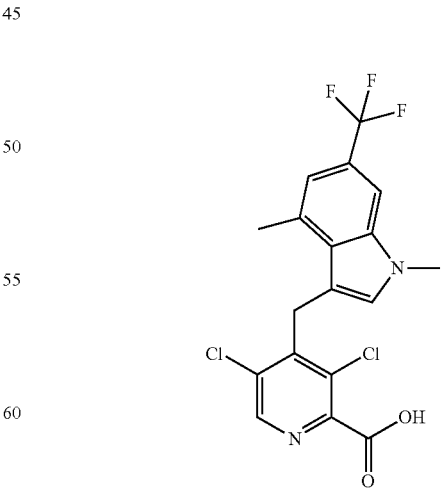

Using a procedure similar to Example A, Step 5, 3,5-dichloro-4-[[1,4-dimethyl-6-(trifluoromethyl)-1H-indol-3-yl]methyl]pyridine-2-carboxylic acid (195 mg, 100% yield, orange solid) was prepared from ethyl 3,5-dichloro-4-[[1,4-dimethyl-6-(trifluoromethyl)-1H-indol-3-yl]methyl]pyridine-2-carboxylate (190 mg, 0.427 mmol). LC/MS (Method j): Rt=1.62 min.; MS m/z: 417 [M+H]+; 1H NMR ((DMSO-d6, 300 MHz): δ 8.60 (s, 1H), 7.62 (s, 1H), 7.10 (s, 1H), 6.64 (s, 1H), 4.59 (s, 2H), 3.70 (s, 3H), 2.82 (s, 3H).

Step 4: methyl 2-[1-[3,5-dichloro-4-[[1,4-dimethyl-6-(trifluoromethyl)-1H-indol-3-yl]methyl]pyridine-2-carbonyl]-4-piperidyl]acetate

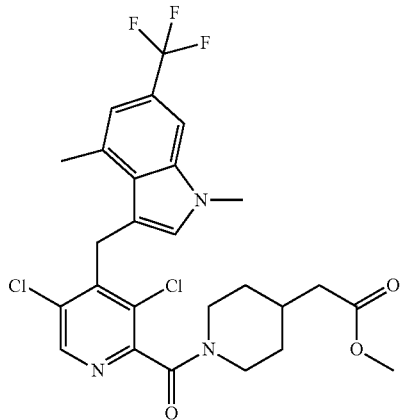 [SMILES: COC(=O)CC1CCN(C(=O)c2ncc(Cl)c(Cc3cn(C)c4cc(C(F)(F)F)cc(C)c34)c2Cl)CC1]

Using a procedure similar to Example A, Step 6, methyl 2-[1-[3,5-dichloro-4-[[1,4-dimethyl-6-(trifluoromethyl)-1H-indol-3-yl]methyl]pyridine-2-carbonyl]-4-piperidyl]acetate (72 mg, 67%) was obtained from 3,5-dichloro-4-[[1,4-dimethyl-6-(trifluoromethyl)-1H-indol-3-yl]methyl]pyridine-2-carboxylic acid (81 mg, 0.194 mmol) and methyl 2-(4-piperidyl)acetate hydrochloride (53 mg, 0.272 mmol). LC/MS (Method j): R$_t$=2.05 min.; MS m/z: 556 [M+H]+; 1H NMR ((DMSO-d6, 300 MHz): δ=8.72 (s, 1H), 7.63 (s, 1H), 7.10 (s, 1H), 6.69 (s, 1H), 4.60 (s, 2H), 4.46 (m, 1H), 3.70 (s, 3H), 3.58 (s, 3H), 3.28 (m, 1H), 3.05 (m, 1H), 2.81 (m, 4H), 2.29 (m, 2H), 1.99 (m, 1H), 1.78 (m, 1H), 1.61 (m, 1H), 1.16 (m, 2H).

Step 5: 2-[1-[3,5-dichloro-4-[[1,4-dimethyl-6-(trifluoromethyl)-1H-indol-3-yl]methyl]pyridine-2-carbonyl]-4-piperidyl]acetic acid

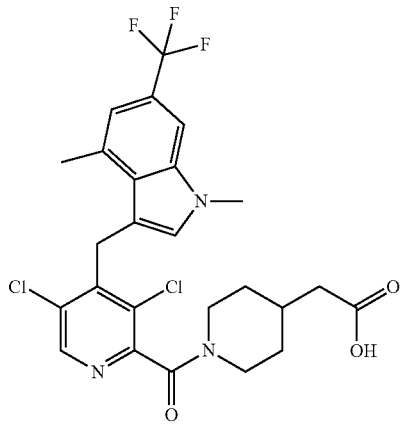 [SMILES: Cc1cc(C(F)(F)F)cc2c1c(Cc1c(Cl)cnc(C(=O)N3CCC(CC(=O)O)CC3)c1Cl)cn2C]

Using a procedure similar to Example A, Step 5, 2-[1-[3,5-dichloro-4-[[1,4-dimethyl-6-(trifluoromethyl)-1H-indol-3-yl]methyl]pyridine-2-carbonyl]-4-piperidyl]acetic acid (62 mg, 89%) was obtained from methyl 2-[1-[3,5-dichloro-4-[[1,4-dimethyl-6-(trifluoromethyl)-1H-indol-3-yl]methyl]pyridine-2-carbonyl]-4-piperidyl]acetate (70 mg, 0.126 mmol). LC/MS (Method g): R$_t$=1.83 min.; MS m/z: 542 [M+H]+ 1H NMR ((DMSO-d6, 400 MHz): δ 8.72 (s, 1H), 7.62 (s, 1H), 7.10 (s, 1H), 6.69 (s, 1H), 4.60 (s, 2H), 4.46 (m, 1H), 3.70 (s, 3H), 3.28 (m, 1H), 3.04 (m, 1H), 2.82 (s, 4H), 2.16 (m, 2H), 1.95 (m, 1H), 1.80 (m, 1H), 1.62 (m, 1H), 1.14 (m, 2H).

Example DX: 2-[1-[3,5-dichloro-4-[[1,4-dimethyl-6-(trifluoromethoxy)-1H-indol-3-yl]methyl]pyridine-2-carbonyl]-4-piperidyl]acetic acid

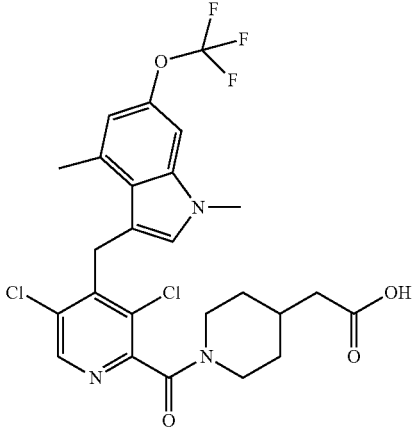 [SMILES: Cc1cc(OC(F)(F)F)cc2c1c(Cc1c(Cl)cnc(C(=O)N3CCC(CC(=O)O)CC3)c1Cl)cn2C]

Step 1: ethyl 3,5-dichloro-4-[[4-methyl-6-(trifluoromethoxy)-1H-indol-3-yl]methyl]pyridine-2-carboxylate

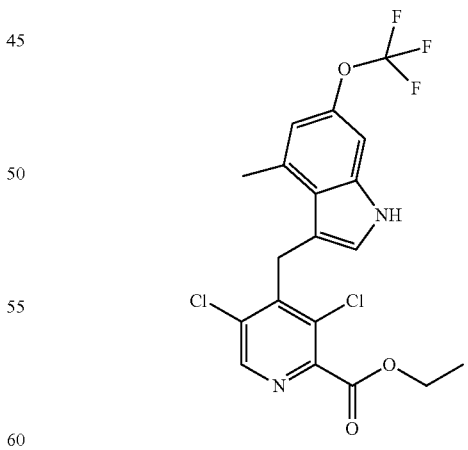

Using a procedure similar to Example DU, Step 1, ethyl 3,5-dichloro-4-[[4-methyl-6-(trifluoromethoxy)-1H-indol-3-yl]methyl]pyridine-2-carboxylate (185 mg, 59%) was obtained from 4-methyl-6-(trifluoromethoxy)-1H-indole (150 mg, 0.697 mmol, (Preparation 80) and ethyl 3,5-dichloro-4-formyl-pyridine-2-carboxylate (190 mg, 0.767 mmol) (Preparation #37, Step D). LC/MS (Method i): $R_t$=2.68 min.; MS m/z: 447 [M+H]$^+$; $^1$H NMR ((DMSO-d$_6$, 300 MHz): δ 11.05 (s, 1H), 8.75 (s, 1H), 7.14 (s, 1H), 6.78 (s, 1H), 6.49 (s, 1H), 4.60 (s, 2H), 4.40 (q, J=7.1 Hz, 2H), 2.77 (s, 3H), 1.33 (t, J=7.1 Hz, 3H).

Step 2: ethyl 3,5-dichloro-4-[[1,4-dimethyl-6-(trifluoromethoxy)-1H-indol-3-yl]methyl]pyridine-2-carboxylate

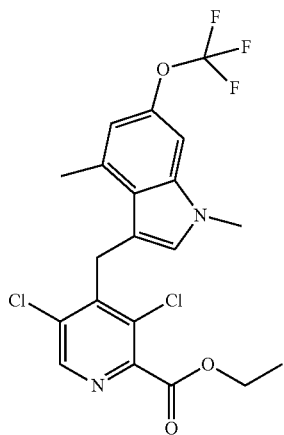 [SMILES: CCOC(=O)c1ncc(Cl)c(Cc2cn(C)c3cc(OC(F)(F)F)cc(C)c23)c1Cl]

Using a procedure similar to Example A, Step 4, ethyl 3,5-dichloro-4-[[1,4-dimethyl-6-(trifluoromethoxy)-1H-indol-3-yl]methyl]pyridine-2-carboxylate (210 mg, 79%) was obtained from ethyl 3,5-dichloro-4-[[4-methyl-6-(trifluoromethoxy)-1H-indol-3-yl]methyl]pyridine-2-carboxylate (185 mg, 0.41 mmol) and methyl iodide (26 μL, 0.41 mmol). LC/MS (Method i): $R_t$=2.82 min.; MS m/z: 461 [M+H]$^+$; $^1$H NMR ((DMSO-d$_6$, 300 MHz): δ=8.76 (s, 1H), 7.25 (s, 1H), 6.82 (s, 1H), 6.56 (s, 1H), 4.60 (s, 2H), 4.40 (q, J=6.9 Hz, 2H), 3.62 (s, 3H), 2.73 (s, 3H), 1.33 (t, J=7.1 Hz, 3H).

Step 3: 3,5-dichloro-4-[[1,4-dimethyl-6-(trifluoromethoxy)-1H-indol-3-yl]methyl]pyridine-2-carboxylic acid

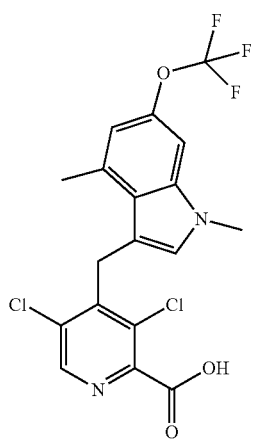 [SMILES: Cc1cc(OC(F)(F)F)cc2c1c(Cc1c(Cl)cnc(C(=O)O)c1Cl)cn2C]

Using a procedure similar to Example A, Step 5, 3,5-dichloro-4-[[1,4-dimethyl-6-(trifluoromethoxy)-1H-indol-3-yl]methyl]pyridine-2-carboxylic acid (180 mg, 84%) was prepared from ethyl 3,5-dichloro-4-[[1,4-dimethyl-6-(trifluoromethoxy)-1H-indol-3-yl]methyl]pyridine-2-carboxylate (210 mg, 0.45 mmol). LC/MS (Method i): $R_t$=2.26 min.; MS m/z: 433 [M+H]$^+$; $^1$H NMR ((DMSO-d$_6$, 300 MHz): δ 8.70 (s, 1H), 7.25 (s, 1H), 6.82 (m, 1H), 6.52 (s, 1H), 4.58 (s, 2H), 3.62 (s, 3H), 2.77 (s, 3H).

Step 4: methyl 2-[1-[3,5-dichloro-4-[[1,4-dimethyl-6-(trifluoromethoxy)-1H-indol-3-yl]methyl]pyridine-2-carbonyl]-4-piperidyl]acetate

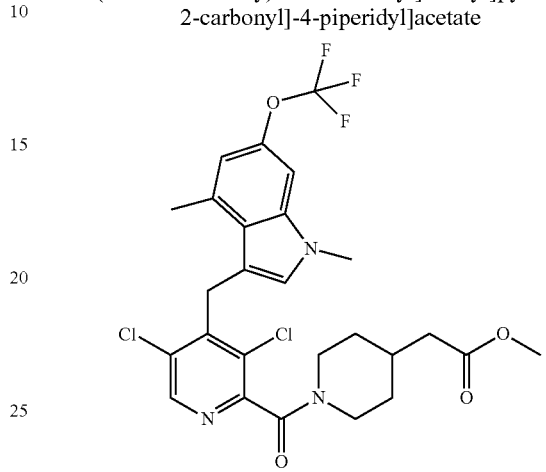

Using a procedure similar to Example A, Step 6, methyl 2-[1-[3,5-dichloro-4-[[1,4-dimethyl-6-(trifluoromethoxy)-1H-indol-3-yl]methyl]pyridine-2-carbonyl]-4-piperidyl]acetate (110 mg, 41%) was obtained from 3,5-dichloro-4-[[1,4-dimethyl-6-(trifluoromethoxy)-1H-indol-3-yl]methyl]pyridine-2-carboxylic acid (180 mg, 0.416 mmol) and methyl 2-(4-piperidyl)acetate hydrochloride (89 mg, 0.457 mmol).

LC/MS (Method i): $R_t$=2.65 min.; MS m/z: 572 [M+H]$^+$; $^1$H NMR ((DMSO-d$_6$, 300 MHz): δ=8.72 (s, 1H), 7.25 (s, 1H), 6.82 (s, 1H), 6.53 (s, 1H), 4.57 (s, 2H), 4.46 (m, 1H), 3.62 (s, 3H), 3.58 (s, 3H), 3.27 (m, 1H), 3.05 (m, 1H), 2.80 (m, 4H), 2.29 (m, 2H), 1.99 (m, 1H), 1.76 (m, 1H), 1.60 (m, 1H), 1.15 (m, 2H).

Step 5: 2-[1-[3,5-dichloro-4-[[1,4-dimethyl-6-(trifluoromethoxy)-1H-indol-3-yl]methyl]pyridine-2-carbonyl]-4-piperidyl]acetic acid

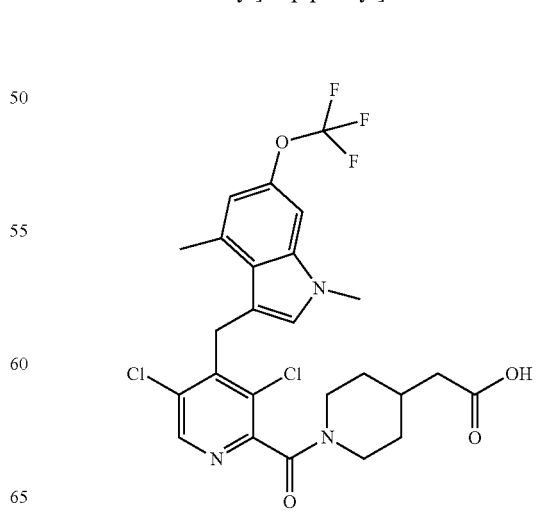

Using a procedure similar to Example A, Step 5, 2-[1-[3,5-dichloro-4-[[1,4-dimethyl-6-(trifluoromethoxy)-1H-indol-3-yl]methyl]pyridine-2-carbonyl]-4-piperidyl]acetic acid 44 mg, 80%) was obtained from methyl 2-[1-[3,5-dichloro-4-[[1,4-dimethyl-6-(trifluoromethoxy)-1H-indol-3-yl]methyl]pyridine-2-carbonyl]-4-piperidyl]acetate (55 mg, 0.096 mmol). LC/MS (Method g): $R_t$=1.86 min.; MS m/z: 558 [M+H]$^+$; $^1$H NMR ((DMSO-$d_6$, 400 MHz): δ 12.11 (s, 1H), 8.72 (s, 1H), 7.25 (s, 1H), 6.82 (s, 1H), 6.53 (s, 1H), 4.57 (s, 2H), 4.46 (m, 1H), 3.62 (s, 3H), 3.27 (m, 1H), 3.05 (m, 1H), 2.84 (m, 1H), 2.77 (m, 3H), 2.18 (m, 2H), 1.96 (m, 1H), 1.80 (m 1H), 1.63 (m, 1H), 1.15 (m, 2H).

Example DY: 2-[1-[4,6-dichloro-5-[[1,4-dimethyl-6-(trifluoromethoxy)-1H-indol-3-yl]methyl]pyridine-3-carbonyl]-4-piperidyl]acetic acid

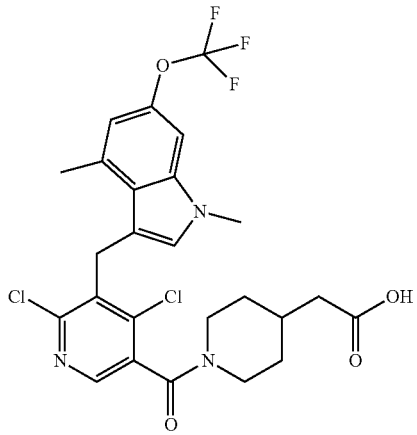 [SMILES: Cc1cc(OC(F)(F)F)cc2c1c(Cc1c(Cl)ncc(C(=O)N3CCC(CC(=O)O)CC3)c1Cl)cn2C]

Step 1: tert-butyl 4,6-dichloro-5-[[4-methyl-6-(trifluoromethoxy)-1H-indol-3-yl]methyl]pyridine-3-carboxylate

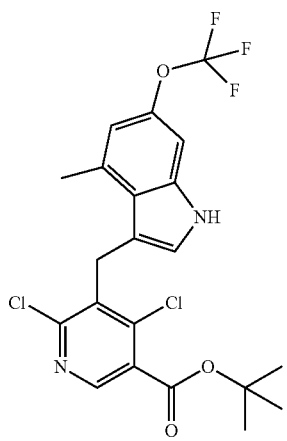 [SMILES: Cc1cc(OC(F)(F)F)cc2[nH]cc(Cc3c(Cl)ncc(C(=O)OC(C)(C)C)c3Cl)c12]

Using a procedure similar to Example DU Step 1, tert-butyl 4,6-dichloro-5-[[4-methyl-6-(trifluoromethoxy)-1H-indol-3-yl]methyl]pyridine-3-carboxylate (100 mg, 45%) was obtained from 4-methyl-6-(trifluoromethoxy)-1H-indole (100 mg, 0.465 mmol) (Preparation 80) and tert-butyl 4,6-dichloro-5-formyl-pyridine-3-carboxylate (141 mg, 0.511 mmol) (Example DO, Step 12). LC/MS (Method i): $R_t$=2.89 min.; MS m/z: 475 [M+H]$^+$; $^1$H NMR ((DMSO-$d_6$, 300 MHz): δ 11.03 (s, 1H), 8.70 (s, 1H), 7.13 (s, 1H), 6.77 (m, 1H), 6.80 (s, 1H), 4.58 (s, 2H), 2.77 (s, 3H), 1.57 (s, 9H).

Step 2: tert-butyl 4,6-dichloro-5-[[1,4-dimethyl-6-(trifluoromethoxy)-1H-indol-3-yl]methyl]pyridine-3-carboxylate

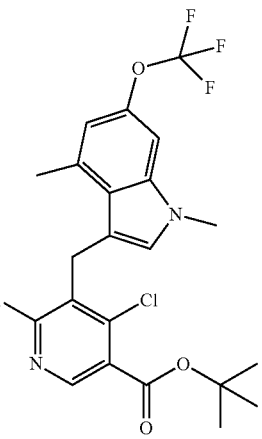

Using a procedure similar to Example A, Step 4, tert-butyl 4,6-dichloro-5-[[1,4-dimethyl-6-(trifluoromethoxy)-1H-indol-3-yl]methyl]pyridine-3-carboxylate (145 mg, 92% yield) was obtained from tert-butyl 4,6-dichloro-5-[[4-methyl-6-(trifluoromethoxy)-1H-indol-3-yl]methyl]pyridine-3-carboxylate (135 mg, 0.28 mmol) and methyl iodide (18 μL, 0.284 mmol). LC/MS (Method j): $R_t$=2.68 min.; MS m/z: 489 [M+H]$^+$; $^1$H NMR ((DMSO-$d_6$, 300 MHz): δ=8.72 (s, 1H), 7.24 (s, 1H), 6.81 (s, 1H), 6.57 (s, 1H), 4.58 (s, 2H), 3.62 (s, 3H), 2.77 (s, 3H), 1.57 (s, 9H).

Step 3: 4,6-dichloro-5-[[1,4-dimethyl-6-(trifluoromethoxy)-1H-indol-3-yl]methyl]pyridine-3-carboxylic acid

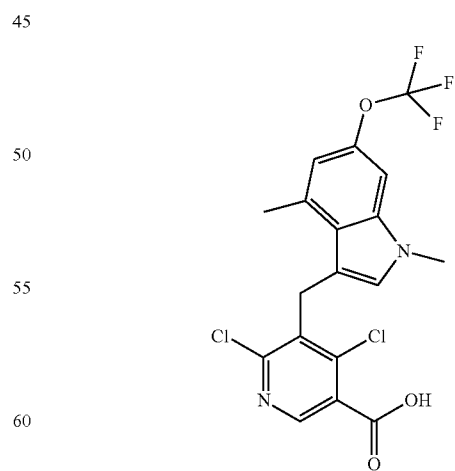

Using a procedure similar to Example DJ, Step 2, 4,6-dichloro-5-[[1,4-dimethyl-6-(trifluoromethoxy)-1H-indol-3-yl]methyl]pyridine-3-carboxylic acid (135 mg, 74% yield) was obtained tert-butyl 4,6-dichloro-5-[[4-methyl-6-(trifluoromethoxy)-1H-indol-3-yl]methyl]pyridine-3-carboxylate (140 mg, 0.286 mmol). LC/MS (Method i): R$_t$=2.32 min.; MS m/z: 433 [M+H]$^+$ Step 4: methyl 2-[1-[4,6-dichloro-5-[[1,4-dimethyl-6-(trifluoromethoxy)-1H-indol-3-yl]methyl]pyridine-3-carbonyl]-4-piperidyl]acetate

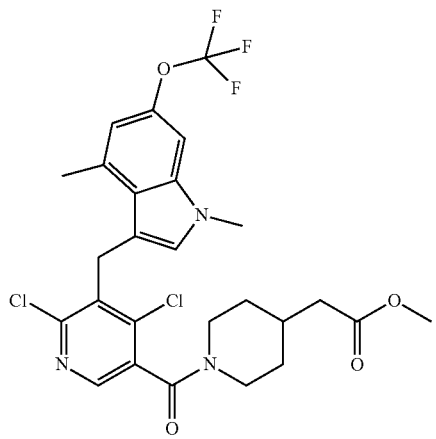 [SMILES: COC(=O)CC1CCN(C(=O)c2cnc(Cl)c(Cc3cn(C)c4cc(OC(F)(F)F)cc(C)c34)c2Cl)CC1]

Using a procedure similar to Example A Step 6, 2-[1-[4,6-dichloro-5-[[1,4-dimethyl-6-(trifluoromethoxy)-1H-indol-3-yl]methyl]pyridine-3-carbonyl]-4-piperidyl]acetate (60 mg, 32% yield) was obtained from 4,6-dichloro-5-[[1,4-dimethyl-6-(trifluoromethoxy)-1H-indol-3-yl]methyl]pyridine-3-carboxylic acid (135 mg, 0.312 mmol) and methyl 2-(4-piperidyl)acetate hydrochloride (66.4 mg, 0.343 mmol). LC/MS (Method i): R$_t$=2.63 min.; MS m/z: 572 [M+H]$^+$; $^1$H NMR ((DMSO-d$_6$, 300 MHz): δ=8.45 and 8.38 (s, 1H), 7.24 (s, 1H), 6.81 (s, 1H), 6.59 and 6.54 (s, 1H), 4.54 (m, 3H), 3.62 (s, 3H), 3.60 and 3.57 (s, 3H), 3.41 (m, 1H), 3.07 (m, 1H), 2.81 (m, 4H), 2.29 (m, 2H), 1.99 (m, 1H), 1.78 (m, 1H), 1.61 (m, 1H), 1.17 (m, 2H).

Step 5: 2-[1-[4,6-dichloro-5-[[1,4-dimethyl-6-(trifluoromethoxy)-1H-indol-3-yl]methyl]pyridine-3-carbonyl]-4-piperidyl]acetic acid

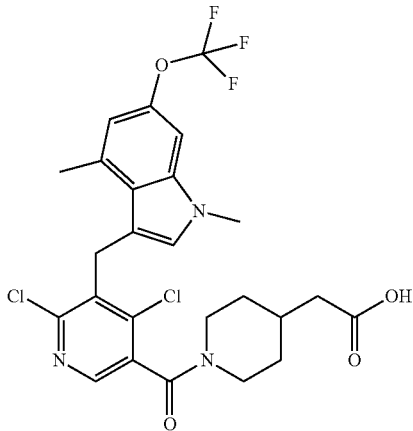 [SMILES: Cc1cc(OC(F)(F)F)cc2c1c(Cc1c(Cl)ncc(C(=O)N3CCC(CC(=O)O)CC3)c1Cl)cn2C]

Using a procedure similar to Example A, Step 5, 2-[1-[4,6-dichloro-5-[[1,4-dimethyl-6-(trifluoromethoxy)-1H-indol-3-yl]methyl]pyridine-3-carbonyl]-4-piperidyl]acetic acid (43 mg, 78%) was obtained from methyl 2-[1-[4,6-dichloro-5-[[1,4-dimethyl-6-(trifluoromethoxy)-1H-indol-3-yl]methyl]pyridine-3-carbonyl]-4-piperidyl]acetate (55 mg, 0.09 mmol). LC/MS (Method g): R$_t$=1.85 min.; MS m/z: 558 [M+H]$^+$; $^1$H NMR ((DMSO-d$_6$, 400 MHz): δ=12.11 (broad, 1H), 8.45 and 8.38 (s, 1H), 7.24 (s, 1H), 6.81 (s, 1H), 6.59 and 6.54 (s, 1H), 4.55 (m, 3H), 3.63 (s, 3H), 3.38 (m, 1H), 3.07 (m, 1H), 2.79 (m, 4H), 2.18 (m, 2H), 1.96 (m, 1H), 1.79 (m, 1H), 1.64 (m, 1H), 1.16 (m, 2H).

Example DZ: 2-(1-(2,4-dichloro-3-((4-methyl-6-(trifluoromethyl)benzofuran-3-yl)methyl)benzoyl)piperidin-4-yl)acetic acid

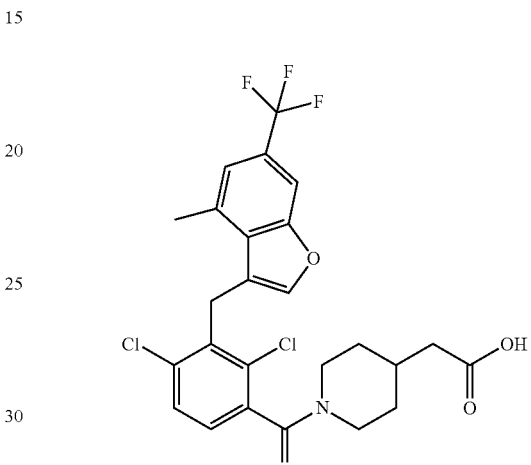

Step 1: tert-butyl 2,4-dichloro-3-(3-(2-iodo-3-methyl-5-(trifluoromethyl)phenoxy)prop-1-en-1-yl)benzoate

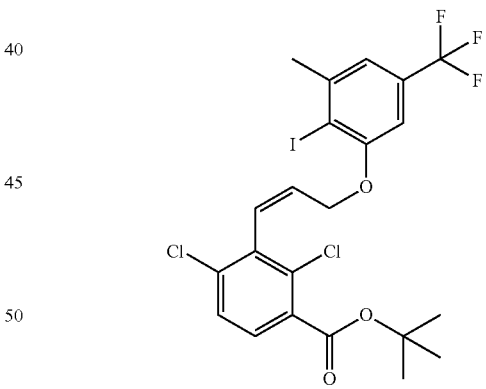

To a solution of tert-butyl 2,4-dichloro-3-(3-((methylsulfonyl)oxy)prop-1-en-1-yl)benzoate (2.95 g, 7.74 mmol) (Preparation 59) in ACN (78 mL) was added potassium carbonate (2.139 g, 15.47 mmol), potassium iodide (1.2 g, 7.74 mmol), and 2-iodo-3-methyl-5-(trifluoromethyl)phenol (2.3 g, 7.74 mmol) (Preparation 85). The reaction mixture was stirred at 50° C. for 45 minutes. The reaction mixture was diluted with H$_2$O and extracted twice with EtOAc. The obtained organic layer was dried over magnesium sulfate, filtered and concentrated under reduced pressure. The residue was purified to give 3,7-dimethyl-5-(trifluoromethoxy)-1H-indole tert-butyl 2,4-dichloro-3-(3-(2-iodo-3-methyl-5-(trifluoromethyl)phenoxy)prop-1-en-1-yl)benzoate (3.6 g, 80%) as a pale yellow solid. LC/MS (Method i): R$_t$=3.07 min ¹H NMR (DMSO-d₆, 300 MHz): δ 7.59 (d, J=8.6 Hz, 1H), 7.54 (d, J=8.6 Hz, 1H), 7.34 (s, 1H), 7.17 (s, 1H), 6.81 (d, J=16.3 Hz, 1H), 6.33 (dt, J=16.3, 4.8 Hz, 1H), 5.03 (m, 2H), 2.6 (s, 3H), 1.54 (s, 9H).

Step 2: tert-butyl 2,4-dichloro-3-((4-methyl-6-(trifluoromethyl)benzofuran-3(2H)-ylidene)methyl)benzoate

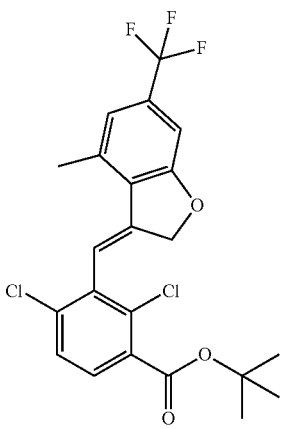 [SMILES: Cc1cc(C(F)(F)F)cc2c1/C(=C/c1c(Cl)ccc(C(=O)OC(C)(C)C)c1Cl)CO2]

To a solution of tert-butyl 2,4-dichloro-3-(3-(2-iodo-3-methyl-5-(trifluoromethyl)phenoxy)prop-1-en-1-yl)benzoate (500 mg, 0.85 mmol) DMF (2.5 mL) was added tetrabutylammonium chloride (260 mg, 0.937 mmol), sodium carbonate (226 mg, 2.129 mmol), sodium formate (57.9 mg, 0.852 mmol) and bis(acetonitrile)dichloropalladium(II) (17.67 mg, 0.068 mmol). The reaction mixture was degassed with Argon and stirred at 80° C. for 18 hours. The reaction mixture was filtered and the filtrate was concentrated under reduced pressure. The residue was purified by column chromatography on silica gel (eluting with 0-10% EtOAc in cyclohexane) to give tert-butyl 2,4-dichloro-3-((4-methyl-6-(trifluoromethyl)benzofuran-3(2H)-ylidene)methyl)benzoate (240 mg, 45%) as a yellow oil. It was used crude in the next step. LC/MS (Method j): R$_t$=2.88 min ¹H NMR (DMSO-d₆, 300 MHz): δ 7.67 (m, 2H), 7.21 (s, 1H), 7.15 (s, 1H), 6.92 (m, 1H), 5.01 (m, 2H), 2.62 (s, 3H), 1.56 (s, 9H).

Step 3: 2,4-dichloro-3-((4-methyl-6-(trifluoromethyl)benzofuran-3-yl)methyl)benzoic acid

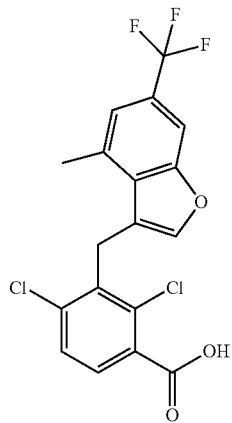 [SMILES: Cc1cc(C(F)(F)F)cc2occ(Cc3c(Cl)ccc(C(=O)O)c3Cl)c12]

Using a procedure similar to Example DJ, Step 2, 2,4-dichloro-3-((4-methyl-6-(trifluoromethyl)benzofuran-3-yl)methyl)benzoic acid (100 mg, 61%) was prepared from crude tert-butyl 2,4-dichloro-3-((4-methyl-6-(trifluoromethyl)benzofuran-3-yl)methyl)benzoate (115 mg, 0.25 mmol) It was used crude in the next step. LC/MS (Method i): R$_t$=2.55 min.; MS m/z: 401 [M−H]⁻; ¹H NMR (DMSO-d₆, 500 MHz): δ 13.59 (broad, 1H), 7.83 (s, 1H), 7.75 (d, J=8.4 Hz, 1H), 7.66 (d, J=8.4 Hz, 1H), 7.42 (s, 1H), 7.26 (s, 1H), 4.55 (s, 2H), 2.83 (s, 3H).

Step 4: methyl 2-(1-(2,4-dichloro-3-((4-methyl-6-(trifluoromethyl)benzofuran-3-yl)methyl)benzoyl)piperidin-4-yl)acetate

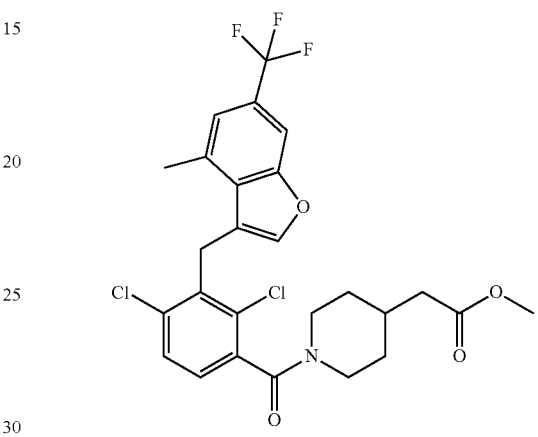

Using a procedure similar to Example A1, methyl 2-(1-(2,4-dichloro-3-((4-methyl-6-(trifluoromethyl)benzofuran-3-yl)methyl)benzoyl)piperidin-4-yl)acetate (54 mg, 50%) was prepared from crude 2,4-dichloro-3-((4-methyl-6-(trifluoromethyl)benzofuran-3-yl)methyl)benzoic acid (66 mg, 0.16 mmol) and methyl (4-piperidyl)acetate hydrochloride (48 mg, 0.25 mmol). LC/MS (Method i): R$_t$=2.73 min.; MS m/z: 542 [M+H]⁺; ¹H NMR (DMSO-d₆, 300 MHz): δ 7.82 (s, 1H), 7.65 and 7.63 (d, J=8.3 Hz, 1H), 7.35 (m, 3H), 4.45 (m, 3H), 3.59 and 3.57 (s, 3H), 3.36 (m, 1H), 3.02 (m, 1H), 2.82 (s, 3H), 2.75 (m, 1H), 2.27 (m, 2H), 1.90 (m, 1H), 1.73 (m, 1H), 1.58 (m, 1H), 1.14 (m, 2H).

Step 5: 2-(1-(2,4-dichloro-3-((4-methyl-6-(trifluoromethyl)benzofuran-3-yl)methyl)benzoyl)piperidin-4-yl)acetic acid

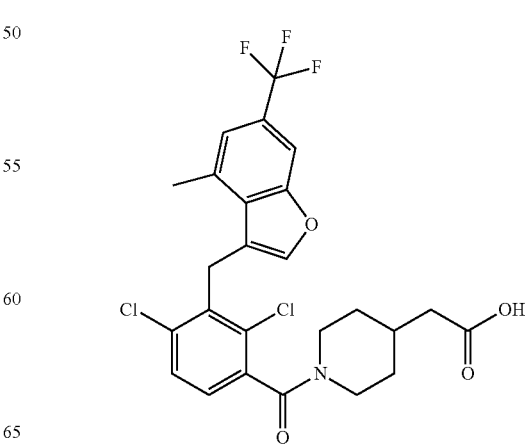

Using a procedure similar to Example A, Step 5, 2-(1-(2,4-dichloro-3-((4-methyl-6-(trifluoromethyl)benzofuran-3-yl)methyl)benzoyl)piperidin-4-yl)acetic acid (25 mg, 50%) was prepared from methyl 2-(1-(2,4-dichloro-3-((4-methyl-6-(trifluoromethyl)benzofuran-3-yl)methyl)benzoyl)piperidin-4-yl)acetate (52 mg, 0.09 mmol). LC/MS (Method g): $R_f$=1.93 min.; MS m/z: 528 [M+H]$^+$; $^1$H NMR (DMSO-d$_6$, 500 MHz): δ 12.11 (m, 1H), 7.82 (s, 1H), 7.64 and 7.63 (d, J=8.3 Hz, 1H), 7.35 (m, 3H), 4.51 (m, 3H), 3.28 (m, 1H), 3.02 (m, 1H), 2.79 (m, 4H), 2.17 (m, 2H), 1.92 (m, 1H), 1.77 (m, 1H), 1.62 (m, 1H), 1.13 (m, 2H).

Example EA: 2-(1-(2,4-dichloro-3-(3,7-dimethyl-5-(trifluoromethyl)-1H-indazole-1-carbonyl)benzoyl)piperidin-4-yl)acetic acid

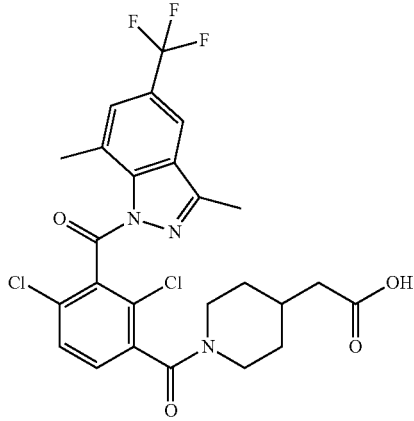 [SMILES: Cc1nn(C(=O)c2c(Cl)ccc(C(=O)N3CCC(CC(=O)O)CC3)c2Cl)c2c(C)cc(C(F)(F)F)cc12]

Step 1: tert-butyl 2,4-dichloro-3-(3,7-dimethyl-5-(trifluoromethyl)-1H-indazole-1-carbonyl)benzoate and tert-butyl 2,4-dichloro-3-(3,7-dimethyl-5-(trifluoromethyl)-2H-indazole-2-carbonyl)benzoate

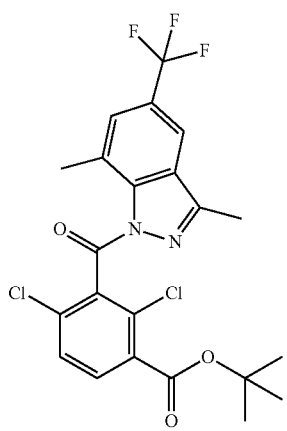

-continued

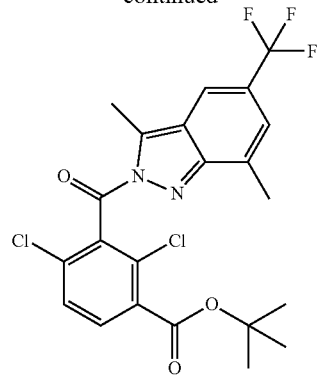

Using a procedure similar to Example DJ, Step 1, tert-butyl 2,4-dichloro-3-(3,7-dimethyl-5-(trifluoromethyl)-1H-indazole-1-carbonyl)benzoate (120 mg, 4%) and tert-butyl 2,4-dichloro-3-(3,7-dimethyl-5-(trifluoromethyl)-2H-indazole-2-carbonyl)benzoate (870 mg, 43%) were prepared from 3,7-dimethyl-5-(trifluoromethyl)-1H-indazole (600 mg, 2.8 mmol) (Preparation #42) and tert-butyl 2,4-dichloro-3-(chlorocarbonyl)benzoate (1.3 g, 4.2 mmol) (Preparation #44).

tert-butyl 2,4-dichloro-3-(3,7-dimethyl-5-(trifluoromethyl)-1H-indazole-1-carbonyl)benzoate. LC/MS (Method j): $R_f$=2.55 min.; MS m/z: 487 [M+H]$^+$; $^1$H NMR (DMSO-d$_6$, 300 MHz): δ 8.20 (s, 1H), 7.91 (d, J=8.4 Hz, 1H), 7.90 (s, 1H), 7.75 (d, J=8.4 Hz, 1H), 2.88 (s, 3H), 2.51 (s, 3H), 1.55 (s, 9H).

tert-butyl 2,4-dichloro-3-(3,7-dimethyl-5-(trifluoromethyl)-2H-indazole-2-carbonyl)benzoate. LC/MS (Method j): $R_f$=2.61 min.; MS m/z: 487 [M+H]$^+$; $^1$H NMR (DMSO-d$_6$, 300 MHz): δ 8.24 (s, 1H), 7.97 (d, J=8.4 Hz, 1H), 7.79 (d, J=8.4 Hz, 1H), 7.33 (s, 1H), 3.07 (s, 3H), 2.31 (s, 3H), 1.55 (s, 9H).

Step 2: 2,4-dichloro-3-(3,7-dimethyl-5-(trifluoromethyl)-1H-indazole-1-carbonyl)benzoic acid

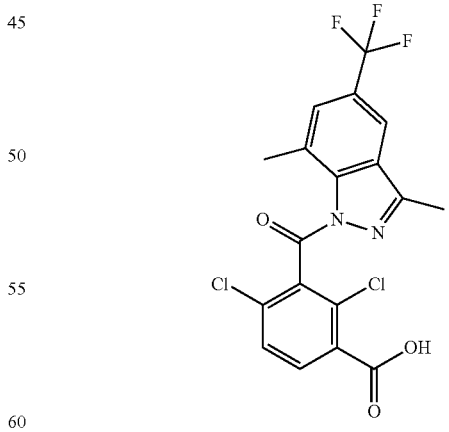

Using a procedure similar to Example DJ, Step 2, 2,4-dichloro-3-(3,7-dimethyl-5-(trifluoromethyl)-1H-indazole-1-carbonyl)benzoic acid (100 mg, 83%) was prepared from tert-butyl 2,4-dichloro-3-(3,7-dimethyl-5-(trifluoromethyl)-1H-indazole-1-carbonyl)benzoate (110 mg, 0.22 mmol). LC/MS (Method j): Rt=1.76 min.; MS m/z: 431 [M+H]$^+$; $^1$H NMR (DMSO-d$_6$, 300 MHz): δ 8.19 (m, 1H), 7.96 (d, J=8.4 Hz, 1H), 7.90 (s, 1H), 7.74 (d, J=8.4 Hz, 1H), 2.88 (s, 3H), 2.49 (s, 3H).

Step 3: methyl 2-(1-(2,4-dichloro-3-(3,7-dimethyl-5-(trifluoromethyl)-1H-indazole-1-carbonyl)benzoyl)piperidin-4-yl)acetate

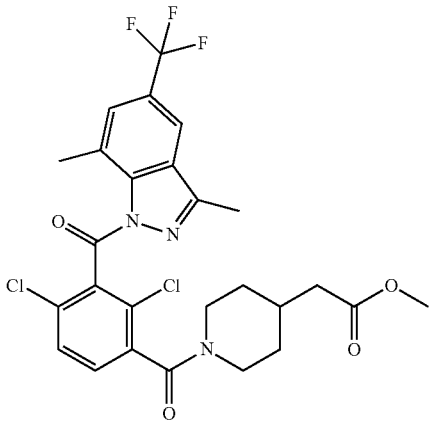 [SMILES: COC(=O)CC1CCN(C(=O)c2ccc(Cl)c(C(=O)n3nc(C)c4cc(C(F)(F)F)cc(C)c43)c2Cl)CC1]

Using a procedure similar to Example A, Step 6, methyl 2-(1-(2,4-dichloro-3-(3,7-dimethyl-5-(trifluoromethyl)-1H-indazole-1-carbonyl)benzoyl)piperidin-4-yl)acetate (64 mg, 42%) was prepared from 2,4-dichloro-dimethyl-5-(trifluoromethyl)-1H-indazole-1-carbonyl)benzoic acid (115 mg, 0.27 mmol) and methyl 2-(piperidin-4-yl)acetate hydrochloride (67 mg, 0.35 mmol). LC/MS (Method i): R$_t$=2.58 min.; MS m/z: 570 [M+H]$^+$; $^1$H NMR (DMSO-d$_6$, 300 MHz): δ 8.21 (s, 1H), 7.91 (s, 1H), 7.72 (m, 1H), 7.56 (m, 1H), 4.7 (m, 1H), 3.59 (m, 4H), 3.21 (m, 1H), 3.09 (m, 2H), 2.89 (m, 3H), 2.82 (m, 1H), 2.48 (m, 1H), 2.29 (m, 2H), 1.99 (m, 1H), 1.74 (m, 1H), 1.64 (m, 1H), 1.15 (m, 2H).

Step 4: 2-(1-(2,4-dichloro-3-(3,7-dimethyl-5-(trifluoromethyl)-1H-indazole-1-carbonyl)benzoyl)piperidin-4-yl)acetic acid

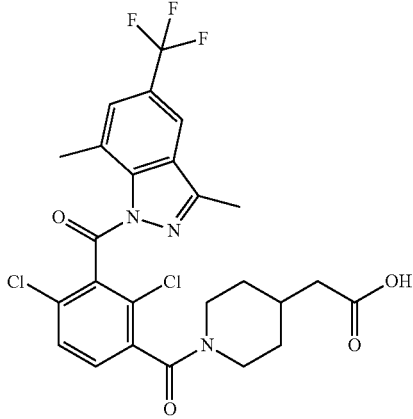 [SMILES: Cc1nn(C(=O)c2c(Cl)ccc(C(=O)N3CCC(CC(=O)O)CC3)c2Cl)c2c(C)cc(C(F)(F)F)cc12]

Using a procedure similar to Example A, Step 5, 2-(1-(2,4-dichloro-3-(3,7-dimethyl-5-(trifluoromethyl)-1H-indazole-1-carbonyl)benzoyl)piperidin-4-yl)acetic acid (53 mg, 86%) was prepared from methyl 2-(1-(2,4-dichloro-3-(3,7-dimethyl-5-(trifluoromethyl)-1H-indazole-1-carbonyl)benzoyl)piperidin-4-yl)acetate (63 mg, 0.11 mmol). LC/MS (Method g): R$_t$=1.86 min.; MS m/z: 556 [M+H]$^+$; $^1$H NMR (DMSO-d$_6$, 400 MHz): δ=12.11 (broad, 1H), 8.21 (m, 1H), 7.91 (s, 1H), 7.73 (m, 1H), 7.63 and 7.55 (m, 1H), 4.47 (m, 1H), 3.27 (m, 1H), 3.09 (m, 1H), 2.85 (m, 4H), 2.47 (m, 3H), 2.18 (m, 2H), 1.95 (m, 1H), 1.78 (m, 1H), 1.65 (m, 1H), 1.18 (m, 2H).

Example EB: 2-(1-(2,4-dichloro-3-(3,7-dimethyl-5-(trifluoromethyl)-2H-indazole-2-carbonyl)benzoyl)piperidin-4-yl)acetic acid

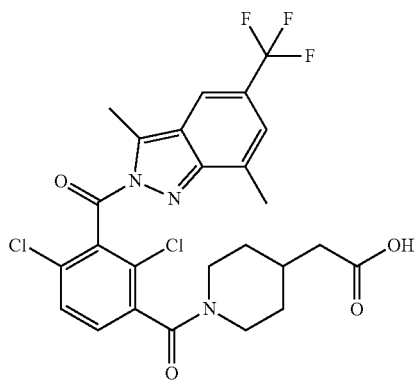 [SMILES: Cc1cc(C(F)(F)F)cc2c(C)n(C(=O)c3c(Cl)ccc(C(=O)N4CCC(CC(=O)O)CC4)c3Cl)nc12]

Step 1: 2,4-dichloro-3-(3,7-dimethyl-5-(trifluoromethyl)-2H-indazole-2-carbonyl)benzoic acid

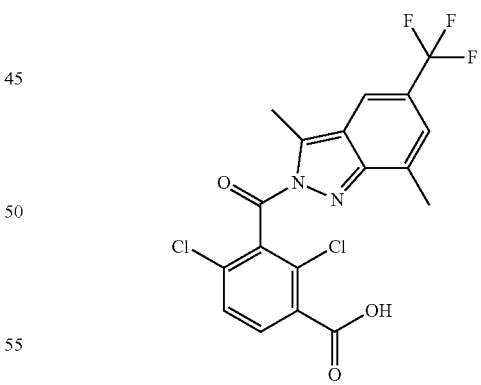

Using a procedure similar to Example DJ, Step 2, 2,4-dichloro-3-(3,7-dimethyl-5-(trifluoromethyl)-2H-indazole-2-carbonyl)benzoic acid (145 mg, 86%) was prepared from tert-butyl 2,4-dichloro-3-(3,7-dimethyl-5-(trifluoromethyl)-2H-indazole-2-carbonyl)benzoate (190 mg, 0.39 mmol) (Example EA, Step 1). LC/MS (Method i): R$_t$=2.42 min.; MS m/z: 431 [M+H]$^+$; $^1$H NMR (DMSO-d$_6$, 300 MHz): δ=8.26 (s, 1H), 8.04 (d, J=8.4 Hz, 1H), 7.79 (d, J=8.4 Hz, 1H), 7.33 (s, 1H), 3.09 (s, 4H), 2.32 (s, 3H).

Step 2: methyl 2-(1-(2,4-dichloro-3-(3,7-dimethyl-5-(trifluoromethyl)-2H-indazole-2-carbonyl)benzoyl)piperidin-4-yl)acetate

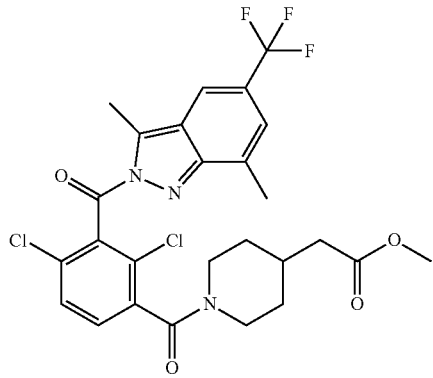 [SMILES: COC(=O)CC1CCN(C(=O)c2ccc(Cl)c(C(=O)n3nc4c(C)cc(C(F)(F)F)cc4c3C)c2Cl)CC1]

Using a procedure similar to Example A, Step 6, methyl 2-(1-(2,4-dichloro-3-(3,7-dimethyl-5-(trifluoromethyl)-2H-indazole-2-carbonyl)benzoyl)piperidin-4-yl)acetate (125 mg, 63%) was prepared from 2,4-dichloro-3-(3,7-dimethyl-5-(trifluoromethyl)-2H-indazole-2-carbonyl)benzoic acid (140 mg, 0.32 mmol) and methyl 2-(piperidin-4-yl)acetate hydrochloride (82 mg, 0.42 mmol). LC/MS (Method i): $R_t$=2.62 min.; MS m/z: 570 [M+H]$^+$; $^1$H NMR (DMSO-d$_6$, 300 MHz): δ 8.26 (s, 1H), 7.70 (m, 2H), 7.33 (s, 1H), 4.46 (m, 1H), 3.56 (m, 3H), 3.29 (m, 1H), 3.08 (s, 4H), 2.81 (m, 1H), 2.28 (m, 5H), 1.99 (m, 1H), 1.75 (m, 1H), 1.60 (m, 1H), 1.17 (m, 2H).

Step 3: 2-(1-(2,4-dichloro-3-(3,7-dimethyl-5-(trifluoromethyl)-2H-indazole-2-carbonyl)benzoyl)piperidin-4-yl)acetic acid

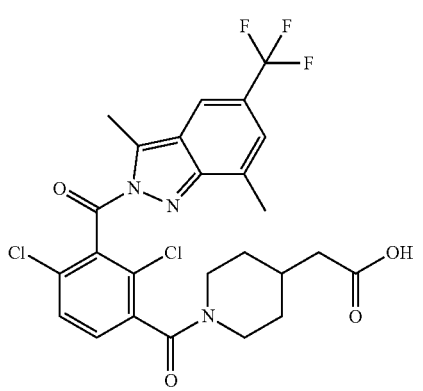 [SMILES: Cc1cc(C(F)(F)F)cc2c(C)n(C(=O)c3c(Cl)ccc(C(=O)N4CCC(CC(=O)O)CC4)c3Cl)nc12]

Using a procedure similar to Example A, Step 5, 2-(1-(2,4-dichloro-3-(3,7-dimethyl-5-(trifluoromethyl)-2H-indazole-2-carbonyl)benzoyl)piperidin-4-yl)acetic acid (102 mg, 87%) was prepared from methyl 2-(1-(2,4-dichloro-3-(3,7-dimethyl-5-(trifluoromethyl)-2H-indazole-2-carbonyl)benzoyl)piperidin-4-yl)acetate (120 mg, 0.21 mmol). LC/MS (Method g): $R_t$=1.89 min.; MS m/z: 556 [M+H]$^+$; $^1$H NMR (DMSO-d$_6$, 400 MHz): b=12.12 (broad, 1H), 8.26 (s, 1H), 7.70 (m, 2H), 7.33 (s, 1H), 4.46 (m, 1H), 3.28 (m, 1H), 3.08 (m, 4H), 2.80 (m, 1H), 2.31 (m, 4H), 2.11 (m, 1H), 1.94 (m, 1H), 1.79 (m, 1H), 1.62 (m, 1H), 0.15 (m, 2H).

Example EC: 2-(1-(2,4-dichloro-3-((7-methyl-5-(trifluoromethyl)-1H-indazol-1-yl)methyl)benzoyl)piperidin-4-yl)acetic acid

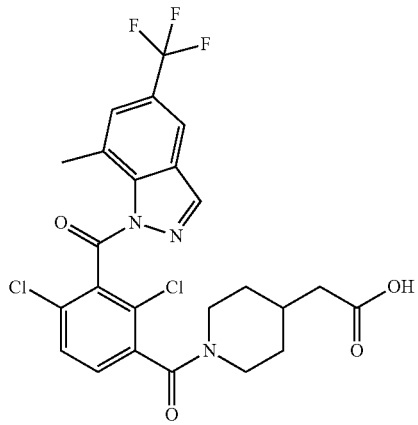 [SMILES: Cc1cc(C(F)(F)F)cc2cnn(C(=O)c3c(Cl)ccc(C(=O)N4CCC(CC(=O)O)CC4)c3Cl)c12]

Step 1: methyl 2-(1-(2,4-dichloro-3-((7-methyl-5-(trifluoromethyl)-1H-indazol-1-yl)methyl)benzoyl)piperidin-4-yl)acetate and methyl 2-(1-(2,4-dichloro-3-((7-methyl-5-(trifluoromethyl)-2H-indazol-2-yl)methyl)benzoyl)piperidin-4-yl)acetate

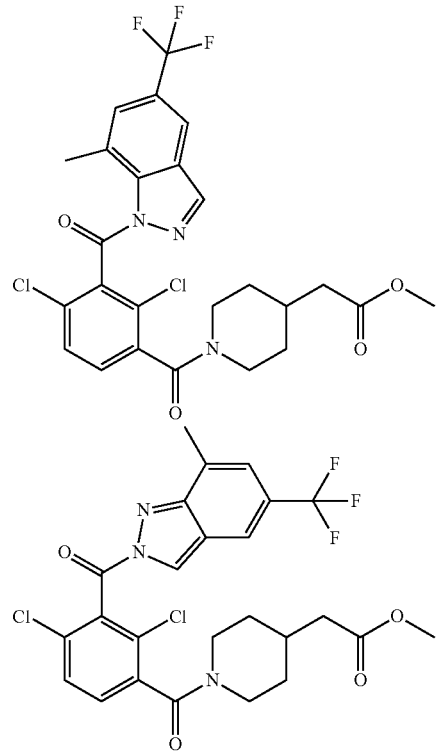

Using a procedure similar to Example DD, Step 1, methyl 2-(1-(2,4-dichloro-3-((7-methyl-5-(trifluoromethyl)-1H-indazol-1-yl)methyl)benzoyl)piperidin-4-yl)acetate (115 mg, 8.5%) and methyl 2-[1-[2,4-dichloro-3-[[7-methyl-5-(trifluoromethyl)-2H-indazol-2-yl]methyl]benzoyl]-4-piperidyl]acetate (350 mg, 26%) were prepared from 7-methyl-5-(trifluoromethyl)-1H-indazole (500 mg, 2.5 mmol) (Preparation 78) and methyl 2-(1-(2,4-dichloro-3-(((methylsulfonyl)oxy)methyl)benzoyl)piperidin-4-yl)acetate (1.4 g, 3.2 mmol) (Preparation 53). methyl 2-(1-(2,4-dichloro-3-((7-methyl-5-(trifluoromethyl)-1H-indazol-1-yl)methyl)benzoyl)piperidin-4-yl)acetate. LC/MS (Method i): $R_t$=2.51 min.; MS m/z: 542 [M+H]$^+$;

$^1$H NMR (DMSO-d$_6$, 400 MHz): δ 8.14 (s, 1H), 8.06 (s, 1H), 7.61 and 7.60 (d, J=8.3 Hz, 1H), 7.50 (s, 1H), 7.45 and 7.37 (d, J=8.3 Hz, 1H), 6.06 and 6.07 (s, 2H), 4.44 (m, 1H), 3.59 and 3.57 (s, 3H), 3.20 (m, 1H), 3.03 (m, 1H), 2.97 (s, 3H), 2.78 (m, 1H), 2.50 (s, 3H), 2.27 (m, 2H), 1.95 (m, 1H), 1.74 (m, 1H), 1.57 (m 1H), 1.13 (m, 2H).

methyl 2-[1-[2,4-dichloro-3-[[7-methyl-5-(trifluoromethyl)-2H-indazol-2-yl]methyl]benzoyl]-4-piperidyl]acetate. LC/MS (Method i): $R_t$=2.47 min.; MS m/z: 542 [M+H]$^+$; $^1$H NMR (DMSO-d$_6$, 300 MHz): δ 8.55 and 8.53 (s, 1H), 8.01 (s, 1H), 7.66 (m, 1H), 7.51 and 7.43 (d, J=8.26 Hz, 1H), 7.22 (s, 1H), 5.97 (s, 2H), 4.45 (m, 1H), 3.59 and 3.58 (s, 3H), 3.28 (m, 1H), 3.05 (m, 1H), 2.80 (m, 1H), 2.50 (m, 3H), 2.27 (m, 2H), 1.96 (m, 1H), 1.76 (m, 1H), 1.57 (m, 1H), 1.17 (m, 2H).

Step 2: 2-(1-(2,4-dichloro-3-((7-methyl-5-(trifluoromethyl)-1H-idazol-1-yl)methyl)benzoyl)piperidin-4-yl)acetic acid

Using a procedure similar to Example A, Step 5, 2-(1-(2,4-dichloro-3-((7-methyl-5-(trifluoromethyl)-1H-indazol-1-yl)methyl)benzoyl)piperidin-4-yl)acetic acid (113 mg, 97%) was prepared from methyl 2-(1-(2,4-dichloro-3-((7-methyl-5-(trifluoromethyl)-1H-indazol-1-yl)methyl)benzoyl)piperidin-4-yl)acetate (119 mg, 0.22 mmol). LC/MS (Method g): $R_t$=1.73 min.; MS m/z: 528 [M+H]$^+$; $^1$H NMR (DMSO-d$_6$, 400 MHz): δ 12.10 (s, 1H), 8.14 (s, 1H), 8.06 (s, 1H), 7.61 and 8.60 (d, J=8.3 Hz, 1H), 7.50 (s, 1H), 7.45 and 7.37 (d, J=8.3 Hz, 1H), 6.08 and 7.07 (s, 2H), 4.44 (m, 1H), 3.21 (m, 1H), 3.02 (m, 1H), 2.97 (s, 3H), 2.78 (m, 1H), 2.16 (m, 2H), 1.92 (m, 1H), 1.76 (m, 1H), 1.59 (m, 1H), 1.12 (m, 2H).

Example ED: 2-(1-(2,4-dichloro-3-((7-methyl-5-(trifluoromethyl)-2H-indazol-2-yl)methyl)benzoyl)piperidin-4-yl)acetic acid

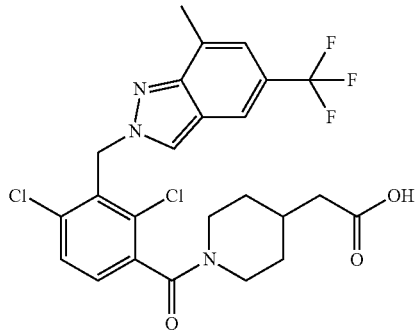 [SMILES: Cc1cc(C(F)(F)F)cc2cn(Cc3c(Cl)ccc(C(=O)N4CCC(CC(=O)O)CC4)c3Cl)nc12]

Using a procedure similar to Example A, Step 5, 2-(1-(2,4-dichloro-3-((7-methyl-5-(trifluoromethyl)-2H-indazol-2-yl)methyl)benzoyl)piperidin-4-yl)acetic acid (76 mg, 64%) was prepared from methyl 2-[1-[2,4-dichloro-3-[[7-methyl-5-(trifluoromethyl)indazol-2-yl]methyl]benzoyl]-4-piperidyl]acetate (121 mg, 0.22 mmol) (example EC, step 1). LC/MS (Method g): $R_t$=1.70 min.; MS m/z: 528 [M+H]$^+$;

$^1$H NMR (DMSO-d$_6$, 400 MHz): δ 12.13 (broad, 1H), 8.55 and 8.53 (s, 1H), 8.01 (s, 1H), 7.67 and 7.65 (d, J=8.4 Hz, 1H), 7.51 and 7.43 (d, J=8.4 Hz, 1H), 7.22 (s, 1H), 597 (m, 2H), 4.47 (m, 1H), 3.31 (m, 4H), 3.03 (m, 1H), 2.80 (m, 1H), 2.17 (m, 2H), 1.93 (m, 1H), 1.76 (m, 1H), 1.60 (m, 1H), 1.17 (m, 2H).

Example EE: 2-(1-(2,4-dichloro-3-((1,4-dimethyl-6-(trifluoromethyl)-1H-indazol-3-yl)methyl)benzoyl)piperidin-4-yl)acetic acid

Step 1: tert-butyl 2,4-dichloro-3-((1,4-dimethyl-6-(trifluoromethyl)-1H-indazol-3-yl)(hydroxy)methyl)benzoate

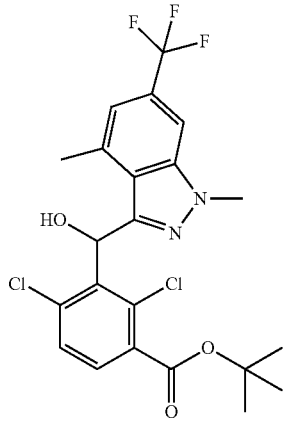 [SMILES: Cc1cc(C(F)(F)F)cc2c1c(C(O)c1c(Cl)ccc(C(=O)OC(C)(C)C)c1Cl)nn2C]

Using a procedure similar to Example FE, Step 1, tert-butyl 2,4-dichloro-3-((1,4-dimethyl-6-(trifluoromethyl)-1H-indazol-3-yl)(hydroxy)methyl)benzoate (149 mg, 63%) was prepared from 1,4-dimethyl-6-(trifluoromethyl)-1H-indazole-3-carbaldehyde (100 mg, 0.41 mmol) (Preparation 79) and tert-butyl 2,4-dichlorobenzoate (153 mg, 0.62 mmol) ((preparation #33, Step A). LC/MS (Method i): $R_t$=2.72 min.; MS m/z: 489 [M+H]$^+$; $^1$H NMR (DMSO-d$_6$, 400 MHz): δ 7.93 (s, 1H), 7.56 (m, 2H), 7.24 (s, 1H), 6.95 (d, J=5.7 Hz, 1H), 6.35 (d, J=5.7 Hz, 1H), 3.96 (s, 3H), 2.88 (s, 3H), 1.55 (s, 9H).

Step 2: 2,4-dichloro-3-((1,4-dimethyl-6-(trifluoromethyl)-1H-indazol-3-yl)methyl)benzoic acid

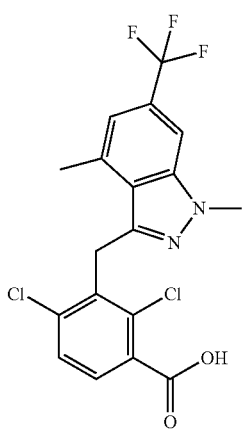 [SMILES: Cc1cc(C(F)(F)F)cc2c1c(Cc1c(Cl)ccc(C(=O)O)c1Cl)nn2C]

Using a procedure similar to Example A, Step 2 and heating at 50° C., 2,4-dichloro-3-((1,4-dimethyl-6-(trifluoromethyl)-1H-indazol-3-yl)methyl)benzoic acid (66 mg, 61%) was prepared from tert-butyl 2,4-dichloro-3-((1,4-dimethyl-6-(trifluoromethyl)-1H-indazol-3-yl)(hydroxy)methyl)benzoate (149 mg, 0.26 mmol). LC/MS (Method i): $R_t$=2.39 min.; MS m/z: 417 [M+H]$^+$; $^1$H NMR (DMSO-d$_6$, 300 MHz): δ=13.50 (broad, 1H), 7.89 (s, 1H), 7.65 (m, 2H), 7.19 (s, 1H), 4.80 (s, 2H), 3.92 (s, 3H), 2.85 (s, 3H).

Step 3: methyl 2-(1-(2,4-dichloro-3-((1,4-dimethyl-6-(trifluoromethyl)-1H-indazol-3-yl)methyl)benzoyl)piperidin-4-yl)acetate

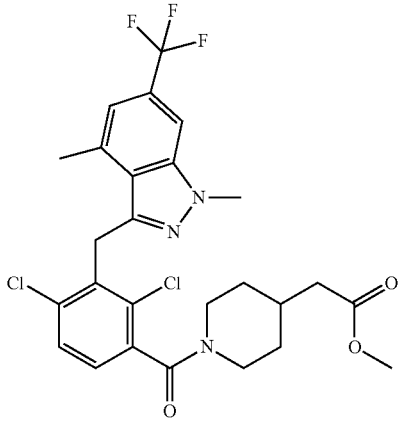 [SMILES: COC(=O)CC1CCN(C(=O)c2ccc(Cl)c(Cc3nn(C)c4cc(C(F)(F)F)cc(C)c34)c2Cl)CC1]

Using a procedure similar to Example A1, methyl 2-(1-(2,4-dichloro-3-((1,4-dimethyl-6-(trifluoromethyl)-1H-indazol-3-yl)methyl)benzoyl)piperidin-4-yl)acetate (110 mg, 82%) was prepared from 2,4-dichloro-3-((1,4-dimethyl-6-(trifluoromethyl)-1H-indazol-3-yl)methyl)benzoic acid (100 mg, 0.24 mmol) and methyl 2-(piperidin-4-yl)acetate hydrochloride (69.6 mmol). LC/MS (Method i): 2.62 min.; MS m/z: 556 [M+H]$^+$; $^1$H NMR (DMSO-d$_6$, 300 MHz): δ 7.89 (s, 1H), 7.59 and 7.56 (d, J=8.3 Hz, 1H), 7.35 and 7.27 (d, J=8.3 Hz, 1H), 7.19 (s, 1H), 4.77 (m, 2H), 4.47 (m, 1H), 3.91 and 3.90 (s, 3H), 3.59 and 3.57 (s, 3H), 3.28 (m, 1H), 3.05 (m, 1H), 2.85 (s, 3H), 2.78 (m, 1H), 2.27 (m, 2H), 1.97 (m, 1H), 1.77 (m, 1H), 1.60 (m, 1H), 1.14 (m, 2H).

Step 4: 2-(1-(2,4-dichloro-3-((1,4-dimethyl-6-(trifluoromethyl)-1H-indazol-3-yl)methyl)benzoyl)piperidin-4-yl)acetic acid

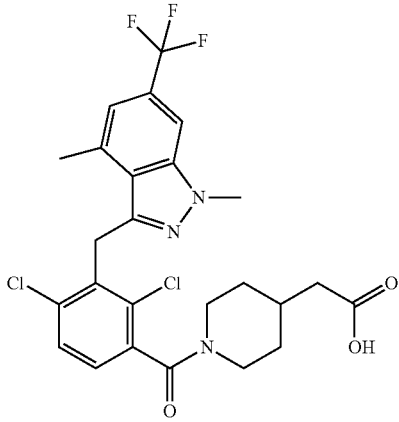 [SMILES: Cc1cc(C(F)(F)F)cc2c1c(Cc1c(Cl)ccc(C(=O)N3CCC(CC(=O)O)CC3)c1Cl)nn2C]

Using a procedure similar to Example A, Step 5 2-(1-(2,4-dichloro-3-((1,4-dimethyl-6-(trifluoromethyl)-1H-indazol-3-yl)methyl)benzoyl)piperidin-4-yl)acetic acid (71 mg, 67%) was prepared from methyl 2-(1-(2,4-dichloro-3-((1,4-dimethyl-6-(trifluoromethyl)-1H-indazol-3-yl)methyl)benzoyl)piperidin-4-yl)acetate (105 mg, 0.19 mmol). LC/MS (Method g): $R_t$=1.78 min.;

MS m/z: 542 [M+H]+; 1H NMR (DMSO-d6, 500 MHz): δ 12.10 (broad, 1H), 7.88 (s, 1H), 7.58 and 7.57 (d, J=8.3 Hz, 1H), 7.36 and 7.28 (d, J=8.3 Hz, 1H), 7.19 (s, 1H), 4.78 (m, 2H), 4.48 (m, 1H), 3.91 and 3.90 (s, 3H), 3.25 (m, 1H), 3.04 (m, 1H), 2.85 (s, 3H), 2.79 (m, 1H), 2.17 (m, 2H), 1.93 (m, 1H), 1.76 (m, 1H), 1.62 (m, 1H), 1.13 (m, 2H).

Example EF: 2-(1-(2,4-dichloro-3-((3-methyl-5-(trifluoromethyl)-1H-indazol-1-yl)methyl)benzoyl)piperidin-4-yl)acetic acid

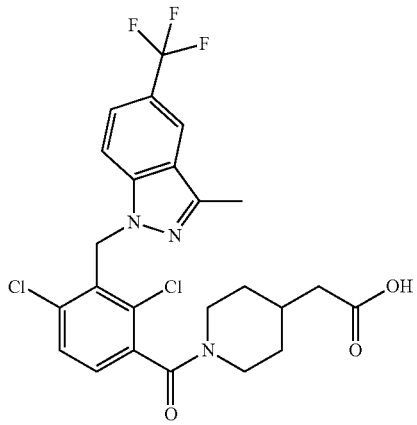 [SMILES: Cc1nn(Cc2c(Cl)ccc(C(=O)N3CCC(CC(=O)O)CC3)c2Cl)c2ccc(C(F)(F)F)cc12]

Step 1: methyl 2,4-dichloro-3-((3-methyl-5-(trifluoromethyl)-1H-indazol-1-yl)methyl)benzoate

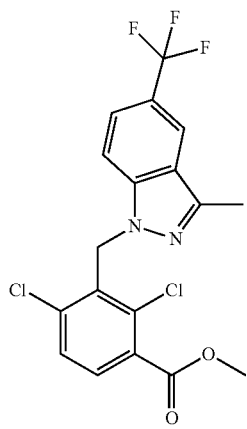 [SMILES: COC(=O)c1ccc(Cl)c(Cn2nc(C)c3cc(C(F)(F)F)ccc32)c1Cl]

Using a procedure similar to Example DD, Step 1 methyl 2,4-dichloro-3-((3-methyl-5-(trifluoromethyl)-1H-indazol-1-yl)methyl)benzoate (1.44 g, 86%) was prepared from 3-methyl-5-(trifluoromethyl)-1H-indazole (800 mg, 4 mmol) and methyl 3-(bromomethyl)-2,4-dichlorobenzoate (1.5 g, 5.2 mmol) (preparation #1, Step B). LC/MS (Method i): R$_t$=2.55 min.; MS m/z: 417 [M+H]+;

1H NMR (DMSO-d6, 500 MHz): δ 8.17 (m, 1H), 7.94 (d, J=8.9 Hz, 1H), 7.77 (d, J=8.4 Hz, 1H), 7.71 (d, J=8.9 Hz, 1H), 7.66 (d, J=8.4 Hz, 1H), 5.82 (s, 2H), 3.84 (s, 3H), 2.45 (s, 3H).

Step 2: 2,4-dichloro-3-((3-methyl-5-(trifluoromethyl)-1H-indazol-1-yl)methyl)benzoic acid

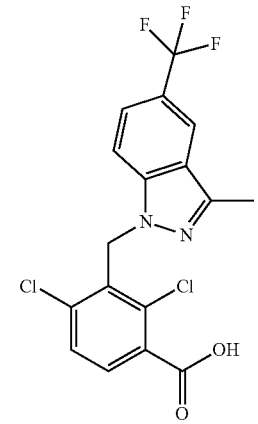 [SMILES: Cc1nn(Cc2c(Cl)ccc(C(=O)O)c2Cl)c2ccc(C(F)(F)F)cc12]

Using a procedure similar to Example A, Step 5, 2,4-dichloro-3-((3-methyl-5-(trifluoromethyl)-1H-indazol-1-yl)methyl)benzoic acid (1.22 g, 88%) was prepared from methyl 2,4-dichloro-3-((3-methyl-5-(trifluoromethyl)-1H-indazol-1-yl)methyl)benzoate (1.44 g, 3.45 mmol). LC/MS (Method i): R$_t$=2.23 min.; MS m/z: 403 [M+H]+; 1H NMR (DMSO-d6, 300 MHz): δ 13.69 (br., 1H), 8.19 (m, 1H), 7.96 (d, J=8.8 Hz, 1H), 7.75 (d, J=8.4 Hz, 1H), 7.73 (d, J=8.8 Hz, 1H), 7.63 (d, J=8.4 Hz, 1H), 5.83 (s, 2H), 2.47 (s, 3H).

Step 3: 2-(1-(2,4-dichloro-3-((3-methyl-5-(trifluoromethyl)-1H-indazol-1-yl)methyl)benzoyl)piperidin-4-yl)acetic acid

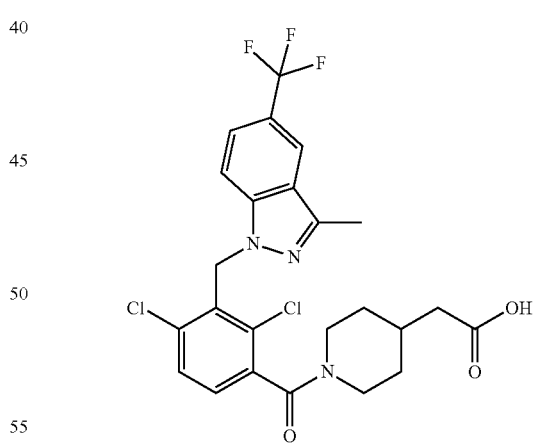

Using a procedure similar to Example A, Step 6 and Example A, Step 5, 2-(1-(2,4-dichloro-3-((3-methyl-5-(trifluoromethyl)-1H-indazol-1-yl)methyl)benzoyl)piperidin-4-yl)acetic acid (104 mg, 79%) was prepared from 2,4-dichloro-3-((3-methyl-5-(trifluoromethyl)-1H-indazol-1-yl)methyl)benzoic acid (100 mg, 0.25 mmol). LC/MS (Method g): R$_t$=1.71 min.; MS m/z: 528 [M+H]+; 1H NMR (DMSO-d6, 400 MHz): δ 12.10 (broad, 1H), 8.19 (s 1H), 94 (d, J=9.0 Hz, 1H), 7.72 (d, J=9.0 Hz, 1H), 7.61 and 7.60 (d, J=8.3 Hz, 1H), 7.33-7.44 and 7.37 (d, J=8.3 Hz, 1H), 5.80 (m, 2H), 4.45 (m, 1H), 3.20 (m, 1H), 3.02 (m, 1H), 2.78 (m, 1H), 2.47 and 2.46 (ds, 3H), 2.16 (m, 2H), 1.92 (m, 1H), 1.76 (m, 1H), 1.59 (m, 1H), 1.14 (m, 2H).

Example EG: 2-[1-[2,4-dichloro-3-[[3,7-dimethyl-5-(trifluoromethoxy)-1H-indol-1-yl]methyl]benzoyl]-4-piperidyl]acetic acid

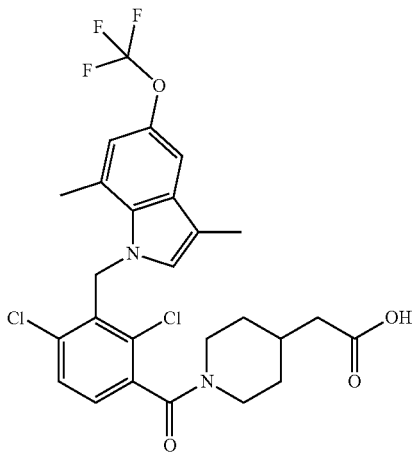 [SMILES: Cc1cn(Cc2c(Cl)ccc(C(=O)N3CCC(CC(=O)O)CC3)c2Cl)c2c(C)cc(OC(F)(F)F)cc12]

Step 1: methyl 2,4-dichloro-3-((3,7-dimethyl-5-(trifluoromethoxy)-1H-indol-1-yl)methyl)benzoate

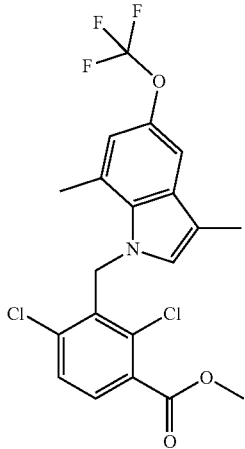 [SMILES: COC(=O)c1ccc(Cl)c(Cn2cc(C)c3cc(OC(F)(F)F)cc(C)c32)c1Cl]

Using a procedure similar to Example DH, Step 1, methyl 2,4-dichloro-3-((3,7-dimethyl-5-(trifluoromethoxy)-1H-indol-1-yl)methyl)benzoate (336 mg, 62%) was prepared from 3,7-dimethyl-5-(trifluoromethoxy)-1H-indole (Preparation #61) (280 mg, 1.22 mmol) and tert-butyl 3-(bromomethyl)-2,4-dichlorobenzoate (498 mg, 1.46 mmol) (Preparation #1, step B). LC/MS (Method i): R$_t$=2.82 min.; MS m/z: 446 [M+H]$^+$; $^1$H NMR (DMSO-d$_6$, 300 MHz): δ 7.87 (d, J=8.4 Hz, 1H), 7.75 (d, J=8.4 Hz, 1H), 7.26 (s, 1H), 6.93 (s, 1H), 6.48 (s, 1H), 5.86 (s, 2H), 3.88 (s, 3H), 2.88 (s, 3H), 2.11 (s, 3H).

Step 2: 2,4-dichloro-3-((3,7-dimethyl-5-(trifluoromethoxy)-1H-indol-1-yl)methyl)benzoic acid

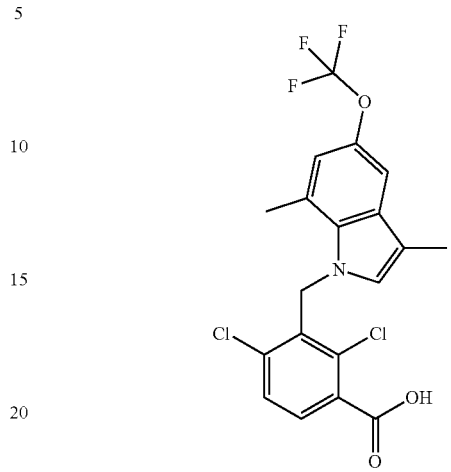

Using a procedure similar to Example A, Step 5, 2,4-dichloro-3-((3,7-dimethyl-5-(trifluoromethoxy)-1H-indol-1-yl)methyl)benzoic acid (272 mg, 85%) was prepared from methyl 2,4-dichloro-3-((3,7-dimethyl-5-(trifluoromethoxy)-1H-indol-1-yl)methyl)benzoate (332 mg, 0.7 mmol). LC/MS (Method i): R$_t$=2.53 min.; MS m/z: 432 [M+H]$^+$; $^1$H NMR (DMSO-d$_6$, 300 MHz): δ 13.65 (broad, 1H), 7.83 (d, J=8.4 Hz, 1H), 7.71 (d, J=8.4 Hz, 1H), 7.26 (s, 1H), 6.93 (m, 1H), 6.47 (s, 1H), 5.86 (s, 2H), 2.88 (s, 3H), 2.11 (s, 3H).

Step 3: methyl 2-(1-(2,4-dichloro-3-((3,7-dimethyl-5-(trifluoromethoxy)-1H-indol-1-yl)methyl)benzoyl)piperidin-4-yl)acetate

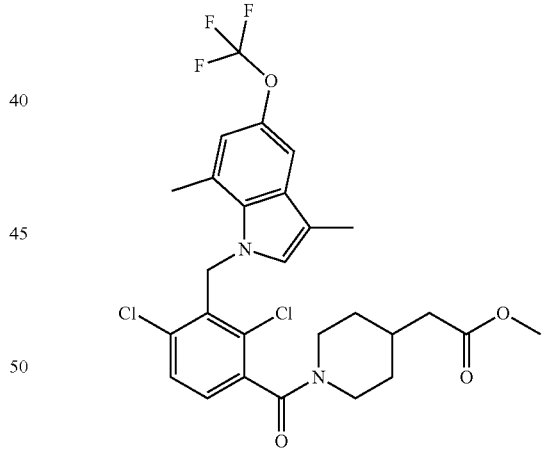

Using a procedure similar to Example A, Step 6, methyl 2-(1-(2,4-dichloro-3-((3,7-dimethyl-5-(trifluoromethoxy)-1H-indol-1-yl)methyl)benzoyl)piperidin-4-yl)acetate (100 mg, 76%) was prepared from 2,4-dichloro-3-((3,7-dimethyl-5-(trifluoromethoxy)-1H-indol-1-yl)methyl)benzoic acid (100 mg, 0.2 mmol) and methyl (4-piperidyl)acetate hydrochloride (90 mg, 0.4 mmol). LC/MS (Method i): R$_t$=2.68 min.; MS m/z: 571 [M+H]$^+$; $^1$H NMR (DMSO-d$_6$, 300 MHz): δ 7.69 and 7.67 (d, J=8.3 Hz, 1H), 7.52 (d, J=8.3 Hz, 0.5H), 7.45 (d, J=8.3 Hz, 0.5H), 7.26 (s, 1H), 6.93 (s, 1H), 6.50 and 6.47 (s, 1H), 5.80 (m, 2H), 4.46 (m, 1H), 3.59 and 3.57 (s, 3H), 3.28 (m, 1H), 2.08 (m, 1H), 2.87 (s, 3H), 2.80 (m, 1H), 2.26 (m, 2H), 2.12 (s, 3H), 1.97 (m, 1H) 1.75 (m, 1H), 1.58 (m, 1H), 1.17 (m, 2H).

Step 4: 2-(1-(2,4-dichloro-3-((3,7-dimethyl-5-(trifluoromethoxy)-1H-indol-1-yl)methyl)benzoyl)piperidin-4-yl)acetic acid

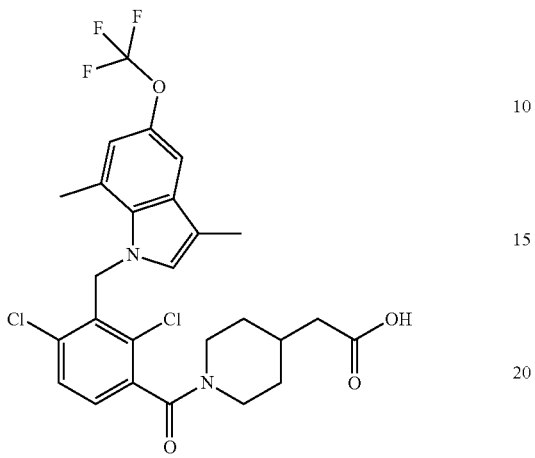

Using a procedure similar to Example 1, Step 5, 2-(1-(2,4-dichloro-3-((3,7-dimethyl-5-(trifluoromethoxy)-1H-indol-1-yl)methyl)benzoyl)piperidin-4-yl)acetic acid (78 mg, 83%) was prepared from methyl 2-(1-(2,4-dichloro-3-((3,7-dimethyl-5-(trifluoromethoxy)-1H-indol-1-yl)methyl)benzoyl)piperidin-4-yl)acetate (96 mg, 0.16 mmol). LC/MS (Method g): $R_t$=1.96 min.; MS m/z: 557 [M+H]$^+$; $^1$H NMR (DMSO-d$_6$, 400 MHz): δ 12.10 (broad, 1H), 7.69 and 7.68 (d, J=8.3 Hz, 1H), 7.52 (d, J=8.3 Hz, 0.5H), 7.46 (d, J=8.3 Hz, 0.5H), 7.26 (s, 1H), 6.93 (s, 1H), 6.50 and 6.46 (s, 1H), 5.82 (m, 2H), 4.46 (m, 1H), 3.27 (m, 1H), 3.04 (m, 1H), 2.87 (s, 3H), 2.82 (m, 1H), 2.18 (m, 2H), 2.12 (s, 3H), 1.94 (m, 1H), 1.77 (m, 1H), 1.61 (m, 1H), 1.17 (m, 2H).

TABLE EG

The following examples were prepared from 2,4-dichloro-3-((3,7-dimethyl-5-(trifluoromethoxy)-1H-indol-1-yl)methyl)benzoic acid (example EG step 2) using the same procedure as described in example EG step 3 and 4 with the appropriate amines.

| Example # | Product | Amine | Intermediate ester $R_t$ min | Intermediate ester m/z ESI+ (M + H)$^+$ | Final acid $R_t$ min | Final acid m/z ESI+ (M + H)$^+$ |
|---|---|---|---|---|---|---|
| EG-1 | (structure) | (structure) | 2.64 (Method i) | 557 | 1.94 (Method g) | 543 |

TABLE EG-continued

The following examples were prepared from 2,4-dichloro-3-((3,7-dimethyl-5-(trifluoromethoxy)-1H-indol-1-yl)methyl)benzoic acid (example EG step 2) using the same procedure as described in example EG step 3 and 4 with the appropriate amines.

| Example # | Product | Amine | Intermediate ester R, min | Intermediate ester m/z ESI+ (M + H)+ | Final acid R, min | Final acid m/z ESI+ (M + H)+ |
|---|---|---|---|---|---|---|
| EG-2 | Chiral 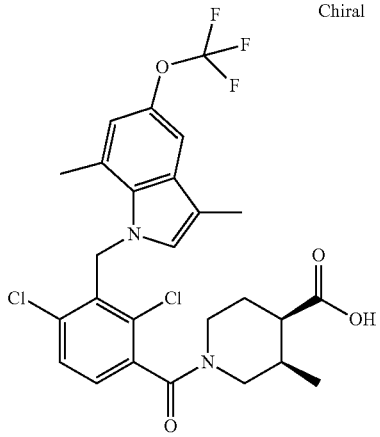 [SMILES: Cc1cn(Cc2c(Cl)ccc(C(=O)N3CC[C@@H](C(=O)O)[C@@H](C)C3)c2Cl)c2c(C)cc(OC(F)(F)F)cc12] | 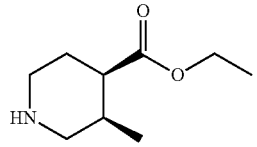 (Preparation 84) | 2.89 (Method i) | 585 | 1.97 (Method g) | 557 |

Example EH: 2-[1-[2,4-dichloro-3-[3,7-dimethyl-5-(trifluoromethoxy)indole-1-carbonyl]benzoyl]-4-piperidyl]acetic acid

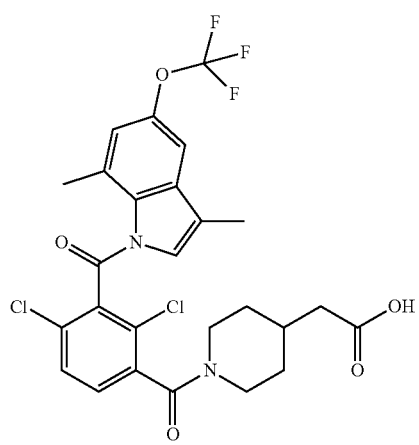 [SMILES: Cc1cn(C(=O)c2c(Cl)ccc(C(=O)N3CCC(CC(=O)O)CC3)c2Cl)c2c(C)cc(OC(F)(F)F)cc12]

Step 1: tert-butyl 2,4-dichloro-3-(3,7-dimethyl-5-(trifluoromethoxy)-1H-indole-1-carbonyl)benzoate

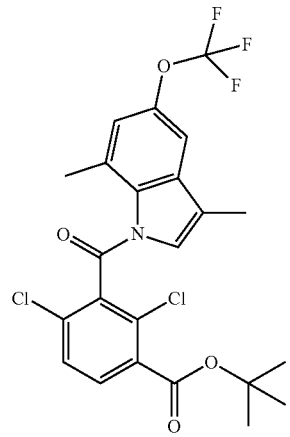 [SMILES: Cc1cn(C(=O)c2c(Cl)ccc(C(=O)OC(C)(C)C)c2Cl)c2c(C)cc(OC(F)(F)F)cc12]

Using a procedure similar to Example DJ, Step 1, tert-butyl 2,4-dichloro-3-(3,7-dimethyl-5-(trifluoromethoxy)-1H-indole-1-carbonyl)benzoate (330 mg, 40%) was prepared from 3,7-dimethyl-5-(trifluoromethoxy)-1H-indole (Preparation 61) (415 mg, 1.81 mmol) and tert-butyl 2,4-dichloro-3-(chlorocarbonyl)benzoate (513 mg, 1.65 mmol) (Preparation #44). LC/MS (Method j): Rt=2.71 min.;

MS m/z: 502 [M+H]+; $^1$H NMR (DMSO-$d_6$, 300 MHz): δ 7.98 (d, J=8.4 Hz, 1H), 7.81 (d, J=8.4 Hz, 1H), 7.43 (s, 1H), 7.27 (m, 1H), 7.21 (s, 1H), 2.69 (s, 3H), 2.16 (d, J=1.3 Hz, 3H), 1.57 (s, 9H).

Step 2: tert-butyl 2,4-dichloro-3-(3,7-dimethyl-5-(trifluoromethoxy)-1H-indole-1-carbonyl)benzoate

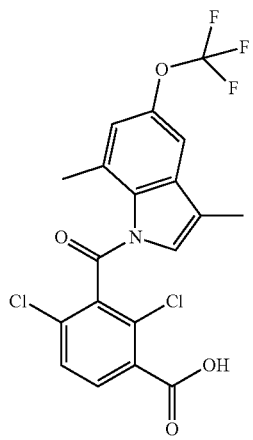 [SMILES: Cc1cn(C(=O)c2c(Cl)ccc(C(=O)O)c2Cl)c2c(C)cc(OC(F)(F)F)cc12]

Using a procedure similar to Example DJ, Step 2, 2,4-dichloro-3-(3,7-dimethyl-5-(trifluoromethoxy)-1H-indole-1-carbonyl)benzoic acid (280 mg, 96%) was prepared from tert-butyl 2,4-dichloro-3-(3,7-dimethyl-5-(trifluoromethoxy)-1H-indole-1-carbonyl)benzoate (330 mg, 0.65 mmol). LC/MS (Method k): $R_t$=2.56 min.; MS m/z: 446 [M+H]$^+$; $^1$H NMR (DMSO-d$_6$, 300 MHz): δ 13.9 (broad, 1H), 8.04 (d, J=8.4 Hz, 1H), 7.80 (d, J=8.4 Hz, 1H), 7.43 (s, 1H), 7.28 (s, 1H), 7.18 (d, J=1.2 Hz, 1H), 2.69 (s, 3H), 2.16 (d, J=1.2 Hz, 3H).

Step 3: methyl 2-(1-(2,4-dichloro-3-(3,7-dimethyl-5-(trifluoromethoxy)-1H-indole-1-carbonyl)benzoyl)piperidin-4-yl)acetate

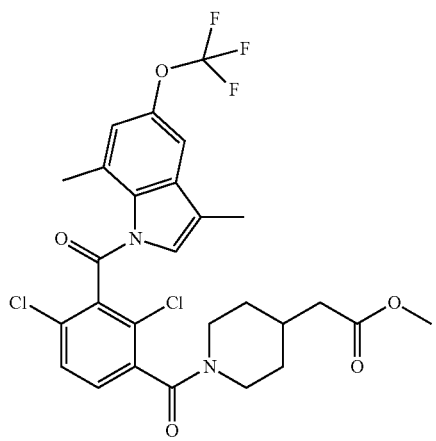 [SMILES: COC(=O)CC1CCN(C(=O)c2ccc(Cl)c(C(=O)n3cc(C)c4cc(OC(F)(F)F)cc(C)c43)c2Cl)CC1]

Using a procedure similar to Example A, Step 6, methyl 2-(1-(2,4-dichloro-3-(3,7-dimethyl-5-(trifluoromethoxy)-1H-indole-1-carbonyl)benzoyl)piperidin-4-yl)acetate (93 mg, 71%) was prepared from 2,4-dichloro-3-(3,7-dimethyl-5-(trifluoromethoxy)-1H-indole-1-carbonyl)benzoic acid (100 mg, 0.22 mmol) and methyl (4-piperidyl)acetate hydrochloride (87 mg, 0.44 mmol). LC/MS (Method k): Rt=2.70 min.; MS m/z: 585 [M+H]$^+$; $^1$H NMR (DMSO-d$_6$, 300 MHz): δ 7.79 (m, 1H), 7.85 (m, 1H), 7.45 (s, 1H), 7.25 (s, 1H), 7.35 and 7.31 and 7.09 (s, 1H), 4.47 (m, 1H), 3.59 (m, 3H), 3.24 (m, 1H), 3.07 (m, 1H), 2.83 (m, 1H), 2.68 (s, 3H), 2.25 (m, 2H), 2.18 (m, 3H), 1.99 (m, 1H), 1.76 (m, 1H), 1.59 (m, 1H), 1.12 (m, 2H).

Step 4: 2-(1-(2,4-dichloro-3-(3,7-dimethyl-5-(trifluoromethoxy)-1H-indole-1-carbonyl)benzoyl)piperidin-4-yl)acetic acid

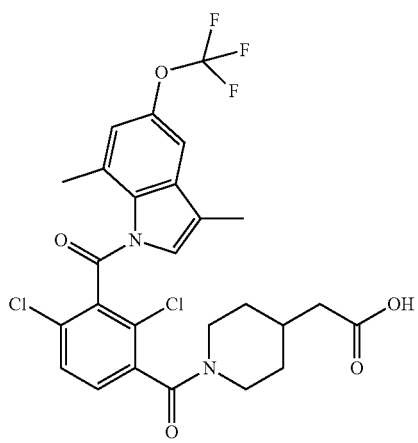 [SMILES: Cc1cn(C(=O)c2c(Cl)ccc(C(=O)N3CCC(CC(=O)O)CC3)c2Cl)c2c(C)cc(OC(F)(F)F)cc12]

Using a procedure similar to Example A, Step 5, 2-(1-(2,4-dichloro-3-(3,7-dimethyl-5-(trifluoromethoxy)-1H-indole-1-carbonyl)benzoyl)piperidin-4-yl)acetic acid (48 mg, 55%) was prepared from methyl 2-(1-(2,4-dichloro-3-(3,7-dimethyl-5-(trifluoromethoxy)-1H-indole-1-carbonyl)benzoyl)piperidin-4-yl)acetate (90 mg, 0.15 mmol). LC/MS (Method g): $R_t$=1.95 min.; MS m/z: 571 [M+H]$^+$; $^1$H NMR (DMSO-d$_6$, 400 MHz): δ 12.11 (broad, 1H), 7.79 (m, 1H), 7.65 (m, 1H), 7.43 (broad, 1H), 7.37 and 7.31 and 7.10 (m, 1H), 7.27 (broad, 1H), 4.47 (m, 1H), 3.57 (m, 1H), 3.24 (m, 1H), 3.05 (m, 1H), 2.80 (m, 1H), 2.68 (s, 3H), 2.15 (m, 5H), 1.95 (m, 1H), 1.78 (m, 1H), 1.65 (m, 1H), 1.15 (m, 2H).

TABLE EH

The following examples were prepared from 2,4-dichloro-3-(3,7-dimethyl-5-(trifluoromethoxy)-1H-indole-1-carbonyl)benzoic acid (example EH, Step 2) using the same procedure as described in example EH, Step 3 and 4 with the appropriate amines.

| Example # | Product | Amine | Intermediate ester $R_t$ min | Intermediate ester m/z ESI+ (M + H)+ | Final acid $R_t$ min | Final acid m/z ESI+ (M + H)+ |
|---|---|---|---|---|---|---|
| EH-1 | 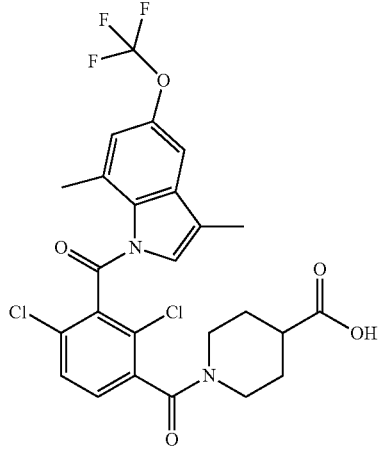 [SMILES: Cc1cn(C(=O)c2c(Cl)ccc(C(=O)N3CCC(C(=O)O)CC3)c2Cl)c2c(C)cc(OC(F)(F)F)cc12] | 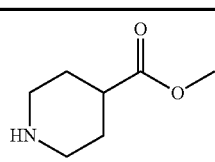 | 2.66 (Method k) | 571 | 1.94 (Method g) | 559 |

Example EI: 2-(1-(2,4-dichloro-3-((5-(trifluoromethoxy)-1H-indol-1-yl)methyl)benzoyl)piperidin-4-yl)acetic acid

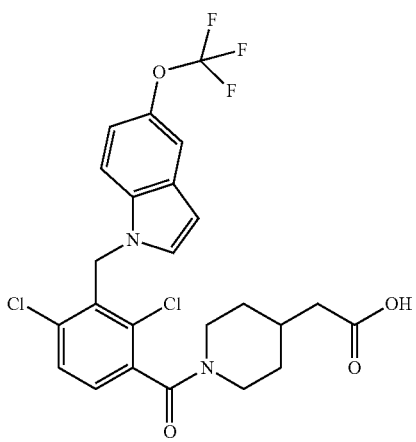 [SMILES: O=C(O)CC1CCN(C(=O)c2ccc(Cl)c(Cn3ccc4cc(OC(F)(F)F)ccc43)c2Cl)CC1]

Step 1: methyl 2-(1-(2,4-dichloro-3-((5-(trifluoromethoxy)-1H-indol-1-yl)methyl)benzoyl)piperidin-4-yl)acetate

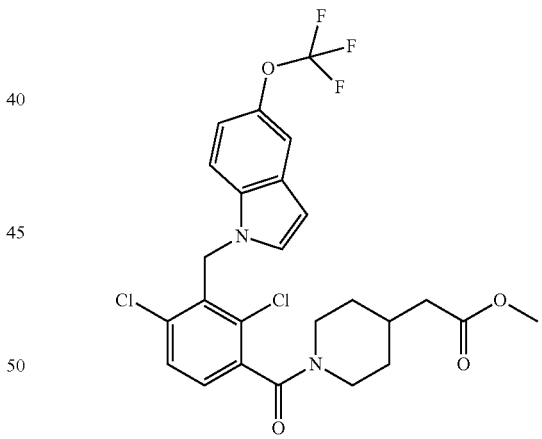

Using a procedure similar to Example DH, Step 1, methyl 2-(1-(2,4-dichloro-3-((5-(trifluoromethoxy)-1H-indol-1-yl)methyl)benzoyl)piperidin-4-yl)acetate (141 mg, 77%) was prepared from 5-(trifluoromethoxy)-1H-indole (68 mg, 0.34 mmol) and methyl 2-(1-(2,4-dichloro-3-(((methylsulfonyl)oxy)methyl)benzoyl)piperidin-4-yl)acetate (Preparation 53) (192 mg, 0.44 mmol).

LC/MS (Method i): $R_t$=2.60 min.; MS m/z: 543 [M+H]+; 1H NMR (DMSO-$d_6$, 300 MHz): δ 7.69 (m, 2H), 7.56 (m, 1H), 7.50 and 7.42 (d, J=8.4 Hz, 1H), 7.15 (m, 2H), 6.54 (m, 1H), 5.62 (m, 2H), 4.45 (m, 1H), 3.59 and 3.58 (s, 3H), 3.20 (m, 1H), 3.01 (m, 1H), 2.79 (m, 1H), 2.27 (m, 2H), 1.97 (m, 1H), 1.75 (m, 1H), 1.57 (m, 1H), 1.13 (m, 2H).

Step 2: 2-(1-(2,4-dichloro-3-((5-(trifluoromethoxy)-1H-indol-1-yl)methyl)benzoyl)piperidin-4-yl)acetic acid

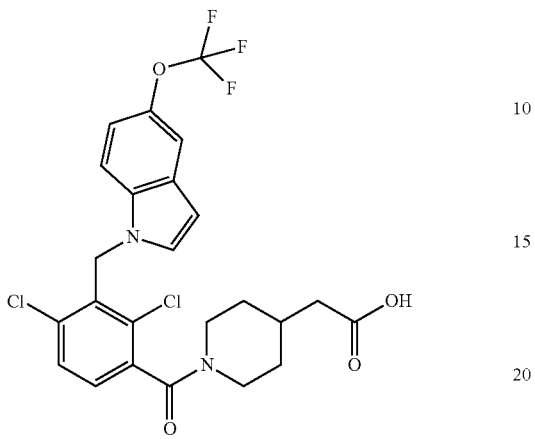

Using a procedure similar to Example A, Step 5, 2-(1-(2,4-dichloro-3-((5-(trifluoromethoxy)-1H-indol-1-yl)methyl)benzoyl)piperidin-4-yl)acetic acid (75 mg, 58%) was prepared from methyl 2-(1-(2,4-dichloro-3-((5-(trifluoromethoxy)-1H-indol-1-yl)methyl)benzoyl)piperidin-4-yl)acetate (132 mg, 0.24 mmol). LC/MS (Method g): $R_t$=1.77 min.; MS m/z: 529 [M+H]$^+$; $^1$H NMR (DMSO-d$_6$, 400 MHz): δ 12.10 (broad, 1H), 7.66 (m, 2H), 7.56 (s, 1H), 7.50 and 7.42 (d, J=8.4 Hz, 1H), 7.14 (m, 2H), 6.54 (m, 1H), 5.62 (m, 2H), 4.45 (m, 1H), 3.23 (m, 1H), 3.02 (m, 1H), 2.78 (m, 1H), 2.16 (m, 2H), 1.93 (m, 1H), 1.77 (m, 1H), 1.59 (m, 1H), 1.13 (m, 2H).

TABLE EI

The following examples were prepared from methyl 2-(1-(2,4-dichloro-3-(((methylsulfonyl)oxy)methyl)benzoyl)piperidin-4-yl)acetate (Preparation 53) using the same procedure as described in example EI, Step 1 and 2 with the appropriate indole.

| Example # | Product | Indole | Intermediate ester $R_t$ min | Intermediate ester m/z ESI+ (M + H)$^+$ | Final acid $R_t$ min | Final acid m/z ESI+ (M + H)$^+$ |
|---|---|---|---|---|---|---|
| EI-1 | | | 2.69 (method i) | 501 | 1.89 (method g) | 487 |

TABLE EI-continued

The following examples were prepared from methyl 2-(1-(2,4-dichloro-3-(((methylsulfonyl)oxy)methyl)benzoyl)piperidin-4-yl)acetate (Preparation 53) using the same procedure as described in example EI, Step 1 and 2 with the appropriate indole.

| Example # | Product | Indole | Intermediate ester R$_t$, min | Intermediate ester m/z ESI+ (M + H)$^+$ | Final acid R$_t$, min | Final acid m/z ESI+ (M + H)$^+$ |
|---|---|---|---|---|---|---|
| EI-2 | | | 2.45 (method i) | 507 | 1.69 (method g) | 491 |
| EI-3 | | | Not isolated | | 1.79 (method g) | 479 |
| EI-4 | | | 1.96 (method g) | 527 | 1.78 (method g) | 513 |

TABLE EI-continued

The following examples were prepared from methyl 2-(1-(2,4-dichloro-3-(((methylsulfonyl)oxy)methyl)benzoyl)piperidin-4-yl)acetate (Preparation 53) using the same procedure as described in example EI, Step 1 and 2 with the appropriate indole.

| Example # | Product | Indole | Intermediate ester R, min | Intermediate ester m/z ESI+ (M + H)+ | Final acid R, min | Final acid m/z ESI+ (M + H)+ |
|---|---|---|---|---|---|---|
| EI-5 | | Preparation 62 | 2.78 (method i) | 561 | 1.96 (method g) | 547 |
| EI-6 | | Preparation 63 | 2.71 (method i) | 555 | 1.91 (method g) | 541 |
| EI-7 | | | 2.55 (method i) | 527 | 1.77 (method g) | 513 |

Example EJ: 2-(1-(2,4-dichloro-3-((7-methyl-5-(trifluoromethoxy)-1H-indol-1-yl)methyl)benzoyl)piperidin-4-yl)acetic acid

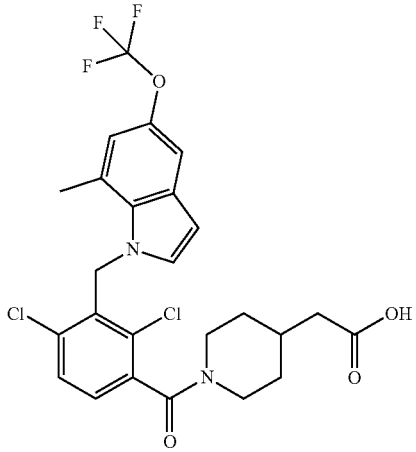 [SMILES: Cc1cc(OC(F)(F)F)cc2ccn(Cc3c(Cl)ccc(C(=O)N4CCC(CC(=O)O)CC4)c3Cl)c12]

Step 1: methyl 2,4-dichloro-3-((7-methyl-5-(trifluoromethoxy)-1H-indol-1-yl)methyl)

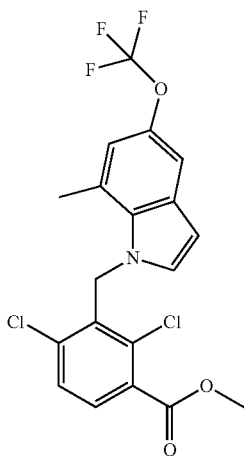 [SMILES: COC(=O)c1ccc(Cl)c(Cn2ccc3cc(OC(F)(F)F)cc(C)c32)c1Cl]

Using a procedure similar to Example DH, Step 1, methyl 2,4-dichloro-3-((7-methyl-5-(trifluoromethoxy)-1H-indol-1-yl)methyl)benzoate (910 mg, 69%) was prepared from 7-methyl-5-(trifluoromethoxy)-1H-indole (Preparation #64) (600 mg, 2.8 mmol) and tert-butyl 3-(bromomethyl)-2,4-dichlorobenzoate (914 mg, 3.07 mmol) (Preparation #1, step B). LC/MS (Method j): $R_t$=2.34 min.; MS m/z: 432 [M+H]$^+$; $^1$H NMR (DMSO-d$_6$, 300 MHz): δ 7.88 (d, J=8.4 Hz, 1H), 7.76 (d, J=8.4 Hz, 1H), 7.37 (s, 1H), 6.94 (s, 1H), 6.67 (d, J=3.3 Hz, 1H), 6.45 (d, J=3.3 Hz, 1H), 5.93 (s, 2H), 3.88 (s, 3H), 2.90 (s, 3H).

Step 2: 2,4-dichloro-3-((7-methyl-5-(trifluoromethoxy)-1H-indol-1-yl)methyl)benzoic acid

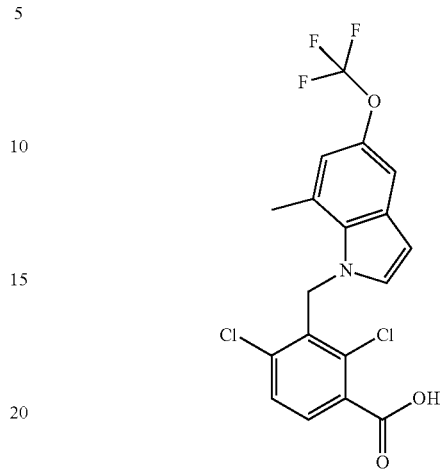

Using a procedure similar to Example A, Step 5, 2,4-dichloro-3-((7-methyl-5-(trifluoromethoxy)-1H-indol-1-yl)methyl)benzoic acid (840 mg, 91%) was prepared from methyl 2,4-dichloro-3-((7-methyl-5-(trifluoromethoxy)-1H-indol-1-yl)methyl)benzoate (900 mg, 2.08 mmol). LC/MS (Method j): $R_t$=1.85 min.; MS m/z: 418 [M+H]$^+$; $^1$H NMR (DMSO-d$_6$, 300 MHz): δ 13.78 (broad, 1H), 7.82 (d, J=8.4 Hz, 1H), 7.70 (d, J=8.4 Hz, 1H), 7.37 (s, 1H), 6.94 (s, 1H), 6.66 (d, J=3.3 Hz, 1H), 6.45 (d, J=3.3 Hz, 1H), 5.92 (s, 2H), 2.90 (s, 3H)

Step 3: methyl 2-(1-(2,4-dichloro-3-((7-methyl-5-(trifluoromethoxy)-1H-indol-1-yl)methyl)benzoyl)piperidin-4-yl)acetate

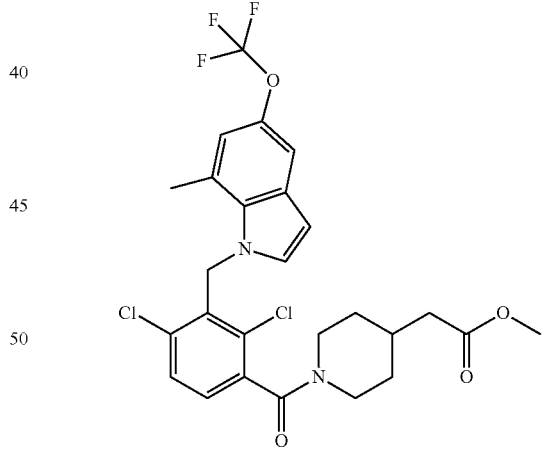

Using a procedure similar to Example A, Step 6, methyl 2-(1-(2,4-dichloro-3-((7-methyl-5-(trifluoromethoxy)-1H-indol-1-yl)methyl)benzoyl)piperidin-4-yl)acetate (240 mg, 82%) was prepared from 2,4-dichloro-3-((7-methyl-5-(trifluoromethoxy)-1H-indol-1-yl)methyl)benzoic acid (200 mg, 0.48 mmol) and methyl (4-piperidyl)acetate hydrochloride (111 mg, 0.57 mmol). LC/MS (Method j): $R_t$=2.14 min.; MS m/z: 557 [M+H]$^+$; $^1$H NMR (DMSO-d$_6$, 300 MHz): δ 7.70 and 7.71 (d, J=8.3 Hz, 1H), 7.53 and 7.45 (d, J=8.3 Hz, 1H), 7.37 (s, 1H), 6.94 (s, 1H), 6.69 (m, 1H), 6.46 (m, 1H), 5.89 (m, 2H), 4.46 (m, 1H), 3.59 and 3.57 (s, 3H), 3.26 (m, 1H), 3.03 (m, 1H), 2.99 (s, 3H), 2.79 (m, 1H), 2.27 (m, 2H), 1.97 (m, 1H), 1.75 (m, 1H), 1.57 (m, 1H), 1.05-1.27 (m, 2H).

Step 4: 2-(1-(2,4-dichloro-3-((7-methyl-5-(trifluoromethoxy)-1H-indol-1-yl)methyl)benzoyl)piperidin-4-yl)acetic acid A-1668537.0

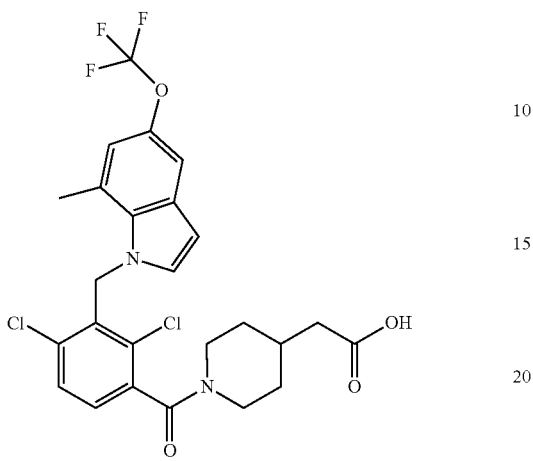

Using a procedure similar to Example A, Step 5, 2-(1-(2,4-dichloro-3-((7-methyl-5-(trifluoromethoxy)-1H-indol-1-yl)methyl)benzoyl)piperidin-4-yl)acetic acid (150 mg, 67%) was prepared from methyl 2-(1-(2,4-dichloro-3-((7-methyl-5-(trifluoromethoxy)-1H-indol-1-yl)methyl)benzoyl)piperidin-4-yl)acetate (230 mg, 0.41 mmol). LC/MS (Method g): $R_t$=1.88 min.;

MS m/z: 543 [M+H]$^+$; $^1$H NMR (DMSO-d$_6$, 400 MHz): δ 12.08 (m, 1H), 7.69 (m, 1H), 7.53 and 7.45 (d, J=8.1 Hz, 1H), 7.37 (s, 1H), 6.93 (s, 1H), 6.69 and 6.68 (d, J=8.1 Hz 1H), 6.46 (m, 1H), 5.89 (m, 2H), 4.46 (m, 1H), 3.29 (m, 1H), 3.03 (m, 1H), 2.89 (s, 3H), 2.80 (m, 1H), 2.15 (m, 2H), 1.93 (m, 1H), 1.77 (m, 1H), 1.60 (m, 1H), 1.12 (m, 2H).

TABLE EJ

The following examples were prepared from 2,4-dichloro-3-((7-methyl-5-(trifluoromethoxy)-1H-indol-1-yl)methyl)benzoic acid (example EJ, Step 2) using the same procedure as described in example EJ, Step 3 and 4 with the appropriate amines.

| Example # | Product | Amine | Intermediate ester $R_t$ min | Intermediate ester m/z ESI+ (M + H)$^+$ | Final acid $R_t$ min | Final acid m/z ESI+ (M + H)$^+$ |
|---|---|---|---|---|---|---|
| EJ-1 | (structure) | (structure) Preparation 82 | 2.16 (method j) | 569 | 1.89 (method g) | 555 |

TABLE EJ-continued

The following examples were prepared from 2,4-dichloro-3-((7-methyl-5-(trifluoromethoxy)-1H-indol-1-yl)methyl)benzoic acid (example EJ, Step 2) using the same procedure as described in example EJ, Step 3 and 4 with the appropriate amines.

| Example # | Product | Amine | Intermediate ester $R_t$ min | Intermediate ester m/z ESI+ (M + H)+ | Final acid $R_t$ min | Final acid m/z ESI+ (M + H)+ |
|---|---|---|---|---|---|---|
| EJ-2 | 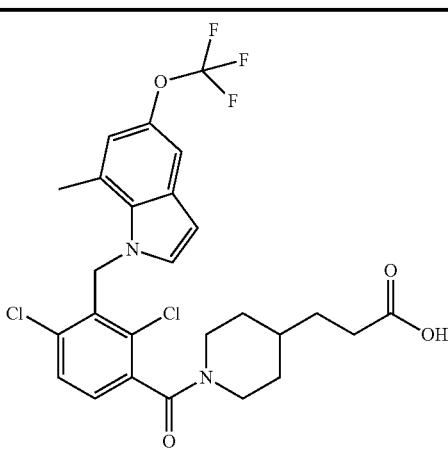 | 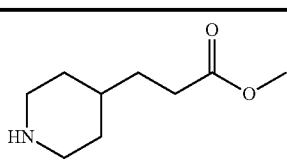 | 2.74 (method i) | 571 | 1.92 (method g) | 557 |

Example EK: 2-(1-(2,4-dimethyl-3-((7-methyl-5-(trifluoromethoxy)-1H-indol-1-yl)methyl)benzoyl)piperidin-4-yl)acetic acid

Step 1: methyl 2,4-dimethyl-3-((7-methyl-5-(trifluoromethoxy)-1H-indol-1-yl)methyl)benzoate

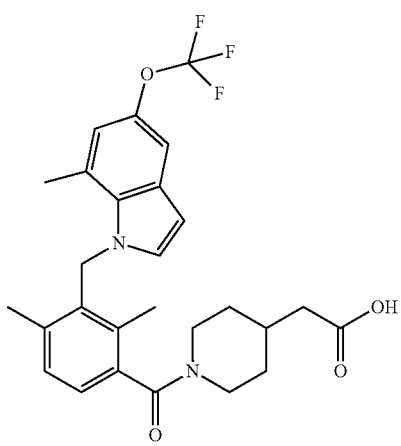 [SMILES: Cc1ccc(C(=O)N2CCC(CC(=O)O)CC2)c(C)c1Cn1ccc2cc(OC(F)(F)F)cc(C)c21]

To a solution of 7-methyl-5-(trifluoromethoxy)-1H-indole (Preparation 64) (200 mg, 0.93 mmol) in ACN (4 mL) was added cesium carbonate (454 mg, 1.4 mmol) and methyl 3-(chloromethyl)-2,4-dimethylbenzoate (227 mg, 1.1 mmol) (Preparation #54) and the reaction mixture was stirred at 70° C. overnight, then filtered and concentrated under reduced pressure. The residue was purified by column chromatography on silica gel (eluting with 10% to 20% ethylacetate in cyclohexane) to give methyl 2,4-dimethyl-3-((7-methyl-5-(trifluoromethoxy)-1H-indol-1-yl)methyl)benzoate (300 mg, 64%).

LC/MS (Method j): $R_t$=2.37 min.; MS m/z: 392 [M+H]+; $^1$H NMR (DMSO-$d_6$, 300 MHz): δ 7.71 (d, J=7.9 Hz, 1H), 7.36 (s, 1H), 7.29 (d, J=7.9 Hz, 1H), 6.92 (s, 1H), 6.46 (d, J=3.3 Hz, 1H), 6.39 (d, J=3.3 Hz, 1H), 5.73 (m, 2H), 3.82 (s, 3H), 2.93 (s, 3H), 2.36 (s, 3H), 2.29 (s, 3H).

Step 2: 2,4-dimethyl-3-((7-methyl-5-(trifluoromethoxy)-1H-indol-1-yl)methyl)benzoic acid

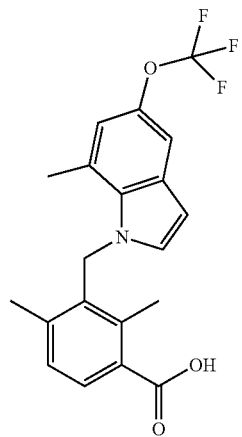 [SMILES: Cc1ccc(C(=O)O)c(C)c1Cn1ccc2cc(OC(F)(F)F)cc(C)c21]

Using a procedure similar to Example A, Step 5, 2,4-dimethyl-3-((7-methyl-5-(trifluoromethoxy)-1H-indol-1-yl)methyl)benzoic acid (245 mg, 84%) was prepared from methyl 2,4-dimethyl-3-((7-methyl-5-(trifluoromethoxy)-1H-indol-1-yl)methyl)benzoate (292 mg, 0.75 mmol). LC/MS (Method j): $R_t$=1.89 min.; MS m/z: 378 [M+H]$^+$; $^1$H NMR (DMSO-d$_6$, 300 MHz): δ 13.01 (broad, 1H), 7.70 (d, J=7.9 Hz, 1H), 7.35 (s, 1H), 7.25 (d, J=7.9 Hz, 1H), 6.92 (s, 1H), 6.47 (d, J=3.3 Hz, 1H), 6.38 (d, J=3.3 Hz, 1H), 5.71 (s, 2H), 2.93 (s, 3H), 2.38 (s, 3H), 2.28 (s, 3H).

Step 3: methyl 2-(1-(2,4-dimethyl-3-((7-methyl-5-(trifluoromethoxy)-1H-indol-1-yl)methyl)benzoyl)piperidin-4-yl)acetate

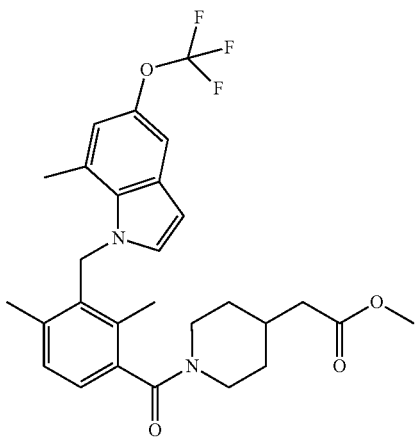

Using a procedure similar to Example A, Step 6, methyl 2-(1-(2,4-dimethyl-3-((7-methyl-5-(trifluoromethoxy)-1H-indol-1-yl)methyl)benzoyl)piperidin-4-yl)acetate (135 mg, 90%) was prepared from 2,4-dimethyl-3-((7-methyl-5-(trifluoromethoxy)-1H-indol-1-yl)methyl)benzoic acid (110 mg, 0.29 mmol) and methyl (4-piperidyl)acetate hydrochloride (68 mg, 0.35 mmol). LC/MS (Method j): $R_t$=2.08 min.; MS m/z: 517 [M+H]$^+$; $^1$H NMR (DMSO-d$_6$, 300 MHz): δ 7.35 (s, 1H), 7.20 (m, 1H), 7.16 and 7.08 (d, J=9 Hz, 1H), 6.91 (s, 1H), 6.49 (m, 1H), 6.40 (m, 1H), 5.68 (s, 2H), 4.52 (m, 1H), 3.59 and 3.57 (s, 3H), 3.27 (m, 1H), 2.97 (m, 1H), 2.92 (s, 3H), 2.76 (m, 1H), 2.30 (m, 2H), 2.24 (s, 3H), 2.10 and 2.05 (s, 3H), 1.92 (m, 1H), 1.75 (m, 1H), 1.55 (m, 1H), 1.12 (m, 2H).

Step 4: 2-(1-(2,4-dimethyl-3-((7-methyl-5-(trifluoromethoxy)-1H-indol-1-yl)methyl)benzoyl)piperidin-4-yl)acetic acid

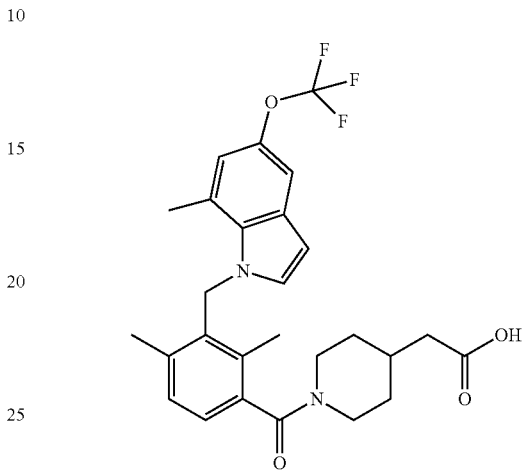

Using a procedure similar to Example A, Step 5, 2-(1-(2,4-dimethyl-3-((7-methyl-5-(trifluoromethoxy)-1H-indol-1-yl)methyl)benzoyl)piperidin-4-yl)acetic acid (115 mg, 85%) was prepared from methyl 2-(1-(2,4-dimethyl-3-((7-methyl-5-(trifluoromethoxy)-1H-indol-1-yl)methyl)benzoyl)piperidin-4-yl)acetate (130 mg, 0.25 mmol). LC/MS (Method g): $R_t$=1.84 min.;
MS m/z: 503 [M+H]$^+$; $^1$H NMR (DMSO-d$_6$, 400 MHz): δ 11.90 (br, 1H), 7.35 (s, 1H), 7.22 and 7.21 (d, J=7.7 Hz, 1H), 7.16 and 7.09 (d, J=7.7 Hz, 1H), 6.91 (s, 1H), 6.49 (m, 1H), 6.40 (m, 1H), 5.68 (m, 2H), 4.51 (m, 1H), 3.27 (m, 1H), 2.98 (m, 1H), 2.92 (s, 3H), 2.75 (m, 1H), 2.25 (s, 3H), 2.16 (m, 2H), 2.10 and 2.05 (s, 3H), 1.92 (m, 1H), 1.74 (m, 1H), 1.53 (m, 1H), 1.05 (m, 2H).

Example EL: 2-(1-(2,4-dichloro-3-(7-methyl-5-(trifluoromethoxy)-1H-indole-1-carbonyl)benzoyl)piperidin-4-yl)acetic acid

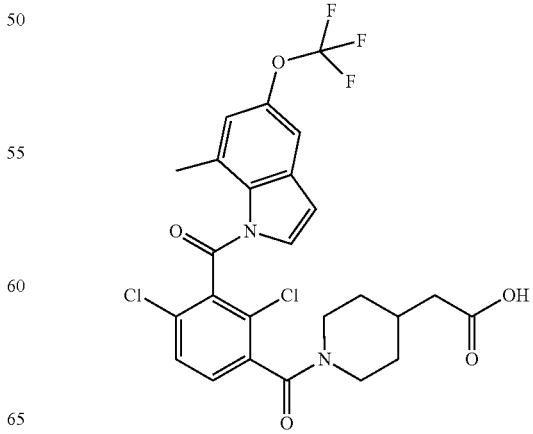

667

Step 1: tert-butyl 2,4-dichloro-3-(7-methyl-5-(trifluoromethoxy)-1H-indole-1-carbonyl)benzoate

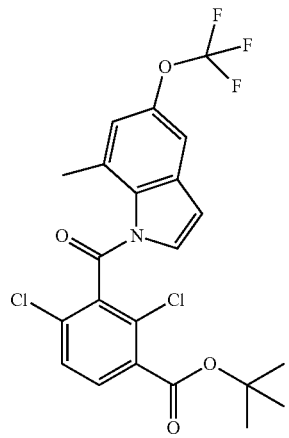 [SMILES: Cc1cc(OC(F)(F)F)cc2ccn(C(=O)c3c(Cl)ccc(C(=O)OC(C)(C)C)c3Cl)c12]

Using a procedure similar to Example DJ, Step 1, tert-butyl 2,4-dichloro-3-(7-methyl-5-(trifluoromethoxy)-1H-indole-1-carbonyl)benzoate (840 mg, 88%) was prepared from 7-methyl-5-(trifluoromethoxy)-1H-indole (Preparation 64) (600 mg, 2.8 mmol) and tert-butyl 2,4-dichloro-3-(fluorocarbonyl)benzoate (631 mg, 2 mmol) (Preparation 55). LC/MS (Method j): $R_t$=2.74 min.; MS m/z: 488 [M+H]$^+$; $^1$H NMR (DMSO-d$_6$, 300 MHz): δ 7.99 (d, J=8.4 Hz, 1H), 7.82 (d, J=8.4 Hz, 1H), 7.54 (s, 1H), 7.41 (d, J=3.8 Hz, 1H), 7.27 (m, 1H), 6.84 (d, J=3.8 Hz, 1H), 2.69 (s, 3H), 1.57 (s, 9H).

Step 2: 2,4-dichloro-3-(7-methyl-5-(trifluoromethoxy)-1H-indole-1-carbonyl)benzoic acid

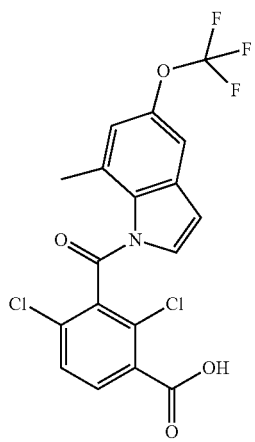 [SMILES: Cc1cc(OC(F)(F)F)cc2ccn(C(=O)c3c(Cl)ccc(C(=O)O)c3Cl)c12]

Using a procedure similar to Example DJ, Step 2, 2,4-dichloro-3-(7-methyl-5-(trifluoromethoxy)-1H-indole-1-carbonyl)benzoic acid (705 mg, 97%) was prepared from tert-butyl 2,4-dichloro-3-(7-methyl-5-(trifluoromethoxy)-1H-indole-1-carbonyl)benzoate (807 mg, 1.65 mmol). LC/MS (Method j): $R_t$=1.77 min.; MS m/z: 432 [M+H]$^+$; $^1$H NMR (DMSO-d$_6$, 300 MHz): δ 13.90 (broad, 1H), 8.03 (d, J=8.6 Hz, 1H), 7.81 (d, J=8.6 Hz, 1H), 7.54 (s, 1H), 7.38 (d, J=3.8 Hz, 1H), 7.27 (m, 1H), 6.84 (d, J=3.8 Hz, 1H), 2.70 (s, 3H).

668

Step 3: methyl 2-(1-(2,4-dichloro-3-(7-methyl-5-(trifluoromethoxy)-1H-indole-1-carbonyl)benzoyl)piperidin-4-yl)acetate

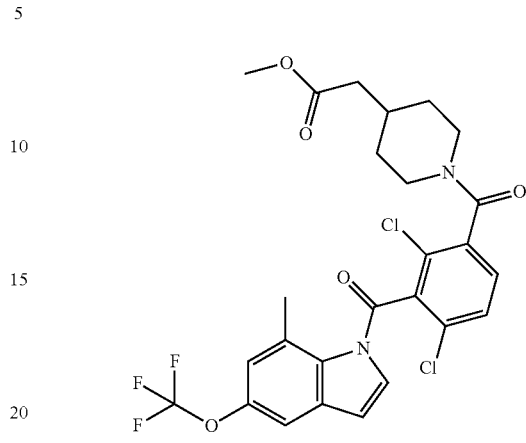

Using a procedure similar to Example A, Step 6, methyl 2-(1-(2,4-dichloro-3-((7-methyl-5-(trifluoromethoxy)-1H-indol-1-yl)methyl)benzoyl)piperidin-4-yl)acetate (240 mg, 82%) was prepared from 2,4-dichloro-3-((7-methyl-5-(trifluoromethoxy)-1H-indol-1-yl)methyl)benzoic acid (200 mg, 0.48 mmol) and methyl (4-piperidyl)acetate hydrochloride (111 mg, 0.57 mmol). LC/MS (Method j): $R_t$=2.14 min.; MS m/z: 557 [M+H]$^+$; $^1$H NMR (DMSO-d$_6$, 300 MHz): δ 7.70 and 7.71 (d, J=8.3 Hz, 1H), 7.53 and 7.45 (d, J=8.3 Hz, 1H), 7.37 (s, 1H), 6.94 (s, 1H), 6.69 (m, 1H), 6.46 (m, 1H), 5.89 (m, 2H), 4.46 (m, 1H), 3.59 and 3.57 (s, 3H), 3.26 (m, 1H), 3.03 (m, 1H), 2.99 (s, 3H), 2.79 (m, 1H), 2.27 (m, 2H), 1.97 (m, 1H), 1.75 (m, 1H), 1.57 (m, 1H), 1.05-1.27 (m, 2H).

Step 4: 2-(1-(2,4-dichloro-3-(7-methyl-5-(trifluoromethoxy)-1H-indole-1-carbonyl)benzoyl)piperidin-4-yl)acetic acid

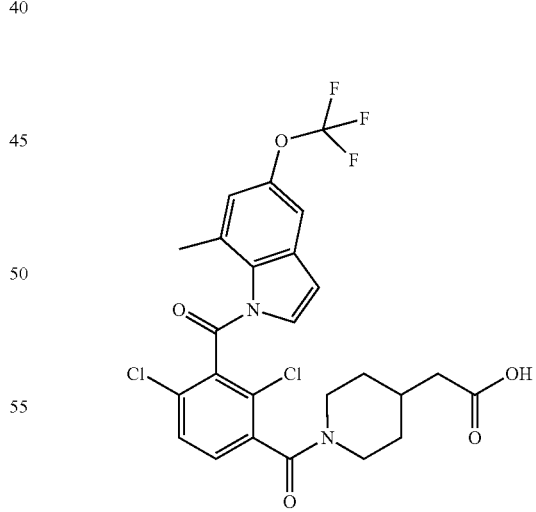

Using a procedure similar to Example A, Step 5, 2-(1-(2,4-dichloro-3-((7-methyl-5-(trifluoromethoxy)-1H-indol-1-yl)methyl)benzoyl)piperidin-4-yl)acetic acid (150 mg, 67%) was prepared from methyl 2-(1-(2,4-dichloro-3-((7-methyl-5-(trifluoromethoxy)-1H-indol-1-yl)methyl)benzoyl)piperidin-4-yl)acetate (230 mg, 0.41 mmol). LC/MS (Method g): $R_t$=1.88 min.;

MS m/z: 543 [M+H]$^+$; $^1$H NMR (DMSO-d$_6$, 400 MHz): δ 12.08 (m, 1H), 7.69 (m, 1H), 7.53 and 7.45 (d, J=8.1 Hz, 1H), 7.37 (s, 1H), 6.93 (s, 1H), 6.69 and 6.68 (d, J=8.1 Hz 1H), 6.46 (m, 1H), 5.89 (m, 2H), 4.46 (m, 1H), 3.29 (m, 1H), 3.03 (m, 1H), 2.89 (s, 3H), 2.80 (m, 1H), 2.15 (m, 2H), 1.93 (m, 1H), 1.77 (m, 1H), 1.60 (m, 1H), 1.12 (m, 2H).

TABLE EL

The following examples were prepared from 2,4-dichloro-3-(7-methyl-5-(trifluoromethoxy)-1H-indole-1-carbonyl)benzoic acid (example EL, Step 2) using the same with the appropriate amines as described in example EL, Step 3 and 4.

| Example # | Product | Amine | Intermediate ester R$_t$ min | Intermediate ester m/z ESI+ (M + H)$^+$ | Final acid R$_t$ min | Final acid m/z ESI+ (M + H)$^+$ |
|---|---|---|---|---|---|---|
| EL-1 | 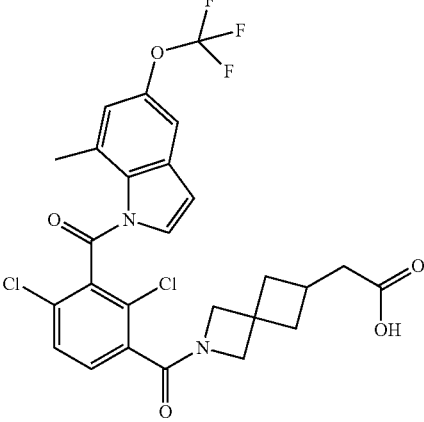 | 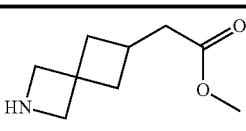 Preparation 82 | 2.15 (method j) | 583 | 1.89 (Method g) | 569 |

Example EM: 2-(1-(2,4-dichloro-3-((5-(difluoromethoxy)-7-methyl-1H-indol-1-yl)methyl)benzoyl)piperidin-4-yl)acetic acid

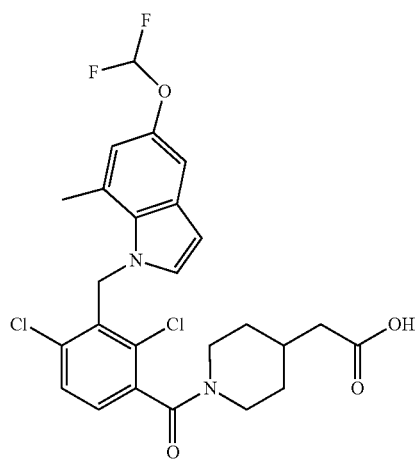 [SMILES: Cc1cc(OC(F)F)cc2ccn(Cc3c(Cl)ccc(C(=O)N4CCC(CC(=O)O)CC4)c3Cl)c12]

Step 1: methyl 2,4-dichloro-3-((5-(difluoromethoxy)-7-methyl-1H-indol-1-yl)methyl)benzoate

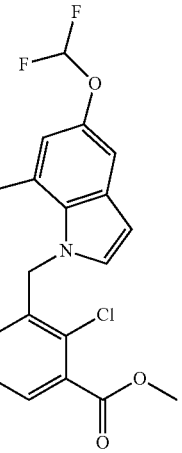

Using a procedure similar to Example DH, Step 1, methyl 2,4-dichloro-3-((5-(difluoromethoxy)-7-methyl-1H-indol-1-yl)methyl)benzoate (300 mg, 47%) was prepared from 5-(difluoromethoxy)-7-methyl-1H-indole (Preparation 65) (280 mg, 1.42 mmol) and methyl 3-(bromomethyl)-2,4-dichlorobenzoate (423 mg, 1.42 mmol) (Preparation #1, step B). LC/MS (Method i): R$_t$=2.63 min.;

MS m/z: 414 [M+H]$^+$; $^1$H NMR (DMSO-d$_6$, 300 MHz): δ 7.87 (d, J=8.4 Hz, 1H), 7.75 (d, J=8.4 Hz, 1H), 7.17 (s, 1H), 7.10 (t, J=75 Hz, 1H), 6.81 (m, 1H), 6.61 (dd, J=3.1 Hz, 1H), 6.39 (d, J=3.1 Hz, 1H), 5.90 (s, 2H), 3.88 (s, 3H), 2.87 (s, 3H).

Step 2: 2,4-dichloro-3-((5-(difluoromethoxy)-7-methyl-1H-indol-1-yl)methyl)benzoic acid

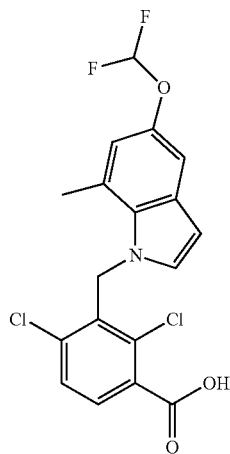 [SMILES: Cc1cc(OC(F)F)cc2ccn(Cc3c(Cl)ccc(C(=O)O)c3Cl)c12]

Using a procedure similar to Example A, Step 5, 2,4-dichloro-3-((5-(difluoromethoxy)-7-methyl-1H-indol-1-yl)methyl)benzoic acid (270 mg, 93%) was prepared from methyl 2,4-dichloro-3-((5-(difluoromethoxy)-7-methyl-1H-indol-1-yl)methyl)benzoate (295 mg, 0.7 mmol). LC/MS (Method i): R$_t$=2.29 min.; MS m/z: 400 [M+H]$^+$; $^1$H NMR (DMSO-d$_6$, 300 MHz): δ 13.74 (broad, 1H), 7.83 (d, J=8.4 Hz, 1H), 7.70 (d, J=8.4 Hz, 1H), 7.17 (m, 1H), 7.10 (t, J=75 Hz, 1H), 6.80 (m, 1H), 6.60 (m, 1H), 6.39 (m, 1H), 5.89 (s, 2H), 2.87 (s, 3H).

Step 3: methyl 2-(1-(2,4-dichloro-3-((5-(difluoromethoxy)-7-methyl-1H-indol-1-yl)methyl)benzoyl)piperidin-4-yl)acetate

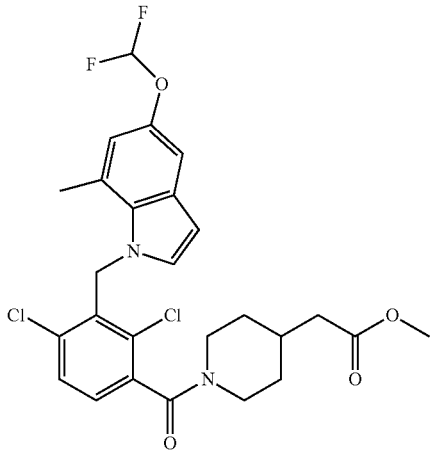 [SMILES: COC(=O)CC1CCN(C(=O)c2ccc(Cl)c(Cn3ccc4cc(OC(F)F)cc(C)c43)c2Cl)CC1]

Using a procedure similar to Example A, Step 6, methyl 2-(1-(2,4-dichloro-3-((5-(difluoromethoxy)-7-methyl-1H-indol-1-yl)methyl)benzoyl)piperidin-4-yl)acetate (120 mg, 83%) was prepared from 2,4-dichloro-3-((5-(difluoromethoxy)-7-methyl-1H-indol-1-yl)methyl)benzoic acid (100 mg, 0.25 mmol) and methyl 2-(piperidin-4-yl)acetate hydrochloride (53 mg, 0.27 mmol). LC/MS (Method i): R$_t$=2.50 min.; MS m/z: 539 [M+H]$^+$; $^1$H NMR (DMSO-d$_6$, 300 MHz): δ 7.69 and 7.68 (m, 1H), 7.52 and 7.44 (d, J=8.3 Hz, 1H), 7.17 (m, 1H), 7.10 (t, J=75 Hz, 1H), 6.80 (m, 1H), 6.63 (m, 1H), 6.40 (m, 1H), 5.87 (m, 2H), 4.46 (m, 1H), 3.59 and 3.57 (s, 3H), 3.26 (m, 1H), 3.03 (m, 1H), 2.88 (s, 3H), 2.81 (m, 1H), 2.28 (m, 2H), 1.97 (m, 1H), 1.75 (m, 1H), 1.56 (m, 1H), 1.13 (m, 2H).

Step 4: 2-(1-(2,4-dichloro-3-((5-(difluoromethoxy)-7-methyl-1H-indol-1-yl)methyl)benzoyl)piperidin-4-yl)acetic acid

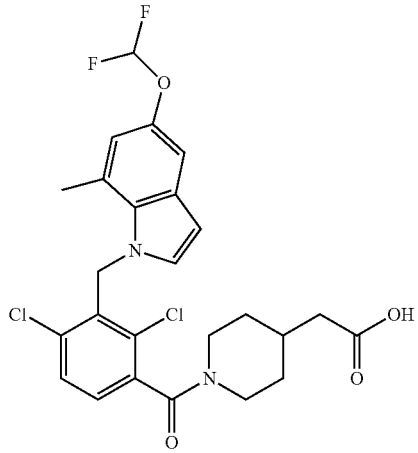 [SMILES: Cc1cc(OC(F)F)cc2ccn(Cc3c(Cl)ccc(C(=O)N4CCC(CC(=O)O)CC4)c3Cl)c12]

Using a procedure similar to Example A, Step 5, 2-(1-(2,4-dichloro-3-((5-(difluoromethoxy)-7-methyl-1H-indol-1-yl)methyl)benzoyl)piperidin-4-yl)acetic acid (105 mg, 85%) was prepared from methyl 2-(1-(2,4-dichloro-3-((5-(difluoromethoxy)-7-methyl-1H-indol-1-yl)methyl)benzoyl)piperidin-4-yl)acetate (120 mg, 0.22 mmol). LC/MS (Method g): R$_t$=1.71 min.; MS m/z: 525 [M+H]$^+$; $^1$H NMR (DMSO-d$_6$, 400 MHz): δ 11.13 (broad, 1H), 7.69 and 7.68 (d, J=8.4 Hz, 1H), 7.52 and 7.45 (d, J=8.4 Hz, 1H), 7.17 (m, 1H), 7.10 (t, J=75 Hz 1H), 6.80 (m, 1H), 6.63 (m, 1H), 6.40 (m, 1H), 5.87 (m, 2H), 4.47 (m, 1H), 3.29 (m, 1H), 3.06 (m, 1H), 2.86 (s, 3H), 2.81 (m, 1H), 2.17 (m, 2H), 1.93 (m, 1H), 1.78 (m, 1H), 1.61 (m, 1H), 1.14 (m, 2H).

Example EN: 2-(1-(2,4-dichloro-3-((5-cyclopropyl-7-fluoro-1H-indol-1-yl)methyl)benzoyl)piperidin-4-yl)acetic acid

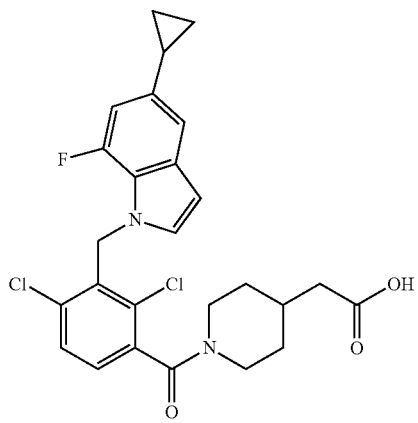 [SMILES: O=C(O)CC1CCN(C(=O)c2ccc(Cl)c(Cn3ccc4cc(C5CC5)cc(F)c43)c2Cl)CC1]

Step 1: methyl 2,4-dichloro-3-((5-cyclopropyl-7-fluoro-1H-indol-1-yl)methyl)benzoate

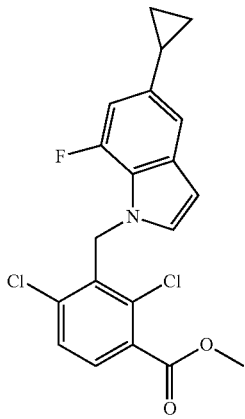 [SMILES: COC(=O)c1ccc(Cl)c(Cn2ccc3cc(C4CC4)cc(F)c32)c1Cl]

Using a procedure similar to Example DH, Step 1, methyl 2,4-dichloro-3-((5-cyclopropyl-7-fluoro-1H-indol-1-yl)methyl)benzoate (610 mg, 68%) was prepared from 5-cyclopropyl-7-fluoro-1H-indole (Preparation 66) (400 mg, 2.28 mmol) and methyl 3-(bromomethyl)-2,4-dichlorobenzoate (680 mg, 2.28 mmol) (Preparation #1, step B). LC/MS (Method i): $R_f$=2.84 min.; MS m/z: 392 [M+H]$^+$; $^1$H NMR (DMSO-d$_6$, 300 MHz): δ 7.83 (d, J=8.4 Hz, 1H), 7.72 (d, J=8.4 Hz, 1H), 7.10 (m, 1H), 6.75 (m, 2H), 6.38 (m, 1H), 5.76 (m, 2H), 3.87 (s, 3H), 1.98 (m, 1H), 0.92 (m, 2H), 0.66 (m, 2H).

Step 2: 2,4-dichloro-3-((5-cyclopropyl-7-fluoro-1H-indol-1-yl)methyl)benzoic acid

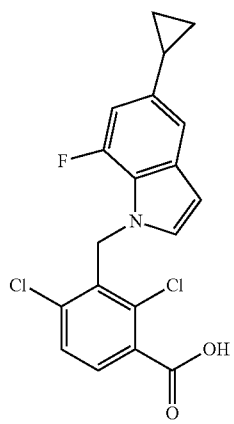 [SMILES: O=C(O)c1ccc(Cl)c(Cn2ccc3cc(C4CC4)cc(F)c32)c1Cl]

Using a procedure similar to Example A, Step 5, 2,4-dichloro-3-((5-cyclopropyl-7-fluoro-1H-indol-1-yl)methyl)benzoic acid (602 mg, 97%) was prepared from methyl 2,4-dichloro-3-((5-cyclopropyl-7-fluoro-1H-indol-1-yl)methyl)benzoate (610 mg, 1.55 mmol). LC/MS (Method i): $R_f$=2.49 min.; MS m/z: 378 [M+H]$^+$; $^1$H NMR (DMSO-d$_6$, 300 MHz): δ 7.77 (d, J=8.4 Hz, 1H), 7.66 (d, J=8.4 Hz, 1H), 7.10 (m, 1H), 6.76 (m, 2H), 6.38 (m, 1H), 5.75 (s, 2H), 1.98 (m, 1H), 0.93 (m, 2H), 0.67 (m, 2H).

Step 3: methyl 2-(1-(2,4-dichloro-3-((5-cyclopropyl-7-fluoro-1H-indol-1-yl)methyl)benzoyl)piperidin-4-yl)acetate

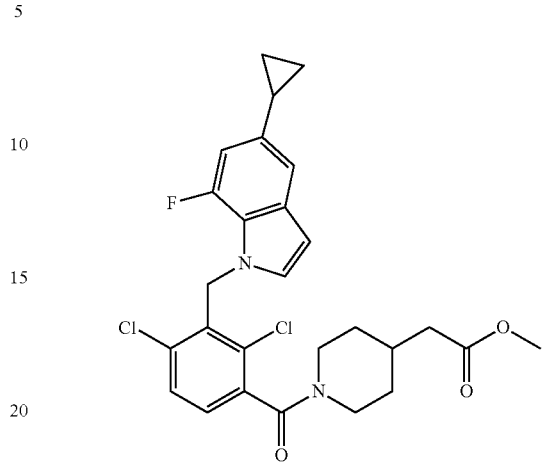

Using a procedure similar to Example A1, methyl 2-(1-(2,4-dichloro-3-((5-cyclopropyl-7-fluoro-1H-indol-1-yl)methyl)benzoyl)piperidin-4-yl)acetate (115 mg, 84%) was prepared from 2,4-dichloro-3-((5-cyclopropyl-7-fluoro-1H-indol-1-yl)methyl)benzoic acid (100 mg, 0.26 mmol) and methyl (4-piperidyl)acetate hydrochloride (102 mg, 0.52 mmol). LC/MS (Method i): $R_f$=2.69 min.; MS m/z: 517 [M+H]$^+$; $^1$H NMR (DMSO-d$_6$, 300 MHz): δ 7.67 and 7.65 (d, J=8.3 Hz, 1H), 7.48 and 7.40 (d, J=8.3 Hz, 1H), 7.10 (m, 1H), 6.80 (m, 1H), 6.74 and 6.69 (s, 1H), 6.39 (m, 1H), 5.69-5.73 (m, 2H), 4.45 (m, 1H), 3.59 and 3.57 (s, 3H), 3.28 (m, 1H), 3.02 (m, 1H), 2.77 (m, 1H), 2.27 (m, 2H), 1.98 (m, 2H), 1.75 (m, 1H), 1.57 (m, 1H), 1.17 (m, 2H), 0.90 (m, 2H), 0.66 (m, 2H).

Step 4: 2-(1-(2,4-dichloro-3-((5-cyclopropyl-7-fluoro-1H-indol-1-yl)methyl)benzoyl)piperidin-4-yl)acetic acid

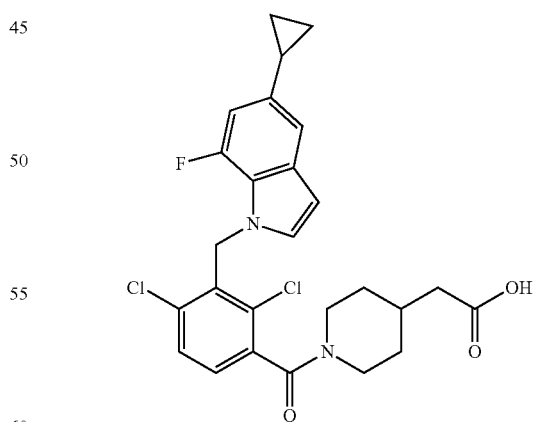

Using a procedure similar to Example A, Step 5, 2-(1-(2,4-dichloro-3-((5-cyclopropyl-7-fluoro-1H-indol-1-yl)methyl)benzoyl)piperidin-4-yl)acetic acid (114 mg, 99%) was prepared from methyl 2-(1-(2,4-dichloro-3-((5-cyclopropyl-7-fluoro-1H-indol-1-yl)methyl)benzoyl)piperidin-4-yl)acetate (115 mg, 0.22 mmol). LC/MS (Method g):

$R_t$=1.88 min.; MS m/z: 503 [M+H]$^+$; $^1$H NMR (DMSO-d$_6$, 400 MHz): δ 12.10 (broad, 1H), 7.66 and 7.64 (d, J=8.4 Hz, 1H), 7.49 and 7.41 (d, J=8.4 Hz, 1H), 7.10 (m, 1H), 6.80 (m, 1H), 6.73 and 6.70 (s, 1H), 6.40 (m, 1H), 5.73 (m, 2H), 4.46 (m, 1H), 3.25 (m, 1H), 3.02 (m, 1H), 2.78 (m, 1H), 2.17 (m, 2H), 1.94 (m, 2H), 1.76 (m, 1H), 1.59 (m, 1H), 1.13 (m, 2H), 0.90 (m, 2H), 0.66 (m, 2H).

Example EO: 2-(1-(2,4-dichloro-3-(5-cyclopropyl-7-fluoro-1H-indole-1-carbonyl)benzoyl)piperidin-4-yl)acetic acid

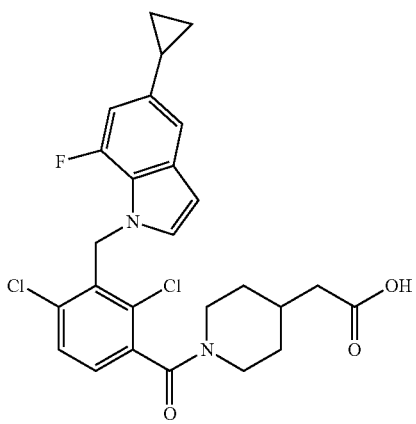

Step 1: tert-butyl 2,4-dichloro-3-(5-cyclopropyl-7-fluoro-1H-indole-1-carbonyl)benzoate

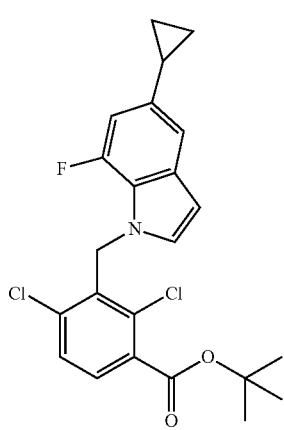 [SMILES: CC(C)(C)OC(=O)c1ccc(Cl)c(Cn2ccc3cc(C4CC4)cc(F)c32)c1Cl]

Using a procedure similar to Example DJ, Step 1, tert-butyl 2,4-dichloro-3-(5-cyclopropyl-7-fluoro-1H-indole-1-carbonyl)benzoate (1.05 g, 94%) was prepared from 5-cyclopropyl-7-fluoro-1H-indole (Preparation 66) (400 mg, 2.28 mmol) and tert-butyl 2,4-dichloro-3-(fluorocarbonyl)benzoate (1 g, 3.4 mmol) (Preparation 55). LC/MS (Method i): $R_t$=2.89 min.; MS m/z: 448 [M+H]$^+$; $^1$H NMR (DMSO-d$_6$, 300 MHz): δ 7.98 (d, J=9 Hz, 1H), 7.79 (d, J=9 Hz, 1H), 7.28 (d, J=3.8 Hz, 1H), 7.21 (s, 1H), 6.99 (m, 1H), 5.76 (s, 1H), 2.05 (m, 1H), 1.56 (m, 9H), 0.99 (m, 2H), 0.75 (m, 2H).

Step 2: 2,4-dichloro-3-(5-cyclopropyl-7-fluoro-1H-indole-1-carbonyl)benzoic acid

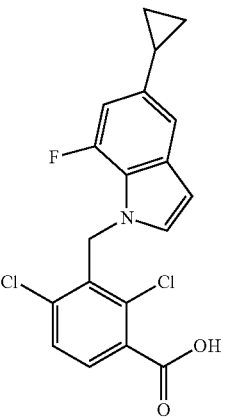 [SMILES: O=C(O)c1ccc(Cl)c(Cn2ccc3cc(C4CC4)cc(F)c32)c1Cl]

Using a procedure similar to Example DJ, Step 2, 2,4-dichloro-3-(5-cyclopropyl-7-fluoro-1H-indole-1-carbonyl)benzoic acid (834 mg, 91%) was prepared from tert-butyl 2,4-dichloro-3-(5-cyclopropyl-7-fluoro-1H-indole-1-carbonyl)benzoate (1 g, 2.3 mmol). LC/MS (Method i): $R_t$=2.23 min.; MS m/z: 392 [M+H]$^+$; $^1$H NMR (DMSO-d$_6$, 300 MHz): δ 13.86 (broad, 1H), 8.03 (d, J=9 Hz, 1H), 7.79 (d, J=9 Hz, 1H), 7.25 (m, 2H), 6.97 (m, 1H), 6.76 (m, 1H), 2.05 (m, 1H), 0.99 (m, 2H), 0.75 (m, 2H).

Step 3: methyl 2-(1-(2,4-dichloro-3-(5-cyclopropyl-7-fluoro-1H-indole-1-carbonyl)benzoyl)piperidin-4-yl)acetate

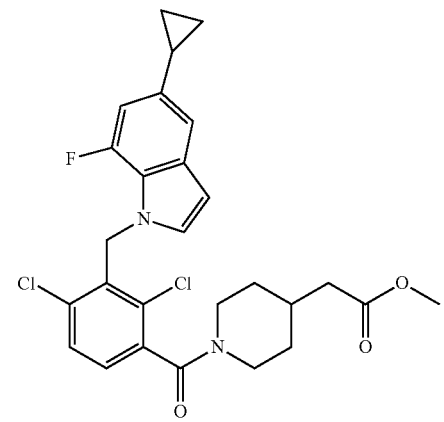 [SMILES: COC(=O)CC1CCN(C(=O)c2ccc(Cl)c(Cn3ccc4cc(C5CC5)cc(F)c43)c2Cl)CC1]

Using a procedure similar to Example A1, methyl 2-(1-(2,4-dichloro-3-(5-cyclopropyl-7-fluoro-1H-indole-1-carbonyl)benzoyl)piperidin-4-yl)acetate (107 mg, 79%) was prepared from 2,4-dichloro-3-(5-cyclopropyl-7-fluoro-1H-indole-1-carbonyl)benzoic acid (100 mg, 0.25 mmol) and methyl (4-piperidyl)acetate hydrochloride (74 mg, 0.38 mmol). LC/MS (Method i): $R_t$=2.50 min.; MS m/z: 531 [M+H]$^+$ $^1$H NMR (DMSO-d$_6$, 300 MHz): δ=8.13-7.14 (m, 4H), 7.02-6.74 (m, 2H), 4.45 (m, 1H), 3.62-3.56 (m, 3H), 3.26-3.15 (m, 1H), 3.05 (m, 1H), 2.80 (m, 1H), 2.28 (m, 2H), 1.99 (m, 2H), 1.76 (m, 1H), 1.60 (m, 1H), 1.15 (m, 2H), 0.97 (m, 2H), 0.73 (m, 2H).

Step 4: 2-(1-(2,4-dichloro-3-(5-cyclopropyl-7-fluoro-1H-indole-1-carbonyl)benzoyl)piperidin-4-yl)acetic acid

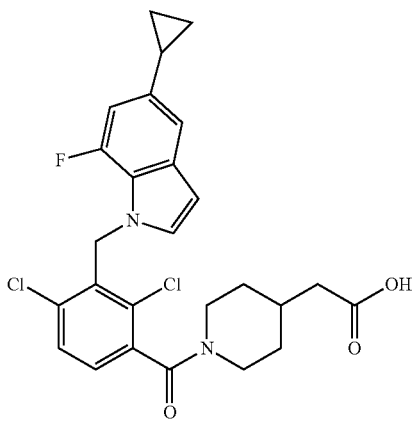

Using a procedure similar to Example A, Step 5, 2-(1-(2,4-dichloro-3-(5-cyclopropyl-7-fluoro-1H-indole-1-carbonyl)benzoyl)piperidin-4-yl)acetic acid (80 mg, 77%) was prepared from methyl 2-(1-(2,4-dichloro-3-(5-cyclopropyl-7-fluoro-1H-indole-1-carbonyl)benzoyl)piperidin-4-yl)acetate (107 mg, 0.2 mmol). LC/MS (Method g): $R_t$=1.72 min.; MS m/z: 517 [M+H]$^+$; $^1$H NMR (DMSO-d$_6$, 500 MHz): δ 12.04 (broad, 1H), 8.12-7.16 (m, 4H), 7.00-6.73 (m, 2H), 4.45 (m, 1H), 3.56 (m, 1H), 3.22 (m, 1H), 3.05 (m, 1H), 2.80 (m, 1H), 2.19 (m, 1H), 2.05 (m, 1H), 1.95 (m, 1H), 1.78 (m, 1H), 1.63 (m, 1H), 1.13 (m, 2H), 0.99 (m, 2H), 0.75 (m, 2H).

Example EP: 2-(1-(2,4-dichloro-3-((7-fluoro-5-(trifluoromethyl)-1H-indol-1-yl)methyl)benzoyl)piperidin-4-yl)acetic acid

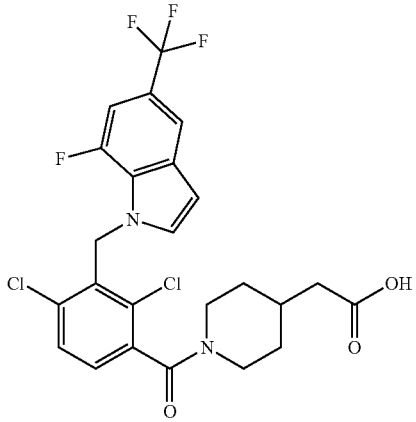

Step 1: methyl 2,4-dichloro-3-((7-fluoro-5-(trifluoromethyl)-1H-indol-1-yl)methyl)benzoate

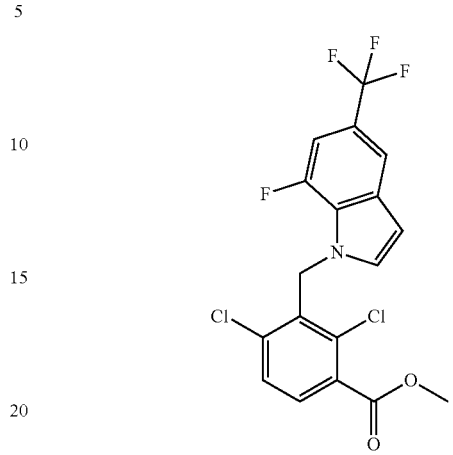

Using a procedure similar to Example DH, Step 1, methyl 2,4-dichloro-3-((7-fluoro-5-(trifluoromethyl)-1H-indol-1-yl)methyl)benzoate (324 mg, 69%) was prepared from 7-fluoro-5-(trifluoromethyl)-1H-indole (Preparation 67) (225 mg, 1.1 mmol) and methyl 3-(bromomethyl)-2,4-dichlorobenzoate (350 mg, 1.1 mmol) (Preparation #1, step B). LC/MS (Method i): $R_t$=2.81 min.; MS m/z: 420 [M+H]$^+$; $^1$H NMR (DMSO-d$_6$, 300 MHz): δ 7.85 (m, 2H), 7.72 (d, J=8.4 Hz, 1H), 7.38 (m, 1H), 7.07 (d, J=3.3 Hz, 1H), 6.71 (m, 1H), 5.88 (s, 2H), 3.87 (s, 3H)

Step 2: 2,4-dichloro-3-((7-fluoro-5-(trifluoromethyl)-1H-indol-1-yl)methyl)benzoic acid

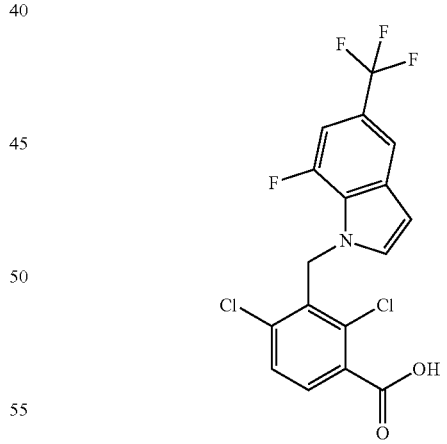

Using a procedure similar to Example A, Step 5, 2,4-dichloro-3-((7-fluoro-5-(trifluoromethyl)-1H-indol-1-yl)methyl)benzoic acid (299 mg, 97%) was prepared from methyl 2,4-dichloro-3-((7-fluoro-5-(trifluoromethyl)-1H-indol-1-yl)methyl)benzoate (320 mg, 0.76 mmol). LC/MS (Method i): $R_t$=2.47 min.; MS m/z: 406 [M+H]$^+$; $^1$H NMR (DMSO-d$_6$, 300 MHz): δ 13.73 (broad, 1H), 7.85 (s, 1H), 7.82 (d, J=8.3 Hz, 1H), 7.70 (J=8.3 Hz, 1H), 7.39 (m, 1H), 7.06 (d, J=3.3 Hz, 1H), 6.71 (m, 1H), 5.88 (s, 2H).

Step 3: methyl 2-(1-(2,4-dichloro-3-((7-fluoro-5-(trifluoromethyl)-1H-indol-1-yl)methyl)benzoyl)piperidin-4-yl)acetate

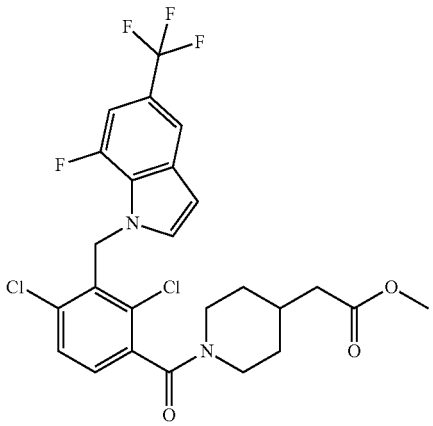 [SMILES: COC(=O)CC1CCN(C(=O)c2ccc(Cl)c(Cn3ccc4cc(C(F)(F)F)cc(F)c43)c2Cl)CC1]

Using a procedure similar to Example A1, methyl 2-(1-(2,4-dichloro-3-((7-fluoro-5-(trifluoromethyl)-1H-indol-1-yl)methyl)benzoyl)piperidin-4-yl)acetate (103 mg, 77%) was prepared from 2,4-dichloro-3-((7-fluoro-5-(trifluoromethyl)-1H-indol-1-yl)methyl)benzoic acid (100 mg, 0.26 mmol) and methyl (4-piperidyl)acetate hydrochloride (71 mg, 0.36 mmol). LC/MS (Method i): $R_t$=2.67 min.; MS m/z: 545 [M+H]$^+$; $^1$H NMR (DMSO-d$_6$, 300 MHz): δ 7.86 (s, 1H), 7.68 and 7.66 (d, J=8.3 Hz, 1H), 7.50 and 7.43 (d, J=8.3 Hz, 1H), 7.38 (m, 1H), 7.08 (m, 1H), 6.72 (m, 1H), 5.84 (m, 2H), 4.45 (m, 1H), 3.59 and 3.57 (s, 3H), 3.28 (m, 1H), 3.02 (m, 1H), 2.77 (m, 1H), 2.27 (m, 2H), 1.96 (m, 1H), 1.76 (m, 1H), 1.56 (m, 1H), 1.14 (m, 2H).

Step 4: 2-(1-(2,4-dichloro-3-((7-fluoro-5-(trifluoromethyl)-1H-indol-1-yl)methyl)benzoyl)piperidin-4-yl)acetic acid

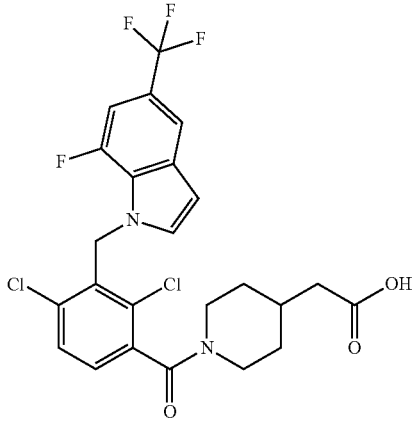

Using a procedure similar to Example A, Step 5, 2-(1-(2,4-dichloro-3-((7-fluoro-5-(trifluoromethyl)-1H-indol-1-yl)methyl)benzoyl)piperidin-4-yl)acetic acid (84 mg, 83%) was prepared from methyl 2-(1-(2,4-dichloro-3-((7-fluoro-5-(trifluoromethyl)-1H-indol-1-yl)methyl)benzoyl)piperidin-4-yl)acetate (103 mg, 0.17 mmol). LC/MS (Method g): $R_t$=1.87 min.; MS m/z: 531 [M+H]$^+$; $^1$H NMR (DMSO-d$_6$, 400 MHz): δ 12.11 (br, 1H), 7.86 (s, 1H), 7.68 and 6.66 (d, J=8.3 Hz, 1H), 7.51 and 7.43 (d, J=8.3 Hz, 1H), 7.38 (m, 1H), 7.08 (m, 1H), 6.72 (m, 1H), 5.84 (m, 2H), 4.45 (m, 1H), 3.27 (m, 1H), 3.02 (m, 1H), 2.80 (m, 1H), 2.17 (m, 2H), 1.92 (m, 1H), 1.76 (m, 1H), 1.59 (m, 1H), 1.14 (m, 2H).

Example EQ: 2-(1-(4,6-dichloro-5-(3,7-dimethyl-5-(trifluoromethyl)-1H-indole-1-carbonyl)nicotinoyl)piperidin-4-yl)acetic acid

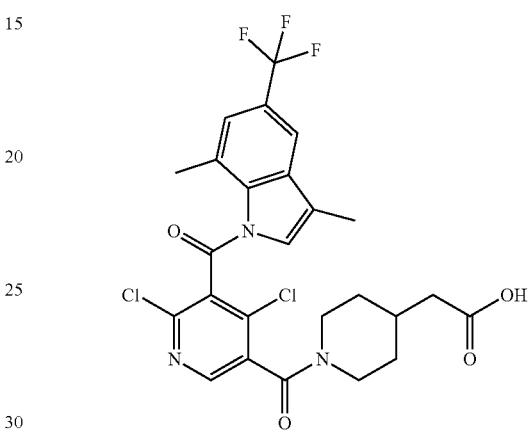

Step 1: tert-butyl 4,6-dichloro-5-(3,7-dimethyl-5-(trifluoromethyl)-1H-indole-1-carbonyl)nicotinate

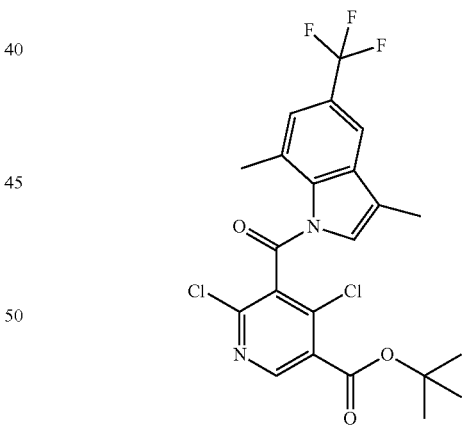

Using a procedure similar to Example DJ, Step 1, tert-butyl 4,6-dichloro-5-(3,7-dimethyl-5-(trifluoromethyl)-1H-indole-1-carbonyl)nicotinate (1.36 g, 63%) was prepared from 3,7-dimethyl-5-(trifluoromethyl)-1H-indole (Preparation #43) (0.95 g, 4.46 mmol) and tert-butyl 4,6-dichloro-5-(chlorocarbonyl)nicotinate (2.07 g, 6.68 mmol) (Preparation 56). LC/MS (Method i): Rt=2.81 min.;

MS m/z: 487 [M+H]$^+$; $^1$H NMR (DMSO-d$_6$, 300 MHz): δ 9.01 (s, 1H), 7.82 (s, 1H), 7.62 (s, 1H), 7.56 (s, 1H), 2.73 (s, 3H), 2.22 (s, 3H), 1.59 (s, 9H).

Step 2: 4,6-dichloro-5-(3,7-dimethyl-5-(trifluoromethyl)-1H-indole-1-carbonyl)nicotinic acid

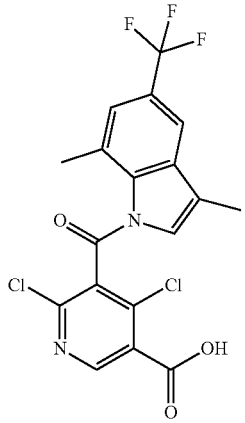 [SMILES: Cc1cn(C(=O)c2c(Cl)ncc(C(=O)O)c2Cl)c2c(C)cc(C(F)(F)F)cc12]

Using a procedure similar to Example DJ, Step 2, 4,6-dichloro-5-(3,7-dimethyl-5-(trifluoromethyl)-1H-indole-1-carbonyl)nicotinic acid (1.48 g, 100%) was prepared tert-butyl 4,6-dichloro-5-(3,7-dimethyl-5-(trifluoromethyl)-1H-indole-1-carbonyl)nicotinate (1.36 g, 2.79 mmol). LC/MS (Method i): $R_t$=2.30 min.; MS m/z: 431 [M+H]$^+$; $^1$H NMR (DMSO-d$_6$, 300 MHz): δ 14.20 (broad, 1H), 9.04 (s, 1H), 7.82 (s, 1H), 7.62 (s, 1H), 7.54 (s, 1H), 2.73 (s, 3H), 2.22 (s, 3H).

Step 3: methyl 2-(1-(4,6-dichloro-5-(3,7-dimethyl-5-(trifluoromethyl)-1H-indole-1-carbonyl)nicotinoyl)piperidin-4-yl)acetate

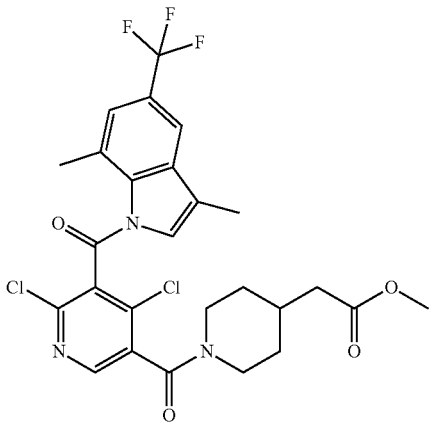 [SMILES: COC(=O)CC1CCN(C(=O)c2cnc(Cl)c(C(=O)n3cc(C)c4cc(C(F)(F)F)cc(C)c43)c2Cl)CC1]

Using a procedure similar to Example A1, methyl 2-(1-(4,6-dichloro-5-(3,7-dimethyl-5-(trifluoromethyl)-1H-indole-1-carbonyl)nicotinoyl)piperidin-4-yl)acetate (280 mg, 42%) was prepared from 4,6-dichloro-5-(3,7-dimethyl-5-(trifluoromethyl)-1H-indole-1-carbonyl)nicotinic acid (500 mg, 1.16 mmol) and methyl (4-piperidyl)acetate hydrochloride (337 mg, 1.74 mmol). LC/MS (Method i): $R_t$=2.48 min.; MS m/z: 570 [M+H]$^+$; $^1$H NMR (DMSO-d$_6$, 300 MHz): δ 8.70 (m, 1H), 7.83 (s, 1H), 7.72 and 7.50 (m, 1H), 7.61 (s, 1H), 4.47 (m, 1H), 3.72 (m, 1H), 3.60 (m, 3H), 3.10 (m, 1H), 2.86 (m, 1H), 2.71 (s, 3H), 2.31 (m, 2H), 2.23 (s, 3H), 2.00 (m, 1H), 1.77 (m, 1H), 1.64 (m, 1H), 1.18 (m, 2H).

Step 4: 2-(1-(4,6-dichloro-5-(3,7-dimethyl-5-(trifluoromethyl)-1H-indole-1-carbonyl)nicotinoyl)piperidin-4-yl)acetic acid

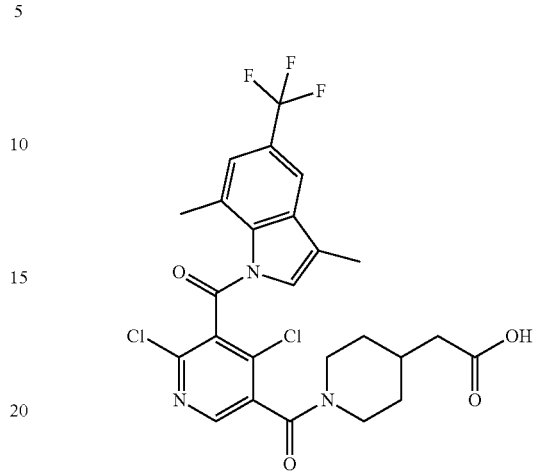

Using a procedure similar to Example A, Step 5, 2-(1-(4,6-dichloro-5-(3,7-dimethyl-5-(trifluoromethyl)-1H-indole-1-carbonyl)nicotinoyl)piperidin-4-yl)acetic acid (176 mg, 64%) was prepared from methyl 2-(1-(4,6-dichloro-5-(3,7-dimethyl-5-(trifluoromethyl)-1H-indole-1-carbonyl)nicotinoyl)piperidin-4-yl)acetate (278 mg, 0.48 mmol). LC/MS (Method g): $R_t$=1.86 min.;

MS m/z: 556 [M+H]$^+$; $^1$H NMR (DMSO-d$_6$, 400 MHz): δ 12.11 (broad, 1H), 8.70 (m, 1H), 7.83 (s, 1H), 7.72 and 7.50 (m, 1H), 7.62 (s, 1H), 4.47 (m, 1H), 3.73 and 3.45 (m, 1H), 3.10 (m, 1H), 2.85 (m, 1H), 2.71 (s, 3H), 2.23 (s, 3H), 2.17 (m, 2H), 1.96 (m, 1H), 1.75 (m, 1H), 1.66 (m, 1H), 1.15 (m, 2H).

Example ER: 2-(1-(4,6-dichloro-5-((3,7-dimethyl-5-(trifluoromethyl)-1H-indol-1-yl)methyl)nicotinoyl)piperidin-4-yl)acetic acid

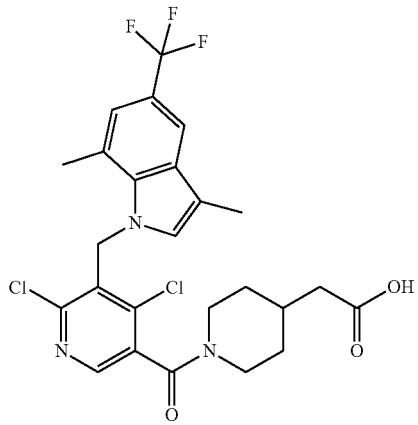 [SMILES: Cc1cn(Cc2c(Cl)ncc(C(=O)N3CCC(CC(=O)O)CC3)c2Cl)c2c(C)cc(C(F)(F)F)cc12]

Step 1: tert-butyl 4,6-dichloro-5-((3,7-dimethyl-5-(trifluoromethyl)-1H-indol-1-yl)methyl)nicotinate

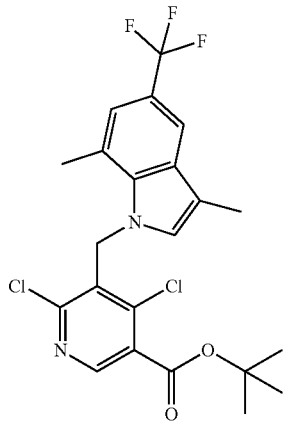 [SMILES: Cc1cn(Cc2c(Cl)ncc(C(=O)OC(C)(C)C)c2Cl)c2c(C)cc(C(F)(F)F)cc12]

Using a procedure similar to Example DH, Step 1, tert-butyl 4,6-dichloro-5-((3,7-dimethyl-5-(trifluoromethyl)-1H-indol-1-yl)methyl)nicotinate (85 mg, 28%) was prepared from 3,7-dimethyl-5-(trifluoromethyl)-1H-indole (Preparation #43) (100 mg, 0.47 mmol) and tert-butyl 4,6-dichloro-5-(((methylsulfonyl)oxy)methyl)nicotinate (167 mg, 0.47 mmol) (Preparation 57). LC/MS (Method j): $R_t$=2.66 min.; MS m/z: 473 [M+H]$^+$; $^1$H NMR (DMSO-d$_6$, 300 MHz): δ 8.82 (s, 1H), 7.69 (s, 1H), 7.23 (s, 1H), 6.74 (s, 1H), 5.90 (s, 2H), 2.91 (s, 3H), 2.18 (s, 3H), 1.57 (s, 9H).

Step 2: 4,6-dichloro-5-((3,7-dimethyl-5-(trifluoromethyl)-1H-indol-1-yl)methyl)nicotinic acid

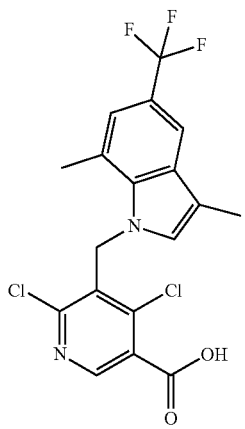 [SMILES: Cc1cn(Cc2c(Cl)ncc(C(=O)O)c2Cl)c2c(C)cc(C(F)(F)F)cc12]

Using a procedure similar to Example DJ, Step 2, 4,6-dichloro-5-((3,7-dimethyl-5-(trifluoromethyl)-1H-indol-1-yl)methyl)nicotinic acid (80 mg, 70%) was prepared from tert-butyl 4,6-dichloro-5-((3,7-dimethyl-5-(trifluoromethyl)-1H-indol-1-yl)methyl)nicotinate (85 mg, 0.18 mmol). LC/MS (Method i): $R_t$=2.30 min.; MS m/z: 417 [M+H]$^+$; $^1$H NMR (DMSO-d$_6$, 300 MHz): δ 14.14 (broad, 1H), 8.85 (s, 1H), 7.69 (s, 1H), 7.23 (s, 1H), 6.72 (s, 1H), 5.91 (s, 2H), 2.91 (s, 3H), 2.18 (s, 3H).

Step 3: methyl 2-(1-(4,6-dichloro-5-((3,7-dimethyl-5-(trifluoromethyl)-1H-indol-1-yl)methyl)nicotinoyl)piperidin-4-yl)acetate

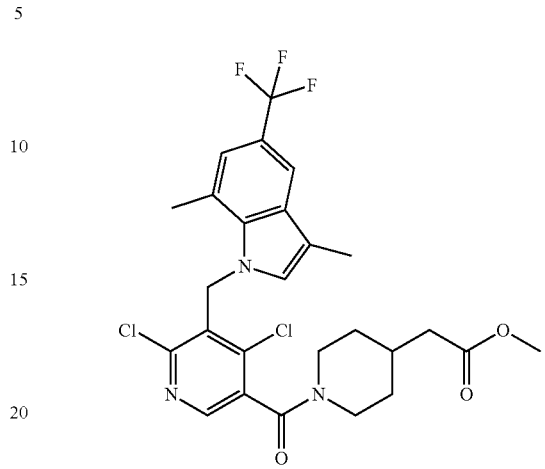

Using a procedure similar to Example A, step 6, methyl 2-(1-(4,6-dichloro-5-((3,7-dimethyl-5-(trifluoromethyl)-1H-indol-1-yl)methyl)nicotinoyl)piperidin-4-yl)acetate (60 mg, 60%) was prepared from 4,6-dichloro-5-((3,7-dimethyl-5-(trifluoromethyl)-1H-indol-1-yl)methyl)nicotinic acid (70 mg, 0.17 mmol) and methyl (4-piperidyl)acetate hydrochloride (41.8 mg, 0.21 mmol). LC/MS (Method i): $R_t$=2.58 min.; MS m/z: 556 [M+H]$^+$; $^1$H NMR (DMSO-d$_6$, 300 MHz): δ 8.56 and 8.49 (s, 1H), 7.69 (s, 1H), 7.23 (s, 1H), 6.76 and 6.73 (s, 1H), 5.88 (m, 2H), 4.46 (m, 1H), 3.50 and 3.57 (s, 3H), 3.40 (m, 1H), 3.07 (m, 1H), 2.90 (s, 3H), 2.84 (m, 1H), 2.29 (s, 2H), 2.19 (s, 3H), 1.99 (m, 1H), 1.76 (m, 1H), 1.60 (m, 1H), 1.17 (m, 2H).

Step 4: 2-(1-(4,6-dichloro-5-((3,7-dimethyl-5-(trifluoromethyl)-1H-indol-1-yl)methyl)nicotinoyl)piperidin-4-yl)acetic acid

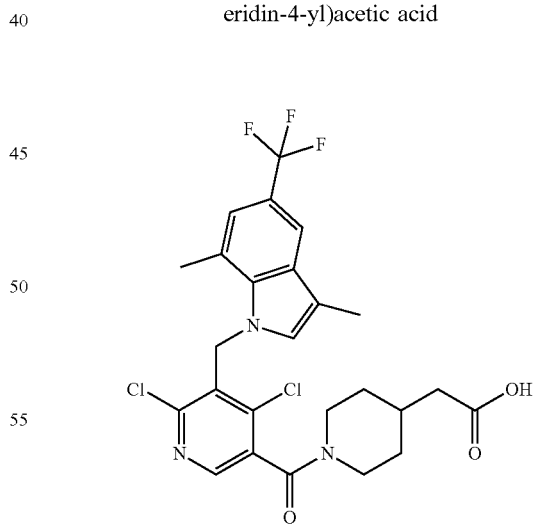

Using a procedure similar to Example O, step 4, 2-(1-(4,6-dichloro-5-((3,7-dimethyl-5-(trifluoromethyl)-1H-indol-1-yl)methyl)nicotinoyl)piperidin-4-yl)acetic acid (36 mg, 70%) was prepared from methyl 2-(1-(4,6-dichloro-5-((3,7-dimethyl-5-(trifluoromethyl)-1H-indol-1-yl)methyl)nicotinoyl)piperidin-4-yl)acetate (50 mg, 0.09 mmol). LC/MS (Method g): $R_t$=1.80 min.;

MS m/z: 542 [M+H]⁺; ¹H NMR (DMSO-d₆, 400 MHz): δ 12.10 (broad, 1H), 8.56 and 8.49 (s, 1H), 7.69 (s, 1H), 7.23 (s, 1H), 6.75 and 6.73 (s, 1H), 5.87 (m, 2H), 4.48 (m, 1H), 3.40 (m, 1H), 3.07 (m, 1H), 2.90 (s, 3H), 2.83 (m, 1H), 2.19 (m, 5H), 1.95 (m, 1H), 1.80 (m, 1H), 1.63 (m, 1H), 1.17 (m, 2H).

Example ES: 2-(1-(2,4-dichloro-3-(7-methyl-5-(trifluoromethyl)-1H-indole-1-carbonyl)benzoyl)piperidin-4-yl)acetic acid

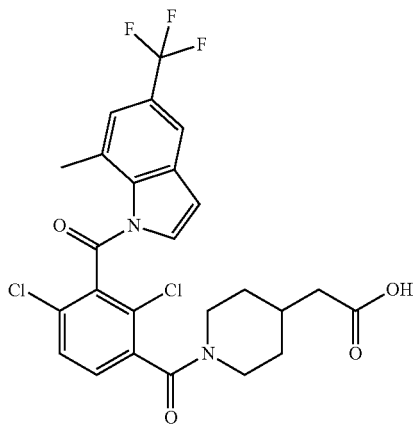 [SMILES: Cc1cc(C(F)(F)F)cc2ccn(C(=O)c3c(Cl)ccc(C(=O)N4CCC(CC(=O)O)CC4)c3Cl)c12]

Step 1: tert-butyl 2,4-dichloro-3-(7-methyl-5-(trifluoromethyl)-1H-indole-1-carbonyl)benzoate

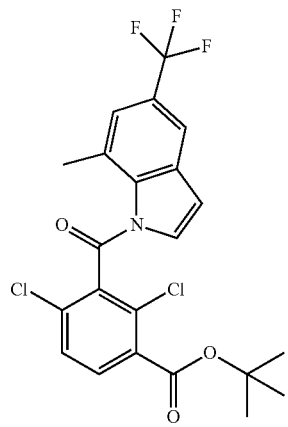 [SMILES: Cc1cc(C(F)(F)F)cc2ccn(C(=O)c3c(Cl)ccc(C(=O)OC(C)(C)C)c3Cl)c12]

Using a procedure similar to Example DJ, Step 1, tert-butyl 2,4-dichloro-3-(7-methyl-5-(trifluoromethyl)-1H-indole-1-carbonyl)benzoate (684 mg, 72%) was prepared from 7-methyl-5-(trifluoromethyl)-1H-indole (Preparation #49) (400 mg, 2 mmol) and tert-butyl 2,4-dichloro-3-(chlorocarbonyl)benzoate (684 mg, 2.2 mmol) (Preparation #44). LC/MS (Method j): R_t=2.61 min.;

MS m/z: 472 [M+H]⁺; ¹H NMR (DMSO-d₆, 300 MHz): δ 8.00 (d, J=8.4 Hz, 1H), 7.93 (s, 1H), 7.83 (d, J=8.4 Hz, 1H), 7.60 (s, 1H), 7.48 (d, J=4.0 Hz, 1H), 6.92 (d, J=4.0 Hz, 1H), 2.74 (s, 3H), 1.57 (s, 9H).

Step 2: 2,4-dichloro-3-(7-methyl-5-(trifluoromethyl)-1H-indole-1-carbonyl)benzoic acid

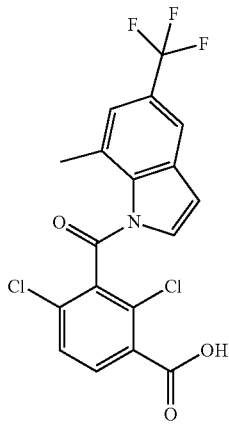 [SMILES: Cc1cc(C(F)(F)F)cc2ccn(C(=O)c3c(Cl)ccc(C(=O)O)c3Cl)c12]

Using a procedure similar to Example DJ, Step 2, 2,4-dichloro-3-(7-methyl-5-(trifluoromethyl)-1H-indole-1-carbonyl)benzoic acid (595 mg, 99%) was prepared from tert-butyl 2,4-dichloro-3-(7-methyl-5-(trifluoromethyl)-1H-indole-1-carbonyl)benzoate (684 mg, 1.5 mmol). LC/MS (Method j): R_t=1.68 min.; MS m/z: 416 [M+H]⁺; ¹H NMR (DMSO-d₆, 300 MHz): δ 13.91 (broad, 1H), 8.06 (d, J=8.4 Hz, 1H), 7.93 (s, 1H), 7.82 (d, J=8.4 Hz, 1H), 7.60 (s, 1H), 7.45 (d, J=3.8 Hz, 1H), 6.92 (d, J=3.8 Hz, 1H), 2.74 (s, 3H).

Step 3: methyl 2-(1-(2,4-dichloro-3-(7-methyl-5-(trifluoromethyl)-1H-indole-1-carbonyl)benzoyl)piperidin-4-yl)acetate

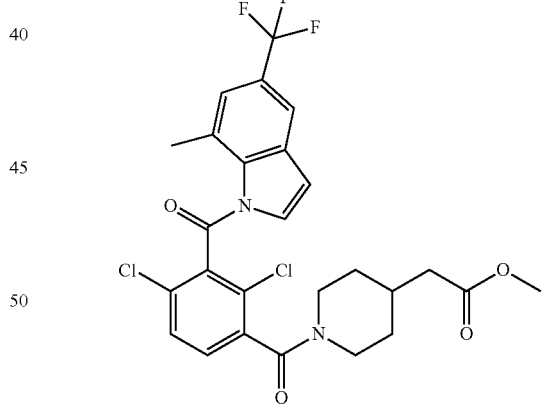

Using a procedure similar to Example A, step 6, methyl 2-(1-(2,4-dichloro-3-(7-methyl-5-(trifluoromethyl)-1H-indole-1-carbonyl)benzoyl)piperidin-4-yl)acetate (118 mg, 88%) was prepared from 2,4-dichloro-3-(7-methyl-5-(trifluoromethyl)-1H-indole-1-carbonyl)benzoic acid (100 mg, 0.24 mmol) and methyl (4-piperidyl)acetate hydrochloride (93 mg, 0.48 mmol). LC/MS (Method i): 2.58 min.; MS m/z: 555 [M+H]⁺; ¹H NMR (DMSO-d₆, 300 MHz): δ 7.93 (m, 1H), 7.82 and 7.80 (d, J=8.4 Hz, 1H), 7.72-7.35 (m, 3H), 6.93 (m, 1H), 4.45 (m, 1H), 3.56 (m, 4H), 3.06 (m, 1H), 2.81 (m, 1H), 2.72 (s, 3H), 2.28 (m, 2H), 1.99 (m, 1H), 1.69-1.77 (m, 1H), 1.61 (m, 1H), 1.18 (m, 2H).

Step 4: 2-(1-(2,4-dichloro-3-(7-methyl-5-(trifluoromethyl)-1H-indol-1-carbonyl)benzoyl)piperidin-4-yl)acetic acid

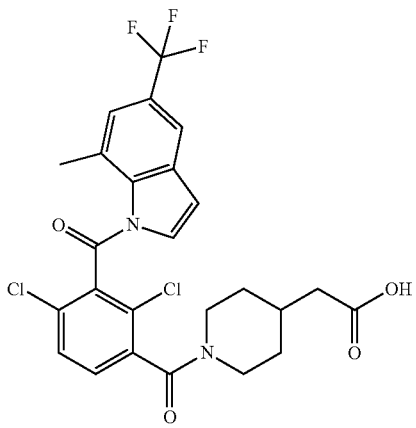 [SMILES: Cc1cc(C(F)(F)F)cc2ccn(C(=O)c3c(Cl)ccc(C(=O)N4CCC(CC(=O)O)CC4)c3Cl)c12]

Using a procedure similar to Example A, step 5, 2-(1-(2,4-dichloro-3-(7-methyl-5-(trifluoromethyl)-1H-indole-1-carbonyl)benzoyl)piperidin-4-yl)acetic acid (99 mg, 84%) was prepared from methyl 2-(1-(2,4-dichloro-3-(7-methyl-5-(trifluoromethyl)-1H-indole-1-carbonyl)benzoyl)piperidin-4-yl)acetate (118 mg, 0.21 mmol). LC/MS (Method g): $R_t$=1.86 min.; MS m/z: 541 [M+H]$^+$; $^1$H NMR (DMSO-d$_6$, 400 MHz): δ 12.16 (broad, 1H), 7.93 (m, 1H), 7.81 and 7.80 (d, J=8.4 Hz, 1H), 7.72-7.36 (m, 3H), 6.93 (m, 1H), 4.47 (m, 1H), 3.55 and 3.24 (m, 1H), 3.06 (m, 1H), 2.81 (m, 1H), 2.72 (s, 3H), 2.18 (m, 2H), 1.95 (m, 1H), 1.77 (m, 1H), 1.63 (m, 1H), 1.16 (m, 2H).

Example ET: (2,4-dichloro-3-((3,7-dimethyl-5-(trifluoromethyl)-1H-pyrrolo[2,3-c]pyridin-1-yl)methyl)phenyl)(morpholino)methanone

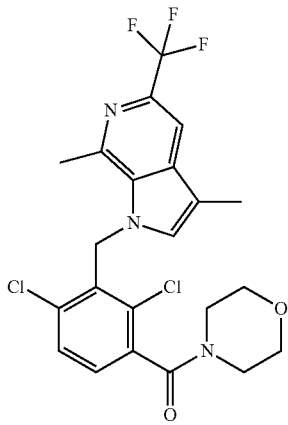 [SMILES: Cc1cn(Cc2c(Cl)ccc(C(=O)N3CCOCC3)c2Cl)c2c(C)nc(C(F)(F)F)cc12]

Using a procedure similar to Example DH, Step 1, (2,4-dichloro-3-((3,7-dimethyl-5-(trifluoromethyl)-1H-pyrrolo[2,3-c]pyridin-1-yl)methyl)phenyl)(morpholino)methanone (101 mg, 67%) was prepared from 3,7-dimethyl-5-(trifluoromethyl)-1H-pyrrolo[2,3-c]pyridine (Preparation 68) (66 mg, 0.31 mmol) and (2,4-dichloro-3-(chloromethyl)phenyl)(morpholino)methanone (105 mg, 0.34 mmol) (Preparation #11). LC/MS (Method g): $R_t$=1.68 min.; MS m/z: 486 [M+H]$^+$; $^1$H NMR (DMSO-d$_6$, 400 MHz): δ 7.87 (s, 1H), 7.73 (d, J=8.4 Hz, 1H), 7.55 (d, J=8.4 Hz, 1H), 6.83 (m, 1H), 5.96 (d, J=15 Hz, 1H), 5.89 (d, J=15 Hz, 1H), 3.64 (m, 4H), 3.54 (m, 2H), 3.19 (m, 2H), 3.08 (s, 3H), 2.20 (m, 3H).

Example EU: 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetic acid

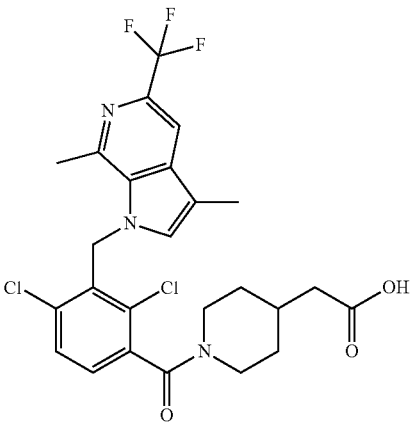 [SMILES: Cc1cn(Cc2c(Cl)ccc(C(=O)N3CCC(CC(=O)O)CC3)c2Cl)c2c(C)nc(C(F)(F)F)cc12]

Step 1: methyl 2,4-dichloro-3-((3,7-dimethyl-5-(trifluoromethyl)-1H-pyrrolo[2,3-c]pyridin-1-yl)methyl)benzoate

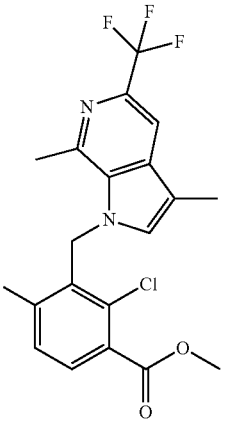

Using a procedure similar to Example DH, Step 1, methyl 2,4-dichloro-3-((3,7-dimethyl-5-(trifluoromethyl)-1H-pyrrolo[2,3-c]pyridin-1-yl)methyl)benzoate (600 mg, 74%) was prepared from 3,7-dimethyl-5-(trifluoromethyl)-1H-pyrrolo[2,3-c]pyridine (Preparation 68) (300 mg, 1.4 mmol) and methyl 3-(bromomethyl)-2,4-dichlorobenzoate (417 mg, 1.4 mmol) ((Preparation #1, step B). LC/MS (Method i): Rt=2.60 min.; MS m/z: 431 [M+H]$^+$; $^1$H NMR (DMSO-d$_6$, 300 MHz): δ 7.90 (d, J=8.4 Hz, 1H), 7.87 (s, 1H), 7.76 (d, J=8.4 Hz, 1H), 6.82 (s, 1H), 5.96 (s, 2H), 3.88 (s, 3H), 3.09 (s, 3H), 2.19 (s, 3H).

Step 2: 2,4-dichloro-3-((3,7-dimethyl-5-(trifluoromethyl)-1H-pyrrolo[2,3-c]pyridin-1-yl)methyl)benzoic acid

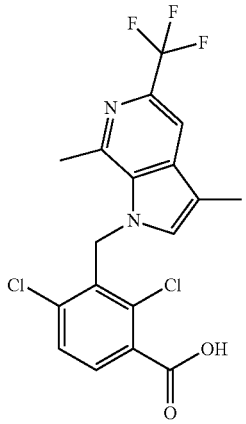 [SMILES: Cc1cn(Cc2c(Cl)ccc(C(=O)O)c2Cl)c2c(C)nc(C(F)(F)F)cc12]

Using a procedure similar to Example A, step 5, 2,4-dichloro-3-((3,7-dimethyl-5-(trifluoromethyl)-1H-pyrrolo[2,3-c]pyridin-1-yl)methyl)benzoic acid (610 mg, 99%) was prepared from methyl 2,4-dichloro-3-((3,7-dimethyl-5-(trifluoromethyl)-1H-pyrrolo[2,3-c]pyridin-1-yl)methyl)benzoate (600 mg, 1.4 mmol). LC/MS (Method i): $R_f$=2.23 min.; MS m/z: 417 [M+H]$^+$; $^1$H NMR (DMSO-d$_6$, 300 MHz): δ 7.86 (s, 1H), 7.70 (d, J=8.4 Hz, 1H), 7.63 (d, J=8.4 Hz, 1H), 6.78 (s, 1H), 5.93 (s, 2H), 3.09 (s, 3H), 2.18 (s, 3H).

Step 3: methyl 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetate

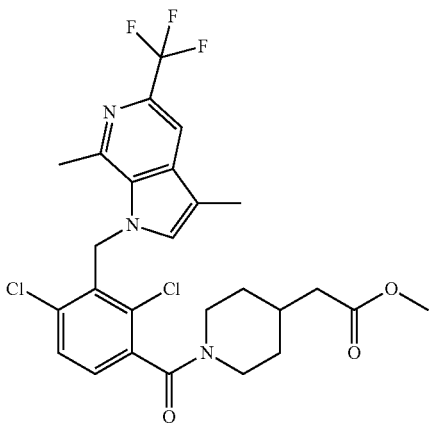 [SMILES: COC(=O)CC1CCN(C(=O)c2ccc(Cl)c(Cn3cc(C)c4cc(C(F)(F)F)nc(C)c43)c2Cl)CC1]

Using a procedure similar to Example A, step 6, methyl 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetate (225 mg, 73%) was prepared from 2,4-dichloro-3-((3,7-dimethyl-5-(trifluoromethyl)-1H-pyrrolo[2,3-c]pyridin-1-yl)methyl)benzoic acid (230 mg, 0.55 mmol) and methyl (4-piperidyl)acetate hydrochloride (117 mg, 0.60 mmol). LC/MS (Method i): $R_f$=2.46 min.; MS m/z: 556 [M+H]$^+$; $^1$H NMR (DMSO-d$_6$, 300 MHz): δ 7.87 (s, 1H), 7.72 and 7.71 (d, J=8.3 Hz, 1H), 7.54 and 7.47 (d, J=8.3 Hz, 1H), 6.82 and 6.80 (s, 1H), 5.92 (m, 2H), 4.44 (m, 1H), 3.59 and 3.57 (s, 3H), 3.27 (m, 1H), 3.08 (s, 3H), 3.02 (m, 1H), 2.81 (m, 1H), 2.28 (m, 2H), 2.20 (s, 3H), 1.99 (m, 1H), 1.72 (m, 1H), 1.57 (m, 1H), 1.14 (m, 2H).

Step 4: 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetic acid

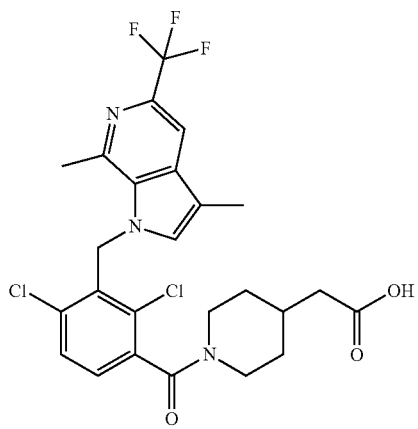 [SMILES: Cc1cn(Cc2c(Cl)ccc(C(=O)N3CCC(CC(=O)O)CC3)c2Cl)c2c(C)nc(C(F)(F)F)cc12]

Using a procedure similar to Example A, step 5, 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetic acid (130 mg, 59%) was prepared from methyl 2-(1-(2,4-dichloro-3-((3,7-dimethyl-5-(trifluoromethyl)-1H-pyrrolo[2,3-c]pyridin-1-yl)methyl)benzoyl)piperidin-4-yl)acetate (225 mg, 0.40 mmol). LC/MS (Method g): $R_f$=1.63 min.; MS m/z: 542 [M+H]$^+$; $^1$H NMR (DMSO-d$_6$, 400 MHz): δ 12.09 (broad, 1H), 7.87 (s, 1H), 7.71 and 7.70 (d, J=8.3 Hz, 1H), 7.55 and 7.53 (d, J=8.3 Hz, 1H), 6.82 and 6.79 (s, 1H), 5.92 (m, 2H), 4.46 (m, 1H), 3.25 (m, 1H), 3.08 (s, 3H), 3.03 (m, 1H), 2.80 (m, 1H), 2.20 (s, 3H), 2.15 (m, 2H), 1.94 (m, 1H), 1.76 (m, 1H), 1.61 (m, 1H), 1.12 (m, 2H).

Example EV: 2-(1-(2,4-dichloro-3-(3,7-dimethyl-5-(trifluoromethyl)-1H-pyrrolo[2,3-c]pyridine-1-carbonyl)benzoyl)piperidin-4-yl)acetic acid

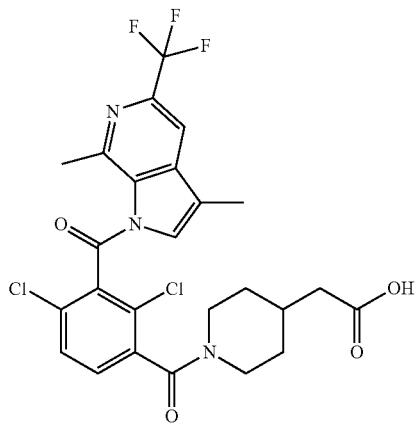 [SMILES: Cc1cn(C(=O)c2c(Cl)ccc(C(=O)N3CCC(CC(=O)O)CC3)c2Cl)c2c(C)nc(C(F)(F)F)cc12]

Step 1: tert-butyl 2,4-dichloro-3-(3,7-dimethyl-5-(trifluoromethyl)-1H-pyrrolo[2,3-c]pyridine-1-carbonyl)benzoate

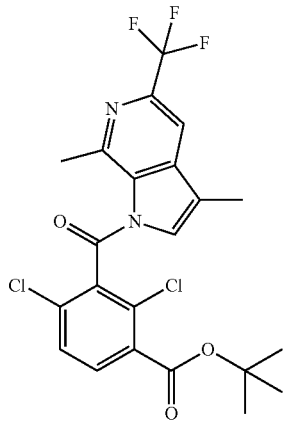 [SMILES: Cc1cn(C(=O)c2c(Cl)ccc(C(=O)OC(C)(C)C)c2Cl)c2c(C)nc(C(F)(F)F)cc12]

Using a procedure similar to Example DJ, Step 1, tert-butyl 2,4-dichloro-3-(3,7-dimethyl-5-(trifluoromethyl)-1H-pyrrolo[2,3-c]pyridin-1-carbonyl)benzoate (690 mg, 68%) was prepared from 3,7-dimethyl-5-(trifluoromethyl)-1H-pyrrolo[2,3-e]pyridine (Preparation 68) (350 mg, 1.6 mmol) and tert-butyl 2,4-dichloro-3-(chlorocarbonyl)benzoate (911 mg, 2.94 mmol) (Preparation #44). LC/MS (Method i): $R_t$=2.80 min.; MS m/z: 487 $[M+H]^+$; $^1$H NMR (DMSO-$d_6$, 300 MHz): δ 8.05 (s, 1H), 8.03 (d, J=8.4 Hz, 1H), 7.84 (d, J=8.4 Hz, 1H), 7.57 (m, 1H), 2.92 (s, 3H), 2.24 (s, 3H), 1.57 (s, 9H).

Step 2: 2,4-dichloro-3-(3,7-dimethyl-5-(trifluoromethyl)-1H-pyrrolo[2,3-c]pyridine-1-carbonyl)benzoic acid

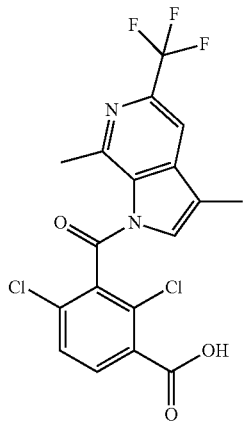 [SMILES: Cc1cn(C(=O)c2c(Cl)ccc(C(=O)O)c2Cl)c2c(C)nc(C(F)(F)F)cc12]

Using a procedure similar to Example DJ, Step 2, 2,4-dichloro-3-(3,7-dimethyl-5-(trifluoromethyl)-1H-pyrrolo[2,3-c]pyridine-1-carbonyl)benzoic acid (370 mg, 52%) was prepared from tert-butyl 2,4-dichloro-3-(3,7-dimethyl-5-(trifluoromethyl)-1H-pyrrolo[2,3-c]pyridine-1-carbonyl)benzoate (690 mg, 1.4 mmol). LC/MS (Method i): $R_t$=2.19 min.; MS m/z: 431 $[M+H]^+$; $^1$H NMR (DMSO-$d_6$, 300 MHz): δ 8.08 (d, J=8.4 Hz, 1H), 8.05 (s, 1H), 7.84 (d, J=8.4 Hz, 1H), 7.55 (d, J=1.3 Hz, 1H), 2.93 (s, 3H), 2.24 (d, J=1.3 Hz, 3H).

Step 3: methyl 2-(1-(2,4-dichloro-3-(3,7-dimethyl-5-(trifluoromethyl)-1H-pyrrolo[2,3-c]pyridine-1-carbonyl)benzoyl)piperidin-4-yl)acetate

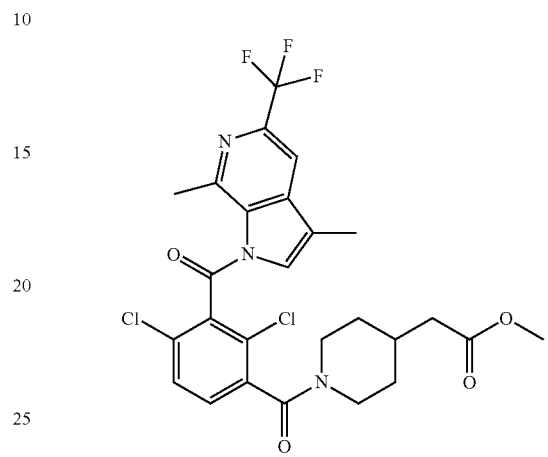

Using a procedure similar to Example A, step 6, methyl 2-(1-(2,4-dichloro-3-(3,7-dimethyl-5-(trifluoromethyl)-1H-pyrrolo[2,3-c]pyridine-1-carbonyl)benzoyl)piperidin-4-yl)acetate (85 mg, 58%) was prepared from 2,4-dichloro-3-(3,7-dimethyl-5-(trifluoromethyl)-1H-pyrrolo[2,3-c]pyridine-1-carbonyl)benzoic acid (100 mg, 0.23 mmol) and methyl (4-piperidyl)acetate hydrochloride (49 mg, 0.25 mmol). LC/MS (Method i): $R_t$=2.45 min.; MS m/z: 570 $[M+H]^+$; $^1$H NMR (DMSO-$d_6$, 300 MHz): δ 8.05 (s, 1H), 7.83 (m, 1H), 7.67 (m, 1.5H), 7.48 (m, 0.5H), 4.46 (m, 1H), 3.60 (m, 3H), 3.28 (m, 1H), 3.06 (m, 1H), 2.91 (s, 3H), 2.82 (m, 1H), 2.30 (m, 2H), 2.25 and 2.24 (s, 3H), 1.98 (m, 1H), 1.77 (m, 1H), 1.62 (m, 1H), 1.17 (m, 2H).

Step 4: 2-(1-(2,4-dichloro-3-(3,7-dimethyl-5-(trifluoromethyl)-1H-pyrrolo[2,3-c]pyridine-1-carbonyl)benzoyl)piperidin-4-yl)acetic acid

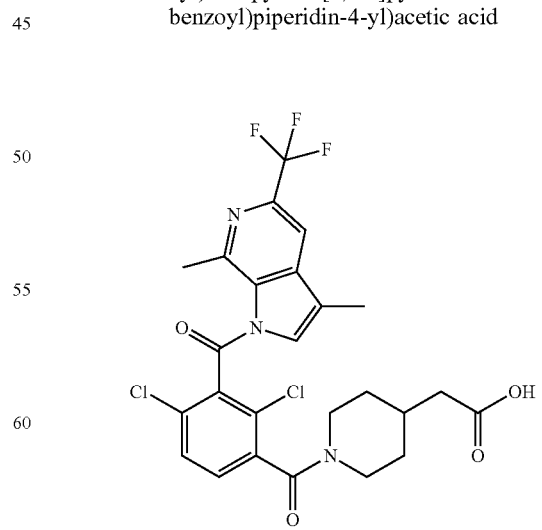

Using a procedure similar to Example A, step 5, 2-(1-(2,4-dichloro-3-(3,7-dimethyl-5-(trifluoromethyl)-1H-pyrrolo

[2,3-c]pyridine-1-carbonyl)benzoyl)piperidin-4-yl)acetic acid (48 mg, 57%) was prepared from methyl 2-(1-(2,4-dichloro-3-(3,7-dimethyl-5-(trifluoromethyl)-1H-pyrrolo[2,3-c]pyridine-1-carbonyl)benzoyl)piperidin-4-yl)acetate (85 mg, 0.15 mmol). LC/MS (Method g): $R_t$=1.73 min.; MS m/z: 556 [M+H]$^+$; $^1$H NMR (DMSO-d$_6$, 400 MHz): δ 8.05 (s, 1H), 7.82 (m, 1H), 7.70 (m, 1.5H), 7.47 (m, 0.5H), 3.60 (m, 1H), 3.25 (m, 1H), 3.09 (m, 1H), 2.92 (s, 3H), 2.84 (m, 1H), 2.25 (s, 3H), 2.17 (m, 2H), 1.94 (m, 1H), 1.77 (m, 1H), 1.65 (m, 1H), 1.14 (m, 2H).

Example EW: 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetic acid

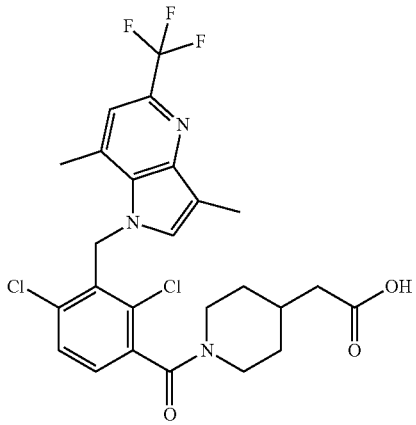 [SMILES: Cc1cn(Cc2c(Cl)ccc(C(=O)N3CCC(CC(=O)O)CC3)c2Cl)c2c(C)cc(C(F)(F)F)nc12]

Step 1: methyl 2,4-dichloro-3-((3,7-dimethyl-5-(trifluoromethyl)-1H-pyrrolo[3,2-b]pyridin-1-yl)methyl)benzoate

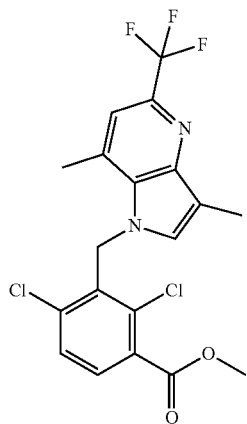 [SMILES: COC(=O)c1ccc(Cl)c(Cn2cc(C)c3nc(C(F)(F)F)cc(C)c32)c1Cl]

Using a procedure similar to Example DH, Step 1, methyl 2,4-dichloro-3-((3,7-dimethyl-5-(trifluoromethyl)-1H-pyrrolo[3,2-b]pyridin-1-yl)methyl)benzoate (579 mg, 96%) was prepared from 3,7-dimethyl-5-(trifluoromethyl)-1H-pyrrolo[3,2-b]pyridine (300 mg, 1.4 mmol) (Preparation 69) and methyl 3-(bromomethyl)-2,4-dichlorobenzoate (417 mg, 1.4 mmol) (Preparation #1, step B). LC/MS (Method i): $R_t$=2.56 min.; MS m/z: 431 [M+H]$^+$; $^1$H NMR (DMSO-d$_6$, 300 MHz): δ 7.89 (d, J=8.0 Hz, 1H), 7.76 (d, J=8.0 Hz, 1H), 7.46 (s, 1H), 6.92 (m, 1H), 5.91 (s, 2H), 3.88 (s, 3H), 2.96 (s, 3H), 2.19 (m, 3H).

Step 2: 2,4-dichloro-3-((3,7-dimethyl-5-(trifluoromethyl)-1H-pyrrolo[3,2-b]pyridin-1-yl)methyl)benzoic acid

Using a procedure similar to Example A, step 5, 2,4-dichloro-3-((3,7-dimethyl-5-(trifluoromethyl)-1H-pyrrolo[3,2-b]pyridin-1-yl)methyl)benzoic acid (545 mg, 97%) was prepared from methyl 2,4-dichloro-3-((3,7-dimethyl-5-(trifluoromethyl)-1H-pyrrolo[3,2-b]pyridin-1-yl)methyl)benzoate (579 mg, 1.34 mmol). LC/MS (Method i): $R_t$=2.23 min.; MS m/z: 417 [M+H]$^+$; $^1$H NMR (DMSO-d$_6$, 300 MHz): δ 13.70 (broad, 1H), 7.85 (d, J=8.4 Hz, 1H), 7.72 (d, J=8.4 Hz, 1H), 7.46 (s, 1H), 6.92 (m, 1H), 5.90 (s, 2H), 2.96 (s, 3H), 2.19 (m, 3H).

Step 3: methyl 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetate

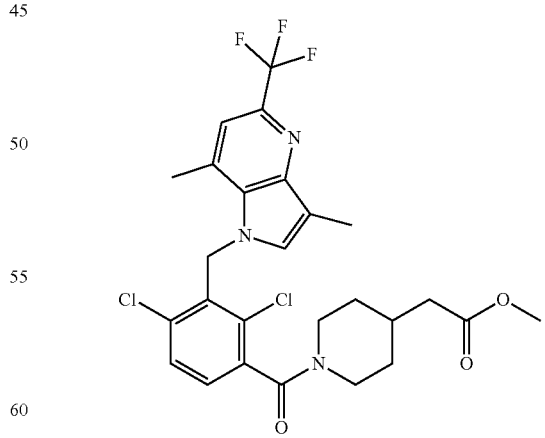

Using a procedure similar to Example A, step 6, methyl 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetate (86 mg, 64%) was prepared from 2,4-dichloro-3-((3,7-dimethyl-5-(trifluoromethyl)-1H-pyrrolo[3,2-b]

pyridin-1-yl)methyl)benzoic acid (100 mg, 0.24 mmol) and methyl (4-piperidyl)acetate hydrochloride (93 mg, 0.48 mmol). LC/MS (Method i): $R_t$=2.44 min.; MS m/z: 556 [M+H]$^+$; $^1$H NMR (DMSO-d$_6$, 300 MHz): δ=7.71 and 7.69 (d, J=8.3 Hz, 1H), 7.53 and 7.46 (d, J=8.3 Hz, 1H), 7.45 (s, 1H), 6.93 and 6.91 (m, 1H), 5.87 (m, 2H), 4.44 (m, 1H), 3.59 and 3.57 (s, 3H), 3.31 (m, 1H), 3.05 (m, 1H), 2.95 (s, 3H), 2.79 (m, 1H), 2.28 (m, 2H), 2.20 (m, 3H), 1.97 (m, 1H), 1.75 (m, 1H), 1.57 (m, 1H), 1.15 (m, 2H).

Step 4: 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetic acid

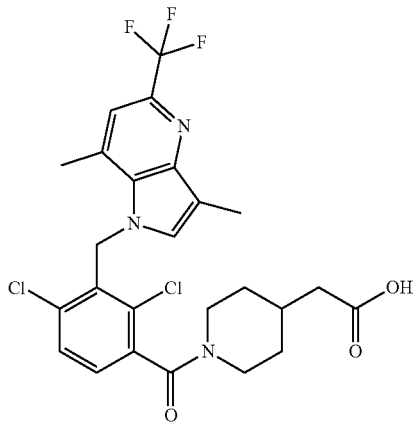 [SMILES: Cc1cn(Cc2c(Cl)ccc(C(=O)N3CCC(CC(=O)O)CC3)c2Cl)c2c(C)cc(C(F)(F)F)nc12]

Using a procedure similar to Example A, step 5, 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetic acid (64 mg, 80%) was prepared from methyl 2-(1-(2,4-dichloro-3-((3,7-dimethyl-5-(trifluoromethyl)-1H-pyrrolo[3,2-b]pyridin-1-yl)methyl)benzoyl)piperidin-4-yl)acetate (81 mg, 0.15 mmol). LC/MS (Method i): $R_t$=2.20 min.; MS m/z: 542 [M+H]$^+$; $^1$H NMR (DMSO-d$_6$, 400 MHz): δ 12.18 (broad, 1H), 7.70 and 7.69 (d, J=8.3 Hz, 1H), 7.53 and 7.46 (d, J=8.3 Hz, 1H), 7.45 (s, 1H), 6.94 and 6.91 (s, 1H), 5.87 (m, 2H), 4.46 (m, 1H), 3.28 (m, 1H), 3.03 (m, 1H), 2.94 (s, 3H), 2.79 (m, 1H), 2.20 (m, 3H), 2.13 (m, 2H), 1.92 (m, 1H), 1.76 (m, 1H), 1.61 (m, 1H), 1.14 (m, 2H).

Example EX: 2-(2,6-dichloro-3-(morpholine-4-carbonyl)benzyl)-1,4-dimethyl-1H-indole-5-carbonitrile

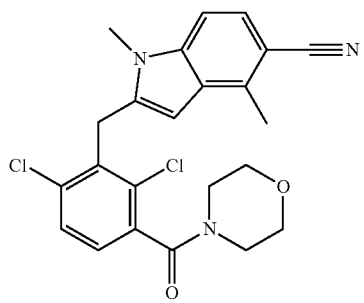 [SMILES: Cc1c(C#N)ccc2c1cc(Cc1c(Cl)ccc(C(=O)N3CCOCC3)c1Cl)n2C]

Step 1: methyl 2,4-dichloro-3-((5-cyano-4-methyl-1-(phenylsulfonyl)-1H-indol-2-yl)(hydroxy)methyl)benzoate

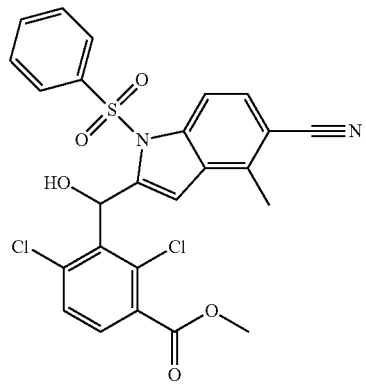 [SMILES: COC(=O)c1ccc(Cl)c(C(O)c2cc3c(C)c(C#N)ccc3n2S(=O)(=O)c2ccccc2)c1Cl]

Using a procedure similar to Example A, Step 1, methyl 2,4-dichloro-3-((5-cyano-4-methyl-1-(phenylsulfonyl)-1H-indol-2-yl)(hydroxy)methyl)benzoate (1.92 g, 76%) was prepared from N-(4-cyano-2-iodo-3-methylphenyl)benzenesulfonamide (1.7 g, 4.3 mmol) (Preparation 70) and methyl 2,4-dichloro-3-(1-hydroxyprop-2-yn-1-yl)benzoate (1.2 g, 4.7 mmol) (Preparation #1). LC/MS (Method i): $R_t$=2.41 min.; MS m/z: 587 [M–H]$^-$+CH$_3$COOH; $^1$H NMR (DMSO-d$_6$, 300 MHz): δ 8.01 (d, J=8.8 Hz, 1H), 7.90 (m, 2H), 7.69 (m, 3H), 7.58 (m, 3H), 7.04 (d, J=5.8 Hz, 1H), 6.88 (s, 1H), 6.73 (d, J=5.8 Hz, 1H), 3.86 (s, 3H), 2.57 (s, 3H).

Step 2: methyl 2,4-dichloro-3-((5-cyano-4-methyl-1-(phenylsulfonyl)-1H-indol-2-yl)methyl)benzoate (10459453-791-001)

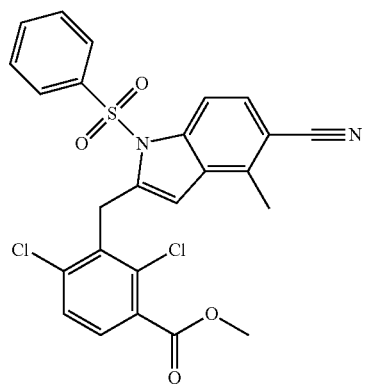 [SMILES: COC(=O)c1ccc(Cl)c(Cc2cc3c(C)c(C#N)ccc3n2S(=O)(=O)c2ccccc2)c1Cl]

Using a procedure similar to Example A, Step 2, methyl 2,4-dichloro-3-((5-cyano-4-methyl-1-(phenylsulfonyl)-1H-indol-2-yl)methyl)benzoate (1.74 g, 85%) was prepared from methyl 2,4-dichloro-3-((5-cyano-4-methyl-1-(phenylsulfonyl)-1H-indol-2-yl)(hydroxy)methyl)benzoate (1.9 g, 3.6 mmol).

LC/MS (Method i): $R_t$=2.74 min.; MS m/z: 513 [M+H]$^+$; $^1$H NMR (DMSO-d$_6$, 300 MHz): δ 8.14 (d, J=8.9 Hz, 1H), 7.99 (m, 2H), 7.82 (m, 2H), 7.86 (m, 4H), 6.05 (s, 1H), 4.62 (s, 2H), 3.87 (s, 3H), 2.46 (s, 3H).

Step 3: methyl 2,4-dichloro-3-((5-cyano-4-methyl-1H-indol-2-yl)methyl)benzoate

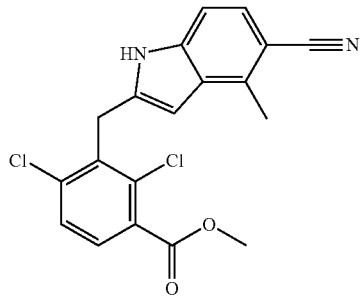 [SMILES: COC(=O)c1ccc(Cl)c(Cc2cc3c(C)c(C#N)ccc3[nH]2)c1Cl]

Using a procedure similar to Example A, Step 3, methyl 2,4-dichloro-3-((5-cyano-4-methyl-1H-indol-2-yl)methyl)benzoate (1.13 g, 83%) was prepared from methyl 2,4-dichloro-3-((5-cyano-4-methyl-1-(Phenylsulfonyl)-1H-indol-2-yl)methyl)benzoate (1.72 g, 3.3 mmol). LC/MS (Method i): $R_t$=2.38 min.; MS m/z: 373 [M+H]$^+$; $^1$H NMR (DMSO-d$_6$, 300 MHz): δ 11.63 (s, 1H), 7.77 (d, J=8.4 Hz, 1H), 7.69 (d, J=8.4 Hz, 1H), 7.31 (s, 2H), 6.03 (m, 1H), 4.48 (s, 2H), 3.87 (s, 3H), 2.53 (s, 3H).

Step 4: methyl 2,4-dichloro-3-((5-cyano-1,4-dimethyl-1H-indol-2-yl)methyl)benzoate

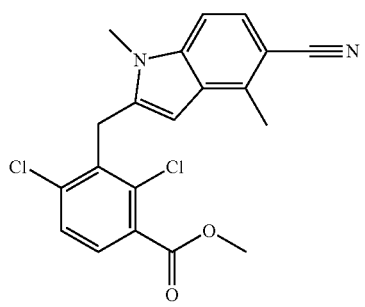 [SMILES: COC(=O)c1ccc(Cl)c(Cc2cc3c(C)c(C#N)ccc3n2C)c1Cl]

Using a procedure similar to Example P, Step 4, methyl 2,4-dichloro-3-((5-cyano-1,4-dimethyl-1H-indol-2-yl)methyl)benzoate (1.1 g, 94%) was prepared from methyl 2,4-dichloro-3-((5-cyano-4-methyl-1H-indol-2-yl)methyl)benzoate (1.1 g, 2.95 mmol). LC/MS (Method i): $R_t$=2.48 min.; MS m/z: 387 [M+H]$^+$; $^1$H NMR (DMSO-d$_6$, 300 MHz): δ 7.80 (d, J=8.1 Hz, 1H), 7.72 (d, J=8.1 Hz, 1H), 7.49 (d, J=8.6 Hz, 1H), 7.40 (d, J=8.6 Hz, 1H), 5.75 (s, 1H), 4.48 (s, 2H), 3.90 (s, 3H), 3.88 (s, 3H), 2.48 (s, 3H).

Step 5: 2,4-dichloro-3-((5-cyano-1,4-dimethyl-1H-indol-2-yl)methyl)benzoic acid

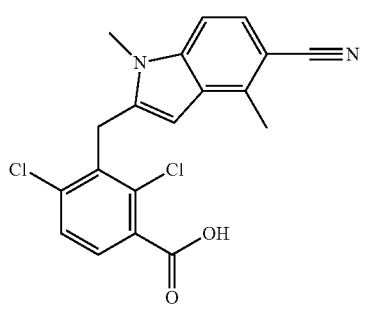 [SMILES: Cc1c(C#N)ccc2c1cc(Cc1c(Cl)ccc(C(=O)O)c1Cl)n2C]

Using a procedure similar to Example A, Step 5, 2,4-dichloro-3-((5-cyano-1,4-dimethyl-1H-indol-2-yl)methyl)benzoic acid (1.01 g, 93%) was prepared from methyl 2,4-dichloro-3-((5-cyano-1,4-dimethyl-1H-indol-2-yl)methyl)benzoate (1.1 g, 2.81 mmol). LC/MS (Method i): $R_t$=2.15 min.; MS m/z: 373 [M+H]$^+$; $^1$H NMR (DMSO-d$_6$, 300 MHz): δ 13.71 (broad, 1H), 7.75 (d, J=8.4 Hz, 1H), 7.67 (d, J=8.4 Hz, 1H), 7.49 (d, J=8.8 Hz, 1H), 7.40 (d, J=8.8 Hz, 1H), 5.75 (s, 1H), 4.47 (s, 2H), 3.89 (s, 3H), 2.49 (s, 3H).

Step 6: 2-(2,6-dichloro-3-(morpholine-4-carbonyl)benzyl)-1,4-dimethyl-1H-indole-5-carbonitrile

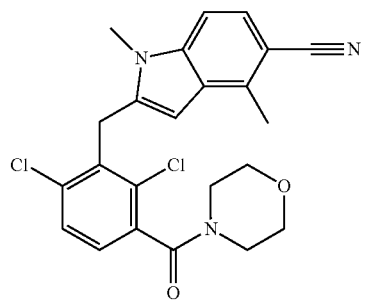 [SMILES: Cc1c(C#N)ccc2c1cc(Cc1c(Cl)ccc(C(=O)N3CCOCC3)c1Cl)n2C]

Using a procedure similar to Example A, Step 6, 2-(2,6-dichloro-3-(morpholine-4-carbonyl)benzyl)-1,4-dimethyl-1H-indole-5-carbonitrile (80 mg, 66%) was prepared from 2,4-dichloro-3-((5-cyano-1,4-dimethyl-1H-indol-2-yl)methyl)benzoic acid (100 mg, 0.27 mmol) and morpholine (28 mg, 0.32 mmol). LC/MS (Method g): $R_t$=1.60 min.; MS m/z: 442 [M+H]$^+$; $^1$H NMR (DMSO-d$_6$, 400 MHz): δ 7.68 (d, J=8.1 Hz, 1H), 7.49 (d, J=8.4 Hz, 1H), 7.46 (d, J=8.4 Hz, 1H), 7.40 (d, J=8.1 Hz, 1H), 5.77 (s, 1H), 4.44 (m, 2H), 3.89 (s, 3H), 3.65 (m, 4H), 3.54 (m, 2H), 3.19 (m, 2H), 2.49 (s, 3H).

Example EY: 2-(1-(2,4-dichloro-3-((5-cyano-1,4-dimethyl-1H-indol-2-yl)methyl)benzoyl)piperidin-4-yl)acetic acid

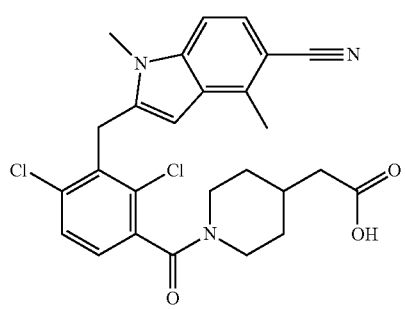

Step 1: methyl 2-(1-(2,4-dichloro-3-((5-cyano-1,4-dimethyl-1H-indol-2-yl)methyl)benzoyl)piperidin-4-yl)acetate

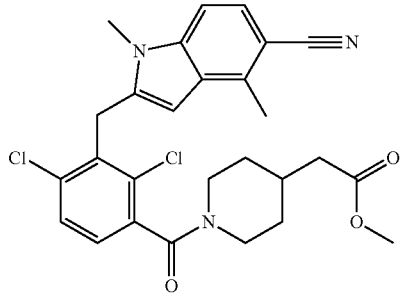 [SMILES: COC(=O)CC1CCN(C(=O)c2ccc(Cl)c(Cc3cc4c(C)c(C#N)ccc4n3C)c2Cl)CC1]

Using a procedure similar to Example A, Step 6, methyl 2-(1-(2,4-dichloro-3-((5-cyano-1,4-dimethyl-1H-indol-2-yl)methyl)benzoyl)piperidin-4-yl)acetate (150 mg, 84%) was prepared from 2,4-dichloro-3-((5-cyano-1,4-dimethyl-1H-indol-2-yl)methyl)benzoic acid (130 mg, 0.35 mmol) (Example EX, step 5) and methyl (4-piperidyl)acetate hydrochloride (81 mg, 0.42 mmol). LC/MS (Method i): $R_t$=2.33 min.; MS m/z: 512 [M+H]$^+$; $^1$H NMR (DMSO-d$_6$, 300 MHz): δ 7.66 and 7.64 (d, J=8.3 Hz, 1H), 7.43 (m, 3H), 5.76 and 7.72 (s, 1H), 4.46 (m, 3H), 3.89 (s, 3H), 3.59 and 3.56 (s, 3H), 3.30 (m, 1H), 3.04 (m, 1H), 2.80 (m, 1H), 2.49 and 2.47 (s, 3H), 2.27 (m, 2H), 1.96 (m, 1H), 1.75 (m, 1H), 1.59 (m, 1H), 1.14 (m, 2H).

Step 2: 2-(1-(2,4-dichloro-3-((5-cyano-1,4-dimethyl-1H-indol-2-yl)methyl)benzoyl)piperidin-4-yl)acetic acid

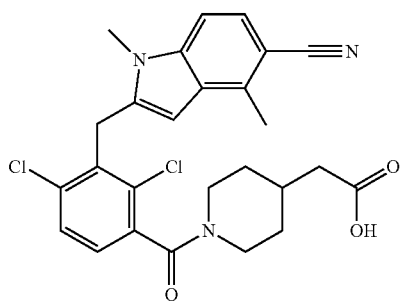 [SMILES: Cc1c(C#N)ccc2c1cc(Cc1c(Cl)ccc(C(=O)N3CCC(CC(=O)O)CC3)c1Cl)n2C]

Using a procedure similar to Example A, Step 5, 2-(1-(2,4-dichloro-3-((5-cyano-1,4-dimethyl-1H-indol-2-yl)methyl)benzoyl)piperidin-4-yl)acetic acid (122 mg, 88%) was prepared from methyl 2-(1-(2,4-dichloro-3-((5-cyano-1,4-dimethyl-1H-indol-2-yl)methyl)benzoyl)piperidin-4-yl)acetate (140 mg, 0.27 mmol). LC/MS (Method g): $R_t$=1.56 min.; MS m/z: 498 [M+H]$^+$; $^1$H NMR (DMSO-d$_6$, 400 MHz): δ 12.10 (broad, 1H), 7.66 and 7.64 (d, J=8.4 Hz, 1H), 7.42 (m, 3H), 5.76 and 5.72 (s, 1H), 4.47 (m, 3H), 3.89 and 3.88 (s, 3H), 3.28 (m, 1H), 3.05 (m, 1H), 2.78 (m, 1H), 2.49 and 2.47 (s, 3H), 2.14 (m, 2H), 1.93 (m, 1H), 1.77 (m, 1H), 1.62 (m, 1H), 1.14 (m, 2H).

Example EZ: (2,4-dichloro-3-((4,6-dichloro-1-methyl-1H-indol-2-yl)methyl)phenyl)(morpholino)methanone

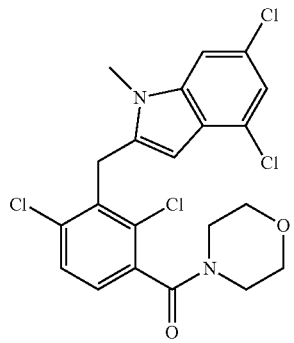

Step 1: tert-butyl 2,4-dichloro-3-((4,6-dichloro-1-(phenylsulfonyl)-1H-indol-2-yl)(hydroxy)methyl)benzoate

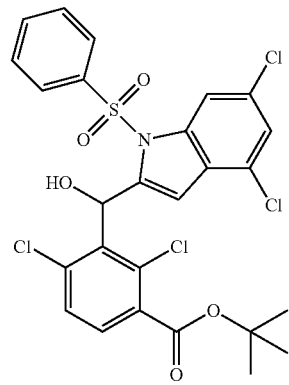 [SMILES: CC(C)(C)OC(=O)c1ccc(Cl)c(C(O)c2cc3c(Cl)cc(Cl)cc3n2S(=O)(=O)c2ccccc2)c1Cl]

Using a procedure similar to Example CJ, Step 1, tert-butyl 2,4-dichloro-3-((4,6-dichloro-1-(phenylsulfonyl)-1H-indol-2-yl)(hydroxy)methyl)benzoate (870 mg, 44%) was prepared from 4,6-dichloro-1-(phenylsulfonyl)-1H-indole (1.08 g, 3.31 mmol) (Preparation 71) and tert-butyl 2,4-dichloro-3-formylbenzoate (900 mg, 3.27 mmol) (Preparation #33, step B). LC/MS (Method j): $R_t$=2.70 min.; MS m/z: 658 [M−H]$^-$+CH3COOH; $^1$H NMR (DMSO-d$_6$, 300 MHz): δ 7.99 (s, 1H), 7.87 (m, 2H), 7.73 (m, 1H), 7.54 (m, 5H), 6.97 (s, 1H), 6.76 (s, 1H), 6.67 (s, 1H), 1.54 (s, 9H).

Step 2: 2,4-dichloro-3-((4,6-dichloro-1-(phenylsulfonyl)-1H-indol-2-yl)methyl)benzoic acid

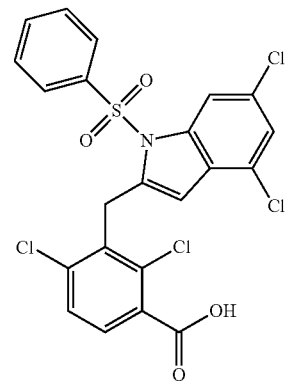 [SMILES: O=C(O)c1ccc(Cl)c(Cc2cc3c(Cl)cc(Cl)cc3n2S(=O)(=O)c2ccccc2)c1Cl]

Using a procedure similar to Example A, Step 2, 2,4-dichloro-3-((4,6-dichloro-1-(phenylsulfonyl)-1H-indol-2-yl)methyl)benzoic acid (565 mg, 60%) was prepared from tert-butyl 2,4-dichloro-3-((4,6-dichloro-1-(phenylsulfonyl)-1H-indol-2-yl)(hydroxy)methyl)benzoate (1 g, 1.76 mmol). LC/MS (Method j): $R_t$=2.30 min.; MS m/z: 526 [M–H]$^-$; $^1$H NMR (DMSO-d$_6$, 300 MHz): δ 13.68 (broad, 1H), 8.14 (m, 1H), 8.02 (m, 2H), 7.80 (m, 2H), 7.69 (m, 3H), 7.55 (m, 1H), 5.71 (m, 1H), 4.57 (m, 2H).

Step 3: 2,4-dichloro-3-((4,6-dichloro-1H-indol-2-yl)methyl)benzoic acid

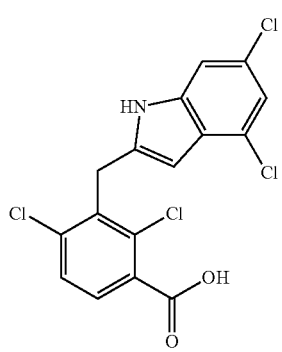 [SMILES: O=C(O)c1ccc(Cl)c(Cc2cc3c(Cl)cc(Cl)cc3[nH]2)c1Cl]

Using a procedure similar to Example A, Step 3, 2,4-dichloro-3-((4,6-dichloro-1H-indol-2-yl)methyl)benzoic acid (416 mg, 53%) was prepared from 2,4-dichloro-3-((4,6-dichloro-1-(Phenylsulfonyl)-1H-indol-2-yl)methyl)benzoic acid (465 mg, 0.9 mmol). LC/MS (Method i): $R_t$=2.42 min.; MS m/z: 386 [M–H]$^-$ Step 4: methyl 2,4-dichloro-3-((4,6-dichloro-1-methyl-1H-indol-2-yl)methyl)benzoate

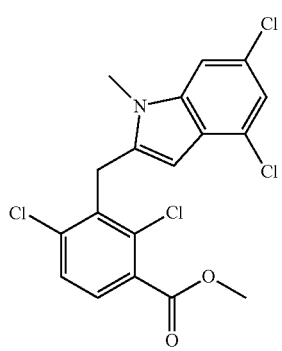 [SMILES: COC(=O)c1ccc(Cl)c(Cc2cc3c(Cl)cc(Cl)cc3n2C)c1Cl]

Using a procedure similar to Example P, Step 4, methyl 2,4-dichloro-3-((4,6-dichloro-1-methyl-1H-indol-2-yl)methyl)benzoate (268 mg, 73%) was prepared from 2,4-dichloro-3-((4,6-dichloro-1H-indol-2-yl)methyl)benzoic acid (342 mg, 0.87 mmol). LC/MS (Method i): $R_t$=2.85 min.; MS m/z: 416 [M+H]$^+$ $^1$H NMR (DMSO-d$_6$, 300 MHz): δ 7.80 (d, J=8.9 Hz, 1H), 7.73 (d, J=8.9 Hz, 1H), 7.67 (dd, J=1.7, 0.8 Hz, 1H), 7.13 (d, J=1.7 Hz, 1H), 5.52 (m, 1H), 4.47 (m, 2H), 3.88 (s, 3H), 3.86 (s, 3H).

Step 5: 2,4-dichloro-3-((4,6-dichloro-1-methyl-1H-indol-2-yl)methyl)benzoic acid

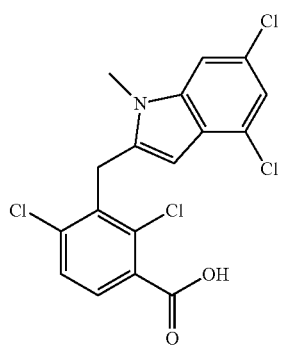 [SMILES: Cn1c(Cc2c(Cl)ccc(C(=O)O)c2Cl)cc2c(Cl)cc(Cl)cc21]

Using a procedure similar to Example A, Step 5, 2,4-dichloro-3-((4,6-dichloro-1-methyl-1H-indol-2-yl)methyl)benzoic acid (165 mg, 51%) was prepared from methyl 2,4-dichloro-3-((4,6-dichloro-1-methyl-1H-indol-2-yl)methyl)benzoate (265 mg, 0.63 mmol). LC/MS (Method i): $R_t$=2.53 min.; MS m/z: 402 [M+H]$^+$; $^1$H NMR (DMSO-d$_6$, 300 MHz): δ 13.68 (broad, 1H), 7.76 (d, J=8.6 Hz, 1H), 7.68 (d, J=8.6 Hz, 1H), 7.67 (m, 1H), 7.14 (d, J=1.7 Hz, 1H), 5.53 (m, 1H), 4.46 (s, 2H), 3.88 (s, 3H).

Step 6: (2,4-dichloro-3-((4,6-dichloro-1-methyl-1H-indol-2-yl)methyl)phenyl)(morpholino)methanone

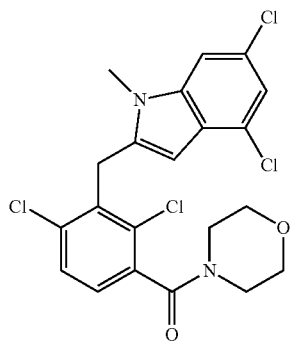

Using a procedure similar to Example A1, (2,4-dichloro-3-((4,6-dichloro-1-methyl-1H-indol-2-yl)methyl)phenyl)(morpholino)methanone (39 mg, 52%) was prepared from 2,4-dichloro-3-((4,6-dichloro-1-methyl-1H-indol-2-yl)methyl)benzoic acid (80 mg, 0.16 mmol) and morpholine (27.7 mg, 0.32 mmol). LC/MS (Method g): $R_t$=1.96 min.; MS m/z: 471 [M+H]$^+$; $^1$H NMR (DMSO-d$_6$, 400 MHz): δ 7.68 (d, J=8.4 Hz, 1H), 7.66 (m, 1H), 7.46 (d, J=8.4 Hz, 1H), 7.13 (d, J=1.5 Hz, 1H), 5.55 (m, 1H), 4.43 (m, 2H), 3.87 (s, 3H), 3.65 (m, 4H), 3.54 (m, 2H), 3.20 (m, 2H).

Example FA: 2-(1-(2,4-dichloro-3-((4,6-dichloro-1-methyl-1H-indol-2-yl)methyl)benzoyl)piperidin-4-yl)acetic acid

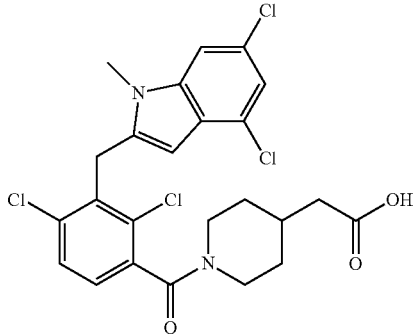 [SMILES: Cn1c(Cc2c(Cl)ccc(C(=O)N3CCC(CC(=O)O)CC3)c2Cl)cc2c(Cl)cc(Cl)cc21]

Step 1: methyl 2-(1-(2,4-dichloro-3-((4,6-dichloro-1-methyl-1H-indol-2-yl)methyl)benzoyl)piperidin-4-yl)acetate

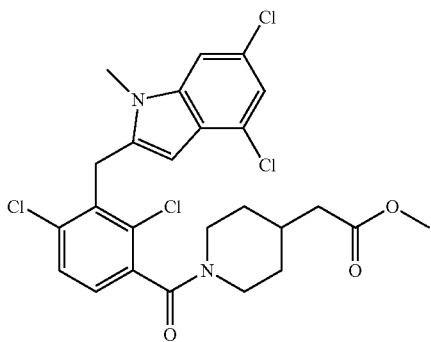

Using a procedure similar to Example A1, methyl 2-(1-(2,4-dichloro-3-((4,6-dichloro-1-methyl-1H-indol-2-yl)methyl)benzoyl)piperidin-4-yl)acetate (32 mg, 47%) was prepared from 2,4-dichloro-3-((4,6-dichloro-1-methyl-1H-indol-2-yl)methyl)benzoic acid (63 mg, 0.12 mmol) (example EZ, Step 5) and methyl (4-piperidyl)acetate hydrochloride (96 mg, 0.5 mmol). LC/MS (Method i): $R_t$=2.69 min.; MS m/z: 541 [M+H]$^+$; $^1$H NMR (DMSO-d$_6$, 300 MHz): δ 7.66 (m, 2H), 7.44 and 7.37 (d, J=8.3 Hz, 1H), 7.13 (m, 1H), 5.52 (m, 1H), 4.44 (m, 3H), 3.87 and 3.86 (s, 3H), 3.59 and 3.56 (s, 3H), 3.23 (m, 1H), 3.05 (m, 1H), 2.80 (m, 1H), 2.25 (m, 2H), 1.86 (m, 1H), 1.77 (m, 1H), 1.59 (m, 1H), 1.14 (m, 2H).

Step 2: 2-(1-(2,4-dichloro-3-((4,6-dichloro-1-methyl-1H-indol-2-yl)methyl)benzoyl)piperidin-4-yl)acetic acid

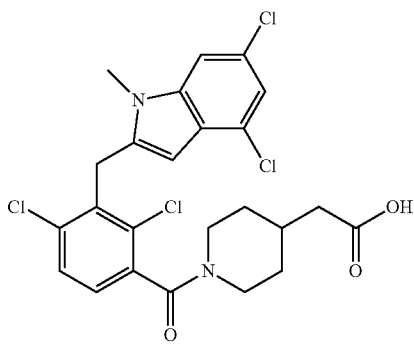 [SMILES: Cn1c(Cc2c(Cl)ccc(C(=O)N3CCC(CC(=O)O)CC3)c2Cl)cc2c(Cl)cc(Cl)cc21]

Using a procedure similar to Example A, Step 5, 2-(1-(2,4-dichloro-3-((4,6-dichloro-1-methyl-1H-indol-2-yl)methyl)benzoyl)piperidin-4-yl)acetic acid (17 mg, 57%) was prepared from methyl 2-(1-(2,4-dichloro-3-((4,6-dichloro-1-methyl-1H-indol-2-yl)methyl)benzoyl)piperidin-4-yl)acetate (30 mg, 0.055 mmol). LC/MS (Method g): $R_t$=1.87 min.; MS m/z: 527 [M+H]$^+$; $^1$H NMR (DMSO-d$_6$, 400 MHz): δ 12.13 (broad, 1H), 7.66 (m, 2H), 7.44 and 7.37 (d, J=8.4 Hz, 1H), 7.13 (m, 1H), 5.53 (m, 1H), 4.44 (m, 3H), 3.87 and 3.86 (s, 3H), 3.24 (m, 1H), 3.05 (m, 1H), 2.80 (m, 1H), 2.15 (m, 2H), 1.93 (m, 1H), 1.77 (m, 1H), 1.61 (m, 1H), 1.14 (m, 2H).

Example FB: 2-((2,4-dichloro-5-(2-oxa-8-azaspiro[4.5]decane-8-carbonyl)pyridin-3-yl)methyl)-1,4-dimethyl-1H-indole-6-carbonitrile

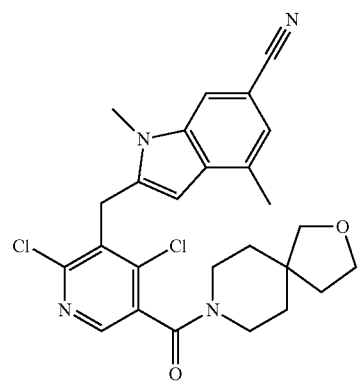 [SMILES: Cc1cc(C#N)cc2c1cc(Cc1c(Cl)ncc(C(=O)N3CCC4(CCOC4)CC3)c1Cl)n2C]

Step 1: ethyl 4,6-dichloro-5-((6-cyano-4-methyl-1-(phenylsulfonyl)-1H-indol-2-yl)(hydroxy)methyl)nicotinate

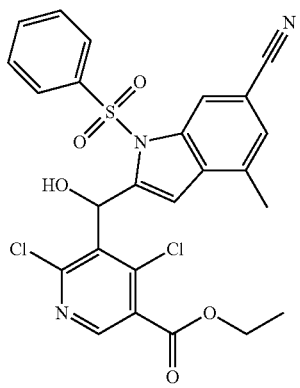 [SMILES: CCOC(=O)c1cnc(Cl)c(C(O)c2cc3c(C)cc(C#N)cc3n2S(=O)(=O)c2ccccc2)c1Cl]

Using a procedure similar to Example A, Step 1, ethyl 4,6-dichloro-5-((6-cyano-4-methyl-1-(phenylsulfonyl)-1H-indol-2-yl)(hydroxy)methyl)nicotinate (4.46 g, 41%) was prepared from N-(5-cyano-2-iodo-3-methylphenyl)benzenesulfonamide (7.91 g, 19.8 mmol) (Preparation #18) and ethyl 4,6-dichloro-5-(1-hydroxyprop-2-yn-1-yl)nicotinate (6.53 g, 23.82 mmol) (Preparation #38). LC/MS (Method i): $R_t$=2.40 min.; MS m/z: 544 [M+H]$^+$; $^1$H NMR (DMSO-d$_6$, 300 MHz): δ 8.70 (s, 1H), 8.24 (s, 1H), 7.89 (m, 2H), 7.71

(m, 1H), 7.56 (m, 3H), 7.07 (s, 1H), 6.93 (s, 2H), 4.37 (q, J=7.1 Hz, 2H), 2.45 (s, 3H), 1.33 (t, J=7.1 Hz, 3H).

Step 2: ethyl 4,6-dichloro-5-((6-cyano-4-methyl-1-(phenylsulfonyl)-1H-indol-2-yl)methyl)nicotinate

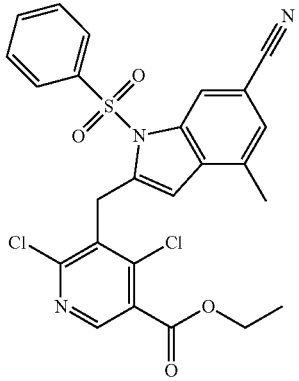 [SMILES: CCOC(=O)c1cnc(Cl)c(Cc2cc3c(C)cc(C#N)cc3n2S(=O)(=O)c2ccccc2)c1Cl]

Using a procedure similar to Example Z, Step 2, ethyl 4,6-dichloro-5-((6-cyano-4-methyl-1-(phenylsulfonyl)-1H-indol-2-yl)methyl)nicotinate (3.6 g, 83%) was prepared from ethyl 4,6-dichloro-5-((6-cyano-4-methyl-1-(phenylsulfonyl)-1H-indol-2-yl)(hydroxy)methyl)nicotinate (4.46 g, 8.19 mmol). LC/MS (Method i): $R_t$=2.71 min.; MS m/z: 528 [M+H]$^+$; $^1$H NMR (DMSO-d$_6$, 300 MHz): δ 8.84 (s, 1H), 8.35 (s, 1H), 8.05 (m, 2H), 7.78 (m, 1H), 7.68 (m, 2H), 7.48 (m, 1H), 6.34 (s, 1H), 4.62 (s, 2H), 4.37 (q, J=7.1 Hz, 2H), 2.33 (s, 3H), 1.34 (t, J=7.1 Hz, 3H).

Step 3: 4,6-dichloro-5-((6-cyano-4-methyl-1H-indol-2-yl)methyl)nicotinic acid

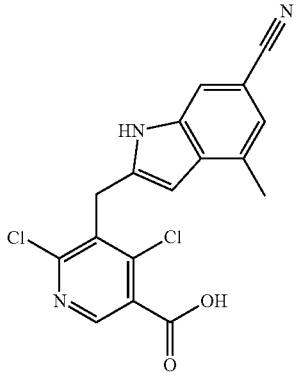 [SMILES: Cc1cc(C#N)cc2[nH]c(Cc3c(Cl)ncc(C(=O)O)c3Cl)cc12]

Using a procedure similar to Example A, Step 3, 4,6-dichloro-5-((6-cyano-4-methyl-1H-indol-2-yl)methyl)nicotinic acid (3.1 g, 100%) was prepared from ethyl 4,6-dichloro-5-((6-cyano-4-methyl-1-(Phenylsulfonyl)-1H-indol-2-yl)methyl)nicotinate (3.55 g, 6.73 mmol). LC/MS (Method i): $R_t$=1.85 min.; MS m/z: 360 [M+H]$^+$; $^1$H NMR (DMSO-d$_6$, 300 MHz): δ 11.67 (s, 1H), 8.63 (s, 1H), 7.63 (s, 1H), 7.09 (s, 1H), 6.08 (s, 1H), 4.47 (s, 2H), 2.39 (s, 3H).

Step 4: methyl 4,6-dichloro-5-((6-cyano-1,4-dimethyl-1H-indol-2-yl)methyl)nicotinate

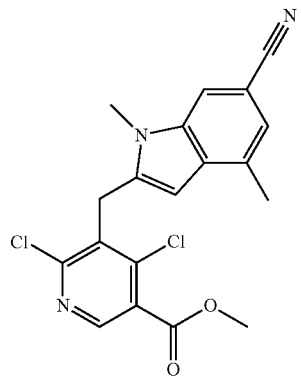 [SMILES: COC(=O)c1cnc(Cl)c(Cc2cc3c(C)cc(C#N)cc3n2C)c1Cl]

Using a procedure similar to Example P, Step 4, methyl 4,6-dichloro-5-((6-cyano-1,4-dimethyl-1H-indol-2-yl)methyl)nicotinate (1.05 g, 31%) was prepared from 4,6-dichloro-5-((6-cyano-4-methyl-1H-indol-2-yl)methyl)nicotinic acid (3.1 g, 8.61 mmol). LC/MS (Method i): $R_t$=2.35 min.; MS m/z: 388 [M+H]$^+$; $^1$H NMR (DMSO-d$_6$, 300 MHz): δ 8.84 (s, 1H), 7.93 (s, 1H), 7.12 (s, 1H), 5.87 (s, 1H), 4.50 (s, 2H), 3.92 (s, 3H), 3.91 (ds, 3H), 2.34 (s, 3H).

Step 5: 4,6-dichloro-5-((6-cyano-1,4-dimethyl-1H-indol-2-yl)methyl)nicotinic acid

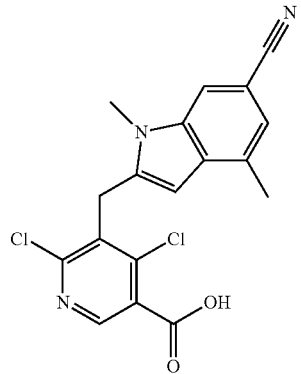 [SMILES: Cc1cc(C#N)cc2c1cc(Cc1c(Cl)ncc(C(=O)O)c1Cl)n2C]

Using a procedure similar to Example A, Step 5, 4,6-dichloro-5-((6-cyano-1,4-dimethyl-1H-indol-2-yl)methyl)nicotinic acid (870 mg, 86%) was prepared from methyl 4,6-dichloro-5-((6-cyano-1,4-dimethyl-1H-indol-2-yl)methyl)nicotinate (1.05 g, 2.7 mmol). LC/MS (Method i): $R_t$=1.87 min.; MS m/z: 374 [M+H]$^+$; $^1$H NMR (DMSO-d$_6$, 300 MHz): δ 8.74 (s, 1H), 7.92 (s, 1H), 7.12 (s, 1H), 5.84 (s, 1H), 4.49 (s, 2H), 3.91 (s, 3H), 2.34 (s, 3H).

Step 6: 2-((2,4-dichloro-5-(2-oxa-8-azaspiro[4.5] decane-8-carbonyl)pyridin-3-yl)methyl)-1,4-dimethyl-1H-indole-6-carbonitrile Example FD: 2-(1-(2,4-dichloro-3-((6-methoxy-1,4-dimethyl-1H-indol-2-yl)methyl)benzoyl)piperidin-4-yl)acetic acid

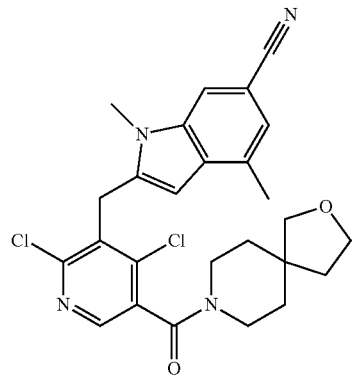 [SMILES: Cc1cc(C#N)cc2c1cc(Cc1c(Cl)ncc(C(=O)N3CCC4(CCOC4)CC3)c1Cl)n2C]

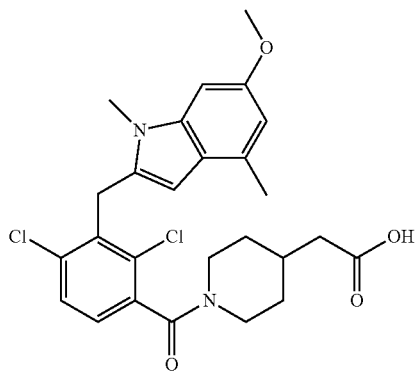

Using a procedure similar to Example A, Step 6, 2-((2,4-dichloro-5-(2-oxa-8-azaspiro[4.5]decane-8-carbonyl)pyridin-3-yl)methyl)-1,4-dimethyl-1H-indole-6-carbonitrile (20 mg, 15%) was prepared from 4,6-dichloro-5-((6-cyano-1,4-dimethyl-1H-indol-2-yl)methyl)nicotinic acid (100 mg, 0.27 mmol) and 2-oxa-8-azaspiro[4.5]decane (49 mg, 0.35 mmol). LC/MS (Method g): $R_t$=1.60 min.; MS m/z: 497 [M+H]$^+$; $^1$H NMR (DMSO-d$_6$, 400 MHz): δ 8.48 (s, 1H), 7.92 (s, 1H), 7.12 (s, 1H), 5.86 (m, 1H), 4.47 (m, 2H), 3.90 (s, 3H), 3.75 (m, 4H), 3.48 (m, 2H), 3.24 (m, 2H), 2.35 (s, 3H), 1.74 (m, 2H), 1.56 (m, 4H).

Example FC: 2-((2,4-dichloro-5-(4-(oxetan-3-yl) piperidine-1-carbonyl)pyridin-3-yl)methyl)-1,4-dimethyl-1H-indole-6-carbonitrile Step 1: tert-butyl 2,4-dichloro-3-(hydroxy(6-methoxy-4-methyl-1-(phenylsulfonyl)-1H-indol-2-yl)methyl)benzoate

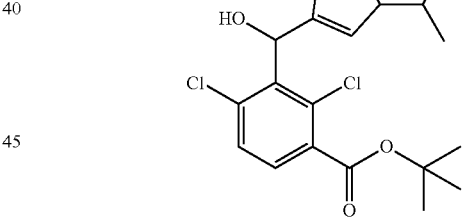

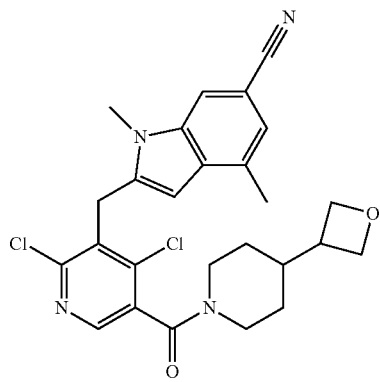 [SMILES: Cc1cc(C#N)cc2c1cc(Cc1c(Cl)ncc(C(=O)N3CCC(C4COC4)CC3)c1Cl)n2C]

Using a procedure similar to Example A, Step 6, 2-((2,4-dichloro-5-(4-(oxetan-3-yl)piperidine-1-carbonyl)pyridin-3-yl)methyl)-1,4-dimethyl-1H-indole-6-carbonitrile (54 mg, 38%) was prepared from 4,6-dichloro-5-((6-cyano-1,4-dimethyl-1H-indol-2-yl)methyl)nicotinic acid (100 mg, 0.27 mmol) and 4-(oxetan-3-yl)piperidine (49 mg, 0.35 mmol) (example FB, Step 5). LC/MS (Method g): $R_t$=1.56 min.; MS m/z: 497 [M+H]$^+$; $^1$H NMR (DMSO-d$_6$, 400 MHz): δ 8.51 and 8.44 (s, 1H), 7.92 (s, 1H), 7.12 (s, 1H), 5.88 and 5.83 (s, 1H), 4.46 (m, 7H), 3.90 (s, 3H), 3.43 (m, 1H), 3.07 (m, 1H), 2.71 (m, 2H), 2.35 and 2.33 (s, 3H), 1.91 (m, 1H), 1.69 (m, 1H), 1.54 (m, 1H), 1.02 (m, 2H).

Using a procedure similar to Example CJ, Step 1, tert-butyl 2,4-dichloro-3-(hydroxy(6-methoxy-4-methyl-1-(phenylsulfonyl)-1H-indol-2-yl)methyl)benzoate (732 mg, 45%) was prepared from 6-methoxy-4-methyl-1-(phenylsulfonyl)-1H-indole (857 mg, 2.84 mmol) (Preparation 72) and tert-butyl 2,4-dichloro-3-formylbenzoate (939 mg, 3.41 mmol) (Preparation #33, step B). LC/MS (Method i): $R_t$=2.71 min.; MS m/z: 634 [M–H]$^-$+CH$_3$COOH; $^1$H NMR (DMSO-d$_6$, 300 MHz): δ 7.90 (m, 2H), 7.67 (m, 1H), 7.57 (m, 4H), 7.31 (m, 1H), 7.01 (m, 1H), 6.71 (m, 1H), 6.53 (s, 1H), 6.46 (m, 1H), 3.78 (s, 3H), 2.30 (s, 3H), 1.54 (s, 9H).

Step 2: 2,4-dichloro-3-((6-methoxy-4-methyl-1-(phenylsulfonyl)-1H-indol-2-yl)methyl)benzoic acid

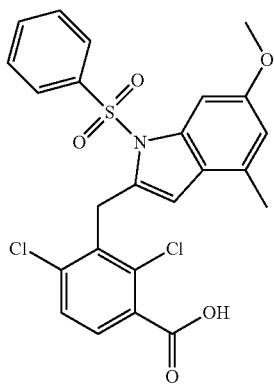 [SMILES: COc1cc(C)c2cc(Cc3c(Cl)ccc(C(=O)O)c3Cl)n(S(=O)(=O)c3ccccc3)c2c1]

Using a procedure similar to Example A, Step 2, 2,4-dichloro-3-((6-methoxy-4-methyl-1-(phenylsulfonyl)-1H-indol-2-yl)methyl)benzoic acid (638 mg, 100%) was prepared from tert-butyl 2,4-dichloro-3-(hydroxy(6-methoxy-4-methyl-1-(phenylsulfonyl)-1H-indol-2-yl)methyl)benzoate (730 mg, 1.27 mmol). LC/MS (Method i): $R_f$=2.44 min.; MS m/z: 504 [M+H]$^+$; $^1$H NMR (DMSO-d$_6$, 300 MHz): δ 13.65 (broad, 1H), 7.92 (m, 2H), 7.75 (m, 2H), 7.66 (m, 3H), 7.47 (m 1H), 6.71 (m, 1H), 5.67 (s, 1H), 4.56 (s, 2H), 3.81 (s, 3H), 2.20 (s, 3H).

Step 3: 2,4-dichloro-3-((6-methoxy-4-methyl-1H-indol-2-yl)methyl)benzoic acid

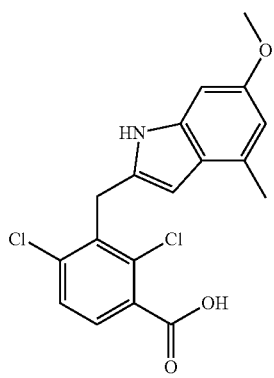 [SMILES: COc1cc(C)c2cc(Cc3c(Cl)ccc(C(=O)O)c3Cl)[nH]c2c1]

Using a procedure similar to Example A, Step 3, 2,4-dichloro-3-((6-methoxy-4-methyl-1H-indol-2-yl)methyl)benzoic acid was prepared from 2,4-dichloro-3-((6-methoxy-4-methyl-1-(phenylsulfonyl)-1H-indol-2-yl)methyl)benzoic acid (55 mg, 1.1 mmol) and used crude in the next step. LC/MS (Method i): $R_f$=2.11 min.; MS m/z: 364 [M+H]$^+$

Step 4: methyl 2,4-dichloro-3-((6-methoxy-1,4-dimethyl-1H-indol-2-yl)methyl)benzoate

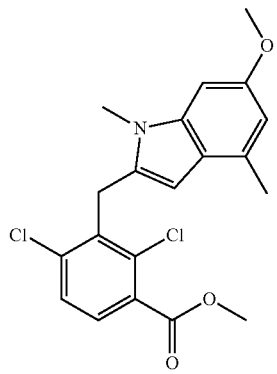 [SMILES: COC(=O)c1ccc(Cl)c(Cc2cc3c(C)cc(OC)cc3n2C)c1Cl]

Using a procedure similar to Example P, Step 4, methyl 2,4-dichloro-3-((6-methoxy-1,4-dimethyl-1H-indol-2-yl)methyl)benzoate (500 mg, 100%) was prepared from crude 2,4-dichloro-3-((6-methoxy-4-methyl-1-(phenylsulfonyl)-1H-indol-2-yl)methyl)benzoic acid. LC/MS (Method i): $R_f$=2.53 min.; MS m/z: 392 [M+H]$^+$; $^1$H NMR (DMSO-d$_6$, 300 MHz): δ 7.77 (d, J=7.8 Hz, 1H), 7.70 (d, J=7.8 Hz, 1H), 6.81 (m, 1H), 6.43 (m, 1H), 5.41 (m, 1H), 4.40 (s, 2H), 3.88 (s, 3H), 3.77 (s, 3H), 3.76 (s, 3H), 2.22 (s, 3H).

Step 5: 2,4-dichloro-3-((6-methoxy-1,4-dimethyl-1H-indol-2-yl)methyl)benzoic acid

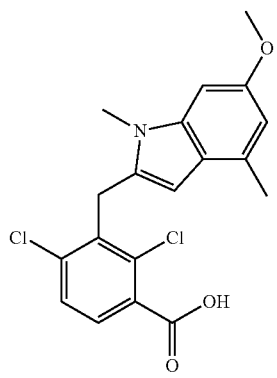 [SMILES: COc1cc(C)c2cc(Cc3c(Cl)ccc(C(=O)O)c3Cl)n(C)c2c1]

Using a procedure similar to Example A, Step 5, 2,4-dichloro-3-((6-methoxy-1,4-dimethyl-1H-indol-2-yl)methyl)benzoic acid (305 mg, 62%) was prepared from methyl 2,4-dichloro-3-((6-methoxy-1,4-dimethyl-1H-indol-2-yl)methyl)benzoate (509 mg, 1.3 mmol). LC/MS (Method i): $R_f$=2.20 min.; MS m/z: 378 [M+H]$^+$; $^1$H NMR (DMSO-d$_6$, 300 MHz): δ 13.59 (broad, 1H), 7.73 (d, J=8.3 Hz, 1H), 7.65 (d, J=8.3 Hz, 1H), 6.81 (d, J=2.0 Hz, 1H), 6.43 (m, 1H), 5.42 (m, 1H), 4.39 (s, 2H), 3.77 (s, 3H), 3.76 (s, 3H), 2.23 (s, 3H).

Step 6: methyl 2-(1-(2,4-dichloro-3-((6-methoxy-1,4-dimethyl-1H-indol-2-yl)methyl)benzoyl)piperidin-4-yl)acetate

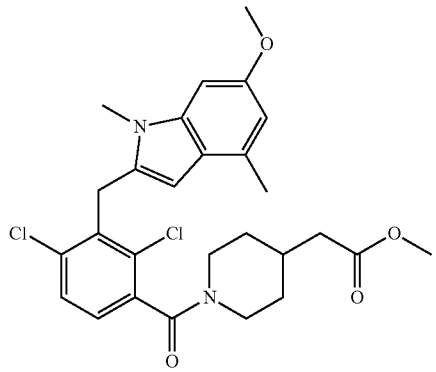 [SMILES: COC(=O)CC1CCN(C(=O)c2ccc(Cl)c(Cc3cc4c(C)cc(OC)cc4n3C)c2Cl)CC1]

Using a procedure similar to Example A, Step 6, methyl 2-(1-(2,4-dichloro-3-((6-methoxy-1,4-dimethyl-1H-indol-2-yl)methyl)benzoyl)piperidin-4-yl)acetate (83 mg, 61%) was prepared from 2,4-dichloro-3-((6-methoxy-1,4-dimethyl-1H-indol-2-yl)methyl)benzoic acid (100 mg, 0.26 mmol) and methyl (4-piperidyl)acetate hydrochloride (102 mg, 0.53 mmol). LC/MS (Method i): $R_t$=2.37 min.;

MS m/z: 517 [M+H]$^+$ $^1$H NMR (DMSO-d$_6$, 300 MHz): δ 7.64 and 7.62 (d, J=8.3 Hz, 1H), 7.41 and 7.34 (d, J=8.3 Hz, 1H), 6.81 (s, 1H), 6.43 (m, 1H), 5.42 and 5.39 (s, 1H), 4.41 (m, 3H), 3.77 (s, 6H), 3.59 and 3.57 (s, 3H), 3.27 (m, 1H), 3.05 (m, 1H), 2.80 (m, 1H), 2.28 (m, 2H), 2.22 and 2.21 (s, 3H), 1.86-2.05 (m, 1H), 1.75 (m, 1H), 1.58 (m, 1H), 1.17 (m, 2H).

Step 7: 2-(1-(2,4-dichloro-3-((6-methoxy-1,4-dimethyl-1H-indol-2-yl)methyl)benzoyl)piperidin-4-yl)acetic acid

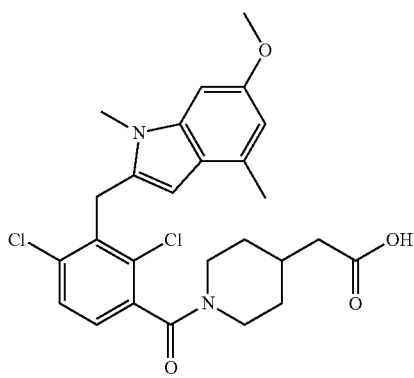 [SMILES: COc1cc(C)c2cc(Cc3c(Cl)ccc(C(=O)N4CCC(CC(=O)O)CC4)c3Cl)n(C)c2c1]

Using a procedure similar to Example A, Step 5, 2-(1-(2,4-dichloro-3-((6-methoxy-1,4-dimethyl-1H-indol-2-yl)methyl)benzoyl)piperidin-4-yl)acetic acid (55 mg, 68%) was prepared from methyl 2-(1-(2,4-dichloro-3-((6-methoxy-1,4-dimethyl-1H-indol-2-yl)methyl)benzoyl)piperidin-4-yl)acetate (80 mg, 0.15 mmol). LC/MS (Method i): $R_t$=2.13 min.; MS m/z: 503 [M+H]$^+$; $^1$H NMR (DMSO-d$_6$, 400 MHz): δ=12.08 (s, 1H), 7.64 and 7.62 (d, J=8.3 Hz, 1H), 7.41 and 7.34 (d, J=8.3 Hz, 1H), 6.80 (s, 1H), 6.43 (s, 1H), 5.43 and 5.40 (s, 1H), 4.36 (m, 3H), 3.77 (s, 6H), 3.27 (m, 1H), 3.04 (m, 1H), 2.80 (m, 1H), 2.21 and 2.21 (s, 3H), 2.14 (m, 2H), 1.95 (m, 1H), 1.79 (m, 1H), 1.61 (m, 1H), 1.16 (m, 2H).

Example FE: 2-(1-(2,4-dichloro-3-((4-fluoro-1-methyl-6-(trifluoromethyl)-1H-indol-2-yl)methyl)benzoyl)piperidin-4-yl)acetic acid

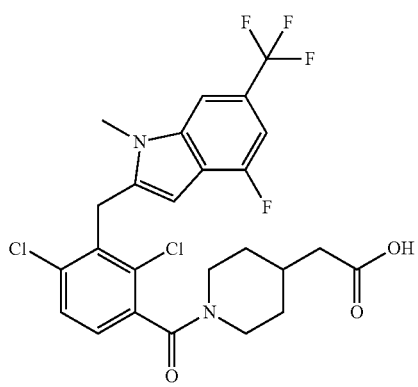

Step 1: tert-butyl 2,4-dichloro-3-((4-fluoro-1-methyl-6-(trifluoromethyl)-1H-indol-2-yl)(hydroxy)methyl)benzoate

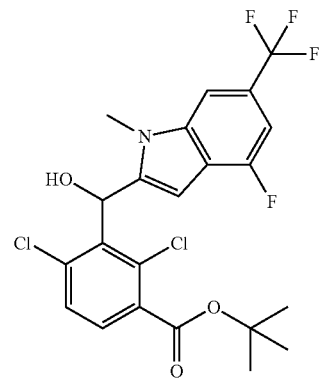 [SMILES: Cn1c(C(O)c2c(Cl)ccc(C(=O)OC(C)(C)C)c2Cl)cc2c(F)cc(C(F)(F)F)cc21]

To a solution of tert-butyl 2,4-dichlorobenzoate (125 mg, 0.507 mmol) (Preparation #33, Step A) in THF (1.5 mL) under argon and cooled at −78° C. was added dropwise lithium diisopropylamide (0.230 mL, 0.461 mmol). The reaction mixture was stirred for 1 hour at −78° C. then 4-fluoro-1-methyl-6-(trifluoromethyl)-1H-indole-2-carbaldehyde (113 mg, 0.461 mmol) (Preparation #73) in solution in THF (1.5 mL) was added. The reaction mixture was stirred for 30 minutes at −78° C. The reaction mixture was quenched with a saturated solution of NaHCO$_3$ and extracted twice with EtOAc. The organic layer was dried over magnesium sulfate, filtered and concentrated under reduced pressure. The residue was purified by silica gel chromatography (eluting with 5-20% EtOAc in cyclohexane) to give tert-butyl 2,4-dichloro-3-((4-fluoro-1-methyl-6-(trifluoromethyl)-1H-indol-2-yl)(hydroxy)methyl)benzoate (156 mg, 69%). LC/MS (Method i): $R_t$=2.76 min.; MS m/z: 492 [M+H]$^+$; $^1$H NMR (DMSO-d$_6$, 300 MHz): δ 7.83 (s, 1H), 7.66 (d, J=8.3 Hz, 1H), 7.61 (d, J=8.3 Hz, 1H), 7.15 (dd, J=10.7, 0.7 Hz, 1H), 6.73 (d, J=5.4 Hz, 1H), 6.59 (d, J=5.6 Hz, 1H), 6.13 (s, 1H), 3.90 (s, 3H), 1.55 (s, 9H).

Step 2: 2,4-dichloro-3-((4-fluoro-1-methyl-6-(trifluoromethyl)-1H-indol-2-yl)methyl)benzoic acid

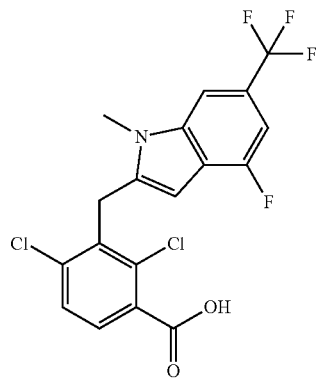 [SMILES: Cn1c(Cc2c(Cl)ccc(C(=O)O)c2Cl)cc2c(F)cc(C(F)(F)F)cc21]

Using a procedure similar to Example A, Step 2, 2,4-dichloro-3-((4-fluoro-1-methyl-6-(trifluoromethyl)-1H-indol-2-yl)methyl)benzoic acid (43 mg, 100%) was prepared from tert-butyl 2,4-dichloro-3-((4-fluoro-1-methyl-6-(trifluoromethyl)-1H-indol-2-yl)(hydroxy)methyl)benzoate (50 mg, 0.1 mmol). LC/MS (Method i): $R_t$=2.43 min.; MS m/z: 420 [M+H]$^+$; $^1$H NMR (DMSO-d$_6$, 300 MHz): δ 13.50 (broad, 1H), 7.83 (s, 1H), 7.77 (d, J=8.9 Hz, 1H), 7.68 (d, J=8.9 Hz, 1H), 7.12 (dd, J=10.4, 0.7 Hz, 1H), 5.69 (d, J=0.7 Hz, 1H), 4.51 (s, 2H), 3.97 (s, 3H).

Step 3: methyl 2-(1-(2,4-dichloro-3-((4-fluoro-1-methyl-6-(trifluoromethyl)-1H-indol-2-yl)methyl)benzoyl)piperidin-4-yl)acetate

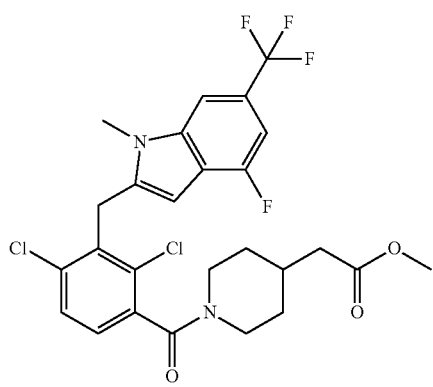 [SMILES: COC(=O)CC1CCN(C(=O)c2ccc(Cl)c(Cc3cc4c(F)cc(C(F)(F)F)cc4n3C)c2Cl)CC1]

Using a procedure similar to Example A1, methyl 2-(1-(2,4-dichloro-3-((4-fluoro-1-methyl-6-(trifluoromethyl)-1H-indol-2-yl)methyl)benzoyl)piperidin-4-yl)acetate (48 mg, 60%) was prepared from 2,4-dichloro-3-((4-fluoro-1-methyl-6-(trifluoromethyl)-1H-indol-2-yl)methyl)benzoic acid (60 mg, 0.14 mmol) and methyl (4-piperidyl)acetate hydrochloride (41 mg, 0.21 mmol). LC/MS (Method i): $R_t$=2.58 min.; MS m/z: 559 [M+H]$^+$; $^1$H NMR (DMSO-d$_6$, 300 MHz): δ 7.83 (s, 1H), 7.66 and 7.65 (d, J=8.2 Hz, 1H), 7.45 and 7.38 (d, J=8.2 Hz, 1H), 7.12 (d, J=10.2 Hz, 1H), 5.72 and 5.68 (s, 1H), 4.47 (m, 3H), 3.97 (s, 3H), 3.59 and 3.56 (s, 3H), 3.27 (m, 1H), 3.05 (m, 1H), 2.81 (m, 1H), 2.26 (m, 2H), 1.95 (m, 1H), 1.75 (m, 1H), 1.56 (m, 1H), 1.15 (m, 2H).

Step 4: 2-(1-(2,4-dichloro-3-((4-fluoro-1-methyl-6-(trifluoromethyl)-1H-indol-2-yl)methyl)benzoyl)piperidin-4-yl)acetic acid

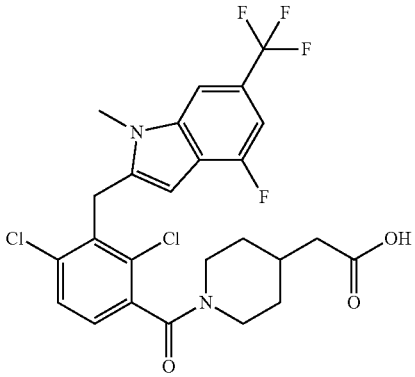 [SMILES: Cn1c(Cc2c(Cl)ccc(C(=O)N3CCC(CC(=O)O)CC3)c2Cl)cc2c(F)cc(C(F)(F)F)cc21]

Using a procedure similar to Example A, Step 5, 2-(1-(2,4-dichloro-3-((4-fluoro-1-methyl-6-(trifluoromethyl)-1H-indol-2-yl)methyl)benzoyl)piperidin-4-yl)acetic acid (40 mg, 86%) was prepared from methyl 2-(1-(2,4-dichloro-3-((4-fluoro-1-methyl-6-(trifluoromethyl)-1H-indol-2-yl)methyl)benzoyl)piperidin-4-yl)acetate (46 mg, 0.08 mmol). LC/MS (Method g): $R_t$=1.83 min.; MS m/z: 545 [M+H]$^+$; $^1$H NMR (DMSO-d$_6$, 400 MHz): δ=12.14 (broad, 1H), 7.82 (s, 1H), 7.66 and 7.65 (d, J=8.2 Hz, 1H), 7.45 and 7.38 (d, J=8.2 Hz, 1H), 7.12 (d, J=10.3 Hz, 1H), 5.72 and 5.68 (s, 1H), 4.47 (m, 3H), 3.97 and 3.96 (s, 3H), 3.24 (m, 1H), 3.04 (m, 1H), 2.80 (m, 1H), 2.15 (m, 2H), 1.93 (m, 1H), 1.79 (m, 1H), 1.60 (m, 1H), 1.14 (m, 2H).

TABLE FE

The following examples were prepared from 2,4-dichloro-3-((4-fluoro-1-methyl-6-(trifluoromethyl)-1H-indol-2-yl)methyl)benzoic acid (example FE, Step 2) using the same procedure with the appropriate amines as described in example FE, Steps 3 and 4.

| Example # | Product | Amine | Intermediate ester R, min | m/z ESI+ (M + H)+ | Final acid R, min | m/z ESI+ (M + H)+ |
|---|---|---|---|---|---|---|
| FE-2 | 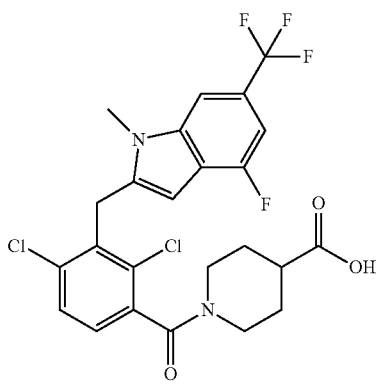 [SMILES: Cn1c(Cc2c(Cl)ccc(C(=O)N3CCC(C(=O)O)CC3)c2Cl)cc2c(F)cc(C(F)(F)F)cc21] | 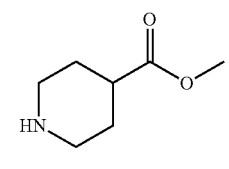 | 2.60 (Method i) | 545 | 1.81 (method g) | 531 |
| FE-3 | 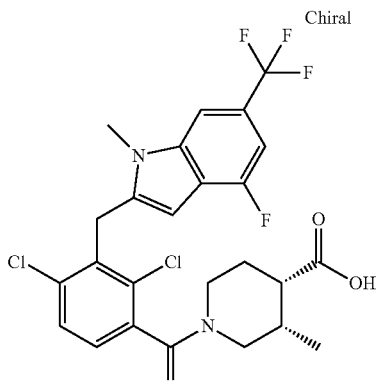 | 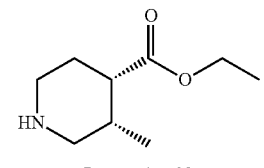 Preparation 83 | 2.76 (method i) | 573 | 1.84 (method g) | 545 |
| FE-4 | 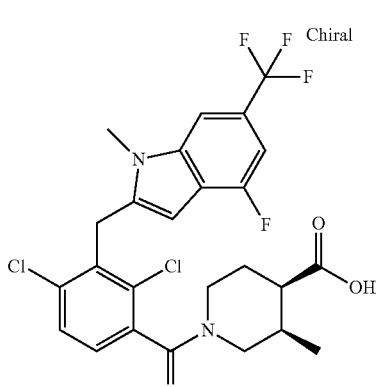 | 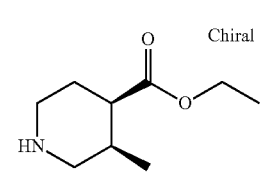 Preparation 84 | 2.76 (method i) | 573 | 1.84 (method g) | 545 |

Example FF: 2-(1-(2,4-dichloro-3-((6-(difluoromethoxy)-1,4-dimethyl-1H-indol-2-yl)methyl)benzoyl)piperidin-4-yl)acetic acid

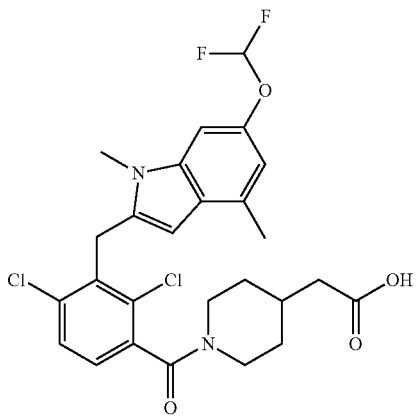 [SMILES: Cc1cc(OC(F)F)cc2c1cc(Cc1c(Cl)ccc(C(=O)N3CCC(CC(=O)O)CC3)c1Cl)n2C]

Step 1: tert-butyl 2,4-dichloro-3-((6-(difluoromethoxy)-4-methyl-1-(phenylsulfonyl)-1H-indol-2-yl)(hydroxy)methyl)benzoate

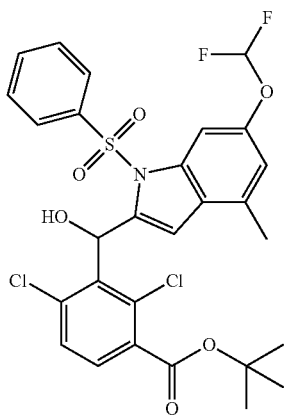 [SMILES: Cc1cc(OC(F)F)cc2c1cc(C(O)c1c(Cl)ccc(C(=O)OC(C)(C)C)c1Cl)n2S(=O)(=O)c1ccccc1]

Using a procedure similar to Example CJ, Step 1, tert-butyl 2,4-dichloro-3-((6-(difluoromethoxy)-4-methyl-1-(phenylsulfonyl)-1H-indol-2-yl)(hydroxy)methyl)benzoate (807 mg, 36%) was prepared from 6-(difluoromethoxy)-4-methyl-1-(phenylsulfonyl)-1H-indole (1.2 g, 3.6 mmol) (Preparation #ZZ-24) and tert-butyl 2,4-dichloro-3-formyl-benzoate (1 g, 3.97 mmol) (Preparation #33, step B).

LC/MS (Method i): $R_t$=2.77 min.; MS M/z: 670 [M−H]$^-$+ CH$_3$COOH; $^1$H NMR (DMSO-d$_6$, 300 MHz): δ 7.88 (m, 2H), 7.68 (m, 1H), 7.56 (m, 5H), 7.23 (t, J=73 Hz, 1H), 6.98 (m, 2H), 6.69 (s, 1H), 6.58 (s, 1H), 2.37 (s, 3H), 1.54 (s, 9H).

Step 2: 2,4-dichloro-3-((6-(difluoromethoxy)-4-methyl-1-(phenylsulfonyl)-1H-indol-2-yl)methyl)benzoic acid

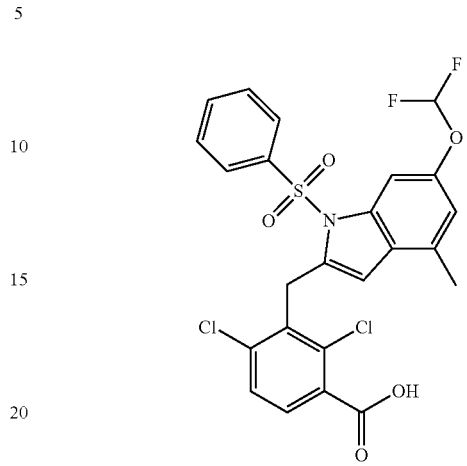

Using a procedure similar to Example A, Step 2, 2,4-dichloro-3-((6-(difluoromethoxy)-4-methyl-1-(phenylsulfonyl)-1H-indol-2-yl)methyl)benzoic acid (666 mg, 100%) was prepared from tert-butyl 2,4-dichloro-3-((6-(difluoromethoxy)-4-methyl-1-(phenylsulfonyl)-1H-indol-2-yl)(hydroxy)methyl)benzoate (655 mg, 1 mmol). LC/MS (Method j): Rt=1.92 min.; MS m/z: 540 [M+H]$^+$; $^1$H NMR (DMSO-d$_6$, 300 MHz): δ 13.6 (broad, 1H), 7.94 (m, 2H), 7.76 (m, 3H), 7.66 (m, 3H), 7.24 (t, J=74.3 Hz, 1H), 6.94 (s, 1H), 5.80 (s, 1H), 4.58 (s, 2H), 2.26 (s, 3H).

Step 3: 2,4-dichloro-3-((6-(difluoromethoxy)-4-methyl-1H-indol-2-yl)methyl)benzoic acid

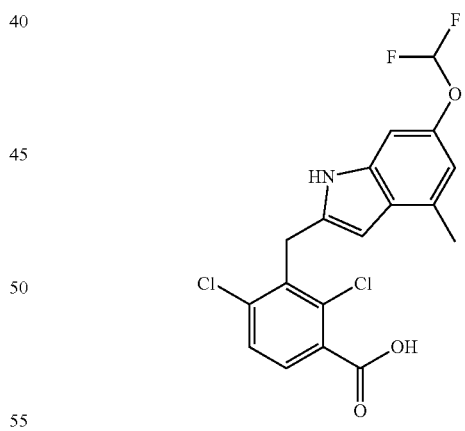

Using a procedure similar to Example A, Step 3, 2,4-dichloro-3-((6-(difluoromethoxy)-4-methyl-1H-indol-2-yl)methyl)benzoic acid (456 mg, 100%) was prepared from 2,4-dichloro-3-((6-(difluoromethoxy)-4-methyl-1-(phenylsulfonyl)-1H-indol-2-yl)methyl)benzoic acid (616 mg, 1.1 mmol) The crude was used in the next step without purification. LC/MS (Method j): $R_t$=1.53 min.;

MS m/z: 400 [M+H]$^+$; $^1$H NMR (DMSO-d$_6$, 300 MHz): δ=11.05 (s, 1H), 7.45 (s, 2H), 7.21 (m, 1H), 6.99 (t, J=75.1 Hz, 1H), 6.85 (s, 1H), 6.51 (s, 1H), 5.73 (s, 1H), 4.31 (s, 2H), 2.24 (s, 3H).

719

Step 4: methyl 2,4-dichloro-3-((6-(difluoromethoxy)-1,4-dimethyl-1H-indol-2-yl)methyl)benzoate

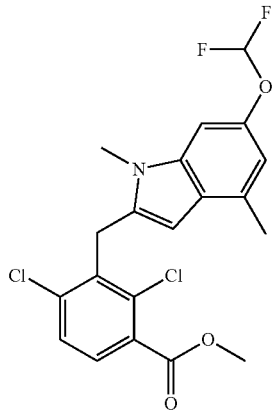 [SMILES: COC(=O)c1ccc(Cl)c(Cc2cc3c(C)cc(OC(F)F)cc3n2C)c1Cl]

Using a procedure similar to Example P, Step 4, methyl 2,4-dichloro-3-((6-(difluoromethoxy)-1,4-dimethyl-1H-indol-2-yl)methyl)benzoate (350 mg, 72%) was prepared from 2,4-dichloro-3-((6-(difluoromethoxy)-4-methyl-1H-indol-2-yl)methyl)benzoic acid (456 mg, 1.1 mmol). LC/MS (Method j): Rt=2.10 min.; MS m/z: 428 [M+H]+; 1H NMR (DMSO-$d_6$, 300 MHz): δ 7.78 (d, J=8.2 Hz, 1H), 7.70 (d, J=8.2 Hz, 1H), 7.14 (s, 1H), 7.11 (t, J=75 Hz, 1H), 6.64 (s, 1H), 5.53 (s, 1H), 4.44 (s, 2H), 3.88 (s, 3H), 3.81 (s, 3H), 2.28 (s, 3H).

Step 5: 2,4-dichloro-3-((6-(difluoromethoxy)-1,4-dimethyl-1H-indol-2-yl)methyl)benzoic acid

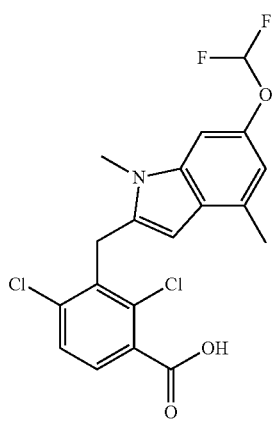 [SMILES: Cc1cc(OC(F)F)cc2c1cc(Cc1c(Cl)ccc(C(=O)O)c1Cl)n2C]

Using a procedure similar to Example A, Step 5, 2,4-dichloro-3-((6-(difluoromethoxy)-1,4-dimethyl-1H-indol-2-yl)methyl)benzoic acid (319 mg, 94%) was prepared from methyl 2,4-dichloro-3-((6-(difluoromethoxy)-1,4-dimethyl-1H-indol-2-yl)methyl)benzoate (349 mg, 0.8 mmol). LC/MS (Method j): Rt=1.62 min.; MS m/z: 414 [M+H]+; 1H NMR (DMSO-$d_6$, 300 MHz): δ 7.70 (d, J=8.2 Hz, 1H), 7.64 (d, J=8.2 Hz, 1H), 7.14 (s, 1H), 7.11 (t, J=75 Hz, 1H), 6.64 (s, 1H), 5.54 (s, 1H), 4.42 (s, 2H), 3.81 (s, 3H), 2.29 (s, 3H).

720

Step 6: methyl 2-(1-(2,4-dichloro-3-((6-(difluoromethoxy)-1,4-dimethyl-1H-indol-2-yl)methyl)benzoyl)piperidin-4-yl)acetate

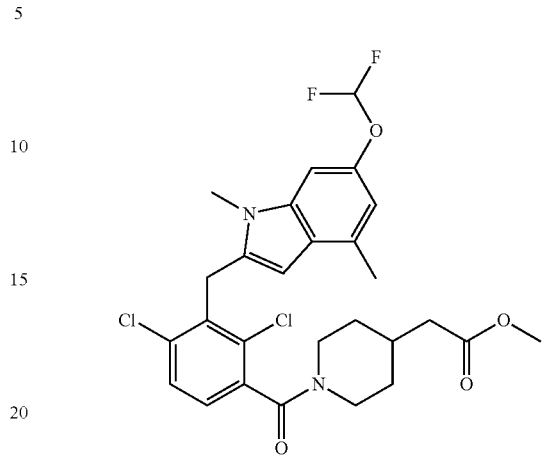

Using a procedure similar to Example A, Step 6, methyl 2-(1-(2,4-dichloro-3-((6-(difluoromethoxy)-1,4-dimethyl-1H-indol-2-yl)methyl)benzoyl)piperidin-4-yl)acetate (123 mg, 92%) was prepared from 2,4-dichloro-3-((6-(difluoromethoxy)-1,4-dimethyl-1H-indol-2-yl)methyl)benzoic acid (100 mg, 0.24 mmol) and methyl 2-(piperidin-4-yl)acetate hydrochloride (51.4 mg, 0.26 mmol). LC/MS (Method j): $R_t$=1.89 min.; MS m/z: 553 [M+H]+; 1H NMR (DMSO-$d_6$, 300 MHz): δ 7.65 (m, 1H), 7.74 and 7.36 (d, J=7.7 Hz, 1H), 7.13 (s, 1H), 7.11 (t, J=75 Hz, 1H), 6.64 (s, 1H), 5.54 and 5.51 (s, 1H), 4.42 (m, 3H), 3.80 (s, 3H), 3.59 and 3.56 (s, 3H), 3.24 (m, 1H), 3.05 (m, 1H), 2.80 (m, 1H), 2.27 (m, 5H), 1.95 (m, 1H), 1.75 (m, 1H), 1.58 (m, 1H), 1.15 (m, 2H).

Step 7: 2-(1-(2,4-dichloro-3-((6-(difluoromethoxy)-1,4-dimethyl-1H-indol-2-yl)methyl)benzoyl)piperidin-4-yl)acetic acid

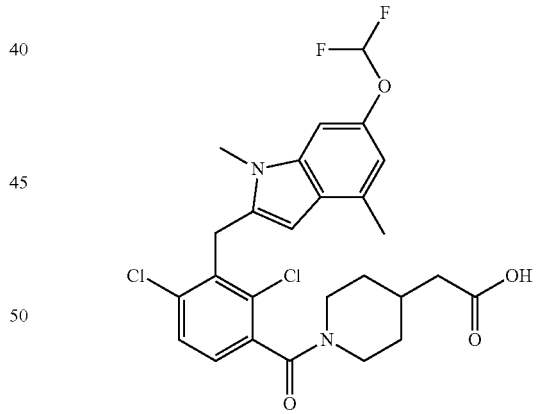

Using a procedure similar to Example A, Step 5, 2-(1-(2,4-dichloro-3-((6-(difluoromethoxy)-1,4-dimethyl-1H-indol-2-yl)methyl)benzoyl)piperidin-4-yl)acetic acid (98 mg, 83%) was prepared from methyl 2-(1-(2,4-dichloro-3-((6-(difluoromethoxy)-1,4-dimethyl-1H-indol-2-yl)methyl)benzoyl)piperidin-4-yl)acetate (120 mg, 0.22 mmol). LC/MS (Method g): $R_t$=1.72 min.;
MS m/z: 539 [M+H]+; 1H NMR (DMSO-$d_6$, 400 MHz): δ 12.07 (broad, 1H), 7.65 and 7.64 (d, J=8.3 Hz, 1H), 7.42 and 7.72 (d, J=8.3 Hz, 1H), 7.13 (s, 1H), 7.11 (t, J=75 Hz, 1H), 6.64 (s, 1H), 5.54 and 5.51 (s, 1H), 4.43 (m, 3H), 3.80 (s, 3H), 3.25 (m, 1H), 3.05 (m, 1H), 2.80 (m, 1H), 2.29 and 2.28 (s, 3H), 2.14 (m, 2H), 1.93 (m, 1H), 1.77 (m, 1H), 1.61 (m, 1H), 1.15 (m, 2H).

TABLE FF

The following examples were prepared from 2,4-dichloro-3-((6-(difluoromethoxy)-1,4-dimethyl-1H-indol-2-yl)methyl)benzoic acid (example FF, Step 5) using the same procedure with the appropriate amines as described in example FF, Steps 6 and 7.

| Example # | Product | Amine | Intermediate ester R$_t$ min | Intermediate ester m/z ESI+ (M + H)+ | Final acid R$_t$ min | Final acid m/z ESI+ (M + H)+ |
|---|---|---|---|---|---|---|
| FF-1 | 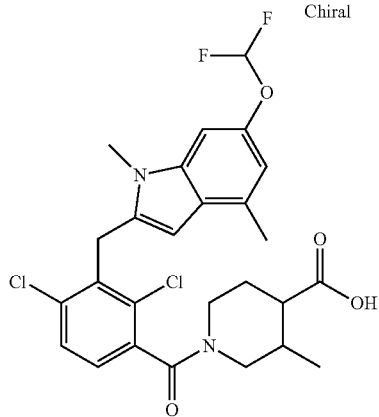 [SMILES: Cc1cc(OC(F)F)cc2c1cc(Cc1c(Cl)ccc(C(=O)N3CCC(C(=O)O)C(C)C3)c1Cl)n2C] Chiral | 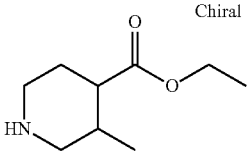 Chiral<br>Preparation 84 | 2.64 (Method i) | 567 | 1.7 (method g) | 539 |
| FF-2 | 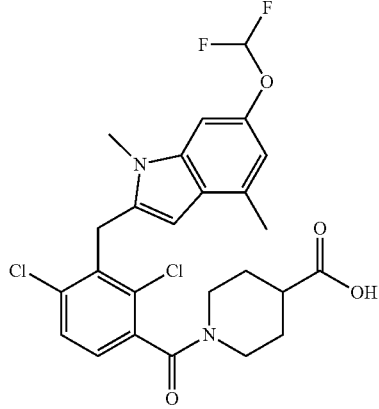 [SMILES: Cc1cc(OC(F)F)cc2c1cc(Cc1c(Cl)ccc(C(=O)N3CCC(C(=O)O)CC3)c1Cl)n2C] | 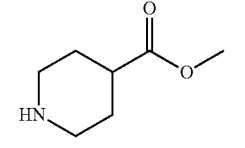 | 2.48 (method i) | 539 | 1.66 (method g) | 525 |

Example FG: 2-(1-(4,6-dichloro-5-(1,4-dimethyl-6-(trifluoromethyl)-1H-indole-2-carbonyl)nicotinoyl)piperidin-4-yl)acetic acid

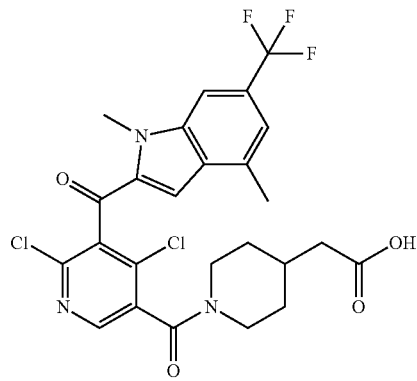

Step 1: tert-butyl 4,6-dichloro-5-(hydroxy(4-methyl-1-(phenylsulfonyl)-6-(trifluoromethyl)-1H-indol-2-yl)methyl)nicotinate

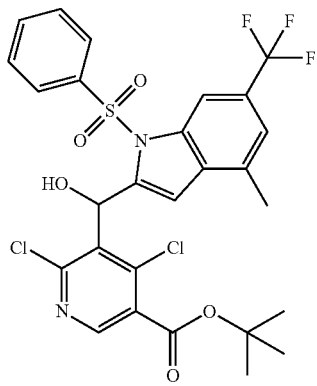 [SMILES: Cc1cc(C(F)(F)F)cc2c1cc(C(O)c1c(Cl)ncc(C(=O)OC(C)(C)C)c1Cl)n2S(=O)(=O)c1ccccc1]

Using a procedure similar to Example A, Step 1, tert-butyl 4,6-dichloro-5-(hydroxy(4-methyl-1-(phenylsulfonyl)-6-(trifluoromethyl)-1H-indol-2-yl)methyl)nicotinate (5.45 g, 55%) was prepared from N-(2-iodo-3-methyl-5-(trifluoromethyl)phenyl)benzenesulfonamide (7.06 g, 16 mmol) (Preparation #16) and tert-butyl 4,6-dichloro-5-(1-hydroxyprop-2-yn-1-yl)nicotinate (5.8 g, 19.2 mmol) (Preparation 60). LC/MS (Method i): $R_f$=2.77 min.; MS m/z: 615 [M+H]$^+$; $^1$H NMR (DMSO-d$_6$, 300 MHz): δ 8.63 (s, 1H), 8.08 (s, 1H), 7.78 (m, 2H), 7.69 (m, 1H), 7.58 (m, 2H), 7.45 (s, 1H), 7.07 (s, 1H), 6.90 (m, 2H), 2.49 (s, 3H), 1.56 (s, 9H).

Step 2: tert-butyl 4,6-dichloro-5-(4-methyl-1-(phenylsulfonyl)-6-(trifluoromethyl)-1H-indole-2-carbonyl)nicotinate

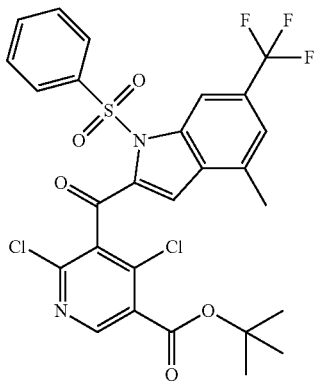 [SMILES: Cc1cc(C(F)(F)F)cc2c1cc(C(=O)c1c(Cl)ncc(C(=O)OC(C)(C)C)c1Cl)n2S(=O)(=O)c1ccccc1]

Using a procedure similar to Example AD, Step 2, tert-butyl 4,6-dichloro-5-(4-methyl-1-(phenylsulfonyl)-6-(trifluoromethyl)-1H-indole-2-carbonyl)nicotinate (3.84 g, 71%) was prepared from tert-butyl 4,6-dichloro-5-(hydroxy(4-methyl-1-(phenylsulfonyl)-6-(trifluoromethyl)-1H-indol-2-yl)methyl)nicotinate (5.4 g, 8.77 mmol). LC/MS (Method i): $R_f$=2.91 min.; MS m/z: 613 [M+H]$^+$; $^1$H NMR (DMSO-d$_6$, 300 MHz): δ 8.97 (s, 1H), 8.33 (m, 1H), 8.12 (m, 3H), 7.80 (m, 1H), 7.71 (m, 2H), 7.59 (s, 1H), 2.58 (s, 3H), 1.57 (s, 9H).

Step 3: 4,6-dichloro-5-(4-methyl-6-(trifluoromethyl)-1H-indole-2-carbonyl)nicotinic acid

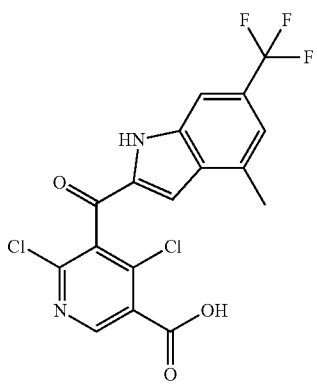 [SMILES: Cc1cc(C(F)(F)F)cc2[nH]c(C(=O)c3c(Cl)ncc(C(=O)O)c3Cl)cc12]

To a solution of tert-butyl 4,6-dichloro-5-(4-methyl-1-(phenylsulfonyl)-6-(trifluoromethyl)-1H-indole-2-carbonyl)nicotinate (3.74 g, 6.1 mmol) in THF (75 mL) was added sodium hydroxide (30.5 mL, 30.5 mmol) and the mixture was stirred 20 hours at room temperature and 6 hours at 50° C. The reaction mixture was partially evaporated and then HCl 1M was added. The formed precipitate was filtrated to give 4,6-dichloro-5-(4-methyl-6-(trifluoromethyl)-1H-indole-2-carbonyl)nicotinic acid (3.25 g, 59%). It is used crude in the next step. LC/MS (Method i): Rt=201 min.; MS m/z: 417 [M+H]$^+$ Step 4: methyl 4,6-dichloro-5-(1,4-dimethyl-6-(trifluoromethyl)-1H-indole-2-carbonyl)nicotinate

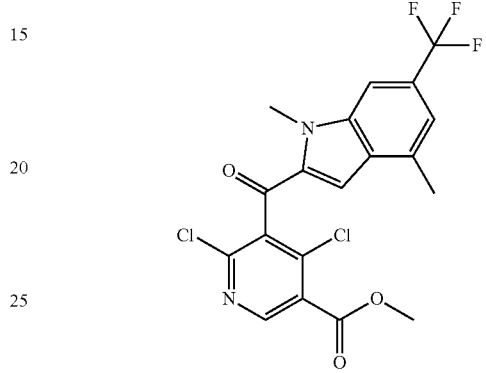

Using a procedure similar to Example P, Step 4, methyl 4,6-dichloro-5-(1,4-dimethyl-6-(trifluoromethyl)-1H-indole-2-carbonyl)nicotinate (850 mg, 24%) was prepared from 4,6-dichloro-5-(4-methyl-6-(trifluoromethyl)-1H-indole-2-carbonyl)nicotinic acid (3.25 g, 7.79 mmol). LC/MS (Method j): $R_f$=2.06 min.; MS m/z: 445 [M+H]$^+$; $^1$H NMR (DMSO-d$_6$, 300 MHz): δ 9.03 (s, 1H), 7.96 (s, 1H), 7.53 (s, 1H), 7.25 (s, 1H), 4.24 (s, 3H), 3.94 (s, 3H), 2.52 (s, 3H).

Step 5: 4,6-dichloro-5-(1,4-dimethyl-6-(trifluoromethyl)-1H-indole-2-carbonyl)nicotinic acid

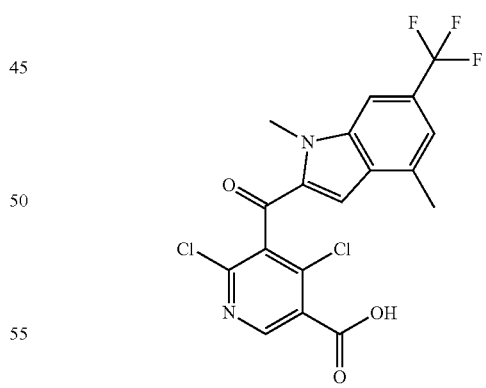

Using a procedure similar to Example A, Step 5, 4,6-dichloro-5-(1,4-dimethyl-6-(trifluoromethyl)-1H-indole-2-carbonyl)nicotinic acid (780 mg, 95%) was prepared from methyl 4,6-dichloro-5-(1,4-dimethyl-6-(trifluoromethyl)-1H-indole-2-carbonyl)nicotinate (0.85 g, 1.9 mmol). LC/MS (Method i): $R_f$=2.20 min.; MS m/z: 431 [M+H]$^+$; $^1$H NMR (DMSO-d$_6$, 300 MHz): δ=14.22 (broad, 1H), 9.00 (s, 1H), 7.96 (s, 1H), 7.51 (s, 1H), 7.24 (s, 1H), 4.24 (s, 3H), 2.53 (s, 3H).

Step 6: 2-(1-(4,6-dichloro-5-(1,4-dimethyl-6-(trifluoromethyl)-1H-indole-2-carbonyl)nicotinoyl)piperidin-4-yl)acetic acid

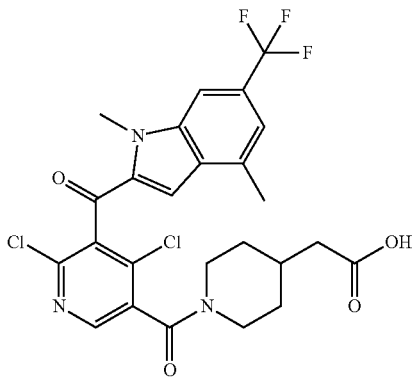

Using a procedure similar to Example A, Step 6, followed by Example A, Step 5, 2-(1-(4,6-dichloro-5-(1,4-dimethyl-6-(trifluoromethyl)-1H-indole-2-carbonyl)nicotinoyl)piperidin-4-yl)acetic acid (59 mg, 46%) was prepared from 4,6-dichloro-5-(1,4-dimethyl-6-(trifluoromethyl)-1H-indole-2-carbonyl)nicotinic acid (100 mg, 0.23 mmol). LC/MS (Method g): $R_f$=1.81 min.; MS m/z: 556 [M+H]⁺; ¹H NMR (DMSO-d₆, 400 MHz): δ 8.66 (m, 1H), 7.96 (s, 1H), 7.55 (m, 1H), 7.24 (s, 1H), 4.46 (m, 1H), 4.23 (s, 3H), 3.74 (m, 1H), 3.11 (m, 1H), 2.85 (m, 1H), 2.53 (s, 3H), 2.19 (m, 1H), 2.13 (m, 1H), 1.96 (m, 1H), 1.80 (m, 1H), 1.66 (m, 1H), 0.18 (m, 2H).

Example FH: 2-(1-(3,5-dichloro-4-((1,4-dimethyl-6-(trifluoromethyl)-1H-indol-2-yl)methyl)picolinoyl)piperidin-4-yl)acetic acid

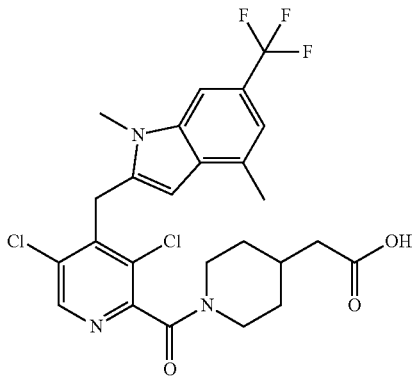

Step 1: methyl 2-(1-(3,5-dichloro-4-((1,4-dimethyl-6-(trifluoromethyl)-1H-indol-2-yl)methyl)picolinoyl)piperidin-4-yl)acetate

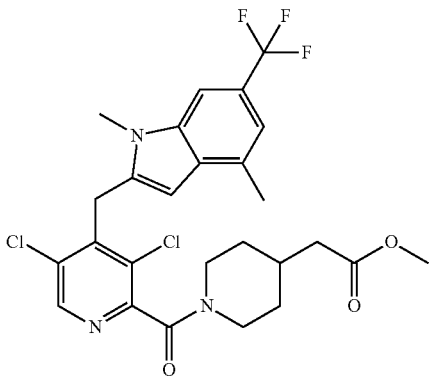 [SMILES: COC(=O)CC1CCN(C(=O)c2ncc(Cl)c(Cc3cc4c(C)cc(C(F)(F)F)cc4n3C)c2Cl)CC1]

Using a procedure similar to Example A, Step 6, methyl 2-(1-(3,5-dichloro-4-((1,4-dimethyl-6-(trifluoromethyl)-1H-indol-2-yl)methyl)picolinoyl)piperidin-4-yl)acetate (89 mg, 74%) was prepared from 3,5-dichloro-4-((1,4-dimethyl-6-(trifluoromethyl)-1H-indol-2-yl)methyl)picolinic acid (90 mg, 0.21 mmol) (example BE, Step 5). LC/MS (Method j): $R_f$=1.85 min.; MS m/z: 556 [M+H]⁺; ¹H NMR (DMSO-d₆, 300 MHz): δ 8.76 (s, 1H), 7.71 (s, 1H), 7.07 (s, 1H), 5.79 (s, 1H), 4.48 (s, 3H), 3.92 (s, 3H), 3.58 (s, 3H), 3.25 (m, 1H), 3.07 (m, 1H), 2.85 (m, 1H), 2.37 (s, 3H), 2.28 (m, 2H), 1.99 (m, 1H), 1.76 (m, 1H), 1.63 (m, 1H), 1.17 (m, 2H).

Step 2: 2-(1-(3,5-dichloro-4-((1,4-dimethyl-6-(trifluoromethyl)-1H-indol-2-yl)methyl)picolinoyl)piperidin-4-yl)acetic acid

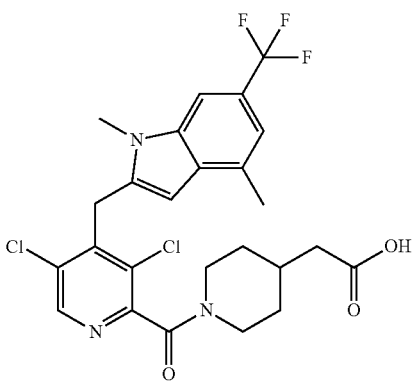 [SMILES: Cc1cc(C(F)(F)F)cc2c1cc(Cc1c(Cl)cnc(C(=O)N3CCC(CC(=O)O)CC3)c1Cl)n2C]

Using a procedure similar to Example A, Step 5, 2-(1-(3,5-dichloro-4-((1,4-dimethyl-6-(trifluoromethyl)-1H-indol-2-yl)methyl)picolinoyl)piperidin-4-yl)acetic acid 60 mg, 70%) was prepared from methyl 2-(1-(3,5-dichloro-4-((1,4-dimethyl-6-(trifluoromethyl)-1H-indol-2-yl)methyl)picolinoyl)piperidin-4-yl)acetate acid (85 mg, 0.15 mmol). LC/MS (Method g): $R_f$=1.76 min.; MS m/z: 542 [M+H]⁺; ¹H NMR (DMSO-d₆, 400 MHz): δ 12.10 (broad, 1H), 8.76 (s, 1H), 7.72 (s, 1H), 7.07 (s, 1H), 5.79 (s, 1H), 4.48 (m, 3H), 3.92 (s, 3H), 3.26 (m, 1H), 3.08 (m, 1H), 2.84 (m, 1H), 2.37 (s, 3H), 2.17 (m, 2H), 1.95 (m, 1H), 1.78 (m, 1H), 1.62 (m, 1H), 1.14 (m, 2H).

Example FI: 2-(1-(2,4-dichloro-3-((1-methyl-6-(trifluoromethoxy)-1H-indol-2-yl)methyl)benzoyl)piperidin-4-yl)acetic acid

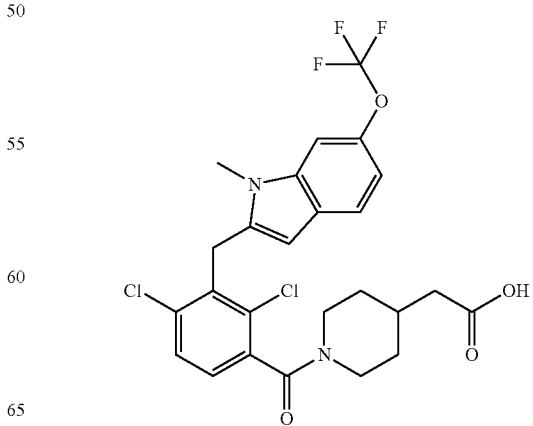

727

Step 1: methyl 2,4-dichloro-3-(hydroxy(1-(phenyl-sulfonyl)-6-(trifluoromethoxy)-1H-indol-2-yl)methyl)benzoate

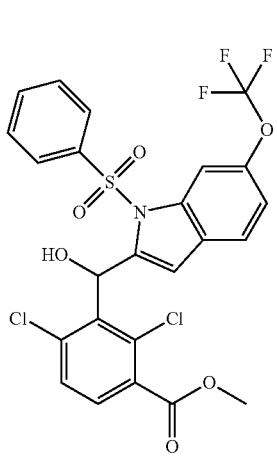 [SMILES: COC(=O)c1ccc(Cl)c(C(O)c2cc3ccc(OC(F)(F)F)cc3n2S(=O)(=O)c2ccccc2)c1Cl]

Using a procedure similar to Example A, Step 1, methyl 2,4-dichloro-3-(hydroxy(1-(phenylsulfonyl)-6-(trifluoromethoxy)-1H-indol-2-yl)methyl)benzoate (2.32 g, 80%) was prepared from N-(2-iodo-5-(trifluoromethoxy)phenyl)benzenesulfonamide (2.2 g, 4.96 mmol) (Preparation 75) and methyl 2,4-dichloro-3-(1-hydroxyprop-2-yn-1-yl)benzoate (1.54 g, 5.96 mmol) (Preparation #1). LC/MS (Method i): $R_t$=2.39 min.; MS m/z: 632 [M–H]⁻+CH₃COOH; ¹H NMR (DMSO-$d_6$, 300 MHz): δ 7.93 (m, 3H), 7.68 (m, 3H), 7.60 (m, 3H), 7.29 (m, 1H), 7.05 (m, 1H), 6.67 (m, 2H), 3.87 (s, 3H).

Step 2: methyl 2,4-dichloro-3-O-(phenylsulfonyl)-6-(trifluoromethoxy)-1H-indol-2-yl)methyl)benzoate

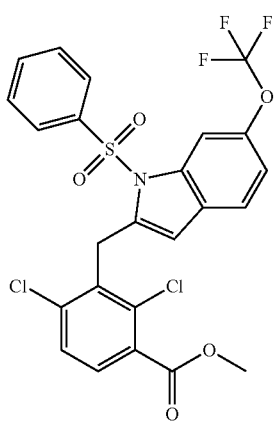 [SMILES: COC(=O)c1ccc(Cl)c(Cc2cc3ccc(OC(F)(F)F)cc3n2S(=O)(=O)c2ccccc2)c1Cl]

Using a procedure similar to Example A, Step 2, methyl 2,4-dichloro-3-((1-(phenylsulfonyl)-6-(trifluoromethoxy)-1H-indol-2-yl)methyl)benzoate (2.25 g, 98%) was prepared from methyl 2,4-dichloro-3-(hydroxy(1-(phenylsulfonyl)-6-(trifluoromethoxy)-1H-indol-2-yl)methyl)benzoate (2.3 g, 4 mmol). LC/MS (Method i): $R_t$=2.68 min.; MS m/z: 558 [M+H]⁺; ¹H NMR (DMSO-$d_6$, 300 MHz): δ=8.04 (s, 1H), 7.96 (m, 2H), 7.82 (m, 1H), 7.76 (m, 1H), 7.69 (m, 3H), 7.57 (m, 1H), 7.28 (m, 1H), 5.91 (m, 1H), 4.61 (m 2H), 3.87 (s, 3H).

728

Step 3: methyl 2,4-dichloro-3-((6-(trifluoromethoxy)-1H-indol-2-yl)methyl)benzoate

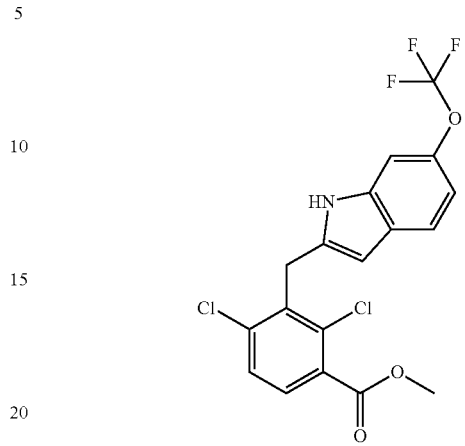

Using a procedure similar to Example A, Step 3, methyl 2,4-dichloro-3-((6-(trifluoromethoxy)-1H-indol-2-yl)methyl)benzoate (1.4 g, 60%) was prepared from methyl 2,4-dichloro-3-((1-(phenylsulfonyl)-6-(trifluoromethoxy)-1H-indol-2-yl)methyl)benzoate (2.6 g, 4.6 mmol). LC/MS (Method i): $R_t$=2.38 min.; MS m/z: 418 [M+H]⁺; ¹H NMR (DMSO-$d_6$, 300 MHz): δ 11.30 (s, 1H), 7.74 (d, J=8.3 Hz, 1H), 7.68 (d, J=8.3 Hz, 1H), 7.44 (d, J=8.6 Hz, 1H), 7.28 (m, 1H), 6.92 (m, 1H), 5.89 (s, 1H), 4.45 (s, 2H), 3.87 (s, 3H).

Step 4: methyl 2,4-dichloro-3-((1-methyl-6-(trifluoromethoxy)-1H-indol-2-yl)methyl)benzoate

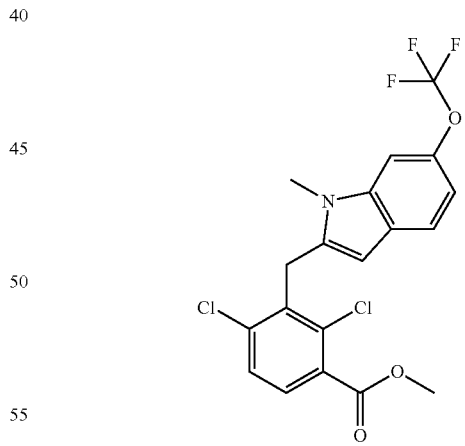

Using a procedure similar to Example P, Step 4, methyl 2,4-dichloro-3-((1-methyl-6-(trifluoromethoxy)-1H-indol-2-yl)methyl)benzoate (1.1 g, 54%) was prepared from methyl 2,4-dichloro-3-((6-(trifluoromethoxy)-1H-indol-2-yl)methyl)benzoate (1.35 g, 3.23 mmol). LC/MS (Method j): $R_t$=1.79 min.; MS m/z: 432 [M+H]⁺; ¹H NMR (DMSO-$d_6$, 300 MHz): δ 7.80 (d, J=8.4 Hz, 1H), 7.71 (d, J=8.4 Hz, 1H), 7.52 (s, 1H), 7.44 (d, J=8.6 Hz, 1H), 6.94 (m, 1H), 5.59 (s, 1H), 4.46 (s, 2H), 3.88 (s, 3H), 3.86 (s, 3H).

Step 5: 2,4-dichloro-3-((1-methyl-6-(trifluoromethoxy)-1H-indol-2-yl)methyl)benzoic acid

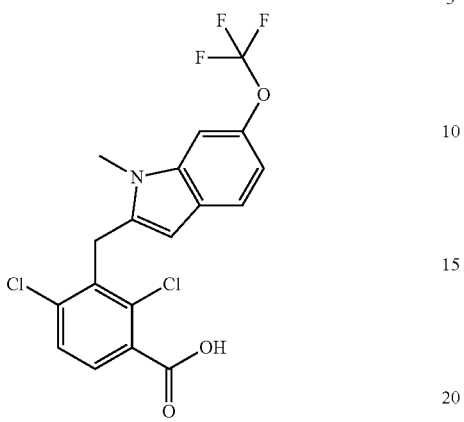

Using a procedure similar to Example A, Step 5, 2,4-dichloro-3-((1-methyl-6-(trifluoromethoxy)-1H-indol-2-yl)methyl)benzoic acid (990 mg, 100%) was prepared from methyl 2,4-dichloro-3-((1-methyl-6-(trifluoromethoxy)-1H-indol-2-yl)methyl)benzoate (1 g, 3.3 mmol). LC/MS (Method i): $R_t$=2.47 min.; MS m/z: 418 [M+H]$^+$; $^1$H NMR (DMSO-d$_6$, 300 MHz): δ=13.64 (broad, 1H), 7.74 (d, J=8.4 Hz, 1H), 7.66 (d, J=8.4 Hz, 1H), 7.52 (s, 1H), 7.44 (d, J=8.6 Hz, 1H), 6.94 (m, 1H), 5.60 (m, 1H), 4.45 (s, 2H), 3.86 (s, 3H).

Step 6: methyl 2-(1-(2,4-dichloro-3-((1-methyl-6-(trifluoromethoxy)-1H-indol-2-yl)methyl)benzoyl)piperidin-4-yl)acetate

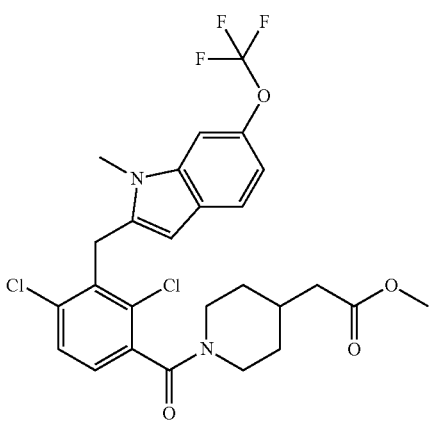 [SMILES: COC(=O)CC1CCN(C(=O)c2ccc(Cl)c(Cc3cc4ccc(OC(F)(F)F)cc4n3C)c2Cl)CC1]

Using a procedure similar to Example A, Step 6, methyl 2-(1-(2,4-dichloro-3-((1-methyl-6-(trifluoromethoxy)-1H-indol-2-yl)methyl)benzoyl)piperidin-4-yl)acetate (180 mg, 88%) was prepared from 2,4-dichloro-3-((1-methyl-6-(trifluoromethoxy)-1H-indol-2-yl)methyl)benzoic acid (150 mg, 0.36 mmol) and methyl 2-(piperidin-4-yl)acetate hydrochloride (83 mg, 0.43 mmol). LC/MS (Method i): $R_t$=2.64 min.; MS m/z: 557 [M+H]$^+$; $^1$H NMR (DMSO-d$_6$, 300 MHz): δ 7.64 and 7.63 (d, J=8.3 Hz, 1H), 7.51 (s, 1H), 7.43 (m, 1.5H), 7.36 (d, J=8.3 Hz, 0.5H), 6.94 (m, 1H), 5.63 and 6.60 (s, 1H), 4.42 (m, 3H), 3.85 (s, 3H), 3.59 and 3.56 (s, 3H), 3.28 (m, 1H), 3.05 (m, 1H), 2.80 (m, 1H), 2.29 (m, 2H), 1.97 (m, 1H), 1.73 (m, 1H), 1.59 (m, 1H), 1.16 (m, 2H).

Step 7: 2-(1-(2,4-dichloro-3-((1-methyl-6-(trifluoromethoxy)-1H-indol-2-yl)methyl)benzoyl)piperidin-4-yl)acetic acid

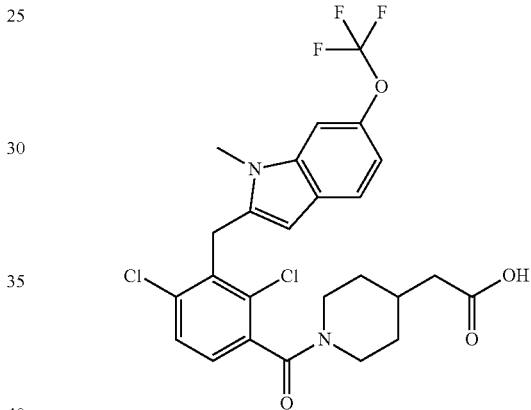

Using a procedure similar to Example A, Step 5, 2-(1-(2,4-dichloro-3-((1-methyl-6-(trifluoromethoxy)-1H-indol-2-yl)methyl)benzoyl)piperidin-4-yl)acetic acid (150 mg, 88%) was prepared from methyl 2-(1-(2,4-dichloro-3-((1-methyl-6-(trifluoromethoxy)-1H-indol-2-yl)methyl)benzoyl)piperidin-4-yl)acetate (170 mg, 0.30 mmol). LC/MS (Method g): $R_t$=1.83 min.;

MS m/z: 543 [M+H]$^+$; $^1$H NMR (DMSO-d$_6$, 400 MHz): δ 7.64 and 7.63 (d, J=8.1 Hz, 1H), 7.51 (s, 1H), 7.44 (m, 1.5H), 7.36 (d, J=8.4 Hz, 0.5H), 6.4 (m, 1H), 5.63 and 5.61 (s, 1H), 4.44 (m, 3H), 3.85 (s, 3H), 3.27 (m, 1H), 3.04 (m, 1H), 2.80 (m, 1H), 2.17 (m, 2H), 1.93 (m, 1H), 1.78 (m, 1H), 1.62 (m, 1H), 1.14 (m, 2H).

TABLE FI

The following examples were prepared from 2,4-dichloro-3-((1-methyl-6-(trifluoromethoxy)-1H-indol-2-yl)methyl)benzoic acid (example FI, Step 5) using the same procedure with the appropriate amines as described in example FI, Steps 6 and 7.

| Example # | Product | Amine | Intermediate ester R, min | Intermediate ester m/z ESI+ (M + H)+ | Final acid R, min | Final acid m/z ESI+ (M + H)+ |
|---|---|---|---|---|---|---|
| FI-1 | 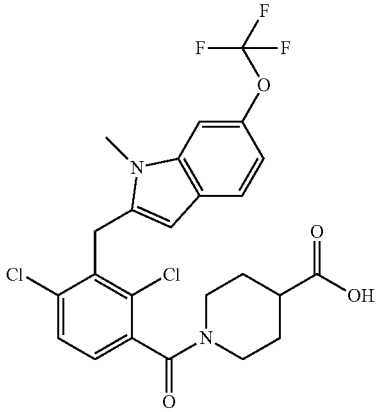 [SMILES: Cn1c(Cc2c(Cl)ccc(C(=O)N3CCC(C(=O)O)CC3)c2Cl)cc2ccc(OC(F)(F)F)cc21] | 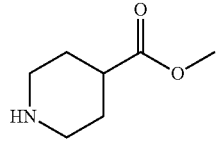 | 2.60 (Method i) | 543 | 1.81 (method g) | 529 |
| FI-2 | 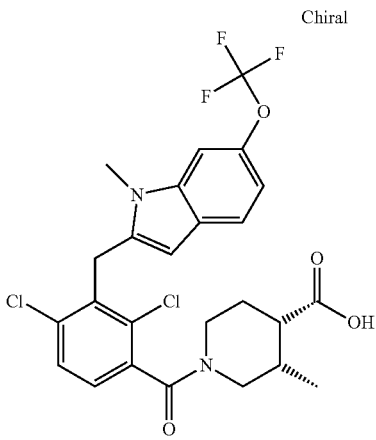 Chiral | 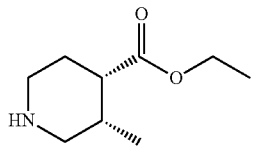 Preparation 83 | 2.76 (Method i) | 571 | 1.84 (method g) | 543 |
| FI-3 | 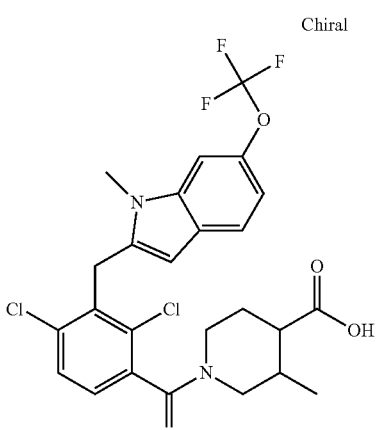 Chiral | 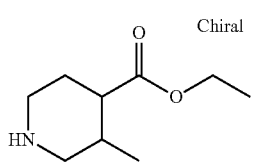 Chiral Preparation 84 | 2.75 (Method i) | 571 | 1.80 (method g) | 543 |

Example FJ: (2,4-dichloro-3-((1,4-dimethyl-6-(trifluoromethyl)-1H-pyrrolo[3,2-c]pyridin-2-yl)methyl)phenyl)(4-(oxetan-3-yl)piperazin-1-yl)methanone

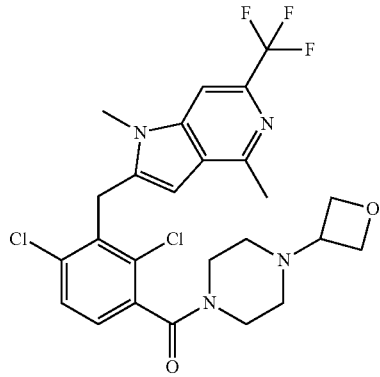

Step 1: methyl 2,4-dichloro-3-(hydroxy(4-methyl-1-(phenylsulfonyl)-6-(trifluoromethyl)-1H-pyrrolo[3,2-c]pyridin-2-yl)methyl)benzoate

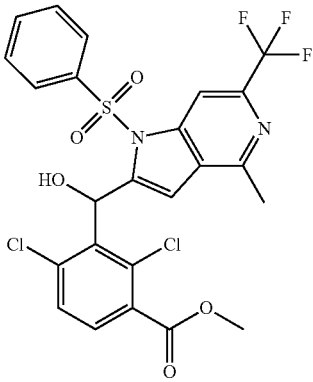 [SMILES: COC(=O)c1ccc(Cl)c(C(O)c2cc3c(C)nc(C(F)(F)F)cc3n2S(=O)(=O)c2ccccc2)c1Cl]

Using a procedure similar to Example A, Step 1, methyl 2,4-dichloro-3-(hydroxy(4-methyl-1-(phenylsulfonyl)-6-(trifluoromethyl)-1H-pyrrolo[3,2-c]pyridin-2-yl)methyl)benzoate (1.16 g, 60%) was prepared from N-(3-iodo-2-methyl-6-(trifluoromethyl)pyridin-4-yl)benzenesulfonamide (1.5 g, 3.4 mmol) (preparation #39) and methyl 2,4-dichloro-3-(1-hydroxyprop-2-yn-1-yl)benzoate (1.0 g, 4 mmol) (preparation #1). LC/MS (Method i): $R_f$=2.46 min.; MS m/z: 573 [M+H]$^+$; $^1$H NMR (DMSO-d$_6$, 300 MHz): δ 8.17 (s, 1H), 7.85 (m, 2H), 7.72 (m, 1H), 7.67 (d, J=8.4 Hz, 1H), 7.60 (m, 2H), 7.52 (d, J=8.4 Hz, 1H), 7.01 (s, 2H), 6.62 (m, 1H), 3.86 (s, 3H), 2.69 (s, 3H).

Step 2: methyl 2,4-dichloro-3-((4-methyl-1-(phenylsulfonyl)-6-(trifluoromethyl)-1H-pyrrolo[3,2-c]pyridin-2-yl)methyl)benzoate

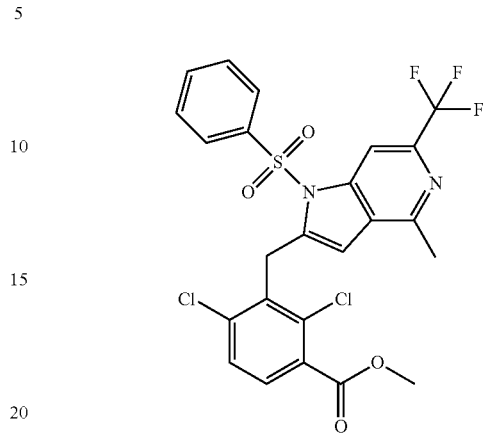

Using a procedure similar to Example Z, Step 2, methyl 2,4-dichloro-3-((4-methyl-1-(phenylsulfonyl)-6-(trifluoromethyl)-1H-pyrrolo[3,2-c]pyridin-2-yl)methyl)benzoate (644 mg, 58%) was prepared from methyl 2,4-dichloro-3-(hydroxy(4-methyl-1-(phenylsulfonyl)-6-(trifluoromethyl)-1H-pyrrolo[3,2-c]pyridin-2-yl)methyl)benzoate (946 mg, 1.6 mmol). LC/MS (Method i): $R_f$=2.79 min.; MS m/z: 557 [M+H]$^+$; $^1$H NMR (DMSO-d$_6$, 300 MHz): δ 8.32 (s, 1H), 8.05 (m 2H), 7.80 (m, 2H), 7.70 (m, 3H), 6.20 (s, 1H), 4.57 (s, 2H), 3.86 (s, 3H), 2.57 (s, 3H).

Step 3: methyl 2,4-dichloro-3-((4-methyl-6-(trifluoromethyl)-1H-pyrrolo[3,2-c]pyridin-2-yl)methyl)benzoate

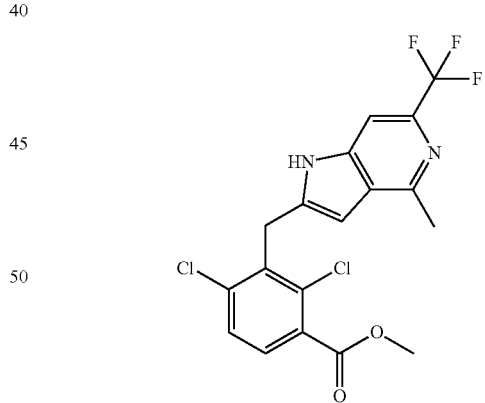

Using a procedure similar to Example A, Step 3, methyl 2,4-dichloro-3-((4-methyl-6-(trifluoromethyl)-1H-pyrrolo[3,2-c]pyridin-2-yl)methyl)benzoate (471 mg, 98%) was prepared from methyl 2,4-dichloro-3-((4-methyl-1-(phenylsulfonyl)-6-(trifluoromethyl)-1H-pyrrolo[3,2-c]pyridin-2-yl)methyl)benzoate (644 mg, 1.15 mmol). LC/MS (Method i): $R_f$=2.30 min.; MS m/z: 417 [M+H]$^+$;

$^1$H NMR (DMSO-d$_6$, 300 MHz): δ=11.95 (broad, 1H), 7.77 (d, J=8.1 Hz, 1H), 7.70 (d, J=8.1 Hz, 1H), 7.61 (s, 1H), 6.13 (m, 1H), 4.52 (s, 2H), 3.88 (s, 3H), 2.58 (s, 3H).

Step 4: methyl 2,4-dichloro-3-((1,4-dimethyl-6-(trifluoromethyl)-1H-pyrrolo[3,2-c]pyridin-2-yl)methyl)benzoate

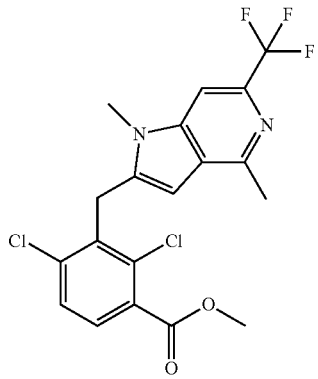 [SMILES: COC(=O)c1ccc(Cl)c(Cc2cc3c(C)nc(C(F)(F)F)cc3n2C)c1Cl]

Using a procedure similar to Example P, Step 4, methyl 2,4-dichloro-3-((1,4-dimethyl-6-(trifluoromethyl)-1H-pyrrolo[3,2-c]pyridin-2-yl)methyl)benzoate (500 mg, 100%) was prepared from methyl 2,4-dichloro-3-((4-methyl-6-(trifluoromethyl)-1H-pyrrolo[3,2-c]pyridin-2-yl)methyl)benzoate (468 mg, 1.12 mmol). LC/MS (Method i): $R_f$=2.42 min.; MS m/z: 431 [M+H]$^+$; $^1$H NMR (DMSO-d$_6$, 300 MHz): δ 7.92 (s, 1H), 7.82 (d, J=8.3 Hz, 1H), 7.73 (d, J=8.3 Hz, 1H), 5.86 (s, 1H), 4.52 (s, 2H), 3.96 (s, 3H), 3.88 (s, 3H), 2.54 (s, 3H).

Step 5: 2,4-dichloro-3-((1,4-dimethyl-6-(trifluoromethyl)-1H-pyrrolo[3,2-c]pyridin-2-yl)methyl)benzoic acid

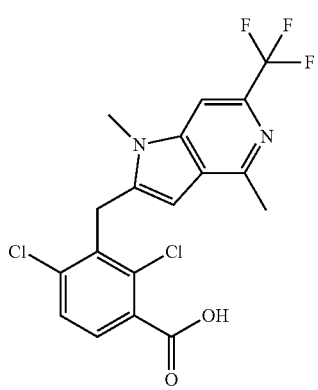 [SMILES: Cc1nc(C(F)(F)F)cc2c1cc(Cc1c(Cl)ccc(C(=O)O)c1Cl)n2C]

Using a procedure similar to Example A, Step 5, 2,4-dichloro-3-((1,4-dimethyl-6-(trifluoromethyl)-1H-pyrrolo[3,2-c]pyridin-2-yl)methyl)benzoic acid (350 mg, 75%) was prepared from methyl 2,4-dichloro-3-((1,4-dimethyl-6-(trifluoromethyl)-1H-pyrrolo[3,2-c]pyridin-2-yl)methyl)benzoate (484 mg, 1.12 mmol). LC/MS (Method i): $R_f$=2.03 min.; MS m/z: 417 [M+H]$^+$; $^1$H NMR (DMSO-d$_6$, 300 MHz): δ 7.92 (s, 1H), 7.65 (m, 2H), 5.84 (s, 1H), 4.49 (s, 2H), 3.96 (s, 3H), 2.53 (s, 3H).

Step 6: (2,4-dichloro-3-((1,4-dimethyl-6-(trifluoromethyl)-1H-pyrrolo[3,2-c]pyridin-2-yl)methyl)phenyl)(4-(oxetan-3-yl)piperazin-1-yl)methanone

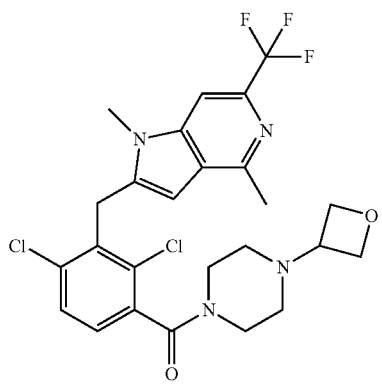 [SMILES: Cc1nc(C(F)(F)F)cc2c1cc(Cc1c(Cl)ccc(C(=O)N3CCN(C4COC4)CC3)c1Cl)n2C]

Using a procedure similar to Example A, Step 6, (2,4-dichloro-3-((1,4-dimethyl-6-(trifluoromethyl)-1H-pyrrolo[3,2-c]pyridin-2-yl)methyl)phenyl)(4-(oxetan-3-yl)piperazin-1-yl)methanone (64 mg, 59%) was prepared from 2,4-dichloro-3-((1,4-dimethyl-6-(trifluoromethyl)-1H-pyrrolo[3,2-c]pyridin-2-yl)methyl)benzoic acid (80 mg, 0.19 mmol) and 1-(oxetan-3-yl)piperazine (41 mg, 0.29 mmol).

LC/MS (Method g): $R_f$=1.39 min.; MS m/z: 541 [M+H]$^+$; $^1$H NMR (DMSO-d$_6$, 400 MHz): δ 7.92 (s, 1H), 7.68 (d, J=8.4 Hz, 1H), 7.44 (d, J=8.4 Hz, 1H), 5.86 (s, 1H), 4.48 (m, 6H), 3.96 (s, 3H), 3.67 (m, 2H), 3.43 (m, 1H), 3.21 (m, 2H), 2.54 (s, 3H), 2.33 (m, 2H), 2.23 (m, 2H).

Example FK: N-(2-(2,6-dichloro-3-(morpholine-4-carbonyl)benzyl)-1,4-dimethyl-1H-indol-6-yl)acetamide

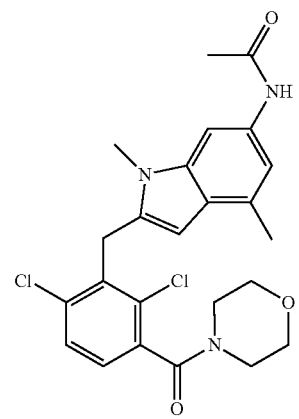 [SMILES: CC(=O)Nc1cc(C)c2cc(Cc3c(Cl)ccc(C(=O)N4CCOCC4)c3Cl)n(C)c2c1]

Step 1: methyl 2,4-dichloro-3-(hydroxy(4-methyl-6-nitro-1-(phenylsulfonyl)-1H-indol-2-yl)methyl)benzoate

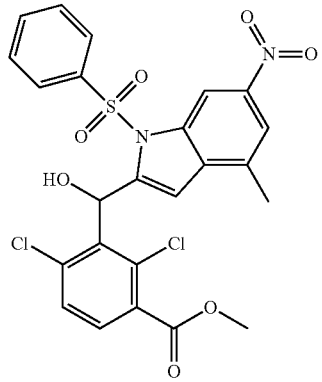 [SMILES: COC(=O)c1ccc(Cl)c(C(O)c2cc3c(C)cc([N+](=O)[O-])cc3n2S(=O)(=O)c2ccccc2)c1Cl]

Using a procedure similar to Example A, Step 1, methyl 2,4-dichloro-3-(hydroxy(4-methyl-6-nitro-1-(phenylsulfonyl)-1H-indol-2-yl)methyl)benzoate (559 mg, 63%) was prepared from N-(2-bromo-3-methyl-5-nitrophenyl)benzenesulfonamide (600 mg, 1.6 mmol) (Preparation 76) and methyl 2,4-dichloro-3-(1-hydroxyprop-2-yn-1-yl)benzoate (544 mg, 2.1 mmol) (Preparation #1). LC/MS (Method i): $R_t$=2.49 min.; MS m/z: 531 [M+H]$^+$–H$_2$O; $^1$H NMR (DMSO-d$_6$, 300 MHz): δ 8.71 (m, 1H), 8.01 (m, 1H), 7.81 (m, 2H), 7.70 (m, 2H), 7.50 (m, 3H), 6.99 (m, 2H), 6.82 (m, 1H), 3.86 (s, 3H), 2.50 (s, 3H).

Step 2: methyl 2,4-dichloro-3-(hydroxy(4-methyl-6-nitro-1H-indol-2-yl)methyl)benzoate

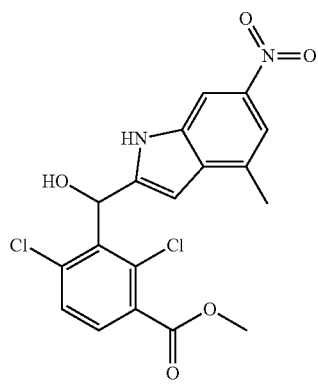 [SMILES: COC(=O)c1ccc(Cl)c(C(O)c2cc3c(C)cc([N+](=O)[O-])cc3[nH]2)c1Cl]

Using a procedure similar to Example A, Step 3, methyl 2,4-dichloro-3-(hydroxy(4-methyl-6-nitro-1H-indol-2-yl)methyl)benzoate (506 mg, 61%) was prepared from methyl 2,4-dichloro-3-(hydroxy(4-methyl-6-nitro-1-(phenylsulfonyl)-1H-indol-2-yl)methyl)benzoate (1.1 g, 2.0 mmol). LC/MS (Method i): $R_t$=2.26 min.; MS m/z: 409 [M+H]$^+$; $^1$H NMR (DMSO-d$_6$, 300 MHz): δ 11.88 (m, 1H), 8.16 (m, 1H), 7.73 (d, J=8.3 Hz, 1H), 7.67 (m, 1H), 7.63 (d, J=8.3 Hz, 1H), 6.82 (m, 2H), 6.14 (s, 1H), 3.86 (s, 3H), 2.45 (s, 3H).

Step 3: methyl 2,4-dichloro-3-((4-methyl-6-nitro-1H-indol-2-yl)methyl)benzoate

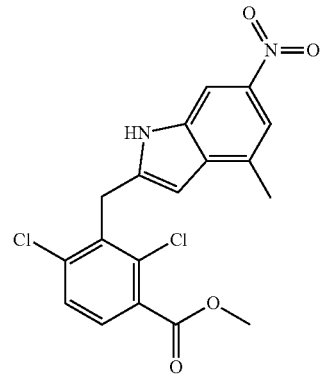 [SMILES: COC(=O)c1ccc(Cl)c(Cc2cc3c(C)cc([N+](=O)[O-])cc3[nH]2)c1Cl]

Using a procedure similar to Example A, Step 2, methyl 2,4-dichloro-3-((4-methyl-6-nitro-1H-indol-2-yl)methyl)benzoate (130 mg, 27%) was prepared from methyl 2,4-dichloro-3-(hydroxy(4-methyl-6-nitro-1H-indol-2-yl)methyl)benzoate (493 mg, 1.2 mmol). LC/MS (Method i): $R_t$=2.52 min.; MS m/z: 393 [M+H]$^+$; $^1$H NMR (DMSO-d$_6$, 300 MHz): δ 11.84 (s, 1H), 8.11 (m, 1H), 7.77 (d, J=8.8 Hz, 1H), 7.70 (d, J=8.8 Hz, 1H), 7.67 (m, 1H), 6.08 (m, 1H), 4.54 (s, 2H), 3.87 (s, 3H), 2.44 (s, 3H).

Step 4: methyl 2,4-dichloro-3-((1,4-dimethyl-6-nitro-1H-indol-2-yl)methyl)benzoate

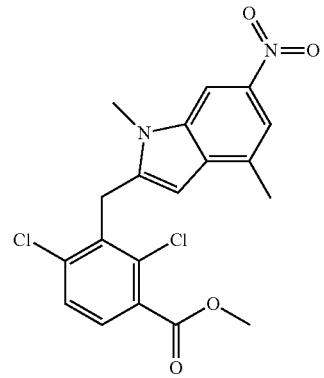 [SMILES: COC(=O)c1ccc(Cl)c(Cc2cc3c(C)cc([N+](=O)[O-])cc3n2C)c1Cl]

Using a procedure similar to Example P, Step 4, methyl 2,4-dichloro-3-((1,4-dimethyl-6-nitro-1H-indol-2-yl)methyl)benzoate (161 mg, 100%) was prepared from methyl 2,4-dichloro-3-((4-methyl-6-nitro-1H-indol-2-yl)methyl)benzoate (152 mg, 0.4 mmol). LC/MS (Method i): $R_t$=2.59 min.; MS m/z: 407 [M+H]$^+$; $^1$H NMR (DMSO-d$_6$, 300 MHz): δ 8.35 (s, 1H), 7.81 (d, J=8.4 Hz, 1H), 7.72 (d, J=8.4 Hz, 1H), 7.70 (s, 1H), 5.76 (s, 1H), 4.54 (s, 2H), 3.98 (s, 3H), 3.88 (s, 3H), 2.39 (s, 3H).

Step 5: 2,4-dichloro-3-((1,4-dimethyl-6-nitro-1H-indol-2-yl)methyl)benzoic acid

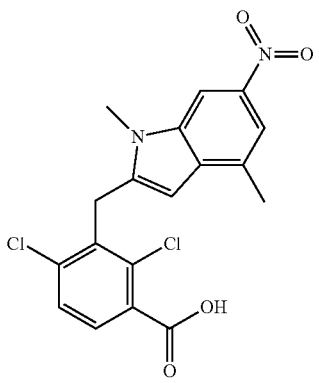 [SMILES: Cc1cc([N+](=O)[O-])cc2c1cc(Cc1c(Cl)ccc(C(=O)O)c1Cl)n2C]

Using a procedure similar to Example A, Step 5, 2,4-dichloro-3-((1,4-dimethyl-6-nitro-1H-indol-2-yl)methyl) benzoic acid (145 mg, 93%) was prepared from methyl 2,4-dichloro-3-((1,4-dimethyl-6-nitro-1H-indol-2-yl) methyl)benzoate (161 mg, 0.39 mmol). LC/MS (Method i): $R_t$=2.24 min.; MS m/z: 393 [M+H]$^+$; $^1$H NMR (DMSO-d$_6$, 300 MHz): δ 13.68 (br., 1H), 8.35 (m, 1H), 7.77 (d, J=8.2 Hz, 1H), 7.71 (m, 1H), 7.68 (d, J=8.2 Hz, 1H), 5.76 (s, 1H), 4.53 (s, 2H), 3.98 (s, 3H), 2.39 (s, 3H).

Step 6: (2,4-dichloro-3-((1,4-dimethyl-6-nitro-1H-indol-2-yl)methyl)phenyl)(morpholino)methanone

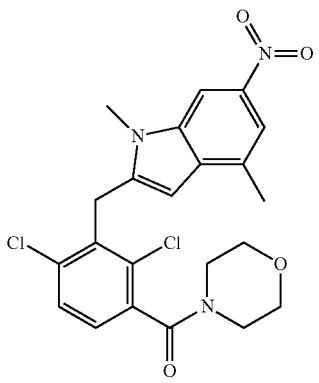 [SMILES: Cc1cc([N+](=O)[O-])cc2c1cc(Cc1c(Cl)ccc(C(=O)N3CCOCC3)c1Cl)n2C]

Using a procedure similar to Example A, Step 6, (2,4-dichloro-3-((1,4-dimethyl-6-nitro-1H-indol-2-yl)methyl) phenyl)(morpholino)methanone (217 mg, 100%) was prepared from 2,4-dichloro-3-((1,4-dimethyl-6-nitro-1H-indol-2-yl)methyl)benzoic acid (145 mg, 0.36 mmol) and morpholine (38.6 mg, 0.44 mmol). LC/MS (Method i): $R_t$=2.27 min.; MS m/z: 462 [M+H]$^+$; $^1$H NMR (DMSO-d$_6$, 300 MHz): δ 8.35 (s, 1H), 7.70 (m, 2H), 7.47 (d, J=8.3 Hz, 1H), 5.79 (m, 1H), 4.50 (m, 2H), 3.98 (s, 3H), 3.65 (s, 4H), 3.55 (m, 2H), 3.18 (m, 2H), 2.39 (s, 3H).

Step 7: (3-((6-amino-1,4-dimethyl-1H-indol-2-yl)methyl)-2,4-dichlorophenyl)(morpholino)methanone

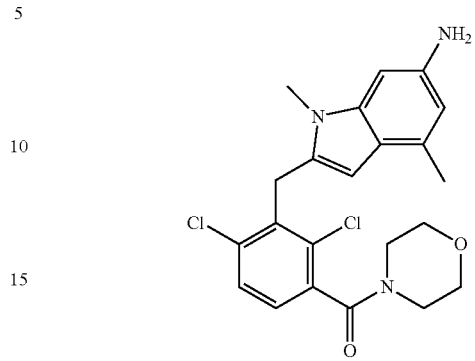

Using a procedure similar to Preparation #18, Step C, (3-((6-amino-1,4-dimethyl-1H-indol-2-yl)methyl)-2,4-dichlorophenyl)(morpholino)methanone (91 mg, 45%) was prepared from (2,4-dichloro-3-((1,4-dimethyl-6-nitro-1H-indol-2-yl)methyl)phenyl)(morpholino)methanone (217 mg, 0.5 mmol). LC/MS (Method i): $R_t$=1.51 min.; MS m/z: 432 [M+H]$^+$; $^1$H NMR (DMSO-d$_6$, 300 MHz): δ 7.65 (d, J=8.2 Hz, 1H), 7.40 (d, J=8.2 Hz, 1H), 6.32 (s, 1H), 6.15 (s, 1H), 5.30 (s, 1H), 4.64 (m, 2H), 4.31 (m, 2H), 3.65 (m, 4H), 3.63 (s, 3H), 3.54 (m, 2H), 3.20 (m, 2H), 2.13 (s, 3H).

Step 8: N-(2-(2,6-dichloro-3-(morpholine-4-carbonyl)benzyl)-1,4-dimethyl-W-indol-6-yl)acetamide

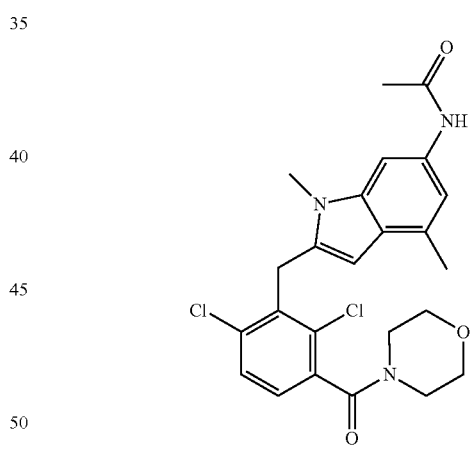

To a solution of (3-((6-amino-1,4-dimethyl-1H-indol-2-yl)methyl)-2,4-dichlorophenyl)(morpholino)methanone (91 mg, 0.21 mmol) in DCM (2 mL) was added acetyl chloride (0.016 mL, 0.232 mmol) and triethylamine (0.053 mL, 0.379 mmol) The reaction mixture was stirred at room temperature for 2 hours. Water was added and the mixture was extracted twice with DCM. The organic layer was dried on magnesium sulfate, filtrate and concentrated. The residue was purified by column chromatography on silica gel (eluting with 10% of DCM in EtOAc) to give N-(2-(2,6-dichloro-3-(morpholine-4-carbonyl)benzyl)-1,4-dimethyl-1H-indol-6-yl)acetamide (57 mg, 54%). LC/MS (Method g): $R_t$=1.34 min.; MS m/z: 474 [M+H]$^+$; $^1$H NMR (DMSO-d$_6$, 500 MHz): δ 9.76 (s, 1H), 7.69 (s, 1H), 7.66 (d, J=8.3 Hz, 1H), 7.43 (d, J=8.3 Hz, 1H), 6.80 (s, 1H), 5.46 (s, 1H), 4.41 (d, J=16.3 Hz, 1H), 4.36 (d, J=16.3 Hz, 1H), 3.74 (s, 3H), 3.65 (m, 4H), 3.54 (m, 2H), 3.17 (m, 2H), 2.24 (s, 3H), 2.03 (s, 3H).

Example FL: 2-(1-(2-chloro-4-cyclopropyl-3-((1-methyl-6-(trifluoromethoxy)-1H-indol-2-yl)methyl)benzoyl)piperidin-4-yl)acetic acid

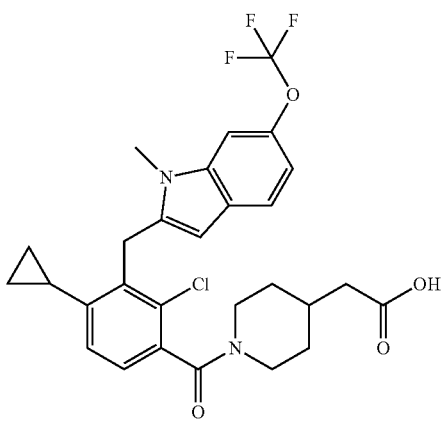 [SMILES: Cn1c(Cc2c(C3CC3)ccc(C(=O)N3CCC(CC(=O)O)CC3)c2Cl)cc2ccc(OC(F)(F)F)cc21]

Step 1: tert-butyl 2-chloro-4-cyclopropyl-3-(hydroxy(1-(phenylsulfonyl)-6-(trifluoromethoxy)-1H-indol-2-yl)methyl)benzoate

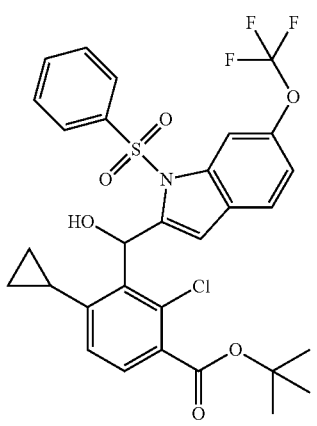 [SMILES: CC(C)(C)OC(=O)c1ccc(C2CC2)c(C(O)c2cc3ccc(OC(F)(F)F)cc3n2S(=O)(=O)c2ccccc2)c1Cl]

Using a procedure similar to Example A, Step 1, tert-butyl 2-chloro-4-cyclopropyl-3-(hydroxy(1-(phenylsulfonyl)-6-(trifluoromethoxy)-1H-indol-2-yl)methyl)benzoate (786 mg, 38%) was prepared from N-(2-iodo-5-(trifluoromethoxy)phenyl)benzenesulfonamide (1.26 g, 2.8 mmol) (Preparation 75) and tert-butyl 2-chloro-4-cyclopropyl-3-(1-hydroxyprop-2-yn-1-yl)benzoate (1.05 g, 3.42 mmol) (Preparation 58). LC/MS (Method j): $R_f$=2.65 min.; MS m/z: 680 [M−H]⁻+CH₃COOH; ¹H NMR (DMSO-d₆, 300 MHz): δ 8.04 (m, 2H), 7.92 (s, 1H), 7.65 (m, 4H), 7.48 (d, J=8.3 Hz, 1H), 7.26 (m, 2H), 6.96 (d, J=8.3 Hz, 1H), 6.60 ppm (d, J=5.6 Hz, 1H), 6.52 (s, 1H), 2.68 (m, 1H), 1.53 (s, 9H), 0.80 (m, 4H).

Step 2: 2-chloro-4-cyclopropyl-3-((1-(phenylsulfonyl)-6-(trifluoromethoxy)-1H-indol-2-yl)methyl)benzoic acid

Using a procedure similar to Example A, Step 2, 2-chloro-4-cyclopropyl-3-((1-(phenylsulfonyl)-6-(trifluoromethoxy)-1H-indol-2-yl)methyl)benzoic acid (223 mg, 81%) was prepared from tert-butyl 2-chloro-4-cyclopropyl-3-(hydroxy(1-(phenylsulfonyl)-6-(trifluoromethoxy)-1H-indol-2-yl)methyl)benzoate (250 mg, 0.4 mmol). LC/MS (Method j): $R_f$=2.17 min.; MS m/z: 548 [M−H]⁻; ¹H NMR (DMSO-d₆, 300 MHz): δ 13.29 (m, 1H), 8.06 (s, 1H), 7.96 (m, 2H), 7.77 (m, 1H), 7.66 (m, 3H), 7.58 (d, J=8.6 Hz, 1H), 7.25 (m, 1H), 7.14 (d, J=8.6 Hz, 1H), 5.83 (s, 1H), 4.62 (s, 2H), 1.69 (m, 1H), 0.68 (m, 4H).

Step 3: 2-chloro-4-cyclopropyl-3-((6-(trifluoromethoxy)-1H-indol-2-yl)methyl)benzoic acid

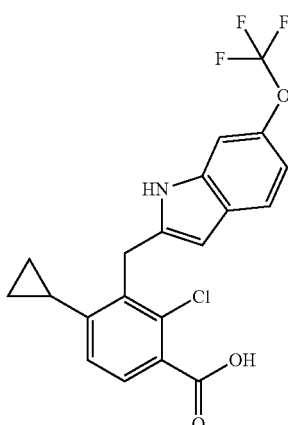

Using a procedure similar to Example A, Step 3, 2-chloro-4-cyclopropyl-3-((6-(trifluoromethoxy)-1H-indol-2-yl)methyl)benzoic acid (164 mg, 100%) was prepared from 2-chloro-4-cyclopropyl-3-((1-(phenylsulfonyl)-6-(trifluoromethoxy)-1H-indol-2-yl)methyl)benzoic acid (220 mg, 0.4 mmol).

LC/MS (Method j): $R_f$=1.77 min.; MS m/z: 410 [M+H]⁺; ¹H NMR (DMSO-d₆, 300 MHz): δ 11.29 (s, 1H), 7.53 (d, J=8.3 Hz, 1H), 7.42 (d, J=8.6 Hz, 1H), 7.27 (s, 1H), 7.08 (d, J=8.1 Hz, 1H), 6.88 (m, 1H), 5.83 (s, 1H), 4.50 (s, 2H), 1.99 (s, 1H), 0.90 (m, 2H), 0.69 (m, 2H).

Step 4: methyl 2-chloro-4-cyclopropyl-3-((1-methyl-6-(trifluoromethoxy)-1H-indol-2-yl)methyl)benzoate

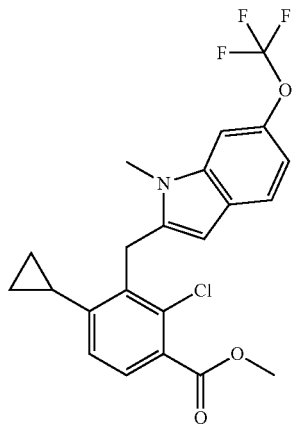 [SMILES: COC(=O)c1ccc(C2CC2)c(Cc2cc3ccc(OC(F)(F)F)cc3n2C)c1Cl]

Using a procedure similar to Example P, Step 4, methyl 2-chloro-4-cyclopropyl-3-((1-methyl-6-(trifluoromethoxy)-1H-indol-2-yl)methyl)benzoate (100 mg, 57%) was prepared from 2-chloro-4-cyclopropyl-3-((6-(trifluoromethoxy)-1H-indol-2-yl)methyl)benzoic acid (131 mg, 0.32 mmol).

LC/MS (Method j): $R_t$=2.37 min.; MS m/z: 438 [M+H]$^+$; $^1$H NMR (DMSO-d$_6$, 300 MHz): δ 7.65 (d, J=8.1 Hz, 1H), 7.51 (s, 1H), 7.42 (d, J=8.4 Hz, 1H), 7.15 (d, J=8.1 Hz, 1H), 6.93 (m, 1H), 5.56 (s, 1H), 4.50 (s, 2H), 3.87 (s, 3H), 3.84 (s, 3H), 1.94 (m, 1H), 0.91 (m, 2H), 0.71 (m, 2H).

Step 5: 2-chloro-4-cyclopropyl-3-((1-methyl-6-(trifluoromethoxy)-1H-indol-2-yl)methyl)benzoic acid

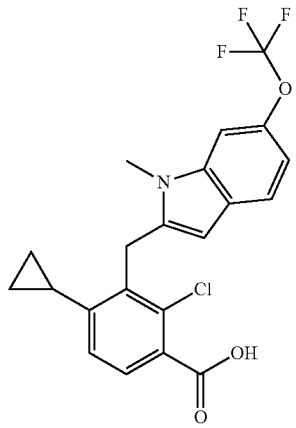 [SMILES: Cn1c(Cc2c(C3CC3)ccc(C(=O)O)c2Cl)cc2ccc(OC(F)(F)F)cc21]

Using a procedure similar to Example A, Step 5, 2-chloro-4-cyclopropyl-3-((1-methyl-6-(trifluoromethoxy)-1H-indol-2-yl)methyl)benzoic acid (77 mg, 81%) was prepared from methyl 2-chloro-4-cyclopropyl-3-((1-methyl-6-(trifluoromethoxy)-1H-indol-2-yl)methyl)benzoate (98 mg, 0.22 mmol). LC/MS (Method j): $R_t$=1.90 min.; MS m/z: 424 [M+H]$^+$; $^1$H NMR (DMSO-d$_6$, 300 MHz): δ 13.34 (broad, 1H), 7.58 (d, J=8.1 Hz, 1H), 7.51 (s, 1H), 7.42 (d, J=8.6 Hz, 1H), 7.10 (d, J=8.1 Hz, 1H), 6.91 (m, 1H), 5.57 (s, 1H), 4.48 (s, 2H), 3.87 (s, 3H), 1.92 (s, 1H), 0.89 (m, 2H), 0.69 (m, 2H).

Step 6: methyl 2-(1-(2-chloro-4-cyclopropyl-3-((1-methyl-6-(trifluoromethoxy)-1H-indol-2-yl)methyl)benzoyl)piperidin-4-yl)acetate

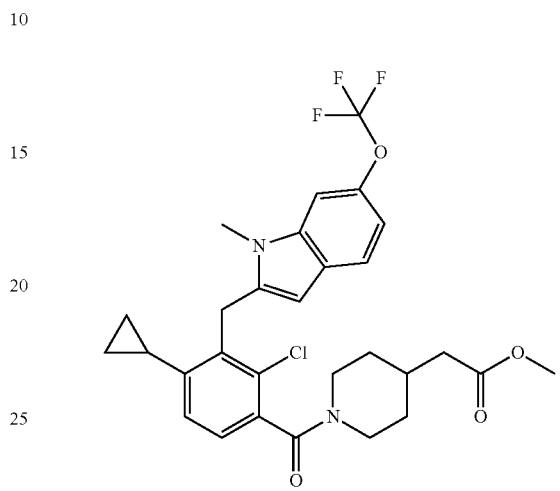

Using a procedure similar to Example A, Step 6, methyl 2-(1-(2-chloro-4-cyclopropyl-3-((1-methyl-6-(trifluoromethoxy)-1H-indol-2-yl)methyl)benzoyl)piperidin-4-yl)acetate (80 mg, 80%) was prepared from 2-chloro-4-cyclopropyl-3-((1-methyl-6-(trifluoromethoxy)-1H-indol-2-yl)methyl)benzoic acid (75 mg, 0.18 mmol) and methyl (4-piperidyl)acetate hydrochloride (38 mg, 0.19 mmol). LC/MS (Method j): $R_t$=2.15 min.; MS m/z: 563 [M+H]$^+$; $^1$H NMR (DMSO-d$_6$, 300 MHz): δ 7.51 (s, 1H), 7.43 and 7.42 (d, J=8.5 Hz, 1H), 7.17 (m, 2H), 6.92 (m, 1H), 5.59 and 5.56 (s, 1H), 4.46 (m, 3H), 3.86 (s, 3H), 3.59 and 3.56 (s, 3H), 3.24 (m, 1H), 3.01 (m, 1H), 2.79 (m, 1H), 2.25 (m, 2H), 1.90 (m, 2H), 174 (m, 1H), 1.58 (m, 1H), 1.14 (m, 2H), 0.87 (m, 2H), 0.67 (m, 2H).

Step 7: 2-(1-(2-chloro-4-cyclopropyl-3-((1-methyl-6-(trifluoromethoxy)-1H-indol-2-yl)methyl)benzoyl)piperidin-4-yl)acetic acid

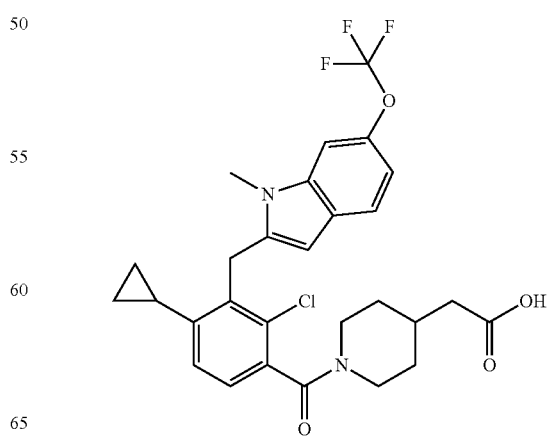

Using a procedure similar to Example A, Step 5, 2-(1-(2-chloro-4-cyclopropyl-3-((1-methyl-6-(trifluoromethoxy)-1H-indol-2-yl)methyl)benzoyl)piperidin-4-yl)acetic acid (66 mg, 84%) was prepared from methyl 2-(1-(2-chloro-4-cyclopropyl-3-((1-methyl-6-(trifluoromethoxy)-1H-indol-2-yl)methyl)benzoyl)piperidin-4-yl)acetate (80 mg, 0.14 mmol). LC/MS (Method g): R$_t$=1.83 min.; MS m/z: 549 [M+H]$^+$; $^1$H NMR (DMSO-d$_6$, 400 MHz): δ 12.21 (m, 1H), 7.51 (s, 1H), 7.43 and 7.42 (d, J=8.6 Hz, 1H), 7.25 and 7.18 (d, J=8.6 Hz, 1H), 7.11 (m, 1H), 6.92 (m, 1H), 5.59 and 5.57 (s, 1H), 4.46 (m, 3H), 3.86 (s, 3H), 3.26 (m, 1H), 3.01 (m, 1H), 2.77 (m, 1H), 2.17 (m, 1H), 2.11 (m, 1H), 1.90 (m, 2H), 1.76 (m, 1H), 1.62 (m, 1H), 1.12 (m, 2H), 0.88 (m, 2H), 0.67 (m, 2H).

Example FM: 2-(1-(2,4-dichloro-3-((6-cyclopropyl-4-fluoro-1-methyl-1H-indol-2-yl)methyl)benzoyl)piperidin-4-yl)acetic acid

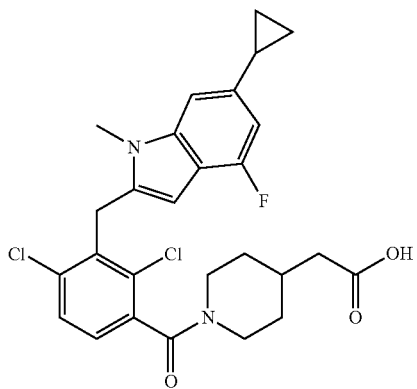 [SMILES: Cn1c(Cc2c(Cl)ccc(C(=O)N3CCC(CC(=O)O)CC3)c2Cl)cc2c(F)cc(C3CC3)cc21]

Step 1: tert-butyl 2,4-dichloro-3-((6-cyclopropyl-4-fluoro-1-(phenylsulfonyl)-1H-indol-2-yl)(hydroxy)methyl)benzoate

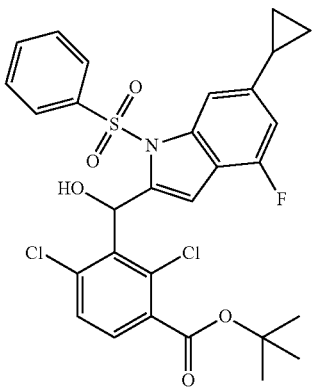 [SMILES: CC(C)(C)OC(=O)c1ccc(Cl)c(C(O)c2cc3c(F)cc(C4CC4)cc3n2S(=O)(=O)c2ccccc2)c1Cl]

Using a procedure similar to Example CJ, Step 1, tert-butyl 2,4-dichloro-3-((6-cyclopropyl-4-fluoro-1-(phenylsulfonyl)-1H-indol-2-yl)(hydroxy)methyl)benzoate (180 mg, 71%) was prepared from 6-cyclopropyl-4-fluoro-1-(phenylsulfonyl)-1H-indole (135 mg, 0.43 mmol) (Preparation 77) and tert-butyl 2,4-dichloro-3-formylbenzoate (177 mg, 0.64 mmol) (Preparation #33, step B). LC/MS (Method j): Rt=2.48 min.; MS m/z: 572 [M+H]$^+$—H$_2$O; $^1$H NMR (DMSO-d$_6$, 300 MHz): δ 7.89 (m, 2H), 7.69 (m, 1H), 7.56 (m, 5H), 6.99 (m, 1H), 6.79 (m, 1H), 6.61 (m, 1H), 6.56 (s, 1H), 2.09 (m, 1H), 1.54 (s, 9H), 1.01 (m, 2H), 0.70 (m, 2H).

Step 2: 2,4-dichloro-3-((6-cyclopropyl-4-fluoro-1-(phenylsulfonyl)-1H-indol-2-yl)methyl)benzoic acid

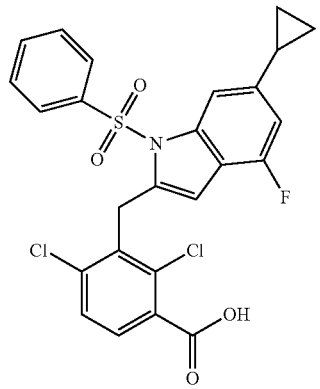 [SMILES: O=C(O)c1ccc(Cl)c(Cc2cc3c(F)cc(C4CC4)cc3n2S(=O)(=O)c2ccccc2)c1Cl]

Using a procedure similar to Example A, Step 2, 2,4-dichloro-3-((6-cyclopropyl-4-fluoro-1-(phenylsulfonyl)-1H-indol-2-yl)methyl)benzoic acid (700 mg, 100%) was prepared from tert-butyl 2,4-dichloro-3-((6-cyclopropyl-4-fluoro-1-(phenylsulfonyl)-1H-indol-2-yl)(hydroxy)methyl)benzoate (920 mg, 1.2 mmol). LC/MS (Method j): R$_t$=2.09 min.; MS m/z: 516 [M−H]$^−$; $^1$H NMR (DMSO-d$_6$, 300 MHz): δ=13.64 (broad, 1H), 7.96 (m, 2H), 7.78 (m, 2H), 7.68 (m, 4H), 6.78 (m, 1H), 5.68 (s, 1H), 4.57 (s, 2H), 2.12 (m, 1H), 1.03 (m, 2H), 0.73 (m, 2H).

Step 3: 2,4-dichloro-3-((6-cyclopropyl-4-fluoro-1H-indol-2-yl)methyl)benzoic acid

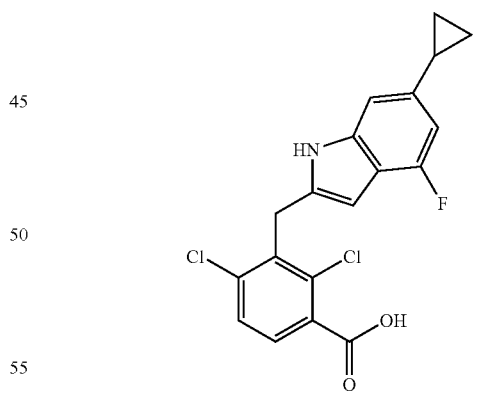

Using a procedure similar to Example A, Step 3, 2,4-dichloro-3-((6-cyclopropyl-4-fluoro-1H-indol-2-yl)methyl)benzoic acid (620 mg, 69%) was prepared from 2,4-dichloro-3-((6-cyclopropyl-4-fluoro-1-(phenylsulfonyl)-1H-indol-2-yl)methyl)benzoic acid (697 mg, 1.3 mmol). LC/MS (Method j): R$_t$=1.59 min.; MS m/z: 378 [M+H]$^+$; $^1$H NMR (DMSO-d$_6$, 300 MHz): δ=13.60 (broad, 1H), 11.17 (s, 1H), 7.70 (d, J=8.6 Hz, 1H), 7.63 (d, J=8.6 Hz, 1H), 6.89 (s, 1H), 6.44 (m, 1H), 5.73 (m, 1H), 4.42 (m, 2H), 1.97 (m, 1H), 0.91 (m, 2H), 0.63 (m, 2H).

747

Step 4: methyl 2,4-dichloro-3-((6-cyclopropyl-4-fluoro-1-methyl-1H-indol-2-yl)methyl)benzoate

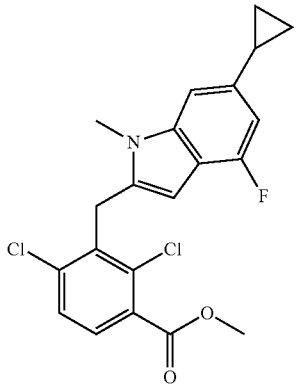 [SMILES: COC(=O)c1ccc(Cl)c(Cc2cc3c(F)cc(C4CC4)cc3n2C)c1Cl]

Using a procedure similar to Example P, Step 4, methyl 2,4-dichloro-3-((6-cyclopropyl-4-fluoro-1-methyl-1H-indol-2-yl)methyl)benzoate (219 mg, 33%) was prepared from 2,4-dichloro-3-((6-cyclopropyl-4-fluoro-1H-indol-2-yl)methyl)benzoic acid (618 mg, 1.6 mmol). LC/MS (Method j): $R_t$=2.26 min.; MS m/z: 406 [M+H]$^+$; $^1$H NMR (DMSO-d$_6$, 300 MHz): δ 7.78 (d, J=8.8 Hz, 1H), 7.70 (d, J=8.8 Hz, 1H), 7.04 (s, 1H), 6.50 (m, 1H), 5.42 (s, 1H), 4.42 (s, 2H), 3.88 (s, 3H), 3.81 (s, 3H), 2.01 (m, 1H), 0.94 (m, 2H), 0.71 (m, 2H).

Step 5: 2,4-dichloro-3-((6-cyclopropyl-4-fluoro-1-methyl-1H-indol-2-yl)methyl)benzoic acid

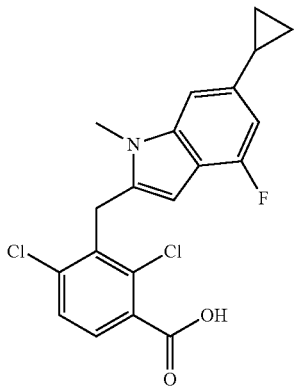 [SMILES: Cn1c(Cc2c(Cl)ccc(C(=O)O)c2Cl)cc2c(F)cc(C3CC3)cc21]

Using a procedure similar to Example A, Step 5, 2,4-dichloro-3-((6-cyclopropyl-4-fluoro-1-methyl-1H-indol-2-yl)methyl)benzoic acid (145 mg, 57%) was prepared from methyl 2,4-dichloro-3-((6-cyclopropyl-4-fluoro-1-methyl-1H-indol-2-yl)methyl)benzoate (263 mg, 0.64 mmol). LC/MS (Method j): Rt=1.78 min.; MS m/z: 392 [M+H]$^+$

748

Step 6: methyl 2-(1-(2,4-dichloro-3-((6-cyclopropyl-4-fluoro-1-methyl-1H-indol-2-yl)methyl)benzoyl)piperidin-4-yl)acetate

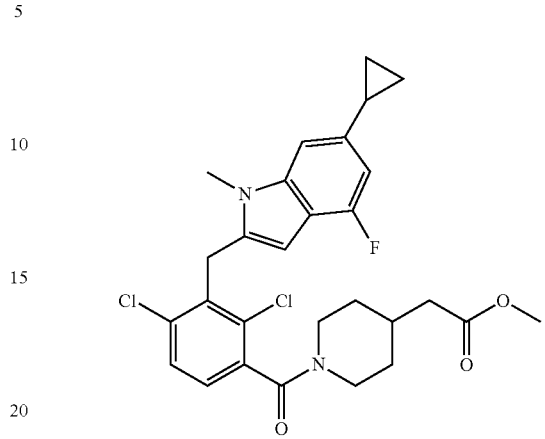

Using a procedure similar to Example A, Step 6, methyl 2-(1-(2,4-dichloro-3-((6-cyclopropyl-4-fluoro-1-methyl-1H-indol-2-yl)methyl)benzoyl)piperidin-4-yl)acetate (81 mg, 84%) was prepared from 2,4-dichloro-3-((6-cyclopropyl-4-fluoro-1-methyl-1H-indol-2-yl)methyl)benzoic acid (71 mg, 0.18 mmol) and methyl (4-piperidyl)acetate hydrochloride (70 mg, 0.36 mmol). LC/MS (Method i): $R_t$=2.63 min.; MS m/z: 531 [M+H]$^+$; $^1$H NMR (DMSO-d$_6$, 300 MHz): δ 7.64 and 7.63 (d, J=8.3 Hz, 1H), 7.42 and 7.35 (d, J=8.3 Hz, 1H), 7.04 (s, 1H), 6.49 (m, 1H), 5.44 (m, 1H), 4.41 (m, 3H), 3.81 (s, 3H), 3.59 and 3.56 (s, 3H), 3.27 (m, 1H), 3.05 (m, 1H), 2.78 (m, 1H), 2.26 (m, 2H), 1.99 (m, 2H), 1.75 (m, 1H), 1.59 (m, 1H), 1.17 (m, 2H), 0.94 (m, 2H), 0.70 (m, 2H).

Step 7: 2-(1-(2,4-dichloro-3-((6-cyclopropyl-4-fluoro-1-methyl-1H-indol-2-yl)methyl)benzoyl)piperidin-4-yl)acetic acid

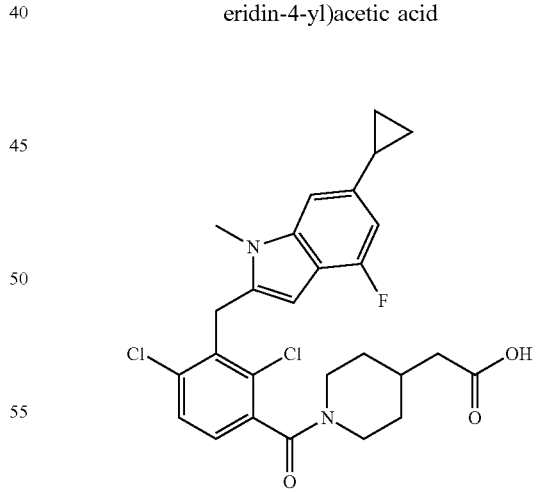

Using a procedure similar to Example A, Step 5, 2-(1-(2,4-dichloro-3-((6-cyclopropyl-4-fluoro-1-methyl-1H-indol-2-yl)methyl)benzoyl)piperidin-4-yl)acetic acid (41 mg, 53%) was prepared from methyl 2-(1-(2,4-dichloro-3-((6-cyclopropyl-4-fluoro-1-methyl-1H-indol-2-yl)methyl)benzoyl)piperidin-4-yl)acetate (79 mg, 0.15 mmol). LC/MS (Method g): $R_t$=1.83 min.; MS m/z: 517 [M+H]$^+$; $^1$H NMR (DMSO-d$_6$, 400 MHz): δ=12.10 (s, 1H), 7.64 and 7.63 (d, J=8.1 Hz, 1H), 7.42 and 7.35 (d, J=8.1 Hz, 1H), 7.04 (s, 1H), 6.49 (s, 1H), 5.45 (m, 1H), 4.42 (m, 3H), 3.81 (s, 3H), 3.26 (m, 1H), 3.04 (m, 1H), 2.80 (m, 1H), 2.15 (m, 2H), 1.97 (m, 2H), 1.77 (m, 1H), 1.61 (m, 1H), 1.14 (m, 2H), 0.93 (m, 2H), 0.70 (m, 2H).

Example FN: 1-(2,4-dichloro-3-((6-cyclopropyl-4-fluoro-1-methyl-1H-indol-2-yl)methyl)benzoyl)piperidine-4-carboxylic acid

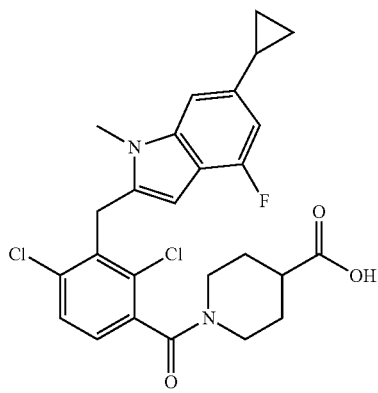 [SMILES: Cn1c(Cc2c(Cl)ccc(C(=O)N3CCC(C(=O)O)CC3)c2Cl)cc2c(F)cc(C3CC3)cc21]

Step 1: methyl 1-(2,4-dichloro-3-((6-cyclopropyl-4-fluoro-1-methyl-1H-indol-2-yl)methyl)benzoyl)piperidine-4-carboxylate

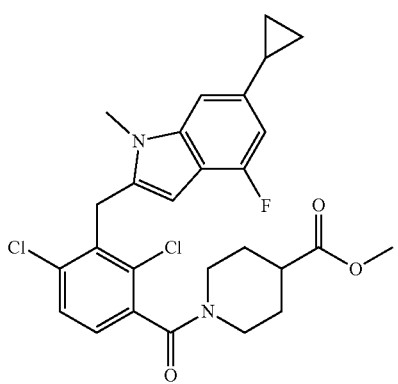 [SMILES: COC(=O)C1CCN(C(=O)c2ccc(Cl)c(Cc3cc4c(F)cc(C5CC5)cc4n3C)c2Cl)CC1]

Using a procedure similar to Example A, Step 6, methyl 1-(2,4-dichloro-3-((6-cyclopropyl-4-fluoro-1-methyl-1H-indol-2-yl)methyl)benzoyl)piperidine-4-carboxylate (74 mg, 80%) was prepared from 2,4-dichloro-3-((6-cyclopropyl-4-fluoro-1-methyl-1H-indol-2-yl)methyl)benzoic acid (70 mg, 0.18 mmol) (example FM, Step 5) and methyl piperidine-4-carboxylate hydrochloride (64 mg, 0.36 mmol). LC/MS (Method j): R$_f$=1.98 min.; MS m/z: 517 [M+H]$^+$; $^1$H NMR (DMSO-d$_6$, 300 MHz): δ 7.64 (d, J=8.3 Hz, 1H), 7.45 and 7.38 (d, J=8.3 Hz, 1H), 7.04 (s, 1H), 6.50 (m, 1H), 5.45 (m, 1H), 4.38 (m, 3H), 3.81 (m, 3H), 3.62 and 3.59 (s, 3H), 3.28 (m, 1H), 3.13 (m, 1H), 2.97 (m, 1H), 2.68 (m, 1H), 1.98 (m, 2H), 1.77 (m, 1H), 1.52 (m, 2H), 0.93 (m, 2H), 0.71 (m, 2H).

Step 2: 1-(2,4-dichloro-3-((6-cyclopropyl-4-fluoro-1-methyl-1H-indol-2-yl)methyl)benzoyl)piperidine-4-carboxylic acid

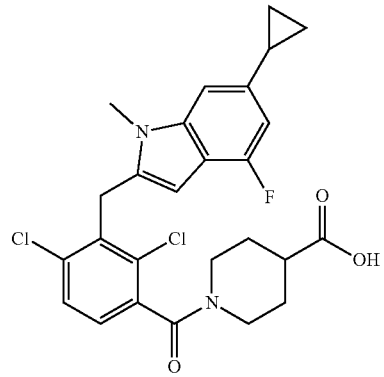 [SMILES: Cn1c(Cc2c(Cl)ccc(C(=O)N3CCC(C(=O)O)CC3)c2Cl)cc2c(F)cc(C3CC3)cc21]

Using a procedure similar to Example A, Step 5, 1-(2,4-dichloro-3-((6-cyclopropyl-4-fluoro-1-methyl-1H-indol-2-yl)methyl)benzoyl)piperidine-4-carboxylic acid (34 mg, 48%) was prepared from methyl 1-(2,4-dichloro-3-((6-cyclopropyl-4-fluoro-1-methyl-1H-indol-2-yl)methyl)benzoyl)piperidine-4-carboxylate (72 mg, 0.13 mmol). LC/MS (Method g): R$_f$=1.81 min.;

MS m/z: 503 [M+H]$^+$; $^1$H NMR (DMSO-d$_6$, 400 MHz): δ 12.33 (broad, 1H), 7.64 (d, J=8.1 Hz, 1H), 7.44 and 7.38 (d, J=8.1 Hz, 1H), 7.04 (s, 1H), 6.50 (m, 1H), 5.45 (m, 1H), 4.38 (m, 3H), 3.81 (s, 3H), 3.25 (m, 1H), 3.08 (m, 1H), 2.98 (m, 1H), 2.54 (m, 1H), 2.01 (m, 1H), 1.92 (m, 1H), 1.78 (m, 1H), 1.49 (m, 2H), 0.94 (m, 2H), 0.71 (m, 2H).

Example FO: 2-[[2,6-dichloro-3-(morpholine-4-carbonyl)phenyl]methyl]-N,N,1,4-tetramethyl-indole-6-carboxamide

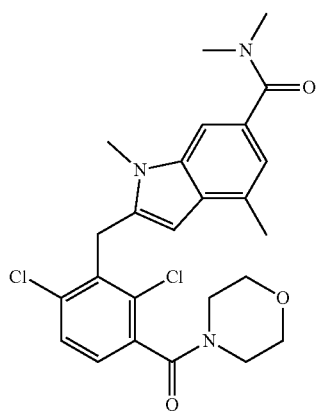 [SMILES: Cc1cc(C(=O)N(C)C)cc2c1cc(Cc1c(Cl)ccc(C(=O)N3CCOCC3)c1Cl)n2C]

751

Step 1: 2-(2,6-dichloro-3-(morpholine-4-carbonyl) benzyl)-1,4-dimethyl-1H-indole-6-carboxylic acid

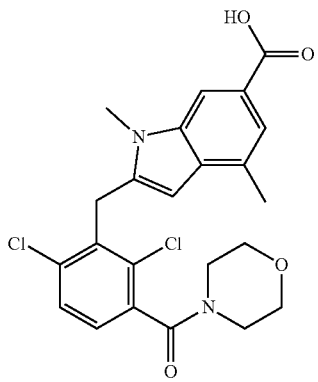 [SMILES: Cc1cc(C(=O)O)cc2c1cc(Cc1c(Cl)ccc(C(=O)N3CCOCC3)c1Cl)n2C]

To a suspension of 2-(2,6-dichloro-3-(morpholine-4-carbonyl)benzyl)-1,4-dimethyl-1H-indole-6-carbonitrile (Example AA-35) in a ethylene glycol (600 μl, 10.76 mmol) was added a 3M solution of potassium hydroxide (400 μL, 1.20 mmol) and the reaction mixture was stirred 1.5 hours at 130° C. under microwaves irradiation. The reaction mixture was diluted with water, and washed twice with DCM. The aqueous layer was acidified with a 1M HCl solution, extracted with DCM, dried over magnesium sulfate, filtered and evaporated. 2-(2,6-dichloro-3-(morpholine-4-carbonyl) benzyl)-1,4-dimethyl-1H-indole-6-carboxylic acid (16 mg, 53.4%) was isolated as broken white powder. LC/MS (Method i): $R_t$=1.90 min.; MS m/z: 461 [M+H]$^+$; $^1$H NMR (DMSO-d$_6$, 300 MHz): δ 12.47 (broad, 1H), 7.92 (s, 1H), 7.68 (d, J=8.4 Hz, 1H), 7.45 (d, J=8.4 Hz, 1H), 7.40 (s, 1H), 5.64 (m, 1H), 4.46 (m, 2H), 3.89 (s, 3H), 3.65 (m, 4H), 3.54 (m, 2H), 3.18 (m, 2H), 2.33 (m, 3H).

Step 2: 2-[[2,6-dichloro-3-(morpholine-4-carbonyl) phenyl]methyl]-N,N,1,4-tetramethyl-indole-6-carboxamide

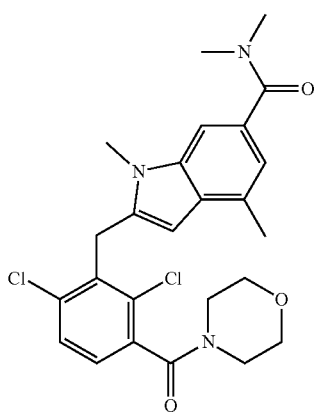 [SMILES: Cc1cc(C(=O)N(C)C)cc2c1cc(Cc1c(Cl)ccc(C(=O)N3CCOCC3)c1Cl)n2C]

Using a procedure similar to Example A, Step 6, 2-[[2,6-dichloro-3-(morpholine-4-carbonyl)phenyl]methyl]-N,N,1,4-tetramethyl-indole-6-carboxamide (29 mg, 55%) was prepared from 2-(2,6-dichloro-3-(morpholine-4-carbonyl) benzyl)-1,4-dimethyl-1H-indole-6-carboxylic acid (50 mg, 0.11 mmol). LC/MS (Method g): $R_t$=1.42 min.; MS m/z: 488

752

[M+H]$^+$; $^1$H NMR (DMSO-d$_6$, 400 MHz): δ=7.68 (d, J=8.1 Hz, 1H), 7.45 (d, J=8.1 Hz, 1H), 7.35 (s, 1H), 6.81 (s, 1H), 5.58 (s, 1H), 4.43 (m, 2H), 3.85 (s, 3H), 3.65 (m, 4H), 3.54 (m, 2H), 3.12-3.26 (m, 2H), 2.98 (s, 6H), 2.30 (s, 3H).

Example FP: 2-[[2,6-dichloro-3-(morpholine-4-carbonyl)phenyl]methyl]-N,1,4-trimethyl-indole-6-carboxamide

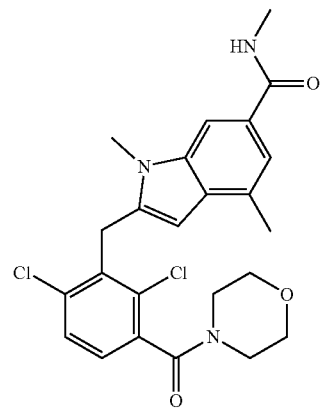 [SMILES: CNC(=O)c1cc(C)c2cc(Cc3c(Cl)ccc(C(=O)N4CCOCC4)c3Cl)n(C)c2c1]

Using a procedure similar to Example A1, 2-[[2,6-dichloro-3-(morpholine-4-carbonyl)phenyl]methyl]-N,1,4-trimethyl-indole-6-carboxamide (35 mg, 68%) was prepared from 2-(2,6-dichloro-3-(morpholine-4-carbonyl)benzyl)-1,4-dimethyl-1H-indole-6-carboxylic acid (50 mg, 0.11 mmol) (example FO, Step 1) and methylamine (0.217 μL, 0.43 mmol). LC/MS (Method g): Rt=1.32 min.; MS m/z: 474 [M+H]$^+$; $^1$H NMR (DMSO-d$_6$, 400 MHz): δ 8.26 (m, 1H), 7.82 (s, 1H), 7.68 (d, J=8.4 Hz, 1H), 7.45 (d, J=8.4 Hz, 1H), 7.31 (m, 1H), 5.59 (s, 1H), 4.44 (m, 2H), 3.87 (s, 3H), 3.65 (m, 4H), 3.54 (m, 2H), 3.19 (m, 2H), 2.80 (d, J=4.4 Hz, 3H), 2.32 (s, 3H).

Example FQ: 1-(2,4-dichloro-3-((1,4-dimethyl-6-(trifluoromethyl)-1H-indol-3-yl)methyl)benzoyl) piperidine-4-carboxylic acid

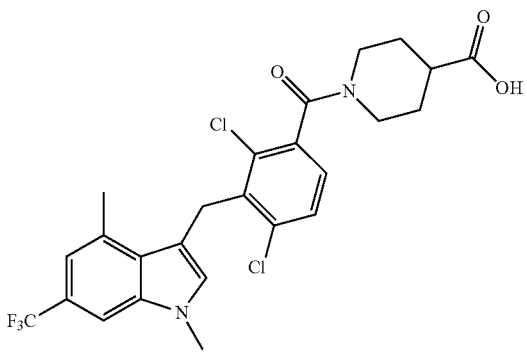 [SMILES: Cc1cc(C(F)(F)F)cc2c1c(Cc1c(Cl)ccc(C(=O)N3CCC(C(=O)O)CC3)c1Cl)cn2C]

753

Step 1: 2-bromo-1-methyl-3-nitro-5-(trifluoromethyl)benzene

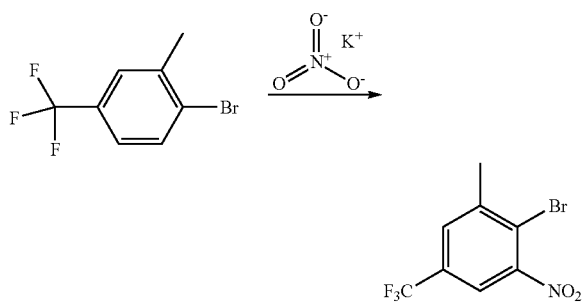

A yellow biphasic solution of 1-bromo-2-methyl-4-(trifluoromethyl)benzene (40.65 g, 170 mmol) (Combi-blocks) and $H_2SO_4$ (203 mL) was cooled in an ice bath and potassium nitrate (20.63 g, 204 mmol) was added in portions, keeping the temperature <25° C. The ice bath was removed and the temperature maintained between 20 and 25° C. After 1.5 hours, LC/MS showed complete reaction. The solution was cooled in an ice bath and water added (400 mL) over 10 minutes, keeping the temp <30° C. Extracted the aqueous layer with MTBE (2×100 mL), washed the organic layer with brine (2×50 mL). The extracts were combined and dried over $Na_2SO_4$, filtered and solvent removed to yield 2-bromo-1-methyl-3-nitro-5-(trifluoromethyl)benzene (45.1 g, 159 mmol, 93% yield), used without further purification. LC/MS (Method i) $R_t$=1.73 min.; MS m/z: 282.13 & 283.95 (M−H)⁻; Crude 1H NMR shows a 5:1 ratio of isomers

Step 2: benzyl 2-cyano-2-(2-methyl-6-nitro-4-(trifluoromethyl)phenyl)acetate

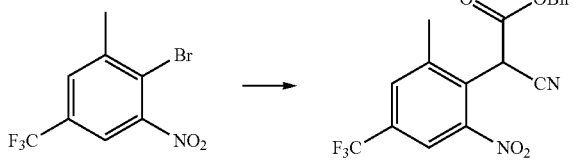

A mixture of 2-bromo-1-methyl-3-nitro-5-(trifluoromethyl)benzene (86.6 g, 305 mmol), DMF (178 mL), benzyl cyanoacetate (46.7 mL, 305 mmol), and potassium carbonate (93 g, 671 mmol) was heated to 80° C. After 90 minutes the solution was cooled to <20° C. by the addition of water/ice (800 mL), followed by 2N HCl (534 mL, 1067 mmol) carefully at <25° C. The crude product was partitioned between the acid aqueous phase and EtOAc (4×150 mL). The organic extracts were combined, washed with water (3×200 mL) and brine (200 mL), dried over $Na_2SO_4$, filtered and solvent removed in vacuo to yield a dark gum that solidified on standing. The solid was triturated with MTBE (100 mL) for 15 minutes before the dropwise addition of heptane (200 mL). The solid was collected and washed with 1:2 MTBE/heptanes (2×50 mL), finally $Et_2O$ (2×20 mL) and dried to yield a beige powdery solid of benzyl 2-cyano-2-(2-methyl-6-nitro-4-(trifluoromethyl)phenyl)acetate (71 g, 184 mmol, 60.3%). LC/MS (Method i) $R_t$=1.73 min.; MS m/z: 377.31 (M−H)⁻.

754

Step 3: 4-methyl-6-(trifluoromethyl)-1H-indole

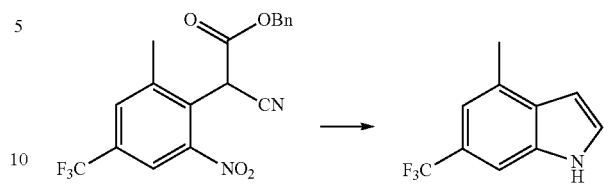

Benzyl 2-cyano-2-(2-methyl-6-nitro-4-(trifluoromethyl)phenyl)acetate (63.5 g, 168 mmol), EtOH (490 mL), water (49 mL), acetic acid (49 mL) were added to 5% Pd/C (wet JM#9) (21.51 g, 101 mmol) in a 1.7 L Parr hydrogenator and shaken for 23 hours at 70 psi and 50° C. The mixture was cooled to rt and filtered concentrated in vacuo at 50° C., diluted with EtOAc (200 mL) and water (200 mL). The aqueous layer was separated and extracted with EtOAc (2×50 mL). Original EtOAC and extracts were combined, washed with 2N HCl (2×80 mL) followed by 10% aqueous $Na_2S_2O_3$ (2×100 mL), saturated aqueous $NaHCO_3$ (3×150 mL) and brine (2×50 mL), dried ($Na_2SO_4$), filtered and solvent distilled to yield a purple liquid that solidified on standing of 4-methyl-6-(trifluoromethyl)-1H-indole (38 g, 191 mmol, 100% yield). Used without further purification. LC/MS (Method i) $R_t$=1.58 min.; MS m/z: 198.23 (M−H)⁻.

Step 4: tert-butyl 2,4-dichloro-3-((4-methyl-6-(trifluoromethyl)-1H-indol-3-yl)methyl)benzoate

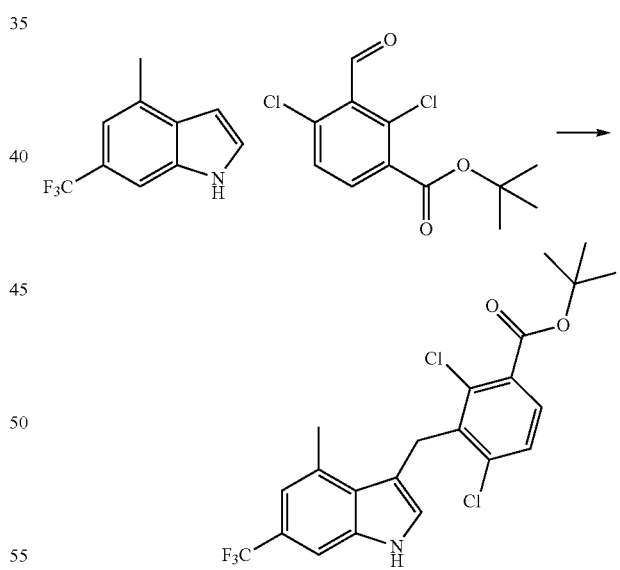

A solution of 4-methyl-6-(trifluoromethyl)-1H-indole (14.4 g, 72.3 mmol) in DCM (75 mL) was cooled to <5° C. and tert-butyl 2,4-dichloro-3-formylbenzoate (21.88 g, 80 mmol) (Preparation #33, Step B), triethylsilane (34.6 mL, 217 mmol), and 2,2,2-TFA (8.36 mL, 108 mmol) were added, keeping the temperature <5° C. After 2 hours the reaction mixture was poured onto a stirred solution of MTBE (200 mL) and saturated $NaHCO_3$ (200 mL). After 30 minutes the organic layer was separated, washed with brine and concentrated in vacuo to provide tert-butyl 2,4-dichloro- 3-((4-methyl-6-(trifluoromethyl)-1H-indol-3-yl)methyl) benzoate as an oil. The crude pdt was used without further purification.

Step 5: 2,4-dichloro-3-((1,4-dimethyl-6-(trifluoromethyl)-1H-indol-3-yl)methyl)benzoic acid

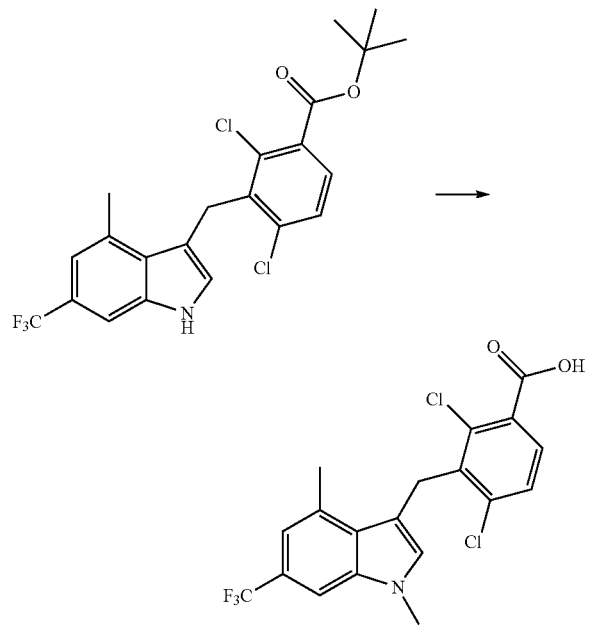

To a solution of the crude tert-butyl 2,4-dichloro-3-((4-methyl-6-(trifluoromethyl)-1H-indol-3-yl)methyl)benzoate (33 g, 72.0 mmol) in DMF (100 mL) was added iodomethane (4.95 mL, 79 mmol) followed by a solution of sodium 2-methylpropan-2-olate (7.61 g, 79 mmol) in DMF (50 mL) while maintaining a temperature of about 25-30° C. After 4 h the reaction mixture was diluted with MTBE (200 mL) and NH$_4$Cl (100 mL). The organic layer was separated, washed with water (100 mL) and brine (100 mL), dried (Na$_2$SO$_4$) filtered and concentrated in vacuo. The crude ester was dissolved in 1,4-dioxane (240 mL) and a 6N solution of hydrogen chloride (120 mL, 720 mmol) The reaction mixture was heated to 85° C. After 48 hours the reaction mixture was cooled to room temperature and MTBE (200 mL) was added. The organic layer was separated washed with brine, dried over Na$_2$SO$_4$, filtered and concentrated in vacuo. The crude material was suspended in ACN (100 mL) briefly heated to 70° C., cooled to room temperature and filtered. Solids contained product and inorganic salts (not soluble in DMSO or MeOH). The solids were dissolved in EtOAc (200 mL) and washed with water (100 mL) and brine (100 mL), dried over Na$_2$SO$_4$, filtered and concentrated in vacuo. The solids were suspended in ACN (100 mL) heated to 70° C. with stirring. After 2 hours the mixture was cooled to room temperature and filtered to provide 2,4-dichloro-3-((1,4-dimethyl-6-(trifluoromethyl)-1H-indol-3-yl)methyl)benzoic acid (20 g, 48.1 mmol, 66.7% as a tan solid. LC/MS (Method i) R$_f$=2.18 min.;
MS m/z: 414 (M−H)$^-$.

Step 6: 1-(2,4-dichloro-3-((1,4-dimethyl-6-(trifluoromethyl)-1H-indol-3-yl)methyl)benzoyl)piperidine-4-carboxylic acid

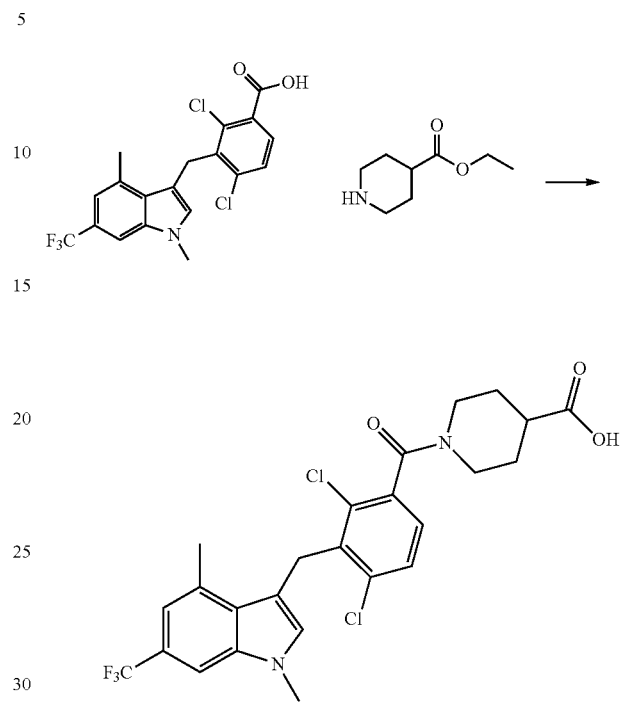

To a slurry of 2,4-dichloro-3-((1,4-dimethyl-6-(trifluoromethyl)-1H-indol-3-yl)methyl)benzoic acid (20 g, 48.1 mmol) in THF (200 mL) was added 2-(3H-[1,2,3]triazolo[4,5-b]pyridin-3-yl)-1,1,3,3-tetramethylisouronium hexafluorophosphate(V) (20.10 g, 52.9 mmol) followed by triethylamine (26.8 mL, 192 mmol). After 10 minutes ethyl piperidine-4-carboxylate, hydrochloric acid (10.24 g, 52.9 mmol) was added in one portion. After 2 hours LC/MS showed reaction complete (yellow nearly homogeneous solution). The mixture was diluted with MTBE (300 mL) and washed with 1N HCl (50 mL×3), 1N NaOH (50 mL×3), saturated NH$_4$Cl (50 mL) and brine (50 mL), dried over Na$_2$SO$_4$, filtered and concentrated in vacuo to a yellow oil. The oil was dissolved in MTBE (200 mL) and decolorizing carbon (15 g) was added. After 30 minutes of stirring the mixture was filtered, and concentrated in vacuo to a foam. To a solution of the ester in 1,4-dioxane (200 mL) was added 2N sodium hydroxide (96 mL, 192 mmol). The reaction mixture was heated to 75° C. MeOH was added until homogeneous. After 1 hour hydrolysis was complete. The solution was cooled to room temperature MTBE added (500 mL) and pH adjusted to 1 with 5N HCl. The organic layer was separated, washed with water (2×100 mL), brine (100 mL), dried over Na$_2$SO$_4$ filtered and concentrated in vacuo to a yellow solid. The solids were suspended in ACN and stirred for about 18 hours. After 15 hours the solids were collected by filtration rinsing with ACN (2×10 mL). After drying for 30 minutes the solids were transferred to a vial and dried in a vacuum oven at 55° C. for about 18 hours to provide 1-(2,4-dichloro-3-((1,4-dimethyl-6-(trifluoromethyl)-1H-indol-3-yl)methyl)benzoyl)piperidine-4-carboxylic acid (24.5 g, 46.5 mmol, 97% yield) as a white solid.

LC/MS (Method i) R$_f$=2.52 min.; MS m/z: 525 (M−H)$^-$.

Example FR: 2-(1-(3,5-dichloro-4-((3,7-dimethyl-5-(trifluoromethyl)-1H-indol-1-yl)methyl)picolinoyl)piperidin-4-yl)acetic acid

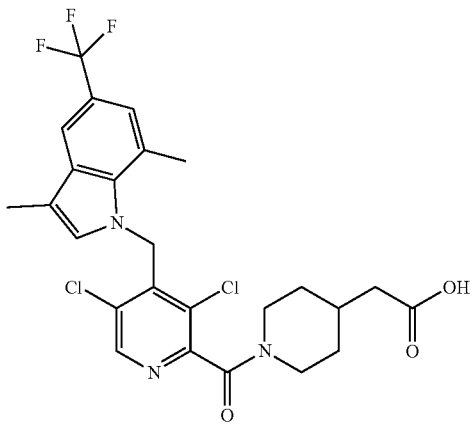 [SMILES: Cc1cn(Cc2c(Cl)cnc(C(=O)N3CCC(CC(=O)O)CC3)c2Cl)c2c(C)cc(C(F)(F)F)cc12]

Step 1: 3,5-dichloro-4-(diethoxymethyl)pyridine 1-oxide

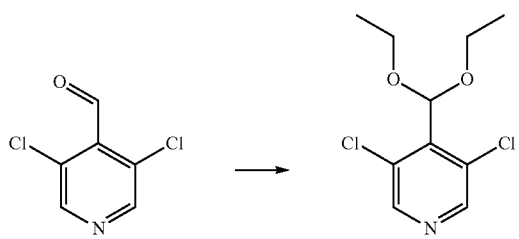

To a solution of 3,5-dichloroisonicotinaldehyde (50 g, 284 mmol) in EtOH (500 mL) was added triethoxymethane (47.3 mL, 284 mmol) followed by sulfuric acid (1.514 mL, 28.4 mmol). The reaction mixture was heated to 75° C. After 4 hours the reaction mixture was cooled to room temperature, partially concentrated in vacuo and solids began to precipitate. The solids were collected by filtration and dried in vacuo to provide 3,5-dichloro-4-(diethoxymethyl)pyridine (41 g, 164 mmol, 57.7%) as an off white solid. The filtrate was partially concentrated in vacuo to about 100 mL, and cooled in an ice bath. After 30 minutes additional solids were collected by filtration, rinsed with ice cold EtOH, and dried in vacuo to provide 3,5-dichloro-4-(diethoxymethyl)pyridine (20.2 g, 81 mmol, 28.4% yield) as an off white solid. The two crops were combined. $^1$H NMR (400 MHz, DMSO-d6) δ 8.60 (s, 1H), 5.89 (s, 1H), 3.73 (dq, J=9.7, 7.1 Hz, 2H), 3.50 (dq, J=9.7, 7.0 Hz, 2H), 1.13 (t, J=7.0 Hz, 6H).

Step 2: 3,5-dichloro-4-(diethoxymethyl)pyridine 1-oxide

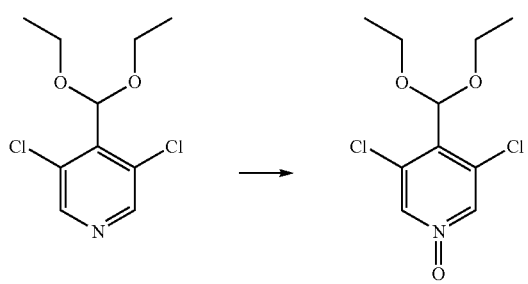 [SMILES: CCOC(OCC)c1c(Cl)cncc1Cl ; CCOC(OCC)c1c(Cl)c[n+]([O-])cc1Cl]

To a solution of 3,5-dichloro-4-(diethoxymethyl)pyridine (41 g, 164 mmol) in DCM (200 mL) was added 3-chlorobenzoperoxoic acid (44.1 g, 197 mmol). After 2 days the reaction mixture was diluted with Et$_2$O (about 300 mL) and washed with 2N NaOH (2×300 mL), brine (100 mL), dried over Na$_2$SO$_4$ filtered and concentrated in vacuo. The resulting solids were slurried in heptane (about 40 mL). After 30 minutes of stirring the solids were collected by filtration and dried in vacuo to provide 3,5-dichloro-4-(diethoxymethyl)pyridine 1-oxide (34.5 g, 130 mmol, 79%) as a tan solid. LC/MS (Method i) R$_t$=1.70 min.; MS m/z: 266 (M+H)$^+$.

Step 3: 3,5-dichloro-4-(hydroxymethyl)picolinate

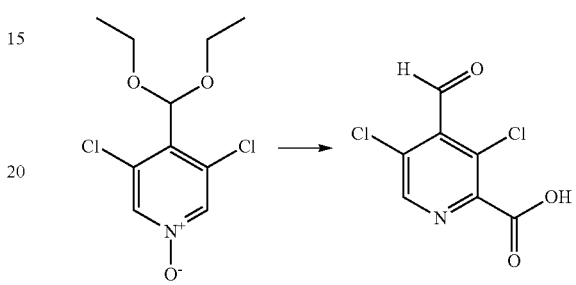

To a solution of 3,5-dichloro-4-(diethoxymethyl)pyridine 1-oxide (67 g, 252 mmol) in ACN (140 mL) was added triethylamine (70.2 mL, 504 mmol) followed by trimethylsilanecarbonitrile (101 mL, 755 mmol) The reaction mixture was flushed with nitrogen. After 10 minutes the reaction mixture was fitted with a reflux condenser and a balloon. The reaction mixture was heated to 80° C. After 15 hours the reaction mixture was cooled to room temperature and concentrated in vacuo. The mixture was diluted with 2N sodium hydroxide (629 mL, 1259 mmol) and dioxane (~60 mL). The reaction mixture was heated to 80° C. After 15 hours the reaction mixture was cooled to room temperature, diluted with EtOAc (about 600 mL) and the pH of the reaction mixture was adjusted to 1 with concentrated HCl. The organic layer was separated, dried over Na$_2$SO$_4$, filtered and concentrated in vacuo. The solids were suspended in heptane (about 100 mL) with stirring. After 2 hours the solids were collected by filtration to provide 3,5-dichloro-4-(diethoxymethyl)picolinic acid. The acetal was suspended in 6N HCl (500 mL) and 1,4-dioxane (about 50 mL). After 2 hours LC/MS showed the aldehyde and significant solids had formed. The solids were dissolved in EtOAc (600 mL). The acid aqueous layer was extracted with EtOAc (3×200 mL). All of the organics were combined, washed with brine, dried over Na$_2$SO$_4$, filtered and concentrated in vacuo using solvent exchange with heptanes during the concentration. The resulting solids were collected by filtration to provide 3,5-dichloro-4-formylpicolinic acid (47 g, 214 mmol, 85% yield) as a tan solid. LC/MS (Method i) R$_t$=0.40 min.; MS m/z: 218 (M−H)$^-$.

Step 4: 3,5-dichloro-4-(hydroxymethyl)picolinate

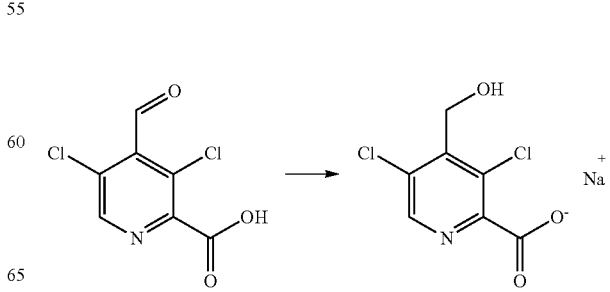

To a solution of 3,5-dichloro-4-formylpicolinic acid (51.6 g, 235 mmol) in EtOH (500 mL) was carefully added sodium tetrahydroborate (18.63 g, 493 mmol) to maintain a temperature of around 35° C. during addition. Precipitate formed shortly after addition. After 2 hours at room temperature MTBE (150 mL) was added slowly. After 30 minutes the solids were collected by filtration rinsing with MTBE and dried in vacuo at 50° C. to obtain crude sodium 3,5-dichloro-4-(hydroxymethyl)picolinate (70 g) which was used in next step without further purification. $^1$H NMR (DMSO, d6): δ 8.30 (s, 1H); 4.64 (s, 2H).

Step 5: 3,5-dichloro-4-(chloromethyl)picolinic acid

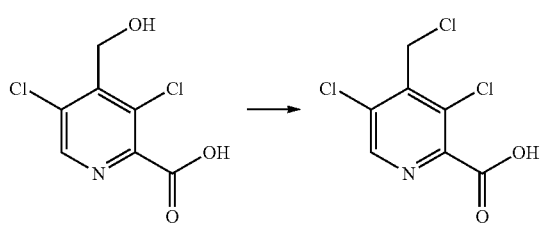 [SMILES: O=C(O)c1ncc(Cl)c(CO)c1Cl ; O=C(O)c1ncc(Cl)c(CCl)c1Cl]

To a slurry of 3,5-dichloro-4-(hydroxymethyl)picolinic acid (70 g, 236 mmol) in DCM (150 mL) was added sulfurous dichloride (69.0 mL, 946 mmol). After 15 hours water (5 mL) then EtOAc (200 mL) was carefully added to control vigorous bubbling. The organic layers were separated, dried over $Na_2SO_4$, filtered and concentrated in vacuo to an off-white solid, 3,5-dichloro-4-(chloromethyl)picolinic acid (50.7 g, 211 mmol, 89%). LC/MS (Method i) $R_t$=0.30 min.; MS m/z: 240 (M–H)$^-$.

Step 6: 3,5-dichloro-4-((3,7-dimethyl-5-(trifluoromethyl)-1H-indol-1-yl)methyl)picolinic

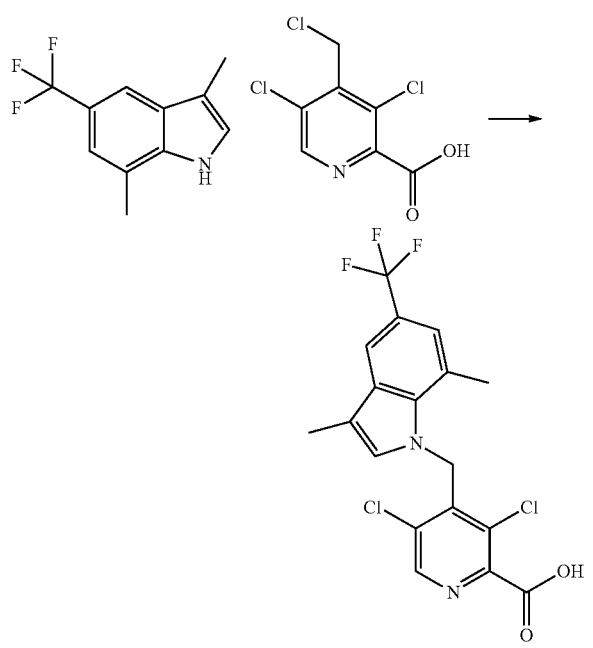

To a solution of 3,7-dimethyl-5-(trifluoromethyl)-1H-indole (38 g, 178 mmol) (Preparation #43) in THF (400 mL) was added sodium hydride (15.68 g, 392 mmol) After 15 minutes 3,5-dichloro-4-(chloromethyl)picolinic acid (42.9 g, 178 mmol) in DMF (100 mL) was added. After 15 hours the reaction mixture had solidified. The reaction mixture was diluted with MTBE (600 mL) and water (600 mL) The pH of the aqueous layer was adjusted to 1 with 5N HCl. The organic layers were separated, washed with brine (300 mL) dried over $Na_2SO_4$ filtered and concentrated in vacuo. The product was concentrated from ACN several times, then suspended in ACN (200 mL) stirred overnight. Solis were collected, rinsed with ACN (20 mL) and dried in vacuo to provide 3,5-dichloro-4-((3,7-dimethyl-5-(trifluoromethyl)-1H-indol-1-yl)methyl)picolinic acid (35.2 g, 84 mmol, 47.3% yield) as a tan solid. LC/MS (Method i) $R_t$=1.20 min.; MS m/z: 417 (M–H)$^-$.

Step 7: methyl 2-(1-(3,5-dichloro-4-((3,7-dimethyl-5-(trifluoromethyl)-1H-indol-1-yl)methyl)picolinoyl) piperidin-4-yl)acetate

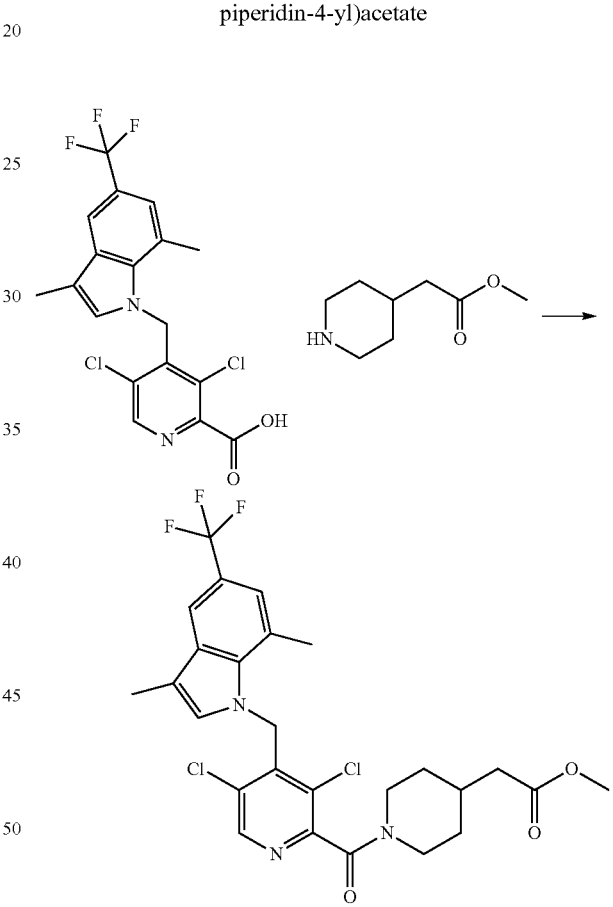

To a slurry of 3,5-dichloro-4-((3,7-dimethyl-5-(trifluoromethyl)-1H-indol-1-yl)methyl)picolinic acid (30 g, 71.9 mmol) in EtOAc (200 mL), DMF (20 mL) was added methyl 2-(piperidin-4-yl)acetate, hydrochloric acid (15.32 g, 79 mmol) followed by 2-(3H-[1,2,3]triazolo[4,5-b]pyridin-3-yl)-1,1,3,3-tetramethylisouronium hexafluorophosphate(V) (30.1 g, 79 mmol). Triethylamine (35.1 mL, 252 mmol) was added slowly maintaining the temperature at 20-25° C. After 30 minutes MTBE (100 mL) and water (200 mL) were added. The organic layer was separated, washed with 1N HCl (100 mL×3), saturated $Na_2CO_3$ (100 mL×2), saturated $NH_4Cl$ (100 mL) and brine (50 mL) and concentrated in vacuo. The crude product was purified via flash column

761 chromatography using DCM/MTBE (5-10%) as eluent on a 330 g×2 SiO₂ column to provide methyl 2-(1-(3,5-dichloro-4-((3,7-dimethyl-5-(trifluoromethyl)-1H-indol-1-yl)methyl)picolinoyl)piperidin-4-yl)acetate (35 g, 62.9 mmol, 87% yield) as a yellow oil. LC/MS (Method i) $R_t$=2.00 min.; MS m/z: 556 (M+H)⁺.

Step 8: 2-(1-(3,5-dichloro-4-((3,7-dimethyl-5-(trifluoromethyl)-1H-indol-1-yl)methyl)picolinoyl)piperidin-4-yl)acetic acid

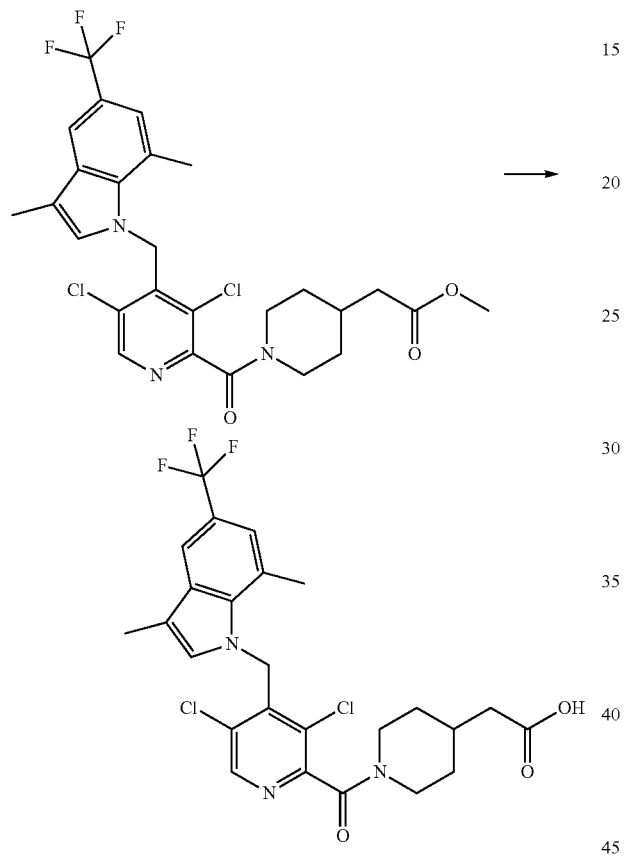

To a solution of methyl 2-(1-(3,5-dichloro-4-((3,7-dimethyl-5-(trifluoromethyl)-1H-indol-1-yl)methyl)picolinoyl)piperidin-4-yl)acetate (40 g, 71.9 mmol) in THF (300 mL) was added a 1M solution of sodium hydroxide (71.9 mL, 144 mmol). The reaction mixture was heated to 45-50° C. and MeOH was added until a homogeneous reaction mixture resulted. After 3 hours the reaction mixture was cooled to room temperature and partially concentrated in vacuo, removing approximately 200 mL of solvent. MTBE (300 mL) and 2N HCl (100 mL) were added. The organic layer was separated, washed with water (100 mL×2), brine (100 mL), dried over Na₂SO₄, filtered and concentrated in vacuo, solvent exchanging with ACN. After three concentration cycles, ACN (400 mL) was added and the resulting slurry was heated to 50° C. After 1 hour the slurry was cooled to room temperature slowly with stirring. After 15 hours the solids were collected by filtration, dried in vacuum oven at 55° C. to provide 2-(1-(3,5-dichloro-4-((3,7-dimethyl-5-(trifluoromethyl)-1H-indol-1-yl)methyl)picolinoyl)piperidin-4-yl)acetic acid (30.5 g, 56.2 mmol, 78%) as a white solid. LC/MS (Method i) $R_t$=1.68 min.; MS m/z: 540 (M−H)⁻.

762

Example FS: 1-(2,4-dichloro-3-((1,4-dimethyl-6-(trifluoromethyl)-1H-pyrrolo[2,3-b]pyridin-2-yl)methyl)benzoyl)piperidine-4-carboxylic acid

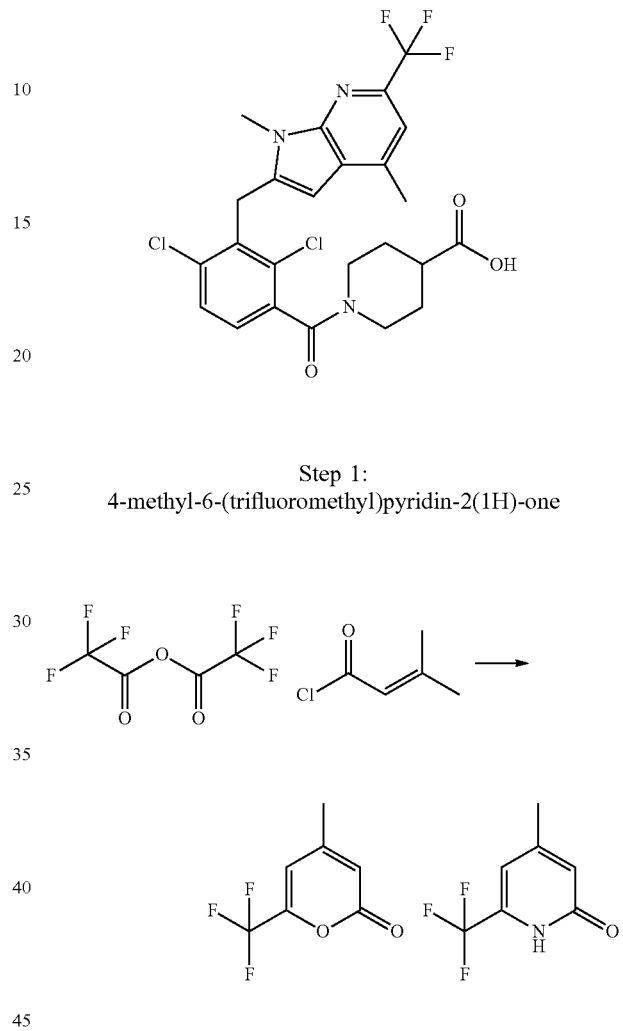

Step 1:
4-methyl-6-(trifluoromethyl)pyridin-2(1H)-one

A flask charged with CHCl₃ (1.25 L) was cooled to 0° C. 2,2,2-Trifluoroacetic anhydride (0.141 L, 1012 mmol) was added followed by 3-methylbut-2-enoyl chloride (0.094 L, 843 mmol). Triethylamine (0.259 L, 1856 mmol) was added dropwise such that the internal temperature was maintained below 10° C. After addition, the mixture was stirred at 0° C. for 1 hour and then warmed to room temperature slowly and stirred for overnight. The reaction mixture was washed with water (1 L), saturated NaHCO₃ (1 L), water/brine (1:1, 500 mL), dried over MgSO₄, filtered and concentrated in vacuo. The residue was dissolved in acetic acid (1.25 L). NH₄OAc (130 g, 1687 mmol) was added. The reaction set up was capped with a balloon and the mixture was heated at 115° C. overnight. After 20 hours the reaction mixture was cooled to 40° C. and concentrated in vacuo. The syrup was poured onto water (approximately 2 L) with stirring. After 1 hour the solids were collected by filtration to provide 4-methyl-6-(trifluoromethyl)pyridin-2(1H)-one (101 g, 570 mmol, 67.6%) as a tan solid. LC/MS (Method i) $R_t$=1.59 min.; MS m/z: 178 (M+H)⁺; 1H NMR (400 MHz, Chloroform-d) δ 6.79 (s, 1H), 6.70 (s, 1H), 2.34 (s, 3H).

Step 2:
2-chloro-4-methyl-6-(trifluoromethyl)pyridine

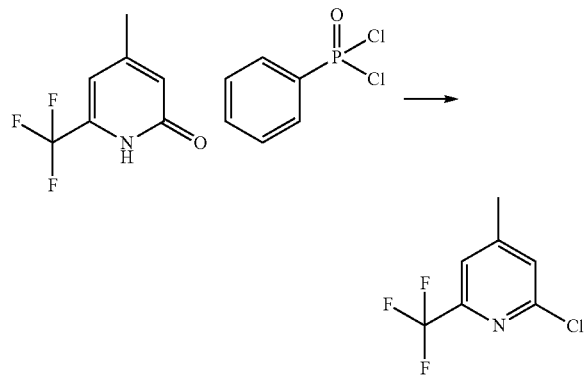

A 50 mL pear-shaped flask fitted with a short path distillation head was charged with 4-methyl-6-(trifluoromethyl)pyridin-2(1H)-one (20 g, 113 mmol). To the flask was added phenylphosphonic dichloride (19.21 mL, 135 mmol). The reaction mixture was heated to 160° C. After 3 hours the pressure on the reaction mixture was slowly reduced to 100 mBar. Distillation began at a temperature of about 120-130° C. When distillation had significantly slowed, the pressure over the reaction mixture was reduced to 80 mBar and the bath temp was raised to 170° C. After 3 hours the distillation had ceased providing 2-chloro-4-methyl-6-(trifluoromethyl) pyridine (12 g, 61.4 mmol, 54.3% yield). 1H NMR (400 MHz, DMSO-d6) δ 7.81 (s, 1H), 7.73 (s, 1H), 2.43 (s, 3H).

Step 3: tert-butyl (4-methyl-6-(trifluoromethyl)pyridin-2-yl)carbamate

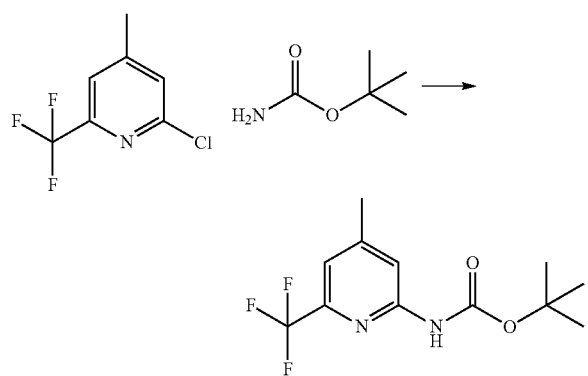

A flask charged with 2-chloro-4-methyl-6-(trifluoromethyl)pyridine (35.12 g, 180 mmol), tert-butyl carbamate (42.1 g, 359 mmol), Pd$_2$(dba)$_3$ (4.11 g, 4.49 mmol), dicyclohexyl(2',4',6'-triisopropyl-[1,1'-biphenyl]-2-yl)phosphine (X-phos) (4.28 g, 8.98 mmol) and cesium carbonate (205 g, 629 mmol) was evacuated and filled with N$_2$ (repeated 3 times) before addition of degassed 1,4-dioxane (350 mL). The mixture was then heated at 80° C. for 2 hours and then cooled to room temperature. The reaction mixture was partitioned between water (300 mL) and EtOAc (300 mL). The aqueous layer was further extracted with EtOAc (2×100 mL). The organic layer was dried over Na$_2$SO$_4$, filtered and concentrated to dryness to give a dark red oil. Used crude in following reaction.

Step 4: 4-methyl-6-(trifluoromethyl)pyridin-2-amine

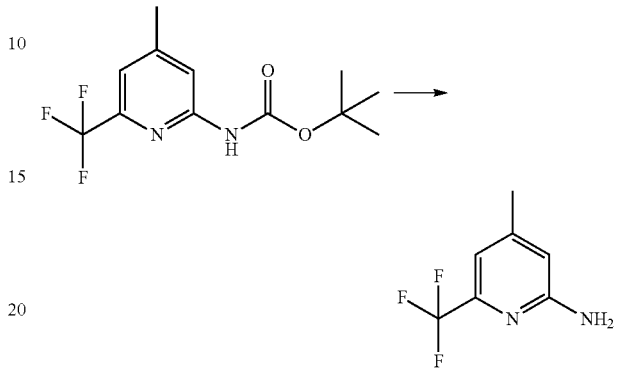

A mixture of tert-butyl (4-methyl-6-(trifluoromethyl)pyridin-2-yl)carbamate (49.6 g, 180 mmol) and hydrogen chloride (4M in 1,4-dioxane) (597 mL, 2388 mmol) was stirred at room temperature for 2 hours. The solvent was removed under reduced pressure. The residue was suspended in EtOAc and filtered. The filtrate was diluted with EtOAc. The organic layer was extracted with 6 N HCl (3×50 mL). The aqueous layer was washed with DCM (4×100 mL). The pH of the aqueous layer was adjusted to pH 8 with addition of Na$_2$CO$_3$. The bright yellow solid was collected by filtration, washed with water. The solid was then dissolved in DCM, washed with brine, dried over Na$_2$SO$_4$, filtered and concentrated to almost dryness. The solids were triturated with petroleum ether. Solid was collected by filtration, washed with petroleum ether and air dried to give 4-methyl-6-(trifluoromethyl)pyridin-2-amine (27.73 g, 157 mmol, 88%) as a pale yellow solid. LC/MS (Method i) R$_t$=2.55 min.; MS m/z: 177 (M+H)$^+$.

Step 5: 3,5-dibromo-4-methyl-6-(trifluoromethyl) pyridin-2-amine

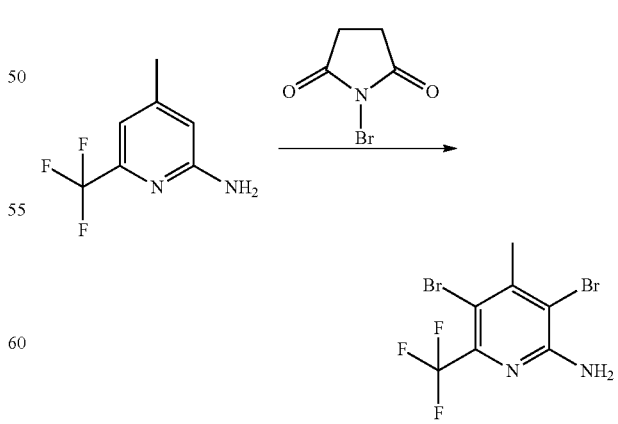

A mixture of 4-methyl-6-(trifluoromethyl)pyridin-2-amine (31.45 g, 179 mmol) and NBS (66.7 g, 375 mmol) in ACN (250 mL) was heated at 70° C. for 2 hours. Approximately 500 mL water was added. The solid was collected by filtration, washed with water and air dried for 5 minutes. The solid was solubilized in DCM, washed with water, dried over Na$_2$SO$_4$, filtered and concentrated to almost dryness. The solids were triturated with heptane. Solid was collected by filtration, washed with heptane and dried to give 3,5-dibromo-4-methyl-6-(trifluoromethyl)pyridin-2-amine (56.99 g, 171 mmol, 96%) as light yellow solid. LC/MS (Method i) R$_t$=2.55 min.; MS m/z: 333 (M+H)$^+$; 1H NMR (400 MHz, DMSO-d6) δ 6.90 (s, 2H), 2.53 (s, 3H).

Step 6: 3-bromo-4-methyl-6-(trifluoromethyl)pyridin-2-amine

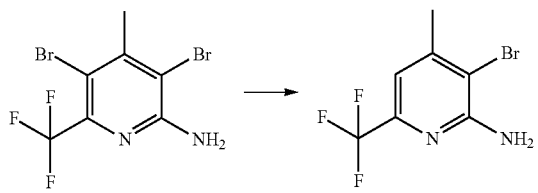

To a light orange solution of 3,5-dibromo-4-methyl-6-(trifluoromethyl)pyridin-2-amine (56.98 g, 171 mmol) in THF (570 mL) at −78° C. was added n-butyllithium (2.5 M in hexane) (68.3 mL, 171 mmol) dropwise. The mixture was stirred at −78° C. for 15 minutes. Stirring was continued at −78° C. for another 30 minutes. A second portion of butyllithium (2.5 M in hexane) (20.48 mL, 51.2 mmol) was added dropwise. After 30 minutes a third portion of butyllithium (2.5 M in hexane) (13.65 mL, 34.1 mmol) was added dropwise. LC/MS after 15 min showed the reaction was complete. The reaction flask was transferred to an ice-water bath. 20 mL water was added quickly and the reaction was allowed to warm up to room temperature. The reaction mixture was partitioned between saturated NH$_4$Cl (300 mL) and EtOAc (300 mL). The organic layer was washed with NaHCO$_3$ (300 mL), dried over Na$_2$SO$_4$, filtered and concentrated to almost dryness. The solids were triturated with heptane. The solid was collected by filtration, washed with hepane to give 3-bromo-4-methyl-6-(trifluoromethyl)pyridin-2-amine (38.87 g, 145 mmol, 85%), as a off-white solid. LC/MS (Method i) R$_t$=2.29 min.; MS m/z: 255 (M+H)$^+$; 1H NMR (400 MHz, DMSO-d6) δ 6.96 (s, 1H), 6.74 (s, 2H), 2.32 (s, 3H).

Step 7: (E)-3-(2-ethoxyvinyl)-4-methyl-6-(trifluoromethyl)pyridin-2-amine

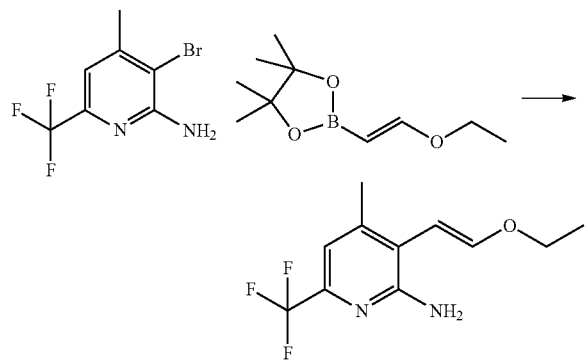

A flask charged with 3-bromo-4-methyl-6-(trifluoromethyl)pyridin-2-amine (38.26 g, 143 mmol), (E)-2-(2-ethoxyvinyl)-4,4,5,5-tetramethyl-1,3,2-dioxaborolane (56.5 g, 285 mmol), diacetoxypalladium (0.960 g, 4.28 mmol), dicyclohexyl(2',4',6'-triisopropyl-[1,1'-biphenyl]-2-yl)phosphine (XPhos) (4.28 g, 8.98 mmol) and cesium carbonate (116 g, 356 mmol) was degassed with N$_2$ for 15 minutes before addition of 320 mL degassed 1,4-dioxane/H$_2$O (4:1). The mixture was heated at 80° C. for 2 hours then cooled to room temperature. The reaction mixture was partitioned between EtOAc (200 mL) and water (200 mL). The aqueous layer was further extracted with EtOAc (2×50 mL). The organic layer was dried over Na$_2$SO$_4$, filtered and concentrated to dryness. The solids were diluted with heptane, filtered, washed with heptane to give an off-white solid (1.45 g) which was discarded. The filtrate was concentrated to dryness again to give a thick black oil, which was left at room temperature overnight. Significant solids formation was noticed. The solids were again diluted with heptane, sonicated and filtered, washed with heptane to give a light brown solid. 15.20 g 95% purity by LC/MS, $^1$H NMR. The filtrate was concentrated to dryness to give a black oil which was purified by flash chromatography (0-25% EtOAc/heptane over 30 minutes; Redi-Sep column, 330 g, 309 nm). Fractions were concentrated to almost dryness. The solid was collected by filtration, washed with a small amount of heptane and dried to give the second crop of product as a light yellow solid. 12.69 g. Two crops combined to give (E)-3-(2-ethoxyvinyl)-4-methyl-6-(trifluoromethyl)pyridin-2-amine (27.89 g, 113 mmol, 79%). LC/MS (Method i) R$_t$=1.48 min.; MS m/z: 247 (M+H)$^+$.

Step 8: 4-methyl-6-(trifluoromethyl)-1H-pyrrolo[2,3-b]pyridine

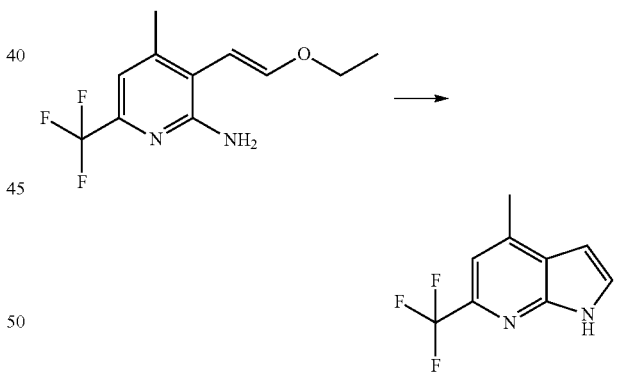

A mixture of (E)-3-(2-ethoxyvinyl)-4-methyl-6-(trifluoromethyl)pyridin-2-amine (27.89 g, 113 mmol) and acetic acid (130 mL) was heated at 100° C. overnight. Cooled to room temperature. The precipitate was collected by filtration, washed with ACN and dried to give the first crop of product. The filtrate was concentrated to about 50 mL. The solid was collected by filtration, washed with ACN and dried to give the second crop of product. The filtrate still had some product in it. The solid was suspended in about 250 mL EtOAc, heated to reflux to dissolve then rotavaped to remove most of the solvent. Heptane was added and the slurry was filtered and dried to give the product as an off-white solid. The three crops of product were combined to give 4-methyl-6-(trifluoromethyl)-1H-pyrrolo[2,3-b]pyridine (19.77 g, 99 mmol, 88%). LC/MS (Method i) $R_t$=1.30 min.; MS m/z: 201 (M+H)$^+$; $^1$H NMR (400 MHz, DMSO-d6) δ 12.13-11.98 (br, 1H), 7.67 (t, J=3.1 Hz, 1H), 7.34 (d, J=1.0 Hz, 1H), 6.63 (dd, J=3.5, 1.9 Hz, 1H), 2.59 (s, 3H).

Step 9: 4-methyl-1-(phenylsulfonyl)-6-(trifluoromethyl)-1H-pyrrolo[2,3-b]pyridine

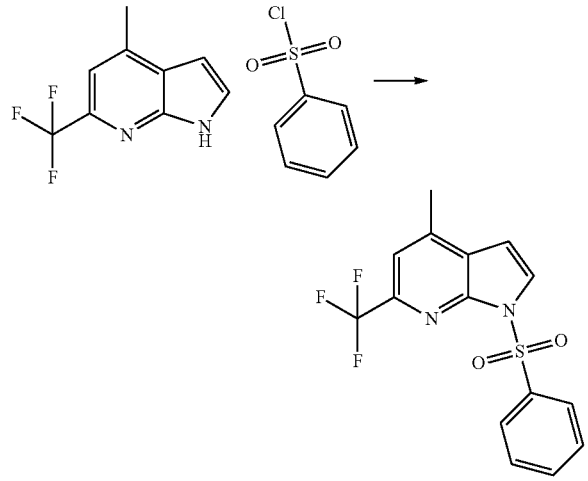

To a suspension of sodium hydride (60% in mineral oil) (4.35 g, 109 mmol) in DMF (40 mL) at 0° C. was added a solution of 4-methyl-6-(trifluoromethyl)-1H-pyrrolo[2,3-b]pyridine (19.77 g, 99 mmol) under N$_2$. After addition, the ice-water bath was removed and the mixture was stirred at room temperature for 30 minutes then it was cooled to 0° C. Benzenesulfonyl chloride (13.27 mL, 104 mmol) was added dropwise. After addition, the reaction was allowed to warm to room temperature and stirred for 1 hour. The reaction was quenched with addition of 100 mL saturated NH$_4$Cl solution followed by addition of 350 mL water. The solid was collected by filtration, washed with water and dried in vacuum oven at 70° C. over the weekend to give an off-white solid. The solids were dissolved in EtOAc, filtered through 70 g silica gel, and washed with EtOAc. The filtrate was dried over Na$_2$SO$_4$, filtered and concentrated to dryness. The solids were triturated with EtOAc/heptane to give 4-methyl-1-(phenylsulfonyl)-6-(trifluoromethyl)-1H-pyrrolo[2,3-b]pyridine (28.52 g, 84 mmol, 85%) as white solid. LC/MS (Method i): $R_t$=1.84 min.; MS m/z: 341 (M+H)$^+$; 1H NMR (400 MHz, DMSO-d6) δ 8.15-8.07 (m, 3H), 7.75-7.67 (m, 1H), 7.64-7.56 (m, 3H), 7.03 (d, J=4.1 Hz, 1H), 2.57 (s, 3H).

Step 10: tert-butyl 2,4-dichloro-3-(hydroxy(4-methyl-1-(phenylsulfonyl)-6-(trifluoromethyl)-1H-pyrrolo[2,3-b]pyridin-2-yl)methyl)benzoate

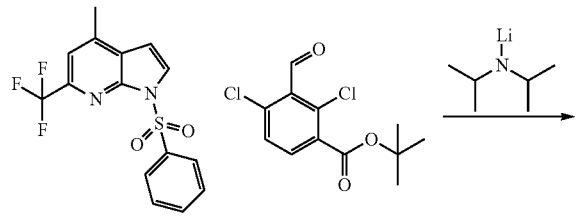

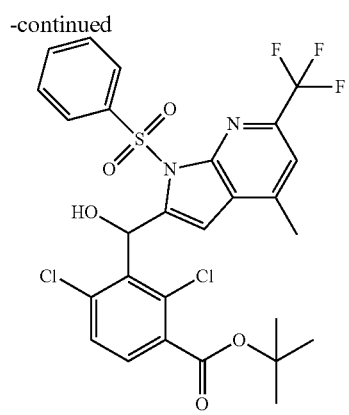
-continued

A colorless solution of 4-methyl-1-(phenylsulfonyl)-6-(trifluoromethyl)-1H-pyrrolo[2,3-b]pyridine (3 g, 8.82 mmol) in THF (45 mL) was cooled down to −78° C. under N$_2$. LDA (1.0 M in THF/hexane) (10.58 mL, 10.58 mmol) was added dropwise (internal temperature <−70° C.) (solution turned dark orange at the end of addition). The mixture was stirred at −78° C. for 0.5 h. A solution of tert-butyl 2,4-dichloro-3-formylbenzoate (2.91 g, 10.58 mmol) in THF (8 mL) was added dropwise (internal temperature maintained below −70° C.) (solution remained red orange). The mixture was stirred at −78° C. for 1 h. The reaction was quenched with saturated NH$_4$Cl (50 mL) and extracted with EtOAc (2×50 mL). The organic layer was dried over Na$_2$SO$_4$, filtered and concentrated to dryness. The solids were purified by flash chromatography (0-25% EtOAc/heptane over 30 min and then hold 25% EtOAc/heptane; Silicycle column, 200 g, 278 nm) to give tert-butyl 2,4-dichloro-3-(hydroxy(4-methyl-1-(phenylsulfonyl)-6-(trifluoromethyl)-1H-pyrrolo[2,3-b]pyridin-2-yl)methyl)benzoate (4.59 g, 7.46 mmol, 85%) as a white solid. LC/MS (Method i) $R_t$=2.18 min.; MS m/z: 615 (M+H)$^+$.

Step 11: 2,4-dichloro-3-((4-methyl-1-(phenylsulfonyl)-6-(trifluoromethyl)-1H-pyrrolo[2,3-b]pyridin-2-yl)methyl)benzoic acid

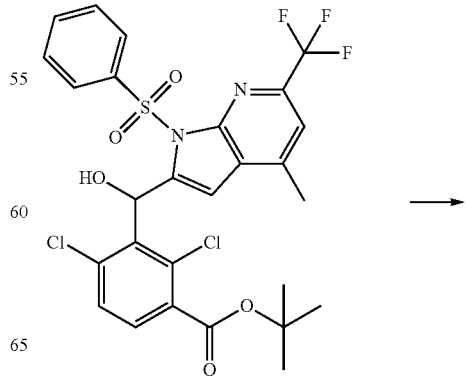

769

-continued

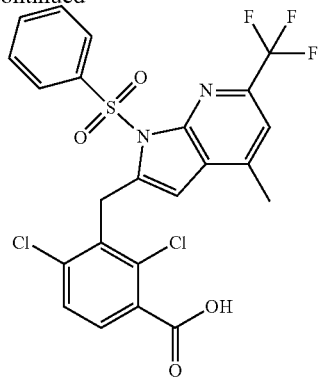

770

-continued

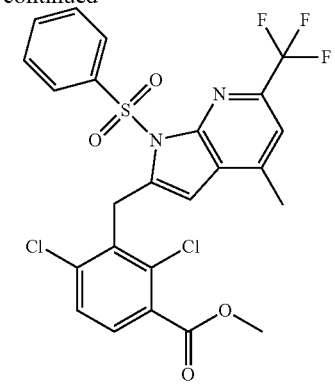

To a solution of tert-butyl 2,4-dichloro-3-(hydroxy(4-methyl-1-(phenylsulfonyl)-6-(trifluoromethyl)-1H-pyrrolo[2,3-b]pyridin-2-yl)methyl)benzoate (2.0571 g, 3.34 mmol) in CHCl₃ (20 mL) was added SOCl₂ (2.440 mL, 33.4 mmol). The mixture was heated at 60° C. overnight. Additional SOCl₂ (2.440 mL, 33.4 mmol) was added, the mixture was heated at 60° C. for another 24 hours. Solvent was removed under reduced pressure. The residue was partitioned between EtOAc (100 mL) and saturated NaHCO₃ (100 mL). The organic layer was concentrated to dryness to give a white foam. TLC (25% EtOAc/heptane) indicated one major peak. The intermediate was dissolved in acetic acid (45 mL). Zinc (1.093 g, 16.71 mmol) was added. The mixture was stirred at room temperature for 0.5 hour, filtered and washed with EtOAc. Filtrate was concentrated to dryness. The residue was partitioned between EtOAc (20 mL) and 1N HCl (20 mL). The organic layer was washed with saturated NaHCO₃ (20 mL), dried over Na₂SO₄, filtered and concentrated to dryness to give a white foam. To the above foam was added DCM (12 mL) followed by TFA (4 mL). The yellow solution was stirred at room temperature for 4 hours. Volatiles were removed under reduced pressure. The residue was partitioned between EtOAc (50 mL) and saturated NH₄Cl (50 mL). The organic layer was dried over Na₂SO₄, filtered and concentrated to dryness to give a white foam, which was used in the next step without further purification.

Step 12: 2,4-dichloro-3-((4-methyl-1-(phenylsulfonyl)-6-(trifluoromethyl)-1H-pyrrolo[2,3-b]pyridin-2-yl)methyl)benzoate To a solution of 2,4-dichloro-3-((4-methyl-1-(phenylsulfonyl)-6-(trifluoromethyl)-1H-pyrrolo[2,3-b]pyridin-2-yl)methyl)benzoic acid (1.816 g, 3.34 mmol) in ACN (54 mL) was added cesium carbonate (3.27 g, 10.03 mmol) followed by dimethyl sulfate (0.634 mL, 6.68 mmol). The mixture was stirred at room temperature for 4 hours and then heated at 40° C. overnight. The reaction mixture was partitioned between EtOAc (20 mL) and water (20 mL). The aqueous layer was further extracted with EtOAc (20 mL). The organic layer was washed with brine (10 mL), dried over Na₂SO₄, filtered and concentrated to dryness. The crude product was purified by flash chromatography (0-50% EtOAc/heptane over 30 min.; Redi-Sep column, 120 g, 254 nm). The major peak was concentrated to dryness to give methyl 2,4-dichloro-3-((4-methyl-1-(phenylsulfonyl)-6-(trifluoromethyl)-1H-pyrrolo[2,3-b]pyridin-2-yl)methyl)benzoate (1.15 g, 2.063 mmol, 61.8%) as a light yellow gum.

LC/MS (Method i) R_f=1.49 min.; MS m/z: 557 (M+H)⁺.

Step 13: 2,4-dichloro-3-((4-methyl-6-(trifluoromethyl)-1H-pyrrolo[2,3-b]pyridin-2-yl)methyl)benzoate

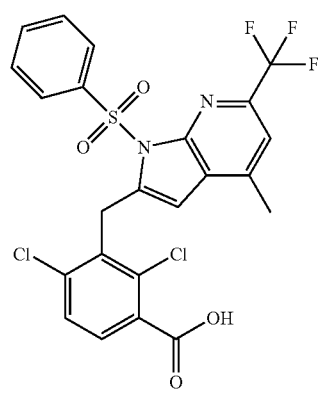 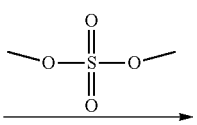 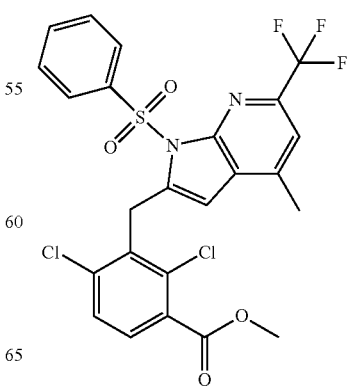

771
-continued

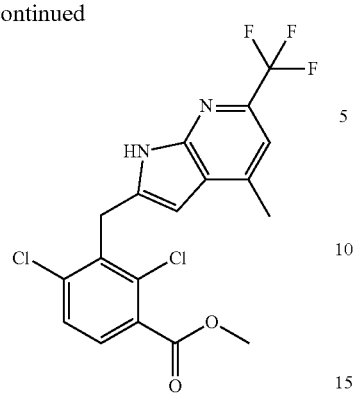

A flask charged with methyl 2,4-dichloro-3-((4-methyl-1-(phenylsulfonyl)-6-(trifluoromethyl)-1H-pyrrolo[2,3-b]pyridin-2-yl)methyl)benzoate (1.15 g, 2.063 mmol) was flushed with $N_2$ for 15 min THF (23 mL) was added to form a yellow solution. TBAF (3.09 mL, 3.09 mmol) was added. The mixture was heated at 50° C. overnight. Solvent was removed under reduced pressure. The residue was dissolved in EtOAc (20 mL), washed with saturated $NaHCO_3$ (2×10 mL), brine (10 mL), dried over $Na_2SO_4$, filtered and concentrated to dryness. The crude product was purified by flash chromatography (0-25% EtOAc/heptane over 30 min.; Redi-Sep column, 80 g, 284 nm) to give methyl 2,4-dichloro-3-((4-methyl-6-(trifluoromethyl)-1H-pyrrolo[2,3-b]pyridin-2-yl)methyl)benzoate (662.7 mg, 1.588 mmol, 77%) as a white solid. LC/MS (Method i) $R_t$=2.01 min.; MS m/z: 417 (M+H)$^+$; $^1$H NMR (400 MHz, DMSO-d6) δ 12.16 (s, 1H), 7.75 (d, J=8.4 Hz, 1H), 7.67 (d, J=8.4 Hz, 1H), 7.28 (d, J=0.8 Hz, 1H), 5.93 (dd, J=2.1, 1.1 Hz, 1H), 4.49 (s, 2H), 3.86 (s, 3H), 2.45 (s, 3H).

Step 14: methyl 2,4-dichloro-3-((1,4-dimethyl-6-(trifluoromethyl)-1H-pyrrolo[2,3-b]pyridin-2-yl)methyl)benzoate 772
-continued

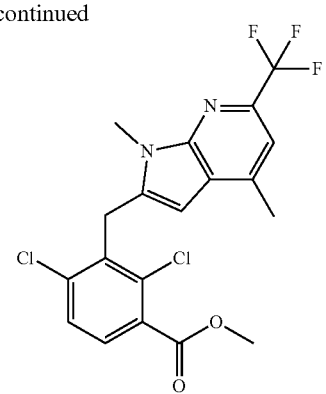

To a solution of methyl 2,4-dichloro-3-((4-methyl-6-(trifluoromethyl)-1H-pyrrolo[2,3-b]pyridin-2-yl)methyl)benzoate (662 mg, 1.587 mmol) in ACN (50 mL) was added cesium carbonate (1551 mg, 4.76 mmol) followed by dimethyl sulfate (0.301 mL, 3.17 mmol). The mixture was stirred at room temperature over the weekend (turned into a thick suspension after about 30 min of stirring). The reaction was quenched with water (20 mL) and extracted with EtOAc (20 mL). The organic layer was washed with brine (3×10 mL), dried over $Na_2SO_4$, filtered and concentrated to dryness. The solids were triturated with $Et_2O$/heptane. The solid was collected by filtration, washed with heptane, dried to give methyl 2,4-dichloro-3-((1,4-dimethyl-6-(trifluoromethyl)-1H-pyrrolo[2,3-b]pyridin-2-yl)methyl)benzoate (632.8 mg, 1.467 mmol, 92%) as a white solid. LC/MS (Method i) $R_t$=2.19 min.;

MS m/z: 431 (M+H)$^+$; $^1$H NMR (400 MHz, DMSO-d6) δ 7.80 (d, J=8.4 Hz, 1H), 7.71 (d, J=8.4 Hz, 1H), 7.32 (d, J=0.8 Hz, 1H), 5.80-5.75 (m, 1H), 4.54 (s, 2H), 3.92 (s, 3H), 3.87 (s, 3H), 2.44 (d, J=0.7 Hz, 3H).

Step 15: 2,4-dichloro-3-((1,4-dimethyl-6-(trifluoromethyl)-1H-pyrrolo[2,3-b]pyridin-2-yl)methyl)benzoic acid

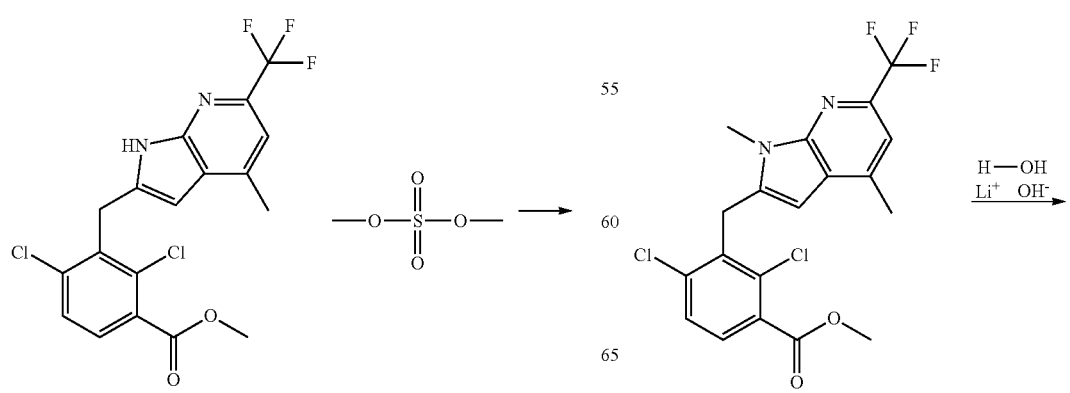

773
-continued

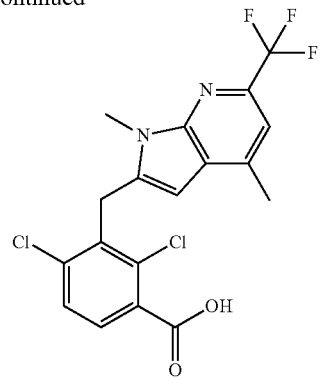

To a yellow solution of methyl 2,4-dichloro-3-((1,4-dimethyl-6-(trifluoromethyl)-1H-pyrrolo[2,3-b]pyridin-2-yl)

774 methyl)benzoate (632.8 mg, 1.467 mmol) in THF (12 mL) was added lithium hydroxide hydrate (123 mg, 2.93 mmol). The mixture was stirred at room temperature overnight. Solvent was removed under reduced pressure. The solution was diluted with water (10 mL). and pH adjusted to 2-3 with 1N HCl. A gel like precipitate was formed. The solid was collected by filtration, washed with water and dried in a vacuum oven at 60° C. overnight to give 2,4-dichloro-3-((1,4-dimethyl-6-(trifluoromethyl)-1H-pyrrolo[2,3-b]pyridin-2-yl)methyl)benzoic acid (389 mg, 64% yield).

LC/MS (Method i) $R_f$=1.42 min.; MS m/z: 417 (M+H)$^+$.
$^1$H NMR (400 MHz, DMSO-d6) δ 13.63 (s, 1H), 7.74 (d, J=8.4 Hz, 1H), 7.65 (d, J=8.4 Hz, 1H), 7.34-7.30 (m, 1H), 5.77 (s, 1H), 4.52 (s, 2H), 3.92 (s, 3H), 2.44 (s, 3H).

Step 16: (2,4-dichloro-3-((1,4-dimethyl-6-(trifluoromethyl)-1H-pyrrolo[2,3-b]pyridin-2-yl)methyl)phenyl)(4-hydroxypiperidin-1-yl)methanone

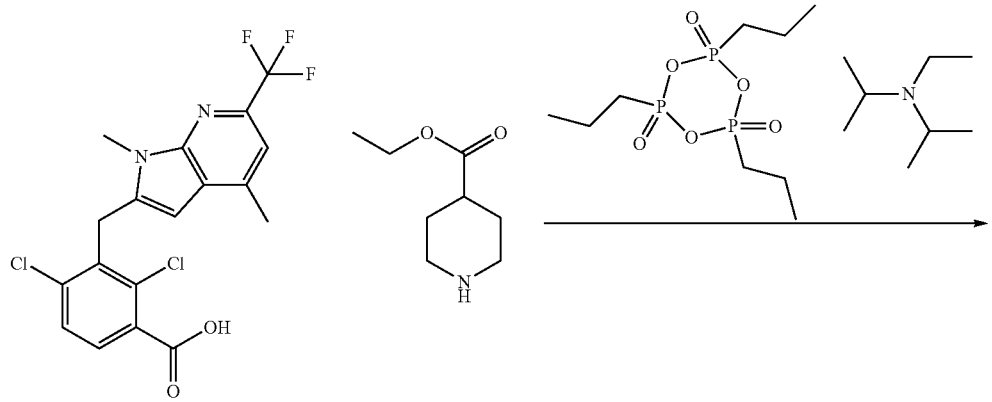

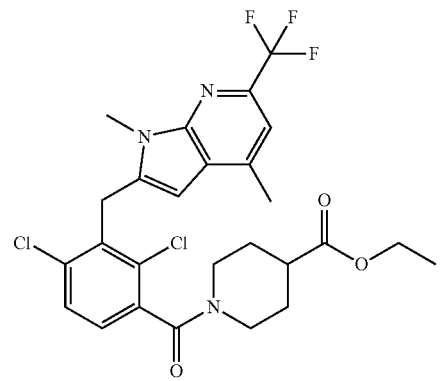

2,4-Dichloro-3-((1,4-dimethyl-6-(trifluoromethyl)-1H-pyrrolo[2,3-b]pyridin-2-yl)methyl)benzoic acid (120 mg, 0.288 mmol) was suspended in EtOAc (2.4 mL). To the suspension ethyl piperidine-4-carboxylate (66.5 μL, 0.431 mmol) and N-ethyl-N-isopropylpropan-2-amine (95 μL, 0.546 mmol) were added. The suspension was cooled to 0-5° C. in an ice bath and added 2,4,6-tripropyl-1,3,5,2,4,6-trioxatriphosphinane 2,4,6-trioxide (308 μL, 0.518 mmol) dropwise (turned into an almost clear solution with addition of T3P). The reaction mixture was stirred for 2 hours at 0-5° C. The mixture was poured into a separatory funnel, washed with 1M HCl (3×20 mL), 1M NaOH (3×20 mL) then dried over sodium sulfate, filtered through a pad of silica gel, rinsing with EtOAc. The filtrate was concentrated to dryness to give ethyl 1-(2,4-dichloro-3-((1,4-dimethyl-6-(trifluoromethyl)-1H-pyrrolo[2,3-b]pyridin-2-yl)methyl)benzoyl)piperidine-4-carboxylate (160 mg, 100%) as a foam.

LC/MS (Method i) $R_t$=2.11 min.; MS m/z: 556 (M+H)+.

Step 17: 1-(2,4-dichloro-3-((1,4-dimethyl-6-(trifluoromethyl)-1H-pyrrolo[2,3-b]pyridin-2-yl)methyl)benzoyl)piperidine-4-carboxylic acid

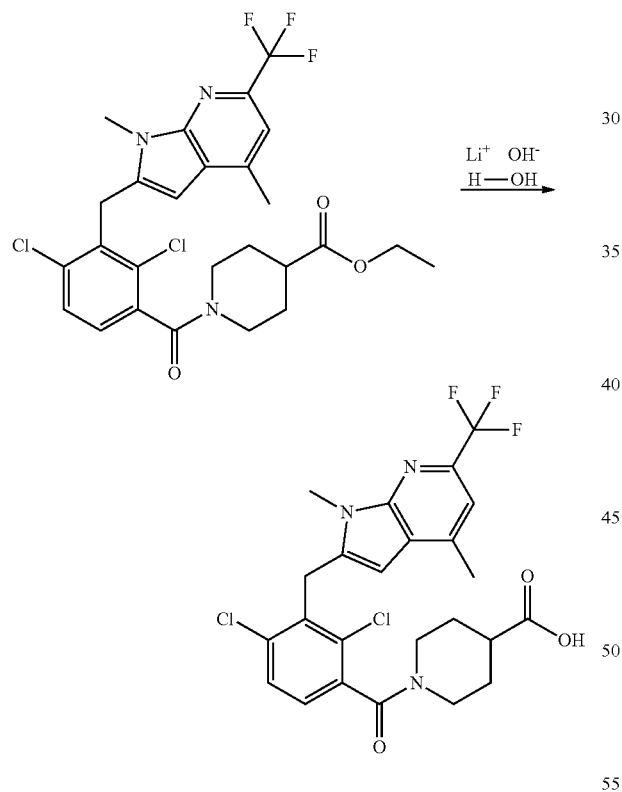

A mixture of ethyl 1-(2,4-dichloro-3-((1,4-dimethyl-6-(trifluoromethyl)-1H-pyrrolo[2,3-b]pyridin-2-yl)methyl)benzoyl)piperidine-4-carboxylate (160 mg, 0.288 mmol) and lithium hydroxide hydrate (12.07 mg, 0.288 mmol) in THF (3 mL) and water (1.000 mL) was stirred at room temperature overnight. The layers were partitioned between EtOAc (10 mL), ACN (2 mL) and 1 N HCl (10 mL). The organic layer was washed with brine (3×5 mL)) then dried over $Na_2SO_4$, filtered and concentrated to dryness. The solids were triturated with ACN. The solid was collected by filtration, washed with $H_2O$ and dried to give 1-(2,4-dichloro-3-((1,4-dimethyl-6-(trifluoromethyl)-1H-pyrrolo[2, 3-b]pyridin-2-yl)methyl)benzoyl)piperidine-4-carboxylic acid (118.7 mg, 0.220 mmol, 77% yield) as a white solid. LC/MS (Method i) Rt=2.41 min.; MS m/z: 528 (M+H)+.

Example FT: (2,4-dichloro-3-((1,4-dimethyl-6-(trifluoromethyl)-1H-pyrrolo[2,3-b]pyridin-2-yl)methyl)phenyl)(4-(2-methoxyethyl)piperidin-1-yl)methanone

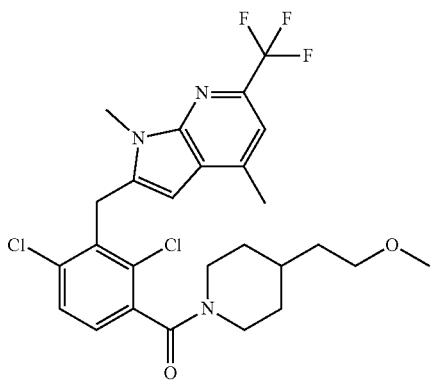 [SMILES: COCCC1CCN(C(=O)c2ccc(Cl)c(Cc3cc4c(C)cc(C(F)(F)F)nc4n3C)c2Cl)CC1]

(2,4-dichloro-3-((1,4-dimethyl-6-(trifluoromethyl)-1H-pyrrolo[2,3-b]pyridin-2-yl)methyl)phenyl)(4-(2-methoxyethyl)piperidin-1-yl)methanone was prepared in a similar way to example FS, step 16.

LC/MS (Method i) $R_t$=3.01 min.; MS m/z: 542 (M+H)+.

Example FT-1:2-(1-(2,4-dichloro-3-((1,4-dimethyl-6-(trifluoromethyl)-1H-pyrrolo[2,3-b]pyridin-2-yl)methyl)benzoyl)piperidin-4-yl)acetic acid

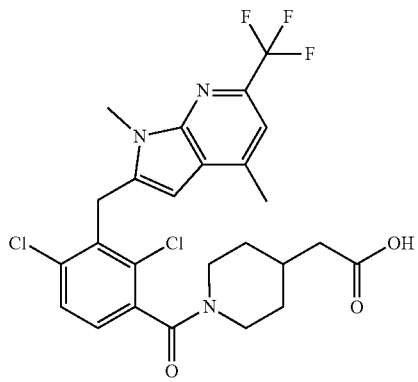 [SMILES: Cc1cc(C(F)(F)F)nc2c1cc(Cc1c(Cl)ccc(C(=O)N3CCC(CC(=O)O)CC3)c1Cl)n2C]

2-(1-(2,4-dichloro-3-((1,4-dimethyl-6-(trifluoromethyl)-1H-pyrrolo[2,3-b]pyridin-2-yl)methyl)benzoyl)piperidin-4-yl)acetic acid was prepared in a similar way to example FS, step 16.

LC/MS (Method i) $R_t$=2.48 min.; MS m/z: 542 (M+H)+.

Example FT-3: ethyl 1-(2,4-dichloro-3-((1,4-dimethyl-6-(trifluoromethyl)-1H-pyrrolo[2,3-b]pyridin-2-yl)methyl)benzoyl)piperidine-4-carboxylate

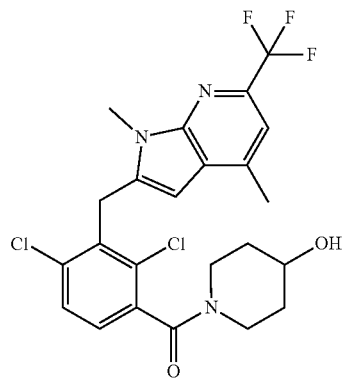 [SMILES: Cc1cc(C(F)(F)F)nc2c1cc(Cc1c(Cl)ccc(C(=O)N3CCC(O)CC3)c1Cl)n2C]

Ethyl 1-(2,4-dichloro-3-((1,4-dimethyl-6-(trifluoromethyl)-1H-pyrrolo[2,3-b]pyridin-2-yl)methyl)benzoyl)piperidine-4-carboxylate was prepared in a similar way to example FS step 16.

LC/MS (Method i) Rt=2.41 min.; MS m/z: 528 (M+H)+.

Example FU: 2-(1-(2,4-dichloro-3-(1,4-dimethyl-6-(trifluoromethyl)-1H-pyrrolo[2,3-b]pyridine-2-carbonyl)benzoyl)piperidin-4-yl)acetic acid

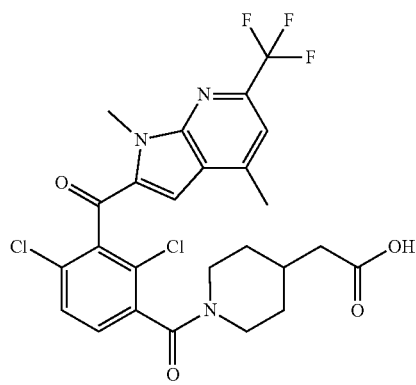

Step 1: tert-butyl 2,4-dichloro-3-(4-methyl-1-(phenylsulfonyl)-6-(trifluoromethyl)-1H-pyrrolo[2,3-b]pyridine-2-carbonyl)benzoate

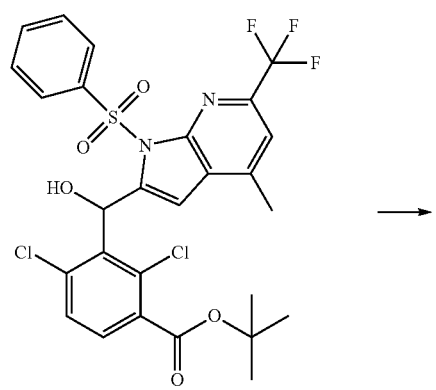

To a clear solution of tert-butyl 2,4-dichloro-3-(hydroxy (4-methyl-1-(phenylsulfonyl)-6-(trifluoromethyl)-1H-pyrrolo[2,3-b]pyridin-2-yl)methyl)benzoate (4.73 g, 7.69 mmol) (example FS, step 10) in CH$_2$Cl$_2$ (50 mL) at 0° C. was added Dess-Martin Periodinane (3.59 g, 8.45 mmol) in one portion. The mixture was stirred at 0° C. for 2 hours then diluted with DCM (50 mL), washed with 5% NaS$_2$O$_3$ (30 mL) and saturated NaHCO$_3$ (30 mL), brine (20 mL), dried over Na$_2$SO$_4$, filtered and concentrated to dryness to give tert-butyl 2,4-dichloro-3-(4-methyl-1-(phenylsulfonyl)-6-(trifluoromethyl)-1H-pyrrolo[2,3-b]pyridine-2-carbonyl) benzoate (4.7 g, 100%) as a white foam.

LC/MS (Method i) R$_f$=2.28 min.; MS m/z: 613 (M+H)$^+$.

Step 2: tert-butyl 2,4-dichloro-3-(4-methyl-6-(trifluoromethyl)-1H-pyrrolo[2,3-b]pyridine-2-carbonyl)benzoate

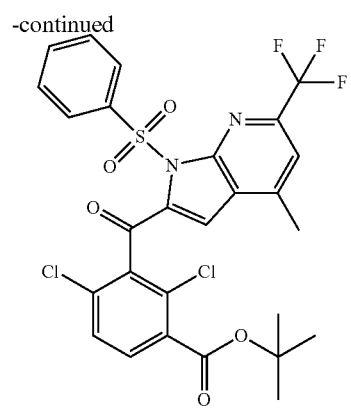

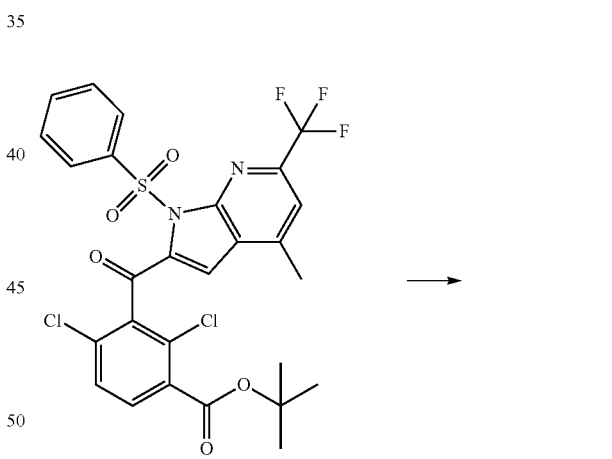

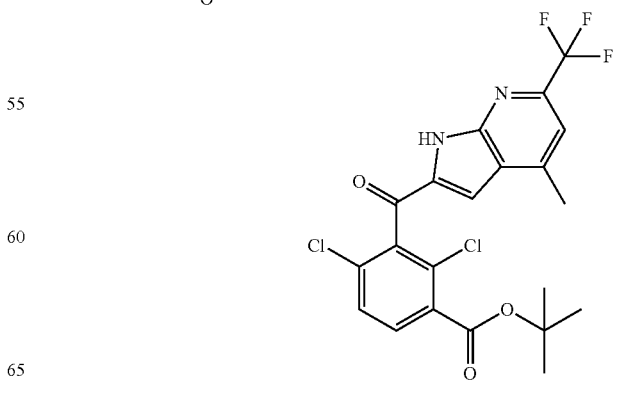

A flask charged with tert-butyl 2,4-dichloro-3-(4-methyl-1-(phenylsulfonyl)-6-(trifluoromethyl)-1H-pyrrolo[2,3-b]pyridine-2-carbonyl)benzoate (4.71 g, 7.68 mmol) was degassed with N₂ for 15 minutes. THF (25 mL) was added to form a light yellow solution. Tetrabutylammonium fluoride (1.0 M in THF) (7.68 mL, 7.68 mmol) was added to form a brown solution. The mixture was heated at 50° C. overnight. Additional tetrabutylammonium fluoride (1.0 M in THF) (7.68 mL, 7.68 mmol) was added and the solution heated at 50° C. for 6 hours. Solvent was removed under reduced pressure. The residue was dissolved in EtOAc (100 mL), filtered to remove insoluble solids then washed with saturated NaHCO₃ (2×50 mL), brine (2×50 mL), dried over Na₂SO₄, filtered and concentrated to dryness. The solids were redissolved in THF (25 mL). Tetrabutylammonium fluoride (4.99 mL, 4.99 mmol) was added. The mixture was heated at 50° C. for 4 h. Solvent was removed under reduced pressure. The residue was dissolved in EtOAc (100 mL), washed with saturated NaHCO₃ (2×50 mL), brine (2×50 mL), dried over Na₂SO₄, filtered and concentrated to dryness. The solids were purified through a pad of silica gel, eluting with 40% EtOAc/heptane. Fractions containing product were concentrated to dryness to give tert-butyl 2,4-dichloro-3-(4-methyl-6-(trifluoromethyl)-1H-pyrrolo[2,3-b]pyridine-2-carbonyl)benzoate (3.7127 g, 7.84 mmol, 102%). LC/MS (Method i) $R_t$=2.16 min.; MS m/z: 473 (M+H)⁺; ¹H NMR (400 MHz, DMSO-d6) δ 13.17 (s, 1H), 7.93 (d, J=8.5 Hz, 1H), 7.74 (d, J=8.4 Hz, 1H), 7.48 (s, 1H), 7.30 (s, 1H), 2.61 (s, 3H), 1.55 (s, 9H).

Step 3: tert-butyl 2,4-dichloro-3-(1,4-dimethyl-6-(trifluoromethyl)-1H-pyrrolo[2,3-b]pyridine-2-carbonyl)benzoate

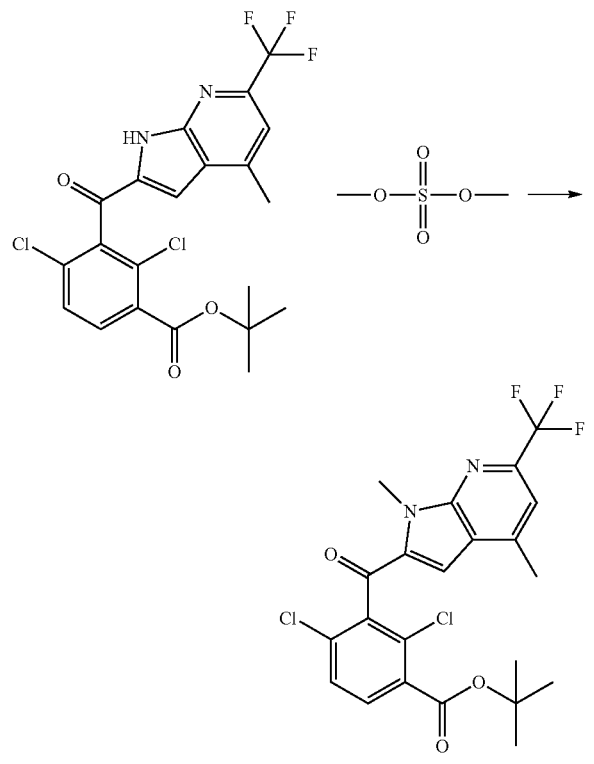

To a yellow solution of tert-butyl 2,4-dichloro-3-(4-methyl-6-(trifluoromethyl)-1H-pyrrolo[2,3-b]pyridine-2-carbonyl)benzoate (3.71 g, 7.84 mmol) in ACN (148 mL) was added cesium carbonate (7.66 g, 23.52 mmol) followed by dimethyl sulfate (1.487 mL, 15.68 mmol) The mixture was stirred at room temperature for about 60 hours. The solution was poured into 300 mL water with stirring. Solid was collected by filtration, washed with water and dried to give tert-butyl 2,4-dichloro-3-(1,4-dimethyl-6-(trifluoromethyl)-1H-pyrrolo[2,3-b]pyridine-2-carbonyl)benzoate (3.4 g, 89%) as a light brown solid. LC/MS (Method i) $R_t$=2.39 min.; MS m/z: 487 (M+H)⁺. ¹H NMR (400 MHz, DMSO-d6) δ 7.94 (d, J=8.4 Hz, 1H), 7.75 (d, J=8.4 Hz, 1H), 7.54 (d, J=0.9 Hz, 1H), 7.35 (s, 1H), 4.18 (s, 3H), 2.61 (d, J=0.8 Hz, 3H), 1.55 (s, 9H).

Step 4: 2,4-dichloro-3-(1,4-dimethyl-6-(trifluoromethyl)-1H-pyrrolo[2,3-b]pyridine-2-carbonyl)benzoic acid

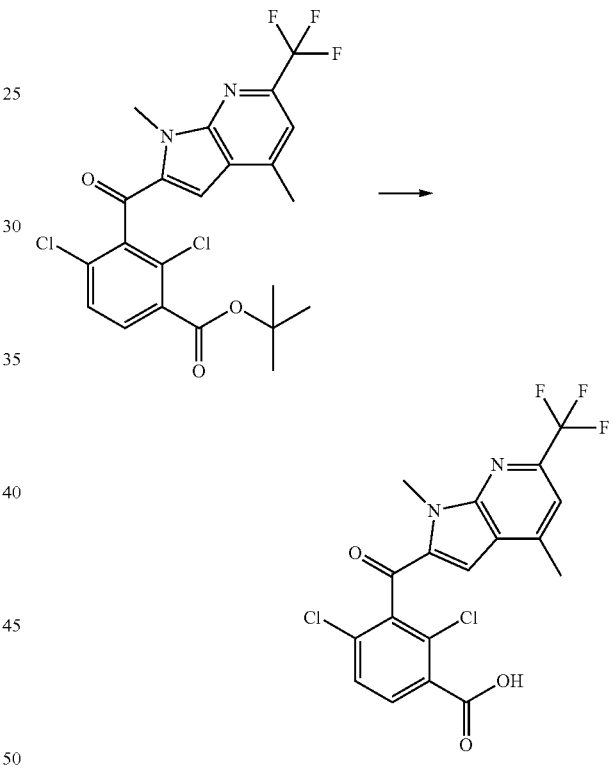

To a yellow solution of tert-butyl 2,4-dichloro-3-(1,4-dimethyl-6-(trifluoromethyl)-1H-pyrrolo[2,3-b]pyridine-2-carbonyl)benzoate (3.4 g, 6.98 mmol) in CH2Cl2 (17 mL) was added TFA (16.13 mL, 209 mmol). The mixture was stirred at room temperature for 2 hours. Solvent was removed under reduced pressure. To the residue was added ether. The solution was sonicated until solid started to form and the resulting slurry was stirred at room temperature for 10 minutes. Solid was collected by filtration, washed with ether and dried to give 2,4-dichloro-3-(1,4-dimethyl-6-(trifluoromethyl)-1H-pyrrolo[2,3-b]pyridine-2-carbonyl)benzoic acid (2.1816 g, 72%) as a white solid. LC/MS (Method i) $R_t$=1.39 min.; MS m/z: 431 (M+H)⁺; ¹H NMR (400 MHz, DMSO-d6) δ 13.76 (s, 1H), 8.00 (d, J=8.5 Hz, 1H), 7.75 (d, J=8.4 Hz, 1H), 7.54 (d, J=1.1 Hz, 1H), 7.31 (s, 1H), 4.18 (s, 3H), 2.61 (s, 3H).

Step 5: ethyl 2-(1-(2,4-dichloro-3-(1,4-dimethyl-6-(trifluoromethyl)-1H-pyrrolo[2,3-b]pyridine-2-carbonyl)benzoyl)piperidin-4-yl)acetate

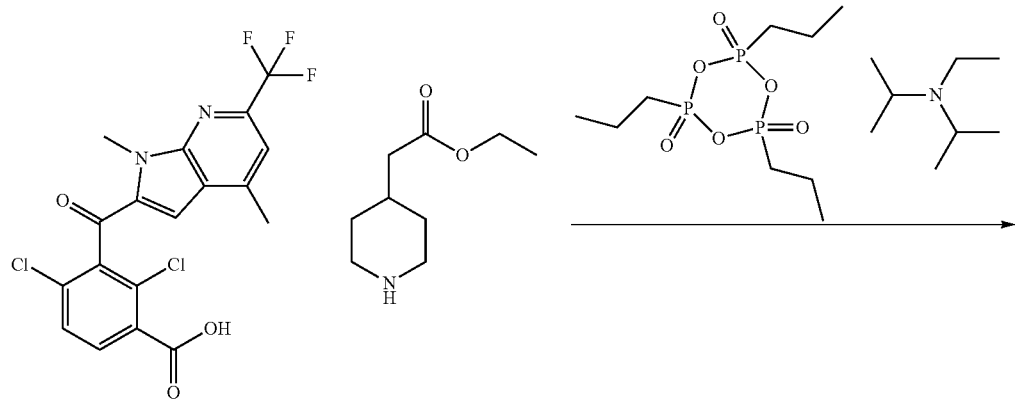

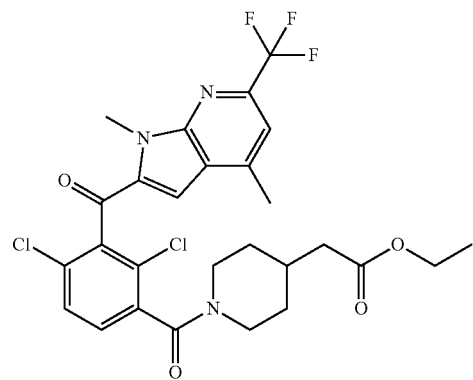

The 2,4-dichloro-3-(1,4-dimethyl-6-(trifluoromethyl)-1H-pyrrolo[2,3-b]pyridine-2-carbonyl)benzoic acid (150 mg, 0.348 mmol) was suspended in EtOAc (2.319 mL). To the suspension ethyl 2-(piperidin-4-yl)acetate (89 mg, 0.522 mmol) and N-ethyl-N-isopropylpropan-2-amine (0.115 mL, 0.661 mmol) were added. The suspension was cooled to 0-5° C. in an ice bath and added 2,4,6-tripropyl-1,3,5,2,4,6-trioxatriphosphinane 2,4,6-trioxide (0.372 mL, 0.626 mmol) dropwise. The reaction mixture was stirred for 2 hours at 0-5° C. 1M HCl (4 mL) was added, and the aqueous mixture was extracted with EtOAc (3×4 mL), The organic layers were concentrated to dryness and purified by flash chromatography (0-75% EtOAc/heptane over 30 minutes; Redi-Sep column, 24 g, 311 nm). Fractions were concentrated to dryness to give ethyl 2-(1-(2,4-dichloro-3-(1,4-dimethyl-6-(trifluoromethyl)-1H-pyrrolo[2,3-b]pyridine-2-carbonyl)benzoyl)piperidin-4-yl)acetate (0.196 g, 0.335 mmol, 96%) as a clear oil. LC/MS (Method i) $R_f$=2.16 min.; MS m/z: 584 $(M+H)^+$.

Step 6: 2-(1-(2,4-dichloro-3-(1,4-dimethyl-6-(trifluoromethyl)-1H-pyrrolo[2,3-b]pyridine-2-carbonyl)benzoyl)piperidin-4-yl)acetic acid

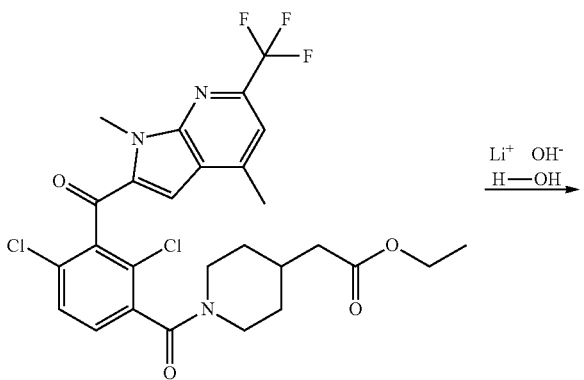

-continued

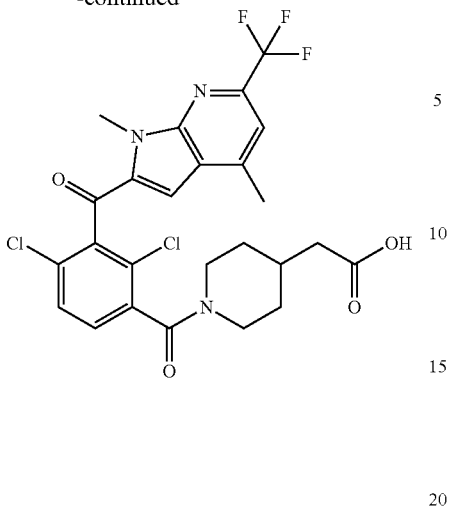

A mixture of ethyl 2-(1-(2,4-dichloro-3-(1,4-dimethyl-6-(trifluoromethyl)-1H-pyrrolo[2,3-b]pyridine-2-carbonyl)benzoyl)piperidin-4-yl)acetate (0.196 g, 0.335 mmol) and lithium hydroxide hydrate (0.014 g, 0.335 mmol) in THF (3 mL) and water (1.000 mL) was stirred at room temperature overnight. Solvent was removed. Water (10 mL) and HCl (1N, 2 mL) were added. The reaction mixture was stirred at room temperature for 2 hours. The suspension was filtered and dried to give 2-(1-(2,4-dichloro-3-(1,4-dimethyl-6-(trifluoromethyl)-1H-pyrrolo[2,3-b]pyridine-2-carbonyl)benzoyl)piperidin-4-yl)acetic acid (0.162 g, 0.291 mmol, 87%) as an off-white solid. LC/MS (Method i) $R_t$=2.52 min.;

MS m/z: 556 (M+H)$^+$.

Example FV: 1-(2,4-dichloro-3-(1,4-dimethyl-6-(trifluoromethyl)-1H-pyrrolo[2,3-b]pyridine-2-carbonyl)benzoyl)piperidine-4-carbonitrile

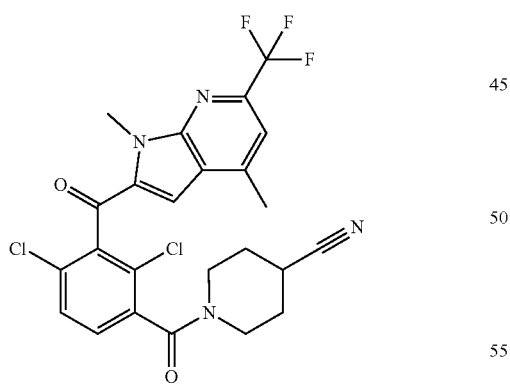

1-(2,4-Dichloro-3-(1,4-dimethyl-6-(trifluoro methyl)-1H-pyrrolo[2,3-b]pyridine-2-carbonyl)benzoyl)piperidine-4-carbonitrile was prepared in a similar way to example FU, step 5.

LC/MS (Method i) $R_t$=2.71 min.; MS m/z: 523 (M+H)+.

Example FW: (2,6-dichloro-3-((3S,4S)-4-hydroxy-3-methylpiperidine-1-carbonyl)phenyl)(1,4-dimethyl-6-(trifluoromethyl)-1H-pyrrolo[2,3-b]pyridin-2-yl)methanone and (2,6-dichloro-3-((3R,4R)-4-hydroxy-3-methylpiperidine-1-carbonyl)phenyl)(1,4-dimethyl-6-(trifluoromethyl)-1H-pyrrolo[2,3-b]pyridin-2-yl)methanone

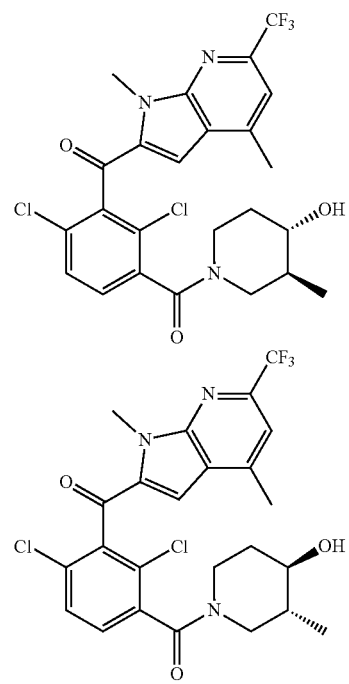

(2,6-dichloro-3-((3S,4S)-4-hydroxy-3-methylpiperidine-1-carbonyl)phenyl)(1,4-dimethyl-6-(trifluoromethyl)-1H-pyrrolo[2,3-b]pyridin-2-yl)methanone and (2,6-dichloro-3-((3R,4R)-4-hydroxy-3-methylpiperidine-1-carbonyl)phenyl)(1,4-dimethyl-6-(trifluoromethyl)-1H-pyrrolo[2,3-b]pyridin-2-yl)methanone were prepared in a similar way to example FU, step 5. LC/MS (Method i) $R_t$=2.71 min.;

MS m/z: 523 (M+H)+.

Example FX: (3R,4R)-1-(2,4-dichloro-3-(1,4-dimethyl-6-(trifluoromethyl)-1H-pyrrolo[2,3-b]pyridine-2-carbonyl)benzoyl)-3-methylpiperidine-4-carboxylic acid

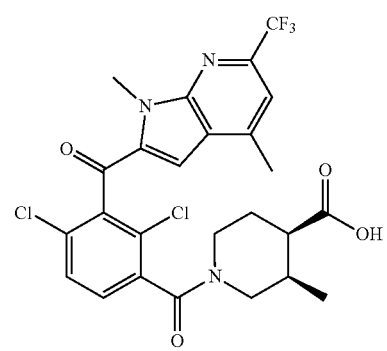 [SMILES: Cc1cc(C(F)(F)F)nc2c1cc(C(=O)c1c(Cl)ccc(C(=O)N3CC[C@@H](C(=O)O)[C@@H](C)C3)c1Cl)n2C]

(3R,4R)-1-(2,4-Dichloro-3-(1,4-dimethyl-6-(trifluoromethyl)-1H-pyrrolo[2,3-b]pyridine-2-carbonyl)benzoyl)-3-methylpiperidine-4-carboxylic acid was prepared in a similar way to example FU, step 6. LC/MS (Method i) R$_t$=2.49 min.; MS m/z: 556 (M+H)+.

Example FY: (2,4-dichloro-3-(1,4-dimethyl-6-(trifluoromethyl)-1H-pyrrolo[2,3-b]pyridine-2-carbonyl)phenyl)(4-(2-methoxyethyl)piperidin-1-yl)methanone

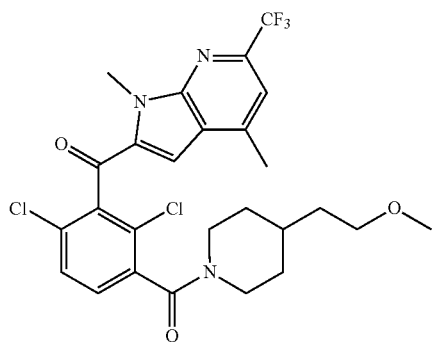 [SMILES: COCCC1CCN(C(=O)c2ccc(Cl)c(C(=O)c3cc4c(C)cc(C(F)(F)F)nc4n3C)c2Cl)CC1]

(2,4-Dichloro-3-(1,4-dimethyl-6-(trifluoromethyl)-1H-pyrrolo[2,3-b]pyridine-2-carbonyl)phenyl)(4-(2-methoxyethyl)piperidin-1-yl)methanone was prepared in a similar way to example FU, step 5.

LC/MS (Method i) R$_t$=2.99 min.; MS m/z: 556 (M+H)+.

Example FZ: (2,4-dichloro-3-(1,4-dimethyl-6-(trifluoromethyl)-1H-pyrrolo[2,3-b]pyridine-2-carbonyl)phenyl)(4-hydroxypiperidin-1-yl)methanone

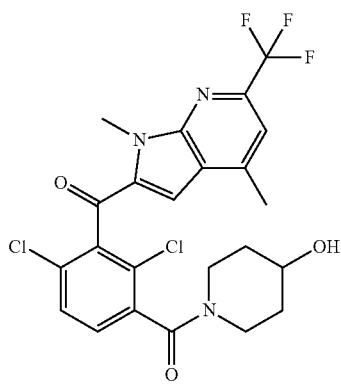 [SMILES: Cc1cc(C(F)(F)F)nc2c1cc(C(=O)c1c(Cl)ccc(C(=O)N3CCC(O)CC3)c1Cl)n2C]

(2,4-dichloro-3-(1,4-dimethyl-6-(trifluoromethyl)-1H-pyrrolo[2,3-b]pyridine-2-carbonyl)phenyl)(4-hydroxypiperidin-1-yl)methanone was prepared in a similar way to example FU, step 5. LC/MS (Method i) R$_t$=2.49 min.; MS m/z: 514 (M+H)+.

Example GA: 2-((3R,4S)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid; 2-((3S,4R)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid; 2-((3S,4S)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid; 2-((3R,4R)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid

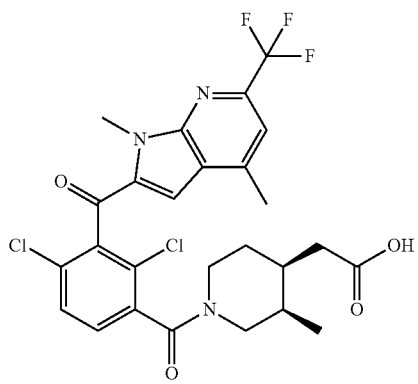

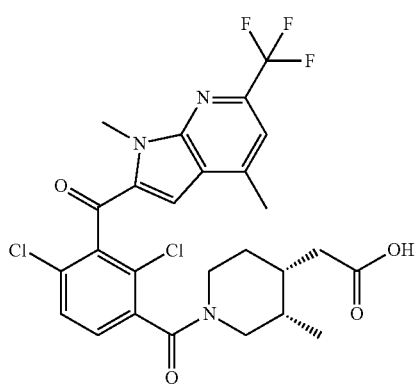

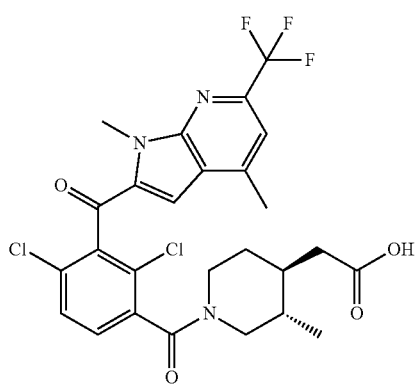

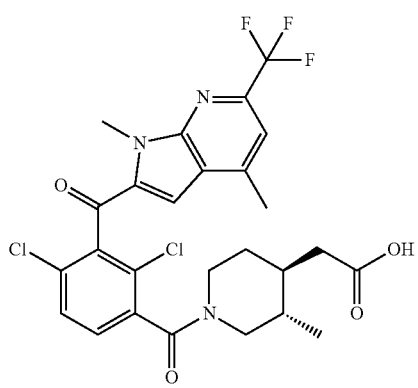

787

-continued

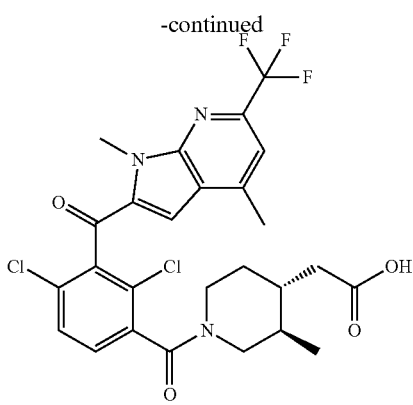

2-((3R,4S)-1-(2,4-dichloro-3-(1,4-dimethyl-6-(trifluoromethyl)-1H-pyrrolo[2,3-b]pyridine-2-carbonyl)benzoyl)-3-methylpiperidin-4-yl)acetic acid was prepared in a similar way to example FU, step 6. LC/MS (Method i) Rt=2.53 min.; MS m/z: 570 (M+H)+. All four isomers of the final product can be isolated by chiral chromatography (chiral method p) or prepared individually from chiral starting materials as exemplified in preparation 83-84.

Example GB: (2,4-dichloro-3-(1,4-dimethyl-6-(trifluoromethyl)-1H-pyrrolo[2,3-b]pyridine-2-carbonyl)phenyl)(4-(methylsulfonyl)piperidin-1-yl)methanone

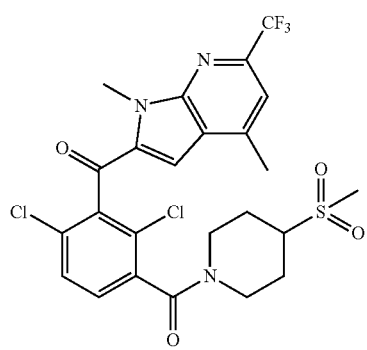 [SMILES: Cc1cc(C(F)(F)F)nc2c1cc(C(=O)c1c(Cl)ccc(C(=O)N3CCC(S(C)(=O)=O)CC3)c1Cl)n2C]

788

(2,4-dichloro-3-(1,4-dimethyl-6-(trifluoromethyl)-1H-pyrrolo[2,3-b]pyridine-2-carbonyl)phenyl)(4-(methylsulfonyl)piperidin-1-yl)methanone was prepared in a similar way to example FU, step 5.

LC/MS (Method i) $R_f$=2.53 min.; MS m/z: 576 (M+H)+.

Example GC: 2-((3S,4R)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetic acid

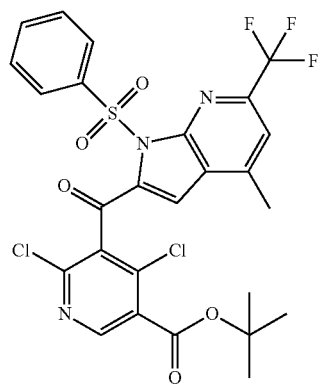

Step 1: tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate

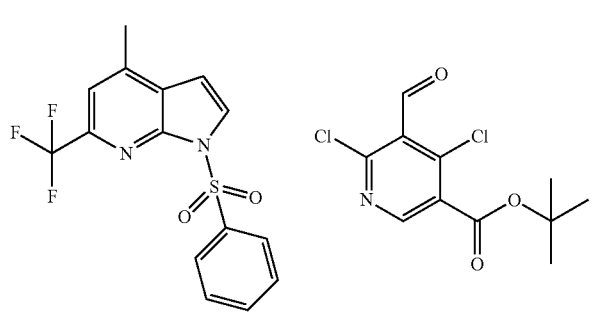

To a solution of 4-methyl-1-(phenylsulfonyl)-6-(trifluoromethyl)-1H-pyrrolo[2,3-b]pyridine (29 g, 85 mmol) (example FS, step 9) in THF (290 mL) was added 2M lithium diisopropylamide in THF (42.6 mL, 85 mmol) dropwise at −78° C. under nitrogen (turned into a reddish orange solution, internal temperature maintained below −70° C.). The mixture was stirred at −78° C. for 30 minutes. A solution of tert-butyl 4,6-dichloro-5-formylnicotinate (25.9 g, 94 mmol) (example DO, step 12) in THF (145 mL) was added dropwise (internal temperature maintained below −75° C.). The mixture was stirred at −78° C. for 1 h. The reaction was quenched with addition of saturated NH₄Cl (120 mL). THF solvent was removed in vacuo and the aqueous layer was diluted with water (200 mL) and the product was partitioned between EtOAc (3×100 mL) and the aqueous layer. Extracts were combined and washed with water (3×70 mL), brine (100 mL) and then dried over Na₂SO₄, filtered and solvent removed in vacuo to dryness to give a tan gum/foam 68 g—solvent wet. The foam was triturated with pentane (3×150 mL), gradually a gum/solid resulted. The suspension was sonicated to produce a fine powder, cooled to about 15° C. and the solid was collected and washed with pentane (3×80 mL) and dried in vacuo to give an off-white solid of crude product 42 g. The solid was stirred with pentane (200 mL), filtered and dried to yield 21.5 g. The solid was stirred with ether (20 mL) for 10 minutes and 30-60° C. petroleum-ether (20 mL) was added dropwise with stirring. The solid was collected and washed with 30-60° C. petroleum-ether (2×30 mL) and dried to yield a white solid of tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate (17.7 g, 28.7 mmol, 33.7%). LC/MS (Method i) $R_t$=2.09 min.; MS m/z: 616 (M+H)⁺.

Step 2: tert-butyl 4,6-dichloro-5-((4-methyl-1-(phenylsulfonyl)-6-(trifluoromethyl)-1H-pyrrolo[2,3-b]pyridin-2-yl)methyl)nicotinate

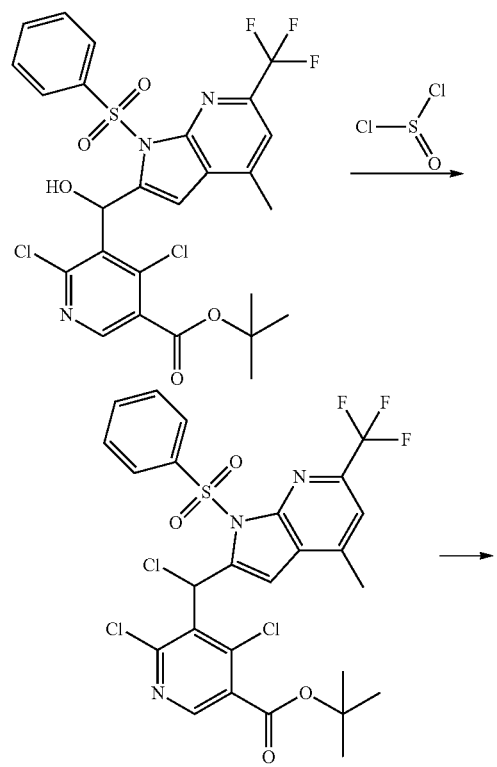

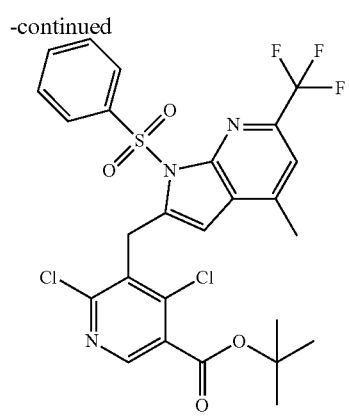

To a solution of tert-butyl 4,6-dichloro-5-(hydroxy(4-methyl-1-(phenylsulfonyl)-6-(trifluoromethyl)-1H-pyrrolo[2,3-b]pyridin-2-yl)methyl)nicotinate (7.9 g, 12.82 mmol) in CHCl₃ (49.4 mL) was added sulfurous dichloride (4.68 mL, 64.1 mmol). The mixture was heated at 60° C. overnight. The reaction mixture was concentrated under reduced pressure to give a pale yellow foam. It was dissolved in acetic acid (26.0 mL). Zinc (4.19 g, 64.1 mmol) was stirred with acetic acid for 10 minutes and filtered, then added to the reaction mixture. After 1.5 hours the reaction was filtered over a pad of Celite® and washed with EtOAc (50 mL). The filtrate was concentrated and purified via analogix (120 g column; 0-20% EtOAc/Heptane over 10 column volumes). The clean fractions were collected and concentrated to give tert-butyl 4,6-dichloro-5-((4-methyl-1-(phenylsulfonyl)-6-(trifluoromethyl)-1H-pyrrolo[2,3-b]pyridin-2-yl)methyl)nicotinate (3.1 g, 5.16 mmol, 40.3%). LC/MS (Method i) $R_t$=2.29 min.; MS m/z: 600, 601, 602 (M+H)⁺.

Step 3: tert-butyl 4,6-dichloro-5-((4-methyl-6-(trifluoromethyl)-1H-pyrrolo[2,3-b]pyridin-2-yl)methyl)nicotinate

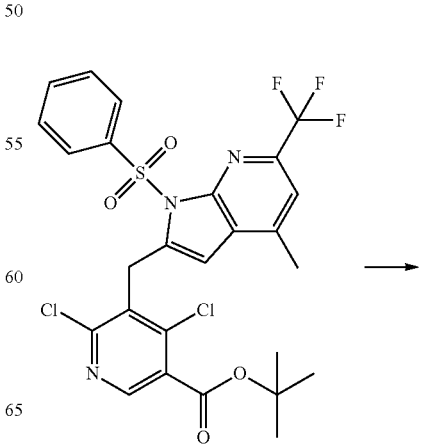

-continued

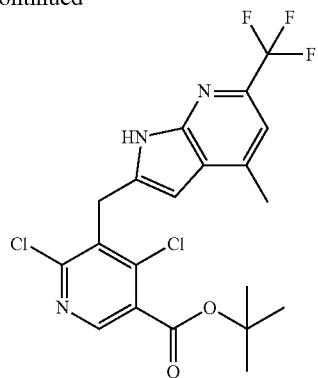

To a solution of tert-butyl 4,6-dichloro-5-((4-methyl-1-(phenylsulfonyl)-6-(trifluoromethyl)-1H-pyrrolo[2,3-b]pyridin-2-yl)methyl)nicotinate (3 g, 5.00 mmol) in THF (50.0 mL) was added tetrabutylammonium fluoride (5.50 mL, 5.50 mmol) The reaction mixture was stirred at room temperature for about 4 hours. The reaction mixture was concentrated and purified via analogix (80 g column; 0-25% EtOAC/Heptane over 7 column volumes) to give tert-butyl 4,6-dichloro-5-((4-methyl-6-(trifluoromethyl)-1H-pyrrolo[2,3-b]pyridin-2-yl)methyl)nicotinate (1.83 g, 3.98 mmol, 80%.

LC/MS (Method i) $R_t$=2.10 min.; MS m/z: 460, 461, 462 (M+H)$^+$.

Step 4: tert-butyl 4,6-dichloro-5-((1,4-dimethyl-6-(trifluoromethyl)-1H-pyrrolo[2,3-b]pyridin-2-yl)methyl)nicotinate

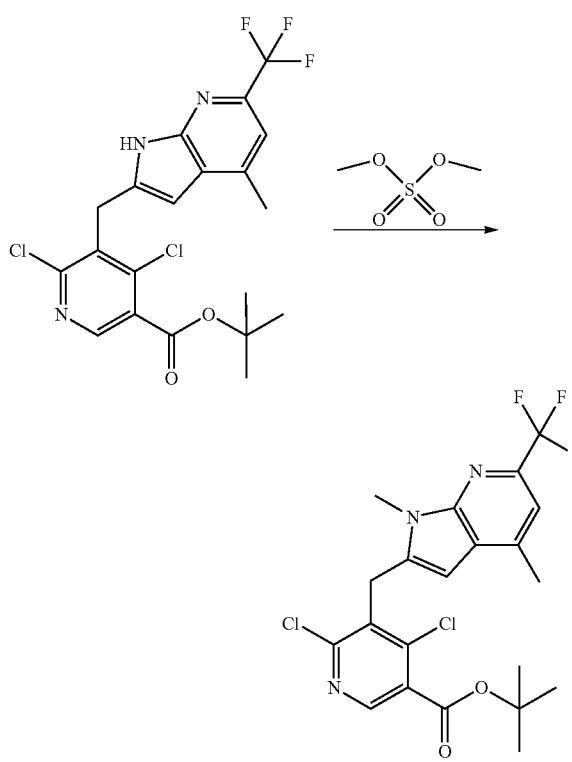

A vial was charged with tert-butyl 4,6-dichloro-5-((4-methyl-6-(trifluoromethyl)-1H-pyrrolo[2,3-b]pyridin-2-yl)methyl)nicotinate (1.48 g, 3.22 mmol) and ACN (1.00 mL) followed by the addition of cesium carbonate (3.14 g, 9.65 mmol) and dimethyl sulfate (0.768 mL, 8.04 mmol) The mixture was stirred at room temperature for about 60 hours. The mixture was concentrated under reduced pressure. The residue was partitioned between water (50 mL) and EtOAC (60 mL). The organic layer was dried over MgSO$_4$, filtered and concentrated. The crude material was purified via Analogix (0-30% EtOAC/DCM; 40 g Silicycle SiliaSep Silica gel column column) The collected fractions were concentrated and suspended in ether and filtered to give a white solid. The material was dried in a vacuum oven at about 60° C. to give tert-butyl 4,6-dichloro-5-((1,4-dimethyl-6-(trifluoromethyl)-1H-pyrrolo[2,3-b]pyridin-2-yl)methyl)nicotinate (1.35 g, 2.85 mmol, 89%). LC/MS (Method i) $R_t$=2.25 min.; MS m/z: 474, 475, 476 (M+H)$^+$.

Step 5: 4,6-dichloro-5-((1,4-dimethyl-6-(trifluoromethyl)-1H-pyrrolo[2,3-b]pyridin-2-yl)methyl)nicotinic acid

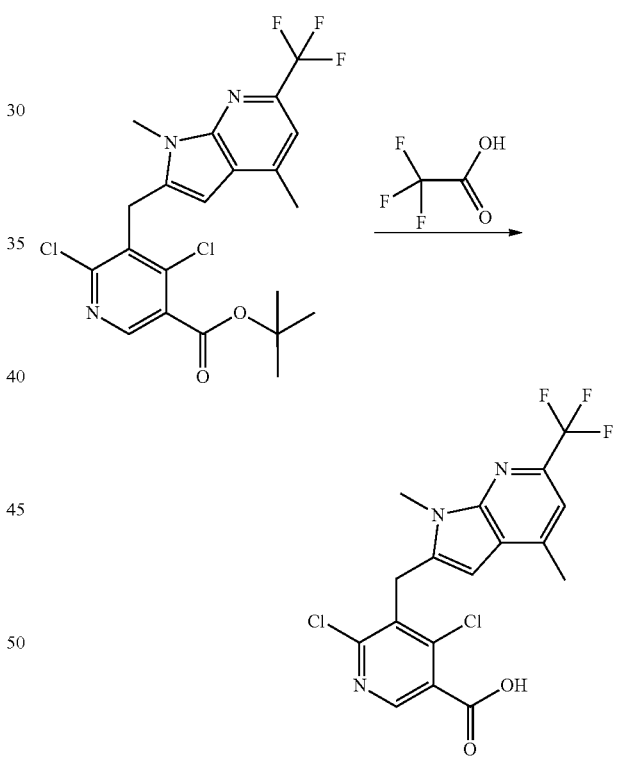

To a yellow solution of tert-butyl 4,6-dichloro-5-((1,4-dimethyl-6-(trifluoromethyl)-1H-pyrrolo[2,3-b]pyridin-2-yl)methyl)nicotinate (1.127 g, 2.376 mmol) in CH$_2$Cl$_2$ (3 mL) was added TFA (6.04 mL, 78 mmol). The mixture was stirred at room temperature for about 5 hours. The mixture was concentrated under reduced pressure and dissolved in DCM. On addition of a saturated solution of sodium bicarbonate, a white precipitate formed which was collected via filtration and washed with water. The precipitate was dried in a vacuum oven at about 60° C. overnight to give 4,6-dichloro-5-((1,4-dimethyl-6-(trifluoromethyl)-1H-pyrrolo

[2,3-b]pyridin-2-yl)methyl)nicotinic acid (820 mg, 1.961 mmol, 83% yield). LC/MS (Method i) R$_t$=1.15 min.; MS m/z: 418, 419, 420 (M+H)+.

Step 6: ethyl 2-((3R,4S)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetate

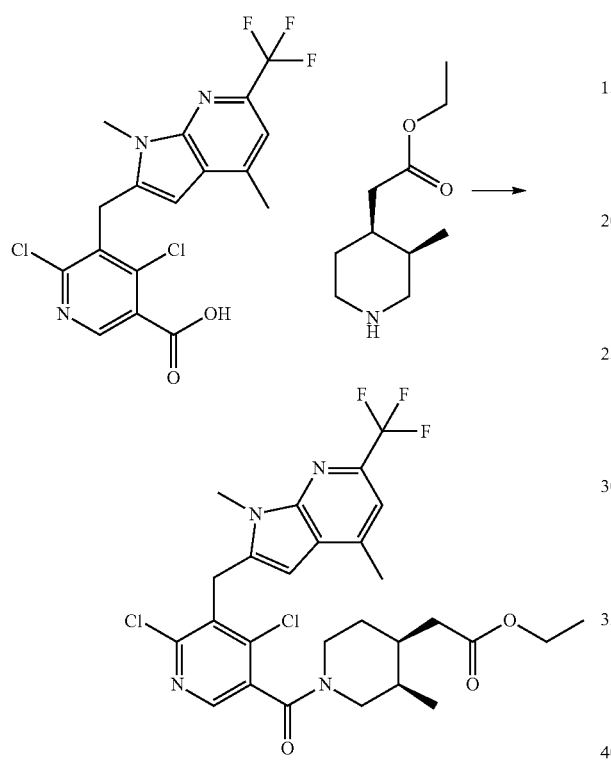

Step 7: 2-((3R,4S)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetic acid

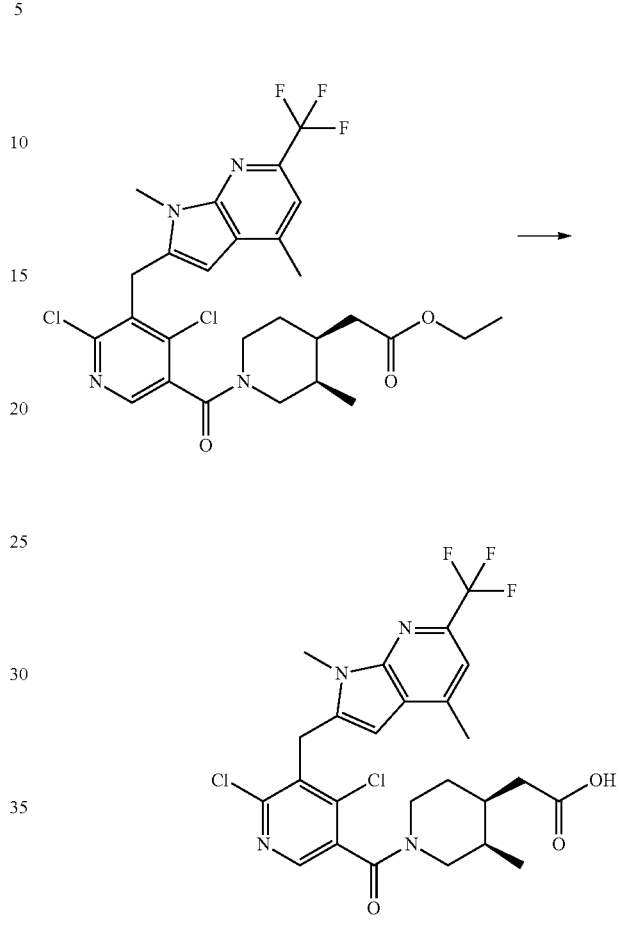

A vial was charged with 4,6-dichloro-5-((1,4-dimethyl-6-(trifluoromethyl)-1H-pyrrolo[2,3-b]pyridin-2-yl)methyl)nicotinic acid (162 mg, 0.387 mmol) and ethyl 2-((3R,4S)-3-methylpiperidin-4-yl)acetate, hydrochloric acid, (150 mg, 0.581 mmol) in EtOAc (2 mL). N-ethyl-N-isopropylpropan-2-amine (0.203 mL, 1.162 mmol) was added, followed by dropwise addition of 2,4,6-tripropyl-1,3,5,2,4,6-trioxatriphosphinane 2,4,6-trioxide (T3P) (0.530 mL, 0.891 mmol). The reaction stirred overnight. Added 2,4,6-tripropyl-1,3,5,2,4,6-trioxatriphosphinane 2,4,6-trioxide (0.230 mL, 0.387 mmol) and N-ethyl-N-isopropylpropan-2-amine (0.101 mL, 0.581 mmol) and stirred 3 hours. The reaction was warmed to about 40° C. After 2 hours 2,4,6-tripropyl-1,3,5,2,4,6-trioxatriphosphinane 2,4,6-trioxide (0.230 mL, 0.387 mmol) was added and the reaction stirred overnight at about 40° C. The reaction mixture was diluted with EtOAC (10 mL) and washed with 1 N HCl (10 mL) then with a solution of NaHCO$_3$ (10 mL). The organic layer was dried over MgSO$_4$, filtered and concentrated and purified via analogix (12 g column, 10-80% EtOAc/Hept) to give ethyl 2-((3R,4S)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetate (152 mg, 0.260 mmol, 67.0% yield). LC/MS (Method i) R$_t$=2.01 min.; MS m/z: 585, 586, 587 (M+H)$^+$.

To a solution of ethyl 2-((3R,4S)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetate (151 mg, 0.258 mmol) in THF (4 mL):water (0.800 mL) was added lithium hydroxide hydrate (16.24 mg, 0.387 mmol) and the reaction was stirred at about 35° C. overnight. The mixture was concentrated under reduced pressure. The residue was dissolved in water (5 mL) and the aqueous layer was extracted with DCM (5 mL). An emulsion formed. The entire mixture was acidified with 1 N HCl to pH of about 1-2. More DCM was added, stirred and allowed to sit for about 1 h. The organic layer was separated. The aq layer was washed with 5% MeoH/DCM. The organic layers were combined, dried over MgSO$_4$, filtered and concentrated. The crude product was purified by RP-HPLC. The fractions obtained were concentrated to 60% the original volume and the resulting solids were collected via filtration and dried in a vacuum at about 60° C. overnight to give 2-((3R,4S)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetic acid (102 mg, 0.183 mmol, 70.9% yield). LC/MS (Method i) R$_t$=2.36 min.; MS m/z: 557, 558, 559 (M+H)$^+$.

Example GD: (2,4-dichloro-3-(1,4-dimethyl-6-(trifluoromethyl)-1H-pyrrolo[2,3-b]pyridine-2-carbonyl)phenyl)(4-(methylsulfonyl)piperidin-1-yl)methanone

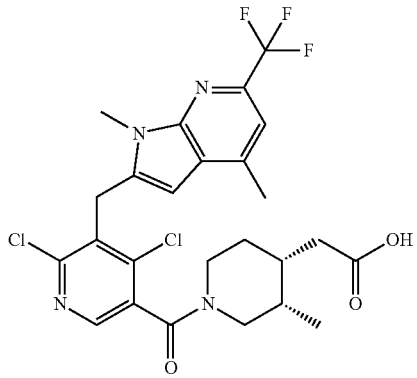 [SMILES: Cc1cc(C(F)(F)F)nc2c1cc(Cc1c(Cl)ncc(C(=O)N3CC[C@H](CC(=O)O)[C@H](C)C3)c1Cl)n2C]

2-((3S,4R)-1-(4,6-dichloro-5-((1,4-dimethyl-6-(trifluoromethyl)-1H-pyrrolo[2,3-b]pyridin-2-yl)methyl)nicotinoyl)-3-methylpiperidin-4-yl)acetic acid (130 mg, 0.233 mmol, 59.6% yield) was prepared in a similar way to example GC, step 7. LC/MS (Method i) $R_f$=2.36 min.; MS m/z: 557, 558, 559 (M+H)$^+$ Example GE: (2,4-dichloro-3-(1,4-dimethyl-6-(trifluoromethyl)-1H-pyrrolo[2,3-b]pyridine-2-carbonyl)phenyl)(4-(methylsulfonyl)piperidin-1-yl)methanone

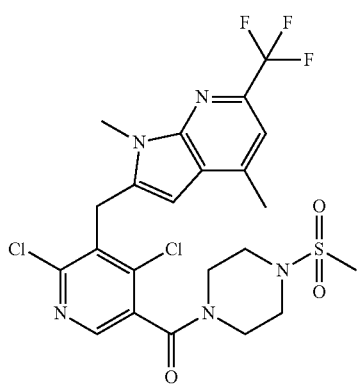 [SMILES: Cc1cc(C(F)(F)F)nc2c1cc(Cc1c(Cl)ncc(C(=O)N3CCN(S(C)(=O)=O)CC3)c1Cl)n2C]

(4,6-dichloro-5-((1,4-dimethyl-6-(trifluoromethyl)-1H-pyrrolo[2,3-b]pyridin-2-yl)methyl)pyridin-3-yl)(4-(methylsulfonyl)piperazin-1-yl)methanone (110 mg, 0.195 mmol, 78% yield) was prepared in a similar way to example GC, step 6. LC/MS (Method i).) $R_f$=2.47 min.; MS m/z: 564, 565, 566 (M+H)$^+$.

Example GF: (4,6-dichloro-5-((1,4-dimethyl-6-(trifluoromethyl)-1H-pyrrolo[2,3-b]pyridin-2-yl)methyl)pyridin-3-yl)(morpholino)methanone

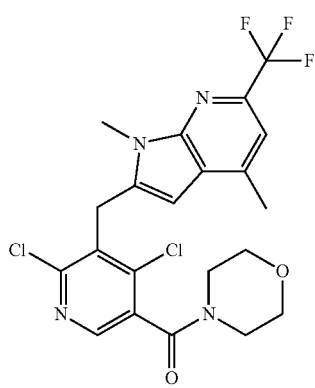 [SMILES: Cc1cc(C(F)(F)F)nc2c1cc(Cc1c(Cl)ncc(C(=O)N3CCOCC3)c1Cl)n2C]

(4,6-dichloro-5-((1,4-dimethyl-6-(trifluoromethyl)-1H-pyrrolo[2,3-b]pyridin-2-yl)methyl)pyridin-3-yl)(morpholino)methanone (102.7 mg, 0.207 mmol, 75% yield) was prepared in a similar way to example GC, step 6. LC/MS (Method i).) $R_f$=2.52 min.; MS m/z: 487 (M+H)+.

Example GG: (4,6-dichloro-5-((1,4-dimethyl-6-(trifluoromethyl)-1H-pyrrolo[2,3-b]pyridin-2-yl)methyl)pyridin-3-yl)(4-(methylsulfonyl)piperidin-1-yl)methanone

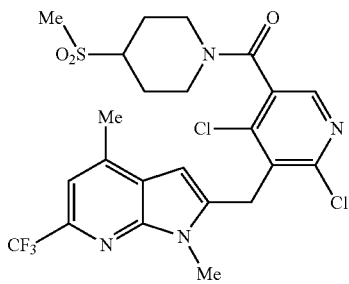 [SMILES: Cc1cc(C(F)(F)F)nc2c1cc(Cc1c(Cl)ncc(C(=O)N3CCC(S(C)(=O)=O)CC3)c1Cl)n2C]

(4,6-dichloro-5-((1,4-dimethyl-6-(trifluoromethyl)-1H-pyrrolo[2,3-b]pyridin-2-yl)methyl)pyridin-3-yl)(4-(methylsulfonyl)piperidin-1-yl)methanone (35 mg, 10% yield) was prepared in a similar way to example GC, step 6. LC/MS (Method i).) $R_f$=1.59 min.; MS m/z: 563, 565, 567 (M+H)+.

797

Example GH: (3,5-dichloro-4-((1,4-dimethyl-6-(trifluoromethyl)-1H-pyrrolo[2,3-b]pyridin-2-yl)methyl)pyridin-2-yl)(morpholino)methanone

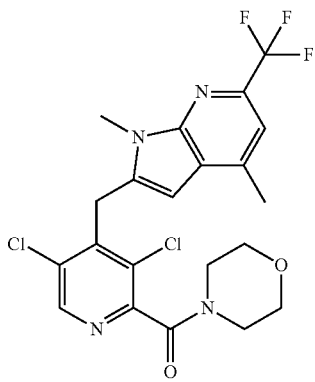 [SMILES: Cc1cc(C(F)(F)F)nc2c1cc(Cc1c(Cl)cnc(C(=O)N3CCOCC3)c1Cl)n2C]

Step 1: 3,5-dichloro-2-(morpholine-4-carbonyl)isonicotinaldehyde

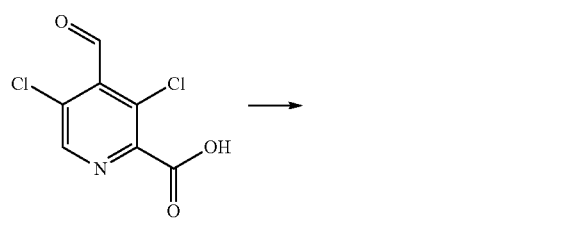

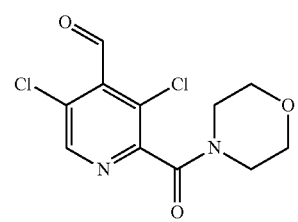

798

To a solution of 3,5-dichloro-4-formylpicolinic acid (1.2 g, 5.45 mmol) (example FR, step 4) and 2-(3H-[1,2,3]triazolo[4,5-b]pyridin-3-yl)-1,1,3,3-tetramethylisouronium hexafluorophosphate(V) (2.281 g, 6.00 mmol) in THF (5 mL) was added morpholine (1.045 mL, 12.00 mmol). After 15 hours the reaction mixture was partitioned between EtOAc (10 mL) and NaHCO$_3$ (10 mL). The organic layer was separated, concentrated in vacuo and purified by chromatography on silica gel (EtOAc/DCM) to give 3,5-dichloro-2-(morpholine-4-carbonyl)isonicotinaldehyde (900 mg, 3.11 mmol, 57.1% yield) as a thick oil. 1H NMR (400 MHz, DMSO-d6) δ 10.29 (s, 1H), 8.81 (s, 1H), 3.51 (t, J=4.8 Hz, 4H), 3.16 (t, J=4.8 Hz, 4H).

Step 2: (3,5-dichloro-4-(hydroxy(4-methyl-1-(phenylsulfonyl)-6-(trifluoromethyl)-1H-pyrrolo[2,3-b]pyridin-2-yl)methyl)pyridin-2-yl)(morpholino)methanone

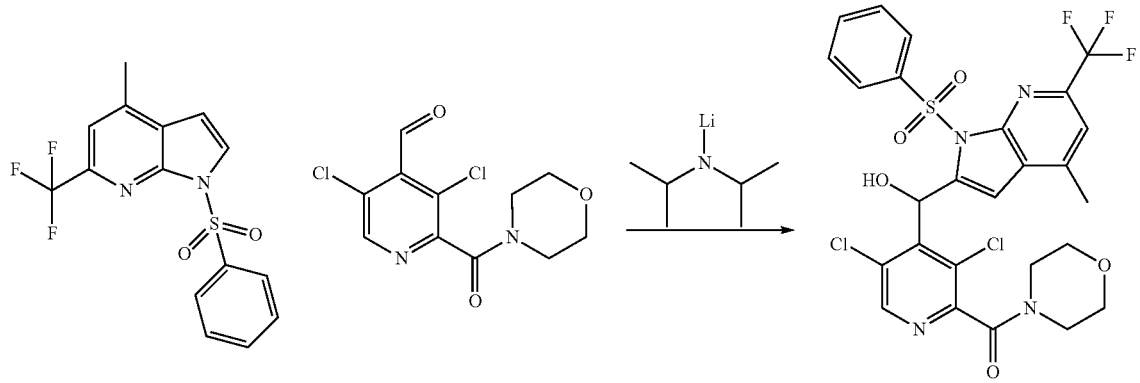

A colorless solution of 4-methyl-1-(phenylsulfonyl)-6-(trifluoromethyl)-1H-pyrrolo[2,3-b]pyridine (900 mg, 2.64 mmol) (example DO, step 10) in THF (15 mL) was cooled to −78° C. under N$_2$. LDA (1.0 M in THF/hexane) (3.17 mL, 3.17 mmol) was added dropwise (keeping internal temperature <−75° C.). The mixture was stirred at −78° C. for 1 hour. A solution of 3,5-dichloro-2-(morpholine-4-carbonyl)isonicotinaldehyde (918 mg, 3.17 mmol) in THF (8 mL) was added dropwise (internal temperature maintained below −75° C.). The mixture was stirred at −78° C. for 1 hour. The solution was quenched with saturated NH$_4$Cl (20 mL). Extracted the aqueous layer with EtOAc (2×30 mL). The organic layer was dried over Na$_2$SO$_4$, filtered and concentrated to dryness. The solid was purified by flash chromatography (25-75% EtOAc/Heptane over 30 min.; Silicycle column, 40 g, 282 nm) to give (3,5-dichloro-4-(hydroxy(4-methyl-1-(phenylsulfonyl)-6-(trifluoromethyl)-1H-pyrrolo[2,3-b]pyridin-2-yl)methyl)pyridin-2-yl)(morpholino)methanone (1.18 g, 1.875 mmol, 70.9% yield) as a white solid.

LC/MS (Method i) R$_t$=2.63 min.; MS m/z: 573 (M+H)$^+$.

Step 3: (3,5-dichloro-4-(chloro(4-methyl-1-(phenylsulfonyl)-6-(trifluoromethyl)-1H-pyrrolo[2,3-b]pyridin-2-yl)methyl)pyridin-2-yl)(morpholino)methanone

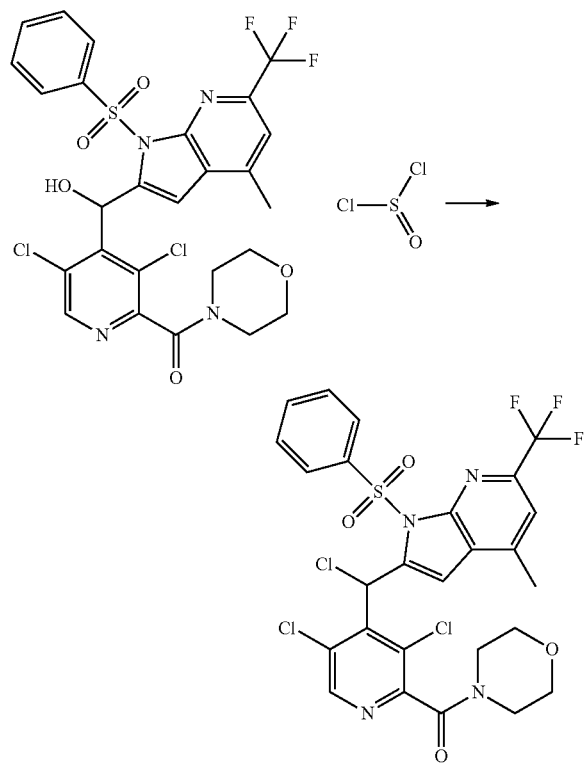

To a clear solution of (3,5-dichloro-4-(hydroxy(4-methyl-1-(phenylsulfonyl)-6-(trifluoromethyl)-1H-pyrrolo[2,3-b]pyridin-2-yl)methyl)pyridin-2-yl)(morpholino)methanone (300 mg, 0.477 mmol) in CHCl$_3$ (3 mL) was added SOCl$_2$ (0.174 mL, 2.383 mmol). The mixture was heated at 60° C. overnight. Solvent was removed under reduced pressure. The residue was partitioned between EtOAc (20 mL) and saturated NaHCO$_3$ (20 mL). The organic layer was concentrated to dryness and purified by flash chromatography (0-75% EtOAc/Heptane over 30 min.; Redi-Sep column, 24 g, 280 nm) to give (3,5-dichloro-4-(chloro(4-methyl-1-(phenylsulfonyl)-6-(trifluoromethyl)-1H-pyrrolo[2,3-b]pyridin-2-yl)methyl)pyridin-2-yl)(morpholino)methanone (200.3 mg, 0.309 mmol, 64.9% yield) as a white solid. LC/MS (Method i) R$_t$=1.99 min.; MS m/z: 647 (M+H)$^+$.

Step 4: (3,5-dichloro-4-((4-methyl-1-(phenylsulfonyl)-6-(trifluoromethyl)-1H-pyrrolo[2,3-b]pyridin-2-yl)methyl)pyridin-2-yl)(morpholino)methanone

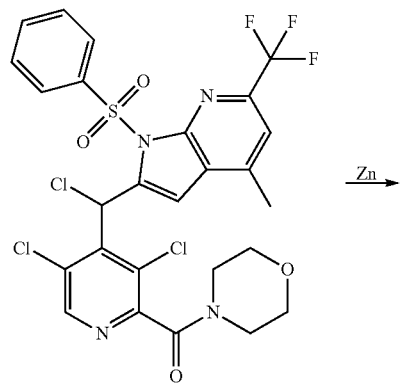

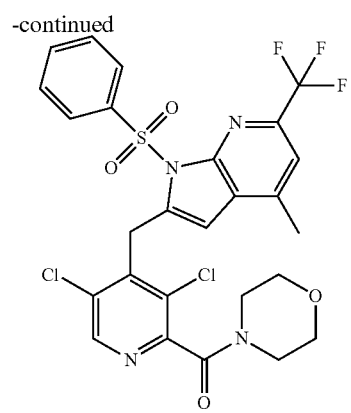

To a solution of (3,5-dichloro-4-(chloro(4-methyl-1-(phenylsulfonyl)-6-(trifluoromethyl)-1H-pyrrolo[2,3-b]pyridin-2-yl)methyl)pyridin-2-yl)(morpholino)methanone (200 mg, 0.309 mmol) in AcOH (2 mL) was added zinc (101 mg, 1.543 mmol) The mixture was stirred at room temperature for 2 hours then filtered and washed with EtOAc. The filtrate was concentrated to dryness. The residue was partitioned between EtOAc (20 mL) and saturated NaHCO$_3$ (20 mL). The aqueous layer was extracted with EtOAc (1×10 mL). The organic layer was dried over Na$_2$SO$_4$, filtered and concentrated to dryness to give (3,5-dichloro-4-((4-methyl-1-(phenylsulfonyl)-6-(trifluoromethyl)-1H-pyrrolo[2,3-b]pyridin-2-yl)methyl)pyridin-2-yl)(morpholino)methanone (176.6 mg, 0.248 mmol, 80% yield) as a white foam. LC/MS (Method i) R$_t$=1.90 min.; MS m/z: 613 (M+H)+.

Step 5: (3,5-dichloro-4-((4-methyl-6-(trifluoromethyl)-1H-pyrrolo[2,3-b]pyridin-2-yl)methyl)pyridin-2-yl)(morpholino)methanone

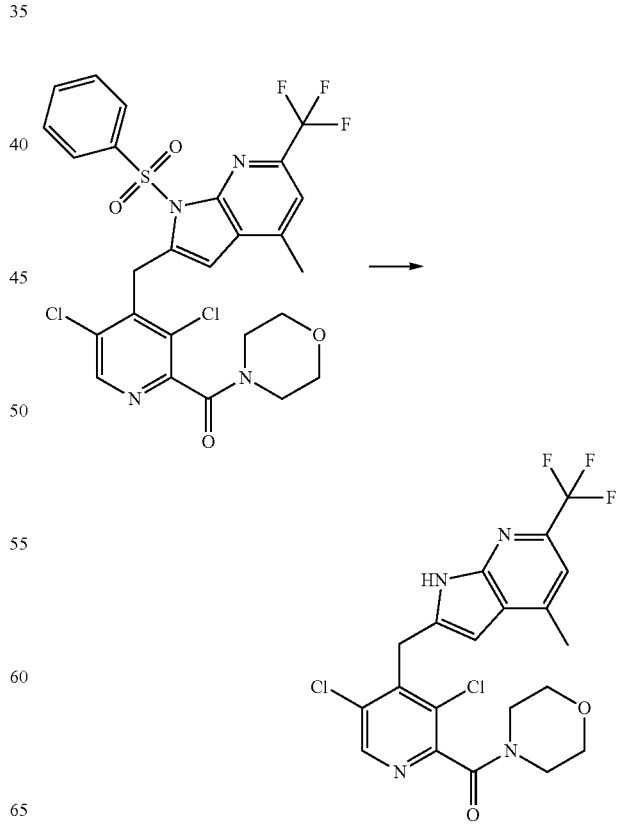

801

To a light yellow solution of (3,5-dichloro-4-((4-methyl-1-(phenylsulfonyl)-6-(trifluoromethyl)-1H-pyrrolo[2,3-b]pyridin-2-yl)methyl)pyridin-2-yl)(morpholino)methanone (176 mg, 0.247 mmol) in THF (3 mL) under N2 was added TBAF (1.0 M in THF) (0.370 mL, 0.370 mmol) The mixture was heated at 50° C. for 4 hours. Solvent was removed under reduced pressure. Purified by flash chromatography (0-75% EtOAc/Heptane over 30 min.; Redi-Sep column, 24 g, 285 nm) to give (3,5-dichloro-4-((4-methyl-6-(trifluoromethyl)-1H-pyrrolo[2,3-b]pyridin-2-yl)methyl)pyridin-2-yl)(morpholino)methanone (139.1 mg, 0.294 mmol, 119% yield) as a white solid. LC/MS (Method i) $R_t$=1.48 min.; MS m/z: 473 (M+H)+.

Step 6: (3,5-dichloro-4-((1,4-dimethyl-6-(trifluoromethyl)-1H-pyrrolo[2,3-b]pyridin-2-yl)methyl)pyridin-2-yl)(morpholino)methanone

802

A vial charged with (3,5-dichloro-4-((4-methyl-6-(trifluoromethyl)-1H-pyrrolo[2,3-b]pyridin-2-yl)methyl)pyridin-2-yl)(morpholino)methanone (139 mg, 0.294 mmol) and cesium carbonate (239 mg, 0.734 mmol) then flushed with $N_2$ for 10 min before addition of ACN (2 mL). The solution was flushed with $N_2$ for another 5 minutes. Dimethyl sulfate (0.042 mL, 0.441 mmol) was added. The mixture was stirred at room temperature for 3 hours. The solution was filtered and washed with EtOAc. The filtrate was concentrated to dryness and purified by flash chromatography (0-75% EtOAc/Heptane over 30 min.; Redi-Sep column, 24 g, 283 nm). It was further purified on Interchim RP-system with 20-95% 0.1% $HCO_2H$ in water/ACN. Fractions containing product were concentrated to remove volatiles and lyophlized to dryness to give (3,5-dichloro-4-((1,4-dimethyl-6-(trifluoromethyl)-1H-pyrrolo[2,3-b]pyridin-2-yl)methyl)pyridin-2-yl)(morpholino)methanone (103 mg, 0.207 mmol, 84% yield) as an off-white powder. LC/MS (Method i) $R_t$=2.56 min.; MS m/z: 487 (M+H)$^+$.

Example GI: 2-(1-(2,4-dichloro-3-(1-methyl-6-(trifluoromethoxy)-1H-indole-2-carbonyl)benzoyl)piperidin-4-yl)acetic acid

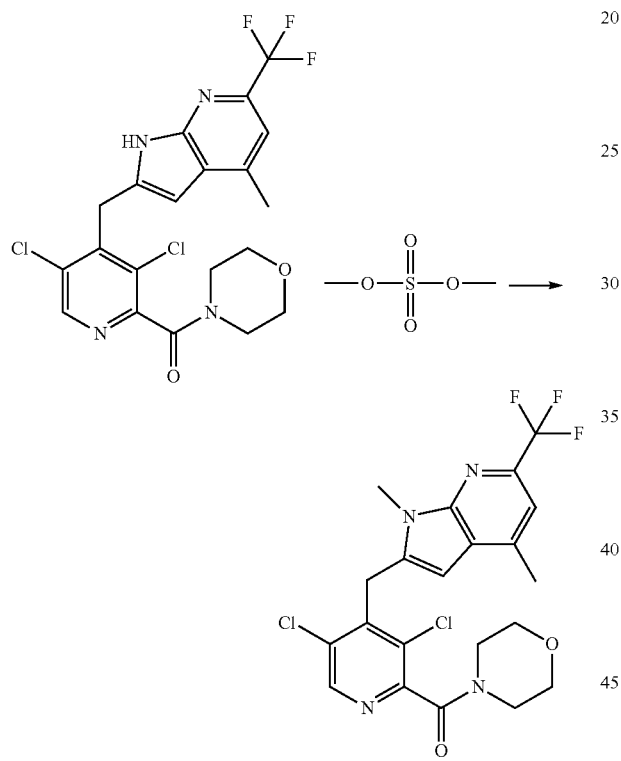

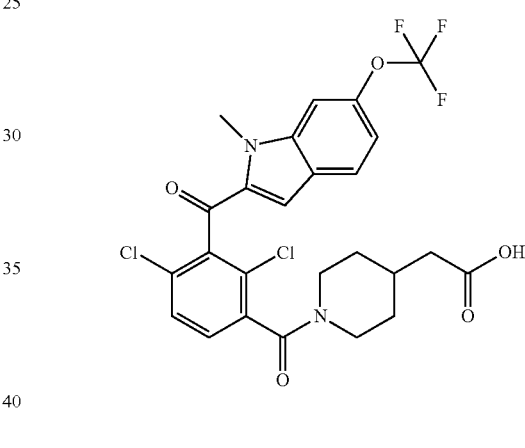

Step 1: tert-butyl 2,4-dichloro-3-(hydroxy(1-methyl-6-(trifluoromethoxy)-1H-indol-2-yl)methyl)benzoate

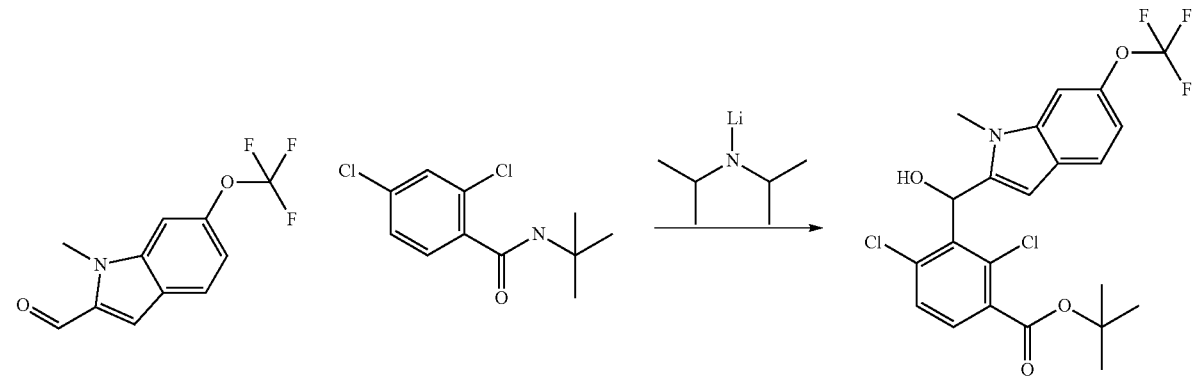

In a reaction vial, 2.0 M lithium diisopropylamide in THF/heptane/ethylbenzene (5.18 mL, 10.36 mmol) in THF (THF) (20 mL) was added to give a colorless solution. The solution was cooled to about −65° C. in a dry ice/acetone bath. A solution of tert-butyl 2,4-dichlorobenzoate (2.56 g, 10.36 mmol) (Preparation #33, Step A) in THF (THF) (15 mL) was added and the mixture was stirred for 2 hours. The solution turned dark on addition. In a separate reaction vial, 1-methyl-6-(trifluoromethoxy)-1H-indole-2-carbaldehyde (2.10 g, 8.64 mmol) (preparation #52, step N) in THF (THF) (20 mL) was added to give a yellow solution and the mixture was cooled to about −78° C. The anion solution was added dropwise via a syringe, keeping the temperature <−65° C. Stirred at about −65° C. for 5 minutes. LC/MS shows about 30% conversion. Made additional anion (1.2 eq) and added. After 5 minutes, almost all starting material was consumed. Added 1.0 M citric acid (100 mL) and extracted with MTBE (100 mL). Washed with brine (50 mL) and dried over magnesium sulfate. The crude product was triturated with heptane (50 mL). The solids were removed by filtration and the heptane layer was allowed to stand. Filtered off additional precipitate which had formed over the weekend. The heptane solvent was removed in vacuo to give 5.27 g of a crude oil. The crude material was chromatographed on the Intelliflash 280 system using a 120 g Redi-Sep silica gel column using the following gradient: A: Heptane; B: EtOAc; 0% B to 60% B over 30 min Gave tert-butyl 2,4-dichloro-3-(hydroxy(1-methyl-6-(trifluoromethoxy)-1H-indol-2-yl)methyl)benzoate (2.072 g, 49% yield). LC/MS (Method i) LC/MS (Method i) Rt=2.17 min.; MS m/z: 490.0 (M+H)+.

Step 2: tert-butyl 2,4-dichloro-3-(1-methyl-6-(trifluoromethoxy)-1H-indole-2-carbonyl)benzoate

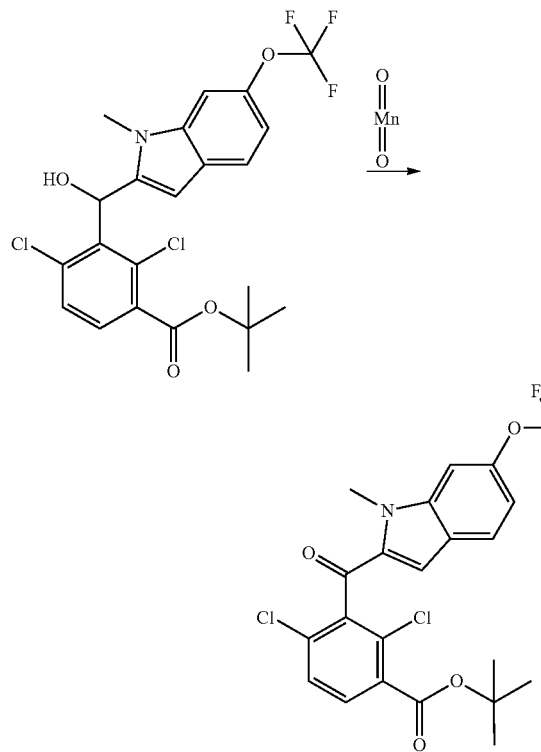

In a round-bottomed flask, tert-butyl 2,4-dichloro-3-(hydroxy(1-methyl-6-(trifluoromethoxy)-1H-indol-2-yl)methyl)benzoate (1.03 g, 2.101 mmol) in DCM (10 mL) and THF (10.00 mL) was added to give a yellow solution. Manganese dioxide (1.826 g, 21.01 mmol) was added and the mixture was stirred at ambient temperature. The mixture was left to react over the weekend. The inorganic layer was filtered off and additional manganese dioxide (1.826 g, 21.01 mmol) was added. After 6 hours, all starting material was consumed. The solution was filtered through a pad of Celite®, washed with DCM. Solvent was removed in vacuo to give 1.020 g of crude product which was used directly in the next step without further purification. LC/MS (Method i) Rt=2.33 min.; MS m/z: 488.18 (M+H)+.

Step 3: 2,4-dichloro-3-(1-methyl-6-(trifluoromethoxy)-1H-indole-2-carbonyl)benzoic acid

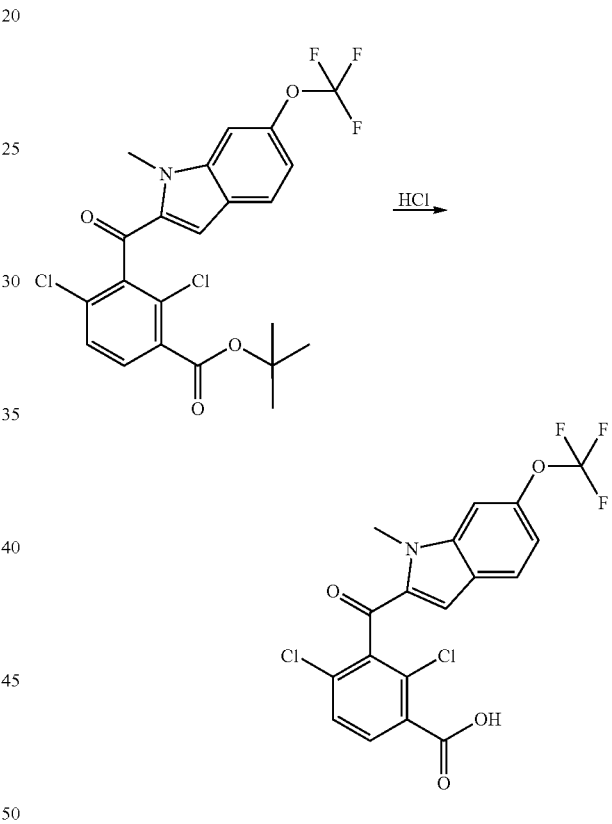

In a round-bottomed flask, tert-butyl 2,4-dichloro-3-(1-methyl-6-(trifluoromethoxy)-1H-indole-2-carbonyl)benzoate (1.020 g, 2.089 mmol) in dioxane (20 mL) was added to give a colorless solution. 5 N hydrochloric acid (2.089 mL, 10.44 mmol) was added and the mixture was heated at 85° C. overnight. All starting material was shown to be converted to product by LC/MS. The solution was cooled to ambient temperature. MBTE (40 mL) and water (20 mL) were added. The layers were separated and the organic layer washed with water (2×10 mL), dried over magnesium sulfate and the solvent removed in vacuo to give 2,4-dichloro-3-(1-methyl-6-(trifluoromethoxy)-1H-indole-2-carbonyl)benzoic acid (0.908 g, 95% yield) as a solid which was used in the next step without further purification. LC/MS (Method i) LC/MS (Method i) Rt=1.32 min.; MS m/z: 432.12 (M+H)+; MS m/z: 430.22 (M−H)−.

805

Step 4: methyl 2-(1-(2,4-dichloro-3-(1-methyl-6-(trifluoromethoxy)-1H-indole-2-carbonyl)benzoyl)piperidin-4-yl)acetate

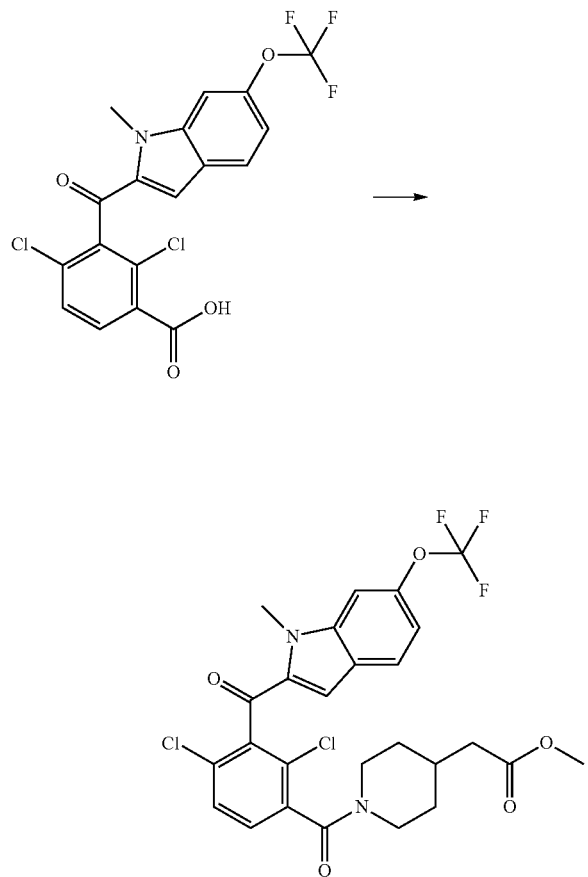 [SMILES: Cn1c(C(=O)c2c(Cl)ccc(C(=O)O)c2Cl)cc2ccc(OC(F)(F)F)cc21 ; COC(=O)CC1CCN(C(=O)c2ccc(Cl)c(C(=O)c3cc4ccc(OC(F)(F)F)cc4n3C)c2Cl)CC1]

In a round-bottomed flask, 2,4-dichloro-3-(1-methyl-6-(trifluoromethoxy)-1H-indole-2-carbonyl)benzoic acid (1.411 g, 3.26 mmol) in EtOAc (15 mL) was added to give a yellow solution. Methyl 2-(piperidin-4-yl)acetate and hydrochloric acid (0.696 g, 3.59 mmol) and N,N-dimethylformamide (3 mL) were added. The solution was stirred for 15 minutes. HATU (1.366 g, 3.59 mmol) was added followed by the dropwise addition of triethylamine (1.593 mL, 11.43 mmol), keeping the temperature <25° C. After 1 hour, MBTE (40 mL) and water (15 mL) were added. The layers were separated and the organic layer was washed with 1 N HCl (3×15 mL), saturated aqueous sodium bicarbonate (2×15 mL), saturated aqueous ammonium chloride (15 mL) and brine (15 mL) then dried over magnesium sulfate and solvent removed in vacuo to give 1.72 g of crude material. The crude material was chromatographed on the Intelliflash 280 system using a 120 g Silicycle SiliaSep Silica gel column using the following gradient: A: Heptane; B: EtOAc; 10% B to 100% B over 30 min Solvent was removed in vacuo from fractions 3-8 to give methyl 2-(1-(2,4-dichloro-3-(1-methyl-6-(trifluoromethoxy)-1H-indole-2-carbonyl)benzoyl)piperidin-4-yl)acetate (1.724 g, 91% yield). LC/MS (Method i) $R_t$=1.99 min.; MS m/z: 571.17 (M+H)+.

806

Step 5: 2-(1-(2,4-dichloro-3-(1-methyl-6-(trifluoromethoxy)-1H-indole-2-carbonyl)benzoyl)piperidin-4-yl)acetic acid

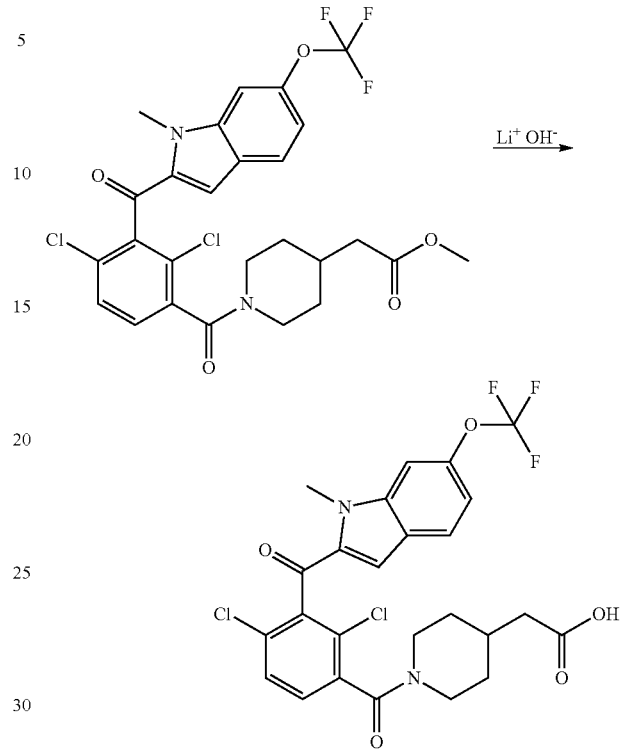

In a round-bottomed flask, methyl 2-(1-(2,4-dichloro-3-(1-methyl-6-(trifluoromethoxy)-1H-indole-2-carbonyl)benzoyl)piperidin-4-yl)acetate (1.59 g, 2.78 mmol) in THF (THF) (30 mL) and Water (10.0 mL) was added to give a colorless solution. Lithium hydroixide (0.133 g, 5.57 mmol) was added and the mixture was stirred at ambient temperature overnight. Concentrated reaction mixture and added water (10 mL). Acidified to pH 3 with 1 N HCl. Gave a clumped up precipitate. Filtered, washing with water. Dissolved the residue in DCM. Separated out the water and dried over magnesium sulfate. Removed solvent in vacuo, drying at 60° C. Lyopholyzed over the weekend (from water/ACN). Gave 2-(1-(2,4-dichloro-3-(1-methyl-6-(trifluoro methoxy)-1H-indole-2-carbonyl)benzoyl)piperidin-4-yl) acetic acid (0.993 g, 63% yield). LC/MS (Method i) $R_t$=1.69 min.; MS m/z: 557.20, 559.19 (M+H)+; MS m/z: 555.20, 557.22 (M−H)−.

Example GJ: 2-(1-(4,6-dichloro-5-((1-methyl-6-(trifluoromethoxy)-1H-indol-2-yl)methyl)nicotinoyl)piperidin-4-yl)acetic acid

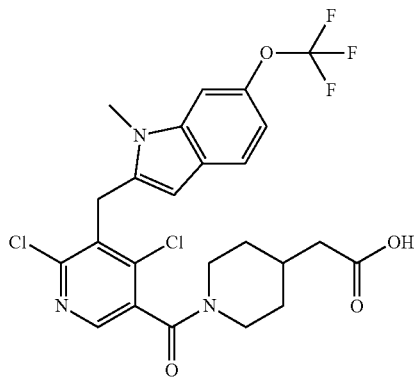 [SMILES: Cn1c(Cc2c(Cl)ncc(C(=O)N3CCC(CC(=O)O)CC3)c2Cl)cc2ccc(OC(F)(F)F)cc21]

807

Step 1: 4,6-dichloro-5-(hydroxy(1-methyl-6-(trifluoromethoxy)-1H-indol-2-yl)methyl)nicotinic acid

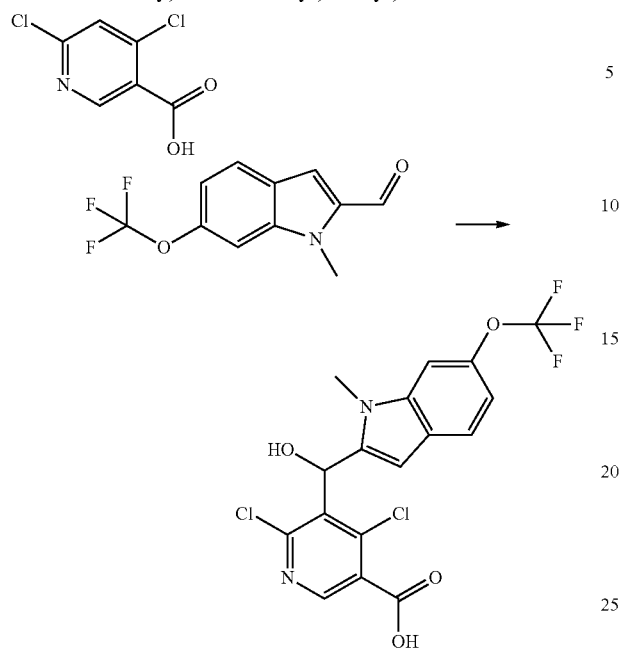

To a solution of diisopropylamine (2.461 mL, 17.27 mmol) in THF (20 mL) at 0° C. was added a 2.5M solution of butyllithium (6.91 mL, 17.27 mmol) in hexanes. After 20 minutes the mixture was cooled to −75° C. and a solution of 4,6-dichloronicotinic acid (1.658 g, 8.64 mmol) in THF (25 mL) was slowly added, temp <65° C. After 30 minutes a solution of 1-methyl-6-(trifluoromethoxy)-1H-indole-2-carbaldehyde (1.05 g, 4.32 mmol) (preparation #52, step n) in THF (5 mL) was added slowly, temperature <70° C. After 30 min 1N HCl (30 mL) was added and the reaction mixture was warmed to room temperature. MTBE/EtOAc (1:1, 50 mL) and water (30 mL) was added. The organic layer was separated, washed with brine (30 mL), dried (Na2SO4) filtered, TEA (10 mL) was added and the mixture was concentrated in vacuo to provide crude 4,6-dichloro-5-(hydroxy(1-methyl-6-(trifluoromethoxy)-1H-indol-2-yl)methyl)nicotinic acid (1.8 g) which was used without further purification.

Step 2: methyl 2-(1-(4,6-dichloro-5-(hydroxy(1-methyl-6-(trifluoromethoxy)-1H-indol-2-yl)methyl)nicotinoyl)piperidin-4-yl)acetate

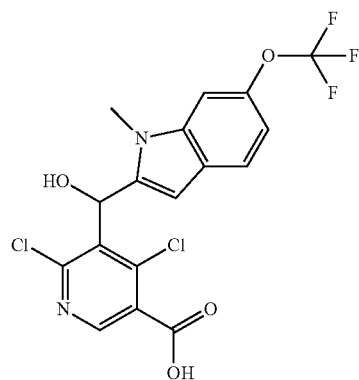

808

-continued

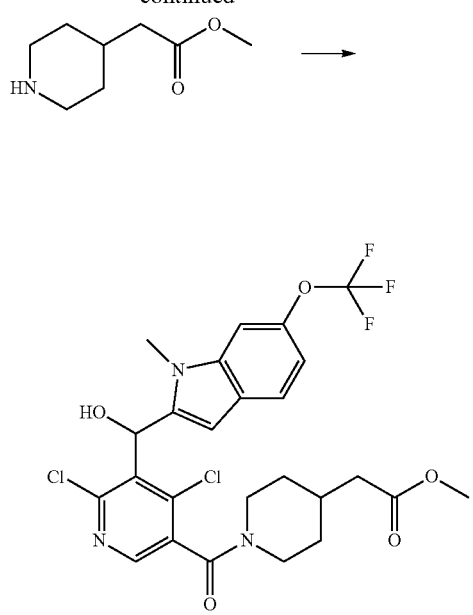

To a solution of 4,6-dichloro-5-(hydroxy(1-methyl-6-(trifluoromethoxy)-1H-indol-2-yl)methyl)nicotinic acid (1.8 g, 4.14 mmol) in EtOAc (EtOAc) (9 mL) and Dimethyl formamide (DMF) (9.00 mL) was added methyl 2-(piperidin-4-yl)acetate, Hydrochloric Acid (1.682 g, 8.69 mmol), 2-(3H-[1,2,3]triazolo[4,5-b]pyridin-3-yl)-1,1,3,3-tetramethylisouronium hexafluorophosphate(V) (3.30 g, 8.69 mmol) and triethylamine (2.88 mL, 20.68 mmol). After 2 h 1N HCl (20 mL) and MTBE (20 mL) were added. The organic layer was separated, washed with NaHCO₃ (20 mL). NH₄Cl (40 mL) was added, organic separated, washed with brine (20 mL) dried (Na₂SO₄) filtered and concd in vacuo. The crude product was purified by FCC on SiO₂ (40 g)(EtOAc/Hep) to provide methyl 2-(1-(4,6-dichloro-5-(hydroxy(1-methyl-6-(trifluoromethoxy)-1H-indol-2-yl)methyl)nicotinoyl)piperidin-4-yl)acetate (1.4 g, 2.437 mmol, 58.9% yield) as a foam. LC/MS (Method i) Rt=1.55 min.; MS m/z: 574 (M+H)+.

Step 3: methyl 2-(1-(4,6-dichloro-5-((1-methyl-6-(trifluoromethoxy)-1H-indol-2-yl)methyl)nicotinoyl)piperidin-4-yl)acetate -continued

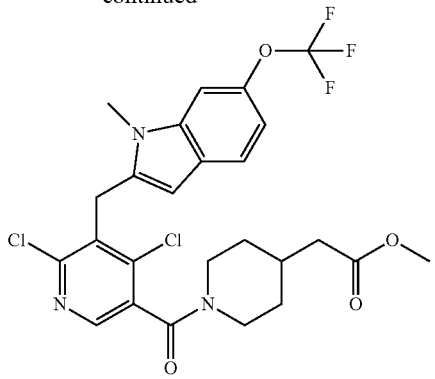

To a solution of methyl 2-(1-(4,6-dichloro-5-(hydroxy(1-methyl-6-(trifluoromethoxy)-1H-indol-2-yl)methyl)nicotinoyl)piperidin-4-yl)acetate (1.4 g, 2.437 mmol) in DCM (DCM) (50 mL) at 0° C. was added triethylsilane (11.68 mL, 73.1 mmol) and 2,2,2-TFA (1.878 mL, 24.37 mmol). After 2 h warm to rt. After 8 h dilute with MTBE (100 mL) and 2N NaOH (50 mL). Organic separated, washed with brine (50 mL), dried (Na$_2$SO$_4$) filtered and concentrated in vacuo. FCC SiO$_2$ (40 g), EtOAc/Hep to provide methyl 2-(1-(4,6-dichloro-5-((1-methyl-6-(trifluoromethoxy)-1H-indol-2-yl)methyl)nicotinoyl)piperidin-4-yl)acetate (800 mg, 1.433 mmol, 58.8% yield) as a foam. LC/MS (Method i) Rt=1.95 min.; MS m/z: 556 (M+H)+.

Step 4: 2-(1-(4,6-dichloro-5-((1-methyl-6-(trifluoromethoxy)-1H-indol-2-yl)methyl)nicotinoyl)piperidin-4-yl)acetic acid

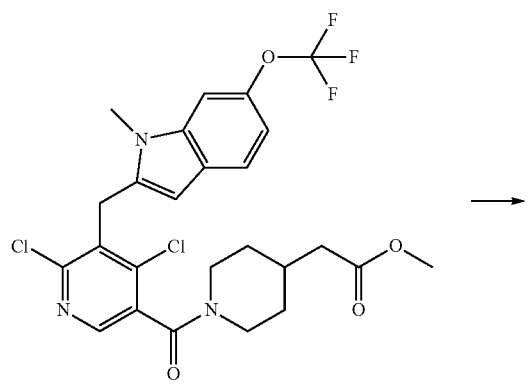

To a solution of methyl 2-(1-(4,6-dichloro-5-((1-methyl-6-(trifluoromethoxy)-1H-indol-2-yl)methyl)nicotinoyl)piperidin-4-yl)acetate (1.2 g, 2.149 mmol) in THF (12 mL) was added a 1N solution of sodium hydroxide (4.30 mL, 4.30 mmol). The reaction mixture was heated to 45° C. and MeOH was added slowly until a homogeneous solution resulted. After 3 hours the reaction mixture was cooled to room temperature and MTBE:EtOAc (1:1, 30 mL) and water (20 mL) were added. The organic layer was separated, washed with brine (20 mL), dried (Na$_2$SO$_4$) filtered and concentrated in vacuo. The residue was concentrated from ACN several times (solids form). The residue was suspended in ACN (3 mL) heated to 60° C., stirred for 2 hours and slowly cooled to room temperature and filtered. The filtrate was partially concentrated under a stream of air and the resulting solids were collected by filtration and combined with the first crop. The solids were dried in vacuo at 50° C. to obtain 2-(1-(4,6-dichloro-5-((1-methyl-6-(trifluoromethoxy)-1H-indol-2-yl)methyl)nicotinoyl)piperidin-4-yl)acetic acid (350 mg, 0.643 mmol, 29.9% yield) as a white solid.

LC/MS (Method i) R$_t$=1.61 min.; MS m/z: 544 (M+H)+.

Example GK: 2-(1-(4,6-dichloro-5-((1-methyl-6-(trifluoromethoxy)-1H-indol-2-yl)methyl)nicotinoyl) piperidin-4-yl)acetic acid

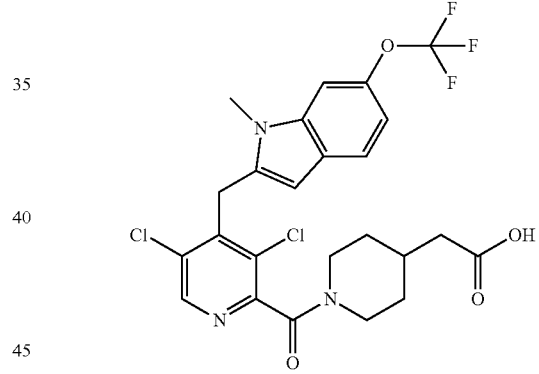

Step 1: methyl 2-(1-(3,5-dichloro-4-((1-methyl-6-(trifluoromethoxy)-1H-indol-2-yl)methyl)picolinoyl) piperidin-4-yl)acetate

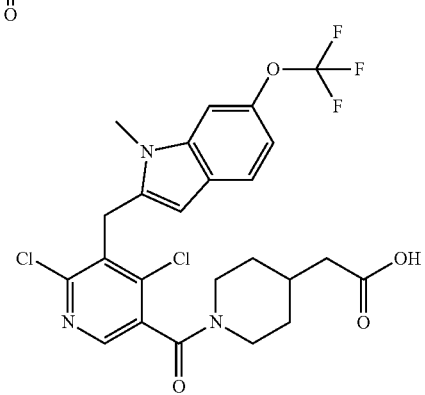

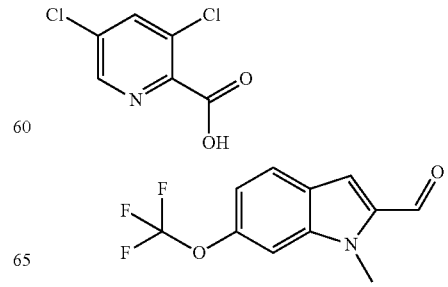

-continued

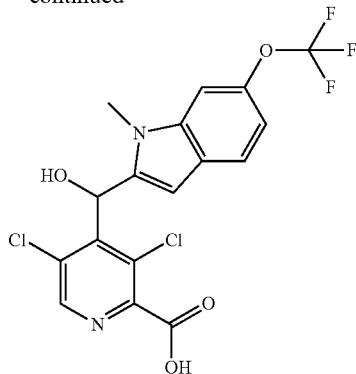

In a 500 mL round-bottomed flask, diisopropylamine (9.12 mL, 64.0 mmol) in THF (53.3 mL) was added to give colorless solution. The solution was cooled to about 0° C. in an ice bath. Butyllithium (2.5 M) (24 mL, 60.0 mmol) and butyllithium (2.0 M in cyclohexane) (2.00 mL, 4.00 mmol) was added dropwise and the solution stirred at 0° C. for about 7 minutes. The solution was cooled to about −78° C. in a dry ice/acetone bath, then stirred at −78° C. for about 15 minutes. A solution of 3,5-dichloropicolinic acid (6.14 g, 32.0 mmol) (Ark Pharm) in THF (53.3 mL) was added dropwise via syringe (use extra 10 mL THF to rinse) for about 32 minutes, and the reaction stirred for about 10 minutes. A solution of 1-methyl-6-(trifluoromethoxy)-1H-indole-2-carbaldehyde (3.89 g, 16.00 mmol) (preparation #52, step n) in THF (53.3 mL) was added dropwise via syringe (use extra 10 mL THF to rinse) for about 9 minutes, and the reaction stirred for about 10 minutes. The reaction mixture was poured into stirring saturated NH₄Cl (200 mL) plus ice (200 g), added EtOAc (400 mL), HCl (1N, 20 mL). The two layers were partitioned, the organic layer was washed with saturated. NH₄Cl (2×100 mL), brine (2×100 mL), dried over MgSO₄, filtered and concentrated to give 3,5-dichloro-4-(hydroxy(1-methyl-6-(trifluoromethoxy)-1H-indol-2-yl)methyl)picolinic acid (11 g) as orange oil. The crude product was used as is in next step. LC/MS (Method i) R$_t$=1.03 min.; MS m/z: 436 (M+H)⁺.

Step 2: methyl 2-(1-(3,5-dichloro-4-((1-methyl-6-(trifluoromethoxy)-1H-indol-2-yl)methyl)picolinoyl)piperidin-4-yl)acetate

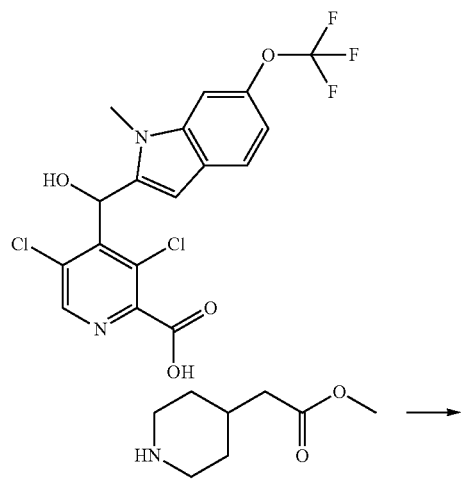

-continued

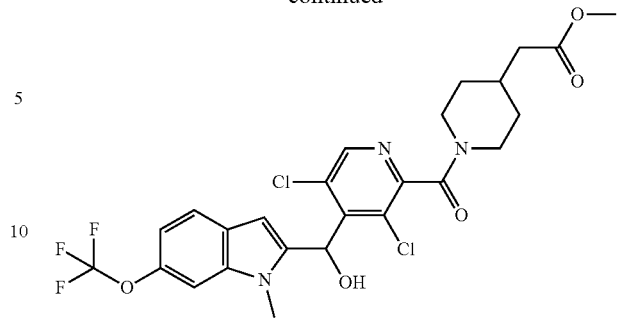

To an orange solution of 3,5-dichloro-4-(hydroxy(1-methyl-6-(trifluoromethoxy)-1H-indol-2-yl)methyl)picolinic acid (6.96 g, 16 mmol) in dimethyl formamide (DMF) (45.0 mL) was added methyl 2-(piperidin-4-yl)acetate, hydrochloric acid (6.51 g, 33.6 mmol), the solution was stirred for about 10 minutes then cooled by ice-bath. 2-(3H-[1,2,3]triazolo[4,5-b]pyridin-3-yl)-1,1,3,3-tetramethylisouronium hexafluorophosphate(V) (12.78 g, 33.6 mmol) was added and the solution stirred for about 10 minutes. Then triethylamine (11.15 mL, 80 mmol) was added slowly. Removed ice bath. The solution was stirred at room temperature for 90 minutes. Added EtOAc (400 mL) and saturated NaHCO₃ (250 mL). The organic layer was washed with saturated NaHCO₃ (2×150 mL) and brine (125 mL) dried (over Na₂SO₄ and MgSO₄) filtered and concentrated in vacuo to give 12.7 g crude. FCC SiO2 (220 g) EtOAc/Hep (45-85%) to provide methyl 2-(1-(3,5-dichloro-4-(hydroxy(1-methyl-6-(trifluoromethoxy)-1H-indol-2-yl)methyl)picolinoyl)piperidin-4-yl)acetate (4.748 g, 8.27 mmol, 49.1% yield). LC/MS (Method i) R$_t$=1.71 min.; MS m/z: 575 (M+H)⁺.

Step 3: methyl 2-(1-(3,5-dichloro-4-((1-methyl-6-(trifluoromethoxy)-1H-indol-2-yl)methyl)picolinoyl)piperidin-4-yl)acetate

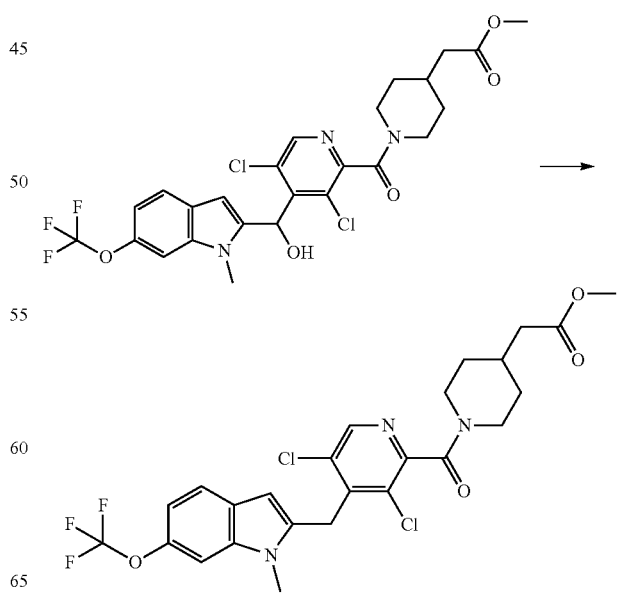

813

In a 2 L round-bottomed flask, methyl 2-(1-(3,5-dichloro-4-(hydroxy(1-methyl-6-(trifluoromethoxy)-1H-indol-2-yl)methyl)picolinoyl)piperidin-4-yl)acetate (4.74 g, 8.25 mmol) in DCM (450 mL) was added to give pale yellow solution. The solution was cooled to about 0° C. in an ice bath. Triethylsilane (52.7 mL, 330 mmol) was added. 2,2,2-TFA (6.36 mL, 83 mmol) was added dropwise. After 1 hour removed ice bath and stirred at room temperature. After 15 hours added triethylsilane (25 mL, 157 mmol), stirred at room temperature overnight. The reaction mixture was concentrated and purified via Isco (35-90% EtOAc/Heptane) on silica gel to provide methyl 2-(1-(3,5-dichloro-4-((1-methyl-6-(trifluoromethoxy)-1H-indol-2-yl)methyl)picolinoyl)piperidin-4-yl)acetate (1.25 g, 2.194 mmol, 26.6% yield). LC/MS (Method i) $R_t$=1.89 min.; MS m/z: 559 (M+H)$^+$.

Step 4: 2-(1-(3,5-dichloro-4-((1-methyl-6-(trifluoromethoxy)-1H-indol-2-yl)methyl)picolinoyl)piperidin-4-yl)acetic acid

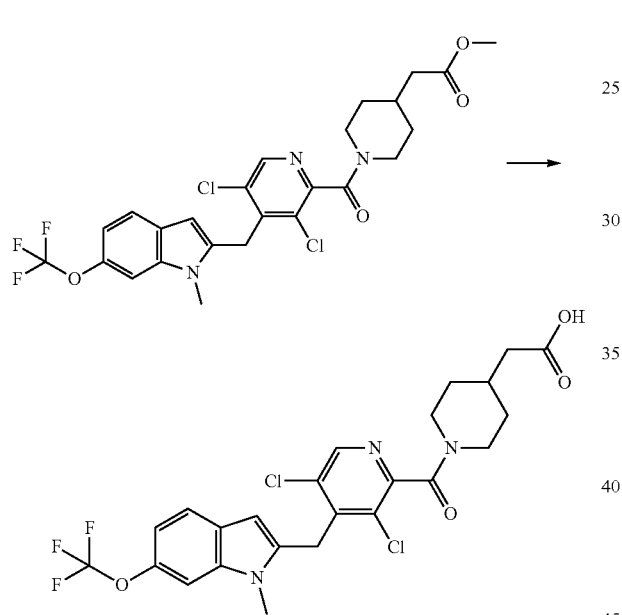

In a 40 mL reaction vial, methyl 2-(1-(3,5-dichloro-4-((1-methyl-6-(trifluoromethoxy)-1H-indol-2-yl)methyl)picolinoyl)piperidin-4-yl)acetate (1.25 g, 2.239 mmol) in MeOH (4.33 mL) and water (2.163 mL) was added to give white suspension. Sodium hydroxide (2N) (2.239 mL, 4.48 mmol) was added, THF (2.2 mL) was added, heated up to 70° C. for 30 minutes, it became clear red solution. The solution was cooled to about 0° C. in an ice bath. Hydrogen chloride (0.895 mL, 4.48 mmol) was added dropwise until pH=1, a white gummy suspension formed, filtered and washed by water (5×10 mL) and pentane (5×10 mL) to give a pale yellow solid. The solid was added 12 mL MeOH (10 mL/g), heated up to 100° C. in capped 40 mL vial for 10 minutes, still pale yellow suspension. The solution was cooled to room temperature slowly, filtered, washed by MeOH (3×2 mL), dried on funnel for 2 hours to give 970 mg pale yellow solid, The solid was dried in vacuum oven over night to give 2-(1-(3,5-dichloro-4-((1-methyl-6-(trifluoromethoxy)-1H-indol-2-yl)methyl)picolinoyl)piperidin-4-yl)acetic acid (0.97 g, 1.764 mmol, 79% yield). LC/MS (Method i) $R_t$=1.62 min.; MS m/z: 545 (M+H)$^+$.

814

Example GL: 2-[1-[2,4-dichloro-3-[[1-methyl-7-(trifluoromethyl)-1H-indol-3-yl]methyl]benzoyl]-4-piperidyl]acetic acid

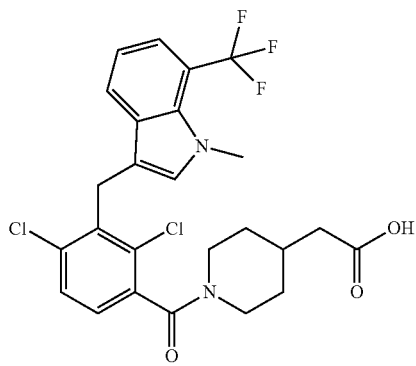 [SMILES: Cn1cc(Cc2c(Cl)ccc(C(=O)N3CCC(CC(=O)O)CC3)c2Cl)c2cccc(C(F)(F)F)c21]

Step 1: tert-butyl 2,4-dichloro-3-[[7-(trifluoromethyl)-1H-indol-3-yl]methyl]benzoate

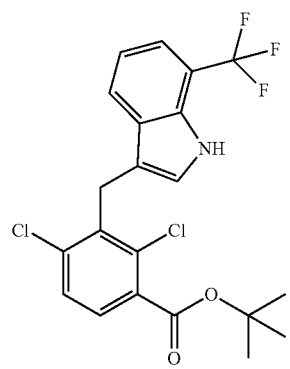 [SMILES: CC(C)(C)OC(=O)c1ccc(Cl)c(Cc2c[nH]c3c(C(F)(F)F)cccc23)c1Cl]

Using a procedure similar to Example DU Step 1, tert-butyl 2,4-dichloro-3-[[7-(trifluoromethyl)-1H-indol-3-yl]methyl]benzoate (190 mg, 71%) was obtained from 7-(trifluoromethyl)-1H-indole (100 mg, 0.540 mmol) and tert-butyl 2,4-dichloro-3-formylbenzoate (182 mg, 0.594 mmol) (Preparation #33, Step B). LC/MS (Method i): $R_t$=2.92 min.; MS m/z: 444 [M+H]$^+$; $^1$H NMR ((DMSO-d$_6$, 300 MHz): δ=δ 11.28 (s, 1H); 7.96 (d, J=8.1 Hz, 1H); 7.60 (m, 2H); 7.46 (d, J=8.1 Hz, 1H); 7.20 (m, 1H); 6.80 (s, 1H); 4.40 (s, 2H); 1.53 (s, 9H)

Step 2: tert-butyl 2,4-dichloro-3-[[1-methyl-7-(trifluoromethyl)-1H-indol-3-yl]methyl]benzoate

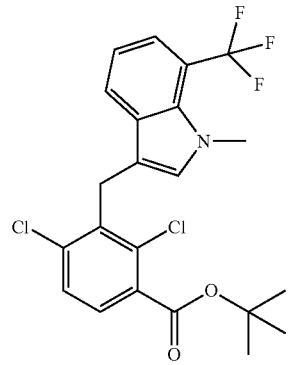 [SMILES: Cn1cc(Cc2c(Cl)ccc(C(=O)OC(C)(C)C)c2Cl)c2cccc(C(F)(F)F)c21]

Using a procedure similar to Example A, Step 4, tert-butyl 2,4-dichloro-3-[[1-methyl-7-(trifluoromethyl)-1H-indol-3-yl]methyl]benzoate (180 mg, 92%) was obtained from tert-butyl 2,4-dichloro-3-[[7-(trifluoromethyl)-1H-indol-3-yl]methyl]benzoate (180 mg, 0.405 mmol) and methyl iodide (27.9 µL, 0.446 mmol). LC/MS (Method i): R$_t$=2.79 min.; MS m/z: 458 [M+H]$^+$; $^1$H NMR ((DMSO-d$_6$, 300 MHz): δ 8.05 (d, J=8.1 Hz, 1H); 7.60 (s, 2H); 7.59 (d, J=8.1 Hz, 1H); 7.25 (m, 1H); 6.89 (s, 1H); 4.38 (s, 2H); 3.78 (s, 3H); 1.54 (s, 9H).

Step 3: 2,4-dichloro-3-[[1-methyl-7-(trifluoromethyl)-1H-indol-3-yl]methyl]benzoic acid

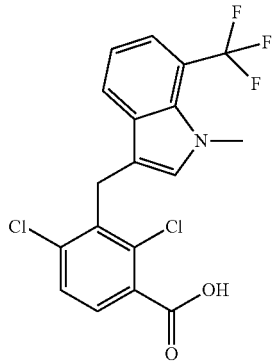 [SMILES: Cn1cc(Cc2c(Cl)ccc(C(=O)O)c2Cl)c2cccc(C(F)(F)F)c21]

Using a procedure similar to Example DJ, Step 2, 2,4-dichloro-3-[[1-methyl-7-(trifluoromethyl)-1H-indol-3-yl]methyl]benzoic acid was obtained (150 mg, 84%) from tert-butyl 2,4-dichloro-3-[[1-methyl-7-(trifluoromethyl)-1H-indol-3-yl]methyl]benzoate (170 mg, 0.371 mmol). LC/MS (Method j): Rt=1.85 min.; MS m/z: 402 [M+H]$^+$; $^1$H NMR ((DMSO-d$_6$, 300 MHz): δ 13.5 (m broad, 1H); 8.04 (d, J=8.4 Hz, 1H); 7.60 (m, 3H); 7.32 (m, 1H); 6.87 (s, 1H); 4.39 (s, 2H); 3.78 (s, 3H).

Step 4: methyl 2-[1-[2,4-dichloro-3-[[1-methyl-7-(trifluoromethyl)-1H-indol-3-yl]methyl]benzoyl]-4-piperidyl]acetate

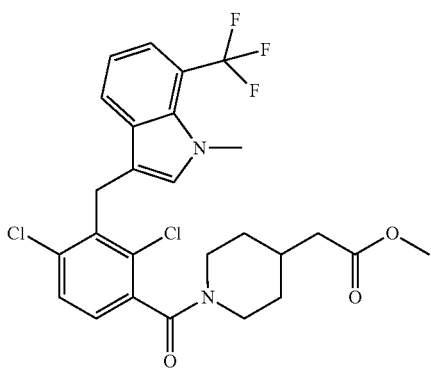 [SMILES: COC(=O)CC1CCN(C(=O)c2ccc(Cl)c(Cc3cn(C)c4c(C(F)(F)F)cccc34)c2Cl)CC1]

Using a procedure similar to Example A, Step 6, methyl 2-[1-[2,4-dichloro-3-[[1-methyl-7-(trifluoromethyl)-1H-indol-3-yl]methyl]benzoyl]-4-piperidyl]acetate (138 mg, 71%) was obtained from 2,4-dichloro-3-[[1-methyl-7-(trifluoromethyl)-1H-indol-3-yl]methyl]benzoic acid (140 mg, 0.348 mmol) and methyl 2-(4-piperidyl)acetate hydrochloride (81 mg, 0.418 mmol). LC/MS (Method j): R$_t$=2.15 min.; MS m/z: 541 [M+H]$^+$; $^1$H NMR ((DMSO-d$_6$, 300 MHz): δ 8.04 (m, 1H); 7.59 (m, 2H); 7.30 and 7.25 (d, J=8.4 Hz, 1H); 7.20 (m, 1H); 6.87 (m, 1H); 4.48 (m, 1H); 4.35 (m, 2H); 3.79 (s, 3H); 3.57 and 3.59 (s, 3H); 3.35 (m, 1H); 3.02 (m, 1H); 2.80 (m, 1H); 2.27 (m, 2H); 1.99 (m, 1H); 1.75 (m, 1H); 1.62 (m, 1H); 1.15 (m, 2H).

Step 5: 2-[1-[2,4-dichloro-3-[[1-methyl-7-(trifluoromethyl)-1H-indol-3-yl]methyl]benzoyl]-4-piperidyl]acetic acid

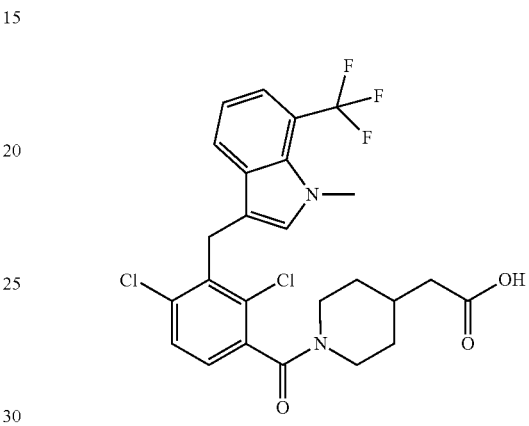

Using a procedure similar to Example A, Step 5, 2-[1-[2,4-dichloro-3-[[1-methyl-7-(trifluoromethyl)-1H-indol-3-yl]methyl]benzoyl]-4-piperidyl]acetic acid (115 mg, 84%) was obtained from methyl 2-[1-[2,4-dichloro-3-[[1-methyl-7-(trifluoromethyl)-1H-indol-3-yl]methyl]benzoyl]-4-piperidyl]acetate (135 mg, 0.249 mmol). LC/MS (Method g): R$_t$=1.90 min.; MS m/z: 527 [M+H]$^+$; $^1$H NMR ((DMSO-d$_6$, 300 MHz): δ 12.11 (m broad, 1H); 8.02 (m, 1H); 7.63 (m, 2H); 7.38 and 7.32 (d, J=8.4 Hz, 1H); 7.22 (m, 1H); 6.88 (m, 1H); 4.50 (m, 1H); 4.38 (m, 2H); 3.78 (s, 3H); 3.27 (m, 1H); 3.00 (m, 1H); 2.80 (m, 1H); 2.16 (m, 2H); 1.95 (m, 1H); 1.76 (m, 1H); 1.60 (m, 1H); 1.13 (m, 2H).

Example GN: 2-[1-[4,6-dichloro-5-[(6-cyclopropyl-4-fluoro-1-methyl-1H-indol-2-yl)methyl]pyridine-3-carbonyl]-4-piperidyl]acetic acid

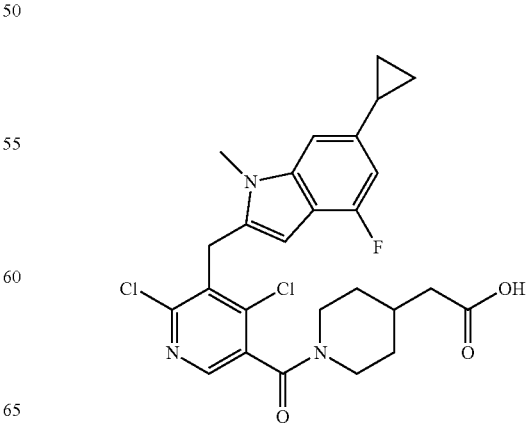

817

Step 1: tert-butyl 5-[[1-(benzenesulfonyl)-6-cyclopropyl-4-fluoro-1H-indol-2-yl]-hydroxy-methyl]-4,6-dichloro-pyridine-3-carboxylate

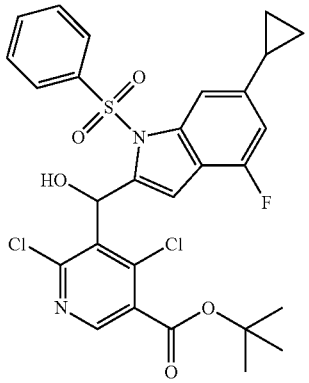 [SMILES: CC(C)(C)OC(=O)c1cnc(Cl)c(C(O)c2cc3c(F)cc(C4CC4)cc3n2S(=O)(=O)c2ccccc2)c1Cl]

Using a procedure similar to Example CJ, Step 1, tert-butyl 5-[[1-(benzenesulfonyl)-6-cyclopropyl-4-fluoro-1H-indol-2-yl]-hydroxy-methyl]-4,6-dichloro-pyridine-3-carboxylate (105 mg, 18%) was prepared from 6-cyclopropyl-4-fluoro-1-(phenylsulfonyl)-1H-indole (170 mg, 0.539 mmol) (Preparation 77) and tert-butyl 4,6-dichloro-5-formyl-pyridine-3-carboxylate (223 mg, 0.809 mmol) (Example DO, Step 12). LC/MS (Method j): $R_t$=2.31 min.; MS m/z: 591 [M+H]$^+$; $^1$H NMR ((DMSO-d$_6$, 300 MHz): δ=8.63 (s, 1H); 7.84 (d, J=7.79 Hz, 2H); 7.66 (m, 1H); 7.59 (m, 2H); 6.89 (m, 1H); 6.78 (m, 2H); 2.10 (m, 1H): 1.6 (s, 9H); 1.52 (m, 1H); 1.39 (s, 1H); 1.00 (m, 2H); 0.71 (m, 2H).

Step 2: 5-[[1-(benzenesulfonyl)-6-cyclopropyl-4-fluoro-1H-indol-2-yl]methyl]-4,6-dichloro-pyridine-3-carboxylic acid

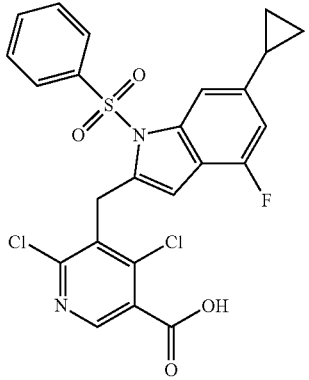 [SMILES: O=C(O)c1cnc(Cl)c(Cc2cc3c(F)cc(C4CC4)cc3n2S(=O)(=O)c2ccccc2)c1Cl]

Using a procedure similar to Example A, Step 2, 5-[[1-(benzenesulfonyl)-6-cyclopropyl-4-fluoro-1H-indol-2-yl]methyl]-4,6-dichloro-pyridine-3-carboxylic acid (176 mg, 100%) was prepared from tert-butyl 5-[[1-(benzenesulfonyl)-6-cyclopropyl-4-fluoro-1H-indol-2-yl]-hydroxy-methyl]-4,6-dichloro-pyridine-3-carboxylate (200 mg, 0.338 mmol). LC/MS (Method j): $R_t$=1.73 min.; MS m/z: 519 [M+H]$^+$

818

Step 3: 4,6-dichloro-5-[(6-cyclopropyl-4-fluoro-1H-indol-2-yl)methyl]pyridine-3-carboxylic acid

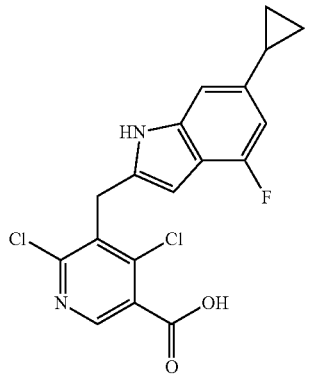 [SMILES: O=C(O)c1cnc(Cl)c(Cc2cc3c(F)cc(C4CC4)cc3[nH]2)c1Cl]

Using a procedure similar to Example A, Step 3, 4,6-dichloro-5-[(6-cyclopropyl-4-fluoro-1H-indol-2-yl)methyl]pyridine-3-carboxylic acid (165 mg, 81%) was prepared from 5-[[1-(benzenesulfonyl)-6-cyclopropyl-4-fluoro-1H-indol-2-yl]methyl]-4,6-dichloro-pyridine-3-carboxylic acid (270 mg, 0.390 mmol). LC/MS (Method i): $R_t$=2.04 min.; no ionization.

Step 4: methyl 4,6-dichloro-5-[(6-cyclopropyl-4-fluoro-1-methyl-1H-indol-2-yl)methyl]pyridine-3-carboxylate

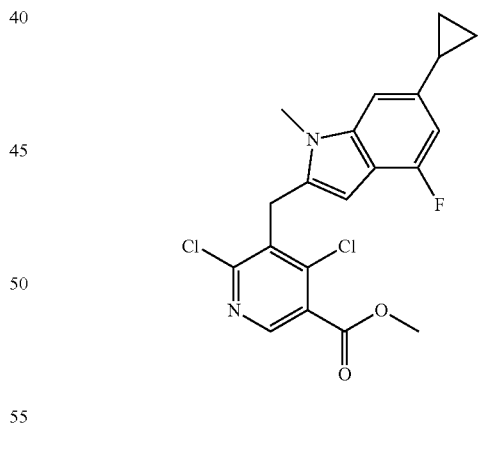

Using a procedure similar to Example P, Step 4, methyl 4,6-dichloro-5-[(6-cyclopropyl-4-fluoro-1-methyl-1H-indol-2-yl)methyl]pyridine-3-carboxylate (172 mg, 100%) was prepared from 4,6-dichloro-5-[(6-cyclopropyl-4-fluoro-1H-indol-2-yl)methyl]pyridine-3-carboxylic acid (160 mg, 0.422 mmol).

LC/MS (Method i): $R_t$=2.60 min.; MS m/z: 407 [M+H]$^+$.

Step 5: 4,6-dichloro-5-[(6-cyclopropyl-4-fluoro-1-methyl-1H-indol-2-yl)methyl]pyridine-3-carboxylic acid

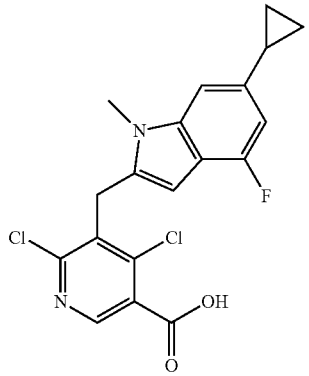 [SMILES: Cn1c(Cc2c(Cl)ncc(C(=O)O)c2Cl)cc2c(F)cc(C3CC3)cc21]

Using a procedure similar to Example A, Step 5, 4,6-dichloro-5-[(6-cyclopropyl-4-fluoro-1-methyl-1H-indol-2-yl)methyl]pyridine-3-carboxylic acid (125 mg, 46%) was prepared from methyl 4,6-dichloro-5-[(6-cyclopropyl-4-fluoro-1-methyl-1H-indol-2-yl)methyl]pyridine-3-carboxylate (200 mg, 0.491 mmol). LC/MS (Method i): $R_t$=2.17 min.; no ionization.

Step 6: methyl 2-[1-[4,6-dichloro-5-[(6-cyclopropyl-4-fluoro-1-methyl-1H-indol-2-yl)methyl]pyridine-3-carbonyl]-4-piperidyl]acetate

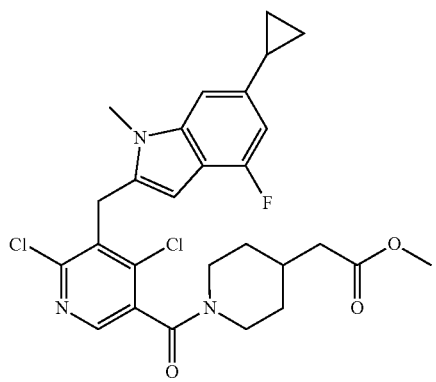 [SMILES: COC(=O)CC1CCN(C(=O)c2cnc(Cl)c(Cc3cc4c(F)cc(C5CC5)cc4n3C)c2Cl)CC1]

Using a procedure similar to Example A, Step 6, methyl 2-[1-[4,6-dichloro-5-[(6-cyclopropyl-4-fluoro-1-methyl-1H-indol-2-yl)methyl]pyridine-3-carbonyl]-4-piperidyl]acetate (80 mg, 38%) was prepared from 4,6-dichloro-5-[(6-cyclopropyl-4-fluoro-1-methyl-1H-indol-2-yl)methyl]pyridine-3-carboxylic acid (120 mg, 0.305 mmol) and methyl (4-piperidyl)acetate hydrochloride (76 mg, 0.397 mmol).

LC/MS (Method i): $R_t$=2.49 min.; MS m/z: 532 [M+H]$^+$; $^1$H NMR ((DMSO-d$_6$, 300 MHz): b=8.44 and 8.40 (s, 1H); 7.05 (s, 1H); 6.50 (d, J=11.7 Hz, 1H); 5.59 (d, J=17 Hz, 1H); 4.48 (m, 2H); 3.81 (s, 3H); 3.59 (s, 3H); 3.39 (m, 1H); 3.08 (m, 1H); 2.83 (m, 1H); 2.27 (m, 1H); 2.03 (m, 3H); 1.75 (m, 1H); 1.40 (m, 1H); 1.15 (m, 2H); 0.93 (m, 2H); 0.70 (m, 2H).

Step 7: 2-[1-[4,6-dichloro-5-[(6-cyclopropyl-4-fluoro-1-methyl-1H-indol-2-yl)methyl]pyridine-3-carbonyl]-4-piperidyl]acetic acid

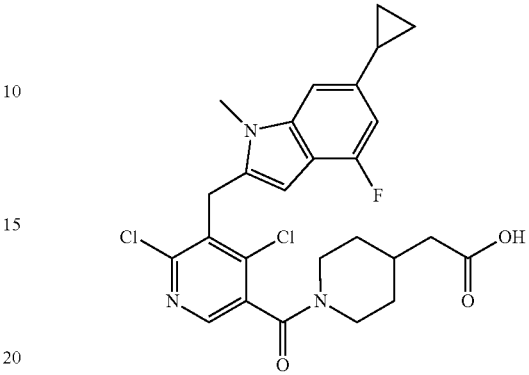

Using a procedure similar to Example A, Step 5, 2-[1-[4,6-dichloro-5-[(6-cyclopropyl-4-fluoro-1-methyl-1H-indol-2-yl)methyl]pyridine-3-carbonyl]-4-piperidyl]acetic acid (65 mg, 83%) was prepared from methyl 2-[1-[4,6-dichloro-5-[(6-cyclopropyl-4-fluoro-1-methyl-1H-indol-2-yl)methyl]pyridine-3-carbonyl]-4-piperidyl]acetate (80 mg, 0.15 mmol). LC/MS (Method g): $R_t$=1.72 min.; MS m/z: 518 [M+H]$^+$; $^1$H NMR ((DMSO-d$_6$, 300 MHz): b=12.1 (m broad, 1H); 8.47 and 8.40 (s, 1H); 7.05 (s, 1H); 6.50 (d, J=11.5 Hz, 1H); 5.61 and 5.56 (s, 1H); 6.38 (m, 1H); 4.35 (s, 2H); 3.80 (s, 3H); 3.39 (m, 1H); 3.05 (m, 1H); 2.84 (m, 1H); 2.15 (m, 2H); 1.99 (m, 2H); 1.78 (m, 1H); 1.60 (m, 1H); 1.18 (m, 2H); 0.90 (m, 2H); 0.65 (m, 2H).

Biological Activity

The primary screen was performed by transient transactivation assays. These cell-based assays were carried out using Cos-7 cells transfected with a chimeric human RORγ-Gal4 receptor expression plasmid and a 5Gal4 pGL3 TK Luc reporter plasmid. Transfections were performed by a chemical agent (Jet PEI). Transfected cells were distributed in 384-wells plates and were allowed to recover for 24 h. The culture medium was then removed and fresh medium containing the compounds to be tested was added (final concentration ranging from $10^{-4}$ M to 3 $10^{-10}$ M). After an overnight incubation, luciferase expression was measured by adding SteadyGlo according to the manufacturer's instructions (Promega). T0901317 at $10^{-5}$ M was used as reference. Results were expressed as fold induction compared to basal level or as percentage activity compared to references taken as 100% (basal) or 0% (T0901317). Dose-effect curves and IC$_{50}$ were calculated using the software Assay Explorer (MDL).

IC$_{50}$ for the different examples are reported in the table using the following categories:
A: IC$_{50}$<0.1 μM; B: 0.1 μM<IC$_{50}$<0.5 μM; C: 0.5 μM<IC$_{50}$<1 μM;
D: 1 μM<IC$_{50}$<10 μM; E: IC$_{50}$>10 μM.

| Example | IC$_{50}$ |
| --- | --- |
| A | A |
| A1 | A |
| A1-11 | A |
| AP-6 | A |

| Example | IC$_{50}$ |
|---|---|
| AQ-3 | A |
| AQ-4 | A |
| AQ-5 | A |
| B | A |
| B-1 | A |
| B-2 | A |
| B-3 | B |
| B-4 | B |
| B-5 | B |
| B-6 | A |
| B-7 | A |
| B-8 | A |
| B-9 | A |
| B-10 | D |
| B-11 | B |
| B-12 | D |
| B-13 | B |
| B-14 | B |
| B-15 | D |
| B-16 | B |
| B-17 | A |
| B-18 | A |
| B-19 | A |
| B-20 | A |
| B-21 | A |
| B-22 | A |
| B-23 | A |
| B-24 | A |
| B-25 | A |
| B-26 | A |
| GH | A |
| BH-2 | B |
| C | D |
| CZ-1 | B |
| CZ-1A | B |
| CZ-2 | A |
| CZ-3 | B |
| D | A |
| D-1 | A |
| D-2 | A |
| D-3 | D |
| DD-1 | A |
| DH1-1 | A |
| DH1-2 | A |
| DJ1-1 | A |
| DJ1-2 | A |
| DJ1-3 | A |
| DP-1 | A |
| DP-2 | A |
| DP-3 | A |
| DU | A |
| DU1-1 | A |
| DU1-2 | A |
| DV | A |
| DW | A |
| DX | A |
| DY | A |
| DZ | A |
| E | B |
| EA | A |
| EB | A |
| EC | A |
| ED | A |
| EE | A |
| EF | A |
| EG | A |
| EG-1 | A |
| EG-2 | A |
| EH | A |
| EH-1 | B |
| EI | A |
| EI-1 | A |
| EI-2 | A |
| EI-3 | A |
| EI-4 | A |
| EI-5 | A |
| EI-6 | A |
| EI-7 | A |
| EJ-2 | A |
| EJ-3 | A |
| EK | A |
| EL | A |
| EL-1 | A |
| EM | A |
| EN | A |
| EO | A |
| EP | A |
| EQ | A |
| ER | A |
| ES | A |
| ET | A |
| EU | B |
| EV | A |
| EW | B |
| EX | A |
| EY | A |
| EZ | A |
| F | A |
| F1-1 | A |
| F1-2 | A |
| F1-3 | A |
| FA | A |
| FB | A |
| FC | A |
| FD | A |
| FE | A |
| FE-2 | A |
| FE-3 | A |
| FE-4 | A |
| FF | A |
| FF-1 | A |
| FF-2 | A |
| FG | A |
| FH | A |
| FI | A |
| FI-1 | A |
| FI-2 | A |
| FI-3 | A |
| FJ | A |
| FK | A |
| FL | A |
| FM | A |
| FN | A |
| FO | A |
| FP | A |
| FQ | A |
| FR | A |
| FS | A |
| FT | A |
| FU | A |
| FV | A |
| FW | B |
| FX | B |
| FY | S |
| FZ | A |
| G | A |
| GA | A |
| GB | A |
| GC | A |
| GE | B |
| GF | A |
| GG | A |
| GI | A |
| GK | A |
| GN | A |
| G1 | B |
| H | D |
| I | B |
| J | A |
| K | B |
| K1 | B |
| L | A |
| L-1 | B |
| L-2 | B |

| Example | IC$_{50}$ |
|---|---|
| L-3 | B |
| L-4 | B |
| L-5 | C |
| M | B |
| N | C |
| O | B |
| P | B |
| Q | B |
| R | A |
| S | A |
| T | B |
| U | A |
| V | A |
| W | B |
| X | D |
| Y | D |
| Y1 | B |
| Z | D |
| AA | A |
| AA-1 | A |
| AA-2 | A |
| AA-3 | A |
| AA-4 | A |
| AA-5 | B |
| AA-6 | B |
| AA-7 | A |
| AA-8 | A |
| AA-9 | B |
| AA-10 | B |
| AA-11 | A |
| AA-12 | B |
| AA-13 | B |
| AA-14 | B |
| AA-15 | B |
| AA-16 | B |
| AA-17 | A |
| AA-18 | A |
| AA-19 | B |
| AA-20 | B |
| AA-21 | B |
| AA-22 | B |
| AA-23 | C |
| AA-24 | B |
| AA-25 | B |
| AA-26 | B |
| AA-27 | A |
| AA-28 | A |
| AA-29 | A |
| AA-30 | A |
| AA-31 | A |
| AA-32 | B |
| AA-35 | A |
| AA-36 | A |
| AA-37 | A |
| AA-39 | B |
| AA-40 | B |
| AB | B |
| AC | B |
| AD | B |
| AE | B |
| AF | B |
| AF1 | C |
| AG | B |
| AG1 | C |
| AH | C |
| AH1 | C |
| AI | B |
| AI1 | A |
| AJ | B |
| AJ1 | B |
| AK | B |
| AK1 | B |
| AL | A |
| AL1 | B |
| AM | D |
| AM-1 | C |
| AM-2 | D |
| AM-3 | B |
| AN | A |
| AN-1 | C |
| AN-2 | A |
| AN-3 | A |
| AN-4 | A |
| AN-5 | A |
| AO | A |
| AP | A |
| AP-1 | A |
| AQ | A |
| AQ-1 | A |
| AQ-2 | B |
| AR | D |
| AS | D |
| AT | B |
| AU | B |
| AV | B |
| AW | A |
| AX | A |
| AY | A |
| AZ | A |
| BA | A |
| BB | C |
| BC | B |
| BD | D |
| BE | B |
| BF | B |
| BF-1 | A |
| BF-2 | B |
| BF-3 | C |
| BF-4 | B |
| BF-5 | D |
| BG | C |
| BH | A |
| BI | D |
| BJ | B |
| BJ-1 | D |
| BJ-2 | D |
| BJ-3 | C |
| BJ-4 | D |
| BJ-5 | B |
| BJ-6 | C |
| BJ-7 | D |
| BJ-8 | A |
| BJ-9 | B |
| BJ-10 | A |
| BJ-11 | B |
| BJ-12 | A |
| BJ-13 | B |
| BJ-14 | B |
| BJ-15 | B |
| BJ-16 | B |
| BJ-17 | A |
| BJ-18 | A |
| BJ-19 | B |
| BJ-20 | B |
| BJ-21 | B |
| BJ-22 | B |
| BJ-24 | C |
| BJ-25 | C |
| BJ-26 | D |
| BJ-27 | D |
| BJ-28 | D |
| BJ-29 | D |
| BJ-30 | B |
| BJ-31 | D |
| BJ-32 | C |
| BJ-33 | B |
| BJ-34 | B |
| BJ-35 | B |
| BJ-36 | B |
| BJ-37 | B |
| BJ-38 | B |
| BJ-39 | D |
| BJ-40 | B |
| BJ-41 | B |

| Example | IC$_{50}$ |
|---|---|
| BJ-42 | B |
| BJ-43 | D |
| BJ-44 | C |
| BK | D |
| BL | D |
| BM | D |
| BN | B |
| BN-1 | NT |
| BN-2 | C |
| BN-3 | B |
| BN-4 | C |
| BN-5 | D |
| BN-6 | B |
| BN-7 | B |
| BN-8 | B |
| BN-9 | D |
| BN-10 | D |
| BN-11 | C |
| BN-12 | B |
| BN-13 | C |
| BN-14 | D |
| BN-15 | D |
| BN-16 | C |
| BN-17 | D |
| BO | C |
| BP | D |
| BR | B |
| BS | B |
| BT | D |
| BU | A |
| BV | NT |
| BW | B |
| BW-1 | B |
| BW-2 | B |
| BW-3 | B |
| BW-4 | B |
| BW-5 | B |
| BW-6 | B |
| BW-7 | B |
| BW-8 | B |
| BW-9 | B |
| BW-10 | B |
| BW-11 | B |
| BW-12 | C |
| BW-13 | B |
| BW-14 | B |
| BW-15 | B |
| BW-16 | D |
| BW-17 | B |
| BW-18 | C |
| BX | C |
| BY | D |
| BZ | B |
| CA | B |
| CB | B |
| CC | D |
| CD | D |
| CE | B |
| CF | C |
| CG | C |
| CH | A |
| CI | D |
| CJ | D |
| CK | D |
| CL | A |
| CL | B |
| CL-1 | A |
| CL-2 | A |
| CM | A |
| CM1 | A |
| CO | D |
| CP | D |
| CQ | D |
| CR | B |
| CS | D |
| CT | B |
| CT-1 | B |
| CT-2 | B |
| CT-3 | A |
| CT-4 | E |
| CT-5 | C |
| CT-6 | A |
| CT-7 | A |
| CT-8 | A |
| CT-9 | B |
| CT-10 | B |
| CT-11 | B |
| CU | B |
| CV | C |
| CV-1 | D |
| CV-2 | C |
| CV-3 | C |
| CV-4 | D |
| CV-5 | B |
| CV-6 | B |
| CW | B |
| CY | D |
| CZ | A |
| DA | D |
| DB | D |
| DC | D |
| DD | B |
| DE | A |
| DF | B |
| DG | A |
| DH | A |
| DI | A |
| DJ | A |
| DK | B |
| DL | A |
| DM | B |
| DN | A |
| DO | A |
| DP | A |
| DQ | A |
| DR | A |
| DS | A |
| DT | A |

Compounds of the invention were also tested in the IL-23 model of Psoriasiform Dermatitis: Female C57BL/6 mice 18-22 g (Charles River Labs) were housed in an AAALAC approved facility under specific pathogen free conditions and provided food and water ad libitum Animals were injected (ear; intradermal) with 1 μg recombinant murine IL-23 on days 0, 1, 2 and 3 under anesthesia (isoflurane). On day 4 animals were humanely euthanized and plasma and ear samples harvested for drug exposures and/or model endpoints. Animals also received vehicle (0.5% hydroxypropyl methylcellulose/0.02% Tween 80 in water) or test compound suspended in vehicle daily via oral gavage, until the study was terminated. Compounds of this invention gave >50% reduction in ear inflammation relative to vehicle control dosed orally at >1 mg/kg.

What is claimed is:
1. A compound of Formula (Ia):

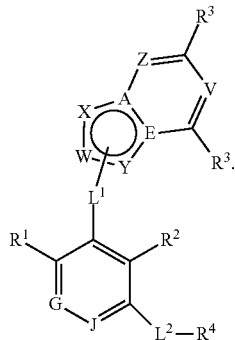

Formula (Ia)

or a pharmaceutically acceptable salt or stereoisomer thereof,
wherein:
G and J are independently CH or N;
W is C or $CR^a$, $L^1$ is connected to W or Y; and
A and E are independently C or N provided both are not N;
V is $CR^3$ or N;
X is $CR^a$, $NR^a$, N, or O;
Y is C, $CR^a$, $NR^a$, N, O or S;
Z is $CR^3$ or N; or
W is N or $NR^a$, $L^1$ is connected to W or Y; and
A and E are independently C or N provided both are not N;
V is $CR^3$ or N;
X is $CR^a$, $NR^a$, or N;
Y is C, $CR^a$, or N;
Z is $CR^3$ or N;
$L^1$ is —CH($R^b$)—, —C($R^b$)($R^d$)—, or —C(O)—;
$L^2$ is —C(O)—;
$R^1$ and $R^2$ are independently halo, —O—($C_1$-$C_3$)alkyl, —O—($C_3$-$C_6$)cycloalkyl, optionally substituted ($C_3$-$C_6$)cycloalkyl, or —($C_1$-$C_3$)alkyl;
each $R^3$ is independently H, $CF_3$, CN, halo, —C(=O)($C_1$-$C_3$)alkyl, —C(O)N($R^e$)$_2$, —$NR^e COR^e$, —$OCHF_2$, $OCF_3$, —O—($C_1$-$C_3$)alkyl, —O—($C_3$-$C_6$)cycloalkyl, —S—($C_1$-$C_3$)alkyl, optionally substituted ($C_1$-$C_6$)alkyl, optionally substituted ($C_3$-$C_6$)cycloalkyl, optionally substituted heteroaryl, or optionally substituted heterocyclyl;
$R^4$ is —$NR^5R^6$, —(CH$_2$)$_m$-optionally substituted heterocyclyl, optionally substituted oxetanyl, or NH—optionally substituted oxetanyl; wherein $R^5$ is H or —($C_1$-$C_3$)alkyl, and $R^6$ is optionally substituted ($C_1$-$C_4$)alkyl, optionally substituted ($C_3$-$C_6$)cycloalkyl or —(CH$_2$)$_m$-optionally substituted heterocyclyl; or $R^5$ and $R^6$, together with the nitrogen atom to which they are attached, form an optionally substituted heterocyclyl;
each $R^a$ is independently H, —C(O)CH$_3$, optionally substituted ($C_1$-$C_6$)alkyl, optionally substituted ($C_3$-$C_6$)cycloalkyl, or —S(O)$_2$-phenyl;
each $R^b$ is independently H, F, OH, —O—($C_1$-$C_3$)alkyl, or ($C_1$-$C_3$)alkyl;
each $R^d$ is independently H, F, or ($C_1$-$C_3$)alkyl; or $R^d$ and $R^b$ form a ($C_3$-$C_5$) spirocycle;

$R^e$ is independently H or —($C_1$-$C_3$)alkyl; and
m is independently 0 or 1;
provided that not more than two of A, E, W, X and Y are N;
wherein heterocyclyl is:
a non-aromatic monocylic, bicyclic, tricyclic, or spirocyclic ring having 5 to 12 ring atoms including at least one nitrogen, oxygen, or sulfur ring atom; or
an azetidinyl ring.

2. The compound according to claim 1, or a pharmaceutically acceptable salt or stereoisomer thereof, wherein G and J are each CH.

3. The compound according to claim 1, or a pharmaceutically acceptable salt or stereoisomer thereof, wherein $L^1$ is —CH$_2$—, —C(O)—, —C(H)(OH)—, —C(H)(OCH$_3$)—, or —C(H)(CH$_3$)—.

4. The compound according to claim 1, or a pharmaceutically acceptable salt or stereoisomer thereof, wherein $R^1$ and $R^2$ are independently halo, —O—($C_1$-$C_3$)alkyl, cyclopropyl, or ($C_1$-$C_3$)alkyl.

5. The compound according to claim 1, or a pharmaceutically acceptable salt or stereoisomer thereof, wherein $R^3$ is independently H, —CF$_3$, —CN, halo, —OCHF$_2$, —OCF$_3$, —C(O)N($R^e$)$_2$, —$NR^e COR^e$, —($C_1$-$C_3$)alkyl, —O—($C_1$-$C_3$)alkyl, —S—($C_1$-$C_3$)alkyl, ($C_3$-$C_6$)cycloalkyl, or morpholinyl.

6. The compound according to claim 1, or pharmaceutically acceptable salt or stereoisomer thereof, wherein $R^4$ is —CH$_2$-optionally substituted tetrahydro-2H-pyranyl, —N(CH$_2$CH$_3$)—CH$_2$CH$_2$OH, —NH—CH$_2$-optionally substituted tetrahydro-2H-pyranyl, —N(H)-optionally substituted ($C_3$-$C_6$)cycloalkyl, —NH-optionally substituted oxetanyl, —NH-optionally substituted tetrahydro-2H-pyranyl, optionally substituted azabicyclo[2.2.1]heptanyl, optionally substituted azabicyclo[3.1.0]hexanyl, optionally substituted azaspiro[3.3]heptanyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted azepanyl, optionally substituted azetidinyl, optionally substituted 1,2-diazepanyl, optionally substituted 1,4-diazepanyl, optionally substituted morpholinyl, optionally substituted oxetanyl, optionally substituted piperazinyl, optionally substituted piperidinyl, optionally substituted pyrrolidinyl, or thiomorpholine 1,1-dioxide.

7. The compound according to claim 6, or a pharmaceutically acceptable salt or stereoisomer thereof,
wherein:
the —NH—CH$_2$-tetrahydro-2H-pyranyl is optionally substituted with one or two —OH or —O($C_1$-$C_4$)alkyl;
the —N(H)—($C_3$-$C_6$)cycloalkyl is optionally substituted with one or more F, —OH, —COOH, or —CO$_2$($C_1$-$C_4$)alkyl;
the azabicyclo[2.2.1]heptanyl and the azabicyclo[3.1.0]hexanyl are each independently optionally substituted with —CO$_2$H or —CO$_2$($C_1$-$C_4$)alkyl;
the azaspiro[3.3]heptanyl is optionally substituted with —CH$_2$CO$_2$H, —CH$_2$CO$_2$CH$_3$, —CO$_2$H, or —CO$_2$CH$_3$;
the 2-oxa-6-azaspiro[3.3]heptanyl, the 2-oxa-7-azaspiro[3.5]nonanyl, or the 2-oxa-8-azaspiro[4.5]decanyl are each independently optionally substituted with —CH$_2$CO$_2$H;
the azetidinyl is optionally substituted with one or two —CH$_3$, —OH, —OCH$_3$, —($C_1$-$C_4$)alkylene-OH, —CH$_2$OCH$_3$, —($C_1$-$C_4$)alkyleneO($C_1$-$C_4$)alkyl, —CO$_2$($C_1$-$C_4$)alkyl, —CO$_2$H, —($C_1$-$C_4$)alkylene- CO$_2$H, —(C$_1$-C$_4$)alkylene-CO$_2$—(C$_1$-C$_4$)alkyl, —N(CH$_3$)$_2$, or pyrrolidinyl;

the 1,2-diazepanyl or the 1,4-diazepanyl is optionally substituted with —(C$_1$-C$_4$)alkylene-OH;

the morpholinyl is optionally substituted with =O; and the piperazinyl, the piperidinyl, and the pyrrolidinyl are each independently optionally substituted with one or more -halo, —CN, —(C$_1$-C$_4$)alkyl, —CH$_2$-cyclopropyl, —(C$_1$-C$_4$)alkylene-F, —CF$_3$, —CH$_2$CF$_3$, —COOH, —(C$_1$-C$_4$)alkyleneCOOH, —CH(OH) CO$_2$H, —COCH$_3$, —CO$_2$(C$_1$-C$_4$)alkyl, —CH(OH) CO$_2$CH$_3$, —(C$_1$-C$_4$)alkylene-C(=O)O(C$_1$-C$_4$)alkyl, —(C$_1$-C$_4$)alkylene-OH, —OH, —O(C$_1$-C$_4$)alkyl, —(C$_1$-C$_4$)alkyleneO(C$_1$-C$_4$)alkyl, —O(C$_1$-C$_4$)alkyleneCO$_2$H, —O(C$_1$-C$_4$)alkyleneC(=O)O(C$_1$-C$_4$)alkyl, —CONHCH$_3$, —SO$_2$—(C$_1$-C$_4$)alkyl, —NH$_2$, —NH(C$_1$-C$_4$)alkyl, —N((C$_1$-C$_4$)alkyl)$_2$, cyclobutanecarboxylic acid, or oxetanyl.

8. The compound according to claim 1, or a pharmaceutically acceptable salt or stereoisomer thereof, wherein R$^1$ and R$^2$ are independently both halo or R$^1$ and R$^2$ are both —CH$_3$.

9. The compound according to claim 1, or a pharmaceutically acceptable salt or stereoisomer thereof, wherein W is C or CH, A is C, and E is C.

10. The compound according to claim 1, or a pharmaceutically acceptable salt or stereoisomer thereof, wherein L$^1$ is —CH$_2$— or —C(O)—.

11. The compound according to claim 1, or a pharmaceutically acceptable salt or stereoisomer thereof, wherein G is CH.

12. The compound according to claim 1, or a pharmaceutically acceptable salt or stereoisomer thereof, wherein J is CH.

13. The compound according to claim 6, or a pharmaceutically acceptable salt or stereoisomer salt thereof, wherein:
W is CH;
X is CR$^a$, wherein R$^a$ is H or —CH$_3$;
Y is N;
A is C;
E is C;
V is CR$^3$, wherein R$^3$ is H;
Z is N or CR$^3$, wherein R$^3$ is H, —CH$_3$, or —CF$_3$;
L$^1$ is connected to Y;
L$^1$ is —CH$_2$— or —C(O)—;
R$^1$ is —Cl or —CH$_3$;
R$^2$ is —Cl or —CH$_3$;
each R$^3$ is independently H, —F, —Cl, —CN, —CH$_3$, —CH(CH$_3$)$_2$, —CF$_3$, —OCHF$_2$, —OCF$_3$, —SCH$_3$, or cyclopropyl; and
R$^4$ is optionally substituted 2-oxa-6-azaspiro[3.3]heptanyl, or optionally substituted piperidinyl.

14. The compound according to claim 6, or a pharmaceutically acceptable salt or stereoisomer thereof, wherein:
W is C;
X is NR$^a$, wherein R$^a$ is —CH$_3$, —CH$_2$CH$_3$, —CH$_2$CH(CH$_3$)$_2$;
Y is N;
A is C;
E is C;
V is CR$^3$, wherein R$^3$ is H, Br, —CN, or —CF$_3$;
Z is CR$^3$ or N, wherein R$^3$ is H or CH$_3$;
L$^1$ is connected to W;
L$^1$ is —CH$_2$— or —C(O)—;
R$^1$ is —Cl or —CH$_3$;
R$^2$ is —Cl or —CH$_3$;

each R$^3$ is independently —Br, —Cl, —CN, —CH$_3$, or —CF$_3$; and

R$^4$ is —N(CH$_2$CH$_3$)—CH$_2$CH$_2$OH, —NH-optionally substituted cyclohexyl, —NH-optionally substituted oxetanyl, optionally substituted azetidinyl, optionally substituted 1,4-diazepanyl, optionally substituted 3-azabicyclo[3.1.0]hexanyl, optionally substituted morpholinyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted piperazinyl, optionally substituted piperidinyl, or optionally substituted pyrrolidinyl.

15. The compound according to claim 1, or a pharmaceutically acceptable salt or stereoisomer thereof, wherein:
W is C;
X is NR$^a$, wherein R$^a$ is H, —CH$_3$, —CH$_2$CH$_3$, —COCH$_3$, or —CH$_2$CH(CH$_3$)$_2$;
Y is CR$^a$, wherein R$^a$ is H;
Z is CR$^3$, wherein R$^3$ is H or —CH$_3$;
A is C;
E is C;
V is CR$^3$, wherein R$^3$ is H, —CN, —CH$_3$, or —CF$_3$;
L$^1$ is connected to W;
L$^1$ is —CH$_2$—, —C(O)—, —CH(OH)—, or —CH(OCH$_3$)—;
R$^1$ is —Cl, —CH$_3$, or cyclopropyl;
R$^2$ is —Cl or —CH$_3$;
each R$^3$ is independently H, —F, —Br, —Cl, —CN, —CH$_3$, —CF$_3$, —OCH$_3$, —OCHF$_2$, —OCF$_3$, —CONHCH$_3$, —CON(CH$_3$)$_2$, —NHCOCH$_3$, cyclopropyl, or morpholinyl; and R$^4$ is —NH—CH$_2$-optionally substituted tetrahydro-2H-pyranyl, —NH-optionally substituted cyclohexyl, —NH-optionally substituted oxetanyl, —NH-optionally substituted tetrahydro-2H-pyranyl, optionally substituted azabicyclo[2.2.1]heptanyl, optionally substituted 3-azabicyclo[3.1.0]hexanyl, optionally substituted azaspiro[3.3]heptanyl, optionally substituted azetidinyl, optionally substituted 1,4-diazepanyl, optionally substituted morpholinyl, optionally substituted 2-oxa-6-azaspiro[3.3]heptanyl, optionally substituted 2-oxa-7-azaspiro[3.5]nonanyl, optionally substituted 2-oxa-8-azaspiro[4.5]decanyl, optionally substituted piperazinyl, optionally substituted piperidinyl, or optionally substituted pyrrolidinyl.

16. The compound according to claim 1, or a pharmaceutically acceptable salt or stereoisomer thereof, wherein:
W is C;
X is CR$^a$, wherein R$^a$ is H;
Y is NR$^a$, wherein R$^a$ is H or —CH$_3$;
Z is N;
A is C;
E is C;
V is CR$^3$, wherein R$^3$ is H or —CF$_3$;
L$^1$ is connected to W;
L$^1$ is —CH$_2$—, —C(O)—, or —CH(OH)—;
R$^1$ is Cl;
R$^2$ is Cl;
each R$^3$ is independently H or —CF$_3$; and
R$^4$ is optionally substituted morpholinyl.

17. The compound according to claim 1, or a pharmaceutically acceptable salt or stereoisomer thereof, wherein:
W is CH;
X is N;
Y is N;
Z is CR$^3$;

A is C;
E is C;
V is CR$^3$; and
L$^1$ is connected to Y.

18. The compound according to claim 1, or a pharmaceutically acceptable salt or stereoisomer thereof, wherein:
W is C;
X is NR$^a$, wherein R$^a$ is H or —CH$_3$;
Y is CR$^a$, wherein R$^a$ is H;
Z is N;
A is C;
E is C;
V is CR$^3$, wherein R$^3$ is H;
L$^1$ is connected to W;
L$^1$ is —CH$_2$— or —C(O)—;
R$^1$ is —Cl;
R$^2$ is —Cl;
each R$^3$ is independently H, —CH$_3$, or —CF$_3$; and
R$^4$ is optionally substituted morpholinyl, optionally substituted piperazinyl, or optionally substituted piperidinyl.

19. The compound according to claim 1, or a pharmaceutically acceptable salt or stereoisomer thereof, wherein:
W is C;
X is CR$^a$, wherein R$^a$ is H or —CH$_3$;
Y is N;
A is N;
E is C;
Z is N;
V is CR$^3$, wherein R$^3$ is H or —CH$_3$;
L$^1$ is connected to W;
L$^1$ is —CH$_2$— or —C(O)—;
R$^1$ is —Cl;
R$^2$ is —Cl;
each R$^3$ is independently H, —Cl, —CN, —CH$_3$, or —CF$_3$; and
R$^4$ is optionally substituted morpholinyl, optionally substituted piperazinyl, or optionally substituted piperidinyl.

20. The compound according to claim 1, or a pharmaceutically acceptable salt or stereoisomer thereof, wherein:
W is C;
X is CR$^a$, wherein R$^a$ is H or —CH$_3$;
Y is N;
Z is CR$^3$, wherein R$^3$ is H;
A is N;
E is C;
V is CR$^3$, wherein R$^3$ is H;
L$^1$ is connected to W;
L$^1$ is —CH$_2$—;
R$^1$ is —Cl;
R$^2$ is —Cl;
each R$^3$ is independently H, —CN, —CH$_3$, or —CF$_3$; and
R$^4$ is optionally substituted morpholinyl, optionally substituted piperazinyl, optionally substituted piperidinyl, or optionally substituted pyrrolidinyl.

21. The compound according to claim 1, or a pharmaceutically acceptable salt or stereoisomer thereof, wherein:
W is N;
X is CR$^a$, wherein R$^a$ is H or —CH$_3$;
Y is N;
Z is CR$^3$, wherein R$^3$ is H;
A is C;
E is C;
V is CR$^3$, wherein R$^3$ is H;
L$^1$ is connected to W;
L$^1$ is —CH$_2$— or —C(O)—;
R$^1$ is —Cl;
R$^2$ is —Cl;
each R$^3$ is independently H, —CH$_3$, or —CF$_3$; and
R$^4$ is optionally substituted morpholinyl or optionally substituted piperidinyl.

22. The compound according to claim 1, or a pharmaceutically acceptable salt or stereoisomer thereof, wherein:
W is N;
X is CR$^a$, wherein R$^a$ is H or —CH$_3$;
Y is N;
Z is CR$^3$, wherein R$^3$ is H;
A is C;
E is C;
V is CR$^3$, wherein R$^3$ is H;
L$^1$ is connected to Y;
L$^1$ is —CH$_2$— or —C(O)—;
R$^1$ is —Cl;
R$^2$ is —Cl;
each R$^3$ is independently H, —CH$_3$, or —CF$_3$; and
R$^4$ is optionally substituted morpholinyl or optionally substituted piperidinyl.

23. The compound according to claim 1, or a pharmaceutically acceptable salt or stereoisomer thereof, wherein:
W is N;
X is NR$^a$, wherein R$^a$ is H or —CH$_3$;
Y is C;
Z is CR$^3$, wherein R$^3$ is H;
A is C;
E is C;
V is CR$^3$, wherein R$^3$ is H;
L$^1$ is connected to Y;
L$^1$ is —CH$_2$—;
R$^1$ is —Cl;
R$^2$ is —Cl;
each R$^3$ is independently H, —CH$_3$, or —CF$_3$; and
R$^4$ is optionally substituted piperidinyl.

24. The compound according to claim 1, or a pharmaceutically acceptable salt or stereoisomer thereof, wherein:
W is C;
X is NR$^a$, wherein R$^a$ is H or CH$_3$;
Y is CR$^a$, wherein R$^a$ is H;
Z is CR$^3$, wherein R$^3$ is H;
A is C;
E is C;
V is N;
L$^1$ is connected to W;
L$^1$ is —CH$_2$—;
R$^1$ is —Cl;
R$^2$ is —Cl;
each R$^3$ is independently H, —CN, —CF$_3$, or —CH$_3$; and
R$^4$ is optionally substituted morpholinyl or optionally substituted piperazinyl.

25. The compound according to claim 1, or a pharmaceutically acceptable salt or stereoisomer thereof, wherein:
W is CR$^a$, wherein R$^a$ is H;
X is O or NR$^a$, wherein R$^a$ is H or —CH$_3$;
Y is C;
Z is CR$^3$, wherein R$^3$ is H or —CF$_3$;
A is C;
E is C;
V is CR$^3$, wherein R$^3$ is H;
L$^1$ is connected to Y;
L$^1$ is —CH$_2$—;
R$^1$ is —Cl;
R$^2$ is —Cl;
each R$^3$ is independently H, —CH$_3$, —CF$_3$, or —OCF$_3$; and
R$^4$ is optionally substituted piperidinyl.

26. The compound according to claim 1, wherein the compound is selected from the group consisting of:
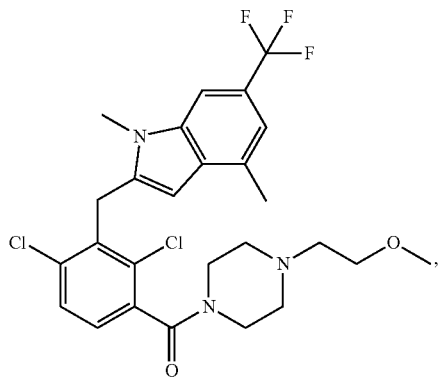
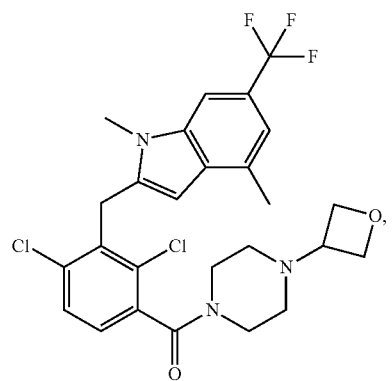
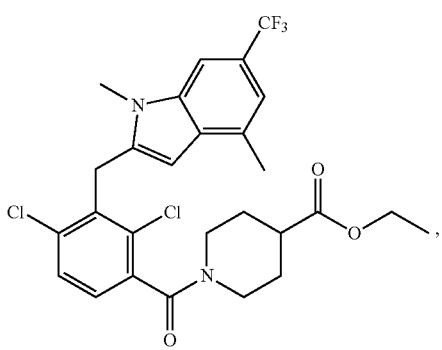
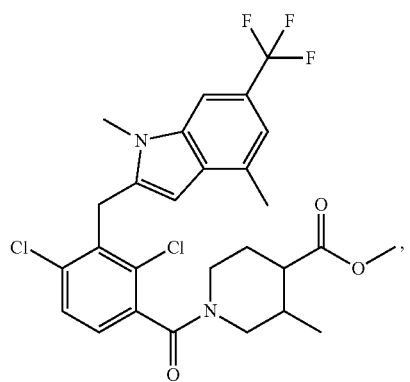
-continued
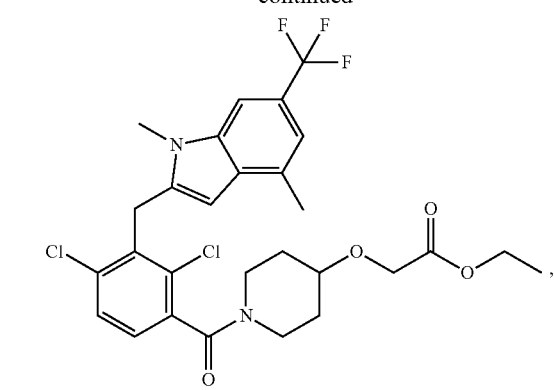
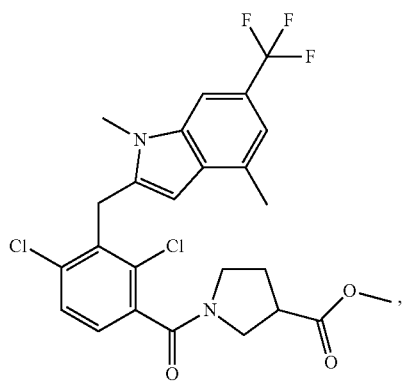
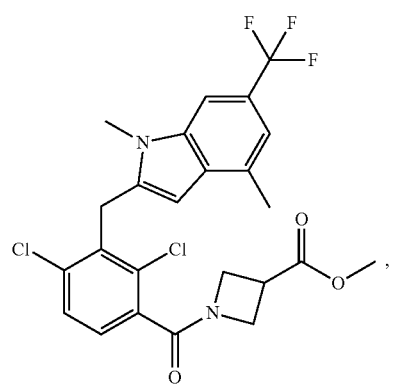
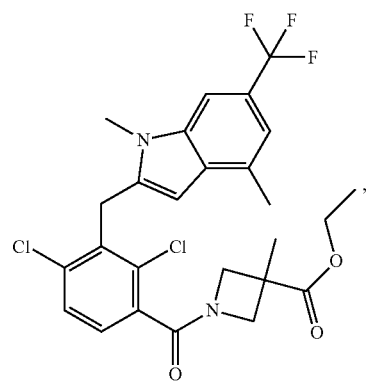

835
-continued
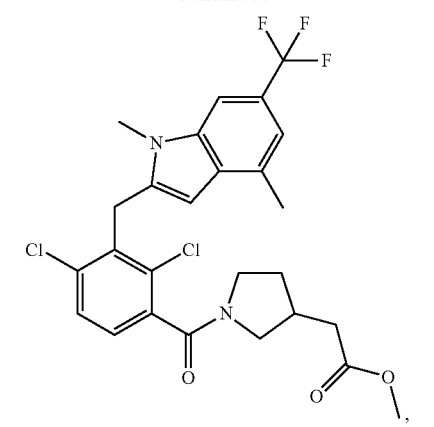
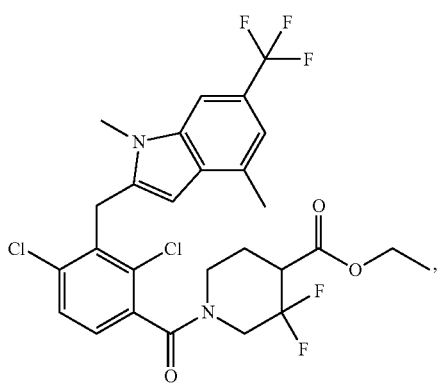
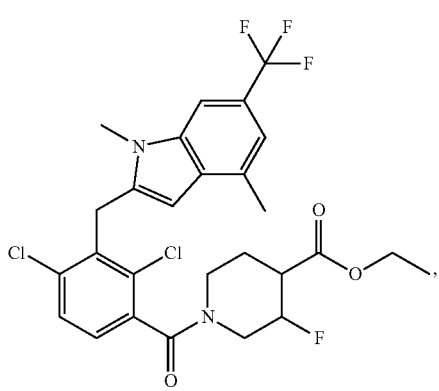
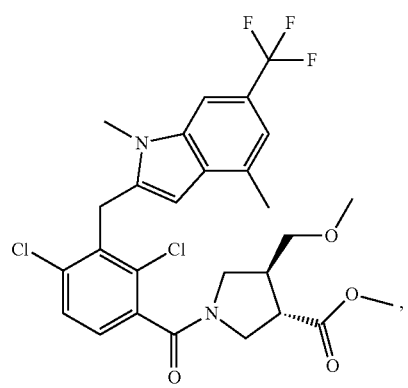
836
-continued
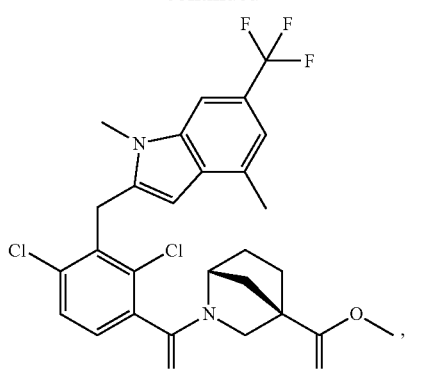
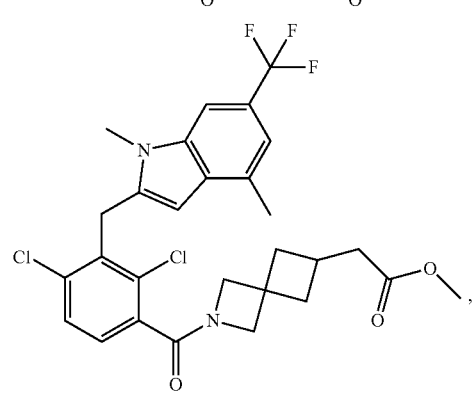
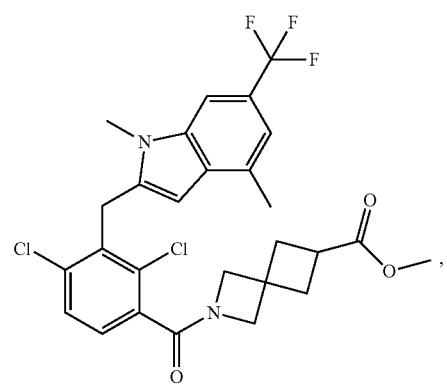
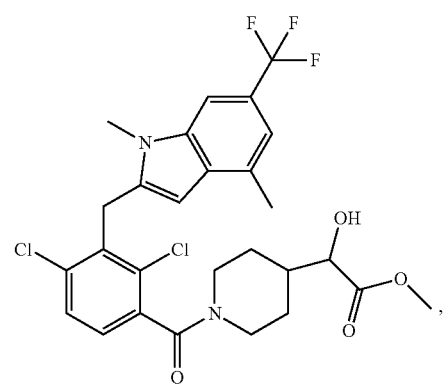

837
-continued
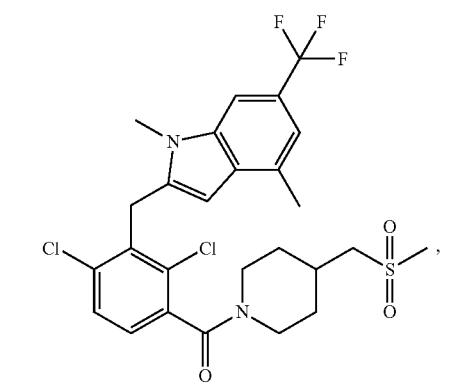
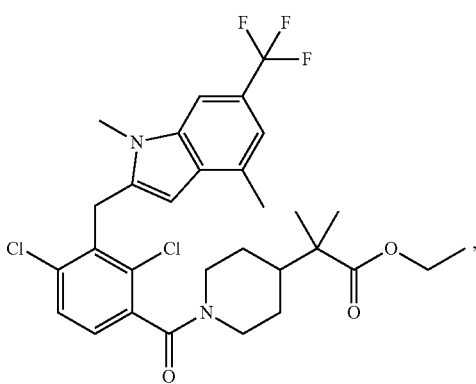
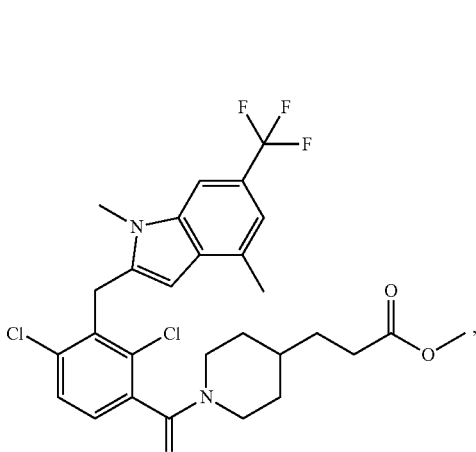
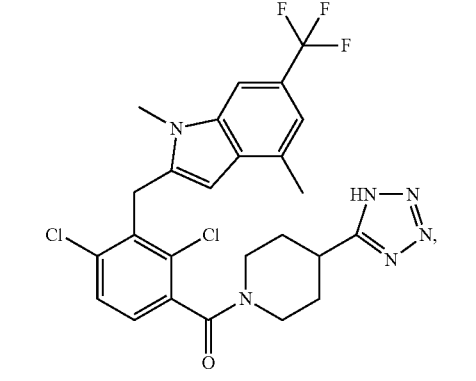
838
-continued
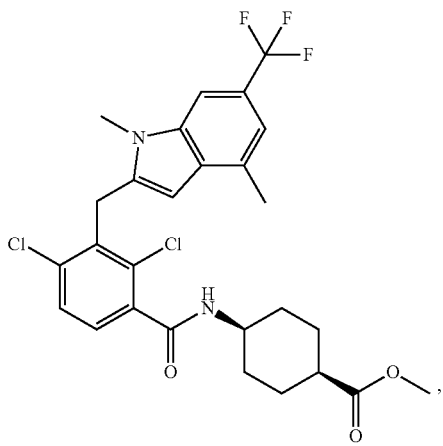
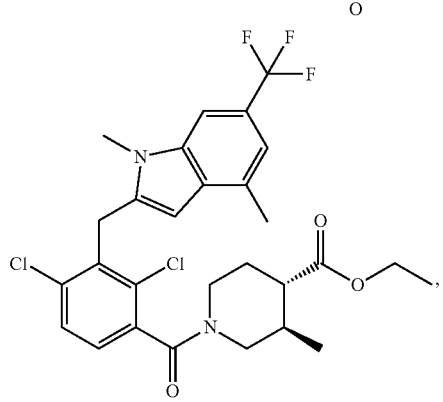
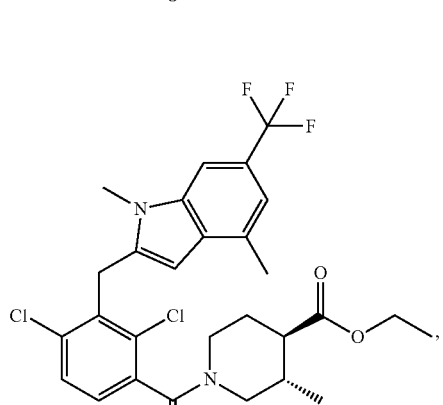
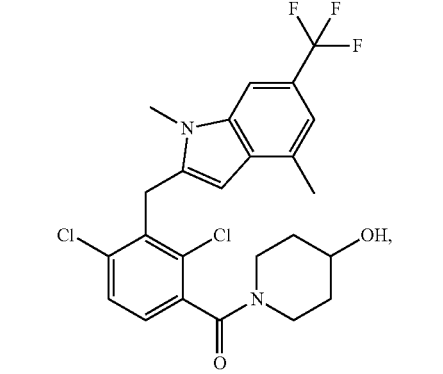

839
-continued
840
-continued
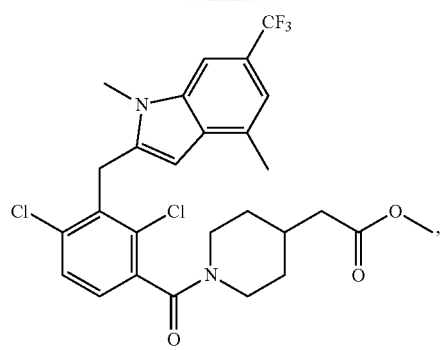
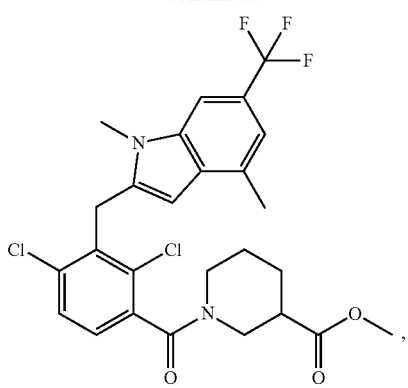

841
-continued
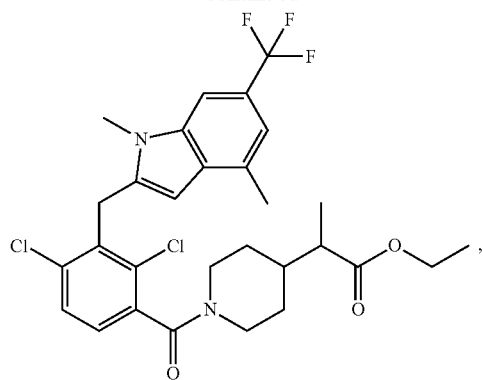
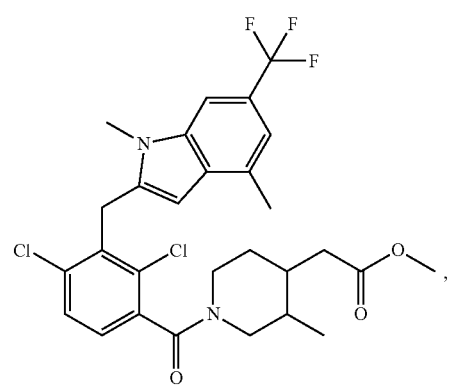
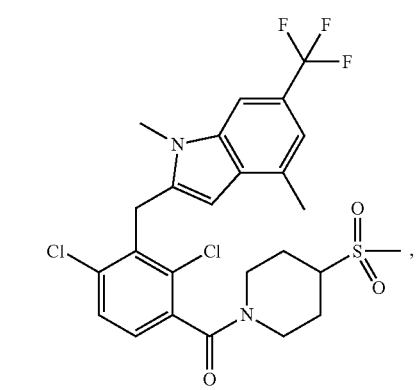
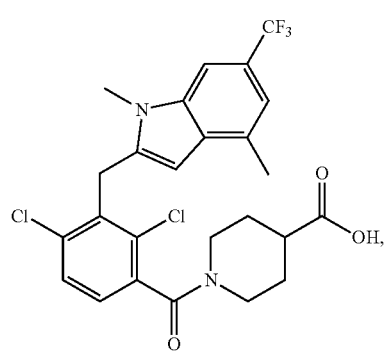
842
-continued
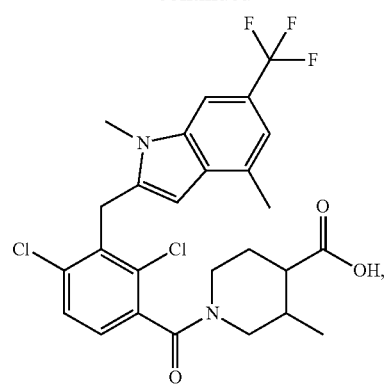
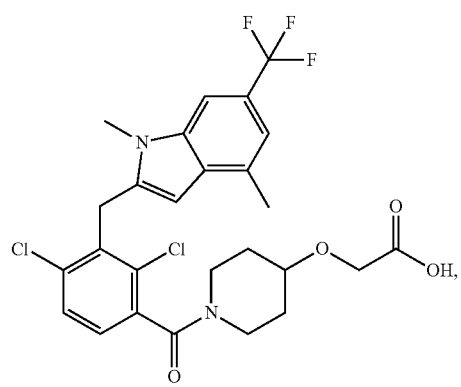
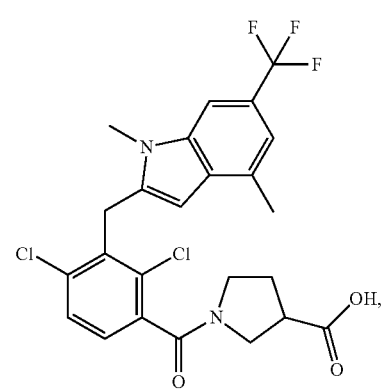
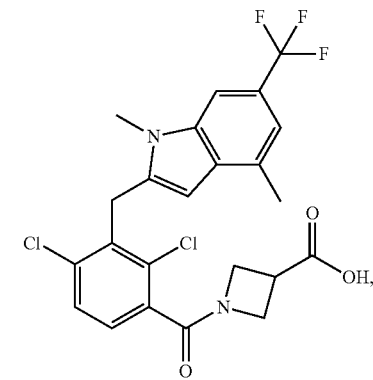

843
-continued
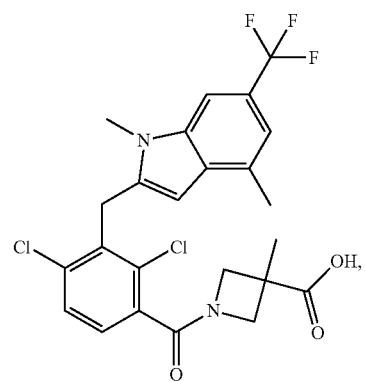
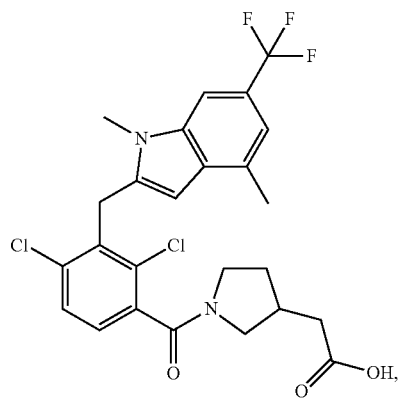
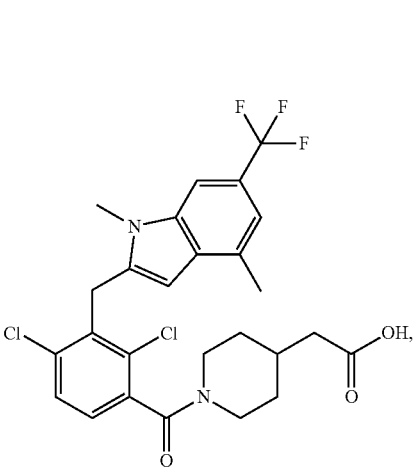
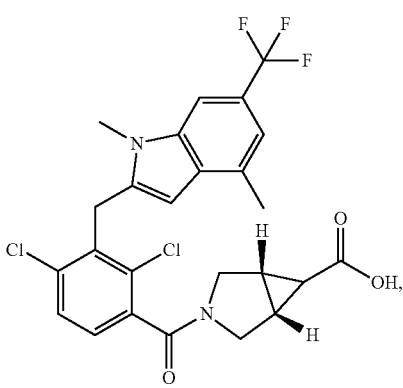
844
-continued
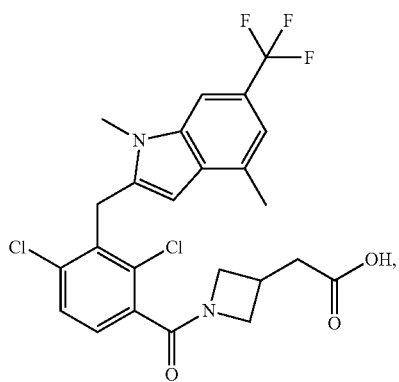
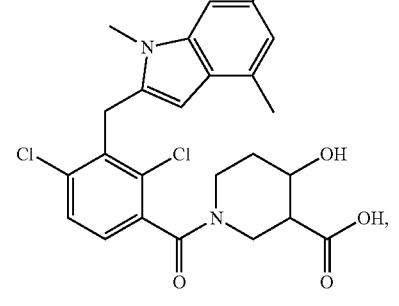
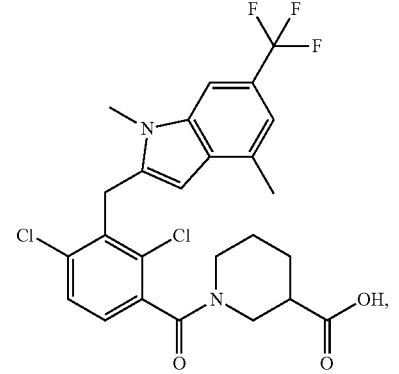
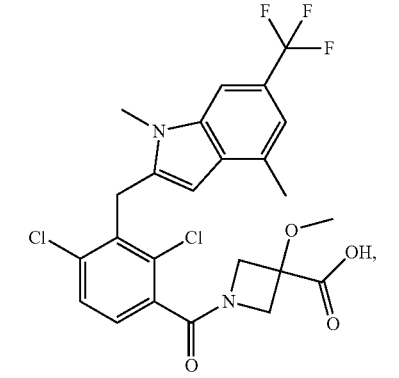

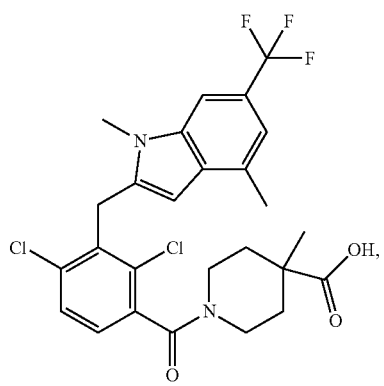
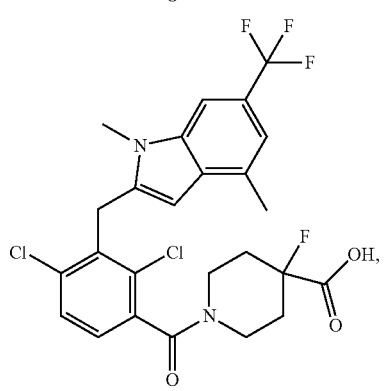
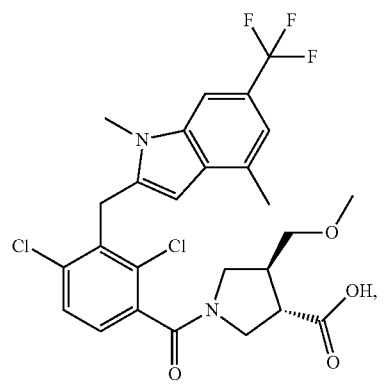
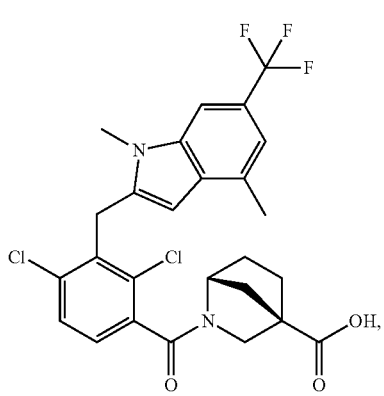
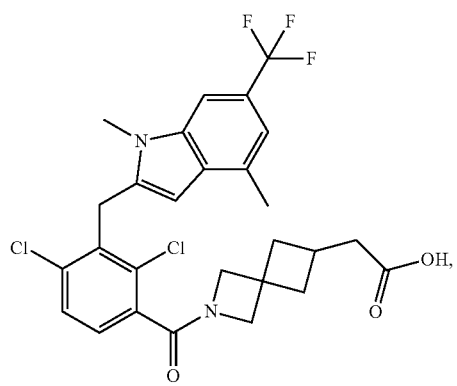
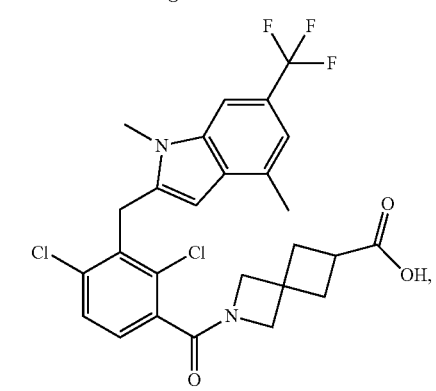
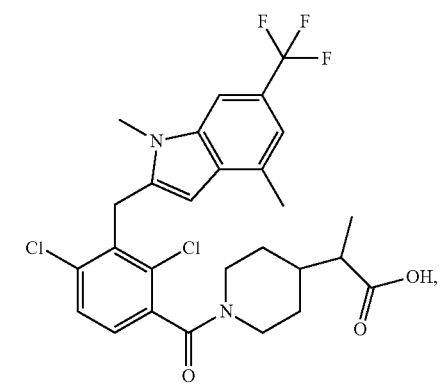
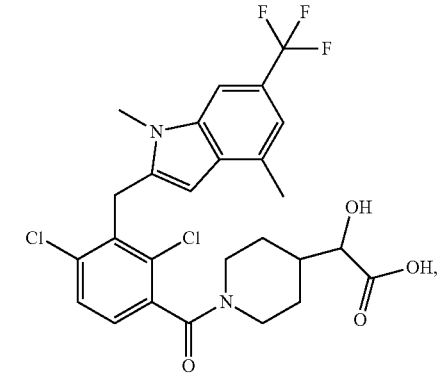

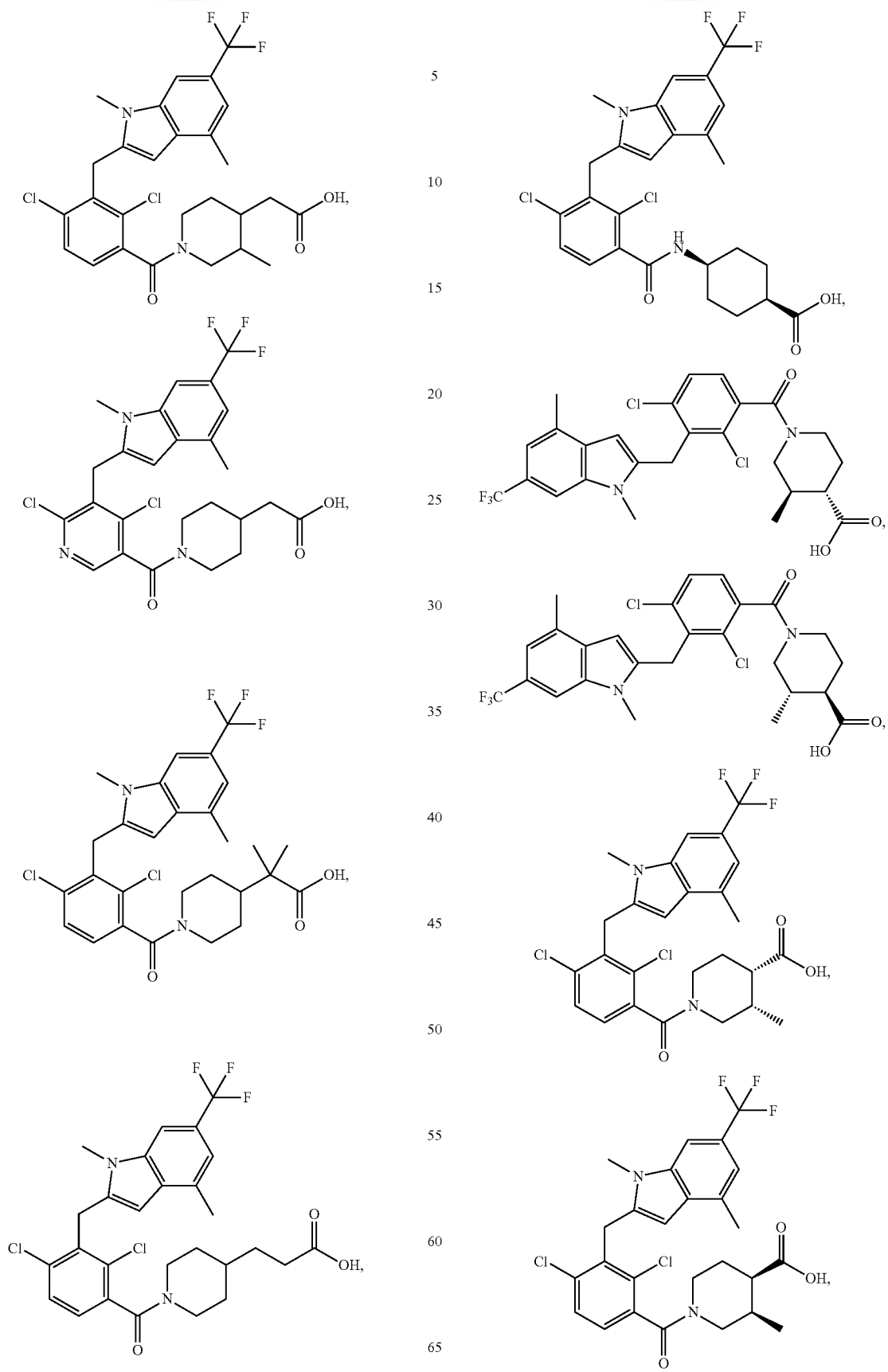

849
-continued
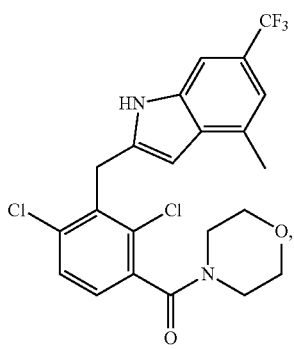
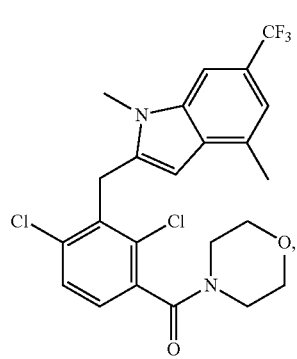
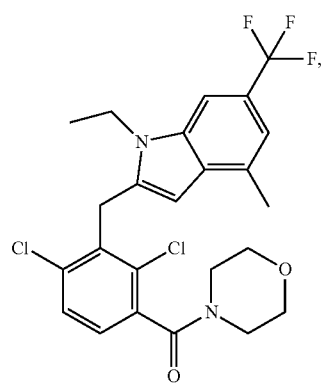
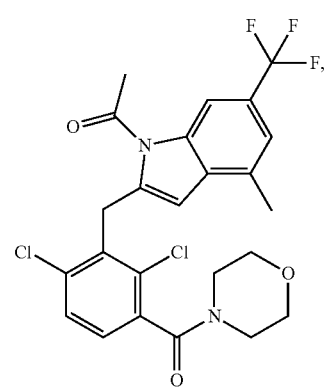
850
-continued
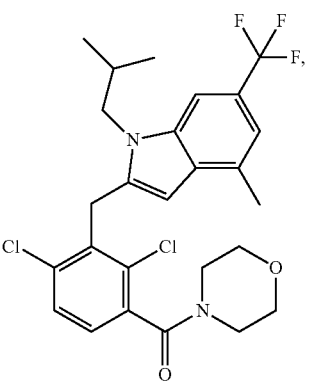
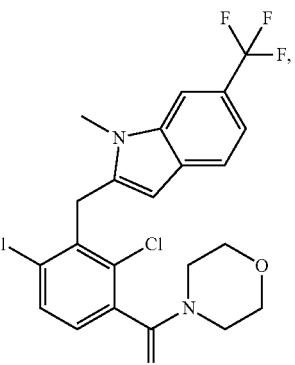
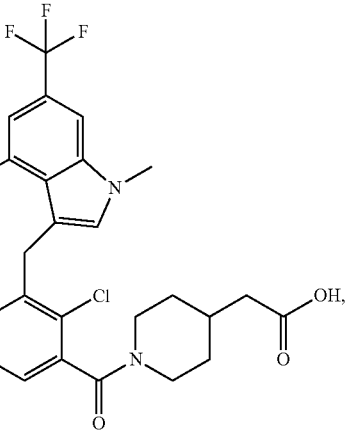
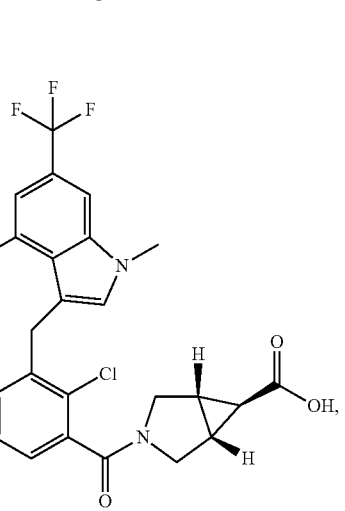

851
-continued
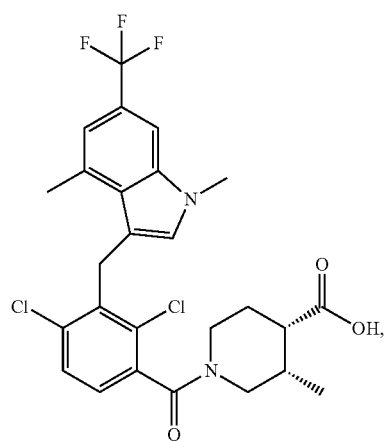
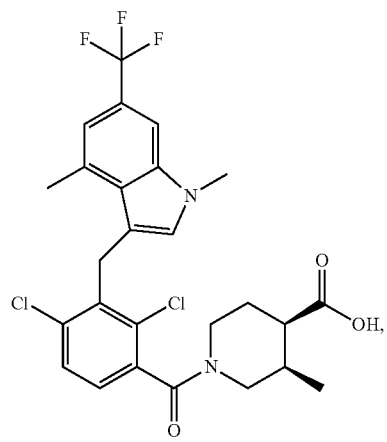
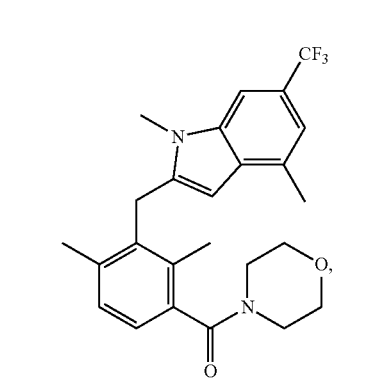
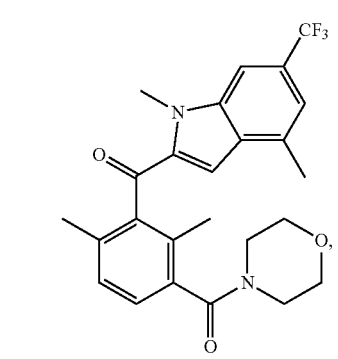
852
-continued
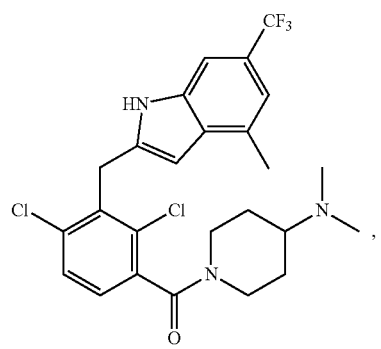
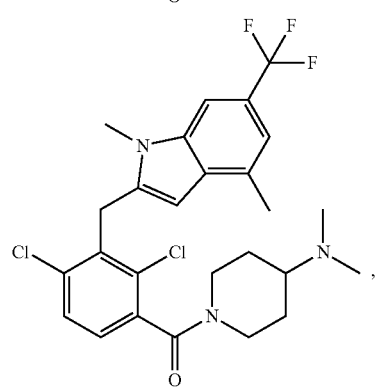
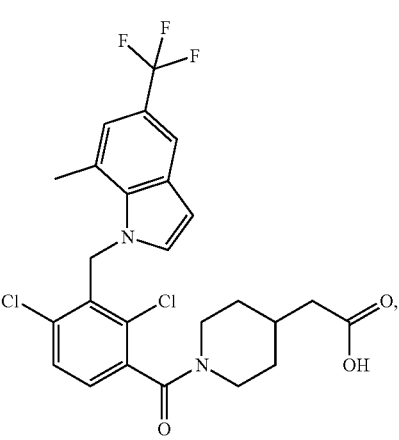
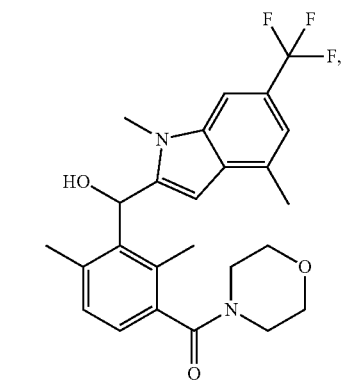

853
-continued
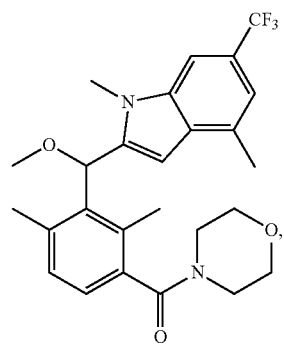
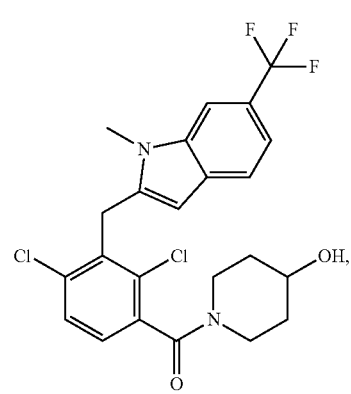
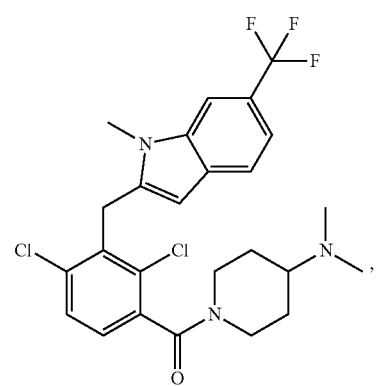
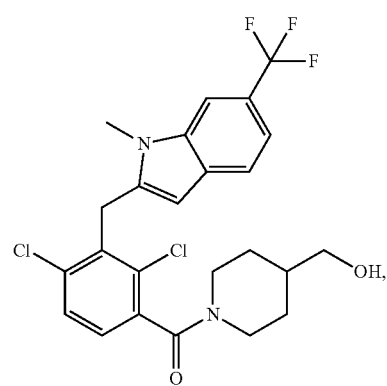
854
-continued
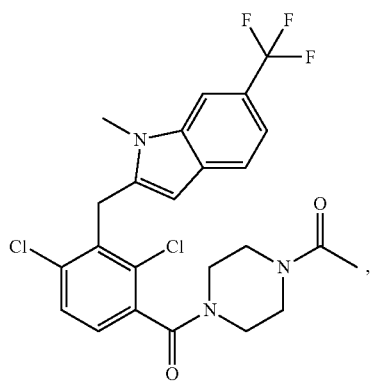
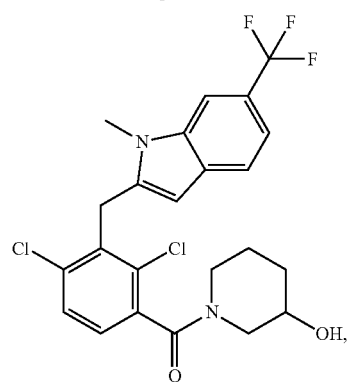
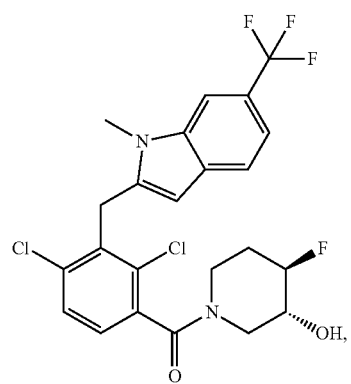
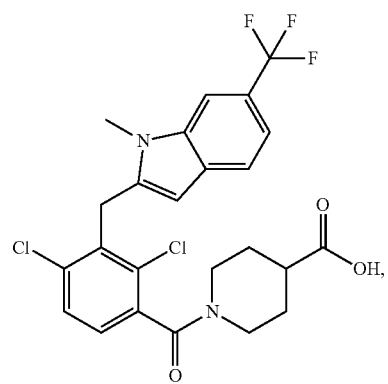

855
-continued
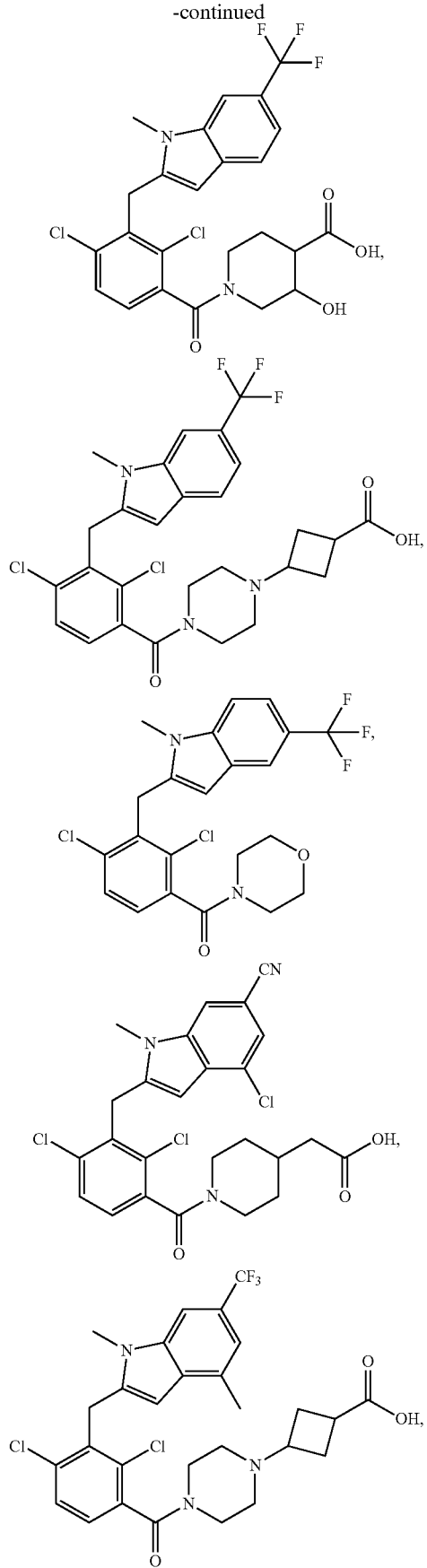
856
-continued
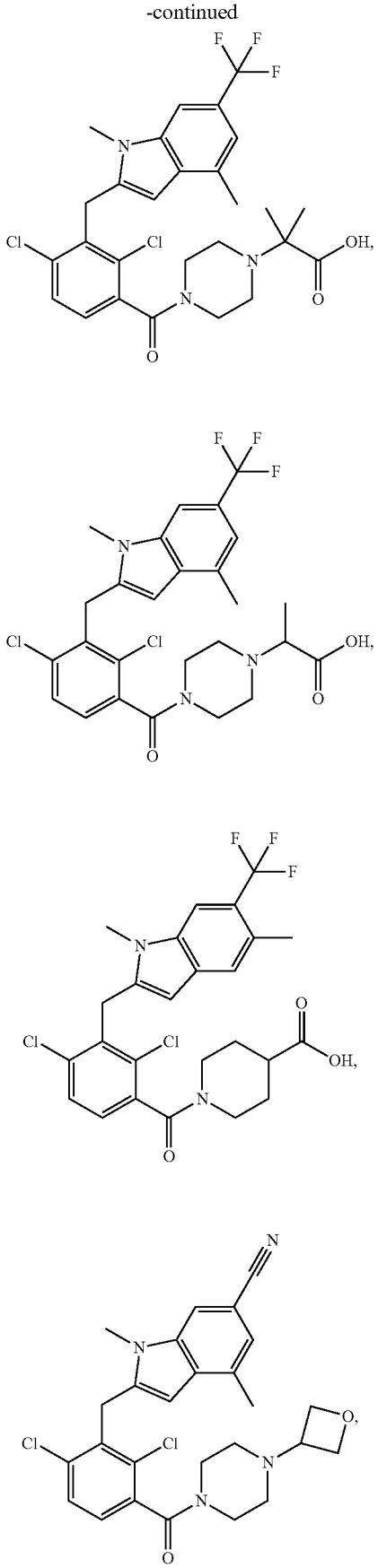

857
-continued
858
-continued
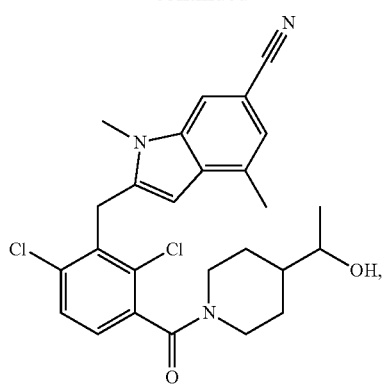
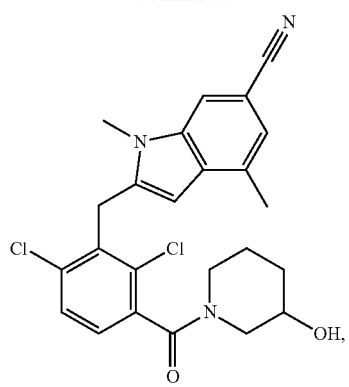

859
-continued
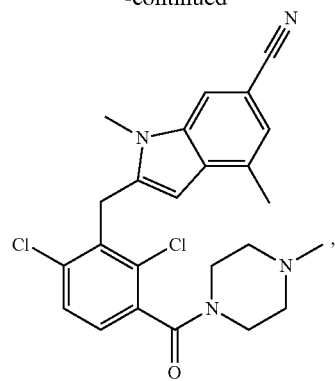
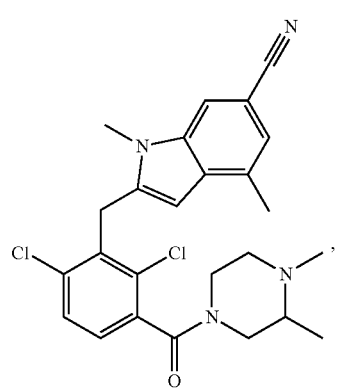
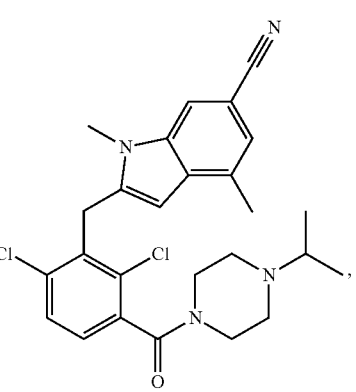
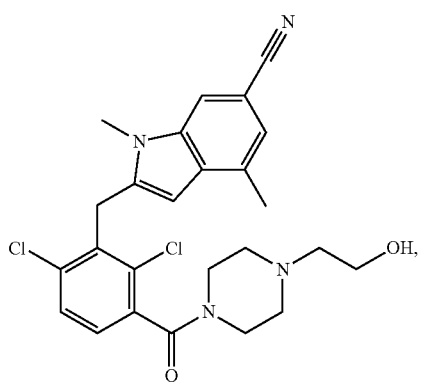
860
-continued
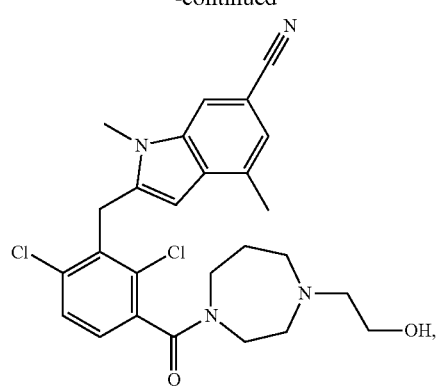
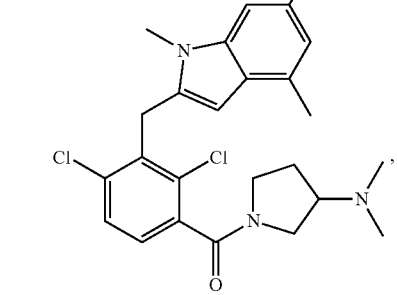
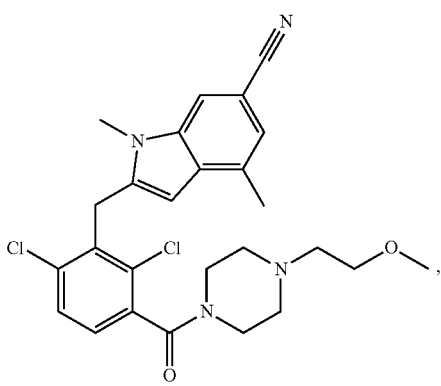
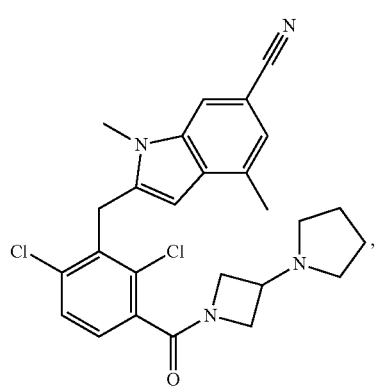

861
-continued
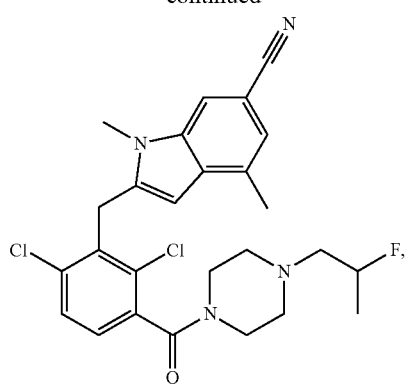
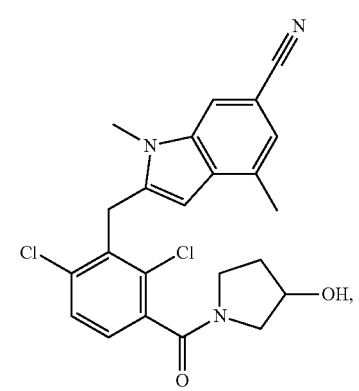
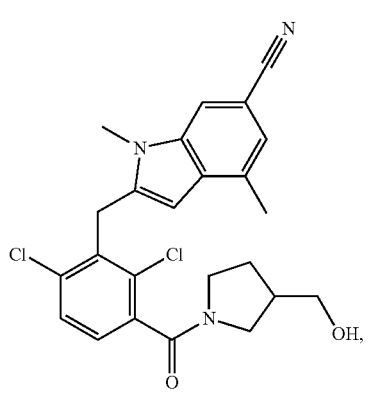
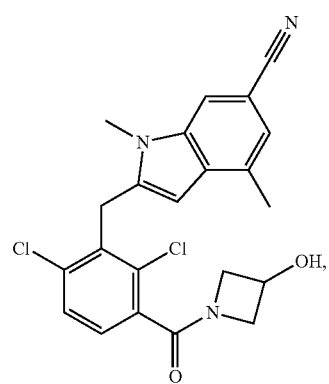
862
-continued
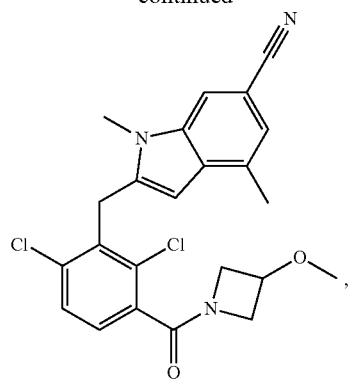
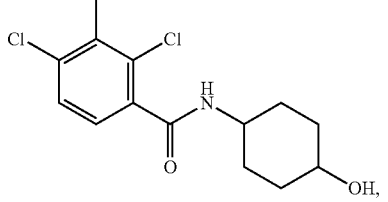
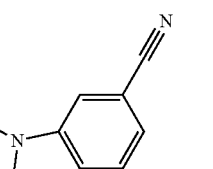
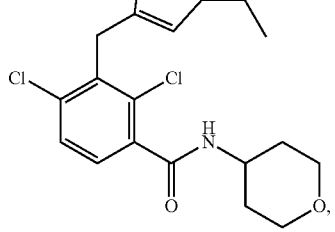
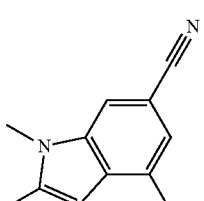
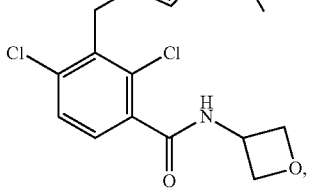

863
-continued
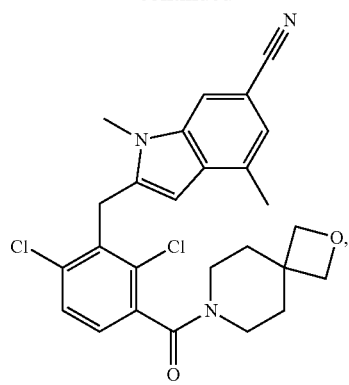
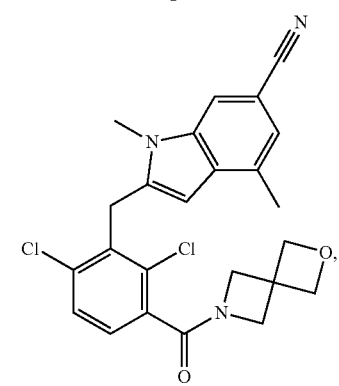
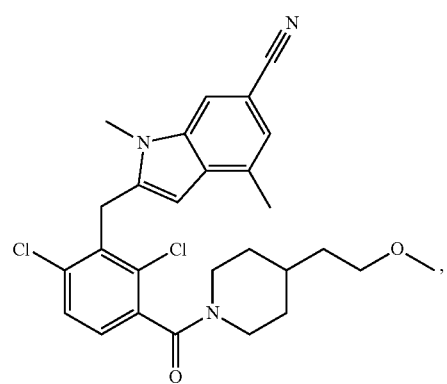
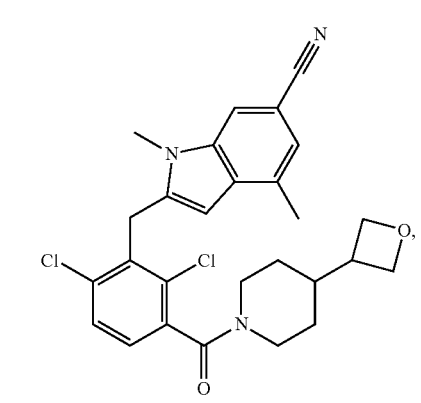
864
-continued
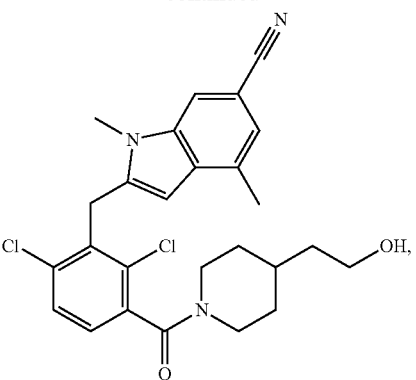
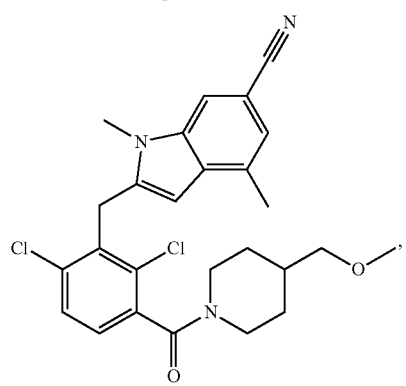
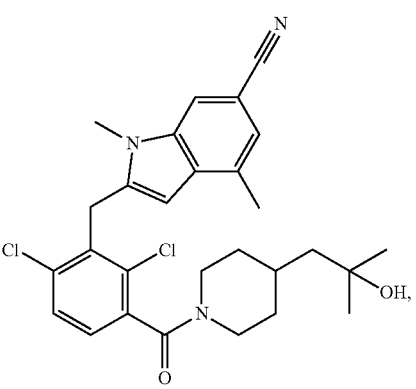
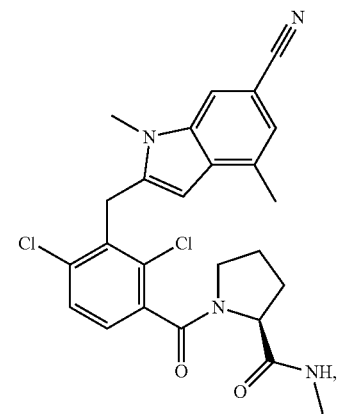

865
-continued
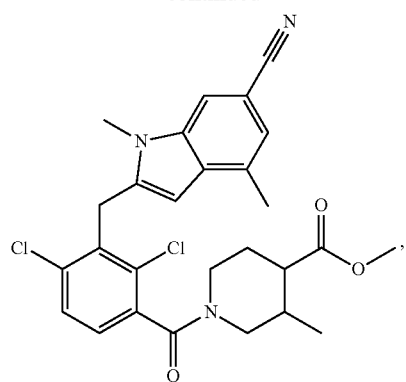
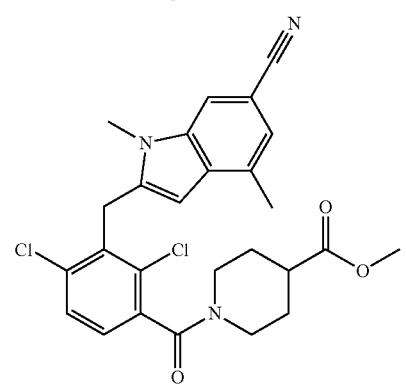
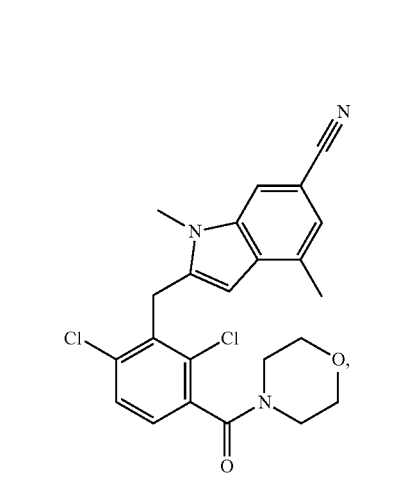
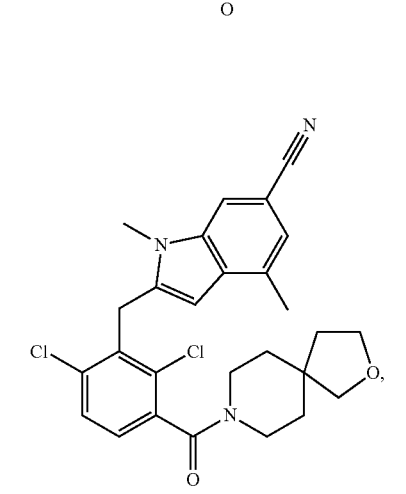
866
-continued
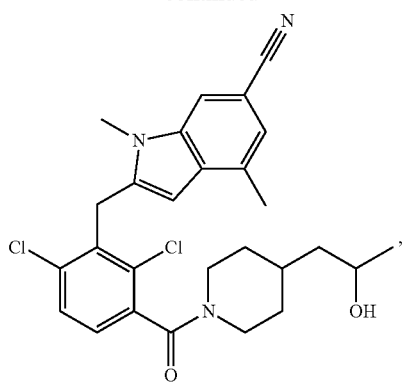
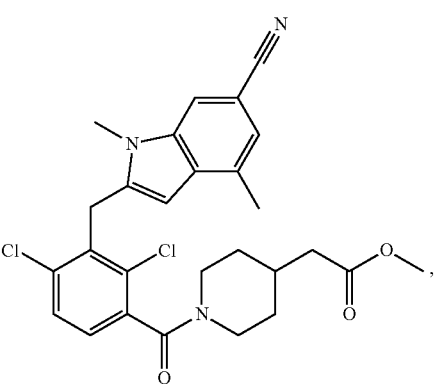
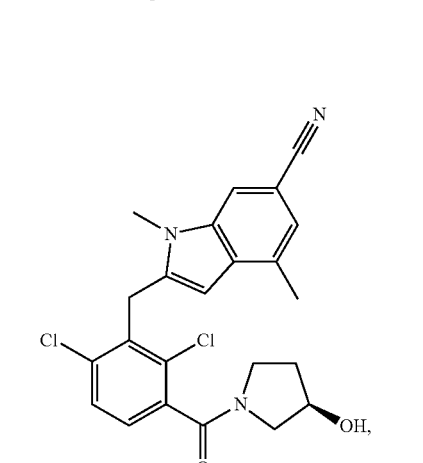
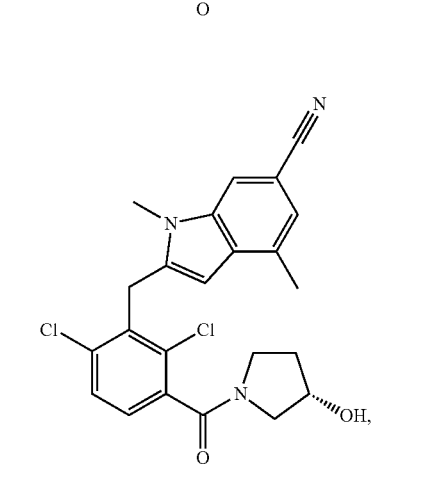

867
-continued
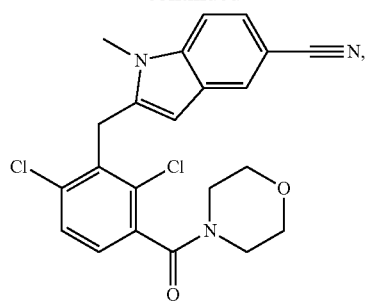
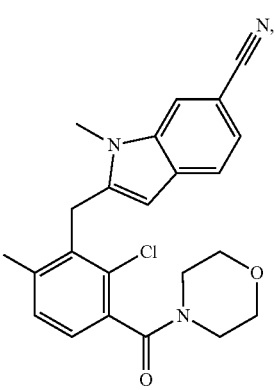
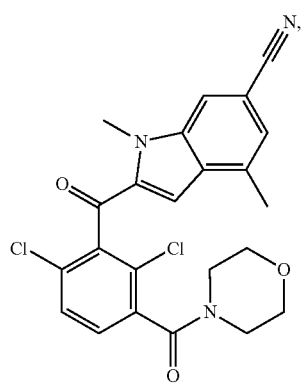
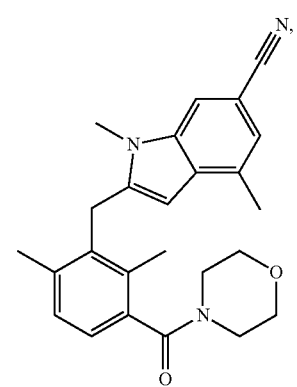
868
-continued
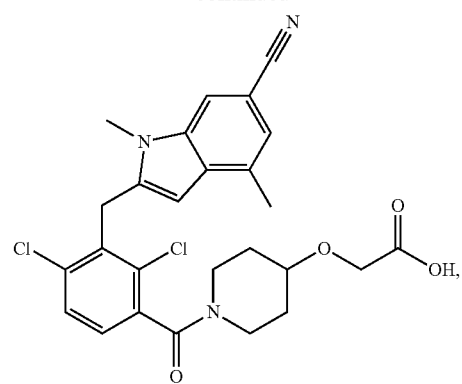
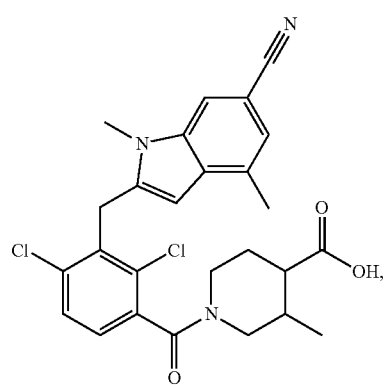
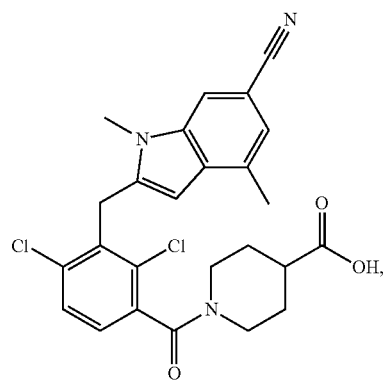
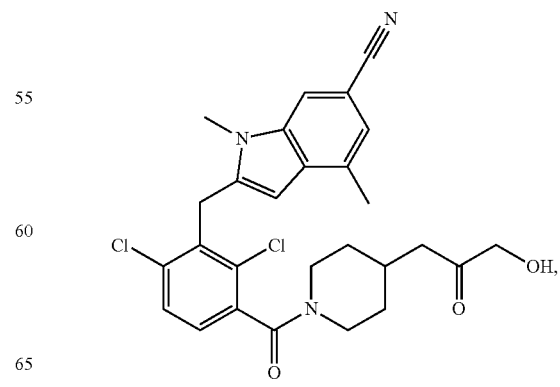

869
-continued
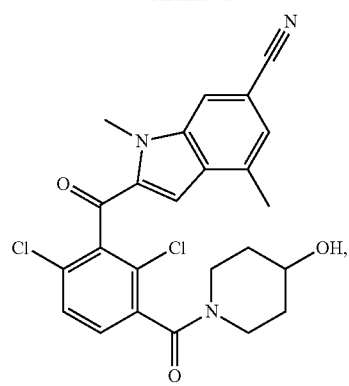
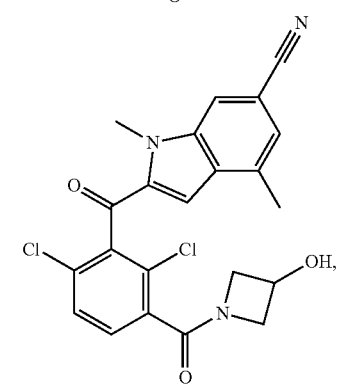
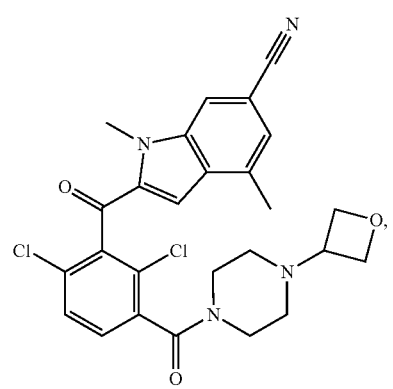
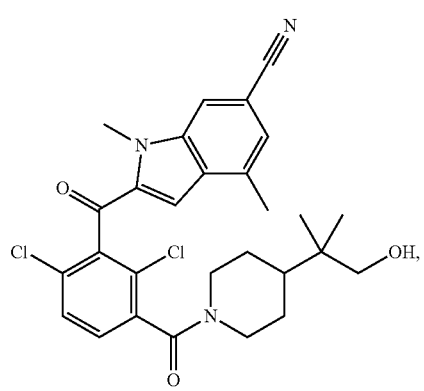
870
-continued
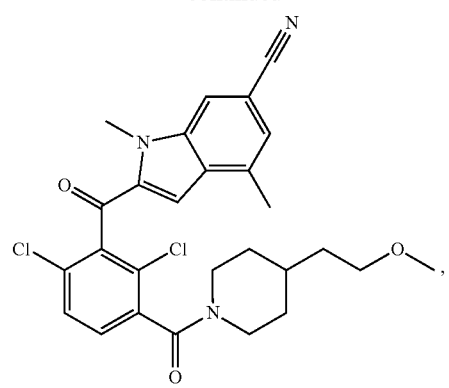
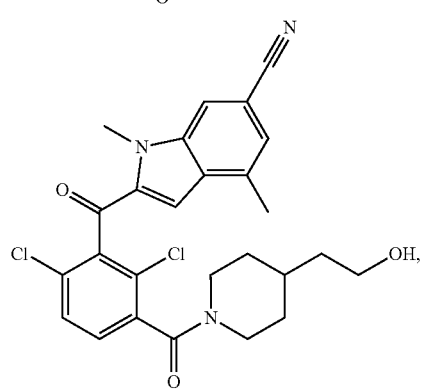
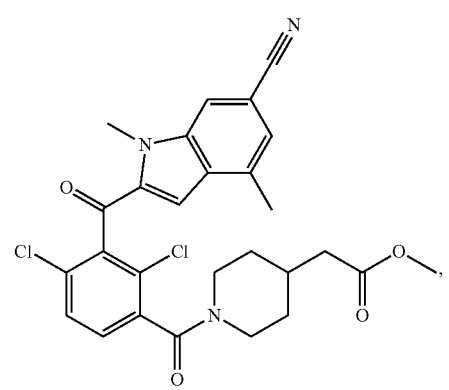
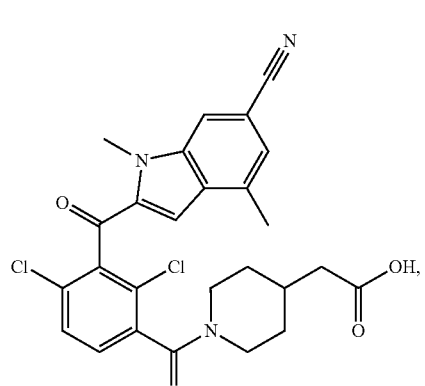

871
-continued
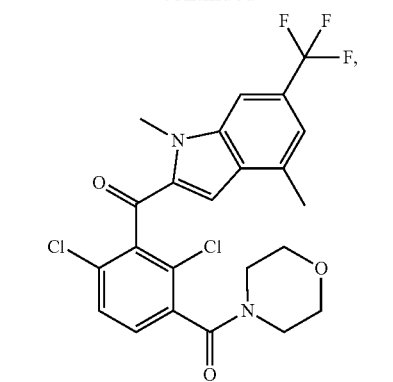
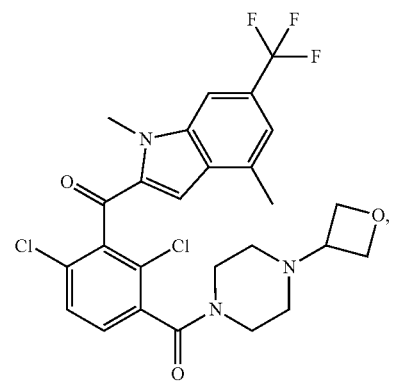
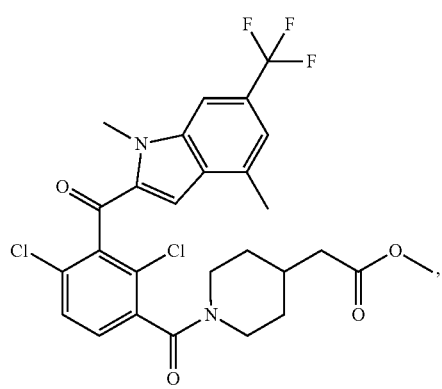
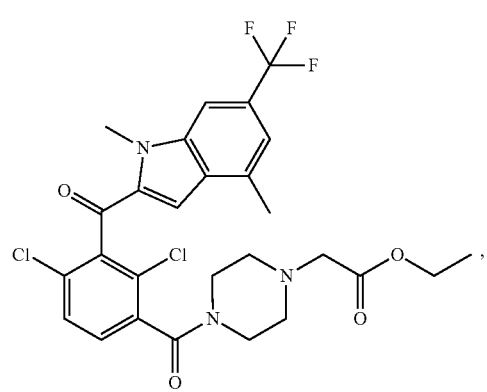
872
-continued
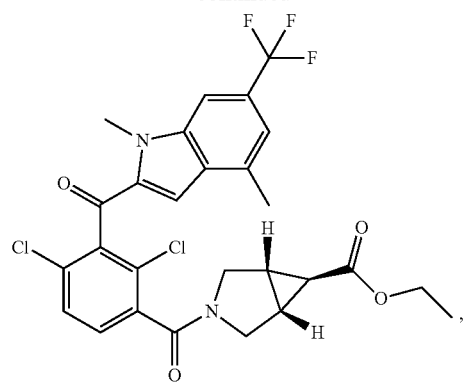
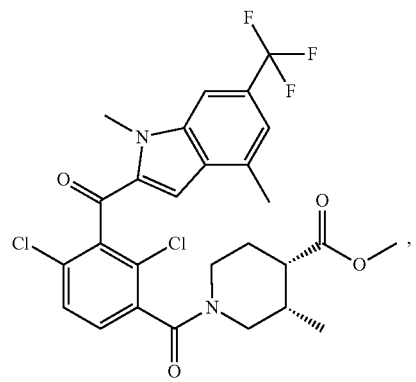
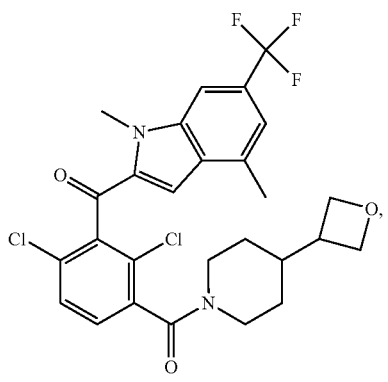
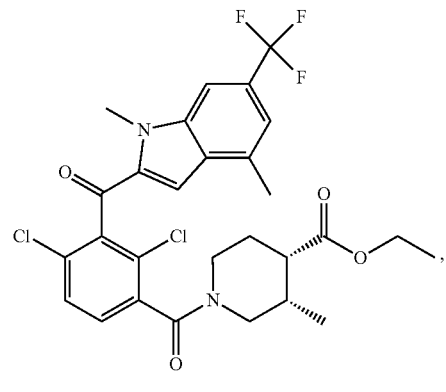

873
-continued
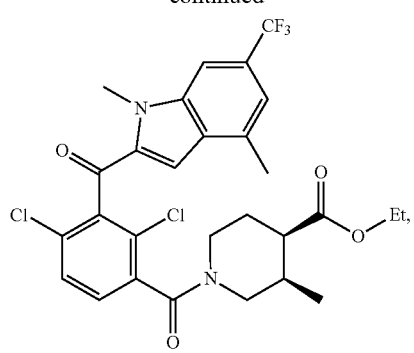
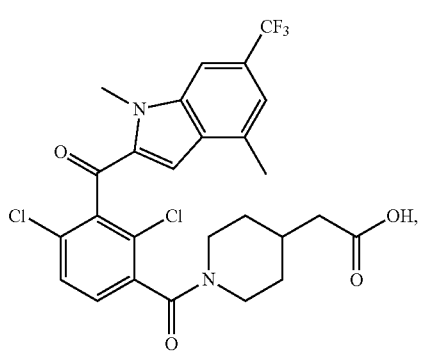
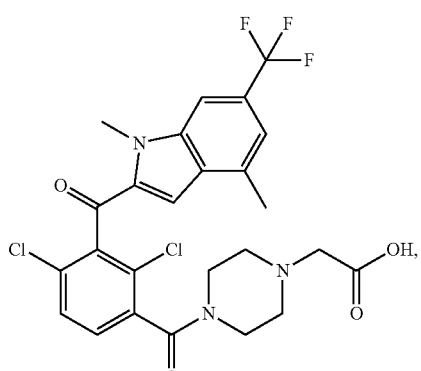
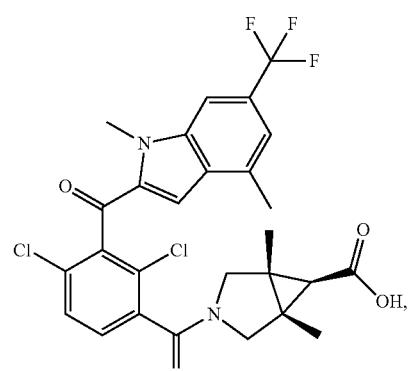
874
-continued
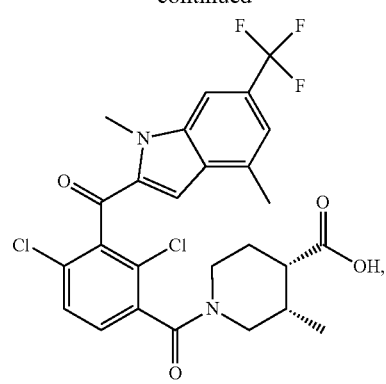
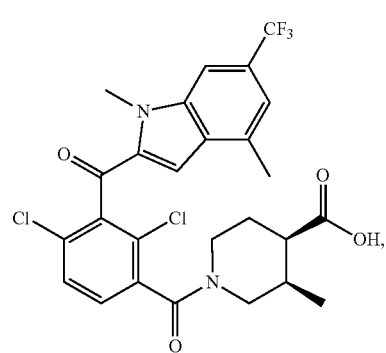
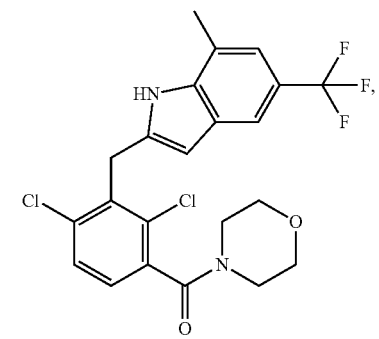
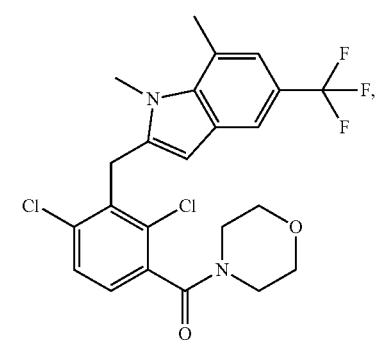

875
-continued

876
-continued

877
-continued
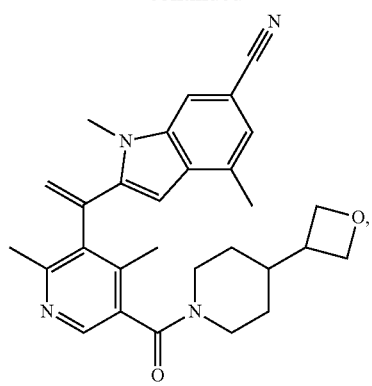
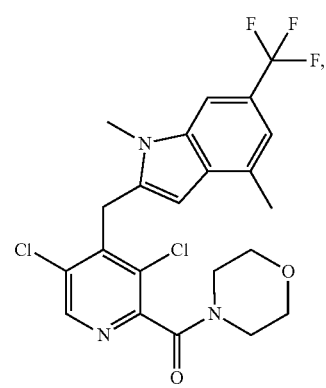
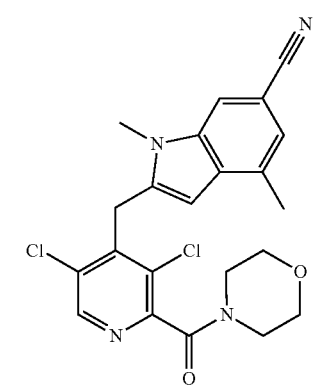
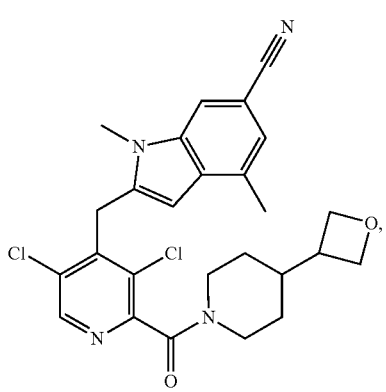
878
-continued
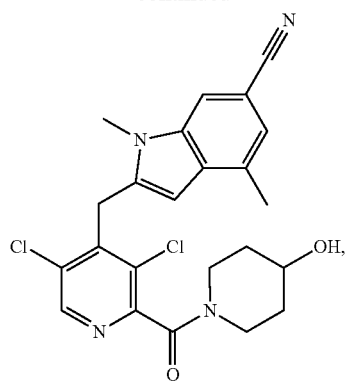
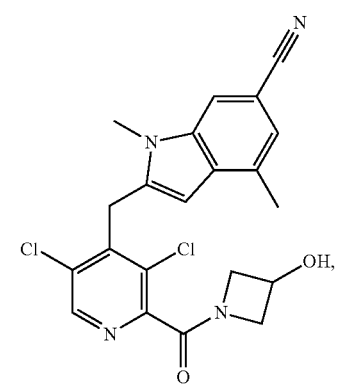
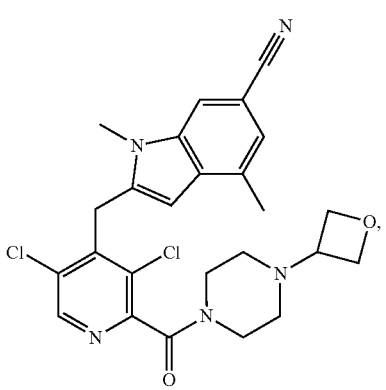
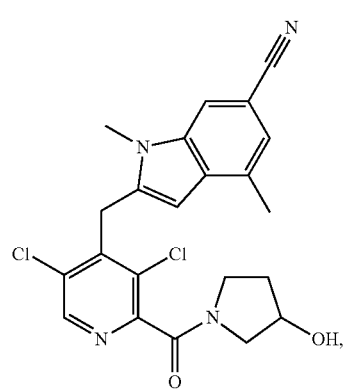

879
-continued
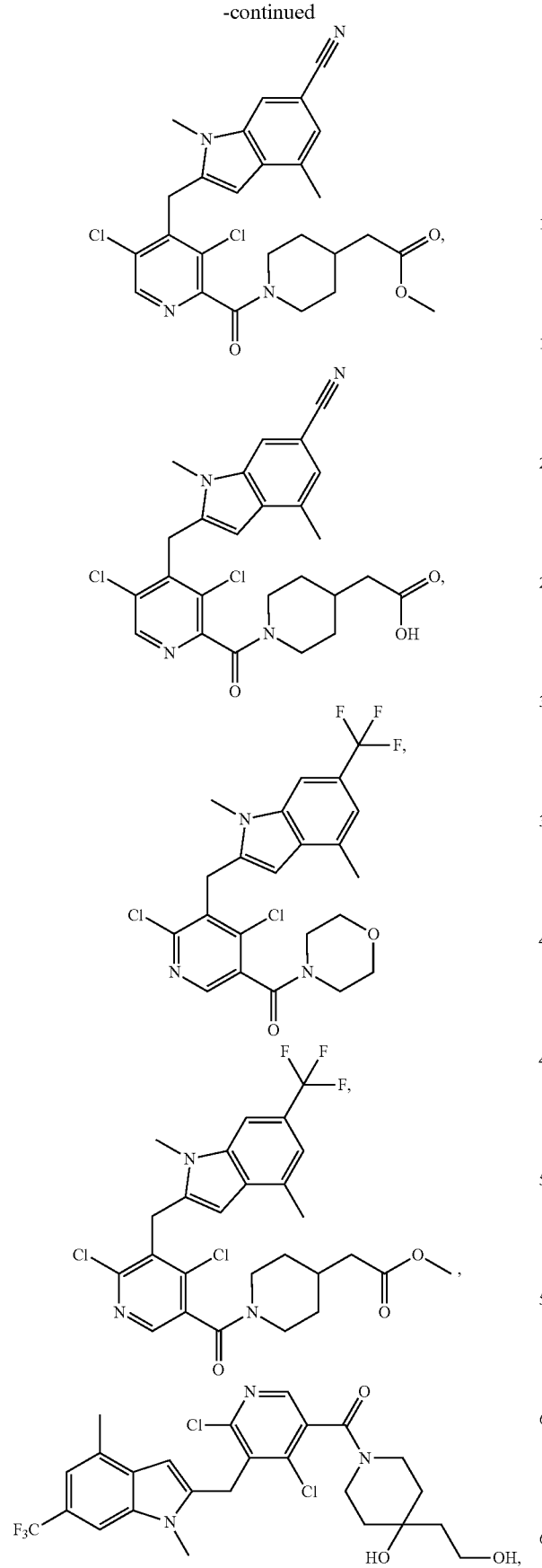
880
-continued
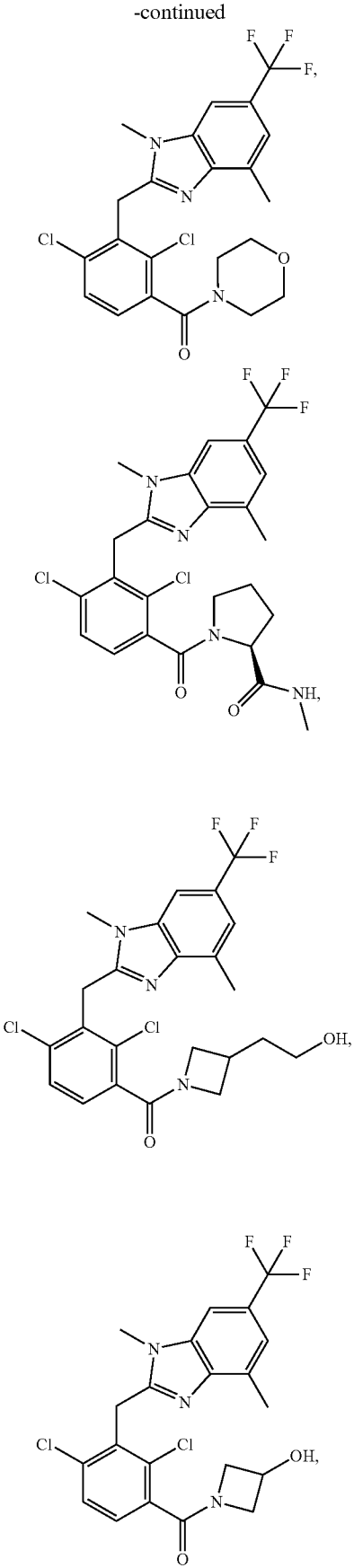

881
-continued
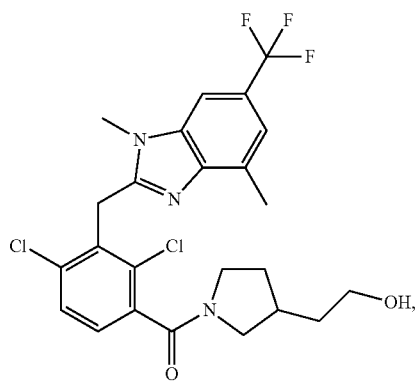
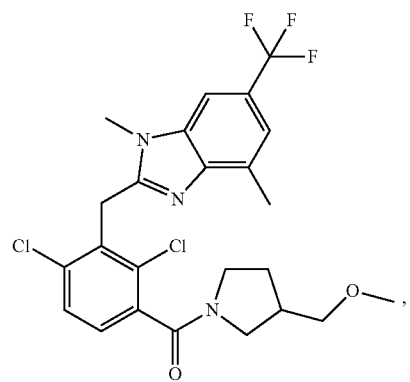
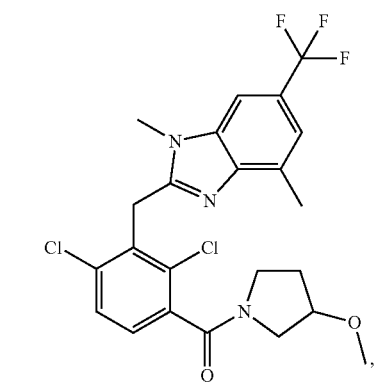
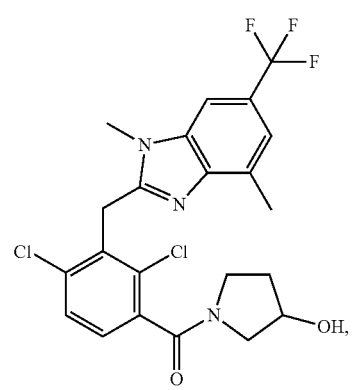
882
-continued
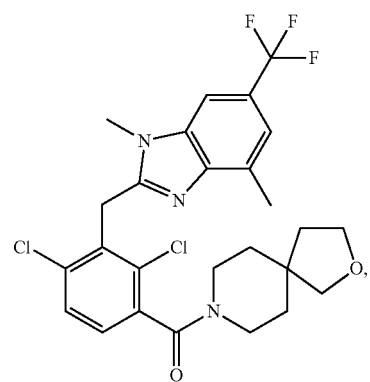
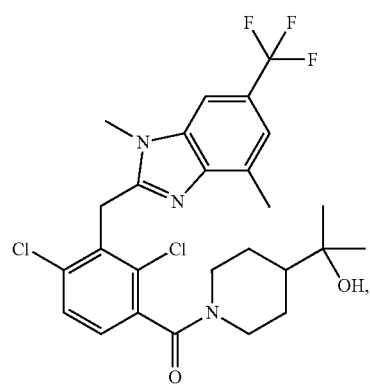
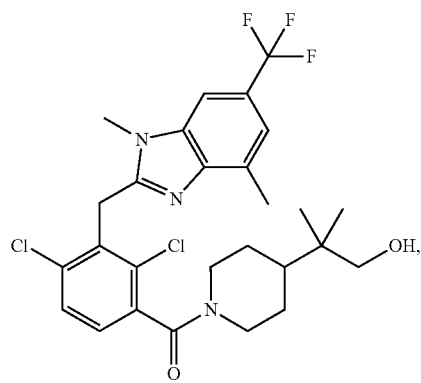
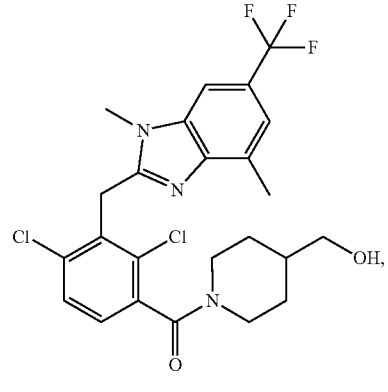

883
-continued
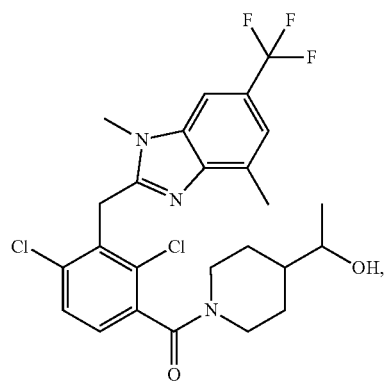
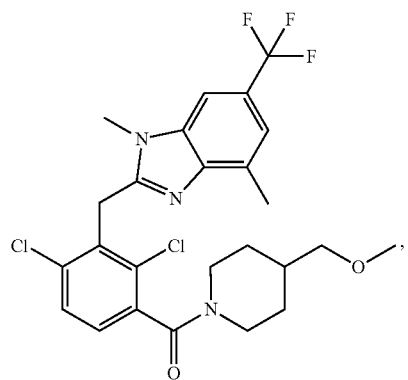
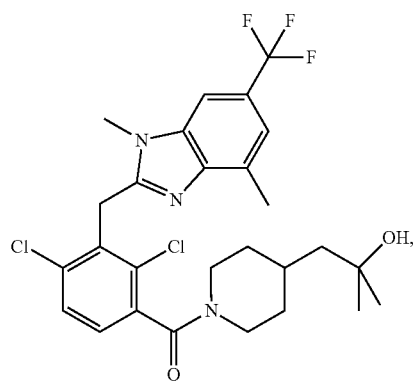
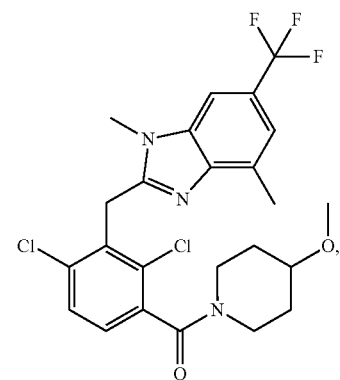
884
-continued
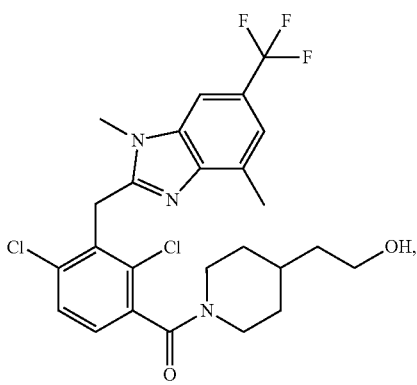
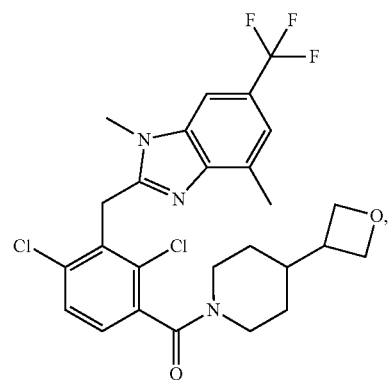
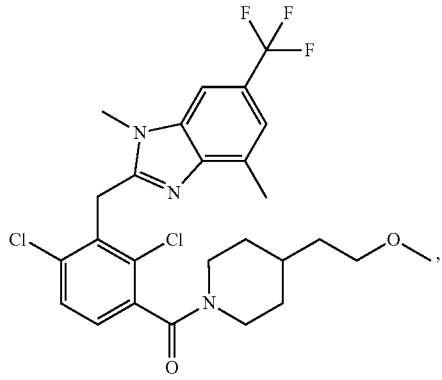
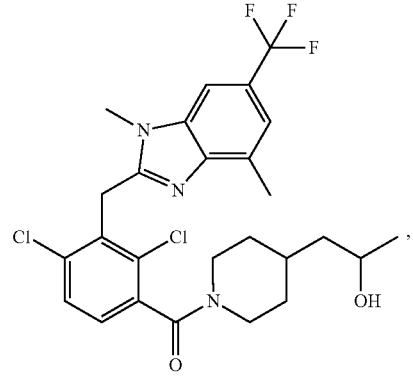

885
-continued
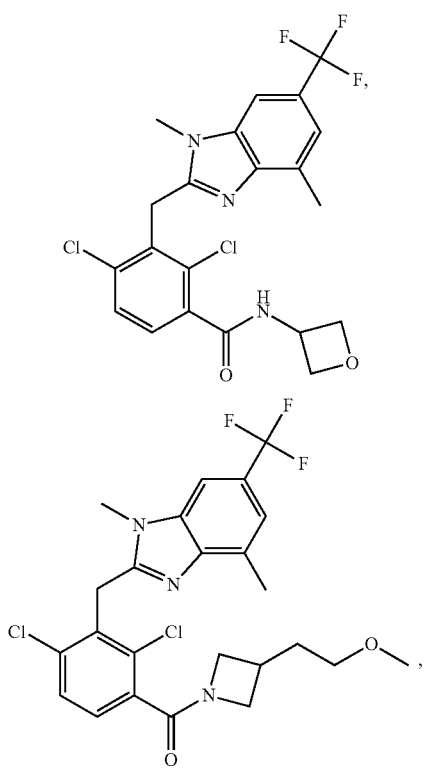
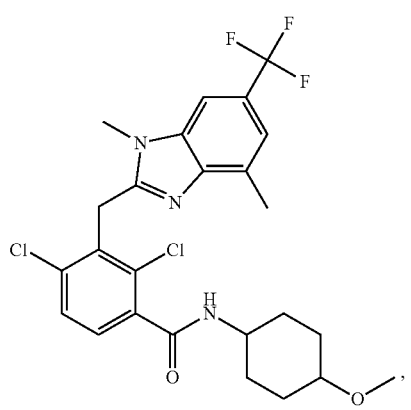
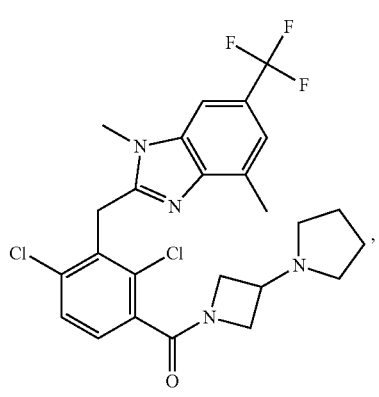
886
-continued
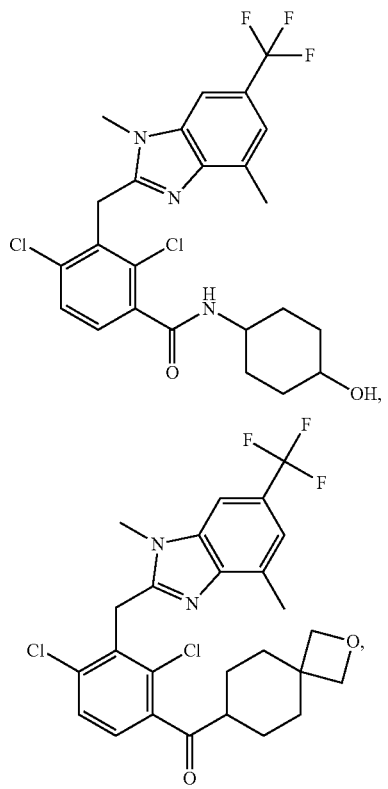
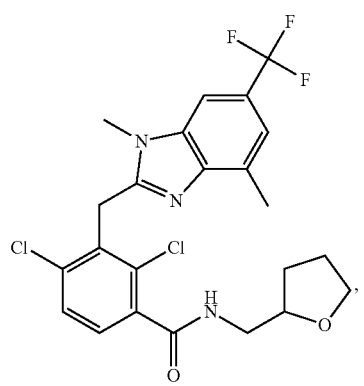
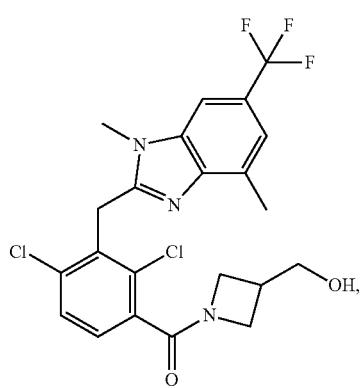

887
-continued
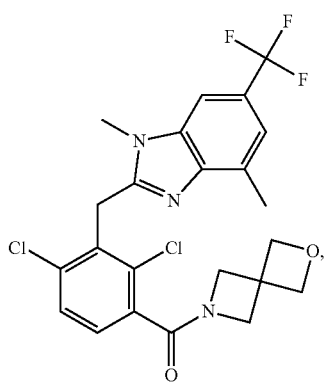
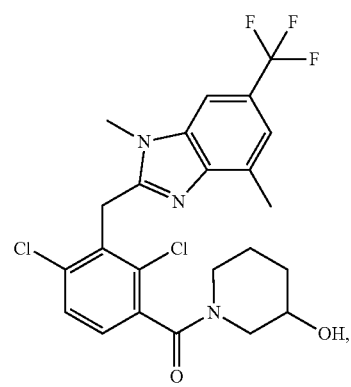
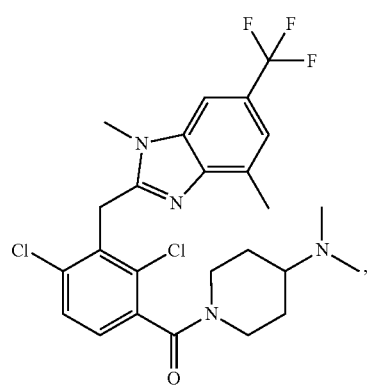
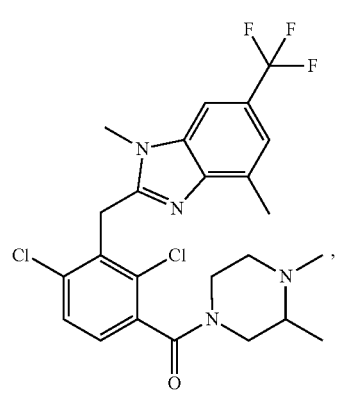
888
-continued
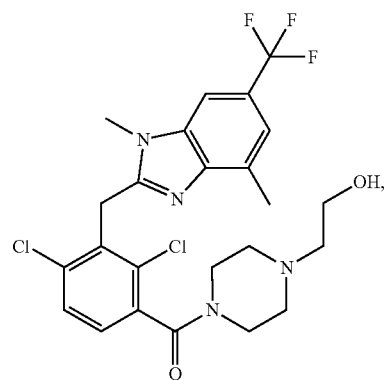
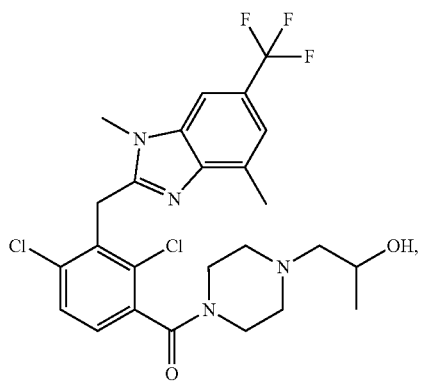
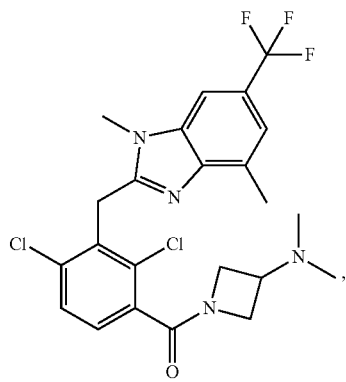
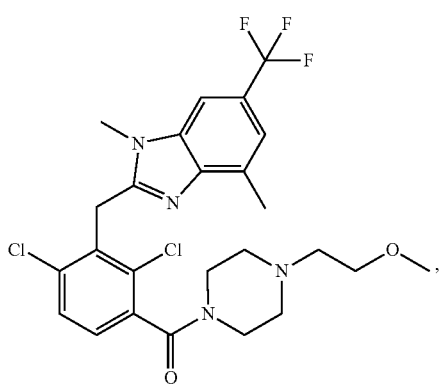

889
-continued
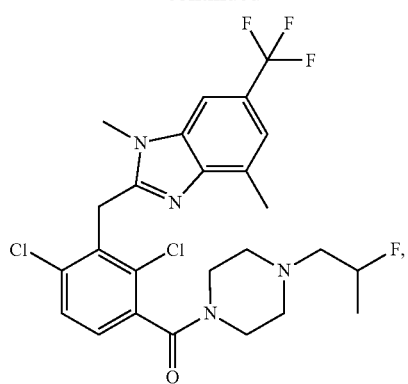
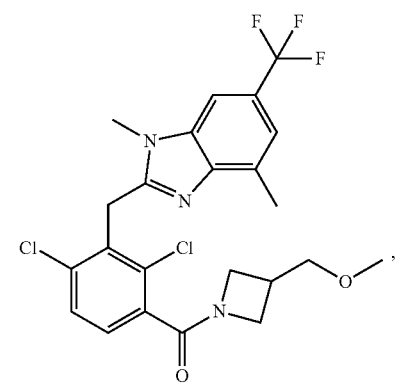
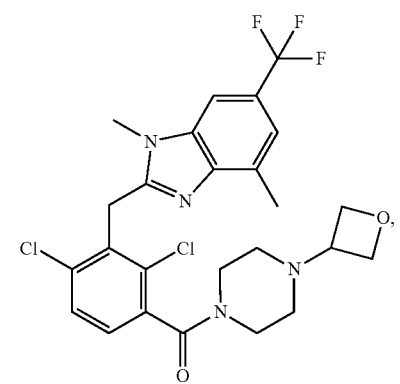
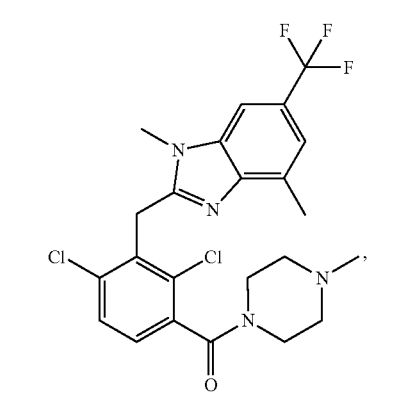
890
-continued
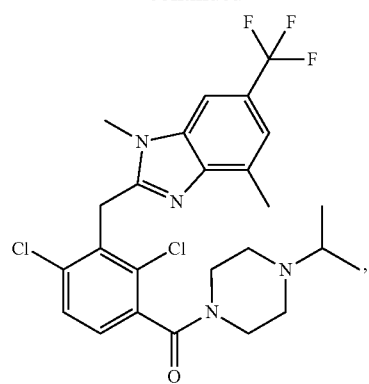
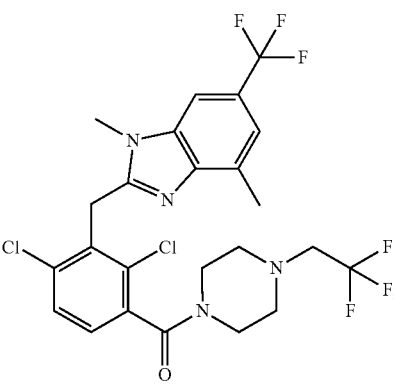
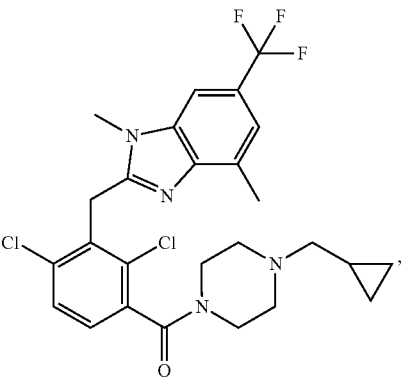
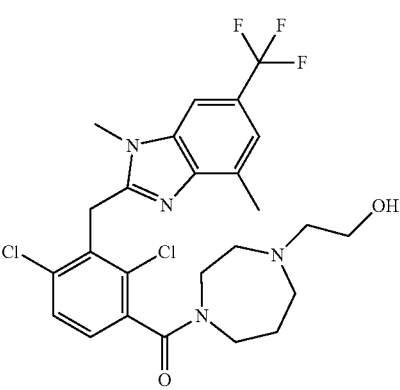

891
-continued
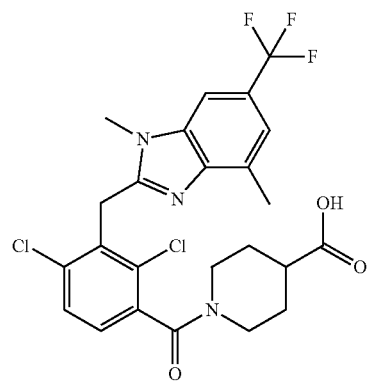
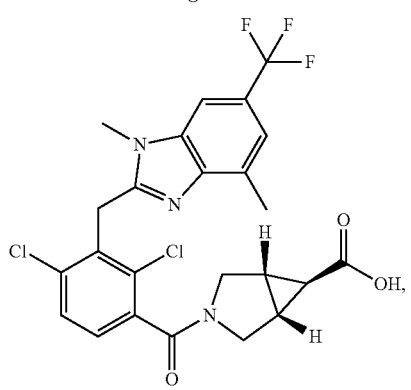
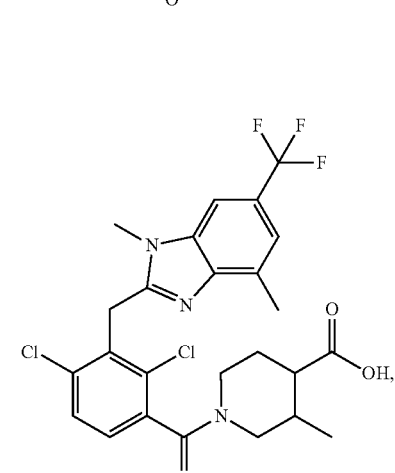
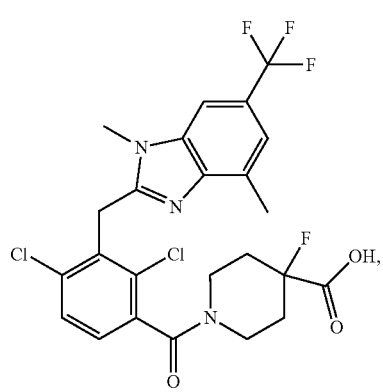
892
-continued
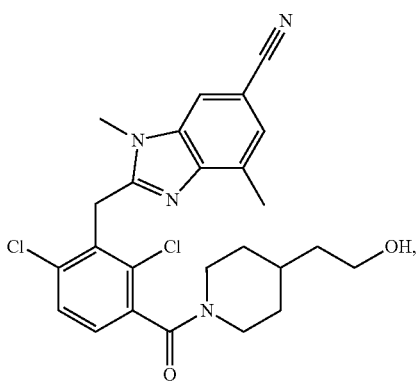
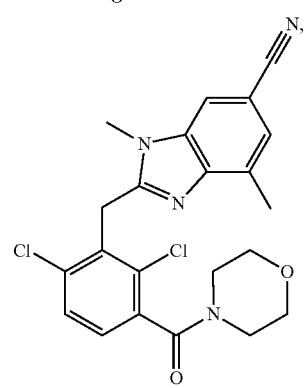
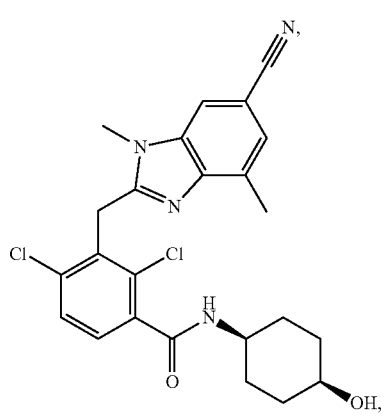
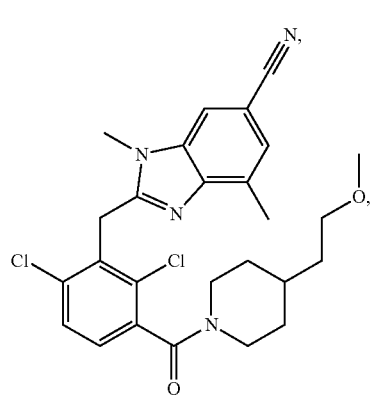

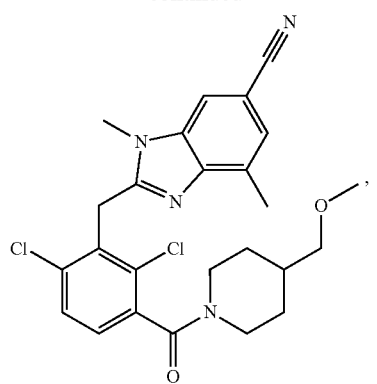
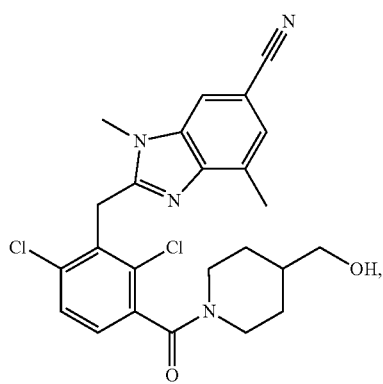
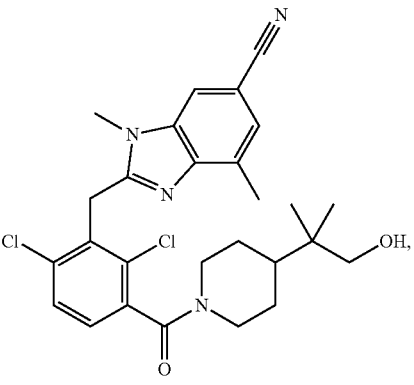
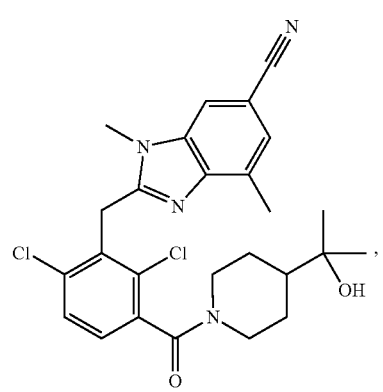
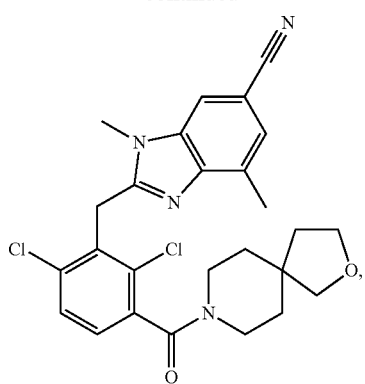
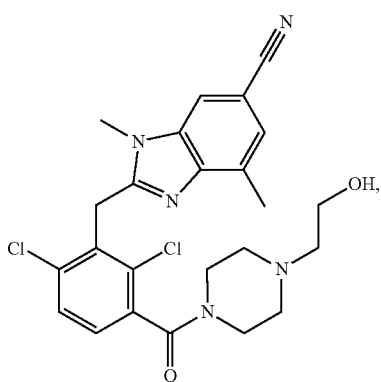
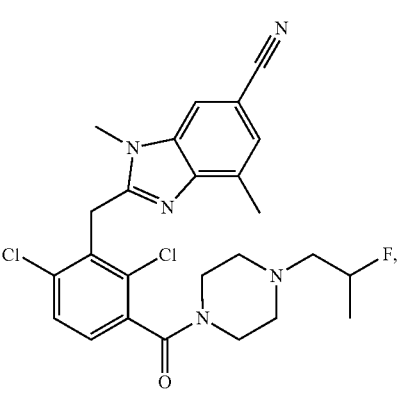

895
-continued
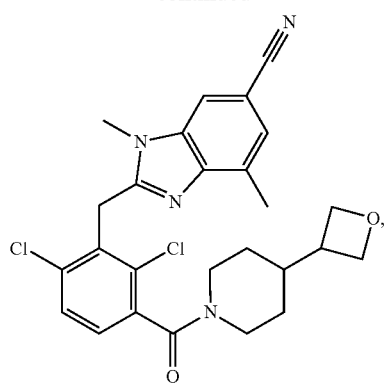
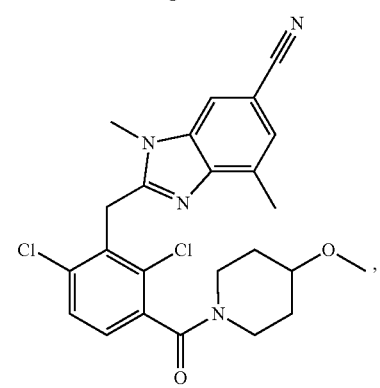
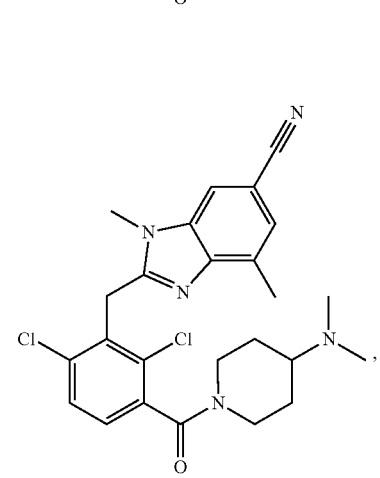
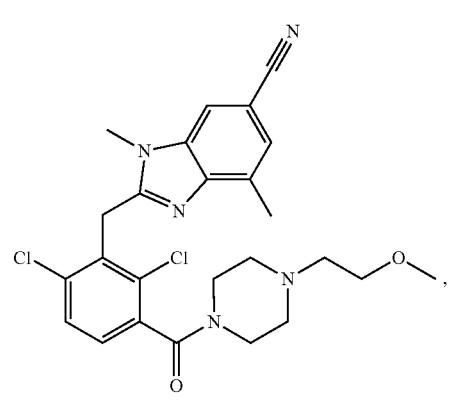
896
-continued
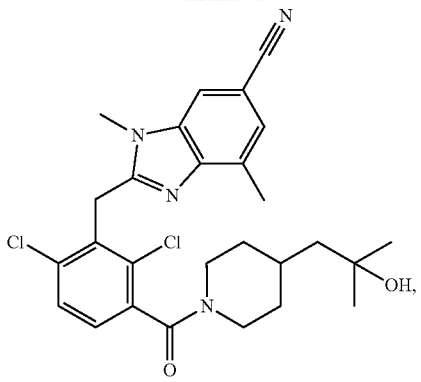
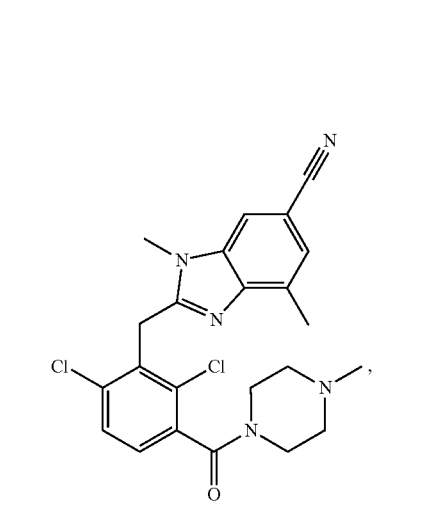
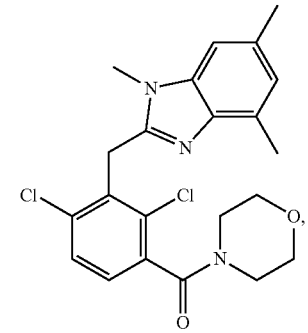
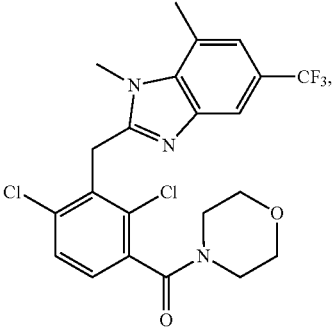

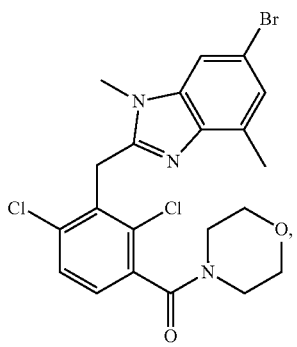
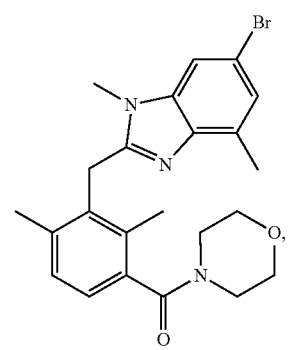
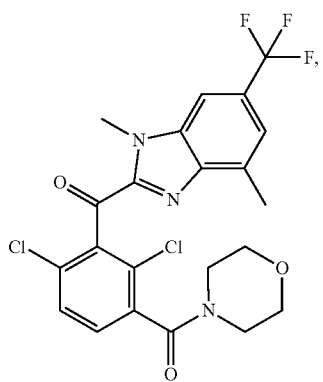
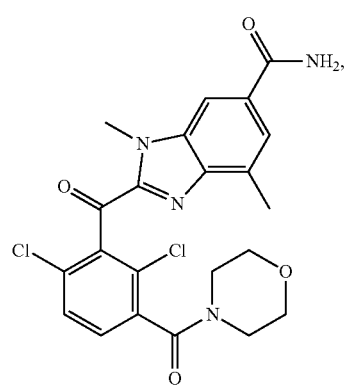
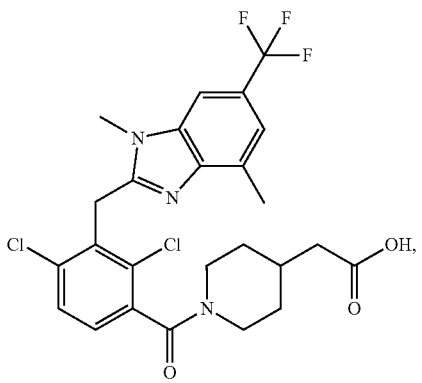
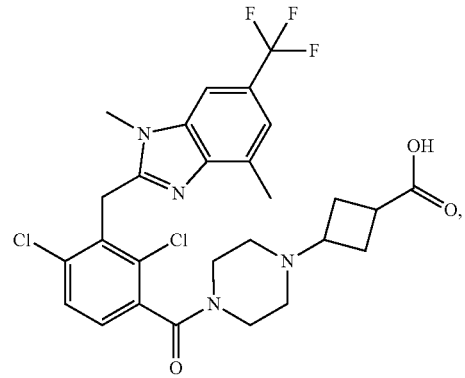
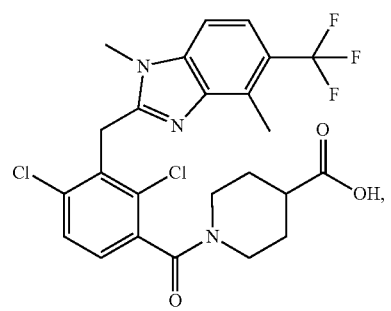
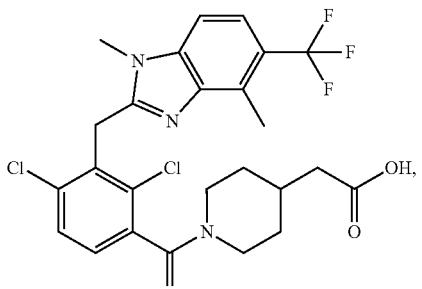
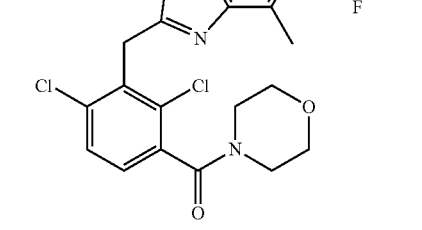

899
-continued
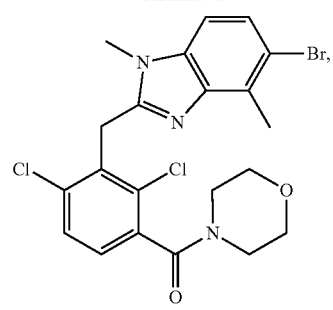
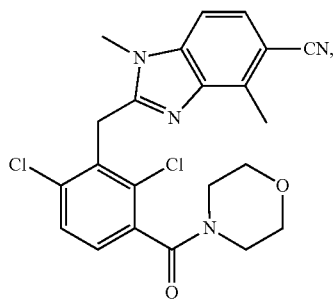
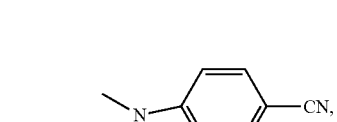
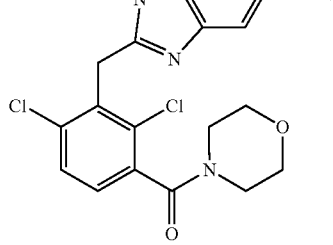
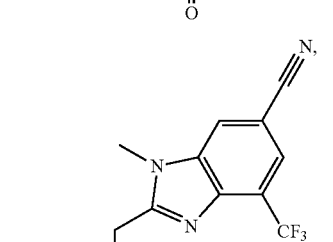
900
-continued
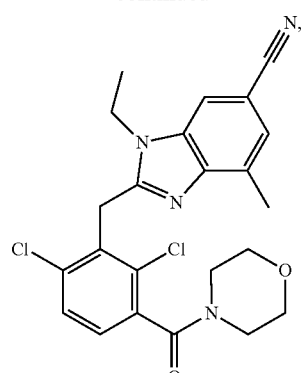
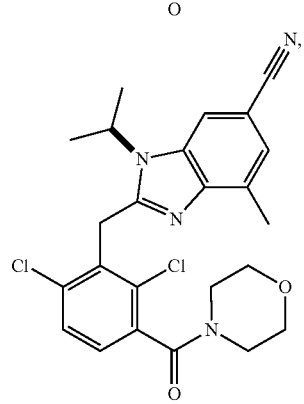
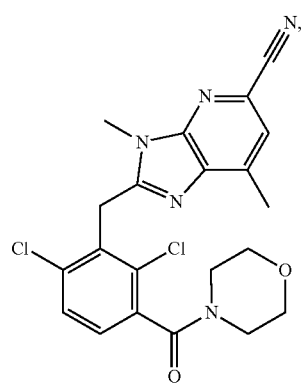
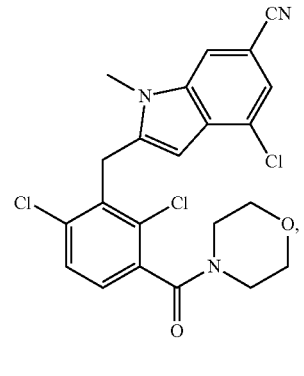

901
-continued
902
-continued
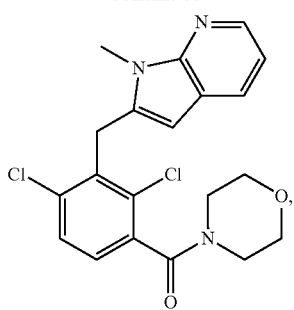
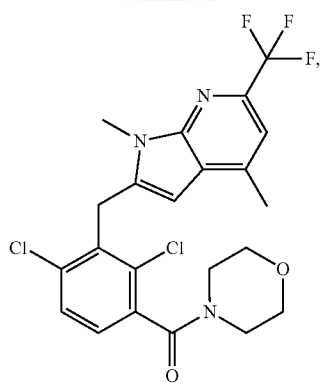
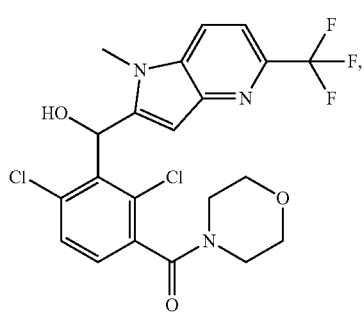
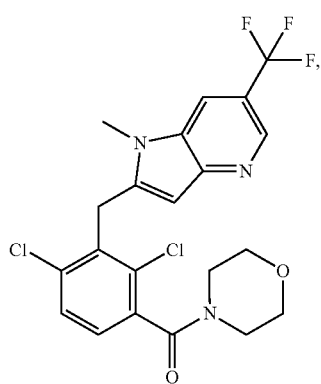

903
-continued
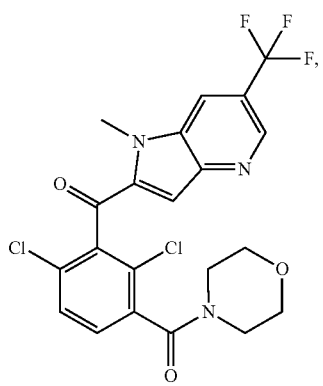
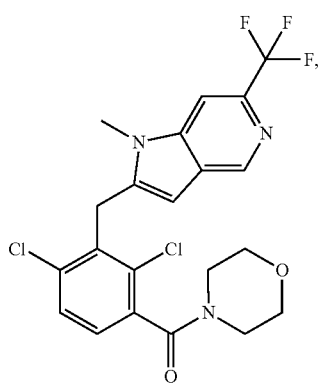
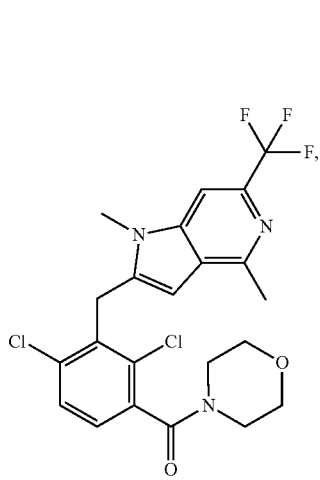
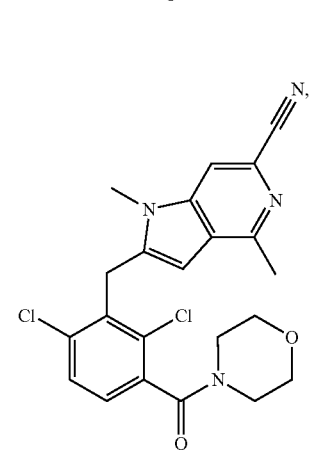
904
-continued
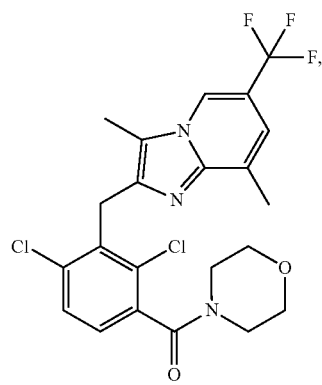
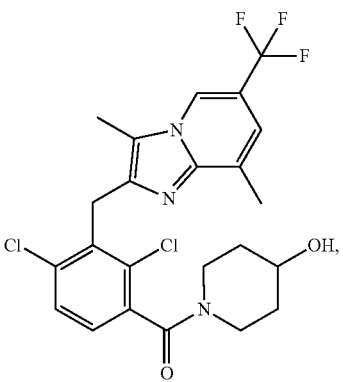
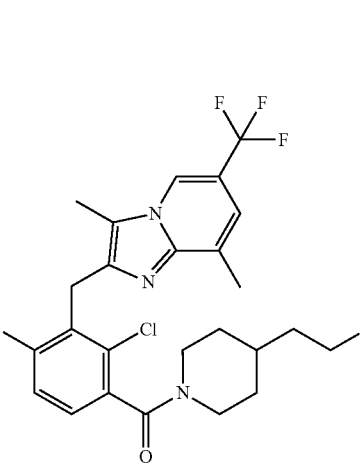
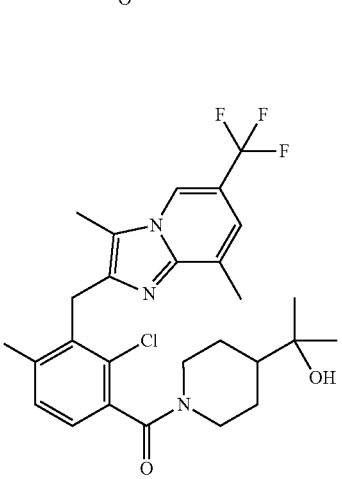

905
-continued
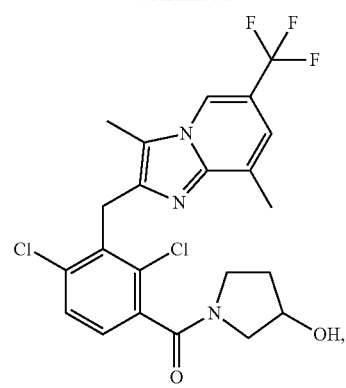
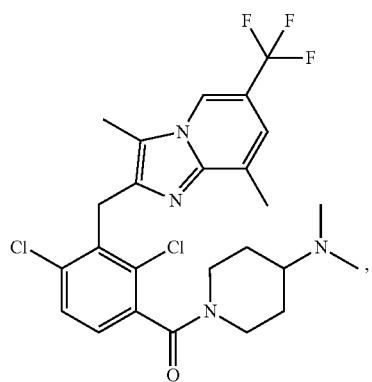
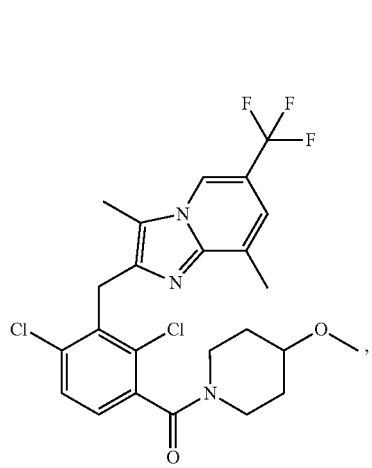
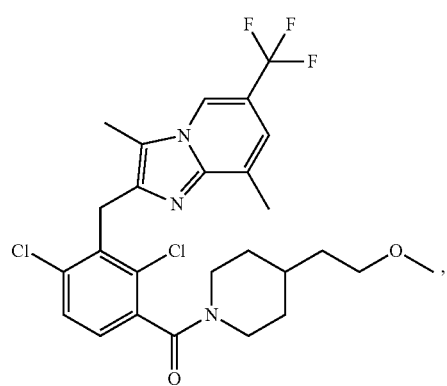
906
-continued
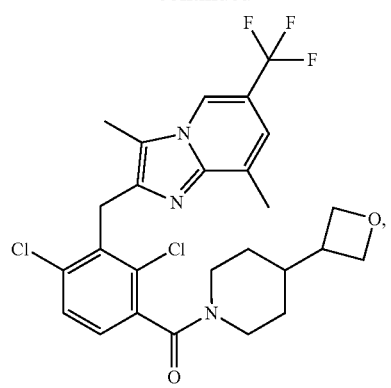
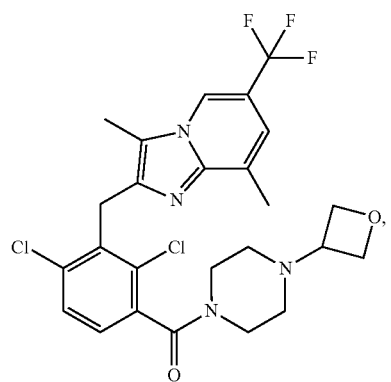
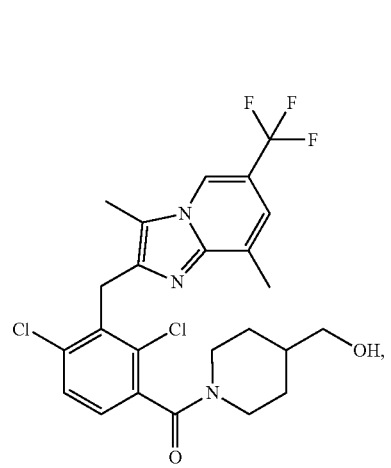
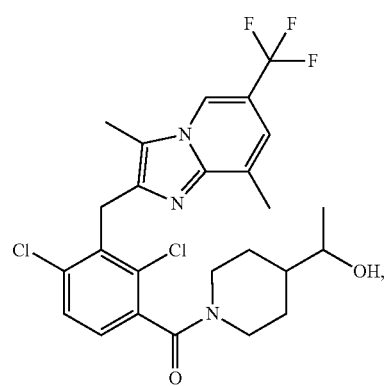

907
-continued
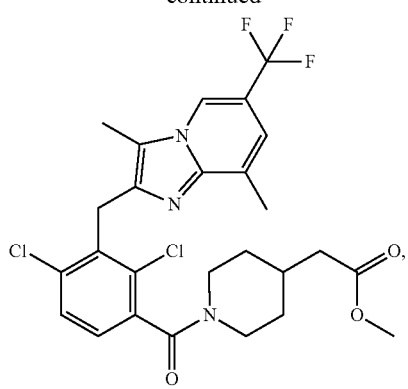
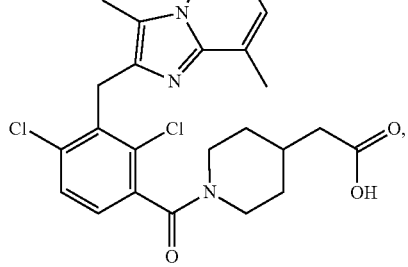
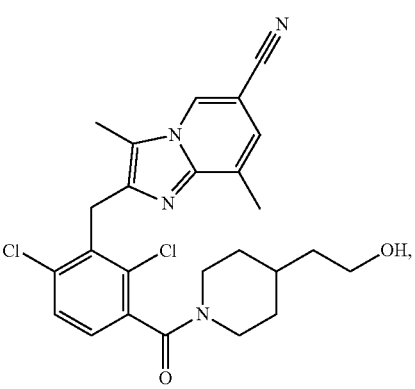
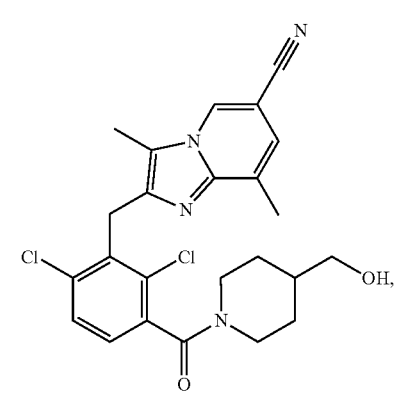
908
-continued
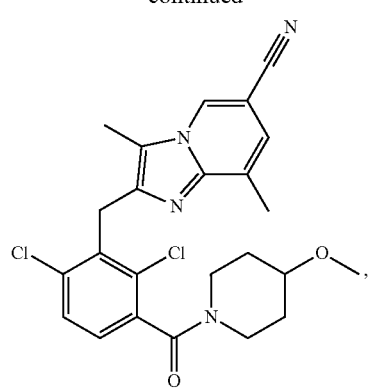
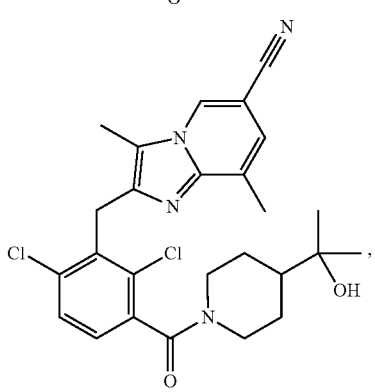
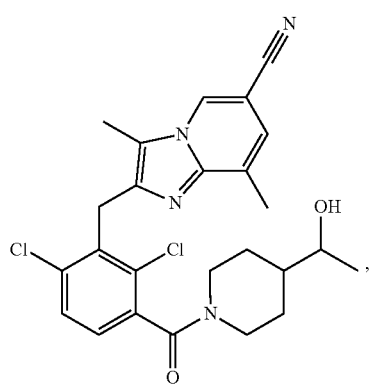
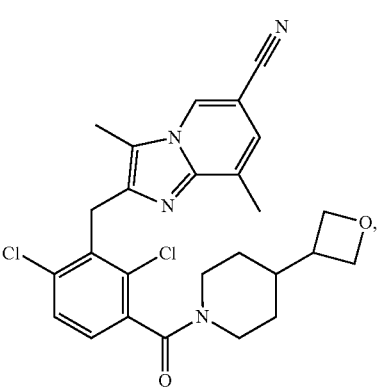

909
-continued
910
-continued
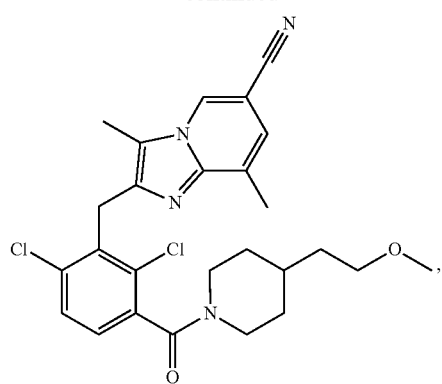
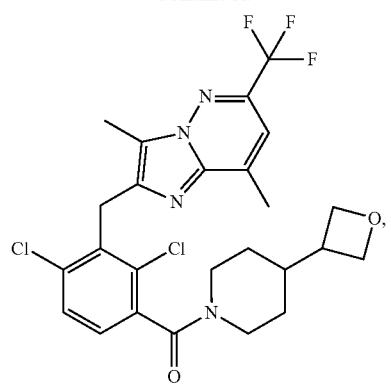

911
-continued
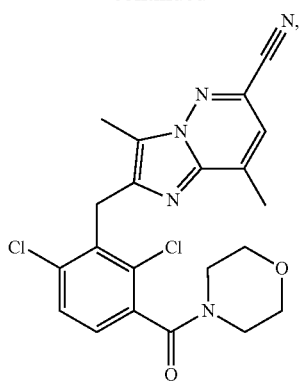
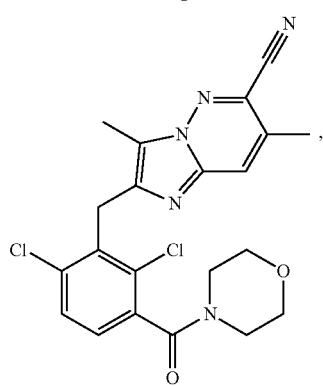
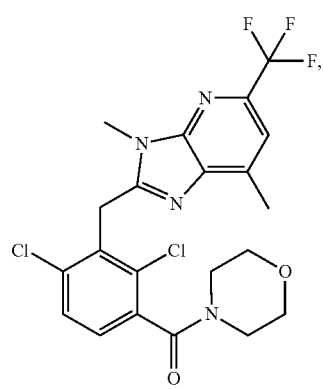
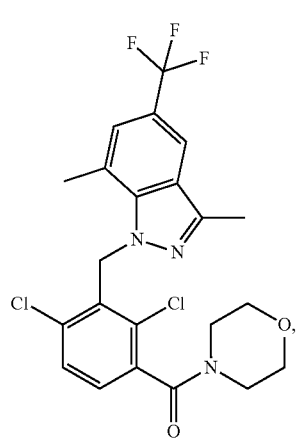
912
-continued
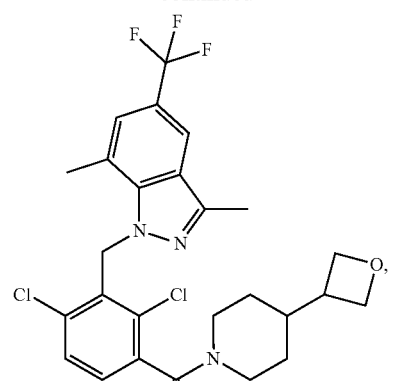
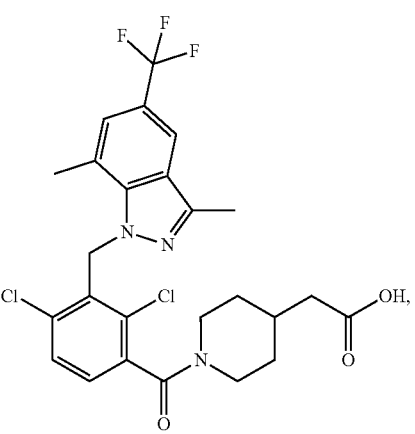
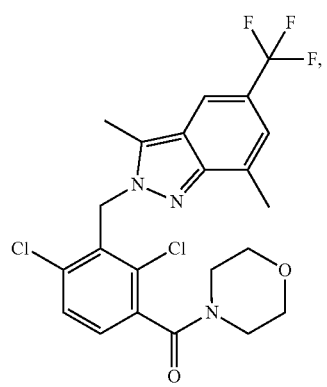
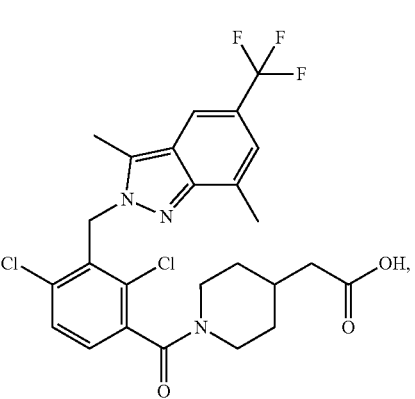

913
-continued
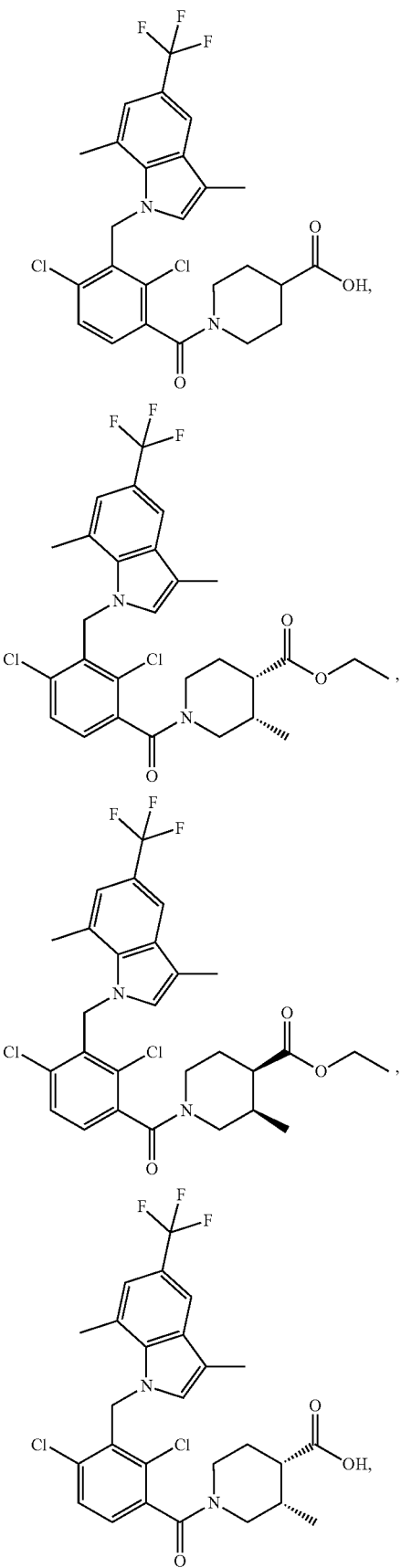
914
-continued
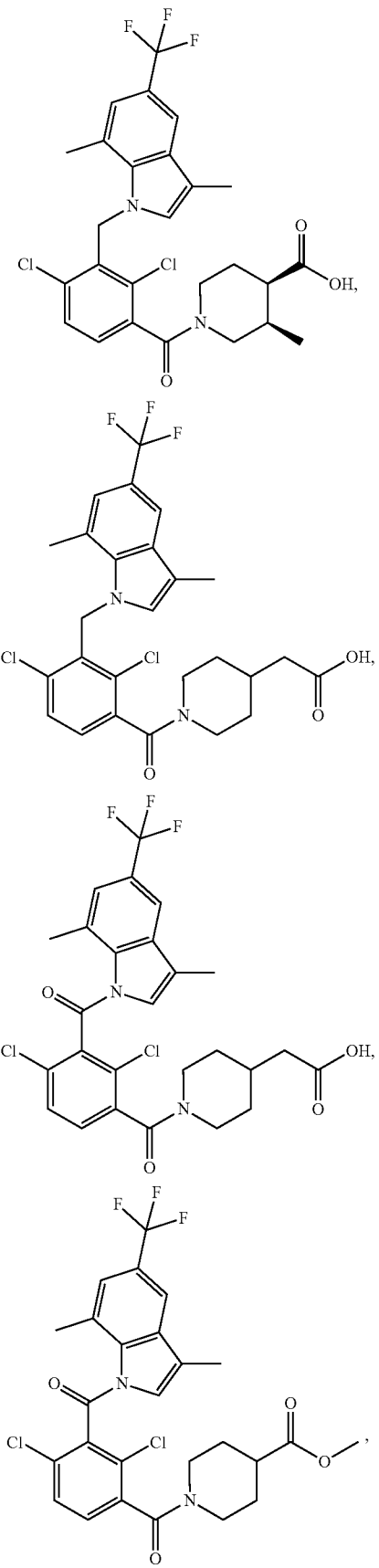

915
-continued
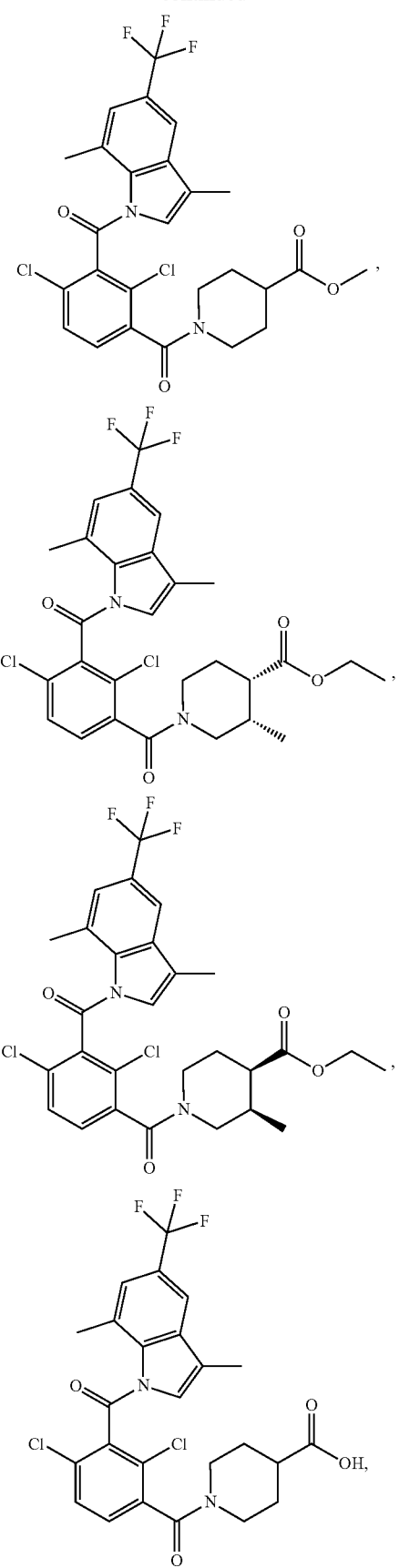
916
-continued
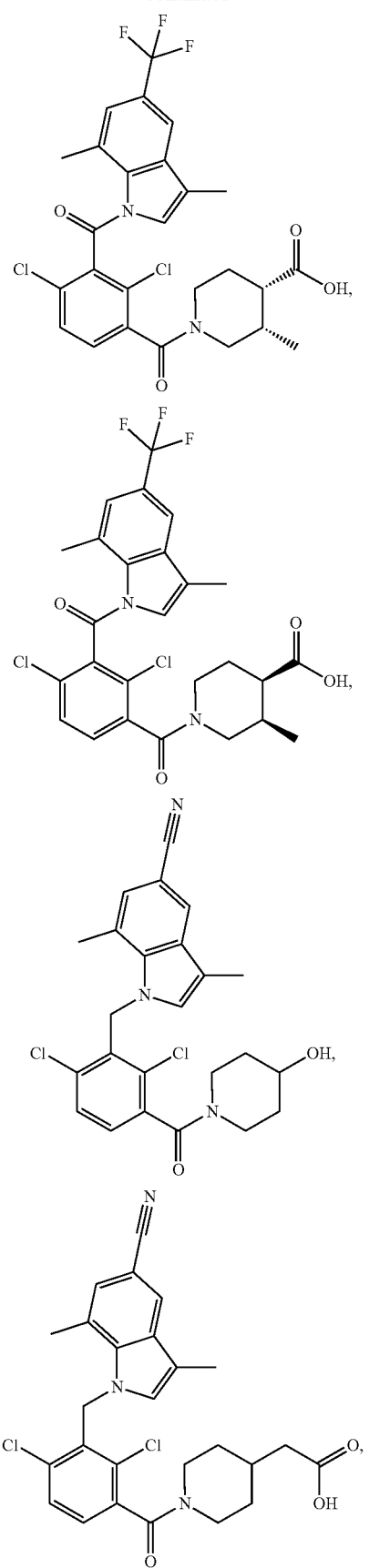

917
-continued
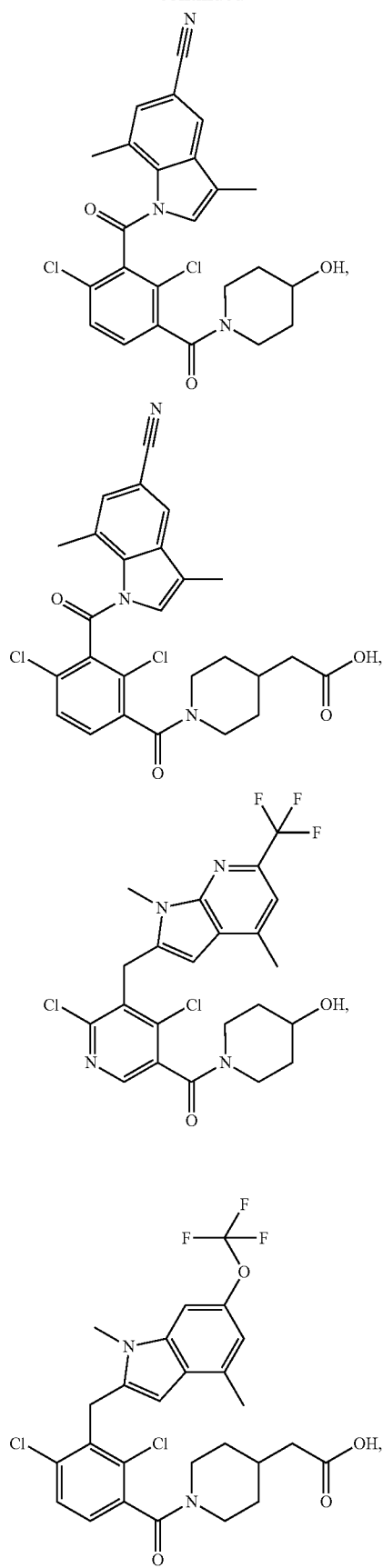
918
-continued
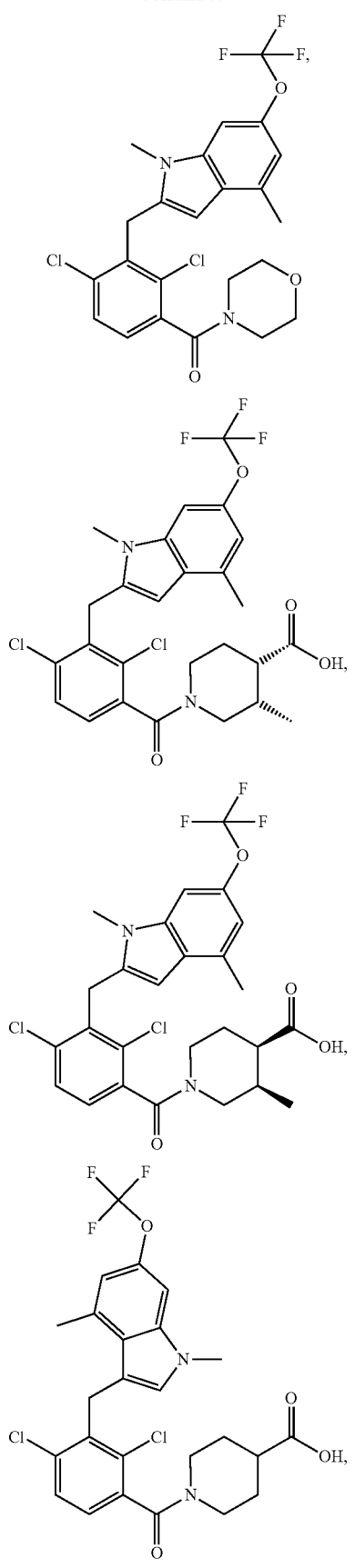

919
-continued
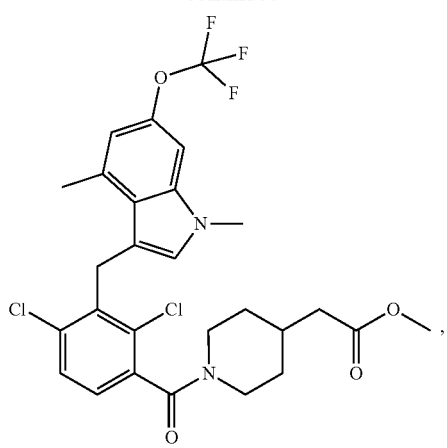
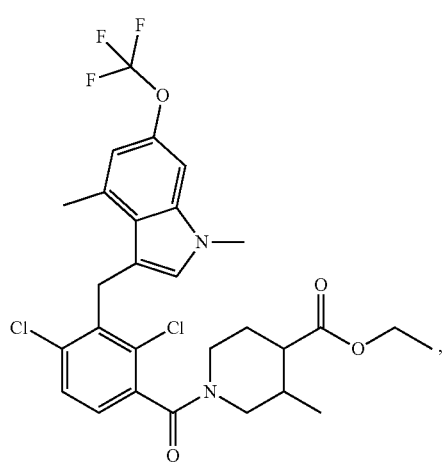
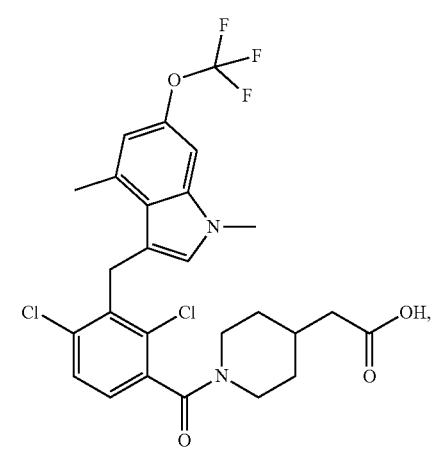
920
-continued
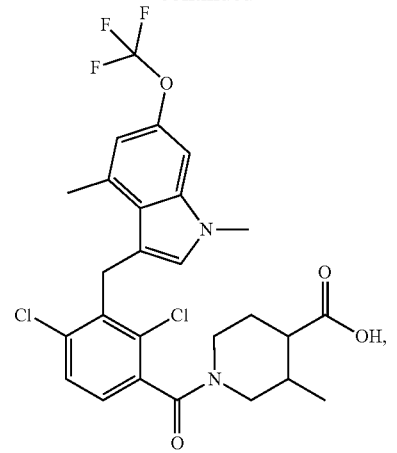
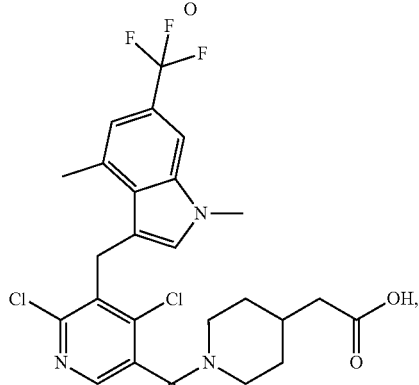
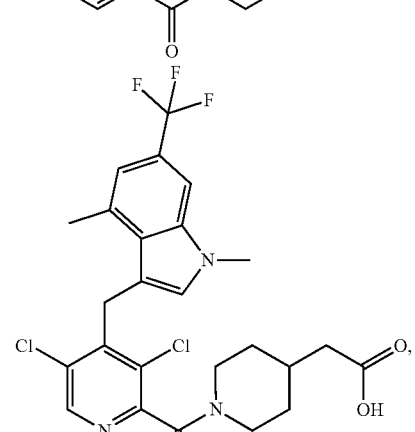
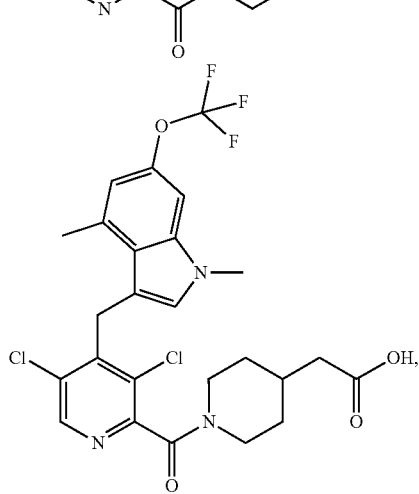

921
-continued
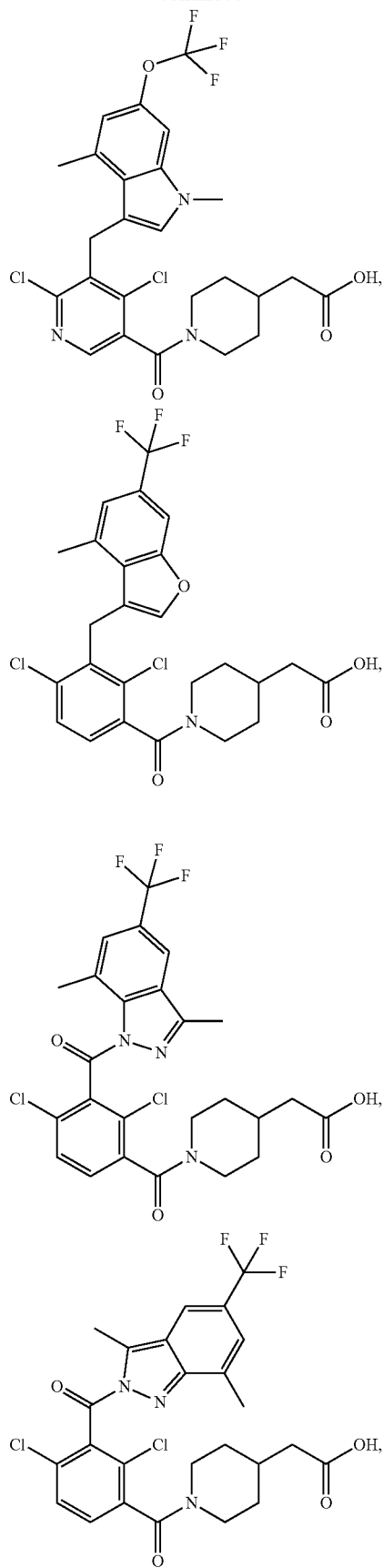
922
-continued
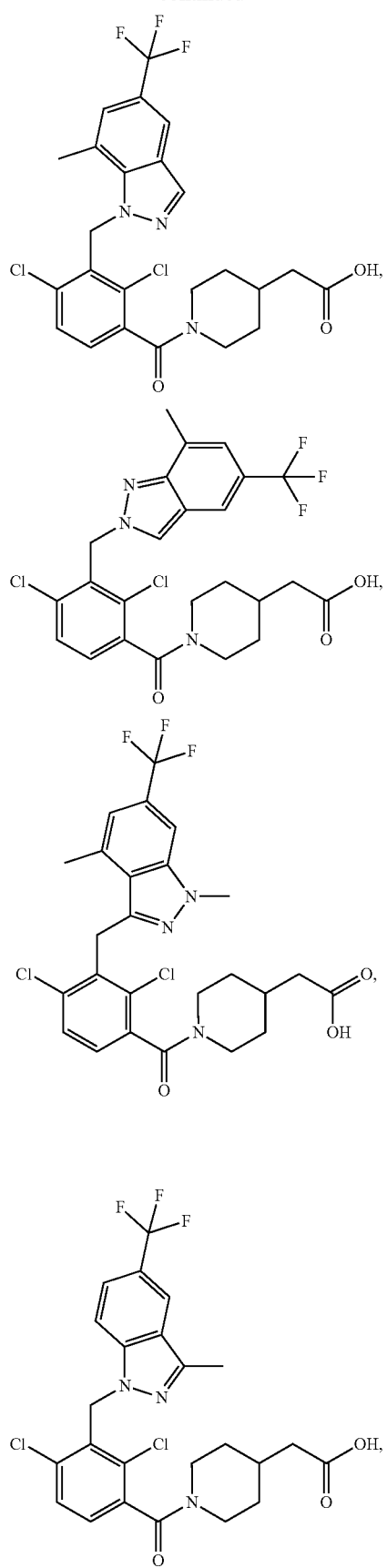

923
-continued
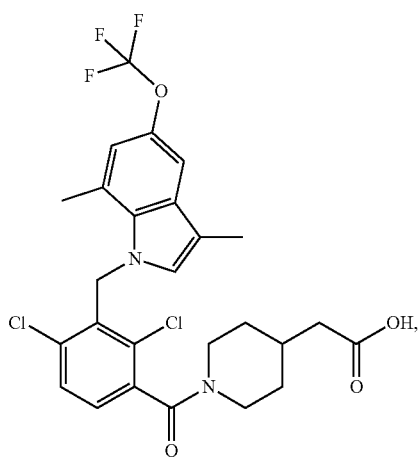
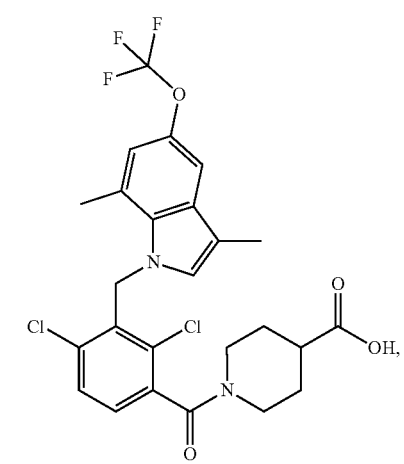
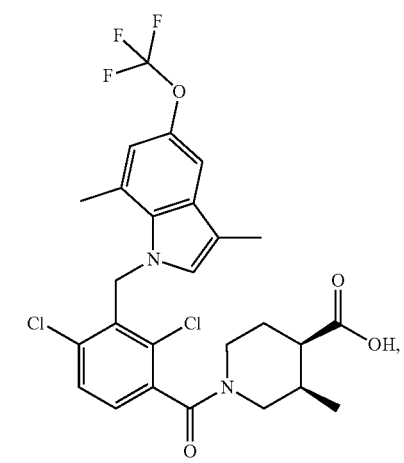
924
-continued
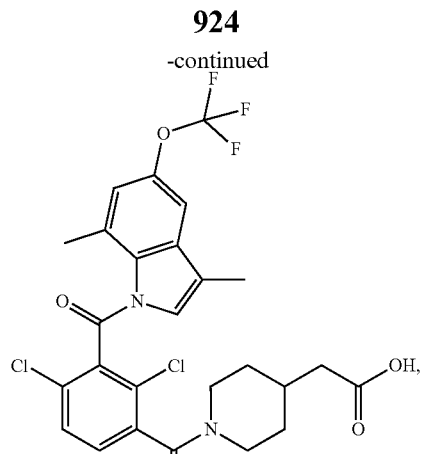
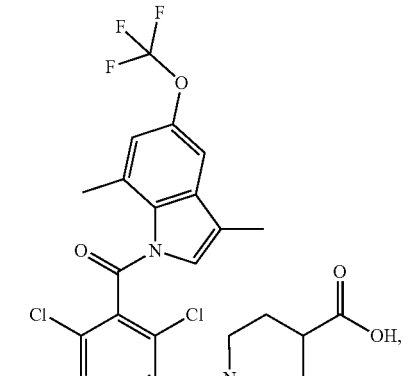
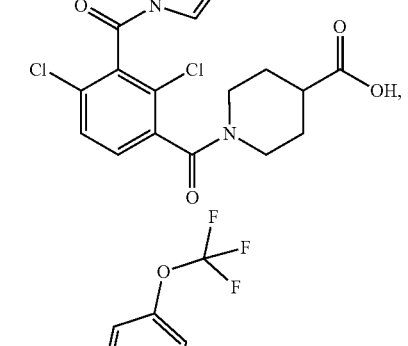
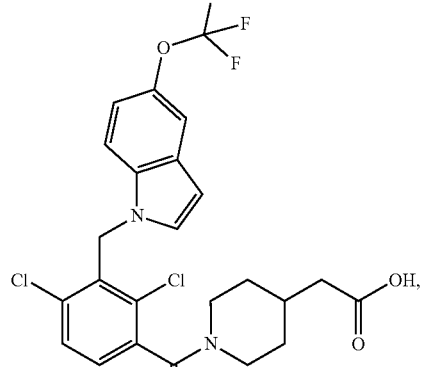
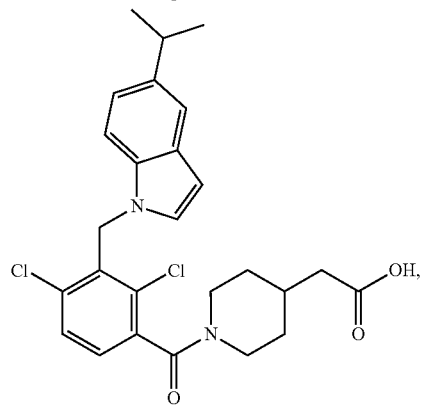

925
-continued
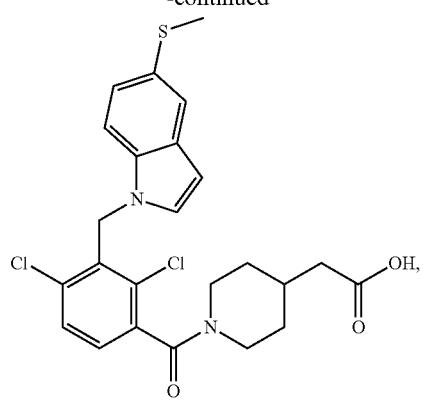
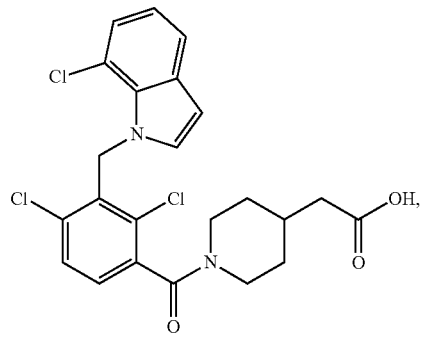
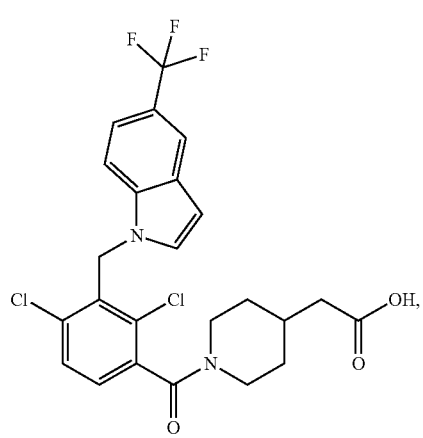
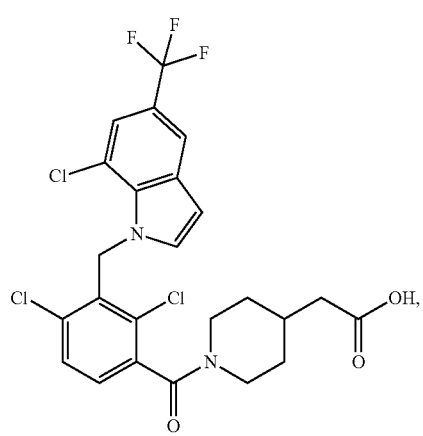
926
-continued
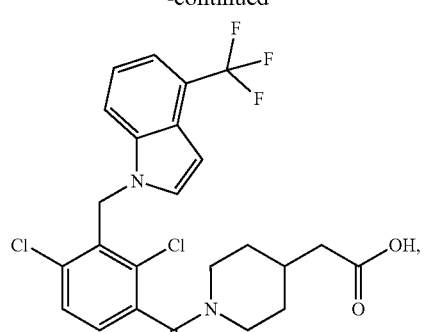
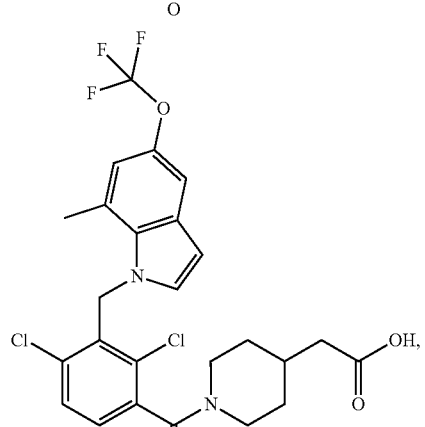
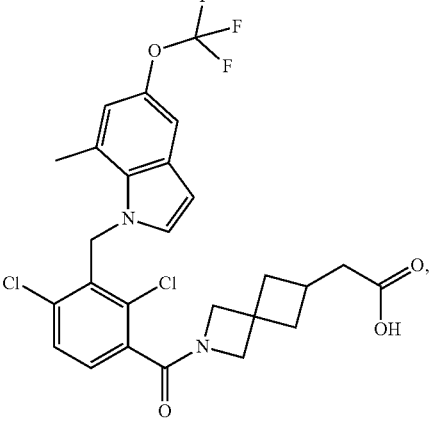
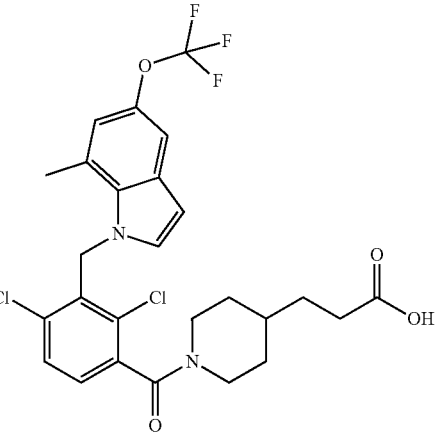

927
-continued
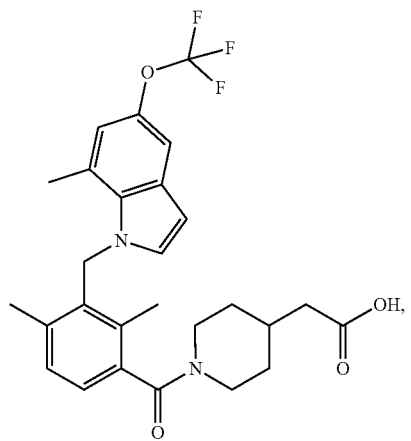
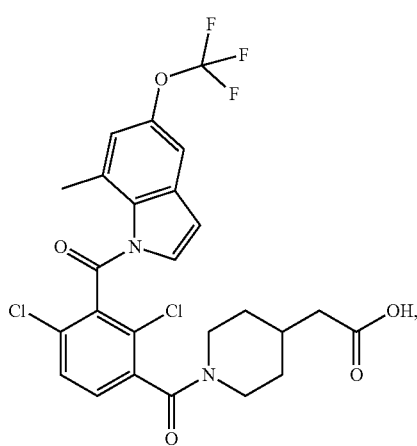
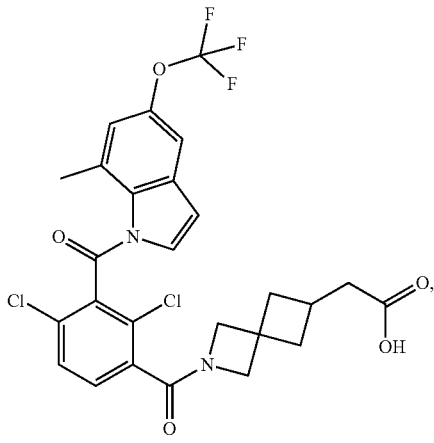
928
-continued
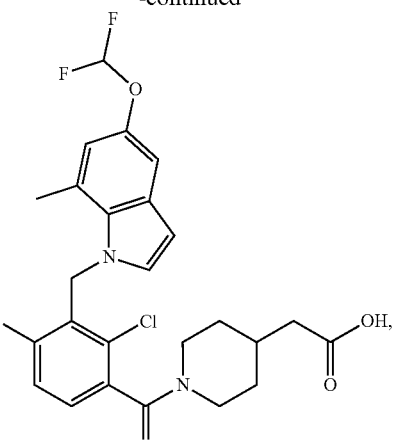
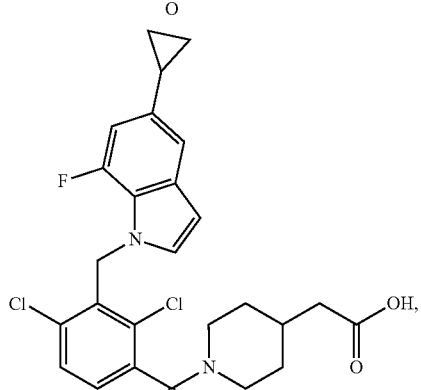
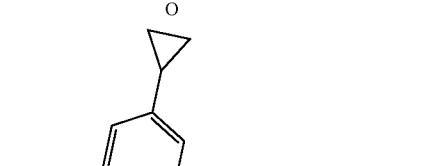
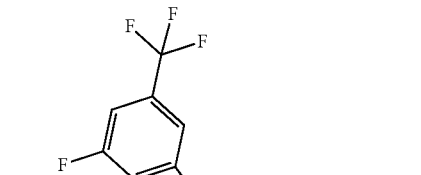
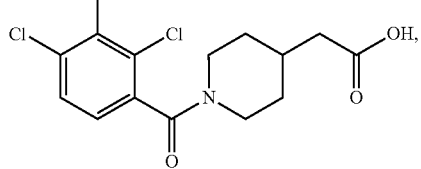

929
-continued
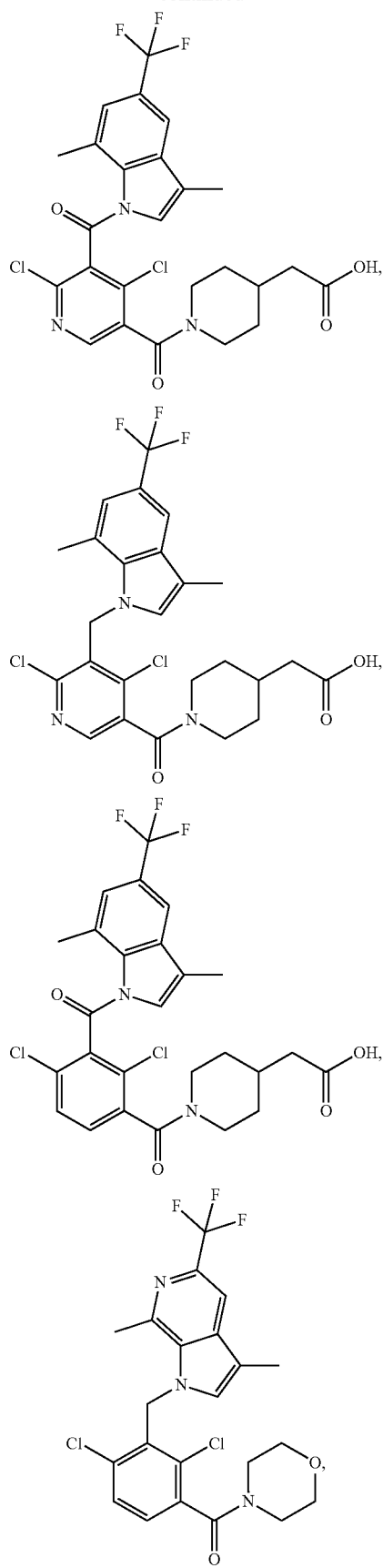
930
-continued
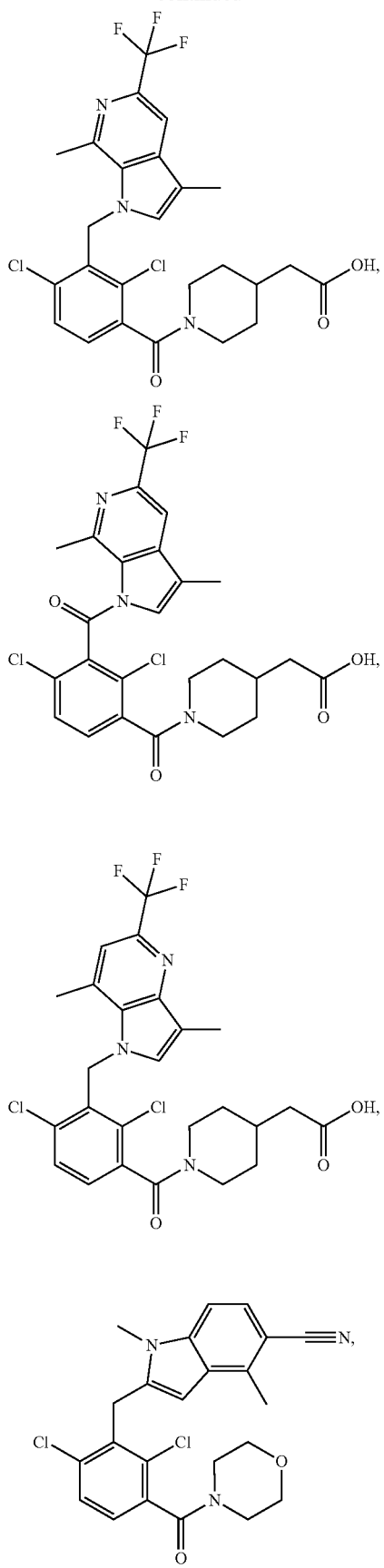

931
-continued
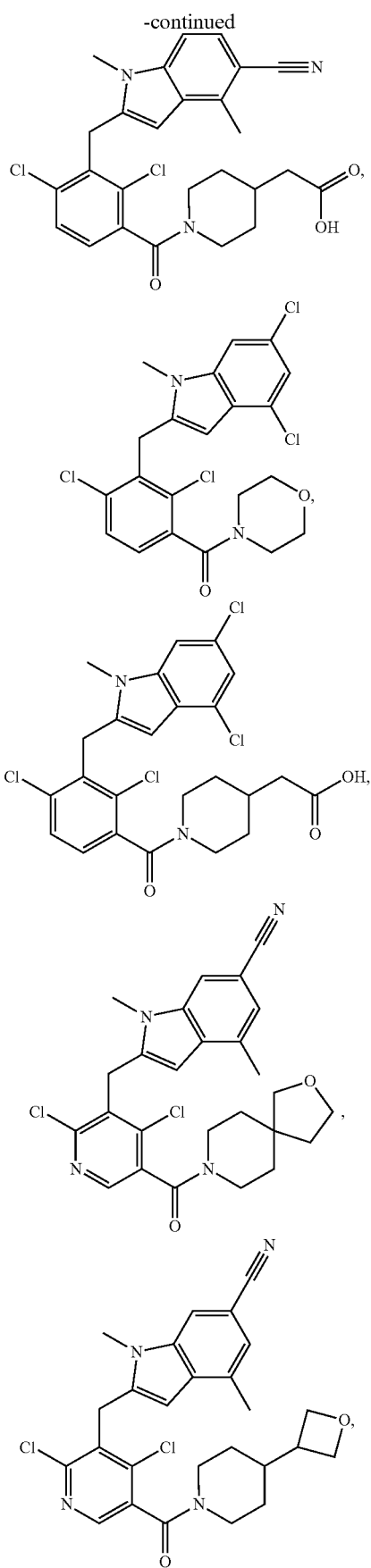
932
-continued
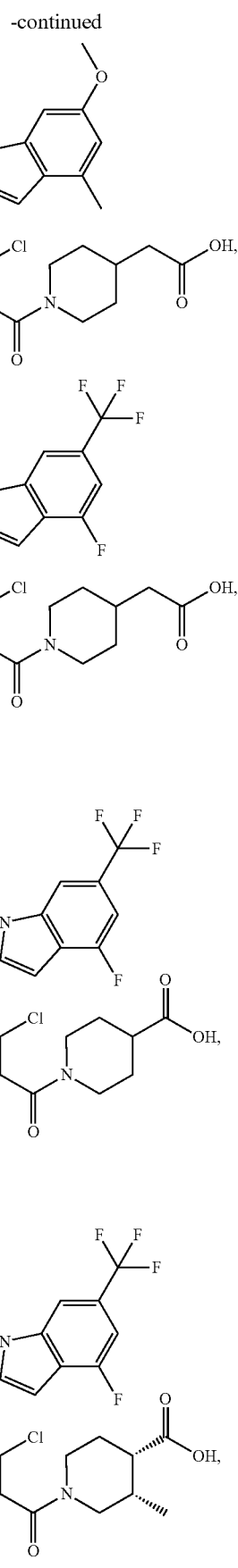

933
-continued
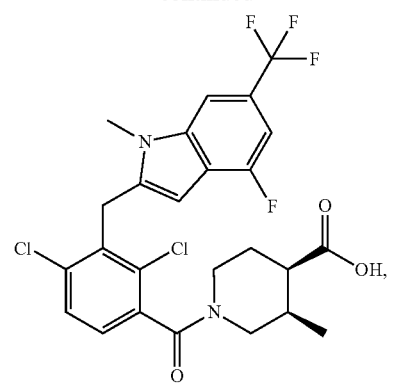
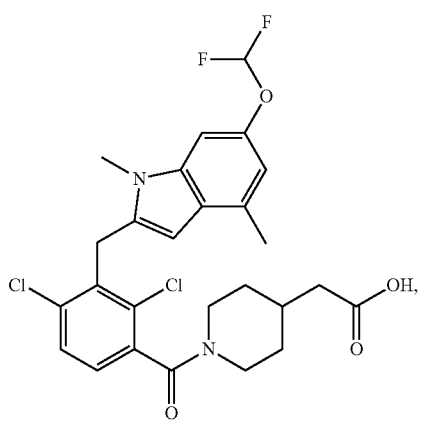
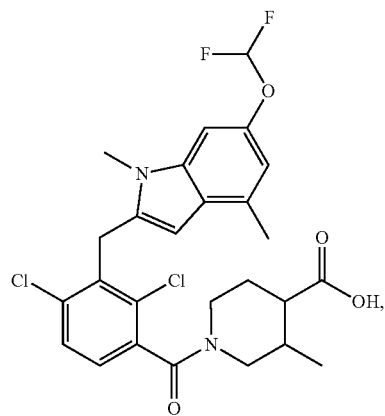
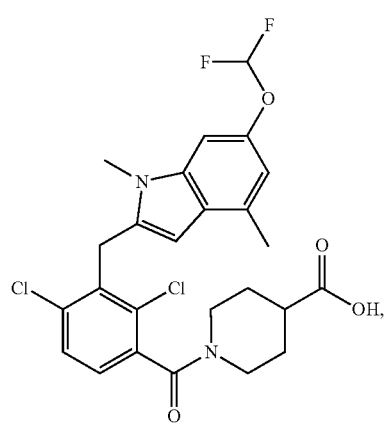
934
-continued
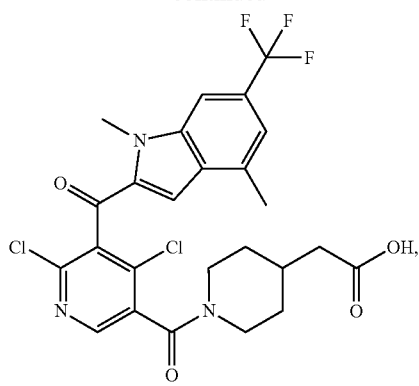
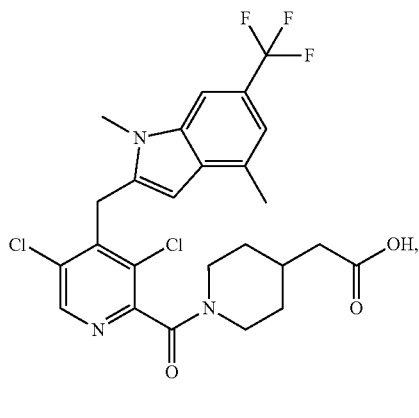
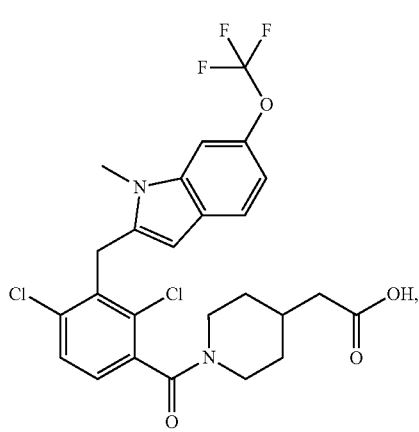
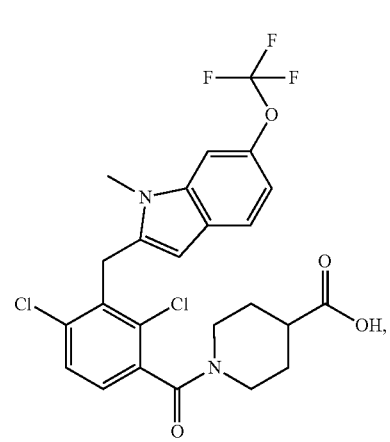

935
-continued
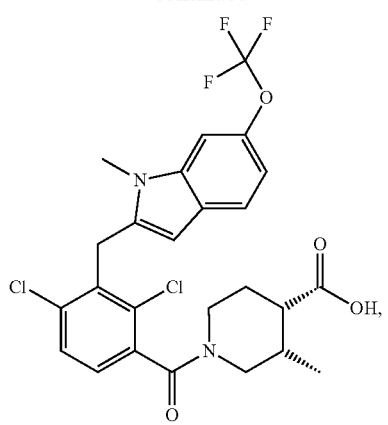
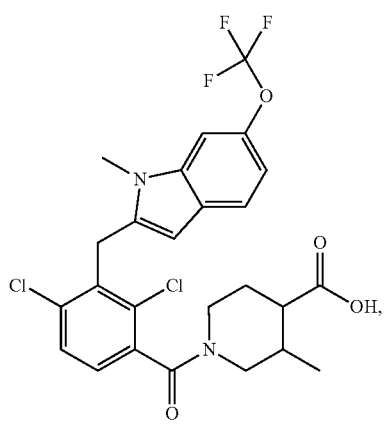
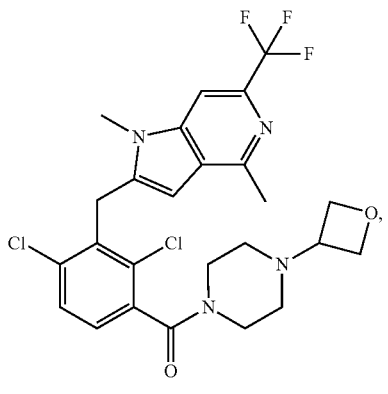
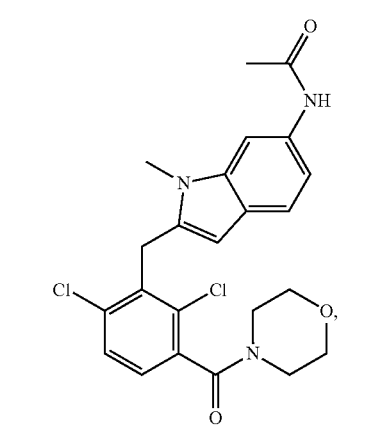
936
-continued
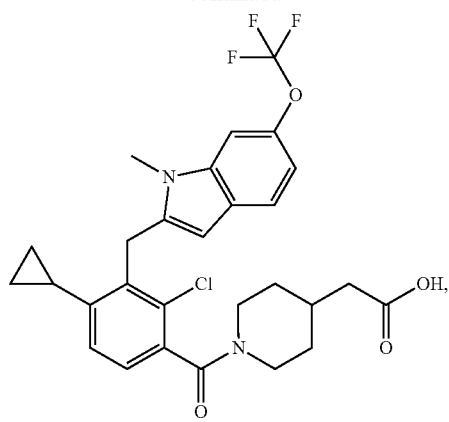
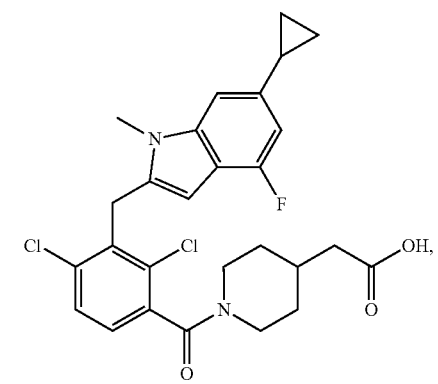
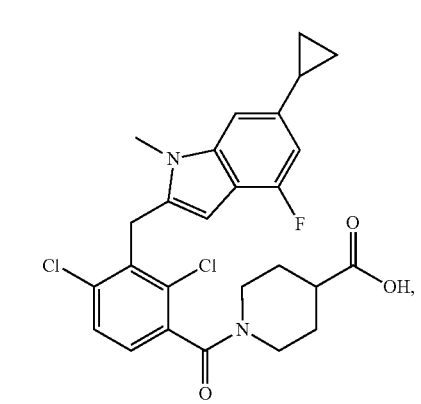
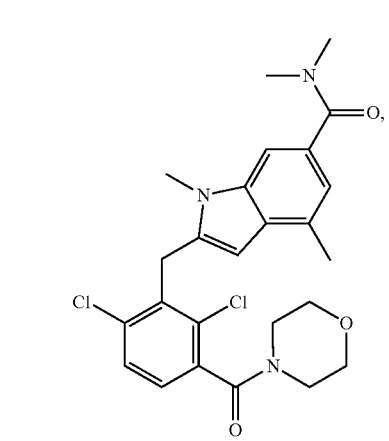

937
-continued
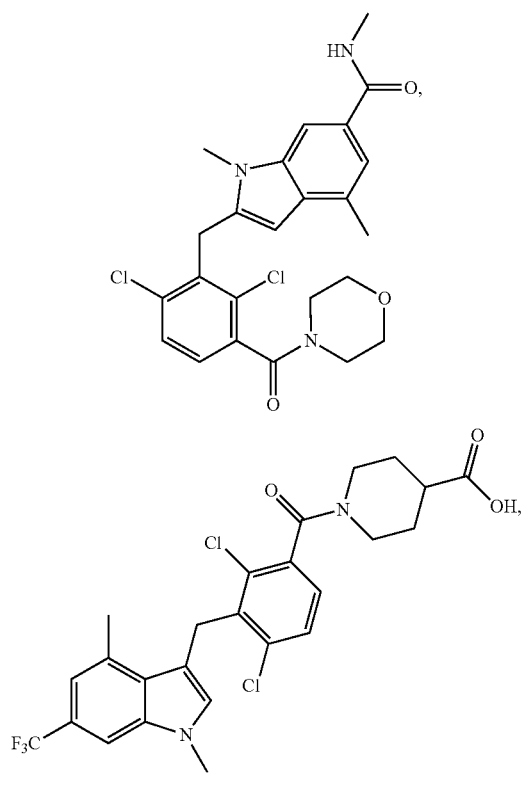
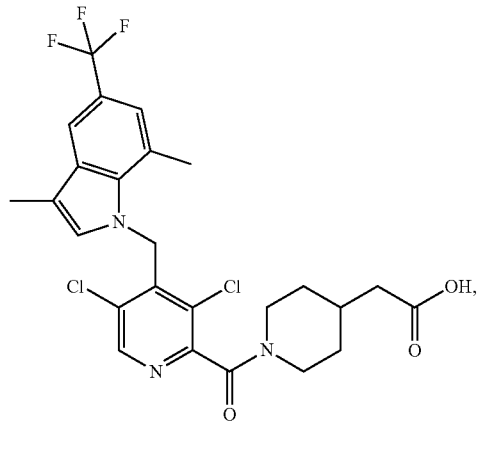
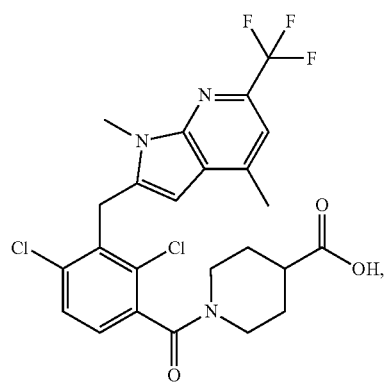
938
-continued
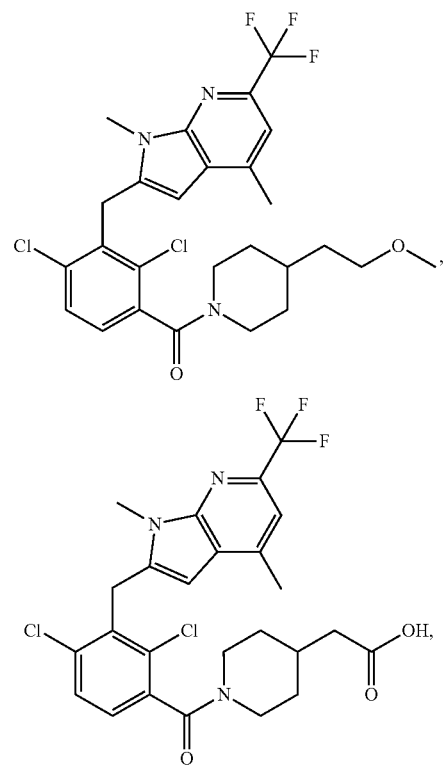
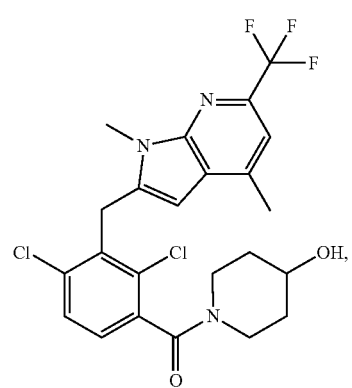
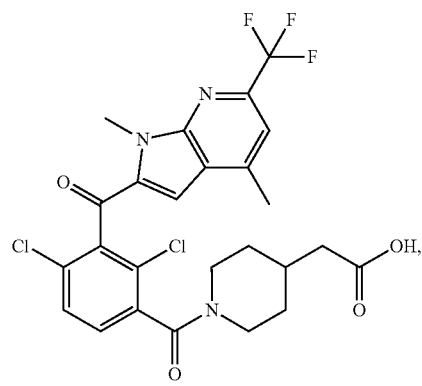

939
-continued
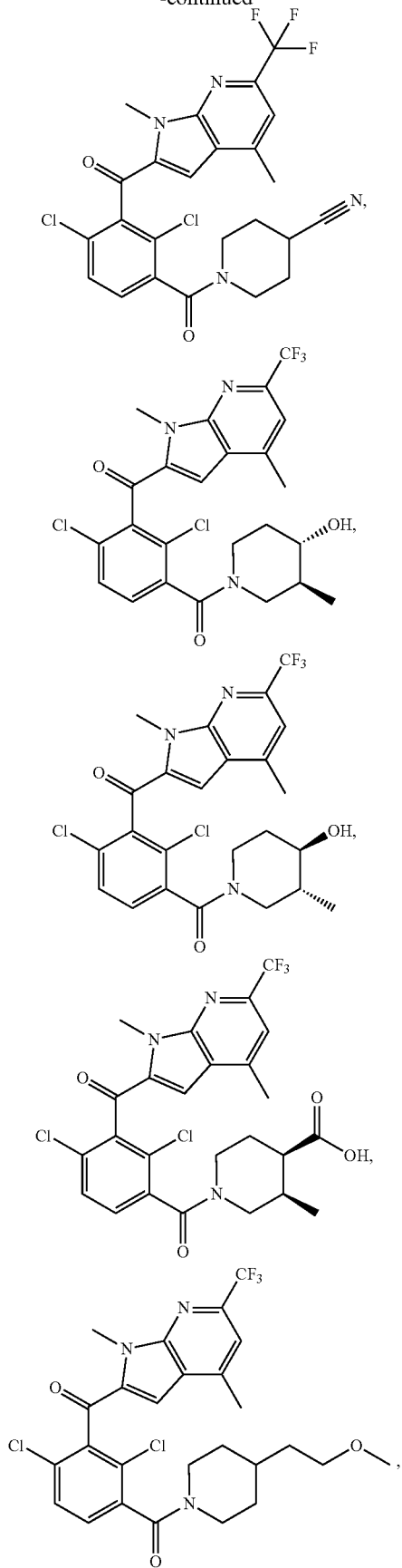
940
-continued
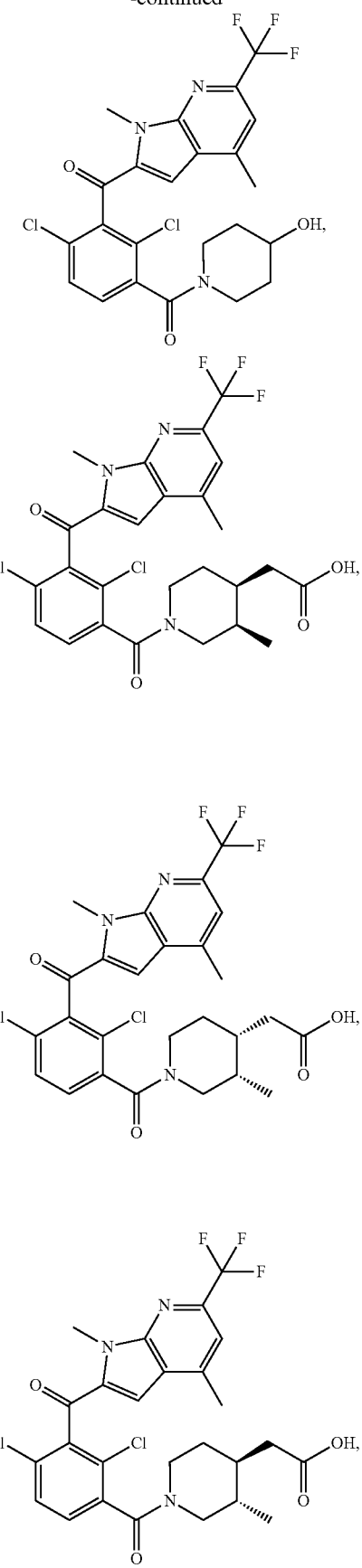

941
-continued
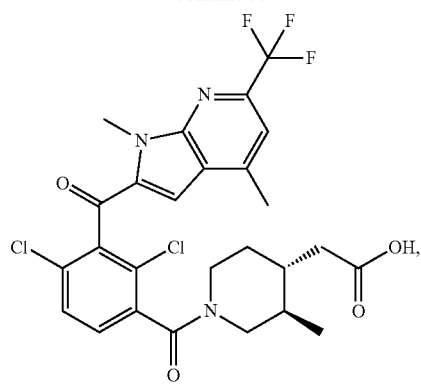
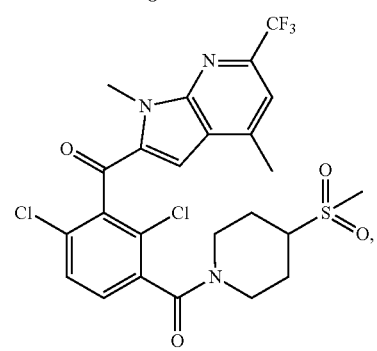
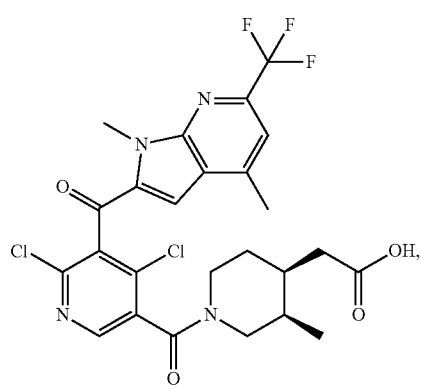
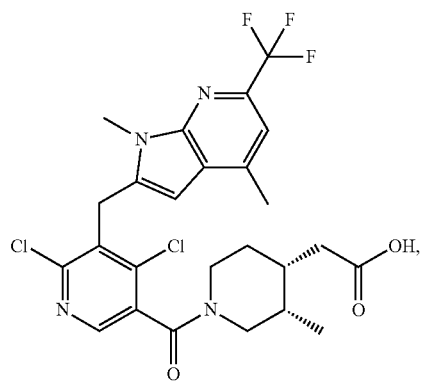
942
-continued
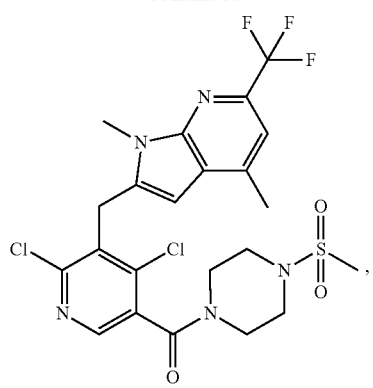
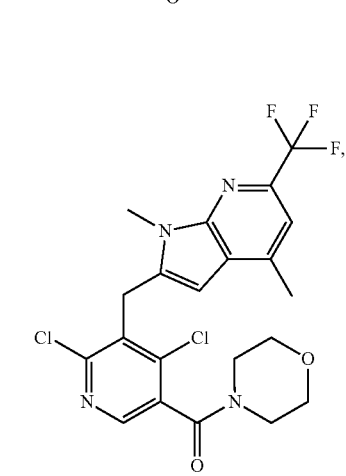
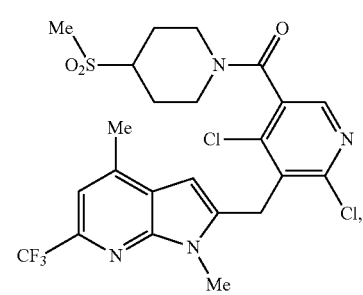
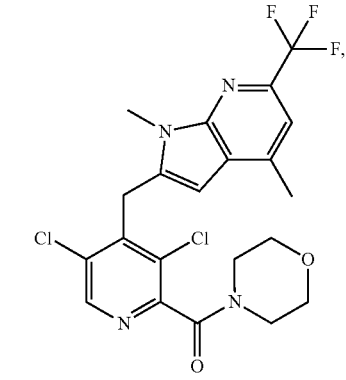

943
-continued

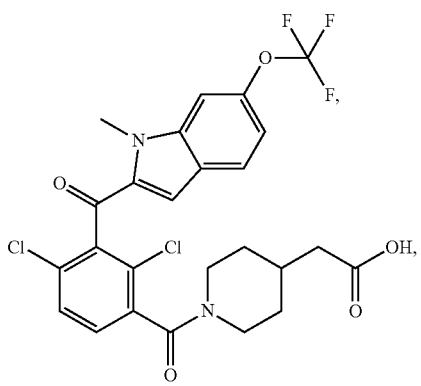

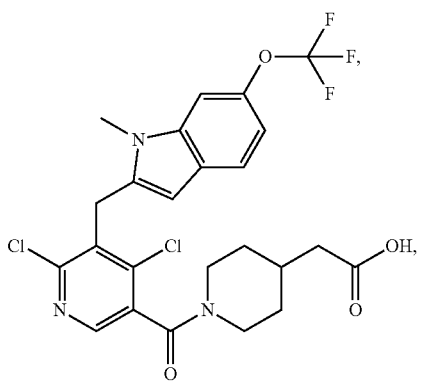

944
-continued

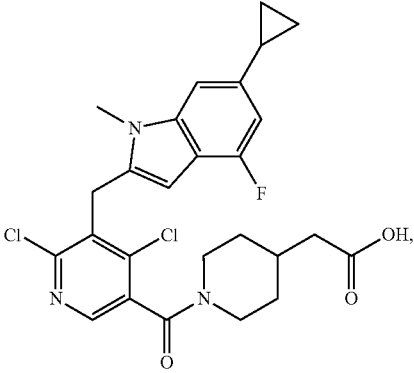

and pharmaceutically acceptable salts thereof.

27. A pharmaceutical composition comprising a compound of claim 1, or a pharmaceutically acceptable salt or stereoisomer thereof, and one or more pharmaceutically acceptable excipients.

28. The compound according to claim 1, or a pharmaceutically acceptable salt or stereoisomer thereof, wherein optionally substituted refers to optional and independent substitution with one or more substituents selected from the group consisting of ($C_1$-$C_8$)alkyl; ($C_2$-$C_8$)alkenyl; ($C_2$-$C_8$)alkynyl; ($C_3$-$C_{10}$)cycloalkyl; halogen; halogenated ($C_1$-$C_8$)alkyl; —O—($C_1$-$C_8$)alkyl; =O; =$CH_2$; —OH; —$CH_2$OH; —$CH_2NH_2$; ($C_1$-$C_4$)alkyl-OH; —$CH_2CH_2OCH_2CH_3$; —S—($C_1$-$C_8$)alkyl; —SH; —NH($C_1$-$C_8$)alkyl; —N(($C_1$-$C_8$)alkyl)$_2$; —$NH_2$; —C(O)$NH_2$; —$CH_2$NHC(O)($C_1$-$C_4$)alkyl; —$CH_2$NHC(O)$CH_2$Cl; —$CH_2$NHC(O)$CH_2$CN; —$CH_2$NHC(O)$CH_2CH_2$N($CH_3$)$_2$; —$CH_2$NHC(O)C(=$CH_2$)$CH_3$; —$CH_2$NHC(O)($C_2$-$C_4$)alkynyl; —$CH_2$NHC(O)$CH_2CH_2$-piperidinyl; —($C_1$-$C_4$)alkyl-morpholinyl; —$CH_2$NHC(O)$CH_2$O—phenyl wherein phenyl is optionally substituted with halogen; ($C_1$-$C_4$) alkoxy; —C(O)($C_1$-$C_4$)alkoxy; —C(O)N($CH_3$)$_2$; —N($CH_3$)$_2$; —NHC(O)($C_1$-$C_4$)alkyl; —NHC(O)($C_2$-$C_4$)alkenyl; —NHC(O)$CH_2$CN; 4-methylpiperazinecarbonyl; —($C_1$-$C_4$)alkylC(O)$NH_2$; —C(O)NH($C_1$-$C_8$)alkyl; —C(O)N(($C_1$-$C_8$)alkyl)$_2$; —C(O)N(H)($C_3$-$C_8$)cycloalkyl; —C(O)($C_1$-$C_4$)alkoxy; —NHC(O)H; —NHC(O)($C_1$-$C_8$)alkyl; —NHC(O)($C_3$-$C_8$)cycloalkyl; —N(($C_1$-$C_8$)alkyl)C(O)H; —N(($C_1$-$C_8$)alkyl)C(O)($C_1$-$C_8$)alkyl; —NHC(O)$NH_2$; —NHC(O)NH($C_1$-$C_8$)alkyl; —N(($C_1$-$C_8$)alkyl)C(O)$NH_2$; —NHC(O)N(($C_1$-$C_8$)alkyl)$_2$; —N(($C_1$-$C_8$)alkyl)C(O)N(($C_1$-$C_8$)alkyl)$_2$; —N(($C_1$-$C_8$)alkyl)C(O)NH(($C_1$-$C_8$)alkyl); —NHCH$_2$-heteroaryl; —OCH$_2$-heteroaryl; —C(O)H; —C(O)($C_1$-$C_8$)alkyl; —CN; —$NO_2$; —S(O)($C_1$-$C_8$)alkyl; —S(O)$_2$($C_1$-$C_8$)alkyl; —S(O)$_2$N(($C_1$-$C_8$)alkyl)$_2$; —S(O)$_2$NH($C_1$-$C_8$)alkyl; —S(O)$_2$NH($C_3$-$C_8$)cycloalkyl; —S(O)$_2$$NH_2$; —NHS(O)$_2$($C_1$-$C_8$)alkyl; —N(($C_1$-$C_5$)alkyl)S(O)$_2$($C_1$-$C_8$)alkyl; —($C_1$-$C_8$)alkyl-O—($C_1$-$C_8$)alkyl; —O—($C_1$-$C_8$)alkyl-O—($C_1$-$C_8$)alkyl; —C(O)OH; —C(O)O($C_1$-$C_8$)alkyl; —NHOH; —NHO($C_1$-$C_8$)alkyl; —O-halogenated ($C_1$-$C_8$)alkyl; —S(O)$_2$-halogenated ($C_1$-$C_8$)alkyl; —S-halogenated ($C_1$-$C_8$)alkyl; pyrrolidine; tetrahydrofuran; pyran; morpholine; tetrazole; imidazole; furan; pyrazine; pyrazole; phenyl; benzyl; —NHC(O)O—($C_1$-$C_6$)alkyl; —N(($C_1$-$C_6$)alkyl)C(O)O—($C_1$-$C_6$)alkyl; —C(=NH)—($C_1$-$C_6$)alkyl; —C(=NOH)—($C_1$-$C_6$)alkyl; and —C(=NO$C_1$-$C_6$alkyl)-($C_1$-$C_6$)alkyl.

29. The compound according to claim 25, or a pharmaceutically acceptable salt or stereoisomer thereof, wherein R⁴ is piperidinyl optionally substituted with —CH₃, —CO₂H, —CH₂CO₂H, —CH₂CO₂CH₃, or —CO₂CH₂CH₃.

30. The compound according to claim 1, wherein the compound is:

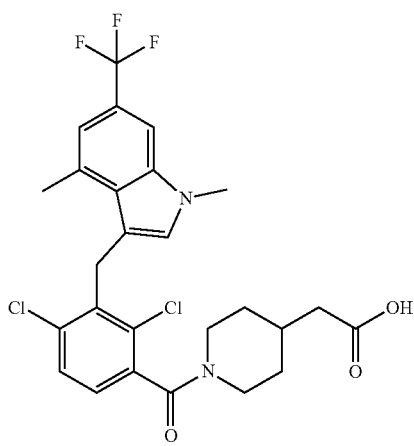 [SMILES: Cc1cc(C(F)(F)F)cc2c1c(Cc1c(Cl)ccc(C(=O)N3CCC(CC(=O)O)CC3)c1Cl)cn2C]

or a pharmaceutically acceptable salt thereof.

31. The compound according to claim 1, wherein the compound is:

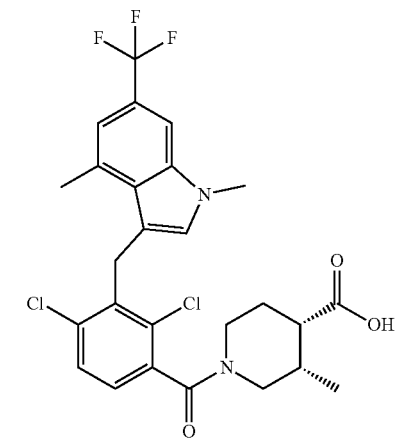 [SMILES: Cc1cc(C(F)(F)F)cc2c1c(Cc1c(Cl)ccc(C(=O)N3CC[C@H](C(=O)O)[C@H](C)C3)c1Cl)cn2C]

or a pharmaceutically acceptable salt thereof.

32. The compound according to claim 1, wherein the compound is:

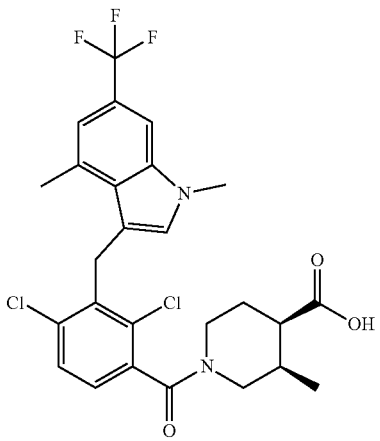 [SMILES: Cc1cc(C(F)(F)F)cc2c1c(Cc1c(Cl)ccc(C(=O)N3CC[C@@H](C(=O)O)[C@@H](C)C3)c1Cl)cn2C]

or a pharmaceutically acceptable salt thereof.

33. The compound according to claim 1, wherein the compound is:

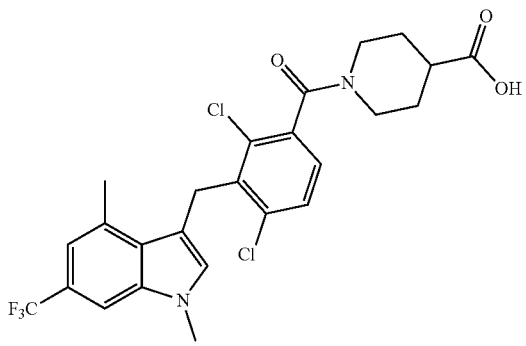 [SMILES: Cc1cc(C(F)(F)F)cc2c1c(Cc1c(Cl)ccc(C(=O)N3CCC(C(=O)O)CC3)c1Cl)cn2C]

or a pharmaceutically acceptable salt thereof.

34. The compound according to claim 1, wherein the compound is:

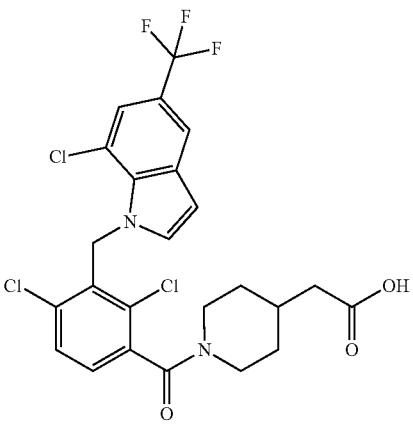 [SMILES: O=C(O)CC1CCN(C(=O)c2ccc(Cl)c(Cn3ccc4cc(C(F)(F)F)cc(Cl)c43)c2Cl)CC1]

or a pharmaceutically acceptable salt thereof.

35. The compound according to claim 1, wherein the compound is:

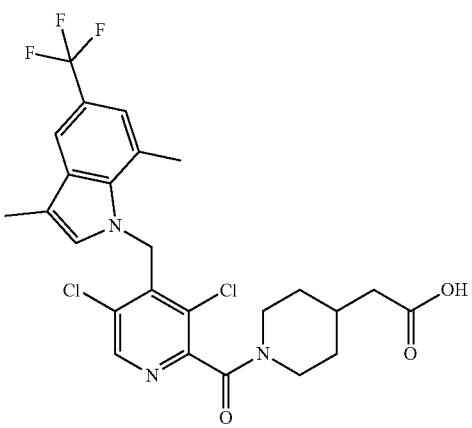 [SMILES: Cc1cn(Cc2c(Cl)cnc(C(=O)N3CCC(CC(=O)O)CC3)c2Cl)c2c(C)cc(C(F)(F)F)cc12]

or a pharmaceutically acceptable salt thereof.

36. A pharmaceutical composition comprising a compound of claim 26, or a pharmaceutically acceptable salt thereof, and one or more pharmaceutically acceptable excipients.

37. The compound according to claim 26, wherein the compound is:

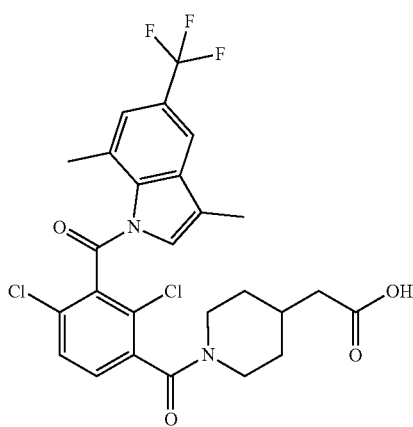 [SMILES: Cc1cn(C(=O)c2c(Cl)ccc(C(=O)N3CCC(CC(=O)O)CC3)c2Cl)c2c(C)cc(C(F)(F)F)cc12]

or a pharmaceutically acceptable salt thereof.

38. The compound according to claim 26, wherein the compound is:

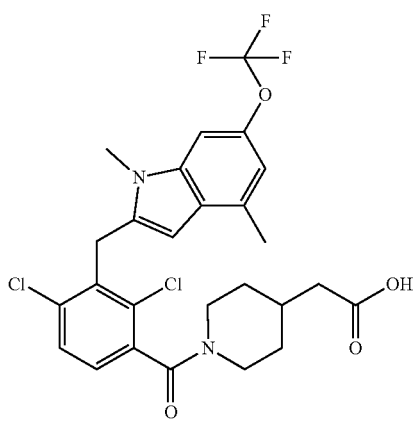

or a pharmaceutically acceptable salt thereof.

39. The compound according to claim 26, wherein the compound is:

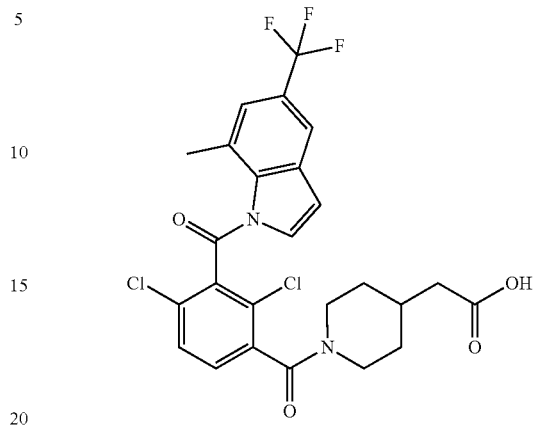

or a pharmaceutically acceptable salt thereof.

40. The compound according to claim 13, or a pharmaceutically acceptable salt or stereoisomer thereof, wherein $R^4$ is piperidinyl optionally substituted with —$CH_3$, —$CO_2H$, —$CH_2CO_2H$, —$CH_2CO_2CH_3$, or —$CO_2CH_2CH_3$.

41. The compound according to claim 1, or a pharmaceutically acceptable salt or stereoisomer thereof, wherein:
W is C;
X is $CR^a$;
Y is $NR^a$;
Z is $CR^3$;
A is C;
E is C;
V is $CR^3$;
$L^1$ is connected to W;
$L^1$ is —$CH_2$— or CO;
$R^1$ is —Cl;
$R^2$ is —Cl; and
$R^4$ is optionally substituted piperidinyl.

42. The compound according to claim 1, or a pharmaceutically acceptable salt or stereoisomer thereof, wherein:
W is $CR^a$, wherein $R^a$ is H;
X is $CR^a$;
Y is N;
Z is $CR^3$;
A is C;
E is C;
V is $CR^3$;
$L^1$ is connected to Y;
$L^1$ is CO;
$R^1$ is —Cl;
$R^2$ is —Cl; and
$R^4$ is optionally substituted piperidinyl.

43. The compound according to claim 41, or a pharmaceutically acceptable salt or stereoisomer thereof, wherein $R^4$ is piperidinyl optionally substituted with —$CH_3$, —$CO_2H$, —$CH_2CO_2H$, —$CH_2CO_2CH_3$, or —$CO_2CH_2CH_3$.

44. The compound according to claim 42, or a pharmaceutically acceptable salt or stereoisomer thereof, wherein $R^4$ is piperidinyl optionally substituted with —$CH_3$, —$CO_2H$, —$CH_2CO_2H$, —$CH_2CO_2CH_3$, or —$CO_2CH_2CH_3$.

45. A pharmaceutical composition comprising a compound of claim 30, or a pharmaceutically acceptable salt thereof, and one or more pharmaceutically acceptable excipients.

46. A pharmaceutical composition comprising a compound of claim 31, or a pharmaceutically acceptable salt thereof, and one or more pharmaceutically acceptable excipients.

47. A pharmaceutical composition comprising a compound of claim 32, or a pharmaceutically acceptable salt thereof, and one or more pharmaceutically acceptable excipients.

48. A pharmaceutical composition comprising a compound of claim 33, or a pharmaceutically acceptable salt thereof, and one or more pharmaceutically acceptable excipients.

49. A pharmaceutical composition comprising a compound of claim 34, or a pharmaceutically acceptable salt thereof, and one or more pharmaceutically acceptable excipients.

50. A pharmaceutical composition comprising a compound of claim 35, or a pharmaceutically acceptable salt thereof, and one or more pharmaceutically acceptable excipients.

51. A pharmaceutical composition comprising a compound of claim 37, or a pharmaceutically acceptable salt thereof, and one or more pharmaceutically acceptable excipients.

52. A pharmaceutical composition comprising a compound of claim 38, or a pharmaceutically acceptable salt thereof, and one or more pharmaceutically acceptable excipients.

53. A pharmaceutical composition comprising a compound of claim 39, or a pharmaceutically acceptable salt thereof, and one or more pharmaceutically acceptable excipients.

* * * * *

UNITED STATES PATENT AND TRADEMARK OFFICE
CERTIFICATE OF CORRECTION

PATENT NO. : 10,106,501 B2  Page 1 of 5
APPLICATION NO. : 15/176309
DATED : October 23, 2018
INVENTOR(S) : Maria A. Argiriadi et al.

It is certified that error appears in the above-identified patent and that said Letters Patent is hereby corrected as shown below:

In the Claims

In Claim 26, Column 877, Lines 2 – 16, delete " 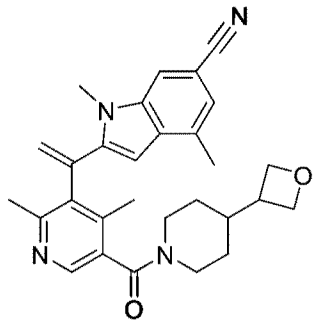 " and insert therefore -- 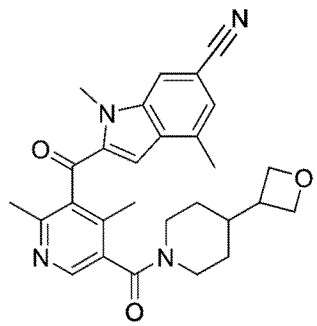 --.

Signed and Sealed this
Eighth Day of January, 2019

Andrei Iancu
*Director of the United States Patent and Trademark Office*

CERTIFICATE OF CORRECTION (continued)
U.S. Pat. No. 10,106,501 B2

In Claim 26, Column 886, Lines 17 – 2, delete " 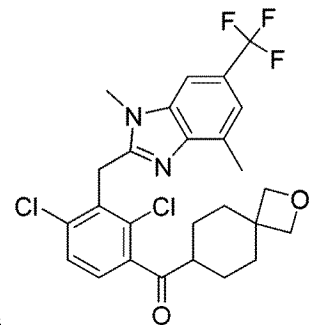 " and insert therefore -- 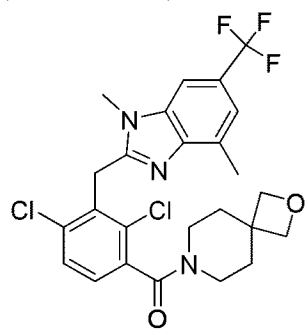 --.

In Claim 26, Column 900, Lines 17 – 2, delete " 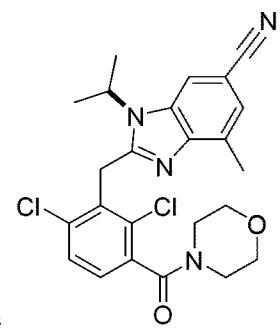 " and insert therefore -- 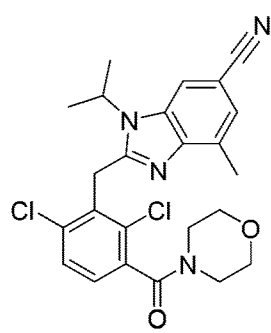 --.

CERTIFICATE OF CORRECTION (continued)
U.S. Pat. No. 10,106,501 B2

In Claim 26, Column 910, Lines 3 – 3, delete " 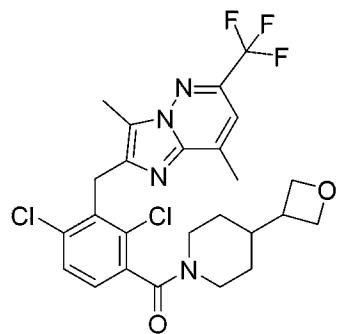 " and insert therefore -- 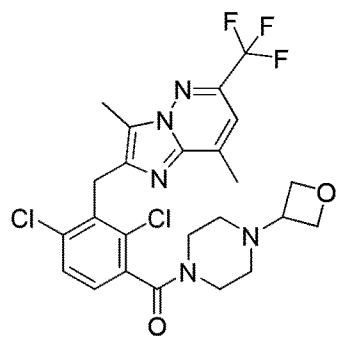 --.

In Claim 26, Column 929, Lines 35 – 50, delete " 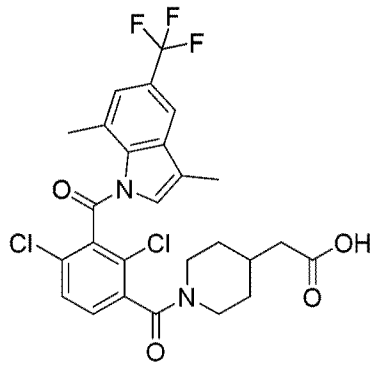 " and insert therefore -- 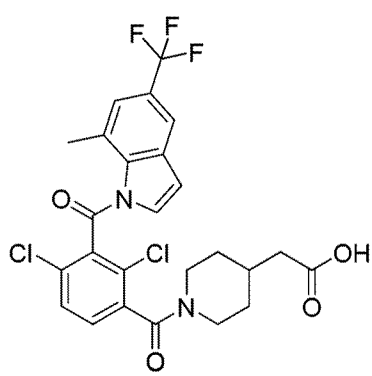 --.

In Claim 26, Column 935, Lines 50 – 65, delete " 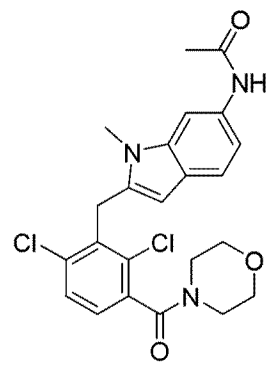 " and insert therefore -- 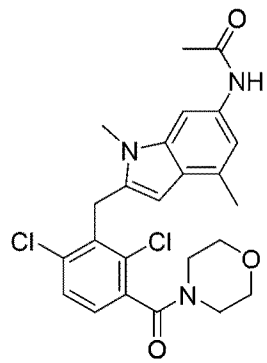 --.
In Claim 28, Column 944, Line 57, delete "-N(($C_1$-$C_5$)alkyl)S(O)$_2$($C_1$-$C_8$)alkyl;" and insert therefore -- -N(($C_1$-$C_8$)alkyl)S(O)$_2$($C_1$-$C_8$)alkyl;--.
In Claim 38, Column 947, Lines 4 – 65, delete " 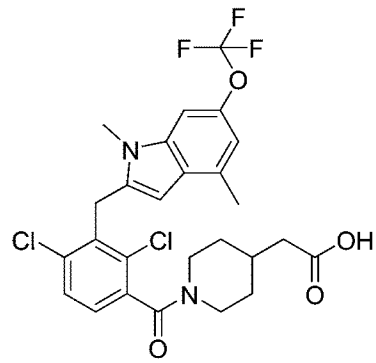 " and insert therefore -- 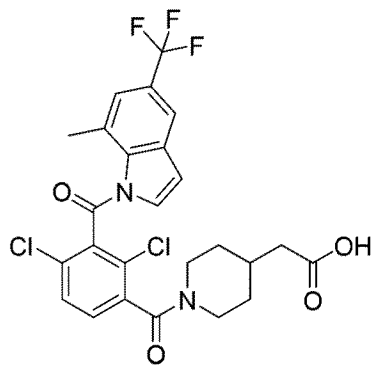 --.

CERTIFICATE OF CORRECTION (continued)
U.S. Pat. No. 10,106,501 B2

In Claim 39, Column 948, Lines 5 – 5, delete " 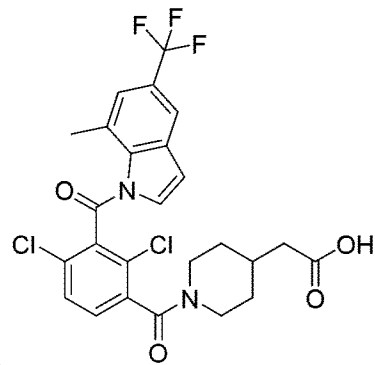 " and insert therefore -- 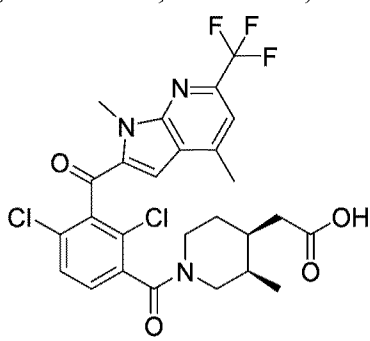 --.